US010364256B2

(12) United States Patent
Callahan et al.

(10) Patent No.: US 10,364,256 B2
(45) Date of Patent: Jul. 30, 2019

(54) BIARYL PYRAZOLES AS NRF2 REGULATORS

(71) Applicants: GlaxoSmithKline Intellectual Property Development Limited, Brentford, Middlesex (GB); Astex Therapeutics Limited, Cambridge, Cambridgeshire (GB)

(72) Inventors: James Callahan, King of Prussia, PA (US); Jeffrey K. Kerns, King of Prussia, PA (US); Peng Li, King of Prussia, PA (US); Tindy Li, King of Prussia, PA (US); Brent W. McCleland, King of Prussia, PA (US); Hong Nie, King of Prussia, PA (US); Joseph E. Pero, Anderson, SC (US); Thomas Glanmor Davies, Cambridge (GB); Maria Grazia Carr, Cambridge (GB); Charlotte Mary Griffiths-Jones, Cambridge (GB); Thomas Daniel Heightman, Cambridge (GB); David Norton, Cambridge (GB); Marinus Leendert Verdonk, Cambridge (GB); Alison Jo-Anne Woolford, Cambridge (GB); Hendrika Maria Gerarda Willems, Cambridge (GB)

(73) Assignees: GlaxoSmithKline Intellectual Property Development Limited, Brentford, Middlesex (GB); Astex Therapeutics Limited, Cambridge, Cambridgeshire (GB)

( * ) Notice: Subject to any disclaimer, the term of this patent is extended or adjusted under 35 U.S.C. 154(b) by 0 days.

(21) Appl. No.: 15/765,354

(22) PCT Filed: Oct. 6, 2016

(86) PCT No.: PCT/IB2016/055996
§ 371 (c)(1),
(2) Date: Apr. 2, 2018

(87) PCT Pub. No.: WO2017/060854
PCT Pub. Date: Apr. 13, 2017

(65) Prior Publication Data
US 2018/0282349 A1    Oct. 4, 2018

Related U.S. Application Data

(60) Provisional application No. 62/237,655, filed on Oct. 6, 2015.

(51) Int. Cl.
C07D 401/04    (2006.01)
C07D 401/06    (2006.01)
C07D 401/10    (2006.01)
C07D 401/12    (2006.01)
(Continued)

(52) U.S. Cl.
CPC ......... *C07D 515/14* (2013.01); *A61K 9/0019* (2013.01); *A61K 9/0053* (2013.01); *A61K 9/0078* (2013.01); *A61P 11/00* (2018.01); *C07D 401/04* (2013.01); *C07D 401/06* (2013.01); *C07D 401/10* (2013.01); *C07D 401/12* (2013.01); *C07D 401/14* (2013.01); *C07D 403/08* (2013.01); *C07D 403/10* (2013.01); *C07D 403/14* (2013.01); *C07D 405/14* (2013.01); *C07D 413/08* (2013.01); *C07D 413/14* (2013.01); *C07D 417/14* (2013.01)

(58) Field of Classification Search
None
See application file for complete search history.

(56) References Cited

U.S. PATENT DOCUMENTS

2003/0191115 A1    10/2003    Pinto et al.
2004/0157919 A1    8/2004    Wu et al.
2015/0018422 A1    1/2015    Miwatashi et al.

FOREIGN PATENT DOCUMENTS

EP    528586 B1    2/1995
EP    0478328 B1    1/1996
(Continued)

OTHER PUBLICATIONS

Antonio R. Damasio, Alzheimer's Disease and Related Dementias, Cecil Textbook of Medicine, 20th edition (1996), vol. 2, pp. 1992-1996 (Year: 1996).
(Continued)

*Primary Examiner* — Alicia L Otton
(74) *Attorney, Agent, or Firm* — Nora L. Stein; Fang Qian; Edward R. Gimmi

(57) ABSTRACT

The present invention relates to biaryl pyrazole compounds of Formula (I)

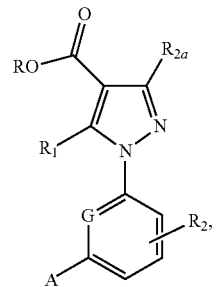

Formula (I)

methods of making them, pharmaceutical compositions containing them and their use as NRF2 regulators.

15 Claims, No Drawings

(51) Int. Cl.

| | | |
|---|---|---|
| *C07D 401/14* | (2006.01) | |
| *C07D 403/08* | (2006.01) | |
| *C07D 403/10* | (2006.01) | |
| *C07D 403/14* | (2006.01) | |
| *C07D 405/14* | (2006.01) | |
| *C07D 413/08* | (2006.01) | |
| *C07D 413/14* | (2006.01) | |
| *C07D 417/14* | (2006.01) | |
| *A61K 31/41* | (2006.01) | |
| *A61K 31/4196* | (2006.01) | |
| *A61K 31/445* | (2006.01) | |
| *A61P 11/00* | (2006.01) | |
| *C07D 515/14* | (2006.01) | |
| *A61K 9/00* | (2006.01) | |

(56) References Cited

FOREIGN PATENT DOCUMENTS

| WO | 1993012075 A1 | 6/1993 |
|---|---|---|
| WO | 1995032710 A1 | 12/1995 |
| WO | 2001025181 A1 | 4/2001 |
| WO | 2001053267 A1 | 7/2001 |
| WO | 2002059080 A2 | 8/2002 |
| WO | 2002080899 A1 | 10/2002 |
| WO | 2002100812 A1 | 12/2002 |
| WO | 2003026652 A1 | 4/2003 |
| WO | 2004007464 A1 | 1/2004 |
| WO | WO 2004/092140 A1 | 10/2004 |
| WO | 2006044133 A1 | 4/2006 |
| WO | 2006118320 A1 | 11/2006 |
| WO | 2008002490 A2 | 1/2008 |
| WO | WO 2009/032249 * | 3/2009 ............ A61P 9/12 |
| WO | WO 2009/032249 A1 | 3/2009 |
| WO | 2010005922 A1 | 1/2010 |
| WO | WO 2010/099054 A1 | 9/2010 |
| WO | 2011097300 A1 | 8/2011 |
| WO | 2012068589 A2 | 5/2012 |
| WO | 2013067036 A1 | 5/2013 |
| WO | 2013122028 A1 | 8/2013 |
| WO | 2013155528 A2 | 10/2013 |
| WO | 2014145642 A2 | 9/2014 |
| WO | 2015092713 A1 | 6/2015 |
| WO | WO2016001875 | 1/2016 |
| WO | WO2016001876 | 1/2016 |
| WO | WO2016001878 | 1/2016 |
| WO | 2016/202253 A1 | 12/2016 |
| WO | 2016/203400 A1 | 12/2016 |
| WO | 2016/203401 A1 | 12/2016 |
| WO | 2017060855 A1 | 4/2017 |

OTHER PUBLICATIONS

FDA mulls drug to slow late-stage Alzheimer's, [retrieved on Sep. 23, 2003]. Retrieved online via Internet, URL: http://www.cnn.com/2003/HEALTH/conditions/09/24/alzheimers.drug.ap/index.html (Year: 2003).

Robert B. Layzer, Section Five—Degenerative Diseases of the Nervous System, Cecil Textbook of Medicine, 20th edition (1996), vol. 2, pp. 2050-2057 (Year: 1996).

TG Davies, et al, "Journal of Medicinal Chemistry Paper — Monoacidic Inhibitors of the Kelch-like ECH-Associated Protein 1: Nuclear Factor Erythroid 2-Related Factor 2 (KEAP1:NRF2) Protein-Protein Interaction with High Cell Potency Identified by Fragment-Based discovery." J Med Chem. Apr. 28, 2016;59(8):3991-4006.

\* cited by examiner

BIARYL PYRAZOLES AS NRF2 REGULATORS

This application is a 371 national stage entry of International Application No. PCT/IB2016/055996, filed Oct. 6, 2016, which claims the benefit of U.S. Provisional Application No. 62/237,655, filed Oct. 6, 2015, which is incorporated herein in its entirety.

FIELD OF THE INVENTION

The present invention relates to biaryl pyrazole compounds, methods of making them, pharmaceutical compositions containing them and their use as NRF2 regulators.

BACKGROUND OF THE INVENTION

NRF2 (NF-E2 related factor 2) is a member of the cap-n-collar family of transcription factors containing a characteristic basic-leucine zipper motif. Under basal conditions, NRF2 levels are tightly controlled by the cytosolic actin-bound repressor, KEAP1 (Kelch-like ECH associating protein 1), which binds to NRF2 and targets it for ubiquitylation and proteasomal degradation via the Cul3-based E3-ubiquitin ligase complex. Under conditions of oxidative stress, DJ1 (PARK7) is activated and stabilizes NRF2 protein by preventing NRF2 from interacting with KEAP1. Also, modification of reactive cysteines on KEAP1 can cause a conformational change in KEAP1 that alters NRF2 binding and promotes NRF2 stabilization. Thus, the levels of NRF2 in the cell are usually kept low in normal conditions but the system is designed to respond quickly to environmental stress by increasing NRF2 levels and thus downstream NRF2 activity.

Inappropriately low NRF2 activity in the face of on-going oxidative stress appears to be a pathological mechanism underlying chronic obstructive pulmonary disease (COPD). Yamada, K., et al. *BMC Pulmonary Medicine,* 2016, 16: 27. This may be a result of an altered equilibrium between NRF2 regulators with both inappropriate lack of positive regulators such as DJ1, and overabundance of negative regulators such as Keap1 and Bach1. Therefore, restoration of NRF2 activity in the lungs of COPD patients should result in repair of the imbalance and mitigation of deleterious processes such as apoptosis of structural cells (including alveolar epithelial and endothelial cells) and inflammation. The results of these effects would be enhanced cytoprotection, preservation of lung structure, and structural repair in the COPD lung, thus slowing disease progression. Therefore, NRF2 modulators may treat COPD (Boutten, A., et al. 2011. *Trends Mol. Med.* 17:363-371) and other respiratory diseases, including asthma and pulmonary fibrosis (Cho, H. Y., and Kleeberger, S. R. 2010. *Toxicol. Appl. Pharmacol.* 244:43-56).

The therapeutic potential of an NRF2 activator is exemplified in pulmonary macrophages from COPD patients where NRF2 pathway appears maladaptive. These cells have impaired bacterial phagocytosis compared with similar cells from control patients, and this effect is reversed by the addition of NRF2 activators in vitro. Therefore, in addition to the effects mentioned above, restoration of appropriate NRF2 activity could also rescue COPD exacerbations by reducing lung infection.

This is demonstrated by the NRF2 activator, Sulforaphane, which increases the expression of Macrophage Receptor with Collagenous structure (MARCO) by COPD macrophages and alveolar macrophages from cigarette smoke-exposed mice, thereby improving in these cells bacterial phagocytosis (*Pseudomonas aeruginosa,* non-typable *Haemophilus influenzae*) and bacterial clearance both ex vivo and in vivo. (Harvey, C. J., et al. 2011. *Sci. Transl. Med.* 3:78ra32).

The therapeutic potential of targeting NRF2 in the lung is not limited to COPD. Rather, targeting the NRF2 pathway could provide treatments for other human lung and respiratory diseases that exhibit oxidative stress components such as chronic asthma and acute asthma, lung disease secondary to environmental exposures including but not limited to ozone, diesel exhaust and occupational exposures, fibrosis, acute lung infection (e.g., viral (Noah, T. L. et al. 2014. PLoS ONE 9(6): e98671), bacterial or fungal), chronic lung infection, α1 antitrypsin disease, and cystic fibrosis (C F, Chen, J. et al. 2008. *PLoS One.* 2008; 3(10):e3367).

A therapy that targets the NRF2 pathway also has many potential uses outside the lung and respiratory system. Many of the diseases for which an NRF2 activator may be useful are autoimmune diseases (psoriasis, IBD, MS), suggesting that an NRF2 activator may be useful in autoimmune diseases in general.

In the clinic, a drug targeting the NRF2 pathway (bardoxolone methyl) has shown efficacy in diabetic patients with diabetic nephropathy/chronic kidney disease (CKD) (Aleksunes, L. M., et al. 2010. *J. Pharmacol. Exp. Ther.* 335:2-12), though phase III trials with this drug in patients with the most severe stage of CKD were terminated. Furthermore, there is evidence to suspect that such a therapy would be effective in sepsis-induced acute kidney injury, other acute kidney injury (AKI) (Shelton, L. M., et al. 2013. *Kidney International.* June 19. doi: 10.1038/ki.2013.248.), and kidney disease or malfunction seen during kidney transplantation.

In the cardiac area, bardoxolone methyl is currently under investigation in patients 30 with Pulmonary Arterial Hypertension and so a drug targeting NRF2 by other mechanisms may also be useful in this disease area. Oxidative stress is increased in the diseased myocardium, resulting in accumulation of reactive oxygen species (ROS) which impairs cardiac function [*Circ* (1987) 76(2); 458-468] and increases susceptibility to arrhythmia [*J of Mol & Cell Cardio* (1991) 23(8); 899-918] by a direct toxic effect of increased necrosis and apoptosis [*Circ Res* (2000) 87(12); 1172-1179]. In a mouse model of pressure overload (TAC), NRF2 gene and protein expression is increased during the early stage of cardiac adaptive hypertrophy, but decreased in the later stage of maladaptive cardiac remodeling associated with systolic dysfunction [*Arterioscler Thromb Vasc Biol* (2009) 29(11); 1843-5 1850; *PLOS ONE* (2012) 7(9); e44899]. In addition, NRF2 activation has been shown to suppress myocardial oxidative stress as well as cardiac apoptosis, fibrosis, hypertrophy, and dysfunction in mouse models of pressure overload [*Arterioscler Thromb Vasc Biol* (2009) 29(11); *J of Mol & Cell Cardio* (2014) 72; 305-315; and 1843-1850; *PLOS ONE* (2012) 7(9); e44899]. NRF2 activation has also been shown to protect against cardiac I/R injury in mice 10 [*Circ Res* (2009) 105(4); 365-374; *J of Mol & Cell Cardio* (2010) 49(4); 576-586] and reduce myocardial oxidative damage following cardiac I/R injury in rat. Therefore, a drug targeting NRF2 by other mechanisms may be useful in a variety of cardiovascular diseases including but not limited to atherosclerosis, hypertension, and heart failure (Oxidative Medicine and Cellular Longevity Volume 2013 (2013), Article ID 104308, 10 pages), acute coronary 15 syndrome, myocardial infarction, myocardial repair, cardiac remodeling, cardiac arrhythmias, heart failure with preserved ejection fraction, heart failure with reduced ejection fraction and diabetic cardiomyopathy.

A drug activating the NRF2 pathway could also be useful for treatment of several neurodegenerative diseases including Parkinson's disease (PD), Alzheimer's disease (AD), amyotrophic lateral sclerosis (ALS) (Brain Res. 2012 Mar. 29; 1446:109-18. 2011.12.064. Epub 2012 Jan. 12) and multiple sclerosis (MS). Multiple in vivo models have shown that NRF2 KO mice are more sensitive to neurotoxic insults than their wild-type counterparts. Treatment of rats with the NRF2 activator tert-butylhydroquinone (tBHQ) reduced cortical damage in rats in a cerebral ischemia-reperfusion model, and cortical glutathione levels were increased in NRF2 wild-type but not KO mice after administration of tBHQ (Shih, A. Y., et al. 2005. *J. Neurosci.* 25: 10321-10335). Tecfidera™ (dimethyl fumarate), which activates NRF2 among other targets, is approved in the U.S. to treat relapsing-remitting multiple sclerosis (MS). Activation of NRF2 may also help treat cases of Friedreich's Ataxia, where increased sensitivity to oxidative stress and impaired NRF2 activation has been reported (Paupe V., et al, 2009. PLoS One; 4(1):e4253. Omaveloxolone (RTA-408) is also in clinical trials for Friedreich's Ataxia.

There is preclinical evidence of the specific protective role of the NRF2 pathway in models of inflammatory bowel disease (IBD, Crohn's Disease and Ulcerative Colitis) and/or colon cancer (Khor, T. O., et al 2008. *Cancer Prev. Res.* (Phila) 1:187-191).

Age-related macular degeneration (AMD) is a common cause of vision loss in people over the age of 50. Cigarette smoking is a major risk factor for the development of non-neovascular (dry) AMD and perhaps also neovascular (wet) AMD. Findings in vitro and in preclinical species support the notion that the NRF2 pathway is involved in the anti-oxidant response of retinal epithelial cells and modulation of inflammation in preclinical models of eye injury (Schimel, et al. 2011. *Am. J. Pathol.* 178:2032-2043). Fuchs Endothelial Corneal Dystrophy (FECD) is a progressive, blinding disease characterized by corneal endothelial cells apoptosis. It is a disease of aging and increased oxidative stress related to low levels of NRF2 expression and/or function (Bitar, M. S., et al. 2012. *Invest Ophthalmol. Vis. Sci.* Aug. 24, 2012 vol. 53 no. 9 5806-5813). In addition, an NRF2 activator may be useful in uveitis or other inflammatory eye conditions.

Non-alcoholic steatohepatitis (NASH) is a disease of fat deposition, inflammation, and damage in the liver that occurs in patients who drink little or no alcohol. In preclinical models, development of NASH is greatly accelerated in KO mice lacking NRF2 when challenged with a methionine- and choline-deficient diet (Chowdhry S., et al. 2010. *Free Rad. Biol. & Med.* 48:357-371). Administration of the NRF2 activators oltipraz and NK-252 in rats on a choline-deficient L-amino acid-defined diet significantly attenuated progression of histologic abnormalities, especially hepatic fibrosis (Shimozono R. et al. 2012. *Molecular Pharmacology.* 84:62-70). Other liver diseases that may be amenable to NRF2 modulation are toxin-induced liver disease (e.g., acetaminophen-induced hepatic disease), viral hepatitis, and cirrhosis (Oxidative Medicine and Cellular Longevity Volume 2013 (2013), Article ID 763257, 9 page).

Recent studies have also begun to elucidate the role of ROS in skin diseases such as psoriasis. A study in psoriasis patients showed an increase in serum malondialdehyde and nitric oxide end products and a decrease in erythrocyte-superoxide dismutase activity, catalase activity, and total antioxidant status that correlated in each case with disease severity index (Dipali P. K., et al. Indian J Clin Biochem. 2010 October; 25(4): 388-392). Also, an NRF2 modulator may be useful in treating the dermatitis/topical effects of radiation (Schafer, M. et al. 2010. *Genes & Devl.* 24:1045-1058), and the immunosuppression due to radiation exposure (Kim, J. H. et al., J. Clin. Invest. 2014 Feb. 3; 124(2): 730-41).

There are also data suggesting that an NRF2 activator may be beneficial in preeclampsia, a disease that occurs in 2-5% of pregnancies and involves hypertension and proteinuria (*Annals of Anatomy—Anatomischer Anzeiaer* Volume 196, Issue 5, September 2014, Pages 268-277).

Preclinical data has shown that compounds with NRF2 activating activity are better at reversing high altitude-induced damage than compounds without NRF2 activity, using animal and cellular models of Acute Mountain Sickness (Lisk C. et al, 2013, Free Radic Biol Med. October 2013; 63: 264-273.)

SUMMARY OF THE INVENTION

In one aspect, this invention provides for biaryl pyrazole analogs, or a salt, particularly a pharmaceutically acceptable salt thereof, and pharmaceutical compositions containing them. In particular, the compounds of this invention include a compound of Formula (I).

In a second aspect, this invention provides for the use of the compounds of Formula (I) as NRF2 regulators.

Accordingly, the present invention is also directed to a method of regulating NRF2 which method comprises contacting a cell with a compound according to Formula (I), or a salt, particularly a pharmaceutically acceptable salt, thereof.

In another aspect, this invention provides for the use of the compounds of Formula (I) for treating and preventing conditions associated with NRF2 imbalance.

In one aspect, the invention is provides a pharmaceutical composition comprising a compound of the invention according to Formula (I), or a salt, particularly a pharmaceutically acceptable salt thereof, and a pharmaceutically acceptable excipient. Particularly, this invention is directed to a pharmaceutical composition for the treatment of an NRF2 regulated disease or disorder, wherein the composition comprises a compound according to Formula (I), or a salt, particularly a pharmaceutically acceptable salt thereof, and a pharmaceutically acceptable excipient.

In a further aspect, this invention provides for a method of treating a respiratory or non-respiratory disorder, including COPD, asthma, fibrosis, chronic asthma and acute asthma, lung disease secondary to environmental exposures, acute lung infection, chronic lung infection, al antitrypsin disease, cystic fibrosis, autoimmune diseases, diabetic nephropathy, chronic kidney disease, sepsis-induced acute kidney injury, acute kidney injury (AKI), kidney disease or malfunction seen during kidney transplantation, Pulmonary Arterial Hypertension, atherosclerosis, hypertension, heart failure, acute coronary syndrome, myocardial infarction, myocardial repair, cardiac remodelling, cardiac arrhythmias, Parkinson's disease (PD), Alzheimer's disease (AD), Friedreich's Ataxia (FA), amyotrophic lateral sclerosis (ALS), multiple sclerosis (MS), inflammatory bowel disease, colon cancer, neovascular (dry) AMD and neovascular (wet) AMD, eye injury, Fuchs Endothelial Corneal Dystrophy (FECD), uveitis or other inflammatory eye conditions, Non-alcoholic Steatohepatitis (NASH), toxin-induced liver disease (e.g., acetaminophen-induced hepatic disease), viral hepatitis, cirrhosis, psoriasis, dermatitis/topical effects of radiation, immunosuppression due to radiation exposure, Preeclampsia, and high altitude sickness, which comprises administering to a human in need thereof, a compound of Formula (I).

In one aspect, this invention relates to a method of treating COPD, which comprises administering to a human in need thereof, a compound of Formula (I), or a salt, particularly a pharmaceutically acceptable salt thereof.

In one aspect, this invention relates to a method of treating heart failure, which comprises administering to a human in need thereof, a compound of Formula (I), or a salt, particularly a pharmaceutically acceptable salt thereof.

In yet another aspect, this invention provides for the use of a compound of Formula (I), or a salt, particularly a pharmaceutically acceptable salt thereof, for the treatment of a respiratory or non-respiratory disorder, including COPD, asthma, fibrosis, chronic asthma and acute asthma, lung disease secondary to environmental exposures, acute lung infection, chronic lung infection, al antitrypsin disease, cystic fibrosis, autoimmune diseases, diabetic nephropathy, chronic kidney disease, sepsis-induced acute kidney injury, acute kidney injury (AKI), kidney disease or malfunction seen during kidney transplantation, Pulmonary Arterial Hypertension, atherosclerosis, hypertension, heart failure, acute coronary syndrome, myocardial infarction, myocardial repair, cardiac remodelling, cardiac arrhythmias, Parkinson's disease (PD), Alzheimer's disease (AD), Friedreich's Ataxia (FA), amyotrophic lateral sclerosis (ALS), multiple sclerosis (MS), inflammatory bowel disease, colon cancer, neovascular (dry) AMD and neovascular (wet) AMD, eye injury, Fuchs Endothelial Corneal Dystrophy (FECD), uveitis or other inflammatory eye conditions, Non-alcoholic Steatohepatitis (NASH), toxin-induced liver disease (e.g., acetaminophen-induced hepatic disease), viral hepatitis, cirrhosis, psoriasis, dermatitis/topical effects of radiation, immunosuppression due to radiation exposure, Preeclampsia, and high altitude sickness.

In one aspect, this invention relates to the use of a compound of Formula (I), or a salt, particularly a pharmaceutically acceptable salt thereof, for the treatment of COPD.

In one aspect, this invention relates to the use of a compound of Formula (I), or a salt, particularly a pharmaceutically acceptable salt thereof, for the treatment of heart failure.

In a further aspect, this invention relates to use of a compound of Formula (I), or a salt, particularly a pharmaceutically acceptable salt thereof, in the manufacture of a medicament for use in the treatment of a respiratory or non-respiratory disorder, including COPD, asthma, fibrosis, chronic asthma and acute asthma, lung disease secondary to environmental exposures, acute lung infection, chronic lung infection, al antitrypsin disease, cystic fibrosis, autoimmune diseases, diabetic nephropathy, chronic kidney disease, sepsis-induced acute kidney injury, acute kidney injury (AKI), kidney disease or malfunction seen during kidney transplantation, Pulmonary Arterial Hypertension, atherosclerosis, hypertension, heart failure, acute coronary syndrome, myocardial infarction, myocardial repair, cardiac remodelling, cardiac arrhythmias, Parkinson's disease (PD), Alzheimer's disease (AD), Friedreich's Ataxia (FA), amyotrophic lateral sclerosis (ALS), multiple sclerosis (MS), inflammatory bowel disease, colon cancer, neovascular (dry) AMD and neovascular (wet) AMD, eye injury, Fuchs Endothelial Corneal Dystrophy (FECD), uveitis or other inflammatory eye conditions, Non-alcoholic Steatohepatitis (NASH), toxin-induced liver disease (e.g., acetaminophen-induced hepatic disease), viral hepatitis, cirrhosis, psoriasis, dermatitis/topical effects of radiation, immunosuppression due to radiation exposure, Preeclampsia, and high altitude sickness.

In one aspect, this invention relates to use of a compound of Formula (I), or a salt, particularly a pharmaceutically acceptable salt thereof, in the manufacture of a medicament for the treatment of COPD.

In one aspect, this invention relates to use of a compound of Formula (I), or a salt, particularly a pharmaceutically acceptable salt thereof, in the manufacture of a medicament for the treatment of heart failure.

In a further aspect, this invention relates to a compound of Formula (I), or a salt, particularly a pharmaceutically acceptable salt thereof, for use in medical therapy. This invention relates to a compound of Formula (I), or a salt, particularly a pharmaceutically acceptable salt thereof, for use in therapy, specifically for use in the treatment of a respiratory or non-respiratory disorder, including COPD, asthma, fibrosis, chronic asthma and acute asthma, lung disease secondary to environmental exposures, acute lung infection, chronic lung infection, al antitrypsin disease, cystic fibrosis, autoimmune diseases, diabetic nephropathy, chronic kidney disease, sepsis-induced acute kidney injury, acute kidney injury (AKI), kidney disease or malfunction seen during kidney transplantation, Pulmonary Arterial Hypertension, atherosclerosis, hypertension, heart failure, acute coronary syndrome, myocardial infarction, myocardial repair, cardiac remodelling, cardiac arrhythmias, Parkinson's disease (PD), Alzheimer's disease (AD), Friedreich's Ataxia (FA), amyotrophic lateral sclerosis (ALS), multiple sclerosis (MS), inflammatory bowel disease, colon cancer, neovascular (dry) AMD and neovascular (wet) AMD, eye injury, Fuchs Endothelial Corneal Dystrophy (FECD), uveitis or other inflammatory eye conditions, Non-alcoholic Steatohepatitis (NASH), toxin-induced liver disease (e.g., acetaminophen-induced hepatic disease), viral hepatitis, cirrhosis, psoriasis, dermatitis/topical effects of radiation, immunosuppression due to radiation exposure, Preeclampsia, and high altitude sickness.

In one aspect, this invention relates to a compound of Formula (I), or a salt, particularly a pharmaceutically acceptable salt thereof, for use in the treatment of COPD.

In one aspect, this invention relates to a compound of Formula (I), or a salt, particularly a pharmaceutically acceptable salt thereof, for use in the treatment of heart failure.

The compounds of Formula (I) and pharmaceutically acceptable salts thereof may be used in combination with one or more other agents which may be useful in the prevention or treatment of allergic disease, inflammatory disease, autoimmune disease, for example; antigen immunotherapy, anti-histamines, corticosteroids, (e.g., fluticasone propionate, fluticasone furoate, beclomethasone dipropionate, budesonide, ciclesonide, mometasone furoate, triamcinolone, flunisolide), NSAIDs, leukotriene modulators (e.g., montelukast, zafirlukast, pranlukast), iNOS inhibitors, tryptase inhibitors, IKK2 inhibitors, p38 inhibitors, Syk inhibitors, protease inhibitors such as elastase inhibitors, integrin antagonists (e.g., beta-2 integrin antagonists), adenosine A2a agonists, mediator release inhibitors such as sodium chromoglycate, 5-lipoxygenase inhibitors (zyflo), DP1 antagonists, DP2 antagonists, PI3K delta inhibitors, ITK inhibitors, LP (lysophosphatidic) inhibitors or FLAP (5-lipoxygenase activating protein) inhibitors (e.g., sodium 3-(3-(tert-butylthio)-1-(4-(6-ethoxypyridin-3-yl)benzyl)-5-((5-methylpyridin-2-yl)methoxy)-1H-indol-2-yl)-2,2-dimethylpropanoate), bronchodilators (e.g., muscarinic antagonists, beta-2 agonists), methotrexate, and similar agents; monoclonal antibody therapy such as anti-IgE, anti-TNF, anti-IL-5, anti-IL-6, anti-IL-12, anti-IL-1 and similar agents; cytokine receptor therapies e.g. etanercept and similar agents; antigen non-specific immunotherapies (e.g. interferon or other cytokines/chemokines, chemokine receptor modulators such as CCR3, CCR4 or CXCR2 antagonists, other cytokine/chemokine agonists or antagonists, TLR agonists and similar agents).

Suitably, for the treatment of asthma, compounds or pharmaceutical formulations of the invention may be administered together with an anti-inflammatory agent such as, for example, a corticosteroid, or a pharmaceutical formulation thereof. For example, a compound of the invention may be formulated together with an anti-inflammatory agent, such as a corticosteroid, in a single formulation, such as a dry powder formulation for inhalation. Alternatively, a pharmaceutical formulation comprising a compound of the invention may be administered in conjunction with a pharmaceutical formulation comprising an anti-inflammatory agent, such as a corticosteroid, either simultaneously or sequentially. In one embodiment, a pharmaceutical formulation comprising a compound of the invention and a pharmaceutical formulation comprising an anti-inflammatory agent, such as a corticosteroid, may each be held in device suitable for the simultaneous administration of both formulations via inhalation.

Suitable corticosteroids for administration together with a compound of the invention include, but are not limited to, fluticasone furoate, fluticasone propionate, beclomethasone diproprionate, budesonide, ciclesonide, mometasone furoate, triamcinolone, flunisolide and prednisilone. In one embodiment of the invention a corticosteroids for administration together with a compound of the invention via inhalation includes fluticasone furoate, fluticasone propionate, beclomethasone diproprionate, budesonide, ciclesonide, mometasone furoate, and, flunisolide.

Suitably, for the treatment of COPD, compounds or pharmaceutical formulations of the invention may be administered together with one or more bronchodilators, or pharmaceutical formulations thereof. For example, a compound of the invention may be formulated together with one or more bronchodilators in a single formulation, such as a dry powder formulation for inhalation. Alternatively, a pharmaceutical formulation comprising a compound of the invention may be administered in conjunction with a pharmaceutical formulation comprising one or more bronchodilators, either simultaneously or sequentially. In a further alternative, a formulation comprising a compound of the invention and a bronchodilator may be administered in conjunction with a pharmaceutical formulation comprising a further bronchodilator. In one embodiment, a pharmaceutical formulation comprising a compound of the invention and a pharmaceutical formulation comprising one or more bronchodilators may each be held in device suitable for the simultaneous administration of both formulations via inhalation. In a further embodiment, a pharmaceutical formulation comprising a compound of the invention together with a bronchodilator and a pharmaceutical formulation comprising a further bronchodilator may each be held in one or more devices suitable for the simultaneous administration of both formulations via inhalation.

Suitable bronchodilators for administration together with a compound of the invention include, but are not limited to, $\beta_2$-adrenoreceptor agonists and anticholinergic agents. Examples of $\beta_2$-adrenoreceptor agonists, include, for example, vilanterol, salmeterol, salbutamol, formoterol, salmefamol, fenoterol carmoterol, etanterol, naminterol, clenbuterol, pirbuterol, flerbuterol, reproterol, bambuterol, indacaterol, terbutaline and salts thereof, for example the xinafoate (1-hydroxy-2-naphthalenecarboxylate) salt of salmeterol, the sulphate salt of salbutamol or the fumarate salt of formoterol. Suitable anticholinergic agents include umeclidinium (for example, as the bromide), ipratropium (for example, as the bromide), oxitropium (for example, as the bromide) and tiotropium (for example, as the bromide). In one embodiment of the invention, a compound of the invention may be administered together with a $\beta_2$-adrenoreceptor agonist, such as vilanterol, and an anticholinergic agent, such as, umeclidinium.

The compounds may also be used in combination with agents for aiding transplantation including Cyclosporines, Tacrolimus, Mycophenolate mofetil, Prednisone, Azathioprine, Sirolimus, Daclizumab, Basiliximab and OKT3.

They may also be used in combination with agents for Diabetes: metformin (biguanides), meglitinides, sulfonylureas, DPP-4 inhibitors, Thiazolidinediones, Alpha-glucosidase inhibitors, Amylin mimetics, Incretin mimetics and insulin.

The compounds may be used in combination with antihypertensives such as diuretics, ACE inhibitors, ARBS, calcium channel blockers, and beta blockers.

Other aspects and advantages of the present invention are described further in the following detailed description of the preferred embodiments thereof.

DETAILED DESCRIPTION OF THE INVENTION

The present invention provides for compounds of Formula (I):

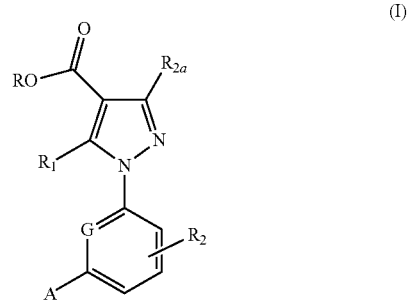

wherein:
R is hydrogen or —$C_{1-5}$alkyl, wherein —$C_{1-5}$alkyl is unsubstituted or substituted by one or two substituents independently selected from —OH, —OC(O)—$C_{1-5}$alkyl, —OC(O)-phenyl, —OC(O)—O—$C_{1-5}$alkyl,

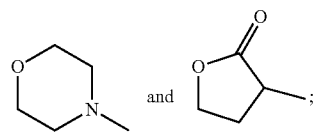

$R_1$ is —$CF_3$, —$C_{3-7}$cycloalkyl, or —$C_{4-7}$heterocycloalkyl, wherein the —$C_{3-7}$cycloalkyl, or —$C_{4-7}$heterocycloalkyl is unsubstituted or substituted by one or two substituents independently selected from —$C_{1-3}$alkyl, phenyl, triazolyl, pyridyl, pyridazinyl, imidazolyl, pyrazolyl, isoxazolyl, halo, —NR$_9$—C(O)—R$_{10}$ and —C(O)R$_{10}$, and wherein each of the phenyl, triazolyl, pyridyl, pyridazinyl, imidazolyl, pyrazolyl and isoxazolyl is unsubstituted or substituted by one or two substituents independently selected from halo, phenyl, and —C$_{1-7}$alkyl optionally substituted with phenyl, —N(CH$_3$)$_2$, —CF$_3$, —OH, —C$_{3-7}$cycloalkyl optionally substituted with —C$_{1-3}$alkyl, and —C$_{3-7}$heterocylcoalkyl optionally substituted with —C$_{1-3}$alkyl or —C(O)—C$_{1-4}$alkyl;

or R$_1$ is —C$_{2-3}$alkyl-R$_{11}$;

R$_{2a}$ is hydrogen, halo, or —C$_{1-3}$alkyl;

R$_2$ is hydrogen, halo, —CN, —O—C$_{1-3}$alkyl, —OH, or —C$_{1-3}$alkyl;

G is CH or N;

A is

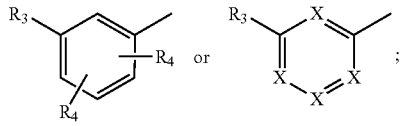

R$_3$ is —(CH$_2$)$_n$—C(O)NR$_5$R$_6$, —(CH$_2$)$_n$—C(R$_{14}$)(R$_{15}$)—NR$_5$R$_6$, —(CH$_2$)$_n$—S(O)NR$_5$R$_6$,

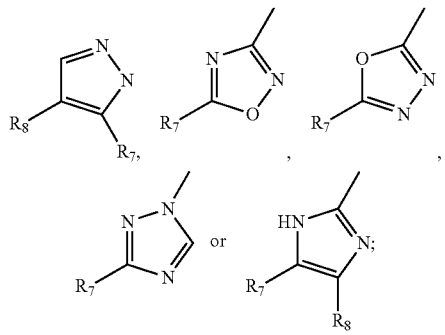

or R$_3$ is —O—C$_{1-6}$alkyl, —C$_{1-6}$ alkyl, —C$_{2-6}$ alkenyl, —C$_{4-7}$ heterocycloalkyl, —O—C$_{4-7}$ heterocycloalkyl, —N—R$_{12}$R$_{13}$, —C$_{3-7}$ cycloalkyl, —O—C$_{3-7}$ cycloalkyl, —S—C$_{1-3}$alkyl, —S—C$_{4-7}$heterocycloalkyl, S—C$_{3-7}$ cycloalkyl, —S(O)—C$_{1-3}$alkyl, —S(O)—C$_{4-7}$ heterocycloalkyl, —S(O)—C$_{3-7}$ cycloalkyl, —S(O)$_2$—C$_{1-3}$alkyl, —S(O)$_2$—C$_{4-7}$ heterocycloalkyl, or —S(O)$_2$—C$_{3-7}$ cycloalkyl, wherein each of —O—C$_{1-6}$alkyl, —C$_{1-6}$ alkyl, —C$_{4-7}$heterocycloalkyl, —O—C$_{4-7}$ heterocycloalkyl, —C$_{3-7}$ cycloalkyl, —O—C$_{3-7}$ cycloalkyl, —S—C$_{1-3}$alkyl, —S—C$_{4-7}$heterocycloalkyl, S—C$_{3-7}$ cycloalkyl, —S(O)—C$_{1-3}$alkyl, —S(O)—C$_{4-7}$ heterocycloalkyl, —S(O)—C$_{3-7}$ cycloalkyl, —S(O)$_2$—C$_{1-3}$alkyl, —S(O)$_2$—C$_{4-7}$ heterocycloalkyl, or —S(O)$_2$—C$_{3-7}$ cycloalkyl, is unsubstituted or substituted by one or two substituents independently selected from —C$_{3-7}$ alkyl, —C$_{3-7}$ cycloalkyl, —OH, =O, —O—C$_{1-5}$ alkyl, CF$_3$, —C$_{4-7}$heterocycloalkyl, phenyl, pyridyl, pyrazolyl, pyridazinyl, pyrimidinyl, pyrazinyl, and triazolyl, and wherein each of —C$_{1-7}$ alkyl, —C$_{3-7}$ cycloalkyl, —O—C$_{1-3}$ alkyl, —C$_{4-7}$ heterocycloalkyl, phenyl, pyridyl, pyrazolyl, pyridazinyl, pyrimidinyl, pyrazinyl, or triazolyl is unsubstituted or further substituted by one or more substituents independently selected from —C$_{1-5}$ alkyl, —CF$_3$, —OC$_{1-3}$alkyl, phenyl, —C(O)—O—C$_{1-5}$alkyl and halo;

Each R$_4$ is independently hydrogen, halo or —C$_{1-3}$alkyl;

R$_5$ and R$_6$ are independently H, —C$_{1-6}$ alkyl, —C$_{3-7}$ cycloalkyl or —C$_{4-7}$ heterocycloalkyl, wherein each of —C$_{1-6}$ alkyl, —C$_{3-7}$ cycloalkyl or —C$_{4-7}$ heterocycloalkyl is unsubstituted or substituted by one or more substituents selected from F, —CH—F$_2$, —CF$_3$, —(CH$_2$)$_n$—O—(CH$_2$)$_m$—CH$_3$, and —C$_{3-7}$cycloalkyl;

or R$_5$ and R$_6$ together with the nitrogen atom to which they are attached form a 5-8-membered ring, an 8-11-membered bicyclic ring or a 9-10-membered bridged bicyclic ring, wherein each 5-8-membered ring, 8-11-membered bicyclic ring, or 9-10-membered bridged bicyclic ring optionally includes one —S(O)$_2$, one or more oxygen ring atoms or one or more nitrogen ring atoms, and wherein each 5-8-membered ring, 8-11-membered bicyclic ring, or 9-10-membered bridged bicyclic ring is unsubstituted or substituted by one, two or three substituents independently selected from —C$_{1-5}$ alkyl, —C$_{3-7}$cycloalkyl, —C$_{4-7}$heterocycloalkyl, halogen, —CHF$_2$, —CF$_3$, and —(CH$_2$)$_n$—O—(CH$_2$)$_m$—CH$_3$;

or R$_5$ and R$_6$ together with the nitrogen atom to which they are attached form 4-azaspiro[2.5]octane, 7-azaspiro[4.5]decane, 2-oxa-8-azaspiro[5.5]undecane, 6-oxa-9-azaspiro[4.5]decane, 2-oxa-8-azaspiro[5.5]undecane, 1-azaspiro[4.5]decane, 2,3,4,5-tetrahydrobenzo[f][1,4]oxazepine or 2,3,4,5-tetrahydro-1H-benzo[c]azepine;

R$_7$ and R$_8$ are independently H, —C$_{1-6}$ alkyl, —C$_{3-7}$ cycloalkyl or —C$_{4-7}$ heterocycloalkyl, wherein each of —C$_{1-6}$ alkyl, —C$_{3-7}$ cycloalkyl or —C$_{4-7}$ heterocycloalkyl is unsubstituted or substituted by one or two substituents independently selected from F, —CHF$_2$, —CF$_3$, and —(CH$_2$)$_n$—O—(CH$_2$)$_m$—CH$_3$;

or R$_7$ and R$_8$ together with the carbon atoms to which they are attached form a 5-8-membered ring, which optionally includes one or more oxygen or nitrogen atoms as ring atoms, and wherein the 5-8-membered ring is unsubstituted or substituted by one or two substituents independently selected from —C$_{1-5}$ alkyl, —C$_{3-7}$ cycloalkyl, —C$_{4-7}$ heterocycloalkyl, F, —CHF$_2$, —CF$_3$, =O, and —(CH$_2$)$_n$—O—(CH$_2$)$_m$—CH$_3$;

R$_9$ is H or —C$_{1-3}$alkyl;

R$_{10}$ is —C$_{1-3}$alkyl;

R$_{11}$ is aryl, triazolyl, pyridyl, pyridazinyl, imidazolyl, or pyrazolyl, wherein each of aryl, triazolyl, pyridyl, pyridazinyl, imidazolyl, or pyrazolyl is unsubstituted or substituted by one or two substituents independently selected from —C$_{1-3}$alkyl and halo;

R$_{12}$ and R$_{13}$ are independently C$_{4-7}$ heterocycloalkyl, —C$_{1-3}$ alkyl or —C$_{3-7}$ cycloalkyl, wherein each of the —C$_{4-7}$ heterocycloalkyl, —C$_{1-3}$ alkyl or —C$_{3-7}$ cycloalkyl is unsubstituted or substituted by one or two substituents independently selected from —C$_{1-7}$alkyl, —C$_{3-7}$cycloalkyl, —OH, =O, —O—C$_{1-5}$alkyl, —C$_{4-7}$heterocycloalkyl, phenyl, pyridyl, pyrazolyl, pyridazinyl, pyrimidinyl, pyrazinyl, and triazolyl, and wherein each of the —C$_{1-7}$alkyl, —C$_{3-7}$ cycloalkyl, —O—C$_{1-5}$alkyl, —C$_{4-7}$heterocycloalkyl, phenyl, pyridyl, pyrazolyl, pyridazinyl, pyrimidinyl, pyrazinyl, or triazolyl is further optionally substituted by one or more substituents independently selected from —C$_{1-5}$alkyl and halo;

R$_{14}$ is hydrogen or —C$_{1-3}$alkyl;

R$_{15}$ is hydrogen or —C$_{1-3}$alkyl;

Each X is CR$_4$ or N provided only one X is N;

Each n is independently 0 or 1;

Each m is independently 0 or 1;

or a pharmaceutically acceptable salt thereof.

"Alkyl" refers to a monovalent saturated hydrocarbon chain having the specified number of carbon member atoms.

For example, $C_{1-4}$ alkyl refers to an alkyl group having from 1 to 4 carbon member atoms. Alkyl groups may be straight or branched. Representative branched alkyl groups have one, two, or three branches. Alkyl includes methyl, ethyl, propyl, (n-propyl and isopropyl), butyl (n-butyl, isobutyl, s-butyl, and t-butyl), pentyl (n-pentyl, tert-pentyl, iso-pentyl), and hexyl (n-hexyl, isohexyl, ter-hexyl).

When used herein, the terms "5-8-membered ring or an 8-10-membered bicyclic ring or a 9-10-membered bridged bicyclic ring" include both saturated and unsaturated ring structures containing the indicated number of carbon atoms. The terms "8-10-membered bicyclic ring or a 9-10-membered bridged bicyclic ring" can be aryl or heteroaryl, and also encompass bicyclic aryl groups containing an aryl ring moiety fused to a cycloalkyl ring moiety.

"Cycloalkyl" refers to a monovalent saturated or unsaturated hydrocarbon ring having the specified number of carbon member atoms. For example, $C_{3-6}$cycloalkyl refers to a cycloalkyl group having from 3 to 6 carbon member atoms. Unsaturated cycloalkyl groups have one or more carbon-carbon double bonds within the ring. Cycloalkyl groups are not aromatic. Cycloalkyl includes cyclopropyl, cyclopropenyl, cyclobutyl, cyclobutenyl, cyclopentyl, cyclopentenyl, cyclohexyl, and cyclohexenyl.

"$C_{4-7}$ heterocycloalkyl" refers to a 4 to 7 membered ring that contains up to 4 hetero atoms, including, nitrogen, oxygen, and sulfur. Examples are azetidine, thietane, thietane 1-oxide, thietane 1,1-dioxide, tetrahydrofuran, pyrrolidine, tetrahydrothiophene, tetrahydrothiophene 1-oxide, tetrahydrothiophene 1,2-dioxide, piperidine, morpholine, thiomorpholine, thiomorpholine 1-oxide, thiomorpholine 1,1-dioxide, tetrahydropyran, tetrahydrothiopyran, tetrahydrothiopyran 1-oxide, tetrahydrothiopyran 1-1 dioxide, piperidine-2-one, azepan-2-one, pyrrolidin-2-one, azepane, oxepane, oxazepane, thiepane, thiepane 1-oxide, thiepane 1,1-dioxide, and thiazepane.

When used herein, the terms 'halogen' and 'halo' include fluorine, chlorine, bromine and iodine, and fluoro, chloro, bromo, and iodo, respectively.

"Substituted" in reference to a group indicates that one or more hydrogen atom attached to a member atom within the group is replaced with a substituent selected from the group of defined substituents. It should be understood that the term "substituted" includes the implicit provision that such substitution be in accordance with the permitted valence of the substituted atom and the substituent and that the substitution results in a stable compound (i.e., one that does not spontaneously undergo transformation such as by rearrangement, cyclization, or elimination and that is sufficiently robust to survive isolation from a reaction mixture). When it is stated that a group may contain one or more substituents, one or more (as appropriate) member atoms within the group may be substituted. In addition, a single member atom within the group may be substituted with more than one substituent as long as such substitution is in accordance with the permitted valence of the atom. Suitable substituents are defined herein for each substituted or optionally substituted group.

The term "independently" means that where more than one substituent is selected from a number of possible substituents, those substituents may be the same or different. That is, each substituent is separately selected from the entire group of recited possible substituents.

The invention also includes various isomers of the compounds of Formula (I) and mixtures thereof. "Isomer" refers to compounds that have the same composition and molecular weight but differ in physical and/or chemical properties. The structural difference may be in constitution (geometric isomers) or in the ability to rotate the plane of polarized light (stereoisomers). The compounds according to Formula (I) contain one or more asymmetric centers, also referred to as chiral centers, and may, therefore, exist as individual enantiomers, diastereomers, or other stereoisomeric forms, or as mixtures thereof. All such isomeric forms are included within the present invention, including mixtures thereof.

Chiral centers may also be present in a substituent such as an alkyl group. Where the stereochemistry of a chiral center present in Formula (I), or in any chemical structure illustrated herein, is not specified the structure is intended to encompass any stereoisomer and all mixtures thereof. Thus, compounds according to Formula (I) containing one or more chiral centers may be used as racemic mixtures, enantiomerically enriched mixtures, or as enantiomerically pure individual stereoisomers.

Individual stereoisomers of a compound according to Formula (I) which contain one or more asymmetric centers may be resolved by methods known to those skilled in the art. For example, such resolution may be carried out (1) by formation of diastereoisomeric salts, complexes or other derivatives; (2) by selective reaction with a stereoisomer-specific reagent, for example by enzymatic oxidation or reduction; or (3) by gas-liquid or liquid chromatography in a chiral environment, for example, on a chiral support such as silica with a bound chiral ligand or in the presence of a chiral solvent. The skilled artisan will appreciate that where the desired stereoisomer is converted into another chemical entity by one of the separation procedures described above, a further step is required to liberate the desired form. Alternatively, specific stereoisomers may be synthesized by asymmetric synthesis using optically active reagents, substrates, catalysts or solvents, or by converting one enantiomer to the other by asymmetric transformation.

For compounds falling within the scope of the invention, the structural conventions used in the Examples are as follows: (a) absolute stereochemistry is defined by the structure; (b) when annotated by "or", then stereochemistry is unknown but resolved; and (c) when annotated by "&" or "and", then stereochemistry is relative, but racemic.

As used herein, "pharmaceutically acceptable" refers to those compounds, materials, compositions, and dosage forms which are, within the scope of sound medical judgment, suitable for use in contact with the tissues of human beings and animals without excessive toxicity, irritation, or other problem or complication, commensurate with a reasonable benefit/risk ratio.

The skilled artisan will appreciate that pharmaceutically acceptable salts of the compounds according to Formula (I) may be prepared. These pharmaceutically acceptable salts may be prepared in situ during the final isolation and purification of the compound, or by separately treating the purified compound in its free acid or free base form with a suitable base or acid, respectively. It will be understood by the skilled artisan that when R of Formula (I) provides an ester, this compound can function as a prodrug and as such, provide the parent acid upon incubation with cells or in vivo.

In certain embodiments, compounds according to Formula (I) may contain an acidic functional group and are, therefore, capable of forming pharmaceutically acceptable base addition salts by treatment with a suitable base. Examples of such bases include a) hydroxides, carbonates, and bicarbonates of sodium, potassium, lithium, calcium, magnesium, aluminum, and zinc; and b) primary, secondary, and tertiary amines including aliphatic amines, aromatic amines, aliphatic diamines, and hydroxy alkylamines such as methylamine, ethylamine, 2-hydroxyethylamine, diethyl-amine, triethylamine, ethylenediamine, ethanolamine, diethanolamine, and cyclohexylamine.

In certain embodiments, compounds according to Formula (I) may contain a basic functional group and are therefore capable of forming pharmaceutically acceptable acid addition salts by treatment with a suitable acid. Suitable acids include pharmaceutically acceptable inorganic acids and organic acids. Representative pharmaceutically acceptable acids include hydrogen chloride, hydrogen bromide, nitric acid, sulfuric acid, sulfonic acid, phosphoric acid, acetic acid, hydroxyacetic acid, phenylacetic acid, propionic acid, butyric acid, valeric acid, maleic acid, acrylic acid, fumaric acid, succinic acid, malic acid, malonic acid, tartaric acid, citric acid, salicylic acid, benzoic acid, tannic acid, formic acid, stearic acid, lactic acid, ascorbic acid, methylsulfonic acid, p-toluenesulfonic acid, oleic acid, lauric acid, and the like.

As used herein, the term "a compound of Formula (I)" or "the compound of Formula (I)" refers to one or more compounds according to Formula (I). The compound of Formula (I) may exist in solid or liquid form. In the solid state, it may exist in crystalline or noncrystalline form, or as a mixture thereof. The skilled artisan will appreciate that pharmaceutically acceptable solvates may be formed from crystalline compounds wherein solvent molecules are incorporated into the crystalline lattice during crystallization. Solvates may involve non-aqueous solvents such as, but not limited to, ethanol, isopropanol, DMSO, acetic acid, ethanolamine, or ethyl acetate, or they may involve water as the solvent that is incorporated into the crystalline lattice. Solvates wherein water is the solvent incorporated into the crystalline lattice are typically referred to as "hydrates." Hydrates include stoichiometric hydrates as well as compositions containing variable amounts of water. The invention includes all such solvates.

The skilled artisan will further appreciate that certain compounds of the invention that exist in crystalline form, including the various solvates thereof, may exhibit polymorphism (i.e., the capacity to occur in different crystalline structures). These different crystalline forms are typically known as "polymorphs." The invention includes all such polymorphs. Polymorphs have the same chemical composition but differ in packing, geometrical arrangement, and other descriptive properties of the crystalline solid state. Polymorphs, therefore, may have different physical properties such as shape, density, hardness, deformability, stability, and dissolution properties. Polymorphs typically exhibit different melting points, IR spectra, and X-ray powder diffraction patterns, which may be used for identification. The skilled artisan will appreciate that different polymorphs may be produced, for example, by changing or adjusting the reaction conditions or reagents, used in making the compound. For example, changes in temperature, pressure, or solvent may result in polymorphs. In addition, one polymorph may spontaneously convert to another polymorph under certain conditions.

The subject invention also includes isotopically-labelled compounds, which are identical to those recited in formula (I) and following, but for the fact that one or more atoms are replaced by an atom having an atomic mass or mass number different from the atomic mass or mass number usually found in nature. Examples of isotopes that can be incorporated into compounds of the invention and pharmaceutically acceptable salts thereof include isotopes of hydrogen, carbon, nitrogen, oxygen, phosphorous, sulphur, fluorine, iodine, and chlorine, such as $^2H$, $^3H$, $^{11}C$, $^{13}C$, $^{14}C$, $^{15}N$, $^{17}O$, $^{18}O$, $^{31}P$, $^{32}P$, $^{35}S$, $^{18}F$, $^{36}Cl$, $^{123}I$ and $^{125}I$.

Compounds of the present invention and pharmaceutically acceptable salts of said compounds that contain the aforementioned isotopes and/or other isotopes of other atoms are within the scope of the present invention. Isotopically-labelled compounds of the present invention, for example those into which radioactive isotopes such as $^3H$, $^{14}O$ are incorporated, are useful in drug and/or substrate tissue distribution assays. Tritiated, i.e., $^3H$, and carbon-14, i.e., $^{14}C$, isotopes are particularly preferred for their ease of preparation and detectability. $^{11}C$ and $^{18}F$ isotopes are particularly useful in PET (positron emission tomography), and $^{125}I$ isotopes are particularly useful in SPECT (single photon emission computerized tomography), all useful in brain imaging. Further, substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances. Isotopically labeled compounds of Formula (I) and following of this invention can generally be prepared by carrying out the procedures disclosed in the Schemes and/or in the Examples below, by substituting a readily available isotopically labeled reagent for a non-isotopically labeled reagent.

Representative Embodiments

In one embodiment, the compound of Formula (I) is substituted as follows:
R is hydrogen or —$C_{1-5}$alkyl which is unsubstituted or substituted by one or two substituents independently selected from —OH, —OC(O)—$C_{1-5}$alkyl, —OC(O)-phenyl, —OC(O)—O—$C_{1-5}$alkyl,

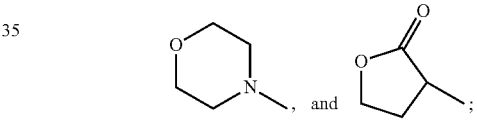, and ;

$R_1$ is —$CF_3$, —$C_{3-7}$cycloalkyl, or —$C_{4-7}$heterocycloalkyl, wherein the —$C_{3-7}$cycloalkyl, or —$C_{4-7}$heterocycloalkyl is unsubstituted or substituted by one or two substituents independently selected from —$C_{1-3}$alkyl, phenyl, triazolyl, pyridyl, pyridazinyl, imidazolyl, pyrazolyl, isoxazolyl, halo, —$NR_9$—C(O)—$R_{10}$ and —C(O)$R_{10}$, and wherein each of the phenyl, triazolyl, pyridyl, pyridazinyl, imidazolyl, pyrazolyl and isoxazolyl is unsubstituted or substituted by one or two substituents independently selected from halo, phenyl, —$C_{1-7}$alkyl optionally substituted with phenyl, —$N(CH_3)_2$, —$CF_3$, —OH, and —$C_{3-7}$cycloalkyl optionally substituted with —$C_{1-3}$alkyl, —$C_{3-7}$heterocylcoalkyl optionally substituted with —$C_{1-3}$alkyl or —C(O)—$C_{1-4}$alkyl;
or $R_1$ is —$C_{2-3}$alkyl-$R_{11}$;
$R_{2a}$ is hydrogen, halo, or —$C_{1-3}$alkyl;
$R_2$ is hydrogen, halo, —CN, —O—$C_{1-3}$alkyl, —OH, or —$C_{1-3}$alkyl;
G is CH or N;
A is

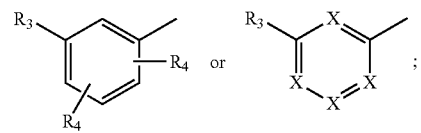;

$R_3$ is —$(CH_2)_n$—$C(O)NR_5R_6$, —$(CH_2)_n$—$C(R_{14})(R_{15})$—$NR_5R_6$, —$(CH_2)_n$—$S(O)NR_5R_6$,

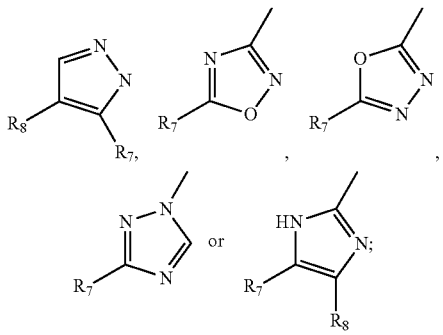

or $R_3$ is —O—$C_{1-6}$alkyl, —$C_{1-6}$alkyl, —$C_{4-7}$heterocycloalkyl, —O—$C_{4-7}$heterocycloalkyl, —N—$R_{12}R_{13}$, —$C_{3-7}$cycloalkyl, —O—$C_{3-7}$cycloalkyl, —S—$C_{1-3}$alkyl, —S—$C_{4-7}$heterocycloalkyl, —S—$C_{3-7}$cycloalkyl, —S(O)—$C_{1-3}$alkyl, —S(O)—$C_{4-7}$ heterocycloalkyl, —S(O)—$C_{3-7}$cycloalkyl, —S(O)$_2$—$C_{1-3}$alkyl, —S(O)$_2$—$C_{4-7}$heterocycloalkyl, or —S(O)$_2$—$C_{3-7}$cycloalkyl, wherein each of —O—$C_{1-6}$alkyl, —$C_{1-6}$alkyl, —$C_{4-7}$heterocycloalkyl, —O—$C_{4-7}$heterocycloalkyl, —$C_{3-7}$cycloalkyl, —O—$C_{3-7}$cycloalkyl, —S—$C_{1-3}$alkyl, —S—$C_{4-7}$heterocycloalkyl, S—$C_{3-7}$cycloalkyl, —S(O)—$C_{1-3}$alkyl, —S(O)—$C_{4-7}$heterocycloalkyl, —S(O)—$C_{3-7}$cycloalkyl, —S(O)$_2$—$C_{1-3}$alkyl, —S(O)$_2$—$C_{4-7}$heterocycloalkyl, or —S(O)$_2$—$C_{3-7}$cycloalkyl, is unsubstituted or substituted by one or two substituents independently selected from —$C_{1-7}$alkyl, —$C_{3-7}$ cycloalkyl, —OH, =O, —O—$C_{1-5}$alkyl, $CF_3$, —$C_{4-7}$ heterocycloalkyl, phenyl, pyridyl, pyrazolyl, pyridazinyl, pyrimidinyl, pyrazinyl, and triazolyl, and wherein each of —$C_{1-7}$alkyl, —$C_{3-7}$cycloalkyl, —O—$C_{1-5}$ alkyl, —$C_{4-7}$heterocycloalkyl, phenyl, pyridyl, pyrazolyl, pyridazinyl, pyrimidinyl, pyrazinyl, and triazolyl is unsubstituted or further substituted by one or more substituents independently selected from —$C_{1-5}$alkyl, —$CF_3$, —$OC_{1-3}$alkyl, phenyl, —C(O)—O—$C_{1-5}$alkyl and halo;

Each $R_4$ is independently hydrogen, halo or —$C_{1-3}$alkyl;

$R_5$ and $R_6$ are independently H, —$C_{1-6}$alkyl, —$C_{3-7}$cycloalkyl or —$C_{4-7}$heterocycloalkyl, wherein each of —$C_{1-6}$ alkyl, —$C_{3-7}$cycloalkyl and —$C_{4-7}$heterocycloalkyl is unsubstituted or substituted by one or more substituents selected from F, —CH—$F_2$, —$CF_3$, —$(CH_2)_n$—O—$(CH_2)_m$—$CH_3$, and —$C_{3-7}$cycloalkyl;

or $R_5$ and $R_6$ together with the nitrogen atom to which they are attached form a 5-8-membered ring, an 8-11-membered bicyclic ring or a 9-10-membered bridged bicyclic ring, wherein each 5-8-membered ring, 8-11-membered bicyclic ring, or 9-10-membered bridged bicyclic ring optionally includes one —S(O)$_2$, one or more oxygen ring atoms or one or more nitrogen ring atoms, and wherein each 5-8-membered ring, 8-11-membered bicyclic ring, or 9-10-membered bridged bicyclic ring is unsubstituted or substituted by one, two or three substituents independently selected from —$C_{1-5}$ alkyl, —$C_{3-7}$cycloalkyl, —$C_{4-7}$heterocycloalkyl, halogen, —$CHF_2$, —$CF_3$, and —$(CH_2)_n$—O—$(CH_2)_m$—$CH_3$;

or $R_5$ and $R_6$ together with the nitrogen atom to which they are attached form 4-azaspiro[2.5]octane, 7-azaspiro[4.5]decane, 2-oxa-8-azaspiro[5.5]undecane, 6-oxa-9-azaspiro[4.5]decane, 2-oxa-8-azaspiro[5.5]undecane, 1-azaspiro[4.5]decane, 2,3,4,5-tetrahydrobenzo[f][1,4]oxazepine or 2,3,4,5-tetrahydro-1H-benzo[c]azepine;

$R_7$ and $R_8$ are independently H, —$C_{1-6}$alkyl, —$C_{3-7}$cycloalkyl or —$C_{4-7}$heterocycloalkyl, wherein each of —$C_{1-6}$ alkyl, —$C_{3-7}$cycloalkyl or —$C_{4-7}$heterocycloalkyl is unsubstituted or substituted by one or more substituents independently selected from F, —$CHF_2$, —$CF_3$, and —$(CH_2)_n$—O—$(CH_2)_m$—$CH_3$;

or $R_7$ and $R_8$ together with the carbon atoms to which they are attached form a 5-8-membered ring, which optionally includes one or more oxygen atoms or one or more nitrogen atoms as ring atoms, and wherein the 5-8-membered ring is unsubstituted or substituted by one or two substituents independently selected from —$C_{1-5}$alkyl, —$C_{3-7}$cycloalkyl, —$C_{4-7}$heterocycloalkyl, F, —$CHF_2$, —$CF_3$, =O, and —$(CH_2)_n$—O—$(CH_2)_m$—$CH_3$;

$R_9$ is H or —$C_{1-3}$alkyl;

$R_{10}$ is —$C_{1-3}$alkyl;

$R_{11}$ is aryl, triazolyl, pyridyl, pyridazinyl, imidazolyl, or pyrazolyl, optionally substituted by one or more substituents independently selected from —$C_{1-3}$alkyl and halo;

$R_{12}$ and $R_{13}$ are independently —$C_{4-7}$heterocycloalkyl, —$C_{1-3}$alkyl or —$C_{3-7}$cycloalkyl, wherein each of —$C_{4-7}$ heterocycloalkyl, —$C_{1-3}$alkyl or —$C_{3-7}$cycloalkyl is unsubstituted or substituted by one or two substituents independently selected from —$C_{1-7}$alkyl, —$C_{3-7}$cycloalkyl, —OH, =O, —O—$C_{1-5}$alkyl, —$C_{4-7}$heterocycloalkyl, phenyl, pyridyl, pyrazolyl, pyridazinyl, pyrimidinyl, pyrazinyl, and triazolyl, and wherein each of —$C_{1-7}$alkyl, —$C_{3-7}$cycloalkyl, —O—$C_{1-3}$alkyl, —$C_{4-7}$heterocycloalkyl, phenyl, pyridyl, pyrazolyl, pyridazinyl, pyrimidinyl, pyrazinyl, or triazolyl is further optionally substituted by one or more substituents independently selected from —$C_{1-5}$alkyl and halo;

$R_{14}$ is hydrogen or —$C_{1-3}$alkyl;

$R_{15}$ is hydrogen or —$C_{1-3}$alkyl;

Each X is $CR_4$ or N, provided only one X is N;

Each n is independently 0 or 1;

Each m is independently 0 or 1;

or a pharmaceutically acceptable salt thereof.

In another embodiment, the compound of Formula (I) is substituted as follows:

R is hydrogen or —$C_{1-5}$alkyl wherein —$C_{1-5}$alkyl is unsubstituted or substituted by one or more substituents independently selected from —OH, —OC(O)—$C_{1-5}$alkyl, —OC(O)-phenyl or —OC(O)—O—$C_{1-5}$alkyl;

$R_1$ is —$CF_3$, —$C_{3-7}$cycloalkyl, wherein the —$C_{3-7}$cycloalkyl is unsubstituted or substituted by one or two substituents independently selected from triazolyl, pyridyl and halo, and wherein each of the triazolyl or pyridyl is unsubstituted or substituted by one or two substituents independently selected from phenyl, halo, —$N(CH_3)_2$, —$CF_3$, —OH, —$C_{1-7}$alkyl optionally substituted with phenyl, —$C_{3-7}$cycloalkyl optionally substituted with —$C_{1-3}$alkyl, and —$C_{3-7}$heterocylcoalkyl optionally further substituted with one or two substituents selected from —$C_{1-3}$alkyl and —C(O)—$C_{1-4}$alkyl;

or $R_1$ is —$C_{2-3}$alkyl-$R_{11}$;

$R_{2a}$ is hydrogen or —$C_{1-3}$alkyl;

$R_2$ is hydrogen, halo or —$C_{1-3}$alkyl;

G is CH or N;

A is

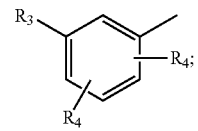

R$_3$ is —(CH$_2$)$_n$—C(O)NR$_5$R$_6$, —(CH$_2$)$_n$—C(R$_{14}$)(R$_{15}$)—N(R$_5$)(R$_6$), or

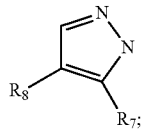

or R$_3$ is —O—C$_{1-6}$alkyl, —C$_{1-6}$alkyl, —C$_{4-7}$heterocycloalkyl, —O—C$_{4-7}$heterocycloalkyl, or —O—C$_{3-7}$cycloalkyl, wherein each of —O—C$_{1-6}$alkyl, —C$_{1-6}$ alkyl, —C$_{4-7}$heterocycloalkyl, —O—C$_{4-7}$ heterocycloalkyl, and —O—C$_{3-7}$cycloalkyl is unsubstituted or substituted by one or two substituents independently selected from —C$_{1-7}$ alkyl, —C$_{3-7}$cycloalkyl, =O, —O—C$_{1-5}$alkyl, and —C$_{4-7}$ heterocycloalkyl, and wherein each of the —C$_{1-7}$alkyl, —C$_{3-7}$cycloalkyl, —O—C$_{1-5}$alkyl, and C$_{4-7}$ heterocycloalkyl, is further substituted by one or two substituents independently selected from —C$_{1-5}$alkyl, CF$_3$, O—C$_{1-3}$ alkyl, phenyl and halo;

Each R$_4$ is independently hydrogen, halo or —C$_{1-3}$ alkyl;
R$_5$ and R$_6$ are independently H, —C$_{1-6}$alkyl, —C$_{3-7}$cycloalkyl or —C$_{4-7}$heterocycloalkyl, wherein each of —C$_{1-6}$alkyl, —C$_{3-7}$cycloalkyl or —C$_{4-7}$heterocycloalkyl is unsubstituted or substituted by one or two substituents independently selected from F, —CH—F$_2$, —CF$_3$, —(CH$_2$)$_n$—O—(CH$_2$)$_m$—CH$_3$, and —C$_{3-7}$cycloalkyl;
or R$_5$ and R$_6$ together with the nitrogen atom to which they are attached form a 5-8-membered ring, an 8-11-membered bicyclic ring or a 9-10-membered bridged bicyclic ring, wherein each 5-8-membered ring, 8-11-membered bicyclic ring, or 9-10-membered bridged bicyclic ring optionally includes one —S(O)$_2$, one or more oxygen ring atoms or one or more nitrogen ring atoms, and wherein each 5-8-membered ring, 8-11-membered bicyclic ring, or 9-10-membered bridged bicyclic ring is unsubstituted or substituted by one, two or three substituents independently selected from —C$_{1-5}$ alkyl, —C$_{3-7}$cycloalkyl, —C$_{4-7}$heterocycloalkyl, halogen, —CHF$_2$, —CF$_3$, and —(CH$_2$)$_n$—O—(CH$_2$)$_m$—CH$_3$;
or R$_5$ and R$_6$ together with the nitrogen atom to which they are attached form 4-azaspiro[2.5]octane, 7-azaspiro[4.5]decane, 2-oxa-8-azaspiro[5.5]undecane, 6-oxa-9-azaspiro[4.5]decane, 2-oxa-8-azaspiro[5.5]undecane, 1-azaspiro[4.5]decane, 2,3,4,5-tetrahydrobenzo[f][1,4]oxazepane, or 2,3,4,5-tetrahydro-1H-benzo[c]azepine;
R$_7$ and R$_8$ are independently H, —C$_{1-6}$alkyl, —C$_{3-7}$cycloalkyl or —C$_{4-7}$heterocycloalkyl, wherein each of —C$_{1-6}$ alkyl, —C$_{3-7}$cycloalkyl or —C$_{4-7}$heterocycloalkyl is unsubstituted or substituted by one or two substituents independently selected from F, —CHF$_2$, —CF$_3$, and —(CH$_2$)$_n$—O—(CH$_2$)$_m$—CH$_3$;
or R$_7$ and R$_8$ together with the carbon atoms to which they are attached form a 5-8-membered ring, which optionally includes one or more oxygen or one or more nitrogen atoms as ring atoms, and wherein the 5-8-membered ring is unsubstituted or substituted by one or two substituents independently selected from —C$_{1-5}$ alkyl, —C$_{3-7}$ cycloalkyl, —C$_{4-7}$ heterocycloalkyl, F, —CHF$_2$, —CF$_3$, =O, or —(CH$_2$)$_n$—O—(CH$_2$)$_m$—CH$_3$;
R$_{11}$ is aryl or triazolyl;
R$_{14}$ is hydrogen or —C$_{1-3}$alkyl;
R$_{15}$ is hydrogen or —C$_{1-3}$alkyl;

Each X is CR$_4$ or N provided only one X is N;
Each n is independently 0 or 1;
Each m is independently 0 or 1;
or a pharmaceutically acceptable salt thereof.

In yet another embodiment, the compound of Formula (I) is substituted as follows:
R is hydrogen;
R$_1$ is —C$_{3-7}$cycloalkyl, wherein the —C$_{3-7}$cycloalkyl may be unsubstituted or substituted by one substituent selected from triazolyl, pyridyl or pyridazinyl, and wherein the, triazolyl, pyridyl, and pyridazinyl is optionally substituted by —C$_{1-3}$alkyl;
R$_{2a}$ is hydrogen or methyl;
R$_2$ is hydrogen or F;
G is CH or N;
A is

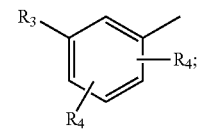

R$_3$ is —(CH$_2$)$_n$—C(O)N(R$_5$)(R$_6$), —(CH$_2$)$_n$—C(R$_{14}$)(R$_{15}$)—N(R$_5$)(R$_6$), or

or R$_3$ is —O—C$_{1-6}$alkyl, —C$_{1-6}$ alkyl, —C$_{4-7}$heterocycloalkyl, —O—C$_{4-7}$heterocycloalkyl, or —O—C$_{3-7}$cycloalkyl, wherein each of —O—C$_{1-6}$alkyl, —C$_{1-6}$ alkyl, —C$_{4-7}$heterocycloalkyl, —O—C$_{4-7}$ heterocycloalkyl, and —O—C$_{3-7}$cycloalkyl is unsubstituted or substituted by one or two substituents independently selected from —C$_{1-7}$ alkyl, —C$_{3-7}$cycloalkyl, =O, —O—C$_{1-5}$alkyl, and —C$_{4-7}$ heterocycloalkyl, and wherein each of the —C$_{1-7}$alkyl, —C$_{3-7}$cycloalkyl, —O—C$_{1-5}$alkyl, and C$_{4-7}$ heterocycloalkyl, is further substituted by one or two substituents independently selected from —C$_{1-5}$alkyl, CF$_3$, O—C$_{1-3}$ alkyl, phenyl and halo;
R$_4$ is independently hydrogen or F;
R$_5$ and R$_6$ together with the nitrogen atom to which they are attached form a 5-8-membered ring, an 8-11-membered bicyclic ring or a 9-10-membered bridged bicyclic ring, wherein each 5-8-membered ring, 8-11-membered bicyclic ring, or 9-10-membered bridged bicyclic ring optionally includes one —S(O)$_2$, one or more oxygen ring atoms or one or more nitrogen ring atoms, and wherein each 5-8-membered ring, 8-11-membered bicyclic ring, or 9-10-membered bridged bicyclic ring is unsubstituted or substituted by one, two or three substituents independently selected from —C$_{1-5}$alkyl, —C$_{3-7}$cycloalkyl, —C$_{4-7}$heterocycloalkyl, halogen, —CHF$_2$, —CF$_3$, and —(CH$_2$)$_n$—O—(CH$_2$)$_m$—CH$_3$;
or R$_5$ and R$_6$ together with the nitrogen atom to which they are attached form 4-azaspiro[2.5]octane, 7-azaspiro[4.5]decane, 2-oxa-8-azaspiro[5.5]undecane, 6-oxa-9-azaspiro[4.5]decane, 2-oxa-8-azaspiro[5.5]undecane, 1-azaspiro[4.5]decane, 2,3,4,5-tetrahydrobenzo[f][1,4]oxazepane, or 2,3,4,5-tetrahydro-1H-benzo[c]azepine;
R$_7$ and R$_8$ are independently H, —C$_{1-6}$ alkyl or —C$_{3-7}$ cycloalkyl, wherein each of —C$_{1-6}$ alkyl, or —C$_{3-7}$ cycloalkyl is unsubstituted or substituted by one or two substituents independently selected from substituted by F, —CHF$_2$, —CF$_3$, and —(CH$_2$)$_n$—O—(CH$_2$)$_m$—CH$_3$;

or R$_7$ and R$_8$ together with the carbon atoms to which they are attached form a 5-8-membered ring, which optionally includes one or more oxygen or one or more nitrogen atoms as ring atoms, and wherein the 5-8-membered ring is unsubstituted or substituted by one or two substituents independently selected from —C$_{1-5}$ alkyl, F, —CHF$_2$, and —CF$_3$;

R$_{14}$ is hydrogen;
R$_{15}$ is hydrogen;
X is CH;
n is independently 0 or 1;
m is independently 0 or 1;
or a pharmaceutically acceptable salt thereof.

In yet another embodiment, the compound of Formula (I) is substituted as follows:

R is hydrogen;
R$_1$ is cyclopropyl, wherein the cyclopropyl ring is unsubstituted or substituted by one substituent selected from halo, triazolyl, pyridyl, and pyridazinyl, and wherein the triazolyl, pyridyl, and pyridazinyl is unsubstituted or substituted by —C$_{1-3}$alkyl;
R$_{2a}$ is hydrogen;
R$_2$ is hydrogen;
G is CH;
A is

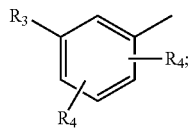

R$_3$ is —(CH$_2$)$_n$—C(O)N(R$_5$)(R$_6$), —(CH$_2$)$_n$—C(R$_{14}$)(R$_{15}$)—N(R$_5$)(R$_6$);

or R$_3$ is —O—C$_{1-6}$alkyl, —C$_{1-6}$ alkyl, —C$_{4-7}$heterocycloalkyl, —O—C$_{4-7}$heterocycloalkyl, or —O—C$_{3-7}$cycloalkyl wherein each of —O—C$_{1-6}$alkyl, —C$_{1-6}$ alkyl, —C$_{4-7}$heterocycloalkyl, —O—C$_{4-7}$ heterocycloalkyl, and —O—C$_{3-7}$cycloalkyl is unsubstituted or substituted by one or two substituents independently selected from —C$_{1-7}$alkyl, —C$_{3-7}$cycloalkyl, =O, —O—C$_{1-5}$alkyl, and —C$_{4-7}$ heterocycloalkyl, and wherein each of the —C$_{1-7}$alkyl, —C$_{3-7}$cycloalkyl, —O—C$_{1-5}$alkyl, and C$_{4-7}$ heterocycloalkyl, is further substituted by one or two substituents independently selected from —C$_{1-5}$alkyl, CF$_3$, O—C$_{1-3}$ alkyl, phenyl and halo;

R$_4$ is independently hydrogen or F;
R$_5$ and R$_6$ together with the nitrogen atom to which they are attached form a 5-8-membered ring, an 8-11-membered bicyclic ring or a 9-10-membered bridged bicyclic ring, wherein each 5-8-membered ring, 8-11-membered bicyclic ring, or 9-10-membered bridged bicyclic ring optionally includes one —S(O)$_2$, one or more oxygen ring atoms or one or more nitrogen ring atoms, and wherein each 5-8-membered ring, 8-11-membered bicyclic ring, or 9-10-membered bridged bicyclic ring is unsubstituted or substituted by one, two or three substituents independently selected from —C$_{1-5}$ alkyl, —C$_{3-7}$cycloalkyl, —C$_{4-7}$heterocycloalkyl, halogen, —CHF$_2$, —CF$_3$, and —(CH$_2$)$_n$—O—(CH$_2$)$_m$—CH$_3$;

or R$_5$ and R$_6$ together with the nitrogen atom to which they are attached form 4-azaspiro[2.5]octane, 7-azaspiro[4.5]decane, 2-oxa-8-azaspiro[5.5]undecane, 6-oxa-9-azaspiro[4.5] decane, 2-oxa-8-azaspiro[5.5]undecane, 1-azaspiro[4.5]decane, 2,3,4,5-tetrahydrobenzo[f][1,4]oxazepane, or 2,3,4,5-tetrahydro-1H-benzo[c]azepine;

R$_{14}$ is hydrogen;
R$_{15}$ is hydrogen;
X is CH;
n is 0;
m is independently 0 or 1;
or a pharmaceutically acceptable salt thereof.

In still another embodiment, the compound of Formula (I) is substituted as follows:

R is hydrogen;
R$_1$ is —CF$_3$, —C$_{3-7}$cycloalkyl, wherein —C$_{3-7}$cycloalkyl is substituted by one or two substituents independently selected from triazolyl, pyridyl and halo, and wherein each of triazolyl or pyridyl is unsubstituted or substituted by one or two substituents independently selected from halo, phenyl, —N(CH$_3$)$_2$, —CF$_3$, —OH, —C$_{1-7}$alkyl optionally substituted with phenyl, —C$_{3-7}$cycloalkyl optionally substituted with —C$_{1-3}$alkyl, and —C$_{3-7}$heterocylcoalkyl optionally substituted with one or two substituents selected from —C$_{1-3}$ alkyl and —C(O)—C$_{1-4}$alkyl;

R$_{2a}$ is hydrogen or methyl;
R$_2$ is hydrogen, halo or —C$_{1-3}$alkyl;
G is CH;
A is

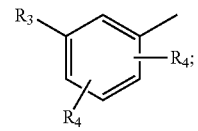

R$_3$ is —(CH$_2$)$_n$—C(O)NR$_5$R$_6$ or

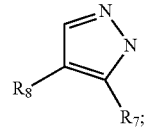

Each R$_4$ is independently hydrogen, halo or —C$_{1-3}$alkyl;
R$_5$ and R$_6$ are independently —C$_{1-6}$alkyl or —C$_{3-7}$cycloalkyl, wherein each of —C$_{1-6}$alkyl, —C$_{3-7}$cycloalkyl is unsubstituted or substituted by one or more substituents selected from F, —CH—F$_2$, —CF$_3$, —(CH$_2$)$_n$—O—(CH$_2$)$_m$—CH$_3$, and —C$_{3-7}$cycloalkyl;

or R$_5$ and R$_6$ together with the nitrogen atom to which they are attached form a 5-8-membered ring, wherein said 5-8-membered ring optionally includes one or more oxygen ring atoms or another nitrogen ring atom, and wherein said 5-8-membered ring is unsubstituted or substituted by —C$_{1-5}$ alkyl;

R$_7$ and R$_8$ are independently H, —C$_{1-6}$alkyl, —C$_{3-7}$ cycloalkyl or —C$_{4-7}$heterocycloalkyl, wherein each of —C$_{1-6}$alkyl, —C$_{3-7}$cycloalkyl or —C$_{4-7}$heterocycloalkyl is unsubstituted or substituted by one or more substituents independently selected from F, —CHF$_2$, —CF$_3$, and —(CH$_2$)$_n$—O—(CH$_2$)$_m$—CH$_3$;

or R$_7$ and R$_8$ together with the carbon atoms to which they are attached form a 5-8-membered ring, which optionally includes one or more oxygen atoms or one or more nitrogen atoms as ring atoms, and wherein the 5-8-membered ring is unsubstituted or substituted by one or two substituents independently selected from —C$_{1-5}$alkyl, —C$_{3-7}$cycloalkyl, —C$_{4-7}$heterocycloalkyl, F, —CHF$_2$, —CF$_3$, =O, and —(CH$_2$)$_n$—O—(CH$_2$)$_m$—CH$_3$;
X is CH;
n is 0;
m is independently 0 or 1;
or a pharmaceutically acceptable salt thereof.

In one embodiment, the compound of Formula (I) is substituted as follows:
R is hydrogen;
R$_1$ is —C$_{3-7}$cycloalkyl, wherein the C$_{3-7}$cycloalkyl is unsubstituted or substituted by one substituent selected from triazolyl, pyridyl and pyridazinyl, and wherein the triazolyl, pyridyl, or pyridazinyl is unsubstituted or substituted by —C$_{1-3}$alkyl;
R$_2$ is hydrogen or F;
R$_{2a}$ is hydrogen;
G is CH or N;
A is

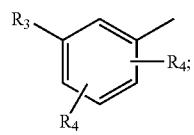

R$_3$ is —(CH$_2$)$_n$—C(O)N(R$_5$)(R$_6$); —(CH$_2$)$_n$—C(R$_{14}$)(R$_{15}$)—N(R$_5$)(R$_6$), or

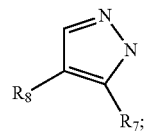

or R$_3$ is —O—C$_{1-3}$alkyl, —C$_{1-6}$alkyl, —C$_{4-7}$heterocycloalkyl, —O—C$_{4-7}$heterocycloalkyl, or, —O—C$_{3-7}$cycloalkyl, wherein each of —O—C$_{1-3}$alkyl, —C$_{1-6}$alkyl, —C$_{4-7}$heterocycloalkyl, —O—C$_{4-7}$heterocycloalkyl, or, —O—C$_{3-7}$cycloalkyl is unsubstituted or substituted by one or two substituents independently selected from —C$_{1-7}$alkyl, —C$_{3-7}$cycloalkyl, =O, —O—C$_{1-5}$alkyl, and —C$_{4-7}$heterocycloalkyl, and wherein each of the —C$_{1-7}$alkyl, —C$_{3-7}$cycloalkyl, —O—C$_{1-3}$alkyl, or —C$_{4-7}$heterocycloalkyl is unsubstituted or further substituted by one or two substituents independently substituted by —C$_{1-5}$alkyl, —CF$_3$, —O—C$_{1-3}$alkyl, phenyl or halo;
Each R$_4$ is independently hydrogen or F;
R$_5$ and R$_6$ together with the nitrogen atom to which they are attached form a 5-8-membered ring, an 8-11-membered bicyclic ring or a 9-10-membered bridged bicyclic ring, wherein each 5-8-membered ring, 8-11-membered bicyclic ring, or 9-10-membered bridged bicyclic ring optionally includes one —S(O)$_2$, one or more oxygen ring atoms or one or more nitrogen ring atoms, and wherein each 5-8-membered ring, 8-11-membered bicyclic ring, or 9-10-membered bridged bicyclic ring is unsubstituted or substituted by one, two or three substituents independently selected from —C$_{1-5}$ alkyl, —C$_{3-7}$cycloalkyl, —C$_{4-7}$heterocycloalkyl, halogen, —CHF$_2$, —CF$_3$, and —(CH$_2$)$_n$—O—(CH$_2$)$_m$—CH$_3$;
or R$_5$ and R$_6$ together with the nitrogen atom to which they are attached form 4-azaspiro[2.5]octane, 7-azaspiro[4.5]decane, 2-oxa-8-azaspiro[5.5]undecane, 6-oxa-9-azaspiro[4.5]decane, 2-oxa-8-azaspiro[5.5]undecane, 1-azaspiro[4.5]decane, 2,3,4,5-tetrahydrobenzo[f][1,4]oxazepine or 2,3,4,5-tetrahydro-1H-benzo[c]azepine;

R$_7$ and R$_8$ are independently H, —C$_{1-6}$ alkyl or —C$_{3-7}$ cycloalkyl wherein each of —C$_{1-6}$ alkyl or —C$_{3-7}$ cycloalkyl is unsubstituted or substituted by one or two substituents independently selected from F, —CHF$_2$, —CF$_3$ and —(CH$_2$)$_n$—O—(CH$_2$)$_m$—CH$_3$;
or R$_7$ and R$_8$ together with the carbon atoms to which they are attached form a 5-8 membered ring, which optionally includes one or more oxygen atoms or one or more nitrogen atoms as ring atoms, and wherein the 5-8-membered ring is unsubstituted or substituted by one or two substituents independently selected from —C$_{1-5}$alkyl, F, —CHF$_2$ and —CF$_3$;
R$_{14}$ is hydrogen;
R$_{15}$ is hydrogen;
Each X is CH;
Each n is independently 0 or 1;
Each m is independently 0 or 1;
or a pharmaceutically acceptable salt thereof.

In still yet another embodiment, the compound of Formula (I) is substituted as follows:
R is hydrogen;
R$_1$ is cyclopropyl, wherein the cyclopropyl is unsubstituted or substituted by one substituent selected from triazolyl, pyridyl, and pyridazinyl, and wherein the triazolyl, pyridyl, or pyridazinyl is unsubstituted or substituted by —C$_{1-3}$alkyl;
R$_2$ is hydrogen;
R$_{2a}$ is hydrogen;
G is CH;
A is

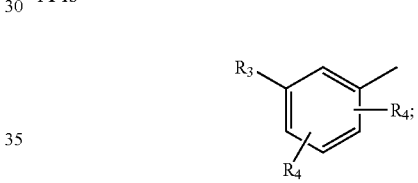

R$_3$ is —(CH$_2$)$_n$—C(O)N(R$_5$)(R$_6$); —(CH$_2$)$_n$—C(R$_{14}$)(R$_{15}$)—N(R$_5$)(R$_6$), —(CH$_2$)$_n$—S(O)NR$_5$R$_6$ or

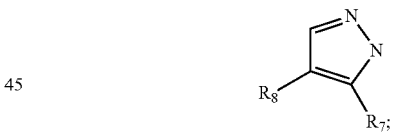

or R$_3$ is —O—C$_{1-3}$alkyl, —C$_{1-6}$ alkyl, —C$_{4-7}$heterocycloalkyl, —O—C$_{4-7}$heterocycloalkyl or —O—C$_{3-7}$ cycloalkyl, wherein each of —O—C$_{1-3}$alkyl, —C$_{1-6}$ alkyl, —C$_{4-7}$heterocycloalkyl, —O—C$_{4-7}$heterocycloalkyl or —O—C$_{3-7}$ cycloalkyl is unsubstituted or substituted by one or two substituents independently selected from —C$_{1-7}$ alkyl, —C$_{3-7}$cycloalkyl, =O, —O—C$_{1-5}$alkyl, and —C$_{4-7}$ heterocycloalkyl, and wherein the —C$_{1-7}$alkyl, —C$_{3-7}$cycloalkyl, —O—C$_{1-3}$alkyl, or —C$_{4-7}$heterocycloalkyl is unsubstituted or further substituted by one or two substituents independently selected from —C$_{1-5}$alkyl, —CF$_3$, —O—C$_{1-3}$alkyl, phenyl and halo;
Each R$_4$ is independently hydrogen or F;
R$_5$ and R$_6$ together with the nitrogen atom to which they are attached form a 5-8-membered ring, an 8-11-membered bicyclic ring or a 9-10-membered bridged bicyclic ring, wherein each 5-8-membered ring, 8-11-membered bicyclic ring, or 9-10-membered bridged bicyclic ring optionally includes one —S(O)$_2$, one or more oxygen ring atoms or one or more nitrogen ring atoms, and wherein each 5-8-membered ring, 8-11-membered bicyclic ring, or 9-10-membered bridged bicyclic ring is unsubstituted or substituted by one, two or three substituents independently selected from —$C_{1-5}$ alkyl, —$C_{3-7}$cycloalkyl, —$C_{4-7}$heterocycloalkyl, halogen, —$CHF_2$, —$CF_3$, and —$(CH_2)_n$—O—$(CH_2)_m$—$CH_3$;

or $R_5$ and $R_6$ together with the nitrogen atom to which they are attached form 4-azaspiro[2.5]octane, 7-azaspiro[4.5]decane, 2-oxa-8-azaspiro[5.5]undecane, 6-oxa-9-azaspiro[4.5]decane, 2-oxa-8-azaspiro[5.5]undecane, 1-azaspiro[4.5]decane, 2,3,4,5-tetrahydrobenzo[f][1,4]oxazepane, or 2,3,4,5-tetrahydro-1H-benzo[c]azepine;

$R_7$ and $R_8$ are independently H, —$C_{1-6}$alkyl or —$C_{3-7}$cycloalkyl, wherein —$C_{1-6}$alkyl or —$C_{3-7}$cycloalkyl is unsubstituted or substituted by one or two substituents selected from F, —$CHF_2$, —$CF_3$, and —$(CH_2)_n$—O—$(CH_2)_m$—$CH_3$; or $R_7$ and $R_8$ together with the carbon atoms to which they are attached form a 5-8-membered ring, which optionally includes one or more oxygen or one or more nitrogen atoms as ring atoms, and wherein the 5-8-membered ring is unsubstituted or substituted by one or two substituents independently selected from —$C_{1-5}$alkyl, F, —$CHF_2$, or —$CF_3$;

$R_{14}$ is hydrogen;
$R_{15}$ is hydrogen;
Each X is CH;
n is 0;
Each m is independently 0 or 1;
or a pharmaceutically acceptable salt thereof.

In another embodiment, the compound of Formula (I) is substituted as follows:
R is hydrogen;
$R_1$ is cyclopropyl, wherein the cyclopropyl ring is unsubstituted or substituted by one substituent selected from halo, triazolyl, pyridyl, and pyridazinyl, and wherein the triazolyl, pyridyl, and pyridazinyl is unsubstituted or substituted by —$C_{1-3}$alkyl;
$R_{2a}$ is —$CH_3$;
$R_2$ is hydrogen;
G is CH;
A is

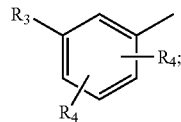

$R_3$ is —$(CH_2)_n$—C(O)N($R_5$)($R_6$), —$(CH_2)_n$—C($R_{14}$)($R_{15}$)—N($R_5$)($R_6$);
or $R_3$ is —O—$C_{1-6}$alkyl, —$C_{1-6}$ alkyl, —$C_{4-7}$heterocycloalkyl, —O—$C_{4-7}$heterocycloalkyl, or —O—$C_{3-7}$cycloalkyl wherein each of —O—$C_{1-6}$alkyl, —$C_{1-6}$ alkyl, —$C_{4-7}$heterocycloalkyl, —O—$C_{4-7}$ heterocycloalkyl, and —O—$C_{3-7}$cycloalkyl is unsubstituted or substituted by one or two substituents independently selected from —$C_{1-7}$ alkyl, —$C_{3-7}$cycloalkyl, =O, —O—$C_{1-5}$alkyl, and —$C_{4-7}$ heterocycloalkyl, and wherein each of the —$C_{3-7}$alkyl, —$C_{3-7}$cycloalkyl, —O—$C_{1-5}$alkyl, and $C_{4-7}$ heterocycloalkyl, is further substituted by one or two substituents independently selected from —$C_{1-5}$alkyl, $CF_3$, O—$C_{1-3}$ alkyl, phenyl and halo;
$R_4$ is independently hydrogen or F;
$R_5$ and $R_6$ together with the nitrogen atom to which they are attached form a 5-8-membered ring, an 8-11-membered bicyclic ring or a 9-10-membered bridged bicyclic ring, wherein each 5-8-membered ring, 8-11-membered bicyclic ring, or 9-10-membered bridged bicyclic ring optionally includes one —S(O)$_2$, one or more oxygen ring atoms or one or more nitrogen ring atoms, and wherein each 5-8-membered ring, 8-11-membered bicyclic ring, or 9-10-membered bridged bicyclic ring is unsubstituted or substituted by one, two or three substituents independently selected from —$C_{1-5}$ alkyl, —$C_{3-7}$cycloalkyl, —$C_{4-7}$heterocycloalkyl, halogen, —$CHF_2$, —$CF_3$, and —$(CH_2)_n$—O—$(CH_2)_m$—$CH_3$;

or $R_5$ and $R_6$ together with the nitrogen atom to which they are attached form 4-azaspiro[2.5]octane, 7-azaspiro[4.5]decane, 2-oxa-8-azaspiro[5.5]undecane, 6-oxa-9-azaspiro[4.5]decane, 2-oxa-8-azaspiro[5.5]undecane, 1-azaspiro[4.5]decane, 2,3,4,5-tetrahydrobenzo[f][1,4]oxazepane, or 2,3,4,5-tetrahydro-1H-benzo[c]azepine;
$R_{14}$ is hydrogen;
$R_{15}$ is hydrogen;
X is CH;
n is 0;
m is independently 0 or 1;
or a pharmaceutically acceptable salt thereof.

In another embodiment, the compound of Formula (I) is substituted as follows:
R is hydrogen;
$R_1$ is cyclopropyl, wherein the cyclopropyl ring is unsubstituted or substituted by one substituent selected from halo, triazolyl, pyridyl, and pyridazinyl, and wherein the triazolyl, pyridyl, and pyridazinyl is unsubstituted or substituted by —$C_{1-3}$alkyl;
$R_{2a}$ is hydrogen;
$R_2$ is halo;
G is CH;
A is

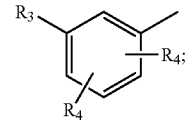

$R_3$ is —$(CH_2)_n$—C(O)N($R_5$)($R_6$), —$(CH_2)_n$—C($R_{14}$)($R_{15}$)—N($R_5$)($R_6$);
or $R_3$ is —O—$C_{1-6}$alkyl, —$C_{1-6}$ alkyl, —$C_{4-7}$heterocycloalkyl, —O—$C_{4-7}$heterocycloalkyl, or —O—$C_{3-7}$cycloalkyl wherein each of —O—$C_{1-6}$alkyl, —$C_{1-6}$ alkyl, —$C_{4-7}$heterocycloalkyl, —O—$C_{4-7}$ heterocycloalkyl, and —O—$C_{3-7}$cycloalkyl is unsubstituted or substituted by one or two substituents independently selected from —$C_{1-7}$ alkyl, —$C_{3-7}$cycloalkyl, =O, —O—$C_{1-5}$alkyl, and —$C_{4-7}$ heterocycloalkyl, and wherein each of the —$C_{1-7}$alkyl, —$C_{3-7}$cycloalkyl, —O—$C_{1-5}$alkyl, and $C_{4-7}$ heterocycloalkyl, is further substituted by one or two substituents independently selected from —$C_{1-5}$alkyl, $CF_3$, O—$C_{1-3}$ alkyl, phenyl and halo;
$R_4$ is independently hydrogen or F;
$R_5$ and $R_6$ together with the nitrogen atom to which they are attached form a 5-8-membered ring, an 8-11-membered bicyclic ring or a 9-10-membered bridged bicyclic ring, wherein each 5-8-membered ring, 8-11-membered bicyclic ring, or 9-10-membered bridged bicyclic ring optionally includes one —S(O)$_2$, one or more oxygen ring atoms or one or more nitrogen ring atoms, and wherein each 5-8-membered ring, 8-11-membered bicyclic ring, or 9-10-membered bridged bicyclic ring is unsubstituted or substituted by one, two or three substituents independently selected from —C$_{1-5}$alkyl, —C$_{3-7}$cycloalkyl, —C$_{4-7}$heterocycloalkyl, halogen, —CHF$_2$, —CF$_3$, and —(CH$_2$)$_n$—O—(CH$_2$)$_m$—CH$_3$;
or R$_5$ and R$_6$ together with the nitrogen atom to which they are attached form 4-azaspiro[2.5]octane, 7-azaspiro[4.5]decane, 2-oxa-8-azaspiro[5.5]undecane, 6-oxa-9-azaspiro[4.5]decane, 2-oxa-8-azaspiro[5.5]undecane, 1-azaspiro[4.5]decane, 2,3,4,5-tetrahydrobenzo[f][1,4]oxazepane, or 2,3,4,5-tetrahydro-1H-benzo[c]azepine;
R$_{14}$ is hydrogen;
R$_{15}$ is hydrogen;
X is CH;
n is 0;
m is independently 0 or 1;
or a pharmaceutically acceptable salt thereof.

In another embodiment, the compound of Formula (I) is substituted as follows:
R is hydrogen;
R$_1$ is cyclopropyl, wherein the cyclopropyl ring is unsubstituted or substituted by one substituent selected from halo, triazolyl, pyridyl, and pyridazinyl, and wherein the triazolyl, pyridyl, and pyridazinyl is unsubstituted or substituted by —C$_{1-3}$alkyl;
R$_{2a}$ is CH$_3$;
R$_2$ is —C$_{1-3}$alkyl;
G is CH;
A is

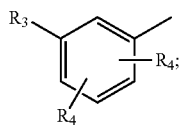

R$_3$ is —(CH$_2$)$_n$—C(O)N(R$_5$)(R$_6$), —(CH$_2$)$_n$—C(R$_{14}$)(R$_{15}$)—N(R$_5$)(R$_6$);
or R$_3$ is —O—C$_{1-6}$alkyl, —C$_{1-6}$ alkyl, —C$_{4-7}$heterocycloalkyl, —O—C$_{4-7}$heterocycloalkyl, or —O—C$_{3-7}$cycloalkyl wherein each of —O—C$_{1-6}$alkyl, —C$_{1-6}$ alkyl, —C$_{4-7}$heterocycloalkyl, —O—C$_{4-7}$ heterocycloalkyl, and —O—C$_{3-7}$cycloalkyl is unsubstituted or substituted by one or two substituents independently selected from —C$_{1-7}$alkyl, —C$_{3-7}$cycloalkyl, =O, —O—C$_{1-5}$alkyl, and —C$_{4-7}$heterocycloalkyl, and wherein each of the —C$_{1-7}$alkyl, —C$_{3-7}$cycloalkyl, —O—C$_{1-5}$alkyl, and C$_{4-7}$ heterocycloalkyl, is further substituted by one or two substituents independently selected from —C$_{1-5}$alkyl, CF$_3$, O—C$_{1-3}$ alkyl, phenyl and halo;
R$_4$ is independently hydrogen or F;
R$_5$ and R$_6$ together with the nitrogen atom to which they are attached form a 5-8-membered ring, an 8-11-membered bicyclic ring or a 9-10-membered bridged bicyclic ring, wherein each 5-8-membered ring, 8-11-membered bicyclic ring, or 9-10-membered bridged bicyclic ring optionally includes one —S(O)$_2$, one or more oxygen ring atoms or one or more nitrogen ring atoms, and wherein each 5-8-membered ring, 8-11-membered bicyclic ring, or 9-10-membered bridged bicyclic ring is unsubstituted or substituted by one, two or three substituents independently selected from —C$_{1-5}$ alkyl, —C$_{3-7}$cycloalkyl, —C$_{4-7}$heterocycloalkyl, halogen, —CHF$_2$, —CF$_3$, and —(CH$_2$)$_n$—O—(CH$_2$)$_m$—CH$_3$;
or R$_5$ and R$_6$ together with the nitrogen atom to which they are attached form 4-azaspiro[2.5]octane, 7-azaspiro[4.5]decane, 2-oxa-8-azaspiro[5.5]undecane, 6-oxa-9-azaspiro[4.5]decane, 2-oxa-8-azaspiro[5.5]undecane, 1-azaspiro[4.5]decane, 2,3,4,5-tetrahydrobenzo[f][1,4]oxazepane, or 2,3,4,5-tetrahydro-1H-benzo[c]azepine;
R$_{14}$ is hydrogen;
R$_{15}$ is hydrogen;
X is CH;
n is 0;
m is independently 0 or 1;
or a pharmaceutically acceptable salt thereof.

In another embodiment, the compound of Formula (I) is substituted as follows:
R is hydrogen;
R$_1$ is cyclopropyl, wherein the cyclopropyl ring is unsubstituted or substituted by one substituent selected from halo, triazolyl, pyridyl, and pyridazinyl, and wherein the triazolyl, pyridyl, and pyridazinyl is unsubstituted or substituted by —C$_{1-3}$alkyl;
R$_{2a}$ is —CH$_3$;
R$_2$ is halo;
G is CH;
A is

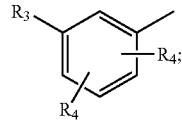

R$_3$ is —(CH$_2$)$_n$—C(O)N(R$_5$)(R$_6$), —(CH$_2$)$_n$—C(R$_{14}$)(R$_{15}$)—N(R$_5$)(R$_6$);
or R$_3$ is —O—C$_{1-6}$alkyl, —C$_{1-6}$ alkyl, —C$_{4-7}$heterocycloalkyl, —O—C$_{4-7}$heterocycloalkyl, or —O—C$_{3-7}$cycloalkyl wherein each of —O—C$_{1-6}$alkyl, —C$_{1-6}$ alkyl, —C$_{4-7}$heterocycloalkyl, —O—C$_{4-7}$ heterocycloalkyl, and —O—C$_{3-7}$cycloalkyl is unsubstituted or substituted by one or two substituents independently selected from —C$_{1-7}$alkyl, —C$_{3-7}$cycloalkyl, =O, —O—C$_{1-5}$alkyl, and —C$_{4-7}$heterocycloalkyl, and wherein each of the —C$_{1-7}$alkyl, —C$_{3-7}$cycloalkyl, —O—C$_{1-5}$alkyl, and C$_{4-7}$ heterocycloalkyl, is further substituted by one or two substituents independently selected from —C$_{1-5}$alkyl, CF$_3$, O—C$_{1-3}$ alkyl, phenyl and halo;
R$_4$ is independently hydrogen or F;
R$_5$ and R$_6$ together with the nitrogen atom to which they are attached form a 5-8-membered ring, an 8-11-membered bicyclic ring or a 9-10-membered bridged bicyclic ring, wherein each 5-8-membered ring, 8-11-membered bicyclic ring, or 9-10-membered bridged bicyclic ring optionally includes one —S(O)$_2$, one or more oxygen ring atoms or one or more nitrogen ring atoms, and wherein each 5-8-membered ring, 8-11-membered bicyclic ring, or 9-10-membered bridged bicyclic ring is unsubstituted or substituted by one, two or three substituents independently selected from —C$_{1-5}$ alkyl, —C$_{3-7}$cycloalkyl, —C$_{4-7}$heterocycloalkyl, halogen, —CHF$_2$, —CF$_3$, and —(CH$_2$)$_n$—O—(CH$_2$)$_m$—CH$_3$;
or R$_5$ and R$_6$ together with the nitrogen atom to which they are attached form 4-azaspiro[2.5]octane, 7-azaspiro[4.5]decane, 2-oxa-8-azaspiro[5.5]undecane, 6-oxa-9-azaspiro[4.5]decane, 2-oxa-8-azaspiro[5.5]undecane, 1-azaspiro[4.5]decane, 2,3,4,5-tetrahydrobenzo[f][1,4]oxazepane, or 2,3,4,5-tetrahydro-1H-benzo[c]azepine;
R$_{14}$ is hydrogen;
R$_{15}$ is hydrogen;
X is CH;
n is 0;
m is independently 0 or 1;
or a pharmaceutically acceptable salt thereof.

In another embodiment, the compound of Formula (I) is substituted as follows:

R is hydrogen;
$R_1$ is cyclopropyl, wherein the cyclopropyl ring is unsubstituted or substituted by one substituent selected from halo, triazolyl, pyridyl, and pyridazinyl, and wherein the triazolyl, pyridyl, and pyridazinyl is unsubstituted or substituted by —$C_{1-3}$alkyl;
$R_{2a}$ is hydrogen;
$R_2$ is —$C_{1-3}$alkyl;
G is CH;
A is

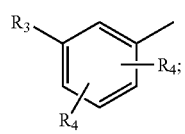

$R_3$ is —$(CH_2)_n$—$C(O)N(R_5)(R_6)$, —$(CH_2)_n$—$C(R_{14})(R_{15})$—$N(R_5)(R_6)$;
or $R_3$ is —O—$C_{1-6}$alkyl, —$C_{1-6}$ alkyl, —$C_{4-7}$heterocycloalkyl, —O—$C_{4-7}$heterocycloalkyl, or —O—$C_{3-7}$cycloalkyl wherein each of —O—$C_{1-6}$alkyl, —$C_{1-6}$ alkyl, —$C_{4-7}$heterocycloalkyl, —O—$C_{4-7}$ heterocycloalkyl, and —O—$C_{3-7}$cycloalkyl is unsubstituted or substituted by one or two substituents independently selected from —$C_{1-7}$ alkyl, —$C_{3-7}$cycloalkyl, =O, —O—$C_{1-5}$alkyl, and —$C_{4-7}$ heterocycloalkyl, and wherein each of the —$C_{1-7}$alkyl, —$C_{3-7}$cycloalkyl, —O—$C_{1-5}$alkyl, and $C_{4-7}$ heterocycloalkyl, is further substituted by one or two substituents independently selected from —$C_{1-5}$alkyl, $CF_3$, O—$C_{1-3}$ alkyl, phenyl and halo;
$R_4$ is independently hydrogen or F;
$R_5$ and $R_6$ together with the nitrogen atom to which they are attached form a 5-8-membered ring, an 8-11-membered bicyclic ring or a 9-10-membered bridged bicyclic ring, wherein each 5-8-membered ring, 8-11-membered bicyclic ring, or 9-10-membered bridged bicyclic ring optionally includes one —$S(O)_2$, one or more oxygen ring atoms or one or more nitrogen ring atoms, and wherein each 5-8-membered ring, 8-11-membered bicyclic ring, or 9-10-membered bridged bicyclic ring is unsubstituted or substituted by one, two or three substituents independently selected from —$C_{1-5}$ alkyl, —$C_{3-7}$cycloalkyl, —$C_{4-7}$heterocycloalkyl, halogen, —$CHF_2$, —$CF_3$, and —$(CH_2)_n$—O—$(CH_2)_m$—$CH_3$;
or $R_5$ and $R_6$ together with the nitrogen atom to which they are attached form 4-azaspiro[2.5]octane, 7-azaspiro[4.5]decane, 2-oxa-8-azaspiro[5.5]undecane, 6-oxa-9-azaspiro[4.5]decane, 2-oxa-8-azaspiro[5.5]undecane, 1-azaspiro[4.5]decane, 2,3,4,5-tetrahydrobenzo[f][1,4]oxazepane, or 2,3,4,5-tetrahydro-1H-benzo[c]azepine;
$R_{14}$ is hydrogen;
$R_{15}$ is hydrogen;
X is CH;
n is 0;
m is independently 0 or 1;
or a pharmaceutically acceptable salt thereof.

In yet another embodiment, the compound of Formula (I) is substituted as follows:
R is hydrogen;
$R_1$ is —$CF_3$;
$R_{2a}$ is hydrogen or methyl;
$R_2$ is hydrogen or F;
G is CH or N;

A is

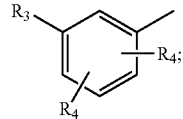

$R_3$ is —$(CH_2)_n$—$C(O)N(R_5)(R_6)$, —$(CH_2)_n$—$C(R_{14})(R_{15})$—$N(R_5)(R_6)$, or

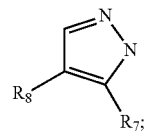

or $R_3$ is —O—$C_{1-6}$alkyl, —$C_{1-6}$ alkyl, —$C_{4-7}$heterocycloalkyl, —O—$C_{4-7}$heterocycloalkyl, or —O—$C_{3-7}$cycloalkyl, wherein each of —O—$C_{1-6}$alkyl, —$C_{1-6}$ alkyl, —$C_{4-7}$heterocycloalkyl, —O—$C_{4-7}$ heterocycloalkyl, and —O—$C_{3-7}$cycloalkyl is unsubstituted or substituted by one or two substituents independently selected from —$C_{1-7}$ alkyl, —$C_{3-7}$cycloalkyl, =O, —O—$C_{1-5}$alkyl, and —$C_{4-7}$ heterocycloalkyl, and wherein each of the —$C_{1-7}$alkyl, —$C_{3-7}$cycloalkyl, —O—$C_{1-5}$alkyl, and $C_{4-7}$ heterocycloalkyl, is further substituted by one or two substituents independently selected from —$C_{1-5}$alkyl, $CF_3$, O—$C_{1-3}$ alkyl, phenyl and halo;
$R_4$ is independently hydrogen or F;
or $R_5$ and $R_6$ together with the nitrogen atom to which they are attached form a 5-8-membered ring, an 8-11-membered bicyclic ring or a 9-10-membered bridged bicyclic ring, wherein each 5-8-membered ring, 8-11-membered bicyclic ring, or 9-10-membered bridged bicyclic ring optionally includes one —$S(O)_2$, one or more oxygen ring atoms or one or more nitrogen ring atoms, and wherein each 5-8-membered ring, 8-11-membered bicyclic ring, or 9-10-membered bridged bicyclic ring is unsubstituted or substituted by one, two or three substituents independently selected from —$C_{1-5}$ alkyl, —$C_{3-7}$cycloalkyl, —$C_{4-7}$heterocycloalkyl, halogen, —$CHF_2$, —$CF_3$, and —$(CH_2)_n$—O—$(CH_2)_m$—$CH_3$;
or $R_5$ and $R_6$ together with the nitrogen atom to which they are attached form 4-azaspiro[2.5]octane, 7-azaspiro[4.5]decane, 2-oxa-8-azaspiro[5.5]undecane, 6-oxa-9-azaspiro[4.5]decane, 2-oxa-8-azaspiro[5.5]undecane, 1-azaspiro[4.5]decane, 2,3,4,5-tetrahydrobenzo[f][1,4]oxazepane, or 2,3,4,5-tetrahydro-1H-benzo[c]azepine;
$R_7$ and $R_8$ are independently H, —$C_{1-6}$ alkyl or —$C_{3-7}$ cycloalkyl, wherein each of —$C_{1-6}$ alkyl, or —$C_{3-7}$ cycloalkyl is unsubstituted or substituted by one or two substituents independently selected from substituted by F, —$CHF_2$, —$CF_3$, and —$(CH_2)_n$—O—$(CH_2)_m$—$CH_3$;
or $R_7$ and $R_8$ together with the carbon atoms to which they are attached form a 5-8-membered ring, which optionally includes one or more oxygen or one or more nitrogen atoms as ring atoms, and wherein the 5-8-membered ring is unsubstituted or substituted by one or two substituents independently selected from —$C_{1-5}$ alkyl, F, —$CHF_2$, and —$CF_3$;
$R_{14}$ is hydrogen;
$R_{15}$ is hydrogen;
X is CH;
n is independently 0 or 1;
m is independently 0 or 1;
or a pharmaceutically acceptable salt thereof.

In one embodiment, the invention is as follows:
A compound of Formula (Ia):

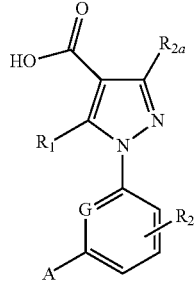

wherein:
R$_1$ is —CF$_3$, —C$_{3-7}$cycloalkyl, or C$_{4-7}$heterocycloalkyl, wherein the —C$_{3-7}$cycloalkyl, or —C$_{4-7}$heterocycloalkyl may be unsubstituted or substituted by one or two substituents independently selected from C$_{1-3}$alkyl, phenyl, triazolyl, pyridyl, pyridazinyl, imidazolyl, pyrazolyl, isoxazolyl, halo, —NR$_9$—C(O)—R$_{10}$ and —C(O)R$_{10}$, and wherein the phenyl, triazolyl, pyridyl, pyridazinyl, imidazolyl, pyrazolyl and isoxazolyl is unsubstituted or substituted by one or two substituents selected from —C$_{1-3}$alkyl and halo;
or R$_1$ is C$_{2-3}$alkyl-R$_{11}$;
R$_{2a}$ is hydrogen, halo, or —C$_{1-3}$alkyl;
R$_2$ is hydrogen, halo, —CN, —O—C$_{1-3}$alkyl, —OH, or C$_{1-3}$alkyl;
G is CH or N;
A is

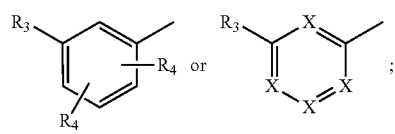

R$_3$ is (CH$_2$)$_n$—C(O)NR$_5$R$_6$, (CH$_2$)$_n$—C(R$_{14}$)(R$_{15}$)—NR$_5$R$_6$,

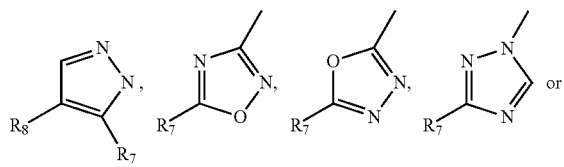

or R$_3$ is O—C$_{1-6}$alkyl, C$_{1-6}$ alkyl, C$_{4-7}$ heterocycloalkyl, O—C$_{4-7}$ heterocycloalkyl, N—R$_{12}$R$_{13}$, C$_{3-7}$ cycloalkyl, O—C$_{3-7}$ cycloalkyl, S—C$_{1-3}$alkyl, S—C$_{4-7}$ heterocycloalkyl, S—C$_{3-7}$ cycloalkyl, S(O)—C$_{1-3}$alkyl, S(O)—C$_{4-7}$ heterocycloalkyl, S(O)—C$_{3-7}$ cycloalkyl, S(O)$_2$—C$_{1-3}$alkyl, S(O)$_2$—C$_{4-7}$ heterocycloalkyl, S(O)$_2$—C$_{3-7}$ cycloalkyl, all of which except for N—R$_{12}$R$_{13}$ may be substituted by one or two substituents chosen from: C$_{1-7}$ alkyl, C$_{3-7}$ cycloalkyl, OH, =O, —O—C$_{1-5}$ alkyl, CF$_3$;

C$_{4-7}$ heterocycloalkyl, phenyl, pyridyl, pyrazolyl, pyridazinyl, pyrimidinyl, pyrazinyl, or triazolyl, and the C$_{1-7}$ alkyl, C$_{3-7}$ cycloalkyl, —O—C$_{1-3}$ alkyl, C$_{4-7}$ heterocycloalkyl, phenyl, pyridyl, pyrazolyl, pyridazinyl, pyrimidinyl, pyrazinyl, or triazolyl may be further substituted by C$_{1-5}$ alkyl, CF$_3$, —OC$_{1-3}$alkyl, phenyl, —C(O)—O—C$_{1-3}$ alkyl or halo;

Each R$_4$ is independently hydrogen, halo or C$_{1-3}$ alkyl;

R$_5$ and R$_6$ are independently H, C$_{1-6}$ alkyl, C$_{3-7}$ cycloalkyl or C$_{4-7}$ heterocycloalkyl, all of which may be substituted by F, CH—F$_2$, CF$_3$, (CH$_2$)$_n$—O—(CH$_2$)$_m$—CH$_3$, or C$_{3-7}$ cycloalkyl;

or R$_5$ and R$_6$ together with the nitrogen atom can form a 5-8 member ring or a 8-11 member bicyclic ring or a 9 or 10-membered bridged bicyclic ring, all of which can optionally include oxygen or another nitrogen as ring atoms, and all of which may be substituted by one or two C$_{1-5}$ alkyl, C$_{3-7}$ cycloalkyl, C$_{4-7}$ heterocycloalkyl, F, CHF$_2$, CF$_3$, or (CH$_2$)$_n$—O—(CH$_2$)$_m$—CH$_3$; or R$_5$ and R$_6$ together with the nitrogen atom can form 4-azaspiro[2.5]octane, 7-azaspiro[4.5]decane, 2-oxa-8-azaspiro[5.5]undecane, 6-oxa-9-azaspiro[4.5]decane, 2-oxa-8-azaspiro[5.5]undecane, 1-azaspiro[4.5]decane, or 2,3,4,5-tetrahydrobenzo[f][1,4]oxazepine; 2,3,4,5-tetrahydro-1H-benzo[c]azepine;

R$_7$ and R$_8$ are independently H, C$_{1-6}$ alkyl, C$_{3-7}$ cycloalkyl or C$_{4-7}$ heterocycloalkyl, of which the C$_{1-6}$ alkyl, C$_{3-7}$ cycloalkyl or C$_{4-7}$ heterocycloalkyl may be substituted by F, CHF$_2$, CF$_3$, (CH$_2$)$_n$—O—(CH$_2$)$_m$—CH$_3$; or R$_7$ and R$_8$ together together with the carbon atoms to which they are attached form a 5-8 member ring, which can optionally include oxygen or nitrogen as ring atoms, which may be substituted by one or two C$_{1-5}$ alkyl, C$_{3-7}$ cycloalkyl, C$_{4-7}$ heterocycloalkyl, F, CHF$_2$, CF$_3$, =O, or (CH$_2$)$_n$—O—(CH$_2$)$_m$—CH$_3$;

R$_9$ is H or C$_{1-3}$ alkyl;

R$_{10}$ is C$_{1-3}$ alkyl;

R$_{11}$ is aryl, triazolyl, pyridyl, pyridazinyl, imidazolyl, or pyrazolyl, all of which may be substituted by C$_{1-3}$alkyl or halo;

R$_{12}$ and R$_{13}$ are independently C$_{4-7}$ heterocycloalkyl, C$_{1-3}$ alkyl or C$_{3-7}$ cycloalkyl all of which may be substituted by one or two substituents chosen from: C$_{1-7}$ alkyl, C$_{3-7}$ cycloalkyl, OH, =O, —O—C$_{1-5}$ alkyl, C$_{4-7}$ heterocycloalkyl, phenyl, pyridyl, pyrazolyl, pyridazinyl, pyrimidinyl, pyrazinyl, or triazolyl, and the C$_{1-7}$ alkyl, C$_{3-7}$ cycloalkyl, —O—C$_{1-3}$ alkyl, C$_{4-7}$ heterocycloalkyl, phenyl, pyridyl, pyrazolyl, pyridazinyl, pyrimidinyl, pyrazinyl, or triazolyl may be further substituted by C$_{1-5}$ alkyl or halo;

R$_{14}$ is hydrogen and C$_{1-3}$ alkyl;

R$_{15}$ is hydrogen and C$_{1-3}$ alkyl;

Each X is CR$_4$ or N provided only one X is N;

Each n is independently 0 or 1;

Each m is independently 0 or 1;

or a pharmaceutically acceptable salt thereof.

In one embodiment, the invention is as follows:
A compound of Formula (Ia):

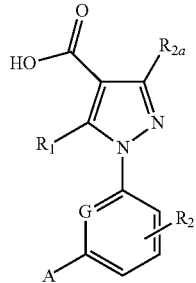

wherein:
$R_1$ is —$CF_3$, —$C_{3-7}$cycloalkyl or —$C_{4-7}$heterocycloalkyl, wherein the —$C_{3-7}$ cycloalkyl or —$C_{4-7}$ heterocycloalkyl is unsubstituted or substituted by one or two substituents selected from —$C_{1-3}$alkyl, phenyl, triazolyl, pyridyl, pyridazinyl, imidazolyl, pyrazolyl, isoxazolyl, halo, —$NR_9$—C(O)—$R_{10}$ and —C(O)$R_{10}$, and wherein the phenyl, triazolyl, pyridyl, pyridazinyl, imidazolyl, pyrazolyl and isoxazolyl is unsubstituted or substituted by one or two substituents independently selected from —$C_{1-3}$alkyl and halo;
or $R_1$ is —$C_{2-3}$alkyl-$R_{11}$;
$R_{2a}$ is hydrogen, halo, or —$C_{1-3}$alkyl;
$R_2$ is hydrogen, halo, —CN, —O—$C_{1-3}$alkyl, —OH, or —$C_{1-3}$alkyl;
G is CH or N;
A is

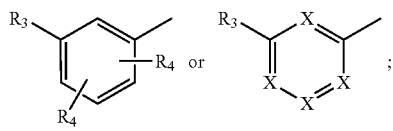

$R_3$ is —$(CH_2)_n$—C(O)$NR_5R_6$, —$(CH_2)_n$—C($R_{14}$)($R_{15}$)—$NR_5R_6$,

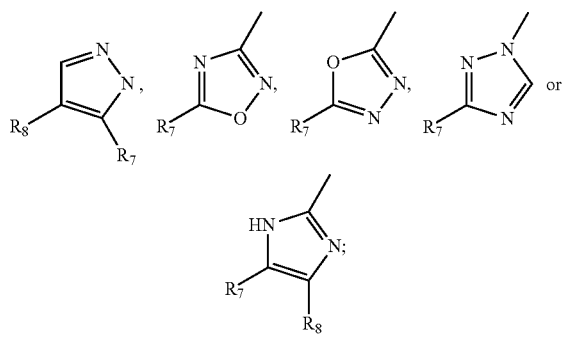

or $R_3$ is —O—$C_{1-6}$alkyl, —$C_{1-6}$alkyl, —$C_{4-7}$heterocycloalkyl, —O—$C_{4-7}$heterocycloalkyl, —N—$R_{12}R_{13}$, —$C_{3-7}$cycloalkyl, —O—$C_{3-7}$ cycloalkyl, —S—$C_{1-3}$alkyl, —S—$C_{4-7}$heterocycloalkyl, —S—$C_{3-7}$cycloalkyl, —S(O)—$C_{1-3}$alkyl, —S(O)—$C_{4-7}$heterocycloalkyl, —S(O)—$C_{3-7}$cycloalkyl, —S(O)$_2$—$C_{1-3}$alkyl, —S(O)$_2$—$C_{4-7}$heterocycloalkyl, —S(O)$_2$—$C_{3-7}$cycloalkyl, wherein —O—$C_{1-6}$alkyl, —$C_{1-6}$alkyl, —$C_{4-7}$heterocycloalkyl, —O—$C_{4-7}$heterocycloalkyl, —$C_{3-7}$cycloalkyl, —O—$C_{3-7}$ cycloalkyl, —S—$C_{3-7}$alkyl, —S—$C_{4-7}$heterocycloalkyl, —S—$C_{3-7}$cycloalkyl, —S(O)—$C_{1-3}$alkyl, —S(O)—$C_{4-7}$heterocycloalkyl, —S(O)—$C_{3-7}$cycloalkyl, —S(O)$_2$—$C_{1-3}$alkyl, —S(O)$_2$—$C_{4-7}$heterocycloalkyl, —S(O)$_2$—$C_{3-7}$cycloalkyl is unsubstituted or substituted by one or two substituents independently selected from —$C_{1-7}$alkyl, —$C_{3-7}$cycloalkyl, —OH, =O, —O—$C_{1-5}$alkyl, —$CF_3$, —$C_{4-7}$heterocycloalkyl, phenyl, pyridyl, pyrazolyl, pyridazinyl, pyrimidinyl, pyrazinyl, and triazolyl, and wherein the —$C_{1-7}$ alkyl, —$C_{3-7}$cycloalkyl, —O—$C_{1-3}$alkyl, $C_{4-7}$heterocycloalkyl, phenyl, pyridyl, pyrazolyl, pyridazinyl, pyrimidinyl, pyrazinyl, or triazolyl is unsubstituted or further substituted by one or two substitutents selected from —$C_{1-5}$alkyl, —$CF_3$, —$OC_{1-3}$alkyl, phenyl, —C(O)—O—$C_{1-5}$alkyl and halo;
Each $R_4$ is independently hydrogen, halo or —$C_{1-3}$alkyl;
$R_5$ and $R_6$ are independently H, —$C_{1-6}$alkyl, —$C_{3-7}$cycloalkyl or —$C_{4-7}$heterocycloalkyl, wherein each of —$C_{1-6}$ alkyl, —$C_{3-7}$cycloalkyl or —$C_{4-7}$heterocycloalkyl is unsubstituted or substituted by one or two substituents independently selected from F, —CH—$F_2$, —$CF_3$, —$(CH_2)_n$—O—$(CH_2)_m$—$CH_3$, and —$C_{3-7}$cycloalkyl;
or $R_5$ and $R_6$ together with the nitrogen atom to which they are attached form a 5-8-membered ring or an 8-11-membered bicyclic ring or a 9-10-membered bridged bicyclic ring, wherein each 5-8-membered ring, 8-11-membered bicyclic ring, or 9-10-membered bridged bicyclic ring optionally includes one or more oxygen ring atoms or another nitrogen ring atom, and wherein each 5-8-membered ring, 8-11-membered bicyclic ring, or 9-10-membered bridged bicyclic ring is unsubstituted or substituted by one or two substituents independently selected from —$C_{1-5}$ alkyl, F, —$CHF_2$, —$CF_3$, and —$(CH_2)_n$—O—$(CH_2)_m$—$CH_3$;
or $R_5$ and $R_6$ together with the nitrogen atom to which they are attached form 4-azaspiro[2.5]octane, 7-azaspiro[4.5]decane, 2-oxa-8-azaspiro[5.5]undecane, 6-oxa-9-azaspiro[4.5]decane, 2-oxa-8-azaspiro[5.5]undecane, 1-azaspiro[4.5]decane, 2,3,4,5-tetrahydrobenzo[f][1,4]oxazepine or 2,3,4,5-tetrahydro-1H-benzo[c]azepine;
$R_7$ and $R_8$ are independently H, —$C_{1-6}$ alkyl, —$C_{3-7}$ cycloalkyl or —$C_{4-7}$ heterocycloalkyl, wherein each of —$C_{1-6}$ alkyl, —$C_{3-7}$ cycloalkyl or —$C_{4-7}$ heterocycloalkyl is unsubstituted or substituted by one or two substituents independently selected from F, —$CHF_2$, —$CF_3$, and —$(CH_2)_n$—O—$(CH_2)_m$—$CH_3$;
or $R_7$ and $R_8$ together with the carbon atoms to which they are attached form a 5-8-membered ring, which optionally includes one or more oxygen or nitrogen atoms as ring atoms, and wherein the 5-8-membered ring is unsubstituted or substituted by one or two substituents independently selected from —$C_{1-5}$ alkyl, —$C_{3-7}$cycloalkyl, —$C_{4-7}$heterocycloalkyl, F, —$CHF_2$, —$CF_3$, =O, and —$(CH_2)_n$—O—$(CH_2)_m$—$CH_3$;
$R_9$ is H or —$C_{1-3}$ alkyl;
$R_{10}$ is —$C_{1-3}$ alkyl;
$R_{11}$ is aryl, triazolyl, pyridyl, pyridazinyl, imidazolyl or pyrazolyl, wherein each of aryl, triazolyl, pyridyl, pyridazinyl, imidazolyl or pyrazolyl is unsubstituted or substituted by one or two substituents independently selected from —$C_{1-3}$alkyl or halo;
$R_{12}$ and $R_{13}$ are independently —$C_{4-7}$ heterocycloalkyl, —$C_{1-3}$alkyl or —$C_{3-7}$cycloalkyl, wherein each of the —$C_{4-7}$ heterocycloalkyl, —$C_{1-3}$alkyl or —$C_{3-7}$cycloalkyl is unsubstituted or substituted by one or two substituents independently selected from —$C_{1-7}$alkyl, —$C_{3-7}$cycloalkyl, —OH, =O, —O—C$_{1-5}$alkyl, —C$_{4-7}$heterocycloalkyl, phenyl, pyridyl, pyrazolyl, pyridazinyl, pyrimidinyl, pyrazinyl and triazolyl, and wherein each of the —C$_{1-7}$alkyl, —C$_{3-7}$cycloalkyl, —O—C$_{1-5}$alkyl, —C$_{4-7}$heterocycloalkyl, phenyl, pyridyl, pyrazolyl, pyridazinyl, pyrimidinyl, pyrazinyl or triazolyl is further optionally substituted by one or more substituents independently selected from —C$_{1-5}$alkyl and halo;

R$_{14}$ is hydrogen and —C$_{1-3}$alkyl;

R$_{15}$ is hydrogen and —C$_{1-3}$alkyl;

Each X is CR$_4$ or N provided only one X is N;

Each n is independently 0 or 1;

Each m is independently 0 or 1;

or a pharmaceutically acceptable salt thereof.

It is to be understood that the present invention covers all combinations of the embodiments and particular groups described hereinabove.

Specific examples of compounds of the present invention include the following:

5-Cyclopentyl-1-{3-[3-(dimethylcarbamoyl)-2-fluorophenyl]phenyl}-1H-pyrazole-4-carboxylic acid 1-{3-[3-(Dimethylcarbamoyl)-2-fluorophenyl]phenyl}-5-(trifluoromethyl)-1H-pyrazole-4-carboxylic acid 1-(3-{3-[Cyclopentyl(methyl)carbamoyl]-2-fluorophenyl}phenyl)-5-cyclopropyl-1H-pyrazole-4-carboxylic acid 5-Cyclopropyl-1-(3-{2-fluoro-3-[methyl(2-methylpropyl)carbamoyl]phenyl}phenyl)-1H-pyrazole-4-carboxylic acid 1-(3-{3-[Cyclohexyl(methyl)carbamoyl]-2-fluorophenyl}phenyl)-5-cyclopropyl-1H-pyrazole-4-carboxylic acid 5-Cyclopropyl-1-{3-[3-(3,3-dimethylpiperidine-1-carbonyl)-2-fluorophenyl]phenyl}-1H-pyrazole-4-carboxylic acid 1-{3-[3-(azepane-1-carbonyl)-2-fluorophenyl]phenyl}-5-cyclopropyl-1H-pyrazole-4-carboxylic acid 1-(3-{3-[Bis(cyclopropylmethyl)carbamoyl]-2-fluorophenyl}phenyl)-5-cyclopropyl-1H-pyrazole-4-carboxylic acid 5-Cyclopropyl-1-(3-{3-[(cyclopropylmethyl)(propyl)carbamoyl]-2-fluorophenyl}phenyl)-1H-pyrazole-4-carboxylic acid 1-{3-[3-(Azepane-1-carbonyl)phenyl]phenyl}-5-cyclopropyl-1H-pyrazole-4-carboxylic acid 1-{3-[3-(propan-2-yloxy)phenyl]phenyl}-5-(trifluoromethyl)-1H-pyrazole-4-carboxylic acid 1-(3-{3-[(Cyclopentylmethyl)(methyl)carbamoyl]-2-fluorophenyl}phenyl)-5-cyclopropyl-1H-pyrazole-4-carboxylic acid 5-[(cis)-3-Acetamidocyclopentyl]-1-{3-[2-fluoro-3-(propan-2-yloxy)phenyl]phenyl}-1H-pyrazole-4-carboxylic acid (cis racemate)

1-(3-{3-[(Cyclopentylmethyl)(cyclopropylmethyl)carbamoyl]-2-fluorophenyl}phenyl)-5-cyclopropyl-1H-pyrazole-4-carboxylic acid 1-(3-{2-Chloro-3-[(cyclopropylmethyl)(propyl)carbamoyl]phenyl}phenyl)-5-cyclopropyl-1H-pyrazole-4-carboxylic acid 5-Cyclopropyl-1-(3-{3-[(cyclopropylmethyl)(propyl)carbamoyl]-2-methylphenyl}phenyl)-1H-pyrazole-4-carboxylic acid 5-Cyclopropyl-1-{3-[2-fluoro-3-(2-propylpiperidine-1-carbonyl)phenyl]phenyl}-1H-pyrazole-4-carboxylic acid 5-Cyclopropyl-1-(3-{2-fluoro-3-[3-(trifluoromethyl)piperidine-1-carbonyl]phenyl}phenyl)-1H-pyrazole-4-carboxylic acid 1-[3-(3-{4-Azaspiro[2.5]octane-4-carbonyl}-2-fluorophenyl)phenyl]-5-cyclopropyl-1H-pyrazole-4-carboxylic acid 5-Cyclopropyl-1-{3-[2-fluoro-3-(piperidine-1-carbonyl)phenyl]phenyl}-1H-pyrazole-4-carboxylic acid 5-Cyclopropyl-1-(3-{3-[(2R,6S)-2,6-dimethylpiperidine-1-carbonyl]-2-fluorophenyl}phenyl)-1H-pyrazole-4-carboxylic acid 5-Cyclopropyl-1-(3-{2-fluoro-3-[2-(methoxymethyl)piperidine-1-carbonyl]phenyl}phenyl)-1H-pyrazole-4-carboxylic acid 5-Cyclopropyl-1-(3-{3-[(cyclopropylmethyl)(3,3,3-trifluoropropyl)carbamoyl]-2-fluorophenyl}phenyl)-1H-pyrazole-4-carboxylic acid 5-Cyclopropyl-1-{3-[3-(2,5-dimethylpyrrolidine-1-carbonyl)-2-fluorophenyl]phenyl}-1H-pyrazole-4-carboxylic acid 1-{3-[3-(2-Propylpiperidine-1-carbonyl)phenyl]phenyl}-5-(trifluoromethyl)-1H-pyrazole-4-carboxylic acid 5-Cyclopropyl-1-{3-[2-fluoro-3-(2-propylpyrrolidine-1-carbonyl)phenyl]phenyl}-1H-pyrazole-4-carboxylic acid 5-Cyclopropyl-1-{3-[2-fluoro-3-(3-propylmorpholine-4-carbonyl)phenyl]phenyl}-1H-pyrazole-4-carboxylic acid 5-Cyclopropyl-1-(3-{2-fluoro-3-[2-(2-methylpropyl)piperidine-1-carbonyl]phenyl}phenyl)-1H-pyrazole-4-carboxylic acid 5-Cyclopropyl-1-{3-[2-fluoro-3-(4-methylazepane-1-carbonyl)phenyl]phenyl}-1H-pyrazole-4-carboxylic acid 5-Cyclopropyl-1-{3-[3-(2,5-dimethylpiperidine-1-carbonyl)-2-fluorophenyl]phenyl}-1H-pyrazole-4-carboxylic acid 5-Cyclopropyl-1-{3-[3-(decahydroquinoline-1-carbonyl)-2-fluorophenyl]phenyl}-1H-pyrazole-4-carboxylic acid 5-cyclopropyl-1-[3-(2-fluoro-3-{3-oxa-8-azabicyclo[3.2.1]octane-8-carbonyl}phenyl)phenyl]-1H-pyrazole-4-carboxylic acid 1-{3-[3-(2-Cyclopentylpiperidine-1-carbonyl)-2-fluorophenyl]phenyl}-5-cyclopropyl-1H-pyrazole-4-carboxylic acid 1-[3-(3-{9-azabicyclo[3.3.1]nonane-9-carbonyl}-2-fluorophenyl)phenyl]-5-cyclopropyl-1H-pyrazole-4-carboxylic acid 1-[3-(3-{7-Azaspiro[4.5]decane-7-carbonyl}-2-fluorophenyl)phenyl]-5-cyclopropyl-1H-pyrazole-4-carboxylic acid 5-Cyclopropyl-1-{3-[3-(5-methyl-1H-pyrazol-1-yl)phenyl]phenyl}-1H-pyrazole-4-carboxylic acid 5-Cyclopropyl-1-(3-{2-fluoro-3-[(2R)-2-propylpiperidine-1-carbonyl]phenyl}phenyl)-1H-pyrazole-4-carboxylic acid 5-Cyclopropyl-1-(3-{2-fluoro-3-[2-(3,3,3-trifluoropropyl)piperidine-1-carbonyl]phenyl}phenyl)-1H-pyrazole-4-carboxylic acid 5-cyclopropyl-1-{3-[2-fluoro-3-(5-methyl-1H-pyrazol-1-yl)phenyl]phenyl}-1H-pyrazole-4-carboxylic acid 1-{3-[3-(2-propylpiperidine-1-carbonyl)phenyl]phenyl}-5-[2-(pyridin-3-yl)cyclopropyl]-1H-pyrazole-4-carboxylic acid 1-[3'-(2-Propyl-piperidine-1-carbonyl)-biphenyl-3-yl]-5-(2-pyridazin-3-yl-cyclopropyl)-1H-pyrazole-4-carboxylic acid 5-[2-(1-methyl-1H-1,2,3-triazol-4-yl)cyclopropyl]-1-{3-[3-(2-propylpiperidine-1-carbonyl)phenyl]phenyl}-1H-pyrazole-4-carboxylic acid 5-Cyclopropyl-1-[3-(2-fluoro-3-{2-oxa-8-azaspiro[5.5]undecane-8-carbonyl}phenyl)phenyl]-1H-pyrazole-4-carboxylic acid 5-cyclopropyl-1-[3-(2-fluoro-3-{6-oxa-9-azaspiro[4.5]decane-9-carbonyl}phenyl)phenyl]-1H-pyrazole-4-carboxylic acid 5-cyclopropyl-1-(3-{2-fluoro-3-[(2S,5R)-2-methyl-5-propylmorpholine-4-carbonyl]phenyl}phenyl)-1H-pyrazole-4-carboxylic acid 5-(1-Acetylpiperidin-4-yl)-1-{3-[3-dimethylcarbamoyl)phenyl]phenyl}-1H-pyrazole-4-carboxylic acid 1-(3-{3-[(cyclopropylmethyl)(methyl)carbamoyl]-2-fluorophenyl}phenyl)-5-(trifluoromethyl)-1H-pyrazole-4-carboxylic acid 5-cyclopropyl-1-(3-{3-[(cyclopropylmethyl)(methyl)carbamoyl]-2-fluorophenyl}phenyl)-1H-pyrazole-4-carboxylic acid 1-{3-[3-(dimethylcarbamoyl)phenyl]phenyl}-5-(3-phenyl-cyclobutyl)-1H-pyrazole-4-carboxylic acid 5-Cyclopropyl-1-[3'-(tetrahydro-furan-2-yl)-biphenyl-3-yl]-1H-pyrazole-4-carboxylic acid 5-[(1S,2S)-2-(1-methyl-1H-1,2,3-triazol-4-yl)cyclopropyl]-1-(3-{3-[(2R)-2-propylpiperidine-1-carbonyl]phenyl}phenyl)-1H-pyrazole-4-carboxylic acid 5-[(1R,2R)-2-(1-methyl-1H-1,2,3-triazol-4-yl)cyclopropyl]-1-(3-{3-[(2R)-2-propylpiperidine-1-carbonyl]phenyl}phenyl)-1H-pyrazole-4-carboxylic acid 1-{3-[3-(2-propylpiperidine-1-carbonyl)phenyl]phenyl}-5-[2-(pyridin-3-yl)cyclopropyl]-1H-pyrazole-4-carboxylic acid 5-Cyclopropyl-1-[3'-(3,5-dimethyl-piperidine-1-carbonyl)-2'-fluoro-biphenyl-3-yl]-1H-pyrazole-4-carboxylic acid 5-Cyclopropyl-1-{3-[2-fluoro-3-((2-S)-2-propylpiperidine-1-carbonyl)phenyl]phenyl}-1H-pyrazole-4-carboxylic acid (R)-1-(2'-Fluoro-3'-(2-propylpiperidine-1-carbonyl)-[1,1'-biphenyl]-3-yl)-5-(2-(1-methyl-1H-1,2,3-triazol-4-yl)ethyl)-1H-pyrazole-4-carboxylic acid 1-(2'-Fluoro-3'-(2-propylpiperidine-1-carbonyl)-[1,1'-biphenyl]-3-yl)-5-(2-(1-methyl-1H-1,2,3-triazol-4-yl)ethyl)-1H-pyrazole-4-carboxylic acid 1-(2'-Fluoro-3'-((R)-2-propylpiperidine-1-carbonyl)-[1,1'-biphenyl]-3-yl)-5-(2-(1-methyl-1H-1,2,3-triazol-4-yl)cyclopropyl)-1H-pyrazole-4-carboxylic acid (R)-5-(2-(1-Methyl-1H-1,2,3-triazol-4-yl)ethyl)-1-(3'-(2-propylpiperidine-1-carbonyl)-[1,1'-biphenyl]-3-yl)-1H-pyrazole-4-carboxylic acid 1-(3'-Isopropoxy-[1,1'-biphenyl]-3-yl)-5-(2-(1-methyl-1H-1,2,3-triazol-4-yl)cyclopropyl)-1H-pyrazole-4-carboxylic acid 1-(3'-(1-Cyclohexylethoxy)-[1,1'-biphenyl]-3-yl)-5-cyclopropyl-1H-pyrazole-4-carboxylic acid 5-Cyclopropyl-1-(3'-(5,6-dihydrocyclopenta[c]pyrazol-1(4H)-yl)-[1,1'-biphenyl]-3-yl)-1H-pyrazole-4-carboxylic acid 5-cyclopropyl-1-(3'-(4,5,6,7-tetrahydro-1H-indazol-1-yl)-[1,1'-biphenyl]-3-yl)-1H-pyrazole-4-carboxylic acid 5-Cyclopropyl-1-(3'-(6,6-dimethyl-5,6-dihydrocyclopenta[c]pyrazol-1(4H)-yl)-[1,1'-biphenyl]-3-yl)-1H-pyrazole-4-carboxylic acid 1-(3'-((S)-1-Cyclohexylethoxy)-[1,1'-biphenyl]-3-yl)-5-((1R,2R)-2-(1-methyl-1H-1,2,3-triazol-4-yl)cyclopropyl)-1H-pyrazole-4-carboxylic acid 1-(3'-(((R)-2-Ethyl-2,3-dihydrobenzo[f][1,4]oxazepin-4(5H)-yl)methyl)-[1,1'-biphenyl]-3-yl)-5-((1R,2R)-2-(1-methyl-1H-1,2,3-triazol-4-yl)cyclopropyl)-1H-pyrazole-4-carboxylic acid 1-(6-(3-Isopropoxyphenyl)pyridin-2-yl)-5-(trifluoromethyl)-1H-pyrazole-4-carboxylic acid 5-(2,2-Difluorocyclopropyl)-1-(3'-((R)-2-propylpiperidine-1-carbonyl)-[1,1'-biphenyl]-3-yl)-1H-pyrazole-4-carboxylic acid 1-(3'-((S)-1-Cyclohexylethoxy)-[1,1'-biphenyl]-3-yl)-5-((1R,2R)-2-(1-methyl-1H-1,2,3-triazol-4-yl)cyclopropyl)-1H-pyrazole-4-carboxylate, Sodium salt Barium 1-(3'-((S)-1-Cyclohexylethoxy)-[1,1'-biphenyl]-3-yl)-5-((1R,2R)-2-(1-methyl-1H-1,2,3-triazol-4-yl)cyclopropyl)-1H-pyrazole-4-carboxylate hydroxide Calcium 1-(3'-((S)-1-Cyclohexylethoxy)-[1,1'-biphenyl]-3-yl)-5-((1R,2R)-2-(1-methyl-1H-1,2,3-triazol-4-yl)cyclopropyl)-1H-pyrazole-4-carboxylate hydroxide 1-(3'-((S)-1-Cyclohexylethoxy)-2'-methyl-[1,1'-biphenyl]-3-yl)-5-(trans-2-(1-methyl-1H-1,2,3-triazol-4-yl)cyclopropyl)-1H-pyrazole-4-carboxylic acid 1-(3'-(Cyclohexylmethoxy)-2'-methyl-[1,1'-biphenyl]-3-yl)-5-(trans-2-(1-methyl-1H-1,2,3-triazol-4-yl)cyclopropyl)-1H-pyrazole-4-carboxylic acid 1-(3'-((S)-1-Cycloheptylethoxy)-[1,1'-biphenyl]-3-yl)-5-((1R,2R)-2-(1-methyl-1H-1,2,3-triazol-4-yl)cyclopropyl)-1H-pyrazole-4-carboxylic acid 1-(3'-((R)-1-Cycloheptylethoxy)-[1,1'-biphenyl]-3-yl)-5-((1R,2R)-2-(1-methyl-1H-1,2,3-triazol-4-yl)cyclopropyl)-1H-pyrazole-4-carboxylic acid 1-(3'-((S)-1-Cyclohexylethoxy)-[1,1'-biphenyl]-3-yl)-5-(trans-2-(1-methyl-1H-1,2,3-triazol-4-yl)cyclopropyl)-1H-pyrazole-4-carboxylic acid 1-(3'-((S)-1-Cyclohexylethoxy)-[1,1'-biphenyl]-3-yl)-5-(trans-2-(1-ethyl-1H-1,2,3-triazol-4-yl)cyclopropyl)-1H-pyrazole-4-carboxylic acid 1-(3'-((S)-1-Cyclohexylethoxy)-[1,1'-biphenyl]-3-yl)-5-(trans-2-(1-(oxetan-3-yl)-1H-1,2,3-triazol-4-yl)cyclopropyl)-1H-pyrazole-4-carboxylic acid 5-(trans-2-(1-Cyclobutyl-1H-1,2,3-triazol-4-yl)cyclopropyl)-1-(3'-((S)-1-cyclohexylethoxy)-[1,1'-biphenyl]-3-yl)-1H-pyrazole-4-carboxylic acid 1-(3'-((S)-1-Cyclohexylethoxy)-[1,1'-biphenyl]-3-yl)-5-(trans-2-(1-cyclopropyl-1H-1,2,3-triazol-4-yl)cyclopropyl)-1H-pyrazole-4-carboxylic acid 5-(trans-2-(1-(1-(tert-Butoxycarbonyl)azetidin-3-yl)-1H-1,2,3-triazol-4-yl)cyclopropyl)-1-(3'-((S)-1-cyclohexylethoxy)-[1,1'-biphenyl]-3-yl)-1H-pyrazole-4-carboxylic acid 5-(trans-2-(1-(1-(tert-Butoxycarbonyl)piperidin-4-yl)-1H-1,2,3-triazol-4-yl)cyclopropyl)-1-(3'-((S)-1-cyclohexylethoxy)-[1,1'-biphenyl]-3-yl)-1H-pyrazole-4-carboxylic acid 1-(3'-((S)-1-Cyclohexylethoxy)-[1,1'-biphenyl]-3-yl)-5-(trans-2-(1-(1-methylpiperidin-4-yl)-1H-1,2,3-triazol-4-yl)cyclopropyl)-1H-pyrazole-4-carboxylic acid 1-(3'-((S)-1-Cyclohexylethoxy)-[1,1'-biphenyl]-3-yl)-5-(trans-2-(1-(tetrahydro-2H-pyran-4-yl)-1H-1,2,3-triazol-4-yl)cyclopropyl)-1H-pyrazole-4-carboxylic acid 5-(trans-2-(1-Cyclohexyl-1H-1,2,3-triazol-4-yl)cyclopropyl)-1-(3'-((S)-1-cyclohexylethoxy)-[1,1'-biphenyl]-3-yl)-1H-pyrazole-4-carboxylic acid 5-(trans-2-(1-(Azetidin-3-yl)-1H-1,2,3-triazol-4-yl)cyclopropyl)-1-(3'-((S)-1-cyclohexylethoxy)-[1,1'-biphenyl]-3-yl)-1H-pyrazole-4-carboxylic acid 1-(3'-((S)-1-cyclohexylethoxy)-[1,1'-biphenyl]-3-yl)-5-(trans-2-(1-(piperidin-4-yl)-1H-1,2,3-triazol-4-yl)cyclopropyl)-1H-pyrazole-4-carboxylic acid 5-(trans-2-(1-Benzyl-1H-1,2,3-triazol-4-yl)cyclopropyl)-1-(3'-((S)-1-cyclohexylethoxy)-[1,1'-biphenyl]-3-yl)-1H-pyrazole-4-carboxylic acid 1-(3'-((S)-1-Cyclohexylethoxy)-[1,1'-biphenyl]-3-yl)-5-(trans-2-(1-(2-(dimethylamino)ethyl)-1H-1,2,3-triazol-4-yl)cyclopropyl)-1H-pyrazole-4-carboxylic acid 1-(3'-((S)-1-Cyclohexylethoxy)-[1,1'-biphenyl]-3-yl)-5-(trans-2-(1-(2,2,2-trifluoroethyl)-1H-1,2,3-triazol-4-yl)cyclopropyl)-1H-pyrazole-4-carboxylic acid 1-(3'-((S)-1-Cyclohexylethoxy)-[1,1'-biphenyl]-3-yl)-5-(trans-2-(1-(2-hydroxyethyl)-1H-1,2,3-triazol-4-yl)cyclopropyl)-1H-pyrazole-4-carboxylic acid 1-(3'-((S)-1-Cyclohexylethoxy)-[1,1'-biphenyl]-3-yl)-5-(trans-2-(1-isopropyl-1H-1,2,3-triazol-4-yl)cyclopropyl)-1H-pyrazole-4-carboxylic acid 1-(3'-((S)-1-Cyclohexylethoxy)-[1,1'-biphenyl]-3-yl)-5-((1,2-trans)-2-(1-phenyl-1H-1,2,3-triazol-4-yl)cyclopropyl)-1H-pyrazole-4-carboxylic acid 5-(trans-2-(1H-1,2,3-Triazol-4-yl)cyclopropyl)-1-(3'-((S)-1-cyclohexylethoxy)-[1,1'-biphenyl]-3-yl)-1H-pyrazole-4-carboxylic acid 1-(3'-((S)-1-Cyclohexylethoxy)-[1,1'-biphenyl]-3-yl)-5-(trans-2-(1-(1-methylazetidin-3-yl)-1H-1,2,3-triazol-4-yl)cyclopropyl)-1H-pyrazole-4-carboxylic acid 1-(3'-((S)-1-Cyclohexylethoxy)-[1,1'-biphenyl]-3-yl)-5-((1R,2R)-2-(1-(tetrahydro-2H-pyran-4-yl)-1H-1,2,3-triazol-4-yl)cyclopropyl)-1H-pyrazole-4-carboxylic acid 1-(3'-((S)-1-Cyclohexylethoxy)-[1,1'-biphenyl]-3-yl)-5-((1S,2S)-2-(1-(tetrahydro-2H-pyran-4-yl)-1H-1,2,3-triazol-4-yl)cyclopropyl)-1H-pyrazole-4-carboxylic acid 1-(3'-((S)-1-Cyclohexylethoxy)-[1,1'-biphenyl]-3-yl)-5-((1R,2R)-2-(1-(2,2,2-trifluoroethyl)-1H-1,2,3-triazol-4-yl)cyclopropyl)-1H-pyrazole-4-carboxylic acid 1-(3'-((S)-1-Cyclohexylethoxy)-[1,1'-biphenyl]-3-yl)-5-((1R,2R)-2-(1-cyclopropyl-1H-1,2,3-triazol-4-yl)cyclopropyl)-1H-pyrazole-4-carboxylic acid 5-((1R,2R)-2-(1H-1,2,3-Triazol-4-yl)cyclopropyl)-1-(3'-((S)-1-cyclohexylethoxy)-[1,1'-biphenyl]-3-yl)-1H-pyrazole-4-carboxylic acid 5-((1S,2S)-2-(1H-1,2,3-Triazol-4-yl)cyclopropyl)-1-(3'-((S)-1-cyclohexylethoxy)-[1,1'-biphenyl]-3-yl)-1H-pyrazole-4-carboxylic acid 1-(3'-((S)-1-cyclohexylethoxy)-[1,1'-biphenyl]-3-yl)-5-(cis-2-(1-methyl-1H-1,2,3-triazol-4-yl)cyclopropyl)-1H-pyrazole-4-carboxylic acid 1-(3'-((S)-1-Cyclohexylethoxy)-[1,1'-biphenyl]-3-yl)-5-(trans-2-(3-hydroxypropyl)cyclopropyl)-1H-pyrazole-4-carboxylic acid 1-(3'-((S)-1-cyclohexylethoxy)-[1,1'-biphenyl]-3-yl)-5-(trans-2-(1-methyl-1H-pyrazol-4-yl)cyclopropyl)-1H-pyrazole-4-carboxylic acid 1-(3'-((S)-1-cyclohexylethoxy)-2'-fluoro-[1,1'-biphenyl]-3-yl)-5-((1R,2R)-2-(1-methyl-1H-1,2,3-triazol-4-yl)cyclopropyl)-1H-pyrazole-4-carboxylic acid Ethyl 1-(3'-((S)-1-cyclohexylethoxy)-[1,1'-biphenyl]-3-yl)-5-((1R,2R)-2-(1-methyl-1H-1,2,3-triazol-4-yl)cyclopropyl)-1H-pyrazole-4-carboxylate 2-Oxotetrahydrofuran-3-yl 1-(3'-((S)-1-cyclohexylethoxy)-[1,1'-biphenyl]-3-yl)-5-((1R,2R)-2-(1-methyl-1H-1,2,3-triazol-4-yl)cyclopropyl)-1H-pyrazole-4-carboxylate 2-Hydroxyethyl 1-(3'-((S)-1-cyclohexylethoxy)-[1,1'-biphenyl]-3-yl)-5-((1R,2R)-2-(1-methyl-1H-1,2,3-triazol-4-yl)cyclopropyl)-1H-pyrazole-4-carboxylate 2-Morpholinoethyl 1-(3'-((S)-1-cyclohexylethoxy)-[1,1'-biphenyl]-3-yl)-5-((1R,2R)-2-(1-methyl-1H-1,2,3-triazol-4-yl)cyclopropyl)-1H-pyrazole-4-carboxylate (Pivaloyloxy)methyl 1-(3'-((S)-1-cyclohexylethoxy)-[1,1'-biphenyl]-3-yl)-5-((1R,2R)-2-(1-methyl-1H-1,2,3-triazol-4-yl)cyclopropyl)-1H-pyrazole-4-carboxylate Acetoxymethyl 1-(3'-((S)-1-cyclohexylethoxy)-[1,1'-biphenyl]-3-yl)-5-((1R,2R)-2-(1-methyl-1H-1,2,3-triazol-4-yl)cyclopropyl)-1H-pyrazole-4-carboxylate (Benzoyloxy)methyl 1-(3'-((S)-1-cyclohexylethoxy)-[1,1'-biphenyl]-3-yl)-5-((1R,2R)-2-(1-methyl-1H-1,2,3-triazol-4-yl)cyclopropyl)-1H-pyrazole-4-carboxylate ((tert-Butoxycarbonyl)oxy)methyl 1-(3'-((S)-1-cyclohexylethoxy)-[1,1'-biphenyl]-3-yl)-5-((1R,2R)-2-(1-methyl-1H-1,2,3-triazol-4-yl)cyclopropyl)-1H-pyrazole-4-carboxylate rac-1-(3'-((E)-2-Cyclohexylvinyl)-[1,1'-biphenyl]-3-yl)-5-(trans-2-(1-methyl-1H-1,2,3-triazol-4-yl)cyclopropyl)-1H-pyrazole-4-carboxylic acid rac-1-(3'-(2-Cyclohexylethyl)-[1,1'-biphenyl]-3-yl)-5-(-2-(1-methyl-1H-1,2,3-triazol-4-yl)cyclopropyl)-1H-pyrazole-4-carboxylic acid 1-(3'-((S)-1-cyclohexylethoxy)-[1,1'-biphenyl]-3-yl)-5-((1R,2R)-2-(3-methylisoxazol-5-yl)cyclopropyl)-1H-pyrazole-4-carboxylic acid 1-(3'-((R) or (S)-2-Cyclohexylpropyl)-[1,1'-biphenyl]-3-yl)-5-((1R,2R)-2-(1-methyl-1H-1,2,3-triazol-4-yl)cyclopropyl)-1H-pyrazole-4-carboxylic acid 1-(3'-((R) or (S)-2-Cyclohexylpropyl)-[1,1'-biphenyl]-3-yl)-5-((1R,2R)-2-(1-methyl-1H-1,2,3-triazol-4-yl)cyclopropyl)-1H-pyrazole-4-carboxylic acid 1-(2'-fluoro-3'-((R)-2-propylpiperidine-1-carbonyl)-[1,1'-biphenyl]-3-yl)-5-(trans-2-(3-methylisoxazol-5-yl)cyclopropyl)-1H-pyrazole-4-carboxylic acid Methyl 1-(3'-((3-ethyl-2,3-dihydrobenzo[f][1,4]oxazepin-4(5H)-yl)methyl)-[1,1'-biphenyl]-3-yl)-5-((1,2-trans)-2-(1-methyl-1H-1,2,3-triazol-4-yl)cyclopropyl)-1H-pyrazole-4-carboxylate 1-(3'-(((S)-3-Ethyl-2,3-dihydrobenzo[f][1,4]oxazepin-4(5H)-yl)methyl)-[1,1'-biphenyl]-3-yl)-5-((1R,2R)-2-(1-methyl-1H-1,2,3-triazol-4-yl)cyclopropyl)-1H-pyrazole-4-carboxylic acid 1-(3'-(((R)-3-Ethyl-2,3-dihydrobenzo[f][1,4]oxazepin-4(5H)-yl)methyl)-[1,1'-biphenyl]-3-yl)-5-((1R,2R)-2-(1-methyl-1H-1,2,3-triazol-4-yl)cyclopropyl)-1H-pyrazole-4-carboxylic acid 1-(3'-(((S)-5-Ethyl-2,3-dihydrobenzo[f][1,4]oxazepin-4(5H)-yl)methyl)-[1,1'-biphenyl]-3-yl)-5-((1R,2R)-2-(1-methyl-1H-1,2,3-triazol-4-yl)cyclopropyl)-1H-pyrazole-4-carboxylic acid (isomer 2)

1-(3'-(((S)-5-Ethyl-2,3-dihydrobenzo[f][1,4]oxazepin-4(5H)-yl)methyl)-[1,1'-biphenyl]-3-yl)-5-((1R,2R)-2-(1-methyl-1H-1,2,3-triazol-4-yl)cyclopropyl)-1H-pyrazole-4-carboxylic acid (isomer 1)

1-(3'-((5-Ethyl-2,3-dihydrobenzo[f][1,4]oxazepin-4(5H)-yl)methyl)-[1,1'-biphenyl]-3-yl)-5-((1,2-trans)-2-(1-methyl-1H-1,2,3-triazol-4-yl)cyclopropyl)-1H-pyrazole-4-carboxylic acid 1-(3'-(((S)-5-Ethyl-2,2-dimethyl-2,3-dihydrobenzo[f][1,4]oxazepin-4(5H)-yl)methyl)-[1,1'-biphenyl]-3-yl)-5-((1R,2R)-2-(1-methyl-1H-1,2,3-triazol-4-yl)cyclopropyl)-1H-pyrazole-4-carboxylic acid (isomer 1)

1-(3'-(((R)-5-Ethyl-2,2-dimethyl-2,3-dihydrobenzo[f][1,4]oxazepin-4(5H)-yl)methyl)-[1,1'-biphenyl]-3-yl)-5-((1R,2R)-2-(1-methyl-1H-1,2,3-triazol-4-yl)cyclopropyl)-1H-pyrazole-4-carboxylic acid (isomer 2)

1-(3'-((4,4-dimethyl-4,5-dihydro-1H-benzo[c]azepin-2(3H)-yl)methyl)-[1,1'-biphenyl]-3-yl)-5-((1,2-trans)-2-(1-methyl-1H-1,2,3-triazol-4-yl)cyclopropyl)-1H-pyrazole-4-carboxylic acid 1-(3'-((1-Ethyl-2,3-dihydro-1H-benzo[e][1,4]diazepin-4 (5H)-yl)methyl)-[1,1'-biphenyl]-3-yl)-5-((1,2-trans)-2-(1-methyl-1H-1,2,3-triazol-4-yl)cyclopropyl)-1H-pyrazole-4-carboxylic acid 1-(3'-(((R)-2-ethyl-2,3-dihydrobenzo[f][1,4]oxazepin-4 (5H)-yl)methyl)-[1,1'-biphenyl]-3-yl)-5-((1,2-trans)-2-(1-isopropyl-1H-1,2,3-triazol-4-yl)cyclopropyl)-1H-pyrazole-4-carboxylic acid 1-(3'-(((R)-2-ethyl-2,3-dihydrobenzo[f][1,4]oxazepin-4 (5H)-yl)methyl)-[1,1'-biphenyl]-3-yl)-5-(2-(1-methyl-1H-1,2,3-triazol-4-yl)cyclopropyl)-1H-pyrazole-4-carboxylic acid 1-(3'-(((R)-4-Methyl-1,1-dioxido-4,5-dihydrobenzo[f][1,2]thiazepin-2(3H)-yl)methyl)-[1,1'-biphenyl]-3-yl)-5-((1R,2R)-2-(1-methyl-1H-1,2,3-triazol-4-yl)cyclopropyl)-1H-pyrazole-4-carboxylic acid 1-(3'-(((S)-8-Bromo-4-methyl-1,1-dioxido-4,5-dihydrobenzo[f][1,2]thiazepin-2(3H)-yl)methyl)-2'-fluoro-[1,1'-biphenyl]-3-yl)-5-((1R,2R)-2-(1-methyl-1H-1,2,3-triazol-4-yl)cyclopropyl)-1H-pyrazole-4-carboxylic acid 1-(3'-(((S)-4-methyl-1,1-dioxido-4,5-dihydrobenzo[f][1,2]thiazepin-2(3H)-yl)methyl)-[1,1'-biphenyl]-3-yl)-5-((1R,2R)-2-(1-methyl-1H-1,2,3-triazol-4-yl)cyclopropyl)-1H-pyrazole-4-carboxylic acid 1-(3'-(((S)-4-methyl-1,1-dioxido-4,5-dihydrobenzo[f][1,2]thiazepin-2(3H)-yl)methyl)-[1,1'-biphenyl]-3-yl)-5-((1S,2S)-2-(1-methyl-1H-1,2,3-triazol-4-yl)cyclopropyl)-1H-pyrazole-4-carboxylic acid 1-(3'-(((S)-8-bromo-4-methyl-1,1-dioxido-4,5-dihydrobenzo[f][1,2]thiazepin-2(3H)-yl)methyl)-[1,1'-biphenyl]-3-yl)-5-((1R,2R)-2-(1-methyl-1H-1,2,3-triazol-4-yl)cyclopropyl)-1H-pyrazole-4-carboxylic acid (isomer 1)

1-(3'-(((R)-8-bromo-4-methyl-1,1-dioxido-4,5-dihydrobenzo[f][1,2]thiazepin-2(3H)-yl)methyl)-[1,1'-biphenyl]-3-yl)-5-((1R,2R)-2-(1-methyl-1H-1,2,3-triazol-4-yl)cyclopropyl)-1H-pyrazole-4-carboxylic acid (isomer 2)

1-(3'-(((S)-4-methyl-1,1-dioxido-4,5-dihydrobenzo[f][1,2]thiazepin-2(3H)-yl)methyl)-[1,1'-biphenyl]-3-yl)-5-((1,2-trans)-2-(1-methyl-1H-1,2,3-triazol-4-yl)cyclopropyl)-1H-pyrazole-4-carboxylic acid 1-(3'-(((R)-4-methyl-1,1-dioxido-4,5-dihydrobenzo[f][1,2]thiazepin-2(3H)-yl)methyl)-[1,1'-biphenyl]-3-yl)-5-((1,2-trans)-2-(1-methyl-1H-1,2,3-triazol-4-yl)cyclopropyl)-1H-pyrazole-4-carboxylic acid 1-(3'-(((R)-4-ethyl-1,1-dioxido-3,4-dihydro-2H-pyrido[2,3-b][1,4,5]oxathiazepin-2-yl)methyl)-[1,1'-biphenyl]-3-yl)-5-((1,2-trans)-2-(1-methyl-1H-1,2,3-triazol-4-yl)cyclopropyl)-1H-pyrazole-4-carboxylic acid 1-(3'-((5-Ethyl-1,1-dioxido-4,5-dihydrobenzo[f][1,2,5]thiadiazepin-2(3H)-yl)methyl)-[1,1'-biphenyl]-3-yl)-5-((1R,2R)-2-(1-methyl-1H-1,2,3-triazol-4-yl)cyclopropyl)-1H-pyrazole-4-carboxylic acid 1-(3'-((5-methyl-1,1-dioxido-4,5-dihydrobenzo[f][1,2,5]thiadiazepin-2(3H)-yl)methyl)-[1,1'-biphenyl]-3-yl)-5-((1,2-trans)-2-(1-methyl-1H-1,2,3-triazol-4-yl)cyclopropyl)-1H-pyrazole-4-carboxylic acid 1-(3'-((2,2-Dimethyl-2,3-dihydrobenzo[f][1,4]oxazepin-4 (5H)-yl)sulfonyl)-[1,1'-biphenyl]-3-yl)-5-((1,2-trans)-2-(1-methyl-1H-1,2,3-triazol-4-yl)cyclopropyl)-1H-pyrazole-4-carboxylic acid 5-((1,2-trans)-2-(1-Methyl-1H-1,2,3-triazol-4-yl)cyclopropyl)-1-(3'-((2-propylpiperidin-1-yl)sulfonyl)-[1,1'-biphenyl]-3-yl)-1H-pyrazole-4-carboxylic acid 5-((1,2-trans)-2-(1-Methyl-1H-1,2,3-triazol-4-yl)cyclopropyl)-1-(3'-(piperidin-1-ylsulfonyl)-[1,1'-biphenyl]-3-yl)-1H-pyrazole-4-carboxylic acid 5-((1,2-trans)-2-(1-Methyl-1H-1,2,3-triazol-4-yl)cyclopropyl)-1-(3'-((tetrahydro-2H-thiopyran-3-yl)methoxy)-[1,1'-biphenyl]-3-yl)-1H-pyrazole-4-carboxylic acid 1-(3'-((4,4-Difluorocyclohexyl)methoxy)-[1,1'-biphenyl]-3-yl)-5-((1,2-trans)-2-(1-methyl-1H-1,2,3-triazol-4-yl)cyclopropyl)-1H-pyrazole-4-carboxylic acid 5-((1,2-trans)-2-(1-Methyl-1H-1,2,3-triazol-4-yl)cyclopropyl)-1-(3'-(((1r,4R)-4-(trifluoromethyl)cyclohexyl)methoxy)-[1,1'-biphenyl]-3-yl)-1H-pyrazole-4-carboxylic acid 5-((1,2-trans)-2-(1-Methyl-1H-1,2,3-triazol-4-yl)cyclopropyl)-1-(3'-((3-(trifluoromethyl)cyclohexyl)methoxy)-[1,1'-biphenyl]-3-yl)-1H-pyrazole-4-carboxylic acid 5-((1,2-trans)-2-(1-Methyl-1H-1,2,3-triazol-4-yl)cyclopropyl)-1-(3'-((2-(trifluoromethyl)cyclohexyl)methoxy)-[1,1'-biphenyl]-3-yl)-1H-pyrazole-4-carboxylic acid 5-((1,2-trans)-2-(1-Methyl-1H-1,2,3-triazol-4-yl)cyclopropyl)-1-(3'-((tetrahydro-2H-thiopyran-4-yl)methoxy)-[1,1'-biphenyl]-3-yl)-1H-pyrazole-4-carboxylic acid 1-(3'-((4-Ethylcyclohexyl)methoxy)-[1,1'-biphenyl]-3-yl)-5-((1,2-trans)-2-(1-methyl-1H-1,2,3-triazol-4-yl)cyclopropyl)-1H-pyrazole-4-carboxylic acid 1-(3'-(Cyclohexylmethoxy)-[1,1'-biphenyl]-3-yl)-5-(2-(1-methyl-1H-1,2,3-triazol-4-yl)ethyl)-1H-pyrazole-4-carboxylic acid 1-(3'-(Cyclohexylmethoxy)-2'-fluoro-[1,1'-biphenyl]-3-yl)-5-((1,2-trans)-2-(1-methyl-1H-1,2,3-triazol-4-yl)cyclopropyl)-1H-pyrazole-4-carboxylic acid 5-Cyclopropyl-1-(3'-(4-(1-methyl-1H-1,2,3-triazol-4-yl)butoxy)-[1,1'-biphenyl]-3-yl)-1H-pyrazole-4-carboxylic acid 5-(2-(1-Methyl-1H-1,2,3-triazol-4-yl)cyclopropyl)-1-(5-methyl-3'-((R)-2-propylpiperidine-1-carbonyl)-[1,1'-biphenyl]-3-yl)-1H-pyrazole-4-carboxylic acid 5-((1R,2R)-2-(1-Methyl-1H-1,2,3-triazol-4-yl)cyclopropyl)-1-(5-methyl-3'-((R)-2-propylpiperidine-1-carbonyl)-[1,1'-biphenyl]-3-yl)-1H-pyrazole-4-carboxylic acid (isomer 1)

5-((1S,2S)-2-(1-methyl-1H-1,2,3-triazol-4-yl)cyclopropyl)-1-(5-methyl-3'-((R)-2-propylpiperidine-1-carbonyl)-[1,1'-biphenyl]-3-yl)-1H-pyrazole-4-carboxylic acid (isomer 2)

1-(3'-(1-Cyclohexyl-2,2,2-trifluoroethoxy)-[1,1'-biphenyl]-3-yl)-5-((1,2-trans)-2-(1-methyl-1H-1,2,3-triazol-4-yl)cyclopropyl)-1H-pyrazole-4-carboxylic acid 1-(3'-(dimethylcarbamoyl)-[1,1'-biphenyl]-3-yl)-5-(2-(1-ethyl-1H-1,2,3-triazol-4-yl)cyclopropyl)-1H-pyrazole-4-carboxylic acid 5-(2-(5-Methylisoxazol-4-yl)cyclopropyl)-1-(3'-((R)-2-propylpiperidine-1-carbonyl)-[1,1'-biphenyl]-3-yl)-1H-pyrazole-4-carboxylic acid 1-(5-Chloro-3'-((R)-2-propylpiperidine-1-carbonyl)-[1,1'-biphenyl]-3-yl)-5-(2-(1-methyl-1H-1,2,3-triazol-4-yl)cyclopropyl)-1H-pyrazole-4-carboxylic acid compound with 2,2,2-trifluoroacetic acid (1:1)

1-(3'-((1-Cyclohexylpropan-2-yl)oxy)-[1,1'-biphenyl]-3-yl)-5-cyclopropyl-1H-pyrazole-4-carboxylic acid 1-(3'-((R)-1-Cyclohexylethoxy)-[1,1'-biphenyl]-3-yl)-5-((1R,2R)-2-(1-methyl-1H-1,2,3-triazol-4-yl)cyclopropyl)-1H-pyrazole-4-carboxylic acid 1-(3'-(1-Cyclohexylethoxy)-[1,1'-biphenyl]-3-yl)-5-((1R,2R)-2-(1-methyl-1H-1,2,3-triazol-4-yl)cyclopropyl)-1H-pyrazole-4-carboxylic acid 1-(3'-(Cyclohexylmethoxy)-[1,1'-biphenyl]-3-yl)-5-(2-(1-methyl-1H-1,2,3-triazol-4-yl)cyclopropyl)-1H-pyrazole-4-carboxylic acid 1-(3'-(1-Cyclohexylethoxy)-[1,1'-biphenyl]-3-yl)-5-((1S,2S)-2-(1-methyl-1H-1,2,3-triazol-4-yl)cyclopropyl)-1H-pyrazole-4-carboxylic acid 1-(3'-(tert-Butoxy)-[1,1'-biphenyl]-3-yl)-5-(2-(1-methyl-1H-1,2,3-triazol-4-yl)cyclopropyl)-1H-pyrazole-4-carboxylic acid 1-(3'-((1-(tert-Butoxycarbonyl)piperidin-4-yl)methoxy)-[1,1'-biphenyl]-3-yl)-5-(2-(1-methyl-1H-1,2,3-triazol-4-yl)cyclopropyl)-1H-pyrazole-4-carboxylic acid 1-(3'-(2-Cyclohexyl-4-methoxybutoxy)-[1,1'-biphenyl]-3-yl)-5-(2-(1-methyl-1H-1,2,3-triazol-4-yl)cyclopropyl)-1H-pyrazole-4-carboxylic acid 5-(2-(1-Methyl-1H-1,2,3-triazol-4-yl)cyclopropyl)-1-(3'-((tetrahydro-2H-pyran-3-yl)methoxy)-[1,1'-biphenyl]-3-yl)-1H-pyrazole-4-carboxylic acid 1-(3'-(2-Cyclohexylethoxy)-[1,1'-biphenyl]-3-yl)-5-(2-(1-methyl-1H-1,2,3-triazol-4-yl)cyclopropyl)-1H-pyrazole-4-carboxylic acid 1-(3'-(Cyclohexylmethoxy)-[1,1'-biphenyl]-3-yl)-5-((1R,2R)-2-(1-methyl-1H-1,2,3-triazol-4-yl)cyclopropyl)-1H-pyrazole-4-carboxylic acid 1-(3'-((2-Cyclohexylpentyl)oxy)-[1,1'-biphenyl]-3-yl)-5-(2-(1-methyl-1H-1,2,3-triazol-4-yl)cyclopropyl)-1H-pyrazole-4-carboxylic acid 1-(3'-(2-Cyclohexylpropoxy)-[1,1'-biphenyl]-3-yl)-5-(2-(1-methyl-1H-1,2,3-triazol-4-yl)cyclopropyl)-1H-pyrazole-4-carboxylic acid 5-(2-(1-Methyl-1H-1,2,3-triazol-4-yl)cyclopropyl)-1-(3'-((tetrahydro-2H-pyran-4-yl)methoxy)-[1,1'-biphenyl]-3-yl)-1H-pyrazole-4-carboxylic acid 5-(2-(1-Methyl-1H-1,2,3-triazol-4-yl)cyclopropyl)-1-(3'-((tetrahydro-2H-pyran-2-yl)methoxy)-[1,1'-biphenyl]-3-yl)-1H-pyrazole-4-carboxylic acid 1-(3'-(((1R,4S)-4-Methoxycyclohexyl)methoxy)-[1,1'-biphenyl]-3-yl)-5-((1,2-trans)-2-(1-methyl-1H-1,2,3-triazol-4-yl)cyclopropyl)-1H-pyrazole-4-carboxylic acid 1-(3'-((2-Methoxycyclohexyl)methoxy)-[1,1'-biphenyl]-3-yl)-5-((1,2-trans)-2-(1-methyl-1H-1,2,3-triazol-4-yl)cyclopropyl)-1H-pyrazole-4-carboxylic acid 1-(3'-((3-Methoxycyclohexyl)methoxy)-[1,1'-biphenyl]-3-yl)-5-((1,2-trans)-2-(1-methyl-1H-1,2,3-triazol-4-yl)cyclopropyl)-1H-pyrazole-4-carboxylic acid 1-(3'-((Cyclohexylmethyl)thio)-[1,1'-biphenyl]-3-yl)-5-(2-(1-methyl-1H-1,2,3-triazol-4-yl)cyclopropyl)-1H-pyrazole-4-carboxylic acid 5-((1,2-trans)-2-(1-Methyl-1H-1,2,3-triazol-4-yl)cyclopropyl)-1-(3'-((R)-1-((1R,4R)-4-(trifluoromethyl)cyclohexyl)ethoxy)-[1,1'-biphenyl]-3-yl)-1H-pyrazole-4-carboxylic acid 1-(2'-Fluoro-3'-isopropoxy-[1,1'-biphenyl]-3-yl)-5-(2-(1-methyl-1H-1,2,3-triazol-4-yl)cyclopropyl)-1H-pyrazole-4-carboxylic acid 1-(3'-(1-Ethoxy-2-methylpropyl)-[1,1'-biphenyl]-3-yl)-5-(2-(1-methyl-1H-1,2,3-triazol-4-yl)cyclopropyl)-1H-pyrazole-4-carboxylic acid 1-(3'-(Cyclopentyl(methoxy)methyl)-[1,1'-biphenyl]-3-yl)-5-(2-(1-methyl-1H-1,2,3-triazol-4-yl)cyclopropyl)-1H-pyrazole-4-carboxylic acid 1-(3'-(1-Methoxy-2-methylpropyl)-[1,1'-biphenyl]-3-yl)-5-(2-(1-methyl-1H-1,2,3-triazol-4-yl)cyclopropyl)-1H-pyrazole-4-carboxylic acid 1-(3'-((4-Chlorocyclohexyl)methoxy)-[1,1'-biphenyl]-3-yl)-5-((1,2-trans)-2-(1-methyl-1H-1,2,3-triazol-4-yl)cyclopropyl)-1H-pyrazole-4-carboxylic acid 1-(3'-((2-chlorocyclohexyl)methoxy)-[1,1'-biphenyl]-3-yl)-5-((1,2-trans)-2-(1-methyl-1H-1,2,3-triazol-4-yl)cyclopropyl)-1H-pyrazole-4-carboxylic acid 1-(3'-((3-chlorocyclohexyl)methoxy)-[1,1'-biphenyl]-3-yl)-5-((1,2-trans)-2-(1-methyl-1H-1,2,3-triazol-4-yl)cyclopropyl)-1H-pyrazole-4-carboxylic acid 1-(3'-(cyclohexylmethoxy)-[1,1'-biphenyl]-3-yl)-3-methyl-5-((1,2-trans)-2-(1-methyl-1H-1,2,3-triazol-4-yl)cyclopropyl)-1H-pyrazole-4-carboxylic acid 1-(5-cyano-3'-(cyclohexylmethoxy)-[1,1'-biphenyl]-3-yl)-5-(2-(1-methyl-1H-1,2,3-triazol-4-yl)cyclopropyl)-1H-pyrazole-4-carboxylic acid 1-(3'-(cyclohexylmethoxy)-[1,1'-biphenyl]-3-yl)-5-(2-(1-methyl-1H-imidazol-4-yl)cyclopropyl)-1H-pyrazole-4-carboxylic acid 1-(3'-(1-cyclohexylethoxy)-[1,1'-biphenyl]-3-yl)-5-((1S,2S)-2-(1-methyl-1H-1,2,3-triazol-4-yl)cyclopropyl)-1H-pyrazole-4-carboxylic acid 1-(3'-(1-cyclohexylethoxy)-[1,1'-biphenyl]-3-yl)-5-((1,2-trans)-2-(1-ethyl-1H-1,2,3-triazol-4-yl)cyclopropyl)-1H-pyrazole-4-carboxylic acid 1-(3'-(1-cyclohexylethoxy)-5-methoxy-[1,1'-biphenyl]-3-yl)-5-((1S,2S)-2-(1-ethyl-1H-1,2,3-triazol-4-yl)cyclopropyl)-1H-pyrazole-4-carboxylic acid 1-(3'-(1-cyclohexylethoxy)-5-methoxy-[1,1'-biphenyl]-3-yl)-5-((1,2-trans)-2-(1-ethyl-1H-1,2,3-triazol-4-yl)cyclopropyl)-1H-pyrazole-4-carboxylic acid 1-(3'-(1-cyclohexylethoxy)-[1,1'-biphenyl]-3-yl)-5-((1,2-trans)-2-(1-isopropyl-1H-1,2,3-triazol-4-yl)cyclopropyl)-1H-pyrazole-4-carboxylic acid 5-(2-(1-Methyl-1H-1,2,3-triazol-4-yl)cyclopropyl)-1-(6-(3-((R)-2-propylpiperidine-1-carbonyl)phenyl)pyridin-2-yl)-1H-pyrazole-4-carboxylic acid 5-(2-(1-Methyl-1H-1,2,3-triazol-4-yl)cyclopropyl)-1-(3-(5-((R)-2-propylpiperidine-1-carbonyl)pyridin-3-yl)phenyl)-1H-pyrazole-4-carboxylic acid 1-(3'-Fluoro-5'-((R)-2-propylpiperidine-1-carbonyl)-[1,1'-biphenyl]-3-yl)-5-(2-(1-methyl-1H-1,2,3-triazol-4-yl)cyclopropyl)-1H-pyrazole-4-carboxylic acid 5-((1,2-trans)-2-(1-methyl-1H-1,2,3-triazol-4-yl)cyclopropyl)-1-(3'-((R)-2-propylpiperidine-1-carbonyl)-[1,1'-biphenyl]-3-yl)-1H-pyrazole-4-carboxylic acid 5-((1,2-trans)-2-(1-Isopropyl-1H-1,2,3-triazol-4-yl)cyclopropyl)-1-(3'-((R)-2-propylpiperidine-1-carbonyl)-[1,1'-biphenyl]-3-yl)-1H-pyrazole-4-carboxylic acid 5-((1,2-trans)-2-(1-Ethyl-1H-1,2,3-triazol-4-yl)cyclopropyl)-1-(3'-((R)-2-propylpiperidine-1-carbonyl)-[1,1'-biphenyl]-3-yl)-1H-pyrazole-4-carboxylic acid 3-Methyl-5-(2-(1-methyl-1H-1,2,3-triazol-4-yl)cyclopropyl)-1-(3'-((R)-2-propylpiperidine-1-carbonyl)-[1,1'-biphenyl]-3-yl)-1H-pyrazole-4-carboxylic acid (R)-5-Cyclopropyl-3-methyl-1-(3'-(2-propylpiperidine-1-carbonyl)-[1,1'-biphenyl]-3-yl)-1H-pyrazole-4-carboxylic acid 1-(6-(3-(6,6-Dimethyl-5,6-dihydrocyclopenta[c]pyrazol-1(4H)-yl)phenyl)pyridin-2-yl)-5-(trifluoromethyl)-1H-pyrazole-4-carboxylic acid 5-Cyclopropyl-1-(3'-(6-methyl-6-propyl-5,6-dihydrocyclopenta[c]pyrazol-1(4H)-yl)-[1,1'-biphenyl]-3-yl)-1H-pyrazole-4-carboxylic acid 1-(3'-(6-Butyl-5,6-dihydrocyclopenta[c]pyrazol-1(4H)-yl)-[1,1'-biphenyl]-3-yl)-5-cyclopropyl-1H-pyrazole-4-carboxylic acid 5-Cyclopropyl-1-(3'-(6-cyclopropyl-5,6-dihydrocyclopenta[c]pyrazol-1(4H)-yl)-[1,1'-biphenyl]-3-yl)-1H-pyrazole-4-carboxylic acid 1-(3'-(6,6-Dimethyl-5,6-dihydrocyclopenta[c]pyrazol-1(4H)-yl)-[1,1'-biphenyl]-3-yl)-5-((1S,2S)-2-(1-methyl-1H-1,2,3-triazol-4-yl)cyclopropyl)-1H-pyrazole-4-carboxylic acid 5-Cyclopropyl-1-(3'-(5-ethyl-1,2,4-oxadiazol-3-yl)-[1,1'-biphenyl]-3-yl)-1H-pyrazole-4-carboxylic acid 5-Cyclopropyl-1-(3'-(5-methyl-1,3,4-oxadiazol-2-yl)-[1,1'-biphenyl]-3-yl)-1H-pyrazole-4-carboxylic acid 5-Cyclopropyl-1-(3'-(5-methyl-1,2,4-oxadiazol-3-yl)-[1,1'-biphenyl]-3-yl)-1H-pyrazole-4-carboxylic acid 1-(3'-(6,6-Dimethyl-5,6-dihydrocyclopenta[c]pyrazol-1(4H)-yl)-[1,1'-biphenyl]-3-yl)-5-(2-(1-methyl-1H-1,2,3-triazol-4-yl)cyclopropyl)-1H-pyrazole-4-carboxylic acid 5-(2-(1-Methyl-1H-pyrazol-4-yl)cyclopropyl)-1-(3'-((R)-2-propylpiperidine-1-carbonyl)-[1,1'-biphenyl]-3-yl)-1H-pyrazole-4-carboxylic acid 1-(2'-Fluoro-3'-((R)-2-propylpiperidine-1-carbonyl)-[1,1'-biphenyl]-3-yl)-5-(2-(1-methyl-1H-pyrazol-4-yl)cyclopropyl)-1H-pyrazole-4-carboxylic acid 1-(3'-(2-Cyclohexylacetyl)-[1,1'-biphenyl]-3-yl)-5-(2-(1-methyl-1H-1,2,3-triazol-4-yl)cyclopropyl)-1H-pyrazole-4-carboxylic acid 1-(3'-(2-Cyclohexyl-1-methoxyethyl)-[1,1'-biphenyl]-3-yl)-5-(2-(1-methyl-1H-1,2,3-triazol-4-yl)cyclopropyl)-1H-pyrazole-4-carboxylic acid 1-(3'-(2-Cyclohexyl-1-hydroxyethyl)-[1,1'-biphenyl]-3-yl)-5-(2-(1-methyl-1H-1,2,3-triazol-4-yl)cyclopropyl)-1H-pyrazole-4-carboxylic acid 1-(3'-((1-Cyclohexylpropan-2-yl)oxy)-[1,1'-biphenyl]-3-yl)-5-(2-(1-methyl-1H-1,2,3-triazol-4-yl)cyclopropyl)-1H-pyrazole-4-carboxylic acid 1-(3'-(1-Cyclohexylethoxy)-[1,1'-biphenyl]-3-yl)-5-(2-(1-methyl-1H-1,2,3-triazol-4-yl)cyclopropyl)-1H-pyrazole-4-carboxylic acid 1-(3'-(Cyclohexyl(hydroxy)methyl)-[1,1'-biphenyl]-3-yl)-5-(2-(1-methyl-1H-1,2,3-triazol-4-yl)cyclopropyl)-1H-pyrazole-4-carboxylic acid 1-(3'-(Benzyloxy)-[1,1'-biphenyl]-3-yl)-5-(2-(1-methyl-1H-1,2,3-triazol-4-yl)cyclopropyl)-1H-pyrazole-4-carboxylic acid 1-(3'-((2-Fluorobenzyl)oxy)-[1,1'-biphenyl]-3-yl)-5-(2-(1-methyl-1H-1,2,3-triazol-4-yl)cyclopropyl)-1H-pyrazole-4-carboxylic acid 1-(3'-((4-Fluorobenzyl)oxy)-[1,1'-biphenyl]-3-yl)-5-(2-(1-methyl-1H-1,2,3-triazol-4-yl)cyclopropyl)-1H-pyrazole-4-carboxylic acid 1-(3'-((3-Fluorobenzyl)oxy)-[1,1'-biphenyl]-3-yl)-5-(2-(1-methyl-1H-1,2,3-triazol-4-yl)cyclopropyl)-1H-pyrazole-4-carboxylic acid 1-(3'-(3,3-Dimethylbutoxy)-[1,1'-biphenyl]-3-yl)-5-(2-(1-methyl-1H-1,2,3-triazol-4-yl)cyclopropyl)-1H-pyrazole-4-carboxylic acid 5-((1,2-trans)-2-(1-Methyl-1H-1,2,3-triazol-4-yl)cyclopropyl)-1-(3'-(neopentyloxy)-[1,1'-biphenyl]-3-yl)-1H-pyrazole-4-carboxylic acid 5-(2-(1-Methyl-1H-1,2,3-triazol-4-yl)cyclopropyl)-1-(3'-(1-(tetrahydro-2H-pyran-4-yl)ethoxy)-[1,1'-biphenyl]-3-yl)-1H-pyrazole-4-carboxylic acid 1-(3'-(1-Cyclopentylethoxy)-[1,1'-biphenyl]-3-yl)-5-(2-(1-methyl-1H-1,2,3-triazol-4-yl)cyclopropyl)-1H-pyrazole-4-carboxylic acid 1-(3'-(Cyclohexyloxy)-[1,1'-biphenyl]-3-yl)-5-(2-(1-methyl-1H-1,2,3-triazol-4-yl)cyclopropyl)-1H-pyrazole-4-carboxylic acid 1-(3'-(1-Cycloheptylethoxy)-[1,1'-biphenyl]-3-yl)-5-((1,2-trans)-2-(1-methyl-1H-1,2,3-triazol-4-yl)cyclopropyl)-1H-pyrazole-4-carboxylic acid 1-(3'-(1-Cyclopropylethoxy)-[1,1'-biphenyl]-3-yl)-5-(2-(1-methyl-1H-1,2,3-triazol-4-yl)cyclopropyl)-1H-pyrazole-4-carboxylic acid 1-(3'-((1-(tert-Butoxycarbonyl)piperidin-3-yl)oxy)-[1,1'-biphenyl]-3-yl)-5-(2-(1-methyl-1H-1,2,3-triazol-4-yl)cyclopropyl)-1H-pyrazole-4-carboxylic acid 1-(3'-(2-Cyclohexylethyl)-[1,1'-biphenyl]-3-yl)-5-(2-(1-methyl-1H-1,2,3-triazol-4-yl)cyclopropyl)-1H-pyrazole-4-carboxylic acid 1-(2'-Fluoro-3'-((tetrahydro-2H-pyran-4-yl)oxy)-[1,1'-biphenyl]-3-yl)-5-(2-(1-methyl-1H-1,2,3-triazol-4-yl)cyclopropyl)-1H-pyrazole-4-carboxylic acid 5-(2-(1-Methyl-1H-1,2,3-triazol-4-yl)cyclopropyl)-1-(3'-(1-phenylethoxy)-[1,1'-biphenyl]-3-yl)-1H-pyrazole-4-carboxylic acid 5-((1,2-trans)-2-(1-Methyl-1H-1,2,3-triazol-4-yl)cyclopropyl)-1-(3'-(pyrimidin-5-ylmethoxy)-[1,1'-biphenyl]-3-yl)-1H-pyrazole-4-carboxylic acid 1-(3'-([1,1'-Biphenyl]-4-ylmethoxy)-[1,1'-biphenyl]-3-yl)-5-((1,2-trans)-2-(1-methyl-1H-1,2,3-triazol-4-yl)cyclopropyl)-1H-pyrazole-4-carboxylic acid 1-(3'-([1,1'-Biphenyl]-3-ylmethoxy)-[1,1'-biphenyl]-3-yl)-5-((1,2-trans)-2-(1-methyl-1H-1,2,3-triazol-4-yl)cyclopropyl)-1H-pyrazole-4-carboxylic acid 1-(3'-(1-([1,1'-Biphenyl]-3-yl)ethoxy)-[1,1'-biphenyl]-3-yl)-5-((1,2-trans)-2-(1-methyl-1H-1,2,3-triazol-4-yl)cyclopropyl)-1H-pyrazole-4-carboxylic acid 1-(3'-(1-([1,1'-Biphenyl]-4-yl)ethoxy)-[1,1'-biphenyl]-3-yl)-5-((1,2-trans)-2-(1-methyl-1H-1,2,3-triazol-4-yl)cyclopropyl)-1H-pyrazole-4-carboxylic acid 1-(4'-(1-Cyclohexylethoxy)-[1,1'-biphenyl]-3-yl)-5-((1,2-trans)-2-(1-methyl-1H-1,2,3-triazol-4-yl)cyclopropyl)-1H-pyrazole-4-carboxylic acid 1-(3'-(1-Cyclohexylpropoxy)-[1,1'-biphenyl]-3-yl)-5-((1,2-trans)-2-(1-methyl-1H-1,2,3-triazol-4-yl)cyclopropyl)-1H-pyrazole-4-carboxylic acid 1-(3'-(Cyclohexanecarbonyl)-[1,1'-biphenyl]-3-yl)-5-(2-(1-methyl-1H-1,2,3-triazol-4-yl)cyclopropyl)-1H-pyrazole-4-carboxylic acid 1-(3'-(Cyclohexyl(methoxy)methyl)-[1,1'-biphenyl]-3-yl)-5-(2-(1-methyl-1H-1,2,3-triazol-4-yl)cyclopropyl)-1H-pyrazole-4-carboxylic acid 1-(3'-(2-cyclohexylethoxy)-[1,1'-biphenyl]-3-yl)-5-(trans-2-(1-methyl-1H-1,2,3-triazol-4-yl)cyclopropyl)-1H-pyrazole-4-carboxylic acid 1-(3-(5-(Cyclohexylmethoxy)pyridin-3-yl)phenyl)-5-(trans-2-(1-methyl-1H-1,2,3-triazol-4-yl)cyclopropyl)-1H-pyrazole-4-carboxylic acid 5-(trans-2-(1-methyl-1H-1,2,3-triazol-4-yl)cyclopropyl)-1-(3'-(piperidin-1-ylmethyl)-[1,1'-biphenyl]-3-yl)-1H-pyrazole-4-carboxylic acid 5-(trans-2-(1-Methyl-1H-1,2,3-triazol-4-yl)cyclopropyl)-1-(3'-(morpholinomethyl)-[1,1'-biphenyl]-3-yl)-1H-pyrazole-4-carboxylic acid 1-(6-(3-(1-Cyclohexylethoxy)phenyl)pyridin-2-yl)-5-(trans-2-(1-methyl-1H-1,2,3-triazol-4-yl)cyclopropyl)-1H-pyrazole-4-carboxylic acid 1-(3'-(6,6-Dimethyl-5,6-dihydrocyclopenta[c]pyrazol-1(4H)-yl)-[1,1'-biphenyl]-3-yl)-5-(trifluoromethyl)-1H-pyrazole-4-carboxylic acid 1-(6-(3-(6,6-Dimethyl-5,6-dihydrocyclopenta[c]pyrazol-1(4H)-yl)phenyl)pyridin-2-yl)-5-(trans-2-(1-methyl-1H-1,2,3-triazol-4-yl)cyclopropyl)-1H-pyrazole-4-carboxylic acid 1-(3'-((4-Ethyl-4,5-dihydro-1H-benzo[c]azepin-2(3H)-yl)methyl)-[1,1'-biphenyl]-3-yl)-5-(trans-2-(1-methyl-1H-1,2,3-triazol-4-yl)cyclopropyl)-1H-pyrazole-4-carboxylic acid 1-(3'-(((R)-2-Ethyl-2,3-dihydrobenzo[f][1,4]oxazepin-4 (5H)-yl)methyl)-[1,1'-biphenyl]-3-yl)-5-(trans-2-(1-methyl-1H-1,2,3-triazol-4-yl)cyclopropyl)-1H-pyrazole-4-carboxylic acid 1-(3'-((2,2-Dimethyl-2,3-dihydrobenzo[f][1,4]oxazepin-4 (5H)-yl)methyl)-[1,1'-biphenyl]-3-yl)-5-(trans-2-(1-methyl-1H-1,2,3-triazol-4-yl)cyclopropyl)-1H-pyrazole-4-carboxylic acid 1-(3'-(((R)-4-Ethyl-1,1-dioxido-3,4-dihydro-2H-benzo[b][1,4,5]oxathiazepin-2-yl)methyl)-[1,1'-biphenyl]-3-yl)-5-(trans-2-(1-methyl-1H-1,2,3-triazol-4-yl)cyclopropyl)-1H-pyrazole-4-carboxylic acid 1-(3'-((2,3-Dihydrobenzo[f][1,4]oxazepin-4(5H)-yl)methyl)-[1,1'-biphenyl]-3-yl)-5-(trans-2-(1-methyl-1H-1,2,3-triazol-4-yl)cyclopropyl)-1H-pyrazole-4-carboxylic acid 1-(3'-((R)-2-Ethyl-2,3,4,5-tetrahydrobenzo[f][1,4]oxazepine-4-carbonyl)-[1,1'-biphenyl]-3-yl)-5-(trans-(2-(1-methyl-1H-1,2,3-triazol-4-yl)cyclopropyl)-1H-pyrazole-4-carboxylic acid 1-(2'-Fluoro-3'-(piperidine-1-carbonyl)-[1,1'-biphenyl]-3-yl)-5-(trans-2-(1-methyl-1H-1,2,3-triazol-4-yl)cyclopropyl)-1H-pyrazole-4-carboxylic acid 1-(2'-Fluoro-3'-(3,3-dimethylpiperidine-1-carbonyl)-[1,1'-biphenyl]-3-yl)-5-(trans-2-(1-methyl-1H-1,2,3-triazol-4-yl)cyclopropyl)-1H-pyrazole-4-carboxylic acid 1-(2'-Fluoro-3'-(azepane-1-carbonyl)-[1,1'-biphenyl]-3-yl)-5-(trans-2-(1-methyl-1H-1,2,3-triazol-4-yl)cyclopropyl)-1H-pyrazole-4-carboxylic acid 1-(3'-((2R,6S)-2,6-Dimethylpiperidine-1-carbonyl)-2'-fluoro-[1,1'-biphenyl]-3-yl)-5-(trans-2-(1-methyl-1H-1,2,3-triazol-4-yl)cyclopropyl)-1H-pyrazole-4-carboxylic acid 1-(3'-((2R,6S)-2,6-dimethylpiperidine-1-carbonyl)-2'-fluoro-[1,1'-biphenyl]-3-yl)-5-(trans-2-(1-methyl-1H-1,2,3-triazol-4-yl)cyclopropyl)-1H-pyrazole-4-carboxylic acid 1-(3'-(3,5-Dimethylpiperidine-1-carbonyl)-2'-fluoro-[1,1'-biphenyl]-3-yl)-5-(2-(1-methyl-1H-1,2,3-triazol-4-yl)cyclopropyl)-1H-pyrazole-4-carboxylic acid 1-(3'-(2-(Methoxymethyl)piperidine-1-carbonyl)-2'-fluoro-[1,1'-biphenyl]-3-yl)-5-(trans-2-(1-methyl-1H-1,2,3-triazol-4-yl)cyclopropyl)-1H-pyrazole-4-carboxylic acid 1-(3'-((Cyclopropylmethyl)carbamoyl)-2'-fluoro-[1,1'-biphenyl]-3-yl)-5-(trans-2-(1-methyl-1H-1,2,3-triazol-4-yl)cyclopropyl)-1H-pyrazole-4-carboxylic acid 1-(2'-Fluoro-3'(isobutyl(methyl)carbamoyl)-[1,1'-biphenyl]-3-yl)-5-(trans-2-(1-methyl-1H-1,2,3-triazol-4-yl)cyclopropyl)-1H-pyrazole-4-carboxylic acid 1-(3'-((S)-2-(Ethoxymethyl)pyrrolidine-1-carbonyl)-[1,1'-biphenyl]-3-yl)-5-(trans-2-(1-methyl-1H-1,2,3-triazol-4-yl)cyclopropyl)-1H-pyrazole-4-carboxylic acid 1-(3'-((R)-2-(Ethoxymethyl)pyrrolidine-1-carbonyl)-[1,1'-biphenyl]-3-yl)-5-(trans-2-(1-methyl-1H-1,2,3-triazol-4-yl)cyclopropyl)-1H-pyrazole-4-carboxylic acid 1-(3'-((R)-2-(Ethoxymethyl)pyrrolidine-1-carbonyl)-[1,1'-biphenyl]-3-yl)-5-(trans-2-(1-methyl-1H-1,2,3-triazol-4-yl)cyclopropyl)-1H-pyrazole-4-carboxylic acid In one embodiment, the invention is directed to compounds which are as follows.

1-(3'-((S)-1-Cyclohexylethoxy)-[1,1'-biphenyl]-3-yl)-5-((1R,2R)-2-(1-methyl-1H-1,2,3-triazol-4-yl)cyclopropyl)-1H-pyrazole-4-carboxylic acid.

1-(3'-((S)-1-Cycloheptylethoxy)-[1,1'-biphenyl]-3-yl)-5-((1R,2R)-2-(1-methyl-1H-1,2,3-triazol-4-yl)cyclopropyl)-1H-pyrazole-4-carboxylic acid.

1-(3'-((S)-1-Cyclohexylethoxy)-[1,1'-biphenyl]-3-yl)-5-((1R,2R)-2-(1-cyclopropyl-1H-1,2,3-triazol-4-yl)cyclopropyl)-1H-pyrazole-4-carboxylic acid.

1-(3'-(((S)-5-Ethyl-2,2-dimethyl-2,3-dihydrobenzo[f][1,4]oxazepin-4(5H)-yl)methyl)-[1,1'-biphenyl]-3-yl)-5-((1R,2R)-2-(1-methyl-1H-1,2,3-triazol-4-yl)cyclopropyl)-1H-pyrazole-4-carboxylic acid (isomer 1).

1-(3'-(((R)-5-Ethyl-2,2-dimethyl-2,3-dihydrobenzo[f][1,4]oxazepin-4(5H)-yl)methyl)-[1,1'-biphenyl]-3-yl)-5-((1R,2R)-2-(1-methyl-1H-1,2,3-triazol-4-yl)cyclopropyl)-1H-pyrazole-4-carboxylic acid (isomer 2).

1-(3'-(2-Cyclohexylethyl)-[1,1'-biphenyl]-3-yl)-5-(2-(1-methyl-1H-1,2,3-triazol-4-yl)cyclopropyl)-1H-pyrazole-4-carboxylic acid.

5-[(1R,2R)-2-(1-methyl-1H-1,2,3-triazol-4-yl)cyclopropyl]-1-(3-{3-[(2R)-2-propylpiperidine-1-carbonyl]phenyl}phenyl)-1H-pyrazole-4-carboxylic acid.

1-(3'-(((R)-8-bromo-4-methyl-1,1-dioxido-4,5-dihydrobenzo[f][1,2]thiazepin-2(3H)-yl)methyl)-[1,1'-biphenyl]-3-yl)-5-((1R,2R)-2-(1-methyl-1H-1,2,3-triazol-4-yl)cyclopropyl)-1H-pyrazole-4-carboxylic acid (isomer 2).

1-(3'-(6,6-Dimethyl-5,6-dihydrocyclopenta[c]pyrazol-(4H)-yl)-[1,1'-biphenyl]-3-yl)-5-((1S,2S)-2-(1-methyl-1H-1,2,3-triazol-4-yl)cyclopropyl)-1H-pyrazole-4-carboxylic acid.

Compound Preparation

The skilled artisan will appreciate that if a substituent described herein is not compatible with the synthetic methods described herein, the substituent may be protected with a suitable protecting group that is stable to the reaction conditions. The protecting group may be removed at a suitable point in the reaction sequence to provide a desired intermediate or target compound. Suitable protecting groups and the methods for protecting and de-protecting different substituents using such suitable protecting groups are well known to those skilled in the art; examples of which may be found in T. Greene and P. Wuts, *Protecting Groups in Chemical Synthesis* (3rd ed.), John Wiley & Sons, NY (1999). In some instances, a substituent may be specifically selected to be reactive under the reaction conditions used. Under these circumstances, the reaction conditions convert the selected substituent into another substituent that is either useful as an intermediate compound or is a desired substituent in a target compound.

The synthesis of the compounds of the general Formula (I) and pharmaceutically acceptable derivatives and salts thereof may be accomplished as outlined below in Schemes 1-12. In the following description, the groups are as defined above for compounds of Formula (I) unless otherwise indicated. Abbreviations are as defined in the Examples section. Starting materials are commercially available or are made from commercially available starting materials using methods known to those skilled in the art.

Scheme 1: Synthesis of Pyrazole Core

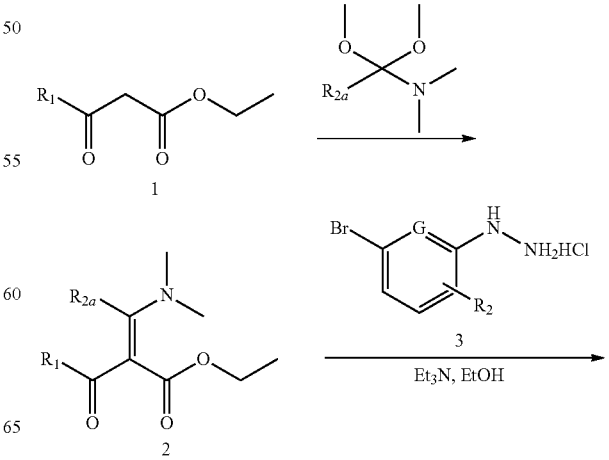

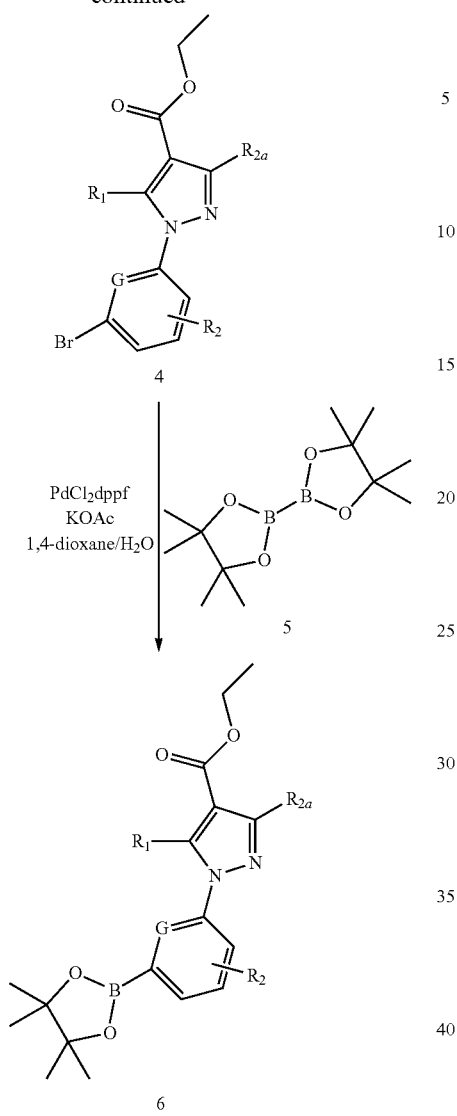

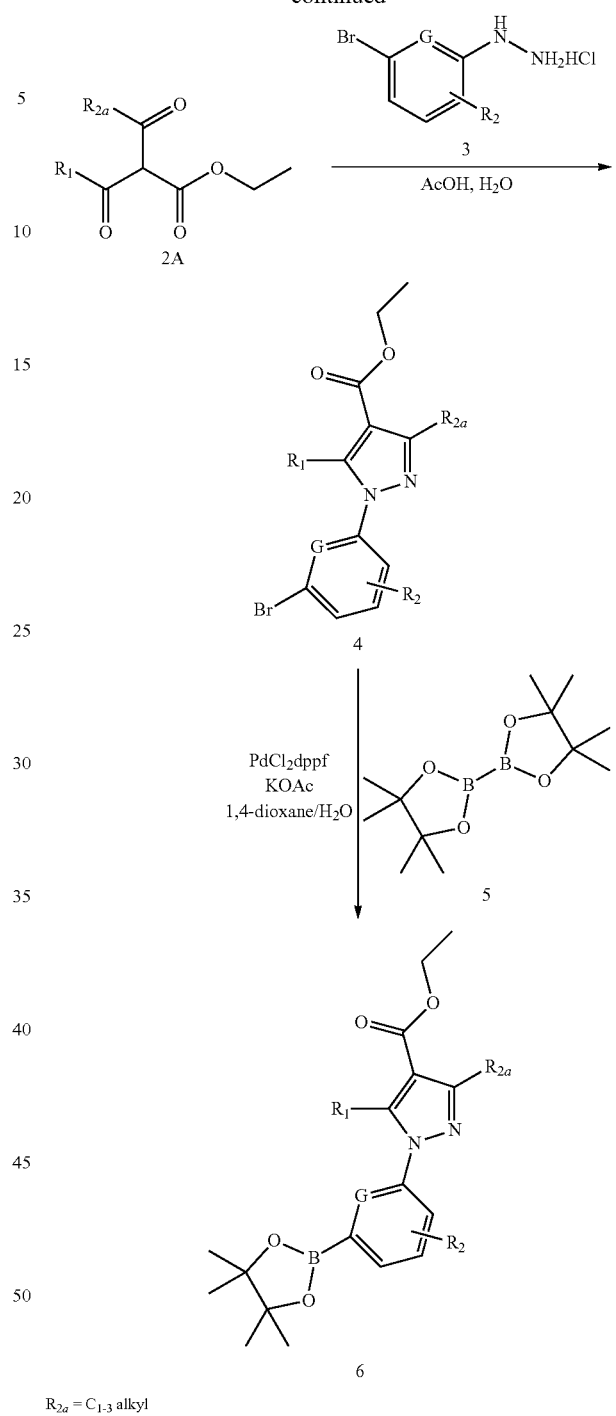

An appropriately substituted ethyl 3-oxyester (1) is stirred with a N,N-dimethylamide acetal at room temperature to provide a dimethylamino-methylene-oxoester intermediate (2). The ethyl 2-((dimethylamino)methylene)-3-oxoester (2) in an alcohol solvent, preferably ethanol is treated with the appropriately substituted bromo-aryl hydrazine (3) along with an amine base such as triethylamine or diisopropylethylamine, to provide the pyrazole intermediate (4). The pyrazole (4) in dioxane is treated with 4,4,4',4',5,5,5',5'-octamethyl-2,2'-bi(1,3,2-dioxaborolane) (5) in the presence of a palladium catalyst such as PdCl$_2$dppf and potassium acetate to give the boronic ester (6).

Scheme 1A: Alternate Synthesis of Pyrazole Core

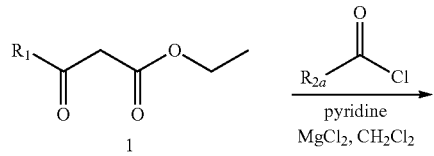

$R_{2a} = C_{1-3}$ alkyl

An appropriately substituted ethyl 3-oxyester (1) is treated with an alkyl acid chloride in methylene chloride along with MgCl$_2$ and pyridine to give intermediate (2A). The intermediate (2A) in acetic acid and water is treated with the appropriately substituted bromo-aryl hydrazine (3) to provide the pyrazole intermediate (4). The pyrazole (4) in dioxane is treated with 4,4,4',4',5,5,5',5'-octamethyl-2,2'-bi(1,3,2-dioxaborolane) (5) in the presence of a palladium catalyst such as PdCl$_2$dppf and potassium acetate to give the boronic ester (6).

Scheme 2: Synthesis of Amide Analogues

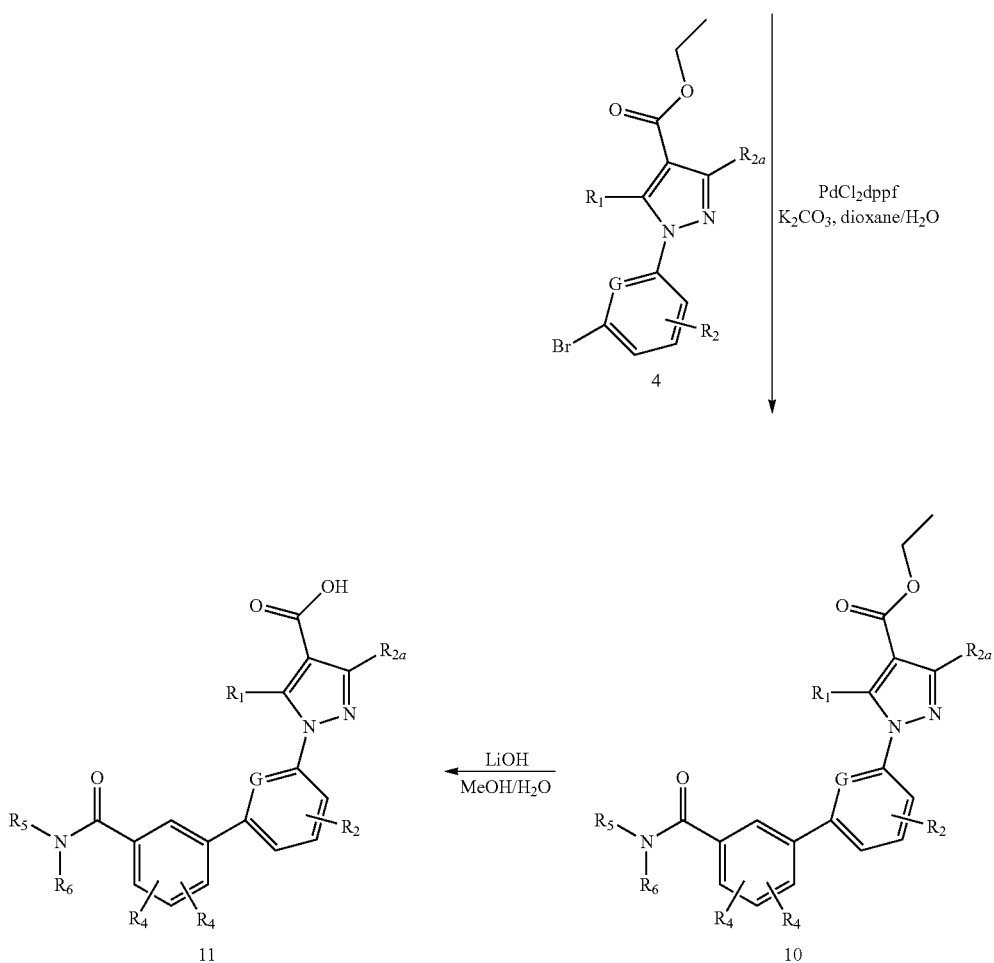

The substituted boronobenzoic acid (7) is dissolved in an appropriate solvent such as DCM, DMF or a mixture of DCM and DMF, and treated with a substituted amine (8) in the presence of a coupling agent like HATU or EDC and an amine base such as triethylamine, or diisopropylethylamine, to provide the boronobenzoic amide (9). The boronobenzoic amide (9) and the pyrazole bromide (4) is dissolved in a mixture of dioxane and water with an inorganic base, such as $K_2CO_3$, and treated with a catalytic amount of a palladium catalyst, such as $PdCl_2dppf$, to give the pyrazole amide ethyl ester (10). Base hydrolysis of the ethyl ester (10) with an inorganic base such as LiOH or NaOH in a mixture of an alcohol such as methanol or ethanol and water provides the pyrazole amide acid (11).

Scheme 3: Synthesis of Amide Analogues

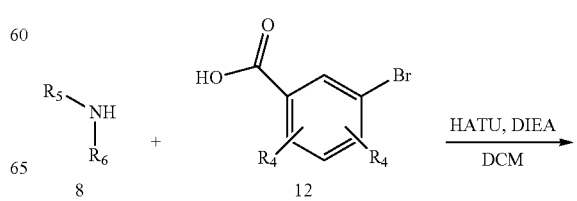

dium catalyst, such as PdCl₂dppf, to give the pyrazole amide ethyl ester (10). Base hydrolysis of the ethyl ester (10) with an inorganic base such as LiOH or NaOH in a mixture of an alcohol, such as methanol or ethanol, and water provides the pyrazole amide acid (11).

Scheme 4: Synthesis of Ether Analogues

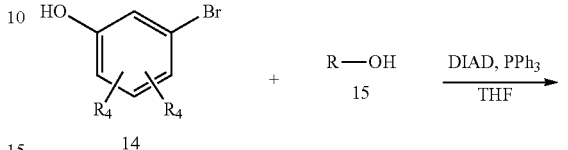

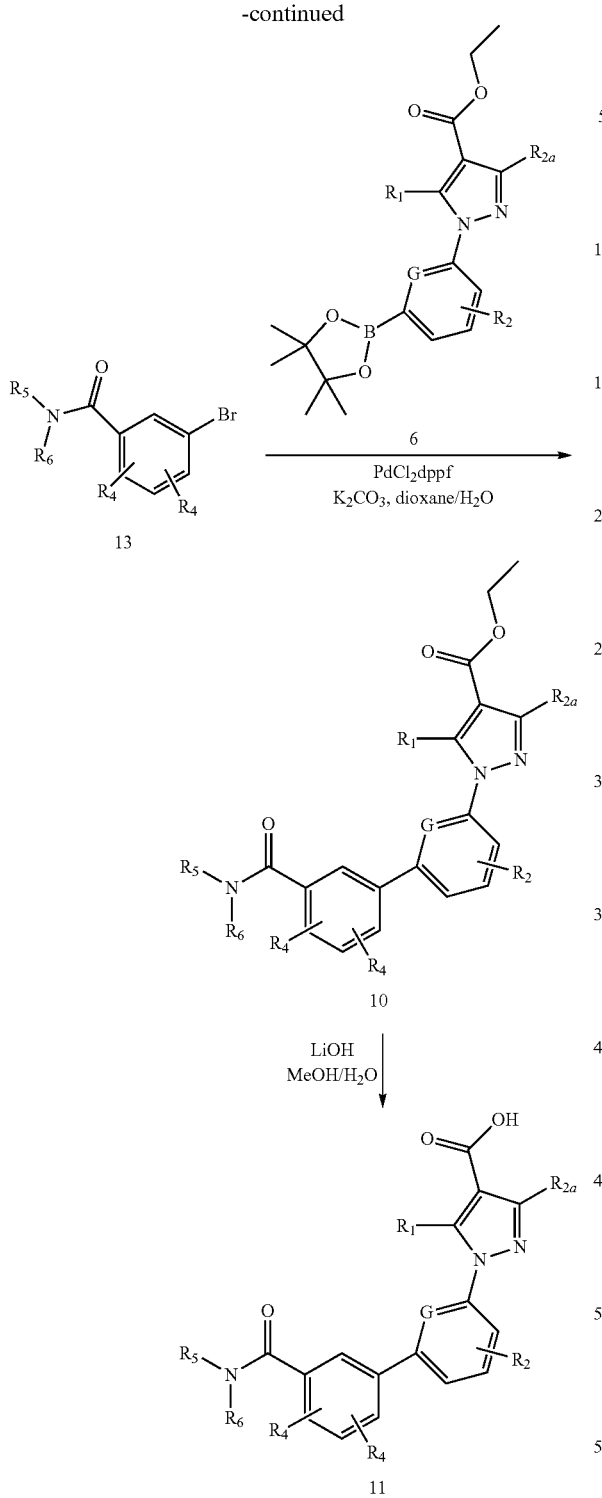

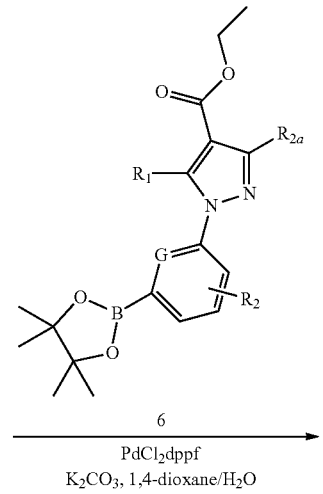

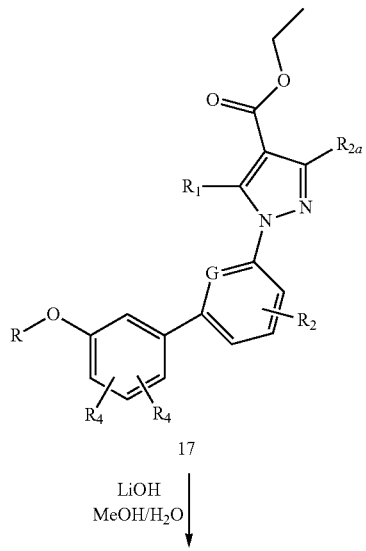

The substituted bromobenzoic acid (12) is dissolved in an appropriate solvent such as DCM, DMF or a mixture of DCM and DMF, and treated with a substituted amine (8) in the presence of a coupling agent like HATU or EDC and an amine base such as triethylamine or diisopropylethylamine, to provide the bromobenzoic amide (13). The bromobenzoic amide (13) and pyrazole boronic ester (6) is dissolved in a mixture of dioxane and water with an inorganic base, such as K₂CO₃, and treated with a catalytic amount of a palla- -continued

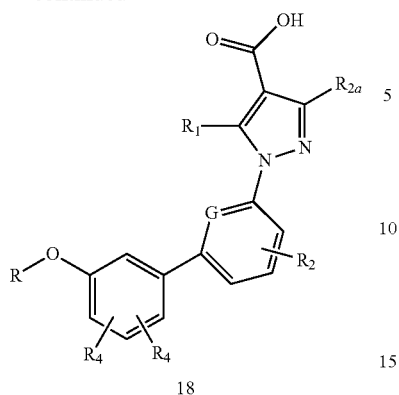

18

R = C$_{1-3}$alkyl, C$_{4-7}$heterocycloalkyl, C$_{3-7}$cycloalkyl; substituted as defined in claim 1

The bromophenyl alcohol (14) and an alkyl, cycloalkyl or heterocycloalkyl primary or secondary alcohol (15) is dissolved in an ethereal solvent like THF and treated with a diazodicarboxylate, such as DEAD or DIAD, in the presence of a trisubstituted phosphine, such as triphenylphosphine or tributylphosphine, to give the bromophenyl ether (16). The bromophenyl ether (16) is dissolved in a mixture of dioxane and water and treated with the pyrazole boronic ester (6) in the presence of an inorganic base, such as K$_2$CO$_3$ and a palladium catalyst such as PdCl$_2$dppf, to give the pyrazole ether ethyl ester (17). Base hydrolysis of the ethyl ester (17) with an inorganic base such as LiOH or NaOH in a mixture of an alcohol, such as methanol or ethanol, and water provides the pyrazole ether acid (18).

Scheme 5: Synthesis of Ether Analogues

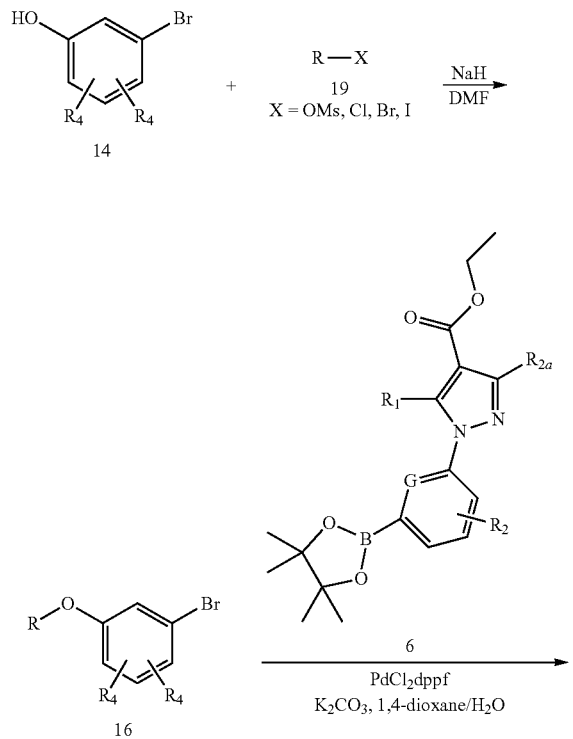

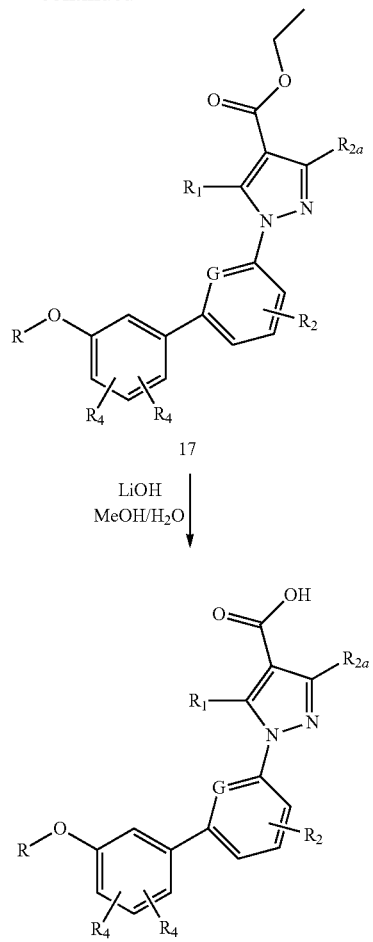

18

R = C$_{1-3}$alkyl, C$_{4-7}$heterocycloalkyl, C$_{3-7}$cycloalkyl; substituted as defined in claim 1

The bromophenyl alcohol (14) and an alkyl, cycloalkyl or heterocycloalkyl chloride, bromide, iodide or mesylate (19) is dissolved in an appropriate solvent, such as DMF, THF or dioxane and treated with a base, such as NaH to give the bromophenyl ether (16). The bromophenyl ether (16) is dissolved in a mixture of dioxane and water and treated with the pyrazole boronic ester (6) in the presence of an inorganic base, such as K$_2$CO$_3$ and a palladium catalyst such as PdCl$_2$dppf, to give the pyrazole ether ethyl ester (17). Base hydrolysis of the ethyl ester (17) with an inorganic base such as LiOH or NaOH in a mixture of an alcohol, such as methanol or ethanol, and water provides the pyrazole ether acid (18).

Scheme 6: Synthesis of Alkyl Alcohol Analogues

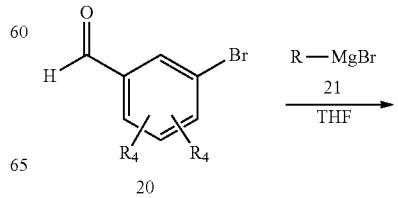

55
-continued

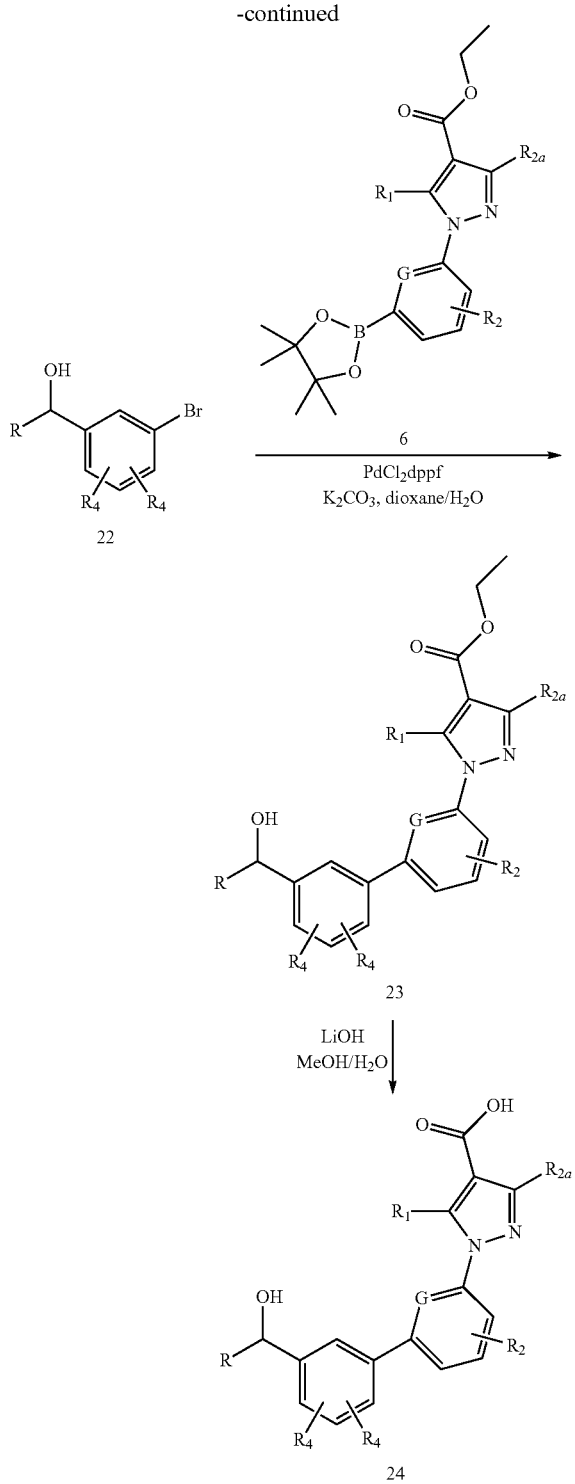

R = $C_{1-7}$alkyl, $C_{3-7}$cycloalkyl, $C_{4-7}$heterocycloalkyl, triazolyl; substituted as defined in claim 1

The bromophenyl aldehyde (20) is dissolved in an ethereal solvent such as diethyl ether or THF and treated with an alkyl, cycloalkyl, heterocycloalkyl or triazolyl Grignard reagent (21) to give the bromophenyl alcohol (22). The bromophenyl alcohol (22) is dissolved in a mixture of dioxane and water and treated with the pyrazole boronic ester (6) in the presence of an inorganic base, such as $K_2CO_3$

56 and a palladium catalyst such as $PdCl_2dppf$ to give the pyrazole alcohol ethyl ester (23). Base hydrolysis of the ethyl ester (23) with an inorganic base such as LiOH or NaOH in a mixture of an alcohol, such as methanol or ethanol, and water provides the pyrazole alcohol acid (24).

Scheme 7: Synthesis of Alkyl Ketone Analogues

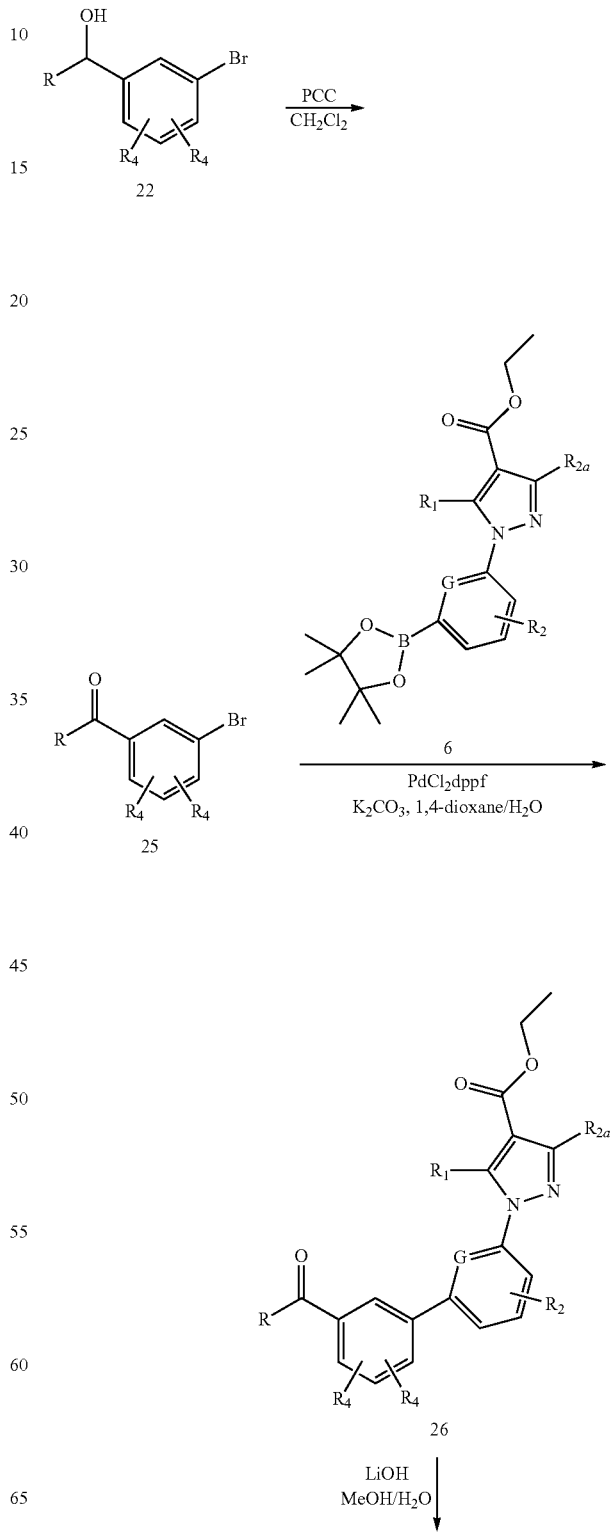

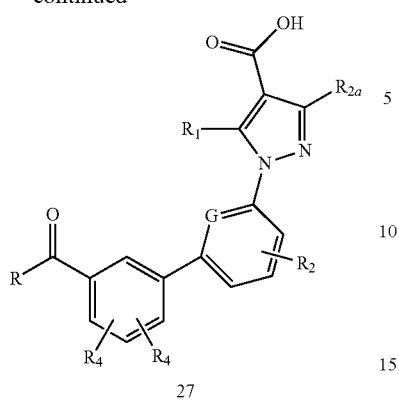

R = C$_{1-7}$alkyl, C$_{3-7}$cycloalkyl, C$_{4-7}$heterocycloalkyl, triazolyl; substituted as defined in claim 1

The bromophenyl alcohol (22) is oxidized to the corresponding bromophenyl ketone (25) using an appropriate oxidizing agent such as pyridium chlorochromate or pyridium dichromate in CH$_2$Cl$_2$. The bromophenyl ketone (25) is dissolved in a mixture of dioxane and water and treated with the pyrazole boronic ester (6) in the presence of an inorganic base, such as K$_2$CO$_3$ and a palladium catalyst such as PdCl$_2$dppf to give the pyrazole ketone ethyl ester (26). Base hydrolysis of the ethyl ester (26) with an inorganic base such as LiOH or NaOH in a mixture of an alcohol, such as methanol or ethanol, and water provides the pyrazole ketone acid (27).

Scheme 8: Synthesis of Alkyl Ether Analogues

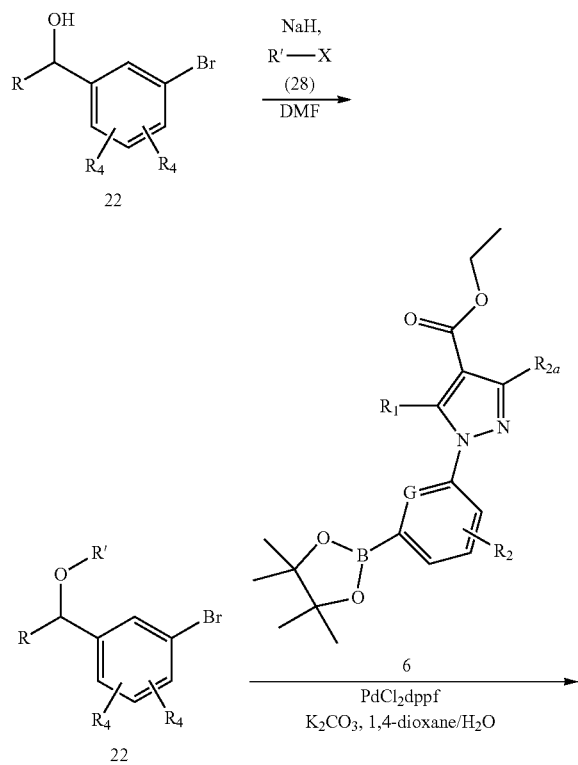

R = C$_{1-7}$alkyl, C$_{3-7}$cycloalkyl, C$_{4-7}$heterocycloalkyl, triazolyl; substituted as defined in claim 1
R' = C$_{1-5}$alkyl
X = Cl, Br, I, OMs The bromophenyl alcohol (22) is dissolved in THF, dioxane or DMF and treated with an alkyl chloride, bromide, iodide or mesylate (28) to provide the bromophenyl ether (29). The bromophenyl ether (29) is dissolved in a mixture of dioxane and water and treated with the pyrazole boronic ester (6) in the presence of an inorganic base, such as K$_2$CO$_3$ and a palladium catalyst such as PdCl$_2$dppf, to give the pyrazole ether ethyl ester (30). Base hydrolysis of the ethyl ester (30) with an inorganic base such as LiOH or NaOH in a mixture of an alcohol, such as methanol or ethanol, and water provides the pyrazole ether acid (31).

Scheme 9: Synthesis of Heteroacyclic Analogues-1
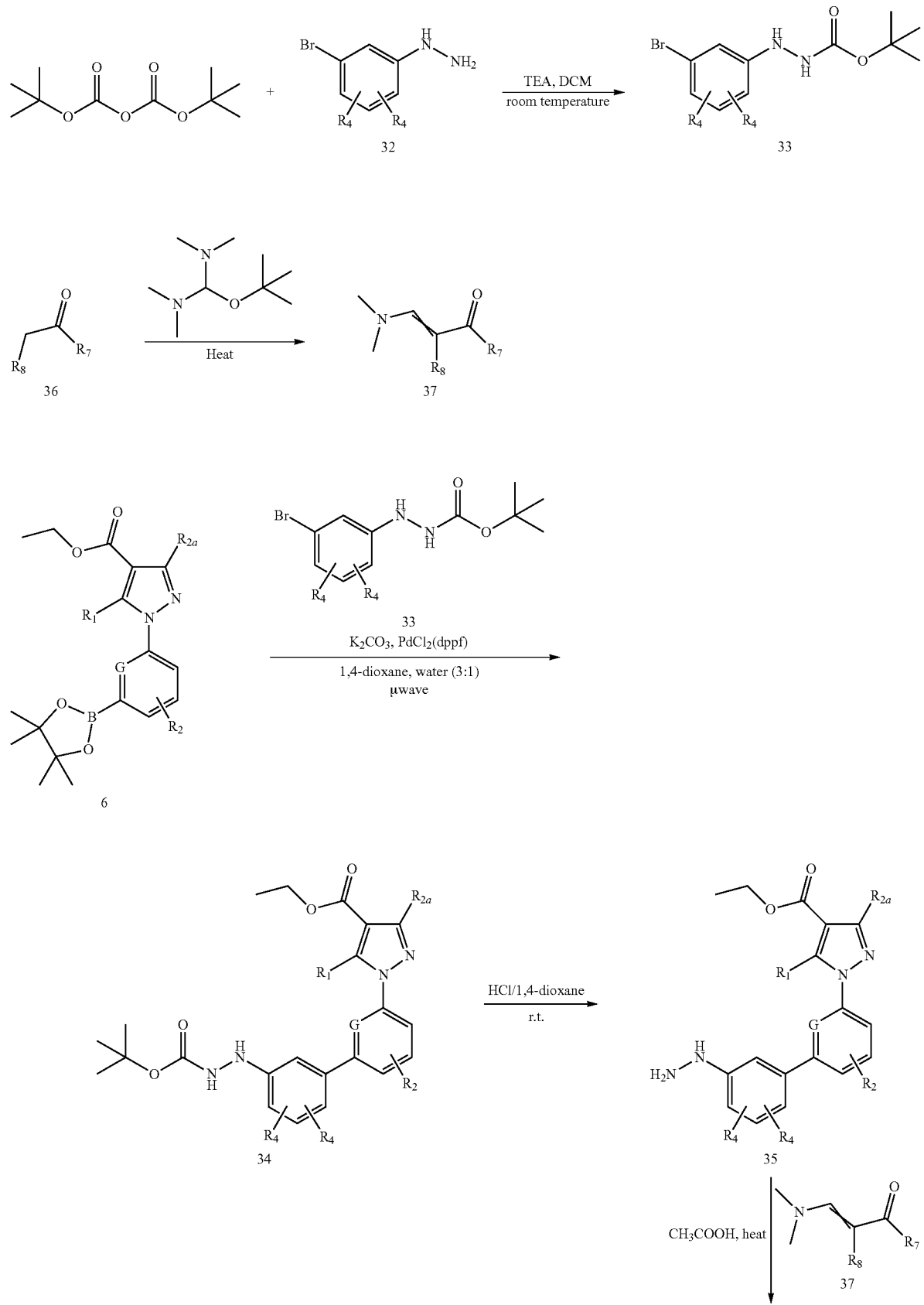

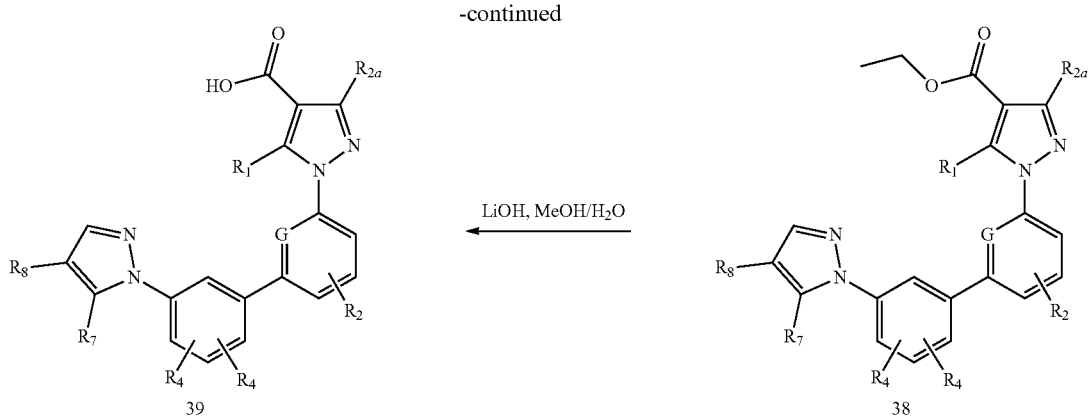

The bromophenyl hydrazine (32) is treated with di-tert-butyl dicarbonate in an appropriate solvent such as DCM, dioxane or t-butanol with a base such as triethyl amide or diisopropylethyl amine to give the protected bromophenyl hydrazine (34). The protected bromophenyl hydrazine (34) is dissolved in a mixture of dioxane and water and treated with the pyrazole boronic ester (6) in the presence of an inorganic base, such as K$_2$CO$_3$ and a palladium catalyst such as PdCl$_2$dppf, to give the protected hydrazine pyrazole ethyl ester (35). The protected hydrazine pyrazole methyl ester (34) is treated under acidic conditions such as HCl in dioxane or TFA in CH$_2$Cl$_2$ to give the hydrazine pyrazole ethyl ester (35). The ketone (36) is heated with 1-tert-butoxy-N,N,N',N'-tetramethylmethanediamine to give the dimethylamino ketone as a mixture of isomers (37). The hydrazine pyrazole ethyl ester (35) is heated with the dimethylamino ketone (37) in acidic acid to give the pyrazole pyrazole ester (38). Base hydrolysis of the ethyl ester (38) with an inorganic base such as LiOH or NaOH in a mixture of an alcohol, such as methanol or ethanol, and water provides the pyrazole pyrazole acid (39).

Scheme 10: Synthesis of Heterocyclic Analogues-2

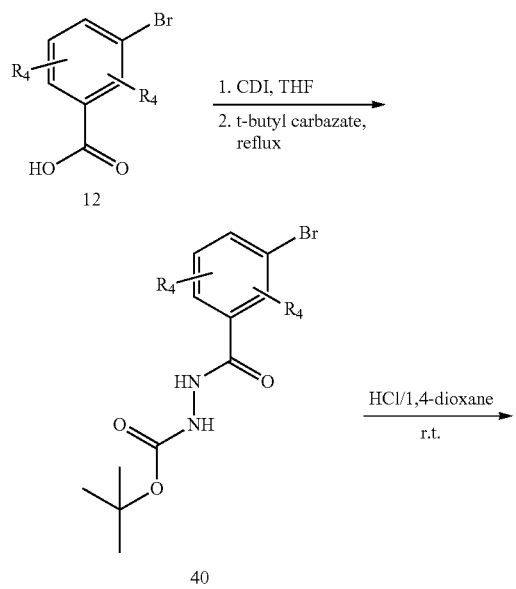

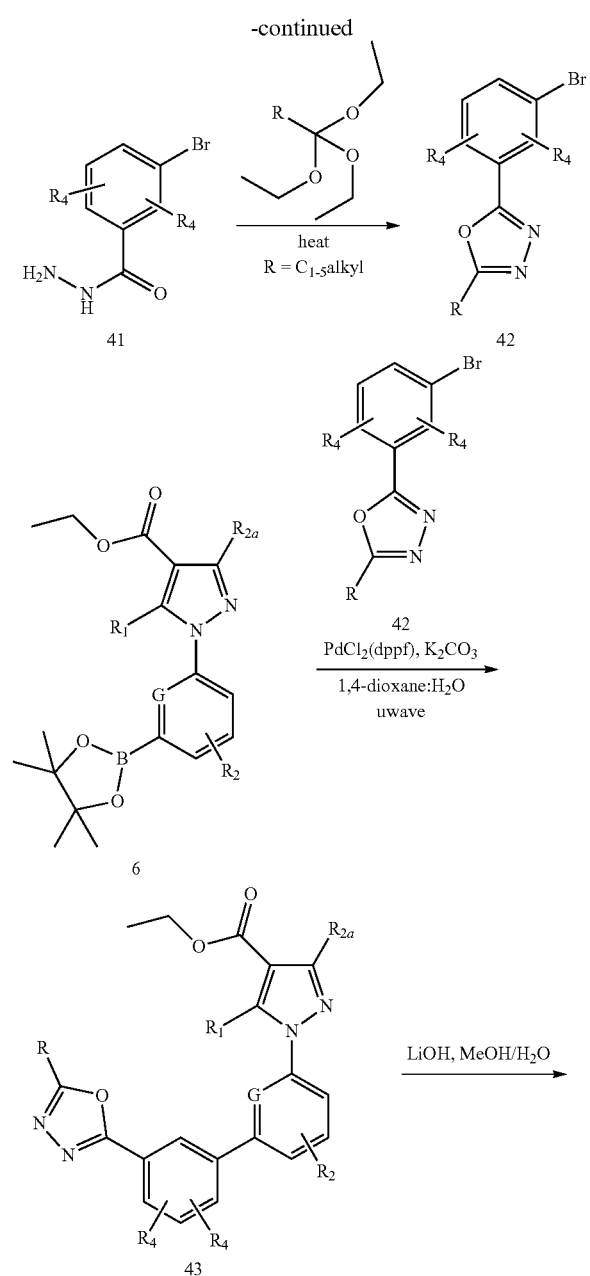

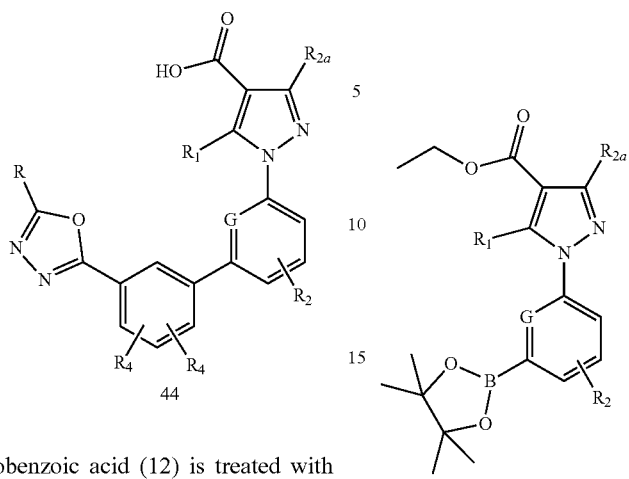

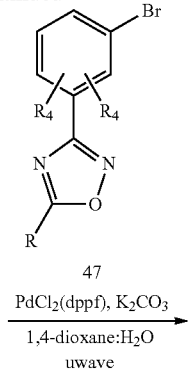

The substituted bromobenzoic acid (12) is treated with CDI in THF followed by heating with t-butyl carbazate to give the Boc-protected bromobenzoylhydrazine carboxylate (40). The Boc-protected bromobenzoylhydrazine carboxylate (40) is treated with acid in an appropriate solvent such as HCl in dioxane or TFA in $CH_2Cl_2$ to give the bromobenzoylhydrazine carboxylate (41). The bromobenzoylhydrazine carboxylate (41) is they heated with the appropriate orthoester to give the bromophenyl-1, 3, 4-oxadiazole (42). The bromophenyl-1, 3, 4-oxadiazole (42) is dissolved in a mixture of dioxane and water and treated with the pyrazole boronic ester (6) in the presence of an inorganic base, such as $K_2CO_3$ and a palladium catalyst such as $PdCl_2dppf$, to give the pyrazole 1, 3, 4-oxadiazole ethyl ester (43). Base hydrolysis of the ethyl ester (43) with an inorganic base such as LiOH or NaOH in a mixture of an alcohol, such as methanol or ethanol, and water provides the pyrazole 1, 3, 4-oxadiazole acid (44).

Scheme 11: Synthesis of Heterocyclic Analogues-3

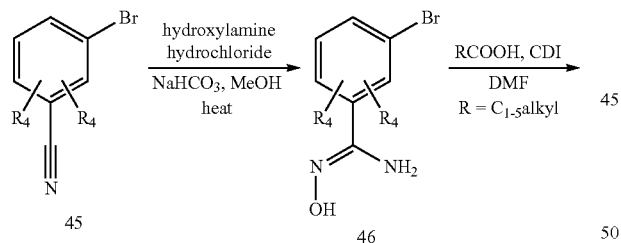

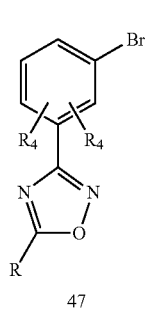

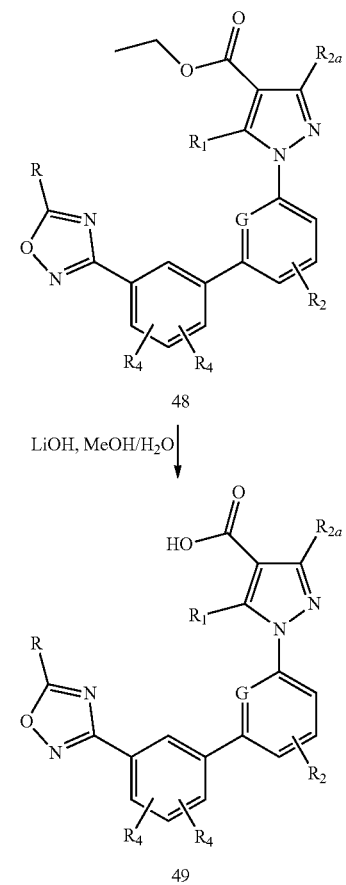

The substituted bromophenyl nitrile (45) in an alcohol solvent like methanol or ethanol is heated with hydroxylamine-hydrochloride in the presence of an inorganic base such as $NaHCO_3$ to give the bromo-N'-hydroxybenzimidamide (46). The bromo-N'-hydroxybenzimidamide (46) is dissolved in DMF along with an alkylcarboxylic acid such as acetic acid or propionic acid in the presence of CDI to give the bromophenyl-1,2,4-oxadiazole (47). The bromophenyl-1,2,4-oxadiazole (46) is dissolved in a mixture of dioxane and water and treated with the pyrazole boronic ester (6) in the presence of an inorganic base, such as $K_2CO_3$ and a palladium catalyst such as $PdCl_2dppf$, to give the pyrazole 1,2,4-oxadiazole ethyl ester (48). Base hydrolysis of the ethyl ester (48) with an inorganic base such as LiOH or NaOH in a mixture of an alcohol, such as methanol or ethanol, and water provides the pyrazole 1,2,4-oxadiazole acid (49).

The substituted bromophenyl nitrile (45) in DMF is heated with NaN3 and NH4Cl followed by aqueous HCl to give the bromophenyl tetrazole (50). The bromophenyl tetrazole (50) is dissolved in a mixture of dioxane and water and treated with the pyrazole boronic ester (6) in the Scheme 12: Synthesis of Heterocyclic Analogues-4

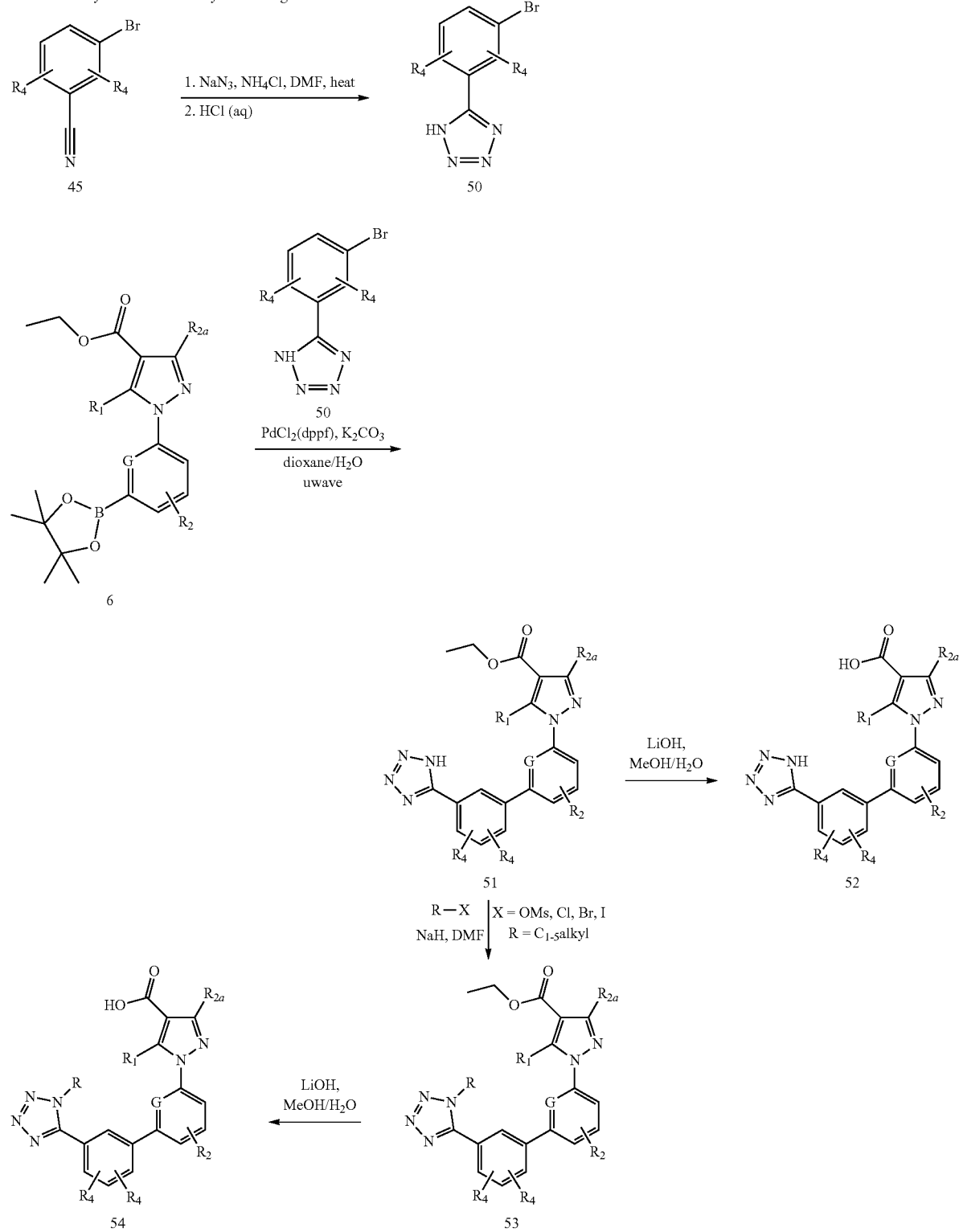

presence of an inorganic base, such as K₂CO₃ and a palladium catalyst such as PdCl₂dppf, to give the pyrazole tetrazole ethyl ester (51). Base hydrolysis of the ethyl ester (51) with an inorganic base such as LiOH or NaOH in a mixture of an alcohol, such as methanol or ethanol, and water provides the pyrazole tetrazole acid (52).

The pyrazole tetrazole ethyl ester (51) is dissolved in an appropriate solvent like THF, dioxane or DMF, with an alkyl bromide, iodide or mesylate in the presence of a base such as NaH to give the pyrazole alkyl tetrazole ethyl ester (53). Base hydrolysis of the ethyl ester (53) with an inorganic base such as LiOH or NaOH in a mixture of an alcohol, such as methanol or ethanol, and water provides the pyrazole alkyl tetrazole acid (54).

Scheme 13. Synthesis of Heterocyclic Analogue-5

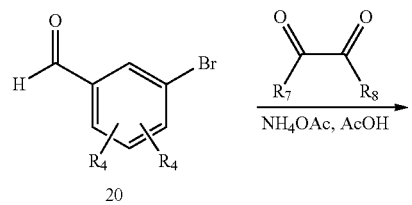

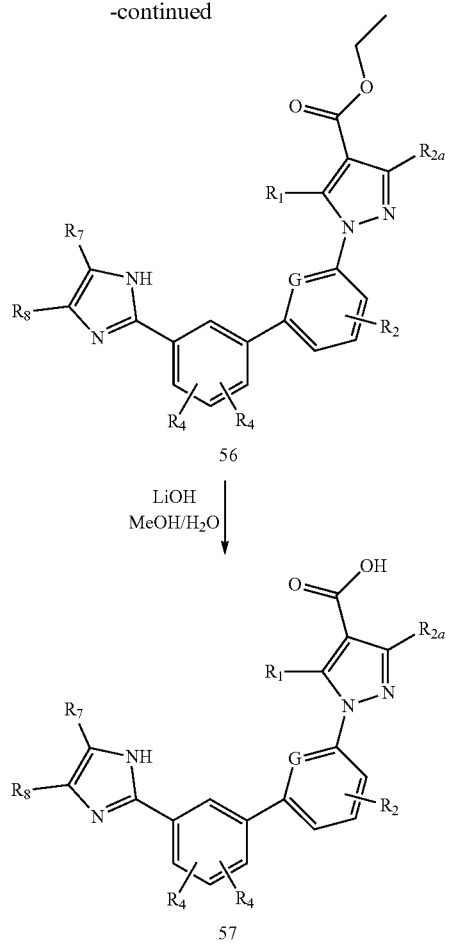

The aldehyde (20) in acetic acid is treated with a 1,2-dicarbonyl containing compound and ammonium acetate to provide the imidazole (55). The imidazole (55) is dissolved in a mixture of dioxane and water and treated with the pyrazole boronic ester (6) in the presence of an inorganic base, such as K₂CO₃ and a palladium catalyst such as PdCl₂dppf, to give the imidazole-pyrazole ester (56). Base hydrolysis of the ester (56) with an inorganic base such as LiOH or NaOH in a mixture of an alcohol, such as methanol or ethanol, and water provides the imidazole-pyrazole acid (57).

Scheme 14. Synthesis of Heterocyclic Analogue-6

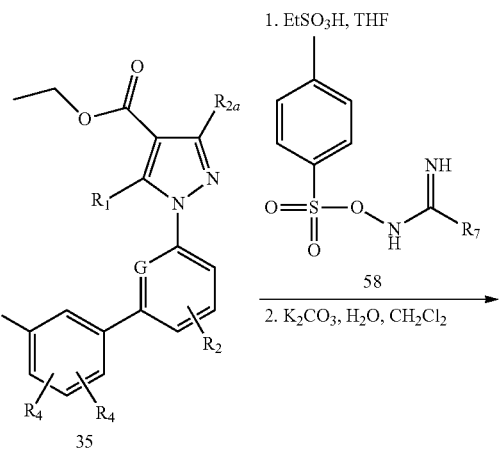

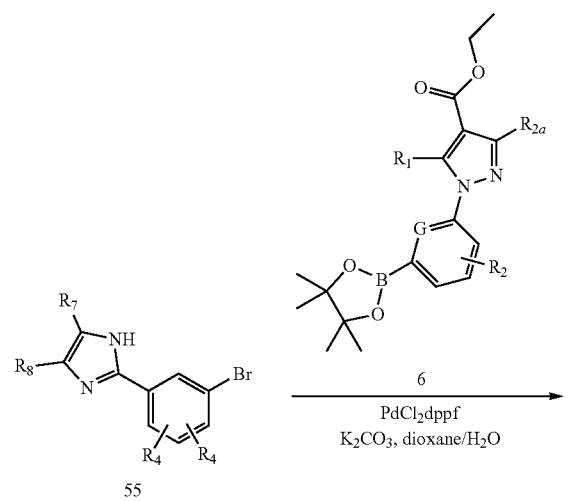

69
-continued

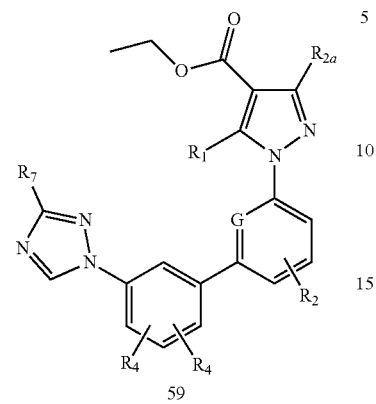

59

LiOH, MeOH/H₂O ↓

70
-continued

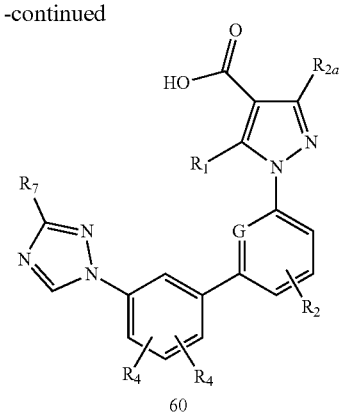

60

The hydrazine pyrazole ethyl ester (35) in THF is treated with a substituted N-(tosyloxy)imidamide (58) and ethanesulfonic acid in THF to give the triazole-pyrazole ester (59). Base hydrolysis of the triazole-pyrazole ester (59) with an inorganic base such as LiOH or NaOH in a mixture of an alcohol, such as methanol or ethanol, and water provides the triazole-pyrazole acid (60).

Scheme 15. Synthesis of Amine (basic) Analogues

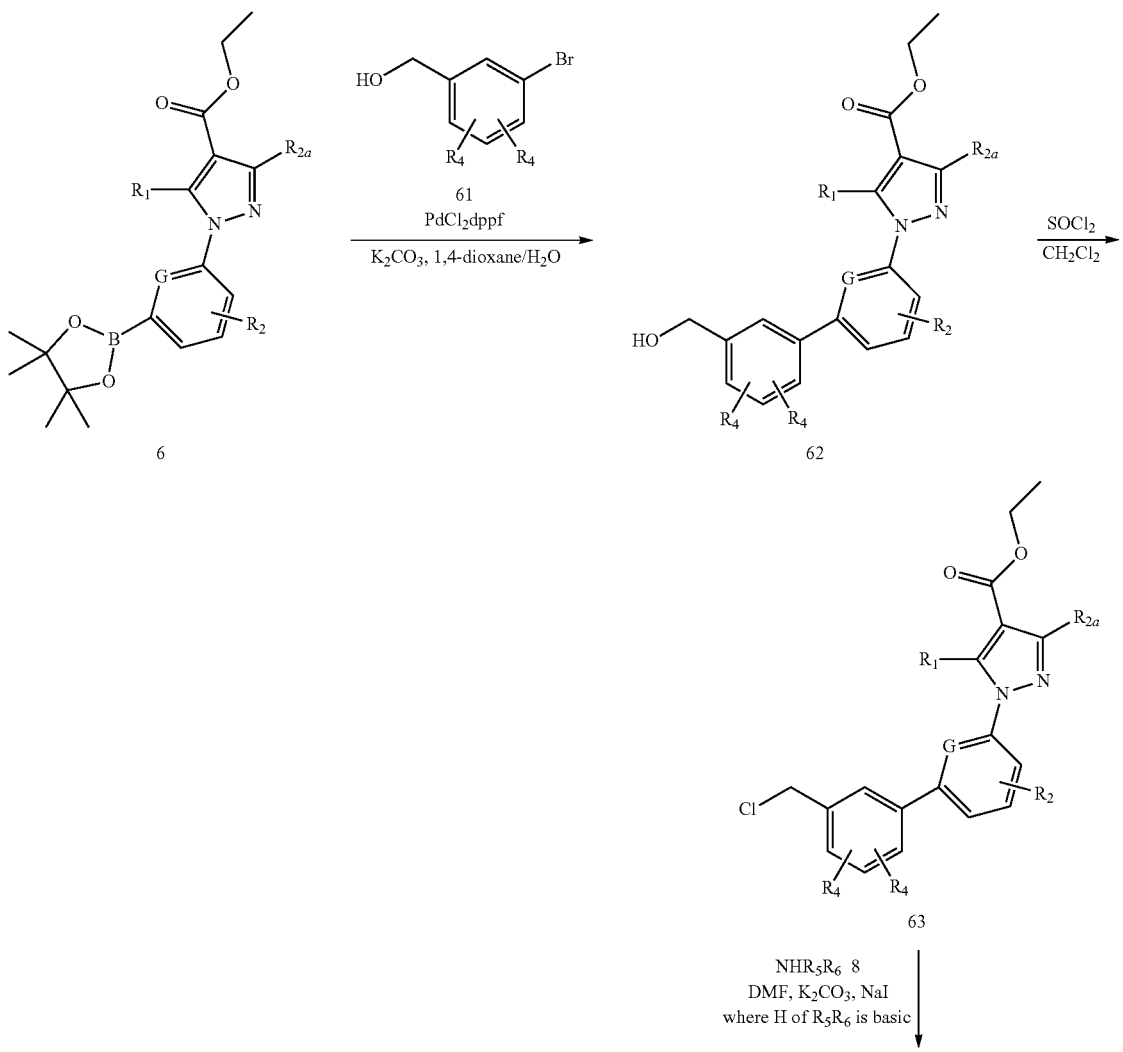

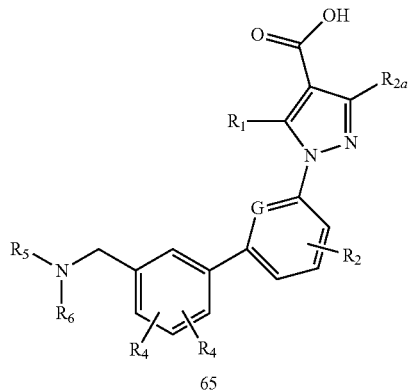 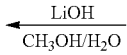 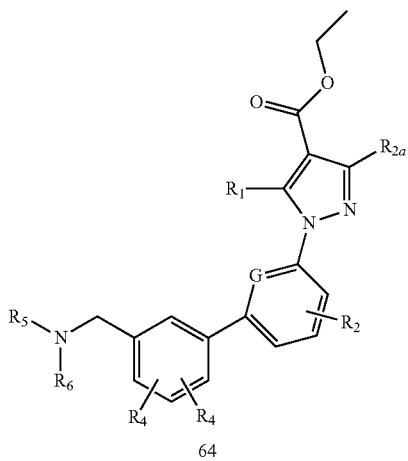

The appropriately substituted (3-bromophenyl)methanol (61) is dissolved in a mixture of dioxane and water and treated with the pyrazole boronic ester (6) in the presence of an inorganic base, such as $K_2CO_3$ and a palladium catalyst such as $PdCl_2dppf$, to give the hydroxymethyl intermediate (62). The hydroxymethyl intermediate (62) is dissolved in dichloromethane and treated with thionylchloride at room temperature to give the corresponding chloride (63). The chloride (63) is added to a mixture of $NHR_5R_6$(8), $K_2CO_3$ and NaI in DMF and the resulting reaction stirred at room temperature to provide ester (64). Base hydrolysis of the ester (64) with an inorganic base such as LiOH or NaOH in a mixture of an alcohol, such as methanol or ethanol, and water provides the pyrazole acid (65).

Scheme 16. Synthesis of Amine (non-basic) Analogues

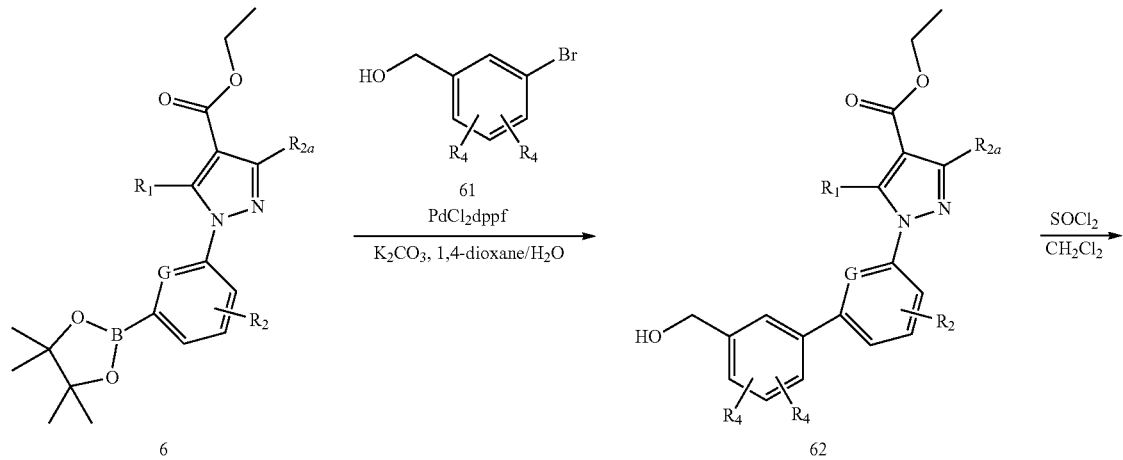

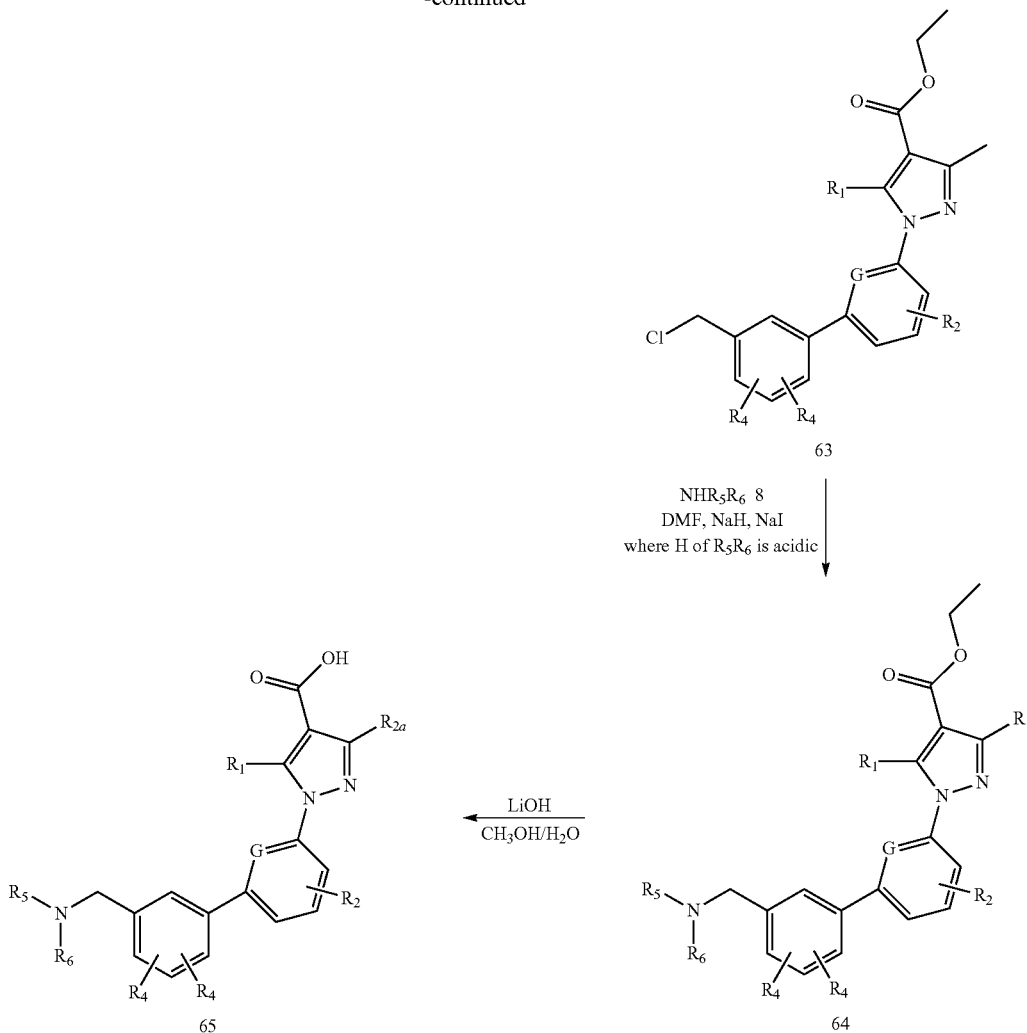

The appropriately substituted (3-bromophenyl)methanol (61) is dissolved in a mixture of dioxane and water and treated with the pyrazole boronic ester (6) in the presence of an inorganic base, such as K₂CO₃ and a palladium catalyst such as PdCl₂dppf, to give the hydroxymethyl intermediate (62). The hydroxymethyl intermediate (62) is dissolved in dichloromethane and treated with thionylchloride at room temperature to give the corresponding chloride (63). The chloride (63) is added to a mixture of NHR₅R₆(8), NaH and NaI in DMF and the resulting reaction stirred at room temperature to provide the ester (64). Base hydrolysis of the ester (64) with an inorganic base such as LiOH or NaOH in a mixture of an alcohol, such as methanol or ethanol, and water provides the pyrazole acid (65).

Biological Activity

As stated above, the compounds according to Formula I are NRF2 regulators, and are useful in the treatment or prevention of human diseases that exhibit oxidative stress components such as respiratory and non-respiratory disorders, including COPD, asthma, fibrosis, chronic asthma and acute asthma, lung disease secondary to environmental exposures, acute lung infection, chronic lung infection, a1 antitrypsin disease, cystic fibrosis, autoimmune diseases, diabetic nephropathy, chronic kidney disease, sepsis-induced acute kidney injury, acute kidney injury (AKI), kidney disease or malfunction seen during kidney transplantation, Pulmonary Arterial Hypertension, atherosclerosis, hypertension, heart failure, acute coronary syndrome, myocardial infarction, myocardial repair, cardiac remodelling, cardiac arrhythmias, Parkinson's disease (PD), Alzheimer's disease (AD), Friedreich's Ataxia (FA), amyotrophic lateral sclerosis (ALS), multiple sclerosis (MS), inflammatory bowel disease, colon cancer, neovascular (dry) AMD and neovascular (wet) AMD, eye injury, Fuchs Endothelial Corneal Dystrophy (FECD), uveitis or other inflammatory eye conditions, Non-alcoholic Steatohepatitis (NASH), toxin-induced liver disease (e.g., acetaminophen-induced hepatic disease), viral hepatitis, cirrhosis, psoriasis, dermatitis/topical effects of radiation, immunosuppression due to radiation exposure, Preeclampsia, and high altitude sickness.

The biological activity of the compounds according to Formula I can be determined using any suitable assay for determining the activity of a candidate compound as a NRF2 antagonist, as well as tissue and in vivo models.

The biological activity of the compounds of Formula (I) are demonstrated by the following tests.

BEAS-2B NQO1 MTT Assay

NAD(P)H:quinone oxidoreductase 1 (NQO1), also called DT diaphorase, is a homodimeric FAD-containing enzyme that catalyzes obligatory NAD(P)H-dependent two-electron reductions of quinones and protects cells against the toxic and neoplastic effects of free radicals and reactive oxygen species arising from one-electron reductions. The transcription of NQO1 is finely regulated by NRF2, and thus NQO1 activity is a good marker for NRF2 activation. On day one, frozen BEAS-2B cells (ATCC) are thawed in a water bath, counted, and re-suspended at a concentration of 250,000 cells/mL. Fifty microliters of cells are plated in 384 well black clear-bottomed plates. Plates are incubated at 37° C., 5% $CO_2$ overnight. On day two, plates are centrifuged and 50 nL of compound or controls are added to the cells. Plates are then incubated at 37° C., 5% $CO_2$ for 48 hours. On day four, medium is aspirated from the plate and crude cell lysates are made by adding 13 uL of 1× Cell Signaling Technologies lysis buffer with 1 Complete, Mini, EDTA-free Protease Inhibitor Tablet (Roche) for each 10 mL of lysis buffer. After lysis plates are incubated for 20 minutes at room temperature. Two microliters of lysate are removed for use in Cell Titer Glo assay (Promega) and MTT cocktail is prepared (Prochaska et. al. 1998) for measurement of NQO1 activity. Fifty microliters of MTT cocktail is added to each well, plate is centrifuged, and analyzed on an Envision plate reader (Perkin Elmer) using Absorbance 570 nm label for 30 minutes. Product formation is measured kinetically and the $pEC_{50}$ of NQO1 specific activity induction is calculated by plotting the change in absorbance (Delta OD/min) versus the log of compound concentration followed by 3-parameter fitting.

$pEC_{50}$ is the negative log of the $EC_{50}$.

All examples described herein possessed NQO1 specific enzyme activity in BEAS-2B cells with $EC_{50}$s between >10 μM-<1 nM unless otherwise noted (see table below). $EC_{50}$s<1 nM (+++++), $EC_{50}$s 10 nM-1 nM (++++), $EC_{50}$s 10-100 nM (+++), $EC_{50}$s 100 nM-1 μM (++), $EC_{50}$s 1-10 μM (+), $EC_{50}$s>10 μM (−), or were not determined (ND).

All examples described herein possessed NQO1 specific enzyme activity in BEAS-2B cells with $EC_{50}$s between >10 uM-<10 nM unless otherwise noted (see table below).

| Ex # | $EC_{50}$ |
|---|---|
| 1 | + |
| *2 | + |
| 3 | + |
| 4 | + |
| 5 | + |
| 6 | + |
| 7 | + |
| 8 | ++ |
| 9 | + |
| 10 | + |
| 11 | + |
| 12 | + |
| *13 | + |
| 14 | ++ |
| 15 | + |
| 16 | + |
| 17 | ++ |
| 18 | + |
| 19 | + |
| 20 | + |
| 21 | ++ |
| 22 | + |
| 23 | + |
| 24 | + |
| 25 | + |
| 26 | + |
| 27 | + |
| 28 | ++ |
| 29 | ++ |
| 30 | ++ |
| 31 | ++ |
| 32 | + |
| 33 | ++ |
| 34 | ++ |
| 35 | ++ |
| 36 | + |
| 37, 54d | ++ |
| 38 | ++ |
| 39 | + |
| 40 | + |
| 41 | + |
| 42 | ++ |
| 43 | + |
| 44 | + |
| 45 | ++ |
| 46 | + |
| 47 | + |
| 48 | + |
| 49 | + |
| *50 | + |
| *51g | + |
| 51h | +++ |
| 52 | + |
| 53 | ++ |
| 54e | ++ |
| *55 | + |
| *56 | + |
| 57 | +++ |
| *58 | + |
| 59 | + |
| *60 | + |
| *61 | ++ |
| 62 | ++ |
| 63 | ++ |
| #64 | +++ |
| 65 | ++ |
| *66 | + |
| 67 | ++ |
| 68 | ++++ |
| 69 | +++++ |
| 70 | +++++ |
| *71 | + |
| 72 | +++ |
| 73 | ++++ |
| 74 | +++ |
| 75 | ++++ |
| 76 | ++++ |
| 77 | +++ |
| 78 | ++++ |
| 79 | ++++ |
| 80 | +++ |
| 81 | +++ |
| 82 | +++ |
| 83 | ++++ |
| 84 | +++ |
| 85 | ++ |
| 86 | ++ |
| 87 | +++ |
| 88 | +++ |
| 89 | ++++ |
| 90 | +++ |
| 91 | ++++ |
| 92 | ++++ |
| 93 | ++++ |
| 94 | +++ |
| 95 | ++++ |
| 96 | ++ |
| 97 | ++++ |
| 98 | ++++ |
| 99 | ++++ |
| 100 | ++ |
| 101 | ++ |
| 102 | ++ |
| 103 | ++ |
| 104 | +++ |
| 105 | +++++ |

-continued

| Ex # | EC$_{50}$ |
|---|---|
| 106 | ++ |
| 107 | ++ |
| 108 | +++ |
| 109 | ++++ |
| 110 | +++++ |
| 111 | ++++ |
| 112 | ++++ |
| 113 | +++ |
| 114 | +++ |
| 115 | ++ |
| 116e | ++++ |
| 116f | ++++ |
| 117 | +++ |
| 118 | ++ |
| 119 | ++ |
| 120 | +++ |
| 121 | +++ |
| 122 | +++ |
| 123 | +++ |
| 124 | +++ |
| 125 | ++++ |
| 126 | ++ |
| 127 | ++ |
| 128 | ++ |
| 129 | ++ |
| 130 | ++ |
| 131 | ++ |
| 132 | ++ |
| 133 | + |
| 134 | ++ |
| 135 | +++ |
| 136 | ++ |
| 137 | +++ |
| 138 | + |
| 139 | + |
| 140 | + |
| 141 | ++ |
| 142 | ++ |
| 143 | ++ |
| 144 | +++ |
| 145 | ++ |
| 146 | +++ |
| 147 | +++ |
| 148 | +++ |
| 149 | ++ |
| 150 | +++ |
| 151 | + |
| 152 | +++ |
| *153 | + |
| 154 | ++ |
| 155 | ++ |
| 156 | ++ |
| 157 | +++ |
| *158 | + |
| 159 | ++ |
| 160 | ++ |
| *161 | ++ |
| 162 | +++ |
| 163 | +++ |
| 164 | +++ |
| 165 | ++++ |
| 166 | ++ |
| 167 | ++ |
| 168 | +++ |
| 169 | + |
| 170 | ++ |
| 171 | +++ |
| 172 | ++ |
| 173 | +++ |
| 174 | + |
| 175 | + |
| 176 | ++ |
| 177 | ++ |
| 178 | ++ |
| 179 | ++++ |
| 180 | ++++ |
| 181 | + |
| 182 | ++ |
| 183 | ++ |
| 184 | ++ |
| 185 | +++ |
| 186 | +++ |
| 187 | +++ |
| 188 | ++ |
| *189 | + |
| 190 | + |
| 191 | ++ |
| 192 | ++++ |
| 193 | ++ |
| 194 | ++ |
| 195 | +++ |
| 196 | ++ |
| 197 | + |
| 198 | ++ |
| 199 | +++ |
| 200 | ++ |
| 201 | ++ |
| 202 | ++ |
| 203 | + |
| 204 | ++ |
| 205 | ++ |
| *206 | ++ |
| 207 | + |
| 208 | +++ |
| *209 | + |
| *210 | ++ |
| *211 | + |
| 212 | ++ |
| 213 | ++ |
| 214 | ++ |
| 215 | ++ |
| 216 | +++ |
| 217 | ++ |
| 218 | +++ |
| 219 | +++ |
| 220 | + |
| 221 | ++ |
| 222 | ++ |
| 223 | ++ |
| 224 | ++ |
| 225 | +++ |
| 226 | +++ |
| 227 | ++ |
| 228 | ++++ |
| 229 | +++ |
| 230 | ++++ |
| 231 | ++ |
| 232 | ++ |
| 233 | ++++ |
| 234 | + |
| 235 | ++ |
| 236 | + |
| 237 | ++ |
| 238 | ++ |
| 239 | ++ |
| 240 | ++ |
| *241 | + |
| 242 | +++ |
| 243 | ++ |
| 244 | ++ |
| 245 | +++ |
| 246 | + |
| 247 | + |
| 248 | + |
| 249 | ++++ |
| 250 | ++ |
| 251 | ++ |
| 252 | ++ |
| 253 | ++ |
| *254 | ++ |
| φ255 | ++ |
| *256 | + |
| *257 | + |
| 258 | ++ |

-continued

| Ex # | EC$_{50}$ |
|---|---|
| 259 | ++ |
| 260 | ++ |
| 261 | +++ |
| 262 | +++ |
| 263 | ++ |
| 264 | ++ |
| 265 | + |
| 266 | ++ |
| 267 | ++ |
| 268 | ++ |
| 269 | + |

*in some determinations EC$_{50}$ values were >10 µM
in some determinations EC$_{50}$ values were <170 pM
*in some determinations EC$_{50}$ values were >10 µM
ϕin two determinations for Example 255 resulted in EC$_{50}$ >1 µM NRF2-Keap1 FP Assay One model for the NRF2-Keap1 interaction is through two binding sites in the Neh2 domain on NRF2. The two sites are referred to as the DLG binding motif (latch domain, uM affinity) and the ETGE binding motif (hinge domain, nM affinity). The Keap1 protein consists of an N-terminal region (NTR), a broad complex, tramtrack, and brick a' brac domain (BTB), an intervening region (IVR), a double glycine repeat domain (DGR or Kelch), and a C-terminal region. The DLG and ETGE motifs of NRF2's Neh2 domain bind to the Kelch domain of Keap1 at different affinities. In the Keap1 Kelch fluorescence polarization (FP) assay, a TAMRA-labeled 16mer peptide (AFFAQLQLDEETGEFL) containing the ETGE motif of NRF2 and the Kelch domain (321-609) of Keap1 is used. The assay determines if a compound interferes with the binding between Keap1 (361-609) and the TAMRA-labeled peptide. Binding of TAMRA-labeled NRF2 peptide to Keap1 (321-609) results in a high FP signal. If a compound interferes with the binding between the peptide and the protein, it will cause the assay signal to decrease. Thus, assay signal is inversely proportional to binding inhibition.

FP Assay 100 nl of 100× compound dose response curves (serial 3-fold dilutions) in DMSO are stamped using an Echo liquid handling system (Labcyte) into 384-well low volume black assay plates (Greiner, #784076), with DMSO in columns 6 and 18. The top concentration of compound is located in columns 1 and 13. Keap1 (321-609) is diluted to 40 nM (2×) in 1× assay buffer (50 mM Tris, pH 8.0, 100 mM NaCl, 5 mM MgCl$_2$, 1 mM DTT, 2 mM CHAPS, and 0.005% BSA) and 5 ul is added using a Multidrop Combi (Thermo Electron Corporation) equipped with a metal tip dispenser to all wells of the compound plate, except column 18. Column 18 receives only 5 ul of assay buffer. Immediately, 5 uL of 16 nM (2×) of Tamra labeled peptide (AFFAQLQLDEET-GEFL, 21$^{st}$ Century Biochemicals) is added to all wells of the plate. The plates are spun at 500 rpm for 1 min, incubated for 1 hr at room temperature, and read on an Analyst GT (Molecular Devices) equipped with excitation (530/25 nm) and emission (580/10 nm) filters designed for Tamra probes. A 561 nm dichroic mirror is also used in the Analyst. The final assay concentrations of Keap1 (321-609) and Tamra labeled peptide are 20 nM and 8 nM, respectively. Fluorescence measurements, represented as mP, are used in the transformation of the data. Compound activity is calculated based on percent inhibition, normalized against controls in the assay (Control 1 contains the Tamra peptide and Keap1 (321-609) together (0% response) and control 2 contains the Tamra peptide alone (100% response)). Data analysis is handled using the software package Abase XE (Surrey, United Kingdom). The % inhibition values are calculated by the equation:

100−(100*((compound response−average control 2)/(average control 1−average control2))).

For calculation of pIC$_{50}$s, Abase XE uses a four parameter equation. pIC$_{50}$ is the negative log of the IC$_{50}$.

All examples described herein possessed activity in the Keap1/Nrf2 FP assay as listed (see table below) unless otherwise noted. IC$_{50}$s<1 nM (+++++), IC$_{50}$s 1 nM-10 nM (++++), IC$_{50}$s 10-100 nM (+++), IC$_{50}$s 100 nM-1 mM (++), IC$_{50}$s 1-10 mM (+), IC$_{50}$s>10 mM (−), or were not determined (ND).

| Ex # | IC$_{50}$ |
|---|---|
| 1 | ++ |
| 2 | ++ |
| 3 | ++ |
| 4 | ++ |
| 5 | ++ |
| 6 | +++ |
| 7 | +++ |
| 8 | +++ |
| 9 | +++ |
| 10 | ++ |
| 11 | + |
| 12 | +++ |
| 13 | + |
| 14 | +++ |
| 15 | ++ |
| 16 | ++ |
| 17 | +++ |
| 18 | ++ |
| 19 | ++ |
| 20 | ++ |
| 21 | +++ |
| 22 | +++ |
| 23 | ++ |
| 24 | ++ |
| 24 | ++ |
| 25 | +++ |
| 26 | +++ |
| 27 | +++ |
| 28 | +++ |
| 29 | +++ |
| 30 | +++ |
| 31 | ++ |
| 32 | ++ |
| 33 | +++ |
| 34 | +++ |
| 35 | +++ |
| 36 | ++ |
| 37, 54d | +++ |
| 38 | +++ |
| 39 | ++ |
| 40 | +++ |
| 41 | +++ |
| 42 | +++ |
| 43 | +++ |
| 44 | +++ |
| 45 | +++ |
| 46 | + |
| 47 | ++ |
| 48 | ++ |
| 49 | ++ |
| 50 | + |
| 51g | ++ |
| 51g | ++ |
| 51h | +++ |
| 52 | ++ |
| 53 | +++ |
| 54e | ++ |
| 55 | +++ |
| 56 | +++ |

-continued

| Ex # | IC$_{50}$ |
|---|---|
| 57 | +++ |
| 58 | +++ |
| 59 | ++ |
| 60 | + |
| 61 | ++ |
| 62 | ++ |
| 63 | ++ |
| 64 | +++ |
| 65 | +++ |
| 66 | + |
| 67 | +++ |
| 68 | +++ |
| 69 | ++++ |
| 70 | +++ |
| 71 | + |
| 72 | ++ |
| 73 | +++ |
| 74 | +++ |
| 75 | +++ |
| 76 | +++ |
| 77 | +++ |
| 77 | +++ |
| 78 | +++ |
| 79 | +++ |
| 80 | ++ |
| 81 | ++ |
| 82 | +++ |
| 83 | +++ |
| 84 | ++ |
| 85 | +++ |
| 86 | +++ |
| 87 | ++ |
| 88 | +++ |
| 89 | +++ |
| 90 | +++ |
| 91 | +++ |
| 92 | +++ |
| 93 | +++ |
| 94 | +++ |
| 95 | +++ |
| 96 | + |
| *97 | +++ |
| 98 | +++ |
| 99 | +++ |
| 100 | + |
| *101 | − |
| 102 | + |
| 103 | + |
| 104 | +++ |
| 104 | +++ |
| *105 | − |
| 106 | − |
| *107 | − |
| *108 | − |
| 109 | − |
| 110 | ++ |
| 111 | − |
| 112 | − |
| 113 | ++ |
| 114 | ++ |
| 115 | ++ |
| 116e | +++ |
| 116f | +++ |
| 117 | +++ |
| 118 | +++ |
| 119 | +++ |
| 120 | +++ |
| 121 | ++++ |
| 122 | +++ |
| 123 | +++ |
| 124 | +++ |
| 125 | +++ |
| 126 | ++ |
| 127 | +++ |
| 128 | +++ |
| 129 | +++ |
| 130 | +++ |

-continued

| Ex # | IC$_{50}$ |
|---|---|
| 130 | +++ |
| 131 | +++ |
| 132 | +++ |
| 133 | ++ |
| 134 | +++ |
| 135 | +++ |
| 136 | +++ |
| 137 | +++ |
| 138 | +++ |
| 139 | +++ |
| 140 | +++ |
| 141 | +++ |
| 142 | +++ |
| 143 | +++ |
| 144 | +++ |
| 145 | +++ |
| 146 | +++ |
| 147 | ++ |
| 148 | +++ |
| 149 | ++ |
| 150 | ++ |
| 151 | + |
| 152 | +++ |
| 153 | + |
| 154 | +++ |
| 155 | +++ |
| 156 | ++ |
| 157 | ++ |
| 158 | ++ |
| 159 | +++ |
| 160 | +++ |
| 161 | + |
| 162 | ++ |
| 163 | ++ |
| 164 | +++ |
| 165 | +++ |
| 166 | +++ |
| 167 | +++ |
| 168 | +++ |
| 169 | ++ |
| 170 | +++ |
| 171 | +++ |
| 172 | ++ |
| 173 | +++ |
| 174 | +++ |
| 175 | +++ |
| 176 | +++ |
| 177 | ++ |
| 178 | +++ |
| 179 | +++ |
| 180 | ++ |
| 181 | ++ |
| 182 | +++ |
| 183 | +++ |
| 184 | +++ |
| 185 | ++ |
| 186 | ++ |
| 187 | ++ |
| 188 | ++ |
| 189 | − |
| 190 | + |
| 191 | ++ |
| 192 | +++ |
| 193 | ++ |
| 194 | ++ |
| 195 | ++ |
| 196 | +++ |
| 197 | +++ |
| 198 | +++ |
| 199 | +++ |
| 200 | +++ |
| 201 | +++ |
| 202 | +++ |
| 203 | + |
| 204 | ++ |
| 205 | ++ |
| 206 | ++ |

| Ex # | IC$_{50}$ |
| --- | --- |
| 207 | ++ |
| 208 | +++ |
| 209 | + |
| 210 | – |
| 211 | – |
| 212 | +++ |
| 213 | +++ |
| 214 | +++ |
| 215 | +++ |
| 216 | +++ |
| 217 | ++ |
| 218 | +++ |
| 219 | +++ |
| 220 | +++ |
| 221 | ++ |
| 222 | +++ |
| 223 | ++ |
| 224 | ++ |
| 225 | +++ |
| 226 | ++ |
| 227 | +++ |
| 228 | +++ |
| 229 | +++ |
| 230 | +++ |
| 231 | +++ |
| 232 | ++ |
| 233 | ++ |
| 234 | +++ |
| 235 | +++ |
| 236 | ++ |
| 237 | ++ |
| 238 | ++ |
| 239 | ++ |
| 240 | ++ |
| 241 | – |
| 242 | +++ |
| 243 | +++ |
| 244 | +++ |
| 245 | +++ |
| 246 | ++ |
| 247 | ++ |
| 248 | ++ |
| 249 | +++ |
| 250 | ++ |
| 251 | +++ |
| 252 | +++ |
| 253 | +++ |
| 254 | +++ |
| 255 | +++ |
| 256 | +++ |
| 257 | +++ |
| 258 | +++ |
| 259 | +++ |
| 260 | +++ |
| 261 | +++ |
| 262 | +++ |
| 263 | +++ |
| 264 | +++ |
| 265 | +++ |
| 266 | +++ |
| 267 | +++ |
| 268 | +++ |
| 269 | ++ |

*in some determinations IC$_{50}$ values were >100 µM

NRF2-Keap1 TR-FRET Assay

In the NRF2-Keap1 TR-FRET (time-resolved fluorescence resonance energy transfer) assay, full length NRF2 protein and full length Keap1 protein (Keap1 exists a dimer) are used. The assay detects the ability of compound to displace the binding of FlagHis-tagged Keap1 with biotinylated, Avi-tagged NRF2 protein. Biotin-NRF2 binds to streptavidin-europium (a component of the detection mix) and Keap1-FlagHis is recognized by anti-Flag APC (allophycocyanin) antibody (also a component of the detection mix). If binding occurs between the two proteins, there will be an energy transfer from the Eu+3 (donor) at 615 nm to the APC (acceptor) at 665 nm. A potential Keap1 inhibitor will cause a reduction in the TR-FRET signal by interfering with the binding of Keap1 to NRF2.

One hundred nanoliters of 100× compound dose response curves (serial 3-fold dilutions) in DMSO are stamped using an Echo liquid handling system (Labcyte) into 384-well, low volume, black assay plates (Greiner, #784076), with DMSO in columns 6 and 18. The top concentration of compound is located in columns 1 and 13. All reagents are diluted in assay buffer (50 mM Tris, pH 8.0, 5 mM MgCl2, 100 mM NaCl, 0.005% BSA, 1 mM DTT, and 2 mM CHAPS). The BSA, DTT, and CHAPS are added to the assay buffer on the day of assay. Using a Multidrop Combi (Thermo Electron Corporation) equipped with a metal tip dispenser, 5 ul of 25 nM Keap1-FlagHis protein is added to all wells of the compound plate, with the exception of the wells in column 18. Wells in column 18 receive 5 ul of assay buffer instead. Plates are centrifuged at 500 rpm for 1 minute, covered with a plate lid, and incubated at 37° C. for 2.25 hours. Plates are then removed from the incubator and allowed to cool to RT for 15 minutes. Five microliters of 50 nM biotin-NRF2 protein is then added to all wells of the plates and the plates are spun at 500 rpm for 1 minute, followed by incubating at 4° C. for 1.25 hours. The plates are then allowed to warm to RT for 15 minutes, followed by the addition of 10 ul of detection mix (1 nM Streptavidin Eu+ W1024 and 5 ug/ml mouse anti-DYKDDDDK IgG conjugated to SureLight APC antibody; both from Columbia Biosciences) to all wells. Plates are spun at 500 rpm for 1 minute, incubated for 1 hour at RT, and read on an Envision plate reader using a 320 nm excitation filter and 615 nm and 665 nm emission filters. Compound response (% inhibition) and potency (pIC50) are calculated based on the ratio of the two emissions (665 nm/615 nm) and then the transformed data is normalized against controls in the assay (control 1=1% DMSO in the presence of NRF2 and Keap1 protein and control 2=1% DMSO in the absence of protein). Data analysis is handled using the software package Abase XE (Surrey, United Kingdom). The % inhibition values are calculated from the ratio (transformed) data by the equation:

100−(100*(compound response−average control 2)/ (average control 1−average control2)).

For calculation of pIC50s, Abase XE uses a four parameter equation. pIC$_{50}$ is the negative log of the IC$_{50}$.

All examples described herein possessed activity in the Nrf2/Keap1 TR-FRET assay as listed (see table below) unless otherwise noted. IC$_{50}$s<10 nM (+++++), IC$_{50}$s 10-100 nM (++++), IC$_{50}$s 100 nM-1 µM (+++), IC$_{50}$s 1-10 µM (++). & IC$_{50}$s 10-100 µM (+), IC$_{50}$s>100 µM (−), or were not determined (ND).

| Ex # | IC$_{50}$ |
| --- | --- |
| 1 | + |
| 2 | ++ |
| 3 | ++ |
| 4 | ++ |
| 5 | ++ |
| 6 | +++ |
| 7 | ++ |
| 8 | +++ |
| 9 | ++ |
| 10 | ++ |
| 11 | + |
| 12 | +++ |
| 13 | + |

-continued

| Ex # | IC$_{50}$ |
|---|---|
| 14 | +++ |
| 15 | ++ |
| 16 | ++ |
| 17 | +++ |
| 18 | ++ |
| 19 | ++ |
| 20 | ++ |
| 21 | +++ |
| 22 | ++ |
| 23 | ++ |
| 24 | ++ |
| 25 | +++ |
| 26 | +++ |
| 27 | +++ |
| 28 | +++ |
| 29 | +++ |
| 30 | ++ |
| 31 | ++ |
| 32 | ++ |
| 33 | +++ |
| 34 | +++ |
| 35 | +++ |
| 36 | ++ |
| 37, 54d | ++ |
| 38 | +++ |
| 39 | ++ |
| 40 | +++ |
| 41 | ++++ |
| 42 | ++++ |
| 43 | +++ |
| 44 | +++ |
| 45 | +++ |
| 46 | + |
| 47 | ++ |
| 48 | ++ |
| 49 | + |
| *50 | − |
| 51g | ++ |
| 51h | ++++ |
| 52 | ++ |
| 53 | +++ |
| 54e | ++ |
| 55 | ++++ |
| 56 | +++ |
| 57 | ++++ |
| 58 | +++ |
| 59 | +++ |
| 60 | + |
| 61 | ++ |
| 62 | ++ |
| 63 | +++ |
| 64 | ND |
| 65 | ND |
| 66 | − |
| 67 | +++ |
| 68 | ND |
| 69 | ND |
| 70 | ND |
| 71 | ND |
| 72 | ND |
| 73 | ND |
| 74 | ND |
| 75 | ND |
| 76 | ND |
| 77 | ND |
| 78 | ND |
| 79 | ND |
| 80 | ND |
| 81 | ND |
| 82 | ND |
| 83 | ND |
| 84 | ND |
| 85 | ND |
| 86 | ND |
| 87 | ND |
| 88 | ND |
| 89 | ND |

-continued

| Ex # | IC$_{50}$ |
|---|---|
| 90 | ND |
| 91 | ND |
| 92 | ND |
| 93 | ND |
| 94 | ND |
| 95 | ND |
| 96 | ND |
| 97 | ND |
| 98 | ND |
| 99 | ND |
| 100 | ND |
| 101 | ND |
| 102 | ND |
| 103 | ND |
| 104 | ND |
| 105 | ND |
| 106 | ND |
| 107 | ND |
| 108 | ND |
| 109 | ND |
| 110 | ND |
| 111 | ND |
| 112 | ND |
| 113 | ND |
| 114 | ND |
| 115 | ND |
| 116e | ND |
| 116f | ND |
| 117 | ND |
| 118 | ND |
| 119 | ND |
| 120 | ND |
| 121 | ND |
| 122 | ND |
| 123 | ND |
| 124 | ND |
| 125 | ND |
| 126 | ND |
| 127 | ND |
| 128 | ND |
| 129 | ++++ |
| 130 | ND |
| 131 | ND |
| 132 | ND |
| 133 | ND |
| 134 | ND |
| 135 | ND |
| 136 | ND |
| 137 | ND |
| 138 | ND |
| 139 | ND |
| 140 | ND |
| 141 | ND |
| 142 | ND |
| 143 | ND |
| 144 | +++ |
| 145 | +++ |
| 146 | +++ |
| 147 | +++ |
| 148 | +++ |
| 149 | +++ |
| 150 | +++ |
| 151 | + |
| 152 | +++ |
| 153 | + |
| 154 | ++++ |
| 155 | ++++ |
| 156 | +++ |
| 157 | +++ |
| 158 | ++ |
| 159 | ++++ |
| 160 | ++++ |
| 161 | + |
| 162 | ND |
| 163 | ++ |
| 164 | +++ |
| 165 | ++++ |

| Ex # | IC$_{50}$ |
|---|---|
| 166 | +++ |
| 167 | +++ |
| 168 | +++ |
| 169 | +++ |
| 170 | ND |
| 171 | +++ |
| 172 | ++ |
| 173 | +++ |
| 174 | +++ |
| 175 | +++ |
| 176 | +++ |
| 177 | +++ |
| 178 | +++ |
| 179 | +++ |
| 180 | ND |
| 181 | ++ |
| 182 | +++ |
| 183 | +++ |
| 184 | +++ |
| 185 | +++ |
| 186 | +++ |
| 187 | +++ |
| 188 | ++ |
| 189 | + |
| 190 | + |
| 191 | +++ |
| 192 | +++ |
| 193 | ND |
| 194 | ND |
| 195 | ND |
| 196 | ++++ |
| 197 | ++++ |
| 198 | ++++ |
| 199 | ++++ |
| 200 | ND |
| 201 | ++++ |
| 202 | ++++ |
| 203 | ++ |
| 204 | ++ |
| 205 | +++ |
| 206 | ++ |
| 207 | ++ |
| 208 | ++++ |
| 209 | + |
| *210 | − |
| 211 | + |
| 212 | ++++ |
| 213 | ++++ |
| 214 | ++++ |
| 215 | +++ |
| 216 | +++ |
| 217 | +++ |
| 218 | +++ |
| 219 | +++ |
| 220 | +++ |
| 221 | +++ |
| 222 | +++ |
| 223 | ++ |
| 224 | +++ |
| 225 | +++ |
| 226 | +++ |
| 227 | ++++ |
| 228 | +++ |
| 229 | +++ |
| 230 | ++++ |
| 231 | +++ |
| 232 | ++++ |
| 233 | +++ |
| 234 | +++ |
| 235 | +++ |
| 236 | ++ |
| 237 | ++ |
| 238 | ++ |
| 239 | +++ |
| 240 | ++ |
| 241 | ND |
| 242 | |
| 243 | +++ |
| 244 | +++ |
| 245 | +++ |
| 246 | ++ |
| 247 | ++ |
| 248 | +++ |
| 249 | ++++ |
| 250 | + |
| 251 | ++++ |
| 252 | +++ |
| 253 | +++ |
| 254 | +++ |
| 255 | ND |
| 256 | ND |
| 257 | ND |
| 258 | ++++ |
| 259 | ++++ |
| 260 | ++++ |
| 261 | ++++ |
| 262 | ++++ |
| 263 | ++++ |
| 264 | ++++ |
| 265 | ++++ |
| 266 | ++++ |
| 267 | ++++ |
| 268 | ++++ |
| 269 | + |

*in some determinations IC$_{50}$ values were >100 μM

NRF2-Keap1 TR-FRET Low Protein Assay

In the NRF2-Keap1 TR-FRET (time-resolved fluorescence resonance energy transfer) low protein assay, full length NRF2 protein and full length Keap1 protein (Keap1 exists a dimer) are used. The assay detects a compound's ability to displace the binding of Keap1 FlagHis with biotinylated Avi-NRF2 protein. Biotin-NRF2 binds to streptavidin-europium (a component of the detection mix) and Keap1 FlagHis is recognized by anti-Flag APC (allophycocyanin) antibody (also a component of the detection mix). If binding occurs between the two proteins, there will be an energy transfer from the Eu+3 (donor) at 615 nm to the APC (acceptor) at 665 nm. A potential NRF2 inhibitor will cause a reduction in the TR-FRET signal by interfering with the binding of Keap1 to NRF2.

Ten nanoliters of 100× compound dose response curves (serial 3-fold dilutions) in DMSO are stamped using an Echo liquid handling system (Labcyte) into 384-well, low volume, black assay plates (Greiner, #784076), with DMSO in columns 6 and 18. An additional 90 nl DMSO is added to each well, to bring the total volume to 100 nl per well. The top concentration of compound is located in columns 1 and 13, with the serial dilutions going across the row. All reagents are diluted in assay buffer (50 mM Tris, pH 8.0, 5 mM MgCl2, 100 mM NaCl, 0.005% BSA, 1 mM DTT, and 2 mM CHAPS. The BSA, DTT, and CHAPS are added to the assay buffer on the day of assay. Using a Multidrop Combi (Thermo Electron Corporation) equipped with a metal tip dispenser, 5 ul of 1.25 nM Keap1 FlagHis protein is added to all wells of the compound plate, with the exception of the wells in column 18. Wells in column 18 receive 5 ul of assay buffer instead. Plates are centrifuged at 500 rpm for 1 minute, covered with a plate lid, and incubated at 37° C. for 2.25 hours. Plates are then removed from the incubator and allowed to cool to RT for 15 minutes. Five microliters of 2.5 nM biotin-NRF2 protein is then added to all wells of the plates and the plates are spun at 500 rpm for 1 minute, followed by incubating at 4° C. for 1.25 hours. The plates are then allowed to warm to RT for 15 minutes, followed by the addition of 10 ul of detection mix (1 nM Streptavidin Eu+W1024 and 5 ug/ml mouse anti-DYKDDDDK IgG conjugated to SureLight APC antibody; both from Columbia Biosciences) to all wells. Plates are spun at 500 rpm for 1 minute, incubated for 1 hour at RT, and read on an Envision plate reader using a 320 nm excitation filter and 615 nm and 665 nm emission filters. Compound response (% inhibition) and potency (pIC50) are calculated based on the ratio of the two emissions (665 nm/615 nm) and then the transformed data is normalized against controls in the assay (control 1=1% DMSO in the presence of NRF2 and Keap1 protein and control 2=1% DMSO in the presence of only the NRF2 protein). Data analysis is handled using the software package Abase XE (Surrey, United Kingdom). The % inhibition values are calculated from the ratio (transformed) data by the equation:

100−(100*(compound response−average control 2)/ (average control 1−average control2)).

For calculation of pIC50s, Abase XE uses a four parameter equation. $pIC_{50}$ is the negative log of the $IC_{50}$.

All examples described herein possessed activity in the Nrf2/Keap1 Low Protein TR-FRET assay as listed (see table below) unless otherwise noted. $IC_{50}$s<10 nM (+++++), $IC_{50}$s 10-100 nM (++++), $IC_{50}$s 100 nM-1 uM (+++), $IC_{50}$s 1-10 uM (++). & $IC_{50}$s 10 uM-100 uM (+), $IC_{50}$s>100 uM (−), or were not determined (ND).

| Ex # | $IC_{50}$ |
|---|---|
| 1 | ND |
| 2 | ND |
| 3 | ND |
| 4 | ND |
| 5 | ND |
| 6 | ND |
| 7 | ND |
| 8 | ++++ |
| 9 | ND |
| 10 | ND |
| 11 | ND |
| 12 | ND |
| 13 | ND |
| 14 | ++++ |
| 15 | ND |
| 16 | ND |
| 17 | ++++ |
| 18 | ND |
| 19 | ND |
| 20 | ND |
| 21 | +++ |
| 22 | ND |
| 23 | ND |
| 24 | ND |
| 25 | ND |
| 26 | ND |
| 27 | ND |
| 28 | ++++ |
| 29 | ++++ |
| 30 | +++ |
| 31 | ++++ |
| 32 | ND |
| 33 | ++++ |
| 34 | ++++ |
| 35 | ++++ |
| 36 | ND |
| 37, 54d | ++++ |
| 38 | ++++ |
| 39 | ND |
| 40 | ND |
| 41 | +++++ |
| 42 | +++++ |
| 43 | ND |
| 44 | ND |
| 45 | ++++ |
| 46 | ND |
| 47 | ND |
| 48 | ND |
| 49 | ND |
| 50 | ND |
| 51g | +++ |
| 51h | +++++ |
| 52 | ND |
| 53 | ++++ |
| 54e | +++ |
| 55 | ++++ |
| 56 | ND |
| 57 | +++++ |
| 58 | ND |
| 59 | +++ |
| 60 | ND |
| 61 | ++ |
| 62 | +++ |
| 63 | ++++ |
| 64 | +++++ |
| #65 | +++++ |
| 66 | ND |
| 67 | ++++ |
| 68 | +++++ |
| 69 | +++++ |
| 70 | +++++ |
| 71 | ++ |
| 72 | +++ |
| 73 | +++++ |
| 74 | ++++ |
| 75 | +++++ |
| 76 | ++++ |
| 77 | ++++ |
| 78 | ++++ |
| 79 | +++++ |
| 80 | ++++ |
| 81 | +++ |
| 82 | ++++ |
| 83 | ++++ |
| 84 | ++++ |
| 85 | ++++ |
| 86 | ++++ |
| 87 | +++ |
| 88 | ++++ |
| 89 | ++++ |
| 90 | +++++ |
| 91 | ++++ |
| 92 | +++ |
| 93 | ++++ |
| 94 | ++++ |
| 95 | +++++ |
| 96 | +++ |
| 97 | ++++ |
| 98 | +++++ |
| 99 | +++++ |
| 100 | +++ |
| *101 | ++ |
| 102 | ++ |
| 103 | ++ |
| 104 | ++++ |
| *105 | ++ |
| 106 | ++ |
| 107 | ++ |
| 108 | ++ |
| 109 | +++ |
| 110 | ++++ |
| 111 | +++ |
| 112 | +++ |
| 113 | +++ |
| 114 | ++++ |
| 115 | +++ |
| 116e | ++++ |
| 116f | ++++ |
| 117 | +++++ |
| 118 | +++++ |
| 119 | +++++ |

| Ex # | IC$_{50}$ |
|---|---|
| 120 | +++++ |
| 121 | +++++ |
| 122 | +++++ |
| 123 | ++++ |
| 124 | +++++ |
| 125 | +++++ |
| 126 | +++ |
| 127 | ++++ |
| 128 | +++++ |
| 129 | +++++ |
| 130 | ++++ |
| 131 | +++++ |
| 132 | +++++ |
| 133 | ++++ |
| 134 | +++++ |
| 135 | ++++ |
| 136 | +++++ |
| 137 | ++++ |
| 138 | +++++ |
| 139 | +++++ |
| 140 | ++++ |
| 141 | ++++ |
| 142 | ++++ |
| 143 | ++++ |
| 144 | ++++ |
| 145 | ++++ |
| 146 | ++++ |
| 147 | ++++ |
| 148 | +++++ |
| 149 | ++++ |
| 150 | ++++ |
| 151 | ND |
| 152 | ++++ |
| 153 | ND |
| 154 | +++++ |
| 155 | +++++ |
| 156 | ND |
| 157 | ++++ |
| 158 | ND |
| 159 | ND |
| 160 | +++++ |
| 161 | ++ |
| 162 | ++++ |
| 163 | +++ |
| 164 | ++++ |
| 165 | +++++ |
| 166 | ND |
| 167 | ++++ |
| 168 | ND |
| 169 | ND |
| 170 | ++++ |
| 171 | ++++ |
| 172 | ND |
| 173 | ND |
| 174 | ND |
| 175 | ND |
| 176 | ++++ |
| 177 | +++ |
| 178 | ++++ |
| 179 | ++++ |
| 180 | ++++ |
| 181 | ND |
| 182 | ND |
| 183 | ++++ |
| 184 | ND |
| 185 | ++++ |
| 186 | ++++ |
| 187 | ++++ |
| 188 | ++ |
| 189 | ND |
| 190 | ND |
| 191 | +++ |
| 192 | ++++ |
| 193 | +++ |
| 194 | ++++ |
| 195 | ++++ |
| 196 | +++++ |
| 197 | +++++ |
| 198 | ND |
| 199 | ND |
| 200 | +++++ |
| #201 | +++++ |
| 202 | +++++ |
| 203 | ND |
| 204 | +++ |
| 205 | ++++ |
| 206 | +++ |
| 207 | ND |
| 208 | +++++ |
| *209 | ++ |
| 210 | + |
| 211 | ND |
| 212 | +++++ |
| 213 | +++++ |
| 214 | +++++ |
| 215 | ++++ |
| 216 | ++++ |
| 217 | ++++ |
| 218 | ++++ |
| 219 | ++++ |
| 220 | ND |
| 221 | +++ |
| 222 | ++++ |
| 223 | +++ |
| 224 | +++ |
| 225 | ++++ |
| 226 | ND |
| 227 | ++++ |
| 228 | ++++ |
| 229 | ++++ |
| 230 | ++++ |
| 231 | ++++ |
| 232 | ++++ |
| 233 | ++++ |
| 234 | ++++ |
| 235 | ++++ |
| 236 | ND |
| 237 | +++ |
| 238 | +++ |
| 239 | +++ |
| 240 | +++ |
| *241 | − |
| 242 | ++++ |
| 243 | ++++ |
| 244 | ++++ |
| 245 | ++++ |
| 246 | +++ |
| 247 | ND |
| 248 | ND |
| 249 | +++++ |
| 250 | +++ |
| 251 | +++++ |
| 252 | ++++ |
| 253 | +++++ |
| 254 | ++++ |
| #255 | +++++ |
| 256 | ++++ |
| 257 | +++++ |
| 258 | +++++ |
| 259 | +++++ |
| 260 | +++++ |
| 261 | +++++ |
| 262 | +++++ |
| 263 | +++++ |
| 264 | +++++ |
| 265 | ND |
| 266 | +++++ |
| 267 | +++++ |
| 268 | +++++ |
| 269 | ND |

*in some determinations IC$_{50}$ values were >100 μM
in some determinations IC$_{50}$ values were <10 nM Rat Model of Myocardial Ischemia and Prolonged Reperfusion Oxidative stress is increased in the diseased myocardium, resulting in accumulation of reactive oxygen species (ROS) which impairs cardiac function [*Circ* (1987) 76(2); 458-468] and increases susceptibility to arrhythmia [*J of Mol & Cell Cardio* (1991) 23(8); 899-918] by a direct toxic effect of increased necrosis and apoptosis [*Circ Res* (2000) 87(12); 1172-1179]. The present study determines whether a small molecule activator of NRF2 that targets the Kelch-domain of Keap1, improves cardiac function in a rodent model of established cardiac dysfunction following myocardial ischemia/reperfusion (I/R) injury.

Cardiac dysfunction is established in rats by 30 minutes of myocardial ischemia induced by occlusion of the left anterior descending coronary artery (LAD) followed by 4 weeks of reperfusion. Compound is administered once a day via subcutaneous injection for 28 days starting 2 hours post-reperfusion at 0.5, 5 and 50 mg/kg/d. Ejection fraction (EF), a measure of cardiac function, is measured as well as cardiac antioxidant enzyme activity, left ventricular fibrosis] and oxidative damage in the heart.

Methods of Use

The compounds of the invention are NRF2 regulators, and are useful in the treatment or prevention of respiratory and non-respiratory disorders, including COPD, asthma, fibrosis, chronic asthma and acute asthma, lung disease secondary to environmental exposures, acute lung infection, chronic lung infection, al antitrypsin disease, cystic fibrosis, autoimmune diseases, diabetic nephropathy, chronic kidney disease, sepsis-induced acute kidney injury, acute kidney injury (AKI), kidney disease or malfunction seen during kidney transplantation, Pulmonary Arterial Hypertension, atherosclerosis, hypertension, heart failure, acute coronary syndrome, myocardial infarction, myocardial repair, cardiac remodelling, cardiac arrhythmias, Parkinson's disease (PD), Alzheimer's disease (AD), Friedreich's Ataxia (FA), amyotrophic lateral sclerosis (ALS), multiple sclerosis (MS), inflammatory bowel disease, colon cancer, neovascular (dry) AMD and neovascular (wet) AMD, eye injury, Fuchs Endothelial Corneal Dystrophy (FECD), uveitis or other inflammatory eye conditions, Non-alcoholic Steatohepatitis (NASH), toxin-induced liver disease (e.g., acetaminophen-induced hepatic disease), viral hepatitis, cirrhosis, psoriasis, dermatitis/topical effects of radiation, immunosuppression due to radiation exposure, Preeclampsia, and high altitude sickness.

Accordingly, in another aspect the invention is directed to methods of treating such conditions.

The methods of treatment of the invention comprise administering a safe and effective amount of a compound according to Formula I or a pharmaceutically-acceptable salt thereof to a patient in need thereof.

As used herein, "treat" in reference to a condition means: (1) to ameliorate or prevent the condition or one or more of the biological manifestations of the condition, (2) to interfere with (a) one or more points in the biological cascade that leads to or is responsible for the condition or (b) one or more of the biological manifestations of the condition, (3) to alleviate one or more of the symptoms or effects associated with the condition, or (4) to slow the progression of the condition or one or more of the biological manifestations of the condition.

The skilled artisan will appreciate that "prevention" is not an absolute term. In medicine, "prevention" is understood to refer to the prophylactic administration of a drug to substantially diminish the likelihood or severity of a condition or biological manifestation thereof, or to delay the onset of such condition or biological manifestation thereof.

As used herein, "safe and effective amount" in reference to a compound of the invention or other pharmaceutically-active agent means an amount of the compound sufficient to treat the patient's condition but low enough to avoid serious side effects (at a reasonable benefit/risk ratio) within the scope of sound medical judgment. A safe and effective amount of a compound will vary with the particular compound chosen (e.g. consider the potency, efficacy, and half-life of the compound); the route of administration chosen; the condition being treated; the severity of the condition being treated; the age, size, weight, and physical condition of the patient being treated; the medical history of the patient to be treated; the duration of the treatment; the nature of concurrent therapy; the desired therapeutic effect; and like factors, but can nevertheless be routinely determined by the skilled artisan.

As used herein, "patient" refers to a human or other animal.

The compounds of the invention may be administered by any suitable route of administration, including both systemic administration and topical administration. Systemic administration includes oral administration, parenteral administration, transdermal administration, rectal administration, and administration by inhalation. Parenteral administration refers to routes of administration other than enteral, transdermal, or by inhalation, and is typically by injection or infusion. Parenteral administration includes intravenous, intramuscular, and subcutaneous injection or infusion. Inhalation refers to administration into the patient's lungs whether inhaled through the mouth or through the nasal passages. Topical administration includes application to the skin as well as intraocular, otic, intravaginal, and intranasal administration.

The compounds of the invention may be administered once or according to a dosing regimen wherein a number of doses are administered at varying intervals of time for a given period of time. For example, doses may be administered one, two, three, or four times per day. Doses may be administered until the desired therapeutic effect is achieved or indefinitely to maintain the desired therapeutic effect. Suitable dosing regimens for a compound of the invention depend on the pharmacokinetic properties of that compound, such as absorption, distribution, and half-life, which can be determined by the skilled artisan. In addition, suitable dosing regimens, including the duration such regimens are administered, for a compound of the invention depend on the condition being treated, the severity of the condition being treated, the age and physical condition of the patient being treated, the medical history of the patient to be treated, the nature of concurrent therapy, the desired therapeutic effect, and like factors within the knowledge and expertise of the skilled artisan. It will be further understood by such skilled artisans that suitable dosing regimens may require adjustment given an individual patient's response to the dosing regimen or over time as individual patient needs change.

Typical daily dosages may vary depending upon the particular route of administration chosen. Typical dosages for oral administration range from 1 mg to 1000 mg per person per day. Preferred dosages are 1-500 mg once daily, more preferred is 1-100 mg per person per day. IV dosages range form 0.1-000 mg/day, preferred is 0.1-500 mg/day, and more preferred is 0.1-100 mg/day. Inhaled daily dosages range from 10 ug-10 mg/day, with preferred 10 ug-2 mg/day, and more preferred 50 uug-500 ug/day.

Additionally, the compounds of the invention may be administered as prodrugs. As used herein, a "prodrug" of a compound of the invention is a functional derivative of the compound which, upon administration to a patient, eventually liberates the compound of the invention in vivo. Administration of a compound of the invention as a prodrug may enable the skilled artisan to do one or more of the following: (a) modify the onset of the compound in vivo; (b) modify the duration of action of the compound in vivo; (c) modify the transportation or distribution of the compound in vivo; (d) modify the solubility of the compound in vivo; and (e) overcome a side effect or other difficulty encountered with the compound. Typical functional derivatives used to prepare prodrugs include modifications of the compound that are chemically or enzymatically cleaved in vivo. Such modifications, which include the preparation of phosphates, amides, ethers, esters, thioesters, carbonates, and carbamates, are well known to those skilled in the art.

Compositions

The compounds of the invention will normally, but not necessarily, be formulated into pharmaceutical compositions prior to administration to a patient. Accordingly, in another aspect the invention is directed to pharmaceutical compositions comprising a compound of the invention and one or more pharmaceutically-acceptable excipient.

The pharmaceutical compositions of the invention may be prepared and packaged in bulk form wherein a safe and effective amount of a compound of the invention can be extracted and then given to the patient such as with powders or syrups. Alternatively, the pharmaceutical compositions of the invention may be prepared and packaged in unit dosage form wherein each physically discrete unit contains a safe and effective amount of a compound of the invention. When prepared in unit dosage form, the pharmaceutical compositions of the invention typically contain from 1 mg to 1000 mg.

The pharmaceutical compositions of the invention typically contain one compound of the invention. However, in certain embodiments, the pharmaceutical compositions of the invention contain more than one compound of the invention. For example, in certain embodiments the pharmaceutical compositions of the invention contain two compounds of the invention. In addition, the pharmaceutical compositions of the invention may optionally further comprise one or more additional pharmaceutically active compounds.

As used herein, "pharmaceutically-acceptable excipient" means a pharmaceutically acceptable material, composition or vehicle involved in giving form or consistency to the pharmaceutical composition. Each excipient must be compatible with the other ingredients of the pharmaceutical composition when commingled such that interactions which would substantially reduce the efficacy of the compound of the invention when administered to a patient and interactions which would result in pharmaceutical compositions that are not pharmaceutically acceptable are avoided. In addition, each excipient must of course be of sufficiently high purity to render it pharmaceutically-acceptable.

The compound of the invention and the pharmaceutically-acceptable excipient or excipients will typically be formulated into a dosage form adapted for administration to the patient by the desired route of administration. For example, dosage forms include those adapted for (1) oral administration such as tablets, capsules, caplets, pills, troches, powders, syrups, elixirs, suspensions, solutions, emulsions, sachets, and cachets; (2) parenteral administration such as sterile solutions, suspensions, and powders for reconstitution; (3) transdermal administration such as transdermal patches; (4) rectal administration such as suppositories; (5) inhalation such as dry powders, aerosols, suspensions, and solutions; and (6) topical administration such as creams, ointments, lotions, solutions, pastes, sprays, foams, and gels.

Suitable pharmaceutically-acceptable excipients will vary depending upon the particular dosage form chosen. In addition, suitable pharmaceutically-acceptable excipients may be chosen for a particular function that they may serve in the composition. For example, certain pharmaceutically-acceptable excipients may be chosen for their ability to facilitate the production of uniform dosage forms. Certain pharmaceutically-acceptable excipients may be chosen for their ability to facilitate the production of stable dosage forms. Certain pharmaceutically-acceptable excipients may be chosen for their ability to facilitate the carrying or transporting of the compound or compounds of the invention once administered to the patient from one organ, or portion of the body, to another organ, or portion of the body. Certain pharmaceutically-acceptable excipients may be chosen for their ability to enhance patient compliance.

Suitable pharmaceutically-acceptable excipients include the following types of excipients: diluents, fillers, binders, disintegrants, lubricants, glidants, granulating agents, coating agents, wetting agents, solvents, co-solvents, suspending agents, emulsifiers, sweeteners, flavoring agents, flavor masking agents, coloring agents, anticaking agents, humectants, chelating agents, plasticizers, viscosity increasing agents, antioxidants, preservatives, stabilizers, surfactants, and buffering agents. The skilled artisan will appreciate that certain pharmaceutically-acceptable excipients may serve more than one function and may serve alternative functions depending on how much of the excipient is present in the formulation and what other ingredients are present in the formulation.

Skilled artisans possess the knowledge and skill in the art to enable them to select suitable pharmaceutically-acceptable excipients in appropriate amounts for use in the invention. In addition, there are a number of resources that are available to the skilled artisan which describe pharmaceutically-acceptable excipients and may be useful in selecting suitable pharmaceutically-acceptable excipients. Examples include *Remington's Pharmaceutical Sciences* (Mack Publishing Company), *The Handbook of Pharmaceutical Additives* (Gower Publishing Limited), and *The Handbook of Pharmaceutical Excipients* (the American Pharmaceutical Association and the Pharmaceutical Press).

The pharmaceutical compositions of the invention are prepared using techniques and methods known to those skilled in the art. Some of the methods commonly used in the art are described in *Remington's Pharmaceutical Sciences* (Mack Publishing Company).

In one aspect, the invention is directed to a solid oral dosage form such as a tablet or capsule comprising a safe and effective amount of a compound of the invention and a diluent or filler. Suitable diluents and fillers include lactose, sucrose, dextrose, mannitol, sorbitol, starch (e.g. corn starch, potato starch, and pre-gelatinized starch), cellulose and its derivatives (e.g. microcrystalline cellulose), calcium sulfate, and dibasic calcium phosphate. The oral solid dosage form may further comprise a binder. Suitable binders include starch (e.g. corn starch, potato starch, and pre-gelatinized starch), gelatin, acacia, sodium alginate, alginic acid, tragacanth, guar gum, povidone, and cellulose and its derivatives (e.g. microcrystalline cellulose). The oral solid dosage form may further comprise a disintegrant. Suitable disintegrants include crospovidone, sodium starch glycolate, croscarmellose, alginic acid, and sodium carboxymethyl cellulose. The oral solid dosage form may further comprise a lubricant. Suitable lubricants include stearic acid, magnesium stearate, calcium stearate, and talc.

In another aspect, the invention is directed to a dosage form adapted for administration to a patient parenterally including subcutaneous, intramuscular, intravenous or intradermal. Pharmaceutical formulations adapted for parenteral administration include aqueous and non-aqueous sterile injection solutions which may contain anti-oxidants, buffers, bacteriostats, and solutes that render the formulation isotonic with the blood of the intended recipient; and aqueous and non-aqueous sterile suspensions which may include suspending agents and thickening agents. The formulations may be presented in unit-dose or multi-dose containers, for example sealed ampules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules, and tablets.

In another aspect, the invention is directed to a dosage form adapted for administration to a patient by inhalation. For example, the compound of the invention may be inhaled into the lungs as a dry powder, an aerosol, a suspension, or a solution.

Dry powder compositions for delivery to the lung by inhalation typically comprise a compound of the invention as a finely divided powder together with one or more pharmaceutically acceptable excipients as finely divided powders. Pharmaceutically acceptable excipients particularly suited for use in dry powders are known to those skilled in the art and include lactose, starch, mannitol, and mono-, di-, and polysaccharides.

The dry powder compositions for use in accordance with the present invention are administered via inhalation devices. As an example, such devices can encompass capsules and cartridges of for example gelatin, or blisters of, for example, laminated aluminum foil. In various embodiments, each capsule, cartridge or blister may contain doses of composition according to the teachings presented herein. Examples of inhalation devices can include those intended for unit dose or multi-dose delivery of composition, including all of the devices set forth herein. As an example, in the case of multi-dose delivery, the formulation can be pre-metered (e.g., as in Diskus®, see GB2242134, U.S. Pat. Nos. 6,032,666, 5,860,419, 5,873,360, 5,590,645, 6,378,519 and 6,536,427 or Diskhaler, see GB 2178965, 2129691 and 2169265, U.S. Pat. Nos. 4,778,054, 4,811,731, 5,035,237) or metered in use (e.g., as in Turbuhaler, see EP 69715, or in the devices described in U.S. Pat. No. 6,321,747). An example of a unit-dose device is Rotahaler (see GB 2064336). In one embodiment, the Diskus® inhalation device comprises an elongate strip formed from a base sheet having a plurality of recesses spaced along its length and a lid sheet peelably sealed thereto to define a plurality of containers, each container having therein an inhalable formulation containing the compound optionally with other excipients and additive taught herein. The peelable seal is an engineered seal, and in one embodiment the engineered seal is a hermetic seal. Preferably, the strip is sufficiently flexible to be wound into a roll. The lid sheet and base sheet will preferably have leading end portions which are not sealed to one another and at least one of the leading end portions is constructed to be attached to a winding means. Also, preferably the engineered seal between the base and lid sheets extends over their whole width. The lid sheet may preferably be peeled from the base sheet in a longitudinal direction from a first end of the base sheet.

A dry powder composition may also be presented in an inhalation device which permits separate containment of two different components of the composition. Thus, for example, these components are administrable simultaneously but are stored separately, e.g., in separate pharmaceutical compositions, for example as described in WO 03/061743 A1 WO 2007/012871 A1 and/or WO2007/068896, as well as U.S. Pat. Nos. 8,113,199, 8,161,968, 8,511,304, 8,534,281, 8,746,242 and 9,333,310.

In one embodiment an inhalation device permitting separate containment of components is an inhaler device having two peelable blister strips, each strip containing pre-metered doses in blister pockets arranged along its length, e.g., multiple containers within each blister strip, e.g., as found in ELLIPTA®. Said device has an internal indexing mechanism which, each time the device is actuated, peels opens a pocket of each strip and positions the blisters so that each newly exposed dose of each strip is adjacent to the manifold which communicates with the mouthpiece of the device. When the patient inhales at the mouthpiece, each dose is simultaneously drawn out of its associated pocket into the manifold and entrained via the mouthpiece into the patient's respiratory tract. A further device that permits separate containment of different components is DUOHALER™ of Innovata. In addition, various structures of inhalation devices provide for the sequential or separate delivery of the pharmaceutical composition(s) from the device, in addition to simultaneous delivery.

Aerosols may be formed by suspending or dissolving a compound of the invention in a liquefied propellant. Suitable propellants include halocarbons, hydrocarbons, and other liquefied gases. Representative propellants include: trichlorofluoromethane (propellant 11), dichlorofluoromethane (propellant 12), dichlorotetrafluoroethane (propellant 114), tetrafluoroethane (HFA-134a), 1,1-difluoroethane (HFA-152a), difluoromethane (HFA-32), pentafluoroethane (HFA-12), heptafluoropropane (HFA-227a), perfluoropropane, perfluorobutane, perfluoropentane, butane, isobutane, and pentane. Aerosols comprising a compound of the invention will typically be administered to a patient via a metered dose inhaler (MDI). Such devices are known to those skilled in the art.

The aerosol may contain additional pharmaceutically acceptable excipients typically used with multiple dose inhalers such as surfactants, lubricants, cosolvents and other excipients to improve the physical stability of the formulation, to improve valve performance, to improve solubility, or to improve taste.

Suspensions and solutions comprising a compound of the invention may also be administered to a patient via a nebulizer. The solvent or suspension agent utilized for nebulization may be any pharmaceutically acceptable liquid such as water, aqueous saline, alcohols or glycols, e.g., ethanol, isopropyl alcohol, glycerol, propylene glycol, polyethylene glycol, etc. or mixtures thereof. Saline solutions utilize salts which display little or no pharmacological activity after administration. Both organic salts, such as alkali metal or ammonium halogen salts, e.g., sodium chloride, potassium chloride or organic salts, such as potassium, sodium and ammonium salts or organic acids, e.g., ascorbic acid, citric acid, acetic acid, tartaric acid, etc. may be used for this purpose.

Other pharmaceutically acceptable excipients may be added to the suspension or solution. The compound of the invention may be stabilized by the addition of an inorganic acid, e.g., hydrochloric acid, nitric acid, sulfuric acid and/or phosphoric acid; an organic acid, e.g., ascorbic acid, citric acid, acetic acid, and tartaric acid, etc., a complexing agent such as EDTA or citric acid and salts thereof; or an antioxidant such as antioxidant such as vitamin E or ascorbic acid. These may be used alone or together to stabilize the compound of the invention. Preservatives may be added such as benzalkonium chloride or benzoic acid and salts thereof. Surfactant may be added particularly to improve the physical stability of suspensions. These include lecithin, disodium dioctylsulphosuccinate, oleic acid and sorbitan esters.

The compounds of Formula (I) and pharmaceutically acceptable salts thereof may be used in combination with one or more other agents which may be useful in the prevention or treatment of allergic disease, inflammatory disease, autoimmune disease, for example; antigen immunotherapy, anti-histamines, corticosteroids, (eg fluticasone propionate, fluticasone furoate, beclomethasone dipropionate, budesonide, ciclesonide, mometasone furoate, triamcinolone, flunisolide), NSAIDs, leukotriene modulators (e.g. montelukast, zafirlukast, pranlukast), iNOS inhibitors, tryptase inhibitors, IKK2 inhibitors, p38 inhibitors, Syk inhibitors, protease inhibitors such as elastase inhibitors, integrin antagonists (e.g., beta-2 integrin antagonists), adenosine A2a agonists, mediator release inhibitors such as sodium chromoglycate, 5-lipoxygenase inhibitors (zyflo), DP1 antagonists, DP2 antagonists, PI3K delta inhibitors, ITK inhibitors, LP (lysophosphatidic) inhibitors or FLAP (5-lipoxygenase activating protein) inhibitors (e.g. sodium 3-(3-(tert-butylthio)-1-(4-(6-ethoxypyridin-3-yl)benzyl)-5-((5-methylpyridin-2-yl)methoxy)-1H-indol-2-yl)-2,2-dimethylpropanoate), bronchodilators (e.g., muscarinic antagonists, beta-2 agonists), methotrexate, and similar agents; monoclonal antibody therapy such as anti-IgE, anti-TNF, anti-IL-5, anti-IL-6, anti-IL-12, anti-IL-1 and similar agents; cytokine receptor therapies e.g. etanercept and similar agents; antigen non-specific immunotherapies (e.g. interferon or other cytokines/chemokines, chemokine receptor modulators such as CCR3, CCR4 or CXCR2 antagonists, other cytokine/chemokine agonists or antagonists, TLR agonists and similar agents).

The compounds may also be used in combination with agents for aiding transplantation including Cyclosporines, Tacrolimus, Mycophenolate mofetil, Prednisone, Azathioprine, Sirolimus, Daclizumab, Basiliximab, or OKT3.

They may also be used in combination with agents for Diabetes: metformin (biguanides), meglitinides, sulfonylureas, DPP-4 inhibitors, Thiazolidinediones, Alpha-glucosidase inhibitors, Amylin mimetics, Incretin mimetics, and insulin.

The compounds may be used in combination with antihypertensives such as diuretics, ACE inhibitors, ARBS, calcium channel blockers, and beta blockers.

One embodiment of the invention encompasses combinations comprising one or two other therapeutic agents. It will be clear to a person skilled in the art that, where appropriate, the other therapeutic ingredient(s) may be used in the form of salts, for example as alkali metal or amine salts or as acid addition salts, or prodrugs, or as esters, for example lower alkyl esters, or as solvates, for example hydrates to optimize the activity and/or stability and/or physical characteristics, such as solubility, of the therapeutic ingredient. It will be clear also that, where appropriate, the therapeutic ingredients may be used in optically pure form.

The combinations referred to above may conveniently be presented for use in the form of a pharmaceutical formulation and thus pharmaceutical formulations comprising a combination as defined above together with a pharmaceutically acceptable diluent or carrier represent a further aspect of the invention.

The individual compounds of such combinations may be administered either sequentially or simultaneously in separate or combined pharmaceutical formulations. In one embodiment, the individual compounds will be administered simultaneously in a combined pharmaceutical formulation. Appropriate doses of known therapeutic agents will readily be appreciated by those skilled in the art.

The invention thus provides, in a further aspect, a pharmaceutical composition comprising a combination of a compound of the invention together with another therapeutically active agent.

EXAMPLES

The following examples illustrate the invention. These examples are not intended to limit the scope of the present invention, but rather to provide guidance to the skilled artisan to prepare and use the compounds, compositions, and methods of the present invention. While particular embodiments of the present invention are described, the skilled artisan will appreciate that various changes and modifications can be made without departing from the spirit and scope of the invention.

All temperatures are given in degrees Celsius, all solvents are highest available purity and all reactions run under anhydrous conditions in an argon (Ar) or nitrogen ($N_2$) atmosphere where necessary.

Analtech Silica Gel GF and E. Merck Silica Gel 60 F-254 thin layer plates were used for thin layer chromatography. Both flash and gravity chromatography were carried out on E. Merck Kieselgel 60 (230-400 mesh) silica gel. The CombiFlash® system used for purification in this application was purchased from Isco, Inc. CombiFlash® purification was carried out using prepacked silica gel columns, a detector with UV wavelength at 254 nm and a variety of solvents or solvent combinations.

Preparative HPLC was performed using a Gilson Preparative System with variable wavelength UV detection or an Agilent Mass Directed AutoPrep (MDAP) system with both mass and variable wavelength UV detection or Waters Preparative System with UV/PDA detection or an Shimadzu PREP LC 20AP. A variety of reverse phase columns, e.g., Luna 5 m C18(2) 100 A, SunFire C18, XBridge C18, Atlantics T3 were used in the purification with the choice of column support dependent upon the conditions used in the purification. The compounds are eluted using a gradient of $CH_3CN$ and water. Neutral conditions used an $CH_3CN$ and water gradient with no additional modifier, acidic conditions used an acid modifier, 0.1% TFA (added to both the $CH_3CN$ and water) or 0.1% formic acid and basic conditions used a basic modifier, 0.1% $NH_4OH$ (added to the water) or 10 mM ammonium bicarbonate.

Analytical HPLC was run using an Agilent system, Shimadzu/Sciex LCMS with variable wavelength UV detection using reverse phase chromatography with a $CH_3CN$ and water gradient with a 0.02 or 0.1% TFA modifier (added to each solvent). LC-MS was determined using either a PE Sciex Single Quadrupole 150EX LC-MS, or Waters ZQ Single Quadrupole LC-MS or Agilent 1200 series SL (dectectors: Agilent 6140 single quadrupole and Agilent 1200 MWD SL) instruments. The compound is analyzed using a reverse phase column, e.g., Thermo Hypersil Gold C18, eluted using a gradient of $CH_3CN$ and water with a low percentage of an acid modifier such as 0.02% TFA or 0.1% formic acid or a base modifier such as 5 mM ammonium bicarbonate (adjusted to pH 10 with aqueous ammonia). When specified "acid method" refers to 0.1% formic acid in water and $CH_3CN$ gradient (1.8 min. 0.9 mL/min flow) with a Waters Acquity UPLC HSS C18; 1.8μ; 2.1×50 mm at 50° C.; "basic method" refers to 95:5 $H_2O+0.1\%$ $NH_4OH$:$CH_3CN$ (pH=9.4) and water gradient (1.8 min. 0.9 mL/min flow) with a Waters Acquity UPLC BEH C18; 1.7μ; 2.1×50 mm at 50° C. and "overnight basic method" refers to 95:5 $H_2O+0.1\%$ $NH_4OH$:$CH_3CN$ (pH=9.4) and water gradient (16 min. 0.8 mL/min flow) with a Waters Acquity UPLC BEH C18; 1.7μ; 2.1×50 mm at 50° C.

Preparative Chiral SFC was performed using a Thar/Waters Preparative SFC System with single wavelength UV detection system or PDA detector. A variety of chiral SFC columns, e.g. Chiralpak IA, IC, AY, AD. OD, OJ, C2 were used in the purification. The compounds are eluted using supercritical fluid $CO_2$ and co-solvents, such as MeOH, EtOH, IPA, and combination of these solvent in different ratio based on the compound selectivity. Modifiers (0.1% of TFA, $NH_4OH$, DEA) would be used as needed.

Analytical Chiral SFC was run using a Thar/Waters SFC system with variable wavelength UV detection or PDA detector. A variety of chiral SFC columns, e.g. Chiralpak IA, IB, IC, ID, AY, AD, AS, CCL4 were used in the purification. The compounds are eluted using supercritical fluid $CO_2$ and co-solvents, such as MeOH, EtOH, IPA, and combination of these solvent in different ratio based on the compound selectivity. Modifiers (0.1% of TFA, $NH_4OH$, DEA) would be used as needed.

Celite® is a filter aid composed of acid-washed diatomaceous silica, and is a registered trademark of Manville Corp., Denver, Colo. Isolute® is a functionalized silica gel based sorbent, and is a registered trademark of Biotage AB Corp., Sweden.

Nuclear magnetic resonance spectra were recorded at 400 MHz using a Bruker AVANCE 400 or Brucker DPX400 or Varian MR400 400 MHz spectrometer. $CDCl_3$ is deuteriochloroform, DMSO-$D_6$ is hexadeuteriodimethylsulfoxide, and MeOD is tetradeuteriomethanol, $CD_2Cl_2$ is deuteriodichloromethane. Chemical shifts are reported in parts per million (δ) downfield from the internal standard tetramethylsilane (TMS) or calibrated to the residual proton signal in the NMR solvent (e.g., $CHCl_3$ in $CDCl_3$). Abbreviations for NMR data are as follows: s=singlet, d=doublet, t=triplet, q=quartet, m=multiplet, dd=doublet of doublets, dt=doublet of triplets, app=apparent, br=broad. J indicates the NMR coupling constant measured in Hertz.

Heating of reaction mixtures with microwave irradiations was carried out on a Biotage Initiator® or CEM microwave reactor, typically employing the high absorbance setting.

Cartridges or columns containing polymer based functional groups (acid, base, metal chelators, etc) can be used as part of compound workup. The "amine" columns or cartridges are used to neutralize or basify acidic reaction mixtures or products. These include $NH_2$ Aminopropyl SPE-ed SPE Cartridges available from Applied Separations and diethylamino SPE cartridges available from United Chemical Technologies, Inc.

General Methods Used in Examples:
Acidic Method (Analytical)
HPLC System: Agilent 1200 series SL
Mass Spec Detector: Agilent 6140 single quadrupole
Second Detector: Agilent 1200 MWD SL
Eluent A: 0.1% Formic Acid in Water
Eluent B: $CH_3CN$
Flow Rate: 0.9 ml/min
Column: Waters Acquity UPLC HSS C18; 1.8μ; 2.1×50 mm
Column T: 50° C.

| Time (mins) | % B |
|---|---|
| 0.0 | 5 |
| 0.1 | 5 |
| 1.11 | 95 |
| 1.67 | 95 |
| 1.68 | 5 |
| 1.80 | 5 |

Capillary voltage: 3000V on ES pos (2700V on ES Neg)
Fragmentor/Gain: 190 on ES pos (160 on ES neg)
Gain: 1
Drying gas flow: 12.0 L/min
Gas Temperature: 345° C.
Nebuliser Pressure: 60 psig
Scan Range: 125-1000 amu
Ionisation Mode: ElectroSpray Positive-Negative switching
Basic Method (Analytical)
HPLC System: Agilent 1200 series SL
Mass Spec Detector: Agilent 6140 single quadrupole
Second Detector: Agilent 1200 MWD SL
Eluent A: 95:5 H2O+0.1% NH4OH:CH3CN (pH=9.4)
Eluent B: $CH_3CN$
Flow Rate: 0.9 ml/min
Column: Waters Acquity UPLC BEH C18; 1.7μ; 2.1×50 mm
Column T: 50° C.

| Time (mins) | % B |
|---|---|
| 0.0 | 5 |
| 0.1 | 5 |
| 1.11 | 95 |
| 1.67 | 95 |
| 1.68 | 5 |
| 1.80 | 5 |

Capillary voltage: 3000V on ES pos (2700V on ES Neg)
Fragmentor/Gain: 190 on ES pos (160 on ES neg)
Gain: 1
Drying gas flow: 12.0 L/min
Gas Temperature: 345° C.
Nebuliser Pressure: 60 psig
Scan Range: 125-1000 amu
Ionisation Mode: ElectroSpray Positive-Negative switching
Overnight Basic Method (Analytical)
HPLC System: Agilent 1200 series SL
Mass Spec Detector: Agilent 6140 single quadrupole
Second Detector: Agilent 1200 MWD SL
Eluent A: 95:5 H2O+0.1% NH4OH:CH3CN (pH=9.4)
Eluent B: $CH_3CN$
Flow Rate: 0.8 ml/min
Column: Waters Acquity UPLC BEH C18; 1.7μ; 2.1×50 mm
Column T: 50° C.

| Time (mins) | % B |
|---|---|
| 0.0 | 5 |
| 0.6 | 5 |
| 11.0 | 95 |
| 14.1 | 95 |

| Time (mins) | % B |
|---|---|
| 14.2 | 5 |
| 16 | 5 |

Capillary voltage: 3000V on ES pos (2700V on ES Neg)
Fragmentor/Gain: 190 on ES pos (160 on ES neg)
Gain: 1
Drying gas flow: 12.0 L/min
Gas Temperature: 345° C.
Nebuliser Pressure: 60 psig
Scan Range: 125-800 amu
Ionisation Mode: ElectroSpray Positive-Negative switching
Abbreviations are listed in the table below. All other abbreviations are as described in the ACS Style Guide (American Chemical Society, Washington, D.C., 1986).

| Table of Abbreviations |
|---|
| [Rh(cod)Cl]$_2$ or [RhCl(cod)]$_2$: di-μ-chlorido-bis[$\eta^2,\eta^2$-(cycloocta-1,5-diene)rhodium |
| ®T3P: 2,4,6-tripropyl-1,3,5,2,4,6-trioxatriphosphorinane 2,4,6-trioxide |
| [C.: degree Celsius |
| AcOH: acetic acid |
| ADDP: (E)-diazene-1,2-diylbis(piperidin-1-ylmethanone) |
| aq = aqueous |
| BINAP: 2,2'-bis(diphenylphosphino)-1,1'-binaphthalene |
| CDI: Carbonyl dimidazole |
| CH$_2$Cl$_2$: dichloromethane |
| CH$_3$CN: acetonitrile |
| CHCl$_3$: chloroform |
| Cs$_2$CO$_3$: cesium carbonate |
| DBU: 1,8-diazabicyclo[5.4.0]undec-7-ene |
| DCE: dichloromethane |
| DCM: dichloromethane |
| DIPEA or DIEA: diisopropylethyl amine |
| DME: dimethyl ether |
| DMF: N,N-dimethylformamide |
| DMF-DMA or DMF-dimethyl acetal: N,N-dimethylformaide-dimethyl acetal |
| DMSO: dimethyl sulfoxide |
| EDC: 1-ethyl-3-(3-dimethylaminopropyl)carbodiimide |
| Et$_2$O: diethyl ether |
| Et$_3$N: triethylamine |
| EtOAc: ethyl acetate |
| EtOH: ethanol |
| g: gram(s) |
| h: hour(s) |
| HATU: O-(7-azabenzotriazol-1-yl)-N,N,N',N'-tetramethyluronium hexafluorophosphate |
| HBTU: N,N,N',N'-tetramethyl-O-(1H-benzotriazol-1-yl)uronium hexafluorophosphate |
| HCl: hydrochloric acid |
| HOAt: 1-hydroxy-7-azabenzotriazole |
| HPLC: high performance liquid chromatography |
| IPA: isopropyl alcohol |
| K$_2$CO$_3$: potassium carbonate |
| KOAc: potassium acetate |
| LAH: lithium aluminum hydride |
| LC: liquid chromatography |
| LC-MS: liquid chromatography-mass spectroscopy |
| LiBH$_4$: lithium borohydride |
| LiHMDS: lithium hexamethyldisilazane |
| LiOH: lithium hydroxide |
| M: molar |
| MeCN: acetonitrile |
| MeI: methyl iodide |
| MeOH: methanol |
| mg: milligram(s) |
| MgCl$_2$: magnesium chloride |
| MgSO$_4$: magnesium sulfate |
| MHz: megahertz |
| min: minute(s) |
| mL: milliliter(s) |
| mmol: millimole(s) |

| Table of Abbreviations |
|---|
| MS: mass spectroscopy |
| N$_2$: nitrogen gas |
| Na$_2$CO$_3$: sodium carbonate |
| Na$_2$SO$_4$: sodium sulfate |
| NaBH$_3$CN or NaCNBH$_3$: sodium cyanoborohydride |
| NaCl: sodium chloride |
| NaH: sodium hydride |
| NaHCO$_3$: sodium bicarbonate |
| NaHMDS: sodium hexamethyldisilazane |
| NaHSO$_4$: sodium bisulfate |
| NaOAc: sodium acetate |
| NaOH: sodium hydroxide |
| NBS: N-bromosuccinimide |
| nBuLi: n-butyl lithium |
| NH$_4$Cl: ammonium chloride |
| NMR: nuclear magnetic resonance |
| P(tBu)$_3$: tri-t-butyl phosphine |
| Pd(PhP$_3$)$_4$: tetrakistriphenylphosphine palladium |
| Pd/C: pallidium on carbon |
| Pd$_2$(dba)$_3$: tris(dibenzylideneacetone)-dipalladium(0) |
| PdCl$_2$(dppf) or Pd(dppf)Cl$_2$: [1,1'-bis(diphenylphosphino)-ferrocene] dichloropalladium(II) |
| Petrol: petroleum ether |
| PS-PPh$_3$: polymer supported triphenylphosphine |
| PtO$_2$: platinum(IV) oxide |
| RT: room temperature |
| T3P: 2,4,6-tripropyl-1,3,5,2,4,6-trioxatriphosphorinane-2,4,6-trioxide solution |
| TEA: triethylamine |
| TFA: trifluoroacetic acid |
| TFFH: tetrafluoroformamidinium hexafluorophosphate |
| THF: tetrahydrofuran |
| triflic anhydride: trifluoromethanesulfonic anhydride |
| TsOH: p-toluenesulfonic acid |
| wt %: weight percent |

INTERMEDIATES

2-Bromo-N-(2-methylallyl)benzenesulfonamide

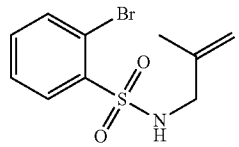

To a solution of 2-bromobenzene-1-sulfonyl chloride (25 g, 98 mmol) in dichloromethane (DCM) (250 mL) at 0° C. was added TEA (13.64 mL, 98 mmol) and 2-methylprop-2-en-1-amine (6.96 g, 98 mmol) and stirred for 10 min. Then it was stirred at RT for 16 h. The reaction mixture was quenched with ice cold water and extracted with DCM (2×200 mL). The combined organic layer washed with ice cold water (2×100 mL), washed with brine solution (100 mL), dried over anhydrous Na$_2$SO$_4$. It was filtered and concentrated to give the title compound (20 g, 68.3 mmol, 69.8% yield). LC-MS m/z 289.81 (M+H)$^+$, 2.20 min (ret. time).

105

4-Methyl-2,3,4,5-tetrahydrobenzo[f][1,2]thiazepine 1,1-dioxide

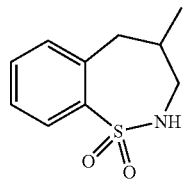

To a solution of 2-bromo-N-(2-methylallyl)benzenesulfonamide (16 g, 55.1 mmol) in toluene (160 mL) at RT was added AIBN (1.811 g, 11.03 mmol). The reaction mixture was heated to 75° C. and added tri-n-butyltin hydride (29.4 mL, 110 mmol). It was heated at 110° C. for 18 h. The reaction mixture was cooled to RT and diluted with ice water (500 mL) and extracted with EtOAc (2×300 mL). The combined organic layer was washed with chilled brine solution (200 mL) and dried over anhydrous $Na_2SO_4$, filtered and concentrated. The crude residue was purified on flash column chromatography eluting with 15% ethyl acetate in hexane. Desired fractions were concentrated to give the title compound (8.51 g, 39.9 mmol, 72.3% yield) as a white solid. LC-MS m/z 211.11 $(M+H)^+$, 1.826 min (ret. time).

(S)-4-Methyl-2,3,4,5-tetrahydrobenzo[f][1,2]thiazepine 1,1-dioxide and (R)-4-methyl-2,3,4,5-tetrahydrobenzo[f][1,2]thiazepine 1,1-dioxide

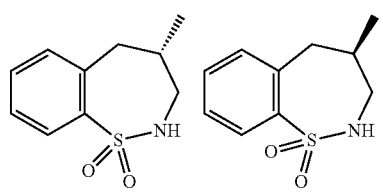

4-Methyl-2,3,4,5-tetrahydrobenzo[f][1,2]thiazepine 1,1-dioxide (4000 mg, 18.93 mmol) was resolved by Chiral SFC (Column: Chiralpak AY 20×250 mm, 5 u; Co-solvent: 20% EtOH; Flow rate: 50 mg/min; Back pressure: 100 Bar) to give single enantiomerically pure (S)-4-methyl-2,3,4,5-tetrahydrobenzo[f][1,2]thiazepine 1,1-dioxide (2.2996 g, 10.88 mmol, 57.5% yield) (chiral SFC ret. time: 1.85 min) LC-MS m/z 211.9 $(M+H)^+$, 0.72 min (ret. time) and single enantiomerically pure (R)-4-methyl-2,3,4,5-tetrahydrobenzo[f][1,2]thiazepine 1,1-dioxide (2.2195 g, 10.50 mmol, 55.5% yield) (chiral SFC ret. time: 2.5 min) LC-MS m/z 211.9 $(M+H)^+$, 0.72 min (ret. time).

106

N-(4-Methoxybenzyl)-2-methylenebutan-1-amine

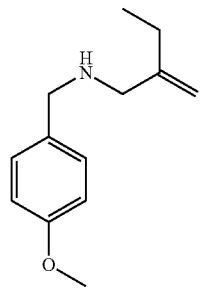

To a solution of (4-methoxyphenyl)methanamine (24.46 g, 178 mmol) in toluene (100 mL) was added 2-methylenebutanal (15 g, 178 mmol). It was heated at 95° C. for 48 h. The reaction mixture was concentrated and dissolved in ethanol (100.0 mL), $NaBH_4$ (6.75 g, 178 mmol) was added at 0° C. and stirred at RT for 4 h. The reaction mixture was concentrated, quenched with water, extracted with DCM twice. The organic layer was dried under anhydrous $Na_2SO_4$, filtered and concentrated. The crude product was purified on flash column chromatography eluting with EtOAc: ether (18:72). Desired fractions were concentrated to give the title compound (13 g, 30.1 mmol, 16.87% yield) as pale yellow liquid. LCMS m/z 206.05 $(M+H)^+$, 3.70 min (ret. time).

2-Bromo-N-(4-methoxybenzyl)-N-(2-methylenebutyl)benzenesulfonamide

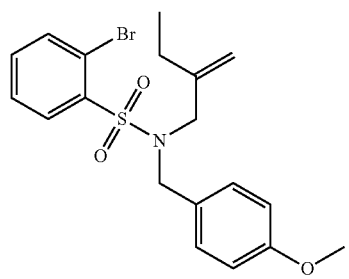 [SMILES: C=C(CC)CN(Cc1ccc(OC)cc1)S(=O)(=O)c1ccccc1Br]

To a solution of 2-bromobenzene-1-sulfonyl chloride (7.60 g, 29.8 mmol) in dichloromethane (DCM) (130 mL) at 0° C. was added N-(4-methoxybenzyl)-2-methylenebutan-1-amine (13 g, 29.8 mmol) and TEA (8.30 mL, 59.5 mmol). The reaction mixture was stirred at RT for 6 h. The reaction mixture was quenched with cold water, extracted with twice DCM, brine solution. The organic layer was dried under anhydrous $Na_2SO_4$, filtered and concentrated. The crude residue was purified by column chromatography eluting with EtOAC:hexane (5:95). Desired fractions were concentrated to give the title compound (9 g, 21.21 mmol, 71.3% yield) as white solid. LCMS m/z 426.05 $(M+H)^+$, 4.18 min (ret. time).

2-Bromo-N-(2-methylenebutyl)benzenesulfonamide

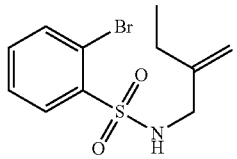 [SMILES: C=C(CC)CNS(=O)(=O)c1ccccc1Br]

To a solution of 2-bromo-N-(4-methoxybenzyl)-N-(2-methylenebutyl)benzenesulfonamide (9 g, 19.67 mmol) in acetonitrile (90 mL) and water (30 mL) at 0° C. was added CAN (43.1 g, 79 mmol). It was stirred at RT for 6 h. The reaction mixture was concentrated, quenched with ice water, extracted with DCM twice. The organic layer was dried under anhydrous $Na_2SO_4$, filtered and concentrated. The crude compound was purified by column chromatography eluting with EtOAC:hexane (15:85). Desired fractions were concentrated. It was then dissolved in methanol (50 mL). $NaBH_4$ (0.744 g, 19.67 mmol) was added at 0° C. The reaction mixture was stirred at ambient temperature for 4 h. The reaction mixture was concentrated, quenched with ice water, extracted with DCM twice. The organic layer was dried over anhydrous $Na_2SO_4$, filtered and concentrated. The crude compound was purified by column chromatography eluting with EtOAC:hexane (06:94) to give the title compound (3 g, 9.14 mmol, 46.5% yield) as white solid. LCMS m/z 303.96 $(M+H)^+$, 2.31 min (ret. time).

4-Ethyl-2,3,4,5-tetrahydrobenzo[f][1,2]thiazepine 1,1-dioxide

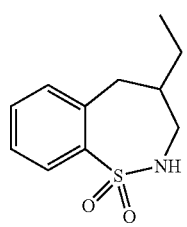

To a solution of 2-bromo-N-(2-methylenebutyl)benzenesulfonamide (3 g, 9.07 mmol) in benzene (30 mL) was added AIBN (0.447 g, 2.72 mmol) and heated at 65° C., tributylstannane (2.90 g, 9.98 mmol) was added at this temperature. The reaction was stirred at 85° C. for 16 h. The reaction mixture was concentrated. The crude product was purified on grace column chromatography with 100-200 silica gel mesh by using EtOAc:hexane (23:77) as solvent. The eluted fractions were concentrated. The product was washed with n-pentane (23 mL) and diethyl ether (10 mL) to give the title compound (980 mg, 4.21 mmol, 46.4% yield) as white solid. LCMS m/z 226.11 $(M-H)^+$, 2.04 min (ret. time) $^1$H NMR (400 MHz, DMSO-d6) δ ppm: 7.77 (dd, J=7.78, 1.21 Hz, 1H) 7.55 (brt, J=6.47 Hz, 1H) 7.45-7.51 (m, 1H) 7.34-7.42 (m, 2H) 3.37 (br s, 1H) 3.04-3.28 (m, 3H) 1.56 (br s, 1H) 1.15 (br s, 2H) 0.87 (t, J=7.34 Hz, 3H).

(S)-4-Ethyl-2,3,4,5-tetrahydrobenzo[f][1,2]thiazepine 1,1-dioxide and (R)-4-ethyl-2,3,4,5-tetrahydrobenzo[f][1,2]thiazepine 1,1-dioxide

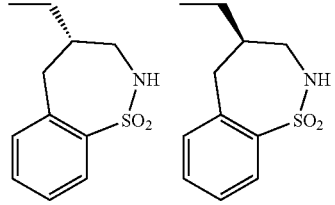

4-Ethyl-2,3,4,5-tetrahydrobenzo[f][1,2]thiazepine 1,1-dioxide (1 g, 4.44 mmol) was resolved by Chiral SFC (Column: Chiralpak AY 20×250 mm, 5 u; Co-solvent: 25% EtOH; Flowrate: 50 g/min; Back pressure: 100 Bar) to give single enantiomerically pure (S)-4-ethyl-2,3,4,5-tetrahydrobenzo[f][1,2]thiazepine 1,1-dioxide (471 mg, 2.090 mmol, 47.1% yield) (chiral SFC ret. time: 1.86 min) LC-MS m/z 226.1 $(M+H)^+$, 0.92 min (ret. time) and (R)-4-ethyl-2,3,4,5-tetrahydrobenzo[f][1,2]thiazepine 1,1-dioxide (472 mg, 2.095 mmol, 47.2% yield) (chiral SFC ret. time: 2.47 min) LC-MS m/z 226.1 $(M+H)^+$, 0.92 min (ret. time).

2,5-Dibromo-N-(2-methylallyl)benzenesulfonamide

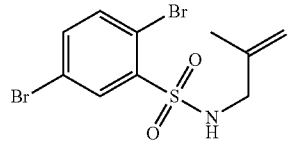

To a solution of 2,5-dibromobenzene-1-sulfonyl chloride (5 g, 14.95 mmol) in dichloromethane (50 mL) at 0° C. was added 2-methylprop-2-en-1-amine (1.063 g, 14.95 mmol) and TEA (2.084 mL, 14.95 mmol). It was stirred for 10 min and then stirred at RT for 16 h. The reaction mixture was quenched with ice cold water and extracted with DCM (2×50 mL). The combined organic layer washed with ice cold water (2×35 mL), washed with brine solution (50 mL), dried over anhydrous $Na_2SO_4$, filtered and concentrated to give the title compound (3.4 g, 8.58 mmol, 57.4% yield) LC-MS m/z 367.8 $(M+H)^+$, 2.58 min (ret. time).

8-Bromo-4-methyl-2,3,4,5-tetrahydrobenzo[f][1,2]thiazepine 1,1-dioxide

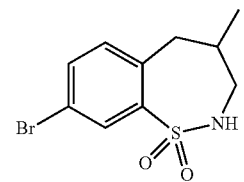

To a solution of 2,5-dibromo-N-(2-methylallyl)benzenesulfonamide (3.4 g, 9.21 mmol) in toluene (35 mL) at RT was added AIBN (0.303 g, 1.842 mmol). The reaction mixture was heated at 75° C. and tri-n-butyltin hydride (4.92 mL, 18.42 mmol) was added. It was stirred at 110° C. for 18 h. The crude residue was diluted with ethyl acetate (100 mL) and washed with brine solution (100 mL). The organic layer was dried over anhydrous Na₂SO₄, filtered and concentrated. The crude residue was purified on flash column chromatography eluting with 15% ethyl acetate in hexane. Desired fractions were concentrated to give the title compound (600 mg, 1.991 mmol, 21.61% yield) as an off-white solid. LC-MS m/z 287.8 (M+H)⁺, 2.29 min (ret. time).

rel-(R or S)-8-Bromo-4-methyl-2,3,4,5-tetrahydrobenzo[f][1,2]thiazepine 1,1-dioxide and rel-(R or S)-8-bromo-4-methyl-2,3,4,5-tetrahydrobenzo[f][1,2]thiazepine 1,1-dioxide

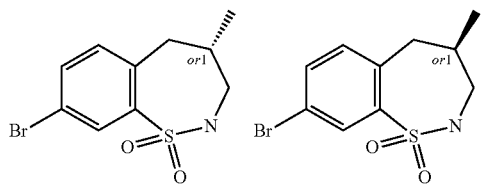

8-Bromo-4-methyl-2,3,4,5-tetrahydrobenzo[f][1,2]thiazepine 1,1-dioxide was resolved by Chiral SFC (Column: Chiralpak AY 20×250 mm, 5 u; Co-solvent: 20% EtOH; Flow rate: 50 g/min; Back pressure: 100 Bar) to give single enantiomerically pure rel-(R or S)-8-bromo-4-methyl-2,3,4,5-tetrahydrobenzo[f][1,2]thiazepine 1,1-dioxide (195 mg, 0.672 mmol, 32.5% yield) (chiral SFC ret. time: 3.06 min) LC-MS m/z 289.8 (M+H)⁺, 0.94 min (ret. time) and single enantiomerically pure rel-(R or S)-8-bromo-4-methyl-2,3,4,5-tetrahydrobenzo[f][1,2]thiazepine 1,1-dioxide (190 mg, 0.655 mmol, 31.7% yield) (chiral SFC ret. time: 4.03 min) LC-MS m/z 289.8 (M+H)⁺, 0.95 min (ret. time).

2-Bromo-N-(2-methylallyl)-5-(trifluoromethyl)benzenesulfonamide

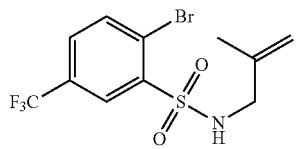 [SMILES: C=C(C)CNS(=O)(=O)c1cc(C(F)(F)F)ccc1Br]

To a suspension of 2-bromo-5-(trifluoromethyl)benzene-1-sulfonyl chloride (5 g, 15.46 mmol) in dichloromethane (DCM) (50 mL) at RT was added 2-methylprop-2-en-1-amine (1.231 g, 17.31 mmol) and triethylamine (4.31 mL, 30.9 mmol). It was stirred for 20 h. The reaction mixture was poured into ice-cold water and extracted with ethyl acetate (2×100 mL). The combined organic layer was washed with brine (100 mL) and dried over Na₂SO₄, filtered and concentrated to give the title compound (5 g, 13.88 mmol, 90% yield) as gummy liquid. LC-MS m/z 355.9 (M+H)⁺, 2.61 min (ret. time).

4-Methyl-8-(trifluoromethyl)-2,3,4,5-tetrahydrobenzo[f][1,2]thiazepine 1,1-dioxide

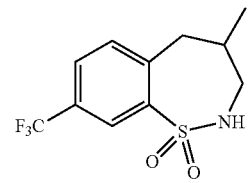 [SMILES: CC1CNS(=O)(=O)c2cc(C(F)(F)F)ccc2C1]

To a solution of 2-bromo-N-(2-methylallyl)-5-(trifluoromethyl)benzenesulfonamide (5 g, 13.96 mmol) in toluene (50 mL) was added AIBN (0.458 g, 2.79 mmol). The reaction mixture was heated to 60° C. and then tributylstannane (8.13 g, 27.9 mmol) was added. It was stirred at 100° C. for 20 h. The reaction mixture was cooled and concentrated. The crude residue was purified on flash column chromatography eluting with 25% EtOAc in hexane. Desired fractions were concentrated to give the title compound (720 mg, 2.52 mmol, 18.02% yield) as a white solid. LC-MS m/z 278.01 (M+H)⁺, 2.37 min (ret. time).

(S)-4-Methyl-8-(trifluoromethyl)-2,3,4,5-tetrahydrobenzo[f][1,2]thiazepine 1,1-dioxide and (R)-4-methyl-8-(trifluoromethyl)-2,3,4,5-tetrahydrobenzo[f][1,2]thiazepine 1,1-dioxide

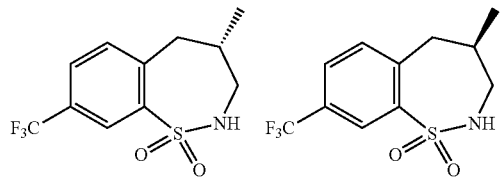 [SMILES: C[C@@H]1CNS(=O)(=O)c2cc(C(F)(F)F)ccc2C1 ; C[C@H]1CNS(=O)(=O)c2cc(C(F)(F)F)ccc2C1]

4-Methyl-8-(trifluoromethyl)-2,3,4,5-tetrahydrobenzo[f][1,2]thiazepine 1,1-dioxide (650 mg, 2.327 mmol) was resolved by Chiral SFC (Column: Chiralpak AD 20×250 mm, 5 u; Co-solvent: 5% IPA in Hexane; Flowrate: 10 mL/min; Back pressure: 100 Bar) to give single enantiomerically pure (S)-4-methyl-8-(trifluoromethyl)-2,3,4,5-tetrahydrobenzo[f][1,2]thiazepine 1,1-dioxide (219 mg, 0.784 mmol, 33.7% yield) (chiral HPLC ret. time: 15.171 min) LC-MS m/z 279.9 (M+H)⁺, 0.95 min (ret. time) and single enantiomerically pure (R)-4-methyl-8-(trifluoromethyl)-2,3,4,5-tetrahydrobenzo[f][1,2]thiazepine 1,1-dioxide (126 mg, 0.451 mmol, 19.38% yield) (chiral HPLC ret. time: 17.076 min) LC-MS m/z 279.9 (M+H)⁺, 0.96 min (ret. time).

2-Bromo-N-(2-methylallyl)-4-(trifluoromethyl)benzenesulfonamide

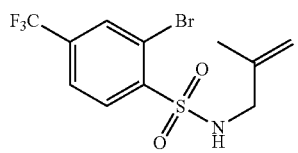 [SMILES: C=C(C)CNS(=O)(=O)c1ccc(C(F)(F)F)cc1Br]

111

To a solution of 2-bromo-4-(trifluoromethyl)benzene-1-sulfonyl chloride (5 g, 15.46 mmol) in dichloromethane (DCM) (50 mL) at 0° C. was added 2-methylprop-2-en-1-amine (1.209 g, 17.00 mmol) and TEA (4.31 mL, 30.9 mmol). The reaction mixture was stirred at RT for 16 h. The reaction mixture was quenched with cold water, extracted with DCM twice. The combined organic layer was washed with brine solution, dried over anhydrous Na$_2$SO$_4$, filtered and concentrated to give the title compound (4.2 g, 11.64 mmol, 75% yield). LC-MS m/z 357.98 (M+H)$^+$, 2.254 min (ret. time).

4-Methyl-7-(trifluoromethyl)-2,3,4,5-tetrahydrobenzo[f][1,2]thiazepine 1,1-dioxide

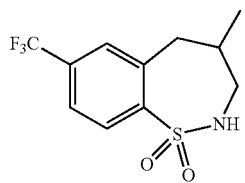 [SMILES: CC1CNS(=O)(=O)c2ccc(C(F)(F)F)cc2C1]

To a solution of 2-bromo-N-(2-methylallyl)-4-(trifluoromethyl)benzenesulfonamide (4.2 g, 11.73 mmol) in toluene (40 mL) was added AIBN (0.385 g, 2.345 mmol) and heated to 75° C. Tributyltin hydride (3.75 g, 12.90 mmol) was added at 75° C. and the reaction mixture was stirred at 110° C. for 16 h. The reaction mixture was cool and concentrated. The crude residue was purified on flash column chromatography eluting with EtOAC:hexane (11:89). Desired fractions were concentrated to give the title compound (1.6 g, 5.61 mmol, 47.8% yield). LC-MS m/z 278.09 (M+H)$^+$, 2.08 min (ret. time).

(R)-4-Methyl-7-(trifluoromethyl)-2,3,4,5-tetrahydrobenzo[f][1,2]thiazepine 1,1-dioxide and (S)-4-methyl-7-(trifluoromethyl)-2,3,4,5-tetrahydrobenzo[f][1,2]thiazepine 1,1-dioxide

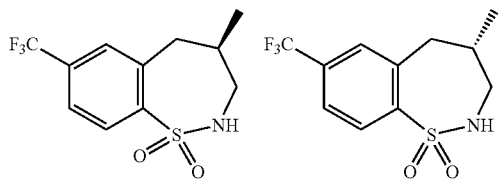

4-Methyl-7-(trifluoromethyl)-2,3,4,5-tetrahydrobenzo[f][1,2]thiazepine 1,1-dioxide (1500 mg, 5.37 mmol) was resolved by Chiral SFC (Column: Chiralpak AD 20×250 mm, 5 u; Co-solvent: 4% IPA/Hexane; Flow rate: 10 mL/min; Back pressure: 30 Bar) to give single enantiomerically pure (R)-4-methyl-7-(trifluoromethyl)-2,3,4,5-tetrahydrobenzo[f][1,2]thiazepine 1,1-dioxide (685 mg, 2.453 mmol, 45.7% yield) (chiral HPLC ret. time: 22.284 min) LC-MS m/z 280.0 (M+H)$^+$, 0.98 min (ret. time) and single enantiomerically pure (S)-4-methyl-7-(trifluoromethyl)-2,3,4,5-tetrahydrobenzo[f][1,2]thiazepine 1,1-dioxide (660 mg, 2.363 mmol, 44.0% yield) (chiral HPLC ret. time: 27.803 min) LC-MS m/z 280.0 (M+H)$^+$, 0.98 min (ret. time).

112

(R)-1-Aminobutan-2-ol

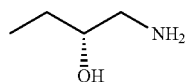

To a solution of ammonium hydroxide (113 mL, 2912 mmol) was added (R)-2-ethyloxirane (21 g, 291 mmol) and the result reaction mixture was stirred at 25° C. for 20 h. The reaction mixture was evaporated under vacuum on lyophilization to give the title compound (16 g, 180 mmol, 61.6% yield). It was carried to next step without further purification.

(R)-2-Chloro-N-(2-hydroxybutyl)pyridine-3-sulfonamide

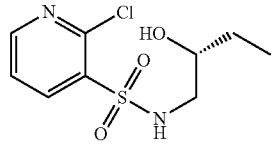 [SMILES: CC[C@@H](O)CNS(=O)(=O)c1cccnc1Cl]

To a solution of (R)-1-aminobutan-2-ol (13.45 g, 151 mmol) in tetrahydrofuran (THF) (50 mL) and water (10 mL) at RT was added K$_2$CO$_3$ (13.03 g, 94 mmol) and 2-chloropyridine-3-sulfonyl chloride (20 g, 94 mmol). It was stirred for 15 h. The reaction mixture was diluted with water (100 mL) and extracted with EtOAc (2×100 mL). The combined organic layer was washed with brine solution (200 mL) and dried over anhydrous Na$_2$SO$_4$, filtered and concentrated to give the title compound (16 g, 48.5 mmol, 51.5% yield) as a gammy liquid. LC-MS m/z 265.16 (M+H)$^+$, 2.61 min (ret. time).

(R)-4-Ethyl-3,4-dihydro-2H-pyrido[2,3-b][1,4,5]oxathiazepine 1,1-dioxide

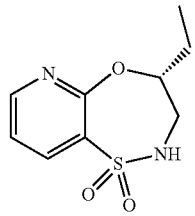

To a solution of (R)-2-chloro-N-(2-hydroxybutyl)pyridine-3-sulfonamide (16 g, 60.4 mmol) in dimethyl sulfoxide (DMSO) (160 mL) at 0° C. was added potassium tert-butoxide (6.78 g, 60.4 mmol). It was stirred at 80° C. for 2 h. The reaction mixture was cooled and diluted with ice water (500 mL) and extracted with EtOAc (2×300 mL). The combined organic layer was washed with chilled brine solution (200 mL) and dried over anhydrous Na$_2$SO$_4$, filtered and concentrated. The crude residue was purified on flash column chromatography eluting with 50% EtOAc in hexane. Desired fractions were concentrated to give the title compound (5.4 g, 23.66 mmol, 39.1% yield) as a pale yellow solid. LC-MS m/z 228.99 (M+H)⁺, 1.424 min (ret. time).

(R)-4-Ethyl-3,4-dihydro-2H-benzo[b][1,4,5]oxathiazepine 1,1-dioxide

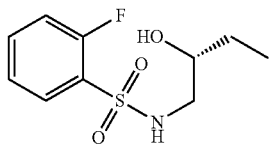 [SMILES: CC[C@@H](O)CNS(=O)(=O)c1ccccc1F]

To a solution of (R)-1-aminobutan-2-ol (14.66 g, 164 mmol) in tetrahydrofuran (THF) (200 mL) and water (60 mL) at RT was added K₂CO₃ (14.20 g, 103 mmol) and 2-fluorobenzene-1-sulfonyl chloride (20 g, 103 mmol). It was stirred for 16 h. The reaction mixture was diluted with water (100 mL) and extracted with EtOAc (2×100 mL). The combined organic layer was washed with brine solution (200 mL) and dried over anhydrous Na₂SO₄, filtered and concentrated to give the title compound (14 g, 53.8 mmol, 52.3% yield) as a gammy liquid. LC-MS m/z 494.83 (2M−H)⁺, 1.660 min (ret. time).

(R)-4-Ethyl-3,4-dihydro-2H-benzo[b][1,4,5]oxathiazepine 1,1-dioxide

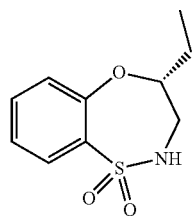

To a solution of (R)-2-fluoro-N-(2-hydroxybutyl)benzenesulfonamide (14 g, 56.6 mmol) in dimethyl sulfoxide (DMSO) (140 mL) at 0° C. was added potassium tert-butoxide (6.35 g, 56.6 mmol). It was then heated at 80° C. for 4 h. The reaction mixture was cooled and neutralized with 1N HCl, diluted with ice water (500 mL) and extracted with EtOAc (2×400 mL). The combined organic layer was washed with chilled brine solution (200 mL) and dried over anhydrous Na₂SO₄, filtered and concentrated. The crude residue was purified on flash column chromatography eluting with 50% EtOAc in hexane. Desired fractions were concentrated to give the title compound (11.12 g, 48.9 mmol, 86% yield) as a white solid. LC-MS m/z 228.05 (M+H)⁺, 1.84 min (ret. time).

2,5-Difluoro-N-(2-hydroxy-2-methylpropyl)benzenesulfonamide

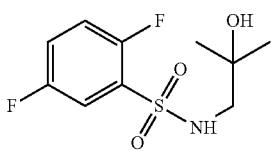 [SMILES: CC(C)(O)CNS(=O)(=O)c1cc(F)ccc1F]

To a solution of 2,5-difluorobenzene-1-sulfonyl chloride (10 g, 47.0 mmol) in tetrahydrofuran (THF) (10 mL) at 0° C. was added 1-amino-2-methylpropan-2-ol (4.19 g, 47.0 mmol) and potassium carbonate (6.50 g, 47.0 mmol). The reaction mixture was stirred at ambient temperature for 4 h. The reaction mixture was extracted with EtOAc (2×100 mL). The combined organic layer washed with brine solution (50 mL), dried over anhydrous Na₂SO₄, filtered and concentrated. The crude product was purified on flash column chromatography eluting with 60% ethyl acetate in n-hexane. Desired fractions were concentrated to give the title compound (7 g, 25.5 mmol, 54.2% yield) as off white solid. LCMS m/z 264 (M−H)⁺, 4.13 min (ret. time).

8-Fluoro-4,4-dimethyl-3,4-dihydro-2H-benzo[b][1,4,5]oxathiazepine 1,1-dioxide

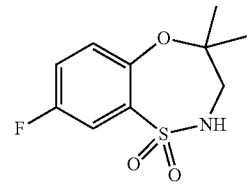 [SMILES: CC1(C)CNS(=O)(=O)c2cc(F)ccc2O1]

To a solution of 2,5-difluoro-N-(2-hydroxy-2-methylpropyl)benzenesulfonamide (7 g, 26.4 mmol) in DMSO (50 mL) at 0° C. was added potassium tert-butoxide (5.92 g, 52.8 mmol). The reaction mixture was stirred at 100° C. for 6 h. The reaction mixture was neutralized with 1N HCl at pH 6-7. It was extracted with ethyl acetate (3×100 mL). The combined organic layer was washed with brine solution (80 mL) and dried over anhydrous Na₂SO₄, filtered and concentrated. The crude residue was purified on flash column chromatography eluting with EtOAc:Hexane (6:4). Desired fractions were concentrated to give the title compound (2.9 g, 10.93 mmol, 41.4% yield) as an off-white solid. LCMS m/z 244.12 (M−H)⁺, 2.28 min (ret. time).

1-((1-(2-Fluorophenyl)propyl)amino)-2-methylpropan-2-ol

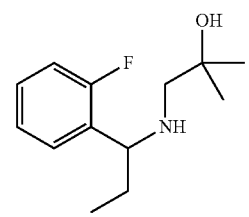 [SMILES: CCC(NCC(C)(C)O)c1ccccc1F]

To a solution of 1-amino-2-methylpropan-2-ol (10.54 g, 118 mmol) in toluene (400 mL) was added 1-(2-fluorophenyl)propan-1-one (15 g, 99 mmol). It was heated at 120° C. for 48 h. NaBH4 (7.46 g, 197 mmol) was added and stirred at RT for 48 h. The reaction mixture was concentrated and quenched with 1 N NaOH solution (80 mL) solution and extracted with ethyl acetate (2×100 mL). The organic layer was concentrated and purified on flash column chromatography eluting with EtOAc:hexane (4:6). Desired fractions were concentrated under vacuum to give the title compound (3.8 g, 10.69 mmol, 10.85% yield) as gummy liquid. LC-MS m/z 226.1 (M+H)⁺, 3.872 min (ret. time).

5-Ethyl-2,2-dimethyl-2,3,4,5-tetrahydrobenzo[f][1,4]oxazepine

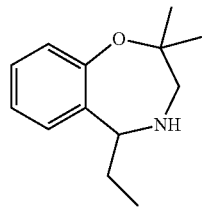

To a solution of 1-((1-(2-fluorophenyl)propyl)amino)-2-methylpropan-2-ol (3.5 g, 15.53 mmol) in dimethyl sulfoxide (DMSO) (20 mL) at 10° C. was added potassium tert-butoxide (8.72 g, 78 mmol). It was heated to 90° C. for 12 h. The reaction mixture was cooled to room temperature and poured in ice water (50 mL), then extracted with ethyl acetate (2×50 mL). The combined organic layer was concentrated. The crude residue was purified on flash column chromatography eluting with EtOAc:hexane (4:6). Desired fractions were concentrated to give the title compound (1.5 g, 4.79 mmol, 30.9% yield) as a gummy liquid. LC-MS m/z 206.2 (M+H)⁺, 3.255 min (ret. time).

Ethyl 3-(2-cyanophenyl)-2,2-dimethylpropanoate

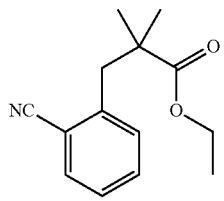

To a solution of ethyl isobutyrate (4.74 g, 40.8 mmol) in tetrahydrofuran (THF) (80 mL) at −78° C. was added LDA (30.6 mL, 61.2 mmol). It was stirred at that temperature for 45 min, then a solution of 2-(bromomethyl)benzonitrile (8 g, 40.8 mmol) in tetrahydrofuran (THF) (30 mL) was added slowly and stirred for at −78° C. for 1 h. The reaction was then allowed to warm to ambient temperature for 3 h. The reaction mixture was quenched with saturated NH₄Cl solution and extracted with DCM (2×30 mL). The combined organic layer was washed with brine solution (50 mL). The organic layer was dried over anhydrous Na₂SO₄, filtered and concentrated. The crude residue was purified by column chromatography eluting with 12% ethyl acetate in n-hexane. Desired fractions were concentrated to give the title compound (6 g, 24.85 mmol, 60.9% yield). ¹H NMR (400 MHz, chloroform-d) δ ppm: 1.11-1.31 (m, 9H) 3.10-3.23 (m, 2H) 4.15 (q, J=7.02 Hz, 2H) 7.26-7.37 (m, 2H) 7.44-7.53 (m, 1H) 7.62 (d, J=7.67 Hz, 1H).

3-(2-(Aminomethyl)phenyl)-2,2-dimethylpropan-1-ol

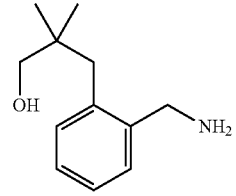

To a solution of ethyl 3-(2-cyanophenyl)-2,2-dimethylpropanoate (6 g, 25.9 mmol) in tetrahydrofuran (THF) (60 mL) at 0° C. was added LAH (78 mL, 78 mmol). It was stirred at 25° C. for 16 h. The reaction mixture was quenched with saturated Na₂SO₄ solution (15 mL), filtered and the filtrate was extracted with ethyl acetate (3×50 mL). The combined organic layer dried over anhydrous Na₂SO₄, filtered and concentrated to give the title compound (3 g, 14.88 mmol, 57.3% yield). LC-MS m/z 194.0 (M+H)⁺, 3.73 min (ret. time).

Ethyl 3-(2-cyanophenyl)-2,2-dimethylpropanoate

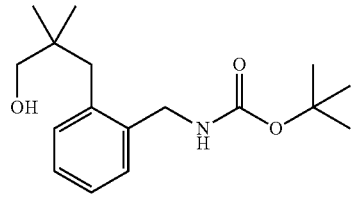 [SMILES: CC(C)(CO)Cc1ccccc1CNC(=O)OC(C)(C)C]

To a solution of 3-(2-(aminomethyl)phenyl)-2,2-dimethylpropan-1-ol (3 g, 15.52 mmol) in dichloromethane (DCM) (30 mL) was added Boc₂O (3.60 mL, 15.52 mmol). It was stirred at ambient temperature for 16 h. The reaction mixture was concentrated and purified by column chromatography eluting with 25% ethyl acetate in n-hexane. Desired fractions were concentrated to give the title compound (6 g, 24.85 mmol, 60.9% yield). LC-MS m/z 294.34 (M+H)⁺, 3.78 min (ret. time).

3-(2-(((tert-Butoxycarbonyl)amino)methyl)phenyl)-2,2-dimethylpropyl Methanesulfonate

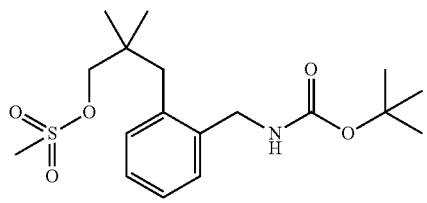 [SMILES: CC(C)(COS(C)(=O)=O)Cc1ccccc1CNC(=O)OC(C)(C)C]

To a solution of tert-butyl 2-(3-hydroxy-2,2-dimethylpropyl)benzylcarbamate (3 g, 10.22 mmol) in dichloromethane (DCM) (35 mL) at 0° C. was added TEA (3.56 mL, 25.6 mmol) and mesyl chloride (1.594 mL, 20.45 mmol). It was stirred at ambient temperature for 2 h. The reaction mixture was quenched with water (20 mL) and extracted with DCM (2×30 mL). The combined organic layer was washed with brine solution (50 mL). The organic layer was dried over anhydrous Na₂SO₄, filtered and concentrated. The crude residue was purified by column chromatography eluting with 20% ethyl acetate in n-hexane. Desired fractions were concentrated under reduced pressure to give the title compound (3 g, 7.70 mmol, 75% yield). LC-MS m/z 372.21 (M+H)⁺, 2.48 min (ret. time).

tert-Butyl 4,4-dimethyl-4,5-dihydro-1H-benzo[c]
azepine-2(3H)-carboxylate

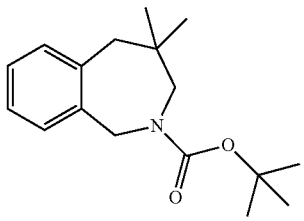 [SMILES: CC1(C)Cc2ccccc2CN(C(=O)OC(C)(C)C)C1]

To a solution of 3-(2-(((tert-butoxycarbonyl)amino)methyl)phenyl)-2,2-dimethylpropyl methanesulfonate (3 g, 8.08 mmol) in isopropanol (50 mL) was added Cs₂CO₃ (7.89 g, 24.23 mmol) and copper(I) iodide (0.154 g, 0.808 mmol). The reaction mixture was heated to 95° C. for 72 h. The reaction mixture was filtered through celite pad and washed with 10% MeOH in DCM (80 mL). The filtrate was concentrated to afford crude residue. The crude residue was purified by column chromatography eluting with 4% ethyl acetate in n-hexane. Desired fractions were concentrated to give the title compound (1.5 g, 4.56 mmol, 56.5% yield). LC-MS m/z 276.62 (M+H)⁺, 5.55 min (ret. time).

4,4-Dimethyl-2,3,4,5-tetrahydro-1H-benzo[c]azepine
Hydrochloride

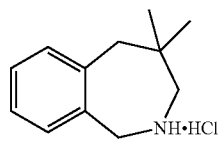

To a solution of tert-butyl 4,4-dimethyl-4,5-dihydro-1H-benzo[c]azepine-2(3H)-carboxylate (1.5 g, 5.45 mmol) in 1,4-dioxane (5 mL) at 0° C. was added 4M HCl in 1,4-dioxane (4 mL, 16.00 mmol). It was stirred at ambient temperature for 2 h. The reaction mixture was concentrated. Diethyl ether (20 mL) was added to the crude residue and stirred for 30 min. It was filtered and dried to give the title compound (1.05 g, 4.93 mmol, 90% yield). LC-MS m/z 176.19 (M+H)⁺, 1.26 min (ret. time).

Ethyl 2-(2-cyanobenzyl)butanoate

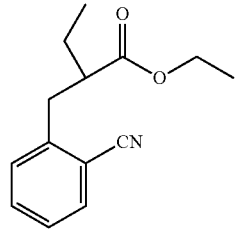 [SMILES: CCOC(=O)C(CC)Cc1ccccc1C#N]

To a solution of ethyl butyrate (0.681 mL, 5.10 mmol) in tetrahydrofuran (THF) (10 mL) at −78° C., was added lithium diisopropylamide (2M in THF) (3.83 mL, 7.65 mmol) slowly. After 30 min, a solution of 2-(bromomethyl)benzonitrile (1 g, 5.10 mmol) in THF (2 mL) was added slowly. It was stirred at −78° C. for 3 h. The reaction mixture was quenched with ammonium chloride solution (50 mL) and extracted with EtOAc (2×20 mL). The combined organic layer was washed with brine solution (20 mL) and dried over Na₂SO₄, filtered and concentrated. The crude residue was purified by silica gel chromatography to give the title compound (600 mg, 2.360 mmol, 46.3% yield) as a colorless liquid. LCMS m/z: 232.17 (M+H)⁺, 3.716 min (ret. time).

2-(2-(Aminomethyl)benzyl)butan-1-ol

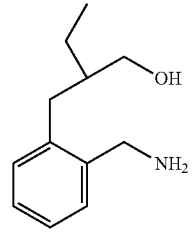

To a solution of ethyl 2-(2-cyanobenzyl)butanoate (600 mg, 2.59 mmol) in tetrahydrofuran (THF) (10 mL) at ambient temperature was added LAH (7.78 mL, 7.78 mmol) slowly. The reaction mixture was stirred for 3 h. The reaction mixture was quenched with ammonium chloride solution and extracted with EtOAc (2×50 mL). The combined organic layer was dried over Na₂SO₄, filtered and concentrated. The crude residue was purified by silica gel chromatography to give the title compound (400 mg, 2.069 mmol, 80% yield). LCMS m/z: 194 (M+H)⁺, 3.036 min (ret. time).

(2-(2-(Chloromethyl)butyl)phenyl)methanamine

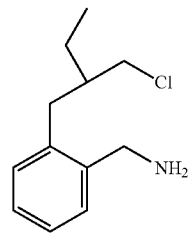

To a solution of 2-(2-(aminomethyl)benzyl)butan-1-ol (400 mg, 2.069 mmol) in 1,2-dichloroethane (DCE) (10 mL) at 5° C. was added sulfurous dichloride (0.302 mL, 4.14 mmol) slowly. The reaction mixture was allowed to stir at ambient temperature for 15 h. It was concentrated and quenched with saturated sodium bicarbonate and extracted with DCM (2×25 mL). The combined organic layer was washed with brine solution (20 mL), dried over $Na_2SO_4$, filtered and concentrated. The crude residue was purified by silica gel chromatography to give the title compound (300 mg, 1.417 mmol, 68.5% yield). LCMS m/z: 212 (M+H)$^+$, 1.94 min (ret. time).

4-Ethyl-2,3,4,5-tetrahydro-1H-benzo[c]azepine

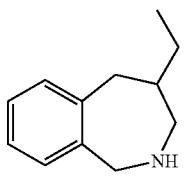

To a solution of (2-(2-(chloromethyl)butyl)phenyl)methanamine (300 mg, 1.417 mmol) in acetonitrile (2 mL) was added DIPEA (1.237 mL, 7.08 mmol). The reaction mixture was stirred at ambient temperature for 16 h. It was concentrated and extracted with DCM (2×50 mL). The organic layer was dried over $Na_2SO_4$, filtered, and concentrated. The crude residue was purified by silica gel chromatography to give the title compound (180 mg, 1.027 mmol, 72.5% yield). LCMS m/z: 176.22 (M+H)$^+$, 1.33 min (ret. time).

1-((2-Bromobenzyl)amino)-2-methylpropan-2-ol

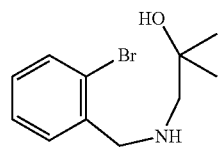

To a solution of 2-bromobenzaldehyde (25 g, 135 mmol) in methanol (250 mL) was added 1-amino-2-methylpropan-2-ol (12.04 g, 135 mmol) and NaOH (13.51 mL, 13.51 mmol). The reaction mixture was stirred under nitrogen atmosphere for 1 h. Then NaBH4 (4.09 g, 108 mmol) was added portion wise for 10 min. It was stirred at 25° C. for 40 h. The reaction mixture was concentrated under reduced pressure. The residue was dissolved in ethyl acetate (500 mL) and washed with brine solution (300 mL). The organic layer was dried over anhydrous $Na_2SO_4$, filtered and concentrated to give the title compound (28 g, 108 mmol, 80% yield). $^1$H NMR (DMSO-d6, 400 MHz): δ=7.55 (ddd, J=19.7, 7.7, 1.1 Hz, 2H), 7.33-7.39 (m, 1H), 7.18 (td, J=7.6, 1.6 Hz, 1H), 4.19 (s, 1H), 3.78 (s, 2H), 2.40 (s, 1H), 1.99 (s, 1H), 1.03-1.13 ppm (m, 6H).

2,2-Dimethyl-2,3,4,5-tetrahydrobenzo[f][1,4]oxazepine

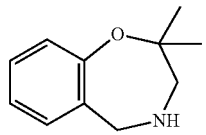

To a solution of 2-((2-bromobenzyl)amino)propan-2-ol (2.0 g, 8.19 mmol) in isopropanol (12 mL) was added $Cs_2CO_3$ (5.34 g, 16.38 mmol) and copper(I) iodide (0.156 g, 0.819 mmol). It was heated in microwave at 130° C. for 1 h. The reaction mixture was filtered through celite pad and washed with ethyl acetate. The filtrate was concentrated and the crude residue was purified by column chromatography eluting with 2% MeOH in DCM. Desired fractions were concentrated under reduced pressure to give the title compound (1.14 g, 4.97 mmol, 60.7% yield). LCMS m/z 178.19 (M+H)$^+$, 2.82 min (ret. time).

tert-Butyl 2,2-dimethyl-2,3-dihydrobenzo[f][1,4]oxazepine-4(5H)-carboxylate

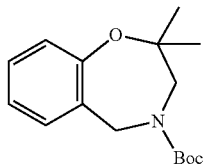 [SMILES: CC(C)(C)OC(=O)N1Cc2ccccc2OC(C)(C)C1]

To a solution of 2,2-dimethyl-2,3,4,5-tetrahydrobenzo[f][1,4]oxazepine (8 g, 45.1 mmol) in dichloromethane (DCM) (80 mL) was added TEA (9.44 mL, 67.7 mmol) and added $Boc_2O$ (15.72 mL, 67.7 mmol) slowly. The reaction mixture was stirred at 25° C. for 16 h. The reaction mixture was diluted with water and extracted with DCM (2×100 mL). The combined organic layer was washed with brine solution (150 mL). The organic layer was dried over anhydrous $Na_2SO_4$, filtered and concentrated. The crude residue was purified by column chromatography eluting with 4% ethyl acetate in n-hexane. Desired fractions were concentrated to give the title compound (9 g, 32.4 mmol, 71.9% yield) $^1$H NMR (CDCl$_3$, 400 MHz): δ=7.11-7.22 (m, 2H), 6.99-7.06 (m, 1H), 6.90-6.97 (m, 1H), 4.36-4.46 (m, 2H), 3.55-3.64 (m, 2H), 1.38-1.45 (m, 9H), 1.20 ppm (s, 6H).

2,2-Dimethyl-2,3,4,5-tetrahydrobenzo[f][1,4]oxazepine Hydrochloride

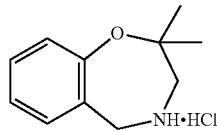

To a solution of tert-butyl 2,2-dimethyl-2,3-dihydrobenzo[f][1,4]oxazepine-4(5H)-carboxylate (9 g, 32.4 mmol) in 1,4-dioxane (50 mL) at 0° C. was added 4M HCl in

1-((2,5-Difluorobenzyl)amino)-2-methylpropan-2-ol

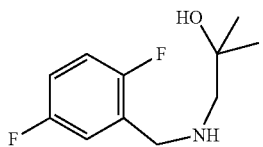

To a solution of 2,5-difluorobenzaldehyde (8 g, 56.3 mmol) in methanol (80 mL) was added 1-amino-2-methylpropan-2-ol (5.02 g, 56.3 mmol) and 1 N sodium hydroxide (5.63 mL, 5.63 mmol). The reaction mixture was stirred for 4 h; sodium tetrahydroborate (2.130 g, 56.3 mmol) was added and then stirred for 16 h. The reaction mixture was concentrated. The crude residue was quenched with ice cold water (80 mL) and extracted with ethyl acetate (3×40 mL). The combined organic layer was washed with brine solution (50 mL). The organic layer was dried over anhydrous Na$_2$SO$_4$, filtered and concentrated. The crude residue was purified by column chromatography using 50% ethyl acetate in n-hexane. Desired fractions were concentrated to give the title compound (6 g, 27.9 mmol, 49.5% yield). LCMS m/z 215.90 (M+H)$^+$, 1.91 min (ret. time).

7-Fluoro-2,2-dimethyl-2,3,4,5-tetrahydrobenzo[f][1,4]oxazepine

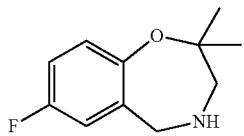

To a solution of 1-((2,5-difluorobenzyl)amino)-2-methylpropan-2-ol (6 g, 27.9 mmol) in dimethyl sulfoxide (DMSO) (50 mL) was added potassium tert-butoxide (7.82 g, 69.7 mmol). It was heated at 90° C. for 16 h. The reaction mixture was cooled and quenched with ice (10 g). It was extracted with ethyl acetate (3×20 mL). The combined organic layer was washed with ice cold water (3×30 mL) and brine solution (30 mL). The organic layer was dried over anhydrous Na$_2$SO$_4$, filtered and concentrated. The crude residue was purified by column chromatography eluting with 70% ethyl acetate in n-hexane. Desired fractions were concentrated to give the title compound (2.8 g, 12.09 mmol, 43.4% yield). LCMS m/z 195.91 (M+H)$^+$, 2.006 min (ret. time).

tert-Butyl 7-fluoro-2,2-dimethyl-2,3-dihydrobenzo[f][1,4]oxazepine-4(5H)-carboxylate

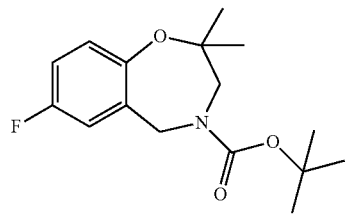 [SMILES: CC(C)(C)OC(=O)N1Cc2cc(F)ccc2OC(C)(C)C1]

To a solution of 7-fluoro-2,2-dimethyl-2,3,4,5-tetrahydrobenzo[f][1,4]oxazepine (2.8 g, 14.34 mmol) in dichloromethane (DCM) (30 mL) at 25° C. was added TEA (1.999 mL, 14.34 mmol) and Boc-anhydride (3.33 mL, 14.34 mmol). It was stirred for 1 h. The reaction mixture was quenched with water (20 mL) and extracted with DCM (2×20 mL). The combined organic layer was washed with brine solution (30 mL). The organic layer was dried over anhydrous Na$_2$SO$_4$, filtered and concentrated. The crude residue was purified by column chromatography eluting with 5% ethyl acetate in n-hexane. Desired fractions were concentrated to give the title compound (2.7 g, 8.83 mmol, 61.6% yield). LCMS m/z 240 (M−56)$^+$, 2.794 min (ret. time).

7-Fluoro-2,2-dimethyl-2,3,4,5-tetrahydrobenzo[f][1,4]oxazepine Hydrochloride

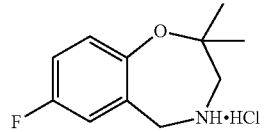

To a solution of tert-butyl 7-fluoro-2,2-dimethyl-2,3-dihydrobenzo[f][1,4]oxazepine-4(5H)-carboxylate (2.7 g, 9.14 mmol) in 1,4-dioxane (15 mL) at 0° C. was added 4M HCl in 1,4-dioxane (6.86 mL, 27.4 mmol). It was stirred 25° C. for 2 h. The reaction mixture was concentrated. Diethyl ether (20 mL) was added to the residue and stirred for 30 min then the solid was filtered, washed with hexane (5 mL) and dried to give the title compound (1.94 g, 8.27 mmol, 91% yield) as a white solid. LCMS 196.1 (M−HCl)$^+$, 4.682 min (ret. time).

1-((5-Bromo-2-fluorobenzyl)amino)-2-methylpropan-2-ol

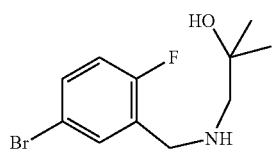

To a solution of 5-bromo-2-fluorobenzaldehyde (1 g, 4.93 mmol) in methanol (50 mL) was added 1-amino-2-methylpropan-2-ol (0.439 g, 4.93 mmol) and 1N sodium hydroxide (0.493 mL, 0.493 mmol). It was stirred for 4 h; sodium tetrahydroborate (0.186 g, 4.93 mmol) was added and stirred for 16 h. The reaction mixture was concentrated, quenched with ice cold water (50 mL) and extracted with ethyl acetate (3×30 mL). The combined organic layer was washed with brine solution (50 mL). The organic layer was dried over anhydrous Na$_2$SO$_4$, filtered and concentrated. The crude residue was purified by column chromatography eluting with 50% ethyl acetate in n-hexane. Desired fractions were concentrated to give the title compound (820 mg, 2.89 mmol, 58.6% yield). LCMS m/z 275.97 (M+H)$^+$, 1.97 min (ret. time).

7-Bromo-2,2-dimethyl-2,3,4,5-tetrahydrobenzo[f][1,4]oxazepine

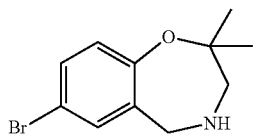

To a solution of 1-((5-bromo-2-fluorobenzyl)amino)-2-methylpropan-2-ol (6 g, 21.73 mmol) in dimethyl sulfoxide (DMSO) (40 mL) was added potassium tert-butoxide (6.10 g, 54.3 mmol). It was heated at 90° C. for 1 h. The reaction mixture was cooled and quenched with ice (10 g). It was extracted with ethyl acetate (3×20 mL). The combined organic layer was washed with ice cold water (3×30 mL) and brine solution (30 mL). The organic layer was dried over anhydrous Na$_2$SO$_4$, filtered and concentrated. The crude residue was purified by column chromatography eluting with 70% ethyl acetate in n-hexane. Desired fractions were concentrated to give the title compound (2.4 g, 3.87 mmol, 17.82% yield). LCMS m/z 257.91 (M+2H)$^+$, 3.42 min (ret. time).

tert-Butyl 7-bromo-2,2-dimethyl-2,3-dihydrobenzo[f][1,4]oxazepine-4(5H)-carboxylate

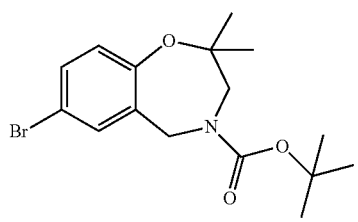 [SMILES: CC(C)(C)OC(=O)N1Cc2cc(Br)ccc2OC(C)(C)C1]

To a solution of 7-bromo-2,2-dimethyl-2,3,4,5-tetrahydrobenzo[f][1,4]oxazepine (7.2 g, 28.1 mmol) in dichloromethane (DCM) (50 mL) was added TEA (5.88 mL, 42.2 mmol) and Boc-anhydride (6.53 mL, 28.1 mmol). It was stirred at ambient temperature for 30 min. The reaction mixture was quenched with water (10 mL) and extracted with DCM (2×20 mL). The combined organic layer washed with brine solution (20 mL). The organic layer was dried over anhydrous Na$_2$SO$_4$, filtered and concentrated. The crude residue was purified by column chromatography eluting with 5% ethyl acetate in n-hexane. Desired fractions were concentrated to give the title compound (3.3 g, 9.08 mmol, 32.3% yield). LCMS m/z 299.91 (M−57)$^+$, 4.26 min (ret. time).

7-Bromo-2,2-dimethyl-2,3,4,5-tetrahydrobenzo[f][1,4]oxazepine Hydrochloride

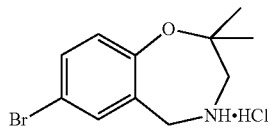

To a solution of tert-butyl 7-bromo-2,2-dimethyl-2,3-dihydrobenzo[f][1,4]oxazepine-4(5H)-carboxylate (3.3 g, 9.26 mmol) in 1,4-dioxane (40 mL) at 0° C. was added 4M HCl in 1,4-dioxane (6.95 mL, 27.8 mmol). It was then stirred at ambient temperature for 2 h. The reaction mixture was concentrated. Diethyl ether (20 mL) was added and stirred for 30 min. Solid was filtered, washed with hexane (5 mL) and dried to give the title compound (2.1 g, 7.08 mmol, 76% yield) as off-white solid. LCMS m/z 256.04 (M−HCl)$^+$, 1.48 min (ret. time).

2,2-Dimethyl-2,3,4,5-tetrahydrobenzo[f][1,4]oxazepine

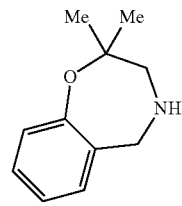 [SMILES: CC1(C)CNCc2ccccc2O1]

A solution of 7-bromo-2,2-dimethyl-2,3,4,5-tetrahydrobenzo[f][1,4]oxazepine hydrochloride (100 mg, 0.342 mmol) in ethanol (13.7 mL) was go through a H-cube hydrogenation flow apparatus equipped with a pre-installed Pd/C cartridge (1 bar, RT). After 15 h and 25 min, the reaction was concentrated to give the title compound as yellow/green oil (83.7 mg). LC-MS m/z 178.1 (M+H)$^+$, 0.49 min (ret. time). $^1$H NMR (400 MHz, methanol-d4) δ ppm 1.35 (s, 6H) 3.41 (s, 2H) 4.33 (s, 2H) 7.05 (d, J=8.03 Hz, 1H) 7.12-7.20 (m, 1H) 7.31-7.40 (m, 2H).

1-(((3-Fluoropyridin-2-yl)methyl)amino)-2-methylpropan-2-ol

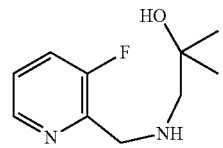

To a solution of 3-fluoropicolinaldehyde (10 g, 80 mmol) in methanol (100 mL) was added 1-amino-2-methylpropan-2-ol (7.13 g, 80 mmol) and Indium(III) trifluoromethanesulfonate (8.99 g, 15.99 mmol). It was stirred under nitrogen atmosphere for 1 h, then NaCNBH$_4$ (5.53 g, 88 mmol) was added portion wise for 10 min. It was stirred at RT for 24 h. It was concentrated and purified on flash column chromatography (Neutral alumina) by using MeOH:DCM (1:9) as solvent. Desired fractions were concentrated to give the title compound (4 g, 13.58 mmol, 16.99% yield) as a colorless liquid. LC-MS m/z 198.91 (M+H)⁺, 1.592 min (ret. time).

2,2-Dimethyl-2,3,4,5-tetrahydropyrido[2,3-f][1,4]oxazepine

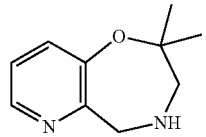

To a solution of 1-(((3-fluoropyridin-2-yl)methyl)amino)-2-methylpropan-2-ol (4 g, 20.18 mmol) in dimethyl sulfoxide (DMSO) (10 mL) was added potassium tert-butoxide (2.264 g, 20.18 mmol). The reaction mixture was heated at 90° C. for 1 h. The reaction mixture was poured in ice water (50 mL) and extracted with ethyl acetate (2×50 mL). The combined organic layer was washed with water (2×40 mL), brine (20 mL), dried over Na₂SO₄, filtered and concentrated. The crude residue was purified on flash column chromatography (Neutral alumina) using 45% ethyl acetate in hexane. The collected the fractions were concentrated to give the title compound (3.2 g, 15.59 mmol, 77% yield) a gummy liquid. LC-MS m/z 178.92 (M+H)⁺, 1.057 min (ret. time).

tert-Butyl 2,2-dimethyl-2,3-dihydropyrido[2,3-f][1,4]oxazepine-4(5H)-carboxylate

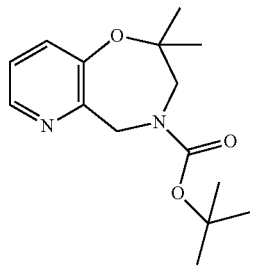 [SMILES: CC(C)(C)OC(=O)N1Cc2ncccc2OC(C)(C)C1]

To a solution of 2,2-dimethyl-2,3,4,5-tetrahydropyrido[2,3-f][1,4]oxazepine (3.2 g, 17.95 mmol) in dichloromethane (DCM) (5 mL) at 0° C. was added TEA (5.00 mL, 35.9 mmol) and Boc-anhydride (5.42 mL, 23.34 mmol). It was stirred at RT for 3 h. The crude residue was diluted with water (10 mL) and extracted with ethyl acetate (2×20 mL). The combined organic layer was washed with brine solution (10 mL), dried over anhydrous Na₂SO₄, filtered and concentrated. The crude residue was purified on flash column chromatography eluting with 3% ethyl acetate in hexane. Desired fractions were concentrated to give the title compound (3.1 g, 9.45 mmol, 52.6% yield) as a colorless liquid. LC-MS m/z 279.13 (M+H)⁺, 3.583 min (ret. time).

2,2-Dimethyl-2,3,4,5-tetrahydropyrido[2,3-f][1,4]oxazepine Hydrochloride

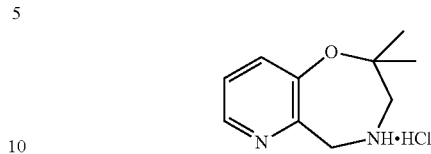

To a solution of tert-butyl 2,2-dimethyl-2,3-dihydropyrido[2,3-f][1,4]oxazepine-4(5H)-carboxylate (3.1 g, 11.14 mmol) in dichloromethane (DCM) (20 mL) at 10° C. was added 4 M HCl in 1,4-dioxane (3.34 mL, 13.36 mmol). It was stirred for 1 h. The obtained precipitation was filtered and the solid was washed with hexane, diethyl ether and dried to give the title compound (2.16 g, 9.85 mmol, 88% yield) as a brown solid. LC-MS m/z 179.1 (M−HCl)⁺, 4.040 min (ret. time)

(R)-1-((2-Bromobenzyl)amino)butan-2-ol

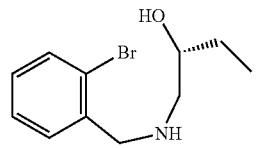

To a solution of 2-bromobenzaldehyde (10 g, 54.0 mmol) in methanol (100 mL) was added (R)-1-aminobutan-2-ol (4.82 g, 54.0 mmol) and NaOH (5.40 mL, 5.40 mmol). It was stirred under nitrogen atmosphere for 1 h. NaBH4 (0.818 g, 21.62 mmol) was added portion wise for 10 min and stirred at RT for 72 h. Solvent was concentrated. The crude product was purified on flash column chromatography (Neutral alumina) eluting with EtOAc:hexane (3:7). Combined fractions were concentrated to give the title compound (10 g, 28.9 mmol, 53.5% yield). as an off-white solid. LC-MS m/z 258.12 (M+H)⁺, 1.302 min (ret. time)

(R)-2-Ethyl-2,3,4,5-tetrahydrobenzo[f][1,4]oxazepine

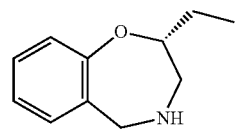

To a solution of (R)-1-((2-bromobenzyl)amino)butan-2-ol (3 g, 11.62 mmol) in isopropanol (30 mL) was added Cs₂CO₃ (7.57 g, 23.24 mmol) and copper(I) iodide (0.443 g, 2.324 mmol). The reaction mixture was heated in microwave reactor at 130° C. for 1 h. The reaction mixture was filtered through celite, washed with isopropanol and concentrated. The crude residue was purified on flash column chromatography eluting with 2.5% MeOH in DCM. Desired fractions were concentrated to give the title compound (1.7 g, 8.77 mmol, 75% yield) as a gummy liquid. LC-MS m/z 178.18 (M+H)⁺, 1.27 min (ret. time).

127

(R)-2-Ethyl-2,3,4,5-tetrahydrobenzo[f][1,4]ox-
azepine hydrochloride

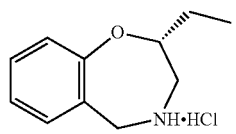

To a solution of (R)-2-ethyl-2,3,4,5-tetrahydrobenzo[f][1,4]oxazepine (5.5 g, 31.0 mmol) in dichloromethane (DCM) (20 mL) at 10° C. was added 4M HCl in 1,4-dioxane (9.31 mL, 37.2 mmol). It was stirred for 1 h. The obtained precipitates were filtered and the solid was washed with hexane and dried to give the title compound (5.1 g, 23.82 mmol, 77% yield) as an off-white solid. LC-MS m/z 178.1 (M+H)$^+$, 1.563 min (ret. time).

Methyl 2-cycloheptylacetate

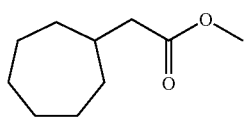

To a solution of 2-cycloheptylacetic acid (4.76 g, 30.5 mmol) in methanol (50 mL) was added sulfuric acid (2.99 g, 30.5 mmol) slowly. Then it was stirred at 70° C. for 16 h. After it was cooled to ambient temperature, the reaction mixture was added to 50 mL of water and extracted with ethyl acetate (3×50 mL), washed with brine, concentrated to obtain the title compound methyl 2-cycloheptylacetate (5.18 g, 28.3 mmol, 92.9% yield). LCMS m/z 171.2 (M+H)$^+$, 1.82 min (Ret. time).

2-Cycloheptylethanol

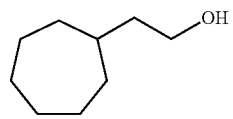

To a solution of methyl 2-cycloheptylacetate (4.33 g, 25.4 mmol) in tetrahydrofuran (THF) (20 mL) was added lithium aluminum hydride (1.931 g, 50.9 mmol) slowly under nitrogen at 0° C. and stirred for 1 hour. Then the reaction mixture was stirred at 25° C. for 16 hours. Then 30 mL of HCl (3 M) was added, extracted with EtOAc (3×30 mL), washed with brine, dried over MgSO$_4$ and concentrated to obtain the title compound 2-cycloheptylethanol (3.28 g, 20.75 mmol, 82% yield) as a white oil. $^1$H NMR (400 MHz, DMSO-d$_6$) δ: 4.26 (t, J=4.9 Hz, 1H), 3.41 (q, J=5.9 Hz, 2H), 1.73-1.29 (m, 13H), 1.22-1.08 (m, 2H).

128

2-Cycloheptylacetaldehyde

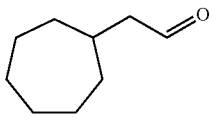

To a solution of 2-cycloheptylethanol (3.28 g, 23.06 mmol) in dichloromethane (DCM) (50 mL) was added PCC (7.46 g, 34.65 mmol) and silica gel (15 g). The reaction mixture was stirred at 25° C. for 16 h. Then it was filtered through a pad of celite. The filtrate was concentrated under vacuum. The crude product was purified by silica gel chromatography (EtOAC:Hexane=1:5) to obtain the title compound 2-cycloheptylacetaldehyde (1.30 g, 8.81 mmol, 38.2% yield) as a yellow oil. $^1$H NMR (400 MHz, CDCl$_3$) δ: 9.74 (s, 1H), 2.32-1.28 (m, 15H).

2-(Cycloheptylmethyl)-1H-imidazole

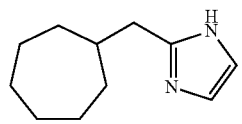 [SMILES: c1c[nH]c(CC2CCCCCC2)n1]

To a solution of 2-cycloheptylacetaldehyde (1.2 g, 8.56 mmol) in methanol (36 mL) and water (36 mL) was added oxaldehyde (0.993 g, 17.12 mmol) and ammonia hydrate (2.189 g, 62.5 mmol). The reaction mixture was stirred at 0° C. for 2 h, then it was stirred at ambient temperature for 18 h. The solid was filtered and dried under vacuum to obtain the title compound 2-(cycloheptylmethyl)-1H-imidazole (680 mg, 3.43 mmol, 40.1% yield) as a white solid. LCMS m/z 179.2 (M+H)$^+$, 1.22 min (ret. time).

1-((1H-Imidazol-2-yl)methyl)piperidine

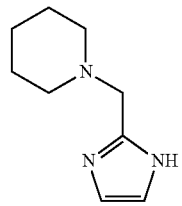 [SMILES: c1c[nH]c(CN2CCCCC2)n1]

To a solution of 1H-imidazole-2-carbaldehyde (2 g, 20.81 mmol) in 1,2-dichloroethane (DCE) (100 mL), piperidine (1.772 g, 20.81 mmol) and acetic acid (0.5 mL) were added. After it was stirred at ambient temperature for 16 h, NaBH(OAc)$_3$ (8.82 g, 41.6 mmol) was added. The reaction mixture was stirred at 25° C. for a further 2 h. The solvent was removed and the residue was purified by reverse-phase HPLC (0.05% NH$_4$HCO$_3$/H$_2$O: CH$_3$CN=5%~95%) to give the title compound 1-((1H-imidazol-2-yl)methyl)piperidine (1.6 g, 9.68 mmol, 46.5% yield) as a yellow solid. LC-MS m/z 166.2 (M+H)$^+$, 1.27 min (ret. time).

129

Example 1. 5-Cyclopentyl-1-{3-[3-(dimethylcarbamoyl)-2-fluorophenyl]phenyl}-1H-pyrazole-4-carboxylic Acid

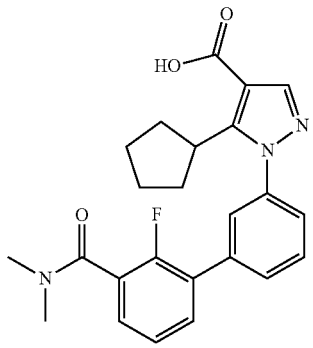 [SMILES: CN(C)C(=O)c1cccc(-c2cccc(-n3ncc(C(=O)O)c3C3CCCC3)c2)c1F]

1a) 3-Bromo-2-fluoro-N,N-dimethyl-benzamide

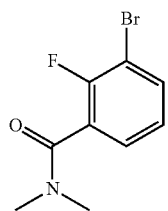

A solution of 3-bromo-2-fluoro-benzoic acid (1.50 g, 6.85 mmol), HATU (3.91 g, 10.3 mmol), dimethylamine (2M in THF, 6.85 mL, 13.7 mmol) and DIPEA (1.77 g, 13.7 mmol) in DMF (20 mL) was stirred for 3 h. Further dimethylamine, DIPEA and HATU was added. After 2 h, the mixture was partitioned between EtOAc and water. The aqueous phase was extracted with EtOAc and the combined organic phases were washed with water (×3) and brine before drying (MgSO$_4$), filtering, and concentrating to give the product (0.121 g, 7%), used without further purification. LC-MS m/z 246 (M+H)$^+$, 1.12 (ret. time), basic method.

1b) 1-(3-Bromo-phenyl)-5-cyclopentyl-1H-pyrazole-4-carboxylic Acid Ethyl Ester

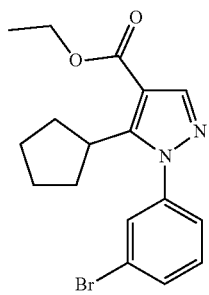 [SMILES: CCOC(=O)c1cnn(-c2cccc(Br)c2)c1C1CCCC1]

A stirred solution of diisopropylamine (8.23 g, 81.4 mmol) in dry THF (10 mL) under N$_2$ at 0° C. was treated with nBuLi (2.5M in hexane, 31.5 mL, 78.7 mmol). After 30 minutes the solution was cooled to −78° C. Dry EtOAc (7.69 mL, 78.7 mmol) was then added dropwise. After 5 min, a solution of cyclopentane carbonyl chloride (3.48 g, 26.2 mmol) in dry THF (2 mL) was added in one go. After 5 min, the cool bath was removed and the mixture was allowed to warm to room temperature. The mixture was diluted with 1N HCl (30 mL) and then extracted with Et$_2$O (2×30 mL). The combined organic phase was dried (MgSO$_4$), filtered, and concentrated 7.8 g of crude 3-cyclopentyl-3-oxo-propionic acid ethyl ester. A mixture of this material (2.4 g, 13.0 mmol) and DMF-dimethyl acetal was stirred in a microwave reactor at 130° C. for 15 min. After cooling, the stirred mixture was diluted with EtOH (10 mL) and treated with 3-bromophenylhydrazine HCl (2.91 g, 13.0 mmol) followed by triethylamine (2.61 g, 26.1 mmol). After 16 h at room temperature the mixture was partitioned between EtOAc and water and then the organic phase washed with water, 0.5 N HCl, water and then brine before it was dried (MgSO$_4$), filtered, and concentrated to give the crude product (4.5 g, 12.4 mmol). LC-MS m/z 363 (M+H)$^+$, 1.61 (ret. time), basic method.

1c) 5-Cyclopentyl-1-[3-(4,4,5,5-tetramethyl-[1,3,2]dioxaborolan-2-yl)-phenyl]-1H-pyrazole-4-carboxylic Acid Ethyl Ester

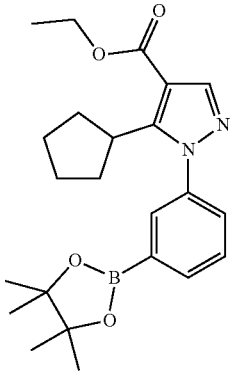 [SMILES: CCOC(=O)c1cnn(-c2cccc(B3OC(C)(C)C(C)(C)O3)c2)c1C1CCCC1]

A mixture of 1-(3-bromo-phenyl)-5-cyclopentyl-1H-pyrazole-4-carboxylic acid ethyl ester (3.00 g, 8.26 mmol), bis(pinacolato)diboron (2.31 g, 9.08 mmol), KOAc (1.62 g, 16.5 mmol) and Pd(dppf)Cl$_2$ (0.332 g, 0.45 mmol) in dioxane (80 mL) was stirred under reflux for 3 hours. The mixture was then concentrated and partitioned between EtOAc and water. The organic phase was washed with water and then brine before it was dried (MgSO$_4$), filtered and concentrated. Purification by silica column, eluting 0-20% EtOAc in petrol gave the product (2.3 g, 5.61 mmol, 68%). LC-MS m/z 329 (M+H)$^+$ for boronic acid, 1.33 (ret. time), basic method. Boronate ester hydrolyses in LC-MS media—retention time is for corresponding boronic acid.

1d) 5-Cyclopentyl-1-{3-[3-(dimethylcarbamoyl)-2-fluorophenyl]phenyl}-1H-pyrazole-4-carboxylic Acid Ethyl Ester

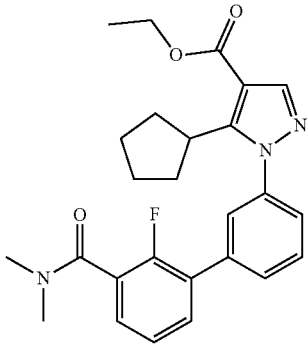 [SMILES: CCOC(=O)c1cnn(-c2cccc(-c3cccc(C(=O)N(C)C)c3F)c2)c1C1CCCC1]

A stirred mixture of 3-bromo-2-fluoro-N,N-dimethylbenzamide (0.150 g, 0.61 mmol), 5-cyclopentyl-1-[3-(4,4,5,5-tetramethyl-[1,3,2]dioxaborolan-2-yl)-phenyl]-1H-pyrazole-4-carboxylic acid ethyl ester (0.300 g, 0.73 mmol), Na$_2$CO$_3$ (0.258 g, 2.44 mmol) and Pd(PPh$_3$)$_4$ (0.042 g, 0.04 mmol) in EtOH (2 mL) and toluene (7 mL) was heated at reflux for 18 h. After cooling the mixture was partitioned between EtOAc (30 mL) and water (20 mL) and the organic phase was washed with water (20 mL) and brine (20 mL) before it was dried (MgSO$_4$), filtered, and concentrated. Purified by silica column (10-40% EtOAc in petrol) to give the product (148 mg, 83%). LC-MS m/z 450 (M+H)$^+$, 1.49 (ret. time), basic method.

1e) 5-Cyclopentyl-1-{3-[3-(dimethylcarbamoyl)-2-fluorophenyl]phenyl}-1H-pyrazole-4-carboxylic Acid

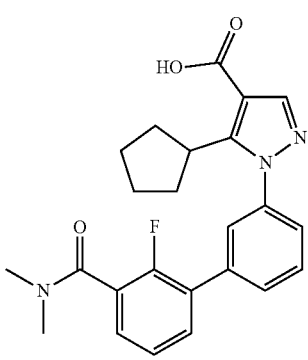 [SMILES: CN(C)C(=O)c1cccc(-c2cccc(-n3ncc(C(=O)O)c3C3CCCC3)c2)c1F]

A stirred solution of 5-cyclopentyl-1-{3-[3-(dimethylcarbamoyl)-2-fluorophenyl]phenyl}-1H-pyrazole-4-carboxylic acid ethyl ester (0.122 g, 0.27 mmol) in EtOH (4 mL) was treated with a solution of NaOH (0.043 g) in water (1 mL). After 60 hours the mixture was acidified with 1N HCl and extracted into EtOAc (2×). The combined organic phases were dried (MgSO$_4$), filtered, and concentrated under vacuum to give the product (0.048 g, 42%). LC-MS m/z 432 (M+H)$^+$, 1.02 (ret. time), basic method. $^1$H NMR (400 MHz, DMSO-d6): 12.31 (1H, s), 7.99 (1H, s), 7.80-7.65 (3H, m), 7.63 (1H, s), 7.57-7.57 (1H, m), 7.57-7.48 (1H, m), 7.48-7.34 (2H, m), 3.27-3.11 (1H, m), 3.03 (3H, s), 2.89 (3H, s), 2.17-2.02 (2H, m), 1.90-1.70 (4H, m), 1.51 (2H, d).

Example 2. 1-{3-[3-(Dimethylcarbamoyl)-2-fluorophenyl]phenyl}-5-(trifluoromethyl)-1H-pyrazole-4-carboxylic Acid

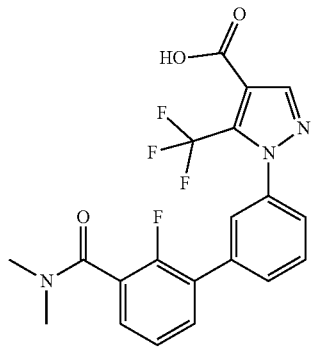 [SMILES: CN(C)C(=O)c1cccc(-c2cccc(-n3ncc(C(=O)O)c3C(F)(F)F)c2)c1F]

2a) 1-(3-Bromo-phenyl)-5-trifluoromethyl-1H-pyrazole-4-carboxylic Acid Ethyl Ester

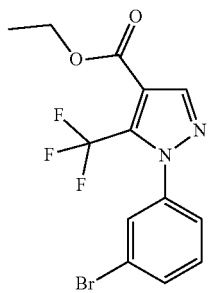

A stirred solution of 2-[1-ethoxy-meth-(Z)-ylidene]-4,4,4-trifluoro-3-oxo-butyric acid ethyl ester (3.09 g, 16.0 mmol) in EtOH (60 mL) was treated with 3-bromophenylhydrazine HCl (5.78 g, 24.0 mmol) followed by DIPEA (4.56 g, 35.3 mmol). After 16 h at room temperature the mixture was partitioned between EtOAc and water and then the organic phase washed with further water, 0.5 N HCl, water, and then brine before it was dried (MgSO$_4$), filtered and concentrated to give the product (6.64 g, quantative). LC-MS m/z 363 (M+H)$^+$, 1.52 (ret. time), basic method.

2b) 1-[3-(4,4,5,5-Tetramethyl-[1,3,2]dioxaborolan-2-yl)-phenyl]-5-trifluoromethyl-1H-pyrazole-4-carboxylic Acid Ethyl Ester

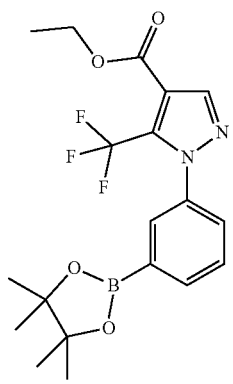 [SMILES: CCOC(=O)c1cnn(-c2cccc(B3OC(C)(C)C(C)(C)O3)c2)c1C(F)(F)F]

A mixture of 1-(3-bromo-phenyl)-5-trifluoromethyl-1H-pyrazole-4-carboxylic acid ethyl ester (3.00 g, 8.26 mmol), bis(pinacolato)diboron (2.31 g, 9.08 mmol), KOAc (1.62 g, 16.5 mmol) and Pd(dppf)Cl$_2$ (0.332 g, 0.45 mmol) in dioxane (80 mL) was stirred under reflux for 3 hours. The mixture was then concentrated and partitioned between EtOAc and water. The organic phase was washed with water and then brine before it was dried (MgSO$_4$), filtered, and concentrated. Purified by silica column, 25S, eluting 0-15% EtOAc in petrol to give the product (1.64 g, 48%).

2c) 1-{3-[3-(Dimethylcarbamoyl)-2-fluorophenyl]phenyl}-5-(trifluoromethyl)-1H-pyrazole-4-carboxylic Acid Ethyl Ester

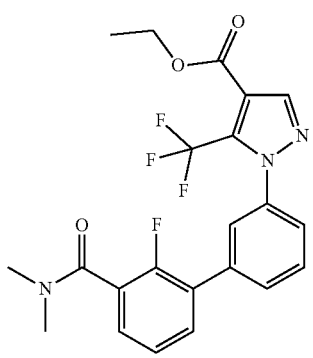 [SMILES: CCOC(=O)c1cnn(-c2cccc(-c3cccc(C(=O)N(C)C)c3F)c2)c1C(F)(F)F]

A stirred mixture of 3-bromo-2-fluoro-N,N-dimethyl-benzamide (0.150 g, 0.61 mmol), 1-[3-(4,4,5,5-tetramethyl-[1,3,2]dioxaborolan-2-yl)-phenyl]-5-trifluoromethyl-1H-pyrazole-4-carboxylic acid ethyl ester (0.300 g, 0.73 mmol), Na$_2$CO$_3$ (0.194 g, 3 mmol) and Pd(PPh$_3$)$_4$ (0.042 g, 0.04 mmol) in EtOH (2 mL) and toluene (7 mL) was heated at reflux for 4 h. After cooling, the mixture was partitioned between EtOAc (30 mL) and water (20 mL) and the organic phase was washed with water (20 mL) and brine (20 mL) before it was dried (MgSO$_4$), filtered, and concentrated. Purified by silica column (30-100% EtOAc in petrol) to give the product (109 mg, 40%). LC-MS m/z 450 (M+H)$^+$, 1.40 (ret. time), basic method.

2d) 1-{3-[3-(Dimethylcarbamoyl)-2-fluorophenyl]phenyl}-5-(trifluoromethyl)-1H-pyrazole-4-carboxylic Acid

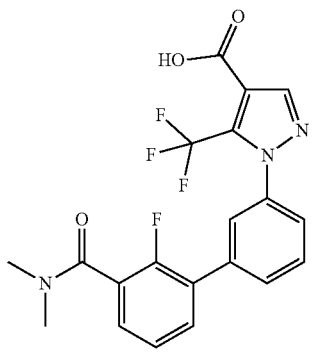 [SMILES: CN(C)C(=O)c1cccc(-c2cccc(-n3ncc(C(=O)O)c3C(F)(F)F)c2)c1F]

A stirred solution of 1-{3-[3-(dimethylcarbamoyl)-2-fluorophenyl]phenyl}-5-(trifluoromethyl)-1H-pyrazole-4-carboxylic acid ethyl ester (0.109 g, 0.24 mmol) in EtOH (3 mL) was treated with a solution of NaOH (0.039 g) in water (0.75 mL). After 60 hours the mixture was acidified with 1N HCl and extracted into EtOAc (×2). The combined organic phases were dried (MgSO$_4$), filtered, and concentrated under vacuum to give the product (0.068 g, 67%). LC-MS m/z 422 (M+H)$^+$, 0.98 (ret. time). 1H NMR (400 MHz, DMSO-d6): 13.34 (1H, s), 8.27 (1H, s), 7.82-7.60 (5H, m), 7.50-7.34 (2H, m), 3.03 (3H, s), 2.89 (3H, s).

Example 3. 1-(3-{3-[Cyclopentyl(methyl)carbamoyl]-2-fluorophenyl}phenyl)-5-cyclopropyl-1H-pyrazole-4-carboxylic Acid

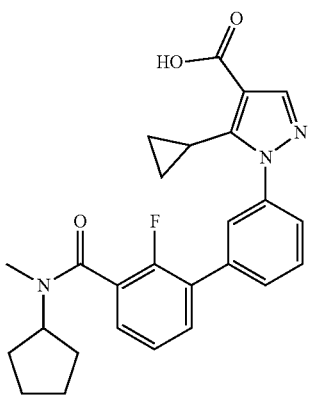 [SMILES: CN(C(=O)c1cccc(-c2cccc(-n3ncc(C(=O)O)c3C3CC3)c2)c1F)C1CCCC1]

3a) 3-Bromo-N-cyclopentyl-2-fluoro-N-methyl-benzamide

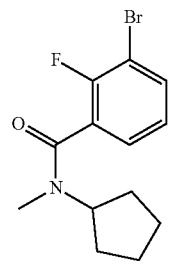 [SMILES: CN(C(=O)c1cccc(Br)c1F)C1CCCC1]

A solution of 3-bromo-2-fluoro-benzoic acid (0.50 g, 2.28 mmol), HATU (0.868 g, 2.28 mmol), N-cyclopropentyl-N-methylamine (0.356 g, 2.63 mmol) and DIPEA (0.885 g, 6.85 mmol) in DCM (20 mL) was stirred for 3 h. The mixture was washed with aqueous NaHCO$_3$ and dried by passage through a phase separation cartridge. Concentration to dryness gave the crude product (0.905 g, quantative), used without further purification.

3b) 1-(3-Bromo-phenyl)-5-cyclopropyl-1H-pyrazole-4-carboxylic Acid Ethyl Ester

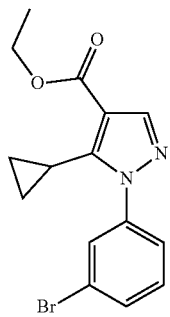

A mixture of ethyl 3-cyclopropyl-3-oxopropanoate (0.731 g, 4.69 mmol) and DMF-dimethyl acetal (0.614 g, 5.15 mmol) was stirred in a microwave reactor at 130° C. for 15 min. After cooling, the stirred mixture was diluted with EtOH (15 mL) and treated with 3-bromophenylhydrazine HCl (1.05 g, 4.69 mmol) followed by triethylamine (1.17 g, 11.7 mmol). After 16 h at room temperature the mixture was partitioned between EtOAc and water and then the organic phase washed with further water, 0.5 N HCl, water and then brine before it was dried (MgSO$_4$), filtered, and concentrated to give the product (1.48 g, 94%). LC-MS m/z no ion observed, 1.50 min (ret. time).

3c) 5-Cyclopropyl-1-[3-(4,4,5,5-tetramethyl-[1,3,2]dioxaborolan-2-yl)-phenyl]-1H-pyrazole-4-carboxylic Acid Ethyl Ester

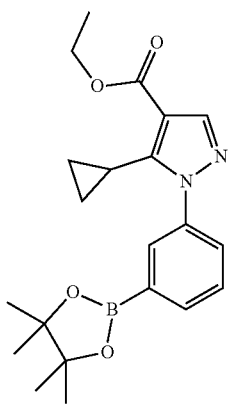 [SMILES: CCOC(=O)c1cnn(-c2cccc(B3OC(C)(C)C(C)(C)O3)c2)c1C1CC1]

A mixture of 1-(3-bromo-phenyl)-5-cyclopropyl-1H-pyrazole-4-carboxylic acid ethyl ester (5.20 g, 15.5 mmol), bis(pinacolato)diboron (4.33 g, 17.1 mmol), KOAc (3.04 g, 31.0 mmol) and Pd(dppf)Cl$_2$ (0.624 g, 0.85 mmol) in dioxane (75 mL) was stirred under reflux for 2 hours. The mixture was then concentrated and partitioned between EtOAc and water. The organic phase washed with water and then brine before it was dried (MgSO$_4$), filtered, and concentrated. It was then purified by silica column, 25S, eluting 3-20% EtOAc in petrol to give the product (6.60 g, quantative.).

3d) 1-(3-{3-[Cyclopentyl(methyl)carbamoyl]-2-fluorophenyl}phenyl)-5-cyclopropyl-1H-pyrazole-4-carboxylic Acid Ethyl Ester

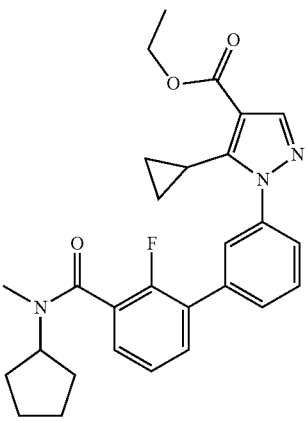 [SMILES: CCOC(=O)c1cnn(-c2cccc(-c3cccc(C(=O)N(C)C4CCCC4)c3F)c2)c1C1CC1]

A stirred mixture of 3-bromo-N-cyclopentyl-2-fluoro-N-methyl-benzamide (0.150 g, 0.50 mmol), 5-cyclopropyl-1-[3-(4,4,5,5-tetramethyl-[1,3,2]dioxaborolan-2-yl)-phenyl]-1H-pyrazole-4-carboxylic acid ethyl ester (0.127 g, 0.33 mmol), aqueous Na$_2$CO$_3$ (3M, 0.33 mL, 3.3 mmol) and Pd(PPh$_3$)$_4$ (0.029 g, 0.02 mmol) in EtOH (1 mL) and toluene (4 mL) was heated at reflux for 3 h. After cooling, the mixture was partitioned between EtOAc (30 mL) and water (20 mL) and the organic phase washed with water (20 mL) and brine (20 mL) before it was dried (MgSO4), filtered, and concentrated to give the product, used without further purification (0.207 g, quantative).

3e) 1-(3-{3-[Cyclopentyl(methyl)carbamoyl]-2-fluorophenyl}phenyl)-5-cyclopropyl-1H-pyrazole-4-carboxylic Acid

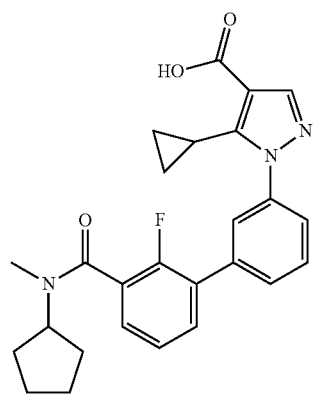 [SMILES: CN(C(=O)c1cccc(-c2cccc(-n3ncc(C(=O)O)c3C3CC3)c2)c1F)C1CCCC1]

A stirred solution of 1-(3-{3-[cyclopentyl(methyl)carbamoyl]-2-fluorophenyl}phenyl)-5-cyclopropyl-1H-pyrazole-4-carboxylic acid ethyl ester (0.207 g, 0.44 mmol) in EtOH (3 mL) was treated with aqueous NaOH (2M, 0.87 mL). After 18 hours the mixture was partitioned between EtOAc and water. The organic phase was discarded and then the aqueous was acidified with 1N HCl and extracted into EtOAc (×2). The combined organic phases were dried (MgSO₄), filtered, and concentrated under vacuum, and the residue purified by preparative HPLC to give the product (0.028 g, 14%). LC-MS m/z 448 (M+H)$^+$, 1.08 (ret. time), basic method. $^1$H NMR (400 MHz, DMSO-d6): 12.21 (1H, s), 7.97 (1H, s), 7.79 (1H, s), 7.72-7.58 (4H, m), 7.39 (2H, d), 4.98-4.85 (0.4H, m), 4.02-3.90 (0.6H, m), 2.90 (2H, s), 2.75 (1H, s), 2.20-2.09 (1H, m), 1.87-1.51 (7H, m), 1.41 (1H, s), 0.87 (2H, d), 0.57 (2H, d). Substituents adjacent to amide N are rotameric peaks.

Example 4. 5-Cyclopropyl-1-(3-{2-fluoro-3-[methyl(2-methylpropyl)carbamoyl]phenyl}phenyl)-1H-pyrazole-4-carboxylic Acid

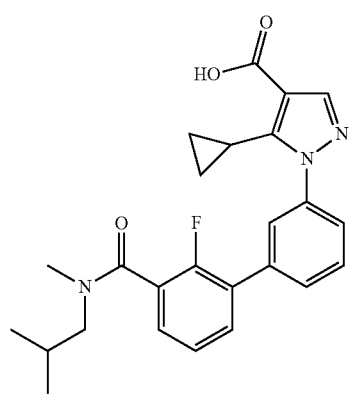 [SMILES: CC(C)CN(C)C(=O)c1cccc(-c2cccc(-n3ncc(C(=O)O)c3C3CC3)c2)c1F]

4a)
3-Bromo-2-fluoro-N-isobutyl-N-methyl-benzamide

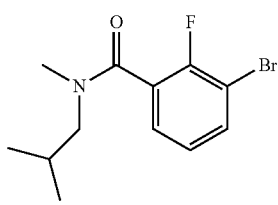 [SMILES: CC(C)CN(C)C(=O)c1cccc(Br)c1F]

A solution of 3-bromo-2-fluoro-benzoic acid (0.50 g, 2.28 mmol), HATU (0.868 g, 2.28 mmol), N-isobutyl-N-methyl-amine (0.229 g, 2.63 mmol) and DIPEA (0.590 g, 4.57 mmol) in DCM (15 mL) was stirred for 3 h. The mixture was washed with aqueous NaHCO₃ and dried by passage through a phase separation cartridge. Concentration to dryness gave the crude product (0.66 g, quantative), used without further purification. LC-MS m/z 288 (M+H)$^+$, 1.43 (ret. time), basic method.

4b) 5-Cyclopropyl-1-(3-{2-fluoro-3-[methyl(2-methylpropyl)carbamoyl]phenyl}phenyl)-1H-pyrazole-4-carboxylic Acid Ethyl Ester

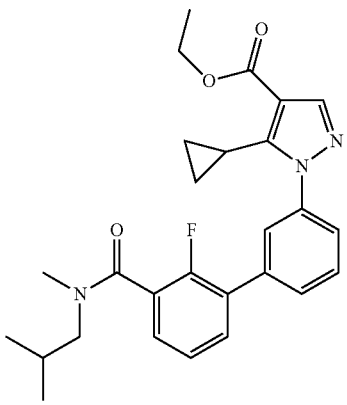 [SMILES: CCOC(=O)c1cnn(-c2cccc(-c3cccc(C(=O)N(C)CC(C)C)c3F)c2)c1C1CC1]

A stirred mixture of 3-bromo-2-fluoro-N-isobutyl-N-methyl-benzamide (0.226 g, 0.78 mmol), 5-cyclopropyl-1-[3-(4,4,5,5-tetramethyl-[1,3,2]dioxaborolan-2-yl)-phenyl]-1H-pyrazole-4-carboxylic acid ethyl ester (0.150 g, 0.39 mmol), aqueous Na₂CO₃ (3M, 0.392 mL) and Pd(PPh₃)₄ (0.045 g, 0.04 mmol) in EtOH (1 mL) and toluene (4 mL) was heated at reflux for 3 h. After cooling, the mixture was partitioned between EtOAc (20 mL) and water (10 mL) and the organic phase washed with water (10 mL) and brine (10 mL) before it was dried (MgSO₄), filtered, concentrated to dryness, and purified by silica chromatography (EtOAc/petrol 20-60% gradient) to give the product (0.110 g, 60%). LC-MS m/z 464 (M+H)$^+$, 1.53 (ret. time), basic method.

4c) 5-Cyclopropyl-1-(3-{2-fluoro-3-[methyl(2-methylpropyl)carbamoyl]phenyl}phenyl)-1H-pyrazole-4-carboxylic Acid

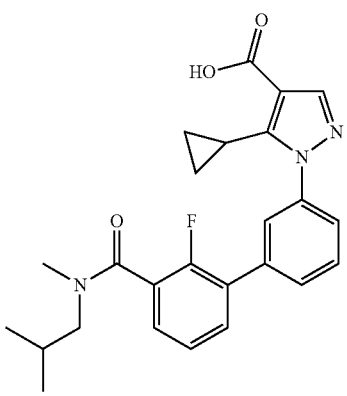 [SMILES: CC(C)CN(C)C(=O)c1cccc(-c2cccc(-n3ncc(C(=O)O)c3C3CC3)c2)c1F]

A stirred solution of 5-cyclopropyl-1-(3-{2-fluoro-3-[methyl(2-methylpropyl)carbamoyl]phenyl}phenyl)-1H-pyrazole-4-carboxylic acid ethyl ester (0.110 g, 0.24 mmol) in EtOH (2 mL) was treated with aqueous NaOH (2M, 0.593 mL). After 60 hours the mixture was partitioned between EtOAc and water. The organic phase was discarded and then the aqueous acidified with 1N HCl and extracted into EtOAc (×2). The combined organic phases were dried (MgSO$_4$), filtered, and concentrated under vacuum, to give the product (0.068 g, 66%). LC-MS m/z 436 (M+H)$^+$, 1.09 (ret. time), basic method. $^1$H NMR (400 MHz, DMSO-d6): 12.44-12.08 (1H, m), 7.97 (1H, s), 7.79 (1H, d), 7.68 (4H, s), 7.44-7.35 (2H, m), 3.09-2.95 (2H, m), 2.87 (2H, s), 2.20-1.98 (2H, m), 0.97-0.79 (6H, m), 0.73 (2H, d), 0.64-0.52 (2H, m). Rotameric peaks around amide and $^1$H underwater peak.

Example 5. 1-(3-{3-[Cyclohexyl(methyl)carbamoyl]-2-fluorophenyl}phenyl)-5-cyclopropyl-1H-pyrazole-4-carboxylic Acid

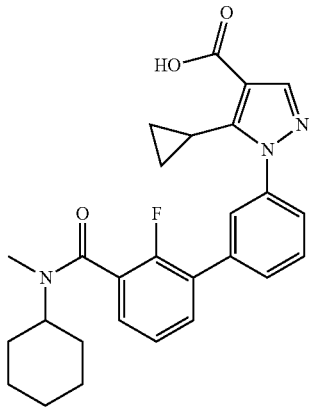 [SMILES: CN(C(=O)c1cccc(-c2cccc(-n3ncc(C(=O)O)c3C3CC3)c2)c1F)C1CCCCC1]

5a)
3-Bromo-N-cyclohexyl-2-fluoro-N-methyl-benzamide

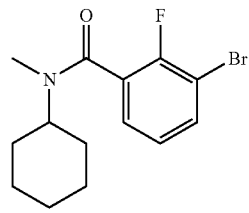 [SMILES: CN(C(=O)c1cccc(Br)c1F)C1CCCCC1]

A solution of 3-bromo-2-fluoro-benzoic acid (0.50 g, 2.28 mmol), HATU (0.868 g, 2.28 mmol), N-cyclohexyl-N-methylamine (0.297 g, 2.63 mmol) and DIPEA (0.590 g, 4.57 mmol) in DCM (15 mL) was stirred for 3 h. The mixture was washed with aqueous NaHCO$_3$ and dried by passage through a phase separation cartridge. Concentration to dryness gave the crude product (0.905 g, quantative), used without further purification. LC-MS m/z 314 (M+H)$^+$, 1.50 (ret. time).

5b) 1-(3-{3-[Cyclohexyl(methyl)carbamoyl]-2-fluorophenyl}phenyl)-5-cyclopropyl-1H-pyrazole-4-carboxylic Acid Ethyl Ester

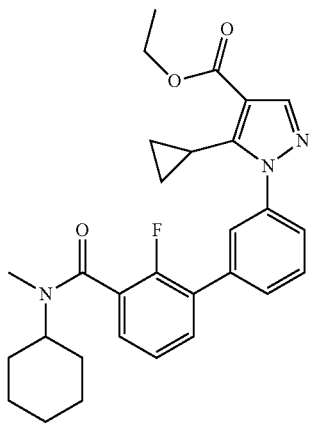 [SMILES: CCOC(=O)c1cnn(-c2cccc(-c3cccc(C(=O)N(C)C4CCCCC4)c3F)c2)c1C1CC1]

A stirred mixture of 3-bromo-N-cyclohexyl-2-fluoro-N-methyl-benzamide (0.226 g, 0.78 mmol), 5-cyclopropyl-1-[3-(4,4,5,5-tetramethyl-[1,3,2]dioxaborolan-2-yl)-phenyl]-1H-pyrazole-4-carboxylic acid ethyl ester (0.150 g, 0.39 mmol), aqueous Na$_2$CO$_3$ (3M, 0.392 mL) and Pd(PPh$_3$)$_4$ (0.045 g, 0.04 mmol) in EtOH (1 mL) and toluene (4 mL) was heated at reflux for 3 h. After cooling, the mixture was partitioned between EtOAc (20 mL) and water (10 mL) and the organic phase washed with water (10 mL) and brine (10 mL) before it was dried (MgSO$_4$), filtered, concentrated to dryness, and purified by silica chromatography (EtOAc/petrol 15-60% gradient) to give the product (0.114 g, 59%). LC-MS m/z 490 (M+H)$^+$, 1.57 (ret. time), basic method.

5c) 1-(3-{3-[Cyclohexyl(methyl)carbamoyl]-2-fluorophenyl}phenyl)-5-cyclopropyl-1H-pyrazole-4-carboxylic Acid

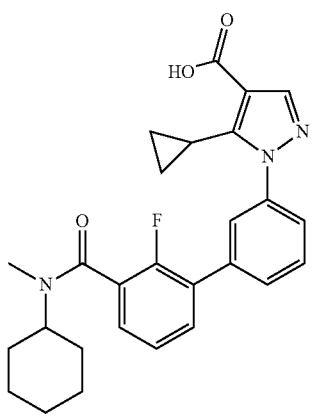 [SMILES: CN(C(=O)c1cccc(-c2cccc(-n3ncc(C(=O)O)c3C3CC3)c2)c1F)C1CCCCC1]

A stirred solution of 1-(3-{3-[cyclohexyl(methyl)carbamoyl]-2-fluorophenyl}phenyl)-5-cyclopropyl-1H-pyrazole-4-carboxylic acid ethyl ester (0.114 g, 0.23 mmol) in EtOH (2 mL) was treated with aqueous NaOH (2M, 0.582 mL). After 60 hours the mixture was partitioned between EtOAc and water. The organic phase was discarded and then the aqueous acidified with 1N HCl and extracted into EtOAc (×2).

The combined organic phases were dried (MgSO$_4$), filtered, and concentrated under vacuum, to give the product (0.084 g, 78%). LC-MS m/z 462 (M+H)$^+$, 1.12 (ret. time), basic method. $^1$H NMR (400 MHz, DMSO-d6): 12.23 (1H, s), 7.97 (1H, d), 7.79 (1H, s), 7.67 (4H, s), 7.51-7.33 (2H, m), 4.42-4.31 (0.5H, m), 3.30-3.19 (0.5H, m), 2.91 (1.5H, s), 2.74 (1.5H, s), 2.21-2.06 (1H, m), 1.81 (1H, d), 1.75-1.45 (6H, m), 1.45-1.29 (1H, m), 1.01 (2H, m), 0.93-0.76 (2H, m), 0.69-0.50 (2H, m). Peaks close to amide are rotameric.

Example 6. 5-Cyclopropyl-1-{3-[3-(3,3-dimethylpiperidine-1-carbonyl)-2-fluorophenyl]phenyl}-1H-pyrazole-4-carboxylic Acid

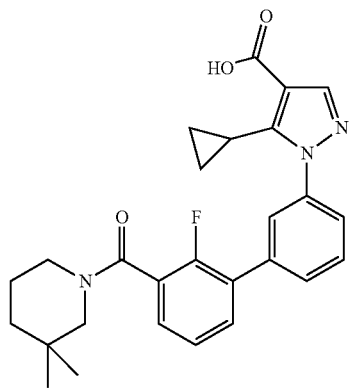 [SMILES: CC1(C)CCCN(C(=O)c2cccc(-c3cccc(-n4ncc(C(=O)O)c4C4CC4)c3)c2F)C1]

6a) (3-Bromo-2-fluoro-phenyl)-(3,3-dimethyl-piperidin-1-yl)-methanone

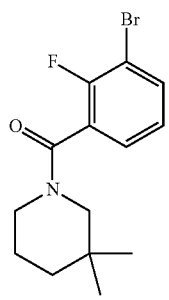

A solution of 3-bromo-2-fluoro-benzoic acid (0.100 g, 0.46 mmol), HATU (0.174 g, 0.46 mmol), 3,3-dimethylpiperidine (0.059 g, 0.53 mmol) and DIPEA (0.118 g, 0.91 mmol) in DCM (15 mL) was stirred for 3 h. The mixture was washed with aqueous NaHCO$_3$ and dried by passage through a phase separation cartridge. Concentration to dryness gave the crude product (0.905 g, quantative), used without further purification. LC-MS m/z 314 (M+H)$^+$, 1.44 (ret. time).

6b) 5-Cyclopropyl-1-{3-[3-(3,3-dimethylpiperidine-1-carbonyl)-2-fluorophenyl]phenyl}-1H-pyrazole-4-carboxylic Acid Ethyl Ester

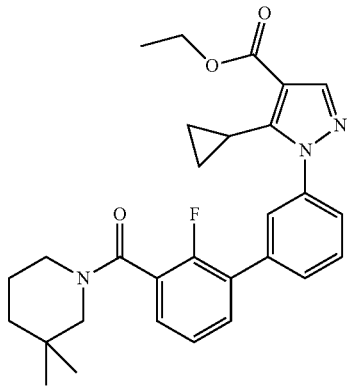 [SMILES: CCOC(=O)c1cnn(-c2cccc(-c3cccc(C(=O)N4CCCC(C)(C)C4)c3F)c2)c1C1CC1]

A stirred mixture of (3-bromo-2-fluoro-phenyl)-(3,3-dimethyl-piperidin-1-yl)-methanone (0.173 g, 0.55 mmol), 5-cyclopropyl-1-[3-(4,4,5,5-tetramethyl-[1,3,2]dioxaborolan-2-yl)-phenyl]-1H-pyrazole-4-carboxylic acid ethyl ester (0.150 g, 0.39 mmol), aqueous Na$_2$CO$_3$ (3M, 0.392 mL) and Pd(PPh$_3$)$_4$ (0.032 g, 0.03 mmol) in EtOH (1 mL) and toluene (4 mL) was heated at reflux for 3 h. After cooling, the mixture was partitioned between EtOAc (20 mL) and water (10 mL) and the organic phase washed with water (10 mL) and brine (10 mL) before it was dried (MgSO$_4$), filtered, concentrated to dryness, and purified by silica chromatography (EtOAc/petrol 10-60% gradient) to give the product (0.119 g, 62%). LC-MS m/z 490 (M+H)$^+$, 1.56 (ret. time).

6c) 5-Cyclopropyl-1-{3-[3-(3,3-dimethylpiperidine-1-carbonyl)-2-fluorophenyl]phenyl}-1H-pyrazole-4-carboxylic Acid

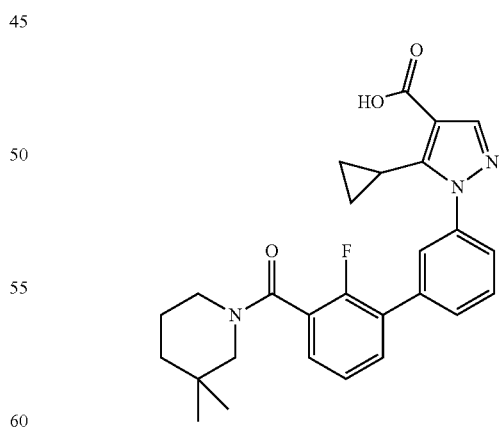

A stirred solution of 5-cyclopropyl-1-{3-[3-(3,3-dimethylpiperidine-1-carbonyl)-2-fluorophenyl]phenyl}-1H-pyrazole-4-carboxylic acid ethyl ester (0.119 g, 0.24 mmol) in EtOH (2 mL) was treated with aqueous NaOH (2M, 0.608 mL). After 60 hours the mixture was partitioned between EtOAc and water. The organic phase was discarded and then the aqueous acidified with 1N HCl and extracted into EtOAc (×2). The combined organic phases were dried (MgSO$_4$), filtered, and concentrated under vacuum to give the product (0.073 g, 65%). LC-MS m/z 462 (M+H)$^+$, 1.12 (ret. time), basic method. $^1$H NMR (400 MHz, DMSO-d6): 12.21 (1H, s), 7.97 (1H, s), 7.79 (1H, d), 7.74-7.58 (4H, m), 7.45-7.34 (2H, m), 3.47 (1H, m), 3.21 (2H, m), 2.98 (1H, m), 2.20-2.08 (1H, m), 1.53 (2H, d), 1.41 (2H, m), 0.96 (3H, s), 0.92-0.83 (2H, m), 0.79 (3H, s), 0.57 (2H, d).

Example 7. 1-{3-[3-(azepane-1-carbonyl)-2-fluorophenyl]phenyl}-5-cyclopropyl-1H-pyrazole-4-carboxylic Acid

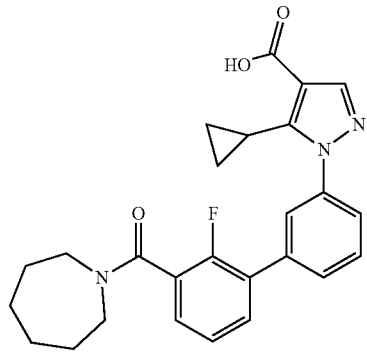 [SMILES: O=C(O)c1cnn(-c2cccc(-c3cccc(C(=O)N4CCCCCC4)c3F)c2)c1C1CC1]

7a) Azepan-1-yl-(3-bromo-2-fluoro-phenyl)-methanone

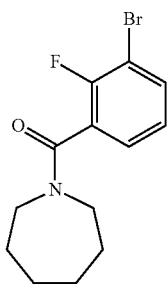 [SMILES: O=C(c1cccc(Br)c1F)N1CCCCCC1]

A solution of 3-bromo-2-fluoro-benzoic acid (0.500 g, 2.28 mmol), HATU (0.868 g, 2.28 mmol), azepane (0.260 g, 2.63 mmol) and DIPEA (0.590 g, 4.57 mmol) in DCM (15 mL) was stirred for 3 h. The mixture was washed with aqueous NaHCO$_3$ and dried by passage through a phase separation cartridge. Concentration to dryness gave the crude product (1.11 g, quantative), used without further purification. LC-MS m/z 300 (M+H)$^+$, 1.36 (ret. time), basic method.

7b) 1-{3-[3-(Azepane-1-carbonyl)-2-fluorophenyl]phenyl}-5-cyclopropyl-1H-pyrazole-4-carboxylic Acid Ethyl Ester

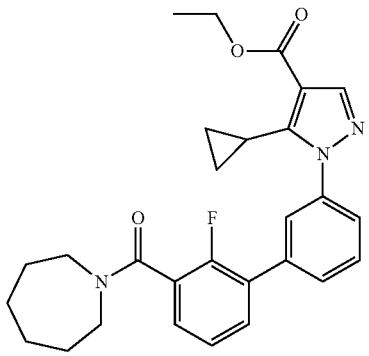 [SMILES: CCOC(=O)c1cnn(-c2cccc(-c3cccc(C(=O)N4CCCCCC4)c3F)c2)c1C1CC1]

A stirred mixture of azepan-1-yl-(3-bromo-2-fluoro-phenyl)-methanone (0.236 g, 0.78 mmol), 5-cyclopropyl-1-[3-(4,4,5,5-tetramethyl-[1,3,2]dioxaborolan-2-yl)-phenyl]-1H-pyrazole-4-carboxylic acid ethyl ester (0.150 g, 0.39 mmol), aqueous Na$_2$CO$_3$ (3M, 0.392 mL) and Pd(PPh$_3$)$_4$ (0.045 g, 0.04 mmol) in EtOH (1 mL) and toluene (4 mL) was heated at reflux for 3 h. After cooling, the mixture was partitioned between EtOAc (20 mL) and water (10 mL). The organic phase was washed with water (10 mL) and brine (10 mL) before it was dried (MgSO$_4$), filtered, concentrated to dryness, and purified by silica chromatography (EtOAc/petrol 15-65% gradient) to give the product (0.093 g, 50%). LC-MS m/z 476 (M+H)$^+$, 1.52 (ret. time), basic method.

7c) 1-{3-[3-(Azepane-1-carbonyl)-2-fluorophenyl]phenyl}-5-cyclopropyl-1H-pyrazole-4-carboxylic Acid

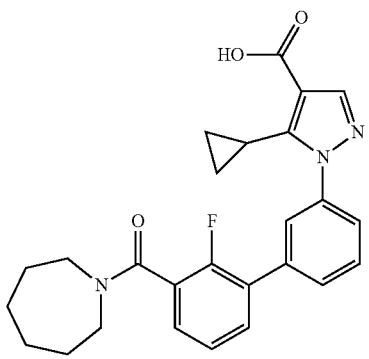 [SMILES: O=C(O)c1cnn(-c2cccc(-c3cccc(C(=O)N4CCCCCC4)c3F)c2)c1C1CC1]

A stirred solution of 1-{3-[3-(azepane-1-carbonyl)-2-fluorophenyl]phenyl}-5-cyclopropyl-1H-pyrazole-4-carboxylic acid ethyl ester (0.093 g, 0.20 mmol) in EtOH (2 mL) was treated with aqueous NaOH (2M, 0.489 mL). After 60 hours the mixture was partitioned between EtOAc and water. The organic phase was discarded and then the aqueous was acidified with 1N HCl and extracted into EtOAc (×2). The combined organic phases were dried (MgSO$_4$), filtered, and concentrated under vacuum, to give the product (0.061 g, 70%). LC-MS m/z 448 (M+H)$^+$, 1.08 (ret. time), basic method. $^1$H NMR (400 MHz, DMSO-d6): 12.21 (1H, s), 7.97 (1H, s), 7.79 (1H, s), 7.72-7.59 (4H, m), 7.45-7.35 (2H, m), 3.60 (2H, s), 3.37-3.24 (2H, m), 2.19-2.08 (1H, m), 1.78-1.65 (2H, m), 1.55 (6H, s), 0.92-0.81 (2H, m), 0.63-0.52 (2H, m).

Example 8. 1-(3-{3-[Bis(cyclopropylmethyl)carbamoyl]-2-fluorophenyl}phenyl)-5-cyclopropyl-1H-pyrazole-4-carboxylic Acid

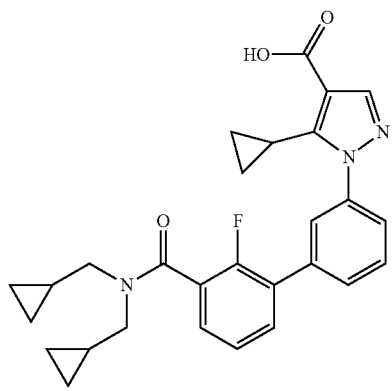 [SMILES: O=C(O)c1cnn(-c2cccc(-c3cccc(C(=O)N(CC4CC4)CC4CC4)c3F)c2)c1C1CC1]

8a) 3-Bromo-N,N-bis-cyclopropylmethyl-2-fluoro-benzamide

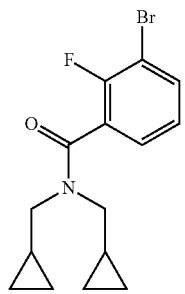 [SMILES: O=C(c1cccc(Br)c1F)N(CC1CC1)CC1CC1]

A solution of 3-bromo-2-fluoro-benzoic acid (0.500 g, 2.28 mmol), HATU (0.868 g, 2.28 mmol), N,N-bis-cyclopropylmethylamine (0.329 g, 2.63 mmol) and DIPEA (0.590 g, 4.57 mmol) in DCM (15 mL) was stirred for 3 h. The mixture was washed with aqueous NaHCO$_3$ and dried by passage through a phase separation cartridge. Concentration to dryness gave the crude product (0.904 g, quantative), used without further purification. LC-MS m/z 326 (M+H)$^+$, 1.46 (ret. time), basic method.

8b) 1-(3-{3-[Bis(cyclopropylmethyl)carbamoyl]-2-fluorophenyl}phenyl)-5-cyclopropyl-1H-pyrazole-4-carboxylic Acid Ethyl Ester

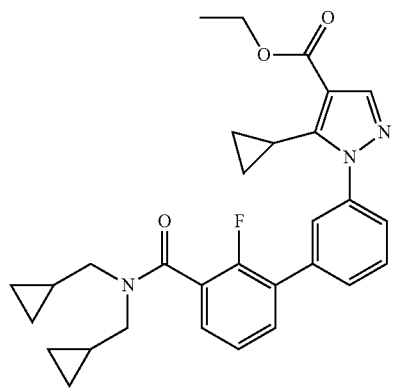 [SMILES: CCOC(=O)c1cnn(-c2cccc(-c3cccc(C(=O)N(CC4CC4)CC4CC4)c3F)c2)c1C1CC1]

A stirred mixture of 3-bromo-N,N-bis-cyclopropylmethyl-2-fluoro-benzamide (0.192 g, 0.59 mmol), 5-cyclopropyl-1-[3-(4,4,5,5-tetramethyl-[1,3,2]dioxaborolan-2-yl)-phenyl]-1H-pyrazole-4-carboxylic acid ethyl ester (0.150 g, 0.39 mmol), aqueous Na$_2$CO$_3$ (3M, 0.392 mL) and Pd(PPh$_3$)$_4$ (0.034 g, 0.03 mmol) in EtOH (1 mL) and toluene (4 mL) was heated at reflux for 3 h. After cooling, the mixture was partitioned between EtOAc (20 mL) and water (10 mL). The organic phase was washed with water (10 mL) and brine (10 mL) before it was dried (MgSO$_4$), filtered, and concentrated to dryness to give the product, used without further purification (0.213 g, quantative). LC-MS no ion observed, 1.57 (ret. time), basic method.

8c) 1-(3-{3-[Bis(cyclopropylmethyl)carbamoyl]-2-fluorophenyl}phenyl)-5-cyclopropyl-1H-pyrazole-4-carboxylic Acid

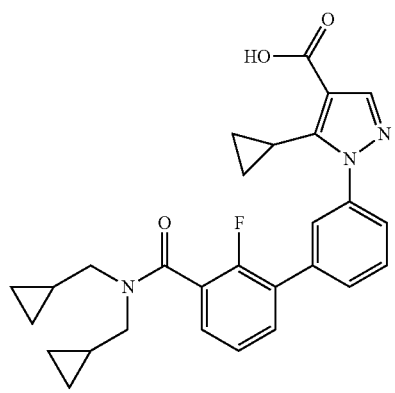 [SMILES: O=C(O)c1cnn(-c2cccc(-c3cccc(C(=O)N(CC4CC4)CC4CC4)c3F)c2)c1C1CC1]

A stirred solution of 1-(3-{3-[bis(cyclopropylmethyl)carbamoyl]-2-fluorophenyl}phenyl)-5-cyclopropyl-1H-pyrazole-4-carboxylic acid ethyl ester (0.213 g, 0.42 mmol) in EtOH (3 mL) was treated with aqueous NaOH (2M, 1.06 mL). After 60 hours the mixture was acidified with 1N HCl and extracted into EtOAc (×2). The combined organic phases were dried (MgSO$_4$), filtered, and concentrated under vacuum, and the residue purified by preparative HPLC to give the product (0.044 g, 22%). LC-MS m/z 474 (M+H)$^+$, 1.14 (ret. time), basic method. $^1$H NMR (400 MHz, DMSO-d6): 12.29 (1H, s), 7.97 (1H, s), 7.79 (1H, s), 7.73-7.56 (4H, m), 7.44-7.35 (2H, m), 3.68-3.39 (2H, m), 3.14 (2H, d), 2.19-2.08 (1H, m), 1.27-1.10 (1H, m), 0.98-0.79 (3H, m), 0.63-0.55 (2H, m), 0.50 (2H, d), 0.43 (2H, d), 0.33 (2H, d), 0.04 (2H, s).

Example 9. 5-Cyclopropyl-1-(3-{3-[(cyclopropylmethyl)(propyl)carbamoyl]-2-fluorophenyl}phenyl)-1H-pyrazole-4-carboxylic Acid

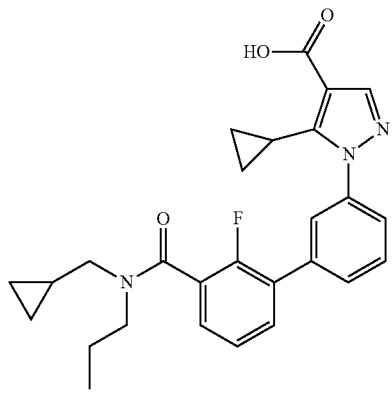 [SMILES: CCCN(CC1CC1)C(=O)c1cccc(-c2cccc(-n3ncc(C(=O)O)c3C3CC3)c2)c1F]

9a) 3-Bromo-N-cyclopropylmethyl-2-fluoro-N-propyl-benzamide

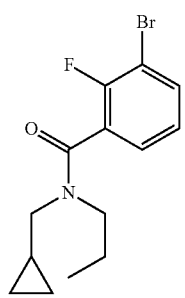 [SMILES: CCCN(CC1CC1)C(=O)c1cccc(Br)c1F]

A solution of 3-bromo-2-fluoro-benzoic acid (0.500 g, 2.28 mmol), HATU (0.868 g, 2.28 mmol), N-cyclopropylmethyl-N-propylamine (0.297 g, 2.63 mmol) and DIPEA (0.590 g, 4.57 mmol) in DCM (15 mL) was stirred for 3 h. The mixture was washed with aqueous NaHCO$_3$ and dried by passage through a phase separation cartridge. Concentration to dryness gave the crude product (1.23 g, quantative), used without further purification. LC-MS m/z 314 (M+H)$^+$, 1.44 (ret. time), basic method.

9b) 5-Cyclopropyl-1-(3-{3-[(cyclopropylmethyl)(propyl)carbamoyl]-2-fluorophenyl}phenyl)-1H-pyrazole-4-carboxylic Acid Ethyl Ester

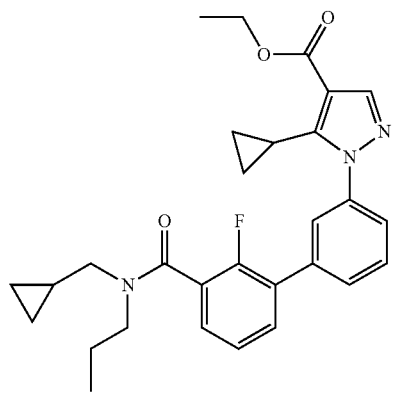 [SMILES: CCCN(CC1CC1)C(=O)c1cccc(-c2cccc(-n3ncc(C(=O)OCC)c3C3CC3)c2)c1F]

A stirred mixture of 3-bromo-N-cyclopropylmethyl-2-fluoro-N-propyl-benzamide (0.247 g, 0.78 mmol), 5-cyclopropyl-1-[3-(4,4,5,5-tetramethyl-[1,3,2]dioxaborolan-2-yl)-phenyl]-1H-pyrazole-4-carboxylic acid ethyl ester (0.150 g, 0.39 mmol), aqueous Na$_2$CO$_3$ (3M, 0.392 mL) and Pd(PPh$_3$)$_4$ (0.045 g, 0.04 mmol) in EtOH (1 mL) and toluene (4 mL) was heated at reflux for 3 h. After cooling, the mixture was partitioned between EtOAc (20 mL) and water (10 mL) and the organic phase washed with water (10 mL) and brine (10 mL) before it was dried (MgSO$_4$), filtered, and concentrated to dryness to give the product, used without further purification (0.250 g, quantative). LC-MS m/z 490 (M+H)$^+$, 1.56 (ret. time), basic method.

9c) 5-Cyclopropyl-1-(3-{3-[(cyclopropylmethyl)(propyl)carbamoyl]-2-fluorophenyl}phenyl)-1H-pyrazole-4-carboxylic Acid A stirred solution of 5-cyclopropyl-1-(3-{3-[(cyclopropylmethyl)(propyl)carbamoyl]-2-fluorophenyl}phenyl)-1H-pyrazole-4-carboxylic acid ethyl ester (0.238 g, 0.49 mmol) in EtOH (3 mL) was treated with aqueous NaOH (2M, 1.215 mL). After 60 hours the mixture was acidified with 1N HCl and extracted into EtOAc (×2). The combined organic phases were dried (MgSO$_4$), filtered, and concentrated under vacuum, and the residue purified by preparative HPLC to give the product (0.034 g, 15%). LC-MS m/z 462 (M+H)$^+$, 1.15 (ret. time), basic method. $^1$H NMR (400 MHz, DMSO-d6): 12.31 (1H, s), 7.97 (1H, d), 7.79 (1H, s), 7.67 (4H, s), 7.44-7.35 (2H, m), 3.69-3.34 (2H, m), 3.21 (1H, t), 3.06 (1H, d), 2.19-2.08 (1H, m), 1.72-1.59 (1H, m), 1.54-1.41 (1H, m), 1.15-1.05 (0.5H, m), 0.96-0.78 (4.5H, m), 0.69 (1H, t), 0.57 (2H, d), 0.54-0.47 (1H, m), 0.43 (1H, d), 0.36-0.27 (1H, m), 0.05 (1H, d). Rotameric peaks around amide.

Example 10. 1-{3-[3-(Azepane-1-carbonyl)phenyl]phenyl}-5-cyclopropyl-1H-pyrazole-4-carboxylic Acid

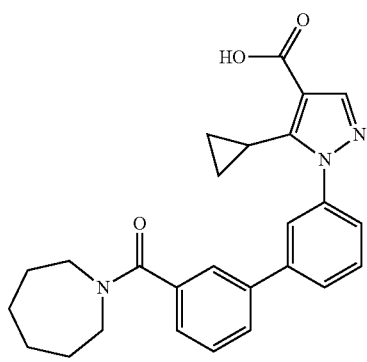 [SMILES: O=C(O)c1cnn(-c2cccc(-c3cccc(C(=O)N4CCCCCC4)c3)c2)c1C1CC1]

10a) Azepan-1-yl-(3-bromo-2-fluoro-phenyl)-methanone

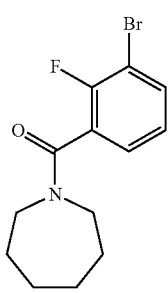 [SMILES: O=C(c1cccc(Br)c1F)N1CCCCCC1]

A solution of 3-bromobenzoic acid (0.500 g, 2.49 mmol), HATU (0.946 g, 2.49 mmol), azepane (0.284 g, 2.86 mmol) and DIPEA (0.643 g, 4.98 mmol) in DCM (15 mL) was stirred for 4 h. The mixture was washed with aqueous NaHCO$_3$ and dried by passage through a phase separation cartridge. Concentration to dryness gave the crude product (1.1 g, quantative), used without further purification. LC-MS m/z 282 (M+H)$^+$, 1.36 (ret. time).

10b) 1-{3-[3-(Azepane-1-carbonyl)phenyl]phenyl}-5-cyclopropyl-1H-pyrazole-4-carboxylic Acid Ethyl Ester

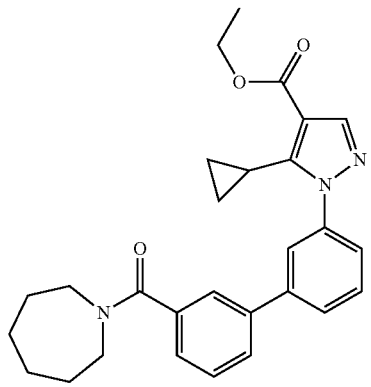 [SMILES: CCOC(=O)c1cnn(-c2cccc(-c3cccc(C(=O)N4CCCCCC4)c3)c2)c1C1CC1]

A stirred mixture of azepan-1-yl-(3-bromophenyl)-methanone (0.243 g, 0.81 mmol), 5-cyclopropyl-1-[3-(4,4,5,5-tetramethyl-[1,3,2]dioxaborolan-2-yl)-phenyl]-1H-pyrazole-4-carboxylic acid ethyl ester (0.155 g, 0.41 mmol), aqueous Na$_2$CO$_3$ (3M, 0.405 mL) and Pd(PPh$_3$)$_4$ (0.047 g, 0.04 mmol) in EtOH (1 mL) and toluene (4 mL) was heated at reflux for 3 h. After cooling, the mixture was partitioned between EtOAc (15 mL) and water (15 mL) and the organic phase washed with water (10 mL) and brine (10 mL) before it was dried (MgSO$_4$), filtered, and concentrated to dryness to give crude product (0.33 g, quantative). LC-MS m/z 458 (M+H)$^+$, 1.53 (ret. time).

10c) 1-{3-[3-(Azepane-1-carbonyl)phenyl]phenyl}-5-cyclopropyl-1H-pyrazole-4-carboxylic Acid

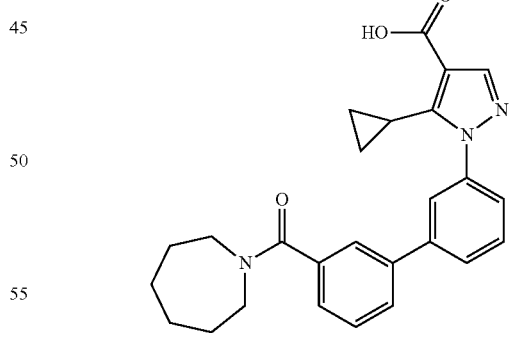

A stirred solution of 1-{3-[3-(azepane-1-carbonyl)phenyl]phenyl}-5-cyclopropyl-1H-pyrazole-4-carboxylic acid ethyl ester (0.330 g, 0.72 mmol) in EtOH (3 mL) was treated with aqueous NaOH (2M, 1.80 mL). After 60 hours the mixture was partitioned between EtOAc and water. The organic phase was discarded and then the aqueous acidified with 1N HCl and extracted into EtOAc (×2). The combined organic phases were dried (MgSO$_4$), filtered, and concentrated under vacuum, and the residue purified by silica chromatography eluting with EtOAc/petrol 50-100% followed by MeOH/EtOAc 0-10% to give the product (0.084 g, 27%). LC-MS m/z 430 (M+H)+, 1.10 (ret. time), basic method. ¹H NMR (400 MHz, DMSO-d6): 12.31 (1H, s), 7.97 (1H, s), 7.95-7.89 (1H, m), 7.87-7.78 (2H, m), 7.71 (1H, s), 7.68-7.59 (2H, m), 7.55 (1H, t), 7.38 (1H, d), 3.58 (2H, t), 3.41-3.33 (2H, m), 2.23-2.12 (1H, m), 1.80-1.65 (2H, m), 1.56 (6H, s), 0.93-0.79 (2H, m), 0.63-0.52 (2H, m).

Example 11. 1-{3-[3-(propan-2-yloxy)phenyl]phenyl}-5-(trifluoromethyl)-1H-pyrazole-4-carboxylic Acid

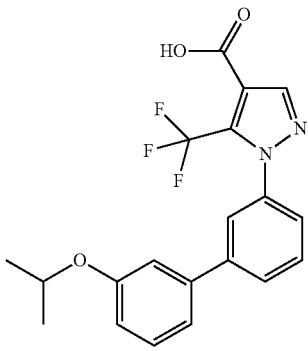 [SMILES: CC(C)Oc1cccc(-c2cccc(-n3ncc(C(=O)O)c3C(F)(F)F)c2)c1]

11a) 1-{3-[3-(Propan-2-yloxy)phenyl]phenyl}-5-(trifluoromethyl)-1H-pyrazole-4-carboxylic Acid Ethyl Ester

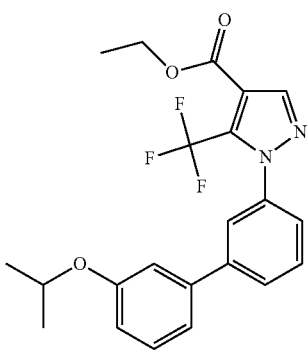 [SMILES: CCOC(=O)c1cnn(-c2cccc(-c3cccc(OC(C)C)c3)c2)c1C(F)(F)F]

A stirred mixture of 1-(3-bromo-phenyl)-5-trifluoromethyl-1H-pyrazole-4-carboxylic acid ethyl ester (0.08 g, 0.22 mmol), 3-isopropoxy-phenylboronic acid (0.050 g, 0.29 mmol), Na₂CO₃ (0.095 g, 0.88 mmol) and Pd(PPh₃)₄ (0.025 g, 0.022 mmol) in DME/water 2:1 (3 mL) was heated at 95° C. for 5 h. After cooling, the mixture was partitioned between EtOAc and water. The organic layer was washed with brine, dried (MgSO₄), filtered, and purified by SiO₂ chromatography (eluting with 50-100% EtOAc/hexanes) to give the product (0.040 g, 43%). LC-MS m/z 419 (M+H)+. 1.67 (ret. time).

11b) 1-{3-[3-(Propan-2-yloxy)phenyl]phenyl}-5-(trifluoromethyl)-1H-pyrazole-4-carboxylic Acid

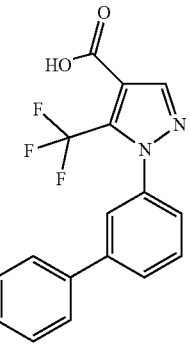

1-(3'-Isopropoxy-biphenyl-3-yl)-5-trifluoromethyl-1H-pyrazole-4-carboxylic acid ethyl ester (0.040 g, 0.096 mmol) was dissolved in MeOH (3 mL) and treated with aqueous LiOH (1M, 1 mL). After 24 hours the mixture was concentrated under vacuum and partitioned between EtOAc and water. The aqueous layer was acidified with 5N aqueous HCl and the product was extracted with DCM (×3). The DCM layer was dried (MgSO₄), filtered and concentrated to dryness to give the product (0.009 g, 24%). LC-MS m/z 391 (M+H)+, 1.17 (ret. time). ¹H-NMR (400 MHz, d6-DMSO): 13.36 (1H, br), 8.26 (1H, s), 7.96-7.82 (2H, m), 7.65 (1H, t), 7.53 (1H, d), 7.39 (1H, t), 7.32-7.19 (2H, m), 6.97 (1H, dd), 4.81-4.68 (1H, m), 1.29 (6H, d).

Example 12. 1-(3-{3-[(Cyclopentylmethyl)(methyl)carbamoyl]-2-fluorophenyl}phenyl)-5-cyclopropyl-1H-pyrazole-4-carboxylic Acid

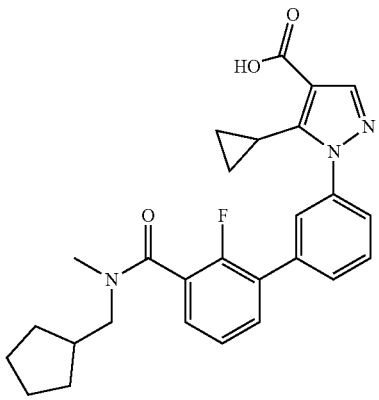 [SMILES: CN(CC1CCCC1)C(=O)c1cccc(-c2cccc(-n3ncc(C(=O)O)c3C3CC3)c2)c1F]

12a) 3-Bromo-N-cyclopentylmethyl-2-fluoro-benzamide

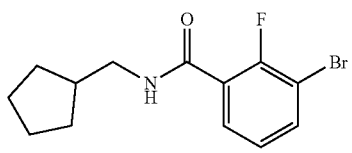 [SMILES: O=C(NCC1CCCC1)c1cccc(Br)c1F]

A solution of 3-bromo-2-fluoro-benzoic acid (1.00 g, 4.57 mmol), HATU (1.74 g, 4.57 mmol), cyclopentylmethylamine (0.712 g, 5.25 mmol) and DIPEA (1.77 g, 13.7 mmol) in DCM (15 mL) was stirred for 4 h. The mixture was washed with aqueous NaHCO$_3$ and dried by passage through a phase separation cartridge. Concentration to dryness gave the crude product (1.40 g, quantative), used without further purification. LC-MS m/z 300 (M+H)$^+$, 1.41 (ret. time).

12b) 3-Bromo-N-cyclopentylmethyl-2-fluoro-N-methyl-benzamide

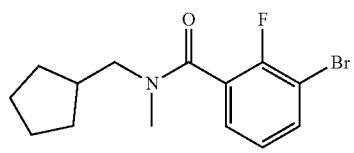 [SMILES: CN(CC1CCCC1)C(=O)c1cccc(Br)c1F]

A stirred solution of 3-bromo-N-cyclopentylmethyl-2-fluoro-benzamide (0.200 g, 0.67 mmol) in dry THF (5 mL) under N$_2$ at 0° C. was treated with NaH (0.019 g, 0.80 mmol). After 30 minutes MeI (0.104 g, 0.75 mmol) was added. After 1 h the reaction was quenched with water and extracted into EtOAc (×2). The combined organic phase was washed with water and brine before it was dried (MgSO4), filtered, and concentrated to give the product (0.124 g, 59%). LC-MS m/z 314 (M+H)$^+$, 1.47 (ret. time).

12c) 1-(3-{3-[(Cyclopentylmethyl)(methyl)carbamoyl]-2-fluorophenyl}phenyl)-5-cyclopropyl-1H-pyrazole-4-carboxylic Acid Ethyl Ester

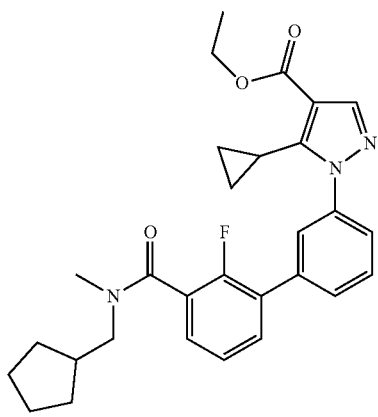 [SMILES: CCOC(=O)c1cnn(-c2cccc(-c3cccc(C(=O)N(C)CC4CCCC4)c3F)c2)c1C1CC1]

A stirred mixture of 3-bromo-N-cyclopentylmethyl-2-fluoro-N-methyl-benzamide (0.123 g, 0.39 mmol), 5-cyclopropyl-1-[3-(4,4,5,5-tetramethyl-[1,3,2]dioxaborolan-2-yl)-phenyl]-1H-pyrazole-4-carboxylic acid ethyl ester (0.100 g, 0.26 mmol), aqueous Na$_2$CO$_3$ (3M, 0.262 mL) and Pd(PPh$_3$)$_4$ (0.023 g, 0.02 mmol) in EtOH (0.75 mL) and toluene (3 mL) was heated at reflux for 3 h. After cooling, the mixture was partitioned between EtOAc (20 mL) and water, (10 mL) and the organic phase was washed with water (10 mL) and brine (10 mL) before it was dried (MgSO$_4$), filtered, and concentrated to dryness. Purification by silica column eluting 5-50% EtOAc in petrol gave the product (0.056 g, 44%). LC-MS m/z 490 (M+H)$^+$, 1.60 (ret. time), basic method.

12d) 1-(3-{3-[(Cyclopentylmethyl)(methyl)carbamoyl]-2-fluorophenyl}phenyl)-5-cyclopropyl-1H-pyrazole-4-carboxylic Acid

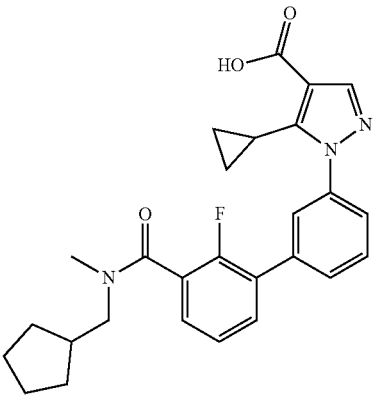 [SMILES: CN(CC1CCCC1)C(=O)c1cccc(-c2cccc(-n3ncc(C(=O)O)c3C3CC3)c2)c1F]

A stirred solution of 1-(3-{3-[(cyclopentylmethyl)(methyl)carbamoyl]-2-fluorophenyl}phenyl)-5-cyclopropyl-1H-pyrazole-4-carboxylic acid ethyl ester (0.056 g, 0.11 mmol) in EtOH (1 mL) was treated with aqueous NaOH (2M, 0.286 mL). After 60 hours the mixture was partitioned between EtOAc and water. The organic phase was discarded and then the aqueous acidified with 1N HCl and extracted into EtOAc (×2). The combined organic phases were dried (MgSO$_4$), filtered and concentrated under vacuum to give the product (0.043 g, 81%). LC-MS m/z 462 (M+H)$^+$, 1.19 (ret. time), basic method. $^1$H NMR (400 MHz, DMSO-d6): 12.25 (1H, s), 7.97 (1H, s), 7.79 (1H, d), 7.73-7.59 (4H, m), 7.44-7.35 (2H, m), 3.45 (1H, s), 3.13 (1H, d), 3.01 (1H, s), 2.88 (2H, s), 2.38-2.24 (1H, m), 2.24-2.12 (1H, m), 1.74-1.49 (4H, m), 1.49-1.22 (3H, m), 1.07-0.92 (1H, m), 0.92-0.79 (2H, m), 0.57 (2H, d).

Example 13. 5-[(cis)-3-Acetamidocyclopentyl]-1-{3-[2-fluoro-3-(propan-2-yloxy)phenyl]phenyl}-1H-pyrazole-4-carboxylic Acid (Cis Racemate)

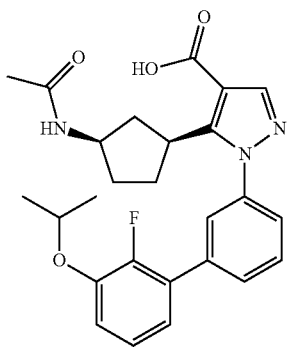 [SMILES: CC(=O)N[C@@H]1CC[C@H](c2c(C(=O)O)cnn2-c2cccc(-c3cccc(OC(C)C)c3F)c2)C1]

13a) 3-(3-tert-Butoxycarbonylamino-cyclopentyl)-3-oxo-propionic Acid Methyl Ester

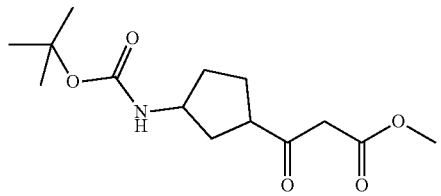 [SMILES: COC(=O)CC(=O)C1CCC(NC(=O)OC(C)(C)C)C1]

A stirred mixture of 3-aminocyclopentanecarboxylic acid (4.00 g, 31.0 mmol) in THF (20 mL) was treated with NaOH (1M aqueous, 57 mL) followed by Boc anhydride (6.76 g, 31.0 mmol). After 16 h the mixture was acidified with 2N HCl and then extracted with EtOAc (2×70 mL). The organic phases were combined, dried (MgSO$_4$), filtered, and concentrated to dryness. The residue was taken up into dry THF (70 mL) and 1,1'-carbonyldiimidazole (2.86 g, 17.6 mmol) was added and the mixture stirred for 1 h. A solid, powdered mixture of MgCl$_2$ (2.10 g, 17.6 mmol) and potassium methyl malonate (5.05 g, 32.3 mmol) was added and the mixture stirred at room temperature for 18 h. The mixture was concentrated and then partitioned between EtOAc and water. The aqueous phase was extracted with EtOAc before the combined organic phase was washed with brine, dried (MgSO$_4$), filtered, and concentrated to dryness to give the product (5 g, quantative) used directly in the next step without purification.

13b) 1-(3-Bromo-phenyl)-5-((cis)-3-tert-butoxycarbonylamino-cyclopentyl)-1H-pyrazole-4-carboxylic Acid Methyl Ester

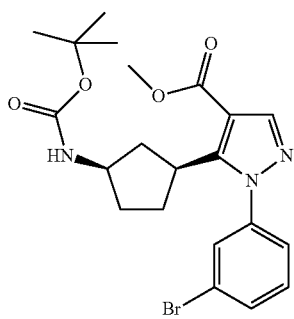 [SMILES: COC(=O)c1cnn(-c2cccc(Br)c2)c1[C@H]1CC[C@@H](NC(=O)OC(C)(C)C)C1]

A mixture of 3-(3-tert-butoxycarbonylamino-cyclopentyl)-3-oxo-propionic acid methyl ester (5.00 g, 17.5 mmol) and DMF-dimethyl acetal (2.30 g, 19.3 mmol) was stirred at room temperature for 16 h. A portion of the residue (3.00 g) was taken up into EtOH (50 mL) and treated with 3-bromophenylhydrazine HCl (1.97 g, 8.81 mmol) followed by triethylamine (2.64 g, 26.4 mmol). After 16 h at room temperature the mixture was partitioned between EtOAc and water and then the organic phase washed with further water, 0.5 N HCl, water and then brine before it was dried (MgSO$_4$), filtered, and concentrated to dryness. Purification by silica chromatography eluting with EtOAc/petrol 10-40% gave the cis product (2.70 g, 66%). LC-MS m/z 464 (M+H)$^+$, 1.55 (ret. time), basic method. A small amount (100 mg) of the trans isomer was also isolated.

13c) 5-((cis)-3-Amino-cyclopentyl)-1-(3-bromo-phenyl)-1H-pyrazole-4-carboxylic Acid Methyl Ester

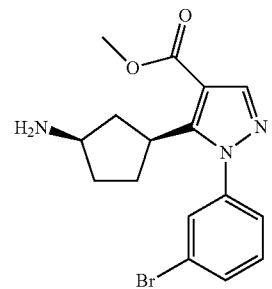 [SMILES: COC(=O)c1cnn(-c2cccc(Br)c2)c1[C@H]1CC[C@@H](N)C1]

A stirred solution of 1-(3-bromo-phenyl)-5-((cis)-3-tert-butoxycarbonylamino-cyclopentyl)-1H-pyrazole-4-carboxylic acid methyl ester (2.70 g, 5.07 mmol) in DCM (40 mL) was treated with HCl (4M in dioxane, 6.34 mL). After 16 h the mixture was diluted with DCM and water, then brought to basic pH with 2M NaOH. The organic layer was dried (MgSO$_4$), filtered and concentrated to give the product (2.19 g, quantative). LC-MS m/z 364 (M+H)$^+$, 1.26 (ret. time), basic method.

13d) 5-((cis)-3-Acetylamino-cyclopentyl)-1-(3-bromo-phenyl)-1H-pyrazole-4-carboxylic Acid Methyl Ester

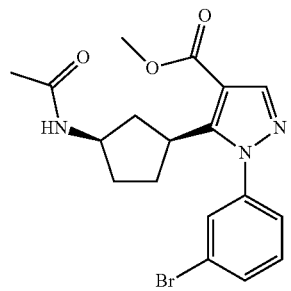 [SMILES: COC(=O)c1cnn(-c2cccc(Br)c2)c1[C@H]1CC[C@@H](NC(C)=O)C1]

A stirred solution of 5-((cis)-3-amino-cyclopentyl)-1-(3-bromo-phenyl)-1H-pyrazole-4-carboxylic acid methyl ester (2.19 g, 6.01 mmol) in DCM (30 mL) was treated with acetic anhydride (0.737 g, 7.22 mmol). After 4 h the mixture was diluted with DCM and washed with water. The organic phase was dried (MgSO$_4$), filtered and concentrated to dryness to give the product (1.80 g, 74%). LC-MS m/z 406 (M+H)$^+$, 1.31 (ret. time), basic method.

13e) 5-[(cis)-3-Acetamidocyclopentyl]-1-{3-[2-fluoro-3-(propan-2-yloxy)phenyl]phenyl}-1H-pyrazole-4-carboxylic Acid Methyl Ester

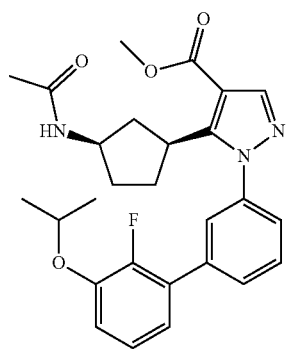 [SMILES: COC(=O)c1cnn(-c2cccc(-c3cccc(OC(C)C)c3F)c2)c1[C@H]1CC[C@@H](NC(C)=O)C1]

A stirred mixture of 2-fluoro-3-isopropoxyphenylboronic acid (0.081 g, 0.45 mmol), 5-((cis)-3-acetylamino-cyclopentyl)-1-(3-bromo-phenyl)-1H-pyrazole-4-carboxylic acid methyl ester (0.153 g, 0.38 mmol), aqueous $Na_2CO_3$ (3M, 0.377 mL) and $Pd(PPh_3)_4$ (0.026 g, 0.02 mmol) in EtOH (1 mL) and toluene (4 mL) was heated at reflux for 3 h. After cooling, the mixture was partitioned between EtOAc (20 mL) and water (10 mL) and the organic phase washed with water (10 mL) and brine (10 mL) before it was dried ($MgSO_4$), filtered, and concentrated to dryness to give the product used without further purification (0.151 g, 84%). LC-MS m/z 480 (M+H)$^+$, 1.47 (ret. time), basic method.

13f) 5-[(cis)-3-Acetamidocyclopentyl]-1-{3-[2-fluoro-3-(propan-2-yloxy)phenyl]phenyl}-1H-pyrazole-4-carboxylic Acid (Cis Racemate)

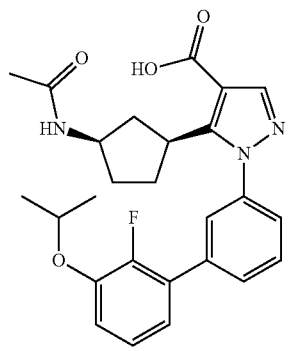 [SMILES: CC(=O)N[C@@H]1CC[C@H](c2c(C(=O)O)cnn2-c2cccc(-c3cccc(OC(C)C)c3F)c2)C1]

A stirred solution of 5-[(cis)-3-acetamidocyclopentyl]-1-{3-[2-fluoro-3-(propan-2-yloxy)phenyl]phenyl}-1H-pyrazole-4-carboxylic acid methyl ester (0.151 g, 0.31 mmol) in EtOH (2 mL) was treated with aqueous NaOH (2M, 0.765 mL). After 60 hours the mixture was partitioned between EtOAc and water. The aqueous layer was acidified with 1N HCl and extracted into EtOAc (×3). The combined organic phases were dried ($MgSO_4$), filtered, and concentrated under vacuum to give the product (0.055 g, 39%). LC-MS m/z 466 (M+H)$^+$, 1.13 (ret. time), basic method. $^1$H NMR (400 MHz, DMSO-d6): 8.01 (1H, s), 7.90 (1H, d), 7.75-7.64 (2H, m), 7.55 (1H, s), 7.51-7.44 (1H, m), 7.27-7.18 (2H, m), 7.16-7.09 (1H, m), 4.72-4.62 (1H, m), 4.02-3.89 (1H, m), 3.28-3.18 (1H, m), 2.24-2.12 (1H, m), 2.09-1.97 (2H, m), 1.91-1.81 (2H, m), 1.79 (3H, s), 1.74-1.61 (1H, m), 1.32 (6H, d).

Example 14. 1-(3-{3-[(Cyclopentylmethyl)(cyclopropylmethyl)carbamoyl]-2-fluorophenyl}phenyl)-5-cyclopropyl-1H-pyrazole-4-carboxylic Acid

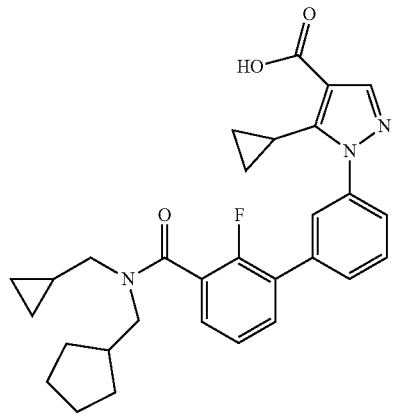 [SMILES: O=C(O)c1cnn(-c2cccc(-c3cccc(C(=O)N(CC4CCCC4)CC4CC4)c3F)c2)c1C1CC1]

14a) 3-Bromo-N-cyclopentylmethyl-N-cyclopropylmethyl-2-fluoro-benzamide

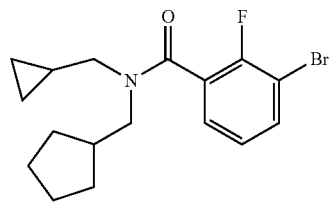 [SMILES: O=C(c1cccc(Br)c1F)N(CC1CCCC1)CC1CC1]

A stirred solution of 3-bromo-N-cyclopentylmethyl-2-fluoro-benzamide (0.300 g, 1.00 mmol) in dry THF (8 mL) under $N_2$ at 0° C. was treated with NaH (0.029 g, 1.20 mmol). After 30 minutes bromomethyl cyclopropane (0.1484 g, 1.10 mmol) was added. After a further 1 h the reaction was quenched with water and extracted into EtOAc (×2). The combined organic phase was washed with water and brine before it was dried (MgSO4), filtered, and concentrated to dryness followed by silica chromatography eluting with EtOAc/petrol 5-30% to give the product (0.193 g, 54%). LC-MS m/z 354 (M+H)$^+$, 1.59 (ret. time).

14b) 1-(3-{3-[(cyclopentylmethyl)(cyclopropylmethyl)carbamoyl]-2-fluorophenyl}phenyl)-5-cyclopropyl-1H-pyrazole-4-carboxylic Acid Ethyl Ester

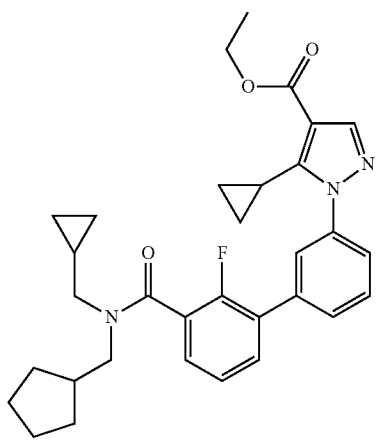 [SMILES: CCOC(=O)c1cnn(-c2cccc(-c3cccc(C(=O)N(CC4CCCC4)CC4CC4)c3F)c2)c1C1CC1]

A stirred mixture of 3-bromo-N-cyclopentylmethyl-N-cyclopropylmethyl-2-fluoro-benzamide (0.110 g, 0.35 mmol), 5-cyclopropyl-1-[3-(4,4,5,5-tetramethyl-[1,3,2]dioxaborolan-2-yl)-phenyl]-1H-pyrazole-4-carboxylic acid ethyl ester (0.112 g, 0.29 mmol), aqueous Na$_2$CO$_3$ (3M, 0.262 mL) and Pd(PPh$_3$)$_4$ (0.020 g, 0.02 mmol) in EtOH (0.75 mL) and toluene (3 mL) was heated at reflux for 3 h. After cooling, the mixture was partitioned between EtOAc (20 mL) and water (10 mL) and the organic phase washed with water (10 mL) and brine (10 mL) before it was dried (MgSO$_4$), filtered, and concentrated to dryness to give the product, used without further purification (0.204 g, quantative). LC-MS m/z no mass ion observed, 1.68 (ret. time).

14c) 1-(3-{3-[(Cyclopentylmethyl)(cyclopropylmethyl)carbamoyl]-2-fluorophenyl}phenyl)-5-cyclopropyl-1H-pyrazole-4-carboxylic Acid

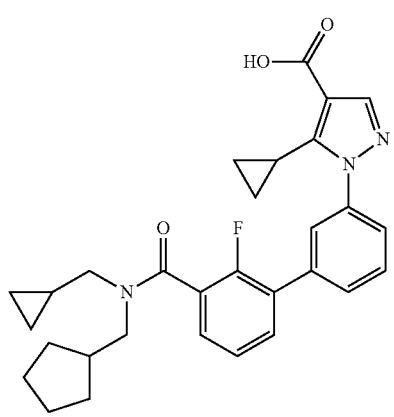 [SMILES: O=C(O)c1cnn(-c2cccc(-c3cccc(C(=O)N(CC4CCCC4)CC4CC4)c3F)c2)c1C1CC1]

A stirred solution of 1-(3-{3-[(cyclopentylmethyl)(cyclopropylmethyl)carbamoyl]-2-fluorophenyl}phenyl)-5-cyclopropyl-1H-pyrazole-4-carboxylic acid ethyl ester (0.204 g, 0.39 mmol) in EtOH (3 mL) was treated with aqueous NaOH (2M, 0.963 mL). After 60 hours the mixture was partitioned between EtOAc and water. The aqueous layer was acidified with 1N HCl and extracted into EtOAc (×3). The combined organic phases were dried (MgSO$_4$), filtered, concentrated under vacuum, and purified by HPLC. The residue was diluted with 1N HCl and extracted into EtOAc (×2). The combined organic phases were dried (MgSO$_4$), filtered, and concentrated under vacuum to give the product (0.055 g, 39%). LC-MS m/z 502 (M+H)$^+$, 1.24 (ret. time), basic method. $^1$H NMR (400 MHz, DMSO-d6): 7.97 (1H, s), 7.78 (1H, d), 7.72-7.61 (4H, m), 7.44-7.35 (2H, m), 3.72 (1H, br, m), 3.45 (1H, br, m), 3.20 (1H, br, m), 3.08 (1H, d), 2.41-2.28 (1H, m), 2.23-2.11 (1H, m), 1.77-1.51 (4H, m), 1.45-1.22 (3H, m), 1.16-0.94 (1H, m), 0.94-0.79 (3H, m), 0.62-0.54 (2H, m), 0.51 (1H, d), 0.48-0.38 (1H, m), 0.32 (1H, d), 0.03 (1H, s).

Example 15. 1-(3-{2-Chloro-3-[(cyclopropylmethyl)(propyl)carbamoyl]phenyl}phenyl)-5-cyclopropyl-1H-pyrazole-4-carboxylic Acid

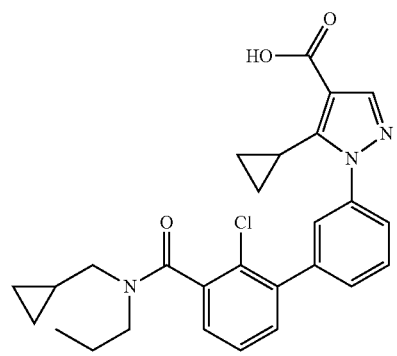 [SMILES: CCCN(CC1CC1)C(=O)c1cccc(-c2cccc(-n3ncc(C(=O)O)c3C3CC3)c2)c1Cl]

15a) 3-Bromo-2-chloro-N-cyclopropylmethyl-N-propyl-benzamide

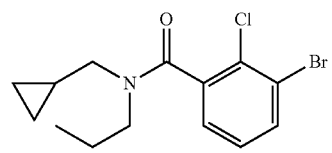

A solution of 3-bromo-2-chloro-benzoic acid (0.500 g, 2.12 mmol), HATU (0.807 g, 2.12 mmol), N-cyclopropylmethyl propylamine (0.402 g, 2.63 mmol) and DIPEA (0.74 mL, 4.2 mmol) in DCM (20 mL) was stirred for 2 h. The mixture was diluted with DCM. The organic phase was washed with aqueous NaHCO$_3$ and dried by passage through a phase separation cartridge. Concentration to dryness gave the crude product (1.21 g, quantative), used without further purification. LC-MS m/z 330 (M+H)$^+$, 1.49 (ret. time).

15b) 1-(3-{2-Chloro-3-[(cyclopropylmethyl)(propyl)carbamoyl]phenyl}phenyl)-5-cyclopropyl-1H-pyrazole-4-carboxylic Acid Ethyl Ester

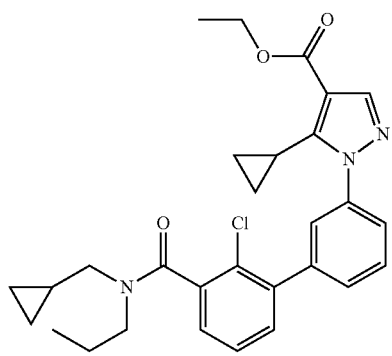 [SMILES: CCCN(CC1CC1)C(=O)c1cccc(-c2cccc(-n3ncc(C(=O)OCC)c3C3CC3)c2)c1Cl]

A stirred mixture of 3-bromo-2-chloro-N-cyclopropylmethyl-N-propyl-benzamide (0.181 g, 0.55 mmol), 5-cyclopropyl-1-[3-(4,4,5,5-tetramethyl-[1,3,2]dioxaborolan-2-yl)-phenyl]-1H-pyrazole-4-carboxylic acid ethyl ester (0.150 g, 0.39 mmol), aqueous Na₂CO₃ (3M, 0.392 mL) and Pd(PPh₃)₄ (0.032 g, 0.04 mmol) in EtOH (1 mL) and toluene (4 mL) was heated at 80° C. for 2 h. After cooling, the mixture was partitioned between EtOAc (20 mL) and water (10 mL) and the organic phase was washed with water (10 mL) and brine (10 mL) before it was dried (MgSO₄), filtered, concentrated to dryness, and purified by silica chromatography eluting with EtOAc/petrol 0-50% to give the product (0.117 g, 59%). LC-MS m/z 506 (M+H)⁺, 1.61 (ret. time).

15c) 1-(3-{2-Chloro-3-[(cyclopropylmethyl)(propyl)carbamoyl]phenyl}phenyl)-5-cyclopropyl-1H-pyrazole-4-carboxylic Acid

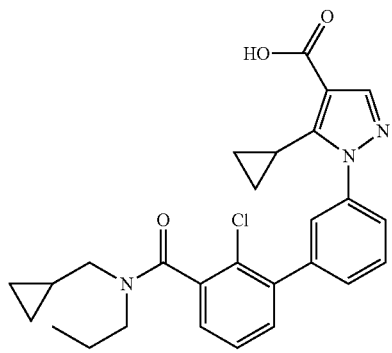

A stirred solution of 1-(3-{2-chloro-3-[(cyclopropylmethyl)(propyl)carbamoyl]phenyl}phenyl)-5-cyclopropyl-1H-pyrazole-4-carboxylic acid ethyl ester (0.117 g, 0.23 mmol) in THF (3 mL) and MeOH (3 mL) was treated with LiOH (98 mg, 4.08 mmol) in water (3 mL). After 40 hours the mixture was concentrated to remove organic solvents and the residue partitioned between EtOAc and water. The aqueous layer was acidified with 1N HCl and extracted into EtOAc (×2). The combined organic phases were dried (MgSO₄), filtered, and concentrated under vacuum to give the product (0.070 g, 63%). LC-MS m/z 478 (M+H)⁺, 1.17 (ret. time). ¹H NMR (400 MHz, DMSO-d6): [presence of rotamers] 12.15 (1H, br s), 7.96 (1H, d), 7.69-7.61 (3H, m), 7.59-7.47 (3H, m), 7.43-7.35 (1H, m), 3.70-3.35 (2H, m), 3.26-2.92 (2H, m), 2.18-2.08 (1H, m), 1.72-1.42 (2H, m), 1.09 (1H, d), 0.97-0.81 (4H, m), 0.71 (1H, t), 0.62-0.25 (5H, m), 0.19-0.04 (1H, m).

Example 16. 5-Cyclopropyl-1-(3-{3-[(cyclopropylmethyl)(propyl)carbamoyl]-2-methylphenyl}phenyl)-1H-pyrazole-4-carboxylic Acid

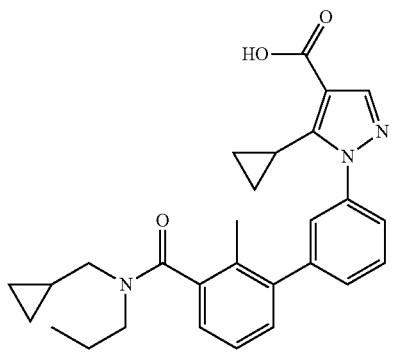 [SMILES: CCCN(CC1CC1)C(=O)c1cccc(-c2cccc(-n3ncc(C(=O)O)c3C3CC3)c2)c1C]

16a) 3-Bromo-2-methyl-N-cyclopropylmethyl-N-propyl-benzamide

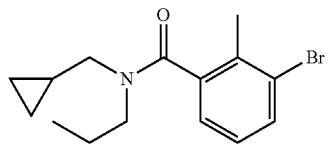 [SMILES: CCCN(CC1CC1)C(=O)c1cccc(Br)c1C]

A solution of 3-bromo-2-methyl-benzoic acid (0.250 g, 1.16 mmol), HATU (0.440 g, 1.16 mmol), N-cyclopropylmethyl propylamine (0.131 g, 1.16 mmol) and DIPEA (0.40 mL, 2.32 mmol) in DCM (10 mL) was stirred for 2 h. The mixture was diluted with DCM and the organic phase was washed with aqueous NaHCO₃ and dried by passage through a phase separation cartridge. Concentration to dryness gave the crude product (0.58 g, quantative), used without further purification. LC-MS m/z 310 (M+H)⁺, 1.50 (ret. time).

16b) 5-Cyclopropyl-1-(3-{3-[(cyclopropylmethyl)(propyl)carbamoyl]-2-methylphenyl}phenyl)-1H-pyrazole-4-carboxylic Acid Ethyl Ester

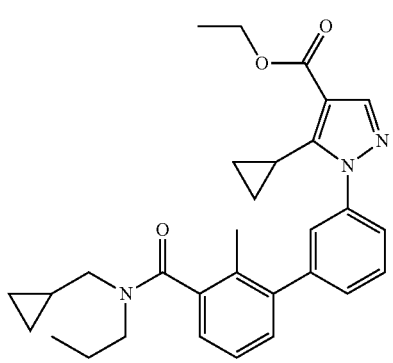 [SMILES: CCCN(CC1CC1)C(=O)c1cccc(-c2cccc(-n3ncc(C(=O)OCC)c3C3CC3)c2)c1C]

A stirred mixture of 3-bromo-2-methyl-N-cyclopropylmethyl-N-propyl-benzamide (0.170 g, 0.55 mmol), 5-cyclopropyl-1-[3-(4,4,5,5-tetramethyl-[1,3,2]dioxaborolan-2-yl)-phenyl]-1H-pyrazole-4-carboxylic acid ethyl ester (0.150 g, 0.39 mmol), aqueous Na$_2$CO$_3$ (3M, 0.392 mL) and Pd(PPh$_3$)$_4$ (0.032 g, 0.04 mmol) in EtOH (1 mL) and toluene (4 mL) was heated at 80° C. for 2 h. After cooling, the mixture was partitioned between EtOAc (20 mL) and water (10 mL) and the organic phase was washed with water (10 mL) and brine (10 mL) before it was dried (MgSO$_4$), filtered, concentrated to dryness, and purified by silica chromatography eluting with EtOAc/petrol 0-50% to give the product (0.107 g, 57%). LC-MS m/z 486 (M+H)$^+$, 1.60 (ret. time).

16c) 5-Cyclopropyl-1-(3-{3-[(cyclopropylmethyl)(propyl)carbamoyl]-2-methylphenyl}phenyl)-1H-pyrazole-4-carboxylic Acid

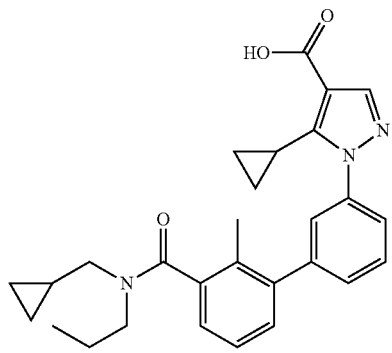 [SMILES: CCCN(CC1CC1)C(=O)c1cccc(-c2cccc(-n3ncc(C(=O)O)c3C3CC3)c2)c1C]

A stirred solution of 5-cyclopropyl-1-(3-{3-[(cyclopropylmethyl)(propyl)carbamoyl]-2-methylphenyl}phenyl)-1H-pyrazole-4-carboxylic acid ethyl ester (0.107 g, 0.22 mmol) in THF (2 mL) and MeOH (2 mL) was treated with LiOH (92 mg, 3.83 mmol) in water (2 mL). After 40 hours the mixture was concentrated to remove organic solvents and the residue partitioned between EtOAc and water. The aqueous layer was acidified with 1N HCl and extracted into EtOAc (×2). The combined organic phases were dried (MgSO$_4$), filtered, and concentrated under vacuum to give the product (0.060 g, 60%). LC-MS m/z 458 (M+H)$^+$, 1.18 (ret. time). $^1$H NMR (400 MHz, DMSO-d6): [presence of rotamers] 12.20 (1H, br s), 7.95 (1H, d), 7.67-7.58 (2H, m), 7.56 (1H, d), 7.49-7.42 (1H, m), 7.38-7.26 (2H, m), 7.23-7.15 (1H, m), 3.67-3.56 (1H, m), 3.47-3.38 (0.4H, m), 3.28-2.98 (2H, m), 2.91 (0.4H, dd), 2.13 (4H, d), 1.66 (1H, dd), 1.56-1.39 (1H, m), 1.20-1.05 (1H, m), 0.97-0.78 (4H, m), 0.69 (1H, t), 0.62-0.25 (4H, m), 0.11-0.05 (1H, m).

Example 17. 5-Cyclopropyl-1-{3-[2-fluoro-3-(2-propylpiperidine-1-carbonyl)phenyl]phenyl}-1H-pyrazole-4-carboxylic Acid

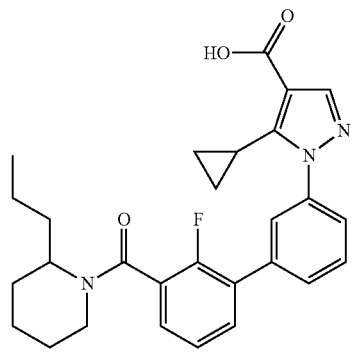 [SMILES: CCCC1CCCCN1C(=O)c1cccc(-c2cccc(-n3ncc(C(=O)O)c3C3CC3)c2)c1F]

17a) (3-Bromo-2-fluoro-phenyl)-(2-propyl-piperidin-1-yl)-methanone

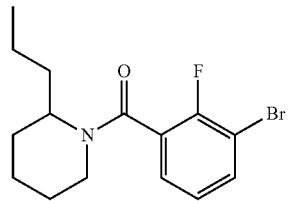 [SMILES: CCCC1CCCCN1C(=O)c1cccc(Br)c1F]

A solution of 3-bromo-2-fluoro-benzoic acid (0.500 g, 2.28 mmol), HATU (0.868 g, 2.28 mmol), 2-propylpiperidine (0.319 g, 2.51 mmol) and DIPEA (0.79 mL, 4.56 mmol) in DCM (20 mL) was stirred for 2 h. The mixture was diluted with DCM and the organic phase washed with aqueous NaHCO$_3$ and dried by passage through a phase separation cartridge. Concentration to dryness gave the crude product (1.33 g, quantative), used without further purification. LC-MS m/z 328 (M+H)$^+$, 1.52 (ret. time).

17b) 5-Cyclopropyl-1-{3-[2-fluoro-3-(2-propylpiperidine-1-carbonyl)phenyl]phenyl}-1H-pyrazole-4-carboxylic Acid Ethyl Ester

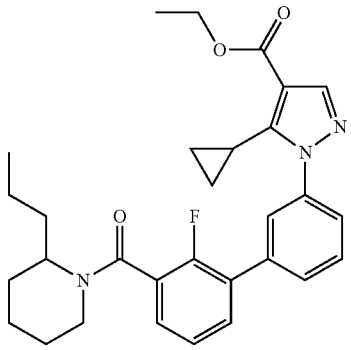 [SMILES: CCCC1CCCCN1C(=O)c1cccc(-c2cccc(-n3ncc(C(=O)OCC)c3C3CC3)c2)c1F]

A stirred mixture of (3-bromo-2-fluoro-phenyl)-(2-propyl-piperidin-1-yl)-methanone (0.180 g, 0.55 mmol), 5-cyclopropyl-1-[3-(4,4,5,5-tetramethyl-[1,3,2]dioxaborolan-2-yl)-phenyl]-1H-pyrazole-4-carboxylic acid ethyl ester (0.150 g, 0.39 mmol), aqueous Na$_2$CO$_3$ (3M, 0.392 mL) and Pd(PPh$_3$)$_4$ (0.032 g, 0.04 mmol) in EtOH (1 mL) and toluene (4 mL) was heated at 80° C. for 2 h. After cooling, the mixture was partitioned between EtOAc (20 mL) and water (10 mL) and the organic phase was washed with water (10 mL) and brine (10 mL) before it was dried (MgSO$_4$), filtered, concentrated to dryness, and purified by silica chromatography eluting with EtOAc/petrol 0-50% to give the product (0.127 g, 65%). LC-MS m/z 504 (M+H)$^+$, 1.63 (ret. time).

17c) 5-Cyclopropyl-1-{3-[2-fluoro-3-(2-propylpiperidine-1-carbonyl)phenyl]phenyl}-1H-pyrazole-4-carboxylic Acid

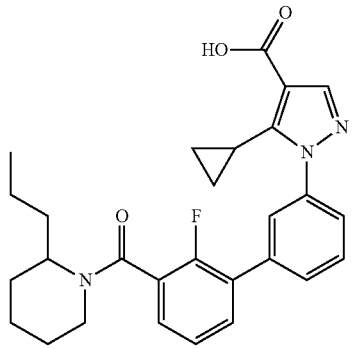 [SMILES: CCCC1CCCCN1C(=O)c1cccc(-c2cccc(-n3ncc(C(=O)O)c3C3CC3)c2)c1F]

A stirred solution of 5-cyclopropyl-1-{3-[2-fluoro-3-(2-propylpiperidine-1-carbonyl)phenyl]phenyl}-1H-pyrazole-4-carboxylic acid ethyl ester (0.127 g, 0.25 mmol) in THF (3 mL) and MeOH (3 mL) was treated with LiOH (106 mg, 4.41 mmol) in water (2 mL). After 40 hours the mixture was concentrated to remove organic solvents and the residue partitioned between EtOAc and water. The aqueous layer was acidified with 1N HCl and extracted into EtOAc (×2). The combined organic phases were dried (MgSO$_4$), filtered, and concentrated under vacuum to give the product (0.070 g, 59%). LC-MS m/z 476 (M+H)$^+$, 1.17 (ret. time). $^1$H NMR (400 MHz, DMSO-d6): [presence of rotamers]12.31 (1H, br s), 7.97 (1H, s), 7.82-7.72 (1H, m), 7.72-7.60 (4H, m), 7.47-7.28 (2H, m), 4.78 (0.6H, br s), 4.44 (0.4H, br s), 3.62-3.52 (0.4H, m), 3.28-3.21 (0.7H, m), 3.20-3.06 (0.6H, m), 2.79 (0.4H, t), 2.19-2.09 (1H, m), 1.87-1.18 (10H, m), 1.01-0.81 (4H, m), 0.79-0.65 (1H, m), 0.58 (2H, d).

Example 18. 5-Cyclopropyl-1-(3-{2-fluoro-3-[3-(trifluoromethyl)piperidine-1-carbonyl]phenyl}phenyl)-1H-pyrazole-4-carboxylic Acid

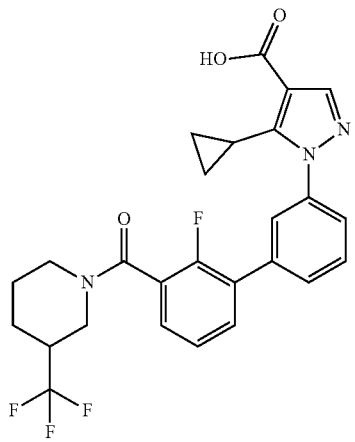 [SMILES: O=C(O)c1cnn(-c2cccc(-c3cccc(C(=O)N4CCCC(C(F)(F)F)C4)c3F)c2)c1C1CC1]

18a) (3-Bromo-2-fluoro-phenyl)-(3-trifluoromethyl-piperidin-1-yl)-methanone

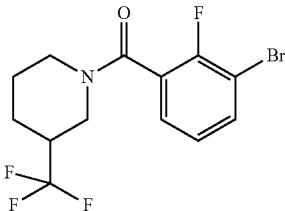 [SMILES: O=C(c1cccc(Br)c1F)N1CCCC(C(F)(F)F)C1]

A solution of 3-bromo-2-fluoro-benzoic acid (0.500 g, 2.28 mmol), HATU (0.868 g, 2.28 mmol), 3-trifluoromethylpiperidine (0.402 g, 2.63 mmol) and DIPEA (0.885 g, 6.85 mmol) in DCM (10 mL) was stirred for 4 h. The mixture was diluted with DCM and the organic phase washed with aqueous NaHCO$_3$ and dried by passage through a phase separation cartridge. Concentration to dryness gave the crude product (1.89 g, quantative), used without further purification. LC-MS m/z 354 (M+H)$^+$, 1.41 (ret. time).

18b) 5-Cyclopropyl-1-(3-{2-fluoro-3-[3-(trifluoromethyl)piperidine-1-carbonyl]phenyl}phenyl)-1H-pyrazole-4-carboxylic Acid Ethyl Ester

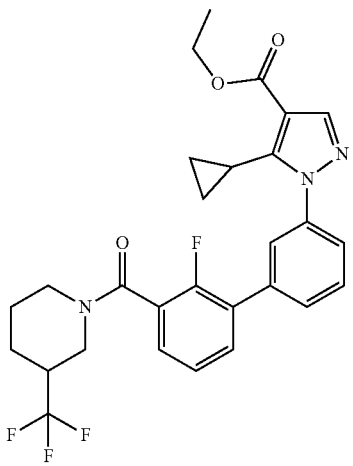 [SMILES: CCOC(=O)c1cnn(-c2cccc(-c3cccc(C(=O)N4CCCC(C(F)(F)F)C4)c3F)c2)c1C1CC1]

A stirred mixture of (3-bromo-2-fluoro-phenyl)-(3-trifluoromethyl-piperidin-1-yl)-methanone (0.222 g, 0.63 mmol), 5-cyclopropyl-1-[3-(4,4,5,5-tetramethyl-[1,3,2]dioxaborolan-2-yl)-phenyl]-1H-pyrazole-4-carboxylic acid ethyl ester (0.120 g, 0.31 mmol), aqueous Na$_2$CO$_3$ (3M, 0.314 mL) and Pd(PPh$_3$)$_4$ (0.036 g, 0.05 mmol) in EtOH (0.75 mL) and toluene (3 mL) was heated at reflux for 3 h. After cooling, the mixture was partitioned between EtOAc (20 mL) and water (10 mL) and the organic phase washed with water (10 mL) and brine (10 mL) before it was dried (MgSO$_4$), filtered, and concentrated to dryness to give the product, used without further purification (0.204 g, quantative). LC-MS m/z 530 (M+H)$^+$, 1.56 (ret. time).

18c) 5-Cyclopropyl-1-(3-{2-fluoro-3-[3-(trifluoromethyl)piperidine-1-carbonyl]phenyl}phenyl)-1H-pyrazole-4-carboxylic Acid

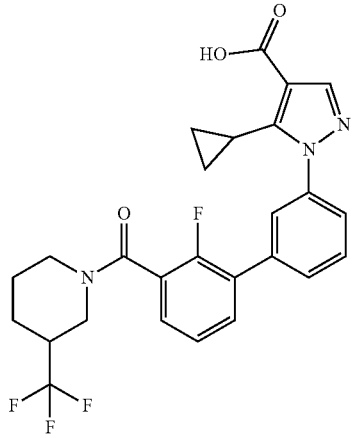 [SMILES: O=C(O)c1cnn(-c2cccc(-c3cccc(C(=O)N4CCCC(C(F)(F)F)C4)c3F)c2)c1C1CC1]

A stirred solution of 5-cyclopropyl-1-(3-{2-fluoro-3-[3-(trifluoromethyl)piperidine-1-carbonyl]phenyl}phenyl)-1H-pyrazole-4-carboxylic acid ethyl ester (0.231 g, 0.44 mmol) in EtOH (3 mL) was treated with aqueous NaOH (2M, 1.09 mL). After 18 hours the mixture was partitioned between EtOAc and water. The aqueous layer was acidified with 1N HCl and extracted into EtOAc (×2). The combined organic phases were dried (MgSO$_4$), filtered, concentrated under vacuum, and purified by HPLC. The residue was diluted with 1N HCl and extracted into EtOAc (×2). The combined organic phases were dried (MgSO$_4$), filtered, and concentrated under vacuum to give the product (0.027 g, 12%). LC-MS m/z 502 (M+H)$^+$, 1.15 (ret. time), basic method. $^1$H NMR (400 MHz, DMSO-d6): 12.36-12.21 (1H, m), 7.97 (1H, s), 7.79 (1H, s), 7.69 (4H, s), 7.57-7.37 (2H, m), 4.54 (0.5H, d), 4.44-4.23 (0.5H, m), 3.64-3.54 (0.5H, m), 3.43 (0.5H, d), 3.27-3.00 (2H, m), 2.20-2.08 (1H, m), 1.99 (1H, s), 1.87-1.74 (1H, m), 1.74-1.53 (2H, m), 1.53-1.39 (1H, m), 0.87 (2H, d), 0.61-0.51 (2H, m). Peaks around amide are rotameric.

Example 19. 1-[3-(3-{4-Azaspiro[2.5]octane-4-carbonyl}-2-fluorophenyl)phenyl]-5-cyclopropyl-1H-pyrazole-4-carboxylic Acid

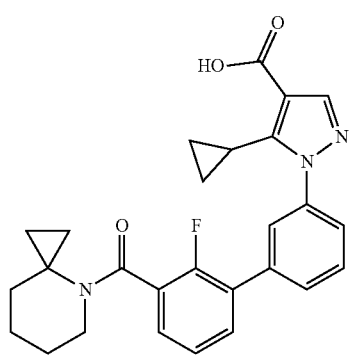 [SMILES: O=C(O)c1cnn(-c2cccc(-c3cccc(C(=O)N4CCCCC45CC5)c3F)c2)c1C1CC1]

19a) (4-Aza-spiro[2.5]oct-4-yl)-(3-bromo-2-fluorophenyl)-methanone

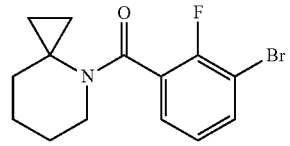 [SMILES: O=C(c1cccc(Br)c1F)N1CCCCC12CC2]

A solution of 3-bromo-2-fluoro-benzoic acid (0.250 g, 1.16 mmol), HATU (0.440 g, 1.16 mmol), 4-azaspiro[2.5]octane hydrochloride (0.171 g, 1.16 mmol) and DIPEA (0.40 mL, 2.32 mmol) in DCM (10 mL) was stirred for 2 h. The mixture was diluted with DCM and the organic phase washed with aqueous NaHCO$_3$ and dried by passage through a phase separation cartridge. Concentration to dryness gave the crude product (0.828 g, quantative), used without further purification. LC-MS m/z 312 (M+H)$^+$, 1.42 (ret. time).

19b) 1-[3-(3-{4-Azaspiro[2.5]octane-4-carbonyl}-2-fluorophenyl)phenyl]-5-cyclopropyl-1H-pyrazole-4-carboxylic Acid Ethyl Ester

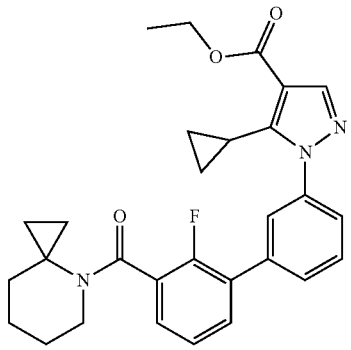 [SMILES: CCOC(=O)c1cnn(-c2cccc(-c3cccc(C(=O)N4CCCCC45CC5)c3F)c2)c1C1CC1]

A stirred mixture of (4-Aza-spiro[2.5]oct-4-yl)-(3-bromo-2-fluoro-phenyl)-methanone (0.143 g, 0.46 mmol), 5-cyclopropyl-1-[3-(4,4,5,5-tetramethyl-[1,3,2]dioxaborolan-2-yl)-phenyl]-1H-pyrazole-4-carboxylic acid ethyl ester (0.125 g, 0.32 mmol), aqueous Na$_2$CO$_3$ (3M, 0.392 mL) and Pd(PPh$_3$)$_4$ (0.032 g, 0.04 mmol) in EtOH (1 mL) and toluene (4 mL) was heated at 80° C. for 2 h. After cooling, the mixture was partitioned between EtOAc (20 mL) and water (10 mL) and the organic phase washed with water (10 mL) and brine (10 mL) before it was dried (MgSO$_4$), filtered, concentrated to dryness, and purified by silica chromatography eluting with EtOAc/petrol 0-60% to give the product (0.094 g, 60%). LC-MS m/z 488 (M+H)$^+$, 1.54 (ret. time).

19c) 1-[3-(3-{4-Azaspiro[2.5]octane-4-carbonyl}-2-fluorophenyl)phenyl]-5-cyclopropyl-1H-pyrazole-4-carboxylic Acid

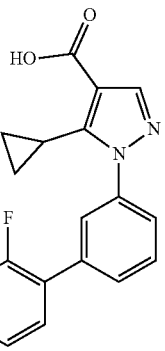

A stirred solution of 1-[3-(3-{4-azaspiro[2.5]octane-4-carbonyl}-2-fluorophenyl)phenyl]-5-cyclopropyl-1H-pyrazole-4-carboxylic acid ethyl ester (0.094 g, 0.193 mmol) in THF (2 mL) and MeOH (2 mL) was treated with LiOH (61 mg, 2.54 mmol) in water (2 mL). After 40 hours the mixture was concentrated to remove organic solvents and the residue partitioned between EtOAc and water. The aqueous layer was acidified with 1N HCl and extracted into EtOAc (×2). The combined organic phases were dried (MgSO$_4$), filtered, and concentrated under vacuum to give the product (0.060 g, 68%). LC-MS m/z 460 (M+H)$^+$, 1.13 (ret. time). $^1$H NMR (400 MHz, DMSO-d6): [presence of rotamers] 12.18 (1H, br s), 7.97 (1H, s), 7.77 (1H, s), 7.70-7.62 (4H, m), 7.46-7.34 (2H, m), 3.70 (1H, br s), 2.18-2.09 (1H, m), 1.82-1.59 (4H, m), 1.59-1.38 (3H, m), 0.99-0.72 (4H, m), 0.62-0.43 (4H, m).

Example 20. 5-Cyclopropyl-1-{3-[2-fluoro-3-(piperidine-1-carbonyl)phenyl]phenyl}-1H-pyrazole-4-carboxylic Acid

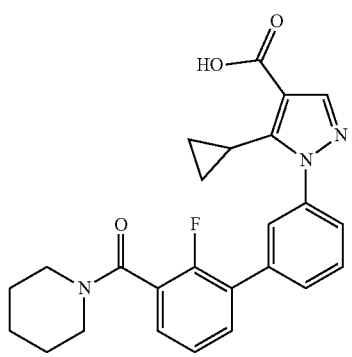

20a) (3-Bromo-2-fluoro-phenyl)-piperidin-1-yl-methanone

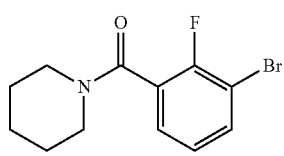 [SMILES: O=C(c1cccc(Br)c1F)N1CCCCC1]

A solution of 3-bromo-2-fluoro-benzoic acid (0.250 g, 1.16 mmol), HATU (0.440 g, 1.16 mmol), piperidine (0.099 g, 1.16 mmol) and DIPEA (0.40 mL, 2.32 mmol) in DCM (10 mL) was stirred for 2 h. The mixture was diluted with DCM and the organic phase washed with aqueous NaHCO$_3$ and dried by passage through a phase separation cartridge. Concentration to dryness gave the crude product (0.644 g, quantitative), used without further purification. LC-MS m/z 286 (M+H)$^+$, 1.34 (ret. time).

20b) 5-Cyclopropyl-1-{3-[2-fluoro-3-(piperidine-1-carbonyl)phenyl]phenyl}-1H-pyrazole-4-carboxylic Acid Ethyl Ester

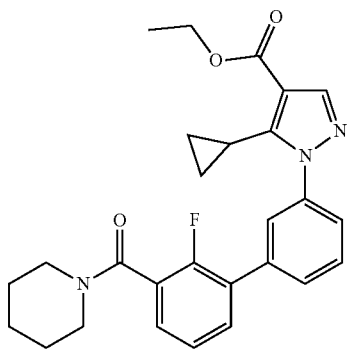 [SMILES: CCOC(=O)c1cnn(-c2cccc(-c3cccc(C(=O)N4CCCCC4)c3F)c2)c1C1CC1]

A stirred mixture of (3-bromo-2-fluoro-phenyl)-piperidin-1-yl-methanone (0.130 g, 0.46 mmol), 5-cyclopropyl-1-[3-(4,4,5,5-tetramethyl-[1,3,2]dioxaborolan-2-yl)-phenyl]-1H-pyrazole-4-carboxylic acid ethyl ester (0.125 g, 0.32 mmol), aqueous Na$_2$CO$_3$ (3M, 0.392 mL) and Pd(PPh$_3$)$_4$ (0.032 g, 0.04 mmol) in EtOH (1 mL) and toluene (4 mL) was heated at 80° C. for 2 h. After cooling, the mixture was partitioned between EtOAc (20 mL) and water (10 mL) and the organic phase washed with water (10 mL) and brine (10 mL) before it was dried (MgSO$_4$), filtered, concentrated to dryness, and purified by silica chromatography eluting with EtOAc/petrol 0-60% to give the product (0.080 g, 54%). LC-MS m/z 462 (M+H)$^+$, 1.51 (ret. time).

20c) 5-Cyclopropyl-1-{3-[2-fluoro-3-(piperidine-1-carbonyl)phenyl]phenyl}-1H-pyrazole-4-carboxylic Acid

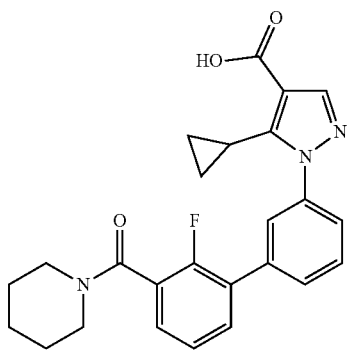 [SMILES: O=C(O)c1cnn(-c2cccc(-c3cccc(C(=O)N4CCCCC4)c3F)c2)c1C1CC1]

A stirred solution of 5-cyclopropyl-1-{3-[2-fluoro-3-(piperidine-1-carbonyl)phenyl]phenyl}-1H-pyrazole-4-carboxylic acid ethyl ester (0.080 g, 0.174 mmol) in THF (2 mL) and MeOH (2 mL) was treated with LiOH (74 mg, 3.08 mmol) in water (2 mL). After 60 hours the mixture was concentrated to remove organic solvents and the residue partitioned between EtOAc and water. The aqueous layer was acidified with 1N HCl and extracted into EtOAc (×2). The combined organic phases were dried (MgSO$_4$), filtered, and concentrated under vacuum to give the product (0.057 g, 76%). $^1$H NMR (400 MHz, DMSO-d6): 12.13 (1H, br s), 7.97 (1H, s), 7.79 (1H, s), 7.71-7.63 (4H, m), 7.45-7.36 (2H, m), 3.63 (2H, br s), 3.24 (2H, t), 2.19-2.10 (1H, m), 1.67-1.51 (4H, m), 1.46 (2H, s), 0.92-0.83 (2H, m), 0.61-0.53 (2H, m).

Example 21. 5-Cyclopropyl-1-(3-{3-[(2R,6S)-2,6-dimethylpiperidine-1-carbonyl]-2-fluorophenyl}phenyl)-1H-pyrazole-4-carboxylic Acid

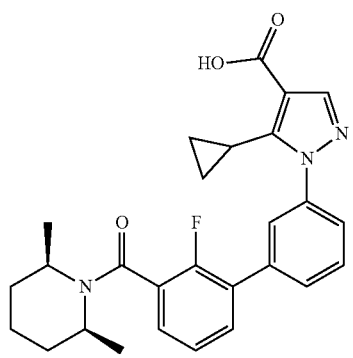 [SMILES: C[C@@H]1CCC[C@H](C)N1C(=O)c1cccc(-c2cccc(-n3ncc(C(=O)O)c3C3CC3)c2)c1F]

21a) (3-Bromo-2-fluoro-phenyl)-((2S,6R)-2,6-dimethyl-piperidin-1-yl)-methanone

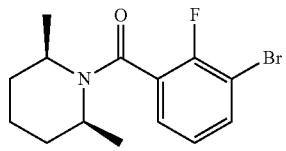 [SMILES: C[C@@H]1CCC[C@H](C)N1C(=O)c1cccc(Br)c1F]

A solution of 3-bromo-2-fluoro-benzoic acid (0.250 g, 1.16 mmol), HATU (0.440 g, 1.16 mmol), cis-2,6-dimethylpiperidine (0.131 g, 1.16 mmol) and DIPEA (0.40 mL, 2.32 mmol) in DCM (10 mL) was stirred for 2 h. The mixture was diluted with DCM and the organic phase washed with aqueous NaHCO$_3$ and dried by passage through a phase separation cartridge. Concentration to dryness gave the crude product (0.722 g, quantative), used without further purification. LC-MS m/z 314 (M+H)$^+$, 1.45 (ret. time).

21b) 5-Cyclopropyl-1-(3-{3-[(2R,6S)-2,6-dimethyl-piperidine-1-carbonyl]-2-fluorophenyl}phenyl)-1H-pyrazole-4-carboxylic Acid Ethyl Ester

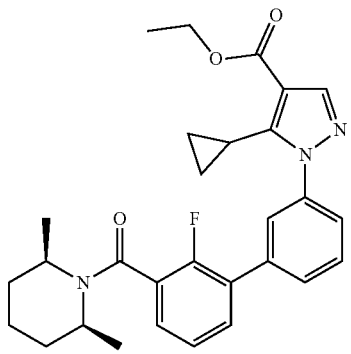 [SMILES: CCOC(=O)c1cnn(-c2cccc(-c3cccc(C(=O)N4[C@H](C)CCC[C@@H]4C)c3F)c2)c1C1CC1]

A stirred mixture of (3-bromo-2-fluoro-phenyl)-((2S,6R)-2,6-dimethyl-piperidin-1-yl)-methanone (0.143 g, 0.46 mmol), 5-cyclopropyl-1-[3-(4,4,5,5-tetramethyl-[1,3,2]dioxaborolan-2-yl)-phenyl]-1H-pyrazole-4-carboxylic acid ethyl ester (0.125 g, 0.32 mmol), aqueous Na$_2$CO$_3$ (3M, 0.392 mL) and Pd(PPh$_3$)$_4$ (0.032 g, 0.04 mmol) in EtOH (1 mL) and toluene (4 mL) was heated at 80° C. for 2 h. After cooling, the mixture was partitioned between EtOAc (20 mL) and water (10 mL) and the organic phase washed with water (10 mL) and brine (10 mL) before it was dried (MgSO$_4$), filtered, concentrated to dryness, and purified by silica chromatography eluting with EtOAc/petrol 0-60% to give the product (0.061 g, 39%). LC-MS m/z 490 (M+H)$^+$, 1.56 (ret. time).

21c) 5-Cyclopropyl-1-(3-{3-[(2R,6S)-2,6-dimethyl-piperidine-1-carbonyl]-2-fluorophenyl}phenyl)-1H-pyrazole-4-carboxylic Acid

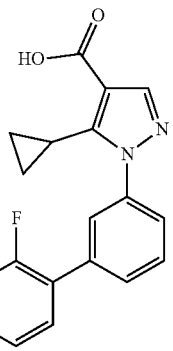

A stirred solution of 5-cyclopropyl-1-(3-{3-[(2R,6S)-2,6-dimethylpiperidine-1-carbonyl]-2-fluorophenyl}phenyl)-1H-pyrazole-4-carboxylic acid ethyl ester (0.061 g, 0.125 mmol) in THF (2 mL) and MeOH (2 mL) was treated with LiOH (52 mg, 3.08 mmol) in water (2 mL). After 60 hours the mixture was concentrated to remove organic solvents and the residue partitioned between EtOAc and water. The aqueous layer was acidified with 1N HCl and extracted into EtOAc (×2). The combined organic phases were dried (MgSO$_4$), filtered, and concentrated under vacuum to give the product (0.032 g, 56%). LC-MS m/z 462 (M+H)$^+$, 1.14 (ret. time). $^1$H NMR (400 MHz, DMSO-d6): [presence of rotamers] 12.28 (1H, br s), 7.97 (1H, s), 7.79 (1H, d), 7.71-7.61 (4H, m), 7.47-7.34 (2H, m), 4.75 (1H, br s), 3.81 (1H, br s), 2.20-2.09 (1H, m), 1.83 (1H, br s), 1.71-1.43 (5H, m), 1.33-1.12 (6H, m), 0.93-0.82 (2H, m), 0.61-0.53 (2H, m).

Example 22. 5-Cyclopropyl-1-(3-{2-fluoro-3-[2-(methoxymethyl)piperidine-1-carbonyl]phenyl}phenyl)-1H-pyrazole-4-carboxylic Acid

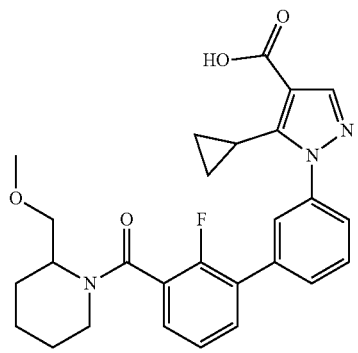 [SMILES: COCC1CCCCN1C(=O)c1cccc(-c2cccc(-n3ncc(C(=O)O)c3C3CC3)c2)c1F]

22a) 3-Bromo-2-fluoro-benzoic Acid Benzyl Ester

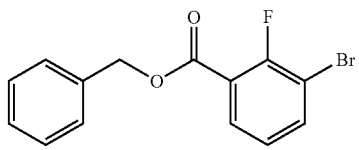 [SMILES: O=C(OCc1ccccc1)c1cccc(Br)c1F]

A stirred solution of 3-bromo-2-fluorobenzoic acid (3.00 g, 13.7 mmol) in DCM (40 mL) was treated with benzyl alcohol (1.48 g, 13.7 mmol), HOAt (2.23 g, 16.4 mmol), EDC (3.15 g, 16.4 mmol) and DIPEA (4.77 mL, 16.4 mmol). After 16 h the mixture was diluted with DCM, and washed sequentially with 5% aqueous citric acid, saturated NaHCO₃ and brine, dried (MgSO₄), filtered, and concentrated to dryness to give the product (3.94 g, 93%) used without further purification. LC-MS m/z 326 (M+H)⁺, 1.54 (ret. time).

22b) 1-(3'-Benzyloxycarbonyl-2'-fluoro-biphenyl-3-yl)-5-cyclopropyl-1H-pyrazole-4-carboxylic Acid Methyl Ester

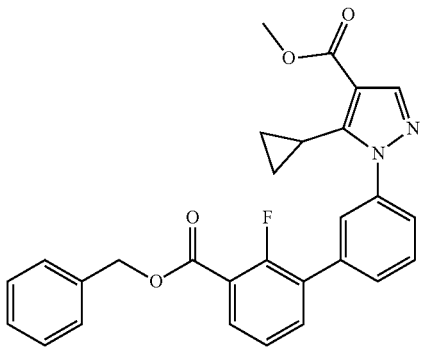 [SMILES: COC(=O)c1cnn(-c2cccc(-c3cccc(C(=O)OCc4ccccc4)c3F)c2)c1C1CC1]

A stirred mixture of 3-bromo-2-fluoro-benzoic acid benzyl ester (0.146 g, 0.47 mmol), 5-cyclopropyl-1-[3-(4,4,5,5-tetramethyl-[1,3,2]dioxaborolan-2-yl)-phenyl]-1H-pyrazole-4-carboxylic acid ethyl ester (0.125 g, 0.32 mmol), aqueous Na₂CO₃ (3M, 0.340 mL) and Pd(PPh₃)₄ (0.028 g, 0.024 mmol) in EtOH (1 mL) and toluene (4 mL) was heated at 80° C. for 2 h. After cooling, the mixture was partitioned between EtOAc (20 mL) and water (10 mL) and the organic phase washed with water (10 mL) and brine (10 mL) before it was dried (MgSO₄), filtered, concentrated to dryness, and purified by silica chromatography eluting with EtOAc/petrol 0-60% to give the product (0.114 g, 72%). LC-MS m/z 472 (M+H)⁺, 1.61 (ret. time).

22c) 1-(3'-Carboxy-2'-fluoro-biphenyl-3-yl)-5-cyclopropyl-1H-pyrazole-4-carboxylic Acid Methyl Ester

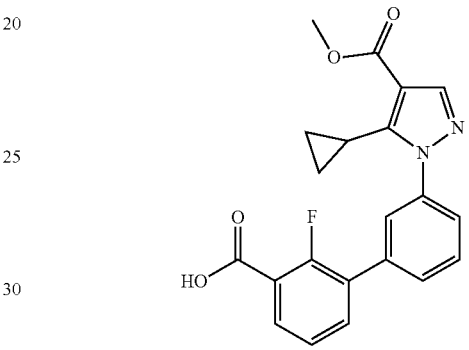

A shaken mixture of 1-(3'-benzyloxycarbonyl-2'-fluoro-biphenyl-3-yl)-5-cyclopropyl-1H-pyrazole-4-carboxylic acid methyl ester (0.114 g, 0.242 mmol) and 10% Pd/C in EtOH (5 mL) and EtOAc (5 mL) was hydrogenated at atmospheric pressure for 16 h. The mixture was then filtered and concentrated to dryness under vacuum to give the product (0.073 g, 79%). LC-MS m/z 381 (M+H)⁺, 1.08 (ret. time).

22d) 5-Cyclopropyl-1-(3-{2-fluoro-3-[2-(methoxymethyl)piperidine-1-carbonyl]phenyl}phenyl)-1H-pyrazole-4-carboxylic Acid Methyl Ester

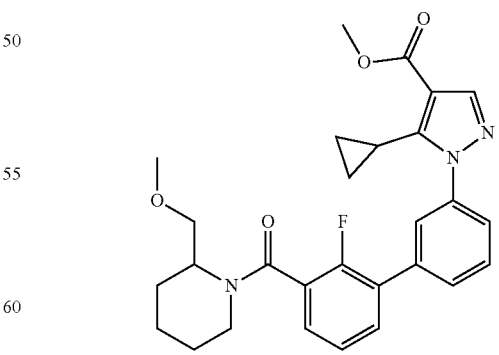

A solution of 1-(3'-carboxy-2'-fluoro-biphenyl-3-yl)-5-cyclopropyl-1H-pyrazole-4-carboxylic acid methyl ester (0.037 g, 0.098 mmol), HATU (0.037 g, 0.097 mmol), 2-methoxymethyl piperidine (0.014 g, 0.108 mmol) and DIPEA (0.033 mL, 0.22 mmol) in DCM (4 mL) was stirred for 16 h. The mixture was diluted with DCM, and the organic phase was washed with water and dried by passage through a phase separation cartridge. Concentration to dryness followed by silica purification eluting with EtOAc/hexane 0-80% gave the product (0.038 g, 79%). LC-MS m/z 492 (M+H)$^+$, 1.48 (ret. time).

22e) 5-Cyclopropyl-1-(3-{2-fluoro-3-[2-(methoxymethyl)piperidine-1-carbonyl]phenyl}phenyl)-1H-pyrazole-4-carboxylic Acid

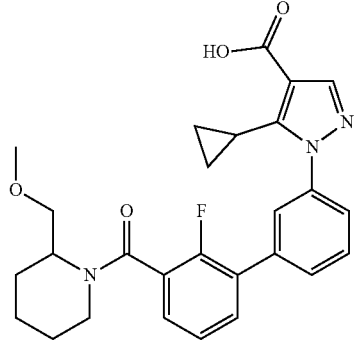 [SMILES: COCC1CCCCN1C(=O)c1cccc(-c2cccc(-n3ncc(C(=O)O)c3C3CC3)c2)c1F]

A stirred solution of 5-cyclopropyl-1-(3-{2-fluoro-3-[2-(methoxymethyl)piperidine-1-carbonyl]phenyl}phenyl)-1H-pyrazole-4-carboxylic acid methyl ester (0.038 g, 0.077 mmol) in THF (0.5 mL) and MeOH (0.5 mL) was treated with LiOH (18 mg, 0.77 mmol) in water (0.5 mL). After 60 hours the mixture was concentrated to remove organic solvents and the residue partitioned between EtOAc and water. The aqueous layer was acidified with 1N HCl and extracted into EtOAc (×2). The combined organic phases were dried (MgSO$_4$), filtered, and concentrated under vacuum to give the product (0.030 g, 82%). LC-MS m/z 478 (M+H)$^+$, 1.19 (ret. time). $^1$H NMR (400 MHz, DMSO-d6): [presence of rotamers] 12.25 (1H, br s), 7.97 (1H, s), 7.79 (1H, br s), 7.71-7.61 (4H, m), 7.46-7.30 (2H, m), 4.92-4.84 (0.5H, m), 4.48-4.41 (0.5H, m), 3.80-3.47 (2H, m), 3.12 (2H, s), 2.18-2.10 (1H, m), 1.76 (1H, d), 1.53 (5H, s), 0.92-0.83 (2H, m), 0.61-0.53 (2H, m) [OMe signal 3H underwater peak].

Example 23. 5-Cyclopropyl-1-(3-{3-[(cyclopropylmethyl)(3,3,3-trifluoropropyl)carbamoyl]-2-fluorophenyl}phenyl)-1H-pyrazole-4-carboxylic Acid

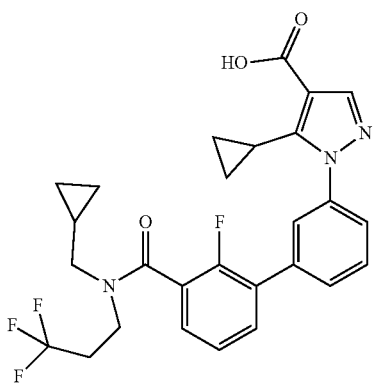 [SMILES: O=C(O)c1cnn(-c2cccc(-c3cccc(C(=O)N(CCC(F)(F)F)CC4CC4)c3F)c2)c1C1CC1]

23a) 3-Bromo-2-fluoro-N-(3,3,3-trifluoro-propyl)-benzamide

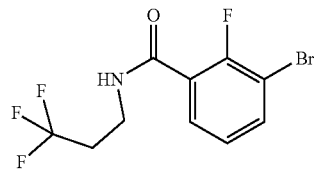 [SMILES: O=C(NCCC(F)(F)F)c1cccc(Br)c1F]

A solution of 3-bromo-2-fluoro-benzoic acid (0.500 g, 2.28 mmol), HATU (0.868 g, 2.28 mmol), 3,3,3-trifluoro-propylamine (0.297 g, 2.63 mmol) and DIPEA (1.19 mL, 6.85 mmol) in DCM (10 mL) was stirred for 4 h. The mixture was diluted with DCM and the organic phase washed with aqueous NaHCO$_3$ and dried by passage through a phase separation cartridge. Concentration to dryness gave the crude product (1.58 g, quantative), used without further purification. LC-MS m/z 315 (M+H)$^+$, 1.33 (ret. time).

23b) 3-Bromo-N-cyclopropylmethyl-2-fluoro-N-(3,3,3-trifluoro-propyl)-benzamide

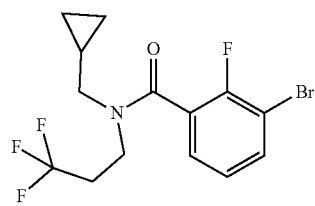 [SMILES: O=C(c1cccc(Br)c1F)N(CCC(F)(F)F)CC1CC1]

A stirred solution of 3-bromo-2-fluoro-N-(3,3,3-trifluoropropyl)-benzamide (0.500 g, 1.59 mmol) in dry THF (14 mL) under N$_2$ at 0° C. was treated with NaH (0.046 g, 1.91 mmol). After 30 minutes bromomethylcyclopropane (0.645 g, 4.78 mmol) was added. After 19 h additional bromomethylcyclopropane (0.645 g, 4.78 mmol) and NaH (0.046 g, 1.91 mmol) were added. After a further 24 h additional bromomethylcyclopropane (0.645 g, 4.78 mmol) was added. After a further 24 h the reaction was quenched with water and extracted into EtOAc (×2). The combined organic phase was washed with water and brine before it was dried (MgSO$_4$), filtered and concentrated, and the residue purified by silica chromatography eluting with EtOAc/petrol 0-60% to give the product (0.210 g, 37%). LC-MS m/z 368 (M+H)$^+$, 1.46 (ret. time).

23c) 5-Cyclopropyl-1-(3-{3-[(cyclopropylmethyl)(3,3,3-trifluoropropyl)carbamoyl]-2-fluorophenyl}phenyl)-1H-pyrazole-4-carboxylic Acid Methyl Ester

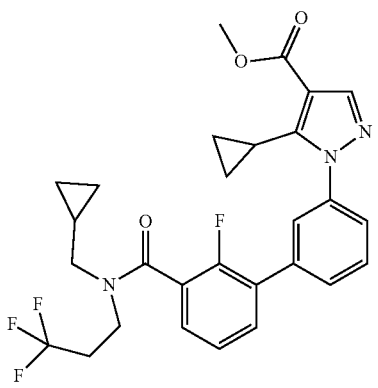 [SMILES: COC(=O)c1cnn(-c2cccc(-c3cccc(C(=O)N(CCC(F)(F)F)CC4CC4)c3F)c2)c1C1CC1]

A stirred mixture of 3-bromo-N-cyclopropylmethyl-2-fluoro-N-(3,3,3-trifluoro-propyl)-benzamide (0.125 g, 0.34 mmol), 5-cyclopropyl-1-[3-(4,4,5,5-tetramethyl-[1,3,2]dioxaborolan-2-yl)-phenyl]-1H-pyrazole-4-carboxylic acid ethyl ester (0.125 g, 0.34 mmol), aqueous $Na_2CO_3$ (3M, 0.340 mL) and $Pd(PPh_3)_4$ (0.028 g, 0.024 mmol) in EtOH (1 mL) and toluene (4 mL) was heated at 80° C. for 2 h. After cooling, the mixture was partitioned between EtOAc (20 mL) and water (10 mL) and the organic phase was washed with water (10 mL) and brine (10 mL) before it was dried ($MgSO_4$), filtered, concentrated to dryness, and purified by silica chromatography eluting with EtOAc/petrol 0-60% to give the product (0.127 g, 71%). LC-MS m/z 530 (M+H)⁺, 1.55 (ret. time).

23d) 5-Cyclopropyl-1-(3-{3-[(cyclopropylmethyl)(3,3,3-trifluoropropyl)carbamoyl]-2-fluorophenyl}phenyl)-1H-pyrazole-4-carboxylic Acid

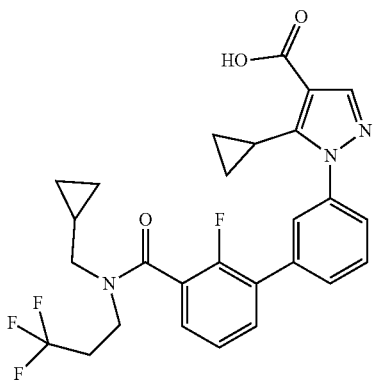 [SMILES: O=C(O)c1cnn(-c2cccc(-c3cccc(C(=O)N(CCC(F)(F)F)CC4CC4)c3F)c2)c1C1CC1]

A stirred solution of 5-cyclopropyl-1-(3-{3-[(cyclopropylmethyl)(3,3,3-trifluoropropyl) carbamoyl]-2-fluorophenyl}phenyl)-1H-pyrazole-4-carboxylic acid methyl ester (0.127 g, 0.240 mmol) in THF (2 mL) and MeOH (2 mL) was treated with LiOH (58 mg, 2.4 mmol) in water (2 mL). After 24 hours the mixture was concentrated to remove organic solvents and the residue partitioned between EtOAc and water. The aqueous layer was acidified with 1N HCl and extracted into EtOAc (×2). The combined organic phases were dried ($MgSO_4$), filtered, and concentrated under vacuum, and the residue purified by HPLC to give the product (0.024 g, 19%). LC-MS m/z 514 (M–H)⁻, 1.14 (ret. time). ¹H NMR (400 MHz, DMSO-d6): [presence of rotamers] 12.24 (1H, br s), 7.87 (1H, s), 7.69 (1H, s), 7.64-7.55 (4H, m), 7.37-7.28 (2H, m), 3.75-3.68 (2H, m), 3.47-3.39 (1H, m), 3.02 (1H, d), 2.69-2.58 (1H, m), 2.56-2.45 (1H, m), 2.08-2.00 (1H, m), 1.04-0.71 (3H, m), 0.50-0.33 (4H, m), 0.27-0.06 (2H, m).

Example 24. 5-Cyclopropyl-1-{3-[3-(2,5-dimethylpyrrolidine-1-carbonyl)-2-fluorophenyl]phenyl}-1H-pyrazole-4-carboxylic Acid

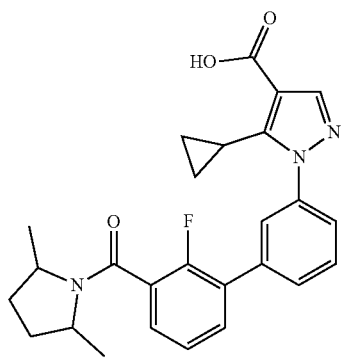 [SMILES: CC1CCC(C)N1C(=O)c1cccc(-c2cccc(-n3ncc(C(=O)O)c3C3CC3)c2)c1F]

24a) 5-Cyclopropyl-1-{3-[3-(2,5-dimethylpyrrolidine-1-carbonyl)-2-fluorophenyl]phenyl}-1H-pyrazole-4-carboxylic Acid Methyl Ester

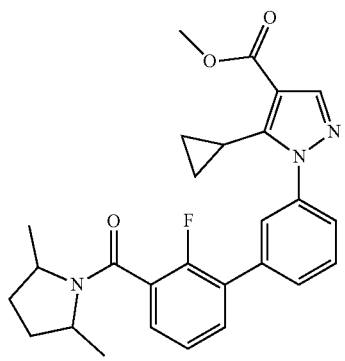 [SMILES: COC(=O)c1cnn(-c2cccc(-c3cccc(C(=O)N4C(C)CCC4C)c3F)c2)c1C1CC1]

A solution of 1-(3'-carboxy-2'-fluoro-biphenyl-3-yl)-5-cyclopropyl-1H-pyrazole-4-carboxylic acid methyl ester (0.037 g, 0.098 mmol), HATU (0.037 g, 0.097 mmol), dimethylpyrrolidine (0.010 g, 0.10 mmol) and DIPEA (0.033 mL, 0.22 mmol) in DCM (4 mL) was stirred for 16 h. The mixture was diluted with DCM, and the organic phase washed with water and dried by passage through a phase separation cartridge. Concentration to dryness followed by silica purification eluting with EtOAc/hexane 0-60% gave the product (0.038 g, 79%). LC-MS m/z 462 (M+H)⁺, 1.47 (ret. time).

24b) 5-Cyclopropyl-1-{3-[3-(2,5-dimethylpyrrolidine-1-carbonyl)-2-fluorophenyl]phenyl}-1H-pyrazole-4-carboxylic Acid

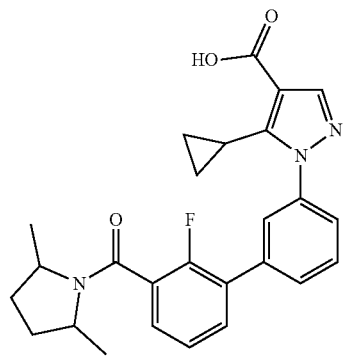 [SMILES: CC1CCC(C)N1C(=O)c1cccc(-c2cccc(-n3ncc(C(=O)O)c3C3CC3)c2)c1F]

A stirred solution of 5-cyclopropyl-1-{3-[3-(2,5-dimethylpyrrolidine-1-carbonyl)-2-fluorophenyl]phenyl}-1H-pyrazole-4-carboxylic acid methyl ester (0.034 g, 0.074 mmol) in THF (0.5 mL) and MeOH (0.5 mL) was treated with LiOH (18 mg, 0.74 mmol) in water (0.5 mL). After 36 hours the mixture was concentrated to remove organic solvents and the residue partitioned between EtOAc and water. The aqueous layer was acidified with 1N HCl and extracted into EtOAc (×2). The combined organic phases were dried (MgSO$_4$), filtered, and concentrated under vacuum to give the product (0.026 g, 79%). $^1$H NMR (400 MHz, DMSO-d6): 12.24 (1H, br s), 7.97 (1H, s), 7.79 (1H, s), 7.71-7.62 (4H, m), 7.47-7.35 (2H, m), 4.31-4.09 (1H, m), 3.92-3.65 (1H, m), 2.18-2.09 (2H, m), 1.99-1.92 (1H, m), 1.78-1.52 (2H, m), 1.34 (3H, d), 0.96 (3H, d), 0.91-0.81 (2H, m), 0.61-0.53 (2H, m).

Example 25. 1-{3-[3-(2-Propylpiperidine-1-carbonyl)phenyl]phenyl}-5-(trifluoromethyl)-1H-pyrazole-4-carboxylic Acid

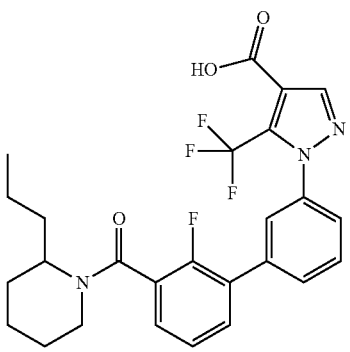 [SMILES: CCCC1CCCCN1C(=O)c1cccc(-c2cccc(-n3ncc(C(=O)O)c3C(F)(F)F)c2)c1F]

25a) [2-Fluoro-3-(4,4,5,5-tetramethyl-[1,3,2]dioxaborolan-2-yl)-phenyl]-(2-propyl-piperidin-1-yl)-methanone

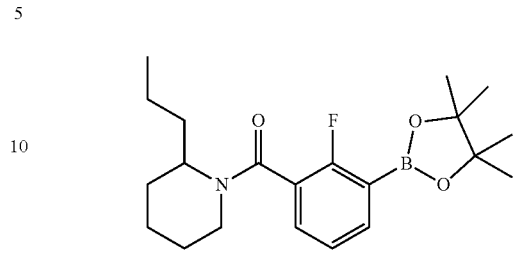

A solution of 2-fluoro-3-(4,4,5,5-tetramethyl-[1,3,2]dioxaborolan-2-yl)-benzoic acid (0.500 g, 1.9 mmol), HATU (0.725 g, 1.9 mmol), 2-propylpiperidine (0.242 g, 1.9 mmol) and DIPEA (0.66 mL, 3.8 mmol) in DCM (20 mL) was stirred for 4 h. The mixture was diluted with DCM and the organic phase was washed with aqueous NaHCO$_3$ and dried by passage through a phase separation cartridge. Concentration to dryness followed by silica chromatography eluting with EtOAc/petrol 0-30% gave the product (0.51 g, 75%). LC-MS m/z 358 (M+H)$^+$, 1.59 (ret. time).

25b) 1-{3-[3-(2-Propylpiperidine-1-carbonyl)phenyl]phenyl}-5-(trifluoromethyl)-1H-pyrazole-4-carboxylic Acid Ethyl Ester

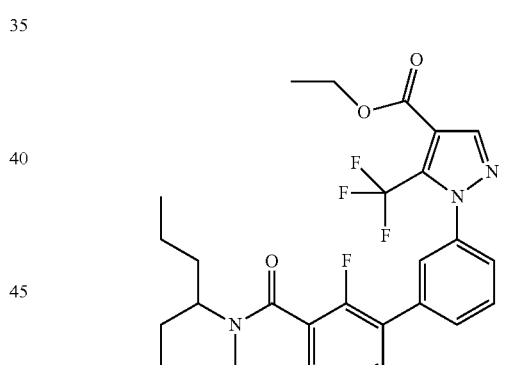

A stirred mixture of 1-(3-bromo-phenyl)-5-trifluoromethyl-1H-pyrazole-4-carboxylic acid ethyl ester (0.170 g, 0.46 mmol), [2-fluoro-3-(4,4,5,5-tetramethyl-[1,3,2]dioxaborolan-2-yl)-phenyl]-(2-propyl-piperidin-1-yl)-methanone (0.125 g, 0.35 mmol), aqueous Na$_2$CO$_3$ (3M, 0.351 mL) and Pd(PPh$_3$)$_4$ (0.030 g, 0.027 mmol) in EtOH (1 mL) and toluene (4 mL) was heated at 80° C. for 2 h. After cooling, the mixture was partitioned between EtOAc (20 mL) and water (10 mL) and the organic phase washed with water (10 mL) and brine (10 mL) before it was dried (MgSO$_4$), filtered, concentrated to dryness, and purified by silica chromatography eluting with EtOAc/petrol 0-60% to give the product (0.127 g, 71%). LC-MS m/z 530 (M+H)$^+$, 1.55 (ret. time).

25c) 1-{3-[3-(2-propylpiperidine-1-carbonyl)phenyl]phenyl}-5-(trifluoromethyl)-1H-pyrazole-4-carboxylic Acid

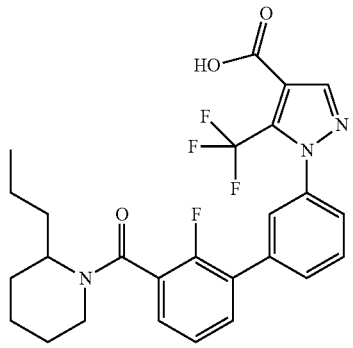 [SMILES: CCCC1CCCCN1C(=O)c1cccc(-c2cccc(-n3ncc(C(=O)O)c3C(F)(F)F)c2)c1F]

A stirred solution of 1-{3-[3-(2-propylpiperidine-1-carbonyl)phenyl]phenyl}-5-(trifluoromethyl)-1H-pyrazole-4-carboxylic acid ethyl ester (0.127 g, 0.248 mmol) in THF (2 mL) and MeOH (2 mL) was treated with LiOH (59 mg, 2.48 mmol) in water (2 mL). After 60 hours the mixture was concentrated to remove organic solvents and the residue partitioned between EtOAc and water. The aqueous layer was acidified with 1N HCl and extracted into EtOAc (×2). The combined organic phases were dried (MgSO$_4$), filtered, and concentrated under vacuum to give the product (0.034 g, 28%). LC-MS m/z 486 (M+H)$^+$, 1.20 (ret. time). $^1$H NMR (400 MHz, DMSO-d6): [presence of rotamers] 13.34 (1H, br s), 8.27 (1H, s), 7.98-7.88 (2H, m), 7.81 (1H, d), 7.73-7.61 (2H, m), 7.61-7.52 (2H, m), 7.36 (1H, d), 4.92-4.16 (1H, m), 3.85-3.36 (1H, m), 3.21-2.74 (1H, m), 1.85-1.26 (10H, m), 1.01-0.54 (3H, m).

Example 26. 5-Cyclopropyl-1-{3-[2-fluoro-3-(2-propylpyrrolidine-1-carbonyl)phenyl]phenyl}-1H-pyrazole-4-carboxylic Acid

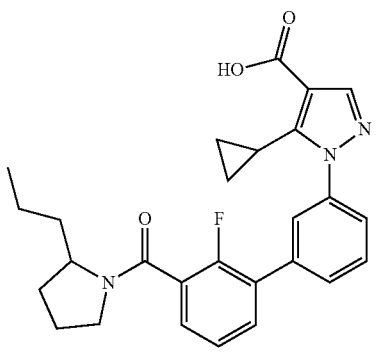 [SMILES: CCCC1CCCN1C(=O)c1cccc(-c2cccc(-n3ncc(C(=O)O)c3C3CC3)c2)c1F]

26a) 5-Cyclopropyl-1-{3-[2-fluoro-3-(2-propylpyrrolidine-1-carbonyl)phenyl]phenyl}-1H-pyrazole-4-carboxylic Acid Methyl Ester

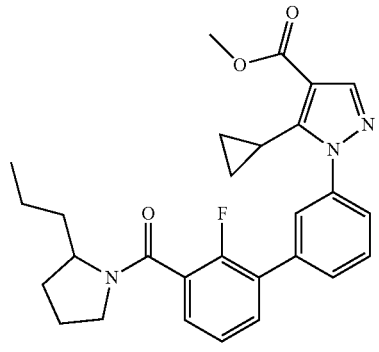 [SMILES: CCCC1CCCN1C(=O)c1cccc(-c2cccc(-n3ncc(C(=O)OC)c3C3CC3)c2)c1F]

A solution of 1-(3'-carboxy-2'-fluoro-biphenyl-3-yl)-5-cyclopropyl-1H-pyrazole-4-carboxylic acid methyl ester (0.113 g, 0.294 mmol), HATU (0.114 g, 0.291 mmol), 2-propylpyrrolidine (0.034 g, 0.30 mmol) and DIPEA (0.099 mL, 0.66 mmol) in DCM (10 mL) was stirred for 16 h. The mixture was diluted with DCM, and the organic phase washed with water and dried by passage through a phase separation cartridge. Concentration to dryness followed by silica purification eluting with EtOAc/hexane 0-60% gave the product (0.052 g, 37%). LC-MS m/z 476 (M+H)$^+$, 1.54 (ret. time).

26b) 5-Cyclopropyl-1-{3-[2-fluoro-3-(2-propylpyrrolidine-1-carbonyl)phenyl]phenyl}-1H-pyrazole-4-carboxylic Acid

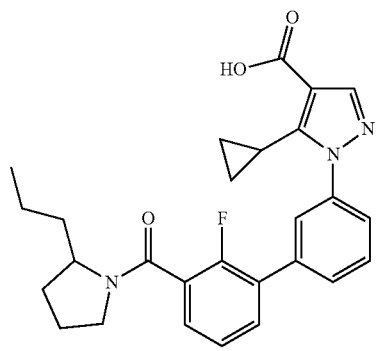 [SMILES: CCCC1CCCN1C(=O)c1cccc(-c2cccc(-n3ncc(C(=O)O)c3C3CC3)c2)c1F]

A stirred solution of 5-cyclopropyl-1-{3-[2-fluoro-3-(2-propylpyrrolidine-1-carbonyl)phenyl]phenyl}-1H-pyrazole-4-carboxylic acid methyl ester (0.052 g, 0.109 mmol) in THF (1 mL) and MeOH (1 mL) was treated with LiOH (26 mg, 1.09 mmol) in water (1 mL). After 36 hours the mixture was concentrated to remove organic solvents and the residue was partitioned between EtOAc and water. The aqueous layer was acidified with 1N HCl and extracted into EtOAc (×2). The combined organic phases were dried (MgSO$_4$), filtered, and concentrated under vacuum to give the product (0.041 g, 82%). LC-MS m/z 462 (M+H)⁺, 1.16 (ret. time). ¹H NMR (400 MHz, DMSO-d6): 12.29 (1H, brs), 7.97 (1H, s), 7.78 (1H, d), 7.72-7.62 (4H, m), 7.50-7.35 (2H, m), 4.16-4.08 (0.7H, m), 3.71-3.54 (0.6H, m), 3.50-3.41 (0.3H, m), 3.29-3.14 (1.3H, m), 2.20-2.09 (1H, m), 2.05-1.92 (1H, m), 1.91-1.61 (3.5H, m), 1.47-1.26 (2.5H, m), 1.16-1.04 (1H, m), 0.93 (2H, t), 0.90-0.81 (2H, m), 0.61-0.54 (2H, m), 0.54-0.48 (1H, m).

Example 27. 5-Cyclopropyl-1-{3-[2-fluoro-3-(3-propylmorpholine-4-carbonyl)phenyl]phenyl}-1H-pyrazole-4-carboxylic Acid

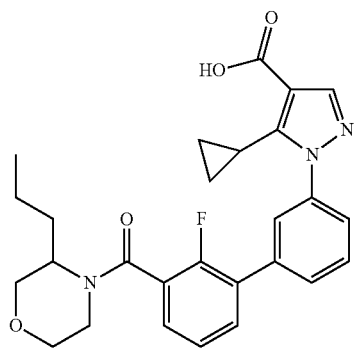 [SMILES: CCCC1COCCN1C(=O)c1cccc(-c2cccc(-n3ncc(C(=O)O)c3C3CC3)c2)c1F]

27a) 5-Cyclopropyl-1-{3-[2-fluoro-3-(3-propylmorpholine-4-carbonyl)phenyl]phenyl}-1H-pyrazole-4-carboxylic Acid Methyl Ester

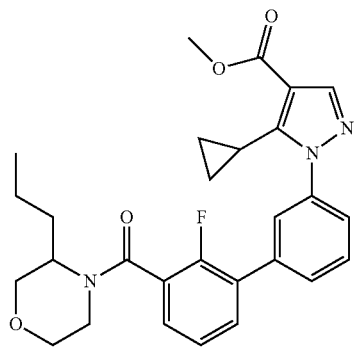 [SMILES: CCCC1COCCN1C(=O)c1cccc(-c2cccc(-n3ncc(C(=O)OC)c3C3CC3)c2)c1F]

A solution of 1-(3'-carboxy-2'-fluoro-biphenyl-3-yl)-5-cyclopropyl-1H-pyrazole-4-carboxylic acid methyl ester (0.050 g, 0.13 mmol), HATU (0.050 g, 0.13 mmol), 2-propylmorpholine (0.017 g, 0.13 mmol) and DIPEA (0.039 mL, 0.26 mmol) in DCM (5 mL) was stirred for 16 h. The mixture was diluted with DCM, and the organic phase washed with water and dried by passage through a phase separation cartridge. Concentration to dryness followed by silica purification eluting with EtOAc/hexane 0-80% gave the product (0.055 g, 85%). LC-MS m/z 492 (M+H)⁺, 1.48 (ret. time).

27b) 5-Cyclopropyl-1-{3-[2-fluoro-3-(3-propylmorpholine-4-carbonyl)phenyl]phenyl}-1H-pyrazole-4-carboxylic Acid

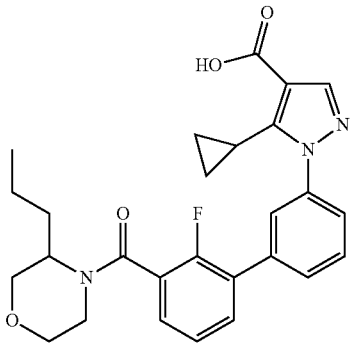 [SMILES: CCCC1COCCN1C(=O)c1cccc(-c2cccc(-n3ncc(C(=O)O)c3C3CC3)c2)c1F]

A stirred solution of 5-cyclopropyl-1-{3-[2-fluoro-3-(3-propylmorpholine-4-carbonyl)phenyl]phenyl}-1H-pyrazole-4-carboxylic acid methyl ester (0.055 g, 0.112 mmol) in THF (1 mL) and MeOH (1 mL) was treated with LiOH (27 mg, 1.12 mmol) in water (1 mL). After 36 hours the mixture was concentrated to remove organic solvents and the residue was partitioned between EtOAc and water. The aqueous layer was acidified with 1N HCl and extracted into EtOAc (×2). The combined organic phases were dried (MgSO₄), filtered, and concentrated under vacuum to give the product (0.042 g, 79%). LC-MS m/z 478 (M+H)⁺, 1.08 (ret. time). ¹H NMR (400 MHz, DMSO-d6): [presence of rotamers] 12.32 (1H, br s), 7.97 (1H, s), 7.79 (1H, br s), 7.68 (4H, s), 7.52-7.33 (2H, m), 4.51 (1H, br s), 4.25 (1H, d), 3.91 (1H, dd), 3.82-3.62 (2H, m), 3.62-3.35 (2H, m), 3.21-3.05 (1H, m), 2.20-2.09 (1H, m), 1.90-1.26 (4H, m), 1.15-1.04 (1H, m), 0.99-0.81 (4H, m), 0.70 (1H, br s), 0.57 (2H, d).

Example 28. 5-Cyclopropyl-1-(3-{2-fluoro-3-[2-(2-methylpropyl)piperidine-1-carbonyl]phenyl}phenyl)-1H-pyrazole-4-carboxylic Acid

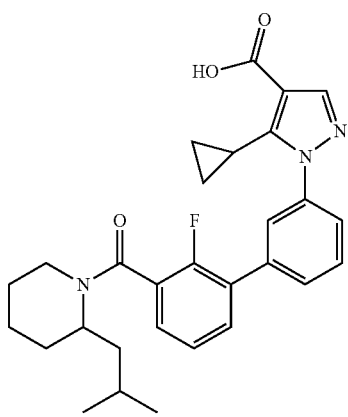 [SMILES: CC(C)CC1CCCCN1C(=O)c1cccc(-c2cccc(-n3ncc(C(=O)O)c3C3CC3)c2)c1F]

28a) 5-Cyclopropyl-1-(3-{2-fluoro-3-[2-(2-methyl-propyl)piperidine-1-carbonyl]phenyl}phenyl)-1H-pyrazole-4-carboxylic Acid Methyl Ester

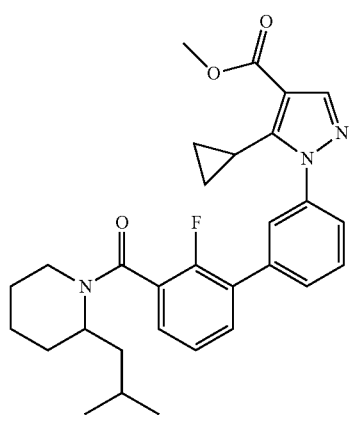 [SMILES: COC(=O)c1cnn(-c2cccc(-c3cccc(C(=O)N4CCCCC4CC(C)C)c3F)c2)c1C1CC1]

A solution of 1-(3'-carboxy-2'-fluoro-biphenyl-3-yl)-5-cyclopropyl-1H-pyrazole-4-carboxylic acid methyl ester (0.050 g, 0.13 mmol), HATU (0.050 g, 0.13 mmol), 2-isobutylpiperidine (0.027 g, 0.15 mmol) and DIPEA (0.069 mL, 0.39 mmol) in DCM (1 mL) was stirred for 4 h. The mixture was diluted with DCM, and the organic phase was washed with water and dried by passage through a phase separation cartridge. Concentration to dryness followed by silica purification eluting with EtOAc/hexane 5-40% gave the product (0.052 g, 79%). LC-MS m/z 504 (M+H)$^+$, 1.63 (ret. time), basic method.

28b) 5-Cyclopropyl-1-(3-{2-fluoro-3-[2-(2-methyl-propyl)piperidine-1-carbonyl]phenyl}phenyl)-1H-pyrazole-4-carboxylic Acid

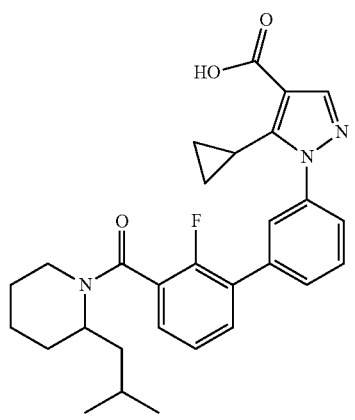 [SMILES: CC(C)CC1CCCCN1C(=O)c1cccc(-c2cccc(-n3ncc(C(=O)O)c3C3CC3)c2)c1F]

A stirred solution of 5-cyclopropyl-1-(3-{2-fluoro-3-[2-(2-methylpropyl)piperidine-1-carbonyl]phenyl}phenyl)-1H-pyrazole-4-carboxylic acid methyl ester (0.052 g, 0.10 mmol) in EtOH (1 mL) was treated with aqueous NaOH (2M, 0.246 mL). After 60 hours the mixture was partitioned between EtOAc and water. The aqueous layer was acidified with 1N HCl and extracted into EtOAc (×2). The combined organic phases were dried (MgSO$_4$), filtered and concentrated under vacuum to give the product (0.038 g, 79%). LC-MS m/z 490 (M+H)$^+$, 1.21 (ret. time), basic method. $^1$H NMR (400 MHz, DMSO-d6): 12.32 (1H, s), 7.97 (1H, s), 7.79 (1H, s), 7.71-7.59 (4H, m), 7.49-7.34 (2H, m), 4.87 (0.5H, m), 4.44 (0.5H, m), 3.68-3.57 (0.5H, m), 3.23 (0.5H, m), 3.15 (0.5H, m), 2.87-2.77 (0.5H, m), 2.19-2.11 (1H, m), 1.73-1.46 (7H, m), 1.39-1.25 (2H, m), 0.99-0.85 (6H, m), 0.65-0.56 (4H, m).

Example 29. 5-Cyclopropyl-1-{3-[2-fluoro-3-(4-methylazepane-1-carbonyl)phenyl]phenyl}-1H-pyrazole-4-carboxylic Acid

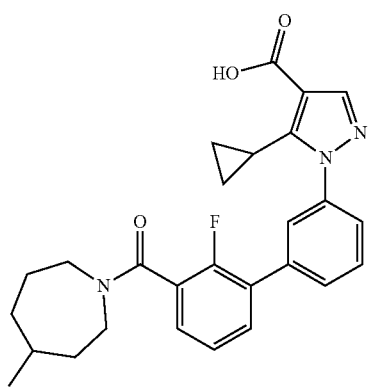 [SMILES: CC1CCCN(C(=O)c2cccc(-c3cccc(-n4ncc(C(=O)O)c4C4CC4)c3)c2F)CC1]

29a) 5-Cyclopropyl-1-{3-[2-fluoro-3-(4-methyl-azepane-1-carbonyl)phenyl]phenyl}-1H-pyrazole-4-carboxylic Acid Methyl Ester

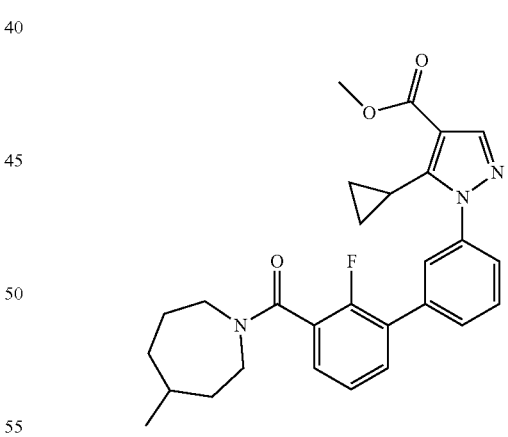

A solution of 1-(3'-carboxy-2'-fluoro-biphenyl-3-yl)-5-cyclopropyl-1H-pyrazole-4-carboxylic acid methyl ester (0.043 g, 0.11 mmol), HATU (0.043 g, 0.11 mmol), 4-methylazepane (0.015 g, 0.13 mmol) and DIPEA (0.039 mL, 0.23 mmol) in DCM (1 mL) was stirred for 4 h. The mixture was diluted with EtOAc, and the organic phase washed with water, dried (MgSO$_4$) and concentrated to dryness. Silica purification eluting with EtOAc/hexane 10-60% gave the product (0.043 g, 80%). LC-MS m/z 476 (M+H)$^+$, 1.54 (ret. time).

29b) 5-Cyclopropyl-1-{3-[2-fluoro-3-(4-methyl-azepane-1-carbonyl)phenyl]phenyl}-1H-pyrazole-4-carboxylic Acid

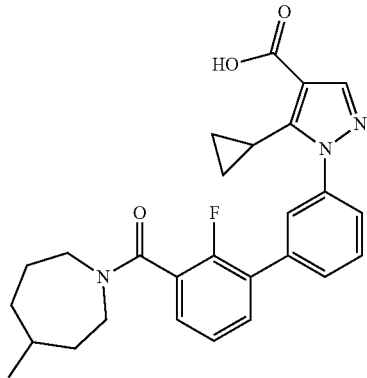 [SMILES: CC1CCCN(C(=O)c2cccc(-c3cccc(-n4ncc(C(=O)O)c4C4CC4)c3)c2F)CC1]

A stirred solution of 5-cyclopropyl-1-{3-[2-fluoro-3-(4-methylazepane-1-carbonyl)phenyl]phenyl}-1H-pyrazole-4-carboxylic acid methyl ester (0.043 g, 0.09 mmol) in EtOH (1 mL) was treated with aqueous NaOH (2M, 0.226 mL). After 60 hours the mixture was partitioned between EtOAc and water. The organic phase was extracted with water and then discarded. The combined aqueous layer was acidified with 1N HCl and extracted into EtOAc (×2). The combined organic phases were dried (MgSO$_4$), filtered and concentrated under vacuum to give the product (0.028 g, 67%). LC-MS m/z 462 (M+H)$^+$, 1.14 (ret. time), basic method. $^1$H NMR (400 MHz, DMSO-d6): 12.29 (1H, s), 7.97 (1H, s), 7.79 (1H, s), 7.67 (4H, m), 7.44-7.35 (2H, m), 3.88-3.79 (0.5H, m), 3.69 (0.5H, m), 3.52 (0.5H, m), 3.43-3.33 (1.5H, m), 3.28-3.17 (1H, m), 2.20-2.08 (1H, m), 1.90-1.76 (1H, m), 1.76-1.46 (4H, m), 1.31-1.12 (2H, m), 0.94 (1.5H, d), 0.91-0.78 (3.5H, m), 0.63-0.51 (2H, m). Azapane peaks are rotameric.

Example 30. 5-Cyclopropyl-1-{3-[3-(2,5-dimethyl-piperidine-1-carbonyl)-2-fluorophenyl]phenyl}-1H-pyrazole-4-carboxylic Acid

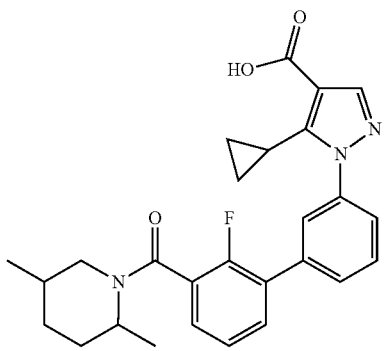 [SMILES: CC1CCC(C)N(C(=O)c2cccc(-c3cccc(-n4ncc(C(=O)O)c4C4CC4)c3)c2F)C1]

30a) 5-Cyclopropyl-1-{3-[3-(2,5-dimethylpiperi-dine-1-carbonyl)-2-fluorophenyl]phenyl}-1H-pyrazole-4-carboxylic Acid Methyl Ester

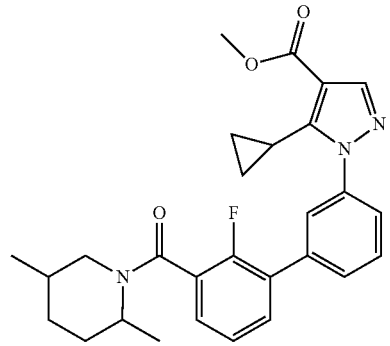 [SMILES: COC(=O)c1cnn(-c2cccc(-c3cccc(C(=O)N4CC(C)CCC4C)c3F)c2)c1C1CC1]

A solution of 1-(3'-carboxy-2'-fluoro-biphenyl-3-yl)-5-cyclopropyl-1H-pyrazole-4-carboxylic acid methyl ester (0.050 g, 0.13 mmol), HATU (0.050 g, 0.13 mmol), 2,5-dimethylpiperidine (0.015 g, 0.13 mmol) and DIPEA (0.046 mL, 0.27 mmol) in DCM (4 mL) was stirred for 16 h. The mixture was diluted with EtOAc, and the organic phase was washed with water, dried (MgSO$_4$), and concentrated to dryness. Silica purification eluting with EtOAc/hexane 0-60% gave the product (0.060 g, 96%.). LC-MS m/z 476 (M+H)$^+$, 1.56 (ret. time).

30b) 5-Cyclopropyl-1-{3-[3-(2,5-dimethylpiperi-dine-1-carbonyl)-2-fluorophenyl]phenyl}-1H-pyrazole-4-carboxylic Acid

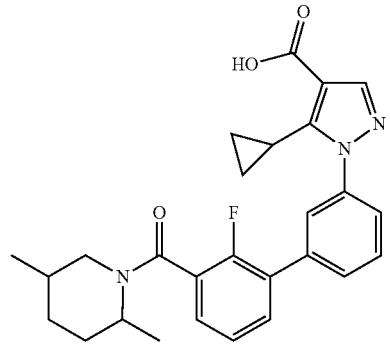 [SMILES: CC1CCC(C)N(C(=O)c2cccc(-c3cccc(-n4ncc(C(=O)O)c4C4CC4)c3)c2F)C1]

A stirred solution of 5-cyclopropyl-1-{3-[3-(2,5-dimethylpiperidine-1-carbonyl)-2-fluorophenyl]phenyl}-1H-pyrazole-4-carboxylic acid methyl ester (0.060 g, 0.126 mmol) in THF (1 mL) and MeOH (1 mL) was treated with LiOH (30 mg, 1.26 mmol) in water (1 mL). After 60 hours the mixture was concentrated to remove organic solvents and the residue partitioned between EtOAc and water. The aqueous layer was acidified with 1N HCl and extracted into EtOAc (×2). The combined organic phases were dried (MgSO$_4$), filtered, and concentrated under vacuum to give the product (0.036 g, 62%). LC-MS m/z 462 (M+H)$^+$, 1.13

(ret. time). ¹H NMR (400 MHz, DMSO-d6): [presence of rotamers] 12.27 (1H, br s), 7.97 (1H, s), 7.79 (1H, br s), 7.73-7.60 (4H, m), 7.45-7.30 (2H, m), 4.86 (0.4H, br s), 4.40-4.14 (0.5H, m), 3.85-3.65 (0.5H, m), 3.51-3.34 (0.3H, m), 3.20-2.96 (1H, m), 2.19-2.09 (1H, m), 1.91-1.76 (2H, m), 1.66-1.08 (6H, m), 1.08-0.71 (5H, m), 0.57 (2H, d).

Example 31. 5-Cyclopropyl-1-{3-[3-(decahydroquinoline-1-carbonyl)-2-fluorophenyl]phenyl}-1H-pyrazole-4-carboxylic Acid

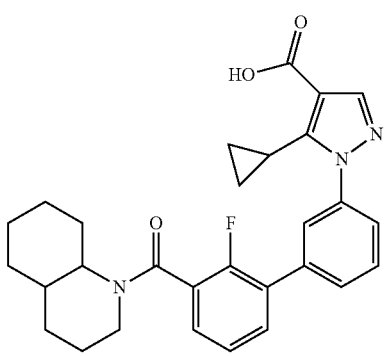 [SMILES: O=C(O)c1cnn(-c2cccc(-c3cccc(C(=O)N4CCCC5CCCCC54)c3F)c2)c1C1CC1]

31a) 5-Cyclopropyl-1-{3-[3-(decahydroquinoline-1-carbonyl)-2-fluorophenyl]phenyl}-1H-pyrazole-4-carboxylic Acid Methyl Ester

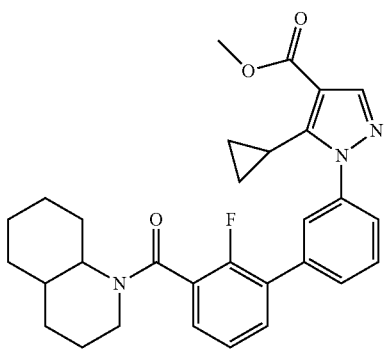 [SMILES: COC(=O)c1cnn(-c2cccc(-c3cccc(C(=O)N4CCCC5CCCCC54)c3F)c2)c1C1CC1]

A solution of 1-(3'-carboxy-2'-fluoro-biphenyl-3-yl)-5-cyclopropyl-1H-pyrazole-4-carboxylic acid methyl ester (0.050 g, 0.13 mmol), HATU (0.050 g, 0.13 mmol), decahydroquinoline (0.018 g, 0.13 mmol) and DIPEA (0.046 mL, 0.27 mmol) in DCM (4 mL) was stirred for 16 h. The mixture was diluted with EtOAc, and the organic phase washed with water, dried (MgSO₄) and concentrated to dryness. Silica purification eluting with EtOAc/hexane 0-60% gave the product (0.061 g, 93%.). LC-MS m/z 502 (M+H)⁺, 1.60 (ret. time).

31b) 5-Cyclopropyl-1-{3-[3-(decahydroquinoline-1-carbonyl)-2-fluorophenyl]phenyl}-1H-pyrazole-4-carboxylic Acid

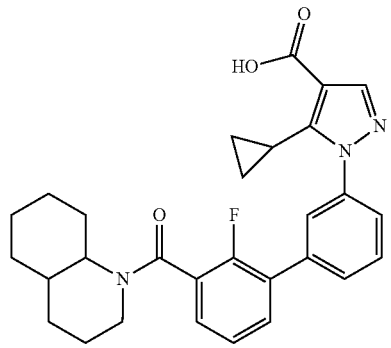 [SMILES: O=C(O)c1cnn(-c2cccc(-c3cccc(C(=O)N4CCCC5CCCCC54)c3F)c2)c1C1CC1]

A stirred solution of 5-cyclopropyl-1-{3-[3-(decahydroquinoline-1-carbonyl)-2-fluorophenyl]phenyl}-1H-pyrazole-4-carboxylic acid methyl ester (0.061 g, 0.122 mmol) in THF (1 mL) and MeOH (1 mL) was treated with LiOH (29 mg, 1.22 mmol) in water (1 mL). After 48 hours the mixture was concentrated to remove organic solvents and the residue partitioned between EtOAc and water. The aqueous layer was acidified with 1N HCl and extracted into EtOAc (×2). The combined organic phases were dried (MgSO₄), filtered, and concentrated under vacuum to give the product (0.033 g, 56%). LC-MS m/z 488 (M+H)⁺, 1.21 (ret. time). ¹H NMR (400 MHz, DMSO-d6): [presence of rotamers] 12.28 (1H, br s), 7.97 (1H, s), 7.78 (1H, br s), 7.71-7.61 (4H, m), 7.45-7.31 (2H, m), 4.61 (0.4H, d), 4.43 (0.3H, d), 3.51-3.33 (1H, m), 3.30-2.74 (2H, m), 2.20-2.06 (1H, m), 1.90-1.22 (12H, m), 0.91-0.82 (2H, m), 0.62-0.53 (2H, m).

Example 32. 5-cyclopropyl-1-[3-(2-fluoro-3-{3-oxa-8-azabicyclo[3.2.1]octane-8-carbonyl}phenyl)phenyl]-1H-pyrazole-4-carboxylic Acid

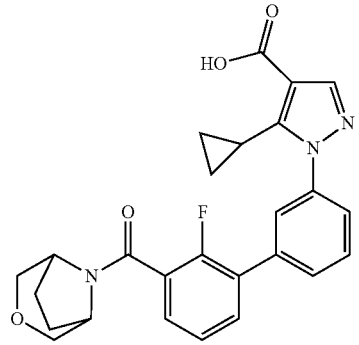 [SMILES: O=C(O)c1cnn(-c2cccc(-c3cccc(C(=O)N4C5CCC4COC5)c3F)c2)c1C1CC1]

32a) 5-Cyclopropyl-1-[3-(2-fluoro-3-{3-oxa-8-azabicyclo[3.2.1]octane-8-carbonyl}phenyl)phenyl]-1H-pyrazole-4-carboxylic Acid Methyl Ester

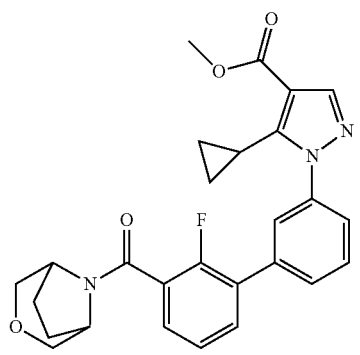 [SMILES: COC(=O)c1cnn(-c2cccc(-c3cccc(C(=O)N4C5CCC4COC5)c3F)c2)c1C1CC1]

A solution of 1-(3'-carboxy-2'-fluoro-biphenyl-3-yl)-5-cyclopropyl-1H-pyrazole-4-carboxylic acid methyl ester (0.043 g, 0.11 mmol), HATU (0.043 g, 0.11 mmol), 3-oxa-8-aza-bicyclo [3.2.1]octane (0.019 g, 0.13 mmol) and DIPEA (0.059 mL, 0.34 mmol) in DCM (1 mL) was stirred for 4 h. The mixture was diluted with DCM, and the organic phase was washed with sat. aqueous NaHCO₃, dried (MgSO₄) and concentrated to dryness. Silica purification eluting with EtOAc/hexane 20-100% gave the product (0.055 g, quantative). LC-MS m/z 476 (M+H)⁺, 1.54 (ret. time), basic method.

32b) 5-Cyclopropyl-1-[3-(2-fluoro-3-{3-oxa-8-azabicyclo[3.2.1]octane-8-carbonyl}phenyl)phenyl]-1H-pyrazole-4-carboxylic Acid

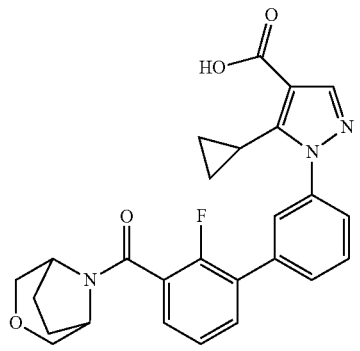 [SMILES: O=C(O)c1cnn(-c2cccc(-c3cccc(C(=O)N4C5CCC4COC5)c3F)c2)c1C1CC1]

A stirred solution of 5-cyclopropyl-1-[3-(2-fluoro-3-{3-oxa-8-azabicyclo[3.2.1]octane-8-carbonyl}phenyl)phenyl]-1H-pyrazole-4-carboxylic acid methyl ester (0.055 g, 0.12 mmol) in EtOH (1.5 mL) was treated with aqueous NaOH (2M, 0.289 mL). After 60 hours the mixture was partitioned between EtOAc and water. The organic phase was further extracted with water and then discarded. The combined aqueous layer was acidified with 1N HCl and extracted into EtOAc (×2). The combined organic phases were dried (MgSO₄), filtered and concentrated under vacuum to give the product (0.035 g, 63%). LC-MS m/z 462 (M+H)⁺, 1.02 (ret. time), basic method. ¹H NMR (400 MHz, DMSO-d6): 12.25 (1H, s), 7.97 (1H, s), 7.81 (1H, s), 7.74-7.61 (4H, m), 7.56-7.47 (1H, m), 7.41 (1H, t), 4.59 (1H, s), 3.77 (1H, s), 3.66 (2H, m), 3.52 (2H, m), 2.20-2.09 (1H, m), 1.97-1.82 (4H, m), 0.93-0.80 (2H, m), 0.62-0.53 (2H, m).

Example 33. 1-{3-[3-(2-Cyclopentylpiperidine-1-carbonyl)-2-fluorophenyl]phenyl}-5-cyclopropyl-1H-pyrazole-4-carboxylic Acid

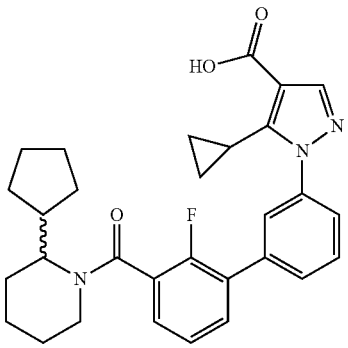 [SMILES: O=C(O)c1cnn(-c2cccc(-c3cccc(C(=O)N4CCCCC4C4CCCC4)c3F)c2)c1C1CC1]

33a) 2-Cyclopentyl-pyridine

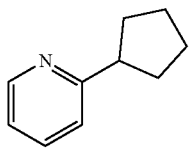 [SMILES: c1ccc(C2CCCC2)nc1]

PdCl₂dppf (231 mg, 0.32 mmol) was added to a solution of 2-bromopyridine (1.0 g, 6.33 mmol) and cyclopentyl zinc bromide (0.5M in THF, 19 mL, 9.5 mmol) in dry dioxane (20 mL) under nitrogen and the reaction was heated to reflux for 2 h. The reaction mixture was concentrated and then partitioned between EtOAc (40 mL) and water (30 mL). The organic phase was washed with water, brine and then dried (MgSO₄), filtered and concentrated. Silica purification eluting with EtOAc/hexane 0-25% gave the product (0.93 g, 99%). LC-MS no mass ion observed, 1.30 (ret. time), basic method.

33b) 2-Cyclopentyl-piperidine

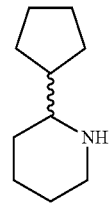

To a solution of 2-cyclopentylpyridine (0.93 g, 6.32 mmol) in ethanol (100 mL) was added HCl in dioxane (4M, 1.74 mL, 9.65 mmol) and PtO₂ (150 mg) and the mixture shaken under a hydrogen atmosphere for 4 h. The catalyst was removed by filtration and then the solution concentrated to dryness to give product (775 mg, 65%) as the HCl salt. ¹H NMR (400 MHz, DMSO-d6): 9.34-8.16 (2H, m), 3.17 (1H, d), 2.93-2.68 (2H, m), 2.11-1.91 (1H, m), 1.85-1.17 (14H, m).

33c) 1-{3-[3-(2-Cyclopentylpiperidine-1-carbonyl)-2-fluorophenyl]phenyl}-5-cyclopropyl-1H-pyrazole-4-carboxylic Acid Methyl Ester

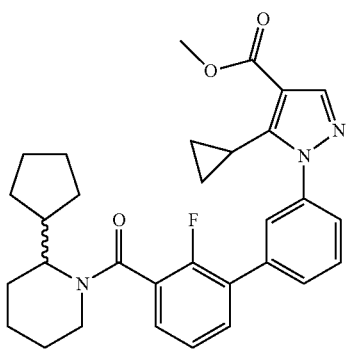 [SMILES: COC(=O)c1cnn(-c2cccc(-c3cccc(C(=O)N4CCCCC4C4CCCC4)c3F)c2)c1C1CC1]

A solution of 1-(3'-carboxy-2'-fluoro-biphenyl-3-yl)-5-cyclopropyl-1H-pyrazole-4-carboxylic acid methyl ester (0.050 g, 0.13 mmol), HATU (0.050 g, 0.13 mmol), 2-cyclopentylpiperidine (0.030 g, 0.16 mmol) and DIPEA (0.069 mL, 0.39 mmol) in DCM (1 mL) was stirred for 2 h. The mixture was diluted with DCM, and the organic phase was washed with sat. aqueous NaHCO$_3$, dried (MgSO$_4$) and concentrated to dryness. Silica purification eluting with EtOAc/hexane 10-60% gave the product (0.049 g, 72%). LC-MS m/z 516 (M+H)$^+$, 1.65 (ret. time), basic method.

33d) 1-{3-[3-(2-Cyclopentylpiperidine-1-carbonyl)-2-fluorophenyl]phenyl}-5-cyclopropyl-1H-pyrazole-4-carboxylic Acid

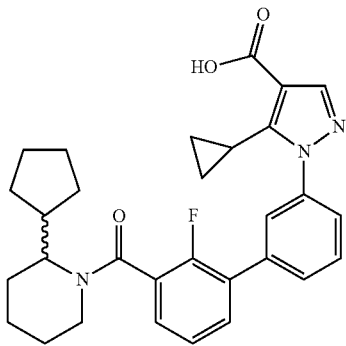 [SMILES: O=C(O)c1cnn(-c2cccc(-c3cccc(C(=O)N4CCCCC4C4CCCC4)c3F)c2)c1C1CC1]

A stirred solution of 1-{3-[3-(2-cyclopentylpiperidine-1-carbonyl)-2-fluorophenyl]phenyl}-5-cyclopropyl-1H-pyrazole-4-carboxylic acid methyl ester (0.049 g, 0.10 mmol) in EtOH (0.75 mL) was treated with aqueous NaOH (2M, 0.238 mL). After 60 hours the mixture was partitioned between EtOAc and water. The organic phase was further extracted with water and then discarded. The combined aqueous layer was acidified with 1N HCl and extracted into EtOAc (×2). The combined organic phases were dried (MgSO$_4$), filtered and concentrated under vacuum to give the product (0.028 g, 59%). LC-MS m/z 502 (M+H)$^+$, 1.25 (ret. time), basic method. $^1$H NMR (400 MHz, DMSO-d6): 12.27 (1H, s), 7.97 (1H, s), 7.78 (1H, s), 7.72-7.60 (4H, m), 7.48-7.24 (2H, m), 4.54-4.42 (1H, m), 3.27-3.07 (1.7H, m), 2.83 (0.3H, t), 2.20-2.08 (1H, m), 1.82-1.38 (11H, m), 1.38-1.13 (3H, m), 1.06-0.91 (1H, m), 0.87 (2H, d), 0.58 (2H, s). Peaks close to amide are rotameric.

Example 34. 1-[3-(3-{9-azabicyclo[3.3.1]nonane-9-carbonyl}-2-fluorophenyl)phenyl]-5-cyclopropyl-1H-pyrazole-4-carboxylic Acid

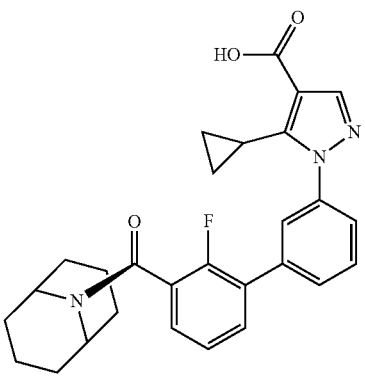

34a) 1-[3-(3-{9-Azabicyclo[3.3.1]nonane-9-carbonyl}-2-fluorophenyl)phenyl]-5-cyclopropyl-1H-pyrazole-4-carboxylic Acid Methyl Ester

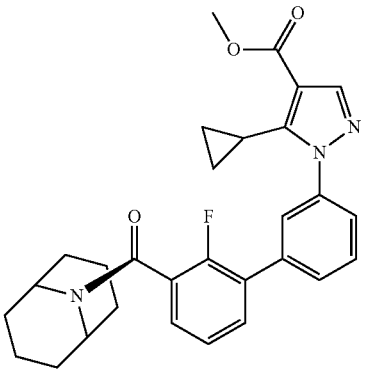

A solution of 1-(3'-carboxy-2'-fluoro-biphenyl-3-yl)-5-cyclopropyl-1H-pyrazole-4-carboxylic acid methyl ester (0.050 g, 0.13 mmol), HATU (0.050 g, 0.13 mmol), 9-azabicyclo[3.3.1] nonane (0.021 g, 0.17 mmol) and DIPEA (0.050 mg, 0.39 mmol) in DCM (4 mL) was stirred for 16 h. The mixture was diluted with DCM, and the organic phase was washed with sat. aqueous NaHCO$_3$ followed by brine, dried (MgSO$_4$), filtered, and concentrated to dryness. Silica purification eluting with EtOAc/hexane 0-60% gave the product (0.062 g, 97%). LC-MS m/z 488 (M+H)$^+$, 1.53 (ret. time).

34b) 1-[3-(3-{9-Azabicyclo[3.3.1]nonane-9-carbonyl}-2-fluorophenyl)phenyl]-5-cyclopropyl-1H-pyrazole-4-carboxylic Acid

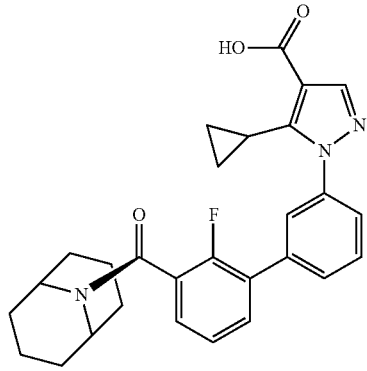

A stirred solution of 1-[3-(3-{9-azabicyclo[3.3.1]nonane-9-carbonyl}-2-fluorophenyl)phenyl]-5-cyclopropyl-1H-pyrazole-4-carboxylic acid methyl ester (0.062 g, 0.127 mmol) in THF (1 mL) and MeOH (1 mL) was treated with LiOH (30 mg, 1.27 mmol) in water (1 mL). After 60 hours the mixture was concentrated to remove organic solvents and the residue partitioned between EtOAc and water. The aqueous layer was acidified with 1N HCl and extracted into EtOAc (×2). The combined organic phases were dried (MgSO₄), filtered, and concentrated under vacuum to give the product (0.044 g, 73%). LC-MS m/z 474 (M+H)$^+$, 1.16 (ret. time). $^1$H NMR (400 MHz, DMSO-d6): [presence of rotamers] 12.26 (1H, br s), 7.97 (1H, s), 7.79 (1H, s), 7.71-7.63 (4H, m), 7.46-7.36 (2H, m), 4.73 (1H, s), 3.60 (1H, s), 2.18-2.00 (3H, m), 1.90-1.53 (10H, m), 0.91-0.83 (2H, m), 0.61-0.54 (2H, m).

Example 35. 1-[3-(3-{7-Azaspiro[4.5]decane-7-carbonyl}-2-fluorophenyl)phenyl]-5-cyclopropyl-1H-pyrazole-4-carboxylic Acid

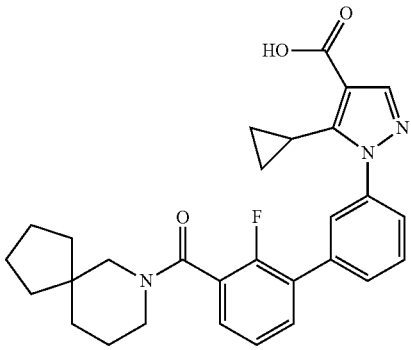 [SMILES: O=C(O)c1cnn(-c2cccc(-c3cccc(C(=O)N4CCCC5(CCCC5)C4)c3F)c2)c1C1CC1]

35a) 1-[3-(3-{7-Azaspiro[4.5]decane-7-carbonyl}-2-fluorophenyl)phenyl]-5-cyclopropyl-1H-pyrazole-4-carboxylic Acid Methyl Ester

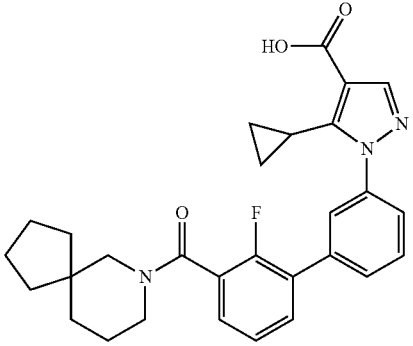 [SMILES: O=C(O)c1cnn(-c2cccc(-c3cccc(C(=O)N4CCCC5(CCCC5)C4)c3F)c2)c1C1CC1]

A solution of 1-(3'-carboxy-2'-fluoro-biphenyl-3-yl)-5-cyclopropyl-1H-pyrazole-4-carboxylic acid methyl ester (0.050 g, 0.13 mmol), HATU (0.050 g, 0.13 mmol), 7-azaspiro[4.5]decane (0.018 g, 0.13 mmol) and DIPEA (0.050 mg, 0.39 mmol) in DCM (4 mL) was stirred for 16 h. The mixture was diluted with DCM, and the organic phase washed with sat. aqueous NaHCO₃ followed by brine, dried (MgSO₄), filtered, and concentrated to dryness. Silica purification eluting with EtOAc/hexane 0-60% gave the product (0.060 g, 91%). LC-MS m/z 502 (M+H)$^+$, 1.60 (ret. time).

35b) 1-[3-(3-{7-Azaspiro[4.5]decane-7-carbonyl}-2-fluorophenyl)phenyl]-5-cyclopropyl-1H-pyrazole-4-carboxylic Acid

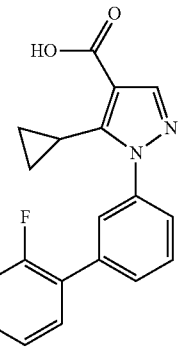

A stirred solution of 1-[3-(3-{9-azabicyclo[3.3.1]nonane-9-carbonyl}-2-fluorophenyl)phenyl]-5-cyclopropyl-1H-pyrazole-4-carboxylic acid methyl ester (0.060 g, 0.120 mmol) in THF (1 mL) and MeOH (1 mL) was treated with LiOH (29 mg, 1.20 mmol) in water (1 mL). After 60 hours the mixture was concentrated to remove organic solvents and the residue partitioned between EtOAc and water. The aqueous layer was acidified with 1N HCl and extracted into EtOAc (×2). The combined organic phases were dried (MgSO₄), filtered, and concentrated under vacuum to give the product (0.044 g, 73%). LC-MS m/z 488 (M+H)$^+$, 1.21 (ret. time). $^1$H NMR (400 MHz, DMSO-d6): [presence of rotamers] 12.29 (1H, br s), 7.97 (1H, s), 7.79 (1H, d), 7.72-7.63 (4H, m), 7.43-7.36 (2H, m), 3.59 (1H, d), 3.27-

3.12 (1H, m), 3.01 (1H, s), 2.19-2.09 (1H, m), 1.70-1.41 (9H, m), 1.41-1.13 (4H, m), 0.92-0.82 (2H, m), 0.61-0.53 (2H, m).

Example 36. 5-Cyclopropyl-1-{3-[3-(5-methyl-1H-pyrazol-1-yl)phenyl]phenyl}-1H-pyrazole-4-carboxylic Acid

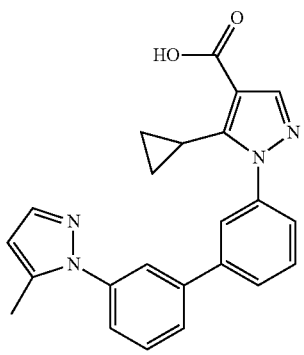 [SMILES: Cc1ccnn1-c1cccc(-c2cccc(-n3ncc(C(=O)O)c3C3CC3)c2)c1]

36a) 1-(3-Bromo-phenyl)-5-methyl-1H-pyrazole-4-carboxylic Acid Ethyl Ester

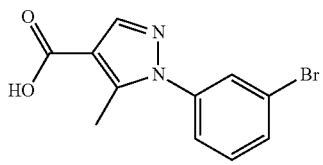 [SMILES: Cc1c(C(=O)O)cnn1-c1cccc(Br)c1]

A mixture of ethyl acetoacetate (6.0 mmol) and DMF-dimethyl acetal (6.0 mmol) was stirred in a microwave reactor at 130° C. for 15 min. After cooling, the stirred mixture was diluted with EtOH (10 mL) and treated with 3-bromophenylhydrazine HCl (1.12 g, 5.0 mmol), followed by triethylamine (0.68 mL, 5.0 mmol) and heated at 80° C. for 3 h. After cooling, the mixture was concentrated to dryness and purified by silica eluting with EtOAc/petrol 10% to give the product (1.50 g, 97%). LC-MS m/z 309 (M+H)$^+$, 1.47 (ret. time).

36b) 1-(3-Bromo-phenyl)-5-methyl-1H-pyrazole-4-carboxylic Acid

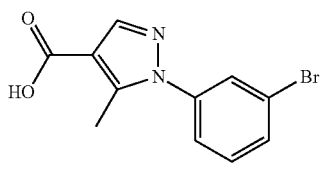 [SMILES: Cc1c(C(=O)O)cnn1-c1cccc(Br)c1]

A stirred solution of 1-(3-bromo-phenyl)-5-methyl-1H-pyrazole-4-carboxylic acid ethyl ester (1.50 g, 4.85 mmol) in MeOH (5 mL) was treated with aqueous NaOH (2M, 4.85 mL) and heated to 60° C. After 2 hours the mixture was partitioned between DCM and water. The aqueous layer was acidified with 1N HCl and extracted into DCM (×3) and IPA/CHCl$_3$ (×2). The combined organic phases were dried (MgSO$_4$), filtered and concentrated under vacuum to give the product (0.792 g, 25%). LC-MS m/z 279 (M+H)$^+$, 0.86 (ret. time).

36c) 1-(3-Bromo-phenyl)-5-methyl-1H-pyrazole

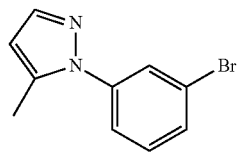

A stirred solution of 1-(3-bromo-phenyl)-5-methyl-1H-pyrazole-4-carboxylic acid (0.372 g, 1.32 mmol) in quinoline (0.5 mL) was heated at 240° C. for 4 h. After cooling the solution was loaded onto a silica column and eluted with EtOAc/petrol 15% to give the product (0.362 g, quantative). 1H NMR (400 MHz, CDCl$_3$): 7.71-7.47 (3H, m), 7.47-7.34 (2H, m), 6.24 (1H, s), 2.38 (3H, s).

36d) 5-Cyclopropyl-1-{3-[3-(5-methyl-1H-pyrazol-1-yl)phenyl]phenyl}-1H-pyrazole-4-carboxylic Acid Methyl Ester

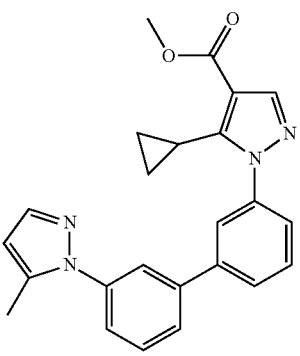 [SMILES: COC(=O)c1cnn(-c2cccc(-c3cccc(-n4nccc4C)c3)c2)c1C1CC1]

A stirred mixture of 1-(3-bromo-phenyl)-5-methyl-1H-pyrazole (0.130 g, 0.55 mmol), 5-cyclopropyl-1-[3-(4,4,5,5-tetramethyl-[1,3,2]dioxaborolan-2-yl)-phenyl]-1H-pyrazole-4-carboxylic acid methyl ester (0.144 g, 0.66 mmol), aqueous Na$_2$CO$_3$ (2M, 2.2 mL) and Pd(PPh$_3$)$_4$ (0.032 g, 0.03 mmol) in DME (11 mL) was heated at 80° C. under N$_2$ for 16 h. After cooling, the mixture was partitioned between EtOAc (20 mL) and water (10 mL) and the organic phase washed with water (10 mL) before it was dried (MgSO$_4$), filtered, concentrated to dryness, and purified by silica chromatography eluting with EtOAc/petrol 30% to give the product (0.090 g, 41%). LC-MS m/z 399 (M+H)$^+$, 1.48 (ret. time).

36e) 5-Cyclopropyl-1-{3-[3-(5-methyl-1H-pyrazol-1-yl)phenyl]phenyl}-1H-pyrazole-4-carboxylic Acid

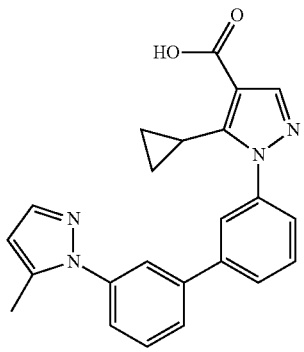 [SMILES: Cc1ccnn1-c1cccc(-c2cccc(-n3ncc(C(=O)O)c3C3CC3)c2)c1]

A stirred solution of 5-cyclopropyl-1-{3-[3-(5-methyl-1H-pyrazol-1-yl)phenyl]phenyl}-1H-pyrazole-4-carboxylic acid methyl ester (0.090 g, 0.23 mmol) in MeOH (1 mL) was treated with aqueous NaOH (2M, 0.5 mL) and heated to 60° C. After 16 hours the mixture was partitioned between DCM and water. The aqueous layer was acidified with 1N HCl and extracted into DCM (×4). The combined organic phases were dried (MgSO$_4$), filtered and concentrated under vacuum, and the residue purified by HPLC to give the product (0.022 g, 25%). LC-MS m/z 385 (M+H)$^+$, 1.07 (ret. time).

Example 37. 5-Cyclopropyl-1-(3-{2-fluoro-3-[(2R)-2-propylpiperidine-1-carbonyl]phenyl}phenyl)-1H-pyrazole-4-carboxylic Acid

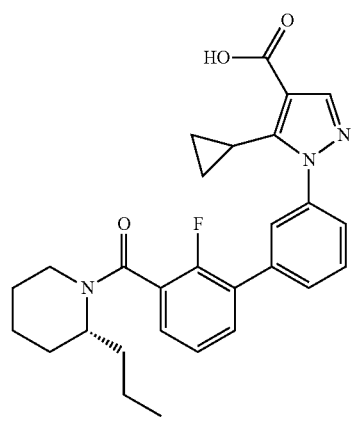 [SMILES: CCC[C@@H]1CCCCN1C(=O)c1cccc(-c2cccc(-n3ncc(C(=O)O)c3C3CC3)c2)c1F]

37a) (R)-2-propyl-piperidine

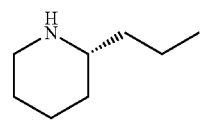

A solution of racemic 2-n-propylpiperidine (3.00 g, 23.6 mmol) in dry MeOH (9.5 mL) was treated with (S)-(+)-mandelic acid (3.59 g, 23.6 mmol) with cooling in an ice bath. Dry ether (21 mL) was then added and the flask left in the fridge for 6 days. The solid was filtered off and rinsed with cold ether. The solid was then redissolved in dry MeOH (6.5 mL) and then dry ether (13 mL) added. Left in fridge overnight and then solid filtered off, again washing with cold ether to give 1.67 g of salt. The salt was dissolved in water (14 mL) and then solid KOH was added until basic. The mixture was extracted with Et$_2$O (×3) before it was dried (MgSO$_4$) and filtered. HCl in Et$_2$O (2M, 3 mL) was added and concentrated to give the product (0.965 g, 25%) as the HCl salt.

37b) (3-Bromo-2-fluoro-phenyl)-((R)-2-propyl-piperidin-1-yl)-methanone

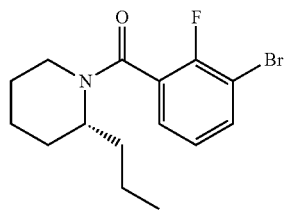 [SMILES: CCC[C@@H]1CCCCN1C(=O)c1cccc(Br)c1F]

A solution of 3-bromo-2-fluoro-benzoic acid (0.090 g, 0.41 mmol), HATU (0.156 g, 0.41 mmol), (R)-2-propyl-piperidine hydrochloride (0.067 g, 0.41 mmol) and DIPEA (0.179 mL, 1.03 mmol) in DCM (2 mL) was stirred for 2 h. The mixture was diluted with DCM and the organic phase washed with aqueous NaHCO$_3$ and dried (MgSO$_4$), filtered, concentrated to dryness, and purified by silica chromatography (EtOAc/petrol 5-30% gradient) to give the product (0.115 g, 64%). Chiral HPLC rt 6.61 min.

37c) 5-Cyclopropyl-1-(3-{2-fluoro-3-[(2R)-2-propylpiperidine-1-carbonyl]phenyl}phenyl)-1H-pyrazole-4-carboxylic Acid Ethyl Ester

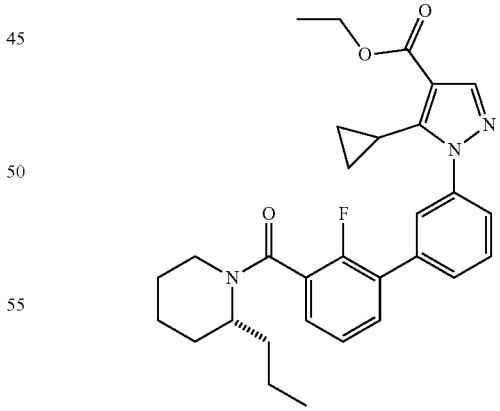

A stirred mixture of (3-bromo-2-fluoro-phenyl)-((R)-2-propyl-piperidin-1-yl)-methanone (0.103 g, 0.31 mmol), 5-cyclopropyl-1-[3-(4,4,5,5-tetramethyl-[1,3,2]dioxaborolan-2-yl)-phenyl]-1H-pyrazole-4-carboxylic acid ethyl ester (0.120 g, 0.31 mmol), aqueous Na$_2$CO$_3$ (3M, 0.314 mL) and Pd(PPh$_3$)$_4$ (0.018 g, 0.02 mmol) in EtOH (1 mL) and toluene (3 mL) was heated at reflux for 2 h. After cooling, the mixture was partitioned between EtOAc (20 mL) and water (15 mL) and the organic phase was washed with water (15 mL) and brine (15 mL) before it was dried (MgSO$_4$), filtered, concentrated to dryness and purified by silica chromatography (EtOAc/petrol 20-70% gradient) to give the product (0.133 g, 84%). LC-MS m/z 504 (M+H)$^+$, 1.64 (ret. time).

37d) 5-Cyclopropyl-1-(3-{2-fluoro-3-[(2R)-2-propylpiperidine-1-carbonyl]phenyl}phenyl)-1H-pyrazole-4-carboxylic Acid

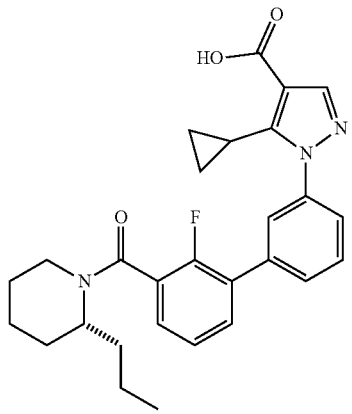 [SMILES: CCC[C@@H]1CCCCN1C(=O)c1cccc(-c2cccc(-n3ncc(C(=O)O)c3C3CC3)c2)c1F]

A stirred solution of 5-cyclopropyl-1-(3-{2-fluoro-3-[(2R)-2-propylpiperidine-1-carbonyl]phenyl}phenyl)-1H-pyrazole-4-carboxylic acid ethyl ester (0.133 g, 0.26 mmol) in EtOH (2 mL) was treated with aqueous NaOH (2M, 0.66 mL). After 60 hours the mixture was partitioned between EtOAc and water. The organic phase was further extracted with water and then discarded. The combined aqueous layer was acidified with 1N HCl and extracted into EtOAc (×2). The combined organic phases were dried (MgSO$_4$), filtered, and concentrated under vacuum to give the product (0.074 g, 59%). LC-MS m/z 476 (M+H)$^+$, 1.18 (ret. time), basic method. $^1$H NMR (400 MHz, DMSO-d6): 12.30 (1H, s), 7.97 (1H, s), 7.82-7.72 (1H, m), 7.72-7.58 (4H, m), 7.48-7.26 (2H, m), 4.78 (0.6H, brs), 4.44 (0.4H, m), 3.56 (0.5H, s), 3.26-3.03 (1H, m), 2.79 (0.5H, t), 2.19-2.08 (1H, m), 1.88-1.39 (7H, m), 1.38-1.14 (3H, m), 1.02-0.81 (4H, m), 0.81-0.62 (1H, m), 0.58 (2H, d).

Example 38. 5-Cyclopropyl-1-(3-{2-fluoro-3-[2-(3,3,3-trifluoropropyl)piperidine-1-carbonyl]phenyl}phenyl)-1H-pyrazole-4-carboxylic Acid

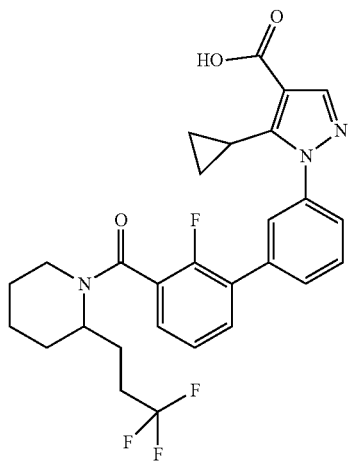 [SMILES: O=C(O)c1cnn(-c2cccc(-c3cccc(C(=O)N4CCCCC4CCC(F)(F)F)c3F)c2)c1C1CC1]

38a) 2-(3,3,3-Trifluoro-propyl)-pyridine

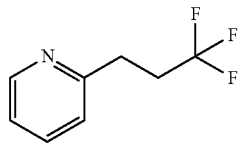 [SMILES: FC(F)(F)CCc1ccccn1]

PdCl$_2$dppf (231 mg, 0.32 mmol) was added to a solution of 2-bromopyridine (1.0 g, 6.33 mmol) and 3,3,3-trifluoropropyl zinc bromide (0.5M in Et$_2$O, 19 mL, 9.5 mmol) in dry dioxane (20 mL) under nitrogen and the reaction heated to reflux for 2 h under N$_2$ (the reflux condenser was not turned on initially to allow loss of ether). The reaction mixture was concentrated and then partitioned between EtOAc (40 mL) and water (30 mL). The organic phase was washed with water, brine, and then dried (MgSO$_4$), filtered, and concentrated. Silica purification eluting with EtOAc/hexane 3-30% gave the product (0.495 g, 45%). LC-MS no mass ion observed, 1.22 (ret. time), basic method.

38b) 2-(3,3,3-Trifluoro-propyl)-piperidine

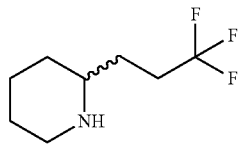 [SMILES: FC(F)(F)CCC1CCCCN1]

To a solution of 2-(3,3,3-Trifluoro-propyl)-pyridine (0.495 g, 2.93 mmol) in ethanol (40 mL) was added HCl in dioxane (4M, 0.78 mL, 3.11 mmol) and PtO$_2$ (60 mg) and the mixture shaken under a hydrogen atmosphere for 4 h. The catalyst was removed by filtration and then the solution concentrated to dryness to give product (480 mg, 78%) as the HCl salt. $^1$H NMR (400 MHz, DMSO-d6): 9.39-8.72 (2H, m), 3.23 (1H, d), 3.06 (1H, s), 2.82 (1H, dd), 2.49-2.24 (2H, m), 2.01-1.82 (2H, m), 1.82-1.68 (3H, m), 1.68-1.50 (1H, m), 1.50-1.33 (2H, m).

38c) (3-Bromo-2-fluoro-phenyl)-[2-(3,3,3-trifluoropropyl)-piperidin-1-yl]-methanone

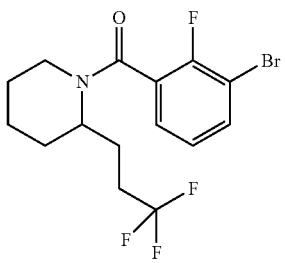 [SMILES: O=C(c1cccc(Br)c1F)N1CCCCC1CCC(F)(F)F]

A solution of 3-bromo-2-fluoro-benzoic acid (0.200 g, 0.91 mmol), HATU (0.347 g, 0.91 mmol), 2-(3,3,3-trifluoropropyl)-piperidine (0.199 g, 0.91 mmol) and DIPEA (0.477 mL, 2.74 mmol) in DCM (5 mL) was stirred for 3 h. The mixture was diluted with DCM and the organic phase was

38d) 5-Cyclopropyl-1-(3-{2-fluoro-3-[2-(3,3,3-trifluoropropyl)piperidine-1-carbonyl]phenyl}phenyl)-1H-pyrazole-4-carboxylic Acid Methyl Ester

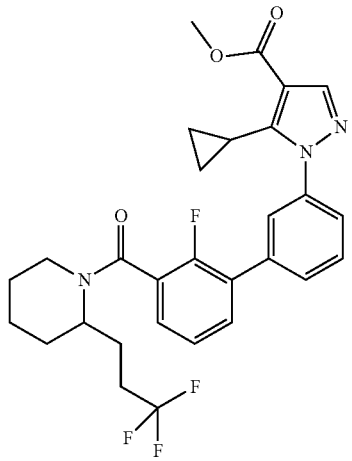 [SMILES: COC(=O)c1cnn(-c2cccc(-c3cccc(C(=O)N4CCCCC4CCC(F)(F)F)c3F)c2)c1C1CC1]

A stirred mixture of (3-bromo-2-fluoro-phenyl)-[2-(3,3,3-trifluoro-propyl)-piperidin-1-yl]-methanone (0.212 g, 0.55 mmol), 5-cyclopropyl-1-[3-(4,4,5,5-tetramethyl-[1,3,2]dioxaborolan-2-yl)-phenyl]-1H-pyrazole-4-carboxylic acid methyl ester (0.170 g, 0.46 mmol), aqueous $Na_2CO_3$ (3M, 0.462 mL) and $Pd(PPh_3)_4$ (0.032 g, 0.05 mmol) in EtOH (1.5 mL) and toluene (4.5 mL) was heated at reflux for 2 h. After cooling, the mixture was partitioned between EtOAc (30 mL) and water (20 mL) and the organic phase was washed with water (20 mL) and brine (20 mL) before it was dried ($MgSO_4$), filtered, concentrated to dryness, and purified by silica chromatography (EtOAc/petrol 10-50% gradient) to give the product (0.141 g, 56%). LC-MS m/z 544 (M+H)$^+$, 1.56 (ret. time), basic method.

38e) 5-cyclopropyl-1-(3-{2-fluoro-3-[2-(3,3,3-trifluoropropyl)piperidine-1-carbonyl]phenyl}phenyl)-1H-pyrazole-4-carboxylic Acid

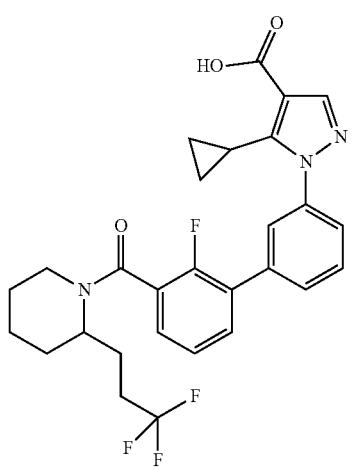 [SMILES: O=C(O)c1cnn(-c2cccc(-c3cccc(C(=O)N4CCCCC4CCC(F)(F)F)c3F)c2)c1C1CC1]

A stirred solution of 5-cyclopropyl-1-(3-{2-fluoro-3-[2-(3,3,3-trifluoropropyl)piperidine-1-carbonyl]phenyl} phenyl)-1H-pyrazole-4-carboxylic acid methyl ester (0.141 g, 0.26 mmol) in EtOH (2 mL) was treated with aqueous NaOH (2M, 0.65 mL). After 60 hours the mixture was partitioned between EtOAc and water. The organic phase was extracted ith further water and then discarded. The combined aqueous layer was acidified with 1N HCl and extracted into EtOAc (×2). The combined organic phases were dried ($MgSO_4$), filtered, and concentrated under vacuum to give the product (0.093 g, 68%). LC-MS m/z 530 (M+H)$^+$, 1.18 (ret. time), basic method. 1H NMR (400 MHz, DMSO-d6): 12.26 (1H, s), 7.97 (1H, s), 7.83-7.72 (1H, m), 7.72-7.60 (4H, m), 7.50-7.36 (2H, m), 4.84 (0.7H, s), 4.46 (0.3H, s), 3.67 (0.3H, s), 3.31-3.23 (0.9H, m), 3.15 (0.8H, d), 2.30 (1H, d), 2.22-2.01 (3H, m), 1.83-1.44 (6H, m), 1.44-1.23 (1H, m), 0.87 (2H, s), 0.57 (2H, d). Peaks close to amide are rotameric.

Example 39. 5-cyclopropyl-1-{3-[2-fluoro-3-(5-methyl-1H-pyrazol-1-yl)phenyl]phenyl}-1H-pyrazole-4-carboxylic Acid

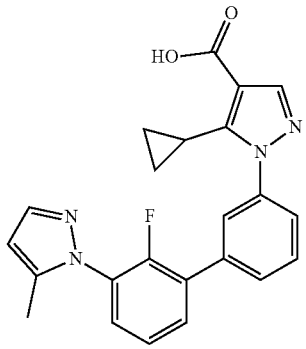 [SMILES: Cc1ccnn1-c1cccc(-c2cccc(-n3ncc(C(=O)O)c3C3CC3)c2)c1F]

39a) 1-(3-chloro-2-fluoro-phenyl)-5-methyl-1H-pyrazole-4-carboxylic Acid Ethyl Ester

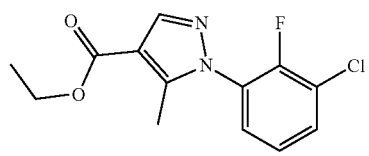 [SMILES: CCOC(=O)c1cnn(-c2cccc(Cl)c2F)c1C]

A mixture of ethyl acetoacetate (2.01 mmol) and DMF-dimethyl acetal (2.01 mmol) was stirred in a microwave reactor at 130° C. for 15 min. After cooling, the stirred mixture was diluted with EtOH (5 mL) and treated with 3-chloro-2-fluorophenylhydrazine HCl (0.330 g, 1.68 mmol), followed by triethylamine (0.23 mL, 1.68 mmol) and heated at 80° C. for 3 h. After cooling, the mixture was concentrated to dryness and purified by silica eluting with EtOAc/petrol 10% to give the product (0.462 g, 97%). LC-MS m/z 283 (M+H)$^+$, 1.44 (ret. time).

39b) 1-(3-Chloro-2-fluoro-phenyl)-5-methyl-1H-pyrazole-4-carboxylic Acid

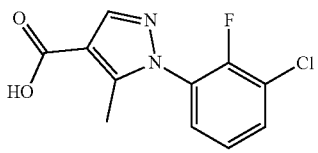 [SMILES: Cc1c(C(=O)O)cnn1-c1cccc(Cl)c1F]

A stirred solution of 1-(3-chloro-2-fluoro-phenyl)-5-methyl-1H-pyrazole-4-carboxylic acid ethyl ester (0.462 g, 1.64 mmol) in MeOH (3 mL) was treated with aqueous NaOH (2M, 4 mL) and heated to 60° C. After 90 min. the mixture was partitioned between DCM and water. The aqueous layer was acidified with 1N HCl and cooled in an ice bath. The resulting precipitate was isolated by filtration, washed with water, and dried to give the product (0.403 g, 90%). LC-MS m/z 255 (M+H)$^+$, 0.86 (ret. time).

39c) 1-(3-Chloro-2-fluoro-phenyl)-5-methyl-1H-pyrazole

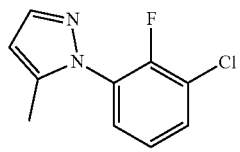

A stirred solution of 1-(3-chloro-2-fluoro-phenyl)-5-methyl-1H-pyrazole-4-carboxylic acid (0.40 3 g, 1.58 mmol) in quinoline (0.5 mL) was heated at 240° C. for 3 h. After cooling the solution was loaded onto a silica column and eluted with EtOAc/petrol 20%. Combined fractions containing the product were concentrated to ⅓ volume and washed with aqueous citric acid (5%), dried (MgSO$_4$), and concentrated to dryness to give the product (0.086 g, 26%). LC-MS m/z 211 (M+H)$^+$, 1.31 (ret. time).

39d) 5-Cyclopropyl-1-{3-[2-fluoro-3-(5-methyl-1H-pyrazol-1-yl)phenyl]phenyl}-1H-pyrazole-4-carboxylic Acid

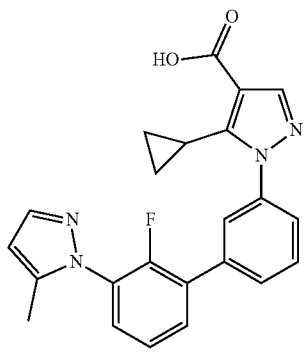 [SMILES: Cc1ccnn1-c1cccc(-c2cccc(-n3ncc(C(=O)O)c3C3CC3)c2)c1F]

A stirred mixture of 1-(3-chloro-2-fluoro-phenyl)-5-methyl-1H-pyrazole (0.86 g, 0.4 mmol), 5-cyclopropyl-1-[3-(4,4,5,5-tetramethyl-[1,3,2]dioxaborolan-2-yl)-phenyl]-1H-pyrazole-4-carboxylic acid methyl ester (0.144 g, 0.66 mmol), aqueous Cs$_2$CO$_3$ (0.156 g, 0.48 mmol) and Pd$_2$dba$_3$ (0.018 g, 0.014 mmol), P($^t$Bu)$_3$ in dioxane (1 mL) under N$_2$ was heated in a microwave at 120° C. for 1 h. After cooling, the mixture was treated with aqueous NaOH (2M, 2 mL). After 16 hours the mixture was partitioned between DCM and water. The aqueous layer was acidified with 1N HCl and extracted into IPA/CHCl$_3$ (1:3 mix, ×4). The combined organic phases were dried (MgSO$_4$), filtered, and concentrated under vacuum, and the residue was purified by HPLC to give the product (0.007 g, 4%). LC-MS m/z 403 (M+H)$^+$, 1.08 (ret. time).

Example 40. 1-{3-[3-(2-propylpiperidine-1-carbonyl)phenyl]phenyl}-5-[2-(pyridin-3-yl)cyclopropyl]-1H-pyrazole-4-carboxylic Acid

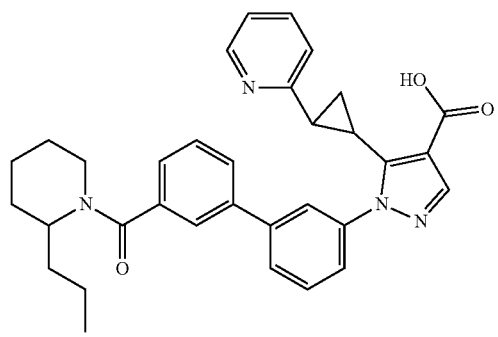 [SMILES: CCCC1CCCCN1C(=O)c1cccc(-c2cccc(-n3ncc(C(=O)O)c3C3CC3c3ccccn3)c2)c1]

40a) (E)-3-Pyridin-2-yl-acrylic Acid Methyl Ester

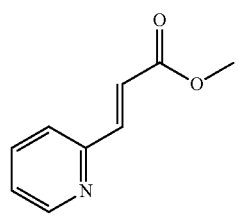

A stirred suspension of 60% sodium hydride (0.48 g, 12.0 mmol) in THF (62 mL) at 0° C. under nitrogen was treated dropwise with (EtO)$_2$P(O)CH$_2$CO$_2$Me (3.97 mL, 24.0 mmol). After 30 min, pyridine-3-carboxaldehyde (1.00 g, 9.24 mmol) in 5 mL of THF was added dropwise. After a further 1.5 h at 0° C., the reaction mixture was partitioned between diethyl ether and water. The organic phase was dried, filtered, and concentrated under vacuum. Silica chromatography with EtOAc in petrol gave the product (1.46 g, 97%). LC-MS m/z 164 (M+H)$^+$, 1.05 (ret. time) basic method.

40b) 2-Pyridin-2-yl-cyclopropanecarboxylic Acid Methyl Ester

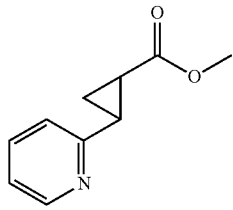

Trimethyl sulfoxonium iodide (2.37 g, 10.7 mmol) was added slowly in small portions over a period of 20 min, to a stirred suspension of sodium hydride (0.43 g, 10.7 mmol) in dry DMSO (60 mL) at RT. After 1 h, a clear solution was formed and a solution of (E)-3-pyridin-2-yl-acrylic acid methyl ester (1.46 g, 8.95 mmol) in dry DMSO (50 mL) was added slowly dropwise. After 30 min, the reaction mixture was poured into ice water (50 mL) and extracted with EtOAc (2×50 mL). The combined extracts were washed with ice water (2×100 mL), brine (50 mL), dried over anhydrous $Na_2SO_4$, filtered, and concentrated to dryness to give the product, used without further purification (0.810 g, 51%). LC-MS m/z 178 (M+H)$^+$, 1.12 (ret. time) basic method.

40c) 2-Pyridin-2-yl-cyclopropanecarboxylic Acid

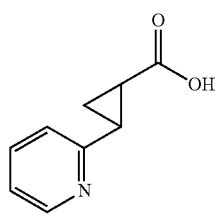 [SMILES: O=C(O)C1CC1c1ccccn1]

A stirred solution of 2-pyridin-2-yl-cyclopropanecarboxylic acid methyl ester (0.80 g, 4.51 mmol) in THF/MeOH (1:1, 23 mL) was treated with a solution of LiOH (0.967 g, 22.6 mmol) in water (23 mL). After 4 hours the reaction was diluted with water and the pH adjusted to pH4 (aqueous citric acid 5%). The mixture was extracted with IPA:CHCl$_3$ (1:3, ×3) and the combined organic layers washed with brine, dried over MgSO$_4$, filtered, and concentrated to dryness. Purification by silica chromatography eluting with EtOAc/petrol gave the product (0.50 g, 68%). LC-MS m/z 164 (M+H)$^+$, 0.20 (ret. time) basic method.

40d) 3-Oxo-3-(2-pyridin-2-yl-cyclopropyl)-propionic Acid Methyl Ester

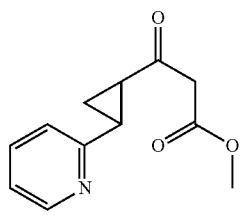 [SMILES: COC(=O)CC(=O)C1CC1c1ccccn1]

1,10-carbonyldiimidazole (0.55 g, 3.37 mmol) was added portionwise over 5 min to a stirred solution of 2-pyridin-2-yl-cyclopropanecarboxylic acid (0.50 g, 3.06 mmol) in anhydrous THF (8 mL) under argon. After 1 h, a mixture of MgCl$_2$ (0.58 g, 6.13 mmol) and potassium hydrogen methyl malonate (1.44 g, 9.19 mmol) was added. After 7 h the mixture was concentrated under vacuum and diluted with ethyl acetate. The mixture was then washed with aqueous NaHSO$_4$ (1M) and brine, and the organic phase dried over Na$_2$SO$_4$, filtered, and concentrated to dryness to give the product, used without further purification (0.80 g, quantative). LC-MS m/z 220 (M+H)$^+$, 1.10 (ret. time), basic method.

40e) 1-(3-Bromo-phenyl)-5-(2-pyridin-2-yl-cyclopropyl)-1H-pyrazole-4-carboxylic Acid Methyl Ester

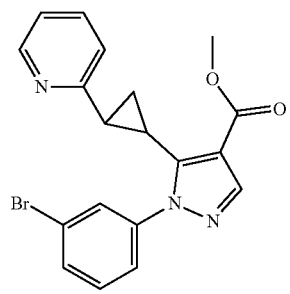 [SMILES: COC(=O)c1cnn(-c2cccc(Br)c2)c1C1CC1c1ccccn1]

A mixture of 3-oxo-3-(2-pyridin-2-yl-cyclopropyl)-propionic acid methyl ester (0.80 g, 3.65 mmol) and DMF-dimethyl acetal (1.455 mL, 11.0 mmol) was stirred at room temperature for 24 h, then concentrated to dryness under vacuum. The residue was treated with toluene and again concentrated to dryness. The residue was taken up into MeCN (12 mL) and, with stirring at 0° C., treated with DIPEA (1.57 mL, 9.02 mmol) and, portionwise, 3-bromophenylhydrazine hydrochloride (0.905 g, 3.97 mmol). The mixture was allowed to warm to room temperature and stirred for 16 h, then diluted with aqueous citric acid (5%) and extracted with EtOAc (×3). The combined organic layers were washed with brine, dried over MgSO$_4$, filtered and concentrated to dryness. Silica purification eluting with EtOAc/petrol gave the product (0.293 g, 20%). LC-MS m/z 398 (M+H)$^+$, 1.44 (ret. time).

40f) 1-{3-[3-(2-propylpiperidine-1-carbonyl)phenyl]phenyl}-5-[2-(pyridin-2-yl)cyclopropyl]-1H-pyrazole-4-carboxylic Acid

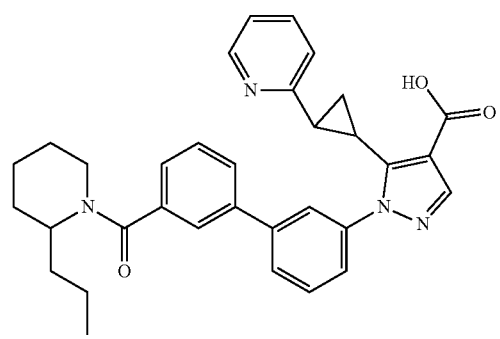 [SMILES: CCCC1CCCCN1C(=O)c1cccc(-c2cccc(-n3ncc(C(=O)O)c3C3CC3c3ccccn3)c2)c1]

A stirred mixture of 1-(3-bromo-phenyl)-5-(2-pyridin-2-yl-cyclopropyl)-1H-pyrazole-4-carboxylic acid methyl ester (0.060 g, 0.15 mmol), 3-(4,4,5,5-tetramethyl-[1,3,2]dioxaborolan-2-yl)-phenyl-(2-propyl-piperidin-1-yl)-methanone (0.059 g, 0.17 mmol), aqueous Na$_2$CO$_3$ (3M, 0.055 mL) and Pd(PPh$_3$)$_4$ (0.006 g, 0.008 mmol) in dioxane/water 1:1 (2 mL) was heated at 100° C. for 2 h. After cooling, the mixture was diluted with MeOH (3 mL) and treated with LiOH (1M, 3 mL). After 24 hours the mixture was acidified with citric acid (5% aqueous) and extracted into EtOAc (×3). The combined organic phases were washed with water and brine, dried (MgSO$_4$), filtered, and concentrated under vacuum. The residue was purified by silica column eluting with EtOAc/MeOH 0-10% to give the product (0.066 g, 82%). LC-MS m/z 535 (M+H)$^+$, 1.14 (ret. time). $^1$H NMR (400 MHz, Me-d$_3$-OD): 8.20 (1H, d), 8.06 (1H, s), 7.95 (1H, s), 7.78-7.69 (2H, m), 7.64-7.47 (5H, m), 7.41-7.30 (2H, m), 7.20 (1H, dd), 4.53 (0.5H, s), 3.82 (0.5H, d), 3.57-3.47 (0.5H, m), 3.23 (1H, br s), 2.94 (0.5H, br s), 2.53-2.45 (1H, m), 2.06 (1H, s), 1.95-1.54 (9H, m), 1.51-1.42 (2H, m), 0.98 (4H, s).

Example 41. 1-[3'-(2-Propyl-piperidine-1-carbonyl)-biphenyl-3-yl]-5-(2-pyridazin-3-yl-cyclopropyl)-1H-pyrazole-4-carboxylic Acid

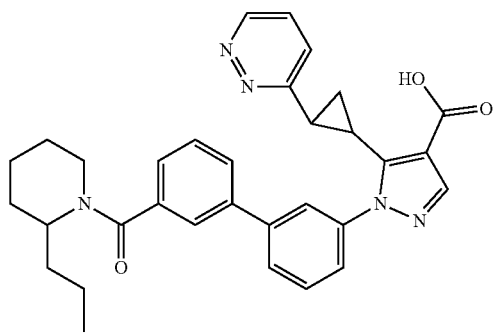 [SMILES: CCCC1CCCCN1C(=O)c1cccc(-c2cccc(-n3ncc(C(=O)O)c3C3CC3c3cccnn3)c2)c1]

41a) 3-(4,4,5,5-Tetramethyl-[1,3,2]dioxaborolan-2-yl)-phenyl-(2-propyl-piperidin-1-yl)-methanone

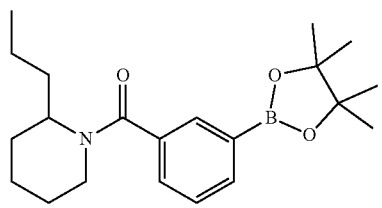 [SMILES: CCCC1CCCCN1C(=O)c1cccc(B2OC(C)(C)C(C)(C)O2)c1]

A solution of 3-(4,4,5,5-tetramethyl-[1,3,2]dioxaborolan-2-yl)-benzoic acid (1.00 g, 3.9 mmol), HBTU (1.97 g, 5.1 mmol), 2-propylpiperidine (0.550 g, 4.3 mmol) and DIPEA (1.02 mL, 5.9 mmol) in DCM (13 mL) was stirred for 16 h. The mixture was diluted with aqueous NaHCO$_3$ and extracted with EtOAc (×2). The combined organic phases were washed with brine, dried (MgSO$_4$), and concentrated to dryness. The residue was purified by silica chromatography eluting with EtOAc/petrol 0-30% to give the product (1.10 g, 79%). LC-MS m/z 275 (M−82)$^+$, 1.24 (ret. time).

41b) (E)-3-Pyridazin-3-yl-acrylic Acid Methyl Ester

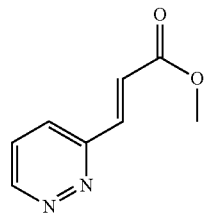

A stirred suspension of 60% sodium hydride (0.48 g, 12.0 mmol) in THF (62 mL) at 0° C. under nitrogen was treated dropwise with (EtO)$_2$P(O)CH$_2$CO$_2$Me (3.97 mL, 24.0 mmol). After 30 min, pyridazine-3-carboxaldehyde (1.00 g, 9.24 mmol) in 5 mL of THF was added dropwise. After a further 1.5 h at 0° C., the reaction mixture was partitioned between diethyl ether and water. The organic phase was dried, filtered, and concentrated under vacuum. Flash chromatography with 5% diethyl ether in petrol gave the product (0.86 g, 57%). LC-MS m/z 165 (M+H)$^+$, 0.60 (ret. time).

41c) 2-Pyridazin-3-yl-cyclopropanecarboxylic Acid

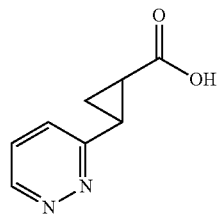

Trimethyl sulfoxonium iodide (1.38 g, 6.29 mmol) was added slowly in small portions over a period of 20 min, to a stirred suspension of sodium hydride (0.25 g, 6.29 mmol) in dry DMSO (35 mL) at RT. After 1 h, a clear solution was formed and a solution of (E)-3-pyridazin-3-yl-acrylic acid methyl ester (0.86 g, 5.24 mmol) in dry DMSO (29 mL) was added slowly dropwise. After 30 min, the reaction mixture was poured into ice water (50 mL) and extracted with EtOAc (2×50 mL). The combined extracts were washed with ice water (2×100 mL), brine (50 mL), dried over anhydrous Na$_2$SO$_4$, filtered, and concentrated to dryness (0.18 g). A stirred solution of the ester (0.1 g, 0.56 mmol) in THF/MeOH (1:1, 3 mL) was treated with a solution of LiOH (0.12 g, 2.81 mmol) in water (3 mL). After 4 hours the reaction was diluted with water and the pH adjusted to pH4 (aqueous citric acid 5%). The mixture was extracted with IPA:CHCl$_3$ (1:3, ×3) and the combined organic layers washed with brine, dried over MgSO$_4$, filtered, and concentrated to dryness. Purification by silica chromatography eluting with EtOAc/petrol gave the product (77 mg, 32%). LC-MS m/z 165 (M+H)$^+$, 0.15 (ret. time).

41d) 3-Oxo-3-(2-pyridazin-3-yl-cyclopropyl)-propionic Acid Methyl Ester

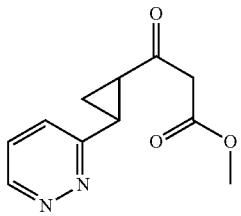 [SMILES: COC(=O)CC(=O)C1CC1c1cccnn1]

1,1-carbonyldiimidazole (84 mg, 0.52 mmol) was added to a stirred solution of 2-pyridazin-3-yl-cyclopropanecarboxylic acid (77 mg, 0.47 mmol) in anhydrous THF (1 mL) under argon. After 1 h, a mixture of MgCl$_2$ (89 mg, 0.94 mmol) and potassium hydrogen methyl malonate (220 mg, 1.41 mmol) was added. After 14 h the mixture was concentrated under vacuum and diluted with ethyl acetate. The mixture was then washed with aqueous NaHSO$_4$ (1M) and brine, and the organic phase dried over Na$_2$SO$_4$, filtered, and concentrated to dryness to give the product, used without further purification (100 mg, 97%). LC-MS m/z 221 (M+H)$^+$, 0.55 (ret. time).

41e) 1-(3-Bromo-phenyl)-5-(2-pyridazin-3-yl-cyclopropyl)-1H-pyrazole-4-carboxylic Acid Methyl Ester

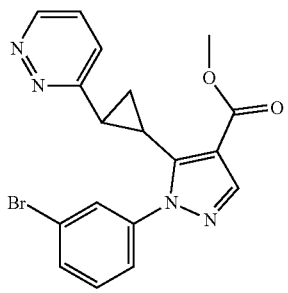 [SMILES: COC(=O)c1cnn(-c2cccc(Br)c2)c1C1CC1c1cccnn1]

A mixture of 3-oxo-3-(2-pyridazin-3-yl-cyclopropyl)-propionic acid methyl ester (0.10 g, 0.45 mmol) and DMF-dimethyl acetal (0.181 mL, 1.36 mmol) was stirred at room temperature for 24 h, then concentrated to dryness under vacuum. The residue was treated with toluene and again concentrated to dryness. The residue was taken up into MeCN and, with stirring at 0° C., treated with DIPEA (2.17 mL, 1.24 mmol) and, portionwise, 3-bromophenylhydrazine hydrochloride (0.125 g, 0.55 mmol). The mixture was allowed to warm to room temperature and stirred for 16 h, then diluted with aqueous citric acid (5%) and extracted with EtOAc (×3). The combined organic layers were washed with brine, dried over MgSO$_4$, filtered, and concentrated to dryness. Silica purification eluting with EtOAc/petrol gave the product (0.293 g, 20%). LC-MS m/z 399 (M+H)$^+$, 1.27 (ret. time).

41f) 1-[3'-(2-Propyl-piperidine-1-carbonyl)-biphenyl-3-yl]-5-(2-pyridazin-3-yl-cyclopropyl)-1H-pyrazole-4-carboxylic Acid

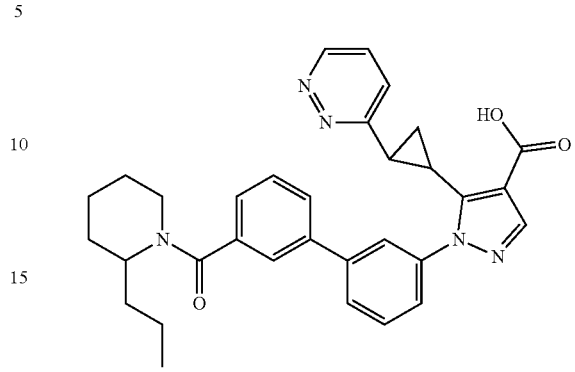

A stirred mixture of 1-(3-bromo-phenyl)-5-(2-pyridazin-3-yl-cyclopropyl)-1H-pyrazole-4-carboxylic acid methyl ester (26 mg, 0.07 mmol), 3-(4,4,5,5-tetramethyl-[1,3,2]dioxaborolan-2-yl)-phenyl-(2-propyl-piperidin-1-yl)-methanone (26 mg, 0.07 mmol), aqueous Na$_2$CO$_3$ (3M, 0.05 mL) and Pd(PPh$_3$)$_4$(3 g, 0.003 mmol) in dioxane/water 1:1 (1 mL) was heated at 100° C. for 2 h. After cooling, the mixture was diluted with MeOH (3 mL) and treated with LiOH (1M, 3 mL). After 24 hours the mixture was acidified with citric acid (5% aqueous) and extracted into EtOAc (×3). The combined organic phases were washed with water and brine, dried (MgSO$_4$), filtered, and concentrated under vacuum. The residue was purified by silica column eluting with EtOAc/MeOH 0-10% to give the product (19 mg, 51%). LC-MS m/z 536 (M+H)$^+$, 1.13 (ret. time). $^1$H NMR (400 MHz, Me-d$_3$-OD): [presence of rotamers] 8.84 (1H, d), 8.07 (1H, s), 7.76 (1H, s), 7.74-7.71 (1H, m), 7.63-7.49 (5H, m), 7.43-7.35 (2H, m), 7.23 (1H, dd), 4.61-4.47 (0.5H, m), 3.90-3.74 (0.5H, m), 3.58-3.53 (0.5H, m), 3.05-2.92 (0.5H, m), 2.92-2.85 (1H, m), 2.37-2.30 (1H, m), 1.94-1.39 (11H, m), 1.24-0.93 (3H, m), 0.81 (1H, br s)

Example 42. 5-[2-(1-methyl-1H-1,2,3-triazol-4-yl)cyclopropyl]-1-{3-[3-(2-propylpiperidine-1-carbonyl)phenyl]phenyl}-1H-pyrazole-4-carboxylic Acid

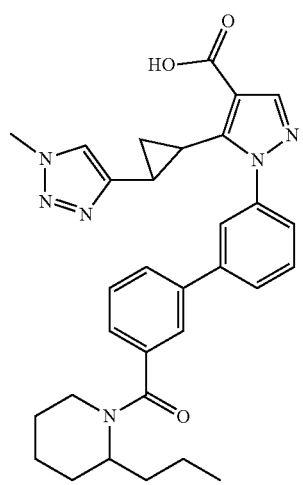 [SMILES: CCCC1CCCCN1C(=O)c1cccc(-c2cccc(-n3ncc(C(=O)O)c3C3CC3c3cn(C)nn3)c2)c1]

42a) (E)-3-(1-Methyl-1H-[1,2,3]triazol-4-yl)-acrylic Acid Benzyl Ester

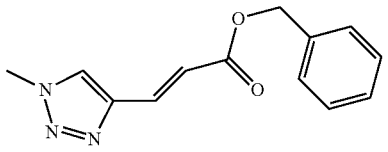 [SMILES: Cn1cc(/C=C/C(=O)OCc2ccccc2)nn1]

A mixture of 1-methyl-1H-1,2,3-triazole-4-carbaldehyde (0.63 g, 5.67 mmol) and benzyl (triphenylphosphoranylidene)acetate (2.69 mL, 6.24 mmol) in toluene (14 mL) was stirred at 120° C. for 2 h. The mixture was then concentrated to dryness under vacuum, and the residue purified by silica chromatography eluting with EtOAc/petrol to give the product (0.764 g, 55%). LC-MS m/z 244 (M+H)$^+$, 1.25 (ret. time).

42b) 2-(1-Methyl-1H-[1,2,3]triazol-4-yl)-cyclopropanecarboxylic Acid Benzyl Ester

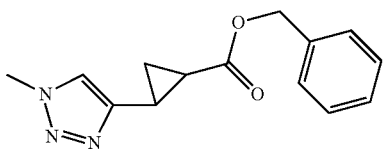 [SMILES: Cn1cc(C2CC2C(=O)OCc2ccccc2)nn1]

Trimethyl sulfoxonium iodide (0.83 g, 3.77 mmol) was added slowly in small portions over a period of 20 min, to a stirred suspension of sodium hydride (0.151 g, 3.77 mmol) in dry DMSO (21 mL) at RT. After 1 h, a clear solution was formed and a solution of (E)-3-(1-methyl-1H-[1,2,3]triazol-4-yl)-acrylic acid benzyl ester (0.764 g, 3.14 mmol) in dry DMSO (17 mL) was added slowly dropwise. After 30 min, the reaction mixture was poured into ice water (50 mL) and extracted with EtOAc (2×50 mL). The combined extracts were washed with ice water (2×100 mL), brine (50 mL), dried over anhydrous Na$_2$SO$_4$, filtered, and concentrated to dryness to give the product, used without further purification (0.60 g, 62%). LC-MS m/z 258 (M+H)$^+$, 1.24 (ret. time).

42c) 2-(1-Methyl-1H-[1,2,3]triazol-4-yl)-cyclopropanecarboxylic Acid

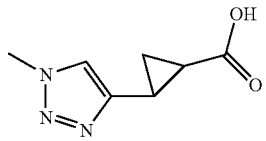

A stirred solution of 2-(1-methyl-1H-[1,2,3]triazol-4-yl)-cyclopropanecarboxylic acid benzyl ester (0.60 g, 2.33 mmol) in THF/MeOH (1:1, 12 mL) was treated with a solution of LiOH (0.499 g, 11.7 mmol) in water (12 mL). After 24 hours the reaction was diluted with water and the pH adjusted to pH4 (aqueous citric acid 5%). The mixture was extracted with EtOAc (×3) and the combined organic layers washed with brine, dried over MgSO$_4$, filtered, and concentrated to dryness to give the product (0.10 g, 26%). $^1$H-NMR (400 MHz, Me-d3-OD): 7.75 (s, 1H), 4.05 (s, 3H), 2.51 (ddd, 1H), 1.95 (ddd, 1H), 1.52 (ddd, 1H), 1.42 (ddd, 1H).

42d) 3-[2-(1-Methyl-1H-[1,2,3]triazol-4-yl)-cyclopropyl]-3-oxo-propionic acid methyl Ester

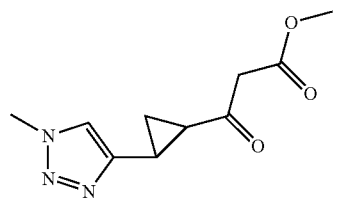

1,10-carbonyldiimidazole (0.109 g, 0.67 mmol) was added portionwise over 5 min to a stirred solution of 2-(1-methyl-1H-[1,2,3]triazol-4-yl)-cyclopropanecarboxylic acid (0.100 g, 0.61 mmol) in anhydrous THF (2 mL) under argon. After 1 h, a mixture of MgCl$_2$ (0.116 g, 1.22 mmol) and potassium hydrogen methyl malonate (0.285 g, 1.83 mmol) was added. After 24 h the mixture was concentrated under vacuum and diluted with ethyl acetate. The mixture was then washed with aqueous NaHSO$_4$ (1M) and brine, and the organic phase dried over Na$_2$SO$_4$, filtered, and concentrated to dryness to give the product, used without further purification (0.187 g, quantative). LC-MS m/z 224 (M+H)$^+$, 0.68 (ret. time).

42e) 1-(3-Bromo-phenyl)-5-[2-(1-methyl-1H-[1,2,3]triazol-4-yl)-cyclopropyl]-1H-pyrazole-4-carboxylic Acid Methyl Ester

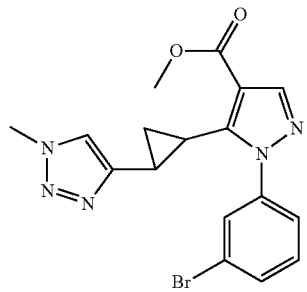 [SMILES: COC(=O)c1cnn(-c2cccc(Br)c2)c1C1CC1c1cn(C)nn1]

A mixture of 3-[2-(1-methyl-1H-[1,2,3]triazol-4-yl)-cyclopropyl]-3-oxo-propionic acid methyl ester (0.187 g, 0.50 mmol) and DMF-dimethyl acetal (0.20 mL, 1.51 mmol) was stirred at room temperature for 24 h, then concentrated to dryness under vacuum. The residue was treated with toluene and again concentrated to dryness. The residue was taken up into MeCN (2 mL) and, with stirring at 0° C., treated with DIPEA (0.218 mL, 1.25 mmol) and, portionwise, 3-bromophenylhydrazine hydrochloride (0.123 g, 0.55 mmol). The mixture was allowed to warm to room temperature and stirred for 16 h, then diluted with aqueous citric acid (5%) and extracted with EtOAc (×3). The combined organic layers were washed with brine, dried over MgSO$_4$, filtered and concentrated to dryness to give the product (0.200 g, 50%), used without further purification. LC-MS m/z 402 (M+H)$^+$+, 1.26 (ret. time).

42f) 5-[2-(1-Methyl-1H-1,2,3-triazol-4-yl)cyclopropyl]-1-{3-[3-(2-propylpiperidine-1-carbonyl)phenyl]phenyl}-1H-pyrazole-4-carboxylic Acid

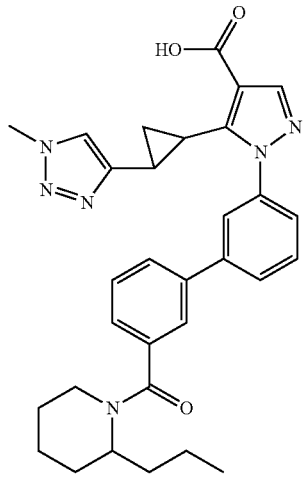 [SMILES: CCCC1CCCCN1C(=O)c1cccc(-c2cccc(-n3ncc(C(=O)O)c3C3CC3c3cn(C)nn3)c2)c1]

A stirred mixture of 1-(3-bromo-phenyl)-5-[2-(1-methyl-1H-[1,2,3]triazol-4-yl)-cyclopropyl]-1H-pyrazole-4-carboxylic acid methyl ester (0.200 g, 0.25 mmol), 3-(4,4,5,5-tetramethyl-[1,3,2]dioxaborolan-2-yl)-phenyl-(2-propyl-piperidin-1-yl)-methanone (0.098 g, 0.27 mmol), aqueous Na$_2$CO$_3$ (3M, 0.029 mL) and Pd(PPh$_3$)$_4$ (0.010 g, 0.012 mmol) in dioxane/water 1:1 (2 mL) was heated at 100° C. for 2 h. After cooling, the mixture was diluted with MeOH (3 mL) and treated with LiOH (1M, 3 mL). After 24 hours the mixture was acidified with citric acid (5% aqueous) and extracted into EtOAc (×3). The combined organic phases were washed with water and brine, dried (MgSO$_4$), filtered, and concentrated under vacuum. The residue was purified by HPLC to give the product (0.042 g, 31%). LC-MS m/z 539 (M+H)$^+$, 1.15 (ret. time). $^1$H-NMR (400 MHz, Me-d3-OD): 8.08 (1H, s), 7.81-7.76 (2H, m), 7.67-7.54 (5H, m), 7.45 (1H, s), 7.40 (1H, d), 4.60-4.43 (0.5H, m), 3.90 (3H, s), 3.89-3.81 (0.5H, m), 3.62-3.51 (0.5H, m), 3.24 (1H, s), 2.96 (0.5H, s), 2.61-2.54 (1H, m), 2.23-2.16 (1H, m), 1.93-1.52 (11H, m), 1.43-1.34 (2H, m), 1.04 (1H, s), 0.81 (1H, d).

Example 43. 5-Cyclopropyl-1-[3-(2-fluoro-3-{2-oxa-8-azaspiro[5.5]undecane-8-carbonyl}phenyl)phenyl]-1H-pyrazole-4-carboxylic Acid

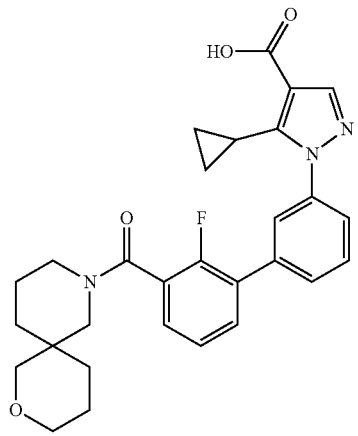 [SMILES: O=C(O)c1cnn(-c2cccc(-c3cccc(C(=O)N4CCCC5(CCCOC5)C4)c3F)c2)c1C1CC1]

43a) 5-Cyclopropyl-1-[3-(2-fluoro-3-{2-oxa-8-azaspiro[5.5]undecane-8-carbonyl}phenyl)phenyl]-1H-pyrazole-4-carboxylic Acid Methyl Ester

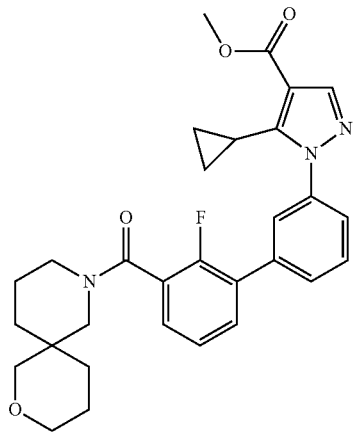 [SMILES: COC(=O)c1cnn(-c2cccc(-c3cccc(C(=O)N4CCCC5(CCCOC5)C4)c3F)c2)c1C1CC1]

A solution of 1-(3'-carboxy-2'-fluoro-biphenyl-3-yl)-5-cyclopropyl-1H-pyrazole-4-carboxylic acid methyl ester (0.065 g, 0.17 mmol), HATU (0.065 g, 0.17 mmol), 2-oxa-8-azaspiro[5.5]undecane (0.032 g, 0.21 mmol) and DIPEA (0.060 mL, 0.34 mmol) in DCM (1.5 mL) was stirred for 18 h. The mixture was diluted with DCM, and the organic phase washed with aqueous NaHCO$_3$, dried (MgSO$_4$), filtered, and concentrated to dryness. Silica purification eluting with EtOAc/hexane 20-70% gave the product (0.092 g, quantative). LC-MS m/z 518 (M+H)$^+$, 1.45 (ret. time), basic method.

43b) 5-Cyclopropyl-1-[3-(2-fluoro-3-{2-oxa-8-azaspiro[5.5]undecane-8-carbonyl}phenyl)phenyl]-1H-pyrazole-4-carboxylic Acid

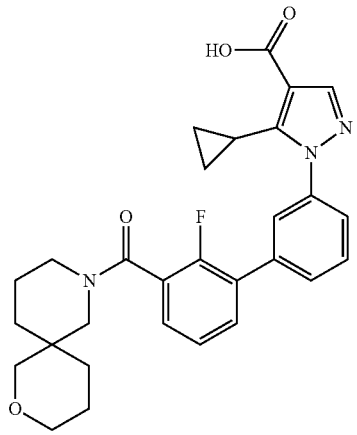 [SMILES: O=C(O)c1cnn(-c2cccc(-c3cccc(C(=O)N4CCCC5(CCCOC5)C4)c3F)c2)c1C1CC1]

A stirred solution of 5-cyclopropyl-1-[3-(2-fluoro-3-{2-oxa-8-azaspiro[5.5]undecane-8-carbonyl}phenyl)phenyl]-1H-pyrazole-4-carboxylic acid methyl ester (0.092 g, 0.18 mmol) in EtOH (1.5 mL) was treated with aqueous NaOH (2M, 0.444 mL). After 60 hours the mixture was partitioned between EtOAc and water. The organic phase was extracted with further water and then discarded. The aqueous layer was acidified with 1N HCl and extracted into EtOAc (×2). The combined organic phases were dried (MgSO$_4$), filtered, and concentrated under vacuum to give the product (0.071 g, 80%). LC-MS m/z 504 (M+H)$^+$, 1.08 (ret. time), basic method. $^1$H NMR (400 MHz, DMSO-d6): 12.46-12.14 (1H, m), 7.97 (1H, s), 7.79 (1H, s), 7.73-7.60 (4H, m), 7.46-7.35 (2H, m), 3.84-3.59 (1H, m), 3.59-3.38 (3H, m), 3.30-3.02 (4H, m), 2.20-2.08 (1H, m), 1.77-1.61 (1H, m), 1.61-1.40 (4H, m), 1.40-1.15 (3H, m), 0.94-0.80 (2H, m), 0.63-0.52 (2H, m).

Example 44. 5-cyclopropyl-1-[3-(2-fluoro-3-{6-oxa-9-azaspiro[4.5]decane-9-carbonyl}phenyl)phenyl]-1H-pyrazole-4-carboxylic Acid

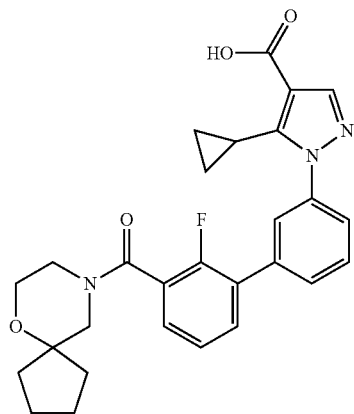 [SMILES: O=C(O)c1cnn(-c2cccc(-c3cccc(C(=O)N4CCOC5(CCCC5)C4)c3F)c2)c1C1CC1]

44a) (3-Bromo-2-fluoro-phenyl)-(6-oxa-9-aza-spiro[4.5]dec-9-yl)-methanone

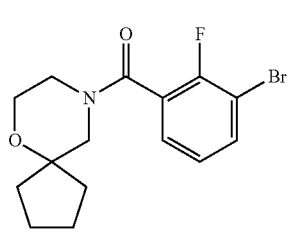 [SMILES: O=C(c1cccc(Br)c1F)N1CCOC2(CCCC2)C1]

A solution of 3-bromo-2-fluoro-benzoic acid (0.200 g, 0.91 mmol), HATU (0.347 g, 0.91 mmol), 6-oxa-9-aza-spiro[4.5]decane (0.129 g, 0.91 mmol) and DIPEA (0.318 mL, 1.83 mmol) in DCM (5 mL) was stirred for 3 h. The mixture was diluted with DCM and the organic phase washed with aqueous NaHCO$_3$ and dried (MgSO$_4$), filtered, and concentrated to dryness to give the product (0.380 g, quantative), used without further purification. LC-MS m/z 342 (M+H)$^+$, 1.36 (ret. time).

44b) 5-Cyclopropyl-1-[3-(2-fluoro-3-{6-oxa-9-azaspiro[4.5]decane-9-carbonyl}phenyl)phenyl]-1H-pyrazole-4-carboxylic Acid Methyl Ester

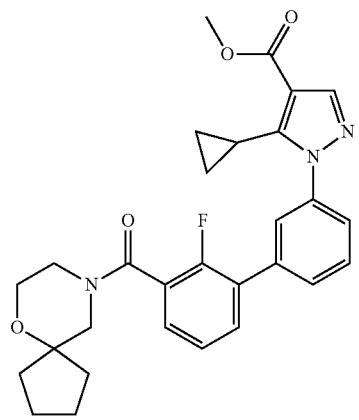 [SMILES: COC(=O)c1cnn(-c2cccc(-c3cccc(C(=O)N4CCOC5(CCCC5)C4)c3F)c2)c1C1CC1]

A stirred mixture of (3-bromo-2-fluoro-phenyl)-(6-oxa-9-aza-spiro[4.5]dec-9-yl)-methanone (0.209 g, 0.61 mmol), 5-cyclopropyl-1-[3-(4,4,5,5-tetramethyl-[1,3,2]dioxaborolan-2-yl)-phenyl]-1H-pyrazole-4-carboxylic acid methyl ester (0.150 g, 0.41 mmol), aqueous Na$_2$CO$_3$ (3M, 0.407 mL) and Pd(PPh$_3$)$_4$ (0.035 g, 0.03 mmol) in EtOH (1 mL) and toluene (3 mL) was heated at reflux for 2 h. After cooling, the mixture was partitioned between EtOAc (30 mL) and water (20 mL) and the organic phase was washed with water (20 mL) and brine (20 mL) before it was dried (MgSO$_4$), filtered, concentrated to dryness, and purified by silica chromatography (EtOAc/petrol 5-80% gradient) to give the product (0.144 g, 70%). LC-MS m/z 504 (M+H)$^+$, 1.50 (ret. time).

44c) 5-Cyclopropyl-1-[3-(2-fluoro-3-{6-oxa-9-azaspiro[4.5]decane-9-carbonyl}phenyl)phenyl]-1H-pyrazole-4-carboxylic Acid

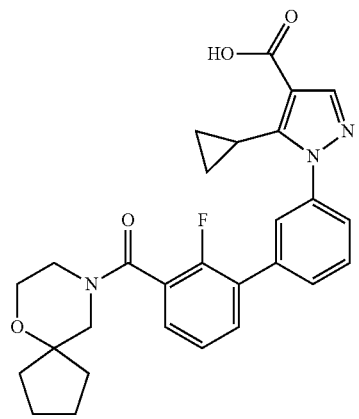 [SMILES: O=C(O)c1cnn(-c2cccc(-c3cccc(C(=O)N4CCOC5(CCCC5)C4)c3F)c2)c1C1CC1]

A stirred solution of 5-cyclopropyl-1-[3-(2-fluoro-3-{6-oxa-9-azaspiro[4.5]decane-9-carbonyl}phenyl)phenyl]-1H-pyrazole-4-carboxylic acid methyl ester (0.144 g, 0.29 mmol) in EtOH (2 mL) was treated with aqueous NaOH (2M, 0.715 mL). After 60 hours the mixture was partitioned between EtOAc and water. The organic phase was further extracted with water. The combined aqueous layer was acidified with 1N HCl and extracted into EtOAc (×2). The combined organic phases were dried (MgSO$_4$), filtered, and concentrated under vacuum to give the product (0.097 g, 69%). LC-MS m/z 490 (M+H)$^+$, 1.12 (ret. time), basic method. $^1$H NMR (400 MHz, DMSO-d6): 12.28 (1H, s), 7.97 (1H, s), 7.80 (1H, d), 7.74-7.62 (4H, m), 7.49-7.37 (2H, m), 3.77-3.59 (2H, m), 3.59-3.43 (2H, m), 3.28 (1H, s), 3.23-3.15 (1H, m), 2.20-2.09 (1H, m), 1.78-1.53 (6H, m), 1.46 (1H, s), 1.38-1.23 (1H, m), 0.92-0.81 (2H, m), 0.62-0.52 (2H, m).

Example 45. 5-cyclopropyl-1-(3-{2-fluoro-3-[(2S, 5R)-2-methyl-5-propylmorpholine-4-carbonyl]phenyl}phenyl)-1H-pyrazole-4-carboxylic Acid

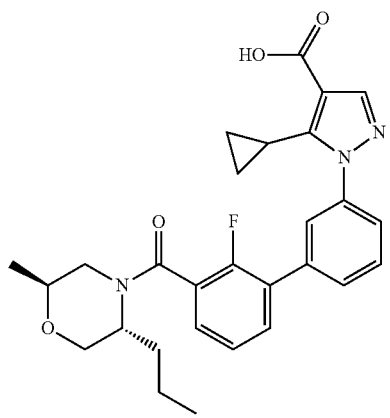 [SMILES: CCC[C@@H]1CO[C@@H](C)CN1C(=O)c1cccc(-c2cccc(-n3ncc(C(=O)O)c3C3CC3)c2)c1F]

45a) (R)-2-((S)-2-Hydroxy-propylamino)-pentan-1-ol

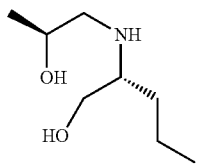

To a solution of (R)-2-amino-pentanol (0.465 g, 4.51 mmol) in water (5 mL) cooled in an ice bath was added (S)-2-methyloxirane (0.288 g, 4.96 mmol) dropwise over 15 minutes. The solution was allowed to warm to rt and stirred for 18 h. The reaction mixture was concentrated to dryness to give the product (0.73 g, 100%) used directly in the next reaction.

45b) N—((R)-1-Hydroxymethyl-butyl)-N—((S)-2-hydroxy-propyl)-4-methyl-benzenesulfonamide

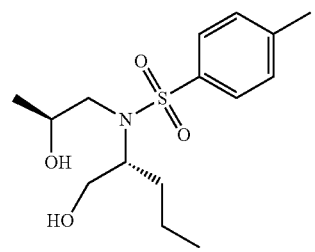 [SMILES: CCC[C@H](CO)N(C[C@H](C)O)S(=O)(=O)c1ccc(C)cc1]

A mixture of (R)-2-((S)-2-Hydroxy-propylamino)-pentan-1-ol (0.73 g, 4.53 mmol), toluenesulfonyl chloride (1.726 g, 9.05 mmol) and triethylamine (13.6 g, 13.6 mmol) in DCM (18 mL) was stirred at rt for 18 h. The reaction mixture was partitioned between further DCM (50 mL) and aqueous Sodium bicarbonate (40 mL). The organic phase was washed with water and brine and then dried (MgSO$_4$), filtered, and concentrated to dryness. Silica chromatography, eluting with 15-60% EtOAc in petroleum ether gave the product (0.423 g, 30%). LC-MS m/z 316 (M+H)$^+$, 1.27 (ret. time), basic method.

45c) (2S,5R)-2-Methyl-5-propyl-4-(toluene-4-sulfonyl)-morpholine

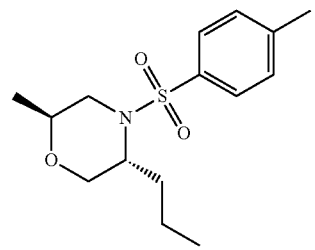

A mixture of N—((R)-1-Hydroxymethyl-butyl)-N—((S)-2-hydroxy-propyl)-4-methyl-benzenesulfonamide (0.423 g, 1.34 mmol) and tosyl imidazole (0.298 g, 1.34 mmol) was stirred at rt for 30 minutes in THF (10 mL). Cooled to 0° C. and sodium hydride (0.134 g, 3.35 mmol) was added. The reaction was stirred at rt for 60 h. The mixture was partitioned between EtOAc and water and then the organic phase was washed with water and brine before it was dried (MgSO$_4$), filtered, and concentrated. Silica chromatography, eluting with 0-40% EtOAc/petroleum ether gave the product (0.349 mg, 88%).

45d) (2S,5R)-2-methyl-5-propylmorpholine

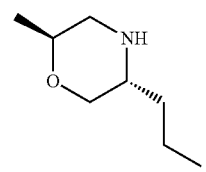

Magnesium turnings (0.31 g, 12.9 mmol) were stirred under a nitrogen atmosphere for 18 h to activate the surface. Dry MeOH (6 mL) was added followed by a solution of (2S,5R)-2-methyl-5-propyl-4-(toluene-4-sulfonyl)-morpholine (0.349 g, 1.17 mmol) in dry MeOH (3 mL) in small batches. There were no initial signs of a reaction, so the flask was left in a room temperature water bath for 2 h. The clear solution had turned grey and the reaction was left to stir for 18 h. The mixture was partitioned between aqueous NH₄Cl and EtOAc and then the aqueous phase extracted with further EtOAc. The combined organic layers were washed with brine, dried (MgSO₄), filtered, and concentrated to dryness to give product (0.175 g, quantative).

45e) 5-Cyclopropyl-1-(3-{2-fluoro-3-[(2S,5R)-2-methyl-5-propylmorpholine-4-carbonyl]phenyl}phenyl)-1H-pyrazole-4-carboxylic Acid Methyl Ester

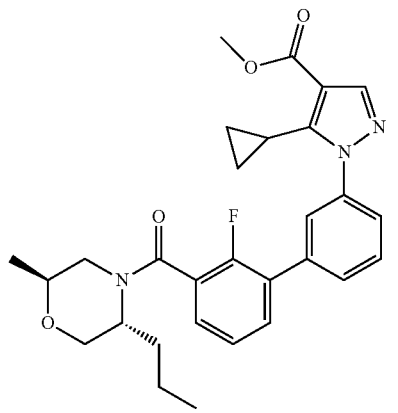 [SMILES: CCC[C@@H]1CO[C@@H](C)CN1C(=O)c1cccc(-c2cccc(-n3ncc(C(=O)OC)c3C3CC3)c2)c1F]

A solution of 1-(3'-carboxy-2'-fluoro-biphenyl-3-yl)-5-cyclopropyl-1H-pyrazole-4-carboxylic acid methyl ester (0.050 g, 0.13 mmol), HATU (0.050 g, 0.13 mmol), (2S,5R)-2-methyl-5-propylmorpholine (0.028 g, 0.16 mmol) and DIPEA (0.057 mL, 0.33 mmol) in DCM (1 mL) was stirred for 2 h. The mixture was diluted with DCM, and the organic phase washed with aqueous NaHCO₃, dried (MgSO₄), filtered, and concentrated to dryness. Silica purification eluting with EtOAc/petrol 15-60% gave the product (0.036 g, 54%). LC-MS m/z 506 (M+H)⁺, 1.50 (ret. time), basic method.

45f) 5-Cyclopropyl-1-(3-{2-fluoro-3-[(2S,5R)-2-methyl-5-propylmorpholine-4-carbonyl]phenyl}phenyl)-1H-pyrazole-4-carboxylic Acid

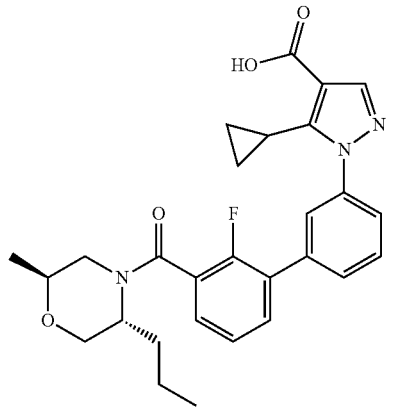 [SMILES: CCC[C@@H]1CO[C@@H](C)CN1C(=O)c1cccc(-c2cccc(-n3ncc(C(=O)O)c3C3CC3)c2)c1F]

A stirred solution of 5-cyclopropyl-1-(3-{2-fluoro-3-[(2S,5R)-2-methyl-5-propylmorpholine-4-carbonyl]phenyl}phenyl)-1H-pyrazole-4-carboxylic acid methyl ester (0.036 g, 0.07 mmol) in EtOH (0.5 mL) was treated with aqueous NaOH (2M, 0.178 mL). After 60 hours the mixture was partitioned between EtOAc and water. The organic phase was extracted with further water and then discarded. The combined aqueous layer was acidified with 1N HCl and extracted into EtOAc (×2). The combined organic phases were dried (MgSO₄), filtered, and concentrated under vacuum to give the product (0.016 g, 46%). LC-MS m/z 492 (M+H)⁺, 1.08 (ret. time), basic method. ¹H NMR (400 MHz, DMSO-d6): 12.36-12.19 (1H, m), 7.97 (1H, s), 7.79 (1H, s), 7.74-7.61 (4H, m), 7.53-7.31 (2H, m), 4.56-4.45 (0.5H, m), 4.16-4.06 (0.5H, m), 4.00-3.75 (2H, m), 3.63-3.36 (2H, m), 3.28-3.17 (0.5H, m), 2.98 (0.5H, d), 2.20-2.08 (1H, m), 1.66-1.45 (1H, m), 1.45-1.25 (2H, m), 1.17-1.06 (3H, m), 1.02-0.81 (5H, m), 0.81-0.63 (1H, m), 0.58 (2H, d).

Example 46. 5-(1-Acetylpiperidin-4-yl)-1-{3-[3-dimethylcarbamoyl)phenyl]phenyl}-1H-pyrazole-4-carboxylic Acid

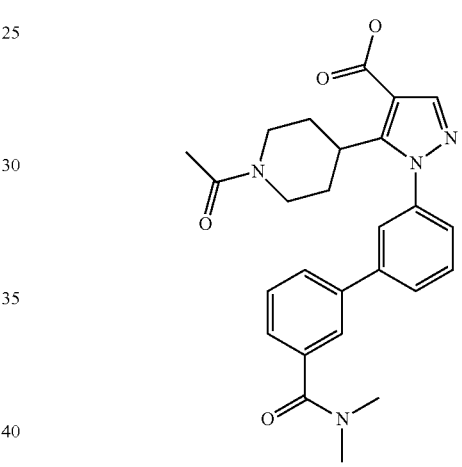

46a) 5-(1-Acetyl-piperidin-4-yl)-1-(3-bromo-phenyl)-1H-pyrazole-4-carboxylic Acid Methyl Ester

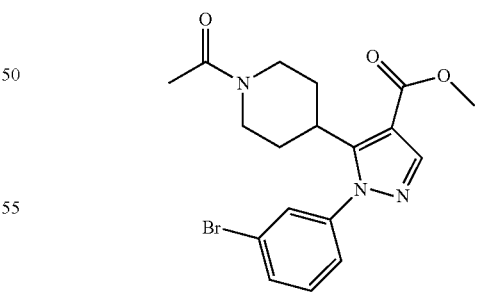

A mixture of 3-(1-acetyl-piperidin-4-yl)-3-oxo-propionic acid methyl ester (250 mg, 1.04 mmol) and dimethylformamide dimethylacetal (0.15 mL, 1.14 mmol) and TsOH (2 mg) was heated at 130° C. in the microwave for 15 min. The mixture was concentrated under vacuum and the residue dissolved in acetonitrile (2 mL). Diisopropylamine (0.271 mL, 1.55 mol) was added followed by 3-bromophenylhydrazine hydrochloride (260 mg, 1.14 mmol). The solution was stirred at room temperature for 16 hours. The reaction

46b) 5-(1-Acetylpiperidin-4-yl)-1-{3-[3-dimethylcarbamoyl)phenyl]phenyl}-1H-pyrazole-4-carboxylic Acid

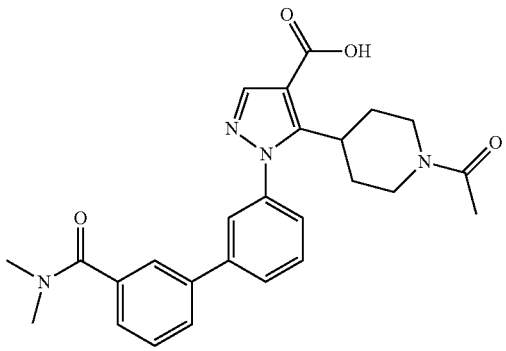 [SMILES: CC(=O)N1CCC(c2c(C(=O)O)cnn2-c2cccc(-c3cccc(C(=O)N(C)C)c3)c2)CC1]

A mixture of 5-(1-acetyl-piperidin-4-yl)-1-(3-bromo-phenyl)-1H-pyrazole-4-carboxylic acid methyl ester (160 mg, 0.39 mmol), N,N-dimethyl-3-(4,4,5,5-tetramethyl-1,3,2-dioxaborolan-2-yl)benzamide (119 mg, 0.43 mmol), sodium carbonate (46 mg, 0.43 mmol) and tetrakistriphenylphosphine palladium (16 mg, 0.02 mmol) in degassed dioxane (2 mL) and water (2 mL) was heated at 100° C. for 4 hours. The reaction was allowed to cool and MeOH (3 mL) and LiOH (1M, 3 mL) were added. The mixture was stirred at room temperature for 16 hours. The aqueous was acidified with citric acid (5% aqueous). The product extracted with EtOAc (×3). The combined organic layers were washed with water, brine and dried over MgSO$_4$. The product was filtered and evaporated to dryness. Purification by prep HPLC gave the title compound (50 mg, 28%). LC-MS m/z 164 (M+H)$^+$, 0.97 (ret. time). $^1$H NMR (400 MHz, Me-d3-OD): 8.07 (1H, s), 7.91 (1H, d), 7.84-7.80 (1H, m), 7.76 (2H, d), 7.72 (1H, t), 7.60 (1H, t), 7.50-7.45 (2H, m), 4.63-4.56 (1H, m), 4.01-3.93 (1H, m), 3.29-3.19 (1H, m), 3.15 (3H, s), 3.09-2.99 (4H, m), 2.58-2.34 (3H, m), 2.10 (3H, s), 1.83-1.67 (2H, m).

Example 47. 1-(3-{3-[(cyclopropylmethyl)(methyl)carbamoyl]-2-fluorophenyl}phenyl)-5-(trifluoromethyl)-1H-pyrazole-4-carboxylic Acid

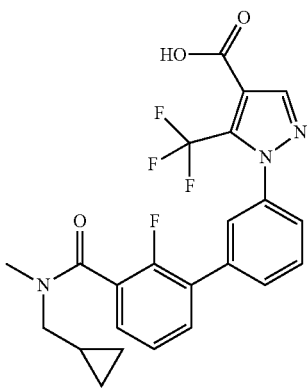 [SMILES: CN(CC1CC1)C(=O)c1cccc(-c2cccc(-n3ncc(C(=O)O)c3C(F)(F)F)c2)c1F]

47a) 3-Bromo-N-cyclopropylmethyl-2-fluoro-N-methyl-benzamide


A solution of 3-bromo-2-fluoro-benzoic acid (0.50 g, 2.28 mmol), HATU (1.30 g, 3.42 mmol), cyclopropylmethyl-methylamine (0.42 g, 3.42 mmol) and DIPEA (0.89 g, 6.85 mmol) in DMF (9 mL) was stirred for 18 h. The mixture was partitioned between EtOAc and water. The aqueous phase was extracted with EtOAc and the combined organic phases washed with water (×2) and brine before drying (MgSO$_4$), filtering, and concentrating to give the product (0.708 g, quantative), used without further purification. LC-MS m/z 573 (2M+H)$^+$, 1.32 (ret. time), basic method.

47b) 1-(3-{3-[(cyclopropylmethyl)(methyl)carbamoyl]-2-fluorophenyl}phenyl)-5-(trifluoromethyl)-1H-pyrazole-4-carboxylic Acid Ethyl Ester

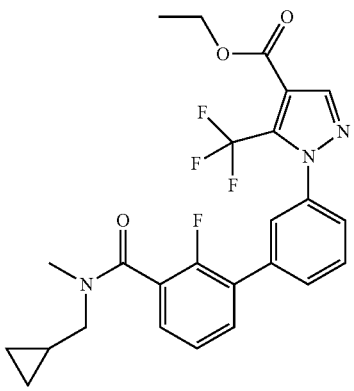 [SMILES: CCOC(=O)c1cnn(-c2cccc(-c3cccc(C(=O)N(C)CC4CC4)c3F)c2)c1C(F)(F)F]

A stirred mixture of 3-bromo-N-cyclopropylmethyl-2-fluoro-N-methyl-benzamide (0.140 g, 0.49 mmol), 1-[3-(4,4,5,5-tetramethyl-[1,3,2]dioxaborolan-2-yl)-phenyl]-5-trifluoromethyl-1H-pyrazole-4-carboxylic acid ethyl ester (0.201 g, 0.49 mmol), Na$_2$CO$_3$ (3M, 0.489 mL) and Pd(PPh$_3$)$_4$ (0.028 g, 0.02 mmol) in EtOH (2 mL) and toluene (7 mL) was heated at reflux for 18 h. After cooling, the mixture was partitioned between EtOAc (150 mL) and water (10 mL) and the organic phase washed with water (10 mL) and brine (10 mL) before it was dried (MgSO$_4$), filtered, and concentrated to give the product (212 mg, 97%). LC-MS m/z 490 (M+H)$^+$, 1.51 (ret. time), basic method.

47c) 1-(3-{3-[(Cyclopropylmethyl)(methyl)carbamoyl]-2-fluorophenyl}phenyl)-5-(trifluoromethyl)-1H-pyrazole-4-carboxylic Acid

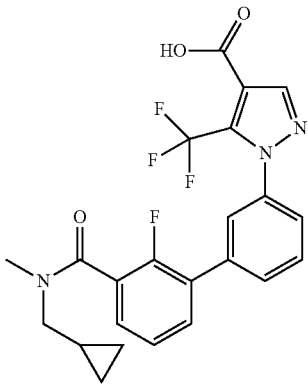 [SMILES: CN(CC1CC1)C(=O)c1cccc(-c2cccc(-n3ncc(C(=O)O)c3C(F)(F)F)c2)c1F]

A stirred solution of 1-(3-{3-[(cyclopropylmethyl)(methyl)carbamoyl]-2-fluorophenyl}phenyl)-5-(trifluoromethyl)-1H-pyrazole-4-carboxylic acid ethyl ester (0.212 g, 0.43 mmol) in EtOH (3 mL) was treated with a solution of NaOH (0.069 g) in water (0.75 mL). After 60 hours the mixture was acidified with 1N HCl and extracted into EtOAc (×2). The combined organic phases were dried (MgSO$_4$), filtered, and concentrated under vacuum to give the product (0.048 g, 24%). LC-MS m/z 462 (M+H)$^+$, 1.09 (ret. time). $^1$H NMR (400 MHz, DMSO-d6): 13.36 (1H, s), 8.27 (1H, s), 7.86-7.57 (5H, m), 7.48-7.35 (2H, m), 3.45-3.35 (1H, m), 3.13-3.01 (2H, m), 2.98-2.89 (1H, m), 1.15-1.02 (1H, m), 0.95-0.83 (1H, m), 0.56-0.48 (1H, m), 0.44 (1H, d), 0.35-0.25 (1H, m), 0.07 (1H, s).

Example 48. 5-cyclopropyl-1-(3-{3-[(cyclopropylmethyl)(methyl)carbamoyl]-2-fluorophenyl}phenyl)-1H-pyrazole-4-carboxylic Acid

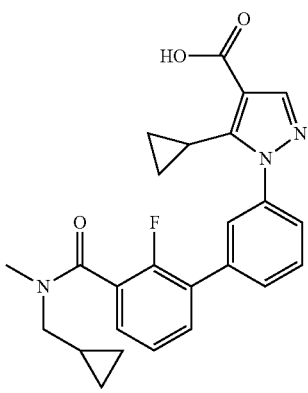 [SMILES: CN(CC1CC1)C(=O)c1cccc(-c2cccc(-n3ncc(C(=O)O)c3C3CC3)c2)c1F]

48a) 5-Cyclopropyl-1-(3-{3-[(cyclopropylmethyl)(methyl)carbamoyl]-2-fluorophenyl}phenyl)-1H-pyrazole-4-carboxylic Acid Ethyl Ester

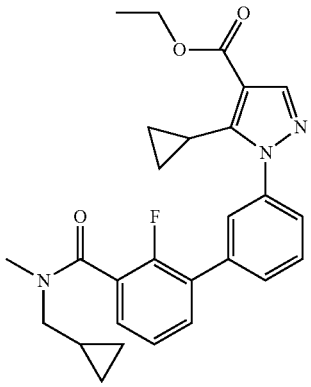 [SMILES: CCOC(=O)c1cnn(-c2cccc(-c3cccc(C(=O)N(C)CC4CC4)c3F)c2)c1C1CC1]

A stirred mixture of 3-bromo-N-cyclopropylmethyl-2-fluoro-N-methyl-benzamide (0.141 g, 0.49 mmol), 1-[3-(4,4,5,5-tetramethyl-[1,3,2]dioxaborolan-2-yl)-phenyl]-5-cyclopropyl-1H-pyrazole-4-carboxylic acid ethyl ester (0.188 g, 0.49 mmol), Na$_2$CO$_3$ (3M, 0.492 mL) and Pd(PPh$_3$)$_4$ (0.028 g, 0.02 mmol) in EtOH (1.5 mL) and toluene (7 mL) was heated at reflux for 3 h. After cooling, the mixture was partitioned between EtOAc (30 mL) and water (20 mL) and the organic phase washed with water (20 mL) and brine (20 mL) before it was dried (MgSO$_4$), filtered, and concentrated to give the product (250 mg, quantative). LC-MS m/z 462 (M+H)$^+$, 1.48 (ret. time), basic method.

48b) 5-Cyclopropyl-1-(3-{3-[(cyclopropylmethyl)(methyl)carbamoyl]-2-fluorophenyl}phenyl)-1H-pyrazole-4-carboxylic Acid

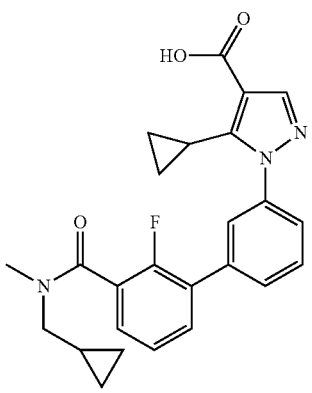 [SMILES: CN(CC1CC1)C(=O)c1cccc(-c2cccc(-n3ncc(C(=O)O)c3C3CC3)c2)c1F]

A stirred solution of 5-cyclopropyl-1-(3-{3-[(cyclopropylmethyl)(methyl)carbamoyl]-2-fluorophenyl}phenyl)-1H-pyrazole-4-carboxylic acid ethyl ester (0.250 g, 0.54 mmol) in EtOH (4 mL) was treated with aqueous NaOH (2M, 1.08 mL). After 60 hours the mixture was acidified with 1N HCl and extracted into EtOAc (×2). The combined organic phases were dried (MgSO$_4$), filtered, and concentrated under vacuum to give the product (0.079 g, 34%). LC-MS m/z 434 (M+H)$^+$, 1.05 (ret. time). $^1$H NMR (400 MHz, DMSO-d6): 12.20 (1H, s), 7.97 (1H, s), 7.79 (1H, s), 7.76-7.57 (4H, m), 7.52-7.34 (2H, m), 3.47-3.36 (1H, m), 3.14-3.01 (2H, m), 2.94 (1H, s), 2.21-2.06 (1H, m), 1.14-1.01 (1H, m), 0.96-0.80 (3H, m), 0.62-0.53 (2H, m), 0.53-0.48 (1H, m), 0.44 (1H, d), 0.36-0.25 (1H, m), 0.07 (1H, d).

Example 49. 1-{3-[3-(dimethylcarbamoyl)phenyl]phenyl}-5-(3-phenylcyclobutyl)-1H-pyrazole-4-carboxylic Acid AT29349/GSK3180353A Astex Example 62

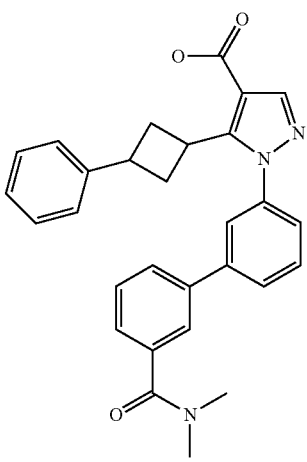 [SMILES: CN(C)C(=O)c1cccc(-c2cccc(-n3ncc(C(=O)O)c3C3CC(c4ccccc4)C3)c2)c1]

49a) 1-(3-Bromo-phenyl)-5-(3-phenyl-cyclobutyl)-1H-pyrazole-4-carboxylic Acid Methyl Ester

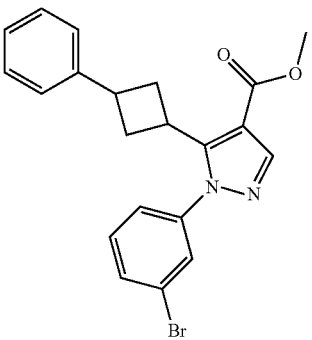 [SMILES: COC(=O)c1cnn(-c2cccc(Br)c2)c1C1CC(c2ccccc2)C1]

Under argon, 1,1-carbonyldiimidazole (552 mg 3.4 mmol) was added portionwise to a solution of 3-phenyl-cyclobutanecarboxylic acid (500 mg, 2.84 mmol) in anhydrous THF (9 mL) and the mixture was stirred at room temperature for 1 hour. Then, a well homogenised and powdered solid mixture of MgCl$_2$ (270 mg, 2.84 mmol) and potassium hydrogen methyl malonate (665 mg, 4.26 mmol) was added and the reaction mixture was stirred at room temperature for 14 hours. The reaction was concentred under vacuum, ethyl acetate was added, and the organic layer was washed with NaHSO$_4$ (1M, aqueous) and then brine. The organic phase was dried over anhydrous Na$_2$SO$_4$, filtered, and the filtrate was concentrated to dryness under vacuum to give 3-oxo-3-(3-phenyl-cyclobutyl)-propionic acid methyl ester (0.63 g). A mixture of 3-oxo-3-(3-phenyl-cyclobutyl)-propionic acid methyl ester (0.63 g), dimethylformamide-dimethylacetal (1.32 mL, 3.12 mmol) and TsOH (5 mg) was stirred at room temperature for 16 hours. The mixture was concentrated under vacuum and dissolved in acetonitrile (9 mL). Diisopropylamine (0.742 mL, 4.26 mmol) was added followed by 3-bromophenylhydrazine hydrochloride (712 mg, 3.12 mmol). The solution was stirred at room temperature for 16 hours. The reaction was diluted with EtOAc and washed with water (×7). The organic phase was dried over MgSO$_4$, filtered, and concentrated under vacuum to afford the title compound (800 mg, 69%) which was used without further purification. LC-MS m/z 411 (M+H)$^+$, 1.61 (ret. time).

49b) 1-{3-[3-(dimethylcarbamoyl)phenyl]phenyl}-5-(3-phenylcyclobutyl)-1H-pyrazole-4-carboxylic Acid

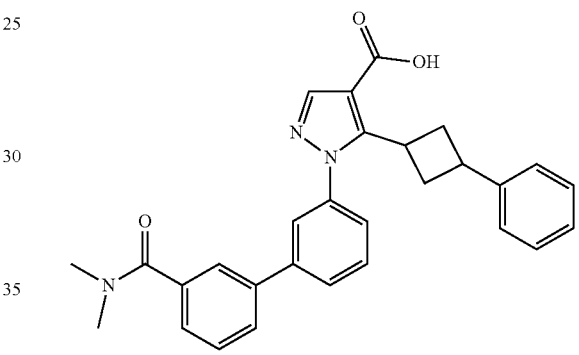

A mixture of cis and trans 1-(3-bromo-phenyl)-5-(3-phenyl-cyclobutyl)-1H-pyrazole-4-carboxylic acid methyl ester (800 mg, 2.5 mmol), N,N-dimethyl-3-(4,4,5,5-tetramethyl-1,3,2-dioxaborolan-2-yl)benzamide (0.86 mg, 3.12 mmol), sodium carbonate (331 mg, 3.12 mmol) and tetrakistriphenylphosphine palladium (117 mg, 0.142 mmol) in degassed dioxane (14 mL) and water (14 mL) was heated at 100° C. for 2 hrs. After cooling, the mixture was diluted with NaHCO$_3$ (sat., aqueous) and extracted with EtOAc (×3). The combined organic layers were washed with water and brine, dried over MgSO$_4$, filtered and concentrated to dryness under vacuum. The residue was treated with MeOH (3 mL) and LiOH (1M, 3 mL). The mixture was stirred at room temperature for 16 hours. The mixture was acidified with citric acid (5% aqueous) and the product extracted with EtOAc (×3). The combined organic layers were washed with water and brine, dried over MgSO$_4$, filtered and concentrated to dryness under vacuum. Purification by preparative HPLC gave the title compound (361 mg, 27%). LC-MS m/z 466 (M+H)$^+$, 1.09 (ret. time). $^1$H NMR (400 MHz, Me-d$_3$-OD): 8.09-8.05 (1H, m), 7.91-7.67 (5H, m), 7.63-7.56 (1H, m), 7.52-7.45 (2H, m), 7.28-7.08 (5H, m), 4.23-4.11 (0.3H, m), 3.99-3.88 (0.7H, m), 3.60-3.50 (0.3H, m), 3.14 (3H, d), 3.06 (3.7H, d), 2.68-2.50 (3.3H, m), 2.46-2.37 (0.7H, m).

Example 50. 5-Cyclopropyl-1-[3'-(tetrahydro-furan-2-yl)-biphenyl-3-yl]-1H-pyrazole-4-carboxylic Acid

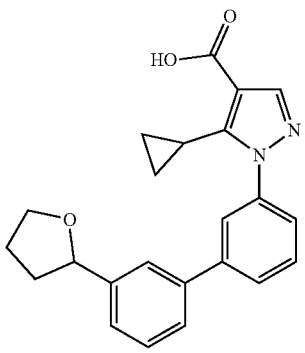 [SMILES: O=C(O)c1cnn(-c2cccc(-c3cccc(C4CCCO4)c3)c2)c1C1CC1]

50a) 3-Furan-2-yl-phenol

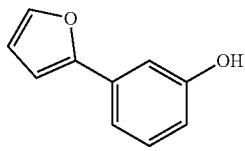 [SMILES: Oc1cccc(-c2ccco2)c1]

A stirred mixture of 2-bromofuran (0.533 g, 0.3.63 mmol), 3-hydroxyphenylboronic acid (0.500 g, 3.63 mmol), aqueous Na₂CO₃ (3M, 3.63 mL, 10.9 mmol) and Pd(PPh₃)₄ (0.210 g, 0.18 mmol) in EtOH (4.5 mL) and toluene (15 mL) was heated at reflux for 3 h. After cooling, the mixture was partitioned between EtOAc (30 mL) and water (20 mL) and the organic phase washed with water (20 mL) and brine (20 mL) before it was dried (MgSO₄), filtered and concentrated. The crude product was purified by silica chromatography (EtOAc/petrol 5-50% gradient) to give the product (0.326 g, 56%). LC-MS m/z 159 (M−H)⁻, 1.21 (ret. time), basic method.

50b) 3-(Tetrahydro-furan-2-yl)-phenol

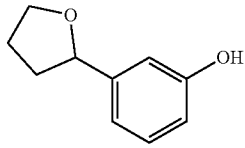 [SMILES: Oc1cccc(C2CCCO2)c1]

To a solution of 3-furan-2-yl-phenol (0.326 g, 2.03 mmol) in ethanol (30 mL) was added Pd/C (10%, 0.050 g) and the mixture shaken under an atmosphere of hydrogen for 4 h. The catalyst was removed by filtration and the solution concentrated to dryness. The crude product was purified by silica chromatography (EtOAc/petrol 10-65% gradient) to give the product (0.076 g, 23%). LC-MS m/z 163 (M−H)⁻, 1.03 (ret. time), basic method.

50c) Trifluoro-methanesulfonic acid 3-(tetrahydro-furan-2-yl)-phenyl Ester

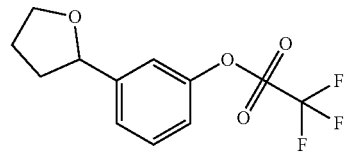

A solution of 3-(tetrahydro-furan-2-yl)-phenol (0.076 g, 0.46 mmol) and triethylamine (0.070 g, 0.69 mmol) in DCM (2 mL) at 0° C. was treated with triflic anhydride (0.509 mL, 1M in DCM, 0.51 mmol) and the reaction stirred at 0° C. for 1 h. The solution was partitioned between DCM and aqueous sodium bicarbonate and then the organic phase dried (MgSO₄), filtered, and concentrated to dryness to give the product (0.137 g, 100%). LC-MS m/z 314 (M+NH₄)⁺, 1.49 (ret. time), basic method.

50d) 5-Cyclopropyl-1-[3'-(tetrahydro-furan-2-yl)-biphenyl-3-yl]-1H-pyrazole-4-carboxylic Acid Ethyl Ester

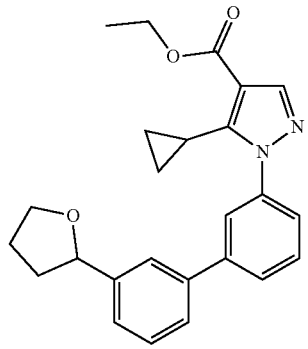 [SMILES: CCOC(=O)c1cnn(-c2cccc(-c3cccc(C4CCCO4)c3)c2)c1C1CC1]

A stirred mixture of trifluoro-methanesulfonic acid 3-(tetrahydro-furan-2-yl)-phenyl ester (0.134 g, 0.45 mmol), 5-cyclopropyl-1-[3-(4,4,5,5-tetramethyl-[1,3,2]dioxaborolan-2-yl)-phenyl]-1H-pyrazole-4-carboxylic acid ethyl ester (0.115 g, 0.30 mmol), aqueous Na₂CO₃ (3M, 0.30 mL, 0.90 mmol) and Pd(PPh₃)₄ (0.017 g, 0.02 mmol) in EtOH (1 mL) and toluene (3 mL) was heated at reflux for 2 h. After cooling, the mixture was partitioned between EtOAc (20 mL) and water (10 mL) and the organic phase washed with water (10 mL) and brine (10 mL) before it was dried (MgSO₄), filtered, and concentrated. The crude product was purified by silica chromatography (EtOAc/petrol 10-30% gradient) to give the product (0.066 g, 55%). LC-MS m/z 403 (M+H)⁺, 1.59 (ret. time), basic method.

50e) 5-Cyclopropyl-1-[3'-(tetrahydro-furan-2-yl)-biphenyl-3-yl]-1H-pyrazole-4-carboxylic Acid

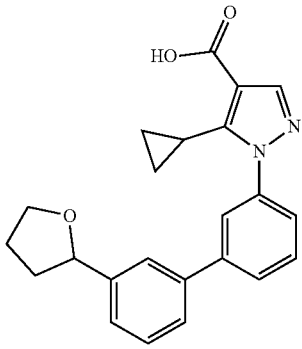 [SMILES: O=C(O)c1cnn(-c2cccc(-c3cccc(C4CCCO4)c3)c2)c1C1CC1]

A solution of 5-cyclopropyl-1-[3'-(tetrahydro-furan-2-yl)-biphenyl-3-yl]-1H-pyrazole-4-carboxylic acid ethyl ester (0.066 g, 0.16 mmol) in EtOH (2.5 mL) was treated with aqueous NaOH (2M, 0.82 mL). After 18 hours the mixture was partitioned between EtOAc and water. The organic phase was extracted with water and then discarded. The combined aqueous layer was acidified with 1N HCl and extracted into EtOAc (×2). The combined organic phases were dried (MgSO$_4$), filtered, and concentrated under vacuum to give the product (0.053 g, 86%). LC-MS m/z 375 (M+H)$^+$, 1.10 (ret. time), basic method. $^1$H NMR (400 MHz, DMSO-d6): 12.45-12.12 (1H, m), 7.97 (1H, s), 7.86 (1H, t), 7.82-7.75 (1H, m), 7.68-7.55 (4H, m), 7.45 (1H, t), 7.36 (1H, d), 4.89 (1H, t), 4.03 (1H, q), 3.84 (1H, q), 2.42-2.29 (1H, m), 2.23-2.11 (1H, m), 2.02-1.92 (2H, m), 1.80-1.68 (1H, m), 0.91-0.78 (2H, m), 0.64-0.51 (2H, m).

Example 51. 5-[(1R,2R)-2-(1-methyl-1H-1,2,3-triazol-4-yl)cyclopropyl]-1-(3-{3-[(2R)-2-propylpiperidine-1-carbonyl]phenyl}phenyl)-1H-pyrazole-4-carboxylic acid and 5-[(1S,2S)-2-(1-methyl-1H-1,2,3-triazol-4-yl)cyclopropyl]-1-(3-{3-[(2R)-2-propylpiperidine-1-carbonyl]phenyl}phenyl)-1H-pyrazole-4-carboxylic Acid

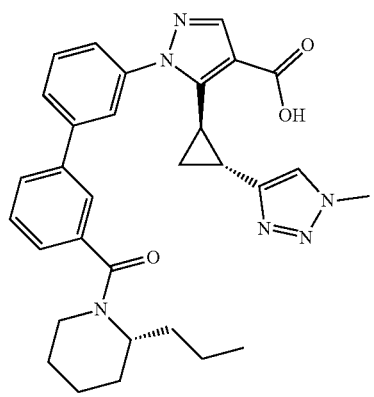

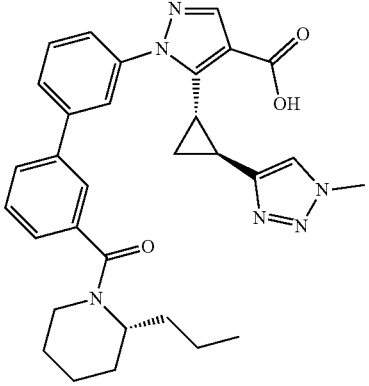

51a) (R)-2-Propyl-piperidine

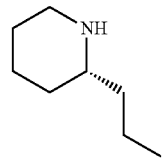

To a solution of racemic 2-propylpiperidine (3.00 g, 23.6 mmol) in dry MeOH (9.5 mL) was added (S)-(+)-mandelic acid whilst cooling in an ice bath. Dry diethyl ether (21 mL) was then added and the mixture left in a fridge for 6 days. The solid was removed by filtration and rinsed with cold ether. The solid was then redissolved in dry MeOH (6.5 mL) and then dry diethyl ether (13 mL) was added. The mixture was left in a fridge for 18 h and then the solid was collected by filtration, and washed with ether to give 1.67 g of the salt. The salt was then dissolved in water (14 mL) and solid KOH added until basic. The aqueous phase was extracted with diethyl ether (×3) and then the combined organic phase was dried (MgSO$_4$), filtered, and concentrated to dryness to give the product (0.965 g, 32%).

51b) ((R)-2-Propyl-piperidin-1-yl)-[3-(4,4,5,5-tetramethyl-[1,3,2]dioxaborolan-2-yl)-phenyl]-methanone

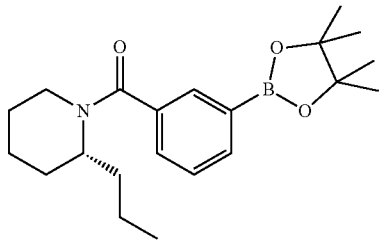 [SMILES: CCC[C@@H]1CCCCN1C(=O)c1cccc(B2OC(C)(C)C(C)(C)O2)c1]

A solution of 3-(pinacolborane)benzoic acid (1.35 g, 5.44 mmol), HATU (2.07 g, 5.44 mmol), (R)-2-propyl-piperidine.HCl (0.891 g, 5.44 mmol) and DIPEA (1.76 g, 13.6 mmol) in DCM (20 mL) was stirred for 2 h. The mixture was washed with aqueous NaHCO$_3$ and dried (MgSO$_4$). Con-

51c) N'-(3-Bromo-phenyl)-hydrazinecarboxylic Acid Tert-Butyl Ester

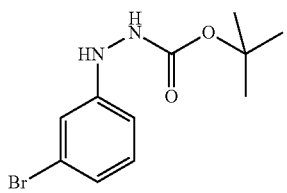 [SMILES: CC(C)(C)OC(=O)NNc1cccc(Br)c1]

A mixture of (3-bromo-phenyl)-hydrazine (4.00 g, 21.4 mmol) and triethylamine (6.42 g, 64.2 mmol) in DCM (40 mL) was treated with di-tertbutyl-dicarbonate (4.67 g, 21.4 mmol) and the reaction stirred for 18 h. The mixture was partitioned between DCM and water and then the organic phase dried (MgSO$_4$), filtered, and concentrated to dryness to give the product (5.77 g, 94%). LC-MS m/z 231 (M+H (−$^t$Bu)+H)$^+$, 1.37 (ret. time), basic method.

51d) N'-[3'-((R)-2-Propyl-piperidine-1-carbonyl)-biphenyl-3-yl]-hydrazinecarboxylic Acid Tert-Butyl Ester

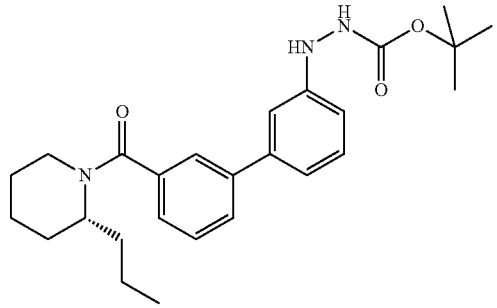 [SMILES: CCC[C@@H]1CCCCN1C(=O)c1cccc(-c2cccc(NNC(=O)OC(C)(C)C)c2)c1]

A stirred mixture of N'-(3-bromo-phenyl)-hydrazinecarboxylic acid tert-butyl ester (1.19 g, 4.13 mmol), ((R)-2-propyl-piperidin-1-yl)-[3-(4,4,5,5-tetramethyl-[1,3,2]dioxaborolan-2-yl)-phenyl]-methanone (1.23 g, 3.44 mmol), aqueous Na$_2$CO$_3$ (3M, 3.44 mL, 10.3 mmol) and Pd(PPh$_3$)$_4$ (0.199 g, 0.17 mmol) in EtOH (10 mL) and toluene (30 mL) was heated at reflux for 2 h. After cooling, the mixture was partitioned between EtOAc (80 mL) and water (40 mL) and the organic phase washed with water (30 mL) and brine (30 mL) before it was dried (MgSO$_4$), filtered, and concentrated. The crude product was purified by silica chromatography (EtOAc/petrol 10-50% gradient) to give the product (0.615 g, 41%). LC-MS m/z 438 (M+H)$^+$, 1.54 (ret. time), basic method.

51e) (3'-Hydrazino-biphenyl-3-yl)-((R)-2-propyl-piperidin-1-yl)-methanone

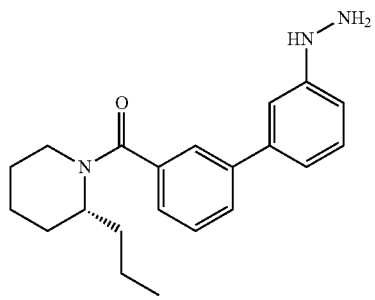 [SMILES: CCC[C@@H]1CCCCN1C(=O)c1cccc(-c2cccc(NN)c2)c1]

A solution of N'-[3'-((R)-2-Propyl-piperidine-1-carbonyl)-biphenyl-3-yl]-hydrazinecarboxylic acid tert-butyl ester (0.615 g, 1.41 mmol) in DCM (15 mL) was treated with HCl in dioxane (4M, 1.76 mL, 7.0 mmol) and the reaction stirred for 18 h. Further DCM was added and water, and the mixture basified with 2M NaOH. The aqueous phase was extracted with further DCM before the combined organic phase was dried (MgSO$_4$), filtered, and concentrated to dryness to give the product (0.455 g, 96%). LC-MS m/z 338 (M+H)$^+$, 1.38 (ret. time), basic method.

51f) 5-[trans-2-(1-Methyl-1H-[1,2,3]triazol-4-yl)-cyclopropyl]-1-[3'-((R)-2-propyl-piperidine-1-carbonyl)-biphenyl-3-yl]-1H-pyrazole-4-carboxylic Acid Methyl Ester

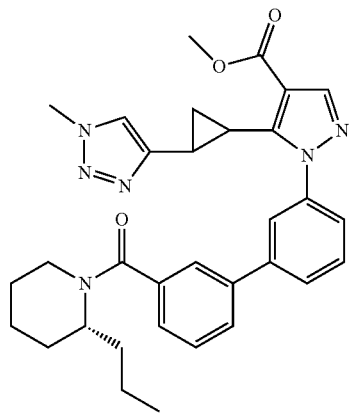 [SMILES: CCC[C@@H]1CCCCN1C(=O)c1cccc(-c2cccc(-n3ncc(C(=O)OC)c3C3CC3c3cn(C)nn3)c2)c1]

A mixture of 3-[2-(1-methyl-1H-[1,2,3]triazol-4-yl)-cyclopropyl]-3-oxo-propionic acid methyl ester (0.505 g, 1.35 mmol) and DMF-dimethyl acetal (0.20 mL, 1.51 mmol) was stirred at room temperature for 24 h, then concentrated to dryness under vacuum. The residue was treated with toluene and again concentrated to dryness to give 3-dimethylamino-2-[2-(1-methyl-1H-[1,2,3]triazol-4-yl)-cyclopropanecarbonyl]-acrylic acid methyl ester (0.375 g, 1.35 mmol). This was taken up in ethanol (20 mL), treated with (3'-hydrazino-biphenyl-3-yl)-((R)-2-propyl-piperidin-1-yl)-methanone (0.455 g, 1.35 mmol) and triethylamine (0.337 g, 3.37 mmol), and stirred at room temperature for 18 h. The reaction mixture was concentrated and then partitioned between EtOAc and water. The aqueous phase was extracted with further EtOAc and then the combined organic phase was washed with brine, dried (MgSO₄), filtered and concentrated to dryness. Purification by silica chromatography (EtOAC/petrol 25-100% gradient) gave the product (0.295 g, 40%). LC-MS m/z 553 (M+H)⁺, 1.45 (ret. time), basic method.

51g) 5-[(1S,2S)-2-(1-methyl-1H-1,2,3-triazol-4-yl)cyclopropyl]-1-(3-{3-[(2R)-2-propylpiperidine-1-carbonyl]phenyl}phenyl)-1H-pyrazole-4-carboxylic Acid and 51h) 5-[(1R,2R)-2-(1-methyl-1H-1,2,3-triazol-4-yl)cyclopropyl]-1-(3-{3-[(2R)-2-propylpiperidine-1-carbonyl]phenyl}phenyl)-1H-pyrazole-4-carboxylic Acid A solution of 5-[trans-2-(1-methyl-1H-[1,2,3]triazol-4-yl)-cyclopropyl]-1-[3'-((R)-2-propyl-piperidine-1-carbonyl)-biphenyl-3-yl]-1H-pyrazole-4-carboxylic acid methyl ester (0.275 g, 0.50 mmol) in EtOH (7.5 mL) was treated with aqueous NaOH (2M, 2.49 mL). After 18 hours the mixture was concentrated to dryness and then partitioned between EtOAc and water, acidifying with 1N HCl. The aqueous layer was extracted with further EtOAc. The combined organic phases were dried (MgSO₄), filtered, and concentrated to dryness. The two trans cyclopropyl diastereoisomers were separated by chiral preparative HPLC (with TFA modifier) and then concentrated to dryness.

51g) 5-[(1S,2S)-2-(1-methyl-1H-1,2,3-triazol-4-yl)cyclopropyl]-1-(3-{3-[(2R)-2-propylpiperidine-1-carbonyl]phenyl}phenyl)-1H-pyrazole-4-carboxylic Acid

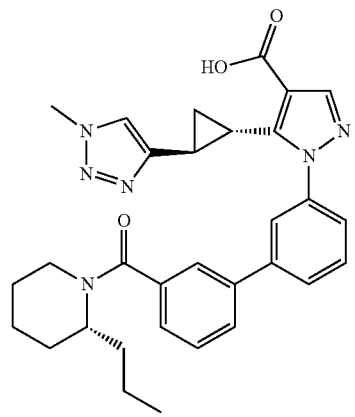 [SMILES: CCC[C@@H]1CCCCN1C(=O)c1cccc(-c2cccc(-n3ncc(C(=O)O)c3[C@H]3C[C@@H]3c3cn(C)nn3)c2)c1]

TFA salt (0.104 g, 32%). LC-MS m/z 539 (M+H)⁺, 1.14 (ret. time), basic method. ¹H NMR (400 MHz, DMSO-d6): 8.02 (1H, s), 7.86-7.73 (2H, m), 7.66-7.38 (6H, m), 7.33 (1H, d), 4.49-4.21 (1H, m), 3.81 (3H, s), 3.65 (0.5H, s), 3.49-3.23 (0.5H, m), 3.23-2.95 (0.5H, m), 2.95-2.71 (0.5H, m), 2.60-2.52 (1H, m), 2.18-2.08 (1H, m), 1.91-0.55 (15H, m).

51h) 5-[(1R,2R)-2-(1-methyl-1H-1,2,3-triazol-4-yl)cyclopropyl]-1-(3-{3-[(2R)-2-propylpiperidine-1-carbonyl]phenyl}phenyl)-1H-pyrazole-4-carboxylic Acid

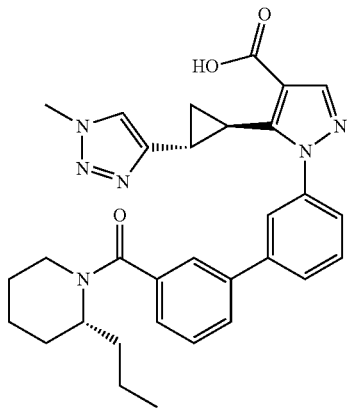 [SMILES: CCC[C@@H]1CCCCN1C(=O)c1cccc(-c2cccc(-n3ncc(C(=O)O)c3[C@@H]3C[C@H]3c3cn(C)nn3)c2)c1]

TFA salt (0.093 mg, 28%). LC-MS m/z 539 (M+H)⁺, 1.13 (ret. time), basic method. ¹H NMR (400 MHz, DMSO-d6): 8.02 (1H, s), 7.86-7.74 (2H, m), 7.66-7.45 (6H, m), 7.33 (1H, d), 4.88-4.24 (2H, m), 3.81 (3H, s), 3.43-3.36 (0.5H, m), 3.18-3.01 (0.5H, m), 2.60-2.54 (1H, m), 2.17-2.08 (1H, m), 1.86-0.53 (15H, m).

Example 52. 1-{3-[3-(2-propylpiperidine-1-carbonyl)phenyl]phenyl}-5-[2-(pyridin-3-yl)cyclopropyl]-1H-pyrazole-4-carboxylic Acid

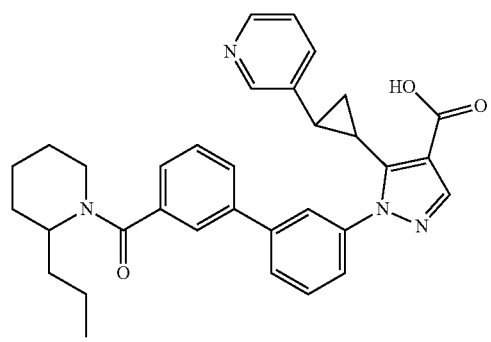 [SMILES: CCCC1CCCCN1C(=O)c1cccc(-c2cccc(-n3ncc(C(=O)O)c3C3CC3c3cccnc3)c2)c1]

52a) (E)-3-Pyridin-3-yl-acrylic Acid Methyl Ester

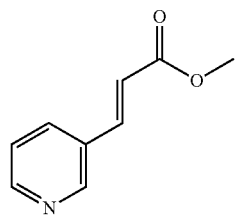

A stirred suspension of 60% sodium hydride (0.48 g, 11.9 mmol) in THF (61 mL) at 0° C. under nitrogen was treated dropwise with (EtO)₂P(O)CH₂CO₂Me (3.93 mL, 23.8 mmol). After 30 min, pyridine-3-carboxaldehyde (1.00 g, 9.15 mmol) in 5 mL of THF was added dropwise. After a further 1.5 h at 0° C., the reaction mixture was partitioned between diethyl ether and water. The organic phase was dried, filtered, and concentrated under vacuum. Flash chromatography with 5% diethyl ether in petrol gave the product (1.39 g, 93%). LC-MS m/z 164 (M+H)⁺, 0.98 (ret. time).

52b) 2-Pyridin-3-yl-cyclopropanecarboxylic Acid Methyl Ester

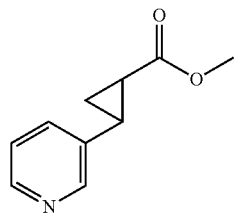

Trimethyl sulfoxonium iodide (2.25 g, 10.2 mmol) was added slowly in small portions over a period of 20 min, to a stirred suspension of sodium hydride (0.41 g, 10.2 mmol) in dry DMSO (57 mL) at RT. After 1 h, a clear solution was formed and a solution of (E)-3-pyridin-3-yl-acrylic acid methyl ester (1.39 g, 8.52 mmol) in dry DMSO (47 mL) was added slowly dropwise. After 30 min, the reaction mixture was poured into ice water (50 mL) and extracted with EtOAc (2×50 mL). The combined extracts were washed with ice water (2×100 mL), brine (50 mL), dried over anhydrous Na₂SO₄, filtered, and concentrated to dryness to give the product, used without further purification (0.60 g, 40%). LC-MS m/z 178 (M+H)⁺, 1.02 (ret. time).

52c) 2-Pyridin-3-yl-cyclopropanecarboxylic Acid

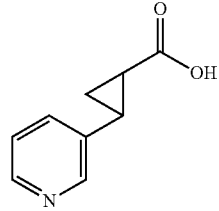 [SMILES: O=C(O)C1CC1c1cccnc1]

A stirred solution of 2-pyridin-3-yl-cyclopropanecarboxylic acid methyl ester (0.50 g, 2.82 mmol) in THF/MeOH (1:1, 14 mL) was treated with a solution of LiOH (0.604 g, 14.1 mmol) in water (14 mL). After 4 hours the reaction was diluted with water and the pH adjusted to pH4 (aqueous citric acid 5%). The mixture was extracted with IPA:CHCl₃ (1:3, ×3) and the combined organic layers washed with brine, dried over MgSO₄, filtered, and concentrated to dryness. Purification by silica chromatography eluting with EtOAc/petrol gave the product (0.30 g, 65%). LC-MS m/z 164 (M+H)⁺, 0.24 (ret. time).

52d) 3-Oxo-3-(2-pyridin-2-yl-cyclopropyl)-propionic Acid Methyl Ester

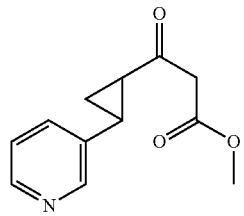

1,10-carbonyldiimidazole (0.33 g, 2.02 mmol) was added portionwise over 5 min to a stirred solution of 2-pyridin-3-yl-cyclopropanecarboxylic acid (0.30 g, 1.84 mmol) in anhydrous THF (5 mL) under argon. After 1 h, a mixture of MgCl₂ (0.35 g, 3.68 mmol) and potassium hydrogen methyl malonate (0.86 g, 5.52 mmol) was added. After 7 h the mixture was concentrated under vacuum and diluted with ethyl acetate. The mixture was then washed with aqueous NaHSO₄ (1M) and brine, and the organic phase dried over Na₂SO₄, filtered, and concentrated to dryness to give the product, used without further purification (0.335 g, 83%). LC-MS m/z 220 (M+H)⁺, 0.99 (ret. time).

52e) 1-(3-Bromo-phenyl)-5-(2-pyridin-3-yl-cyclopropyl)-1H-pyrazole-4-carboxylic Acid Methyl Ester

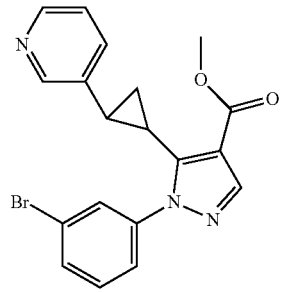 [SMILES: COC(=O)c1cnn(-c2cccc(Br)c2)c1C1CC1c1cccnc1]

A mixture of 3-oxo-3-(2-pyridin-3-yl-cyclopropyl)-propionic acid methyl ester (0.335 g, 1.53 mmol) and DMF-dimethyl acetal (0.609 mL, 4.58 mmol) was stirred at room temperature for 24 h, then concentrated to dryness under vacuum. The residue was treated with toluene and again concentrated to dryness. The residue was taken up into MeCN (5 mL) and, with stirring at 0° C., treated with DIPEA (0.635 mL, 3.65 mmol) and, portionwise, 3-bromophenylhydrazine hydrochloride (0.366 g, 1.60 mmol). The mixture was allowed to warm to room temperature and stirred for 16 h, then diluted with aqueous citric acid (5%) and extracted with EtOAc (×3). The combined organic layers were washed with brine, dried over MgSO₄, filtered, and concentrated to dryness. Silica purification eluting with EtOAc/petrol gave the product (0.126 g, 21%). LC-MS m/z 398 (M+H)⁺, 1.37 (ret. time).

52f) 1-{3-[3-(2-propylpiperidine-1-carbonyl)phenyl]phenyl}-5-[2-(pyridin-3-yl)cyclopropyl]-1H-pyrazole-4-carboxylic Acid

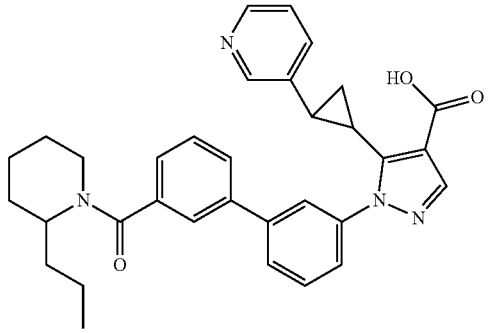 [SMILES: CCCC1CCCCN1C(=O)c1cccc(-c2cccc(-n3ncc(C(=O)O)c3C3CC3c3cccnc3)c2)c1]

A stirred mixture of 1-(3-bromo-phenyl)-5-(2-pyridin-3-yl-cyclopropyl)-1H-pyrazole-4-carboxylic acid methyl ester (0.100 g, 0.25 mmol), 3-(4,4,5,5-tetramethyl-[1,3,2]dioxaborolan-2-yl)-phenyl-(2-propyl-piperidin-1-yl)-methanone (0.099 g, 0.28 mmol), aqueous $Na_2CO_3$ (3M, 0.029 mL) and $Pd(PPh_3)_4$ (0.010 g, 0.013 mmol) in dioxane/water 1:1 (3 mL) was heated at 100° C. for 2 h. After cooling, the mixture was diluted with MeOH (3 mL) and treated with LiOH (1M, 3 mL). After 24 hours the mixture was acidified with citric acid (5% aqueous) and extracted into EtOAc (×3). The combined organic phases were washed with water and brine, dried ($MgSO_4$), filtered, and concentrated under vacuum. The residue was purified by silica column eluting with EtOAc/MeOH 0-10% to give the product (0.110 g, 82%). LC-MS m/z 535 $(M+H)^+$, 1.18 (ret. time). $^1$H NMR (400 MHz, Me-$d_3$-OD): 8.84 (1H, d), 8.07 (1H, s), 7.76 (1H, s), 7.74-7.71 (1H, m), 7.63-7.49 (5H, m), 7.43-7.35 (2H, m), 7.23 (1H, dd), 4.61-4.47 (0.5H, m), 3.90-3.74 (0.5H, m), 3.58-3.53 (0.5H, m), 3.05-2.92 (0.5H, m), 2.92-2.85 (1H, m), 2.37-2.30 (1H, m), 1.94-1.39 (11H, m), 1.24-0.93 (3H, m), 0.81 (1H, br s).

Example 53. 5-Cyclopropyl-1-[3'-(3,5-dimethyl-piperidine-1-carbonyl)-2'-fluoro-biphenyl-3-yl]-1H-pyrazole-4-carboxylic Acid

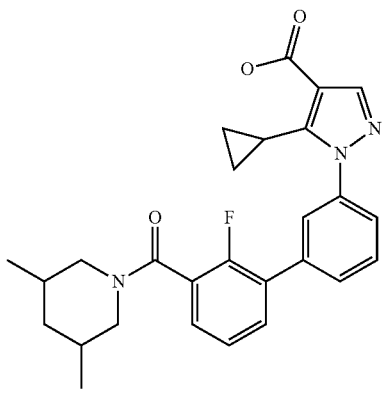 [SMILES: CC1CC(C)CN(C(=O)c2cccc(-c3cccc(-n4ncc(C(=O)O)c4C4CC4)c3)c2F)C1]

53a) 5-Cyclopropyl-1-[3-(4,4,5,5-tetramethyl-[1,3,2]dioxaborolan-2-yl)-phenyl]-1H-pyrazole-4-carboxylic Acid Methyl Ester

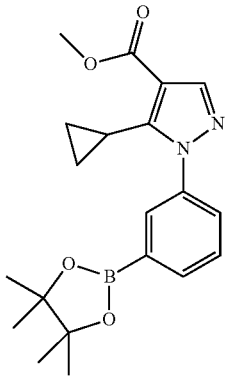 [SMILES: COC(=O)c1cnn(-c2cccc(B3OC(C)(C)C(C)(C)O3)c2)c1C1CC1]

A mixture of 1-(3-bromo-phenyl)-5-cyclopropyl-1H-pyrazole-4-carboxylic acid methyl ester (5.22 g, 16.26 mmol), bis(pinacolato)diboron (4.55 g, 17.88 mmol), KOAc (3.19 g, 35.52 mmol) and $Pd(dppf)Cl_2$ (0.595 g, 0.813 mmol) in dioxane (75 mL) was stirred under reflux for 2 hours, still starting material present 10% excess of reagents added stirred under reflux for further hour. The mixture was then concentrated and partitioned between EtOAc and water. The organic phase was washed with water and then brine before it was dried ($MgSO_4$), filtered, and concentrated. Purified by silica column, eluting 0-20% EtOAc/petrol to give the product (3.0 g, 50%). LC-MS m/z 286 [fragment] $(M+H)^+$, 1.16 (ret. time).

53b) 3-Bromo-2-fluoro-benzoic Acid Benzyl Ester

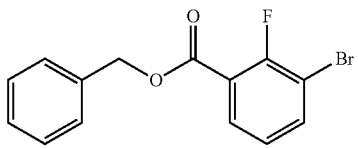 [SMILES: O=C(OCc1ccccc1)c1cccc(Br)c1F]

A stirred solution of 3-bromo-2-fluorobenzoic acid (3.00 g, 13.7 mmol) in DCM (40 mL) was treated with benzyl alcohol (1.48 g, 13.7 mmol), HOAt (2.23 g, 16.4 mmol), EDC (3.15 g, 16.4 mmol) and DIPEA (4.77 mL, 16.4 mmol). After 16 h the mixture was diluted with DCM, and washed sequentially with 5% aq. citric acid, saturated $NaHCO_3$ and brine, dried ($MgSO_4$), filtered, and concentrated to dryness to give the product (3.94 g, 93%) used without further purification. LC-MS m/z 326 $(M+H)^+$, 1.54 (ret. time).

53c) 1-(3'-Benzyloxycarbonyl-2'-fluoro-biphenyl-3-yl)-5-cyclopropyl-1H-pyrazole-4-carboxylic Acid Methyl Ester

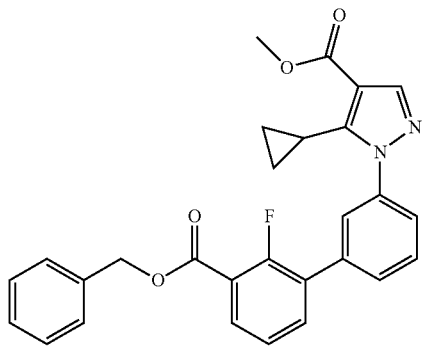 [SMILES: COC(=O)c1cnn(-c2cccc(-c3cccc(C(=O)OCc4ccccc4)c3F)c2)c1C1CC1]

A stirred mixture of 3-bromo-2-fluoro-benzoic acid benzyl ester (1.81 g, 5.85 mmol), 5-cyclopropyl-1-[3-(4,4,5,5-tetramethyl-[1,3,2]dioxaborolan-2-yl)-phenyl]-1H-pyrazole-4-carboxylic acid methyl ester (1.55 g, 4.41 mmol), aq. Na$_2$CO$_3$ (3M, 4.21 mL) and Pd(PPh$_3$)$_4$ (0.347 g, 0.3 mmol) in EtOH (12.4 mL) and toluene (49.6 mL) was heated at 80° C. for 2 h. After cooling, the mixture was partitioned between EtOAc and water and the organic phase washed with water and brine before it was dried (MgSO$_4$), filtered, concentrated to dryness, and purified by silica column eluting with 0-60% EtOAc/petrol to give the product (1.31 g, 62%). LC-MS m/z 471 (M+H)$^+$, 1.61 (ret. time).

53d) 1-(3'-Carboxy-2'-fluoro-biphenyl-3-yl)-5-cyclopropyl-1H-pyrazole-4-carboxylic Acid Methyl Ester

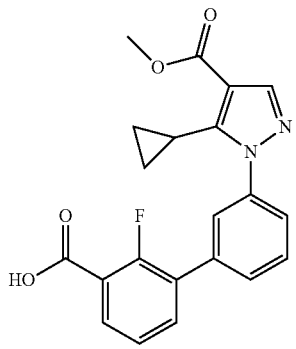 [SMILES: COC(=O)c1cnn(-c2cccc(-c3cccc(C(=O)O)c3F)c2)c1C1CC1]

A shaken mixture of 1-(3'-benzyloxycarbonyl-2'-fluoro-biphenyl-3-yl)-5-cyclopropyl-1H-pyrazole-4-carboxylic acid methyl ester (1.31 g, 2.78 mmol) and 10% Pd/C in EtOH (30 mL) and EtOAc (30 mL) was hydrogenated at atmospheric pressure for 16 h. The mixture was then filtered and fresh catalyst added and left further 24 h, the mixture was filtered then concentrated to dryness under vacuum to give the product (0.7 g, 67%). LC-MS m/z 381 (M+H)$^+$, 1.08 (ret. time).

53e) 5-Cyclopropyl-1-[3'-(3,5-dimethyl-piperidine-1-carbonyl)-2'-fluoro-biphenyl-3-yl]-1H-pyrazole-4-carboxylic Acid Methyl Ester

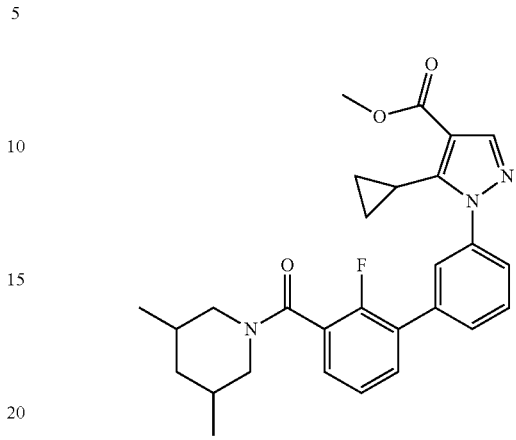

A solution of 1-(3'-carboxy-2'-fluoro-biphenyl-3-yl)-5-cyclopropyl-1H-pyrazole-4-carboxylic acid methyl ester (0.057 g, 0.131 mmol), HATU (0.050 g, 0.097 mmol), 3,5-dimethylpiperidine (0.015 g, 0.131 mmol) and DIPEA (0.046 mL, 0.26 mmol) in DCM (4 mL) was stirred for 16 h. The mixture was diluted with DCM, and the organic phase washed with saturated NaHCO$_3$ brine then dried (MgSO$_4$), concentrated to dryness and purified by silica column eluting with 0-60% EtOAc/hexane to give the product (0.059 g, 95%). LC-MS m/z 476 (M+H)$^+$, 1.56 (ret. time).

53f) 5-Cyclopropyl-1-[3'-(3,5-dimethyl-piperidine-1-carbonyl)-2'-fluoro-biphenyl-3-yl]-1H-pyrazole-4-carboxylic Acid

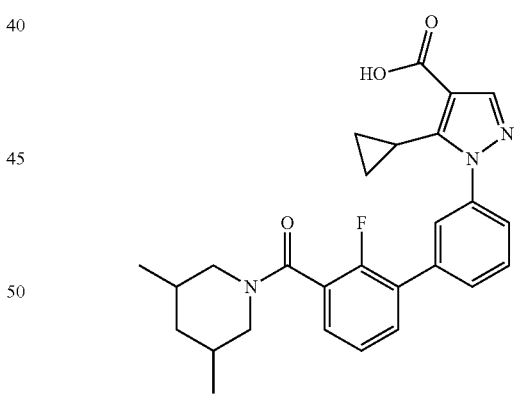

A stirred solution of 5-cyclopropyl-1-[3'-(3,5-dimethyl-piperidine-1-carbonyl)-2'-fluoro-biphenyl-3-yl]-1H-pyrazole-4-carboxylic acid methyl ester (0.059 g, 0.124 mmol) in THF (1 ml) and MeOH (1 mL) was treated with LiOH (52 mg, 1.2 mmol) in water (0.5 mL). After 36 hours the mixture was concentrated to remove organic solvents and the residue partitioned between EtOAc and water. The aqueous layer was acidified with 1N HCl and extracted into EtOAc (×2). The combined organic phases were dried (MgSO$_4$), filtered and concentrated under vacuum to give the product (0.042 g, 73%). LC-MS m/z 462 (M+H)$^+$, 1.17 (ret. time). $^1$H NMR (400 MHz, DMSO-d6): [presence of rotamers] 12.29 (1H, s), 7.97 (1H, s), 7.79 (1H, s), 7.68 (4H, s), 7.40 (2H, d), 4.51 (1H, d), 3.36 (1H, d), 2.62 (1H, s), 2.26 (1H, t), 2.19-2.09 (1H, m), 1.80 (1H, d), 1.57 (2H, s), 0.98-0.69 (9H, m), 0.61-0.53 (2H, m).

Example 54. 5-Cyclopropyl-1-{3-[2-fluoro-3-(2-propylpiperidine-1-carbonyl)phenyl]phenyl}-1H-pyrazole-4-carboxylic Acid and 5-Cyclopropyl-1-{3-[2-fluoro-3-(2-propylpiperidine-1-carbonyl)phenyl]phenyl}-1H-pyrazole-4-carboxylic Acid

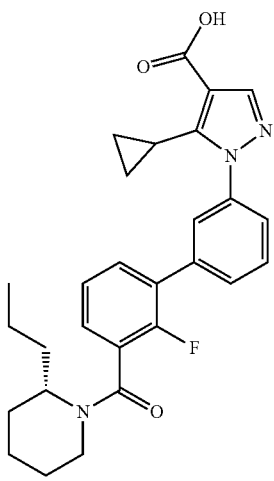

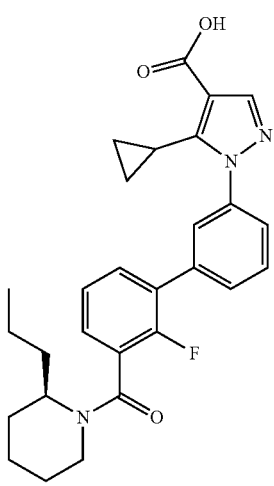

54a) (3-Bromo-2-fluoro-phenyl)-(2-propyl-piperidin-1-yl)-methanone

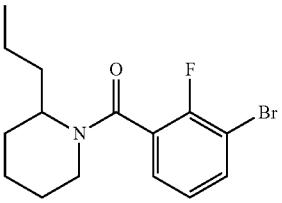 [SMILES: CCCC1CCCCN1C(=O)c1cccc(Br)c1F]

A solution of 3-bromo-2-fluoro-benzoic acid (0.500 g, 2.28 mmol), HATU (0.868 g, 2.28 mmol), 2-propylpiperidine (0.319 g, 2.51 mmol) and DIPEA (0.79 mL, 4.56 mmol) in DCM (20 mL) was stirred for 2 h. The mixture was diluted with DCM and the organic phase washed with aq. NaHCO$_3$ and dried (MgSO$_4$), filtered and concentrated under vacuum to give the crude product (1.33 g, quantitative), used without further purification. LC-MS m/z 328 (M+H)$^+$, 1.52 (ret. time).

54b) 5-Cyclopropyl-1-{3-[2-fluoro-3-(2-propylpiperidine-1-carbonyl)phenyl]phenyl}-1H-pyrazole-4-carboxylic Acid Ethyl Ester A stirred mixture of (3-bromo-2-fluoro-phenyl)-(2-propyl-piperidin-1-yl)-methanone (1 g, 3.03 mmol), 5-cyclopropyl-1-[3-(4,4,5,5-tetramethyl-[1,3,2]dioxaborolan-2-yl)-phenyl]-1H-pyrazole-4-carboxylic acid methyl ester (0.8 g, 2.17 mmol), aqueous Na$_2$CO$_3$ (3M, 2.18 mL) and Pd(PPh$_3$)$_4$ (0.178 g, 0.154 mmol) in EtOH (5 mL) and toluene (20 mL) was heated at 80° C. for 2 h. After cooling, the mixture was partitioned between EtOAc and water (and the organic phase washed with water and brine before it was dried (MgSO$_4$), filtered, concentrated to dryness, and purified by silica column eluting with 0-50% EtOAc/petrol to give the product (0.75 g, 71%). LC-MS m/z 490 (M+H)$^+$, 1.60 (ret. time).

54c) 5-Cyclopropyl-1-{3-[2-fluoro-3-(2-propylpiperidine-1-carbonyl)phenyl]phenyl}-1H-pyrazole-4-carboxylic Acid

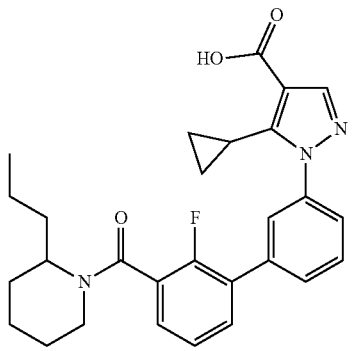 [SMILES: CCCC1CCCCN1C(=O)c1cccc(-c2cccc(-n3ncc(C(=O)O)c3C3CC3)c2)c1F]

A stirred solution of 5-cyclopropyl-1-{3-[2-fluoro-3-(2-propylpiperidine-1-carbonyl)phenyl]phenyl}-1H-pyrazole-4-carboxylic acid methyl ester (0.75 g, 1.53 mmol) in THF (15 mL) and MeOH (15 mL) was treated with LiOH (0.64 g, 15.33 mmol) in water (15 mL). After 48 hours the mixture was concentrated to remove organic solvents and the residue partitioned between EtOAc and water. The aqueous layer was acidified with 1N HCl and extracted into EtOAc (×2). The combined organic phases were dried (MgSO$_4$), filtered, and concentrated under vacuum to give the product (0.714 g, 98%). LC-MS m/z 476 (M+H)$^+$, 1.18 (ret. time). $^1$H NMR (400 MHz, DMSO-d6): [presence of rotamers]12.23 (1H, br s), 7.97 (1H, s), 7.82-7.71 (1H, m), 7.71-7.60 (4H, m), 7.47-7.28 (2H, m), 4.79 (0.6H, br s), 4.44 (0.4H, br s), 3.61-3.52 (0.4H, m), 3.29-3.21 (1H, m), 3.20-3.04 (0.6H, m), 2.79 (0.3H, t), 2.19-2.08 (1H, m), 1.88-1.21 (10H, m), 1.01-0.79 (4H, m), 0.79-0.65 (1H, m), 0.58 (2H, d).

54d) 5-Cyclopropyl-1-{3-[2-fluoro-3-((2R)-2-propylpiperidine-1-carbonyl)phenyl]phenyl}-1H-pyrazole-4-carboxylic Acid and

54e) 5-Cyclopropyl-1-{3-[2-fluoro-3-((2-S)-2-propylpiperidine-1-carbonyl)phenyl]phenyl}-1H-pyrazole-4-carboxylic Acid

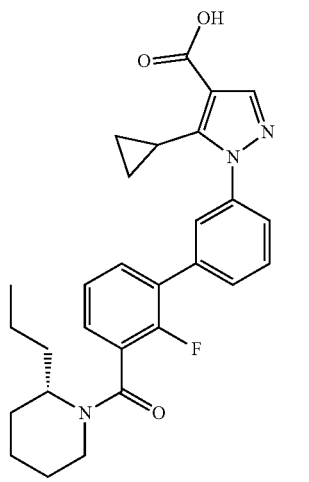 [SMILES: CCC[C@H]1CCCCN1C(=O)c1cccc(-c2cccc(-n3ncc(C(=O)O)c3C3CC3)c2)c1F]

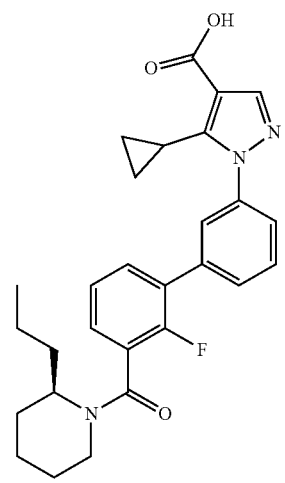 [SMILES: CCC[C@@H]1CCCCN1C(=O)c1cccc(-c2cccc(-n3ncc(C(=O)O)c3C3CC3)c2)c1F]

5-Cyclopropyl-1-{3-[2-fluoro-3-(2-propylpiperidine-1-carbonyl)phenyl]phenyl}-1H-pyrazole-4-carboxylic acid (580 mg) was separated into its enantiomers using the SFC system with a Chiralpak AY, 20×250 mm, 5 u column and 30% ethanol as co-solvent and a flow rate of 50 g/min and backpressure of 100 bar. The desired fractions were collected and dried by RotorVap. The dried samples were transferred to pre-weighed 20 mL vial with MeOH, and dried under nitrogen stream at 45° C. to yield 0.260 g of 5-cyclopropyl-1-{3-[2-fluoro-3-((2R)-2-propylpiperidine-1-carbonyl)phenyl]phenyl}-1H-pyrazole-4-carboxylic acid and 0.254 g of 5-cyclopropyl-1-{3-[2-fluoro-3-((2-S)-2-propylpiperidine-1-carbonyl)phenyl]phenyl}-1H-pyrazole-4-carboxylic acid. The absolute configuration of each enantiomer was confirmed by VCD analysis.

Example 55. (R)-1-(2'-Fluoro-3'-(2-propylpiperidine-1-carbonyl)-[1,1'-biphenyl]-3-yl)-5-(2-(1-methyl-1H-1,2,3-triazol-4-yl)ethyl)-1H-pyrazole-4-carboxylic Acid

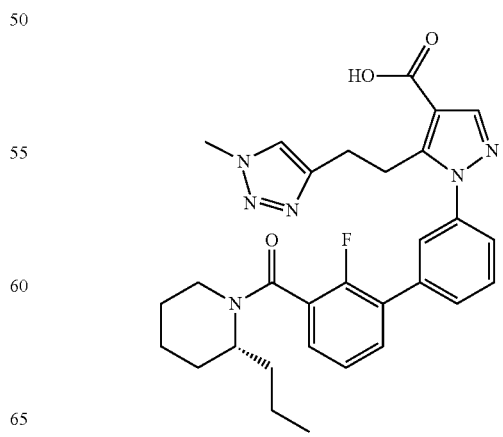

55a) (R)-2-Propylpiperidine

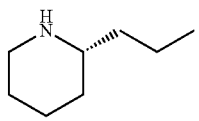

To a solution of 2-propylpiperidine (1.322 mL, 23.58 mmol) in methanol (9.5 mL) at 0° C. was added (S)-(+)-mandelic acid (3.59 g, 23.58 mmol). Diethyl ether (21 mL) was added and the flask left in the fridge for 3 days. Solid was filtered off and rinsed with cold ether. Solid was then redissolved in dry MeOH (9.5 mL) and then ether (20 mL) was added. It was left in fridge for 18 h and solid was filtered off, washing with cold ether to give white solid. The white solid was filtered and washed with cool ether to obtain 2.54 g of salt. The salt was dissolved in water (20 mL) and then solid KOH added until basic. It was extracted with Et$_2$O (×3). The combined organic layer was dried over sodium sulfate, filtered and concentrated to give the title compound (1.17 g, 9.20 mmol, 39.0% yield). LC-MS m/z 128.0 (M+H)$^+$, 0.48 min (ret. time).

55b) (R)-(2-Fluoro-3-(4,4,5,5-tetramethyl-1,3,2-dioxaborolan-2-yl)phenyl)(2-propylpiperidin-1-yl) methanone and (R)-(2-fluoro-3-(2-propylpiperidine-1-carbonyl)phenyl)boronic Acid

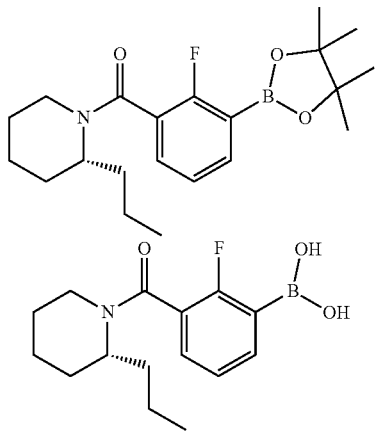

A solution of 50 wt % T$_3$P in EtOAc (1.600 mL, 2.69 mmol) was added to a solution of 2-fluoro-3-(4,4,5,5-tetramethyl-1,3,2-dioxaborolan-2-yl)benzoic acid (550 mg, 2.067 mmol), (R)-2-propylpiperidine (276 mg, 2.170 mmol), and TEA (1.146 mL, 8.27 mmol) in DCM (10 mL) at RT. It was stirred at room temperature for 18 h. The reaction was quenched with saturated NaHCO$_3$, and extracted with DCM twice. The combined organic layer was washed with brine, and dried (Na$_2$SO$_4$). It was filtered and concentrated to give a mixture of (R)-(2-fluoro-3-(4,4,5,5-tetramethyl-1,3,2-dioxaborolan-2-yl)phenyl)(2-propylpiperidin-1-yl)methanone and (R)-(2-fluoro-3-(2-propylpiperidine-1-carbonyl)phenyl)boronic acid (790 mg, 2.105 mmol, 102% yield). It was carried to the next step without purification. LC-MS m/z 376.2 (M+H)$^+$, 1.27 min (ret. time) LC-MS m/z 274.1 (M+H)$^+$, 0.86 min (ret. time).

55c) (R)-1-(2'-Fluoro-3'-(2-propylpiperidine-1-carbonyl)-[1,1'-biphenyl]-3-yl)-5-(2-(1-methyl-1H-1,2,3-triazol-4-yl)ethyl)-1H-pyrazole-4-carboxylic Acid

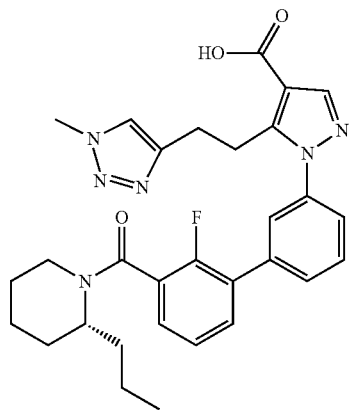 [SMILES: CCC[C@@H]1CCCCN1C(=O)c1cccc(-c2cccc(-n3ncc(C(=O)O)c3CCc3cn(C)nn3)c2)c1F]

A mixture of (R)-(3-(2-propylpiperidine-1-carbonyl)phenyl)boronic acid and (R)-(2-propylpiperidin-1-yl)(3-(4,4,5,5-tetramethyl-1,3,2-dioxaborolan-2-yl)phenyl)methanone (100 mg), methyl 1-(3-bromophenyl)-5-(2-(1-methyl-1H-1,2,3-triazol-4-yl)ethyl)-1H-pyrazole-4-carboxylate (80 mg, 0.205 mmol), Na$_2$CO$_3$ (65.2 mg, 0.615 mmol) and PdCl$_2$(dppf) (15.00 mg, 0.021 mmol) in 1,4-dioxane (3 mL) and water (1 mL) was degassed for 5 min and then heated under microwave for 15 min at 100° c. It was passed through a PL-Thiol MP SPE$^+$ and washed with ethyl acetate. It was then quenched with water and then extracted with ethyl acetate. The organic layer was washed with brine and then concentrated to give crude product. It was redissolved in MeOH (3 mL), and 2M LiOH (0.615 mL, 1.230 mmol) was added and heated under microwave for 30 min at 80° C. The reaction mixture was acidified with 1 N HCl to pH 1. 1 mL of DMSO was added and concentrated. It was purified with acidic reverse-phase HPLC to give the title compound (101 mg, 0.185 mmol, 90% yield). LC-MS m/z 545.3 (M+H)$^+$, 1.00 min (ret. time).

Example 56. 1-(2'-Fluoro-3'-(2-propylpiperidine-1-carbonyl)-[1,1'-biphenyl]-3-yl)-5-(2-(1-methyl-1H-1,2,3-triazol-4-yl)ethyl)-1H-pyrazole-4-carboxylic Acid

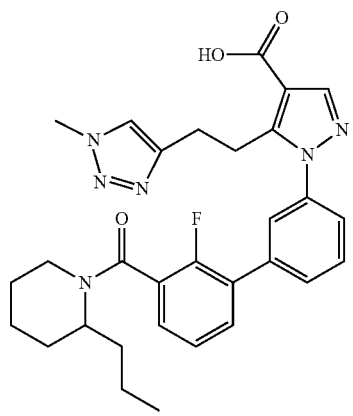 [SMILES: CCCC1CCCCN1C(=O)c1cccc(-c2cccc(-n3ncc(C(=O)O)c3CCc3cn(C)nn3)c2)c1F]

56a) (2-Fluoro-3-(4,4,5,5-tetramethyl-1,3,2-dioxaborolan-2-yl)phenyl)(2-propylpiperidin-1-yl)methanone and (2-Fluoro-3-(2-propylpiperidine-1-carbonyl)phenyl)boronic Acid

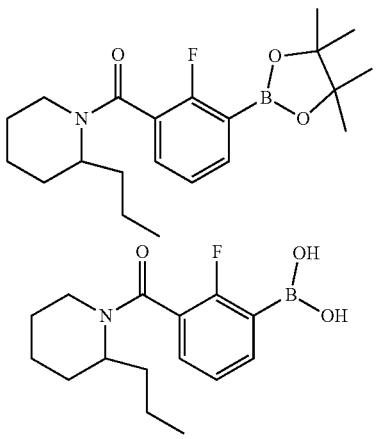

A solution of 50 wt % T₃P in EtOAc (1.891 mL, 3.18 mmol) was added to a solution of 2-fluoro-3-(4,4,5,5-tetramethyl-1,3,2-dioxaborolan-2-yl)benzoic acid (650 mg, 2.443 mmol), 2-propylpiperidine (326 mg, 2.57 mmol), and TEA (1.355 mL, 9.77 mmol) in DCM (10 mL) at RT. It was stirred at room temperature for 18 h. The reaction was quenched with saturated NaHCO₃, and extracted with DCM twice. The combined organic layer was washed with brine, dried (Na₂SO₄). It was filtered and concentrated to give a mixture of (2-fluoro-3-(4,4,5,5-tetramethyl-1,3,2-dioxaborolan-2-yl)phenyl)(2-propylpiperidin-1-yl)methanone and (2-fluoro-3-(2-propylpiperidine-1-carbonyl)phenyl)boronic acid (1.1 g, 2.93 mmol, 120% yield). It was carried to the next step without purification. LC-MS m/z 376.4 (M+H)⁺, 1.25 min (ret. time) LC-MS m/z 294.1 (M+H)⁺, 0.82 min (ret. time).

56b) 1-(2'-Fluoro-3'-(2-propylpiperidine-1-carbonyl)-[1,1'-biphenyl]-3-yl)-5-(2-(1-methyl-1H-1,2,3-triazol-4-yl)ethyl)-1H-pyrazole-4-carboxylic Acid

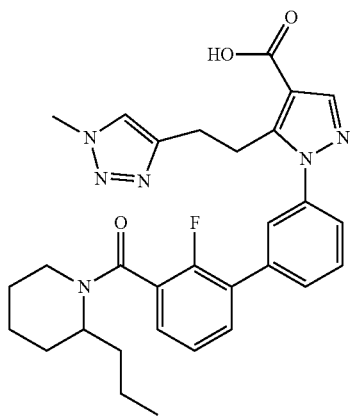 [SMILES: CCCC1CCCCN1C(=O)c1cccc(-c2cccc(-n3ncc(C(=O)O)c3CCc3cn(C)nn3)c2)c1F]

A mixture of (2-fluoro-3-(4,4,5,5-tetramethyl-1,3,2-dioxaborolan-2-yl)phenyl)(2-propylpiperidin-1-yl)methanone and (2-fluoro-3-(2-propylpiperidine-1-carbonyl)phenyl)boronic acid (85 mg, 0.226 mmol), methyl 1-(3-bromophenyl)-5-(2-(1-methyl-1H-1,2,3-triazol-4-yl)ethyl)-1H-pyrazole-4-carboxylate (0.075 mL, 0.205 mmol), Na₂CO₃ (65.2 mg, 0.615 mmol) and PdCl₂(dppf) (15.00 mg, 0.021 mmol), 1,4-Dioxane (3 mL) and water (1 mL) was degassed for 5 min and then heated under microwave for 15 min at 100° C. It was passed through Celite® and washed with ethyl acetate. It was then extracted with ethyl acetate twice. The combined organic layer was washed with brine and then concentrated to give the crude product. It was redissolved in MeOH (3 mL), 2M LiOH (0.615 mL, 1.230 mmol) was added and heated under microwave for 30 min at 80° C. The reaction mixture was acidified with 1 N HCl to pH around 1, 1 mL of DMSO was added and concentrated. It was purified with acidic reverse-phase HPLC to give the title compound (60.9 mg, 0.112 mmol, 54.5% yield). LC-MS m/z 545.5 (M+H)⁺, 0.98 min (ret. time).

Example 57. 1-(2'-Fluoro-3'-((R)-2-propylpiperidine-1-carbonyl)-[1,1'-biphenyl]-3-yl)-5-(2-(1-methyl-1H-1,2,3-triazol-4-yl)cyclopropyl)-1H-pyrazole-4-carboxylic Acid

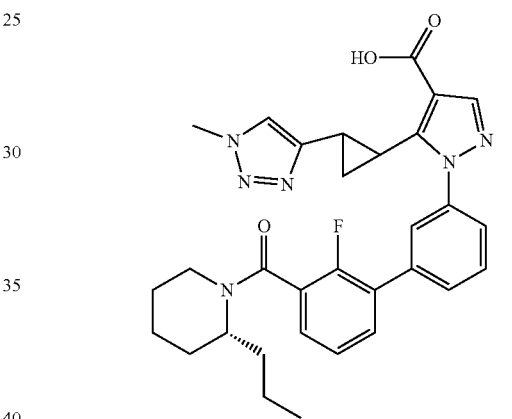

57a) Ethyl 3-(2-(1-methyl-1H-1,2,3-triazol-4-yl)cyclopropyl)-3-oxopropanoate

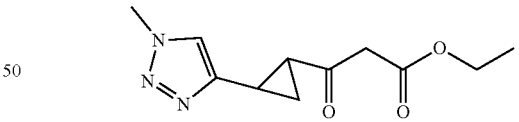

To a solution of 2-(1-methyl-1H-1,2,3-triazol-4-yl)cyclopropanecarboxylic acid (2 g, 11.96 mmol) in tetrahydrofuran (THF) (20 mL) stirred under nitrogen at room temp was added CDI (2.134 g, 13.16 mmol). The reaction mixture was stirred at RT for 1 h, then magnesium chloride (1.366 g, 14.36 mmol) and methyl potassium malonate (5.60 g, 35.9 mmol) were added and stirred at RT for 24 h. The reaction mixture was poured in ice water (30 mL), and extracted with ethyl acetate (20 mL×2). The combined organic layer was washed with brine (20 mL) and concentrated under reduced pressure to give crude compound. The crude residue was purified with silica gel chromatography eluting with 2% MeOH in DCM to give the title compound (1.1 g, 4.47 mmol, 37.3% yield) as a gummy liquid. LC-MS m/z 237.9 (M+H)⁺, 2.83 min (ret. time).

57b) (E)-Ethyl 3-(dimethylamino)-2-(2-(1-methyl-1H-1,2,3-triazol-4-yl)cyclopropanecarbonyl)acrylate

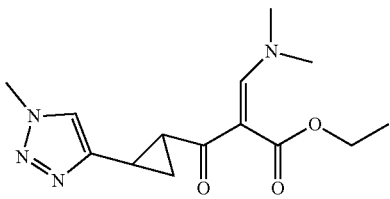 [SMILES: CCOC(=O)/C(=C\N(C)C)C(=O)C1CC1c1cn(C)nn1]

To a solution of ethyl 3-(2-(1-methyl-1H-1,2,3-triazol-4-yl)cyclopropyl)-3-oxopropanoate (2.4 g, 10.12 mmol) in DMF-DMA (4.06 ml, 30.3 mmol) under nitrogen was added p-TsOH (0.019 g, 0.101 mmol). The reaction mixture was stirred at 100° C. for 2 h. It was concentrated under reduced pressure, and co-distilled with toluene. The crude residue was purified with silica gel chromatography eluting with 2.5% MeOH in DCM to give the title compound (1.8 g, 5.85 mmol, 57.9% yield) as a gummy brown liquid. LC-MS m/z 292.9 (M+H)$^+$, 2.74 min (ret. time).

57c) Ethyl 1-(3-bromophenyl)-5-(2-(1-methyl-1H-1,2,3-triazol-4-yl)cyclopropyl)-1H-pyrazole-4-carboxylate

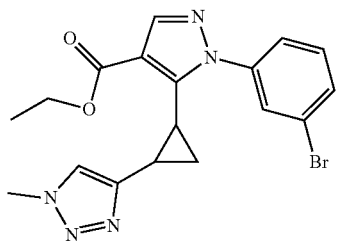 [SMILES: CCOC(=O)c1cnn(-c2cccc(Br)c2)c1C1CC1c1cn(C)nn1]

A mixture of (Z)-ethyl 3-(dimethylamino)-2-(2-(1-methyl-1H-1,2,3-triazol-4-yl)cyclopropanecarbonyl)acrylate (300 mg, 1.026 mmol), (3-bromophenyl)hydrazine, hydrochloride (275 mg, 1.231 mmol) and DIEA (0.538 mL, 3.08 mmol) in ethanol (6 mL) was stirred at RT for 19 h. Solid precipitated out from reaction mixture. Solid was filtered and washed with ether to give the title compound (380 mg, 0.913 mmol, 89% yield) as white solid. LC-MS m/z 416.2 (M+H)$^+$, 0.91 min (ret. time).

57d) Ethyl 1-(2'-fluoro-3'-((R)-2-propylpiperidine-1-carbonyl)-[1,1'-biphenyl]-3-yl)-5-(2-(1-methyl-1H-1,2,3-triazol-4-yl)cyclopropyl)-1H-pyrazole-4-carboxylate

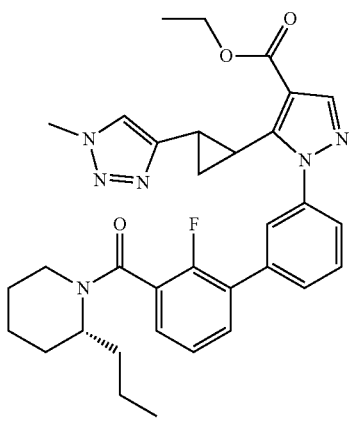 [SMILES: CCC[C@@H]1CCCCN1C(=O)c1cccc(-c2cccc(-n3ncc(C(=O)OCC)c3C3CC3c3cn(C)nn3)c2)c1F]

A mixture of (R)-(2-fluoro-3-(4,4,5,5-tetramethyl-1,3,2-dioxaborolan-2-yl)phenyl)(2-propylpiperidin-1-yl)methanone and (R)-(2-fluoro-3-(2-propylpiperidine-1-carbonyl)phenyl)boronic acid (79 mg, 0.211 mmol), ethyl 1-(3-bromophenyl)-5-(2-(1-methyl-1H-1,2,3-triazol-4-yl)cyclopropyl)-1H-pyrazole-4-carboxylate (0.075 mL, 0.192 mmol), Na$_2$CO$_3$ (61.1 mg, 0.577 mmol) and PdCl$_2$(dppf) (14.06 mg, 0.019 mmol) in 1,4-dioxane (3 mL) and water (1 mL) was degassed for 5 min and then heated under microwave for 15 min at 100° C. It was passed through Celite® and washed with ethyl acetate twice. The combined organic layer was washed with brine and then concentrated to give the crude product. The reaction mixture was purified with reverse-phase HPLC under neutral conditions to give the title compound (74 mg, 0.127 mmol, 65.9% yield). LC-MS m/z 585.2 (M+H)$^+$, 1.14 min (ret. time).

57e) 1-(2'-Fluoro-3'-((R)-2-propylpiperidine-1-carbonyl)-[1,1'-biphenyl]-3-yl)-5-(2-(1-methyl-1H-1,2,3-triazol-4-yl)cyclopropyl)-1H-pyrazole-4-carboxylic Acid

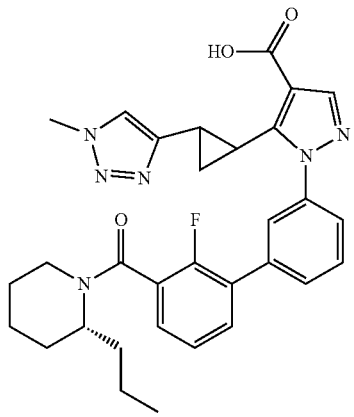 [SMILES: CCC[C@@H]1CCCCN1C(=O)c1cccc(-c2cccc(-n3ncc(C(=O)O)c3C3CC3c3cn(C)nn3)c2)c1F]

To a solution of ethyl 1-(2'-fluoro-3'-((R)-2-propylpiperidine-1-carbonyl)-[1,1'-biphenyl]-3-yl)-5-(2-(1-methyl-1H-1,2,3-triazol-4-yl)cyclopropyl)-1H-pyrazole-4-carboxylate (74 mg, 0.127 mmol) in Methanol (2 mL) was added 2M LiOH (0.345 mL, 0.690 mmol). The mixture was heated under microwave for 30 min at 80° C. The reaction mixture was acidified with 1 N HCl to pH around 1, 1 mL of DMSO was added and concentrated. It was purified with reverse-phase HPLC under acidic conditions to give the title compound (62 mg, 0.111 mmol, 97% yield). LC-MS m/z 557.0 (M+H)$^+$, 0.98 min (ret. time).

Example 58. (R)-5-(2-(1-Methyl-1H-1,2,3-triazol-4-yl)ethyl)-1-(3'-(2-propylpiperidine-1-carbonyl)-[1,1'-biphenyl]-3-yl)-1H-pyrazole-4-carboxylic Acid

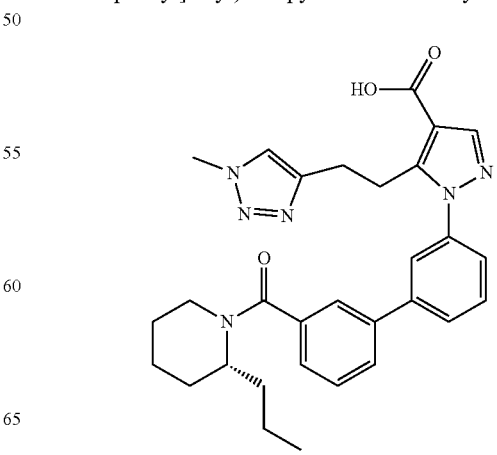

58a) (R)-(2-Propylpiperidin-1-yl)(3-(4,4,5,5-tetramethyl-1,3,2-dioxaborolan-2-yl)phenyl)methanone and (R)-(3-(2-propylpiperidine-1-carbonyl)phenyl) boronic Acid

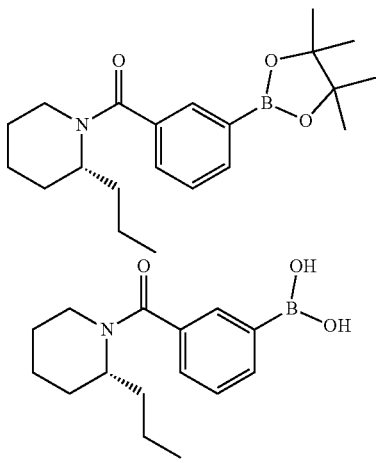

A solution of 50 wt % T$_3$P in EtOAc (1.560 mL, 2.62 mmol) was added to a solution of 3-(4,4,5,5-tetramethyl-1,3,2-dioxaborolan-2-yl)benzoic acid (500 mg, 2.015 mmol), (R)-2-propylpiperidine (269 mg, 2.116 mmol), and TEA (1.118 mL, 8.06 mmol) in DCM (10 mL) at 0° C. The ice bath was removed, and the reaction was stirred at room temperature for 1 h, storing in freezer for 76 h. The reaction was quenched with saturated NaHCO$_3$, and extracted with DCM twice. The organic layer was washed with brine, dried (Na$_2$SO$_4$). It was filtered and concentrated to give a mixture of (R)-(2-propylpiperidin-1-yl)(3-(4,4,5,5-tetramethyl-1,3,2-dioxaborolan-2-yl)phenyl)methanone (650 mg, 1.819 mmol, 90% yield) and (R)-(3-(2-propylpiperidine-1-carbonyl)phenyl)boronic acid. It was carried to the next step without purification. LC-MS m/z 358.3 (M+H)$^+$, 1.28 min (ret. time) LC-MS m/z 276.2 (M+H)$^+$, 0.86 min (ret. time).

58b) (R)-5-(2-(1-Methyl-1H-1,2,3-triazol-4-yl)ethyl)-1-(3'-(2-propylpiperidine-1-carbonyl)-[1,1'-biphenyl]-3-yl)-1H-pyrazole-4-carboxylic Acid

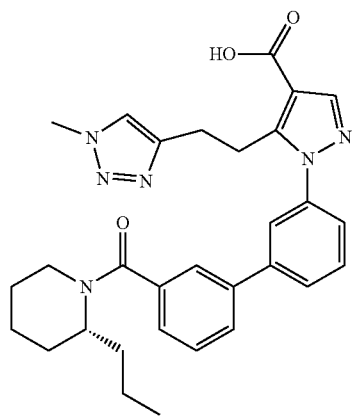 [SMILES: CCC[C@@H]1CCCCN1C(=O)c1cccc(-c2cccc(-n3ncc(C(=O)O)c3CCc3cn(C)nn3)c2)c1]

A mixture of (R)-(3-(2-propylpiperidine-1-carbonyl)phenyl)boronic acid and (R)-(2-propylpiperidin-1-yl)(3-(4,4,5,5-tetramethyl-1,3,2-dioxaborolan-2-yl)phenyl)methanone (100 mg, 0.280 mmol), methyl 1-(3-bromophenyl)-5-(2-(1-methyl-1H-1,2,3-triazol-4-yl)ethyl)-1H-pyrazole-4-carboxylate (109 mg, 0.280 mmol), Na$_2$CO$_3$ (89 mg, 0.840 mmol) and PdCl$_2$(dppf) (20.48 mg, 0.028 mmol) in 1,4-dioxane (3 mL) and water (1 mL) was degassed for 5 min and then heated under microwave for 15 min at 100° C. 30 mg of (R)-(3-(2-propylpiperidine-1-carbonyl)phenyl)boronic acid and (R)-(2-propylpiperidin-1-yl)(3-(4,4,5,5-tetramethyl-1,3,2-dioxaborolan-2-yl)phenyl)methanone was added and heated under microwave for 10 min at 100° C. It was passed through Celite® and washed with ethyl acetate twice. The combined organic layer was washed with brine and then concentrated to give crude product. It was redissolved in MeOH (3 mL), 2 M LiOH (0.840 mL, 1.679 mmol) was added and heated under microwave for 30 min at 80° C. The reaction mixture was acidified with 1 N HCl to pH around 1, 1 mL of DMSO was added and concentrated. It was purified with reverse-phase HPLC under acidic conditions to give the title compound (63.7 mg, 0.121 mmol, 43.2% yield) was obtained. LC-MS m/z 527.1 (M+H)$^+$, 0.99 min (ret. time).

Example 59. 1-(3'-Isopropoxy-[1,1'-biphenyl]-3-yl)-5-(2-(1-methyl-1H-1,2,3-triazol-4-yl)cyclopropyl)-1H-pyrazole-4-carboxylic Acid

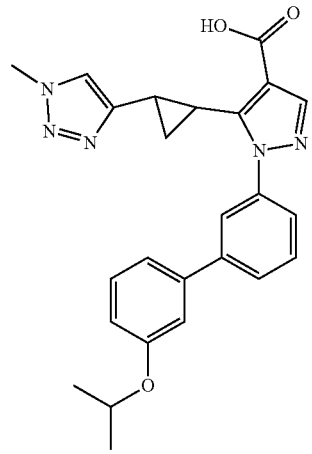 [SMILES: CC(C)Oc1cccc(-c2cccc(-n3ncc(C(=O)O)c3C3CC3c3cn(C)nn3)c2)c1]

59a) Ethyl 1-(3'-isopropoxy-[1,1'-biphenyl]-3-yl)-5-(2-(1-methyl-1H-1,2,3-triazol-4-yl)cyclopropyl)-1H-pyrazole-4-carboxylate

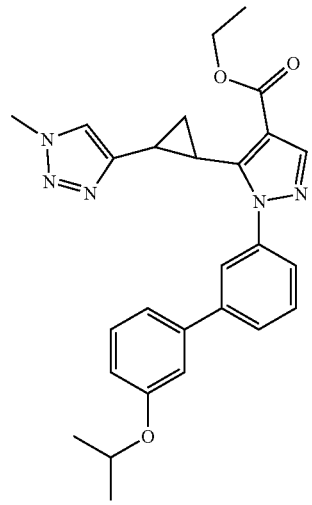 [SMILES: CCOC(=O)c1cnn(-c2cccc(-c3cccc(OC(C)C)c3)c2)c1C1CC1c1cn(C)nn1]

To a solution of ethyl 1-(3-bromophenyl)-5-(2-(1-methyl-1H-1,2,3-triazol-4-yl)cyclopropyl)-1H-pyrazole-4-carboxylate (100 mg, 0.240 mmol) in tetrahydrofuran (THF) (5 mL) and water (1 mL) was added sodium carbonate (50.9 mg, 0.480 mmol), (3-isopropoxyphenyl)boronic acid (51.9 mg, 0.288 mmol). The reaction mixture was purged with nitrogen for 10 min, and Pd(Ph₃P)₄ (27.8 mg, 0.024 mmol) was added. It was heated to 70° C. for 5 h. The crude residue was diluted with water (20 mL) and extracted with ethyl acetate (20 mL×2). The organic layer was washed with brine solution (10 mL) and dried over anhydrous Na₂SO₄, filtered, and concentrated. The crude residue was purified with silica gel chromatography eluting with 15% ethyl acetate in hexane to afford the title compound (50 mg, 0.088 mmol, 36.8% yield) as white solid. LC-MS m/z 472.07 (M+H)⁺, 2.657 min (ret. time).

59b) 1-(3'-Isopropoxy-[1,1'-biphenyl]-3-yl)-5-(2-(1-methyl-1H-1,2,3-triazol-4-yl)cyclopropyl)-1H-pyrazole-4-carboxylic Acid

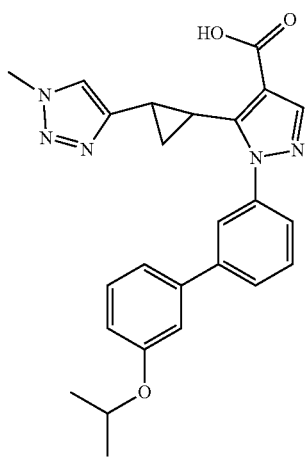 [SMILES: CC(C)Oc1cccc(-c2cccc(-n3ncc(C(=O)O)c3C3CC3c3cn(C)nn3)c2)c1]

To a solution of ethyl 1-(3'-isopropoxy-[1,1'-biphenyl]-3-yl)-5-(2-(1-methyl-1H-1,2,3-triazol-4-yl)cyclopropyl)-1H-pyrazole-4-carboxylate (200 mg, 0.424 mmol) in Ethanol (5 mL) was added 1M NaOH in water (0.424 mL, 0.424 mmol). It was stirred at 25° C. for 5 h. The reaction mixture was concentrated. The residue was cooled and acidified with 1N HCl solution to pH 4. Solid was filtered, washed with water and dried to afford title compound (70 mg, 0.150 mmol, 35.4% yield) as off-white solid. LC-MS m/z 223.90 (M+H)⁺, 2.97 min (ret. time)

Example 60. 1-(3'-(1-Cyclohexylethoxy)-[1,1'-biphenyl]-3-yl)-5-cyclopropyl-1H-pyrazole-4-carboxylic Acid

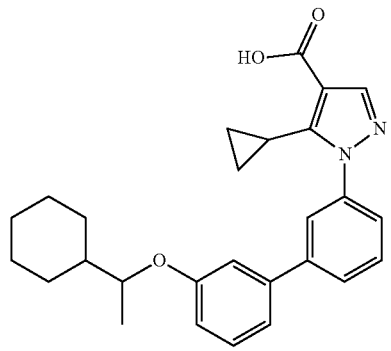 [SMILES: CC(Oc1cccc(-c2cccc(-n3ncc(C(=O)O)c3C3CC3)c2)c1)C1CCCCC1]

60a) Ethyl 5-cyclopropyl-1-(3'-hydroxy-[1,1'-biphenyl]-3-yl)-1H-pyrazole-4-carboxylate

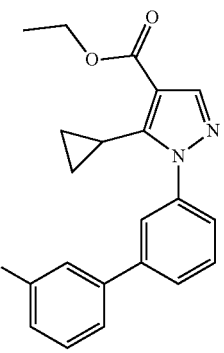

To a solution of ethyl 1-(3-bromophenyl)-5-cyclopropyl-1H-pyrazole-4-carboxylate (1 g, 2.98 mmol) in tetrahydrofuran (THF) (4 mL) was added (3-hydroxyphenyl)boronic acid (0.617 g, 4.47 mmol), sodium carbonate (0.632 g, 5.97 mmol) and water (1 mL). The reaction mixture was degassed with argon for 10 min and then added tetrakis(triphenylphosphine)palladium(0) (0.345 g, 0.298 mmol) was added and stirred at 80° C. for 16 h. The reaction mixture was diluted with water and extracted with ethyl acetate (3×80 mL). The combined organic layer was washed with brine solution (100 mL), dried over anhydrous Na₂SO₄ and concentrated. The crude residue was purified with silica gel chromatography, eluting with 40% ethyl acetate in n-Hexane. Desired fractions were combined to give the title compound (900 mg, 2.58 mmol, 87% yield). ¹H NMR (400 MHz, CDCl₃) δ: 8.04 (s, 1H), 7.71 (t, J=1.9 Hz, 1H), 7.60 (dt, J=7.4, 1.7 Hz, 1H), 7.56-7.45 (m, 2H), 7.31 (t, J=7.9 Hz, 1H), 7.20-7.13 (m, 1H), 7.04 (t, J=2.0 Hz, 1H), 6.84 (ddd, J=8.0, 2.5, 1.0 Hz, 1H), 5.14 (s, 1H), 4.34 (q, J=7.1 Hz, 2H), 2.02 (tt, J=8.5, 5.5 Hz, 1H), 1.38 (t, J=7.1 Hz, 3H), 1.01-0.90 (m, 2H), 0.73-0.64 (m, 2H).

60b) (1-Chloroethyl)cyclohexane

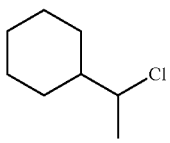

To a solution of 1-cyclohexylethanol (1 g, 7.80 mmol) in dichloromethane (DCM) (15 mL) was added thionyl chloride (1.139 mL, 15.60 mmol) at 0° C. and stirred for 15 min. The reaction mixture was stirred at RT for 2 h. The reaction mixture was quenched with saturated bicarbonate solution and extracted with DCM (3×30 mL). The combined organic layer was washed with water (50 mL) and brine solution (50 mL), dried over anhydrous $Na_2SO_4$, and concentrated to give the title compound (650 mg, 4.43 mmol, 56.8% yield). This material was carried to next step without further purification.

60c) Ethyl 1-(3'-(1-cyclohexylethoxy)-[1,1'-biphenyl]-3-yl)-5-cyclopropyl-1H-pyrazole-4-carboxylate

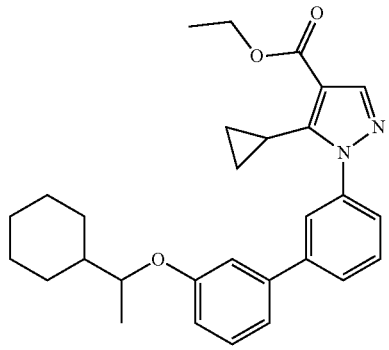 [SMILES: CCOC(=O)c1cnn(-c2cccc(-c3cccc(OC(C)C4CCCCC4)c3)c2)c1C1CC1]

To a solution of ethyl 5-cyclopropyl-1-(3'-hydroxy-[1,1'-biphenyl]-3-yl)-1H-pyrazole-4-carboxylate (450 mg, 1.292 mmol) in N,N-dimethylformamide (DMF) (10 mL) was added cesium carbonate (842 mg, 2.58 mmol) and heated to 100° C. for 1 h in Microwave. The reaction mixture was diluted with ice water and extracted with ethyl acetate (3×40 mL). The combined organic layer was washed with chilled water (3×50 mL) and washed brine solution (100 mL), dried over anhydrous $Na_2SO_4$ and concentrated. The crude residue was purified with silica gel chromatography eluting with 10% ethyl acetate in n-Hexane. Title compound (140 mg, 0.285 mmol, 22.06% yield) was obtained. LC-MS m/z 459.20 (M+H)+, 4.89 min (ret. time).

60d) 1-(3'-(1-Cyclohexylethoxy)-[1,1'-biphenyl]-3-yl)-5-cyclopropyl-1H-pyrazole-4-carboxylic Acid

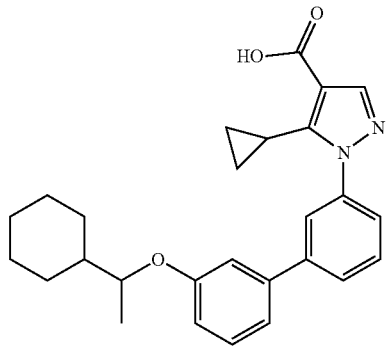 [SMILES: CC(Oc1cccc(-c2cccc(-n3ncc(C(=O)O)c3C3CC3)c2)c1)C1CCCCC1]

To a solution of ethyl 1-(3'-(1-cyclohexylethoxy)-[1,1'-biphenyl]-3-yl)-5-cyclopropyl-1H-pyrazole-4-carboxylate (140 mg, 0.305 mmol) in ethanol (5 mL) was added 2 M NaOH (0.153 mL, 0.305 mmol). It was stirred 25° C. for 3 h. The reaction mixture was concentrated and then diluted with ice. It was acidified with 1N HCl solution till pH 2. It was extracted with ethyl acetate (3×30 mL). The combined organic layer was washed with brine solution (50 mL), and dried over anhydrous $Na_2SO_4$, and concentrated. The crude residue was purified with silica gel chromatography by eluting with MeOH:DCM (0.5:9.5) to give the title compound (60 mg, 0.135 mmol, 44.1% yield) as gummy solid. LC-MS m/z 431.25 (M+H)+, 3.17 min (ret. time).

60e) 1-(3'-(1-Cyclohexylethoxy)-[1,1'-biphenyl]-3-yl)-5-cyclopropyl-1H-pyrazole-4-carboxylic Acid

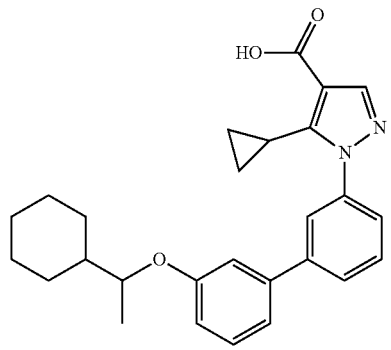 [SMILES: CC(Oc1cccc(-c2cccc(-n3ncc(C(=O)O)c3C3CC3)c2)c1)C1CCCCC1]

A solution of 1-(3'-(1-cyclohexylethoxy)-[1,1'-biphenyl]-3-yl)-5-cyclopropyl-1H-pyrazole-4-carboxylic acid (10 mM, 695 μL in DMSO) was concentrated on the V10 evaporator to afford the title compound (25.7 mg, 0.060 mmol). LC-MS m/z 431.4 (M+H)+, 1.39 min (ret. time)

Example 61: 5-Cyclopropyl-1-(3'-(5,6-dihydrocyclopenta[c]pyrazol-1(4H)-yl)-[1,1'-biphenyl]-3-yl)-1H-pyrazole-4-carboxylic Acid

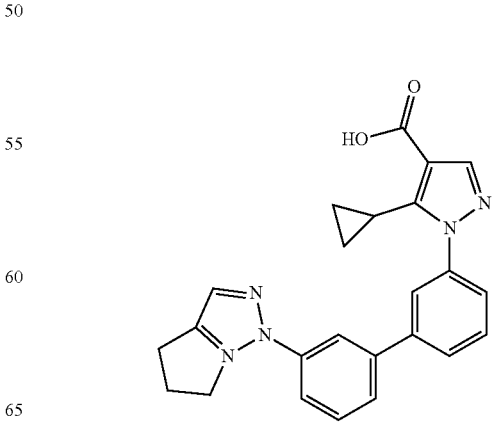

61a) 2-((Dimethylamino)methylene)cyclopentanone

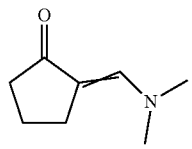

To a solution of cyclopentanone (0.559 mL, 5.94 mmol) in toluene (2 mL) was added N,N-dimethylformamide dimethyl acetal (0.796 ml, 5.94 mmol). The reaction mixture was stirred at 100° C. for 19 hr. The reaction mixture was concentrated to afford the title compound 2-((dimethylamino)methylene)cyclopentanone (237.7 mg, 1.708 mmol, 28.7% yield) which was carried forward without further purification. LC-MS m/z 139.9 M+, 0.88 min (ret. time). 1H NMR (400 MHz, methanol-d4) δ ppm 1.89 (quin, J=7.50 Hz, 2H) 2.22 (t, J=7.91 Hz, 2H) 2.92 (t, J=7.15 Hz, 2H) 3.16 (s, 6H) 7.31 (s, 1H).

61b) Tert-butyl 2-(3-bromophenyl)hydrazinecarboxylate

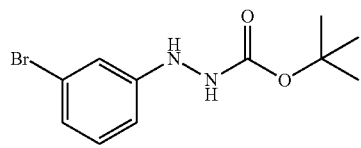 [SMILES: CC(C)(C)OC(=O)NNc1cccc(Br)c1]

To a solution of (3-bromophenyl)hydrazine hydrochloride (3.28 g, 14.66 mmol) and triethylamine (6.13 mL, 44.0 mmol) in dichloromethane (20 mL) was added di-tert-butyl dicarbonate (3.40 mL, 14.66 mmol). The reaction mixture was stirred at ambient temperature for 93 hr. The reaction mixture was quenched with water and extracted with DCM (2×). The combined organic layer was dried over sodium sulfate, filtered and concentrated to afford the title compound tert-butyl 2-(3-bromophenyl)hydrazinecarboxylate (4.1815 g, 14.56 mmol, 99% yield) which was carried forward without further purification. LC-MS m/z 287.0 (M+H)+, 0.96 min (ret. time).

61c) Ethyl 1-(3'-(2-(tert-butoxycarbonyl)hydrazinyl)-[1,1'-biphenyl]-3-yl)-5-cyclopropyl-1H-pyrazole-4-carboxylate

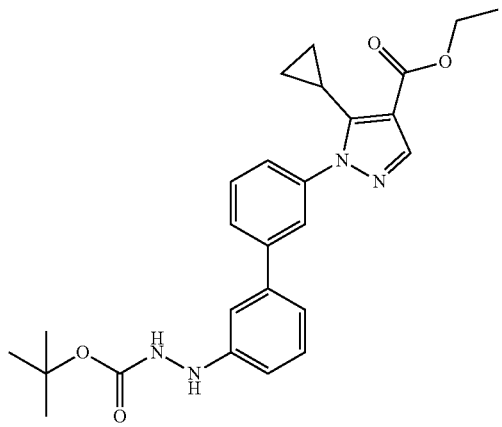 [SMILES: CCOC(=O)c1cnn(-c2cccc(-c3cccc(NNC(=O)OC(C)(C)C)c3)c2)c1C1CC1]

To a solution of ethyl 5-cyclopropyl-1-(3-(4,4,5,5-tetramethyl-1,3,2-dioxaborolan-2-yl)phenyl)-1H-pyrazole-4-carboxylate (1.00 g, 2.62 mmol) and tert-butyl 2-(3-bromophenyl)hydrazinecarboxylate (1.127 g, 3.92 mmol) in a mixture of 1,4-dioxane (12.00 mL) and water (4.00 mL) was added potassium carbonate (0.723 g, 5.23 mmol) and PdCl$_2$(dppf) (0.191 g, 0.262 mmol). The reaction vessel was heated in a Biotage microwave at high absorption for 15 min at 100° C. The reaction was filtered, extracted with EtOAc (3×20 mL) and concentrated to afford the crude product. The crude product was purified by silica gel chromatography to afford the title compound ethyl 1-(3'-(2-(tert-butoxycarbonyl)hydrazinyl)-[1,1'-biphenyl]-3-yl)-5-cyclopropyl-1H-pyrazole-4-carboxylate (650 mg, 1.405 mmol, 74.8% yield). LC-MS m/z 463.2 (M+H)+, 1.18 min (ret. time).

61d) Ethyl 5-cyclopropyl-1-(3'-hydrazinyl-[1,1'-biphenyl]-3-yl)-1H-pyrazole-4-carboxylate Hydrochloride

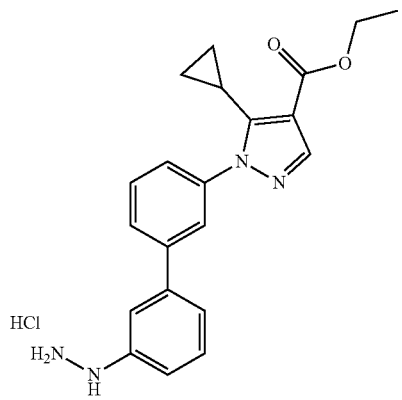 [SMILES: Cl ; CCOC(=O)c1cnn(-c2cccc(-c3cccc(NN)c3)c2)c1C1CC1]

To a solution of ethyl 1-(3'-(2-(tert-butoxycarbonyl)hydrazinyl)-[1,1'-biphenyl]-3-yl)-5-cyclopropyl-1H-pyrazole-4-carboxylate (650 mg, 1.405 mmol) in dichloromethane (6 mL) was added 4 N HCl in dioxane (1.405 mL, 5.62 mmol). The reaction mixture was stirred at ambient temperature for 17 hr. The reaction mixture was concentrated to afford the crude product. Soluble impurities were removed from the crude product via trituration in ether to afford the title compound, ethyl 5-cyclopropyl-1-(3'-hydrazinyl-[1,1'-biphenyl]-3-yl)-1H-pyrazole-4-carboxylate hydrochloride (260.2 mg, 0.718 mmol, 76.4% yield). LC-MS m/z 363.1 (M+H)+, 0.83 min (ret. time).

61d) 5-Cyclopropyl-1-(3'-(5,6-dihydrocyclopenta[c]pyrazol-1(4H)-yl)-[1,1'-biphenyl]-3-yl)-1H-pyrazole-4-carboxylic Acid

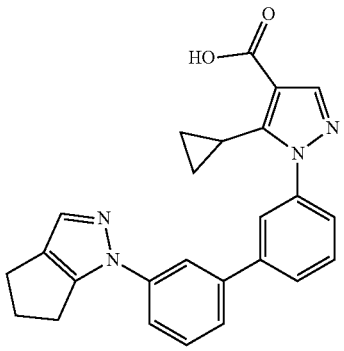 [SMILES: O=C(O)c1cnn(-c2cccc(-c3cccc(-n4ncc5c4CCC5)c3)c2)c1C1CC1]

To a solution of 2-((dimethylamino)methylene)cyclopentanone (30.7 mg, 0.221 mmol) and sodium acetate (18.11 mg, 0.221 mmol) in ethanol (1.5 mL) was added ethyl 5-cyclopropyl-1-(3'-hydrazinyl-[1,1'-biphenyl]-3-yl)-1H-pyrazole-4-carboxylate hydrochloride (80 mg, 0.221 mmol). The reaction mixture was stirred at 70° C. under nitrogen atmosphere for 18 hr. The reaction mixture was concentrated to remove excess solvent. The crude product was dissolved in methanol (2 mL) and to the reaction mixture was added 2 M LiOH (0.441 mL, 0.883 mmol). The reaction vessel was heated in a Biotage microwave at high absorption for 10 min at 100° C. The reaction was neutralized with 1 N HCl (1 mL) and concentrated to afford the crude product. The crude product was dissolved in DMSO (2 mL), filtered through a 0.45 μm acrodisc, and purified with reverse-phase HPLC under acidic conditions to afford the title compound 5-cyclopropyl-1-(3'-(5,6-dihydrocyclopenta[c]pyrazol-1(4H)-yl)-[1,1'-biphenyl]-3-yl)-1H-pyrazole-4-carboxylic acid (13.57 mg, 0.033 mmol, 14.98% yield). LC-MS m/z 411.1 (M+H)+, 1.10 min (ret. time). 1H NMR (400 MHz, methanol-d4) δ ppm 0.68 (d, J=5.27 Hz, 2H) 0.97 (d, J=8.03 Hz, 2H) 2.10-2.19 (m, 1H) 2.71 (m, J=15.90, 6.10 Hz, 4H) 3.09 (t, J=6.65 Hz, 2H) 7.43 (s, 1H) 7.57-7.73 (m, 5H) 7.86 (d, J=7.28 Hz, 1H) 7.91 (s, 1H) 7.98 (s, 1H) 8.05 (s, 1H).

Example 62: 5-cyclopropyl-1-(3'-(4,5,6,7-tetrahydro-1H-indazol-1-yl)-[1,1'-biphenyl]-3-yl)-1H-pyrazole-4-carboxylic Acid

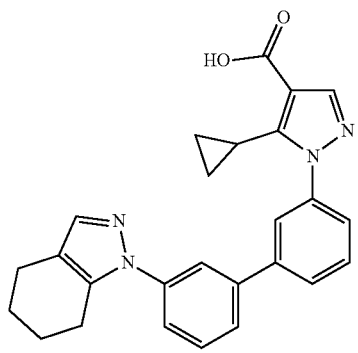 [SMILES: O=C(O)c1cnn(-c2cccc(-c3cccc(-n4ncc5c4CCCC5)c3)c2)c1C1CC1]

62a) 2-((Dimethylamino)methylene)cyclohexanone

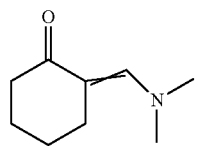

1-Tert-butoxy-N,N,N',N'-tetramethylmethanediamine (533 mg, 3.06 mmol) was added drop wise to cyclohexanone (300 mg, 3.06 mmol). The reaction mixture was stirred at ambient temperature under nitrogen atmosphere for 1.5 hr, then at 110° C. for 4 hr. The reaction mixture was diluted with water (1 mL) and extracted with EtOAc (3×1 mL). The combined organic layer was concentrated to afford the title compound 2-((dimethylamino)methylene)cyclohexanone (296.2 mg, 1.933 mmol, 63.2% yield). LC-MS m/z 154.9 (M+H)+, 0.67 min (ret. time).

62b) Tert-butyl 2-(3-bromophenyl)hydrazinecarboxylate

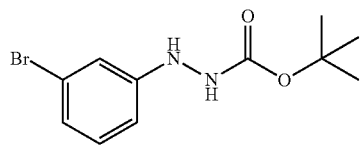 [SMILES: CC(C)(C)OC(=O)NNc1cccc(Br)c1]

To a solution of (3-bromophenyl)hydrazine hydrochloride (3.28 g, 14.66 mmol) and triethylamine (6.13 mL, 44.0 mmol) in dichloromethane (20 mL) was added di-tert-butyl dicarbonate (3.40 mL, 14.66 mmol). The reaction mixture was stirred at ambient temperature for 93 hr. The reaction mixture was quenched with water and extracted with DCM (2×). The combined organic layer was dried over sodium sulfate, filtered, and concentrated to afford the title compound tert-butyl 2-(3-bromophenyl)hydrazinecarboxylate (4.1815 g, 14.56 mmol, 99% yield) which was carried forward without further purification. LC-MS m/z 287.0 (M+H)+, 0.96 min (ret. time).

62c) Ethyl 1-(3'-(2-(tert-butoxycarbonyl)hydrazinyl)-[1,1'-biphenyl]-3-yl)-5-cyclopropyl-1H-pyrazole-4-carboxylate

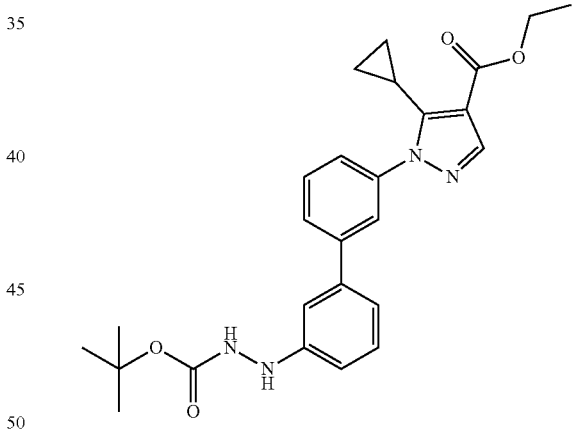

To a solution of ethyl 5-cyclopropyl-1-(3-(4,4,5,5-tetramethyl-1,3,2-dioxaborolan-2-yl)phenyl)-1H-pyrazole-4-carboxylate (1.00 g, 2.62 mmol) and tert-butyl 2-(3-bromophenyl)hydrazinecarboxylate (1.127 g, 3.92 mmol) in a mixture of 1,4-dioxane (12.00 mL) and water (4.00 mL) was added potassium carbonate (0.723 g, 5.23 mmol) and PdCl2(dppf) (0.191 g, 0.262 mmol). The reaction vessel was heated in a Biotage microwave at high absorption for 15 min at 100° C. The reaction was filtered, extracted with ethyl acetate (3×20 mL) and concentrated to afford the crude product. The crude product was purified by silica gel chromatography to afford the title compound ethyl 1-(3'-(2-(tert-butoxycarbonyl)hydrazinyl)-[1,1'-biphenyl]-3-yl)-5-cyclopropyl-1H-pyrazole-4-carboxylate (650 mg, 1.405 mmol, 74.8% yield). LC-MS m/z 463.2 (M+H)+, 1.18 min (ret. time).

62d) Ethyl 5-cyclopropyl-1-(3'-hydrazinyl-[1,1'-biphenyl]-3-yl)-1H-pyrazole-4-carboxylate Hydrochloride

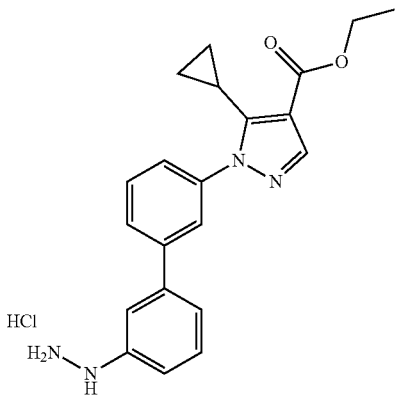

To a solution of ethyl 1-(3'-(2-(tert-butoxycarbonyl)hydrazinyl)-[1,1'-biphenyl]-3-yl)-5-cyclopropyl-1H-pyrazole-4-carboxylate (650 mg, 1.405 mmol) in dichloromethane (6 mL) was added 4 N HCl in dioxane (1.405 mL, 5.62 mmol). The reaction mixture was stirred at ambient temperature for 17 hr. The reaction mixture was concentrated to afford the crude product. Soluble impurities were removed from the crude product via trituration in ether to afford the title compound, ethyl 5-cyclopropyl-1-(3'-hydrazinyl-[1,1'-biphenyl]-3-yl)-1H-pyrazole-4-carboxylate hydrochloride (260.2 mg, 0.718 mmol, 76.4% yield). LC-MS m/z 363.1 (M+H)$^+$, 0.83 min (ret. time).

62e) Ethyl 5-cyclopropyl-1-(3'-(4,5,6,7-tetrahydro-1H-indazol-1-yl)-[1,1'-biphenyl]-3-yl)-1H-pyrazole-4-carboxylate

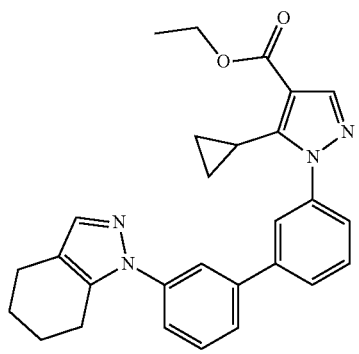 [SMILES: CCOC(=O)c1cnn(-c2cccc(-c3cccc(-n4ncc5c4CCCC5)c3)c2)c1C1CC1]

To a solution of ethyl 5-cyclopropyl-1-(3'-hydrazinyl-[1,1'-biphenyl]-3-yl)-1H-pyrazole-4-carboxylate (80 mg, 0.221 mmol) in acetic acid (1.5 mL) was added 2-((dimethylamino)methylene)cyclohexanone (33.8 mg, 0.221 mmol). The reaction mixture was stirred at 100° C. for 3 hr. The reaction mixture was concentrated to afford the crude product. The crude product was dissolved in DMSO (2 mL) and purified with reverse-phase HPLC under neutral conditions to afford the title compound, ethyl 5-cyclopropyl-1-(3'-(4,5,6,7-tetrahydro-1H-indazol-1-yl)-[1,1'-biphenyl]-3-yl)-1H-pyrazole-4-carboxylate (33.6 mg, 0.074 mmol, 33.6% yield). LC-MS m/z 453.2 (M+H)$^+$, 1.34 min (ret. time). $^1$H NMR (400 MHz, methanol-d$_4$) δ ppm 0.65 (d, J=5.27 Hz, 2H) 0.97 (d, J=8.53 Hz, 2H) 1.41 (t, J=7.03 Hz, 3H) 1.86 (d, J=5.02 Hz, 4H) 2.10-2.20 (m, 1H) 2.60-2.67 (m, 2H) 2.77-2.85 (m, 2H) 4.35 (q, J=7.11 Hz, 2H) 7.49 (s, 1H) 7.53 (d, J=8.03 Hz, 1H) 7.58-7.71 (m, 3H) 7.75 (d, J=7.78 Hz, 1H) 7.81-7.88 (m, 2H) 7.90 (s, 1H) 8.05 (s, 1H).

62f) 5-Cyclopropyl-1-(3'-(4,5,6,7-tetrahydro-1H-indazol-1-yl)-[1,1'-biphenyl]-3-yl)-1H-pyrazole-4-carboxylic Acid

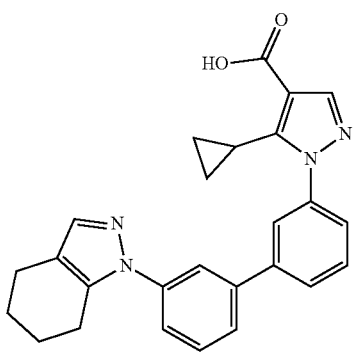 [SMILES: O=C(O)c1cnn(-c2cccc(-c3cccc(-n4ncc5c4CCCC5)c3)c2)c1C1CC1]

To a solution of ethyl 5-cyclopropyl-1-(3'-(4,5,6,7-tetrahydro-1H-indazol-1-yl)-[1,1'-biphenyl]-3-yl)-1H-pyrazole-4-carboxylate (33.6 mg, 0.074 mmol) in methanol (1 mL) was added 2M LiOH (0.223 mL, 0.445 mmol). The reaction vessel was heated in a Biotage microwave at high absorption for 30 min at 80° C. The reaction mixture was neutralized with 1 N HCl (1 mL) and concentrated. The crude product was dissolved in DMSO (2 mL) and purified with reverse-phase HPLC under acidic conditions to afford the title compound 5-cyclopropyl-1-(3'-(4,5,6,7-tetrahydro-1H-indazol-1-yl)-[1,1'-biphenyl]-3-yl)-1H-pyrazole-4-carboxylic acid (24.0 mg, 0.057 mmol, 76% yield). LC-MS m/z 425.4 (M+H)$^+$, 1.08 min (ret. time). $^1$H NMR (400 MHz, METHANOL-d$_4$) δ ppm 0.67 (d, J=5.27 Hz, 2H) 0.95 (d, J=8.28 Hz, 2H) 1.86 (d, J=4.77 Hz, 4H) 2.08-2.17 (m, 1H) 2.61-2.66 (m, 2H) 2.77-2.82 (m, 2H) 7.51-7.55 (m, 2H) 7.58-7.71 (m, 3H) 7.75 (d, J=7.78 Hz, 1H) 7.83 (s, 2H) 7.89 (s, 1H) 8.04 (s, 1H).

Example 63: 5-Cyclopropyl-1-(3'-(6,6-dimethyl-5,6-dihydrocyclopenta[c]pyrazol-1(4H)-yl)-[1,1'-biphenyl]-3-yl)-1H-pyrazole-4-carboxylic Acid

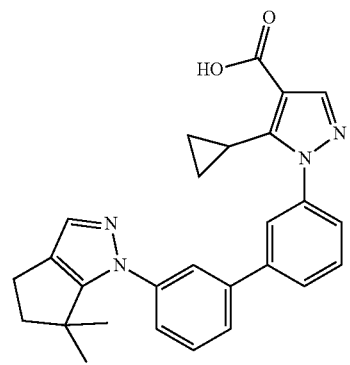 [SMILES: CC1(C)CCc2cnn(-c3cccc(-c4cccc(-n5ncc(C(=O)O)c5C5CC5)c4)c3)c21]

63a) 5-((Dimethylamino)methylene)-2,2-dimethylcyclopentanone

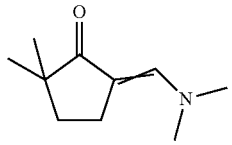

To a solution of 2,2-dimethylcyclopentanone (200 mg, 1.783 mmol) in toluene (1 mL) was added N,N-dimethylformamide dimethyl acetal (0.239 mL, 1.783 mmol). The reaction mixture was stirred at 100° C. for 22 hr. The reaction mixture was concentrated to afford the title compound 5-((dimethylamino)methylene)-2,2-dimethylcyclopentanone (288.8 mg, 1.727 mmol, 97% yield) which was carried forward without further purification. LC-MS m/z 167.9 (M+H)$^+$, 0.69 min (ret. time).

63b) Tert-butyl 2-(3-bromophenyl)hydrazinecarboxylate

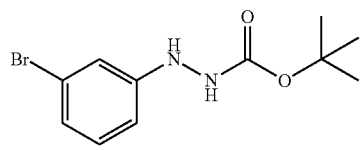

To a solution of (3-bromophenyl)hydrazine hydrochloride (3.28 g, 14.66 mmol) and triethylamine (6.13 mL, 44.0 mmol) in dichloromethane (20 mL) was added di-tert-butyl dicarbonate (3.40 mL, 14.66 mmol). The reaction mixture was stirred at ambient temperature for 93 hr. The reaction mixture was quenched with water and extracted with DCM (2×). The combined organic layer was dried over sodium sulfate, filtered and concentrated to afford the title compound tert-butyl 2-(3-bromophenyl)hydrazinecarboxylate (4.1815 g, 14.56 mmol, 99% yield) which was carried forward without further purification. LC-MS m/z 287.0 (M+H)$^+$, 0.96 min (ret. time).

63c) Ethyl 1-(3'-(2-(tert-butoxycarbonyl)hydrazinyl)-[1,1'-biphenyl]-3-yl)-5-cyclopropyl-1H-pyrazole-4-carboxylate

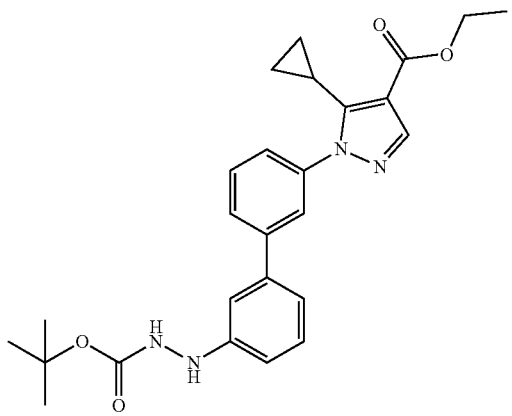 [SMILES: CCOC(=O)c1cnn(-c2cccc(-c3cccc(NNC(=O)OC(C)(C)C)c3)c2)c1C1CC1]

To a solution of tert-butyl 2-(3-bromophenyl)hydrazinecarboxylate (1.127 g, 3.92 mmol) and ethyl 5-cyclopropyl-1-(3-(4,4,5,5-tetramethyl-1,3,2-dioxaborolan-2-yl)phenyl)-1H-pyrazole-4-carboxylate (1.00 g, 2.62 mmol) in a mixture of 1,4-dioxane (12 mL) and water (4.00 mL) was added potassium carbonate (0.723 g, 5.23 mmol) and PdCl$_2$(dppf) (0.191 g, 0.262 mmol). The reaction vessel was heated in a Biotage microwave at high absorption for 15 min at 100° C. The reaction was filtered, extracted with ethyl acetate (3×20 mL), and concentrated to afford the crude product. The crude product was purified by silica gel chromatography to afford the title compound ethyl 1-(3'-(2-(tert-butoxycarbonyl)hydrazinyl)-[1,1'-biphenyl]-3-yl)-5-cyclopropyl-1H-pyrazole-4-carboxylate (650 mg, 1.405 mmol, 74.8% yield). LC-MS m/z 463.2 (M+H)$^+$, 1.18 min (ret. time).

63d) Ethyl 5-cyclopropyl-1-(3'-hydrazinyl-[1,1'-biphenyl]-3-yl)-1H-pyrazole-4-carboxylate Hydrochloride

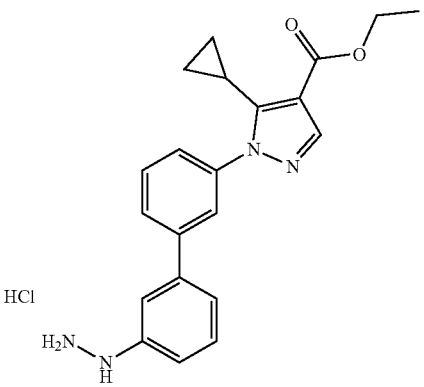 [SMILES: Cl ; CCOC(=O)c1cnn(-c2cccc(-c3cccc(NN)c3)c2)c1C1CC1]

To a solution of ethyl 1-(3'-(2-(tert-butoxycarbonyl)hydrazinyl)-[1,1'-biphenyl]-3-yl)-5-cyclopropyl-1H-pyrazole-4-carboxylate (650 mg, 1.405 mmol) in dichloromethane (6 mL) was added 4 N HCl in dioxane (1.405 mL, 5.62 mmol). The reaction mixture was stirred at ambient temperature for 17 hr. The reaction mixture was concentrated to afford the crude product. Soluble impurities were removed from the crude product via trituration in ether to afford the title compound, ethyl 5-cyclopropyl-1-(3'-hydrazinyl-[1,1'-biphenyl]-3-yl)-1H-pyrazole-4-carboxylate hydrochloride (260.2 mg, 0.718 mmol, 76.4% yield).

63e) Ethyl 5-cyclopropyl-1-(3'-(6,6-dimethyl-5,6-dihydrocyclopenta[c]pyrazol-1(4H)-yl)-[1,1'-biphenyl]-3-yl)-1H-pyrazole-4-carboxylate (N31313-1)

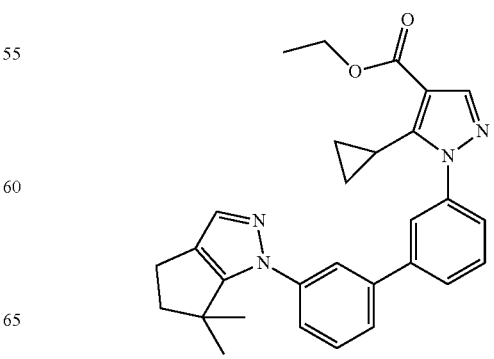

To a solution of 5-((dimethylamino)methylene)-2,2-dimethylcyclopentanone (23.07 mg, 0.138 mmol) in acetic acid (1.5 mL) was added ethyl 5-cyclopropyl-1-(3'-hydrazinyl-[1,1'-biphenyl]-3-yl)-1H-pyrazole-4-carboxylate (50 mg, 0.138 mmol). The reaction mixture was stirred at 100° C. for 3 hr. The reaction mixture was stirred at ambient temperature for an additional 16 hr. The reaction mixture was concentrated and the crude product was dissolved in DMSO (2 mL) and purified with reverse-phase HPLC under neutral conditions to afford the title compound ethyl 5-cyclopropyl-1-(3'-(6,6-dimethyl-5,6-dihydrocyclopenta[c]pyrazol-1(4H)-yl)-[1,1'-biphenyl]-3-yl)-1H-pyrazole-4-carboxylate (19.9 mg, 0.043 mmol, 30.9% yield). LC-MS m/z 467.2 (M+H)+, 1.39 min (ret. time).

63f) 5-Cyclopropyl-1-(3'-(6,6-dimethyl-5,6-dihydrocyclopenta[c]pyrazol-1(4H)-yl)-[1,1'-biphenyl]-3-yl)-1H-pyrazole-4-carboxylic Acid

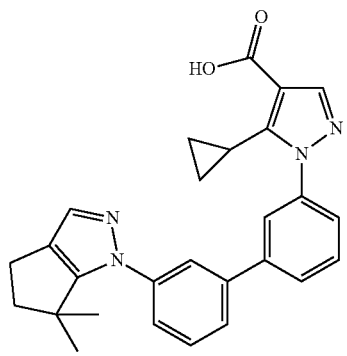 [SMILES: CC1(C)CCc2cnn(-c3cccc(-c4cccc(-n5ncc(C(=O)O)c5C5CC5)c4)c3)c21]

To a solution of ethyl 5-cyclopropyl-1-(3'-(6,6-dimethyl-5,6-dihydrocyclopenta[c]pyrazol-1(4H)-yl)-[1,1'-biphenyl]-3-yl)-1H-pyrazole-4-carboxylate (19.9 mg, 0.043 mmol) in MeOH (1 mL) was added 2M LiOH (0.085 mL, 0.171 mmol). The reaction vessel was heated in a Biotage microwave at high absorption for 30 min at 80° C. The reaction mixture was neutralized with 1 N HCl (1 mL) and concentrated to afford the crude product. The crude product was dissolved in DMSO (2 mL) and purified with reverse-phase HPLC under acidic conditions to afford the title compound, 5-cyclopropyl-1-(3'-(6,6-dimethyl-5,6-dihydrocyclopenta[c]pyrazol-1(4H)-yl)-[1,1'-biphenyl]-3-yl)-1H-pyrazole-4-carboxylic acid (3.53 mg, 8.05 µmol, 18.87% yield). LC-MS m/z 439.4 (M+H)+, 1.13 min (ret. time). $^1$H NMR (400 MHz, methanol-$d_4$) δ ppm 0.67 (d, J=5.27 Hz, 2H) 0.95 (d, J=8.28 Hz, 2H) 1.30 (s, 6H) 2.44 (t, J=6.78 Hz, 2H) 2.65-2.73 (m, 3H) 7.38 (s, 1H) 7.52 (d, J=8.03 Hz, 1H) 7.60-7.73 (m, 3H) 7.78-7.87 (m, 3H) 7.90 (s, 1H) 8.04 (s, 1H).

Example 64. 1-(3'-((S)-1-Cyclohexylethoxy)-[1,1'-biphenyl]-3-yl)-5-((1R,2R)-2-(1-methyl-1H-1,2,3-triazol-4-yl)cyclopropyl)-1H-pyrazole-4-carboxylic Acid

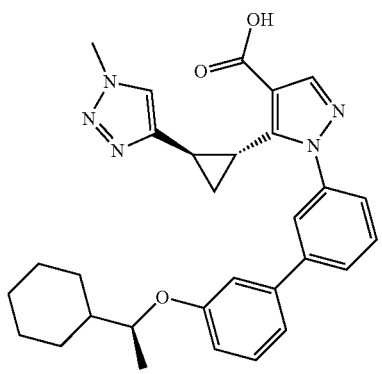 [SMILES: C[C@H](Oc1cccc(-c2cccc(-n3ncc(C(=O)O)c3[C@@H]3C[C@H]3c3cn(C)nn3)c2)c1)C1CCCCC1]

64a) 4-(Diethoxymethyl)-1-methyl-1H-1,2,3-triazole

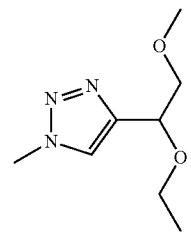

A solution of iodomethane (166 g, 1170 mmol) in tert-butanol (500 mL) was added to NaHCO$_3$ (98 g, 1170 mmol), copper(II) sulfate (12.45 g, 78 mmol), sodium azide (76 g, 1170 mmol) and sodium (R)-2-((S)-1,2-dihydroxyethyl)-4-hydroxy-5-oxo-2,5-dihydrofuran-3-olate (30.9 g, 156 mmol) in water (500 mL) slowly at room temperature. Then 3,3-diethoxyprop-1-yne (50 g, 390 mmol) was added. The reaction mixture was stirred at 60° C. for 16 h. The reaction mixture was extracted with ethyl acetate (3×1000 mL). The combined organic layer was dried with MgSO$_4$ and concentrated to obtain the title compound 4-(diethoxymethyl)-1-methyl-1H-1,2,3-triazole (46 g, 236 mmol, 60.5% yield) which was carried over to next step without further purification. LC-MS m/z 186.1 (M+H)+, 1.46 min (ret. time).

64b) 1-Methyl-1H-1,2,3-triazole-4-carbaldehyde

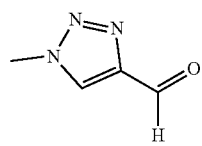

To a solution of 4-(diethoxymethyl)-1-methyl-1H-1,2,3-triazole (46 g, 248 mmol) in water (200 mL), TFA (100 mL, 649 mmol) was added. The reaction mixture was stirred at room temperature for 1 h. The water was evaporated and dried under vacuum to get the title compound, 1-methyl-1H-1,2,3-triazole-4-carbaldehyde (26 g, 234 mmol, 94% yield) as a yellow solid. LC-MS m/z 112.2 (M+H)+, 0.51 min (ret. time).

64c) (Z)-Tert-butyl 3-(1-methyl-1H-1,2,3-triazol-4-yl)acrylate

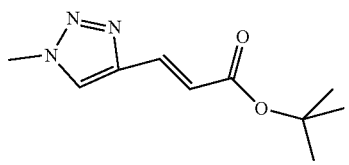

To a solution of tert-butyl 2-(diethoxyphosphoryl)acetate (62.4 g, 248 mmol) in tetrahydrofuran (500 mL), sodium hydride (10.80 g, 270 mmol, 60%) was added at 0° C. The reaction mixture was stirred at 0° C. under $N_2$ for 10 min. Then a solution of 1-methyl-1H-1,2,3-triazole-4-carbaldehyde (25 g, 225 mmol) in THF (500 mL) was added dropwise and the reaction mixture was stirred at 0° C. for 15 min. Water (500 mL) was added and extracted with ethyl acetate (3×300 mL). The combined organic layer was washed with water (2×100 mL) and brine (2×100 mL), dried over $Na_2SO_4$ and concentrated. The crude product was purified by Combiflash chromatography (hexane:ethyl acetate=1:5) to give the title compound (Z)-tert-butyl 3-(1-methyl-1H-1,2,3-triazol-4-yl)acrylate (40 g, 184 mmol, 82% yield) as an oil. LC-MS m/z 210.1 (M+H)+, 1.73 min (ret. time).

64d) tert-Butyl 2-(1-methyl-1H-1,2,3-triazol-4-yl)cyclopropanecarboxylate

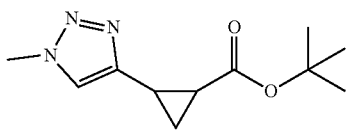

To a solution of trimethylsulfoxonium iodide (126 g, 573 mmol) in dimethyl sulfoxide (300 mL), sodium hydride (16.06 g, 401 mmol) was added at 0° C. The reaction mixture was stirred at room temperature under $N_2$ for 1 h. Then a solution of (E)-tert-butyl 3-(1-methyl-1H-1,2,3-triazol-4-yl)acrylate (40 g, 191 mmol) in tetrahydrofuran (300 mL) was added dropwise. The reaction mixture was stirred at room temperature for 1 hr and heated to 50° C. for another 1 h. Then 200 mL of ethyl acetate and 250 mL of water were added. The water layer was extracted with ethyl acetate (3×250 mol), the combined organic layer was dried with $Na_2SO_4$ and concentrated to get tert-butyl 2-(1-methyl-1H-1,2,3-triazol-4-yl)cyclopropanecarboxylate (36 g, 144 mmol, 75% yield). LC-MS m/z 224.1 (M+H)+, 1.69 min (ret. time).

64e) 2-(1-Methyl-1H-1,2,3-triazol-4-yl)cyclopropanecarboxylic Acid

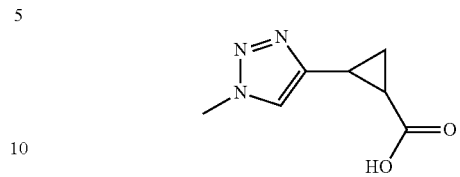

A solution of tert-butyl 2-(1-methyl-1H-1,2,3-triazol-4-yl)cyclopropanecarboxylate (36 g, 161 mmol) in dichloromethane (400 mL), TFA (200 mL, 2596 mmol) was added slowly under nitrogen at room temperature. The reaction mixture was stirred at room temperature for 4 h Then it was concentrated. 100 mL of ethyl acetate and 100 mL of water were added to residue. The water layer was extracted with ethyl acetate (3×100 mL). The combined organic phase was dried with $MgSO_4$ and concentrated to get title compound 2-(1-methyl-1H-1,2,3-triazol-4-yl)cyclopropanecarboxylic acid (24 g, 134 mmol, 83% yield) as a white solid. LC-MS m/z 168.1 (M+H)+, 1.16 min (ret. time).

64f) Methyl 3-(2-(1-methyl-1H-1,2,3-triazol-4-yl)cyclopropyl)-3-oxopropanoate

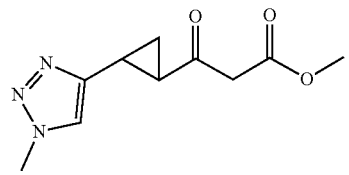 [SMILES: COC(=O)CC(=O)C1CC1c1cn(C)nn1]

To a solution of 2-(1-methyl-1H-1,2,3-triazol-4-yl)cyclopropanecarboxylic acid (24 g, 144 mmol) in tetrahydrofuran (700 mL), was added CDI (30.3 g, 215 mmol) was added. The reaction mixture was stirred at room temperature for 2 h. Then potassium 3-methoxy-3-oxopropanoate (67.3 g, 431 mmol) was added. The reaction mixture was stirred at room temperature for 18 h. The solvent was evaporated and re-dissolved in ethyl acetate (200 mL). Then it was washed with 1 M $KHSO_4$ (150 mL), saturated $NaHCO_3$ (150 mL) and brine (150 mL). The organic layer was dried with $Na_2SO_4$ and concentrated to obtain the title compound methyl 3-(2-(1-methyl-1H-1,2,3-triazol-4-yl)cyclopropyl)-3-oxopropanoate (20 g, 85 mmol, 59.3% yield) as an oil. LC-MS m/z 224.1 (M+H)+, 1.39 min (ret. time).

64 g) Methyl 2-(isopropylimino)-3-(2-(1-methyl-1H-1,2,3-triazol-4-yl)cyclopropyl)-3-oxopropanoate

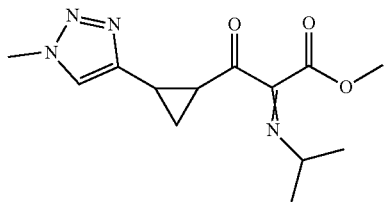

A mixture of methyl 3-(2-(1-methyl-1H-1,2,3-triazol-4-yl)cyclopropyl)-3-oxopropanoate (19 g, 85 mmol) 1,1-dimethoxy-N,N-dimethylmethanamine (11.16 g, 94 mmol) was stirred at 25° C. for 12 h. The reaction mixture was concentrated to obtain the title compound methyl 3-(dimethylamino)-2-(2-(1-methyl-1H-1,2,3-triazol-4-yl)cyclopropanecarbonyl)acrylate (24 g, 77 mmol, 90% yield) as an oil which was used in next step without further purification. LC-MS m/z 279.1 (M+H)⁺, 1.61 min (ret. time).

64h) Methyl 1-(3-bromophenyl)-5-(2-(1-methyl-1H-1,2,3-triazol-4-yl)cyclopropyl)-1H-pyrazole-4-carboxylate

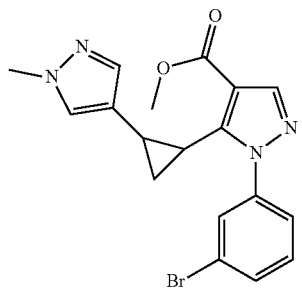 [SMILES: COC(=O)c1cnn(-c2cccc(Br)c2)c1C1CC1c1cnn(C)c1]

A solution of methyl 3-(dimethylamino)-2-(2-(1-methyl-1H-1,2,3-triazol-4-yl)cyclopropanecarbonyl)acrylate (10 g, 35.9 mmol) in acetonitrile (100 mL) was added to (3-bromophenyl)hydrazine hydrochloride (9.64 g, 43.1 mmol) slowly under nitrogen at room temperature. The reaction mixture was stirred at room temperature for 16 h. Then 200 mL of water was added and extracted with ethyl acetate (3×500 mL). The combined organic layer was dried with Na₂SO₄ and concentrated. The crude product was purified by Combiflash chromatography (hexane:ethyl acetate=4:1) to give the title compound methyl 1-(3-bromophenyl)-5-(2-(1-methyl-1H-1,2,3-triazol-4-yl)cyclopropyl)-1H-pyrazole-4-carboxylate (14 g, 34.8 mmol, 97% yield). LC-MS m/z 204.1 (M+H)₊, 1.81 min (ret. time).

64i) Methyl 5-(2-(1-methyl-1H-1,2,3-triazol-4-yl)cyclopropyl)-1-(3-(4,4,5,5-tetramethyl-1,3,2-dioxaborolan-2-yl)phenyl)-1H-pyrazole-4-carboxylate

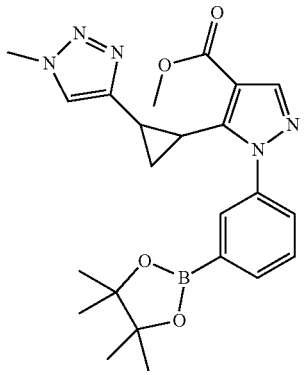 [SMILES: COC(=O)c1cnn(-c2cccc(B3OC(C)(C)C(C)(C)O3)c2)c1C1CC1c1cn(C)nn1]

To a solution of methyl 1-(3-bromophenyl)-5-(2-(1-methyl-1H-1,2,3-triazol-4-yl)cyclopropyl)-1H-pyrazole-4-carboxylate (14 g, 34.8 mmol) in 1,4-dioxane (200 mL) was added potassium acetate (6.83 g, 69.6 mmol), bis(pinacolato)diboron (13.26 g, 52.2 mmol) and the reaction mixture was degassed with argon for 30 min and then PdCl₂(dppf)-CH₂Cl₂ adduct (2.84 g, 3.48 mmol) was added. The reaction mixture was stirred at 100° C. for 16 h. After it was cooled to room temperature, it was filtered through Celite pad and the filtrate was concentrated. The crude product was purified by Combiflash chromatography (hexane:ethyl acetate=2:1) to get the title compound methyl 5-(2-(1-methyl-1H-1,2,3-triazol-4-yl)cyclopropyl)-1-(3-(4,4,5,5-tetramethyl-1,3,2-dioxaborolan-2-yl)phenyl)-1H-pyrazole-4-carboxylate (15 g, 23.37 mmol, 67.1% yield) as white solid. LC-MS m/z 450.1 (M+H)⁺, 1.69 min (ret. time).

64j) (3-(4-(Methoxycarbonyl)-5-((1R,2R)-2-(1-methyl-1H-1,2,3-triazol-4-yl)cyclopropyl)-1H-pyrazol-1-yl)phenyl)boronic Acid

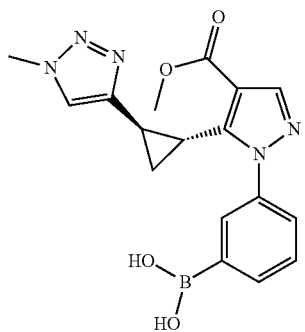 [SMILES: COC(=O)c1cnn(-c2cccc(B(O)O)c2)c1[C@@H]1C[C@H]1c1cn(C)nn1]

To a solution of methyl 5-(2-(1-methyl-1H-1,2,3-triazol-4-yl)cyclopropyl)-1-(3-(4,4,5,5-tetramethyl-1,3,2-dioxaborolan-2-yl)phenyl)-1H-pyrazole-4-carboxylate (15 g, 33.4 mmol) in acetone (100 mL), ammonium acetate (100 mL, 100 mmol) was added, then sodium periodate (21.42 g, 100 mmol) in water (50 mL) was added slowly under nitrogen at room temperature. The reaction mixture was stirred at room temperature for 16 h. Then it was extracted with ethyl acetate (3×100 mL). The combined organic phase was dried with Na₂SO₄ and concentrated. The crude product was purified by Combiflash chromatography (DCM:MeOH=5:1) to obtain the racemate title compound (3-(4-(methoxycarbonyl)-5-(2-(1-methyl-1H-1,2,3-triazol-4-yl)cyclopropyl)-1H-pyrazol-1-yl)phenyl)boronic acid (9.02 g, 26.1 mmol, 72% yield). Then it was separated by chiral column (Chiralpak AY 20×250 mm, 5 u, SFC) to get single isomer-title compound (3-(4-(Methoxycarbonyl)-5-((1R,2R)-2-(1-methyl-1H-1,2,3-triazol-4-yl)cyclopropyl)-1H-pyrazol-1-yl)phenyl)boronic acid (4.303 g, 34.34%). LC-MS m/z 368.0 (M+H)⁺, 1.32 min (ret. time).

64k) (S)-1-Bromo-3-(1-cyclohexylethoxy)benzene

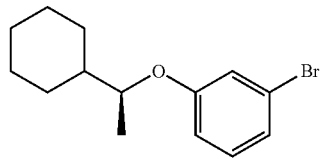 [SMILES: C[C@H](Oc1cccc(Br)c1)C1CCCCC1]

To a solution of 3-bromophenol (2.407 mL, 23.12 mmol) in THF (60 mL), (R)-1-cyclohexylethanol (3.83 mL, 27.7 mmol) DIAD (5.39 mL, 27.7 mmol) and Ph₃P (7277 mg, 27.7 mmol) were added. The reaction mixture was stirred at room temperature for 16 h. The solvent was evaporated and purified by Combiflash chromatography (hexane/ethyl acetate) to get the title compound (S)-1-bromo-3-(1-cyclohexylethoxy)benzene (4.8 g, 16.95 mmol, 73.3%). ¹H NMR (400 MHz, CDCl3) δ=7.16-7.05 (m, 3H), 6.84-6.82 (d, J=8.0 Hz 1H), 4.14 (t, J=8.0 Hz, 1H), 1.94-1.57 (m, 6H), 1.30-1.04 (m, 8H).

64l) Methyl 1-(3'-((S)-1-cyclohexylethoxy)-[1,1'-biphenyl]-3-yl)-5-((1R,2R)-2-(1-methyl-1H-1,2,3-triazol-4-yl)cyclopropyl)-1H-pyrazole-4-carboxylate

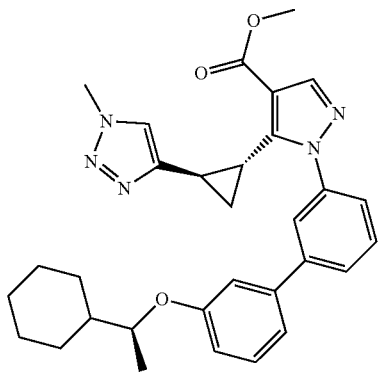 [SMILES: COC(=O)c1cnn(-c2cccc(-c3cccc(O[C@@H](C)C4CCCCC4)c3)c2)c1[C@@H]1C[C@H]1c1cn(C)nn1]

To a solution of (3-(4-(methoxycarbonyl)-5-((1R,2R)-2-(1-methyl-1H-1,2,3-triazol-4-yl)cyclopropyl)-1H-pyrazol-1-yl)phenyl)boronic acid (1.13 g, 3.08 mmol in a mixture of 1,4-Dioxane (18 mL) and water (6.00 mL), (S)-1-bromo-3-(1-cyclohexylethoxy)benzene (1.307 g, 4.62 mmol), potassium carbonate (1.276 g, 9.23 mmol) and PdCl₂(dppf) (0.225 g, 0.308 mmol) were added. The reaction was heated in a microwave at 120° C. for 80 min. Then it was partitioned between ethyl acetate and water. The water layer was extracted with ethyl acetate (3×). The combined organic layer was dried with MgSO₄ and concentrated to get crude product which was purified by Combiflash chromatography (hexane/ethyl acetate) to get the title compound methyl 1-(3'-((S)-1-cyclohexylethoxy)-[1,1'-biphenyl]-3-yl)-5-((1R,2R)-2-(1-methyl-1H-1,2,3-triazol-4-yl)cyclopropyl)-1H-pyrazole-4-carboxylate (1.28 g, 2.435 mmol, 79%). LC-MS m/z 526.4 (M+H)⁺, 1.44 min (ret. time).

64m) 1-(3'-((S)-1-Cyclohexylethoxy)-[1,1'-biphenyl]-3-yl)-5-((1R,2R)-2-(1-methyl-1H-1,2,3-triazol-4-yl)cyclopropyl)-1H-pyrazole-4-carboxylic Acid

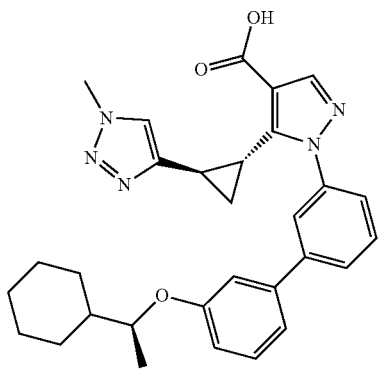 [SMILES: C[C@H](Oc1cccc(-c2cccc(-n3ncc(C(=O)O)c3[C@@H]3C[C@H]3c3cn(C)nn3)c2)c1)C1CCCCC1]

To a solution of methyl 1-(3'-((S)-1-cyclohexylethoxy)-[1,1'-biphenyl]-3-yl)-5-((1R,2R)-2-(1-methyl-1H-1,2,3-triazol-4-yl)cyclopropyl)-1H-pyrazole-4-carboxylate (1.28 g, 2.435 mmol) in a mixture of methanol (30.00 mL) and tetrahydrofuran (16.00 mL), LiOH (0.737 g, 30.8 mmol) and 6.0 mL of water were added. Then the reaction mixture was stirred at room temperature for 18 h. The solvent was evaporated. The residue was partitioned between ethyl acetate and 1N HCl. The water layer was extracted with ethyl acetate (3×). The combined organic phase was dried with MgSO₄ and concentrated to get crude product which was purified by reverse-phase HPLC under acidic condition to get the title compound 1-(3'-((S)-1-cyclohexylethoxy)-[1,1'-biphenyl]-3-yl)-5-((1R,2R)-2-(1-methyl-1H-1,2,3-triazol-4-yl)cyclopropyl)-1H-pyrazole-4-carboxylic acid (700 mg, 1.368 mmol, 44.5%). LC-MS m/z 512.6 (M+H)⁺, 1.34 min (ret. time).

Example 65. 1-(3'-(((R)-2-Ethyl-2,3-dihydrobenzo[f][1,4]oxazepin-4(5H)-yl)methyl)-[1,1'-biphenyl]-3-yl)-5-((1R,2R)-2-(1-methyl-1H-1,2,3-triazol-4-yl)cyclopropyl)-1H-pyrazole-4-carboxylic Acid

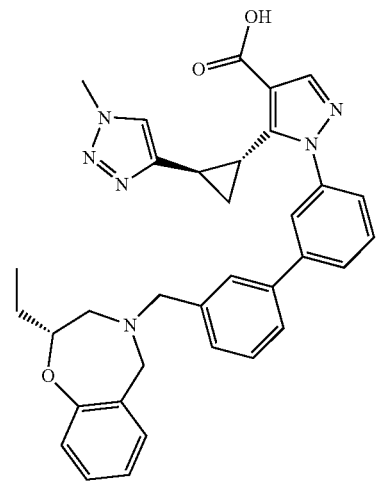 [SMILES: CC[C@@H]1CN(Cc2cccc(-c3cccc(-n4ncc(C(=O)O)c4[C@@H]4C[C@H]4c4cn(C)nn4)c3)c2)Cc2ccccc2O1]

65a) Methyl 1-(3'-(hydroxymethyl)-[1,1'-biphenyl]-3-yl)-5-((1R,2R)-2-(1-methyl-1H-1,2,3-triazol-4-yl)cyclopropyl)-1H-pyrazole-4-carboxylate

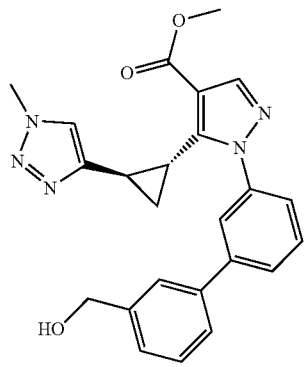 [SMILES: COC(=O)c1cnn(-c2cccc(-c3cccc(CO)c3)c2)c1[C@@H]1C[C@H]1c1cn(C)nn1]

To a solution of (3-(4-(methoxycarbonyl)-5-((1R,2R)-2-(1-methyl-1H-1,2,3-triazol-4-yl)cyclopropyl)-1H-pyrazol-1-yl)phenyl)boronic acid (200 mg, 0.545 mmol) and water (1.5 mL) (3-bromophenyl)methanol (153 mg, 0.817 mmol), $K_2CO_3$ (226 mg, 1.634 mmol) and $PdCl_2$(dppf) (39.9 mg, 0.054 mmol) were added. The reaction was heated in a microwave at 120° C. for 30 min. The solvent was evaporated and purified by Combiflash chromatography (hexane/ethyl acetate) to get the title compound methyl 1-(3'-(hydroxymethyl)-[1,1'-biphenyl]-3-yl)-5-((1R,2R)-2-(1-methyl-1H-1,2,3-triazol-4-yl)cyclopropyl)-1H-pyrazole-4-carboxylate (60 mg, 0.140 mmol, 25.6%). LC-MS m/z 430.0 (M+H)$^+$, 0.88 min (ret. time).

65b) Methyl 1-(3'-(chloromethyl)-[1,1'-biphenyl]-3-yl)-5-((1R,2R)-2-(1-methyl-1H-1,2,3-triazol-4-yl)cyclopropyl)-1H-pyrazole-4-carboxylate

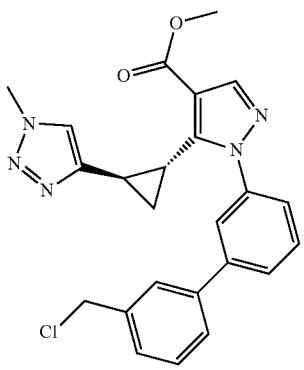 [SMILES: COC(=O)c1cnn(-c2cccc(-c3cccc(CCl)c3)c2)c1[C@@H]1C[C@H]1c1cn(C)nn1]

To a solution of methyl 1-(3'-(hydroxymethyl)-[1,1'-biphenyl]-3-yl)-5-((1R,2R)-2-(1-methyl-1H-1,2,3-triazol-4-yl)cyclopropyl)-1H-pyrazole-4-carboxylate (60 mg, 0.140 mmol) in dichloromethane (2 mL), sulfurous dichloride (49.9 mg, 0.419 mmol) was added. The reaction mixture was stirred at room temperature for 1 h. The solvent was evaporated to obtain the title compound methyl 1-(3'-(chloromethyl)-[1,1'-biphenyl]-3-yl)-5-((1R,2R)-2-(1-methyl-1H-1,2,3-triazol-4-yl)cyclopropyl)-1H-pyrazole-4-carboxylate (60 mg, 0.134 mmol, 96%) which was carried over to next step without further purification. LC-MS m/z 448.1 (M+H)$^+$, 1.01 min (ret. time).

65c) Methyl 1-(3'-(((R)-2-ethyl-2,3-dihydrobenzo[f][1,4]oxazepin-4(5H)-yl)methyl)-[1,1'-biphenyl]-3-yl)-5-((1R,2R)-2-(1-methyl-1H-1,2,3-triazol-4-yl)cyclopropyl)-1H-pyrazole-4-carboxylate

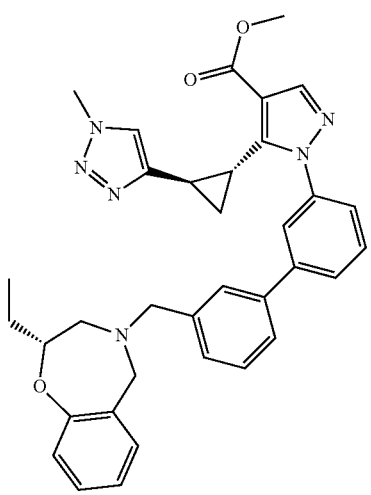 [SMILES: CC[C@@H]1CN(Cc2cccc(-c3cccc(-n4ncc(C(=O)OC)c4[C@@H]4C[C@H]4c4cn(C)nn4)c3)c2)Cc2ccccc2O1]

To a solution of methyl 1-(3'-(chloromethyl)-[1,1'-biphenyl]-3-yl)-5-((1R,2R)-2-(1-methyl-1H-1,2,3-triazol-4-yl)cyclopropyl)-1H-pyrazole-4-carboxylate (60 mg, 0.134 mmol in N,N-dimethylformamide (2 mL), (R)-2-ethyl-2,3,4,5-tetrahydrobenzo[f][1,4]oxazepine (47.5 mg, 0.268 mmol), $K_2CO_3$ (74.1 mg, 0.536 mmol) and sodium iodide (40.2 mg, 0.268 mmol) were added. The reaction mixture was stirred at room temperature for 16 h. The reaction mixture was partitioned between ethyl acetate and water. The organic layer was dried with $MgSO_4$ and concentrated to get the title compound methyl 1-(3'-(((R)-2-ethyl-2,3-dihydrobenzo[f][1,4]oxazepin-4(5H)-yl)methyl)-[1,1'-biphenyl]-3-yl)-5-((1R,2R)-2-(1-methyl-1H-1,2,3-triazol-4-yl)cyclopropyl)-1H-pyrazole-4-carboxylate (60 mg, 0.102 mmol, 76%) which was carried over to next step without further purification. LC-MS m/z 589.1 (M+H)$^+$, 0.89 min (ret. time).

65d) 1-(3'-(((R)-2-Ethyl-2,3-dihydrobenzo[f][1,4]oxazepin-4(5H)-yl)methyl)-[1,1'-biphenyl]-3-yl)-5-((1R,2R)-2-(1-methyl-1H-1,2,3-triazol-4-yl)cyclopropyl)-1H-pyrazole-4-carboxylic Acid

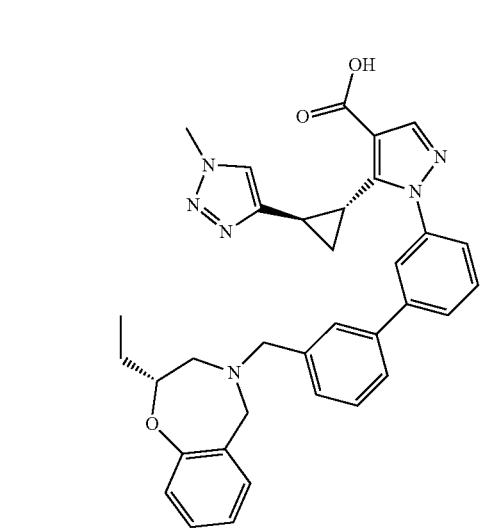 [SMILES: CC[C@@H]1CN(Cc2cccc(-c3cccc(-n4ncc(C(=O)O)c4[C@@H]4C[C@H]4c4cn(C)nn4)c3)c2)Cc2ccccc2O1]

To a solution of methyl 1-(3'-(((R)-2-ethyl-2,3-dihydrobenzo[f][1,4]oxazepin-4(5H)-yl)methyl)-[1,1'-biphenyl]-3-yl)-5-((1R,2R)-2-(1-methyl-1H-1,2,3-triazol-4-yl)cyclopropyl)-1H-pyrazole-4-carboxylate (60 mg, 0.102 mmol) in a mixture of methanol (2.000 mL) and tetrahydrofuran (2.000 mL) LiOH (32.1 mg, 1.340 mmol) and 0.1 mL of water were added. The reaction mixture was stirred at RT for 48 h. The solvent was evaporated and 1 N HCl was added to reaction mixture to pH=1. The solvent was evaporated and purified by reverse-phase HPLC under neutral condition to get the title compound (39.2 mg, 0.068 mmol, 50.9%). LC-MS m/z 575.4 (M+H)$^+$, 0.85 min (ret. time).

Example 66. 1-(6-(3-Isopropoxyphenyl)pyridin-2-yl)-5-(trifluoromethyl)-1H-pyrazole-4-carboxylic Acid

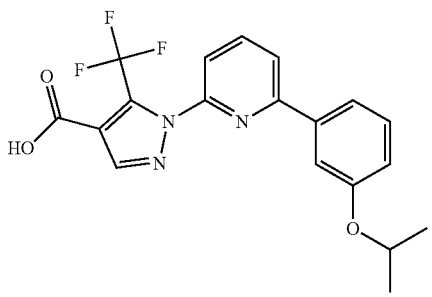 [SMILES: CC(C)Oc1cccc(-c2cccc(-n3ncc(C(=O)O)c3C(F)(F)F)n2)c1]

66a) Ethyl 1-(6-chloropyridin-2-yl)-5-(trifluoromethyl)-1H-pyrazole-4-carboxylate

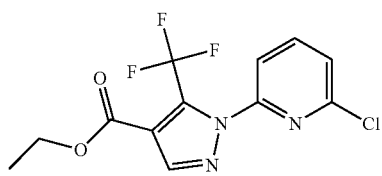 [SMILES: CCOC(=O)c1cnn(-c2cccc(Cl)n2)c1C(F)(F)F]

To a mixture of 2-chloro-6-hydrazinylpyridine (0.5 g, 3.48 mmol) in ethanol (17 mL) was added ethyl 2-(ethoxymethylene)-4,4,4-trifluoro-3-oxobutanoate (0.677 mL, 3.48 mmol). The result reaction mixture was heated at 80° C. for 1 h. The reaction mixture was evaporated down, diluted in EtOAc and then washed with brine. The organic layer was dried with MgSO$_4$, filtered, and evaporated down to give the title compound (1.1350 g, 2.84 mmol, 82% yield). LC-MS m/z 320.0 (M+H)$^+$, 1.16 min (ret. time).

66b) Ethyl 1-(6-(3-isopropoxyphenyl)pyridin-2-yl)-5-(trifluoromethyl)-1H-pyrazole-4-carboxylate

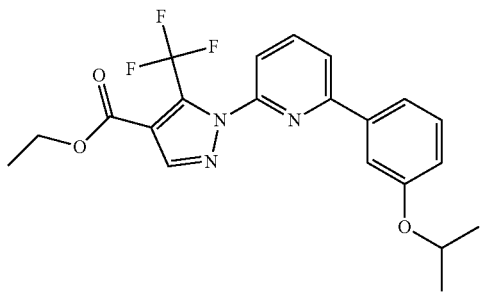 [SMILES: CCOC(=O)c1cnn(-c2cccc(-c3cccc(OC(C)C)c3)n2)c1C(F)(F)F]

To a mixture of ethyl 1-(6-chloropyridin-2-yl)-5-(trifluoromethyl)-1H-pyrazole-4-carboxylate (0.188 g, 0.587 mmol) and (3-isopropoxyphenyl)boronic acid (0.16 g, 0.889 mmol) in 1,4-dioxane (2.2 mL) and water (0.733 mL) was added Pd(Ph$_3$)$_4$ (2.054 g, 1.778 mmol) and sodium carbonate (0.147 mL, 0.293 mmol). The result reaction mixture was heated with microwave at 130° C. for 30 min. The reaction mixture was filtered and washed with water. The aqueous layer was extracted with EtOAc. The combined organic layers were evaporated down the purified with flash chromatograph to give the title compound (0.2125 g, 0.507 mmol, 57.0% yield). LC-MS m/z 420.2 (M+H)$^+$, 1.45 min (ret. time).

66c) 1-(6-(3-Isopropoxyphenyl)pyridin-2-yl)-5-(trifluoromethyl)-1H-pyrazole-4-carboxylic Acid (61.0 mg, 0.156 mmol, 66.7% Yield)

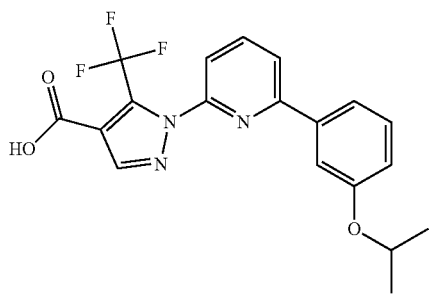 [SMILES: CC(C)Oc1cccc(-c2cccc(-n3ncc(C(=O)O)c3C(F)(F)F)n2)c1]

To ethyl 1-(6-(3-isopropoxyphenyl)pyridin-2-yl)-5-(trifluoromethyl)-1H-pyrazole-4-carboxylate (98 mg, 0.234 mmol) was added to a mixture of sodium hydroxide (6 N) (0.195 mL, 1.168 mmol) in tetrahydrofuran (1 mL). The result mixture was stirred at room temperature for 21 h then was heated at 50° C. for 3 h. This reaction mixture was acidified with HCl (0.195 mL, 6 N), evaporated down under vacuum, purified by reverse phase HPLC (TFA modifier) to give the title compound (61.0 mg, 0.156 mmol, 66.7% yield). LC-MS m/z 392.1 (M+H)$^+$, 1.13 min (ret. time).

Example 67. 5-(2,2-Difluorocyclopropyl)-1-(3'-((R)-2-propylpiperidine-1-carbonyl)-[1,1'-biphenyl]-3-yl)-1H-pyrazole-4-carboxylic Acid

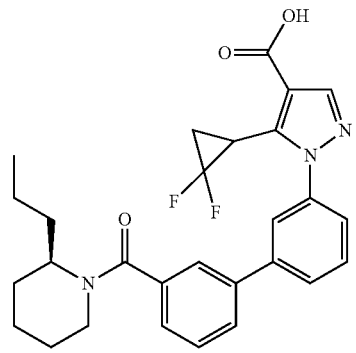 [SMILES: CCC[C@@H]1CCCCN1C(=O)c1cccc(-c2cccc(-n3ncc(C(=O)O)c3C3CC3(F)F)c2)c1]

67a) Methyl 3-(2,2-difluorocyclopropyl)-3-oxopropanoate

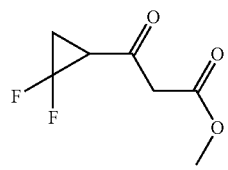

To a solution of 2,2-difluorocyclopropanecarboxylic acid (5.00 g, 41.0 mmol) in Tetrahydrofuran (THF) (50 ml) was added CDI (7.97 g, 49.2 mmol), portionwise, and stirred at room temperature for 3 h. Then, the reaction was diluted with Tetrahydrofuran (THF) (25 ml) and magnesium chloride (5.15 g, 54.1 mmol) and potassium methyl malonate (12.79 g, 82 mmol) were added and the reaction was stirred for 18 h. Afterwards, the reaction was diluted with water (50.0 ml) and the pH was adjusted to pH=7 with 1M HCl (47.5 ml, 47.5 mmol). The aqueous layer was extracted with EtOAc (2×). The combined organics were washed with 1N HCl and brine, dried with MgSO₄ and the solvent was concentrated. The residue was re-dissolved in EtOAc and washed with sat. K₂CO₃ (3×), brine, dried with MgSO₄, and concentrated to provide the title compound (1.86 g, 25% yield). ¹H NMR (400 MHz, Chloroform-d) δ ppm 1.72-1.84 (m, 1H) 2.21-2.32 (m, 1H) 2.89-3.01 (m, 1H) 3.57-3.68 (m, 2H) 3.80 (s, 3H).

67b) (Z)-Methyl 2-(2,2-difluorocyclopropanecarbonyl)-3-(dimethylamino)acrylate

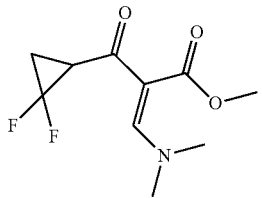 [SMILES: COC(=O)/C(=C\N(C)C)C(=O)C1CC1(F)F]

To a solution of methyl 3-(2,2-difluorocyclopropyl)-3-oxopropanoate (1.86 g, 10.44 mmol) in dichloromethane (DCM) (12 mL) was added DMF-DMA (1.678 mL, 12.53 mmol) and TsOH (0.020 g, 0.104 mmol) and stirred at room temperature for 18 hours. Additional DMF-DMA (0.419 mL, 3.13 mmol) was added and the reaction was and heated to 40° C. for 5 h. The solvent was concentrated and the residue was purified by flash chromatography eluting with 0-2% MeOH/DCM to provide the title compound (2.31 g, 74% yield). LC/MS m/z=234 (M+H)⁺, 0.60 min (ret. time).

67c) Methyl 1-(3-bromophenyl)-5-(2,2-difluorocyclopropyl)-1H-pyrazole-4-carboxylate

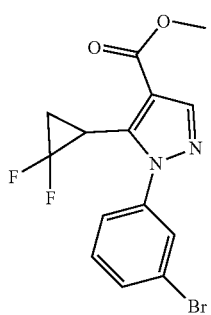 [SMILES: COC(=O)c1cnn(-c2cccc(Br)c2)c1C1CC1(F)F]

To a solution of (Z)-methyl 2-(2,2-difluorocyclopropanecarbonyl)-3-(dimethylamino)acrylate (2.31 g, 7.73 mmol) in Methanol (30 mL) was added triethylamine (1.615 mL, 11.59 mmol) and (3-bromophenyl)hydrazine, hydrochloride (1.727 g, 7.73 mmol) and stirred at room temperature for 4 h. Additional (3-bromophenyl)hydrazine, hydrochloride (0.086 g, 0.386 mmol) was added and stirred for 1.5 h. The solvent was concentrated and the residue was dissolved in EtOAc, washed with water (3×), brine, dried with MgSO₄, and the solvent was concentrated. The residue was purified by flash chromatography eluting with 0-5% EtOAc/DCM to provide the title compound (2.63 g, 95% yield). LC/MS m/z=357 (M+H)⁺, 1.04 min (ret. time).

67d) Methyl 5-(2,2-difluorocyclopropyl)-1-(3'-((R)-2-propylpiperidine-1-carbonyl)-[1,1'-biphenyl]-3-yl)-1H-pyrazole-4-carboxylate

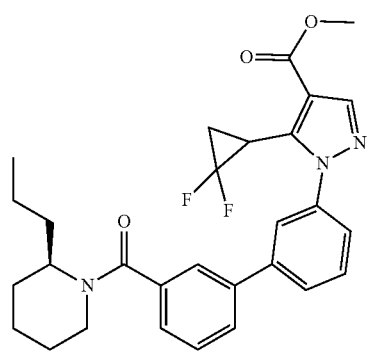 [SMILES: CCC[C@@H]1CCCCN1C(=O)c1cccc(-c2cccc(-n3ncc(C(=O)OC)c3C3CC3(F)F)c2)c1]

A mixture of (R)-(2-propylpiperidin-1-yl)(3-(4,4,5,5-tetramethyl-1,3,2-dioxaborolan-2-yl)phenyl)methanone (100 mg, 0.280 mmol), methyl 1-(3-bromophenyl)-5-(2,2-difluorocyclopropyl)-1H-pyrazole-4-carboxylate (116 mg, 0.325 mmol), and Na₂CO₃ (89 mg, 0.840 mmol) were dissolved/suspended in 1,4-dioxane (3 mL) and water (1 mL) in a 10 mL microwave reaction vessel. The solvent was purged with nitrogen and then PdCl₂(dppf)-CH₂Cl₂ adduct (22.86 mg, 0.028 mmol) was added. The reaction was heated on microwave to 100° C. for 10 min. The reaction was heated a second time at 100° C. for 10 min. The reaction was filtered through a PL-Thiol-MP-SPE cartridge and the solvent was concentrated. The residue was purified by flash chromatography eluting with 0-10% EtOAc/DCM to provide the title compound (0.135 g, 90% yield). LC/MS m/z=508 (M+H)⁺, 1.27 min (ret. time).

67e) 5-(2,2-Difluorocyclopropyl)-1-(3'-((R)-2-propylpiperidine-1-carbonyl)-[1,1'-biphenyl]-3-yl)-1H-pyrazole-4-carboxylic Acid

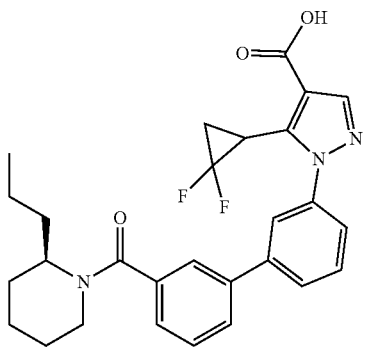 [SMILES: CCC[C@@H]1CCCCN1C(=O)c1cccc(-c2cccc(-n3ncc(C(=O)O)c3C3CC3(F)F)c2)c1]

To a mixture of methyl 5-(2,2-difluorocyclopropyl)-1-(3'-((R)-2-propylpiperidine-1-carbonyl)-[1,1'-biphenyl]-3-yl)-1H-pyrazole-4-carboxylate (135 mg, 0.266 mmol) in tetrahydrofuran (THF) (3 mL) and water (1 mL) was added LiOH (31.8 mg, 1.330 mmol) and stirred at room temperature for 18 h. The reaction was then heated to 45° C. for 9 hours. Additional LiOH (31.8 mg, 1.330 mmol) was added and the reaction was heated for 18 h. The temperature was increased to 60° C. and the reaction was heated for 26 h. The solvent was then concentrated and the reaction was diluted with water and acidified with 6N HCl. The aqueous layer was extracted with EtOAc (3×) and the combined organics were washed with water, brine and dried with MgSO₄. The solvent was concentrated and the residue was purified by reverse phase preparative HPLC under neutral conditions to provide the title compound (0.071 g, 54% yield). LC/MS m/z=494 (M+H)⁺, 1.10 min (ret. time).

Example 68. 1-(3'-((S)-1-Cyclohexylethoxy)-[1,1'-biphenyl]-3-yl)-5-((1R,2R)-2-(1-methyl-1H-1,2,3-triazol-4-yl)cyclopropyl)-1H-pyrazole-4-carboxylate, Sodium salt

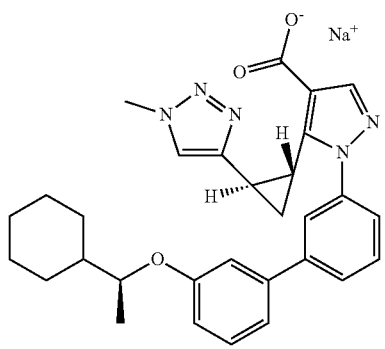 [SMILES: C[C@H](Oc1cccc(-c2cccc(-n3ncc(C(=O)[O-])c3[C@@H]3C[C@H]3c3cn(C)nn3)c2)c1)C1CCCCC1 ; [Na+]]

1-(3'-((S)-1-cyclohexylethoxy)-[1,1'-biphenyl]-3-yl)-5-((1R,2R)-2-(1-methyl-1H-1,2,3-triazol-4-yl)cyclopropyl)-1H-pyrazole-4-carboxylic acid (51 mg, 0.100 mmol) was weighed out and Water (1 mL) was added followed by 2M NaOH (0.050 mL, 0.100 mmol). The solution was stirred overnight and then concentrated. The crude product was dissolved in DMSO (2 mL) and purified with reverse-phase HPLC under neutral conditions to afford the title compound (53.49 mg, 101% yield). LC-MS m/z 512.3 (M+H)⁺, 1.25 min (ret. time). ¹H NMR (DMSO-de) δ: 7.81 (s, 1H), 7.68-7.73 (m, 2H), 7.48-7.60 (m, 3H), 7.33 (s, 1H), 7.12 (s, 1H), 7.07 (d, J=7.8 Hz, 1H), 6.94 (s, 1H), 4.30-4.38 (m, 1H), 3.84 (s, 3H), 2.33-2.42 (m, 1H), 1.83-1.93 (m, 1H), 1.74 (d, J=10.3 Hz, 3H), 1.51-1.67 (m, 3H), 1.02-1.37 (m, 1 OH).

Example 69. Barium 1-(3'-((S)-1-Cyclohexylethoxy)-[1,1'-biphenyl]-3-yl)-5-((1R,2R)-2-(1-methyl-1H-1,2,3-triazol-4-yl)cyclopropyl)-1H-pyrazole-4-carboxylate Hydroxide

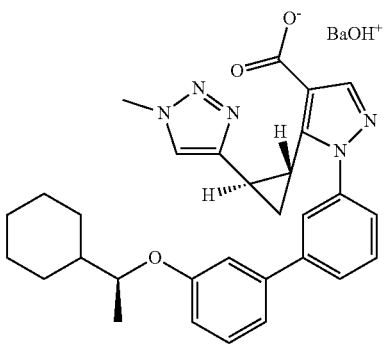

Water (1 mL) was added to 1-(3'-((S)-1-cyclohexylethoxy)-[1,1'-biphenyl]-3-yl)-5-((1R,2R)-2-(1-methyl-1H-1,2,3-triazol-4-yl)cyclopropyl)-1H-pyrazole-4-carboxylic acid (52.5 mg, 0.103 mmol), followed by barium hydroxide (16.19 mg, 0.051 mmol). Not much dissolved. The reaction was heated to 40° C. Added MeOH (1 mL) and, still not all went into solution, after heating for 2 hours. Added THF (1 mL) and all went into solution. The solution was heated overnight and then concentrated. The crude product was dissolved in DMSO (2 mL) and purified with reverse-phase HPLC under neutral conditions to afford the title compound (40.52 mg, 59.4% yield). LC-MS m/z 512.4 (M+H)⁺, 1.35 min (ret. time). ¹H NMR (DMSO-d₆) δ: 7.79 (br. s., 1H), 7.65-7.70 (m, 2H), 7.62 (s, 1H), 7.53 (s, 1H), 7.48 (s, 1H), 7.32 (s, 1H), 7.12 (br. s., 1H), 7.04 (d, J=7.5 Hz, 1H), 6.93 (d, J=8.3 Hz, 1H), 4.34 (s, 1H), 3.83 (s, 3H), 2.59-2.70 (m, 1H), 2.24-2.35 (m, 1H), 1.84-1.93 (m, 1H), 1.68-1.82 (m, 5H), 1.60-1.67 (m, 1H), 1.49-1.59 (m, 1H), 1.30-1.36 (m, 1H), 1.01-1.25 (m, 8H).

Example 70. Calcium 1-(3'-((S)-1-Cyclohexylethoxy)-[1,1'-biphenyl]-3-yl)-5-((1R,2R)-2-(1-methyl-1H-1,2,3-triazol-4-yl)cyclopropyl)-1H-pyrazole-4-carboxylate Hydroxide

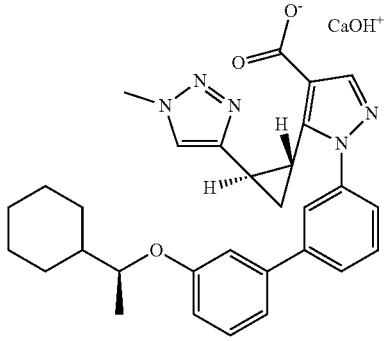

Water (1 mL) was added to 1-(3'-((S)-1-cyclohexylethoxy)-[1,1'-biphenyl]-3-yl)-5-((1R,2R)-2-(1-methyl-1H-1,2,3-triazol-4-yl)cyclopropyl)-1H-pyrazole-4-carboxylic acid (54.2 mg, 0.106 mmol), followed by calcium hydroxide (3.92 mg, 0.053 mmol). Not much dissolved. The reaction was heated to 40° C. Added MeOH (1 mL) and, still not all went into solution, after heating for 2 h. Added THF (1 mL) and all went into solution. The solution was heated overnight and then concentrated. The crude product was dissolved in DMSO (2 mL) and purified with reverse-phase HPLC under neutral conditions to afford the title compound (39.2 mg, 65.2% yield). LC-MS m/z 512.4 (M+H)⁺, 1.34 min (ret. time). ¹H NMR (DMSO-d₆) δ: 7.78-7.98 (m, 1H), 7.69 (br. s., 3H), 7.46-7.57 (m, 2H), 7.28-7.35 (m, 1H), 7.12 (br. s., 1H), 7.05 (d, J=6.8 Hz, 1H), 6.93 (d, J=8.0 Hz, 1H), 4.29-4.40 (m, 1H), 3.82 (br. s., 3H), 3.18 (br. s., 1H), 2.32 (br. s., 1H), 1.87 (d, J=12.0 Hz, 1H), 1.50-1.76 (m, 6H), 1.39 (br. s., 1H), 0.99-1.26 (m, 8H). Theoretical Elemental Analysis: C, 63.47; H, 5.86; N, 12.34; Found Elemental Analysis: C, 63.82; H, 6.10; N, 12.04.

Example 71. 1-(3'-((S)-1-Cyclohexylethoxy)-2'-methyl-[1,1'-biphenyl]-3-yl)-5-(trans-2-(1-methyl-1H-1,2,3-triazol-4-yl)cyclopropyl)-1H-pyrazole-4-carboxylic Acid

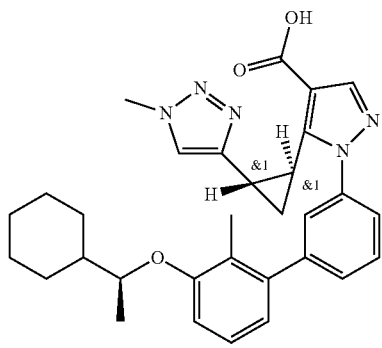 [SMILES: Cc1c(O[C@@H](C)C2CCCCC2)cccc1-c1cccc(-n2ncc(C(=O)O)c2[C@H]2C[C@@H]2c2cn(C)nn2)c1]

71a) (S)-1-Bromo-3-(1-cyclohexylethoxy)-2-methylbenzene

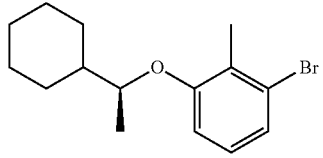 [SMILES: Cc1c(Br)cccc1O[C@@H](C)C1CCCCC1]

Dissolved 3-bromo-2-methylphenol (255 mg, 1.363 mmol) and Ph3P (429 mg, 1.636 mmol) in Tetrahydrofuran (THF) (5 mL). Added (R)-1-cyclohexylethanol (0.226 mL, 1.636 mmol) followed by DIAD (0.318 mL, 1.636 mmol). The reaction was stirred for 22 h and then concentrated. The compound was purified by flash chromatography with silica running from 100% Hex to 100% EtOAc. The desired fractions were concentrated to give the title compound (183.6 mg, 45.3% yield). LC-MS 1.70 min (ret. time).

71b) Methyl 1-(3'-((S)-1-Cyclohexylethoxy)-2'-methyl-[1,1'-biphenyl]-3-yl)-5-(2-(1-methyl-1H-1,2,3-triazol-4-yl)cyclopropyl)-1H-pyrazole-4-carboxylate

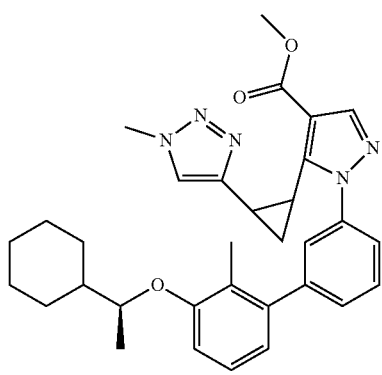 [SMILES: COC(=O)c1cnn(-c2cccc(-c3cccc(O[C@@H](C)C4CCCCC4)c3C)c2)c1C1CC1c1cn(C)nn1]

Weighed out (S)-1-bromo-3-(1-cyclohexylethoxy)-2-methylbenzene (182 mg, 0.612 mmol), (3-(4-(methoxycarbonyl)-5-((1R,2R)-2-(1-methyl-1H-1,2,3-triazol-4-yl)cyclopropyl)-1H-pyrazol-1-yl)phenyl)boronic acid (158.7 mg, 0.432 mmol) and cesium carbonate (352 mg, 1.081 mmol). Added 1,4-dioxane (5 mL) followed by water (1.000 mL), then the flask was flushed with nitrogen. Tetrakis (49.9 mg, 0.043 mmol) was added and the reaction was sealed and heated to 80° C. for 15 h. The reaction was cooled to RT and more tetrakis (49.9 mg, 0.043 mmol) was added and reheated to 80° C. for 1 day. The reaction was concentrated and purified by flash chromatography on silica running from 100% Hex to 100% EtOAc. The desired fractions were concentrated to give the title compound (134.0 mg, 57.4% yield). LC-MS m/z 540.2 (M+H)$^+$, 1.48 min (ret. time).

71c) 1-(3'-((S)-1-Cyclohexylethoxy)-2'-methyl-[1,1'-biphenyl]-3-yl)-5-(trans-2-(1-methyl-1H-1,2,3-triazol-4-yl)cyclopropyl)-1H-pyrazole-4-carboxylic Acid

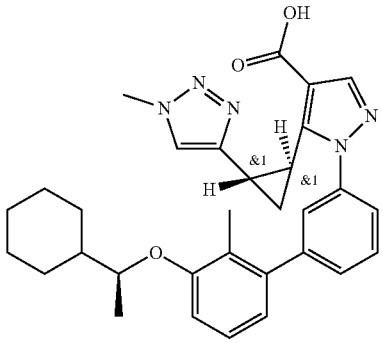 [SMILES: Cc1c(O[C@@H](C)C2CCCCC2)cccc1-c1cccc(-n2ncc(C(=O)O)c2[C@H]2C[C@@H]2c2cn(C)nn2)c1]

To a solution of methyl 1-(3'-((S)-1-cyclohexylethoxy)-2'-methyl-[1,1'-biphenyl]-3-yl)-5-(2-(1-methyl-1H-1,2,3-triazol-4-yl)cyclopropyl)-1H-pyrazole-4-carboxylate (134.0 mg, 0.248 mmol) in a mix of methanol (2 mL) and tetrahydrofuran (THF) (1.000 mL) was added LiOH (104 mg, 2.483 mmol) and water (0.400 mL). The reaction was heated to 50° C. for 2 h and then concentrated. To the residue was added acetonitrile (5 mL), then the reaction was acidified with 1 M HCl to pH=3. The reaction was concentrated. The crude product was dissolved in DMSO (5 mL) and purified with reverse-phase HPLC under acidic conditions to afford the title compound (82.9 mg, 63.5%). LC-MS m/z 526.2 (M+H)$^+$, 1.36 min (ret. time). $^1$H NMR (400 MHz, DMSO-$d_6$) δ=7.99 (s, 1H), 7.59 (s, 1H), 7.54 (s, 2H), 7.44 (s, 1H), 7.38 (d, J=5.8 Hz, 1H), 7.17 (t, J=7.9 Hz, 1H), 6.97 (d, J=8.3 Hz, 1H), 6.62 (d, J=7.5 Hz, 1H), 4.29 (t, J=5.8 Hz, 1H), 3.91 (s, 3H), 2.26-2.16 (m, 1H), 2.00 (s, 3H), 1.90 (d, J=12.0 Hz, 1H), 1.74 (d, J=10.5 Hz, 3H), 1.69-1.53 (m, 2H), 1.39-1.32 (m, 1H), 1.30-1.05 (m, 10H).

Example 72. 1-(3'-(Cyclohexylmethoxy)-2'-methyl-[1,1'-biphenyl]-3-yl)-5-(trans-2-(1-methyl-1H-1,2,3-triazol-4-yl)cyclopropyl)-1H-pyrazole-4-carboxylic Acid

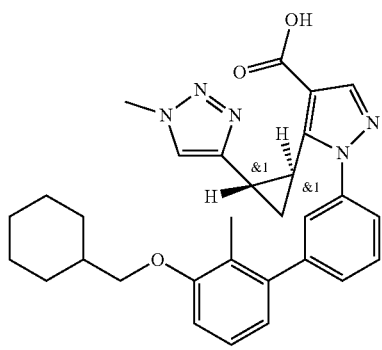 [SMILES: Cc1c(OCC2CCCCC2)cccc1-c1cccc(-n2ncc(C(=O)O)c2[C@H]2C[C@@H]2c2cn(C)nn2)c1]

72a) 1-Bromo-3-(cyclohexylmethoxy)-2-methylbenzene

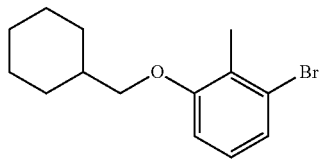

Dissolved 3-bromo-2-methylphenol (251 mg, 1.342 mmol) and Ph₃P (422 mg, 1.610 mmol) in tetrahydrofuran (THF) (5 mL). Added cyclohexylmethanol (0.204 mL, 1.610 mmol) followed by DIAD (0.313 mL, 1.610 mmol). The reaction was stirred for 22 h and then concentrated. The compound was purified by flash chromatography with silica running from 100% Hex to 100% EtOAc. The desired fractions were concentrated to give the title compound (281.1 mg, 74.0% yield). LC-MS 1.67 min (ret. time).

72b) Methyl 1-(3'-(cyclohexylmethoxy)-2'-methyl-[1,1'-biphenyl]-3-yl)-5-(2-(1-methyl-1H-1,2,3-triazol-4-yl)cyclopropyl)-1H-pyrazole-4-carboxylate

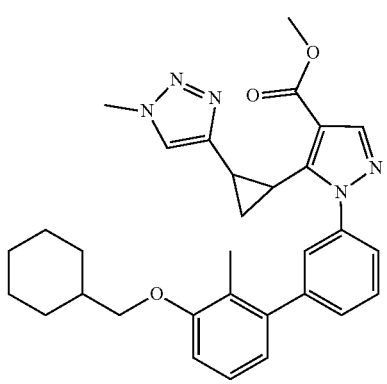 [SMILES: COC(=O)c1cnn(-c2cccc(-c3cccc(OCC4CCCCC4)c3C)c2)c1C1CC1c1cn(C)nn1]

Weighed out 1-bromo-3-(cyclohexylmethoxy)-2-methylbenzene (278 mg, 0.982 mmol), (3-(4-(methoxycarbonyl)-5-((1R,2R)-2-(1-methyl-1H-1,2,3-triazol-4-yl)cyclopropyl)-1H-pyrazol-1-yl)phenyl)boronic acid (236.6 mg, 0.644 mmol) and cesium carbonate (525 mg, 1.611 mmol). Added 1,4-dioxane (25 mL) followed by water (5.00 mL), then the flask was flushed with nitrogen. Tetrakis (74.5 mg, 0.064 mmol) was added and the reaction was sealed and heated to 80° C. for 18 h. Added more tetrakis (74.5 mg, 0.064 mmol) and reheated to 80° C. for 1 day. The reaction was concentrated and purified by flash chromatography on silica running from 100% Hex to 100% EtOAc. The desired fractions were concentrated to give the title compound (194.2 mg, 57.3% yield). LC-MS m/z 526.4 (M+H)⁺, 1.48 min (ret. time).

72c) 1-(3'-(cyclohexylmethoxy)-2'-methyl-[1,1'-biphenyl]-3-yl)-5-(trans-2-(1-methyl-1H-1,2,3-triazol-4-yl)cyclopropyl)-1H-pyrazole-4-carboxylic Acid

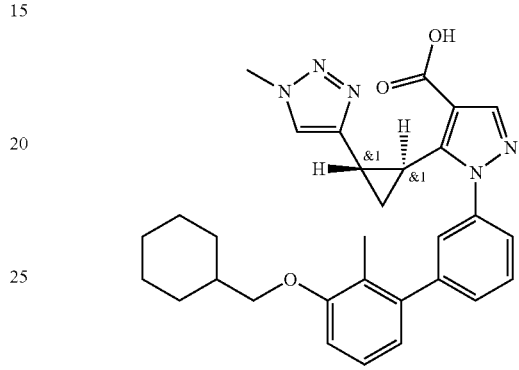

To a solution of methyl 1-(3'-(cyclohexylmethoxy)-2'-methyl-[1,1'-biphenyl]-3-yl)-5-(2-(1-methyl-1H-1,2,3-triazol-4-yl)cyclopropyl)-1H-pyrazole-4-carboxylate (194.2 mg, 0.369 mmol) in a mix of methanol (2 mL) and tetrahydrofuran (THF) (1.000 mL) was added LiOH (155 mg, 3.69 mmol) and Water (0.400 mL). The reaction was heated at 50° C. for 90 min and then concentrated. To the residue was added acetonitrile (5 mL), then the reaction was acidified with 1 M HCl to pH=3. The reaction was concentrated. The crude product was dissolved in DMSO (4 mL) and purified with reverse-phase HPLC under acidic conditions to afford the title compound (29.4 mg, 15.5%). LC-MS m/z 512.2 (M+H)⁺, 1.32 min (ret. time). ¹H NMR (400 MHz, DMSO-d6) δ=7.99 (s, 1H), 7.57 (d, J=13.3 Hz, 3H), 7.44 (s, 1H), 7.38 (d, J=4.5 Hz, 1H), 7.22-7.15 (m, 1H), 6.96 (d, J=8.3 Hz, 1H), 6.65 (d, J=7.5 Hz, 1H), 3.90 (s, 3H), 3.83 (d, J=5.5 Hz, 2H), 2.25-2.16 (m, 1H), 2.01 (s, 3H), 1.90-1.63 (m, 6H), 1.38-1.04 (m, 8H).

Example 73. 1-(3'-((S)-1-Cycloheptylethoxy)-[1,1'-biphenyl]-3-yl)-5-((1R,2R)-2-(1-methyl-1H-1,2,3-triazol-4-yl)cyclopropyl)-1H-pyrazole-4-carboxylic Acid

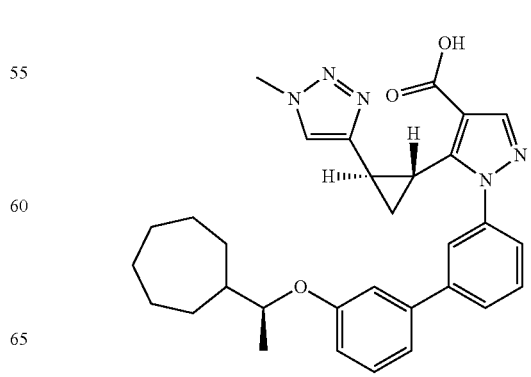

73a) (S)-(1-(3-Bromophenoxy)ethyl)cycloheptane

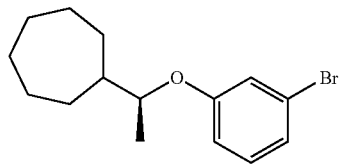 [SMILES: C[C@H](Oc1cccc(Br)c1)C1CCCCCC1]

Dissolved 3-bromophenol (0.15 mL, 1.413 mmol) and Ph$_3$P (446 mg, 1.700 mmol) in tetrahydrofuran (THF) (5 mL). Added (R)-1-cycloheptylethanol (245 mg, 1.722 mmol) followed by DIAD (0.33 mL, 1.697 mmol). The reaction was stirred for 19 h and then concentrated. The compound was purified by flash chromatography with silica running from 100% Hex to 60% Hex/40% EtOAc. The desired fractions were concentrated to give the title compound (229.8 mg, 54.7% yield). LC-MS 1.61 min (ret. time).

73b) Methyl 1-(3'-((S)-1-cycloheptylethoxy)-[1,1'-biphenyl]-3-yl)-5-((1R,2R)-2-(1-methyl-1H-1,2,3-triazol-4-yl)cyclopropyl)-1H-pyrazole-4-carboxylate

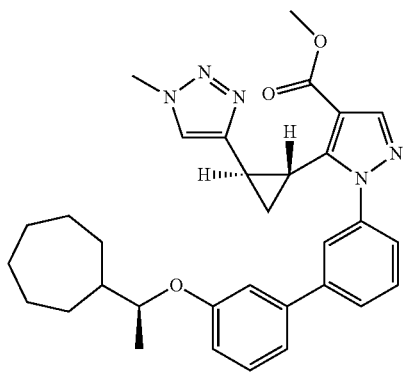 [SMILES: COC(=O)c1cnn(-c2cccc(-c3cccc(O[C@@H](C)C4CCCCCC4)c3)c2)c1[C@@H]1C[C@H]1c1cn(C)nn1]

Weighed out (S)-(1-(3-bromophenoxy)ethyl)cycloheptane (229.8 mg, 0.773 mmol), (3-(4-(methoxycarbonyl)-5-((1R,2R)-2-(1-methyl-1H-1,2,3-triazol-4-yl)cyclopropyl)-1H-pyrazol-1-yl)phenyl)boronic acid (201 mg, 0.547 mmol) and cesium carbonate (447 mg, 1.372 mmol). Added 1,4-dioxane (8 mL) followed by water (1.600 mL). Then the flask was flushed with nitrogen. Tetrakis (190 mg, 0.164 mmol) was added and the reaction was sealed and heated to 80° C. for 18 h. The reaction was cooled to room temp and concentrated. The residue was taken back up in DCM (100 mL) and washed with water (25 mL). The organic layer was concentrated. The compound was purified by flash chromatography on silica running from 100% Hex to 100% EtOAc. The desired fractions were concentrated to give the title compound (302.8 mg, 102% yield). LC-MS m/z 540.2 (M+H)$^+$, 1.46 min (ret. time).

73c) 1-(3'-((S)-1-Cycloheptylethoxy)-[1,1'-biphenyl]-3-yl)-5-((1R,2R)-2-(1-methyl-1H-1,2,3-triazol-4-yl)cyclopropyl)-1H-pyrazole-4-carboxylic Acid

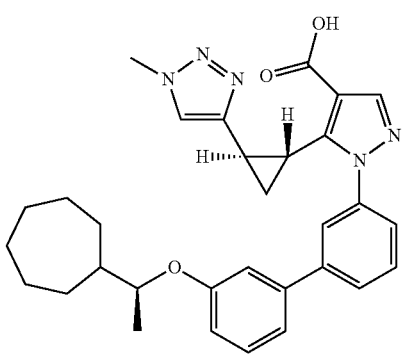 [SMILES: C[C@H](Oc1cccc(-c2cccc(-n3ncc(C(=O)O)c3[C@@H]3C[C@H]3c3cn(C)nn3)c2)c1)C1CCCCCC1]

To a solution of methyl 1-(3'-((S)-1-cycloheptylethoxy)-[1,1'-biphenyl]-3-yl)-5-((1R,2R)-2-(1-methyl-1H-1,2,3-triazol-4-yl)cyclopropyl)-1H-pyrazole-4-carboxylate (310 mg, 0.574 mmol) in a mix of Methanol (5 mL) and Tetrahydrofuran (THF) (2.500 mL) was added LiOH (245 mg, 5.84 mmol) and Water (1.000 mL). The reaction was stirred at RT for 19 h and then concentrated. The residue was partitioned between EtOAc (50 mL) and 1N HCl (25 mL). The water layer was extracted with EtOAc (25 mL) and the combined organics were dried MgSO$_4$, filtered and concentrated in vacuo. The crude product was dissolved in DMSO and purified with reverse-phase HPLC under acidic conditions (0.1% formic acid) to afford the title compound. The compound was crystallized from EtOAc and hexane to give the title compound (85.5 mg, 28.3% yield). LC-MS m/z 526.4 (M+H)$^+$, 1.29 min (ret. time). $^1$H NMR (400 MHz, DMSO-d$_6$) δ: 12.42-12.32 (m, 1H), 8.01 (s, 1H), 7.81-7.72 (m, 2H), 7.57 (d, J=10.8 Hz, 2H), 7.47 (s, 1H), 7.34 (t, J=7.8 Hz, 1H), 7.14-7.07 (m, 2H), 6.94 (d, J=8.3 Hz, 1H), 4.47-4.37 (m, 1H), 3.82 (s, 3H), 2.15 (d, J=7.8 Hz, 1H), 1.86-1.64 (m, 5H), 1.59-1.25 (m, 9H), 1.20 (d, J=6.0 Hz, 3H).

Example 74. 1-(3'-((R)-1-Cycloheptylethoxy)-[1,1'-biphenyl]-3-yl)-5-((1R,2R)-2-(1-methyl-1H-1,2,3-triazol-4-yl)cyclopropyl)-1H-pyrazole-4-carboxylic Acid

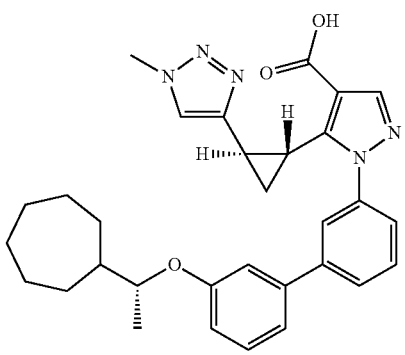 [SMILES: C[C@@H](Oc1cccc(-c2cccc(-n3ncc(C(=O)O)c3[C@@H]3C[C@H]3c3cn(C)nn3)c2)c1)C1CCCCCC1]

289

74a) (R)-(1-(3-Bromophenoxy)ethyl)cycloheptane

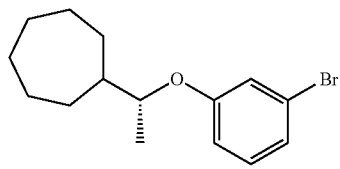 [SMILES: C[C@@H](Oc1cccc(Br)c1)C1CCCCCC1]

Dissolved 3-bromophenol (0.15 mL, 1.413 mmol) and Ph₃P (452 mg, 1.723 mmol) in tetrahydrofuran (THF) (5 mL). Added (S)-1-cycloheptylethanol (245 mg, 1.722 mmol) followed by DIAD (0.33 mL, 1.697 mmol). The reaction was stirred for 19 h and then concentrated. The compound was purified by flash chromatography with silica running from 100% Hex to 60% Hex/40% EtOAc. The desired fractions were concentrated to give the title compound (225.6 mg, 53.7% yield). LC-MS 1.61 min (ret. time).

74b) Methyl 1-(3'-((R)-1-cycloheptylethoxy)-[1,1'-biphenyl]-3-yl)-5-((1R,2R)-2-(1-methyl-1H-1,2,3-triazol-4-yl)cyclopropyl)-1H-pyrazole-4-carboxylate

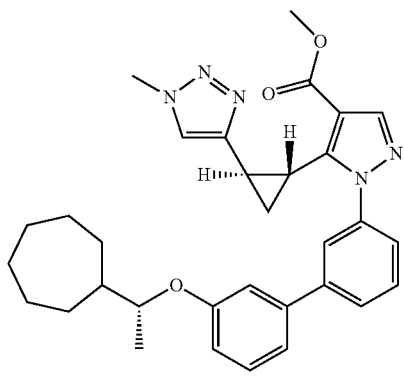 [SMILES: COC(=O)c1cnn(-c2cccc(-c3cccc(O[C@H](C)C4CCCCCC4)c3)c2)c1[C@@H]1C[C@H]1c1cn(C)nn1]

Weighed out (R)-(1-(3-bromophenoxy)ethyl)cycloheptane (225.6 mg, 0.759 mmol), (3-(4-(methoxycarbonyl)-5-((1R,2R)-2-(1-methyl-1H-1,2,3-triazol-4-yl)cyclopropyl)-1H-pyrazol-1-yl)phenyl)boronic acid (204 mg, 0.556 mmol) and cesium carbonate (462 mg, 1.418 mmol). Added 1,4-dioxane (8 mL) followed by water (1.600 mL). The flask was flushed with nitrogen. Tetrakis (193 mg, 0.167 mmol) was added and the reaction was sealed and heated to 80° C. for 18 h. The reaction was cooled to room temp and concentrated. The residue was taken back up in DCM (100 mL) and washed with water (25 mL). The organic layer was concentrated. The compound was purified by flash chromatography on silica running from 100% Hex to 100% EtOAc. The desired fractions were concentrated to give the title compound (293.3 mg, 98% yield). LC-MS m/z 540.2 (M+H)⁺, 1.46 min (ret. time).

290

74c) 1-(3'-((R)-1-Cycloheptylethoxy)-[1,1'-biphenyl]-3-yl)-5-((1R,2R)-2-(1-methyl-1H-1,2,3-triazol-4-yl)cyclopropyl)-1H-pyrazole-4-carboxylic Acid

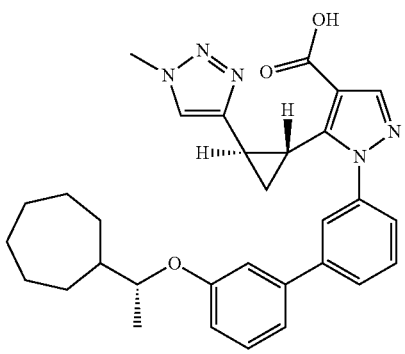 [SMILES: C[C@@H](Oc1cccc(-c2cccc(-n3ncc(C(=O)O)c3[C@@H]3C[C@H]3c3cn(C)nn3)c2)c1)C1CCCCCC1]

To a solution of methyl 1-(3'-((R)-1-cycloheptylethoxy)-[1,1'-biphenyl]-3-yl)-5-((1R,2R)-2-(1-methyl-1H-1,2,3-triazol-4-yl)cyclopropyl)-1H-pyrazole-4-carboxylate (310 mg, 0.574 mmol) in a mix of Methanol (5 mL) and Tetrahydrofuran (THF) (2.500 mL) was added LiOH (241 mg, 5.74 mmol) and Water (1.000 mL). The reaction was stirred at RT for 19 h and then concentrated. The residue was partitioned between EtOAc (50 mL) and 1N HCl (25 mL). The water layer was extracted with EtOAc (25 mL) and the combined organics were dried MgSO₄, filtered and concentrated in vacuo. The crude product was dissolved in DMSO and purified with reverse-phase HPLC under acidic conditions (0.1% formic acid) to afford the title compound. The compound was crystallized from EtOAc and hexane to give the title compound (185.1 mg, 61.3% yield). LC-MS m/z 526.3 (M+H)⁺, 1.37 min (ret. time). ¹H NMR (400 MHz, DMSO-d6) δ: 12.51-12.26 (m, 1H), 8.02 (s, 1H), 7.81-7.72 (m, 2H), 7.61-7.51 (m, 2H), 7.47 (s, 1H), 7.34 (t, J=7.9 Hz, 1H), 7.15-7.06 (m, 2H), 6.94 (d, J=8.0 Hz, 1H), 4.47-4.39 (m, 1H), 3.82 (s, 3H), 2.19-2.12 (m, 1H), 2.08 (s, 1H), 1.85-1.63 (m, 5H), 1.59-1.25 (m, 10H), 1.19 (d, J=5.8 Hz, 3H).

Example 75. 1-(3'-((S)-1-Cyclohexylethoxy)-[1,1'-biphenyl]-3-yl)-5-(trans-2-(1-methyl-1H-1,2,3-triazol-4-yl)cyclopropyl)-1H-pyrazole-4-carboxylic Acid

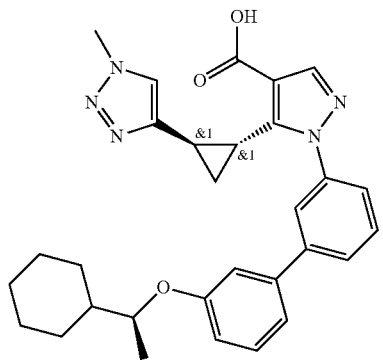 [SMILES: C[C@H](Oc1cccc(-c2cccc(-n3ncc(C(=O)O)c3[C@@H]3C[C@H]3c3cn(C)nn3)c2)c1)C1CCCCC1]

75a) Ethyl 2-(2,2-dibromovinyl)cyclopropanecarboxylate

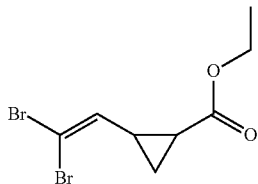

To a solution of triphenylphosphine (258 g, 985 mmol) in dichloromethane (DCM) (300 mL) was added a solution of carbon tetrabromide (163 g, 492 mmol) in dichloromethane (DCM) (300 mL) dropwise at 0° C. After addition, the mixture was stirred for 10 min, a solution of ethyl 2-formylcyclopropanecarboxylate (35 g, 246 mmol) in dichloromethane (DCM) (50 mL) was then added dropwise. After addition, the reaction mixture was stirred for 30 min at 0° C. The ice bath was removed and the reaction mixture was stirred for additional 30 min. The mixture was filtered and the filtrate was concentrated. The residue was triturated with hexanes and filtered through celite. The filtrate was filtered again through celite. To the filtrate was added isolute and concentrated. The isolute was loaded onto a cartridge and purified on the Torrent column chromatography (750 g silica gel, gold) eluting with a gradient of 0-5% ethyl acetate in hexanes. The title compound was obtained as clear colorless oil (43.7 g, 147 mmol, 59.6% yield). LC-MS m/z 296.9 $(M+H)^+$, 1.14 min (ret. time).

75b) 2-(2,2-Dibromovinyl)cyclopropanecarboxylic Acid

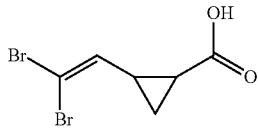

To a solution of ethyl 2-(2,2-dibromovinyl)cyclopropanecarboxylate (43.7 g, 147 mmol) in tetrahydrofuran (THF) (70 mL) and methanol (70 mL) was added 6.0 N NaOH (73.3 mL, 440 mmol). The reaction mixture was stirred for 1.0 hour at room temperature. The mixture was acidified with 6.0 N HCl (aq) and extracted with ethyl acetate. The organic extract was washed with water and dried over anhydrous magnesium sulfate. It was filtered and the filtrated was concentrated to give the title compound (37.6 g, 139 mmol, 95% yield) as white solid used in the next step without further purification. LC-MS m/z 268.5 $(M+H)^+$, 0.86 min (ret. time).

75c) Methyl 3-(2-(2,2-dibromovinyl)cyclopropyl)-3-oxopropanoate

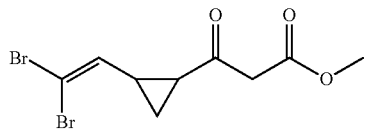

To a solution of 2-(2,2-dibromovinyl)cyclopropanecarboxylic acid (37.6 g, 139 mmol) in tetrahydrofuran (THF) (350 mL) was added CDI (33.9 g, 209 mmol). The mixture was stirred for 2 hours at room temperature, potassium 3-methoxy-3-oxopropanoate (65.3 g, 418 mmol) was added, followed by magnesium chloride (15.92 g, 167 mmol). The resulting reaction mixture was stirred overnight at room temperature. The mixture was neutralized with 6.0 N HCl and diluted with water, extracted with ethyl acetate. The organic extract was washed with brine and dried over anhydrous magnesium sulfate. It was filtered and the filtrate was concentrated. The residue was dissolved in DCM and purified on the Torrent flash column chromatography (750 g silica gel) eluting with a gradient of 0-25% ethyl acetate in hexanes. The title compound was obtained as clear yellow oil (45.4 g, 139 mmol, 100% yield). LC-MS m/z 324.8 $(M+H)^+$, 1.0 min (ret. time).

75d) Methyl 2-(2-(2,2-dibromovinyl)cyclopropanecarbonyl)-3-(dimethylamino)acrylate

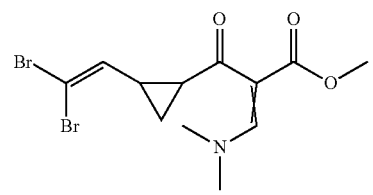 [SMILES: COC(=O)C(=CN(C)C)C(=O)C1CC1C=C(Br)Br]

A mixture of methyl 3-(2-(2,2-dibromovinyl)cyclopropyl)-3-oxopropanoate (45.4 g, 139 mmol) and 1,1-dimethoxy-N,N-dimethylmethanamine (24 ml, 180 mmol) in 1,4-Dioxane (24 mL) was stirred overnight at room temperature. The mixture was concentrated by rotavap. 1,4-dioxane (25 mL) was added and concentrated by rotavap (repeated one more time) to give the title compound (50 g, 131 mmol, 94% yield) as yellow oil used in the next step without further purification. LC-MS m/z 379.9 $(M+H)^+$, 0.99 (ret. time).

75e) Methyl 1-(3-bromophenyl)-5-(2-(2,2-dibromovinyl)cyclopropyl)-1H-pyrazole-4-carboxylate

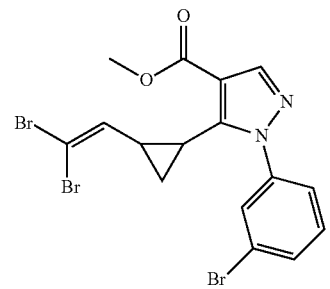 [SMILES: COC(=O)c1cnn(-c2cccc(Br)c2)c1C1CC1C=C(Br)Br]

To a solution of methyl 2-(2-(2,2-dibromovinyl)cyclopropanecarbonyl)-3-(dimethylamino)acrylate (50 g, 131 mmol) in Ethanol (300 mL) was added (3-bromophenyl)hydrazine hydrochloride (32.3 g, 144 mmol). To the resulting suspension was added TEA (36.6 mL, 262 mmol). The mixture turned to clear solution and it was stirred for 2.0 hours at room temperature. The mixture was filtered and the solid 75f) rac-Methyl 1-(3-bromophenyl)-5-((1,2-E)-2-ethynylcyclopropyl)-1H-pyrazole-4-carboxylate

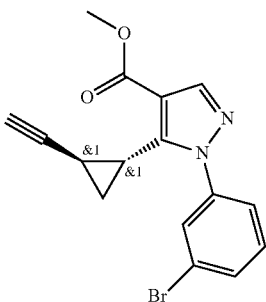 [SMILES: C#C[C@@H]1C[C@H]1c1c(C(=O)OC)cnn1-c1cccc(Br)c1]

A mixture of methyl 1-(3-bromophenyl)-5-((1R,2R)-2-(2,2-dibromovinyl)cyclopropyl)-1H-pyrazole-4-carboxylate (10 g, 19.80 mmol) and cesium carbonate (16.13 g, 49.5 mmol) in dimethyl sulfoxide (DMSO) (100 mL) was stirred for 2 days at 115° C. After cooled to the room temperature, the mixture was diluted with 200 mL of ethyl acetate and hexanes (3:2, V:V). It was filtered through celite, washed with the solution of ethyl acetate and hexanes (3:2, V:V). The resulting mixture was diluted with water (200 mL). The layers were separated and the organic layer was washed with water (2×200 mL), dried over anhydrous magnesium sulfate. It was filtered and the filtrate was concentrated to give the crude product. The crude product was dissolved in dichloromethane (20 mL) and loaded onto a silica gel column (330 g, gold), purified by Combiflash eluting with a gradient of 0-20% ethyl acetate in hexanes. The title compound was obtained as clear light yellow oil (5.2 g, 15.06 mmol, 76% yield). LC-MS m/z 344.8 (M+H)$^+$, 1.12 min (ret. time).

75 g) (S)-2-(3-(1-Cyclohexylethoxy)phenyl)-4,4,5,5-tetramethyl-1,3,2-dioxaborolane

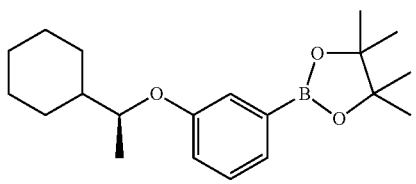 [SMILES: C[C@H](Oc1cccc(B2OC(C)(C)C(C)(C)O2)c1)C1CCCCC1]

A mixture of (S)-1-bromo-3-(1-cyclohexylethoxy)benzene (0.75 g, 2.65 mmol), 4,4,4',4',5,5,5',5'-octamethyl-2,2'-bi(1,3,2-dioxaborolane) (1.009 g, 3.97 mmol), potassium acetate (0.520 g, 5.30 mmol), and PdCl$_2$(dppf)-CH$_2$Cl$_2$ adduct (0.108 g, 0.132 mmol) in 1,4-dioxane (10 mL) was stirred for 2 hours at 100° C., the LCMS showed desired and little starting material. The mixture was stirred overnight at 80° C., the LCMS showed a complete reaction. After cooled to the room temperature, the mixture was filtered through celite, the filtrate was diluted with water and extracted with ethyl acetate. The organic extract was dried over anhydrous magnesium sulfate. It was filtered and the filtrate was concentrated. The crude product was purified on the Combiflash column chromatography eluting with a gradient of 0-5% ethyl acetate in hexanes. The title compound was obtained as clear colorless oil (0.668 g, 2.023 mmol, 76% yield). LC-MS m/z 331.1 (M+H)$^+$, 1.67 min (ret. time).

75h) Methyl 1-(3'-((S)-1-cyclohexylethoxy)-[1,1'-biphenyl]-3-yl)-5-(trans-2-ethynylcyclopropyl)-1H-pyrazole-4-carboxylate

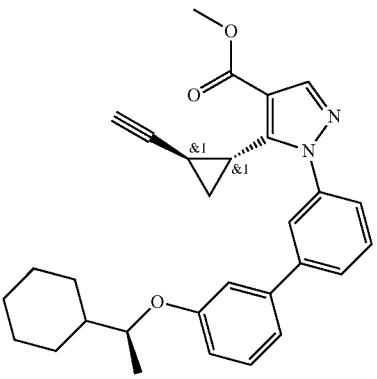 [SMILES: C#C[C@@H]1C[C@H]1c1c(C(=O)OC)cnn1-c1cccc(-c2cccc(O[C@@H](C)C3CCCCC3)c2)c1]

A mixture of (S)-2-(3-(1-cyclohexylethoxy)phenyl)-4,4,5,5-tetramethyl-1,3,2-dioxaborolane (550 mg, 1.665 mmol), rac-methyl 1-(3-bromophenyl)-5-((1R,2R)-2-ethynylcyclopropyl)-1H-pyrazole-4-carboxylate (575 mg, 1.665 mmol), tetrakis (96 mg, 0.083 mmol), and 10% Na$_2$CO$_3$ (aq) (3530 mg, 3.33 mmol) in 1,4-dioxane (10 mL) was stirred for 20 min at 100° C. After cooled to the room temperature, the mixture was diluted with water and extracted with ethyl acetate. The organic extract was washed with water and dried over anhydrous magnesium sulfate. It was filtered and the filtrate was concentrate to give the crude product which was then purified on the Combiflash (silica gel column 120 g, gold) eluting with a gradient of 0-15% ethyl acetate in hexanes. The title compound was obtained as clear colorless oil (560 mg, 1.195 mmol, 71.8% yield). LC-MS m/z 469.1 (M+H)$^+$, 1.64 min (ret. time).

75i) methyl 1-(3'-((S)-1-cyclohexylethoxy)-[1,1'-biphenyl]-3-yl)-5-(trans-2-(1-methyl-1H-1,2,3-triazol-4-yl)cyclopropyl)-1H-pyrazole-4-carboxylate

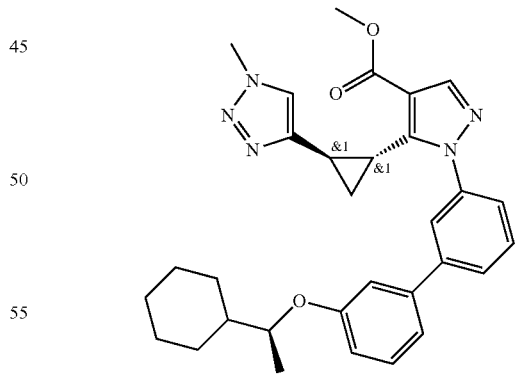

A mixture of rac-methyl 1-(3'-((S)-1-cyclohexylethoxy)-[1,1'-biphenyl]-3-yl)-5-((1R,2R)-2-ethynylcyclopropyl)-1H-pyrazole-4-carboxylate (60 mg, 0.128 mmol), iodomethane (0.020 mL, 0.320 mmol), sodium azide (22 mg, 0.338 mmol), copper(I) iodide (6.0 mg, 0.032 mmol) and DIPEA (0.022 mL, 0.128 mmol) in tert-butanol (2.0 mL) and water (1.0 mL) was irritated via microwave reactor for 40 min at 70° C. After cooled to the room temperature, the mixture was diluted with water and extracted with ethyl acetate. The organic extract was dried over anhydrous magnesium sulfate. It was filtered and the filtrate was concentrated. The crude product was purified on the Combiflash eluting with a gradient of 0-50% ethyl acetate in hexanes. The title compound was obtained as white solid (42 mg, 0.08 mmol, 62.4% yield). LC-MS m/z 526.1 (M+H)+, 1.43 min (ret. time).

75j) 1-(3'-((S)-1-Cyclohexylethoxy)-[1,1'-biphenyl]-3-yl)-5-(trans-2-(1-methyl-1H-1,2,3-triazol-4-yl)cyclopropyl)-1H-pyrazole-4-carboxylic Acid

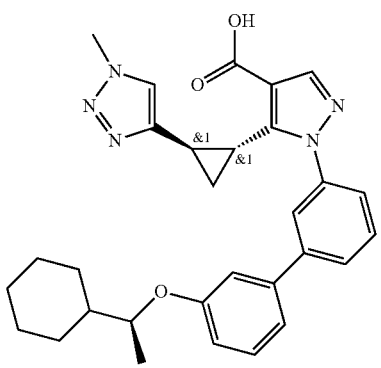 [SMILES: C[C@H](Oc1cccc(-c2cccc(-n3ncc(C(=O)O)c3[C@@H]3C[C@H]3c3cn(C)nn3)c2)c1)C1CCCCC1]

A mixture of methyl 1-(3'-((S)-1-cyclohexylethoxy)-[1,1'-biphenyl]-3-yl)-5-(trans-2-(1-methyl-1H-1,2,3-triazol-4-yl)cyclopropyl)-1H-pyrazole-4-carboxylate (42 mg, 0.080 mmol) and LiOH 50 mg/mL in water (0.765 mL, 1.598 mmol) in tetrahydrofuran (THF) (1.0 mL) and methanol (1.0 mL) was stirred for 18 hours at room temperature. The mixture was concentrated (still some water left) and neutralized with 1.0 N HCl. It was extracted with ethyl acetate. The solvent was evaporated and the crude product was then purified on the prep HPLC eluting with a gradient of 30-100% acetonitrile in water. The title compound was obtained as white solid (34 mg, 0.063 mmol, 79% yield). LC-MS m/z 512.1 (M+H)+, 1.30 min (ret. time).

The compounds in Table 1 were prepared by a method similar to the one described for the preparation of 1-(3'-((S)-1-Cyclohexylethoxy)-[1,1'-biphenyl]-3-yl)-5-(trans-2-(1-methyl-1H-1,2,3-triazol-4-yl)cyclopropyl)-1H-pyrazole-4-carboxylic acid. As is appreciated by those skilled in the art, these analogous examples may involve variations in general reaction conditions.

TABLE 1

| Example | Structure | Name | LCMS [M + H]+ | Retention Time (min) |
|---|---|---|---|---|
| 76 | 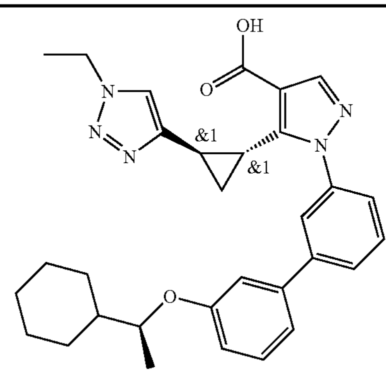 | 1-(3'-((S)-1-Cyclohexylethoxy)-[1,1'-biphenyl]-3-yl)-5-(trans-2-(1-ethyl-1H-1,2,3-triazol-4-yl)cyclopropyl)-1H-pyrazole-4-carboxylic acid | 526.1 | 1.34 |
| 77 | 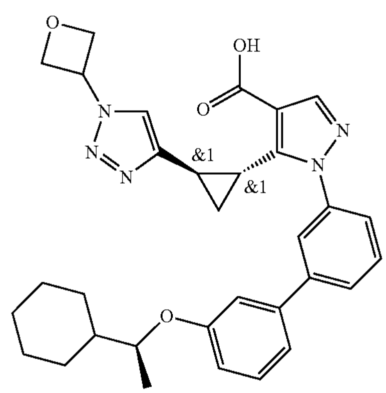 [SMILES: C[C@H](Oc1cccc(-c2cccc(-n3ncc(C(=O)O)c3[C@@H]3C[C@H]3c3cn(C4COC4)nn3)c2)c1)C1CCCCC1] | 1-(3'-((S)-1-Cyclohexylethoxy)-[1,1'-biphenyl]-3-yl)-5-(trans-2-(1-(oxetan-3-yl)-1H-1,2,3-triazol-4-yl)cyclopropyl)-1H-pyrazole-4-carboxylic acid | 554.1 | 1.28 |

TABLE 1-continued

| Example | Structure | Name | LCMS [M + H]+ | Retention Time (min) |
|---|---|---|---|---|
| 78 | 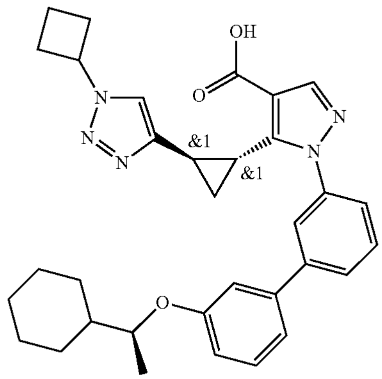 [SMILES: C[C@H](Oc1cccc(-c2cccc(-n3ncc(C(=O)O)c3[C@@H]3C[C@H]3c3cn(C4CCC4)nn3)c2)c1)C1CCCCC1] | 5-(trans-2-(1-Cyclobutyl-1H-1,2,3-triazol-4-yl)cyclopropyl)-1-(3'-((S)-1-cyclohexylethoxy)-[1,1'-biphenyl]-3-yl)-1H-pyrazole-4-carboxylic acid | 552.2 | 1.43 |
| 79 | 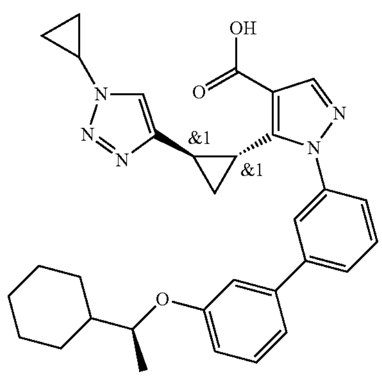 [SMILES: C[C@H](Oc1cccc(-c2cccc(-n3ncc(C(=O)O)c3[C@@H]3C[C@H]3c3cn(C4CC4)nn3)c2)c1)C1CCCCC1] | 1-(3'-((S)-1-Cyclohexylethoxy)-[1,1'-biphenyl]-3-yl)-5-(trans-2-(1-cyclopropyl-1H-1,2,3-triazol-4-yl)cyclopropyl)-1H-pyrazole-4-carboxylic acid | 538.1 | 1.38 |
| 80 | 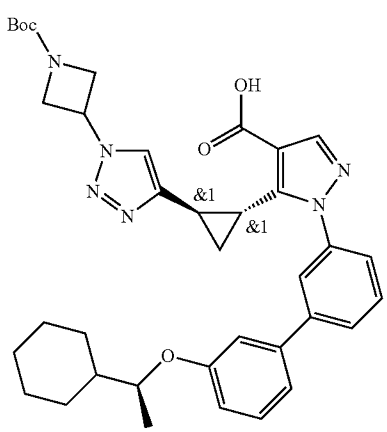 [SMILES: C[C@H](Oc1cccc(-c2cccc(-n3ncc(C(=O)O)c3[C@@H]3C[C@H]3c3cn(C4CN(C(=O)OC(C)(C)C)C4)nn3)c2)c1)C1CCCCC1] | 5-(trans-2-(1-(1-(tert-Butoxycarbonyl)azetidin-3-yl)-1H-1,2,3-triazol-4-yl)cyclopropyl)-1-(3'-((S)-1-cyclohexylethoxy)-[1,1'-biphenyl]-3-yl)-1H-pyrazole-4-carboxylic acid | 653.3 | 1.45 |

TABLE 1-continued

| Example | Structure | Name | LCMS [M + H]+ | Retention Time (min) |
|---|---|---|---|---|
| 81 | 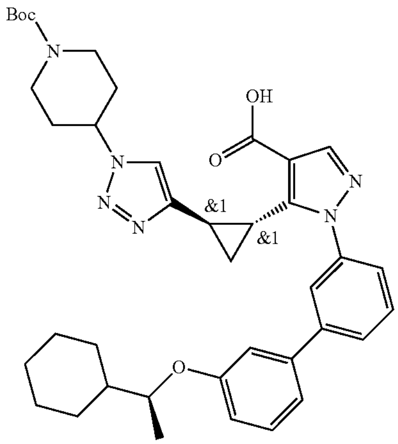 [SMILES: C[C@H](Oc1cccc(-c2cccc(-n3ncc(C(=O)O)c3[C@@H]3C[C@H]3c3cn(C4CCN(C(=O)OC(C)(C)C)CC4)nn3)c2)c1)C1CCCCC1] | 5-(trans-2-(1-(1-(tert-Butoxycarbonyl)piperidin-4-yl)-1H-1,2,3-triazol-4-yl)cyclopropyl)-1-(3'-((S)-1-cyclohexylethoxy)-[1,1'-biphenyl]-3-yl)-1H-pyrazole-4-carboxylic acid | 681.4 | 1.50 |
| 82 | 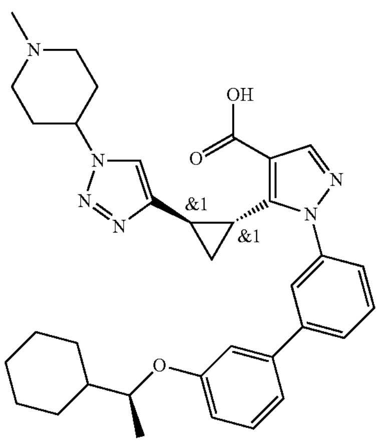 [SMILES: C[C@H](Oc1cccc(-c2cccc(-n3ncc(C(=O)O)c3[C@@H]3C[C@H]3c3cn(C4CCN(C)CC4)nn3)c2)c1)C1CCCCC1] | 1-(3'-((S)-1-Cyclohexylethoxy)-[1,1'-biphenyl]-3-yl)-5-(trans-2-(1-(1-methylpiperidin-4-yl)-1H-1,2,3-triazol-4-yl)cyclopropyl)-1H-pyrazole-4-carboxylic acid | 595.3 | 1.09 |
| 83 | 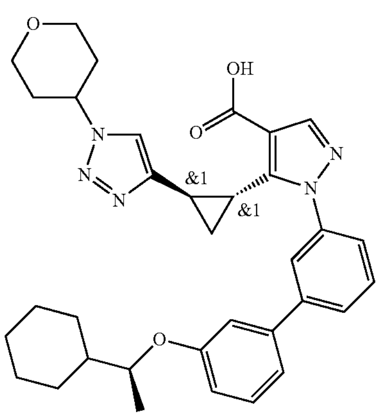 [SMILES: C[C@H](Oc1cccc(-c2cccc(-n3ncc(C(=O)O)c3[C@@H]3C[C@H]3c3cn(C4CCOCC4)nn3)c2)c1)C1CCCCC1] | 1-(3'-((S)-1-Cyclohexylethoxy)-[1,1'-biphenyl]-3-yl)-5-(trans-2-(1-(tetrahydro-2H-pyran-4-yl)-1H-1,2,3-triazol-4-yl)cyclopropyl)-1H-pyrazole-4-carboxylic acid | 582.1 | 1.31 |

TABLE 1-continued

| Example | Structure | Name | LCMS [M + H]+ | Retention Time (min) |
|---|---|---|---|---|
| 84 | 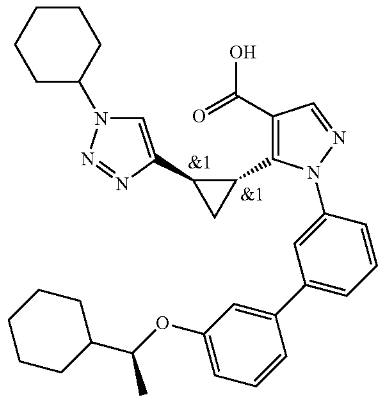 [SMILES: C[C@H](Oc1cccc(-c2cccc(-n3ncc(C(=O)O)c3[C@@H]3C[C@H]3c3cn(C4CCCCC4)nn3)c2)c1)C1CCCCC1] | 5-(trans-2-(1-Cyclohexyl-1H-1,2,3-triazol-4-yl)cyclopropyl)-1-(3'-((S)-1-cyclohexylethoxy)-[1,1'-biphenyl]-3-yl)-1H-pyrazole-4-carboxylic acid | 580.1 | 1.52 |

Example 85. 5-(trans-2-(1-(Azetidin-3-yl)-1H-1,2,3-triazol-4-yl)cyclopropyl)-1-(3'-((S)-1-cyclohexylethoxy)-[1,1'-biphenyl]-3-yl)-1H-pyrazole-4-carboxylic Acid

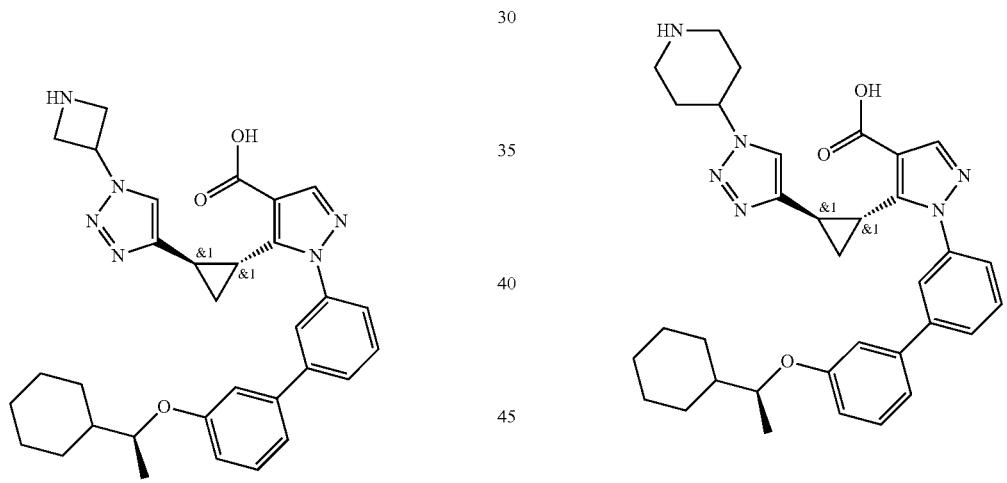

A mixture of 5-(trans-2-(1-(1-(tert-butoxycarbonyl)azetidin-3-yl)-1H-1,2,3-triazol-4-yl)cyclopropyl)-1-(3'-((S)-1-cyclohexylethoxy)-[1,1'-biphenyl]-3-yl)-1H-pyrazole-4-carboxylic acid (100 mg, 0.153 mmol) and TFA (0.5 mL, 6.49 mmol) in dichloromethane (DCM) (1.0 mL) was stirred for 1.0 hour at room temperature. The mixture was neutralized with saturated NaHCO$_3$ (aq) and the mixture was passed through a SCX cartridge flashed with methanol, followed by 2.0 M NH$_3$ in methanol solution. The NH$_3$ solution was collected and concentrated to give the title compound as white solid (80 mg, 0.138 mmol, 90% yield). LC-MS m/z 553.3 (M+H)+, 1.10 min (ret. time).

Example 86. 1-(3'-((S)-1-cyclohexylethoxy)-[1,1'-biphenyl]-3-yl)-5-(trans-2-(1-(piperidin-4-yl)-1H-1,2,3-triazol-4-yl)cyclopropyl)-1H-pyrazole-4-carboxylic Acid To a solution of 5-(trans-2-(1-(1-(tert-butoxycarbonyl)piperidin-4-yl)-1H-1,2,3-triazol-4-yl)cyclopropyl)-1-(3'-((S)-1-cyclohexylethoxy)-[1,1'-biphenyl]-3-yl)-1H-pyrazole-4-carboxylic acid (42 mg, 0.062 mmol) in dichloromethane (DCM) (0.6 mL) was added TFA (0.3 mL, 3.89 mmol). The reaction mixture was stirred for 1.0 hour at room temperature. The mixture was concentrated and the residue was diluted with water and neutralized with saturated NaHCO$_3$ (aq). The resulting mixture was passed through a SCX cartridge, flashed with methanol, followed by 2.0 M ammonia in methanol solution. The ammonia solution was collected and concentrated to give the title compound as white solid (31.5 mg, 0.052 mmol, 84% yield). LC-MS m/z 581.3 (M+H)+, 1.10 min (ret. time).

Example 87. 5-(trans-2-(1-Benzyl-1H-1,2,3-triazol-4-yl)cyclopropyl)-1-(3'-((S)-1-cyclohexylethoxy)-[1,1'-biphenyl]-3-yl)-1H-pyrazole-4-carboxylic Acid

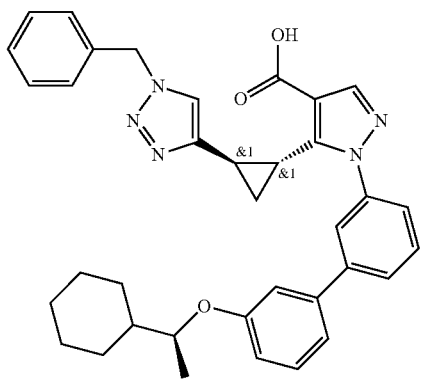 [SMILES: C[C@H](Oc1cccc(-c2cccc(-n3ncc(C(=O)O)c3[C@@H]3C[C@H]3c3cn(Cc4ccccc4)nn3)c2)c1)C1CCCCC1]

87a) Methyl 5-(trans-2-(1-benzyl-1H-1,2,3-triazol-4-yl)cyclopropyl)-1-(3'-((S)-1-cyclohexylethoxy)-[1,1'-biphenyl]-3-yl)-1H-pyrazole-4-carboxylate

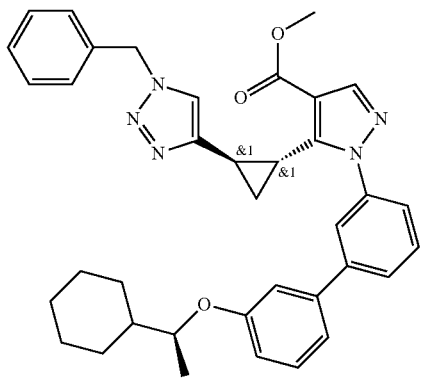 [SMILES: COC(=O)c1cnn(-c2cccc(-c3cccc(O[C@@H](C)C4CCCCC4)c3)c2)c1[C@@H]1C[C@H]1c1cn(Cc2ccccc2)nn1]

A mixture of methyl 1-(3'-((S)-1-cyclohexylethoxy)-[1,1'-biphenyl]-3-yl)-5-(trans-2-ethynylcyclopropyl)-1H-pyrazole-4-carboxylate (100 mg, 0.213 mmol), (azidomethyl)benzene (71.0 mg, 0.534 mmol), copper(I) iodide (8.2 mg, 0.043 mmol), and DIPEA (12 µl, 0.069 mmol) in Tert-Butanol (2.0 mL) and Water (1.0 mL) was irritated via microwave reactor on high absorption for 50 min at 70° C. After cooled to the room temperature, the mixture was diluted with ethyl acetate and filtered through celite. The filtrate was diluted with brine and the layers were separated. The organic layer was washed with brine and dried over anhydrous magnesium sulfate. It was filtered and the filtrate was concentrate to give the crude product which was then purified on the Combiflash eluting with a gradient of 0-40% ethyl acetate in hexanes. The title compound was obtained as white solid (102 mg, 0.17 mmol, 79% yield). LC-MS m/z 602.1 (M+H)$^+$, 1.59 min (ret. time).

87b) 5-(trans-2-(1-Benzyl-1H-1,2,3-triazol-4-yl)cyclopropyl)-1-(3'-((S)-1-cyclohexylethoxy)-[1,1'-biphenyl]-3-yl)-1H-pyrazole-4-carboxylic Acid

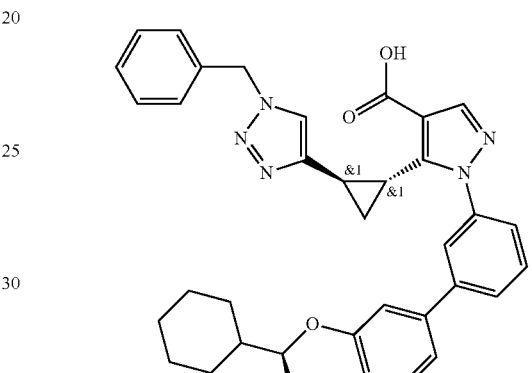

A mixture of methyl 5-(trans-2-(1-benzyl-1H-1,2,3-triazol-4-yl)cyclopropyl)-1-(3'-((S)-1-cyclohexylethoxy)-[1,1'-biphenyl]-3-yl)-1H-pyrazole-4-carboxylate (102 mg, 0.170 mmol) and LiOH (50 mg/mL) (0.812 mL, 1.695 mmol) in tetrahydrofuran (THF) (1.5 mL) and methanol (1.5 mL) was stirred for 7 days at room temperature. The mixture was concentrated (some water left) and the residue was neutralized with 1.0 N HCl (aq), extracted with ethyl acetate. The organic extract was concentrated and the crude product was purified on the prep HPLC eluting with a gradient of 40-100% acetonitrile in water. The title compound was obtained as white solid (82 mg, 0.133 mmol, 78% yield). LC-MS m/z 588.1 (M+H)$^+$, 1.47 min (ret. time).

The compounds in Table 2 were prepared by a method similar to the one described for the preparation of 5-(trans-2-(1-Benzyl-1H-1,2,3-triazol-4-yl)cyclopropyl)-1-(3'-((S)-1-cyclohexylethoxy)-[1,1'-biphenyl]-3-yl)-1H-pyrazole-4-carboxylic acid. As is appreciated by those skilled in the art, these analogous examples may involve variations in general reaction conditions.

TABLE 2

| Example | Structure | Name | LCMS [M + H]+ | Retention Time (min) |
|---|---|---|---|---|
| 88 | 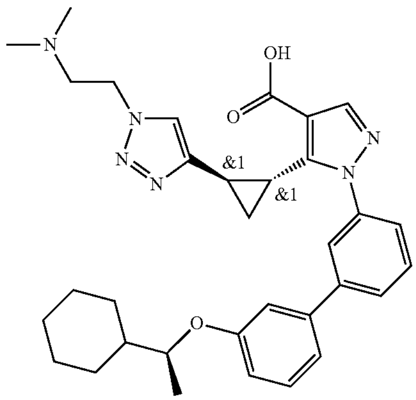 [SMILES: C[C@H](Oc1cccc(-c2cccc(-n3ncc(C(=O)O)c3[C@@H]3C[C@H]3c3cn(CCN(C)C)nn3)c2)c1)C1CCCCC1] | 1-(3'-((S)-1-Cyclohexylethoxy)-[1,1'-biphenyl]-3-yl)-5-(trans-2-(1-(2-(dimethylamino)ethyl)-1H-1,2,3-triazol-4-yl)cyclopropyl)-1H-pyrazole-4-carboxylic acid | 569.2 | 1.11 |
| 89 | 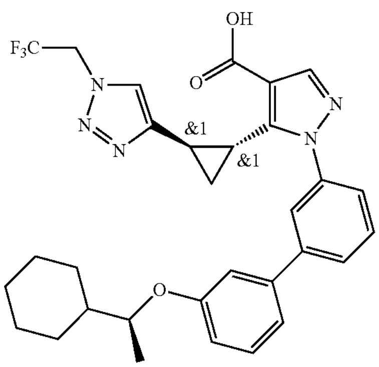 [SMILES: C[C@H](Oc1cccc(-c2cccc(-n3ncc(C(=O)O)c3[C@@H]3C[C@H]3c3cn(CC(F)(F)F)nn3)c2)c1)C1CCCCC1] | 1-(3'-((S)-1-Cyclohexylethoxy)-[1,1'-biphenyl]-3-yl)-5-(trans-2-(1-(2,2,2-trifluoroethyl)-1H-1,2,3-triazol-4-yl)cyclopropyl)-1H-pyrazole-4-carboxylic acid | 580.1 | 1.43 |
| 90 | 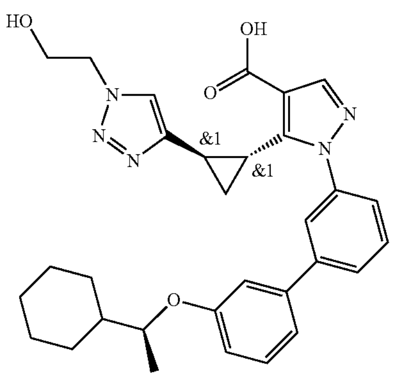 [SMILES: C[C@H](Oc1cccc(-c2cccc(-n3ncc(C(=O)O)c3[C@@H]3C[C@H]3c3cn(CCO)nn3)c2)c1)C1CCCCC1] | 1-(3'-((S)-1-Cyclohexylethoxy)-[1,1'-biphenyl]-3-yl)-5-(trans-2-(1-(2-hydroxyethyl)-1H-1,2,3-triazol-4-yl)cyclopropyl)-1H-pyrazole-4-carboxylic acid | 542.1 | 1.23 |
| 91 | 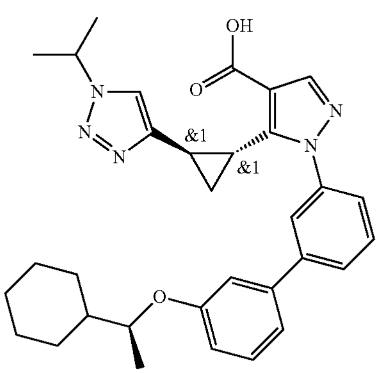 [SMILES: CC(C)n1cc([C@@H]2C[C@H]2c2c(C(=O)O)cnn2-c2cccc(-c3cccc(O[C@@H](C)C4CCCCC4)c3)c2)nn1] | 1-(3'-((S)-1-Cyclohexylethoxy)-[1,1'-biphenyl]-3-yl)-5-(trans-2-(1-isopropyl-1H-1,2,3-triazol-4-yl)cyclopropyl)-1H-pyrazole-4-carboxylic acid | 540.1 | 1.38 |

TABLE 2-continued

| Example | Structure | Name | LCMS [M + H]+ | Retention Time (min) |
|---|---|---|---|---|
| 92 | 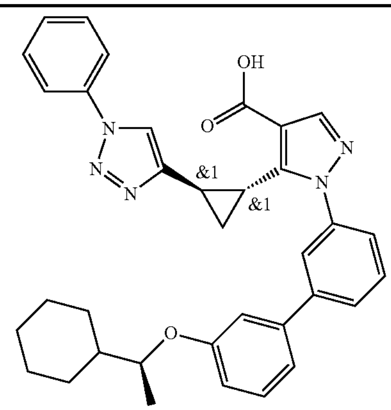 | 1-(3'-((S)-1-Cyclohexylethoxy)-1,1'-biphenyl]-3-yl)-5-((1,2-trans)-2-(1-phenyl-1H-1,2,3-triazol-4-yl)cyclopropyl)-1H-pyrazole-4-carboxylic acid | 574.1 | 1.48 |

Example 93. 5-(trans-2-(1H-1,2,3-Triazol-4-yl)cyclopropyl)-1-(3'-((S)-1-cyclohexylethoxy)-[1,1'-biphenyl]-3-yl)-1H-pyrazole-4-carboxylic Acid Example 94. 1-(3'-((S)-1-Cyclohexylethoxy)-[1,1'-biphenyl]-3-yl)-5-(trans-2-(1-(1-methylazetidin-3-yl)-1H-1,2,3-triazol-4-yl)cyclopropyl)-1H-pyrazole-4-carboxylic Acid

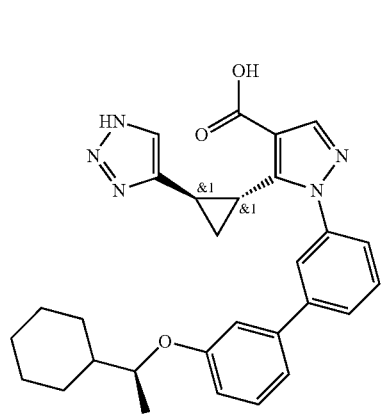 [SMILES: C[C@H](Oc1cccc(-c2cccc(-n3ncc(C(=O)O)c3[C@@H]3C[C@H]3c3c[nH]nn3)c2)c1)C1CCCCC1]

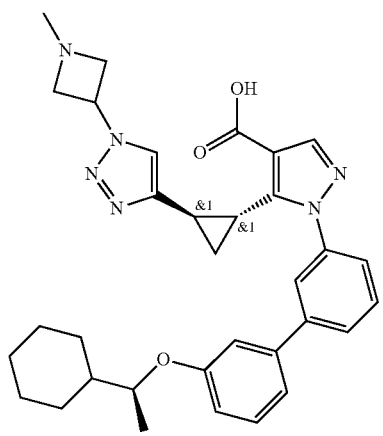 [SMILES: C[C@H](Oc1cccc(-c2cccc(-n3ncc(C(=O)O)c3[C@@H]3C[C@H]3c3cn(C4CN(C)C4)nn3)c2)c1)C1CCCCC1]

A solution of 5-(trans-2-(1-benzyl-1H-1,2,3-triazol-4-yl)cyclopropyl)-1-(3'-((S)-1-cyclohexylethoxy)-[1,1'-biphenyl]-3-yl)-1H-pyrazole-4-carboxylic acid (69 mg, 0.117 mmol) in Ethyl acetate (4.0 mL) and methanol (4.0 mL) was conducted hydrogenation on a H-Cube with 10% Pd/C catalyst (1.0 mL/min flow rate) at room temperature. Very little product was produced after a few hours. Rising the pressure to 50 bars and let it go two days. The LCMS showed little starting material left. The mixture was concentrated and the crude product was purified on the prep HPLC eluting with a gradient of 30-100% acetonitrile in water. The title compound was obtained as white solid (12 mg, 0.023 mmol, 19.5% yield). LC-MS m/z 498.1 (M+H)+, 1.28 min (ret. time).

To a solution of 5-((1R,2R)-2-(1-(azetidin-3-yl)-1H-1,2,3-triazol-4-yl)cyclopropyl)-1-(3'-((S)-1-cyclohexylethoxy)-[1,1'-biphenyl]-3-yl)-1H-pyrazole-4-carboxylic acid (50 mg, 0.090 mmol) in methanol (1.0 mL) was added formaldehyde (25 µl, 0.336 mmol). After stirring for 30 min at room temperature, sodium borohydride (12 mg, 0.317 mmol) was added. The reaction mixture was stirred for 3 days at room temperature. The LCMS showed almost no reaction. The staring material was recovered by a SCX cartridge. The recovered starting material was dissolve in methanol (1.0 mL), paraformaldehyde (13 mg, 0.433 mmol) was added, followed by decaborane (4.0 mg, 0.033 mmol). The reaction mixture was stirred for 2 days at room temperature. The LCMS showed an almost complete reaction but also some impurities appeared. The mixture was passed through a SCX cartridge flashed with methanol, followed by 2.0 M ammonia in methanol solution. The ammonia solution was collected and the concentrated to give the crude product. The crude product was then purified on the prep HPLC eluting with a gradient of 10-90% acetonitrile (0.1% TFA) in water (0.1% TFA). The desired fraction was concentrated and the product was neutralized with saturated NaHCO$_3$ (aq). The resulting mixture was passed through a SCX cartridge flashed with methanol, followed by 2.0 M ammonia in methanol solution. The ammonia solution was collected and concentrated to give the fee base product (9.9 mg, 0.015 mmol, 16.6% yield). LC-MS m/z 567.2 (M+H)$^+$, 1.10 min (ret. time).

Example 95. 1-(3'-((S)-1-Cyclohexylethoxy)-[1,1'-biphenyl]-3-yl)-5-((1R,2R)-2-(1-(tetrahydro-2H-pyran-4-yl)-1H-1,2,3-triazol-4-yl)cyclopropyl)-1H-pyrazole-4-carboxylic Acid

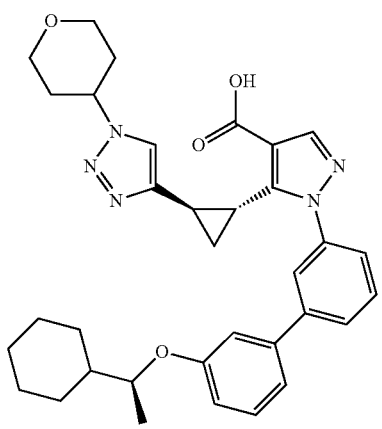 [SMILES: C[C@H](Oc1cccc(-c2cccc(-n3ncc(C(=O)O)c3[C@@H]3C[C@H]3c3cn(C4CCOCC4)nn3)c2)c1)C1CCCCC1]

95a) Methyl 1-(3'-((S)-1-cyclohexylethoxy)-[1,1'-biphenyl]-3-yl)-5-((1R,2R)-2-ethynylcyclopropyl)-1H-pyrazole-4-carboxylate and methyl 1-(3'-((S)-1-cyclohexylethoxy)-[1,1'-biphenyl]-3-yl)-5-((1S,2S)-2-ethynylcyclopropyl)-1H-pyrazole-4-carboxylate

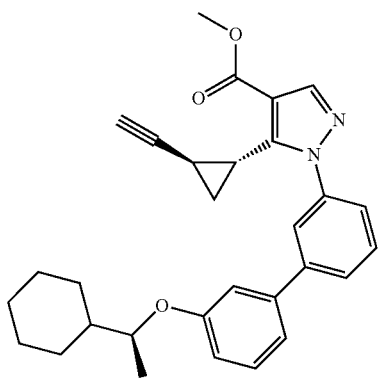

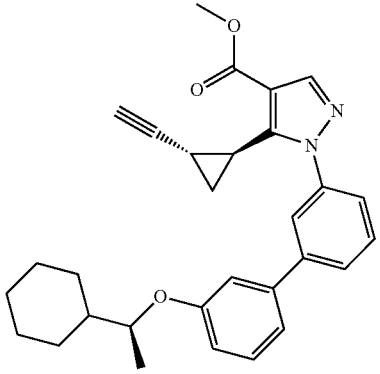

Methyl 1-(3'-((S)-1-cyclohexylethoxy)-[1,1'-biphenyl]-3-yl)-5-(trans-2-ethynylcyclopropyl)-1H-pyrazole-4-carboxylate (700 mg) was resolved by Chiral SFC: Column: Chiralpak AY 20×250 mm, 5 u; Co-solvent: 25% IPA; Flow rate: 50 g/min; Back pressure: 100 Bar; Sample was dissolved in EtOH (70 mg/mL, 0.5 ml/inj). Two single enanteomers were separated and both were obtained as clear colorless oil: methyl 1-(3'-((S)-1-cyclohexylethoxy)-[1,1'-biphenyl]-3-yl)-5-((1R,2R)-2-ethynylcyclopropyl)-1H-pyrazole-4-carboxylate (277.3 mg, 0.592 mmol, 39.6% yield), LC-MS m/z 469.2 (M+H)$^+$, 1.63 min (ret. time); methyl 1-(3'-((S)-1-cyclohexylethoxy)-[1,1'-biphenyl]-3-yl)-5-((1S,2S)-2-ethynylcyclopropyl)-1H-pyrazole-4-carboxylate (305.9 mg, 0.653 mmol, 43.7% yield), LC-MS m/z 469.2 (M+H)$^+$, 1.63 min (ret. time).

95b) Methyl 1-(3'-((S)-1-cyclohexylethoxy)-[1,1'-biphenyl]-3-yl)-5-((1R,2R)-2-(1-(tetrahydro-2H-pyran-4-yl)-1H-1,2,3-triazol-4-yl)cyclopropyl)-1H-pyrazole-4-carboxylate

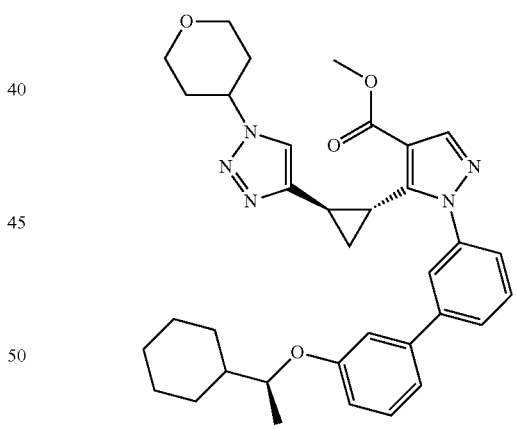

A mixture of 4-iodotetrahydro-2H-pyran (122 mg, 0.576 mmol), sodium azide (49.9 mg, 0.768 mmol), and DIPEA (0.101 mL, 0.576 mmol) in N,N-dimethylformamide (DMF) (1.2 mL) was stirred for 2.0 hours at 80° C. The resulting organic azide intermediate solution was transferred to a microwave reaction tube, and it was diluted with Tert-Butanol (1.5 mL) and Water (0.5 mL). Methyl 1-(3'-((S)-1-cyclohexylethoxy)-[1,1'-biphenyl]-3-yl)-5-((1R,2R)-2-ethynylcyclopropyl)-1H-pyrazole-4-carboxylate (90 mg, 0.192 mmol) and copper(I) iodide (7.32 mg, 0.038 mmol) were added. The reaction mixture was irritated via microwave reactor for 40 min at 70° C. After cooled to the room temperature, the mixture was diluted with brine and extracted with ethyl acetate. The organic extract was washed with brine and dried over anhydrous magnesium sulfate. It was filtered and the filtrate was concentrated. The crude product was purified on the Combiflash eluting with a gradient of 0-60% ethyl acetate in hexanes. The title compound was obtained as white solid (88 mg, 0.148 mmol, 77% yield). LC-MS m/z 596.2 (M+H)$^+$, 1.46 min (ret. time).

95c) 1-(3'-((S)-1-Cyclohexylethoxy)-[1,1'-biphenyl]-3-yl)-5-((1R,2R)-2-(1-(tetrahydro-2H-pyran-4-yl)-1H-1,2,3-triazol-4-yl)cyclopropyl)-1H-pyrazole-4-carboxylic Acid

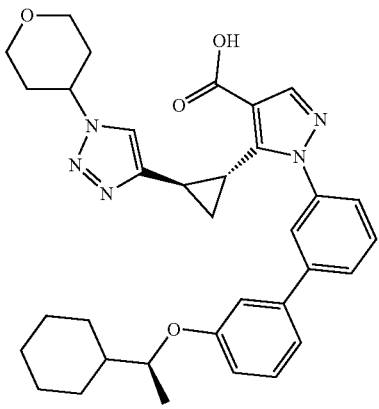 [SMILES: C[C@H](Oc1cccc(-c2cccc(-n3ncc(C(=O)O)c3[C@@H]3C[C@H]3c3cn(C4CCOCC4)nn3)c2)c1)C1CCCCC1]

A mixture of methyl 1-(3'-((S)-1-cyclohexylethoxy)-[1,1'-biphenyl]-3-yl)-5-((1R,2R)-2-(1-(tetrahydro-2H-pyran-4-yl)-1H-1,2,3-triazol-4-yl)cyclopropyl)-1H-pyrazole-4-carboxylate (88 mg, 0.148 mmol) and LiOH (50 mg/mL in H$_2$O) (1.0 mL, 4.18 mmol) in methanol (1.0 mL) and tetrahydrofuran (THF) (1.0 mL) was stirred for 1.0 hour at 40° C. The mixture was concentrated (some water left), the residue was diluted with water (2.0 mL) and neutralized with 1.0 N HCl. The resulting suspension was extracted with ethyl acetate. The organic extract was concentrated and the crude product was purified by prep HPLC eluting with a gradient of 45% to 85% acetonitrile in water. The title compound was obtained as white solid (61 mg, 0.100 mmol, 67.4% yield). LC-MS m/z 582.1 (M+H)$^+$, 1.32 min (ret. time).

The compounds in Table 3 were prepared by a method similar to the one described for the preparation of 1-(3'-((S)-1-Cyclohexylethoxy)-[1,1'-biphenyl]-3-yl)-5-((1R,2R)-2-(1-(tetrahydro-2H-pyran-4-yl)-1H-1,2,3-triazol-4-yl)cyclopropyl)-1H-pyrazole-4-carboxylic acid. As is appreciated by those skilled in the art, these analogous examples may involve variations in general reaction conditions.

TABLE 3

| Example | Structure | Name | LCMS [M + H]$^+$ | Retention Time (min) |
|---|---|---|---|---|
| 96 | 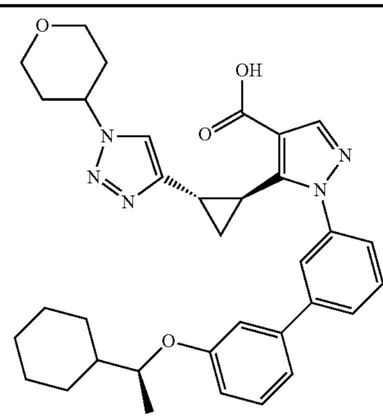 | 1-(3-((S)-1-Cyclohexylethoxy)-[1,1'-biphenyl]-3-yl)-5-((1S,2S)-2-(1-(tetrahydro-2H-pyran-4-yl)-1H-1,2,3-triazol-4-yl)cyclopropyl)-1H-pyrazole-4-carboxylic acid | 582.1 | 1.32 |
| 97 | 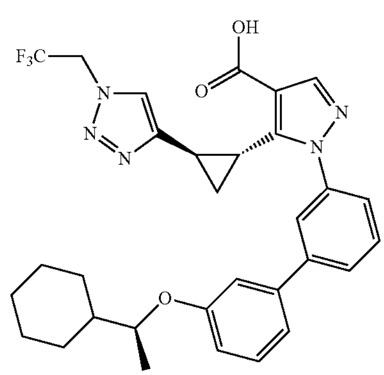 [SMILES: C[C@H](Oc1cccc(-c2cccc(-n3ncc(C(=O)O)c3[C@@H]3C[C@H]3c3cn(CC(F)(F)F)nn3)c2)c1)C1CCCCC1] | 1-(3'-((S)-1-Cyclohexylethoxy)-[1,1'-biphenyl]-3-yl)-5-((1R,2R)-2-(1-(2,2,2-trifluoroethyl)-1H-1,2,3-triazol-4-yl)cyclopropyl)-1H-pyrazole-4-carboxylic acid | 580.0 | 1.44 |

TABLE 3-continued

| Example | Structure | Name | LCMS [M + H]+ | Retention Time (min) |
|---|---|---|---|---|
| 98 | 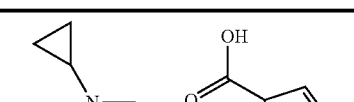 | 1-(3'-((S)-1-Cyclohexylethoxy)-[1,1'-biphenyl]-3-yl)-5-((1R,2R)-2-(1-cyclopropyl-1H-1,2,3-triazol-4-yl)cyclopropyl)-1H-pyrazole-4-carboxylic acid | 538.0 | 1.39 |

Example 99. 5-((1R,2R)-2-(1H-1,2,3-Triazol-4-yl)cyclopropyl)-1-(3'-((S)-1-cyclohexylethoxy)-[1,1'-biphenyl]-3-yl)-1H-pyrazole-4-carboxylic Acid

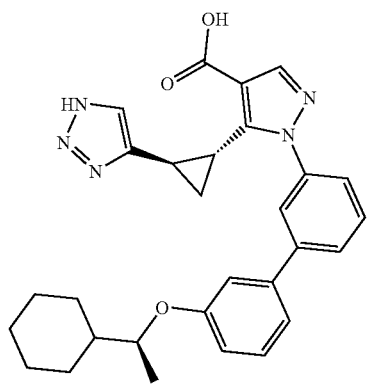 [SMILES: C[C@H](Oc1cccc(-c2cccc(-n3ncc(C(=O)O)c3[C@@H]3C[C@H]3c3c[nH]nn3)c2)c1)C1CCCCC1]

99a) Methyl 1-(3'-((S)-1-cyclohexylethoxy)-[1,1'-biphenyl]-3-yl)-5-((1R,2R)-2-(1-((pivaloyloxy)methyl)-1H-1,2,3-triazol-4-yl)cyclopropyl)-1H-pyrazole-4-carboxylate

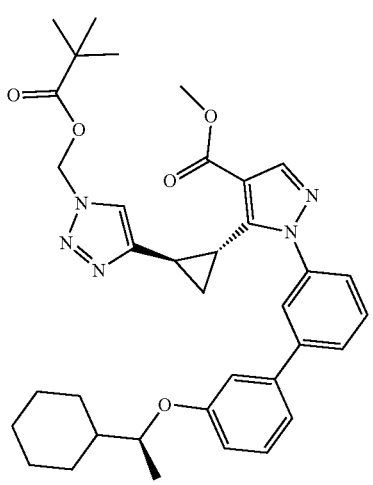 [SMILES: COC(=O)c1cnn(-c2cccc(-c3cccc(O[C@@H](C)C4CCCCC4)c3)c2)c1[C@@H]1C[C@H]1c1cn(COC(=O)C(C)(C)C)nn1]

A mixture of methyl 1-(3'-((S)-1-cyclohexylethoxy)-[1,1'-biphenyl]-3-yl)-5-((1R,2R)-2-ethynylcyclopropyl)-1H-pyrazole-4-carboxylate (96 mg, 0.205 mmol), azidomethyl pivalate (0.078 mL, 0.512 mmol), DIPEA (0.072 mL, 0.410 mmol) and copper(I) iodide (7.80 mg, 0.041 mmol) in N,N-Dimethylformamide (DMF) (0.5 mL), Water (0.5 mL) and Tert-Butanol (1.5 mL) was irritated via microwave reactor for 40 min at 70° C. The mixture was diluted with water and extracted with ethyl acetate. The organic extract was washed with water and dried over anhydrous magnesium sulfate. It was filtered and the filtrate was concentrated. The crude product was purified on the Combiflash eluting with a gradient of 0 to 30% ethyl acetate in hexanes. The title compound was obtained as colorless wax (103 mg, 0.165 mmol, 80% yield). LC-MS m/z 626.4 (M+H)+, 1.68 min (ret. time).

99b) 5-((1R,2R)-2-(1H-1,2,3-Triazol-4-yl)cyclopropyl)-1-(3'-((S)-1-cyclohexylethoxy)-[1,1'-biphenyl]-3-yl)-1H-pyrazole-4-carboxylic Acid

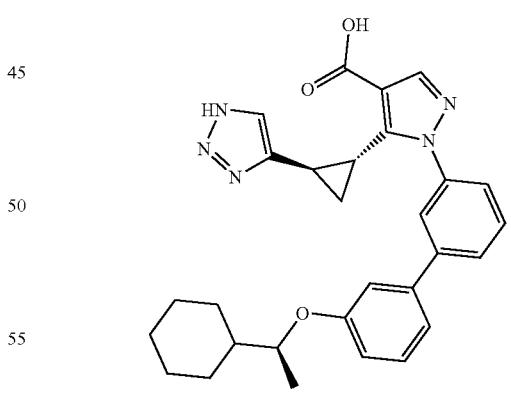

A mixture of methyl 1-(3'-((S)-1-cyclohexylethoxy)-[1,1'-biphenyl]-3-yl)-5-((1R,2R)-2-(1-((pivaloyloxy)methyl)-1H-1,2,3-triazol-4-yl)cyclopropyl)-1H-pyrazole-4-carboxylate (103 mg, 0.165 mmol) and 3.0 N NaOH (aq) (0.8 mL, 4.80 mmol) in tetrahydrofuran (THF) (1.2 mL) and methanol (1.2 mL) was stirred 3 days at room temperature. The mixture was concentrated and the residue was re-dissolved in water. The resulting clear solution was neutralized with 1.0 N HCl (aq). Precipitate formed and it was filtered, washed with water. The solid was re-dissolved in ethanol/THF (1.0 mL/1.0 mL), 3.0 N NaOH (aq) (0.3 mL) was added and it was stirred overnight at room temperature, the LCMS showed pure desired product. The mixture was concentrated and the residue was diluted with water, neutralized with 1.0 N HCl (aq). The precipitate was filtered and washed with water. The white solid was the pure desired product (61 mg, 0.116 mmol, 70.8% yield). LC-MS m/z 498.1 (M+H)+, 1.31 min (ret. time).

Example 100. 5-((1S,2S)-2-(1H-1,2,3-Triazol-4-yl) cyclopropyl)-1-(3'-((S)-1-cyclohexylethoxy)-[1,1'-biphenyl]-3-yl)-1H-pyrazole-4-carboxylic Acid

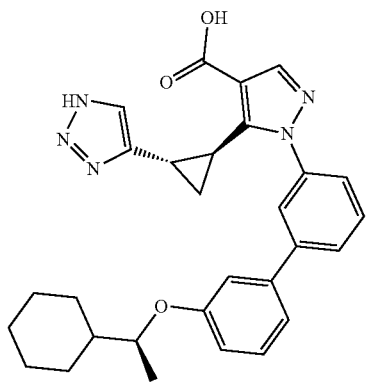 [SMILES: C[C@H](Oc1cccc(-c2cccc(-n3ncc(C(=O)O)c3[C@H]3C[C@@H]3c3c[nH]nn3)c2)c1)C1CCCCC1]

100a) Methyl 1-(3'-((S)-1-cyclohexylethoxy)-[1,1'-biphenyl]-3-yl)-5-((1S,2S)-2-(1-((pivaloyloxy) methyl)-1H-1,2,3-triazol-4-yl)cyclopropyl)-1H-pyrazole-4-carboxylate

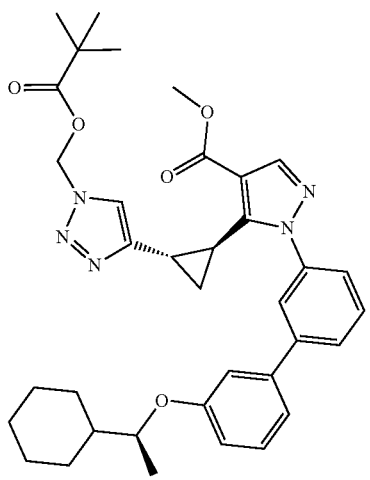 [SMILES: COC(=O)c1cnn(-c2cccc(-c3cccc(O[C@@H](C)C4CCCCC4)c3)c2)c1[C@H]1C[C@@H]1c1cn(COC(=O)C(C)(C)C)nn1]

A mixture of methyl 1-(3'-((S)-1-cyclohexylethoxy)-[1,1'-biphenyl]-3-yl)-5-((1S,2S)-2-ethynylcyclopropyl)-1H-pyrazole-4-carboxylate (50 mg, 0.107 mmol), azidomethyl pivalate (0.041 mL, 0.267 mmol), DIPEA (0.037 mL, 0.213 mmol) and copper(I) iodide (4.06 mg, 0.021 mmol) in N,N-Dimethylformamide (DMF) (0.5 mL), Water (0.5 mL) and Tert-Butanol (1.5 mL) was irritated via microwave reactor for 40 min at 70° C. The mixture was diluted with water and extracted with ethyl acetate. The organic extract was washed with water and dried over anhydrous magnesium sulfate. It was filtered and the filtrate was concentrated. The crude product was purified on the Combiflash eluting with a gradient of 0 to 30% ethyl acetate in hexanes. The title compound was obtained as white solid (55 mg, 0.088 mmol, 82% yield). LC-MS m/z 626.1 (M+H)+, 1.67 min (ret. time).

100b) 5-((1S,2S)-2-(1H-1,2,3-Triazol-4-yl)cyclopropyl)-1-(3'-((S)-1-cyclohexylethoxy)-[1,1'-biphenyl]-3-yl)-1H-pyrazole-4-carboxylic Acid

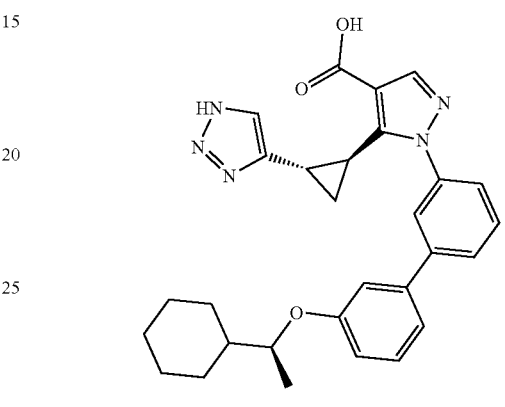

A mixture of methyl 1-(3'-((S)-1-cyclohexylethoxy)-[1,1'-biphenyl]-3-yl)-5-((1S,2S)-2-(1-((pivaloyloxy)methyl)-1H-1,2,3-triazol-4-yl)cyclopropyl)-1H-pyrazole-4-carboxylate (55 mg, 0.088 mmol) and 3.0 N NaOH (aq) (0.8 mL, 2.400 mmol) in tetrahydrofuran (THF) (1.000 mL) and methanol (1.0 mL) was stirred 3 days at room temperature. The mixture was concentrated (some water left) and diluted with water, neutralized with 1.0 N HCl (aq). The resulting suspension was extracted with ethyl acetate. The organic extract was concentrated and the crude product was purified by prep HPLC eluting with a gradient of 45% to 95% acetonitrile in water. The title compound was obtained as white solid (10 mg, 0.019 mmol, 21.7% yield). LC-MS m/z 498.1 (M+H)+, 1.31 min (ret. time).

Example 101. 1-(3'-((S)-1-cyclohexylethoxy)-[1,1'-biphenyl]-3-yl)-5-(cis-2-(1-methyl-1H-1,2,3-triazol-4-yl)cyclopropyl)-1H-pyrazole-4-carboxylic Acid

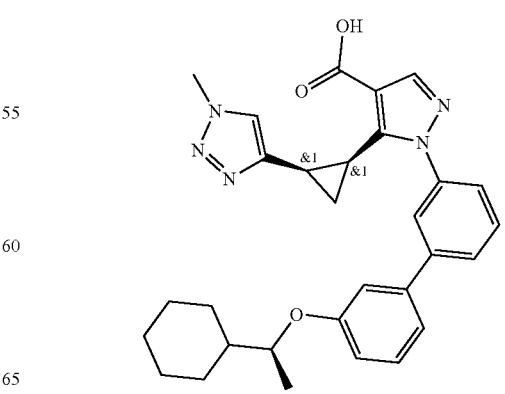

101a) rac-Methyl 1-(3-bromophenyl)-5-((1S,2R)-2-ethynylcyclopropyl)-1H-pyrazole-4-carboxylate

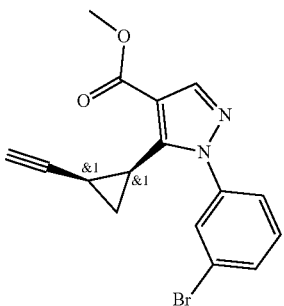 [SMILES: C#C[C@@H]1C[C@@H]1c1c(C(=O)OC)cnn1-c1cccc(Br)c1]

A mixture of methyl 1-(3-bromophenyl)-5-(2-(2,2-dibromovinyl)cyclopropyl)-1H-pyrazole-4-carboxylate (1.0 g, 1.980 mmol) and cesium carbonate (3.23 g, 9.90 mmol) in dimethyl sulfoxide (DMSO) (15 mL) was stirred for 18 hours at 120° C. The LCMS showed trans and cis isomers. After cooled to the room temperature, the mixture was diluted with ethyl acetate and it was filtered through celite. The filtrate was diluted with water and the organic layer was separated and washes with water, dried over anhydrous MgSO$_4$. It was filtered and the filtrate was concentrated. The crude product was purified on the Combiflash eluting with a gradient of 0-20% ethyl acetate in hexanes. Trans and cis isomers were separated and the desired cis isomer was obtained as clear colorless oil (0.16 g, 0.464 mmol, 23.4% yield). LC-MS m/z 344.8 (M+H)$^+$, 1.08 min (ret. time).

101b) Methyl 1-(3'-((S)-1-cyclohexylethoxy)-[1,1'-biphenyl]-3-yl)-5-(cis-2-ethynylcyclopropyl)-1H-pyrazole-4-carboxylate

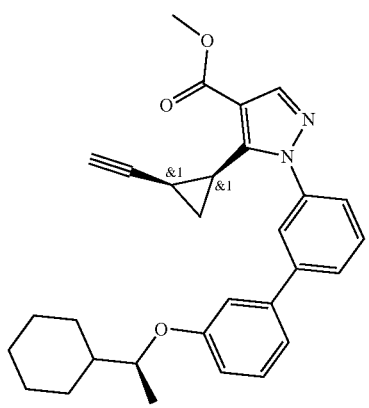 [SMILES: C#C[C@@H]1C[C@@H]1c1c(C(=O)OC)cnn1-c1cccc(-c2cccc(O[C@@H](C)C3CCCCC3)c2)c1]

A mixture of (S)-2-(3-(1-cyclohexylethoxy)phenyl)-4,4,5,5-tetramethyl-1,3,2-dioxaborolane (153 mg, 0.464 mmol), rac-methyl 1-(3-bromophenyl)-5-((1S,2R)-2-ethynylcyclopropyl)-1H-pyrazole-4-carboxylate (160 mg, 0.464 mmol), tetrakis (26.8 mg, 0.023 mmol), and sodium carbonate 10% Wt. in H$_2$O (1474 mg, 1.391 mmol) in 1,4-Dioxane (3.0 mL) was stirred for 30 min at 100° C. After cooled to the room temperature, the mixture was diluted with water and extracted with ethyl acetate. The organic extract was washed with water and dried over anhydrous MgSO$_4$. It was filtered and the filtrate was concentrated. The crude product was purified on the Combiflash eluting with a gradient of 0 to 15% ethyl acetate in hexanes. The title compound was obtained as colorless oil, and it was solidified after standing (121 mg, 0.258 mmol, 55.7% yield). LC-MS m/z 469.0 (M+H)$^+$, 1.60 min (ret. time).

101c) methyl 1-(3'-((S)-1-cyclohexylethoxy)-[1,1'-biphenyl]-3-yl)-5-(cis-2-(1-methyl-1H-1,2,3-triazol-4-yl)cyclopropyl)-1H-pyrazole-4-carboxylate

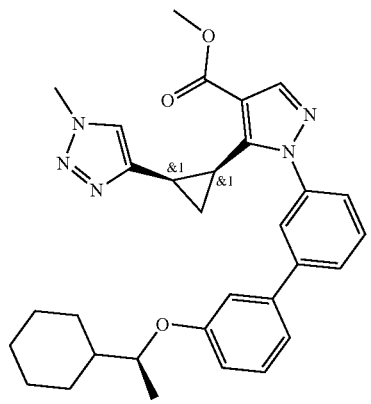 [SMILES: COC(=O)c1cnn(-c2cccc(-c3cccc(O[C@@H](C)C4CCCCC4)c3)c2)c1[C@H]1C[C@H]1c1cn(C)nn1]

A mixture of methyl 1-(3'-((S)-1-cyclohexylethoxy)-[1,1'-biphenyl]-3-yl)-5-(cis-2-ethynylcyclopropyl)-1H-pyrazole-4-carboxylate (120 mg, 0.256 mmol), iodomethane (0.040 mL, 0.640 mmol), sodium azide (45 mg, 0.692 mmol), copper(I) iodide (10 mg, 0.053 mmol), and DIPEA (0.045 mL, 0.256 mmol) in Tert-Butanol (2.0 mL) and Water (1.0 mL) was irritated via microwave reactor for 40 min at 70° C. on normal absorption. After cooled to the room temperature, the mixture was diluted with water and extracted with ethyl acetate. The organic extract was washed with water and dried over anhydrous magnesium sulfate. It was filtered and the filtrate was concentrated. The crude product was purified on the Combiflash eluting with a gradient of 0-60% ethyl acetate in hexanes. The title compound was obtained as thick yellow oil (114 mg, 0.217 mmol, 85% yield). LC-MS m/z 526.0 (M+H)$^+$, 1.43 min (ret. time).

101d) 1-(3'-((S)-1-Cyclohexylethoxy)-[1,1'-biphenyl]-3-yl)-5-(cis-2-(1-methyl-1H-1,2,3-triazol-4-yl)cyclopropyl)-1H-pyrazole-4-carboxylic Acid

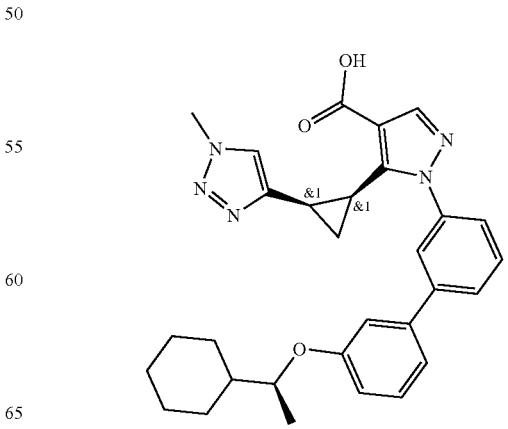

A mixture of rac-methyl 1-(3'-((S)-1-cyclohexylethoxy)-[1,1'-biphenyl]-3-yl)-5-(cis-2-(1-methyl-1H-1,2,3-triazol-4-yl)cyclopropyl)-1H-pyrazole-4-carboxylate (114 mg, 0.217 mmol) and LiOH (50 mg/mL in H₂O) (1.0 mL, 2.088 mmol) in tetrahydrofuran (THF) (1.5 mL) and methanol (1.5 mL) was stirred for overnight at room temperature, the LCMS showed a incomplete reaction. The mixture was stirred for another overnight, the LCMS showed a complete reaction. The mixture was concentrated (some water left) and the residue was dissolved in water. The resulting solution was neutralized with 1.0 N HCl (aq) and extracted with ethyl acetate. The organic extract was concentrated and the crude product was purified on the prep HPLC eluting with a gradient of 40-100% acetonitrile in water. The title compound was obtained as white solid (91 mg, 0.169 mmol, 78% yield). LC-MS m/z 512.0 (M+H)⁺, 1.30 min (ret. time).

Example 102. 1-(3'-((S)-1-Cyclohexylethoxy)-[1,1'-biphenyl]-3-yl)-5-(trans-2-(3-hydroxypropyl)cyclopropyl)-1H-pyrazole-4-carboxylic Acid

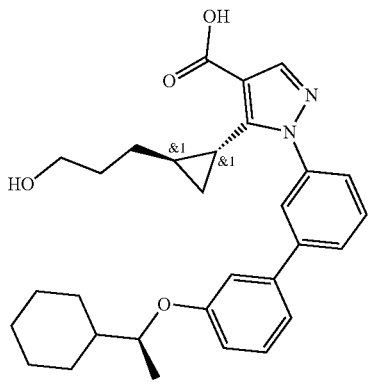 [SMILES: C[C@H](Oc1cccc(-c2cccc(-n3ncc(C(=O)O)c3[C@@H]3C[C@H]3CCCO)c2)c1)C1CCCCC1]

102a) Methyl 1-(3'-((S)-1-cyclohexylethoxy)-[1,1'-biphenyl]-3-yl)-5-(trans-2-(3-hydroxyprop-1-yn-1-yl)cyclopropyl)-1H-pyrazole-4-carboxylate

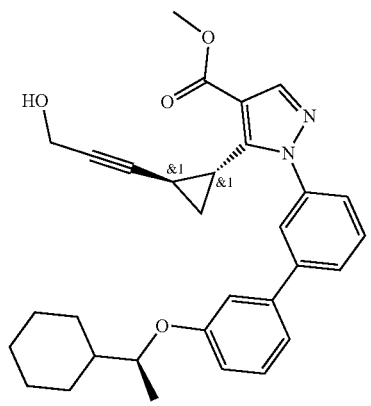 [SMILES: COC(=O)c1cnn(-c2cccc(-c3cccc(O[C@@H](C)C4CCCCC4)c3)c2)c1[C@@H]1C[C@H]1C#CCO]

A mixture of methyl 1-(3'-((S)-1-cyclohexylethoxy)-[1,1'-biphenyl]-3-yl)-5-(trans-2-ethynylcyclopropyl)-1H-pyrazole-4-carboxylate (120 mg, 0.256 mmol), paraformaldehyde (15 mg, 0.500 mmol), and cesium carbonate (167 mg, 0.512 mmol) in dimethyl sulfoxide (DMSO) (2.5 mL) was stirred for 5.0 hours at 100° C., the LCMS showed an incomplete reaction. To the mixture was added additional paraformaldehyde (15 mg, 0.500 mmol) and the reaction mixture was stirred for another 2.0 hours at 100° C., the LCMS showed little change. After cooled to the room temperature, the mixture was diluted with ethyl acetate and filtered through celite. The filtrate was diluted with brine and extracted with ethyl acetate. The organic extract was washed with saturated NH₄Cl (aq) and dried over anhydrous magnesium sulfate. It was filtered and the filtrate was concentrate to give the crude product which was then purified on the Combiflash eluting with a gradient of 0-35% ethyl acetate in hexanes. The title compound was obtained as white solid (34.5 mg, 0.069 mmol, 27% yield). LC-MS m/z 499.1 (M+H)⁺, 1.48 min (ret. time).

102b) methyl 1-(3'-((S)-1-cyclohexylethoxy)-[1,1'-biphenyl]-3-yl)-5-(trans-2-(3-hydroxypropyl)cyclopropyl)-1H-pyrazole-4-carboxylate

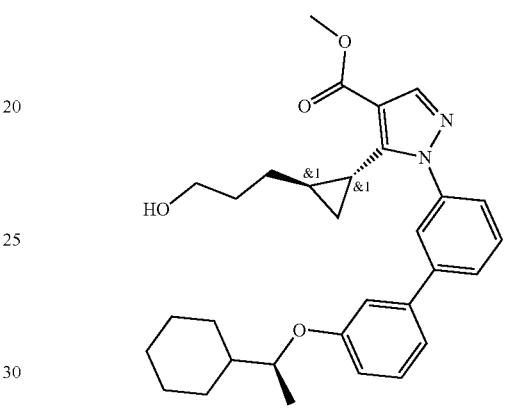

Methyl 1-(3'-((S)-1-cyclohexylethoxy)-[1,1'-biphenyl]-3-yl)-5-(trans-2-(3-hydroxyprop-1-yn-1-yl)cyclopropyl)-1H-pyrazole-4-carboxylate (34 mg, 0.068 mmol) was dissolve in methanol (5.0 mL). The resulting solution was conducted hydrogenation on the H-cube using 10% Pd/C cartridge at 50 bars and room temperature for 1.0 hour. The mixture was concentrated and the residue was purified on the Combiflash eluting with a gradient of 0-35% ethyl acetate in hexanes. The title compound was obtained as colorless wax (13.5 mg, 0.027 mmol, 39.4% yield). LC-MS m/z 503.2 (M+H)⁺, 1.51 min (ret. time).

102c) 1-(3'-((S)-1-Cyclohexylethoxy)-[1,1'-biphenyl]-3-yl)-5-(trans-2-(3-hydroxypropyl)cyclopropyl)-1H-pyrazole-4-carboxylic Acid

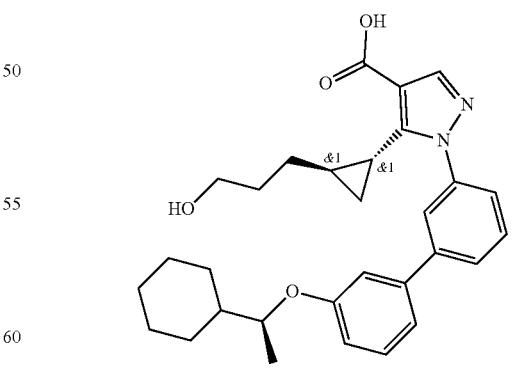

A mixture of methyl 1-(3'-((S)-1-cyclohexylethoxy)-[1,1'-biphenyl]-3-yl)-5-(trans-2-(3-hydroxypropyl)cyclopropyl)-1H-pyrazole-4-carboxylate (13.5 mg, 0.027 mmol) and LiOH (50 mg/mL in water) (0.5 mL, 1.044 mmol) in methanol (1.0 mL) and tetrahydrofuran (THF) (1.0 mL) was stirred for 2 days at 35° C. The mixture was neutralized with 1.0 N HCl and extracted with ethyl acetate. The organic extract was concentrated and the crude product was purified by the prep HPLC eluting with a gradient of 40-100% acetonitrile in water.

The title compound was obtained as white solid (12.4 mg, 0.024 mmol, 90% yield). LC-MS m/z 489.1 (M+H)$^+$, 1.39 min (ret. time).

Example 103. 1-(3'-((S)-1-cyclohexylethoxy)-[1,1'-biphenyl]-3-yl)-5-(trans-2-(1-methyl-1H-pyrazol-4-yl)cyclopropyl)-1H-pyrazole-4-carboxylic Acid

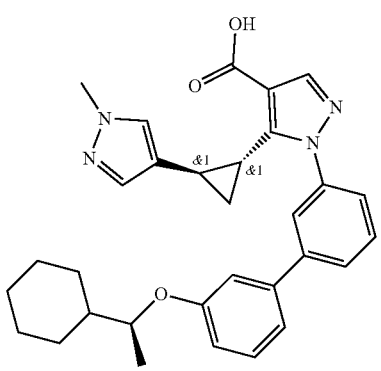 [SMILES: C[C@H](Oc1cccc(-c2cccc(-n3ncc(C(=O)O)c3[C@@H]3C[C@H]3c3cnn(C)c3)c2)c1)C1CCCCC1]

103a) (E)-tert-Butyl 3-(1-methyl-1H-pyrazol-4-yl)acrylate

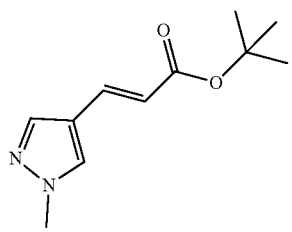

To a solution of tert-butyl 2-(diethoxyphosphoryl)acetate (12.60 g, 49.9 mmol) in tetrahydrofuran (THF) (30 mL) was added NaH 60% dispersion in mineral oil (2.179 g, 54.5 mmol) slowly. The mixture was stirred for 10 min at room temperature. A solution of 1-methyl-1H-pyrazole-4-carbaldehyde (5.0 g, 45.4 mmol) in tetrahydrofuran (THF) (30 mL) was added slowly. After addition, the reaction mixture was stirred for 20 min at room temperature. The LCMS showed a complete reaction. The mixture was diluted with water and extracted with ethyl acetate. The organic extract was washed with water and dried over anhydrous MgSO$_4$. It was filtered and the filtrate was concentrated to give the crude product which was then purified on the Combiflash column chromatography eluting with a gradient of 0 to 50% ethyl acetate in hexanes. The title compound was obtained as clear colorless oil (9.0 g, 43.2 mmol, 95% yield). LC-MS m/z 208.9 (M+H)$^+$, 0.93 min (ret. time).

103b) rac-tert-Butyl (1R,2R)-2-(1-methyl-1H-pyrazol-4-yl)cyclopropane-1-carboxylate

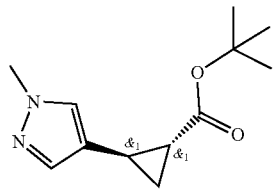 [SMILES: Cn1cc([C@@H]2C[C@H]2C(=O)OC(C)(C)C)cn1]

To a solution of trimethylsulfoxonium iodide (22.19 g, 101 mmol) in dimethyl sulfoxide (DMSO) (80 mL) was added NaH 60% dispersion in mineral oil (2.96 g, 73.9 mmol) at room temperature. The mixture was stirred for 1.0 hour at room temperature under N$_2$. A solution of tert-butyl (E)-3-(1-methyl-1H-pyrazol-4-yl)acrylate (7.0 g, 33.6 mmol) in tetrahydrofuran (THF) (80 mL) was then added slowly. After addition, the reaction mixture was stirred for 1.0 hour at room temperature, and then stirred for additional 1.0 hour at 50° C. The LCMS showed unfinished reaction. The reaction mixture was stirred overnight at room temperature, the LCMS showed a complete reaction. The mixture was diluted with brine/H$_2$O (1:1) and extracted with ethyl acetate. The organic extract was washed with brine and dried over anhydrous MgSO$_4$. It was filtered and the filtrate was concentrated to give the product as clear colorless oil (6.3 g, 28.3 mmol, 84% yield). LC-MS m/z 222.9 (M+H)$^+$, 0.94 min (ret. time).

103c) rac-(1R,2R)-2-(1-Methyl-1H-pyrazol-4-yl)cyclopropane-1-carboxylic Acid

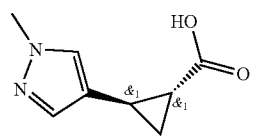

A mixture of rac-tert-butyl (1R,2R)-2-(1-methyl-1H-pyrazol-4-yl)cyclopropane-1-carboxylate (6.3 g, 28.3 mmol) and TFA (21.84 mL, 283 mmol) in dichloromethane (DCM) (20 mL) was stirred for 2.0 hours at room temperature, the LCMS showed a complete reaction. The mixture was concentrated by rotavap and the residue was diluted with water (40 mL), extracted with ethyl acetate (40 mL). The aqueous layer was concentrated to give the desired product as clear colorless oil (3.76 g, 22.63 mmol, 80% yield). LC-MS m/z 166.8 (M+H)$^+$, 0.53 min (ret. time).

103d) rac-Methyl 3-((1R,2R)-2-(1-methyl-1H-pyrazol-4-yl)cyclopropyl)-3-oxopropanoate

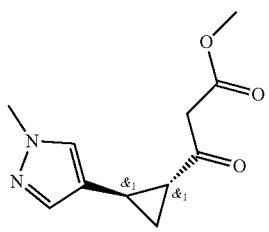 [SMILES: COC(=O)CC(=O)[C@@H]1C[C@H]1c1cnn(C)c1]

To a solution of rac-(1R,2R)-2-(1-methyl-1H-pyrazol-4-yl)cyclopropane-1-carboxylic acid (3.76 g, 22.63 mmol) in tetrahydrofuran (THF) (50 mL) was added CDI (5.50 g, 33.9 mmol). The mixture was stirred for 2 hours at room temperature. methyl potassium malonate (10.60 g, 67.9 mmol) was added, followed by magnesium chloride (2.58 g, 27.2 mmol). The resulting reaction mixture was stirred overnight at room temperature. The mixture was neutralized with 6.0 N HCl and diluted with water, extracted with ethyl acetate. The organic extract was washed with brine and dried over anhydrous magnesium sulfate. It was filtered and the filtrate was concentrated. The residue was dissolved in DCM and purified on the Combiflash column chromatography (80 g silica gel, solution load) eluting with a gradient of 0-5% methanol in dichloromethane. The title compound was obtained as clear light yellow oil (2.37 g, 10.66 mmol, 47.1% yield). LC-MS m/z 223.0 (M+H)$^+$, 0.63 min (ret. time).

103e) rac-Methyl 3-(dimethylamino)-2-((1R,2R)-2-(1-methyl-1H-pyrazol-4-yl)cyclopropanecarbonyl)acrylate

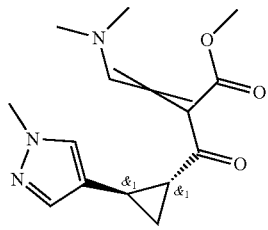 [SMILES: COC(=O)C(C(=O)[C@@H]1C[C@H]1c1cnn(C)c1)C(C)(C)CN(C)C]

A mixture of rac-methyl 3-((1R,2R)-2-(1-methyl-1H-pyrazol-4-yl)cyclopropyl)-3-oxopropanoate (2.35 g, 10.57 mmol) and N,N-dimethylformamide dimethylacetal (1.8 ml, 13.55 mmol) in 1,4-Dioxane (20 mL) was stirred for 18 hours at room temperature. The mixture was concentrated to give the title compound as light orange oil used in the next step without further purification (2.7 g, 9.74 mmol, 92% yield). LC-MS m/z 278.0 (M+H)$^+$, 0.63 min (ret. time).

103f) rac-Methyl 1-(3-bromophenyl)-5-((1R,2R)-2-(1-methyl-1H-pyrazol-4-yl)cyclopropyl)-1H-pyrazole-4-carboxylate

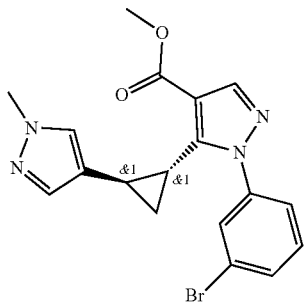 [SMILES: COC(=O)c1cnn(-c2cccc(Br)c2)c1[C@@H]1C[C@H]1c1cnn(C)c1]

To a solution of methyl 3-(dimethylamino)-2-(2-(1-methyl-1H-pyrazol-4-yl)cyclopropanecarbonyl)acrylate (450 mg, 1.623 mmol) in Ethanol (10 mL) was added (3-bromophenyl)hydrazine hydrochloride (399 mg, 1.785 mmol). To the resulting suspension was added TEA (0.565 mL, 4.06 mmol). It was turned to lear solution, and was stirred for 1.0 hour at room temperature. The LCMS showed a complete reaction. The mixture was concentrated and the crude product was purified on the Combiflash column chromatography eluting with a gradient of 0-65% ethyl acetate in hexanes. The product was obtained as light yellow oil and solidified upon standing (550 mg, 1.371 mmol, 84% yield). LC-MS m/z 401.0 (M+H)$^+$, 1.02 min (ret. time).

103g) Methyl 1-(3'-((S)-1-cyclohexylethoxy)-[1,1'-biphenyl]-3-yl)-5-(trans-2-(1-methyl-1H-pyrazol-4-yl)cyclopropyl)-1H-pyrazole-4-carboxylate

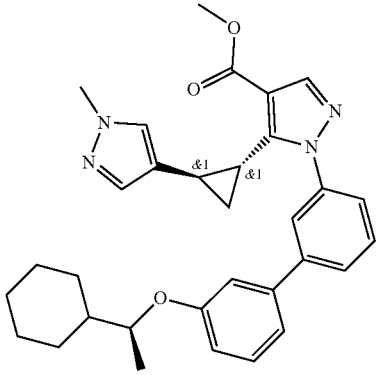 [SMILES: COC(=O)c1cnn(-c2cccc(-c3cccc(O[C@@H](C)C4CCCCC4)c3)c2)c1[C@@H]1C[C@H]1c1cnn(C)c1]

A mixture of rac-methyl 1-(3-bromophenyl)-5-((1R,2R)-2-(1-methyl-1H-pyrazol-4-yl)cyclopropyl)-1H-pyrazole-4-carboxylate (98 mg, 0.244 mmol), (S)-2-(3-(1-cyclohexylethoxy)phenyl)-4,4,5,5-tetramethyl-1,3,2-dioxaborolane (81 mg, 0.244 mmol), tetrakis (14.5 mg, 0.013 mmol), and 10% $Na_2CO_3$ (aq) (777 mg, 0.733 mmol) in 1,4-dioxane (2.0 mL) was stirred for 40 min at 100° C. The LCMS showed a complete reaction. After cooled to the room temperature, the mixture was diluted with water and extracted with ethyl acetate. The organic extract was washed with brine and dried over anhydrous magnesium sulfate. It was filtered and the filtrate was concentrated to give the crude product which was then purified on the Combiflash column chromatography eluting with a gradient of 0-50% ethyl acetate in hexanes. The title compound was obtained as thick colorless oil (100 mg, 0.191 mmol, 78% yield). LC-MS m/z 525.3 (M+H)$^+$, 1.53 min (ret. time).

103h) 1-(3'-((S)-1-Cyclohexylethoxy)-[1,1'-biphenyl]-3-yl)-5-(trans-2-(1-methyl-1H-pyrazol-4-yl)cyclopropyl)-1H-pyrazole-4-carboxylic Acid

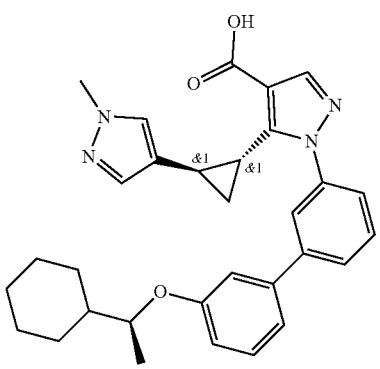 [SMILES: C[C@H](Oc1cccc(-c2cccc(-n3ncc(C(=O)O)c3[C@@H]3C[C@H]3c3cnn(C)c3)c2)c1)C1CCCCC1]

A mixture of methyl 1-(3'-((S)-1-cyclohexylethoxy)-[1,1'-biphenyl]-3-yl)-5-(trans-2-(1-methyl-1H-pyrazol-4-yl)cyclopropyl)-1H-pyrazole-4-carboxylate (100 mg, 0.191 mmol) and 3.0 N NaOH (aq) (0.8 mL, 2.400 mmol) in tetrahydrofuran (THF) (1.000 mL) and methanol (1.0 mL) was stirred 3 days at room temperature. The mixture was concentrated (some water left) and diluted with water, neutralized with 1.0 N HCl (aq). The resulting suspension extracted with ethyl acetate. The organic extract was concentrated and the crude product was purified on the prep HPLC eluting with a gradient of 30-100% acetonitrile in water. The title compound was obtained as white solid (68 mg, 0.127 mmol, 66.4% yield). LC-MS m/z 511.3 (M+H)⁺, 1.38 min (ret. time).

Example 104. 1-(3'-((S)-1-cyclohexylethoxy)-2'-fluoro-[1,1'-biphenyl]-3-yl)-5-((1R,2R)-2-(1-methyl-1H-1,2,3-triazol-4-yl)cyclopropyl)-1H-pyrazole-4-carboxylic Acid 104a) Ethyl 1-(3'-((S)-1-cyclohexylethoxy)-2'-fluoro-[1,1'-biphenyl]-3-yl)-5-((1R,2R)-2-(1-methyl-1H-1,2,3-triazol-4-yl)cyclopropyl)-1H-pyrazole-4-carboxylate

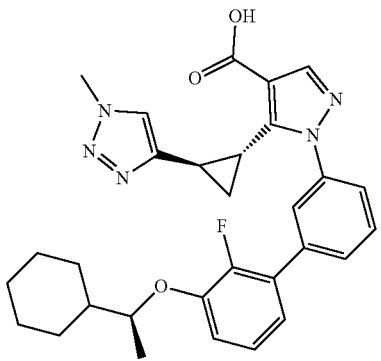 [SMILES: C[C@H](Oc1cccc(-c2cccc(-n3ncc(C(=O)O)c3[C@@H]3C[C@H]3c3cn(C)nn3)c2)c1F)C1CCCCC1]

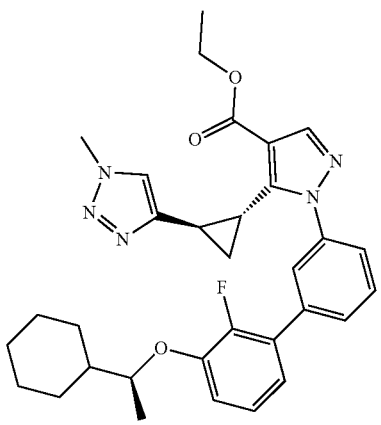 [SMILES: CCOC(=O)c1cnn(-c2cccc(-c3cccc(O[C@@H](C)C4CCCCC4)c3F)c2)c1[C@@H]1C[C@H]1c1cn(C)nn1]

A mixture of ethyl 1-(3-bromophenyl)-5-((1R,2R)-2-(1-methyl-1H-1,2,3-triazol-4-yl)cyclopropyl)-1H-pyrazole-4-carboxylate (60 mg, 0.144 mmol), (S)-2-(3-(1-cyclohexylethoxy)-2-fluorophenyl)-4,4,5,5-tetramethyl-1,3,2-dioxaborolane (50.2 mg, 0.144 mmol), tetrakis (10 mg, 8.65 µmol), and 10% Na$_2$CO$_3$ (aq) (458 mg, 0.432 mmol) in 1,4-dioxane (2.0 mL) was stirred for 40 min at 100° C. The LCMS showed a complete reaction. After cooled to the room temperature, the mixture was diluted with water and extracted with ethyl acetate. The organic extract was washed with brine and dried over anhydrous magnesium sulfate. It was filtered and the filtrate was concentrated to give the crude product which was then purified on the Combiflash column chromatography eluting with a gradient of 0-50% ethyl acetate in hexanes. The title compound was obtained as thick colorless oil (39 mg, 0.07 mmol, 48.5% yield). LC-MS m/z 558.3 (M+H)⁺, 1.51 min (ret. time).

104b) 1-(3'-((S)-1-cyclohexylethoxy)-2'-fluoro-[1,1'-biphenyl]-3-yl)-5-((1R,2R)-2-(1-methyl-1H-1,2,3-triazol-4-yl)cyclopropyl)-1H-pyrazole-4-carboxylic Acid

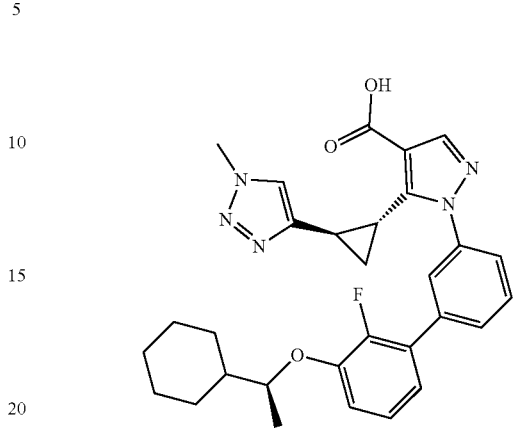

A mixture of ethyl 1-(3'-((S)-1-cyclohexylethoxy)-2'-fluoro-[1,1'-biphenyl]-3-yl)-5-((1R,2R)-2-(1-methyl-1H-1,2,3-triazol-4-yl)cyclopropyl)-1H-pyrazole-4-carboxylate (39 mg, 0.070 mol) and 3.0 N Noah (as) (0.5 mol, 1.500 mol) in tetrahydrofuran (THF) (1.0 mL) and methanol (1.0 mL) was stirred 3 days at room temperature. The mixture was concentrated (some water left) and diluted with water, neutralized with 1.0 N HCl (aq). The resulting suspension was extracted with ethyl acetate. The organic extract was concentrated and the crude product was purified on the prep HPLC eluting with a gradient of 30-100% acetonitrile in water.

The title compound was obtained as white solid (32 mg, 0.057 mmol, 82% yield). LC-MS m/z 530.3 (M+H)⁺, 1.32 min (ret. time).

Example 105. Ethyl 1-(3'-((S)-1-cyclohexylethoxy)-[1,1'-biphenyl]-3-yl)-5-((1R,2R)-2-(1-methyl-1H-1,2,3-triazol-4-yl)cyclopropyl)-1H-pyrazole-4-carboxylate

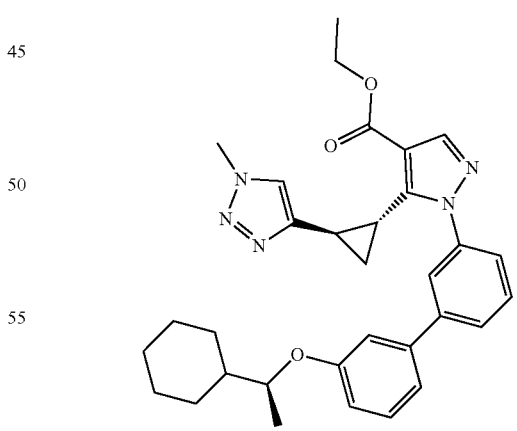

A mixture of ethyl 1-(3-bromophenyl)-5-((1R,2R)-2-(1-methyl-1H-1,2,3-triazol-4-yl)cyclopropyl)-1H-pyrazole-4-carboxylate (0.94 g, 2.258 mmol), (S)-2-(3-(1-cyclohexylethoxy)phenyl)-4,4,5,5-tetramethyl-1,3,2-dioxaborolane (0.746 g, 2.258 mmol), tetrakis (0.130 g, 0.113 mmol), and 10% Na$_2$CO$_3$ (aq) (7.18 g, 6.77 mmol) in 1,4-dioxane (25 mL) was stirred for 40 min at 100° C. After cooled to the room temperature, the mixture was diluted with water and extracted with ethyl acetate. The organic extract was washed with brine and dried over anhydrous magnesium sulfate. It was filtered and the filtrate was concentrated to give the crude product which was then purified on the Combiflash column chromatography eluting with a gradient of 0-50% ethyl acetate in hexanes. The product was obtained as thick colorless oil (1.1 g, 2.038 mmol, 90% yield). LC-MS m/z 540.4 (M+H)$^+$, 1.50 min (ret. time). 60 mg of this product was taken for further purification by prep HPLC eluting with a gradient of 55% to 85% acetonitrile in water. The pure compound was obtained as white solid (40 mg, 0.07 mmol). LCMS (N40279-87-A2): m/z 540.3 (M+H)$^+$, Rt. 1.51 min.

Example 106. 2-Oxotetrahydrofuran-3-yl 1-(3'-((S)-1-cyclohexylethoxy)-[1,1'-biphenyl]-3-yl)-5-((1R, 2R)-2-(1-methyl-1H-1,2,3-triazol-4-yl)cyclopropyl)-1H-pyrazole-4-carboxylate

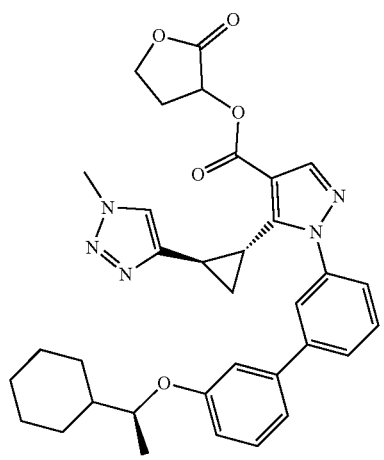 [SMILES: C[C@H](Oc1cccc(-c2cccc(-n3ncc(C(=O)OC4CCOC4=O)c3[C@@H]3C[C@H]3c3cn(C)nn3)c2)c1)C1CCCCC1]

A mixture of 1-(3'-((S)-1-cyclohexylethoxy)-[1,1'-biphenyl]-3-yl)-5-((1R,2R)-2-(1-methyl-1H-1,2,3-triazol-4-yl)cyclopropyl)-1H-pyrazole-4-carboxylic acid (60 mg, 0.117 mmol), 3-bromodihydrofuran-2(3H)-one (0.022 mL, 0.235 mmol) and potassium carbonate (48.6 mg, 0.352 mmol) in N,N-dimethylformamide (DMF) (1.0 mL) was stirred for 1.0 hour at room temperature. The LCMS showed an almost complete reaction. The mixture was left stirring overnight. The LCMS showed a complete reaction. The mixture was diluted with ethyl acetate and filtered through celite. The filtrate was washed with water. The organic layer was separated and washed with water, dried over anhydrous magnesium sulfate. It was filtered and the filtrate was concentrated. The crude product was purified by prep HPLC eluting with a gradient of 55% to 85% acetonitrile in water. The pure title compound was obtained as white solid (45 mg, 0.072 mmol, 61.2% yield). LC-MS m/z 596.3 (M+H)$^+$, 1.42 min (ret. time).

The compounds in Table 4 were prepared by a method similar to the one described for the preparation of 2-Oxotetrahydrofuran-3-yl 1-(3'-((S)-1-cyclohexylethoxy)-[1,1'-biphenyl]-3-yl)-5-((1R,2R)-2-(1-methyl-1H-1,2,3-triazol-4-yl)cyclopropyl)-1H-pyrazole-4-carboxylate. As is appreciated by those skilled in the art, these analogous examples may involve variations in general reaction conditions.

TABLE 4

| Example | Structure | Name | LCMS [M + H]$^+$ | Retention Time (min) |
|---|---|---|---|---|
| 107 | 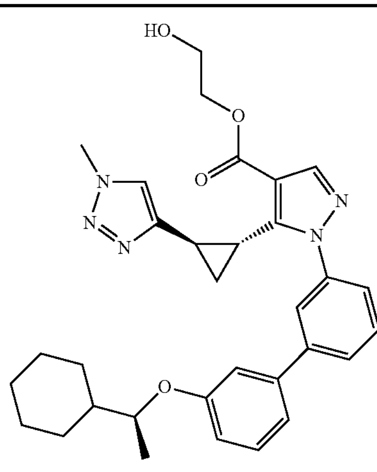 | 2-Hydroxyethyl 1-(3'-((S)-1-cyclohexylethoxy)-[1,1'-biphenyl]-3-yl)-5-((1R,2R)-2-(1-methyl-1H-1,2,3-triazol-4-yl)cyclopropyl)-1H-pyrazole-4-carboxylate | 556.3 | 1.32 |

TABLE 4-continued

| Example | Structure | Name | LCMS [M + H]+ | Retention Time (min) |
|---------|-----------|------|---------------|----------------------|
| 108 | 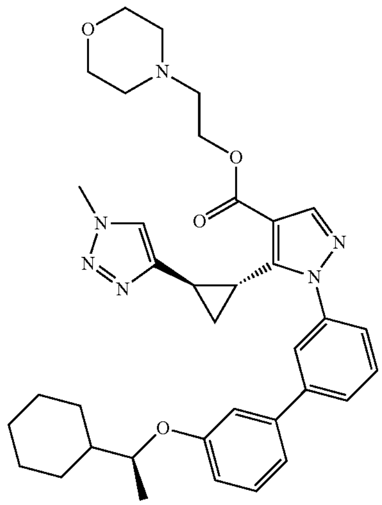 [SMILES: C[C@H](Oc1cccc(-c2cccc(-n3ncc(C(=O)OCCN4CCOCC4)c3[C@@H]3C[C@H]3c3cn(C)nn3)c2)c1)C1CCCCC1] | 2-Morpholinoethyl 1-(3'-((S)-1-cyclohexylethoxy)-[1,1'-biphenyl]-3-yl)-5-((1R,2R)-2-(1-methyl-1H-1,2,3-triazol-4-yl)cyclopropyl)-1H-pyrazole-4-carboxylate | 625.4 | 1.19 |
| 109 | 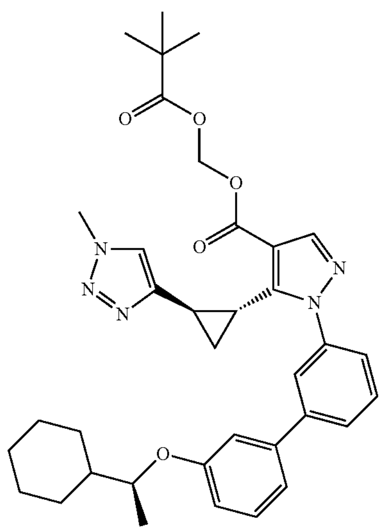 [SMILES: C[C@H](Oc1cccc(-c2cccc(-n3ncc(C(=O)OCOC(=O)C(C)(C)C)c3[C@@H]3C[C@H]3c3cn(C)nn3)c2)c1)C1CCCCC1] | (Pivaloyloxy)methyl 1-(3'-((S)-1-cyclohexylethoxy)-[1,1'-biphenyl]-3-yl)-5-((1R,2R)-2-(1-methyl-1H-1,2,3-triazol-4-yl)cyclopropyl)-1H-pyrazole-4-carboxylate | 626.4 | 1.63 |
| 110 | 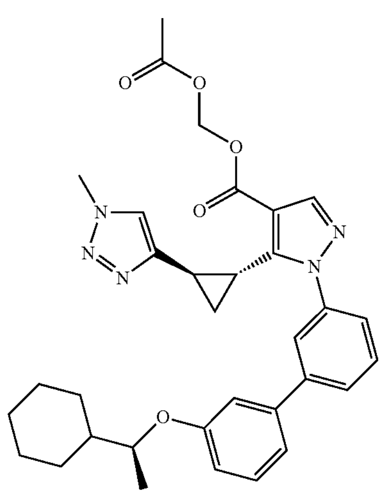 [SMILES: CC(=O)OCOC(=O)c1cnn(-c2cccc(-c3cccc(O[C@@H](C)C4CCCCC4)c3)c2)c1[C@@H]1C[C@H]1c1cn(C)nn1] | Acetoxymethyl 1-(3'-((S)-1-cyclohexylethoxy)-[1,1'-biphenyl]-3-yl)-5-((1R,2R)-2-(1-methyl-1H-1,2,3-triazol-4-yl)cyclopropyl)-1H-pyrazole-4-carboxylate | 584.3 | 1.47 |

TABLE 4-continued

| Example | Structure | Name | LCMS [M + H]+ | Retention Time (min) |
|---|---|---|---|---|
| 111 | 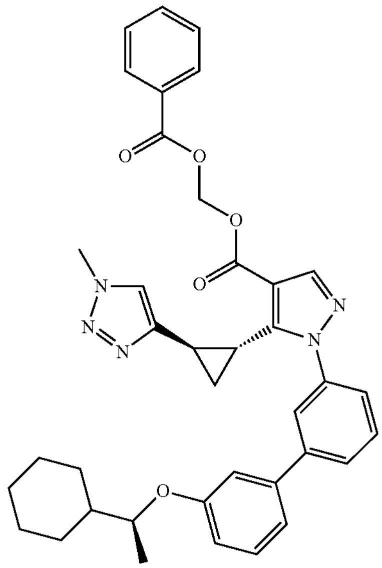 [SMILES: C[C@H](Oc1cccc(-c2cccc(-n3ncc(C(=O)OCOC(=O)c4ccccc4)c3[C@@H]3C[C@H]3c3cn(C)nn3)c2)c1)C1CCCCC1] | (Benzoyloxy)methyl 1-(3'-((S)-1-cyclohexylethoxy)-[1,1'-biphenyl]-3-yl)-5-((1R,2R)-2-(1-methyl-1H-1,2,3-triazol-4-yl)cyclopropyl)-1H-pyrazole-4-carboxylate | 646.4 | 1.61 |
| 112 | 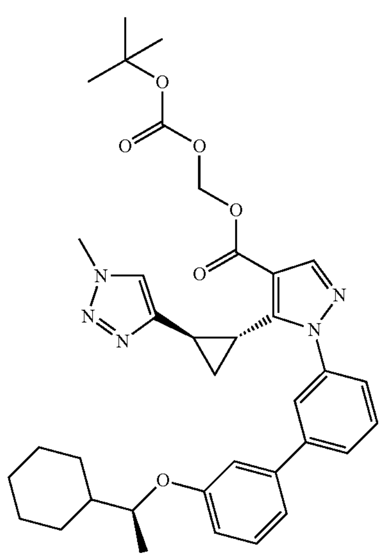 [SMILES: C[C@H](Oc1cccc(-c2cccc(-n3ncc(C(=O)OCOC(=O)OC(C)(C)C)c3[C@@H]3C[C@H]3c3cn(C)nn3)c2)c1)C1CCCCC1] | ((tert-Butoxycarbonyl)oxy)methyl 1-(3'-((S)-1-cyclohexylethoxy)-[1,1'-biphenyl]-3-yl)-5-((1R,2R)-2-(1-methyl-1H-1,2,3-triazol-4-yl)cyclopropyl)-1H-pyrazole-4-carboxylate | 642.4 | 1.60 |

333

Example 113. rac-1-(3'-((E)-2-Cyclohexylvinyl)-[1,1'-biphenyl]-3-yl)-5-(trans-2-(1-methyl-1H-1,2,3-triazol-4-yl)cyclopropyl)-1H-pyrazole-4-carboxylic Acid

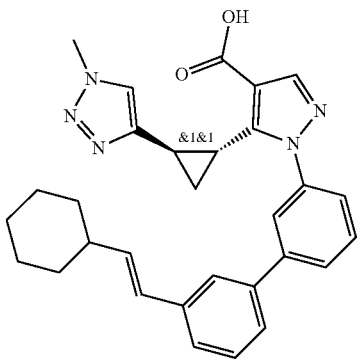 [SMILES: Cn1cc([C@@H]2C[C@H]2c2c(C(=O)O)cnn2-c2cccc(-c3cccc(/C=C/C4CCCCC4)c3)c2)nn1]

113a) (E)-1-Bromo-3-(2-cyclohexylvinyl)benzene

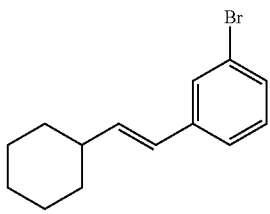 [SMILES: Brc1cccc(/C=C/C2CCCCC2)c1]

A mixture of (E)-(2-cyclohexylvinyl)boronic acid (0.657 g, 4.27 mmol), 1-bromo-3-iodobenzene (0.518 mL, 4.06 mmol), tetrakis (0.235 g, 0.203 mmol), and sodium carbonate 10% wt. in water (12.93 g, 12.19 mmol) in 1,4-dioxane (20 mL) was stirred for 2.0 hours at 100° C., the LCMS showed a complete reaction with a major product (the product did not show desired mass). After cooled to the room temperature, the mixture was diluted with water and extracted with ethyl acetate. The organic extract was dried over anhydrous magnesium sulfate. It was filtered and the filtrate was concentrated. The crude product was purified on the Combiflash eluting with 100% hexanes. The title compound was obtained as clear colorless oil (1.0 g, 3.77 mmol, 93% yield). $^1$H NMR (400 MHz, chloroform-d) δ ppm 1.13-1.41 (m, 5H) 1.71 (m, 1H) 1.80 (m, 4H) 2.10-2.20 (m, 1H) 6.16-6.25 (m, 1H) 6.25-6.33 (m, 1H) 7.12-7.21 (m, 1H) 7.26 (d, J=7.78 Hz, 1H) 7.32 (d, J=7.78 Hz, 1H) 7.52 (s, 1H).

334

113b) (E)-2-(3-(2-Cyclohexylvinyl)phenyl)-4,4,5,5-tetramethyl-1,3,2-dioxaborolane

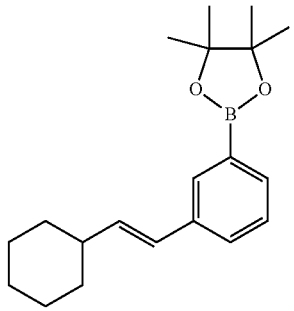 [SMILES: CC1(C)OB(c2cccc(/C=C/C3CCCCC3)c2)OC1(C)C]

A mixture of (E)-1-bromo-3-(2-cyclohexylvinyl)benzene (1.0 g, 3.77 mmol), bis(pinacolato)diboron (1.4 g, 5.51 mmol), PdCl$_2$(dppf)-CH$_2$Cl$_2$ adduct (0.154 g, 0.189 mmol), and potassium acetate (0.740 g, 7.54 mmol) in 1,4-dioxane (20 mL) was stirred for 20 hours at 100° C., the LCMS showed a complete reaction. After cooled to the room temperature, the mixture was filtered through celite and the filtrate was diluted with water and extracted with ethyl acetate. The organic extract was dried over anhydrous magnesium sulfate. It was filtered and the filtrate was concentrated. The crude product was purified on the Combiflash eluting with a gradient of 0-5% ethyl acetate in hexanes. The title compound was obtained as clear colorless oil (0.854 g, 2.73 mmol, 72.5% yield). LC-MS m/z 313.1 (M+H)$^+$, 1.76 min (ret. time).

113c) rac-Methyl 1-(3'-((E)-2-cyclohexylvinyl)-[1,1'-biphenyl]-3-yl)-5-((1R,2R)-2-(1-methyl-1H-1,2,3-triazol-4-yl)cyclopropyl)-1H-pyrazole-4-carboxylate

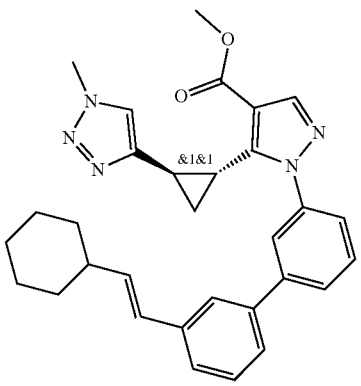 [SMILES: COC(=O)c1cnn(-c2cccc(-c3cccc(/C=C/C4CCCCC4)c3)c2)c1[C@@H]1C[C@H]1c1cn(C)nn1]

A mixture of rac-methyl 1-(3-bromophenyl)-5-((1R,2R)-2-(1-methyl-1H-1,2,3-triazol-4-yl)cyclopropyl)-1H-pyrazole-4-carboxylate (50 mg, 0.124 mmol), (E)-2-(3-(2-cyclohexylvinyl)phenyl)-4,4,5,5-tetramethyl-1,3,2-dioxaborolane (46.6 mg, 0.149 mmol), tetrakis (7.18 mg, 6.22 μmol), and sodium carbonate 10% wt. in water (395 mg, 0.373 mmol) in 1,4-dioxane (2.0 mL) was stirred for 1.0 hour at 100° C. After cooled to the room temperature, the mixture was diluted with water and extracted with ethyl acetate. The organic extract was dried over anhydrous magnesium sulfate. It was filtered and the filtrate was concentrated. The crude product was purified on the Combiflash eluting with a gradient of 0-55% ethyl acetate in hexanes. The title compound was obtained as clear colorless oil (24 mg, 0.047 mmol, 38.0% yield). LC-MS m/z 508.3 (M+H)+, 1.50 min (ret. time).

113d) rac-1-(3'-((E)-2-Cyclohexylvinyl)-[1,1'-biphenyl]-3-yl)-5-(trans-2-(1-methyl-1H-1,2,3-triazol-4-yl)cyclopropyl)-1H-pyrazole-4-carboxylic Acid

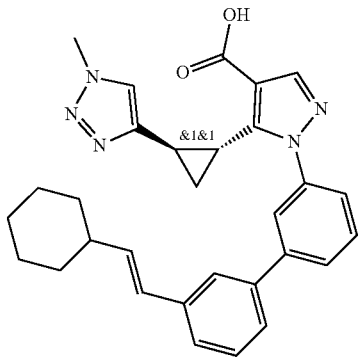 [SMILES: Cn1cc([C@@H]2C[C@H]2c2c(C(=O)O)cnn2-c2cccc(-c3cccc(/C=C/C4CCCCC4)c3)c2)nn1]

A mixture of rac-methyl 1-(3'-((E)-2-cyclohexylvinyl)-[1,1'-biphenyl]-3-yl)-5-((1R,2R)-2-(1-methyl-1H-1,2,3-triazol-4-yl)cyclopropyl)-1H-pyrazole-4-carboxylate (23 mg, 0.045 mmol) and 6.0 N NaOH (0.3 mL, 1.800 mmol) in tetrahydrofuran (THF) (1.0 mL) and methanol (1.0 mL) was stirred for 18 hours at 40° C. The mixture was concentrated and the residue was diluted with water (3 mL), neutralized with 2.0 N HCl (aq). The resulting precipitate was filtered and washed with water, dried to give the title compound as white solid (19 mg, 0.037 mmol, 81.0% yield). LC-MS m/z 494.2 (M+H)+, 1.37 min (ret. time).

Example 114. rac-1-(3'-(2-Cyclohexylethyl)-[1,1'-biphenyl]-3-yl)-5-(-2-(1-methyl-1H-1,2,3-triazol-4-yl)cyclopropyl)-1H-pyrazole-4-carboxylic Acid

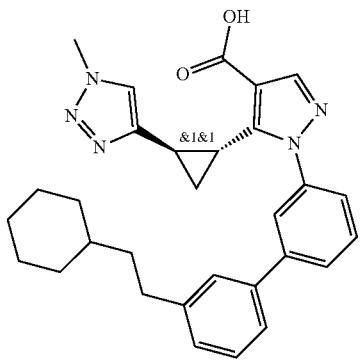 [SMILES: Cn1cc([C@@H]2C[C@H]2c2c(C(=O)O)cnn2-c2cccc(-c3cccc(CCC4CCCCC4)c3)c2)nn1]

114a) 2-(3-(2-Cyclohexylethyl)phenyl)-4,4,5,5-tetramethyl-1,3,2-dioxaborolane

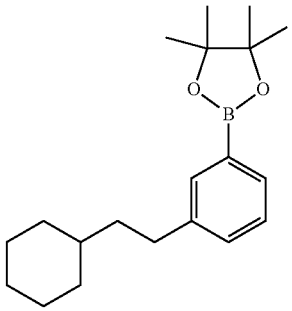 [SMILES: CC1(C)OB(c2cccc(CCC3CCCCC3)c2)OC1(C)C]

To a solution of (E)-2-(3-(2-cyclohexylvinyl)phenyl)-4,4,5,5-tetramethyl-1,3,2-dioxaborolane (370 mg, 1.185 mmol) in Ethanol (10 mL) was added Pd/C 10 wt. % on activated carbon (70 mg, 0.066 mmol). The mixture was stirred for 18 hours at room temperature under hydrogen atmosphere. The mixture was filtered through celite and the filtrate was concentrated to give the title compound white solid (320 mg, 1.018 mmol, 86.0% yield). LC-MS m/z 315.2 (M+H)+, 1.80 min (ret. Time).

114b) rac-Methyl 1-(3'-(2-cyclohexylethyl)-[1,1'-biphenyl]-3-yl)-5-(-2-(1-methyl-1H-1,2,3-triazol-4-yl)cyclopropyl)-1H-pyrazole-4-carboxylate

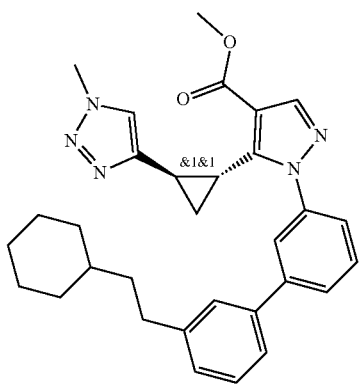 [SMILES: COC(=O)c1cnn(-c2cccc(-c3cccc(CCC4CCCCC4)c3)c2)c1[C@@H]1C[C@H]1c1cn(C)nn1]

A mixture of rac-methyl 1-(3-bromophenyl)-5-((1R,2R)-2-(1-methyl-1H-1,2,3-triazol-4-yl)cyclopropyl)-1H-pyrazole-4-carboxylate (50 mg, 0.124 mmol), 2-(3-(2-cyclohexylethyl)phenyl)-4,4,5,5-tetramethyl-1,3,2-dioxaborolane (46.9 mg, 0.149 mmol), tetrakis (7.18 mg, 6.22 µmol), and sodium carbonate 10 wt. % in water (395 mg, 0.373 mmol) in 1,4-dioxane (2.0 mL) was stirred for 30 min at 100° C. After cooled to the room temperature, the mixture was diluted with water and extracted with ethyl acetate. The organic extract was dried over anhydrous magnesium sulfate. It was filtered and the filtrate was concentrated. The crude product was purified on the Combiflash eluting with a gradient of 0-50% ethyl acetate in hexanes. The title compound was obtained as clear colorless oil (40 mg, 0.078 mmol, 63.1% yield). LC-MS m/z 510.3 (M+H)+, 1.54 min (ret. time).

114c) rac-1-(3'-(2-Cyclohexylethyl)-[1,1'-biphenyl]-3-yl)-5-(-2-(1-methyl-1H-1,2,3-triazol-4-yl)cyclopropyl)-1H-pyrazole-4-carboxylic Acid

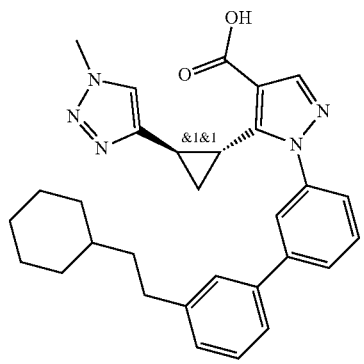 [SMILES: Cn1cc([C@@H]2C[C@H]2c2c(C(=O)O)cnn2-c2cccc(-c3cccc(CCC4CCCCC4)c3)c2)nn1]

A mixture of rac-methyl 1-(3'-(2-cyclohexylethyl)-[1,1'-biphenyl]-3-yl)-5-((1R,2R)-2-(1-methyl-1H-1,2,3-triazol-4-yl)cyclopropyl)-1H-pyrazole-4-carboxylate (38 mg, 0.075 mmol) and 6.0 N NaOH (0.4 mL, 2.400 mmol) in tetrahydrofuran (THF) (1.0 mL) and methanol (1.0 mL) was stirred for 18 hours at 40° C. The mixture was concentrated and the residue was diluted with water (3 mL), neutralized with 2.0 N HCl (aq). The resulting precipitate was filtered and washed with water, dried to give the title compound as white solid (37 mg, 0.071 mmol, 95.0% yield). LC-MS m/z 496.2 (M+H)+, 1.42 (ret. time).

Example 115. 1-(3'-((S)-1-cyclohexylethoxy)-[1,1'-biphenyl]-3-yl)-5-((1R,2R)-2-(3-methylisoxazol-5-yl)cyclopropyl)-1H-pyrazole-4-carboxylic Acid

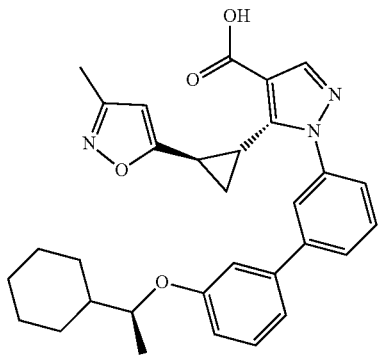

115a) Methyl 1-(3'-((S)-1-cyclohexylethoxy)-[1,1'-biphenyl]-3-yl)-5-((1R,2R)-2-(3-methylisoxazol-5-yl)cyclopropyl)-1H-pyrazole-4-carboxylate

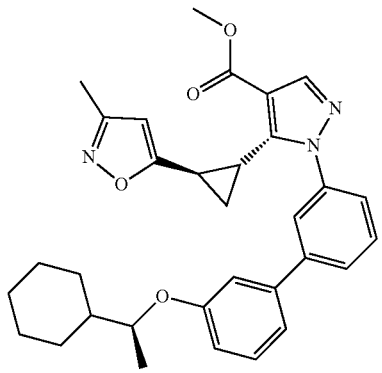

To a solution of acetaldehyde oxime (15 μl, 0.246 mmol) in N,N-dimethylformamide (DMF) (1.0 mL) was added NCS (36.3 mg, 0.272 mmol) and pyridine (2.0 μl, 0.025 mmol) at room temperature. After 1.0 h of stirring, a diluted solution of methyl 1-(3'-((S)-1-cyclohexylethoxy)-[1,1'-biphenyl]-3-yl)-5-((1R,2R)-2-ethynylcyclopropyl)-1H-pyrazole-4-carboxylate (75 mg, 0.160 mmol) in N,N-dimethylformamide (DMF) (1.0 mL) was added slowly, and after 30 min, TEA (45 μl, 0.323 mmol) was added dropwise successively. After addition, the mixture was stirred overnight at room temperature, the LCMS showed small conversion of alkyne to the desired. In another vial, acetaldehyde oxime (75 uL) was dissolved in N,N-dimethylformamide (DMF) (1.0 mL), NCS (181.5 mg) was added, followed by 10 uL pyridine. After stirred for 1.0 hour at room temperature, the mixture was transferred into the first batch reaction vial and the reaction mixture was stirred for 30 min, TEA (225 uL) was then added and the reaction mixture was stirred for 1.0 hour at 50° C. After cooled to the room temperature, the mixture was diluted with water and extracted with ethyl acetate. The organic extract was washed with water and dried over anhydrous magnesium sulfate. It was filtered and the filtrate was concentrated. The crude product was purified on the Combiflash eluting with a gradient of 0-50% ethyl acetate in hexanes. The title compound was obtained as colorless wax (52 mg, 0.099 mmol, 61.8% yield). LC-MS m/z 526.4 (M+H)+, 1.59 (ret. time).

115b) 1-(3'-((S)-1-Cyclohexylethoxy)-[1,1'-biphenyl]-3-yl)-5-((1R,2R)-2-(3-methylisoxazol-5-yl)cyclopropyl)-1H-pyrazole-4-carboxylic Acid

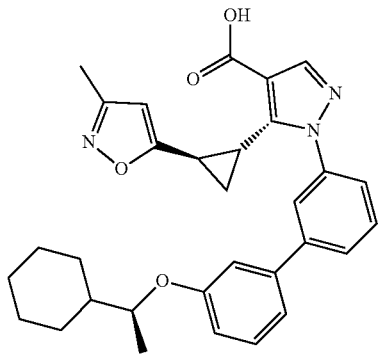

A mixture of methyl 1-(3'-((S)-1-cyclohexylethoxy)-[1,1'-biphenyl]-3-yl)-5-((1R,2R)-2-(3-methylisoxazol-5-yl)cyclopropyl)-1H-pyrazole-4-carboxylate (50 mg, 0.095 mmol) and 6.0 N NaOH (aq) (0.4 mL, 2.400 mmol) in tetrahydrofuran (THF) (0.6 mL) and methanol (0.6 mL) was stirred overnight at room temperature. The mixture was concentrated and the residue was diluted with water (3 mL), neutralized with 2.0 N HCl (aq). The resulting precipitate was extracted with ethyl acetate. The organic extract was concentrated and the crude product was purified on the prep HPLC eluting with a gradient of 40-100% acetonitrile in water. The title compound was obtained as white solid (43 mg, 0.08 mmol, 84.0% yield). LC-MS m/z 512.3 (M+H)+, 1.46 (ret. time).

Example 116. 1-(3'-((R) or (S)-2-Cyclohexylpropyl)-[1,1'-biphenyl]-3-yl)-5-((1R,2R)-2-(1-methyl-1H-1,2,3-triazol-4-yl)cyclopropyl)-1H-pyrazole-4-carboxylic Acid

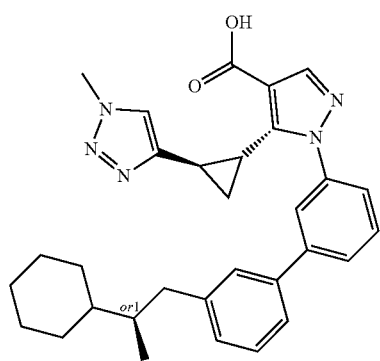

116a) 1-(3-Bromophenyl)propan-2-ol

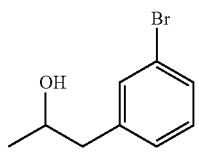

To a solution of 1-(3-bromophenyl)propan-2-one (4.8 g, 22.53 mmol) in Ethanol (50 mL) was added sodium borohydride (1.705 g, 45.1 mmol). The reaction mixture was stirred overnight at room temperature. Water was added and the mixture was extracted with ethyl acetate. The organic extract was washed with 30 mL of 1.0 N HCl (aq) and water, dried over anhydrous magnesium sulfate. It was filtered and the filtrate was concentrated to give the title compound as clear colorless oil (4.8 g, 22.32 mmol, 99.0% yield) used as intermediate without further purification. LC-MS m/z 237.9 (M+Na)+, 0.88 (ret. time).

116b) 1-(3-Bromophenyl)propan-2-yl 4-methylbenzenesulfonate

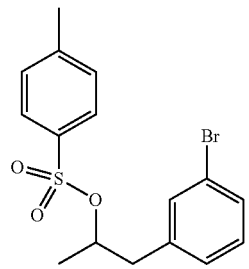 [SMILES: Cc1ccc(S(=O)(=O)OC(C)Cc2cccc(Br)c2)cc1]

To a solution of 1-(3-bromophenyl)propan-2-ol (4.5 g, 20.92 mmol) and pyridine (4.23 mL, 52.3 mmol) in dichloromethane (DCM) (30 mL) was added p-toluenesulfonyl chloride (4.79 g, 25.1 mmol). The reaction mixture was stirred overnight at room temperature. The mixture was diluted with water and extracted with dichloromethane. The organic extract was dried over anhydrous magnesium sulfate. It was filtered and the filtrate was concentrated. The crude product was purified on the Combiflash eluting with a gradient of 0-10% ethyl acetate in hexanes. The title compound was obtained as white solid (5.52 g, 14.95 mmol, 71.4% yield). LC-MS m/z 368.9 (M+H)+, 1.26 (ret. time).

116c) 1-Bromo-3-(2-cyclohexylpropyl)benzene

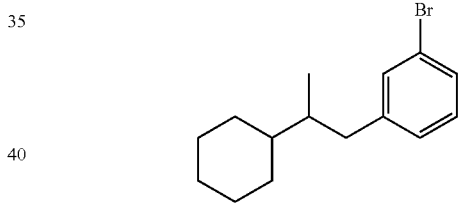

In air, 1-(3-bromophenyl)propan-2-yl 4-methylbenzenesulfonate (4.82 g, 13.05 mmol), copper(I) iodide (0.249 g, 1.305 mmol), and lithium methanolate (0.496 g, 13.05 mmol) were added to a vial equipped with a sir bar. The vial was evacuated and filled with nitrogen. tetrahydrofuran (THF) (50 mL) was then added through the syringe. The mixture was cooled to −10° C., TMEDA (0.394 mL, 2.61 mmol) was added, followed by cyclohexylmagnesium bromide 1.0 M in THF (26.1 mL, 26.1 mmol). The reaction mixture was stirred overnight at 0° C. The mixture was diluted with saturated NH4Cl (aq) and extracted with ethyl acetate. The organic extract was washed with brine and dried over anhydrous magnesium sulfate. It was filtered and the filtrate was concentrated. The crude product was purified on the Combiflash eluting with 100% hexanes. The pure fractions were combined and concentrated to give 1.07 g of the desired product. The overlapped the mixture was concentrated and purified again on the Combiflash to give additional 0.3 g of the desired product. The title compound was obtained as clear colorless oil (1.37 g, 4.867 mmol, 37.3% yield). 1H NMR (400 MHz, DMSO-de) δ ppm: 0.73 (d, J=6.78 Hz, 3H) 0.97-1.26 (m, 6H) 1.51-1.79 (m, 6H) 2.23-2.36 (m, 1H) 2.70 (dd, J=13.18, 5.14 Hz, 1H) 7.14-7.20 (m, 1H) 7.25 (t, J=7.78 Hz, 1H) 7.34-7.41 (m, 2H).

116d) Methyl 1-(3'-((R) or (S)-2-cyclohexylpropyl)-[1,1'-biphenyl]-3-yl)-5-((1R,2R)-2-(1-methyl-1H-1,2,3-triazol-4-yl)cyclopropyl)-1H-pyrazole-4-carboxylate

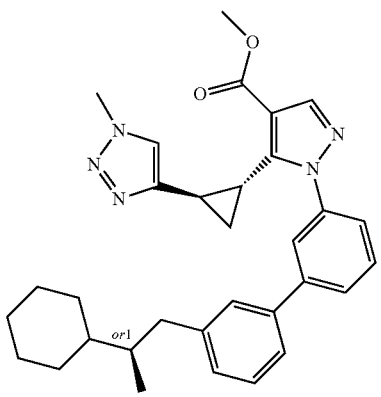 [SMILES: COC(=O)c1cnn(-c2cccc(-c3cccc(C[C@@H](C)C4CCCCC4)c3)c2)c1[C@@H]1C[C@H]1c1cn(C)nn1]

A mixture of (3-(4-(methoxycarbonyl)-5-((1R,2R)-2-(1-methyl-1H-1,2,3-triazol-4-yl)cyclopropyl)-1H-pyrazol-1-yl)phenyl)boronic acid (300 mg, 0.817 mmol), 1-bromo-3-(2-cyclohexylpropyl)benzene (241 mg, 0.858 mmol), tetrakis (56.7 mg, 0.049 mmol), and sodium carbonate (260 mg, 2.451 mmol) in 1,4-dioxane (4.0 mL) and Water (2.0 mL) was stirred for 1.0 hour at 100° C. After cooled to the room temperature, the mixture was diluted with water and extracted with ethyl acetate. The organic extract was dried over anhydrous magnesium sulfate. It was filtered and the filtrate was concentrated. The crude product was purified on the Combiflash eluting with a gradient of 0-50% ethyl acetate in hexanes. The racemic product was obtained as white solid and it was resolved by prep chiral HPLC: Chiralcel OJ-H 5 u 30×250 mm column; eluted with heptane:EtOH (90:10, V:V) with a flow rate of 45 mL/min at room temperature; UV at 254 nm. The two isomers of the title compound were obtained as white solids; peak 1: (145 mg, 0.277 mmol, 33.9% yield). LC-MS m/z 524.4 (M+H)+, 1.57 (ret. time); peak 2: (137 mg, 0.262 mmol, 32.0% yield). LC-MS m/z 524.4 (M+H)+, 1.57 (ret. time).

116e) 1-(3'-((R) or (S)-2-Cyclohexylpropyl)-[1,1'-biphenyl]-3-yl)-5-((1R,2R)-2-(1-methyl-1H-1,2,3-triazol-4-yl)cyclopropyl)-1H-pyrazole-4-carboxylic Acid

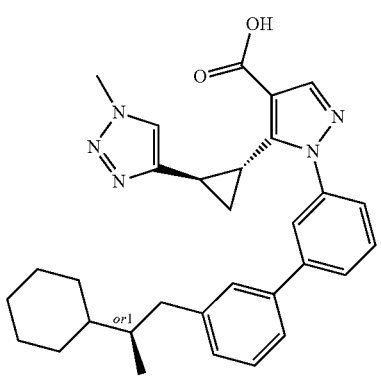 [SMILES: C[C@H](Cc1cccc(-c2cccc(-n3ncc(C(=O)O)c3[C@@H]3C[C@H]3c3cn(C)nn3)c2)c1)C1CCCCC1]

A mixture of methyl 1-(3'-((R) or (S)-2-cyclohexylpropyl)-[1,1'-biphenyl]-3-yl)-5-((1R,2R)-2-(1-methyl-1H-1,2,3-triazol-4-yl)cyclopropyl)-1H-pyrazole-4-carboxylate (first peak from Chiralcel OJ-H 5 u 30×250 mm column; 143 mg, 0.273 mmol) and 6.0 N NaOH (aq) (2.5 mL, 15.00 mmol) in tetrahydrofuran (THF) (2.5 mL) and methanol (2.5 mL) was stirred for 30 min at room temperature, the LCMS showed desired and little starting material. A small portion of the reaction mixture was taken out by pipet and it was acidified with 2.0 N HCl (aq), extracted with ethyl acetate. The organic extract was washed with water and concentrated. The crude product was purified on the prep HPLC eluting with a gradient of 30-100% acetonitrile in water. The title compound was obtained as white solid (8.0 mg, 0.015 mmol, 5.5% yield). LC-MS m/z 510.5 (M+H)+, 1.43 (ret. time).

116f) 1-(3'-((R) or (S)-2-Cyclohexylpropyl)-[1,1'-biphenyl]-3-yl)-5-((1R,2R)-2-(1-methyl-1H-1,2,3-triazol-4-yl)cyclopropyl)-1H-pyrazole-4-carboxylic Acid

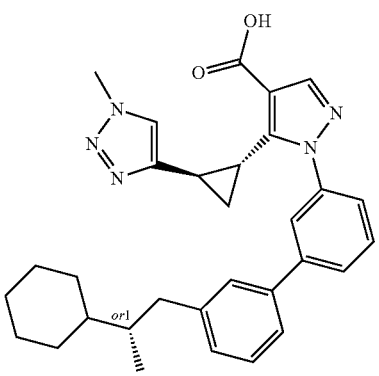 [SMILES: C[C@@H](Cc1cccc(-c2cccc(-n3ncc(C(=O)O)c3[C@@H]3C[C@H]3c3cn(C)nn3)c2)c1)C1CCCCC1]

A mixture of methyl 1-(3'-((S) or (R)-2-cyclohexylpropyl)-[1,1'-biphenyl]-3-yl)-5-((1R,2R)-2-(1-methyl-1H-1,2,3-triazol-4-yl)cyclopropyl)-1H-pyrazole-4-carboxylate (second peak from Chiralcel OJ-H 5 u 30×250 mm column; 135 mg, 0.258 mmol) and 6.0 N NaOH (aq) (2.5 mL, 15.00 mmol) in tetrahydrofuran (THF) (2.5 mL) and methanol (2.5 mL) was stirred for 30 min at room temperature, the LCMS showed desired and also some starting material. 1.0 mL of the reaction mixture was acidified with 2.0 N HCl (aq) and extracted with ethyl acetate. The organic extract was washed with water and concentrated. The crude product was purified on the prep HPLC eluting with a gradient of 30-100% acetonitrile in water. The title compound was obtained as white solid (6.0 mg, 0.011 mmol, 4.3% yield). LC-MS m/z 510.5 (M+H)+, 1.43 (ret. time).

Example 117. 1-(2'-fluoro-3'-((R)-2-propylpiperidine-1-carbonyl)-[1,1'-biphenyl]-3-yl)-5-(trans-2-(3-methylisoxazol-5-yl)cyclopropyl)-1H-pyrazole-4-carboxylic Acid

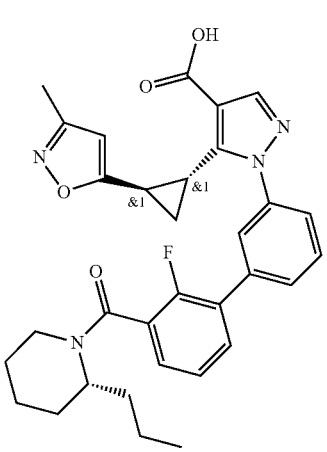 [SMILES: CCC[C@@H]1CCCCN1C(=O)c1cccc(-c2cccc(-n3ncc(C(=O)O)c3[C@@H]3C[C@H]3c3cc(C)no3)c2)c1F]

117a) rac-Methyl 1-(3-bromophenyl)-5-((1R,2R)-2-(3-methylisoxazol-5-yl)cyclopropyl)-1H-pyrazole-4-carboxylate

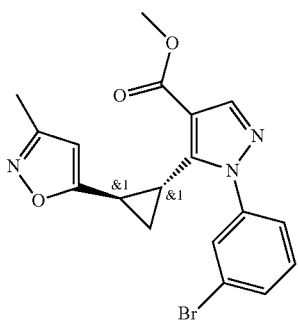 [SMILES: COC(=O)c1cnn(-c2cccc(Br)c2)c1[C@@H]1C[C@H]1c1cc(C)no1]

To a solution of acetaldehyde oxime (0.177 mL, 2.90 mmol) in N,N-dimethylformamide (DMF) (1.2 mL) was added NCS (402 mg, 3.01 mmol) and pyridine (0.023 mL, 0.290 mmol) at room temperature. After 1.0 h of stirring, rac-methyl 1-(3-bromophenyl)-5-((1R,2R)-2-ethynylcyclopropyl)-1H-pyrazole-4-carboxylate (200 mg, 0.579 mmol) in N,N-dimethylformamide (DMF) (1.2 mL) was added, and the mixture was stirred for 30 min, TEA (0.485 mL, 3.48 mmol) was added. The mixture was stirred overnight at 50° C. After cooled to the room temperature, the mixture was diluted with water and extracted with ethyl acetate. The organic extract was washed with water and dried over anhydrous magnesium sulfate. It was filtered and the filtrate was concentrated. The crude product was purified on the Combiflash eluting with a gradient of 0-30% ethyl acetate in hexanes. The title compound was obtained as white solid (192 mg, 0.477 mmol, 82% yield). LC-MS m/z 420.1 (M+H)$^+$, 1.09 (ret. time).

117b) (R)-(2-Fluoro-3-(4,4,5,5-tetramethyl-1,3,2-dioxaborolan-2-yl)phenyl)(2-propylpiperidin-1-yl)methanone

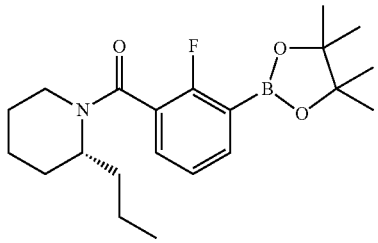 [SMILES: CCC[C@@H]1CCCCN1C(=O)c1cccc(B2OC(C)(C)C(C)(C)O2)c1F]

To a solution of (R)-2-propylpiperidine (158 mg, 1.240 mmol) and 2-fluoro-3-(4,4,5,5-tetramethyl-1,3,2-dioxaborolan-2-yl)benzoic acid (300 mg, 1.128 mmol) in N,N-dimethylformamide (DMF) (3.0 mL) was added BOP (549 mg, 1.240 mmol), followed by DIPEA (0.295 mL, 1.691 mmol). The reaction mixture was stirred for 1.0 hour at room temperature. The mixture was diluted with water and extracted with ethyl acetate. The organic extract was washed with water and dried over anhydrous MgSO$_4$. It was filtered and the filtrate was concentrated. The crude product was purified on the Combiflash eluting with a gradient of 0-35% ethyl acetate in hexanes. The title compound was obtained as clear colorless oil (192 mg, 0.512 mmol, 45.4% yield). LC-MS m/z 376.2 (M+H)$^+$, 1.32 (ret. time).

117c) Methyl 1-(2'-fluoro-3'-((R)-2-propylpiperidine-1-carbonyl)-[1,1'-biphenyl]-3-yl)-5-(trans-2-(3-methylisoxazol-5-yl)cyclopropyl)-1H-pyrazole-4-carboxylate

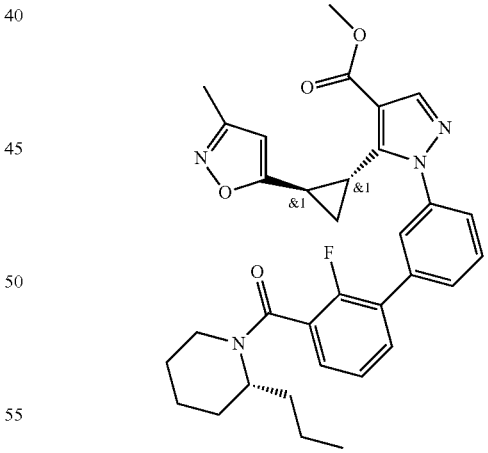

A mixture of (R)-(2-fluoro-3-(4,4,5,5-tetramethyl-1,3,2-dioxaborolan-2-yl)phenyl)(2-propylpiperidin-1-yl)methanone (39.2 mg, 0.104 mmol), rac-methyl 1-(3-bromophenyl)-5-(trans-2-(3-methylisoxazol-5-yl)cyclopropyl)-1H-pyrazole-4-carboxylate (40 mg, 0.099 mmol), tetrakis (7.0 mg, 6.06 µmol), and sodium carbonate (31.6 mg, 0.298 mmol) in 1,4-dioxane (1.2 mL) and Water (0.35 mL) was stirred for 1.0 hour at 100° C. After cooled to the room temperature, the mixture was diluted with water and extracted with ethyl acetate. The organic extract was dried over anhydrous magnesium sulfate. It was filtered and the filtrate was concentrated. The crude product was purified on the Combiflash eluting with a gradient of 0 to 50% ethyl acetate in hexanes. The title compound was obtained as white solid (35 mg, 0.061 mmol, 61.7% yield). LC-MS m/z 571.5 (M+H)⁺, 1.31 (ret. time).

117d) 1-(2'-Fluoro-3'-((R)-2-propylpiperidine-1-carbonyl)-[1,1'-biphenyl]-3-yl)-5-(trans-2-(3-methylisoxazol-5-yl)cyclopropyl)-1H-pyrazole-4-carboxylic Acid

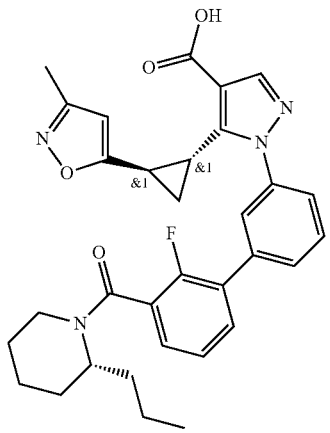 [SMILES: CCC[C@@H]1CCCCN1C(=O)c1cccc(-c2cccc(-n3ncc(C(=O)O)c3[C@@H]3C[C@H]3c3cc(C)no3)c2)c1F]

A mixture of methyl 1-(2'-fluoro-3'-((R)-2-propylpiperidine-1-carbonyl)-[1,1'-biphenyl]-3-yl)-5-(trans-2-(3-methylisoxazol-5-yl)cyclopropyl)-1H-pyrazole-4-carboxylate (35 mg, 0.061 mmol) and 6.0 N NaOH (aq) (0.5 mL, 3.00 mmol) in tetrahydrofuran (THF) (0.8 mL) and methanol (0.8 mL) was stirred overnight at room temperature, the LCMS showed a complete reaction. The mixture was concentrated and the residue was diluted with water (3 mL), neutralized with 2.0 N HCl (aq). The resulting precipitate was extracted with ethyl acetate. The organic extract was concentrated and the crude product was purified on the prep HPLC eluting with a gradient of 20-95% acetonitrile in water. The title compound was obtained as white solid (28 mg, 0.048 mmol, 78% yield). LC-MS m/z 557.4 (M+H)⁺, 1.19 (ret. time).

Example 118. Methyl 1-(3'-((3-ethyl-2,3-dihydrobenzo[f][1,4]oxazepin-4(5H)-yl)methyl)-[1,1'-biphenyl]-3-yl)-5-((1,2-trans)-2-(1-methyl-1H-1,2,3-triazol-4-yl)cyclopropyl)-1H-pyrazole-4-carboxylate

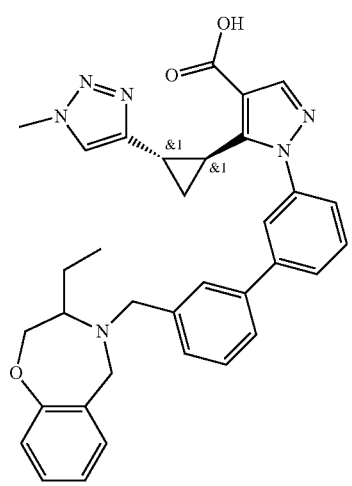 [SMILES: CCC1COc2ccccc2CN1Cc1cccc(-c2cccc(-n3ncc(C(=O)O)c3[C@H]3C[C@@H]3c3cn(C)nn3)c2)c1]

118a) 2-(((1-Hydroxybutan-2-yl)amino)methyl)phenol

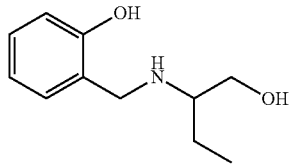

A solution of 2-hydroxybenzaldehyde (1000 mg, 8.19 mmol) in ethanol (50 mL) was added 2-aminobutan-1-ol (876 mg, 9.83 mmol) slowly under nitrogen at 25° C. After the reaction mixture was stirred at 25° C. for 2 h, NaBH₄ (620 mg, 16.38 mmol) was added slowly. The reaction mixture was stirred at room temperature for 4 h. 50 mL of water was added and extracted with ethyl acetate (3×). The combined organic layer was washed with brine, dried over Na₂SO₄ and concentrated under a stream of nitrogen at 50° C. to obtain the title compound 2-(((1-hydroxybutan-2-yl)amino)methyl)phenol (1.7 g, 7.40 mmol, 90% yield) which was used in next step without further purification. LC-MS m/z 196.1 (M+H)⁺, 1.02 min (ret. time).

118b) tert-Butyl 2-hydroxybenzyl(1-hydroxybutan-2-yl)carbamate

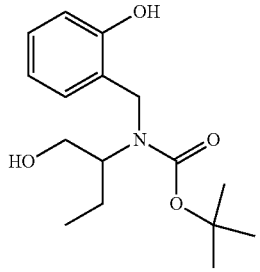

A solution of 2-(((1-hydroxybutan-2-yl)amino)methyl) phenol (1.7 g, 8.71 mmol) in dichloromethane (DCM) (20 mL) was added Boc₂O (2.426 mL, 10.45 mmol) and TEA (2.427 mL, 17.41 mmol) slowly under nitrogen at 25° C. The reaction mixture was stirred at 25° C. for 20 h. The reaction mixture was concentrated and re-dissolved in 50 mL of methanol, and then 5 g of K₂CO₃ was added. Then the reaction mixture was stirred at room temperature for 4 h. 30 mL of water was added and extracted with ethyl acetate (3×). The combined organic layers was washed with brine, dried over Na₂SO₄ and concentrated under a stream of nitrogen at 50° C. to obtain the title compound tert-butyl 2-hydroxybenzyl(1-hydroxybutan-2-yl)carbamate (2.4 g, 8.13 mmol, 93% yield) which was used in next step without further purification. LC-MS m/z 318.1 (M+H)⁺, 1.66 min (ret. time).

118c) tert-Butyl 3-ethyl-2,3-dihydrobenzo[f][1,4]oxazepine-4(5H)-carboxylate

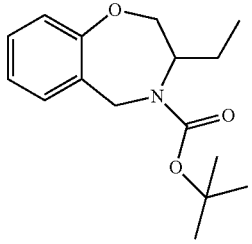 [SMILES: CCC1COc2ccccc2CN1C(=O)OC(C)(C)C]

A solution of tert-butyl 2-hydroxybenzyl(1-hydroxybutan-2-yl)carbamate (2000 mg, 6.77 mmol), triphenylphosphine (5328 mg, 20.31 mmol) in tetrahydrofuran (THF) (25 mL) was added DIAD (3.95 mL, 20.31 mmol) in tetrahydrofuran (THF) (25 mL) slowly under nitrogen at 0° C. The reaction mixture was stirred at room temperature for 16 h. Then the reaction mixture was concentrated. The crude product was purified ion silica gel chromatography (hexane:ethyl acetate=50:1) to obtain the title compound tert-butyl 3-ethyl-2,3-dihydrobenzo[f][1,4]oxazepine-4(5H)-carboxylate (1.4 g, 5.05 mmol, 74.5% yield). LC-MS m/z 300.1 (M+Na)$^+$, 1.8 min (ret. time).

118d) 3-Ethyl-2,3,4,5-tetrahydrobenzo[f][1,4]oxazepine

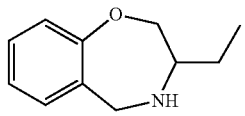

A solution of tert-butyl 3-ethyl-2,3-dihydrobenzo[f][1,4]oxazepine-4(5H)-carboxylate (412 mg, 1.485 mmol) in dichloromethane (DCM) (3 mL) was added TFA (2 ml, 26.0 mmol) slowly under nitrogen at 25° C. The reaction mixture was stirred at 25° C. for 16 h. Then the reaction mixture was concentrated under a stream of nitrogen at 50° C. to obtain the title compound 3-ethyl-2,3,4,5-tetrahydrobenzo[f][1,4]oxazepine trifluoroacetic acid salt (455 mg, 1.485 mmol, 100% yield) which was used in next step without further purification. LC-MS m/z 178.1 (M+Na)$^+$, 1.07 min (ret. time).

118e) 4-(3-Bromobenzyl)-3-ethyl-2,3,4,5-tetrahydrobenzo[f][1,4]oxazepine

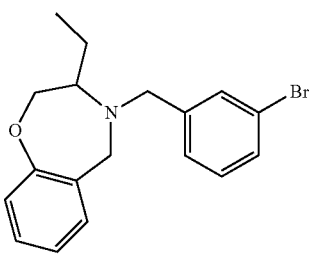 [SMILES: CCC1COc2ccccc2CN1Cc1cccc(Br)c1]

A solution of 3-ethyl-2,3,4,5-tetrahydrobenzo[f][1,4]oxazepine trifluoroacetic acid salt (455 mg, 1.562 mmol) in acetonitrile (20 mL) was added DIPEA (0.818 mL, 4.69 mmol) and 1-bromo-3-(bromomethyl)benzene (390 mg, 1.562 mmol) slowly under nitrogen at room temperature. The reaction mixture was stirred at 90° C. for 2 h. 30 mL of water was added and extracted with ethyl acetate (3×). The combined organic layer was washed with brine, dried over Na$_2$SO$_4$ and concentrated under a stream of nitrogen at 50° C. The crude product was purified by reverse-phase HPLC (0.05% TFA/H$_2$O:CH$_3$CN=5%~95%) to obtain the title compound 4-(3-bromobenzyl)-3-ethyl-2,3,4,5-tetrahydrobenzo[f][1,4]oxazepine (350 mg, 0.960 mmol, 61.5% yield). LC-MS m/z 346.0 (M+Na)$^+$, 1.53 min (ret. time).

118f) Methyl 1-(3'-((3-ethyl-2,3-dihydrobenzo[f][1,4]oxazepin-4(5H)-yl)methyl)-[1,1'-biphenyl]-3-yl)-5-((1,2-trans)-2-(1-methyl-1H-1,2,3-triazol-4-yl)cyclopropyl)-1H-pyrazole-4-carboxylate

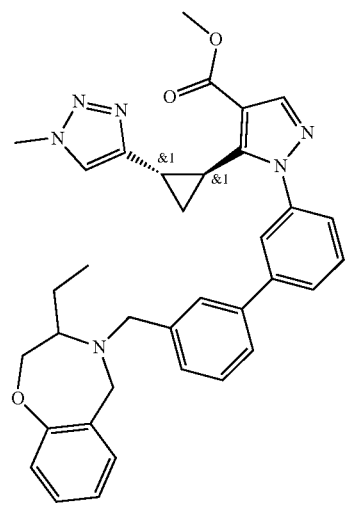 [SMILES: CCC1COc2ccccc2CN1Cc1cccc(-c2cccc(-n3ncc(C(=O)OC)c3[C@H]3C[C@@H]3c3cn(C)nn3)c2)c1]

A mixture of methyl 5-((1,2-trans)-2-(1-methyl-1H-1,2,3-triazol-4-yl)cyclopropyl)-1-(3-(4,4,5,5-tetramethyl-1,3,2-dioxaborolan-2-yl)phenyl)-1H-pyrazole-4-carboxylate (100 mg, 0.223 mmol), 4-(3-bromobenzyl)-3-ethyl-2,3,4,5-tetrahydrobenzo[f][1,4]oxazepine (100 mg, 0.289 mmol), Na$_2$CO$_3$ (0.223 mL, 0.668 mmol) and PdCl$_2$(dppf)-CH$_2$Cl$_2$ adduct (18.18 mg, 0.022 mmol) in a mixture of toluene (5 mL) and methanol (5.00 mL) under nitrogen was stirred at 110° C. for 2 h. 10 mL of water was added and extracted with ethyl acetate (3×). The combined organic layer was washed with brine, dried over Na$_2$SO$_4$ and concentrated under a stream of nitrogen at 50° C. The crude product was purified on silica gel chromatography (hexane:ethyl acetate=1:1) to obtain the title compound methyl 1-(3'-((3-ethyl-2,3-dihydrobenzo[f][1,4]oxazepin-4(5H)-yl)methyl)-[1,1'-biphenyl]-3-yl)-5-((1,2-trans)-2-(1-methyl-1H-1,2,3-triazol-4-yl)cyclopropyl)-1H-pyrazole-4-carboxylate (65 mg, 0.105 mmol, 47.1% yield). LC-MS m/z 589.3 (M+H)$^+$, 2.39 min (ret. time).

349

118g) 1-(3'-((3-Ethyl-2,3-dihydrobenzo[f][1,4]ox-azepin-4(5H)-yl)methyl)-[1,1'-biphenyl]-3-yl)-5-((1,2-trans)-2-(1-methyl-1H-1,2,3-triazol-4-yl)cyclopropyl)-1H-pyrazole-4-carboxylic Acid GSK3

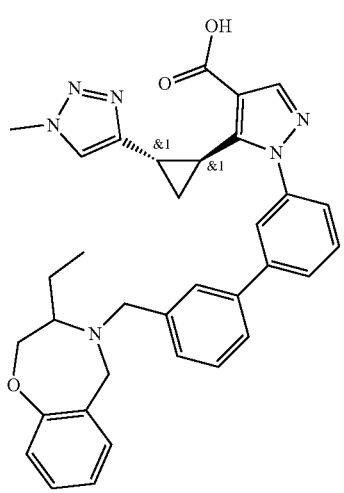 [SMILES: CCC1COc2ccccc2CN1Cc1cccc(-c2cccc(-n3ncc(C(=O)O)c3[C@H]3C[C@@H]3c3cn(C)nn3)c2)c1]

A mixture of methyl 1-(3'-((3-ethyl-2,3-dihydrobenzo[f][1,4]oxazepin-4(5H)-yl)methyl)-[1,1'-biphenyl]-3-yl)-5-((1,2-trans)-2-(1-methyl-1H-1,2,3-triazol-4-yl)cyclopropyl)-1H-pyrazole-4-carboxylate (65 mg, 0.110 mmol) and LiOH (26.4 mg, 1.104 mmol) in water (2 mL) and tetrahydrofuran (THF) (2.000 mL) under nitrogen was stirred at 25° C. for 16 h. After THF was removed, the reaction mixture was adjusted pH to 6 with 1 N HCl. The solid was filtered to provide the title compound 1-(3'-((3-ethyl-2,3-dihydrobenzo[f][1,4]oxazepin-4(5H)-yl)methyl)-[1,1'-biphenyl]-3-yl)-5-((1,2-trans)-2-(1-methyl-1H-1,2,3-triazol-4-yl)cyclopropyl)-1H-pyrazole-4-carboxylic acid (55 mg, 0.091 mmol, 82% yield). LC-MS m/z 575.2 (M+H)+, 1.35 min (ret. time)

Example 119. 1-(3'-(((S)-3-Ethyl-2,3-dihydrobenzo[f][1,4]oxazepin-4(5H)-yl)methyl)-[1,1'-biphenyl]-3-yl)-5-((1R,2R)-2-(1-methyl-1H-1,2,3-triazol-4-yl)cyclopropyl)-1H-pyrazole-4-carboxylic Acid

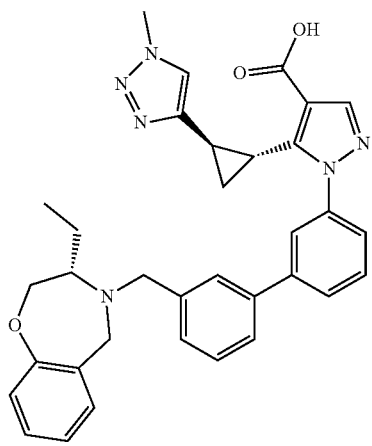 [SMILES: CC[C@H]1COc2ccccc2CN1Cc1cccc(-c2cccc(-n3ncc(C(=O)O)c3[C@@H]3C[C@H]3c3cn(C)nn3)c2)c1]

350

119a) Methyl 1-(3'-(hydroxymethyl)-[1,1'-biphenyl]-3-yl)-5-((1R,2R)-2-(1-methyl-1H-1,2,3-triazol-4-yl)cyclopropyl)-1H-pyrazole-4-carboxylate

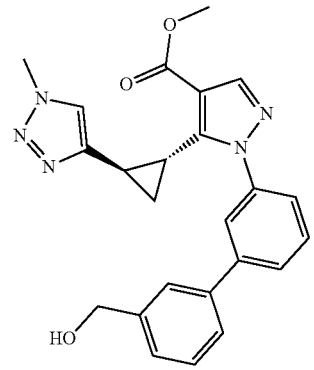 [SMILES: COC(=O)c1cnn(-c2cccc(-c3cccc(CO)c3)c2)c1[C@@H]1C[C@H]1c1cn(C)nn1]

To a solution of (3-(4-(ethoxycarbonyl)-5-((1R,2R)-2-(1-methyl-1H-1,2,3-triazol-4-yl)cyclopropyl)-1H-pyrazol-1-yl)phenyl)boronic acid (1500 mg, 3.94 mmol) in a mixture of 1,4-dioxane (24 mL) and water (8 mL), (3-bromophenyl)methanol (883 mg, 4.72 mmol) and K$_2$CO$_3$ (1632 mg, 11.81 mmol) were added. After it was degassed with nitrogen for 5 mins, PdCl$_2$(dppf) (288 mg, 0.394 mmol) was added. The reaction was heated in a microwave at 120° C. (high absorption) for 40 mins. Then reaction mixture was partitioned between ethyl acetate and water. The water layer was extracted with ethyl acetate (2×). The combined organic phase was dried over MgSO$_4$ and concentrated. The crude product was then purified on a silica cartridge (40 g) with a Combiflash Companion, eluting at 40 mL/min with a gradient running from 100% hexanes to 100% ethyl acetate/hexanes over 35 min) to provide the title compound methyl 1-(3'-(hydroxymethyl)-[1,1'-biphenyl]-3-yl)-5-((1R,2R)-2-(1-methyl-1H-1,2,3-triazol-4-yl)cyclopropyl)-1H-pyrazole-4-carboxylate (480 mg, 1.118 mmol, 27.4% yield). LC-MS m/z 430.1 (M+H)+, 1.84 min (ret. time).

119b) Methyl 1-(3'-(chloromethyl)-[1,1'-biphenyl]-3-yl)-5-((1R,2R)-2-(1-methyl-1H-1,2,3-triazol-4-yl)cyclopropyl)-1H-pyrazole-4-carboxylate

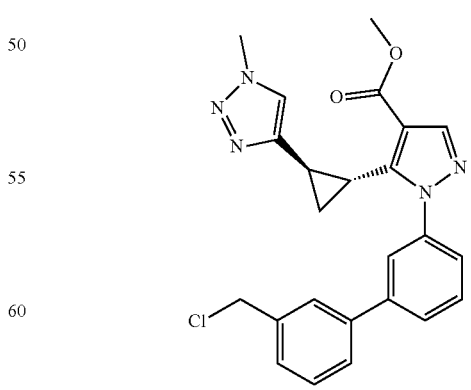

To a solution of methyl 1-(3'-(hydroxymethyl)-[1,1'-biphenyl]-3-yl)-5-((1R,2R)-2-(1-methyl-1H-1,2,3-triazol-4-yl)cyclopropyl)-1H-pyrazole-4-carboxylate (162 mg, 0.377 mmol) in dichloromethane (DCM) (2 mL), thionyl chloride (0.055 mL, 0.754 mmol) was added. The reaction mixture was stirred at room temperature for 30 mins. The solvent was evaporated under Biotage V-10 to give the title compound methyl 1-(3'-(chloromethyl)-[1,1'-biphenyl]-3-yl)-5-((1R,2R)-2-(1-methyl-1H-1,2,3-triazol-4-yl)cyclopropyl)-1H-pyrazole-4-carboxylate (150 mg, 0335 mmol, 89%) which was carried over in next step without further purification. LC-MS m/z 448.1 (M+H)+, 1.07 min (ret. time).

119c) (S)-2-(((1-Hydroxybutan-2-yl)amino)methyl)phenol

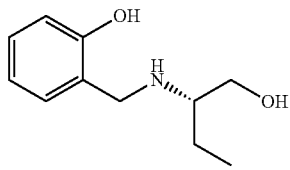

A solution of 2-hydroxybenzaldehyde (2 g, 16.38 mmol) in ethanol (100 mL) was added (S)-2-aminobutan-1-ol (1.752 g, 19.65 mmol) slowly under nitrogen at 25° C. The reaction mixture was stirred at 25° C. for 2 h. Then sodium borohydride (1.239 g, 32.8 mmol) was added slowly and it was stirred at 25° C. for 4 h. 100 mL of water was added and extracted with ethyl acetate (3×). The combined organic layer was dried over $Na_2SO_4$ and concentrated to give the title compound (S)-2-(((1-hydroxybutan-2-yl)amino)methyl)phenol (3 g, 13.00 mmol, 79% yield) which was used in next step without further purification. LC-MS m/z 196.2 (M+H)+, 0.94 min (ret. time).

119d) (S)-tert-butyl 2-Hydroxybenzyl (1-hydroxybutan-2-yl)carbonate

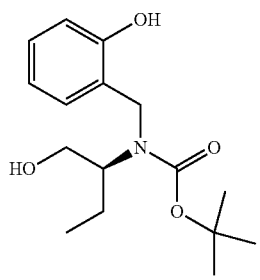 [SMILES: CC[C@@H](CO)N(Cc1ccccc1O)C(=O)OC(C)(C)C]

A solution of (S)-2-(((1-hydroxybutan-2-yl)amino)methyl)phenol (3 g, 15.36 mmol) in DCM (40 mL) was added $Boc_2O$ (4.02 g, 18.44 mmol), TEA (4.28 mL, 30.7 mmol) slowly under nitrogen at 25° C. The reaction mixture was stirred at 25° C. for 20 h. Then the mixture was concentrated and was dissolved in 50 mL of methanol. 5 g of $K_2CO_3$ was added and stirred at 25° C. for 4 h. It was added to 50 mL of water and extracted with ethyl acetate (3×). The combined organic layer was dried over $Na_2SO_4$ and concentrated to obtain the title compound (S)-tert-butyl 2-hydroxybenzyl(1-hydroxybutan-2-yl)carbamate (4 g, 8.81 mmol, 57.4% yield) which was used for next step without further purification. LC-MS m/z 318.2 (M+Na)+, 1.69 min (ret. time).

119e) (S)-tert-Butyl 3-thyl-2,3-dihydrobenzo[f][1,4]oxazepine-4(5H)-carboxylate

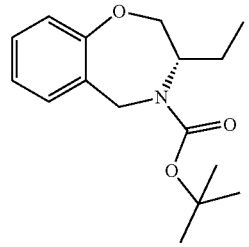 [SMILES: CC[C@H]1COc2ccccc2CN1C(=O)OC(C)(C)C]

A solution of (S)-tert-butyl 2-hydroxybenzyl(1-hydroxybutan-2-yl)carbamate (3.1 g, 10.50 mmol) and triphenylphosphine (4.13 g, 15.74 mmol) in tetrahydrofuran (THF) (30 mL), a solution of DIAD (3.06 mL, 15.74 mmol) in tetrahydrofuran (THF) (5 mL) was added slowly under nitrogen at 0° C. The reaction mixture was stirred at 20° C. for 16 h. Then 15 mL of water was added and extracted with ethyl acetate (3×). The combined organic layer was dried over $Na_2SO_4$ and concentrated. The crude product was then purified on silica gel chromatography (petroleum ether:ethyl acetate=25:1) to give the title compound (S)-tert-butyl 3-ethyl-2,3-dihydrobenzo[f][1,4]oxazepine-4(5H)-carboxylate (2.3 g, 8.11 mmol, 77% yield). LC-MS m/z 300.2 (M+H)+, 1.91 min (ret. time).

119f) (S)-3-Ethyl-2,3,4,5-tetrahydrobenzo[f][1,4]oxazepine

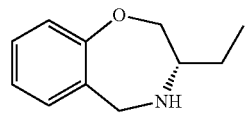

A solution of (S)-tert-butyl 3-ethyl-2,3-dihydrobenzo[f][1,4]oxazepine-4(5H)-carboxylate (4.2 g, 15.14 mmol) in dichloromethane (DCM) (100 mL) was added TFA (8 ml, 104 mmol) slowly under nitrogen at 25° C. The reaction mixture was stirred at 25° C. for 16 h. Then it was concentrated under a stream of nitrogen at 50° C. to give the title compound (S)-3-ethyl-2,3,4,5-tetrahydrobenzo[f][1,4]oxazepine trifluoroacetic acid salt (4.5 g, 14.44 mmol, 95% yield). LC-MS m/z 178.1 (M+H)+, 1.01 min (ret. time).

119g) 1-(3'-(((S)-3-Ethyl-2,3-dihydrobenzo[f][1,4]oxazepin-4(5H)-yl)methyl)-[1,1'-biphenyl]-3-yl)-5-((1R,2R)-2-(1-methyl-1H-1,2,3-triazol-4-yl)cyclopropyl)-1H-pyrazole-4-carboxylic Acid

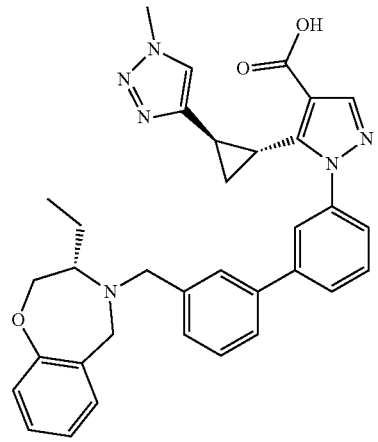 [SMILES: CC[C@H]1COc2ccccc2CN1Cc1cccc(-c2cccc(-n3ncc(C(=O)O)c3[C@@H]3C[C@H]3c3cn(C)nn3)c2)c1]

To a solution of methyl 1-(3'-(chloromethyl)-[1,1'-biphenyl]-3-yl)-5-((1R,2R)-2-(1-methyl-1H-1,2,3-triazol-4-yl)cyclopropyl)-1H-pyrazole-4-carboxylate (50 mg, 0.112 mmol) in methanol (2.00 mL) was added (S)-3-ethyl-2,3,4,5-tetrahydrobenzo[f][1,4]oxazepine (29.7 mg, 0.167 mmol) and DIEA (0.058 mL, 0.335 mmol). The reaction was heated in a microwave at 120° C. (high absorption) for 6 h. The solvent was evaporated under Biotage V-10 and purified by reverse-phase HPLC to give the title compound the methyl 1-(3'-(((S)-3-ethyl-2,3-dihydrobenzo[f][1,4]oxazepin-4(5H)-yl)methyl)-[1,1'-biphenyl]-3-yl)-5-((1R,2R)-2-(1-methyl-1H-1,2,3-triazol-4-yl)cyclopropyl)-1H-pyrazole-4-carboxylate (24.3 mg, 0.041 mmol, 37% yield). LC-MS m/z 589.4 (M+H)+, 0.9 min (ret. time). To it in methanol (2.00 mL), LiOH (26.7 mg, 1.116 mmol) and 0.1 mL of water were added. The reaction mixture was stirred at room temperature for 3 days. It was acidified with 1N HCl. Then it was concentrated and purified by reverse-phase HPLC to obtain the title compound (7.2 mg, 0.013 mmol, 11.22% yield) as solid. LC-MS m/z 575.3 (M+H)+, 0.8 min (ret. time).

Example 120. 1-(3'-(((R)-3-Ethyl-2,3-dihydrobenzo[f][1,4]oxazepin-4(5H)-yl)methyl)-[1,1'-biphenyl]-3-yl)-5-((1R,2R)-2-(1-methyl-1H-1,2,3-triazol-4-yl)cyclopropyl)-1H-pyrazole-4-carboxylic Acid

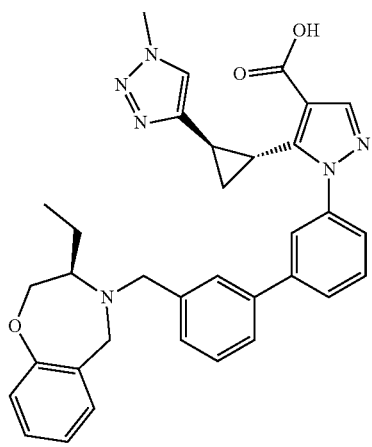 [SMILES: CC[C@@H]1COc2ccccc2CN1Cc1cccc(-c2cccc(-n3ncc(C(=O)O)c3[C@@H]3C[C@H]3c3cn(C)nn3)c2)c1]

120a) (R)-2-(((1-Hydroxybutan-2-yl)amino)methyl)phenol

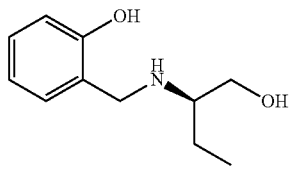

A solution of 2-hydroxybenzaldehyde (5.3 g, 43.4 mmol) in ethanol (100 mL) was added (R)-2-aminobutan-1-ol (4.64 g, 52.1 mmol) slowly under nitrogen at 25° C. The reaction mixture was stirred at 25° C. for 2 h. Then sodium borohydride (3.28 g, 87 mmol) was added slowly. It was stirred at 25° C. for 4 h. 100 mL of water was added and extracted with ethyl acetate (3×). The combined organic layer was concentrated under a stream of nitrogen to obtain the title compound (R)-2-(((1-hydroxybutan-2-yl)amino)methyl)phenol (7.8 g, 33.3 mmol, 77% yield) which was used in next step without further purification. LC-MS m/z 196.2 (M+H)+, 0.9 min (ret. time).

120b) (R)-tert-Butyl 2-hydroxybenzyl(1-hydroxybutan-2-yl)carbamate

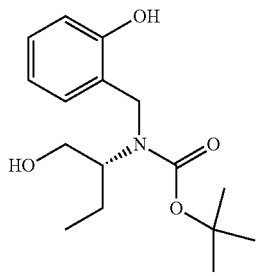 [SMILES: CC[C@H](CO)N(Cc1ccccc1O)C(=O)OC(C)(C)C]

A solution of (R)-2-(((1-hydroxybutan-2-yl)amino)methyl)phenol (3.9 g, 19.97 mmol) in dichloromethane (20 mL) was added Boc$_2$O (5.56 mL, 23.97 mmol) and TEA (5.57 mL, 39.9 mmol) slowly under nitrogen at 25° C. The reaction mixture was stirred at 25° C. for 20 h. Then it was concentrated and dissolved in 50 mL of methanol. 5 g of K$_2$CO$_3$ was added and stirred at 25° C. for 4 h. Then 30 mL of water was added and extracted with ethyl acetate (3×). The combined organic layer was concentrated under a stream of nitrogen at 50° C. to obtain the title compound (R)-tert-butyl 2-hydroxybenzyl(1-hydroxybutan-2-yl)carbamate (6 g, 15.11 mmol, 76% yield) which was used in next step without further purification. LC-MS m/z 318.1 (M+Na)+, 1.69 min (ret. time).

120d) (R)-tert-Butyl 3-ethyl-2,3-dihydrobenzo[f][1,4]oxazepine-4(5H)-carboxylate

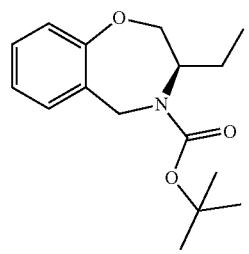 [SMILES: CC[C@@H]1COc2ccccc2CN1C(=O)OC(C)(C)C]

A solution of (R)-tert-butyl 2-hydroxybenzyl(1-hydroxybutan-2-yl)carbamate (4.2 g, 14.22 mmol) and triphenylphosphine (5.59 g, 21.33 mmol) in tetrahydrofuran (THF) (50 mL) was added DIAD (4.15 mL, 21.33 mmol) in tetrahydrofuran (10 mL) slowly under nitrogen at 0° C. The reaction mixture was stirred at 20° C. for 7 h. Then the mixture was washed with water and extracted with ethyl acetate (3×). The combined organic layer was dried over Na$_2$SO$_4$ and concentrated in vacuum. The crude product was then purified on silica gel chromatography (petroleum ether:ethyl acetate=25:1) to obtain the title compound (R)-tert-butyl 3-ethyl-2,3-dihydrobenzo[f][1,4]oxazepine-4(5H)- carboxylate (2.5 g, 8.34 mmol, 58.6% yield). LC-MS m/z 300.2 (M+Na)⁺, 1.91 min (ret. time).

120e) (R)-3-Ethyl-2,3,4,5-tetrahydrobenzo[f][1,4]oxazepine

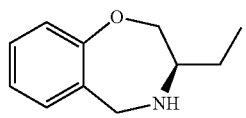

A solution of (R)-tert-butyl 3-ethyl-2,3-dihydrobenzo[f][1,4]oxazepine-4(5H)-carboxylate (3.5 g, 12.62 mmol) in 1,4-dioxane (30 mL) was added hydrogen chloride in 1,4 dioxane (4M, 12.62 mL, 50.5 mmol) slowly under nitrogen at 25° C. The reaction mixture was stirred at 25° C. for 16 h. Then the mixture was concentrated under a stream of nitrogen at 50° C. to obtain the title compound (R)-3-ethyl-2,3,4,5-tetrahydrobenzo[f][1,4]oxazepine hydrochloride (2.8 g, 12.22 mmol, 97% yield). LC-MS m/z 178.2 (M+Na)⁺, 1.01 min (ret. time).

120f) 1-(3'-(((R)-3-Ethyl-2,3-dihydrobenzo[f][1,4]oxazepin-4(5H)-yl)methyl)-[1,1'-biphenyl]-3-yl)-5-((1R,2R)-2-(1-methyl-1H-1,2,3-triazol-4-yl)cyclopropyl)-1H-pyrazole-4-carboxylic Acid

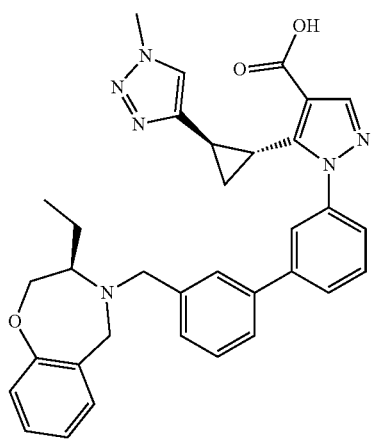 [SMILES: CC[C@@H]1COc2ccccc2CN1Cc1cccc(-c2cccc(-n3ncc(C(=O)O)c3[C@@H]3C[C@H]3c3cn(C)nn3)c2)c1]

To a solution of methyl 1-(3'-(chloromethyl)-[1,1'-biphenyl]-3-yl)-5-((1R,2R)-2-(1-methyl-1H-1,2,3-triazol-4-yl)cyclopropyl)-1H-pyrazole-4-carboxylate (50 mg, 0.112 mmol) in acetonitrile (3 mL), (R)-3-ethyl-2,3,4,5-tetrahydrobenzo[f][1,4]oxazepine (29.7 mg, 0.167 mmol) and DIEA (0.058 mL, 0.335 mmol) were added. The reaction mixture was stirred at 90° C. for 16 h. The solvent was evaporated. The residue was purified by reverse-phase HPLC under acidic condition to provide methyl 1-(3'-(((R)-3-ethyl-2,3-dihydrobenzo[f][1,4]oxazepin-4(5H)-yl)methyl)-[1,1'-biphenyl]-3-yl)-5-((1R,2R)-2-(1-methyl-1H-1,2,3-triazol-4-yl)cyclopropyl)-1H-pyrazole-4-carboxylate (49 mg, 0.083 mmol, 74.6% yield). To it in methanol (2.00 mL), LiOH (26.7 mg, 1.116 mmol) and 0.1 mL of water were added. The reaction mixture was stirred at room temperature for 3 days. 1 N of HCl was added to pH=1. The solvent was evaporated and was purified by reverse-phase HPLC to obtain the title compound (9.85 mg, 0.017 mmol, 15.35% yield). LC-MS m/z 589.4 (M+H)⁺, 0.9 min (ret. time).

Example 121. 1-(3'-(((S)-5-Ethyl-2,3-dihydrobenzo[f][1,4]oxazepin-4(5H)-yl)methyl)-[1,1'-biphenyl]-3-yl)-5-((1R,2R)-2-(1-methyl-1H-1,2,3-triazol-4-yl)cyclopropyl)-1H-pyrazole-4-carboxylic Acid (Isomer 2)

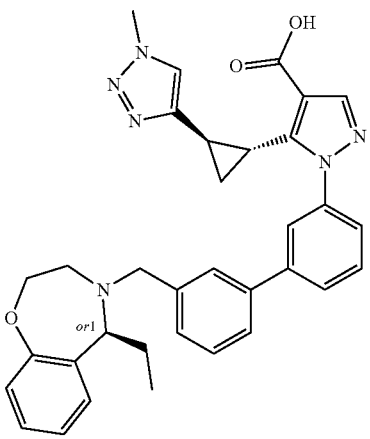 [SMILES: CC[C@H]1c2ccccc2OCCN1Cc1cccc(-c2cccc(-n3ncc(C(=O)O)c3[C@@H]3C[C@H]3c3cn(C)nn3)c2)c1]

121a) 2-(1-((2-Hydroxyethyl)amino)propyl)phenol

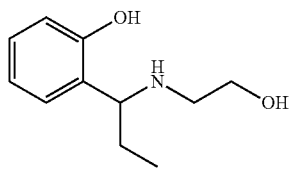

A solution of 1-(2-hydroxyphenyl)propan-1-one (5 g, 33.3 mmol) in toluene (50.0 mL) was added 2-aminoethanol (2.440 g, 40.0 mmol) slowly under nitrogen at 25° C. The reaction mixture was stirred at 130° C. for 22 h. Then toluene was concentrated. The ethanol (50 mL) and NaBH₄ (2.52 g, 66.6 mmol) were added to residue slowly. Then the reaction mixture was stirred at 70° C. for 4 h. 50 mL of water was added and extracted with ethyl acetate (3×). The combined organic layer was washed with water, brine and dried over anhydrous Na₂SO₄. The solvent was concentrated to obtain the title compound 2-(1-((2-hydroxyethyl)amino)propyl)phenol (6.2 g, 30.1 mmol, 90% yield) which was used in next step without further purification. LC-MS m/z 196.2 (M+H)⁺, 1.6 min (ret. time).

121b) tert-Butyl (2-hydroxyethyl)(1-(2-hydroxyphenyl)propyl)carbamate

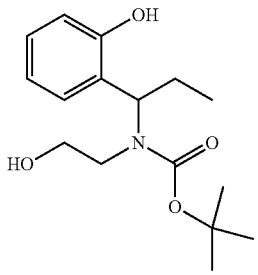 [SMILES: CCC(c1ccccc1O)N(CCO)C(=O)OC(C)(C)C]

A solution of 2-(1-((2-hydroxyethyl)amino)propyl)phenol (6.2 g, 31.8 mmol) in dichloromethane (DCM) (20 mL) was added Boc₂O (8.85 mL, 38.1 mmol), triethylamine (6.64 mL, 47.6 mmol) and DMAP (0.388 g, 3.18 mmol) under nitrogen at 25° C. The reaction mixture was stirred at 25° C. for 20 h. After it was concentrated and was dissolved in 50 mL of methanol. Then 5 g of K₂CO₃ was added and stirred at room temperature for 4 h. 50 mL of water was added and extracted with ethyl acetate (3×). The combined organic layer was washed with water, brine, dried over anhydrous Na₂SO₄ and concentrated. The crude product was then purified on a silica gel chromatography (hexane:ethyl acetate=10:1) to give the title compound tert-butyl (2-hydroxyethyl)(1-(2-hydroxyphenyl)propyl)carbamate (8 g, 24.93 mmol, 79% yield) as a white solid. LC-MS m/z 240.2 (M+H)⁺, 1.87 min (ret. time).

121c) tert-Butyl 5-ethyl-2,3-dihydrobenzo[f][1,4]oxazepine-4(5H)-carboxylate

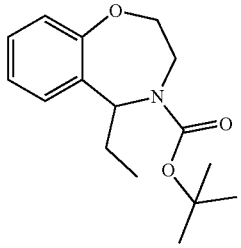 [SMILES: CCC1c2ccccc2OCCN1C(=O)OC(C)(C)C]

To a solution of tert-butyl (2-hydroxyethyl)(1-(2-hydroxyphenyl)propyl)carbamate (8 g, 27.1 mmol) and triphenylphosphine (10.66 g, 40.6 mmol) in tetrahydrofuran (THF) (100 mL) was added DIAD (7.90 mL, 40.6 mmol) in tetrahydrofuran (THF) (16 mL) slowly under nitrogen at 0° C. The reaction mixture was stirred at 20° C. for 16 h. The solvent was concentrated. The residue was purified on silica gel chromatography (hexane:ethyl acetate=50:1) to obtain the title compound tert-butyl 5-ethyl-2,3-dihydrobenzo[f][1,4]oxazepine-4(5H)-carboxylate (5.6 g, 19.98 mmol, 73.8% yield) as a yellow oil. LC-MS m/z 178.2 (M−100+H)⁺, 2.18 min (ret. time).

121d) 5-Ethyl-2,3,4,5-tetrahydrobenzo[f][1,4]oxazepine

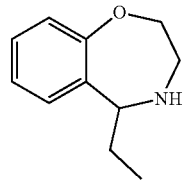

A mixture of tert-butyl 5-ethyl-2,3-dihydrobenzo[f][1,4]oxazepine-4(5H)-carboxylate (5.6 g, 20.19 mmol) in hydrogen chloride in 1,4-dioxane (20.19 ml, 81 mmol) was stirred at 25° C. for 1 h. The solvent was concentrated to obtain the title compound 5-ethyl-2,3,4,5-tetrahydrobenzo[f][1,4]oxazepine, hydrochloride (4.2 g, 19.65 mmol, 97% yield) a white solid. LC-MS m/z 178.2 (M+H)⁺, 1.66 min (ret. time).

121e) Ethyl 1-(3'-((5-ethyl-2,3-dihydrobenzo[f][1,4]oxazepin-4(5H)-yl)methyl)-[1,1'-biphenyl]-3-yl)-5-((1R,2R)-2-(1-methyl-1H-1,2,3-triazol-4-yl)cyclopropyl)-1H-pyrazole-4-carboxylate

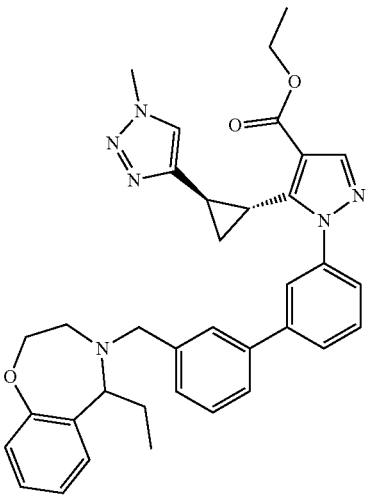

To a solution of ethyl 1-(3'-(chloromethyl)-[1,1'-biphenyl]-3-yl)-5-((1R,2R)-2-(1-methyl-1H-1,2,3-triazol-4-yl)cyclopropyl)-1H-pyrazole-4-carboxylate (110 mg, 0.238 mmol) in acetonitrile (5 mL), 5-ethyl-2,3,4,5-tetrahydrobenzo[f][1,4]oxazepine (84 mg, 0.476 mmol) and DIEA (0.208 mL, 1.191 mmol) were added. The reaction mixture was stirred at 80° C. for 4 h. The solvent was evaporated and the crude product was then purified on a silica cartridge (12 g) with a Combiflash Companion, eluting at 20 mL/min with a gradient running from 100% hexanes to 50% ethyl acetate/hexanes over 35 min) to obtain the title compound (128 mg, 0.212 mmol, 89% yield). LC-MS m/z 603.3 (M+H)⁺, 0.94 min (ret. time).

121f) Ethyl 1-(3'-(((S)-5-ethyl-2,3-dihydrobenzo[f]
[1,4]oxazepin-4(5H)-yl)methyl)-[1,1'-biphenyl]-3-
yl)-5-((1R,2R)-2-(1-methyl-1H-1,2,3-triazol-4-yl)
cyclopropyl)-1H-pyrazole-4-carboxylate (isomer 1)
and ethyl 1-(3'-(((S)-5-ethyl-2,3-dihydrobenzo[f][1,
4]oxazepin-4(5H)-yl)methyl)-[1,1'-biphenyl]-3-yl)-
5-((1R,2R)-2-(1-methyl-1H-1,2,3-triazol-4-yl)cyclo-
propyl)-1H-pyrazole-4-carboxylate (Isomer 2)

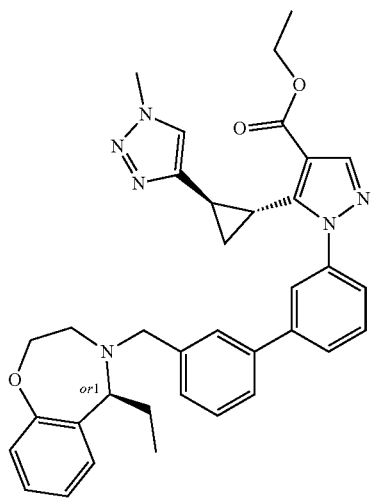

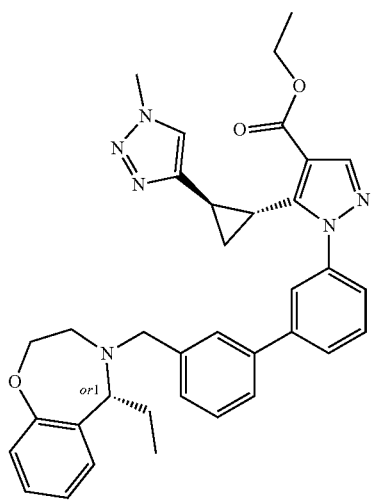 [SMILES: CCOC(=O)c1cnn(-c2cccc(-c3cccc(CN4CCOc5ccccc5C4CC)c3)c2)c1[C@@H]1C[C@H]1c1cn(C)nn1]

This was resolved by Chiral SFC (Column: Chiralpak OJ 20×250 mm, 5 u; Co-solvent: 50% IPA; Flowrate: 50 g/min; Back pressure: 100 Bar) to give single enantiomerically pure ethyl 1-(3'-(((S)-5-ethyl-2,3-dihydrobenzo[f][1,4]oxazepin-4(5H)-yl)methyl)-[1,1'-biphenyl]-3-yl)-5-((1R,2R)-2-(1-methyl-1H-1,2,3-triazol-4-yl)cyclopropyl)-1H-pyrazole-4-carboxylate (isomer 1) (36.5 mg) (chiral SFC ret. time: 5.44 min) LC-MS m/z 603.3 (M+H)$^+$, 0.96 min (ret. time) and single enantiomerically pure ethyl 1-(3'-(((S)-5-ethyl-2,3-dihydrobenzo[f][1,4]oxazepin-4(5H)-yl)methyl)-[1,1'-biphenyl]-3-yl)-5-((1R,2R)-2-(1-methyl-1H-1,2,3-triazol-4-yl)cyclopropyl)-1H-pyrazole-4-carboxylate (isomer 2) (37.5 mg) (chiral SFC ret. time: 6.88 min).

121g) 1-(3'-(((S)-5-ethyl-2,3-dihydrobenzo[f][1,4]
oxazepin-4(5H)-yl)methyl)-[1,1'-biphenyl]-3-yl)-5-
((1R,2R)-2-(1-methyl-1H-1,2,3-triazol-4-yl)cyclo-
propyl)-1H-pyrazole-4-carboxylic Acid (Isomer 2)

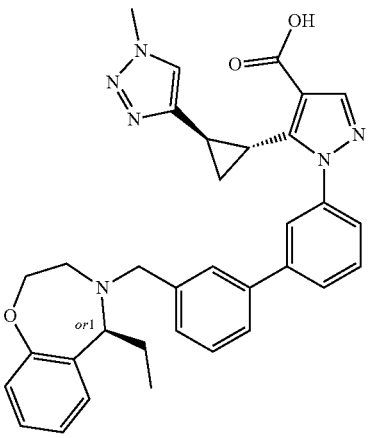 [SMILES: CC[C@H]1c2ccccc2OCCN1Cc1cccc(-c2cccc(-n3ncc(C(=O)O)c3[C@@H]3C[C@H]3c3cn(C)nn3)c2)c1]

To a solution of ethyl 1-(3'-(((S)-5-ethyl-2,3-dihydrobenzo[f][1,4]oxazepin-4(5H)-yl)methyl)-[1,1'-biphenyl]-3-yl)-5-((1R,2R)-2-(1-methyl-1H-1,2,3-triazol-4-yl)cyclopropyl)-1H-pyrazole-4-carboxylate (isomer 2) (37.5 mg, 0.062 mmol) in acetonitrile (5 mL), LiOH (14.90 mg, 0.622 mmol) and 0.1 mL of water were added. The reaction mixture was stirred at room temperature for 20 h. 1N HCl was added to pH=1. The solvent was evaporated and purified by reverse-phase HPLC to obtain the title compound (7.44 mg, 0.013 mmol, 20.81% yield). LC-MS m/z 575.2 (M+H)$^+$, 0.82 min (ret. time).

Example 122. 1-(3'-(((S)-5-Ethyl-2,3-dihydrobenzo
[f][1,4]oxazepin-4(5H)-yl)methyl)-[1,1'-biphenyl]-3-
yl)-5-((1R,2R)-2-(1-methyl-1H-1,2,3-triazol-4-yl)
cyclopropyl)-1H-pyrazole-4-carboxylic Acid
(Isomer 1)

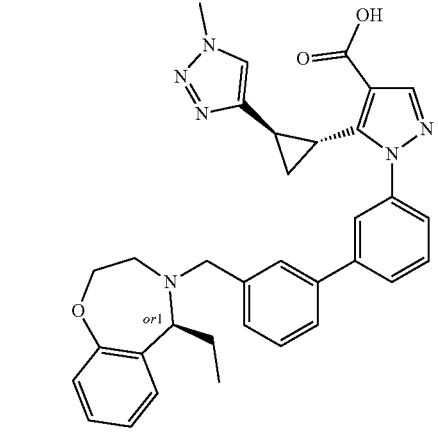 [SMILES: CC[C@H]1c2ccccc2OCCN1Cc1cccc(-c2cccc(-n3ncc(C(=O)O)c3[C@@H]3C[C@H]3c3cn(C)nn3)c2)c1]

To a solution of ethyl 1-(3'-(((S)-5-ethyl-2,3-dihydrobenzo[f][1,4]oxazepin-4(5H)-yl)methyl)-[1,1'-biphenyl]-3-yl)-5-((1R,2R)-2-(1-methyl-1H-1,2,3-triazol-4-yl)cyclopropyl)-1H-pyrazole-4-carboxylate (isomer 1) (36 mg, 0.060 mmol) in methanol (2 mL), LiOH (14.30 mg, 0.597 mmol) and 0.1 mL of water were added. The reaction mixture was stirred at room temperature for 20 h. 1N HCl was added to pH=1. The solvent was evaporated and purified by reverse HPLC to obtain the title compound (5.47 mg, 0.095 mmol, 15.94% yield). LC-MS m/z 575.2 (M+H)+, 0.81 min (ret. time).

Example 123. 1-(3'-((5-Ethyl-2,3-dihydrobenzo[f][1,4]oxazepin-4(5H)-yl)methyl)-[1,1'-biphenyl]-3-yl)-5-((1,2-trans)-2-(1-methyl-1H-1,2,3-triazol-4-yl)cyclopropyl)-1H-pyrazole-4-carboxylic Acid

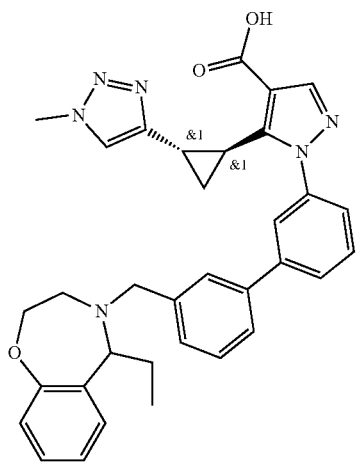 [SMILES: CCC1c2ccccc2OCCN1Cc1cccc(-c2cccc(-n3ncc(C(=O)O)c3[C@H]3C[C@@H]3c3cn(C)nn3)c2)c1]

123a) 4-(3-Bromobenzyl)-5-ethyl-2,3,4,5-tetrahydrobenzo[f][1,4]oxazepine

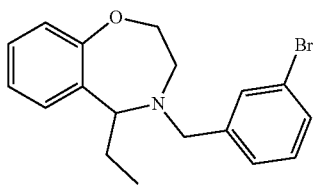 [SMILES: CCC1c2ccccc2OCCN1Cc1cccc(Br)c1]

A mixture of 1-bromo-3-(bromomethyl)benzene (282 mg, 1.128 mmol), 5-ethyl-2,3,4,5-tetrahydrobenzo[f][1,4]oxazepine (200 mg, 1.128 mmol) and DIPEA (0.394 mL, 2.257 mmol) in acetonitrile (5 mL) under nitrogen was stirred at 90° C. for 2 h. 10 mL of water was added and extracted with ethyl acetate (3×). The combined organic layer was concentrated under a stream of nitrogen at 50° C. The crude product was purified on silica gel chromatography (hexane:ethyl acetate=10:1) to obtain the title compound 4-(3-bromobenzyl)-5-ethyl-2,3,4,5-tetrahydrobenzo[f][1,4]oxazepine (230 mg, 0.651 mmol, 57.7% yield) which was used in next step without further purification. LC-MS m/z 346.0 (M+H)+, 1.46 min (ret. time).

123b) Methyl 1-(3'-((5-ethyl-2,3-dihydrobenzo[f][1,4]oxazepin-4(5H)-yl)methyl)-[1,1'-biphenyl]-3-yl)-5-((1,2-trans)-2-(1-methyl-1H-1,2,3-triazol-4-yl)cyclopropyl)-1H-pyrazole-4-carboxylate

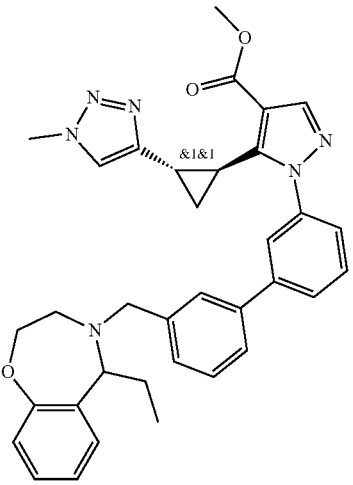 [SMILES: CCC1c2ccccc2OCCN1Cc1cccc(-c2cccc(-n3ncc(C(=O)OC)c3[C@H]3C[C@@H]3c3cn(C)nn3)c2)c1]

A mixture of methyl 5-((1,2-trans)-2-(1-methyl-1H-1,2,3-triazol-4-yl)cyclopropyl)-1-(3-(4,4,5,5-tetramethyl-1,3,2-dioxaborolan-2-yl)phenyl)-1H-pyrazole-4-carboxylate (100 mg, 0.223 mmol), Na₂CO₃ (0.223 mL, 0.668 mmol) and PdCl₂(dppf)-CH₂Cl₂ adduct (18.18 mg, 0.022 mmol) in a mixture of toluene (5 mL) and methanol (5.00 mL) under nitrogen was stirred at 110° C. for 2 h. 10 mL of water was added and extracted with ethyl acetate (3×). The combined organic layer was washed with brine, dried over Na₂SO₄ and concentrated under a stream of nitrogen at 50° C. The crude product was purified on silica gel chromatography (hexane:ethyl acetate=1:1) to obtain the title compound methyl 1-(3'-((5-ethyl-2,3-dihydrobenzo[f][1,4]oxazepin-4(5H)-yl)methyl)-[1,1'-biphenyl]-3-yl)-5-((1,2-trans)-2-(1-methyl-1H-1,2,3-triazol-4-yl)cyclopropyl)-1H-pyrazole-4-carboxylate (60 mg, 0.089 mmol, 39.8% yield). LC-MS m/z 589.2 (M+H)+, 1.91 min (ret. time).

123c) 1-(3'-((5-Ethyl-2,3-dihydrobenzo[f][1,4]oxazepin-4(5H)-yl)methyl)-[1,1'-biphenyl]-3-yl)-5-((1,2-trans)-2-(1-methyl-1H-1,2,3-triazol-4-yl)cyclopropyl)-1H-pyrazole-4-carboxylic Acid

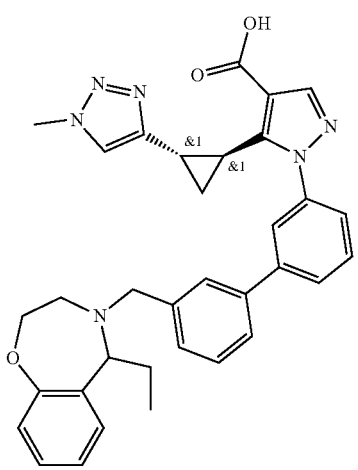 [SMILES: CCC1c2ccccc2OCCN1Cc1cccc(-c2cccc(-n3ncc(C(=O)O)c3[C@H]3C[C@@H]3c3cn(C)nn3)c2)c1]

A mixture of methyl 1-(3'-((5-ethyl-2,3-dihydrobenzo[f][1,4]oxazepin-4(5H)-yl)methyl)-[1,1'-biphenyl]-3-yl)-5-((1,2-trans)-2-(1-methyl-1H-1,2,3-triazol-4-yl)cyclopropyl)-1H-pyrazole-4-carboxylate (65 mg, 0.110 mmol) and LiOH (26.4 mg, 1.104 mmol) in water (2 mL) and tetrahydrofuran (THF) (2.000 mL) under nitrogen was stirred at 25° C. for 16 h. Then THF was removed. The mixture was adjusted pH to 6 with 1 N HCl. The solid was filtered and was purified by reverse-phase HPLC (0.05% TFA/H₂O:CH₃CN= 5%~95%) to obtain the title compound 1-(3'-((5-ethyl-2,3-dihydrobenzo[f][1,4]oxazepin-4(5H)-yl)methyl)-[1,1'-biphenyl]-3-yl)-5-((1,2-trans)-2-(1-methyl-1H-1,2,3-triazol-4-yl)cyclopropyl)-1H-pyrazole-4-carboxylic acid (43 mg, 0.073 mmol, 66.4% yield) as a solid. LC-MS m/z 575.2 (M+H)⁺, 1.34 min (ret. time).

Example 124. 1-(3'-(((S)-5-Ethyl-2,2-dimethyl-2,3-dihydrobenzo[f][1,4]oxazepin-4(5H)-yl)methyl)-[1,1'-biphenyl]-3-yl)-5-((1R,2R)-2-(1-methyl-1H-1,2,3-triazol-4-yl)cyclopropyl)-1H-pyrazole-4-carboxylic Acid (Isomer 1)

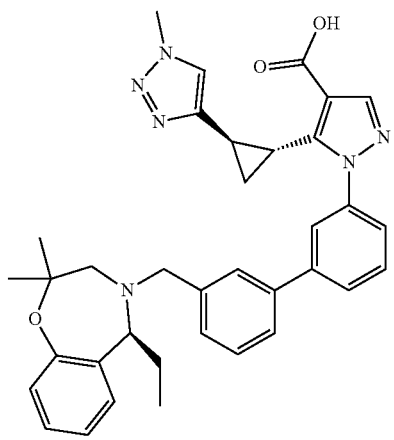 [SMILES: CC[C@H]1c2ccccc2OC(C)(C)CN1Cc1cccc(-c2cccc(-n3ncc(C(=O)O)c3[C@@H]3C[C@H]3c3cn(C)nn3)c2)c1]

124a) Ethyl 1-(3'-(hydroxymethyl)-[1,1'-biphenyl]-3-yl)-5-((1S,2S)-2-(1-methyl-1H-1,2,3-triazol-4-yl)cyclopropyl)-1H-pyrazole-4-carboxylate

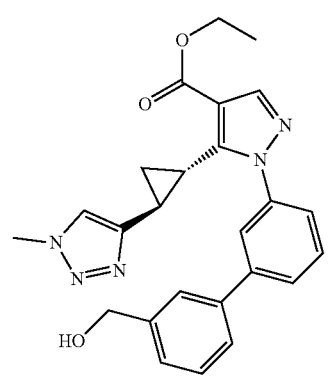 [SMILES: CCOC(=O)c1cnn(-c2cccc(-c3cccc(CO)c3)c2)c1[C@H]1C[C@@H]1c1cn(C)nn1]

To a solution of ethyl 1-(3-bromophenyl)-5-((1S,2S)-2-(1-methyl-1H-1,2,3-triazol-4-yl)cyclopropyl)-1H-pyrazole-4-carboxylate (382 mg, 0.918 mmol) in 1,4-dioxane (9 mL) and water (3 mL), (3-(hydroxymethyl)phenyl)boronic acid (279 mg, 1.835 mmol), K₂CO₃ (380 mg, 2.75 mmol) and PdCl₂(dppf) (67.1 mg, 0.092 mmol) were added. The reaction mixture was heated in a microwave at 120° C. (high absorption) for 40 mins. The solvent was evaporated. The residue was partitioned between ethyl acetate and water. The water layer was extracted with ethyl acetate (2×). The combined organic phase was dried over anhydrous MgSO₄ and concentrated. The crude product was purified on silica gel chromatography (hexane/ethyl acetate) to obtain the title compound (277 mg, 0.625 mmol, 68.1% yield). LC-MS m/z 444.2 (M+H)⁺, 0.89 min (ret. time).

124b) Ethyl 1-(3'-(chloromethyl)-[1,1'-biphenyl]-3-yl)-5-((1R,2R)-2-(1-methyl-1H-1,2,3-triazol-4-yl)cyclopropyl)-1H-pyrazole-4-carboxylate

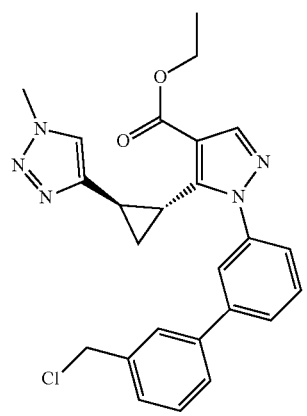 [SMILES: CCOC(=O)c1cnn(-c2cccc(-c3cccc(CCl)c3)c2)c1[C@@H]1C[C@H]1c1cn(C)nn1]

To a solution of ethyl 1-(3'-(hydroxymethyl)-[1,1'-biphenyl]-3-yl)-5-((1R,2R)-2-(1-methyl-1H-1,2,3-triazol-4-yl)cyclopropyl)-1H-pyrazole-4-carboxylate (200 mg, 0.451 mmol) in dichloromethane (DCM) (2.000 mL), thionyl chloride (0.083 mL, 1.132 mmol) was added. The reaction mixture was stirred at room temperature for 30 mins. The solvent was evaporated under Biotage V-10 to obtain the title compound (150 mg, 0.339 mmol, 89% yield) which was carried over in next step without further purification. LC-MS m/z 462.2 (M+H)⁺, 1.13 min (ret. time).

124c) Ethyl 1-(3'-((5-ethyl-2,2-dimethyl-2,3-dihydrobenzo[f][1,4]oxazepin-4(5H)-yl)methyl)-[1,1'-biphenyl]-3-yl)-5-((1R,2R)-2-(1-methyl-1H-1,2,3-triazol-4-yl)cyclopropyl)-1H-pyrazole-4-carboxylate

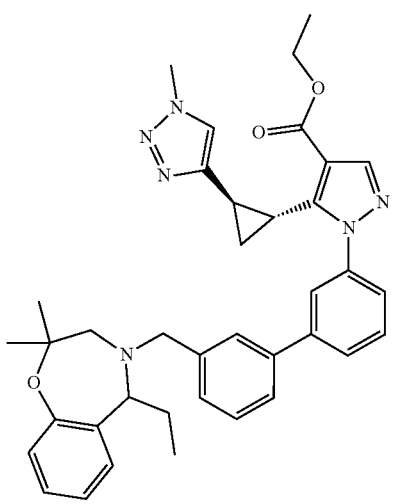 [SMILES: CCOC(=O)c1cnn(-c2cccc(-c3cccc(CN4CC(C)(C)Oc5ccccc5C4CC)c3)c2)c1[C@@H]1C[C@H]1c1cn(C)nn1]

To a reaction of ethyl 1-(3'-(chloromethyl)-[1,1'-biphenyl]-3-yl)-5-((1R,2R)-2-(1-methyl-1H-1,2,3-triazol-4-yl)cyclopropyl)-1H-pyrazole-4-carboxylate (130 mg, 0.281 mmol) in acetonitrile (3 mL), 5-ethyl-2,2-dimethyl-2,3,4,5-tetrahydrobenzo[f][1,4]oxazepine (116 mg, 0.563 mmol) and DIEA (0.147 mL, 0.844 mmol) were added. The reaction mixture was stirred at 90° C. for 9 h. Then the solvent was concentrated. The crude product was then purified on a silica cartridge (40 g) with a Combiflash Companion with Hexane:ethyl acetate to obtain the title compound (95 mg, 0.151 mmol, 53.35% yield). LC-MS m/z 631.4 (M+H)$^+$, 1.03 min (ret. time).

124d) Ethyl 1-(3'-(((S)-5-ethyl-2,2-dimethyl-2,3-dihydrobenzo[f][1,4]oxazepin-4(5H)-yl)methyl)-[1,1'-biphenyl]-3-yl)-5-((1R,2R)-2-(1-methyl-1H-1,2,3-triazol-4-yl)cyclopropyl)-1H-pyrazole-4-carboxylate (isomer 1) and ethyl 1-(3'-(((R)-5-ethyl-2,2-dimethyl-2,3-dihydrobenzo[f][1,4]oxazepin-4(5H)-yl)methyl)-[1,1'-biphenyl]-3-yl)-5-((1R,2R)-2-(1-methyl-1H-1,2,3-triazol-4-yl)cyclopropyl)-1H-pyrazole-4-carboxylate (Isomer 2)

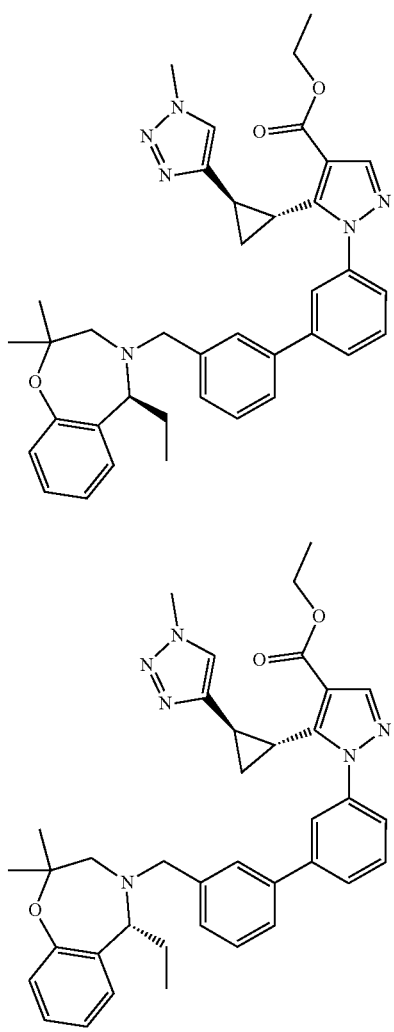

This was resolved by Chiral SFC (Column: Chiralpak OJ 20×250 mm, 5 u; Co-solvent: 30% IPA; Flowrate: 50 g/min; Back pressure: 100 Bar) to give single enantiomerically pure) Ethyl 1-(3'-(((S)-5-ethyl-2,2-dimethyl-2,3-dihydrobenzo[f][1,4]oxazepin-4(5H)-yl)methyl)-[1,1'-biphenyl]-3-yl)-5-((1R,2R)-2-(1-methyl-1H-1,2,3-triazol-4-yl)cyclopropyl)-1H-pyrazole-4-carboxylate (isomer 1) (36.7 mg) (chiral SFC ret. time: 2.97 min) LC-MS m/z 631.3 (M+H)$^+$, 1.05 min (ret. time) and single enantiomerically pure ethyl 1-(3'-(((R)-5-ethyl-2,2-dimethyl-2,3-dihydrobenzo[f][1,4]oxazepin-4(5H)-yl)methyl)-[1,1'-biphenyl]-3-yl)-5-((1R,2R)-2-(1-methyl-1H-1,2,3-triazol-4-yl)cyclopropyl)-1H-pyrazole-4-carboxylate (isomer 2) (35.8 mg) (chiral SFC ret. time: 4.83 min).

124f) 1-(3'-(((S)-5-Ethyl-2,2-dimethyl-2,3-dihydrobenzo[f][1,4]oxazepin-4(5H)-yl)methyl)-[1,1'-biphenyl]-3-yl)-5-((1R,2R)-2-(1-methyl-1H-1,2,3-triazol-4-yl)cyclopropyl)-1H-pyrazole-4-carboxylic Acid (Isomer 1)

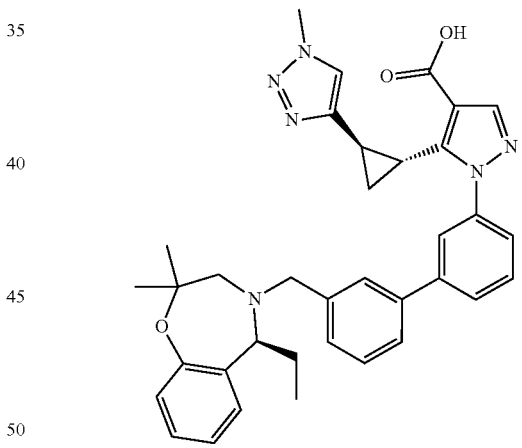

To a solution of ethyl 1-(3'-(((S)-5-ethyl-2,2-dimethyl-2,3-dihydrobenzo[f][1,4]oxazepin-4(5H)-yl)methyl)-[1,1'-biphenyl]-3-yl)-5-((1R,2R)-2-(1-methyl-1H-1,2,3-triazol-4-yl)cyclopropyl)-1H-pyrazole-4-carboxylate (isomer 1) (36.7 mg, 0.058 mmol) in methanol (2 mL), LiOH (13.93 mg, 0.582 mmol) and 0.1 mL of water were added. The reaction mixture was stirred at room temperature for 22 h. 1N HCl was added until pH=1. The solvent was evaporated and was purified by reverse-phase HPLC to obtain the title compound (16.08 mg, 0.025 mmol, 43.6% yield). LC-MS m/z 630.3 (M+H)$^+$, 0.89 min (ret. time).

Example 125. 1-(3'-(((R)-5-Ethyl-2,2-dimethyl-2,3-dihydrobenzo[f][1,4]oxazepin-4(5H)-yl)methyl)-[1,1'-biphenyl]-3-yl)-5-((1R,2R)-2-(1-methyl-1H-1,2,3-triazol-4-yl)cyclopropyl)-1H-pyrazole-4-carboxylic Acid (Isomer 2)

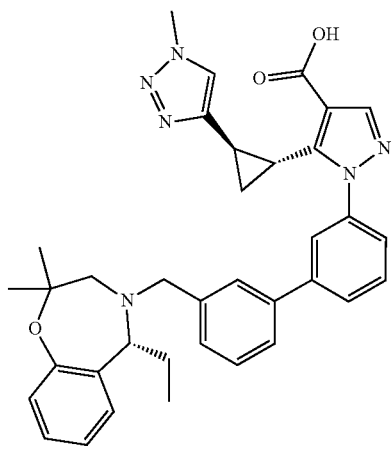 [SMILES: CC[C@@H]1c2ccccc2OC(C)(C)CN1Cc1cccc(-c2cccc(-n3ncc(C(=O)O)c3[C@@H]3C[C@H]3c3cn(C)nn3)c2)c1]

To a solution of ethyl 1-(3'-(((S)-5-ethyl-2,2-dimethyl-2,3-dihydrobenzo[f][1,4]oxazepin-4(5H)-yl)methyl)-[1,1'-biphenyl]-3-yl)-5-((1R,2R)-2-(1-methyl-1H-1,2,3-triazol-4-yl)cyclopropyl)-1H-pyrazole-4-carboxylate (isomer 2) (35.8 mg, 0.057 mmol) in methanol (2 mL), LiOH (13.59 mg, 0.568 mmol) and 0.1 mL of water were added. The reaction mixture was stirred at room temperature for 24 h. 1N of HCl was added until pH=1. The solvent was evaporated and was purified by reverse-phase HPLC to obtain the title compound (19.46 mg, 0.032 mmol, 56.9% yield). LC-MS m/z 630.3 (M+H)$^+$, 0.89 min (ret. time).

Example 126. 1-(3'-((4,4-dimethyl-4,5-dihydro-1H-benzo[c]azepin-2(3H)-yl)methyl)-[1,1'-biphenyl]-3-yl)-5-((1,2-trans)-2-(1-methyl-1H-1,2,3-triazol-4-yl)cyclopropyl)-1H-pyrazole-4-carboxylic Acid

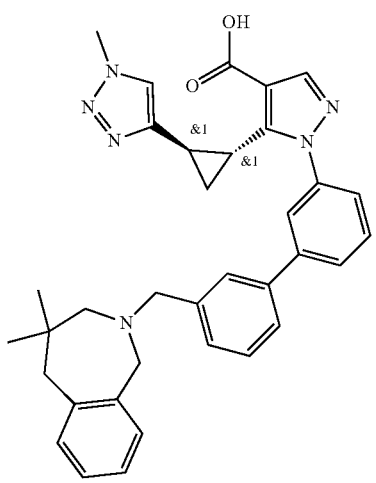 [SMILES: Cn1cc([C@@H]2C[C@H]2c2c(C(=O)O)cnn2-c2cccc(-c3cccc(CN4Cc5ccccc5CC(C)(C)C4)c3)c2)nn1]

126a) Ethyl 3-((1,2-trans)-2-(1-methyl-1H-1,2,3-triazol-4-yl)cyclopropyl)-3-oxopropanoate

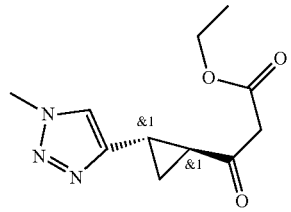 [SMILES: CCOC(=O)CC(=O)[C@H]1C[C@@H]1c1cn(C)nn1]

To a solution of 2-(1-methyl-1H-1,2,3-triazol-4-yl)cyclopropanecarboxylic acid (30 g, 179 mmol) in tetrahydrofuran (THF) (500 mL) at room temperature, CDI (32.0 g, 197 mmol) was added. The reaction mixture was stirred at room temperature for 1 h, then magnesium chloride (20.48 g, 215 mmol) and methylpottasium malonate (56.0 g, 359 mmol) were added. The reaction mixture was stirred at room temperature for 24 h. Then it was poured in ice water and extracted with ethyl acetate (2×). The combined organic layer was washed with brine, dried over $Na_2SO_4$ and concentrated under reduced pressure. The crude product was then purified on a silica cartridge (100-200 silica gel mesh) with a Combiflash Companion with DCM:MeOH to give the title compound ethyl 3-((1,2-trans)-2-(1-methyl-1H-1,2,3-triazol-4-yl)cyclopropyl)-3-oxopropanoate (20 g, 64.7 mmol, 36.0% yield). LC-MS m/z 236.0 (M+H)$^+$, 3.45 min (ret. time).

126b) (Z)-Ethyl 3-(dimethylamino)-2-((1,2-trans)-2-(1-methyl-1H-1,2,3-triazol-4-yl)cyclopropanecarbonyl)acrylate

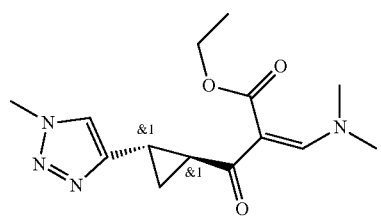

A mixture of ethyl 3-((1,2-trans)-2-(1-methyl-1H-1,2,3-triazol-4-yl)cyclopropyl)-3-oxopropanoate (16 g, 67.4 mmol and pTsOH (1.283 g, 6.74 mmol) in DMF-DMA (27.1 ml, 202 mmol) was stirred under nitrogen at 100° C. for 2 h. The reaction mixture was concentrated under reduced pressure. The crude residue was purified on silica gel chromatography (2.5% MeOH in DCM) to afford the title compound (Z)-ethyl 3-(dimethylamino)-2-((1,2-trans)-2-(1-methyl-1H-1,2,3-triazol-4-yl)cyclopropanecarbonyl)acrylate (15 g, 46.8 mmol, 69.5% yield) as a pale yellow solid. LC-MS m/z 293.2 (M+H)$^+$, 1.38 min (ret. time).

126c) Ethyl 1-(3-bromophenyl)-5-((1,2-trans)-2-(1-methyl-1H-1,2,3-triazol-4-yl)cyclopropyl)-1H-pyrazole-4-carboxylate

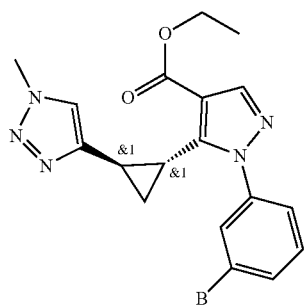

To a solution of (Z)-ethyl 3-(dimethylamino)-2-((1,2-trans)-2-(1-methyl-1H-1,2,3-triazol-4-yl)cyclopropanecarbonyl)acrylate (15.00 g, 51.3 mmol) in ethanol (150 mL), DIPEA (8.96 mL, 51.3 mmol) was added. After it was cooled to 0° C., (3-bromophenyl)hydrazine (70.4 mg, 0.376 mmol) was added and stirred at room temperature for 16 h. The solid was filtered and washed with hexane, diethyl ether and dried to afford the title compound ethyl 1-(3-bromophenyl)-5-((1,2-trans)-2-(1-methyl-1H-1,2,3-triazol-4-yl)cyclopropyl)-1H-pyrazole-4-carboxylate (16 g, 38.4 mmol, 74.8% yield) as a off-white solid. LC-MS m/z 415.2 (M+H)$^+$, 2.15 min (ret. time).

126d) (3-(4-(Ethoxycarbonyl)-5-((1,2-trans)-2-(1-methyl-1H-1,2,3-triazol-4-yl)cyclopropyl)-1H-pyrazol-1-yl)phenyl)boronic Acid

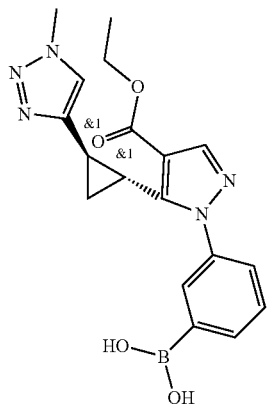 [SMILES: CCOC(=O)c1cnn(-c2cccc(B(O)O)c2)c1[C@@H]1C[C@H]1c1cn(C)nn1]

To a solution of ethyl 1-(3-bromophenyl)-5-((1,2-trans)-2-(1-methyl-1H-1,2,3-triazol-4-yl)cyclopropyl)-1H-pyrazole-4-carboxylate (2 g, 4.80 mmol) in 1,4-dioxane (20 mL), 4,4,4',4',5,5,5',5'-octamethyl-2,2'-bi(1,3,2-dioxaborolane) (2.440 g, 9.61 mmol), potassium acetate (1.415 g, 14.41 mmol) and PdCl$_2$(dppf) (0.352 g, 0.480 mmol) were added. The reaction mixture was stirred at 100° C. for 90 mins. The solvent was evaporated. The crude product was partitioned between ethyl acetate and water. The organic layer was washed with brine, dried over MgSO$_4$ and concentrated. The crude product was purified on silica gel chromatography (hexane/ethyl acetate) to obtain the rac-ethyl 5-((1,2-trans)-2-(1-methyl-1H-1,2,3-triazol-4-yl)cyclopropyl)-1-(3-(4,4,5,5-tetramethyl-1,3,2-dioxaborolan-2-yl)phenyl)-1H-pyrazole-4-carboxylate (1.5447 g, 3.33 mmol, 69.4% yield). To it in acetone (20.00 mL), sodium periodate (3.08 g, 14.41 mmol) and ammonium acetate (7.21 mL, 7.21 mmol) were added. Then the reaction mixture was stirred at 35° C. for 18 h. The solvent was evaporated and was purified on silica gel chromatography (DCM/10% MeOH in DCM) to obtain the title compound (3-(4-(ethoxycarbonyl)-5-((1,2-trans)-2-(1-methyl-1H-1,2,3-triazol-4-yl)cyclopropyl)-1H-pyrazol-1-yl)phenyl)boronic acid (1.4139 g, 3.71 mmol, 77% yield).

126e) (3-(4-(Ethoxycarbonyl)-5-((1R,2R)-2-(1-methyl-1H-1,2,3-triazol-4-yl)cyclopropyl)-1H-pyrazol-1-yl)phenyl)boronic acid and (3-(4-(ethoxycarbonyl)-5-((1S,2S)-2-(1-methyl-1H-1,2,3-triazol-4-yl)cyclopropyl)-1H-pyrazol-1-yl)phenyl)boronic Acid

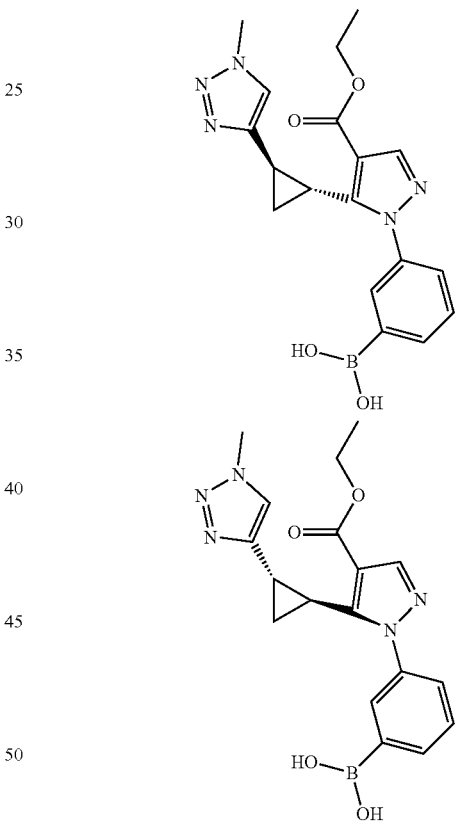

This was resolved by Chiral SFC (Column: Chiralpak OJ 20×250 mm, 5 u; Co-solvent: 20% reagent alcohol; Flow-rate: 50 g/min; Back pressure: 100 Bar) to give single enantiomerically pure) (3-(4-(Ethoxycarbonyl)-5-((1R,2R)-2-(1-methyl-1H-1,2,3-triazol-4-yl)cyclopropyl)-1H-pyrazol-1-yl)phenyl)boronic acid (623 mg) (chiral SFC ret. time: 2.08 min) LC-MS m/z 382.3 (M+H)$^+$, 0.71 min (ret. time) and single enantiomerically pure (R)-3-(3-((2,2-dimethyl-2,3-dihydrobenzo[f][1,4]oxazepin-4(5H)-yl)methyl)-4-methylphenyl)-3-(1-ethyl-4-fluoro-1H-benzo[d][1,2,3]triazol-5-yl)propanoic acid (602 mg) (chiral SFC ret. time: 3.37 min).

126f) Ethyl 1-(3'-(hydroxymethyl)-[1,1'-biphenyl]-3-yl)-5-((1,2-trans)-2-(1-methyl-1H-1,2,3-triazol-4-yl)cyclopropyl)-1H-pyrazole-4-carboxylate

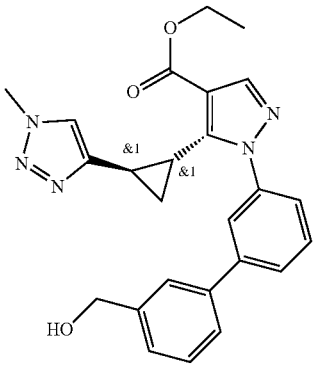

To a solution of ethyl 1-(3-bromophenyl)-5-((1,2-trans)-2-(1-methyl-1H-1,2,3-triazol-4-yl)cyclopropyl)-1H-pyrazole-4-carboxylate (940 mg, 2.258 mmol) in a mixture of 1,4-dioxane (24 mL) and water (8 mL), (3-(hydroxymethyl)phenyl)boronic acid (686 mg, 4.52 mmol) and $K_2CO_3$ (936 mg, 6.77 mmol) were added. After it was degassed with nitrogen for 5 mins, $PdCl_2$(dppf) (165 mg, 0.226 mmol) was added. The reaction was heated in a microwave at 120° C. (high absorption) for 40 mins. The combined mixture was partitioned between ethyl acetate and water. The water layer was extracted with ethyl acetate (2×). The combined organic phase was dried over $MgSO_4$ and concentrated. The crude product was then purified on a silica cartridge (40 g) with a Combiflash Companion, eluting at 40 mL/min with a gradient running from 100% hexanes to 100% ethyl acetate/hexanes over 35 min) to get the title compound (950 mg, 2.142 mmol, 95%). LC-MS m/z 444.3 (M+H)+, 0.9 min (ret. time).

126g) Ethyl 1-(3'-(chloromethyl)-[1,1'-biphenyl]-3-yl)-5-((1,2-trans)-2-(1-methyl-1H-1,2,3-triazol-4-yl)cyclopropyl)-1H-pyrazole-4-carboxylate 1

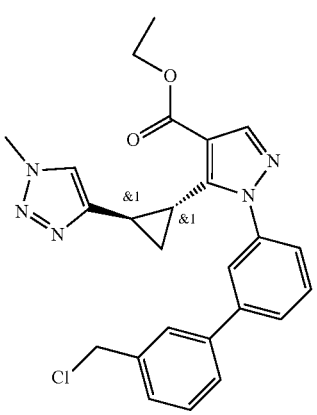 [SMILES: CCOC(=O)c1cnn(-c2cccc(-c3cccc(CCl)c3)c2)c1[C@@H]1C[C@H]1c1cn(C)nn1]

To a solution of ethyl 1-(3'-(hydroxymethyl)-[1,1'-biphenyl]-3-yl)-5-((1,2-trans)-2-(1-methyl-1H-1,2,3-triazol-4-yl)cyclopropyl)-1H-pyrazole-4-carboxylate (80 mg, 0.180 mmol) in dichloromethane (DCM) (2 mL), sulfurous dichloride (64.4 mg, 0.541 mmol) was added. The reaction mixture was stirred at room temperature for 1 h. The solvent was evaporated to obtain the title compound (80 mg, 0.173 mmol, 96%) which was carried over in next step without further purification. LC-MS m/z 642.2 (M+H)+, 1.14 min (ret. time).

126h) 1-(3'-((4,4-Dimethyl-4,5-dihydro-1H-benzo[c]azepin-2(3H)-yl)methyl)-[1,1'-biphenyl]-3-yl)-5-((1,2-trans)-2-(1-methyl-1H-1,2,3-triazol-4-yl)cyclopropyl)-1H-pyrazole-4-carboxylic Acid

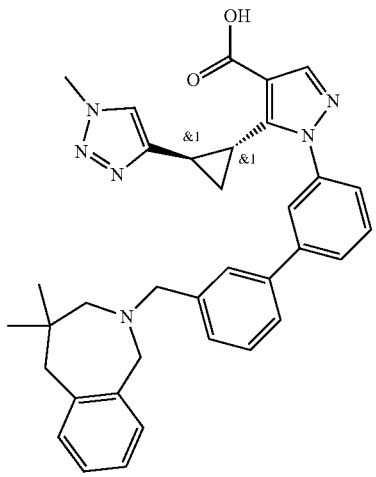 [SMILES: Cn1cc([C@@H]2C[C@H]2c2c(C(=O)O)cnn2-c2cccc(-c3cccc(CN4Cc5ccccc5CC(C)(C)C4)c3)c2)nn1]

To a solution of ethyl 1-(3'-(chloromethyl)-[1,1'-biphenyl]-3-yl)-5-((1,2-trans)-2-(1-methyl-1H-1,2,3-triazol-4-yl)cyclopropyl)-1H-pyrazole-4-carboxylate (80 mg, 0.173 mmol) in N,N-dimethylformamide (DMF) (3 mL), 4,4-dimethyl-2,3,4,5-tetrahydro-1H-benzo[c]azepine (60.7 mg, 0.346 mmol) and $K_2CO_3$ (96 mg, 0.693 mmol) were added. The reaction mixture was stirred at room temperature for 16 h. Then the reaction mixture was partitioned between ethyl acetate and water. The organic phase was washed with brine and dried over $MgSO_4$. After it was concentrated, the crude product was then purified on a silica cartridge (12 g) with a Combiflash Companion, eluting at 30 mL/min with a gradient running from 100% hexanes to 100% ethyl acetate/hexanes over 35 min) to get methyl 1-(3'-((4,4-dimethyl-4,5-dihydro-1H-benzo[c]azepin-2(3H)-yl)methyl)-[1,1'-biphenyl]-3-yl)-5-((1,2-trans)-2-(1-methyl-1H-1,2,3-triazol-4-yl)cyclopropyl)-1H-pyrazole-4-carboxylate (48 mg, 0.08 mmol, 46.1% yield). To it in methanol (3.00 mL), LiOH (41.5 mg, 1.732 mmol) and 0.2 mL of water were added. The reaction mixture was stirred at room temperature for 2 days. 1N HCl was added to pH=1. The solvent was evaporated was purified by reverse-phase HPLC to obtain the title compound (9.9 mg, 0.017 mmol, 9.98% yield). LC-MS m/z 578.4 (M+H)+, 0.87 min (ret. time).

Example 127. 1-(3'-((1-Ethyl-2,3-dihydro-1H-benzo[e][1,4]diazepin-4(5H)-yl)methyl)-[1,1'-biphenyl]-3-yl)-5-((1,2-trans)-2-(1-methyl-1H-1,2,3-triazol-4-yl)cyclopropyl)-1H-pyrazole-4-carboxylic Acid

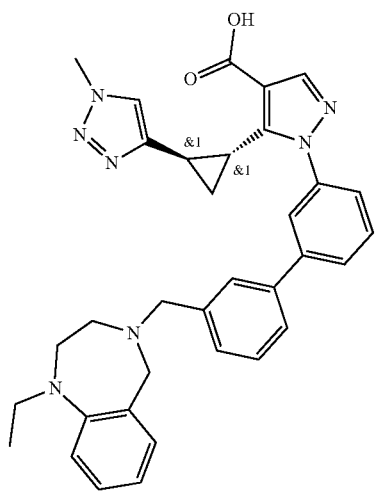 [SMILES: CCN1CCN(Cc2cccc(-c3cccc(-n4ncc(C(=O)O)c4[C@@H]4C[C@H]4c4cn(C)nn4)c3)c2)Cc2ccccc21]

To a solution of ethyl 1-(3'-(chloromethyl)-[1,1'-biphenyl]-3-yl)-5-((1,2-trans)-2-(1-methyl-1H-1,2,3-triazol-4-yl)cyclopropyl)-1H-pyrazole-4-carboxylate (80 mg, 0.173 mmol) in N,N-dimethylformamide (DMF) (2 mL), 1-ethyl-2,3,4,5-tetrahydro-1H-benzo[e][1,4]diazepine (61.0 mg, 0.346 mmol), K$_2$CO$_3$ (96 mg, 0.693 mmol) and sodium iodide (51.9 mg, 0.346 mmol) were added. The reaction mixture was stirred at room temperature for 16 h. Then it was partitioned between ethyl acetate and water. The organic layer was washed with brine and dried over MgSO$_4$. After it was concentrated, the crude product was then purified on a silica cartridge (12 g) with a Combiflash Companion, eluting at 30 mL/min with a gradient running from 100% hexanes to 100% Ethyl acetate/hexanes over 35 min) to get ethyl 1-(3'-((1-ethyl-2,3-dihydro-1H-benzo[e][1,4]diazepin-4(5H)-yl)methyl)-[1,1'-biphenyl]-3-yl)-5-((1,2-trans)-2-(1-methyl-1H-1,2,3-triazol-4-yl)cyclopropyl)-1H-pyrazole-4-carboxylate (70 mg, 0.116 mmol, 67.2% yield). To it in methanol (3.00 mL), LiOH (41.5 mg, 1.732 mmol) and 0.2 mL of water were added. The reaction mixture was stirred at room temperature for 3 days. 1N HCl was added to pH=1. The solvent was evaporated was purified by reverse-phase HPLC to obtain the title compound (40 mg, 0.067 mmol, 38.7% yield). LC-MS m/z 602.5 (M+H)$^+$, 0.98 min (ret. time).

Example 128. 1-(3'-(((R)-2-ethyl-2,3-dihydrobenzo[f][1,4]oxazepin-4(5H)-yl)methyl)-[1,1'-biphenyl]-3-yl)-5-((1,2-trans)-2-(1-isopropyl-1H-1,2,3-triazol-4-yl)cyclopropyl)-1H-pyrazole-4-carboxylic Acid

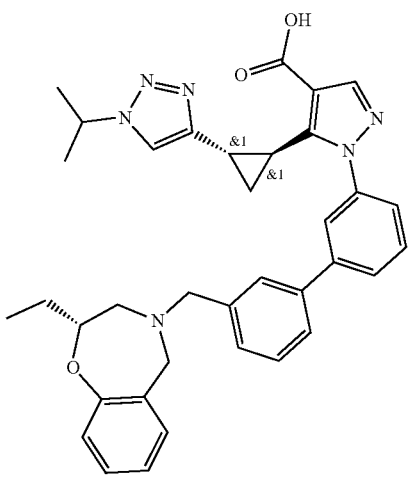 [SMILES: CC[C@@H]1CN(Cc2cccc(-c3cccc(-n4ncc(C(=O)O)c4[C@H]4C[C@@H]4c4cn(C(C)C)nn4)c3)c2)Cc2ccccc2O1]

128a) (R)-4-(3-Bromobenzyl)-2-ethyl-2,3,4,5-tetrahydrobenzo[f][1,4]oxazepine

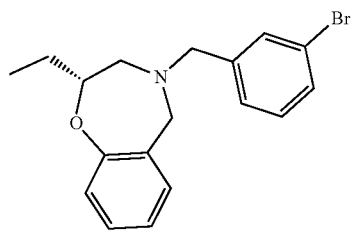 [SMILES: CC[C@@H]1CN(Cc2cccc(Br)c2)Cc2ccccc2O1]

A solution of (R)-2-ethyl-2,3,4,5-tetrahydrobenzo[f][1,4]oxazepine (90 mg, 0.508 mmol) in acetonitrile (20 mL) was added DIPEA (0.098 mL, 0.559 mmol) and 1-bromo-3-(bromomethyl)benzene (140 mg, 0.559 mmol) slowly under nitrogen at room temperature. The reaction mixture was stirred at 90° C. for 2 h. 30 mL of water was added and extracted with ethyl acetate (3×). The combined organic layer was washed with brine, dried over Na$_2$SO$_4$ and concentrated under a stream of nitrogen at 50° C. The crude product was purified by reverse-phase HPLC (0.05% TFA/H$_2$O:CH$_3$CN=5%~95%) to provide the title compound (R)-4-(3-bromobenzyl)-2-ethyl-2,3,4,5-tetrahydrobenzo[f][1,4]oxazepine (150 mg, 0.390 mmol, 77% yield). LC-MS m/z 346.0 (M+H)$^+$, 1.45 min (ret. time).

128b) Methyl 5-((1,2-trans)-2-(1-isopropyl-1H-1,2,3-triazol-4-yl)cyclopropyl)-1-(3-(4,4,5,5-tetramethyl-1,3,2-dioxaborolan-2-yl)phenyl)-1H-pyrazole-4-carboxylate

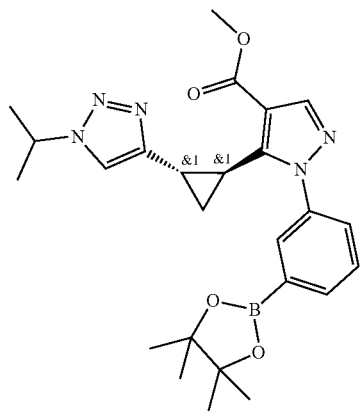 [SMILES: COC(=O)c1cnn(-c2cccc(B3OC(C)(C)C(C)(C)O3)c2)c1[C@H]1C[C@@H]1c1cn(C(C)C)nn1]

To a solution of methyl 1-(3-bromophenyl)-5-(2-(1-isopropyl-1H-1,2,3-triazol-4-yl)cyclopropyl)-1H-pyrazole-4-carboxylate (180 mg, 0.418 mmol) in 1,4-dioxane (100 mL) was added potassium acetate (82 mg, 0.837 mmol) and bis(pinacolato)diboron (159 mg, 0.627 mmol). After the reaction mixture was degassed with argon for 30 mins, PdCl$_2$(dppf)-CH$_2$Cl$_2$ adduct (34.2 mg, 0.042 mmol) was added. The reaction mixture was stirred at 100° C. for 16 h. After the reaction mixture was cooled to room temperature, it was filtered through celite pad and the filtrate was concentrated under vacuum. The residue was purified on silica gel chromatography (ethyl acetate:hexane=1:2) and recrystallized from hexane to obtain the title compound methyl 5-((1,2-trans)-(2-(1-isopropyl-1H-1,2,3-triazol-4-yl)cyclopropyl)-1-(3-(4,4,5,5-tetramethyl-1,3,2-dioxaborolan-2-yl)phenyl)-1H-pyrazole-4-carboxylate (170 mg, 0.214 mmol, 51.1% yield) as white solid. LC-MS m/z 478.2 (M+H)$^+$, 1.80 min (ret. time).

128c) Methyl 1-(3'-(((R)-2-ethyl-2,3-dihydrobenzo[f][1,4]oxazepin-4(5H)-yl)methyl)-[1,1'-biphenyl]-3-yl)-5-((1,2-trans)-2-(1-isopropyl-1H-1,2,3-triazol-4-yl)cyclopropyl)-1H-pyrazole-4-carboxylate

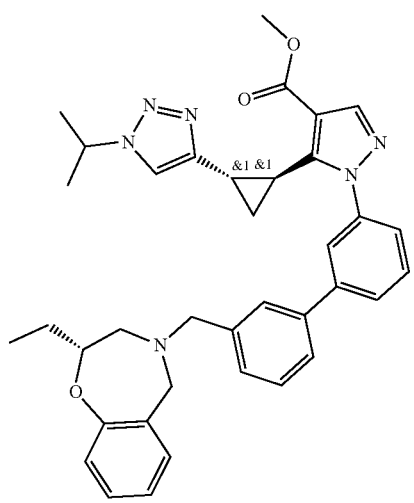 [SMILES: CC[C@@H]1CN(Cc2cccc(-c3cccc(-n4ncc(C(=O)OC)c4[C@H]4C[C@@H]4c4cn(C(C)C)nn4)c3)c2)Cc2ccccc2O1]

11c) A mixture of methyl 5-((1,2-trans)-2-(1-isopropyl-1H-1,2,3-triazol-4-yl)cyclopropyl)-1-(3-(4,4,5,5-tetramethyl-1,3,2-dioxaborolan-2-yl)phenyl)-1H-pyrazole-4-carboxylate (170 mg, 0.356 mmol), (R)-4-(3-bromobenzyl)-2-ethyl-2,3,4,5-tetrahydrobenzo[f][1,4]oxazepine (148 mg, 0.427 mmol), Na$_2$CO$_3$ (0.356 mL, 1.068 mmol) and PdCl$_2$(dppf)-CH$_2$Cl$_2$ adduct (29.1 mg, 0.036 mmol) in toluene (5 mL) and methanol (5.00 mL) under nitrogen was stirred at 110° C. for 2 h. 10 mL of water was added and extracted with ethyl acetate (3×). The combined organic layer was washed with brine, dried over Na$_2$SO$_4$ and concentrated under a stream of nitrogen at 50° C. The crude product was purified on silica gel chromatography (hexane:ethyl acetate=1:1) to obtain the title compound methyl 1-(3'-(((R)-2-ethyl-2,3-dihydrobenzo[f][1,4]oxazepin-4(5H)-yl)methyl)-[1,1'-biphenyl]-3-yl)-5-((1,2-trans)-2-(1-isopropyl-1H-1,2,3-triazol-4-yl)cyclopropyl)-1H-pyrazole-4-carboxylate (65 mg, 0.095 mmol, 26.6% yield). LC-MS m/z 617.3 (M+H)$^+$, 1.91 min (ret. time).

128d) 1-(3'-(((R)-2-Ethyl-2,3-dihydrobenzo[f][1,4]oxazepin-4(5H)-yl)methyl)-[1,1'-biphenyl]-3-yl)-5-((1,2-trans)-2-(1-isopropyl-1H-1,2,3-triazol-4-yl)cyclopropyl)-1H-pyrazole-4-carboxylic Acid

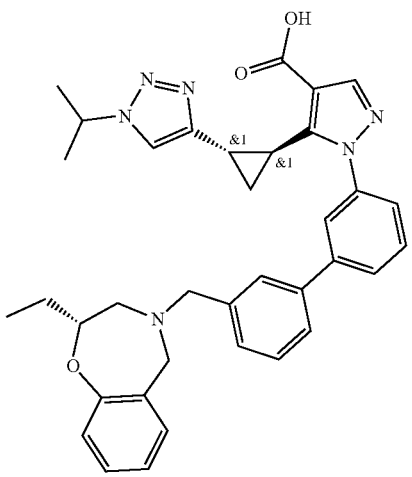 [SMILES: CC[C@@H]1CN(Cc2cccc(-c3cccc(-n4ncc(C(=O)O)c4[C@H]4C[C@@H]4c4cn(C(C)C)nn4)c3)c2)Cc2ccccc2O1]

A mixture of methyl 1-(3'-(((R)-2-ethyl-2,3-dihydrobenzo[f][1,4]oxazepin-4(5H)-yl)methyl)-[1,1'-biphenyl]-3-yl)-5-((1,2-trans)-2-(1-isopropyl-1H-1,2,3-triazol-4-yl)cyclopropyl)-1H-pyrazole-4-carboxylate (65 mg, 0.105 mmol) and LiOH (25.2 mg, 1.054 mmol) in a mixture of water (2 mL) and tetrahydrofuran (THF) (2.000 mL) under nitrogen was stirred at 25° C. for 16 h. After THF was removed, the reaction mixture was adjusted pH to 6 with 1 N HCl. The solid was filtered and purified by prep-HPLC (0.05% TFA/H$_2$O:CH$_3$CN=5%~95%) to obtain the title compound 1-(3'-(((R)-2-ethyl-2,3-dihydrobenzo[f][1,4]oxazepin-4(5H)-yl)methyl)-[1,1'-biphenyl]-3-yl)-5-((1,2-trans)-2-(1-isopropyl-1H-1,2,3-triazol-4-yl)cyclopropyl)-1H-pyrazole-4-carboxylic acid (15 mg, 0.024 mmol, 22.43% yield) as a solid. LC-MS m/z 603.2 (M+H)$^+$, 1.40 min (ret. time).

Example 129. 1-(3'-(((R)-2-ethyl-2,3-dihydrobenzo[f][1,4]oxazepin-4(5H)-yl)methyl)-[1,1'-biphenyl]-3-yl)-5-(2-(1-methyl-1H-1,2,3-triazol-4-yl)cyclopropyl)-1H-pyrazole-4-carboxylic Acid

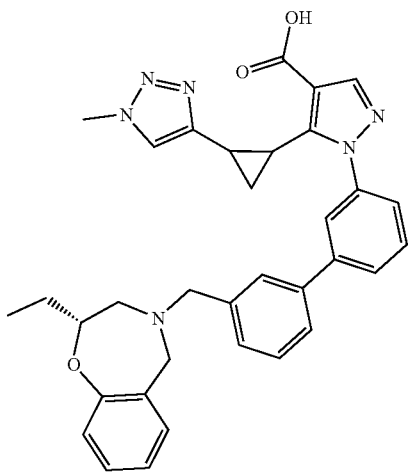 [SMILES: CC[C@@H]1CN(Cc2cccc(-c3cccc(-n4ncc(C(=O)O)c4C4CC4c4cn(C)nn4)c3)c2)Cc2ccccc2O1]

129a) (R)-4-(3-Bromobenzyl)-2-ethyl-2,3,4,5-tetrahydrobenzo[f][1,4]oxazepine

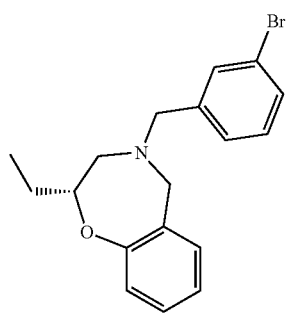 [SMILES: CC[C@@H]1CN(Cc2cccc(Br)c2)Cc2ccccc2O1]

A solution of (R)-2-ethyl-2,3,4,5-tetrahydrobenzo[f][1,4]oxazepine hydrochloride salt (220 mg, 1.029 mmol) in acetonitrile (5 mL) was added 1-bromo-3-(bromomethyl)benzene (257 mg, 1.029 mmol) and DIPEA (0.539 mL, 3.09 mmol) slowly under nitrogen at 25° C. The reaction mixture was stirred at 25° C. for 16 h. 10 mL of water was added and extracted with ethyl acetate (3×). The combined organic layer was concentrated under a stream of nitrogen at 50° C. to obtain the title compound (R)-4-(3-bromobenzyl)-2-ethyl-2,3,4,5-tetrahydrobenzo[f][1,4]oxazepine (382 mg, 0.883 mmol, 86% yield) which was used in next step without further purification. LC-MS m/z 346.0 (M+H)+, 1.91 min (ret. time).

129b) Methyl 1-(3'-(((R)-2-ethyl-2,3-dihydrobenzo[f][1,4]oxazepin-4(5H)-yl)methyl)-[1,1'-biphenyl]-3-yl)-5-(2-(1-methyl-1H-1,2,3-triazol-4-yl)cyclopropyl)-1H-pyrazole-4-carboxylate

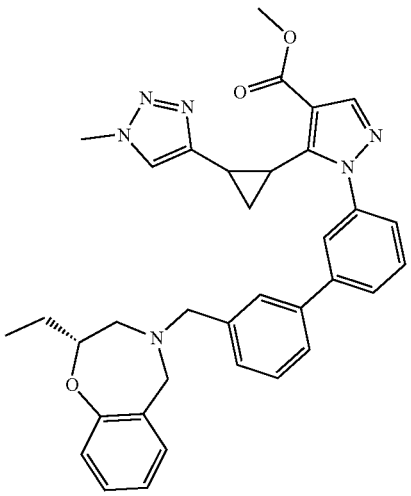 [SMILES: CC[C@@H]1CN(Cc2cccc(-c3cccc(-n4ncc(C(=O)OC)c4C4CC4c4cn(C)nn4)c3)c2)Cc2ccccc2O1]

A mixture of (3-(4-(methoxycarbonyl)-5-(2-(1-methyl-1H-1,2,3-triazol-4-yl)cyclopropyl)-1H-pyrazol-1-yl)phenyl)boronic acid (200 mg, 0.545 mmol), (R)-4-(3-bromobenzyl)-2-ethyl-2,3,4,5-tetrahydrobenzo[f][1,4]oxazepine (386 mg, 0.892 mmol), Na$_2$CO$_3$ (0.545 mL, 1.634 mmol) and PdCl$_2$(dppf)-CH$_2$Cl$_2$ adduct (44.5 mg, 0.054 mmol) in a mixture of toluene (5 mL) and methanol (5.00 mL) under nitrogen was stirred at 110° C. for 2 h. It was adjusted pH to 6 and extracted with ethyl acetate (3×). The combined organic layer was concentrated under a stream of nitrogen at 50° C. to obtain the title compound methyl 1-(3'-(((R)-2-ethyl-2,3-dihydrobenzo[f][1,4]oxazepin-4(5H)-yl)methyl)-[1,1'-biphenyl]-3-yl)-5-(2-(1-methyl-1H-1,2,3-triazol-4-yl)cyclopropyl)-1H-pyrazole-4-carboxylate (110 mg, 0.166 mmol, 30.5% yield) which was used in next step without further purification. LC-MS m/z 589.3 (M+H)+, 1.93 min (ret. time).

129c) 1-(3'-(((R)-2-Ethyl-2,3-dihydrobenzo[f][1,4]oxazepin-4(5H)-yl)methyl)-[1,1'-biphenyl]-3-yl)-5-(2-(1-methyl-1H-1,2,3-triazol-4-yl)cyclopropyl)-1H-pyrazole-4-carboxylic Acid

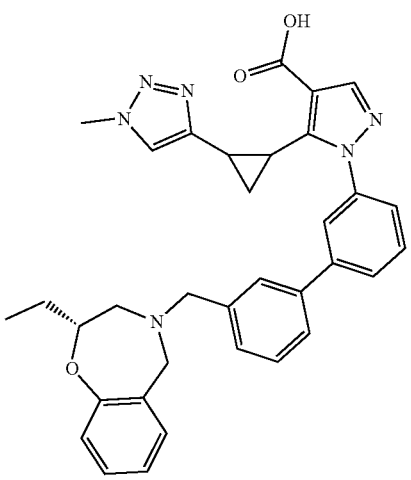 [SMILES: CC[C@@H]1CN(Cc2cccc(-c3cccc(-n4ncc(C(=O)O)c4C4CC4c4cn(C)nn4)c3)c2)Cc2ccccc2O1]

A mixture of methyl 1-(3'-(((R)-2-ethyl-2,3-dihydrobenzo[f][1,4]oxazepin-4(5H)-yl)methyl)-[1,1'-biphenyl]-3-yl)-5-

(2-(1-methyl-1H-1,2,3-triazol-4-yl)cyclopropyl)-1H-pyrazole-4-carboxylate (110 mg, 0.187 mmol) and LiOH (44.7 mg, 1.869 mmol) in a mixture of water (2 mL) and tetrahydrofuran (THF) (2.000 mL) under nitrogen was stirred at 25° C. for 16 h. After THF was removed, the reaction mixture was adjusted pH to 6 with 1 N HCl. The solid was filtered and washed with ethyl acetate and methyl tert-butyl ether. Then it was purified by prep-HPLC (0.05% TFA/H$_2$O: CH$_3$CN=5%~95%) to obtain the title compound 1-(3'-(((R)-2-ethyl-2,3-dihydrobenzo[f][1,4]oxazepin-4(5H)-yl)methyl)-[1,1'-biphenyl]-3-yl)-5-(2-(1-methyl-1H-1,2,3-triazol-4-yl)cyclopropyl)-1H-pyrazole-4-carboxylic acid (50 mg, 0.087 mmol, 46.6% yield) as a solid. LC-MS m/z 575.2 (M+H)$^+$, 1.74 min (ret. time).

Example 130. 1-(3'-(((R)-4-Methyl-1,1-dioxido-4,5-dihydrobenzo[f][1,2]thiazepin-2(3H)-yl)methyl)-[1,1'-biphenyl]-3-yl)-5-((1R,2R)-2-(1-methyl-1H-1,2,3-triazol-4-yl)cyclopropyl)-1H-pyrazole-4-carboxylic Acid

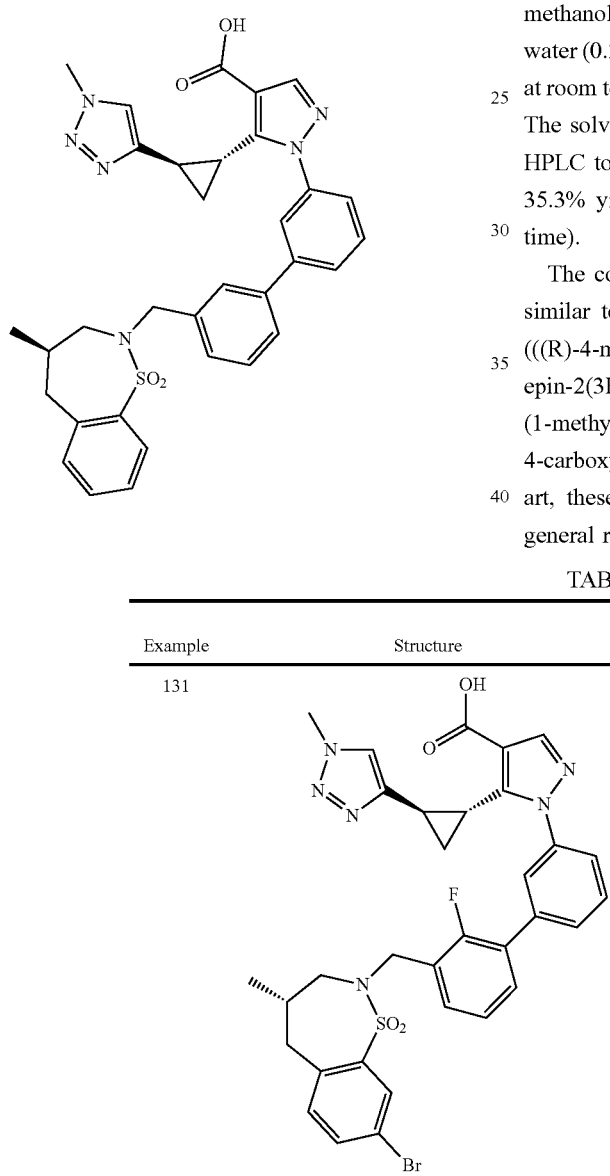

To a solution of methyl 1-(3'-(hydroxymethyl)-[1,1'-biphenyl]-3-yl)-5-((1R,2R)-2-(1-methyl-1H-1,2,3-triazol-4-yl)cyclopropyl)-1H-pyrazole-4-carboxylate (40 mg, 0.093 mmol) in tetrahydrofuran (THF) (10 mL), (R)-4-methyl-2,3,4,5-tetrahydrobenzo[f][1,2]thiazepine 1,1-dioxide (39.4 mg, 0.186 mmol), (E)-diazene-1,2-diylbis(piperidin-1-yl-methanone) (47.0 mg, 0.186 mmol) and tributylphosphine (0.047 mL, 0.186 mmol) were added. The reaction mixture was stirred at room temperature for 18 h. The solvent was evaporated under Biotage V-10 and purified by reverse-phase HPLC under acidic condition to get methyl 1-(3'-(((R)-4-methyl-1,1-dioxido-4,5-dihydrobenzo[f][1,2]thiazepin-2(3H)-yl)methyl)-[1,1'-biphenyl]-3-yl)-5-((1R,2R)-2-(1-methyl-1H-1,2,3-triazol-4-yl)cyclopropyl)-1H-pyrazole-4-carboxylate (48 mg, 0.077 mmol, 83% yield). To it in methanol (2.00 mL), LiOH (2.230 mg, 0.093 mmol) and water (0.2 mL) were added. The reaction mixture was stirred at room temperature for 3 days. 1N HCl was added to pH=1. The solvent was evaporated and purified by reverse-phase HPLC to obtain the title compound (20 mg, 0.033 mmol, 35.3% yield). LC-MS m/z 609.2 (M+H)$^+$, 1.14 min (ret. time).

The compounds in Table 5 were prepared by a method similar to the one described for the preparation of 1-(3'-(((R)-4-methyl-1,1-dioxido-4,5-dihydrobenzo[f][1,2]thiazepin-2(3H)-yl)methyl)-[1,1'-biphenyl]-3-yl)-5-((1R,2R)-2-(1-methyl-1H-1,2,3-triazol-4-yl)cyclopropyl)-1H-pyrazole-4-carboxylic acid. As is appreciated by those skilled in the art, these analogous examples may involve variations in general reaction conditions.

TABLE 5

| Example | Structure | Name | LCMS [M + H]$^+$ | Retention Time (min) |
|---|---|---|---|---|
| 131 | 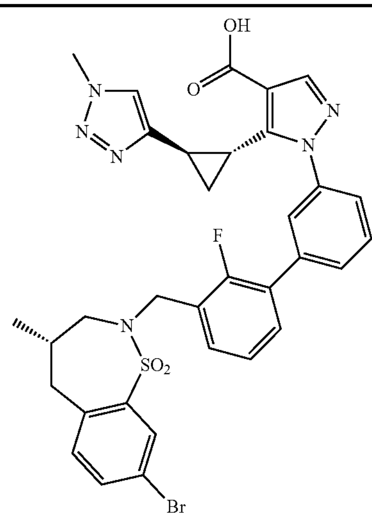 | 1-(3'-(((S)-8-Bromo-4-methyl-1,1-dioxido-4,5-dihydrobenzo[f][1,2]thiazepin-2(3H)-yl)methyl)-2'-fluoro-[1,1'-biphenyl]-3-yl)-5-((1R,2R)-2-(1-methyl-1H-1,2,3-triazol-4-yl)cyclopropyl)-1H-pyrazole-4-carboxylic acid | 705.1/ 707.2 | 1.22 |

TABLE 5-continued

| Example | Structure | Name | LCMS [M + H]⁺ | Retention Time (min) |
|---|---|---|---|---|
| 132 | 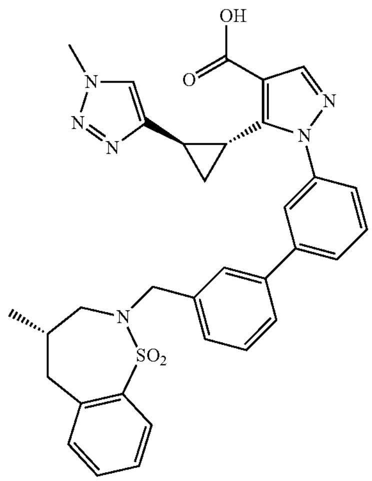 [SMILES: C[C@H]1Cc2ccccc2S(=O)(=O)N(Cc2cccc(-c3cccc(-n4ncc(C(=O)O)c4[C@@H]4C[C@H]4c4cn(C)nn4)c3)c2)C1] | 1-(3'-(((S)-4-methyl-1,1-dioxido-4,5-dihydrobenzo[f][1,2]thiazepin-2(3H)-yl)methyl)-[1,1'-biphenyl]-3-yl)-5-((1R,2R)-2-(1-methyl-1H-1,2,3-triazol-4-yl)cyclopropyl)-1H-pyrazole-4-carboxylic acid | 609.3 | 1.14 |
| 133 | 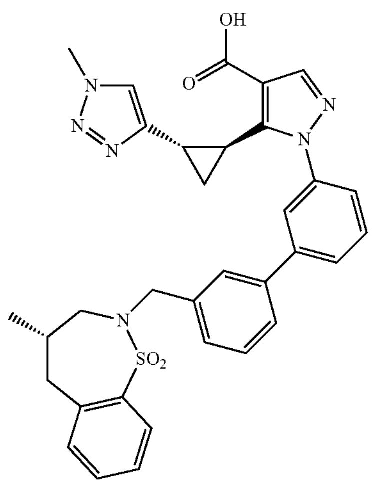 [SMILES: C[C@H]1Cc2ccccc2S(=O)(=O)N(Cc2cccc(-c3cccc(-n4ncc(C(=O)O)c4[C@H]4C[C@@H]4c4cn(C)nn4)c3)c2)C1] | 1-(3'-(((S)-4-methyl-1,1-dioxido-4,5-dihydrobenzo[f][1,2]thiazepin-2(3H)-yl)methyl)-[1,1'-biphenyl]-3-yl)-5-((1S,2S)-2-(1-methyl-1H-1,2,3-triazol-4-yl)cyclopropyl)-1H-pyrazole-4-carboxylic acid | 609.3 | 1.14 |
| 134 | 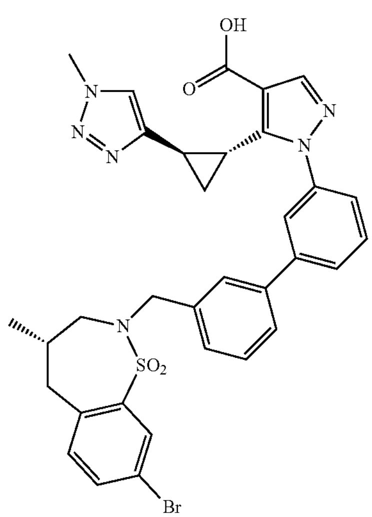 [SMILES: C[C@H]1Cc2ccc(Br)cc2S(=O)(=O)N(Cc2cccc(-c3cccc(-n4ncc(C(=O)O)c4[C@@H]4C[C@H]4c4cn(C)nn4)c3)c2)C1] | 1-(3'-(((S)-8-bromo-4-methyl-1,1-dioxido-4,5-dihydrobenzo[f][1,2]thiazepin-2(3H)-yl)methyl)-[1,1'-biphenyl]-3-yl)-5-((1R,2R)-2-(1-methyl-1H-1,2,3-triazol-4-yl)cyclopropyl)-1H-pyrazole-4-carboxylic acid (isomer 1) | 687.3/ 689.3 | 1.23 |

TABLE 5-continued

| Example | Structure | Name | LCMS [M + H]+ | Retention Time (min) |
|---|---|---|---|---|
| 135 | 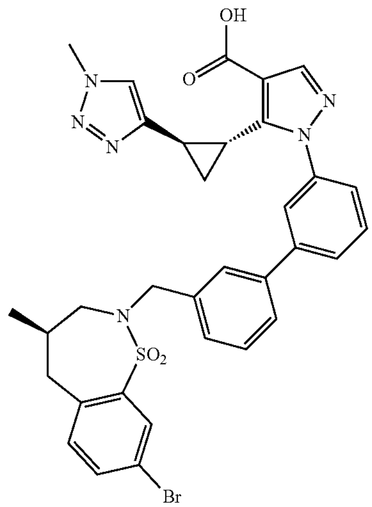 [SMILES: C[C@@H]1Cc2ccc(Br)cc2S(=O)(=O)N(Cc2cccc(-c3cccc(-n4ncc(C(=O)O)c4[C@@H]4C[C@H]4c4cn(C)nn4)c3)c2)C1] | 1-(3'-(((R)-8-bromo-4-methyl-1,1-dioxido-4,5-dihydrobenzo[f][1,2]thiazepin-2(3H)-yl)methyl)-[1,1'-biphenyl]-3-yl)-5-((1R,2R)-2-(1-methyl-1H-1,2,3-triazol-4-yl)cyclopropyl)-1H-pyrazole-4-carboxylic acid (isomer 2) | 687.3/ 689.3 | 1.23 |
| 136 | 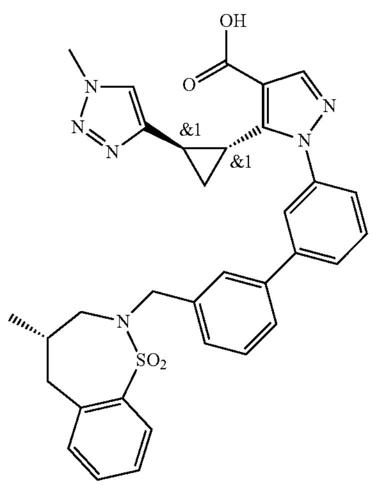 [SMILES: C[C@H]1Cc2ccccc2S(=O)(=O)N(Cc2cccc(-c3cccc(-n4ncc(C(=O)O)c4[C@@H]4C[C@H]4c4cn(C)nn4)c3)c2)C1] | 1-(3'-(((S)-4-methyl-1,1-dioxido-4,5-dihydrobenzo[f][1,2]thiazepin-2(3H)-yl)methyl)-[1,1'-biphenyl]-3-yl)-5-((1,2-trans)-2-(1-methyl-1H-1,2,3-triazol-4-yl)cyclopropyl)-1H-pyrazole-4-carboxylic acid | 609.4 | 1.13 |
| 137 | 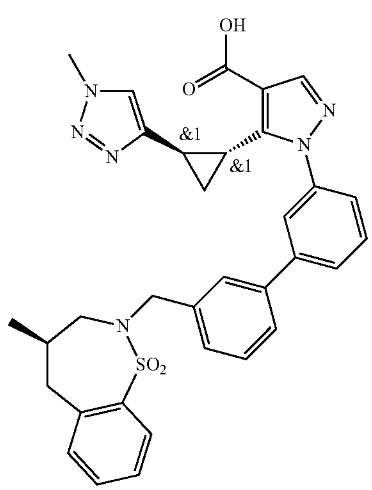 [SMILES: C[C@@H]1Cc2ccccc2S(=O)(=O)N(Cc2cccc(-c3cccc(-n4ncc(C(=O)O)c4[C@@H]4C[C@H]4c4cn(C)nn4)c3)c2)C1] | 1-(3'-(((R)-4-methyl-1,1-dioxido-4,5-dihydrobenzo[f][1,2]thiazepin-2(3H)-yl)methyl)-[1,1'-biphenyl]-3-yl)-5-((1,2-trans)-2-(1-methyl-1H-1,2,3-triazol-4-yl)cyclopropyl)-1H-pyrazole-4-carboxylic acid | 609.3 | 1.13 |

TABLE 5-continued

| Example | Structure | Name | LCMS [M + H]+ | Retention Time (min) |
|---|---|---|---|---|
| 138 | 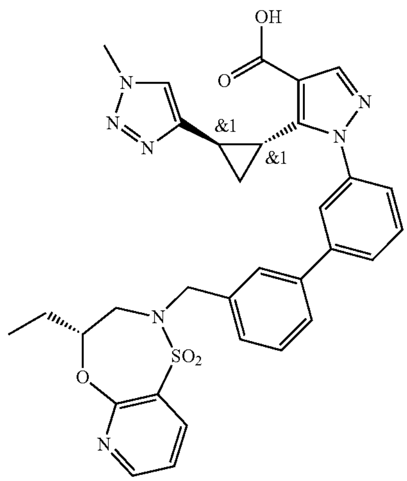 [SMILES: CC[C@@H]1CN(Cc2cccc(-c3cccc(-n4ncc(C(=O)O)c4[C@@H]4C[C@H]4c4cn(C)nn4)c3)c2)S(=O)(=O)c2cccnc2O1] | 1-(3'-(((R)-4-ethyl-1,1-dioxido-3,4-dihydro-2H-pyrido[2,3-b][1,4,5]oxathiazepin-2-yl)methyl)-[1,1'-biphenyl]-3-yl)-5-((1,2-trans)-2-(1-methyl-1H-1,2,3-triazol-4-yl)cyclopropyl)-1H-pyrazole-4-carboxylic acid | 626.5 | 0.97 |
| 139 | 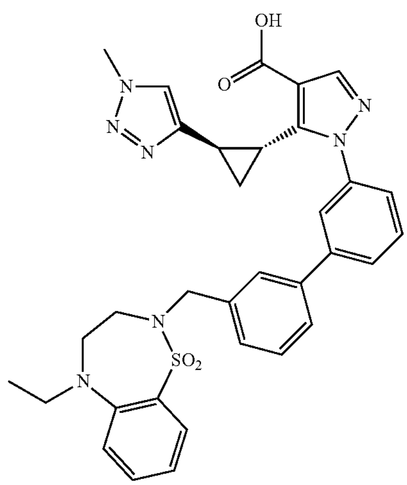 [SMILES: CCN1CCN(Cc2cccc(-c3cccc(-n4ncc(C(=O)O)c4[C@@H]4C[C@H]4c4cn(C)nn4)c3)c2)S(=O)(=O)c2ccccc21] | 1-(3'-((5-Ethyl-1,1-dioxido-4,5-dihydrobenzo[f][1,2,5]thiadiazepin-2(3H)-yl)methyl)-[1,1'-biphenyl]-3-yl)-5-((1R,2R)-2-(1-methyl-1H-1,2,3-triazol-4-yl)cyclopropyl)-1H-pyrazole-4-carboxylic acid | 624.3 | 1.09 |
| 140 | 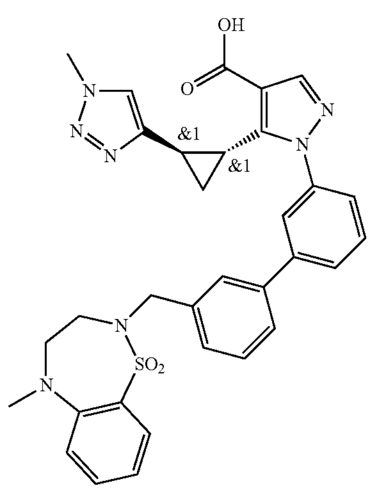 [SMILES: CN1CCN(Cc2cccc(-c3cccc(-n4ncc(C(=O)O)c4[C@@H]4C[C@H]4c4cn(C)nn4)c3)c2)S(=O)(=O)c2ccccc21] | 1-(3'-((5-methyl-1,1-dioxido-4,5-dihydrobenzo[f][1,2,5]thiadiazepin-2(3H)-yl)methyl)-[1,1'-biphenyl]-3-yl)-5-((1,2-trans)-2-(1-methyl-1H-1,2,3-triazol-4-yl)cyclopropyl)-1H-pyrazole-4-carboxylic acid | 610.3 | 1.06 |

131a) Ethyl 3-(dimethylamino)-2-((1,2-trans)-2-(1-methyl-1H-1,2,3-triazol-4-yl)cyclopropanecarbonyl)acrylate

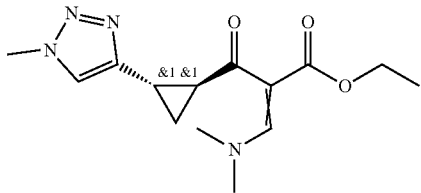 [SMILES: CCOC(=O)C(=CN(C)C)C(=O)[C@H]1C[C@@H]1c1cn(C)nn1]

A mixture of ethyl 3-((1,2-trans)-2-(1-methyl-1H-1,2,3-triazol-4-yl)cyclopropyl)-3-oxopropanoate (15 g, 63.2 mmol) and 1,1-dimethoxy-N,N-dimethylmethanamine (8.29 g, 69.5 mmol) was stirred at 25° C. for 12 h. The reaction mixture was concentrated. The crude product was purified on silica gel chromatography (hexane:ethyl acetate=1:1) to obtain the title compound ethyl 3-(dimethylamino)-2-((1,2-trans)-2-(1-methyl-1H-1,2,3-triazol-4-yl)cyclopropanecarbonyl)acrylate (15.8 g, 40.5 mmol, 64.1% yield) as an oil. LC-MS m/z 293.2 (M+H)$^+$, 1.50 min (ret. time).

131b) Ethyl 3-(dimethylamino)-2-((1R,2R)-2-(1-methyl-1H-1,2,3-triazol-4-yl)cyclopropanecarbonyl)acrylate

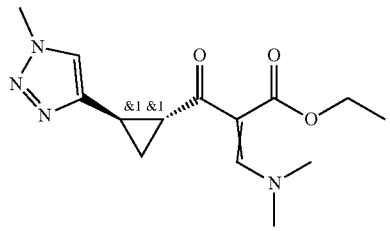 [SMILES: CCOC(=O)C(=CN(C)C)C(=O)[C@@H]1C[C@H]1c1cn(C)nn1]

This was resolved by Chiral SFC (Column: Chiralpak OJ 20×250 mm, 5 u; Co-solvent: 20% Ethanol; Flowrate: 50 g/min; Back pressure: 100 Bar) to give single enantiomerically pure ethyl 3-(dimethylamino)-2-((1R,2R)-2-(1-methyl-1H-1,2,3-triazol-4-yl)cyclopropanecarbonyl)acrylate (5.295 g) (chiral SFC ret. time: 2.52 min) LC-MS m/z 293.0 (M+H)$^+$, 0.55 min (ret. time) and single enantiomerically pure ethyl 3-(dimethylamino)-2-((1S,2S)-2-(1-methyl-1H-1,2,3-triazol-4-yl)cyclopropanecarbonyl)acrylate (5.0 g) (chiral SFC ret. time: 4.05 min).

131c) Ethyl 1-(3-bromophenyl)-5-((1S,2S)-2-(1-methyl-1H-1,2,3-triazol-4-yl)cyclopropyl)-1H-pyrazole-4-carboxylate

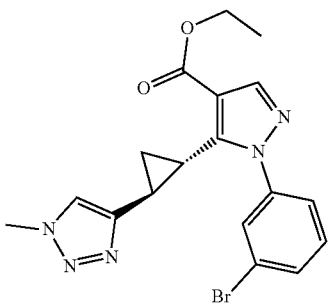 [SMILES: CCOC(=O)c1cnn(-c2cccc(Br)c2)c1[C@H]1C[C@@H]1c1cn(C)nn1]

To a solution of ethyl 3-(dimethylamino)-2-((1R,2R)-2-(1-methyl-1H-1,2,3-triazol-4-yl)cyclopropanecarbonyl)acrylate (1.4 g, 4.79 mmol) in ethanol (20 mL), (3-bromophenyl)hydrazine hydrochloride (1.070 g, 4.79 mmol) and triethylamine (9.58 mmol) were added. The reaction mixture was stirred at room temperature for 4 h. The solid was filtered to obtain the title compound ethyl 1-(3-bromophenyl)-5-((1S,2S)-2-(1-methyl-1H-1,2,3-triazol-4-yl)cyclopropyl)-1H-pyrazole-4-carboxylate (1.2 g, 2.88 mmol, 60.2% yield). LC-MS m/z 430.0/432.0 (M+H)$^+$, 0.98 min (ret. time).

131d) Ethyl 1-(2'-fluoro-3'-(hydroxymethyl)-[1,1'-biphenyl]-3-yl)-5-((1S,2S)-2-(1-methyl-1H-1,2,3-triazol-4-yl)cyclopropyl)-1H-pyrazole-4-carboxylate

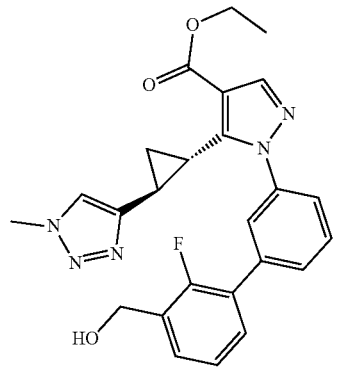 [SMILES: CCOC(=O)c1cnn(-c2cccc(-c3cccc(CO)c3F)c2)c1[C@H]1C[C@@H]1c1cn(C)nn1]

To a solution of ethyl 1-(3-bromophenyl)-5-((1S,2S)-2-(1-methyl-1H-1,2,3-triazol-4-yl)cyclopropyl)-1H-pyrazole-4-carboxylate (600 mg, 1.441 mmol) in 1,4-dioxane (9 mL) and water (3 mL), (2-fluoro-3-(hydroxymethyl)phenyl)boronic acid (490 mg, 2.88 mmol), K$_2$CO$_3$ (598 mg, 4.32 mmol) and PdCl$_2$(dppf) (105 mg, 0.144 mmol) were added. The reaction was heated in a microwave at 120° C. (high absorption) for 40 mins. The solvent was evaporated. The residue was partitioned between ethyl acetate and water. The water layer was extracted with ethyl acetate (2×). The combined organic phase was dried over MgSO$_4$ and concentrated. The crude product was then purified on a silica cartridge (40 g) with a Combiflash Companion, eluting at 20 mL/min with a gradient running from 100% hexanes to 100% Ethyl acetate/hexanes over 35 min to get title compound ethyl 1-(2'-fluoro-3'-(hydroxymethyl)-[1,1'-biphenyl]-3-yl)-5-((1S,2S)-2-(1-methyl-1H-1,2,3-triazol-4-yl)cyclopropyl)-1H-pyrazole-4-carboxylate (450 mg, 0.975 mmol, 67.7% yield). LC-MS m/z 462.2 (M+H)$^+$, 0.95 min (ret. time).

139a) 2-(Ethyl(2-hydroxyethyl)amino)benzenesulfonamide

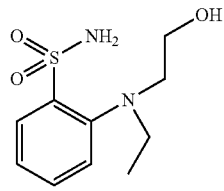 [SMILES: CCN(CCO)c1ccccc1S(N)(=O)=O]

2-Fluorobenzenesulfonamide (1.0 g, 5.71 mmol) in 2-(ethylamino)ethanol (5.09 g, 57.1 mmol) was heated in a microwave at 130° C. (high absorption) for 1 h. The crude product was then purified on a silica cartridge (40 g) with a Combiflash Companion, eluting at 40 mL/min with a gradient running from 100% hexanes to 100% Ethyl acetate/hexanes over 35 min) to obtain the title compound (500 mg, 4.56 mmol, 80% yield). LC-MS m/z 244.9 (M+H)$^+$, 0.57 min (ret. time).

139b) 5-Ethyl-2,3,4,5-tetrahydrobenzo[f][1,2,5]thiadiazepine 1,1-dioxide

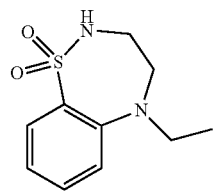

To a solution of 2-((2-hydroxyethyl)(methyl)amino)benzenesulfonamide (500 mg, 2.171 mmol) in tetrahydrofuran (THF) (10 mL), DIAD (0.844 mL, 4.34 mmol) and triphenylphosphine (1139 mg, 4.34 mmol) were added. The reaction mixture was stirred at room temperature for 18 h. The solvent was evaporated and was then purified on a silica cartridge (40 g) with a Combiflash Companion, eluting at 40 mL/min with a gradient running from 100% hexanes to 50% Ethyl acetate/hexanes over 35 min) to provide the title compound (500 mg, 2.21 mmol, 48.5% yield). LC-MS m/z 226.9 (M+H)$^+$, 0.67 min (ret. time).

140a) 2-((2-Hydroxyethyl)(methyl)amino)benzenesulfonamide

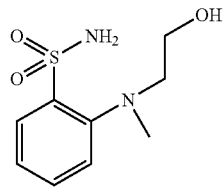

2-Fluorobenzenesulfonamide (1.2 g, 6.85 mmol) in 2-(methylamino)ethanol (5.50 mL, 68.5 mmol) was heated with microwave at 130° C. for 1 h. The crude product was then purified on a silica cartridge (40 g) with a Combiflash Companion, eluting at 40 mL/min with a gradient running from 100% hexanes to 100% Ethyl acetate/hexanes over 35 min) to obtain the title compound (500 mg, 2.17 mmol, 31.7% yield). LC-MS m/z 231.0 (M+H)$^+$, 0.49 min (ret. time).

140b) 5-Methyl-2,3,4,5-tetrahydrobenzo[f][1,2,5]thiadiazepine 1,1-dioxide

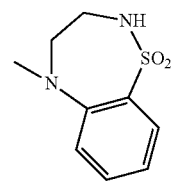

To a solution of 2-((2-hydroxyethyl)(methyl)amino)benzenesulfonamide (500 mg, 2.171 mmol) in tetrahydrofuran (THF) (10 mL), DIAD (0.844 mL, 4.34 mmol) and triphenylphosphine (1139 mg, 4.34 mmol) were added. The reaction mixture was stirred at room temperature for 18 h. The solvent was evaporated and the crude product was then purified on a silica cartridge (30 g) with a Combiflash Companion, eluting at 30 mL/min with a gradient running from 100% hexane to 100% Ethyl acetate/hexanes over 35 min) to obtain the title compound (400 mg, 188 mmol, 87% yield). LC-MS m/z 213.0 (M+H)$^+$, 0.53 min (ret. time).

Example 141. 1-(3'-((2,2-Dimethyl-2,3-dihydrobenzo[f][1,4]oxazepin-4(5H)-yl)sulfonyl)-[1,1'-biphenyl]-3-yl)-5-((1,2-trans)-2-(1-methyl-1H-1,2,3-triazol-4-yl)cyclopropyl)-1H-pyrazole-4-carboxylic Acid

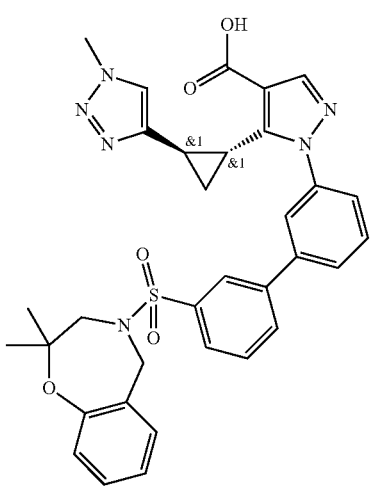 [SMILES: Cn1cc([C@@H]2C[C@H]2c2c(C(=O)O)cnn2-c2cccc(-c3cccc(S(=O)(=O)N4Cc5ccccc5OC(C)(C)C4)c3)c2)nn1]

141a) Methyl 5-((1,2-trans)-2-(1-methyl-1H-1,2,3-triazol-4-yl)cyclopropyl)-1-(3-(4,4,5,5-tetramethyl-1,3,2-dioxaborolan-2-yl)phenyl)-1H-pyrazole-4-carboxylate

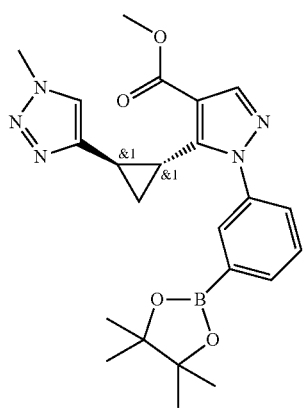 [SMILES: COC(=O)c1cnn(-c2cccc(B3OC(C)(C)C(C)(C)O3)c2)c1[C@@H]1C[C@H]1c1cn(C)nn1]

To a solution of methyl 1-(3-bromophenyl)-5-((1,2-trans)-(2-(1-methyl-1H-1,2,3-triazol-4-yl)cyclopropyl)-1H-pyrazole-4-carboxylate (5.9 g, 14.67 mmol) in 1,4-dioxane (200 mL) was added potassium acetate (2.88 g, 29.3 mmol), bis(pinacolato)diboron (5.59 g, 22.00 mmol). The reaction mixture was degassed with argon for 30 mins, then PdCl$_2$(dppf)-CH$_2$Cl$_2$ adduct (1.198 g, 1.467 mmol) was added. The reaction mixture was stirred at 100° C. for 16 h. The solid was filtered and the filtrate was concentrated under vacuum. The residue was purified on silica gel chromatography (ethyl acetate:hexane=1:2) to afford the product which was then recrystallized from hexane to obtain the title compound methyl 5-(1,2-trans)-(2-(1-methyl-1H-1,2,3-triazol-4-yl)cyclopropyl)-1-(3-(4,4,5,5-tetramethyl-1,3,2-dioxaborolan-2-yl)phenyl)-1H-pyrazole-4-carboxylate (5.6 g, 12.46 mmol, 85% yield) as white solid. LC-MS m/z 450.1 (M+H)$^+$, 1.98 min (ret. time).

141b) (3-(4-(Methoxycarbonyl)-5-((1,2-trans)-2-(1-methyl-1H-1,2,3-triazol-4-yl)cyclopropyl)-1H-pyrazol-1-yl)phenyl)boronic Acid

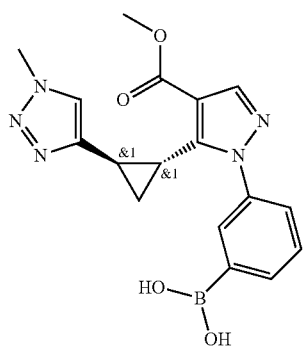 [SMILES: COC(=O)c1cnn(-c2cccc(B(O)O)c2)c1[C@@H]1C[C@H]1c1cn(C)nn1]

A mixture of methyl 5-((1,2-trans)-(2-(1-methyl-1H-1,2,3-triazol-4-yl)cyclopropyl)-1-(3-(4,4,5,5-tetramethyl-1,3,2-dioxaborolan-2-yl)phenyl)-1H-pyrazole-4-carboxylate (5.6 g, 12.46 mmol) in acetone (50 mL), ammonium acetate (37.4 mL, 37.4 mmol) and sodium periodate (8.00 g, 37.4 mmol) in water (25 mL) were added slowly under nitrogen at 25° C. The reaction mixture was stirred at 25° C. for 16 h. Then it was extracted with ethyl acetate (3×). The combined organic layer was concentrated. Then It was washed with hexane and ethyl acetate to obtain the title compound (3-(4-(methoxycarbonyl)-5-(1,2-trans)-(2-(1-methyl-1H-1,2,3-triazol-4-yl)cyclopropyl)-1H-pyrazol-1-yl)phenyl)boronic acid (3.26 g, 8.52 mmol, 68.4% yield) which was used in next step without further purification. LC-MS m/z 368.0 (M+H)$^+$, 1.32 min (ret. time).

141c) (3-(4-(Methoxycarbonyl)-5-((1R,2R)-2-(1-methyl-1H-1,2,3-triazol-4-yl)cyclopropyl)-1H-pyrazol-1-yl)phenyl)boronic acid and (3-(4-(methoxycarbonyl)-5-((1S,2S)-2-(1-methyl-1H-1,2,3-triazol-4-yl)cyclopropyl)-1H-pyrazol-1-yl)phenyl)boronic Acid

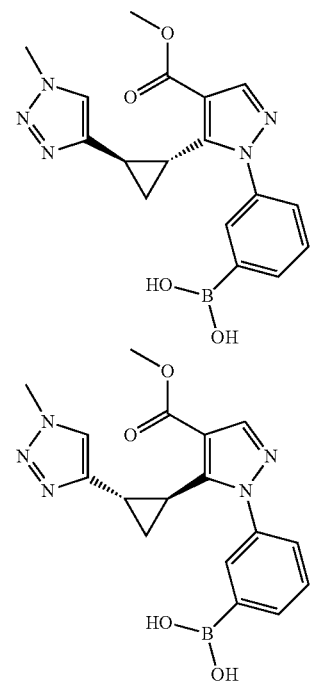

This was resolved by Chiral SFC (Column: Chiralpak AY 20×250 mm, 5 u; Co-solvent: 20% reagent alcohol; Flow-rate: 50 g/min; Back pressure: 100 Bar) to give single enantiomerically pure (3-(4-(methoxycarbonyl)-5-((1R,2R)-2-(1-methyl-1H-1,2,3-triazol-4-yl)cyclopropyl)-1H-pyrazol-1-yl)phenyl)boronic acid (2.93 g) (chiral SFC ret. time: 2.18 min) LC-MS m/z 368.1 (M+H)$^+$, 1.27 min (ret. time) and single enantiomerically pure (3-(4-(methoxycarbonyl)-5-((1S,2S)-2-(1-methyl-1H-1,2,3-triazol-4-yl)cyclopropyl)-1H-pyrazol-1-yl)phenyl)boronic acid (2.6 g) (chiral SFC ret. time: 4.64 min).

141d) 4-((3-Bromophenyl)sulfonyl)-2,2-dimethyl-2,3,4,5-tetrahydrobenzo[f][1,4]oxazepine

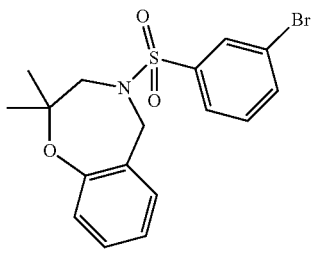 [SMILES: CC1(C)CN(S(=O)(=O)c2cccc(Br)c2)Cc2ccccc2O1]

To a solution of 3-bromobenzene-1-sulfonyl chloride (200 mg, 0.783 mmol) in dichloromethane (DCM) (2 mL), 2,2-dimethyl-2,3,4,5-tetrahydrobenzo[f][1,4]oxazepine (166 mg, 0.939 mmol) was added. The reaction mixture was stirred at room temperature for 1 h. The solvent was evaporated and the crude product was then purified on a silica cartridge (24 g) with a Combiflash Companion, eluting at 30 mL/min with a gradient running from 100% hexanes to 50% Ethyl acetate/hexanes over 35 min) to obtain the title compound (330 mg, 0.833 mmol, 106% yield which had some solvent). LC-MS m/z 396.0/398.0 (M+H)$^+$, 1.26 min (ret. time).

141e) 1-(3'-((2,2-Dimethyl-2,3-dihydrobenzo[f][1,4]oxazepin-4(5H)-yl)sulfonyl)-[1,1'-biphenyl]-3-yl)-5-((1,2-trans)-2-(1-methyl-1H-1,2,3-triazol-4-yl)cyclopropyl)-1H-pyrazole-4-carboxylic Acid

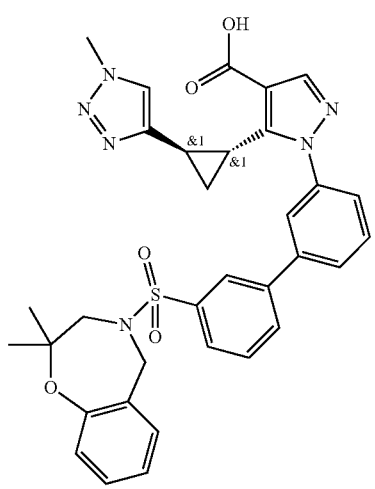 [SMILES: Cn1cc([C@@H]2C[C@H]2c2c(C(=O)O)cnn2-c2cccc(-c3cccc(S(=O)(=O)N4Cc5ccccc5OC(C)(C)C4)c3)c2)nn1]

To a solution of rac-(3-(4-(methoxycarbonyl)-5-((1,2-trans)-2-(1-methyl-1H-1,2,3-triazol-4-yl)cyclopropyl)-1H-pyrazol-1-yl)phenyl)boronic acid (93 mg, 0.252 mmol) in mixture of water (1.00 mL) and methanol (1.000 mL), 4-((3-bromophenyl)sulfonyl)-2,2-dimethyl-2,3,4,5-tetrahydrobenzo[f][1,4]oxazepine (100 mg, 0.252 mmol) and K$_2$CO$_3$ (105 mg, 0.757 mmol) were added, then PdCl$_2$(dppf) (18.46 mg, 0.025 mmol) was added. The reaction was heated in a microwave at 120° C. (high absorption) for 30 mins. The solvent was evaporated and the crude product was then purified on a silica cartridge (12 g) with a Combiflash Companion, eluting at 20 mL/min with a gradient running from 100% hexanes to 50% Ethyl acetate/hexanes over 35 min) to get rac-methyl 1-(3'-((2,2-dimethyl-2,3-dihydrobenzo[f][1,4]oxazepin-4(5H)-yl)sulfonyl)-[1,1'-biphenyl]-3-yl)-5-((1,2-trans)-2-(1-methyl-1H-1,2,3-triazol-4-yl)cyclopropyl)-1H-pyrazole-4-carboxylate (90 mg, 0.141 mmol, 55.8% yield). To it in methanol (1.000 mL), LiOH (60.4 mg, 2.52 mmol) and 0.2 mL of water were added. The reaction mixture was stirred at room temperature for 20 h. 1 N HCl was added to reaction mixture until pH=1. The solvent was evaporated and purified by reverse-phase HPLC to obtain the title compound (47.3 mg, 0.076 mmol, 30.0% yield). LC-MS m/z 635.4 (M+H)$^+$, 1.11 min (ret. time).

Example 142. 5-((1,2-trans)-2-(1-Methyl-1H-1,2,3-triazol-4-yl)cyclopropyl)-1-(3'-((2-propylpiperidin-1-yl)sulfonyl)-[1,1'-biphenyl]-3-yl)-1H-pyrazole-4-carboxylic Acid

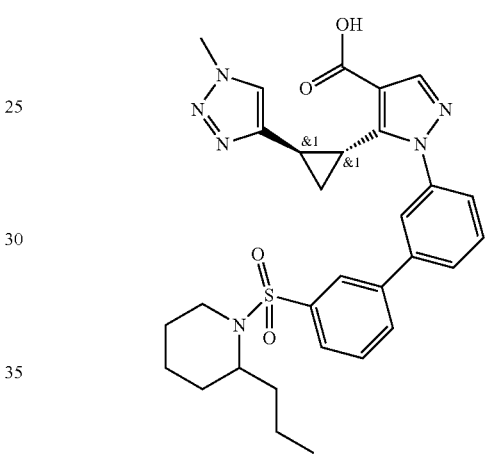

142a) 1-((3-Bromophenyl)sulfonyl)-2-propylpiperidine

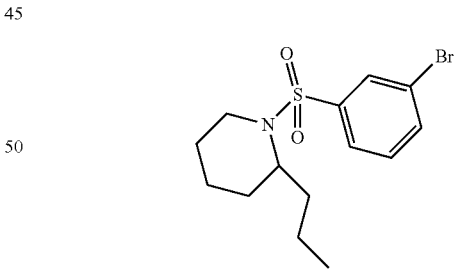

To a solution of 3-bromobenzene-1-sulfonyl chloride (200 mg, 0.783 mmol) in dichloromethane (DCM) (2 mL), 2-propylpiperidine (120 mg, 0.939 mmol) was added, and then the reaction mixture was stirred at room temperature for 90 mins. The solvent was evaporated and the crude product was then purified on a silica cartridge (12 g) with a Combiflash Companion, eluting at 20 mL/min with a gradient running from 100% hexanes to 50% Ethyl acetate/hexanes over 35 min) to obtain the title compound (140 mg, 0.404 mmol, 51.7%). LC-MS m/z 346.0/348.0 (M+H)$^+$, 1.31 min (ret. time).

142b) 5-((1,2-trans)-2-(1-Methyl-1H-1,2,3-triazol-4-yl)cyclopropyl)-1-(3'-((2-propylpiperidin-1-yl)sulfonyl)-[1,1'-biphenyl]-3-yl)-1H-pyrazole-4-carboxylic Acid

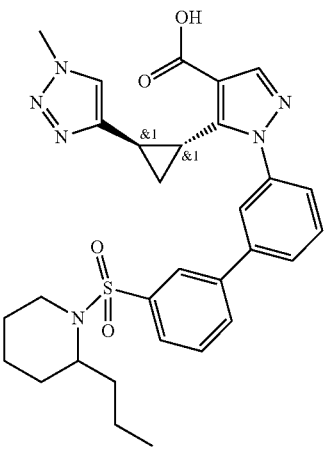 [SMILES: CCCC1CCCCN1S(=O)(=O)c1cccc(-c2cccc(-n3ncc(C(=O)O)c3[C@@H]3C[C@H]3c3cn(C)nn3)c2)c1]

To a solution of 1-((3-bromophenyl)sulfonyl)-2-propylpiperidine (100 mg, 0.289 mmol) in a mixture of 1,4-dioxane (3 mL) and water (1.00 mL), (3-(4-(methoxycarbonyl)-5-((1,2-trans)-2-(1-methyl-1H-1,2,3-triazol-4-yl)cyclopropyl)-1H-pyrazol-1-yl)phenyl)boronic acid (106 mg, 0.289 mmol) and K$_2$CO$_3$ (120 mg, 0.866 mmol) were added, then PdCl$_2$(dppf) (21.13 mg, 0.029 mmol) was added. The reaction was heated in a microwave at 120° C. (high absorption) for 30 min. The solvent was evaporated and the crude product was then purified on a silica cartridge (12 g) with a Combiflash Companion, eluting at 20 mL/min with a gradient running from 100% hexanes to 50% Ethyl acetate/hexanes over 35 min) to get methyl 5-((1,2-trans)-2-(1-methyl-1H-1,2,3-triazol-4-yl)cyclopropyl)-1-(3'-((2-propylpiperidin-1-yl)sulfonyl)-[1,1'-biphenyl]-3-yl)-1H-pyrazole-4-carboxylate (100 mg, 0.17 mmol, 58.8% yield). To it in methanol (2.00 mL), LiOH (69.2 mg, 2.89 mmol) and 0.2 mL of water were added. The reaction mixture was stirred at room temperature for 3 days. 1N HCl was added to reaction mixture until pH=1. The solvent was evaporated and purified by reverse-phase HPLC to obtain the title compound (49.4 mg, 0.086 mmol, 29.8% yield). LC-MS m/z 575.4 (M+H)$^+$, 1.13 min (ret. time).

Example 143. 5-((1,2-trans)-2-(1-Methyl-1H-1,2,3-triazol-4-yl)cyclopropyl)-1-(3'-(piperidin-1-ylsulfonyl)-[1,1'-biphenyl]-3-yl)-1H-pyrazole-4-carboxylic Acid

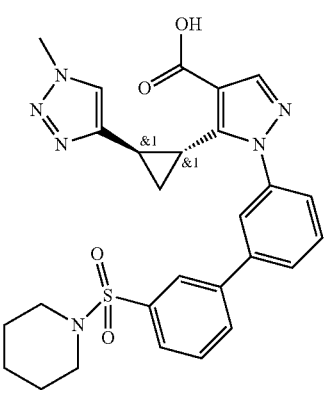 [SMILES: Cn1cc([C@@H]2C[C@H]2c2c(C(=O)O)cnn2-c2cccc(-c3cccc(S(=O)(=O)N4CCCCC4)c3)c2)nn1]

143a) 1-((3-Bromophenyl)sulfonyl)piperidine

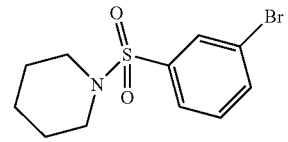 [SMILES: O=S(=O)(c1cccc(Br)c1)N1CCCCC1]

To a solution of 3-bromobenzene-1-sulfonyl chloride (200 mg, 0.783 mmol) in dichloromethane (DCM) (5 mL), piperidine (80 mg, 0.939 mmol) was added. The reaction mixture was stirred at room temperature for 1 h. The solvent was evaporated and the crude product was then purified on a silica cartridge (12 g) with a Combiflash Companion, eluting at 20 mL/min with a gradient running from 100% hexanes to 100% ethyl acetate/hexanes over 35 min) to obtain the title compound (200 mg, 0.657 mmol, 84% yield). LC-MS m/z 303.9/305.9 (M+H)$^+$, 1.1 min (ret. time).

143b) 5-((1,2-trans)-2-(1-Methyl-1H-1,2,3-triazol-4-yl)cyclopropyl)-1-(3'-(piperidin-1-ylsulfonyl)-[1,1'-biphenyl]-3-yl)-1H-pyrazole-4-carboxylic Acid

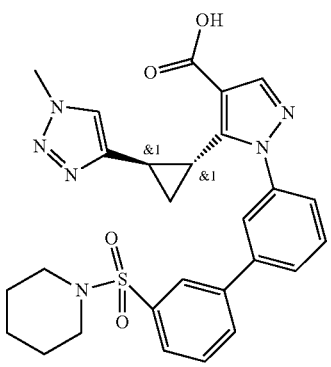 [SMILES: Cn1cc([C@@H]2C[C@H]2c2c(C(=O)O)cnn2-c2cccc(-c3cccc(S(=O)(=O)N4CCCCC4)c3)c2)nn1]

To a solution of 1-((3-bromophenyl)sulfonyl)piperidine (100 mg, 0.329 mmol) in a mixture of 1,4-dioxane (3 mL) and water (1.00 mL), (3-(4-(methoxycarbonyl)-5-((1,2-trans)-2-(1-methyl-1H-1,2,3-triazol-4-yl)cyclopropyl)-1H-pyrazol-1-yl)phenyl)boronic acid (121 mg, 0.329 mmol), K$_2$CO$_3$ (136 mg, 0.986 mmol) and PdCl$_2$(dppf) (24.05 mg, 0.033 mmol) were added. The reaction was heated in a microwave at 120° C. (high absorption) for 40 mins. The solvent was evaporated and the crude product was then purified on a silica cartridge (12 g) with a Combiflash Companion, eluting at 20 mL/min with a gradient running from 100% hexanes to 50% Ethyl acetate/hexanes over 35 min) to obtain rac-methyl 5-((1,2-trans)-2-(1-methyl-1H-1,2,3-triazol-4-yl)cyclopropyl)-1-(3'-(piperidin-1-ylsulfonyl)-[1,1'-biphenyl]-3-yl)-1H-pyrazole-4-carboxylate (90 mg, 0.165 mmol, 50.1% yield). To it in methanol (3.00 mL), LiOH (79 mg, 3.29 mmol) and 0.2 mL of water were added. The reaction mixture was stirred at room temperature for 4 days. 1N HCl was added to pH=1. The solvent was evaporated under Biotage V-10 and purified by reverse-phase HPLC to obtain the title compound (35.8 mg, 0.067 mmol, 20.45% yield). LC-MS m/z 533.0 (M+H)$^+$, 0.98 min (ret. time).

Example 144. 5-((1,2-trans)-2-(1-Methyl-1H-1,2,3-triazol-4-yl)cyclopropyl)-1-(3'-((tetrahydro-2H-thiopyran-3-yl)methoxy)-[1,1'-biphenyl]-3-yl)-1H-pyrazole-4-carboxylic Acid

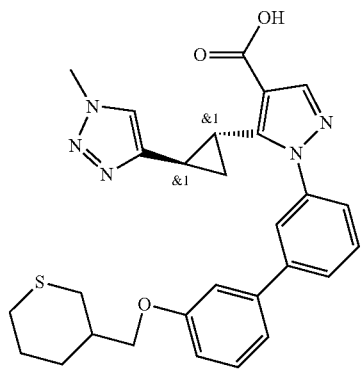 [SMILES: Cn1cc([C@@H]2C[C@H]2c2c(C(=O)O)cnn2-c2cccc(-c3cccc(OCC4CCCSC4)c3)c2)nn1]

144a) Methyl 1-(3'-Hydroxy-[1,1'-biphenyl]-3-yl)-5-((1,2-trans)-2-(1-methyl-1H-1,2,3-triazol-4-yl)cyclopropyl)-1H-pyrazole-4-carboxylate

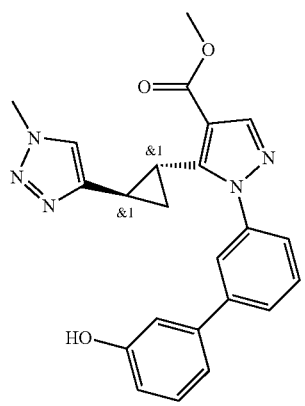 [SMILES: COC(=O)c1cnn(-c2cccc(-c3cccc(O)c3)c2)c1[C@@H]1C[C@H]1c1cn(C)nn1]

To a solution of methyl 1-(3-bromophenyl)-5-((1,2-trans)-(2-(1-methyl-1H-1,2,3-triazol-4-yl)cyclopropyl)-1H-pyrazole-4-carboxylate (1.5 g, 3.73 mmol) in mixture of 1,4-dioxane (12 mL) and water (4 mL), (3-hydroxyphenyl)boronic acid (1.029 g, 7.46 mmol), K$_2$CO$_3$ (1.546 g, 11.19 mmol) and PdCl$_2$(dppf) (0.273 g, 0.373 mmol) were added. The reaction was heated in a microwave at 120° C. (high absorption) for 20 mins. The solvent was evaporated. The residue was partitioned between ethyl acetate and water. The water layer was extracted with ethyl acetate (2×). The combined organic phase was washed with brine, dried over MgSO$_4$ and concentrated. The crude product was then purified on a silica cartridge (40 g) with a Combiflash Companion, eluting at 40 mL/min with a gradient running from 100% hexanes to 100% ethyl acetate/hexanes over 35 min) to obtain the title compound (1.5 g, 3.61 mmol, 97% yield). LC-MS m/z 416.3 (M+H)$^+$, 0.8 min (ret. time).

144b) (Tetrahydro-2H-thiopyran-3-yl)methanol

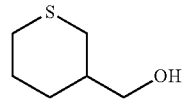

To a solution of tetrahydro-2H-thiopyran-3-carboxylic acid (400 mg, 2.74 mmol) in tetrahydrofuran (THF) (5 mL) at 20° C., LiAlH$_4$ (5.47 mL, 5.47 mmol) was added. The reaction mixture was stirred at 10-20° C. for 2 h. H$_2$O (0.5 mL) and NaOH (0.5 mL) were added to the reaction. The solid was filtered. The liquid was evaporated to obtain the title compound (350 mg, 2.65 mmol, 97% yield). $^1$H NMR (400 MHz, chloroform-d) ⌊ ppm 1.01-2.31 (m, 6H) 2.33-3.04 (m, 4H) 3.35-4.01 (m, 2H).

144c) 5-((1,2-trans)-2-(1-Methyl-1H-1,2,3-triazol-4-yl)cyclopropyl)-1-(3'-((tetrahydro-2H-thiopyran-3-yl)methoxy)-[1,1'-biphenyl]-3-yl)-1H-pyrazole-4-carboxylic Acid

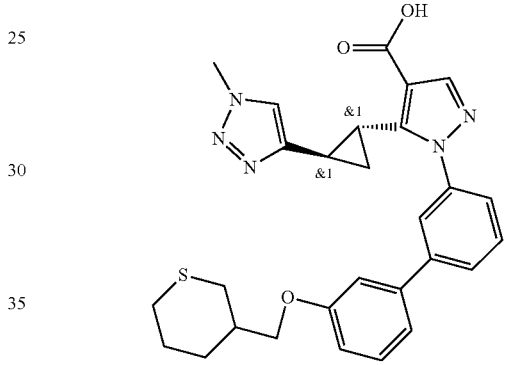

To a solution of methyl 1-(3'-hydroxy-[1,1'-biphenyl]-3-yl)-5-((1,2-trans)-2-(1-methyl-1H-1,2,3-triazol-4-yl)cyclopropyl)-1H-pyrazole-4-carboxylate (300 mg, 0.722 mmol) in tetrahydrofuran (THF) (10 mL), (tetrahydro-2H-thiopyran-3-yl)methanol (191 mg, 1.444 mmol), (E)-diisopropyl diazene-1,2-dicarboxylate (292 mg, 1.444 mmol) and Ph$_3$P (379 mg, 1.444 mmol) were added under nitrogen. The reaction mixture was stirred at room temperature for 18 h. The solvent was evaporated and the crude product was then purified on a silica cartridge (24 g) with a Combiflash Companion, eluting at 30 mL/min with a gradient running from 100% hexanes to 10% ethyl acetate/hexanes over 35 min) to obtain rac-methyl 5-((1,2-trans)-2-(1-methyl-1H-1,2,3-triazol-4-yl)cyclopropyl)-1-(3'-((tetrahydro-2H-thiopyran-3-yl)methoxy)-[1,1'-biphenyl]-3-yl)-1H-pyrazole-4-carboxylate (340 mg, 0.642 mmol, 89% yield). To 100 mg of it in MeOH (1 mL), LiOH (43.7 mg, 1.89 mmol) and 0.1 mL of water were added. The reaction mixture was stirred at room temperature for 3 days. 1N HCl was added until pH=1. The solvent was evaporated and purified by reverse-phase HPLC to obtain the title compound (29.3 mg, 0.057 mmol). LC-MS m/z 516.4 (M+H)$^+$, 1.05 min (ret. time).

The compounds in Table 6 were prepared by a method similar to the one described for the preparation of 5-((1,2-trans)-2-(1-methyl-1H-1,2,3-triazol-4-yl)cyclopropyl)-1-(3'-((tetrahydro-2H-thiopyran-3-yl)methoxy)-[1,1'-biphenyl]-3-yl)-1H-pyrazole-4-carboxylic acid. As is appreciated by those skilled in the art, these analogous examples may involve variations in general reaction conditions.

TABLE 6

| Example | Structure | Name | LCMS [M + H]+ | Retention Time (min) |
|---|---|---|---|---|
| 145 | 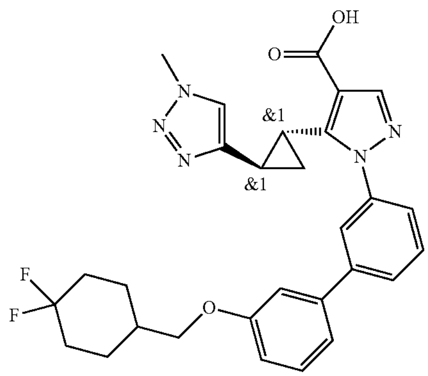 [SMILES: Cn1cc([C@@H]2C[C@H]2c2c(C(=O)O)cnn2-c2cccc(-c3cccc(OCC4CCC(F)(F)CC4)c3)c2)nn1] | 1-(3'-((4,4-Difluorocyclohexyl)methoxy)-[1,1'-biphenyl]-3-yl)-5-((1,2-trans)-2-(1-methyl-1H-1,2,3-triazol-4-yl)cyclopropyl)-1H-pyrazole-4-carboxylic acid | 534.1 | 1.08 |
| 146 | 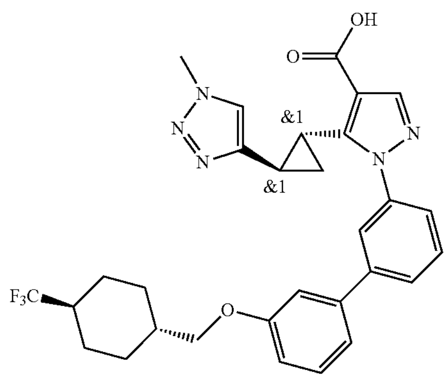 [SMILES: Cn1cc([C@@H]2C[C@H]2c2c(C(=O)O)cnn2-c2cccc(-c3cccc(OC[C@H]4CC[C@H](C(F)(F)F)CC4)c3)c2)nn1] | 5-((1,2-trans)-2-(1-Methyl-1H-1,2,3-triazol-4-yl)cyclopropyl)-1-(3'-(((1r,4R)-4-(trifluoromethyl)cyclohexyl)methoxy)-[1,1'-biphenyl]-3-yl)-1H-pyrazole-4-carboxylic acid | 566.5 | 1.02 |
| 147 | 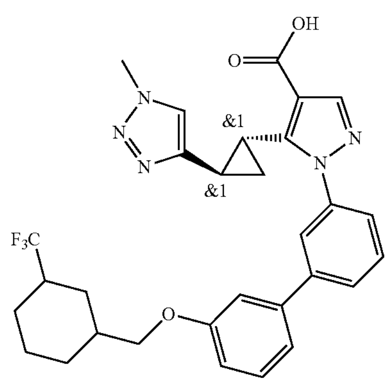 [SMILES: Cn1cc([C@@H]2C[C@H]2c2c(C(=O)O)cnn2-c2cccc(-c3cccc(OCC4CCCC(C(F)(F)F)C4)c3)c2)nn1] | 5-((1,2-trans)-2-(1-Methyl-1H-1,2,3-triazol-4-yl)cyclopropyl)-1-(3'-((3-(trifluoromethyl)cyclohexyl)methoxy)-[1,1'-biphenyl]-3-yl)-1H-pyrazole-4-carboxylic acid | 566.4 | 1.21 |
| 148 | 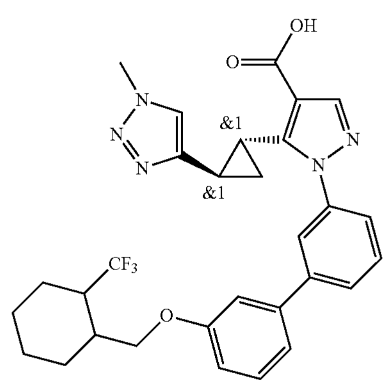 [SMILES: Cn1cc([C@@H]2C[C@H]2c2c(C(=O)O)cnn2-c2cccc(-c3cccc(OCC4CCCCC4C(F)(F)F)c3)c2)nn1] | 5-((1,2-trans)-2-(1-Methyl-1H-1,2,3-triazol-4-yl)cyclopropyl)-1-(3'-((2-(trifluoromethyl)cyclohexyl)methoxy)-[1,1'-biphenyl]-3-yl)-1H-pyrazole-4-carboxylic acid | 566.5 | 1.17 & 1.2 |

TABLE 6-continued

| Example | Structure | Name | LCMS [M + H]+ | Retention Time (min) |
|---|---|---|---|---|
| 149 | 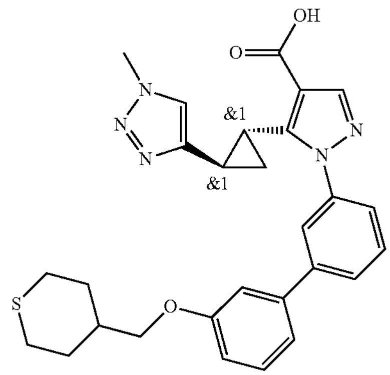 [SMILES: Cn1cc([C@@H]2C[C@H]2c2c(C(=O)O)cnn2-c2cccc(-c3cccc(OCC4CCSCC4)c3)c2)nn1] | 5-((1,2-trans)-2-(1-Methyl-1H-1,2,3-triazol-4-yl)cyclopropyl)-1-(3'-((tetrahydro-2H-thiopyran-4-yl)methoxy)-[1,1'-biphenyl]-3-yl)-1H-pyrazole-4-carboxylic acid | 516.5 | 1.02 |
| 150 | 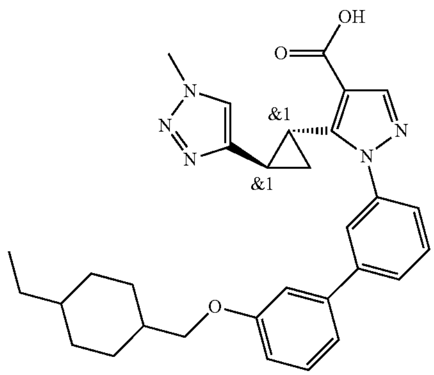 [SMILES: CCC1CCC(COc2cccc(-c3cccc(-n4ncc(C(=O)O)c4[C@@H]4C[C@H]4c4cn(C)nn4)c3)c2)CC1] | 1-(3'-((4-Ethylcyclohexyl)methoxy)-[1,1'-biphenyl]-3-yl)-5-((1,2-trans)-2-(1-methyl-1H-1,2,3-triazol-4-yl)cyclopropyl)-1H-pyrazole-4-carboxylic acid | 526.5 | 1.37 |
| 151 | 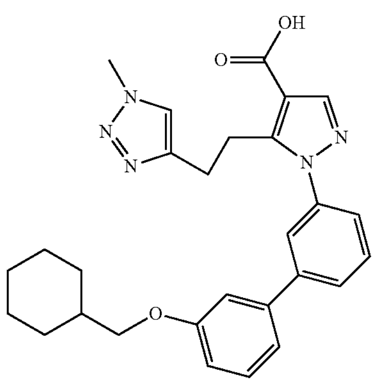 [SMILES: Cn1cc(CCc2c(C(=O)O)cnn2-c2cccc(-c3cccc(OCC4CCCCC4)c3)c2)nn1] | 1-(3-(Cyclohexylmethoxy)-[1,1'-biphenyl]-3-yl)-5-(2-(1-methyl-1H-1,2,3-triazol-4-yl)ethyl)-1H-pyrazole-4-carboxylic acid | 486.4 | 1.22 |

The compounds in Table 7 were prepared by a method similar to the one described for the preparation of (tetrahydro-2H-thiopyran-3-yl)methanol). As is appreciated by those skilled in the art, these analogous examples may involve variations in general reaction conditions.

TABLE 7

| Example | Structure | Name | $^1$H NMR |
|---|---|---|---|
| 145a | 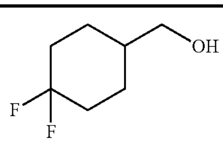 | (4,4-Difluorocyclohexyl)methanol | $^1$H NMR (400 MHz, chloroform-d) [ppm 0.92-2.51 (m, 10H) 3.21-4.18 (m, 2H) |

TABLE 7-continued

| Example | Structure | Name | ¹H NMR |
|---|---|---|---|
| 146a | F₃C-cyclohexyl-CH₂OH | ((1r,4r)-4-(Trifluoromethyl)cyclohexyl)methanol | ¹H NMR (400 MHz, chloroform-d) [ppm 0.80-2.47 (m, 11H) 3.43-4.48 (m, 2H) |
| 147a | 3-CF₃-cyclohexyl-CH₂OH | (3-(Trifluoromethyl)cyclohexyl)methanol | ¹H NMR (400 MHz, chloroform-d) [ppm 0.71-2.54 (m, 11H) 3.43-3.99 (m, 2H) |
| 148a | 2-CF₃-cyclohexyl-CH₂OH | (2-(Trifluoromethyl)cyclohexyl)methanol | ¹H NMR (400 MHz, chloroform-d) [ppm 1.06-2.56 (m, 11H) 3.48-4.04 (m, 2H) |
| 149a | S-tetrahydrothiopyran-CH₂OH | (Tetrahydro-2H-thiopyran-4-yl)methanol | ¹H NMR (400 MHz, chloroform-d) [ppm 1.32-1.64 (m, 4H) 1.99-2.17 (m, 2H) 2.56-2.82 (m, 4H) 3.48 (d, J = 6.02 Hz, 2H) |

151a) Methyl 1-(3'-hydroxy-[1,1'-biphenyl]-3-yl)-5-(2-(1-methyl-1H-1,2,3-triazol-4-yl)ethyl)-1H-pyrazole-4-carboxylate

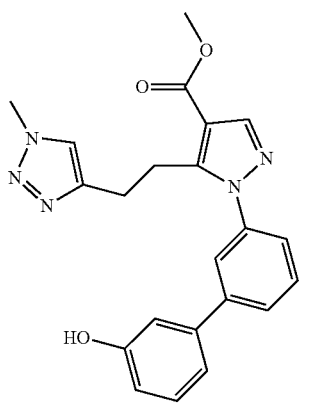 [SMILES: COC(=O)c1cnn(-c2cccc(-c3cccc(O)c3)c2)c1CCc1cn(C)nn1]

To a solution of methyl 1-(3-bromophenyl)-5-(2-(1-methyl-1H-1,2,3-triazol-4-yl)ethyl)-1H-pyrazole-4-carboxylate (150 mg, 0.384 mmol) in 1,4-dioxane (6 mL) and water (2.00 mL), (3-hydroxyphenyl)boronic acid (63.6 mg, 0.461 mmol), PdCl₂(dppf) (28.1 mg, 0.038 mmol) and K₂CO₃ (159 mg, 1.153 mmol) were added. The reaction mixture was stirred at 100° C. for 50 mins. The solvent was evaporated and the crude product was then purified on a silica cartridge (12 g) with a Combiflash Companion, eluting at 20 mL/min with a gradient running from 100% hexanes to 100% ethyl acetate/hexanes over 35 min) to obtain the title compound (203 mg, 0.503 mmol) LC-MS m/z 404.2 (M+H)⁺, 0.83 min (ret. time).

Example 152. 1-(3'-(Cyclohexylmethoxy)-2'-fluoro-[1,1'-biphenyl]-3-yl)-5-((1,2-trans)-2-(1-methyl-1H-1,2,3-triazol-4-yl)cyclopropyl)-1H-pyrazole-4-carboxylic Acid

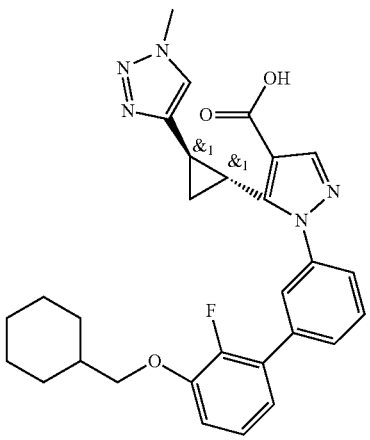 [SMILES: Cn1cc([C@@H]2C[C@H]2c2c(C(=O)O)cnn2-c2cccc(-c3cccc(OCC4CCCCC4)c3F)c2)nn1]

152a)
1-Bromo-3-(cyclohexylmethoxy)-2-fluorobenzene

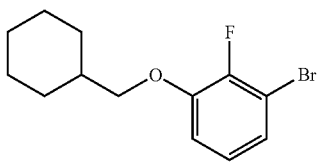

To a solution of 3-bromo-2-fluorophenol (200 mg, 1.047 mmol) in tetrahydrofuran (THF) (10 mL) at room temperature, cyclohexylmethanol (239 mg, 2.094 mmol), DIAD (0.407 mL, 2.094 mmol) and Ph$_3$P (549 mg, 2.094 mmol) were added. The reaction mixture was stirred at room temperature for 16 h. The solvent was evaporated and the crude product was then purified on a silica cartridge (24 g) with a Combiflash Companion, eluting at 30 mL/min with a gradient running from 100% hexanes to 100% ethyl acetate/hexanes over 35 min) to obtain the title compound (250 mg, 0.871 mmol, 83% yield). LC-MS m/z 286.9/288.8 (M+H)$^+$, 1.44 min (ret. time).

152b) 1-(3'-(Cyclohexylmethoxy)-2'-fluoro-[1,1'-biphenyl]-3-yl)-5-((1,2-trans)-2-(1-methyl-1H-1,2,3-triazol-4-yl)cyclopropyl)-1H-pyrazole-4-carboxylic Acid

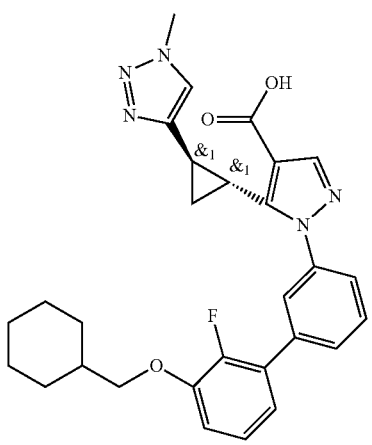 [SMILES: Cn1cc([C@@H]2C[C@H]2c2c(C(=O)O)cnn2-c2cccc(-c3cccc(OCC4CCCCC4)c3F)c2)nn1]

To a solution of 1-bromo-3-(cyclohexylmethoxy)-2-fluorobenzene (125 mg, 0.435 mmol) in a mixture of 1,4-dioxane (3 mL) and water (1 ml), (3-(4-(ethoxycarbonyl)-5-((1,2-trans)-(2-(1-methyl-1H-1,2,3-triazol-4-yl)cyclopropyl)-1H-pyrazol-1-yl)phenyl)boronic acid (249 mg, 0.653 mmol), K$_2$CO$_3$ (241 mg, 1.741 mmol) and PdCl$_2$(dppf) (31.9 mg, 0.044 mmol) were added. The reaction was heated in a microwave at 120° C. (high absorption) for 20 mins. The solvent was evaporated. The crude product was purified on silica gel chromatography (hexane/ethyl acetate) to obtain the ethyl 1-(3'-(cyclohexylmethoxy)-2'-fluoro-[1,1'-biphenyl]-3-yl)-5-(1,2-trans)-(2-(1-methyl-1H-1,2,3-triazol-4-yl)cyclopropyl)-1H-pyrazole-4-carboxylate (200 mg, 0.368 mmol, 85% yield). To it in methanol (2.000 ml), LiOH (104 mg, 4.35 mmol) and 0.1 mL of water were added. The reaction mixture was stirred at room temperature for 40 h. 1N HCl was added to pH=1 and extracted with ethyl acetate (3×). The combined organic phase was dried over MgSO$_4$ and concentrated. The crude product was purified by reverse-phase HPLC to obtain the title compound (110 mg, 0.213 mmol, 49.0% yield). LC-MS m/z 516.5 (M+H)$^+$, 1.2 min (ret. time).

Example 153. 5-Cyclopropyl-1-(3'-(4-(1-methyl-1H-1,2,3-triazol-4-yl)butoxy)-[1,1'-biphenyl]-3-yl)-1H-pyrazole-4-carboxylic Acid

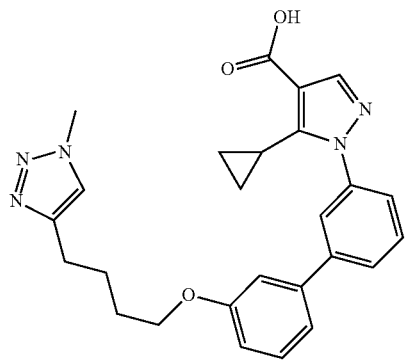 [SMILES: Cn1cc(CCCCOc2cccc(-c3cccc(-n4ncc(C(=O)O)c4C4CC4)c3)c2)nn1]

153a) Ethyl 5-cyclopropyl-1-(3'-(hex-5-yn-1-yloxy)-[1,1'-biphenyl]-3-yl)-1H-pyrazole-4-carboxylate

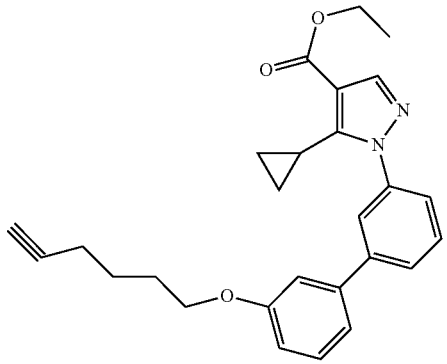 [SMILES: C#CCCCCOc1cccc(-c2cccc(-n3ncc(C(=O)OCC)c3C3CC3)c2)c1]

To a solution of ethyl 5-cyclopropyl-1-(3'-hydroxy-[1,1'-biphenyl]-3-yl)-1H-pyrazole-4-carboxylate (200 mg, 0.574 mmol) in tetrahydrofuran (THF) (10 mL), hex-5-yn-1-ol (113 mg, 1.148 mmol) and DIAD (0.223 mL, 1.148 mmol) were added. Then Ph$_3$P (301 mg, 1.148 mmol) was added. The reaction mixture was stirred at room temperature for 16 h under nitrogen. The solvent was evaporated and purified by reverse-phase HPLC to obtain the title compound (230 mg, 0.537 mmol, 93% yield). LC-MS m/z 429.2 (M+H)$^+$, 1.38 min (ret. time).

153b) 5-Cyclopropyl-1-(3'-(4-(1-methyl-1H-1,2,3-triazol-4-yl)butoxy)-[1,1'-biphenyl]-3-yl)-1H-pyrazole-4-carboxylic Acid

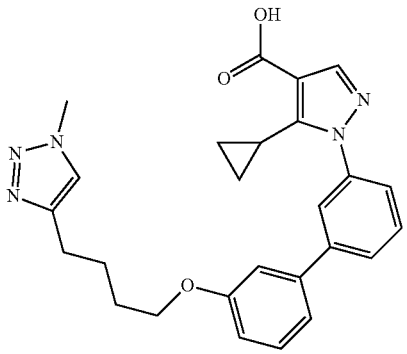 [SMILES: Cn1cc(CCCCOc2cccc(-c3cccc(-n4ncc(C(=O)O)c4C4CC4)c3)c2)nn1]

A mixture of ethyl 5-cyclopropyl-1-(3'-(hex-5-yn-1-yloxy)-[1,1'-biphenyl]-3-yl)-1H-pyrazole-4-carboxylate (230 mg, 0.537 mmol), sodium azide (105 mg, 1.610 mmol) and copper(I) iodide (10.22 mg, 0.054 mmol) in a mixture of water (3.00 mL) and tetrahydrofuran (THF) (5.00 mL). The reaction mixture was stirred at 70° C. for 17 h. The solvent was evaporated and purified by reverse-phase HPLC to obtain the ethyl 5-cyclopropyl-1-(3'-(4-(1-methyl-1H-1,2,3-triazol-4-yl)butoxy)-[1,1'-biphenyl]-3-yl)-1H-pyrazole-4-carboxylate (33 mg, 0.068 mmol, 12.66% yield). To it in methanol (2.00 mL), LiOH (64.3 mg, 2.68 mmol) and 0.1 mL of water was added. The reaction mixture was stirred at room temperature for 2 days. 1N HCl was added until pH=1. The solvent was evaporated and purified by reverse-phase HPLC to obtain the title compound (17.2 mg, 0.038 mmol, 7.0% yield). LC-MS m/z 458.5 (M+H)$^+$, 0.95 min (ret. time).

Example 154. 5-(2-(1-Methyl-1H-1,2,3-triazol-4-yl)cyclopropyl)-1-(5-methyl-3'-((R)-2-propylpiperidine-1-carbonyl)-[1,1'-biphenyl]-3-yl)-1H-pyrazole-4-carboxylic Acid

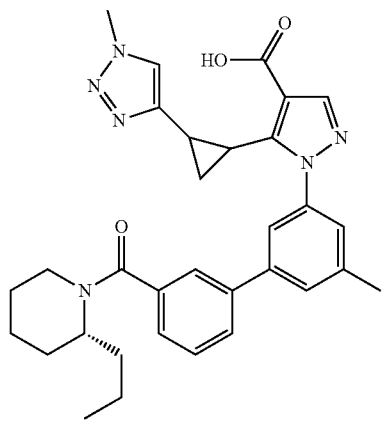 [SMILES: CCC[C@@H]1CCCCN1C(=O)c1cccc(-c2cc(C)cc(-n3ncc(C(=O)O)c3C3CC3c3cn(C)nn3)c2)c1]

154a) Methyl 1-(3-bromo-5-methylphenyl)-5-(2-(1-methyl-1H-1,2,3-triazol-4-yl)cyclopropyl)-1H-pyrazole-4-carboxylate

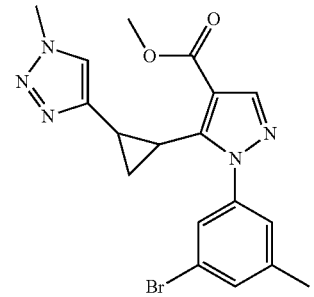 [SMILES: COC(=O)c1cnn(-c2cc(C)cc(Br)c2)c1C1CC1c1cn(C)nn1]

To a solution of methyl 3-(dimethylamino)-2-(2-(1-methyl-1H-1,2,3-triazol-4-yl)cyclopropanecarbonyl)acrylate (235 mg, 0.846 mmol in acetonitrile (5 mL), (3-bromo-5-methylphenyl)hydrazine (170 mg, 0.846 mmol) and DIPEA (0.295 mL, 1.691 mmol) was added. The reaction mixture was stirred at 15° C. for 16 h. The solvent was removed and the residue was purified by reverse-phase TLC (petroleum ether:ethyl acetate=2:1) to obtain the title compound methyl 1-(3-bromo-5-methylphenyl)-5-(2-(1-methyl-1H-1,2,3-triazol-4-yl)cyclopropyl)-1H-pyrazole-4-carboxylate (160 mg, 0.373 mmol, 44.1% yield) as a yellow solid. LC-MS m/z 416.0 (M+H)$^+$, 1.86 min (ret. time).

154b) Methyl 1-(3'-(tert-butoxycarbonyl)-5-methyl-[1,1'-biphenyl]-3-yl)-5-(2-(1-methyl-1H-1,2,3-triazol-4-yl)cyclopropyl)-1H-pyrazole-4-carboxylate

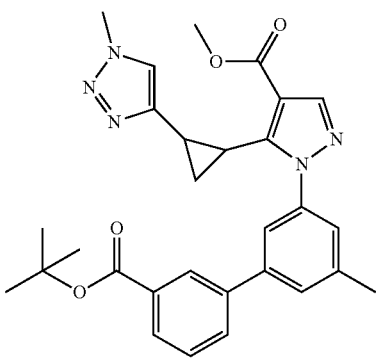 [SMILES: COC(=O)c1cnn(-c2cc(C)cc(-c3cccc(C(=O)OC(C)(C)C)c3)c2)c1C1CC1c1cn(C)nn1]

To a solution of methyl 1-(3-bromo-5-methylphenyl)-5-(2-(1-methyl-1H-1,2,3-triazol-4-yl)cyclopropyl)-1H-pyrazole-4-carboxylate (160 mg, 0.384 mmol) in 1,4-dioxane (2 ml) and water (0.500 ml), K$_2$CO$_3$ (106 mg, 0.769 mmol) and (3-(tert-butoxycarbonyl)phenyl)boronic acid (94 mg, 0.423 mmol) were added. Then PdCl$_2$(dppf)-CH$_2$Cl$_2$ adduct (31.4 mg, 0.038 mmol) was added under N$_2$ and the reaction mixture was stirred at 90° C. for 6 h. The solvent was removed and the residue was purified by prep-TLC (petroleum ether:ethyl acetate=2:1) to give the title compound methyl 1-(3'-(tert-butoxycarbonyl)-5-methyl-[1,1'-biphenyl]-3-yl)-5-(2-(1-methyl-1H-1,2,3-triazol-4-yl)cyclopropyl)-1H-pyrazole-4-carboxylate (165 mg, 0.296 mmol, 77% yield) as a yellow solid. LC-MS m/z 514.2 (M+H)$^+$, 2.10 min (ret. time).

154c) 3'-(4-(Methoxycarbonyl)-5-(2-(1-methyl-1H-1,2,3-triazol-4-yl)cyclopropyl)-1H-pyrazol-1-yl)-5'-methyl-[1,1'-biphenyl]-3-carboxylic Acid

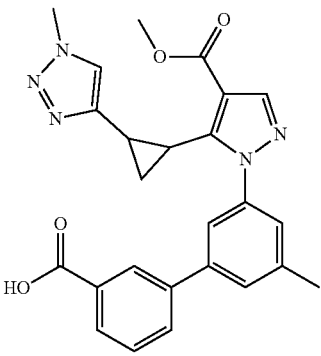 [SMILES: COC(=O)c1cnn(-c2cc(C)cc(-c3cccc(C(=O)O)c3)c2)c1C1CC1c1cn(C)nn1]

To a solution of methyl 1-(3'-(tert-butoxycarbonyl)-5-methyl-[1,1'-biphenyl]-3-yl)-5-(2-(1-methyl-1H-1,2,3-triazol-4-yl)cyclopropyl)-1H-pyrazole-4-carboxylate (165 mg, 0.321 mmol) in dichloromethane (DCM) (3 mL) was added TFA (0.248 mL, 3.21 mmol). The reaction mixture was stirred at 30° C. for 16 h. The solvent was removed to obtain the title compound 3'-(4-(methoxycarbonyl)-5-(2-(1-methyl-1H-1,2,3-triazol-4-yl)cyclopropyl)-1H-pyrazol-1-yl)-5'-methyl-[1,1'-biphenyl]-3-carboxylic acid (150 mg, 0.311 mmol, 97% yield) as a brown oil which was used for next step without further purification. LC-MS m/z 458.1 (M+H)$^+$, 1.54 min (ret. time).

154d) Methyl 5-(2-(1-methyl-1H-1,2,3-triazol-4-yl)cyclopropyl)-1-(5-methyl-3'-((R)-2-propylpiperidine-1-carbonyl)-[1,1'-biphenyl]-3-yl)-1H-pyrazole-4-carboxylate

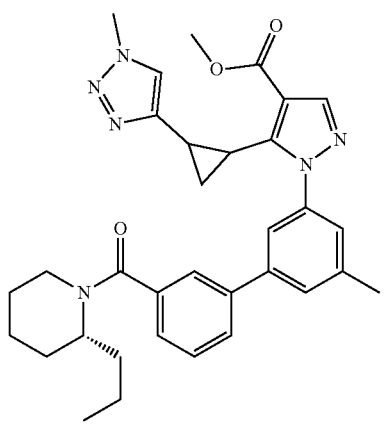 [SMILES: CCC[C@@H]1CCCCN1C(=O)c1cccc(-c2cc(C)cc(-n3ncc(C(=O)OC)c3C3CC3c3cn(C)nn3)c2)c1]

To a solution of 3'-(4-(methoxycarbonyl)-5-(2-(1-methyl-1H-1,2,3-triazol-4-yl)cyclopropyl)-1H-pyrazol-1-yl)-5'-methyl-[1,1'-biphenyl]-3-carboxylic acid (150 mg, 0.328 mmol) in dichloromethane (DCM) (10 mL), HATU (150 mg, 0.393 mmol), (R)-2-propylpiperidine (41.7 mg, 0.328 mmol) and DIPEA (0.172 mL, 0.984 mmol) were added. The reaction mixture was stirred at 25° C. for 16 h. The solvent was removed and the residue was purified by prep-TLC (ethyl acetate=100%) to give the title compound methyl 5-(2-(1-methyl-1H-1,2,3-triazol-4-yl)cyclopropyl)-1-(5-methyl-3'-((R)-2-propylpiperidine-1-carbonyl)-[1,1'-biphenyl]-3-yl)-1H-pyrazole-4-carboxylate (80 mg, 0.141 mmol, 43.1% yield) as a yellow oil. LC-MS m/z 567.3 (M+H)$^+$, 1.80 min (ret. time).

154e) 5-(2-(1-Methyl-1H-1,2,3-triazol-4-yl)cyclopropyl)-1-(5-methyl-3'-((R)-2-propylpiperidine-1-carbonyl)-[1,1'-biphenyl]-3-yl)-1H-pyrazole-4-carboxylic Acid

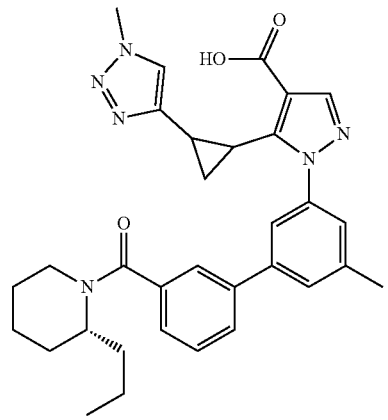 [SMILES: CCC[C@@H]1CCCCN1C(=O)c1cccc(-c2cc(C)cc(-n3ncc(C(=O)O)c3C3CC3c3cn(C)nn3)c2)c1]

To a solution of methyl 5-(2-(1-methyl-1H-1,2,3-triazol-4-yl)cyclopropyl)-1-(5-methyl-3'-((R)-2-propylpiperidine-1-carbonyl)-[1,1'-biphenyl]-3-yl)-1H-pyrazole-4-carboxylate (80 mg, 0.141 mmol) in tetrahydrofuran (THF) (3 mL) and methanol (1 mL) was added LiOH (5.54 mg, 0.231 mmol) in water (1 mL). The reaction mixture was stirred at 60° C. for 16 h. Then organic solvent was evaporated. The residue was adjusted to pH=5 with HCl (3M, 1.5 mL). The resulting was filtrated and washed with water to obtain the title compound 5-(2-(1-methyl-1H-1,2,3-triazol-4-yl)cyclopropyl)-1-(5-methyl-3'-((R)-2-propylpiperidine-1-carbonyl)-[1,1'-biphenyl]-3-yl)-1H-pyrazole-4-carboxylic acid (40 mg, 0.065 mmol, 46.1% yield). LC-MS m/z 553.3 (M+H)$^+$, 1.65 min (ret. time).

Example 155. 5-((1R,2R)-2-(1-Methyl-1H-1,2,3-triazol-4-yl)cyclopropyl)-1-(5-methyl-3'-((R)-2-propylpiperidine-1-carbonyl)-[1,1'-biphenyl]-3-yl)-1H-pyrazole-4-carboxylic Acid (Isomer 1)

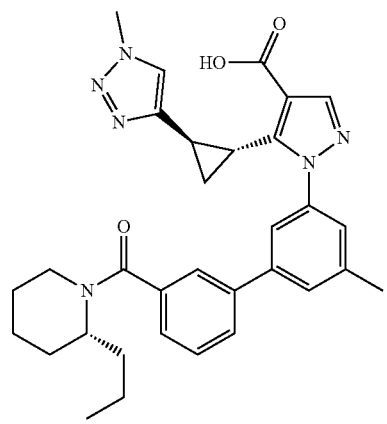 [SMILES: CCC[C@@H]1CCCCN1C(=O)c1cccc(-c2cc(C)cc(-n3ncc(C(=O)O)c3[C@@H]3C[C@H]3c3cn(C)nn3)c2)c1]

155a) Methyl 5-((1R,2R)-2-(1-methyl-1H-1,2,3-triazol-4-yl)cyclopropyl)-1-(5-methyl-3'-((R)-2-propylpiperidine-1-carbonyl)-[1,1'-biphenyl]-3-yl)-1H-pyrazole-4-carboxylate (Isomer 1) and methyl 5-((1S,2S)-2-(1-methyl-1H-1,2,3-triazol-4-yl)cyclopropyl)-1-(5-methyl-3'-((R)-2-propylpiperidine-1-carbonyl)-[1,1'-biphenyl]-3-yl)-1H-pyrazole-4-carboxylate (Isomer 2)

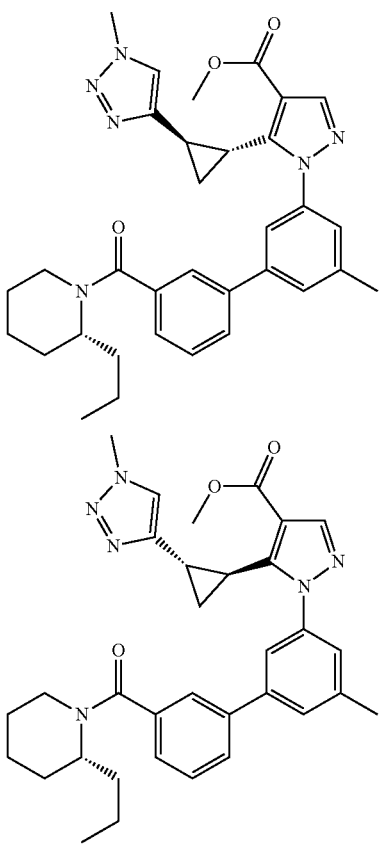

To a solution of 5-(2-(1-methyl-1H-1,2,3-triazol-4-yl)cyclopropyl)-1-(5-methyl-3'-((R)-2-propylpiperidine-1-carbonyl)-[1,1'-biphenyl]-3-yl)-1H-pyrazole-4-carboxylic acid (30 mg, 0.054 mmol) in methanol (3.00 mL) at 0° C., acetyl chloride (7.72 µl, 0.109 mmol) was added. The reaction mixture was stirred for 16 h. Then the other 1 eq. of acetyl chloride was added and stirred at room temperature for other 4 more days. The solvent was evaporated under Biotage-V10 to get crude product. This was resolved by Chiral SFC (Column: Chiral pack IA 20×250 mm, 5 u; Co-solvent: 25% MeOH:IPA (1:1); Flowrate: 50 g/min; Back pressure: 100 Bar) to give single enantiomerically pure methyl 5-((1R,2R)-2-(1-methyl-1H-1,2,3-triazol-4-yl)cyclopropyl)-1-(5-methyl-3'-((R)-2-propylpiperidine-1-carbonyl)-[1,1'-biphenyl]-3-yl)-1H-pyrazole-4-carboxylate (isomer 1) (7.6 mg) (chiral SFC ret. time: 7.21 min) LC-MS m/z 567.6 (M+H)$^+$, 1.15 min (ret. time) and single enantiomerically pure methyl 5-((1S,2S)-2-(1-methyl-1H-1,2,3-triazol-4-yl)cyclopropyl)-1-(5-methyl-3'-((R)-2-propylpiperidine-1-carbonyl)-[1,1'-biphenyl]-3-yl)-1H-pyrazole-4-carboxylate (isomer 2) (9.1 mg) (chiral SFC ret. time: 9.54 min).

155b) 5-((1R,2R)-2-(1-Methyl-1H-1,2,3-triazol-4-yl)cyclopropyl)-1-(5-methyl-3'-((R)-2-propylpiperidine-1-carbonyl)-[1,1'-biphenyl]-3-yl)-1H-pyrazole-4-carboxylic Acid (Isomer 1)

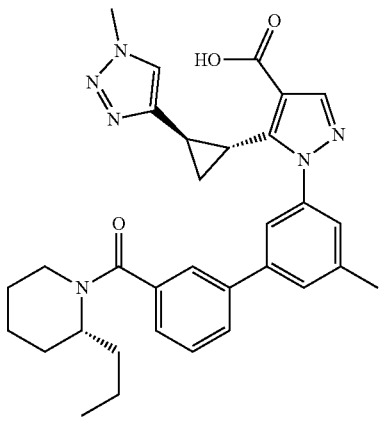 [SMILES: CCC[C@@H]1CCCCN1C(=O)c1cccc(-c2cc(C)cc(-n3ncc(C(=O)O)c3[C@@H]3C[C@H]3c3cn(C)nn3)c2)c1]

To a solution of methyl 5-((1R,2R)-2-(1-methyl-1H-1,2,3-triazol-4-yl)cyclopropyl)-1-(5-methyl-3'-((R)-2-propylpiperidine-1-carbonyl)-[1,1'-biphenyl]-3-yl)-1H-pyrazole-4-carboxylate (7.4 mg, 0.013 mmol) in methanol (1.5 mL) at 25° C., LiOH (6.25 mg, 0.261 mmol) was added. The reaction mixture was stirred for 16 h. Then it was acidified with 1H HCl and solvent was evaporated. The crude product was purified by reverse-phase HPLC to obtain the title compound (3.6 mg, 0.0065 mmol, 49.9% yield). LC-MS m/z 553.5 (M+H)$^+$, 1.02 min (ret. time) (isomer 2).

Example 156. 5-((1S,2S)-2-(1-methyl-1H-1,2,3-triazol-4-yl)cyclopropyl)-1-(5-methyl-3'-((R)-2-propylpiperidine-1-carbonyl)-[1,1'-biphenyl]-3-yl)-1H-pyrazole-4-carboxylic Acid (Isomer 2)

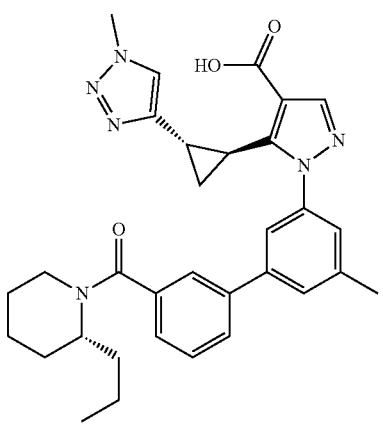 [SMILES: CCC[C@@H]1CCCCN1C(=O)c1cccc(-c2cc(C)cc(-n3ncc(C(=O)O)c3[C@H]3C[C@@H]3c3cn(C)nn3)c2)c1]

To a solution of methyl 5-((1S,2S)-2-(1-methyl-1H-1,2,3-triazol-4-yl)cyclopropyl)-1-(5-methyl-3'-((R)-2-propylpiperidine-1-carbonyl)-[1,1'-biphenyl]-3-yl)-1H-pyrazole-4-carboxylate (9 mg, 0.016 mmol) in MeOH (1.5 mL) at 25° C., LiOH (6.25 mg, 0.261 mmol) was added. The reaction mixture was stirred for 16 h. Then it was acidified by 1H HCl and solvent was evaporated. The crude product was purified by reverse-phase HPLC to obtain the title compound (3.5 mg, 0.0063 mmol, 48.5% yield). LC-MS m/z 553.5 (M+H)⁺, 1.02 min (ret. time) (isomer 1).

Example 157. 1-(3'-(1-Cyclohexyl-2,2,2-trifluoroethoxy)-[1,1'-biphenyl]-3-yl)-5-((1,2-trans)-2-(1-methyl-1H-1,2,3-triazol-4-yl)cyclopropyl)-1H-pyrazole-4-carboxylic Acid

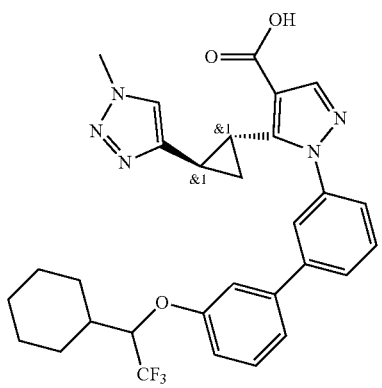 [SMILES: Cn1cc([C@@H]2C[C@H]2c2c(C(=O)O)cnn2-c2cccc(-c3cccc(OC(C4CCCCC4)C(F)(F)F)c3)c2)nn1]

157a) 1-Cyclohexyl-2,2,2-trifluoroethanol

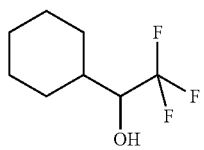 [SMILES: OC(C1CCCCC1)C(F)(F)F]

To a solution of 1-cyclohexyl-2,2,2-trifluoroethanone (500 mg, 2.78 mmol) in THF (10 mL), NaBH₄ (210 mg, 5.55 mmol) was added. The reaction mixture was stirred at 25° C. for 16 h. 1NHCl was added. Then the reaction mixture was extracted with ethyl acetate (3×). The combined organic phase was washed with brine, dried over MgSO₄ and concentrated to obtain the title compound (450 mg, 2.470 mmol, 89% yield). ¹H NMR (400 MHz, chloroform-d) ppm: 0.96-1.44 (m, 5H) 1.57-2.24 (m, 7H) 3.49-3.95 (m, 1H).

157b) 1-Cyclohexyl-2,2,2-trifluoroethyl trifluoromethanesulfonate

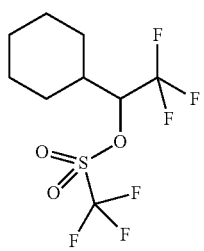 [SMILES: O=S(=O)(OC(C1CCCCC1)C(F)(F)F)C(F)(F)F]

To a solution of 1-cyclohexyl-2,2,2-trifluoroethanol (200 mg, 1.098 mmol) in pyridine (1 mL) under nitrogen at 0° C., trifluoromethanesulfonic anhydride (465 mg, 1.647 mmol) was added by dropwise. After addition, the reaction mixture was stirred at 0° C. for 1.5 h. Then the reaction mixture was partitioned between ether and water. The ether layer was washed with brine, dried over MgSO₄ and concentrated to obtain the title compound (230 mg, 0.732 mmol, 66.7% yield). ¹H NMR (400 MHz, chloroform-d) ppm: 1.26-2.14 (m, 11H) 4.57-5.31 (m, 1H).

157c) 1-(3'-(1-Cyclohexyl-2,2,2-trifluoroethoxy)-[1,1'-biphenyl]-3-yl)-5-((1,2-trans)-2-(1-methyl-1H-1,2,3-triazol-4-yl)cyclopropyl)-1H-pyrazole-4-carboxylic Acid

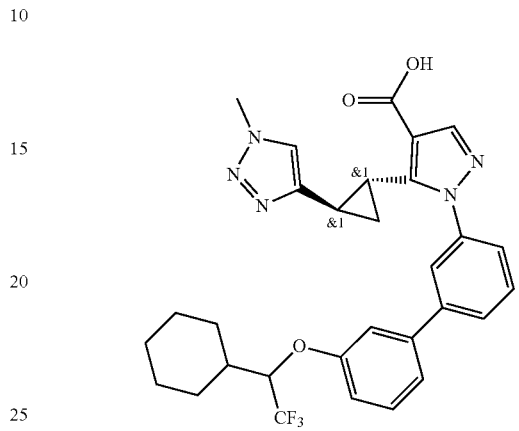

To a solution of methyl 1-(3'-hydroxy-[1,1'-biphenyl]-3-yl)-5-(1,2-trans)-(2-(1-methyl-1H-1,2,3-triazol-4-yl)cyclopropyl)-1H-pyrazole-4-carboxylate (30 mg, 0.072 mmol) in N,N-dimethylformamide (DMF) (1 mL), 1-cyclohexyl-2,2,2-trifluoroethyl trifluoromethanesulfonate (68.1 mg, 0.217 mmol), K₂CO₃ (39.9 mg, 0.289 mmol) and sodium iodide (10.82 mg, 0.072 mmol) were added. The reaction mixture was stirred at 80° C. for 2 days. Then the solvent was evaporated and the crude product was then purified on a silica cartridge (12 g) with a Combiflash Companion, eluting at 20 mL/min with a gradient running from 100% hexanes to 100% ethyl acetate/hexanes over 35 min) to get methyl 1-(3'-(1-cyclohexyl-2,2,2-trifluoroethoxy)-[1,1'-biphenyl]-3-yl)-5-((1,trans)-2-(1-methyl-1H-1,2,3-triazol-4-yl)cyclopropyl)-1H-pyrazole-4-carboxylate (22 mg, 0.038 mmol, 52.6% yield). To it in MeOH (1.000 mL), LiOH (17.29 mg, 0.722 mmol) and 0.1 mL of water were added. The reaction mixture was stirred at room temperature for 16 h. 1N HCl was added to pH=1. The solvent was evaporated under V-10 and the crude product was purified by reverse-phase HPLC to obtain the title compound (12 mg, 0.021 mmol, 29.4% yield). LC-MS m/z 566.5 (M+H)⁺, 1.26 min (ret. time).

Example 158. 1-(3'-(dimethylcarbamoyl)-[1,1'-biphenyl]-3-yl)-5-(2-(1-ethyl-1H-1,2,3-triazol-4-yl)cyclopropyl)-1H-pyrazole-4-carboxylic Acid

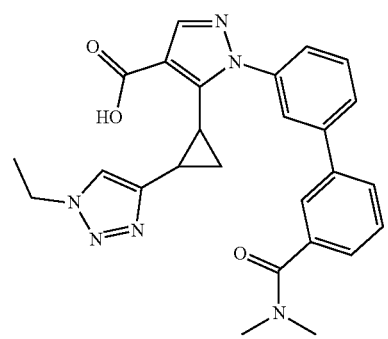 [SMILES: CCn1cc(C2CC2c2c(C(=O)O)cnn2-c2cccc(-c3cccc(C(=O)N(C)C)c3)c2)nn1]

158a) Methyl 1-(3'-(dimethylcarbamoyl)-[1,1'-biphenyl]-3-yl)-5-(2-(1-ethyl-1H-1,2,3-triazol-4-yl)cyclopropyl)-1H-pyrazole-4-carboxylate

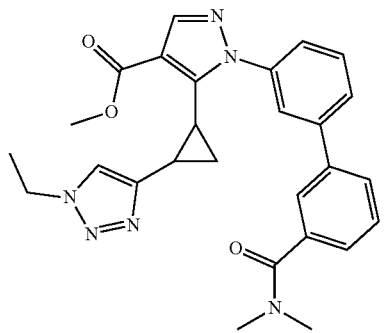 [SMILES: CCn1cc(C2CC2c2c(C(=O)OC)cnn2-c2cccc(-c3cccc(C(=O)N(C)C)c3)c2)nn1]

To a solution of (Z)-methyl 3-(dimethylamino)-2-(2-(1-ethyl-1H-1,2,3-triazol-4-yl)cyclopropanecarbonyl)acrylate (200 mg, 0.684 mmol) in acetonitrile (10 mL), N-ethyl-N-isopropylpropan-2-amine (265 mg, 2.052 mmol) was added under $N_2$ at 0° C. After 5 mins, 3'-hydrazinyl-N,N-dimethyl-[1,1'-biphenyl]-3-carboxamide (210 mg, 0.821 mmol) was added. The reaction mixture was stirred at 0° C. to 30° C. for 6 h. The solvent was removed and the residue was purified on silica gel chromatography (DCM:MeOH=0% to 30%) to obtain the title compound methyl 1-(3'-(dimethylcarbamoyl)-[1,1'-biphenyl]-3-yl)-5-(2-(1-ethyl-1H-1,2,3-triazol-4-yl)cyclopropyl)-1H-pyrazole-4-carboxylate (18 mg, 0.035 mmol, 5.05% yield) as white solid. LC-MS m/z 485.0 $(M+H)^+$, 1.77 min (ret. time).

158b) 1-(3'-(Dimethylcarbamoyl)-[1,1'-biphenyl]-3-yl)-5-(2-(1-ethyl-1H-1,2,3-triazol-4-yl)cyclopropyl)-1H-pyrazole-4-carboxylic Acid

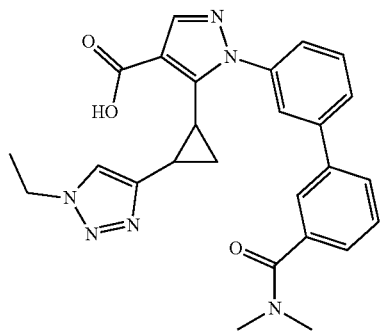 [SMILES: CCn1cc(C2CC2c2c(C(=O)O)cnn2-c2cccc(-c3cccc(C(=O)N(C)C)c3)c2)nn1]

To a solution of methyl 1-(3'-(dimethylcarbamoyl)-[1,1'-biphenyl]-3-yl)-5-(2-(1-ethyl-1H-1,2,3-triazol-4-yl)cyclopropyl)-1H-pyrazole-4-carboxylate (18 mg, 0.037 mmol) in tetrahydrofuran (THF) (4 mL) and water (1 mL), lithium hydroxide (1.779 mg, 0.074 mmol) was added. The reaction mixture was stirred at 25° C. for 16 h. The solvent was removed and the residue was purified by reverse-phase HPLC to afford the title compound 1-(3'-(dimethylcarbamoyl)-[1,1'-biphenyl]-3-yl)-5-(2-(1-ethyl-1H-1,2,3-triazol-4-yl)cyclopropyl)-1H-pyrazole-4-carboxylic acid (15 mg, 0.032 mmol, 85% yield) as white solid. LC-MS m/z 471.0 $(M+H)^+$, 1.38 min (ret. time).

Example 159. 5-(2-(5-Methylisoxazol-4-yl)cyclopropyl)-1-(3'-((R)-2-propylpiperidine-1-carbonyl)-[1,1'-biphenyl]-3-yl)-1H-pyrazole-4-carboxylic Acid

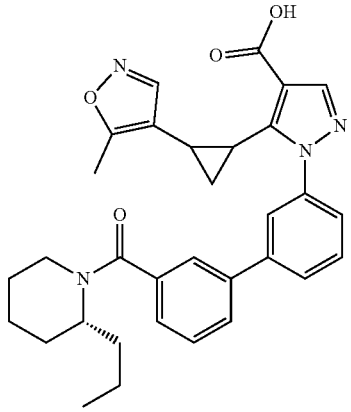 [SMILES: CCC[C@@H]1CCCCN1C(=O)c1cccc(-c2cccc(-n3ncc(C(=O)O)c3C3CC3c3cnoc3C)c2)c1]

159a) (E)-tert-Butyl 3-(5-methylisoxazol-3-yl)acrylate

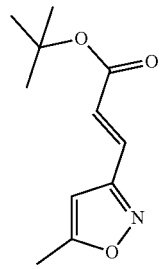

To a solution of tert-butyl 2-(diethoxyphosphoryl)acetate (9.74 g, 38.6 mmol) in tetrahydrofuran (THF) (120 mL), sodium hydride (1.685 g, 42.1 mmol) was added. The reaction mixture was stirred at 0° C. under $N_2$ for 10 mins. Then a solution of 5-methylisoxazole-3-carbaldehyde (3.9 g, 35.1 mmol) in THF (500 mL) was added by dropwise and the reaction was stirred at 0° C. for 15 mins. Then water was added and extracted with ethyl acetate (3×). The combined organic layer was washed with water (2×), brine (2×), dried over $Na_2SO_4$ and concentrated. The crude product was purified on silica gel chromatography (hexane:ethyl acetate=1:5) to obtain the title compound (E)-tert-butyl 3-(5-methylisoxazol-3-yl)acrylate (6 g, 28.1 mmol, 80% yield) as an oil. LC-MS m/z 209.9 $(M+H)^+$, 1.73 min (ret. time).

159b) tert-Butyl 2-(5-methylisoxazol-3-yl)cyclopropanecarboxylate

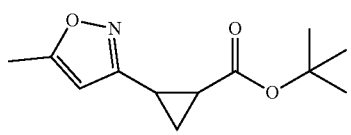 [SMILES: Cc1cc(C2CC2C(=O)OC(C)(C)C)no1]

To a solution of trimethylsulfoxonium iodide (18.93 g, 86 mmol) in dimethyl sulfoxide (DMSO) (45 mL), sodium hydride (3.44 g, 86 mmol) was added. The reaction mixture was stirred at 25° C. under N₂ for 1 h. Then a solution of (Z)-tert-butyl 3-(5-methylisoxazol-3-yl)acrylate (6 g, 28.7 mmol) in tetrahydrofuran (THF) (45.0 mL) was added dropwise and the reaction mixture was stirred at 25° C. for 1 h and stirred at 50° C. for another 1 h. 200 mL of ethyl acetate and 50 mL of water were added. The water layer was extracted with ethyl acetate (3×). The combined organic phase was dried over Na₂SO₄ and concentrated to obtain tert-butyl 2-(5-methylisoxazol-3-yl)cyclopropanecarboxylate (2.3 g, 9.27 mmol, 32.3% yield). LC-MS m/z 223.9 (M+H)⁺, 1.78 min (ret. time).

159c) 2-(5-Methylisoxazol-3-yl)cyclopropanecarboxylic Acid

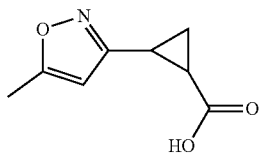

A solution of tert-butyl 2-(5-methylisoxazol-3-yl)cyclopropanecarboxylate (2.1 g, 9.41 mmol) in dichloromethane (DCM) (3 mL) was added TFA (2.174 mL, 28.2 mmol) slowly under nitrogen at 25° C. The reaction mixture was stirred at 25° C. for 4 h. 100 mL of ethyl acetate and 100 mL of water were added. The water layer was concentrated to obtain the title compound 2-(5-methylisoxazol-3-yl)cyclopropanecarboxylic acid (1.660 g, 8.94 mmol, 95% yield) as a white solid. LC-MS m/z 168.0 (M+H)⁺, 1.38 min (ret. time).

159d) Methyl 3-(2-(1-methyl-1H-1,2,3-triazol-4-yl)cyclopropyl)-3-oxopropanoate

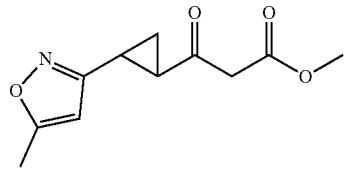 [SMILES: COC(=O)CC(=O)C1CC1c1cc(C)on1]

A solution of 2-(5-methylisoxazol-3-yl)cyclopropanecarboxylic acid (1650 mg, 9.87 mmol) in tetrahydrofuran (THF) (200 mL) was added CDI (2087 mg, 14.81 mmol). The reaction mixture was stirred at 25° C. for 2 h. It was added potassium 3-methoxy-3-oxopropanoate (4625 mg, 29.6 mmol) and potassium 3-methoxy-3-oxopropanoate (4625 mg, 29.6 mmol). The reaction mixture was stirred at room temperature for 18 h. Then the solvent was evaporated and re-dissolved in ethyl acetate (20 mL). The suspension thus obtained was washed with 1 M KHSO₄, saturated NaHCO₃, and brine. The organic layer was dried over Na₂SO₄ and concentrated to obtain the title compound methyl 3-(2-(1-methyl-1H-1,2,3-triazol-4-yl)cyclopropyl)-3-oxopropanoate (2.1 g, 9.41 mmol, 95% yield) as an oil. LC-MS m/z 223.9 (M+H)⁺, 1.52 min (ret. time).

159e) (Z)-Methyl 3-(dimethylamino)-2-(2-(5-methylisoxazol-3-yl)cyclopropanecarbonyl)acrylate

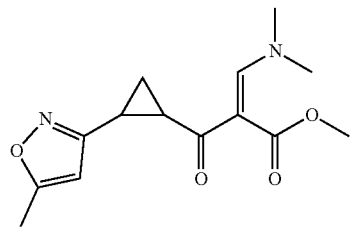 [SMILES: COC(=O)/C(=C\N(C)C)C(=O)C1CC1c1cc(C)on1]

To the solution of methyl 3-(2-(5-methylisoxazol-3-yl)cyclopropyl)-3-oxopropanoate (200 mg, 0.896 mmol) in toluene (3 ml), 1,1-dimethoxy-N,N-dimethylmethanamine (128 mg, 1.075 mmol) was added. Then it was stirred at 90° C. under N₂ for 4 h. The solvent was evaporated to give the title compound (Z)-methyl 3-(dimethylamino)-2-(2-(5-methylisoxazol-3-yl)cyclopropanecarbonyl)acrylate (200 mg, 0.110 mmol, 12.23% yield) as green oil. LC-MS m/z 279.1 (M+H)⁺, 1.60 min (ret. time).

159f) Methyl 1-(3-bromophenyl)-5-(2-(5-methylisoxazol-4-yl)cyclopropyl)-1H-pyrazole-4-carboxylate

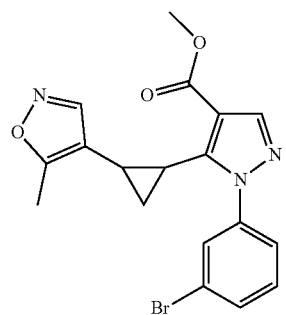 [SMILES: COC(=O)c1cnn(-c2cccc(Br)c2)c1C1CC1c1cnoc1C]

To a solution of (Z)-methyl 3-(dimethylamino)-2-(2-(5-methylisoxazol-3-yl)cyclopropanecarbonyl)acrylate (2 g, 7.19 mmol) in acetonitrile (15 mL), phenylhydrazine hydrochloride (1.039 g, 7.19 mmol) and DIPEA (1.255 mL, 7.19 mmol) was added. The reaction mixture was stirred at 25° C. for 2 h. Then 15 mL of water was added and extracted with Ethyl acetate (3×). The combined organic phase was washed with brine (20 mL), dried over Na₂SO₄ and concentrated. The crude product was purified on silica gel chromatography (ethyl acetate:petroleum ether=1:1) to give the title product methyl 1-(3-bromophenyl)-5-(2-(5-methylisoxazol-4-yl)cyclopropyl)-1H-pyrazole-4-carboxylate (1.6 g, 3.05 mmol, 42.4% yield). LC-MS m/z 401.7 (M+H)⁺, 1.81 min (ret. time).

159g) 3'-(4-(Methoxycarbonyl)-5-(2-(5-methylisoxazol-4-yl)cyclopropyl)-1H-pyrazol-1-yl)-[1,1'-biphenyl]-3-carboxylic Acid

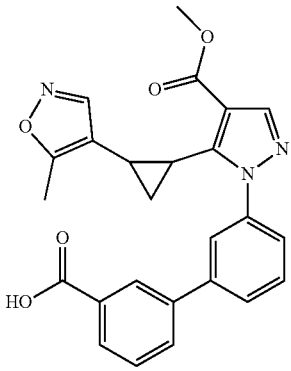 [SMILES: COC(=O)c1cnn(-c2cccc(-c3cccc(C(=O)O)c3)c2)c1C1CC1c1cnoc1C]

To a solution of methyl 1-(3-bromophenyl)-5-(2-(5-methylisoxazol-4-yl)cyclopropyl)-1H-pyrazole-4-carboxylate (250 mg, 0.622 mmol) in methanol (4.00 mL) and toluene (4 mL), tert-butyl 3-(dimethoxyboryl)benzoate (155 mg, 0.622 mmol), $K_2CO_3$ (258 mg, 1.865 mmol) and 1,1'-Bis(diphenylphosphino)ferrocene-palladium(II)dichloride dichloromethane complex (50.8 mg, 0.062 mmol) were added. The reaction mixture was stirred at 90° C. for 4 h. Then it was cooled to 25° C. It was concentrated to obtain methyl 1-(3'-(tert-butoxycarbonyl)-[1,1'-biphenyl]-3-yl)-5-(2-(5-methylisoxazol-4-yl)cyclopropyl)-1H-pyrazole-4-carboxylate (290 mg, 0.581 mmol, 90% yield). To a solution of methyl 1-(3'-(tert-butoxycarbonyl)-[1,1'-biphenyl]-3-yl)-5-(2-(5-methylisoxazol-4-yl)cyclopropyl)-1H-pyrazole-4-carboxylate (290 mg, 0.581 mmol in dichloromethane (DCM) (9 mL), TFA (0.134 mL, 1.742 mmol) was added and the mixture was stirred for 2 h. It was concentrated to obtain the title compound 3'-(4-(methoxycarbonyl)-5-(2-(5-methylisoxazol-4-yl)cyclopropyl)-1H-pyrazol-1-yl)-[1,1'-biphenyl]-3-carboxylic acid (240 mg, 0.487 mmol, 84% yield) as a light yellow solid. LC-MS m/z 444.1 $(M+H)^+$, 1.89 min (ret. time).

159h) Methyl 5-(2-(5-methylisoxazol-4-yl)cyclopropyl)-1-(3'-((R)-2-propylpiperidine-1-carbonyl)-[1,1'-biphenyl]-3-yl)-1H-pyrazole-4-carboxylate

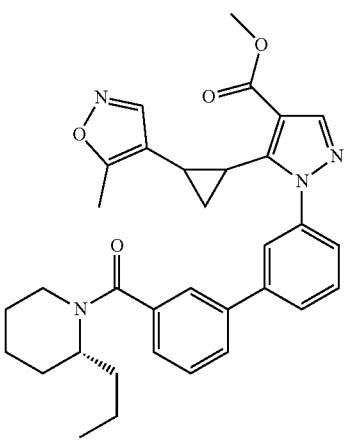 [SMILES: CCC[C@@H]1CCCCN1C(=O)c1cccc(-c2cccc(-n3ncc(C(=O)OC)c3C3CC3c3cnoc3C)c2)c1]

To a solution of 3'-(4-(methoxycarbonyl)-5-(2-(5-methylisoxazol-4-yl)cyclopropyl)-1H-pyrazol-1-yl)-[1,1'-biphenyl]-3-carboxylic acid (257 mg, 0.580 mmol) in N,N-dimethylformamide (DMF) (15 mL) at 0° C., HATU (220 mg, 0.580 mmol) was added and the reaction mixture was stirred at 0° C. for 10 mins. Then (R)-2-propylpiperidine (73.7 mg, 0.580 mmol) was added. The reaction mixture was stirred at 25° C. for 1 h. The reaction mixture was quenched with water (15 mL) and extracted with ethyl acetate (3×). The combined organic phase was dried over $Na_2SO_4$ and concentrated. The residue was purified on silica gel chromatography (ethyl acetate:petroleum ether=1:1) to obtain the title compound methyl 5-(2-(5-methylisoxazol-4-yl)cyclopropyl)-1-(3'-((R)-2-propylpiperidine-1-carbonyl)-[1,1'-biphenyl]-3-yl)-1H-pyrazole-4-carboxylate (250 mg, 0.407 mmol, 70.2% yield) as white solid. LC-MS m/z 553.3 $(M+H)^+$, 2.20 min (ret. time).

159i) 5-(2-(5-Methylisoxazol-4-yl)cyclopropyl)-1-(3'-((R)-2-propylpiperidine-1-carbonyl)-[1,1'-biphenyl]-3-yl)-1H-pyrazole-4-carboxylic Acid

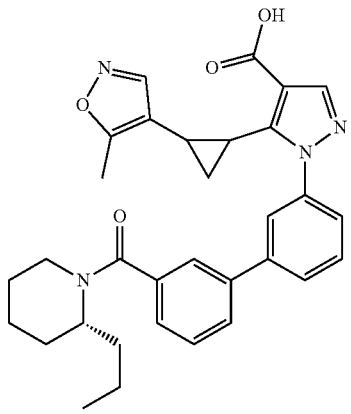 [SMILES: CCC[C@@H]1CCCCN1C(=O)c1cccc(-c2cccc(-n3ncc(C(=O)O)c3C3CC3c3cnoc3C)c2)c1]

To a solution of methyl 5-(2-(5-methylisoxazol-4-yl)cyclopropyl)-1-(3'-((R)-2-propylpiperidine-1-carbonyl)-[1,1'-biphenyl]-3-yl)-1H-pyrazole-4-carboxylate (250 mg, 0.452 mmol) in methanol (5 mL) and water (1.667 mL), LiOH (10.83 mg, 0.452 mmol) was added. The reaction mixture was stirred at 25° C. for 1 h. It was quenched with 5 mL of HCl (1N) and extracted with ethyl acetate (3×). The combined organic layer was washed with brine, dried over $Na_2SO_4$ and concentrated. The crude product was purified by reverse-phase HPLC to obtain the title compound 5-(2-(5-methylisoxazol-4-yl)cyclopropyl)-1-(3'-((R)-2-propylpiperidine-1-carbonyl)-[1,1'-biphenyl]-3-yl)-1H-pyrazole-4-carboxylic acid (200 mg, 0.364 mmol, 80% yield). LC-MS m/z 539.2 $(M+H)^+$, 2.01 min (ret. time).

Example 160. 1-(5-Chloro-3'-((R)-2-propylpiperi-dine-1-carbonyl)-[1,1'-biphenyl]-3-yl)-5-(2-(1-methyl-1H-1,2,3-triazol-4-yl)cyclopropyl)-1H-pyrazole-4-carboxylic Acid Compound with 2,2,2-trifluoroacetic Acid (1:1)

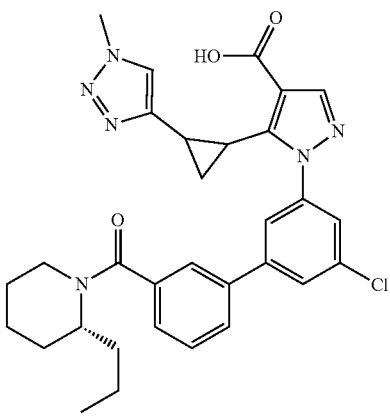 [SMILES: CCC[C@@H]1CCCCN1C(=O)c1cccc(-c2cc(Cl)cc(-n3ncc(C(=O)O)c3C3CC3c3cn(C)nn3)c2)c1]

160a) Methyl 1-(3-bromo-5-chlorophenyl)-5-(2-(1-methyl-1H-1,2,3-triazol-4-yl)cyclopropyl)-1H-pyrazole-4-carboxylate

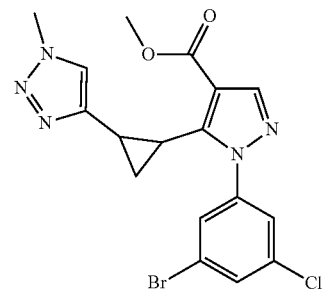 [SMILES: COC(=O)c1cnn(-c2cc(Cl)cc(Br)c2)c1C1CC1c1cn(C)nn1]

To a solution of methyl 3-(dimethylamino)-2-(2-(1-methyl-1H-1,2,3-triazol-4-yl)cyclopropanecarbonyl)acrylate (452 mg, 1.625 mmol) in acetonitrile (10 mL), (3-bromo-5-chlorophenyl)hydrazine (360 mg, 1.625 mmol) and DIPEA (0.568 mL, 3.25 mmol) was added. The reaction mixture was stirred at 15° C. for 16 h. The solvent was removed and the residue was purified by Prep-TLC (petroleum ether:ethyl acetate=2:1, Rf=0.3) to obtain the title compound methyl 1-(3-bromo-5-chlorophenyl)-5-(2-(1-methyl-1H-1,2,3-triazol-4-yl)cyclopropyl)-1H-pyrazole-4-carboxylate (350 mg, 0.801 mmol, 49.3% yield) as a yellow solid. LC-MS m/z 435.9 (M+H)+, 1.89 min (ret. time).

160b) 3'-Chloro-5'-(4-(methoxycarbonyl)-5-(2-(1-methyl-1H-1,2,3-triazol-4-yl)cyclopropyl)-1H-pyrazol-1-yl)-[1,1'-biphenyl]-3-carboxylic Acid

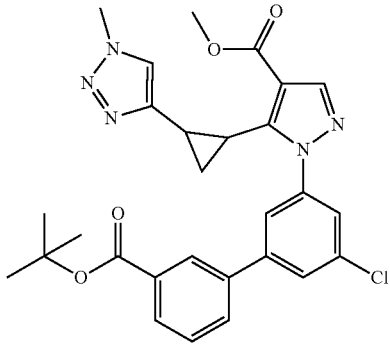 [SMILES: COC(=O)c1cnn(-c2cc(Cl)cc(-c3cccc(C(=O)OC(C)(C)C)c3)c2)c1C1CC1c1cn(C)nn1]

To a solution of methyl 1-(3-bromo-5-chlorophenyl)-5-(2-(1-methyl-1H-1,2,3-triazol-4-yl)cyclopropyl)-1H-pyrazole-4-carboxylate (350 mg, 0.801 mmol) in 1,4-dioxane (12 ml) and water (3.00 ml), K$_2$CO$_3$ (222 mg, 1.603 mmol) and (3-(tert-butoxycarbonyl)phenyl)boronic acid (196 mg, 0.882 mmol) were added. Then PdCl$_2$(dppf)-CH$_2$C2 adduct (65.5 mg, 0.080 mmol) was added under N$_2$ and the reaction mixture was stirred at 90° C. for 6 h. The solvent was evaporated and the residue was purified by Prep-TLC (petroleum ether:ethyl acetate=2:1, Rf=0.3) to obtain the title compound methyl 1-(3'-(tert-butoxycarbonyl)-5-chloro-[1,1'-biphenyl]-3-yl)-5-(2-(1-methyl-1H-1,2,3-triazol-4-yl)cyclopropyl)-1H-pyrazole-4-carboxylate (300 mg, 0.427 mmol, 53.3% yield) as a yellow solid. LC-MS m/z 534.1 (M+H)+, 1.89 min (ret. time).

160c) 3'-Chloro-5'-(4-(methoxycarbonyl)-5-(2-(1-methyl-1H-1,2,3-triazol-4-yl)cyclopropyl)-1H-pyrazol-1-yl)-[1,1'-biphenyl]-3-carboxylic Acid

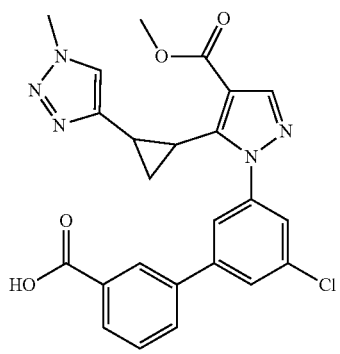 [SMILES: COC(=O)c1cnn(-c2cc(Cl)cc(-c3cccc(C(=O)O)c3)c2)c1C1CC1c1cn(C)nn1]

To a solution of methyl 1-(3'-(tert-butoxycarbonyl)-5-chloro-[1,1'-biphenyl]-3-yl)-5-(2-(1-methyl-1H-1,2,3-triazol-4-yl)cyclopropyl)-1H-pyrazole-4-carboxylate (300 mg, 0.562 mmol) in dichloromethane (DCM) (10 mL) was added TFA (0.433 mL, 5.62 mmol). The reaction mixture was stirred at 30° C. for 16 h. The solvent was removed to obtain the title compound (260 mg, 0.511 mmol, 91% yield) which was used in next step without further purification. LC-MS m/z 478.0 (M+H)+, 1.58 min (ret. time).

160d) Methyl 1-(5-chloro-3'-((R)-2-propylpiperidine-1-carbonyl)-[1,1'-biphenyl]-3-yl)-5-(2-(1-methyl-1H-1,2,3-triazol-4-yl)cyclopropyl)-1H-pyrazole-4-carboxylate

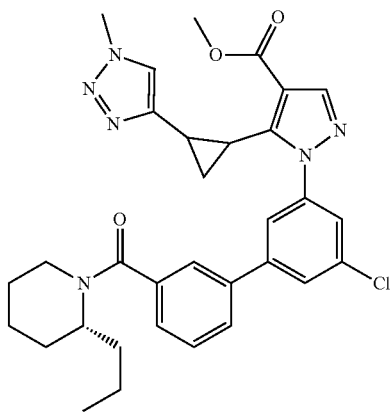 [SMILES: CCC[C@@H]1CCCCN1C(=O)c1cccc(-c2cc(Cl)cc(-n3ncc(C(=O)OC)c3C3CC3c3cn(C)nn3)c2)c1]

To a solution of 3'-chloro-5'-(4-(methoxycarbonyl)-5-(2-(1-methyl-1H-1,2,3-triazol-4-yl)cyclopropyl)-1H-pyrazol-1-yl)-[1,1'-biphenyl]-3-carboxylic acid (160 mg, 0.335 mmol) in dichloromethane (DCM) (5 mL), HATU (153 mg, 0.402 mmol), (R)-2-propylpiperidine (42.6 mg, 0.335 mmol) and DIPEA (0.175 mL, 1.004 mmol) were added. The reaction mixture was stirred at 25° C. for 16 h. The solvent was removed and the residue was purified by Prep-TLC (EA=100%) to obtain the title compound methyl 1-(5-chloro-3'-((R)-2-propylpiperidine-1-carbonyl)-[1,1'-biphenyl]-3-yl)-5-(2-(1-methyl-1H-1,2,3-triazol-4-yl)cyclopropyl)-1H-pyrazole-4-carboxylate (100 mg, 0.135 mmol, 40.2% yield) as a yellow oil. LC-MS m/z 587.2 (M+H)$^+$, 1.86 min (ret. time).

160e) 1-(5-Chloro-3'-((R)-2-propylpiperidine-1-carbonyl)-[1,1'-biphenyl]-3-yl)-5-(2-(1-methyl-1H-1,2,3-triazol-4-yl)cyclopropyl)-1H-pyrazole-4-carboxylic acid compound with 2,2,2-trifluoroacetic Acid (1:1)

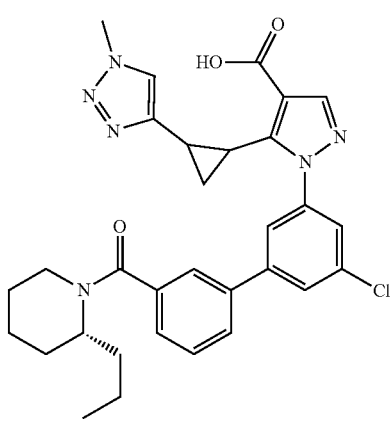 [SMILES: CCC[C@@H]1CCCCN1C(=O)c1cccc(-c2cc(Cl)cc(-n3ncc(C(=O)O)c3C3CC3c3cn(C)nn3)c2)c1]

To a solution of methyl 1-(5-chloro-3'-((R)-2-propylpiperidine-1-carbonyl)-[1,1'-biphenyl]-3-yl)-5-(2-(1-methyl-1H-1,2,3-triazol-4-yl)cyclopropyl)-1H-pyrazole-4-carboxylate (100 mg, 0.170 mmol) in tetrahydrofuran (THF) (3 mL) and methanol (1 mL) was added LiOH (5.54 mg, 0.231 mmol) in water (1 mL). The reaction mixture was stirred at 60° C. for 16 h. Then organic solvent was evaporated. The residue was adjusted pH=5 with HCl (3M, 1.5 mL) and extracted with CH$_2$Cl$_2$ (3×). The organic layer was washed with brine (30 mL), dried over Na$_2$SO$_4$ and concentrated. The crude product was purified by reverse-phase HPLC (0.05% TFA/H$_2$O:CH$_3$CN=5%~95%) to obtain the title compound, 1-(5-chloro-3'-((R)-2-propylpiperidine-1-carbonyl)-[1,1'-biphenyl]-3-yl)-5-(2-(1-methyl-1H-1,2,3-triazol-4-yl)cyclopropyl)-1H-pyrazole-4-carboxylic acid, compound with 2,2,2-trifluoroacetic acid (1:1). (35 mg, 0.051 mmol, 29.9% yield). LC-MS m/z 573.2 (M+H)$^+$, 1.70 min (ret. time).

Example 161

1-(3'-((1-Cyclohexylpropan-2-yl)oxy)-[1,1'-biphenyl]-3-yl)-5-cyclopropyl-1H-pyrazole-4-carboxylic Acid

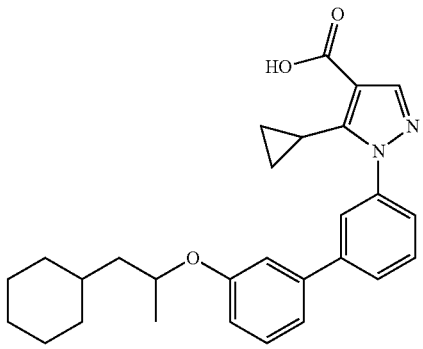 [SMILES: CC(CC1CCCCC1)Oc1cccc(-c2cccc(-n3ncc(C(=O)O)c3C3CC3)c2)c1]

161a) (2-Chloropropyl)cyclohexane

To a solution of 1-cyclohexylpropan-2-ol (400 mg, 2.81 mmol) in dichloromethane (DCM) (10 mL) was added SOCl$_2$ (0.205 mL, 2.81 mmol) slowly at 10° C. The reaction mixture was stirred for 3 h. Then it was diluted with NaHCO$_3$ solution and extracted with ethyl acetate (2×). The combined organic layer was washed with brine solution, dried over anhydrous Na$_2$SO$_4$ and concentrated to obtain the title compound (2-chloropropyl)cyclohexane (300 mg, 1.867 mmol, 66.4% yield) as a color less liquid. $^1$H NMR (400 MHz, chloroform-d) δ ppm: 4.57-4.81 (m, 1H) 1.78 (br d, J=12.28 Hz, 1H) 1.50-1.73 (m, 5H) 1.12-1.43 (m, 7H) 0.77-1.00 (m, 3H).

161b) Ethyl 5-cyclopropyl-1-(3'-hydroxy-[1,1'-biphenyl]-3-yl)-1H-pyrazole-4-carboxylate

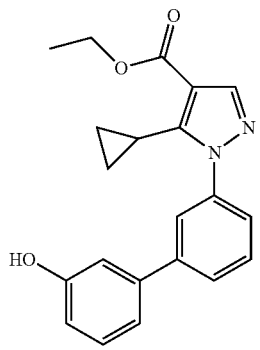 [SMILES: CCOC(=O)c1cnn(-c2cccc(-c3cccc(O)c3)c2)c1C1CC1]

To a solution of ethyl 1-(3-bromophenyl)-5-cyclopropyl-1H-pyrazole-4-carboxylate (1 g, 2.98 mmol) in tetrahydrofuran (THF) (4 mL) was added (3-hydroxyphenyl)boronic acid (0.617 g, 4.47 mmol) sodium carbonate (0.632 g, 5.97 mmol) and water (1 mL). The reaction mixture was degassed with argon for 10 mins and then added tetrakis(triphenylphosphine)palladium(0) (0.345 g, 0.298 mmol) under argon and stirred at 80° C. for 16 h. The reaction mixture was diluted with water and extracted with ethyl acetate (3×). The combined organic layer was washed with brine, dried over anhydrous Na$_2$SO$_4$ and concentrated. The residue was purified on silica gel chromatography (hexane:ethyl acetate=5:2) to afford the title compound ethyl 5-cyclopropyl-1-(3'-hydroxy-[1,1'-biphenyl]-3-yl)-1H-pyrazole-4-carboxylate (900 mg, 2.58 mmol, 87% yield).

161c) Ethyl 1-(3'-((1-cyclohexylpropan-2-yl)oxy)-[1,1'-biphenyl]-3-yl)-5-cyclopropyl-1H-pyrazole-4-carboxylate

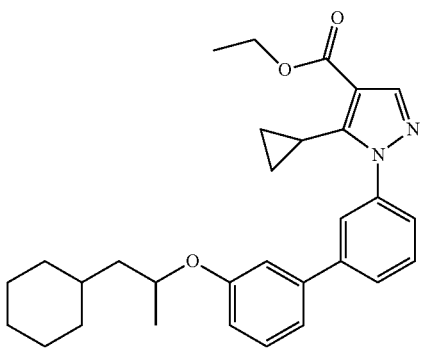 [SMILES: CCOC(=O)c1cnn(-c2cccc(-c3cccc(OC(C)CC4CCCCC4)c3)c2)c1C1CC1]

To a solution of ethyl 5-cyclopropyl-1-(3'-hydroxy-[1,1'-biphenyl]-3-yl)-1H-pyrazole-4-carboxylate (400 mg, 1.148 mmol) and (2-chloropropyl)cyclohexane (295 mg, 1.837 mmol) in N,N-dimethylformamide (DMF) (5 mL) was added Cs$_2$CO$_3$ (374 mg, 1.148 mmol). The reaction was heated in a microwave at 150° C. (high absorption) for 3 h. The reaction mixture was diluted with water and extracted with ethyl acetate (2×). The combined organic layer was washed with brine solution, dried over anhydrous Na$_2$SO$_4$ and concentrated. The crude product was purified on silica gel chromatography (ethyl acetate:hexane=6:4) to obtain the title compound ethyl 1-(3'-((1-cyclohexylpropan-2-yl)oxy)-[1,1'-biphenyl]-3-yl)-5-cyclopropyl-1H-pyrazole-4-carboxylate (150 mg, 0.241 mmol, 20.98% yield) as a gammy liquid. LC-MS m/z 472.9 (M+H)$^+$, 5.04 min (ret. time).

161d) 1-(3'-((1-Cyclohexylpropan-2-yl)oxy)-[1,1'-biphenyl]-3-yl)-5-cyclopropyl-1H-pyrazole-4-carboxylic Acid GSK3336916A

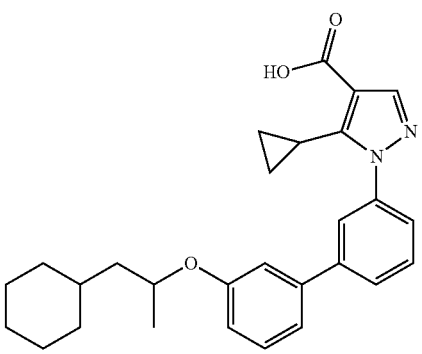 [SMILES: CC(CC1CCCCC1)Oc1cccc(-c2cccc(-n3ncc(C(=O)O)c3C3CC3)c2)c1]

To a solution of ethyl 1-(3'-((1-cyclohexylpropan-2-yl)oxy)-[1,1'-biphenyl]-3-yl)-5-cyclopropyl-1H-pyrazole-4-carboxylate (150 mg, 0.317 mmol) in ethanol (5 mL) was added NaOH (0.159 mL, 0.317 mmol). The reaction mixture was stirred for 5 h. The residue was diluted with ice water and acidified with 2N HCl to pH=2. Then the aqueous layer was extracted with DCM (2×). The combined organic layer was washed with brine, dried over anhydrous Na$_2$SO$_4$ and concentrated. The crude product was purified on silica gel chromotography (MeOH:DCM=0.5:9.5) to obtain the title compound 1-(3'-((1-cyclohexylpropan-2-yl)oxy)-[1,1'-biphenyl]-3-yl)-5-cyclopropyl-1H-pyrazole-4-carboxylic acid (80 mg, 0.179 mmol, 56.3% yield) as an off-white solid. LC-MS m/z 445.25 (M+H)$^+$, 3.26 min (ret. time).

Example 162. 1-(3'-((R)-1-Cyclohexylethoxy)-[1,1'-biphenyl]-3-yl)-5-((1R,2R)-2-(1-methyl-1H-1,2,3-triazol-4-yl)cyclopropyl)-1H-pyrazole-4-carboxylic Acid

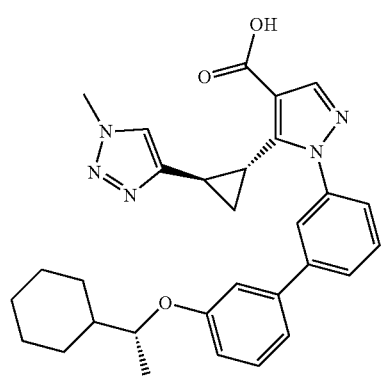 [SMILES: C[C@@H](Oc1cccc(-c2cccc(-n3ncc(C(=O)O)c3[C@@H]3C[C@H]3c3cn(C)nn3)c2)c1)C1CCCCC1]

162a) (R)-1-Bromo-3-(1-cyclohexylethoxy)benzene

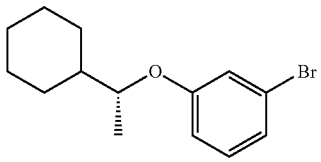 [SMILES: C[C@@H](Oc1cccc(Br)c1)C1CCCCC1]

To a solution of 3-bromophenol (100 mg, 0.578 mmol), Ph₃P (182 mg, 0.694 mmol) and 1-cyclohexylethanol (89 mg, 0.694 mmol) in tetrahydrofuran (THF) (5 mL), DIAD (0.135 mL, 0.694 mmol) in tetrahydrofuran (THF) (2 mL) was added slowly under nitrogen at 25° C. The reaction mixture was stirred at room temperature for 16 h. The solvent was evaporated and purified by reverse-phase HPLC to obtain the title compound (224 mg, 0.791 mmol). $^1$H NMR (400 MHz, chloroform-d) | ppm: 0.97-1.27 (m, 7H) 1.49-2.05 (m, 7H) 4.11 (quin, J=6.15 Hz, 1H) 6.83 (ddd, J=8.16, 2.38, 1.00 Hz, 1H) 7.04-7.20 (m, 3H).

162b) 1-(3'-((R)-1-Cyclohexylethoxy)-[1,1'-biphenyl]-3-yl)-5-((1R,2R)-2-(1-methyl-1H-1,2,3-triazol-4-yl)cyclopropyl)-1H-pyrazole-4-carboxylic Acid To a solution of (3-(4-(methoxycarbonyl)-5-((1R,2R)-2-(1-methyl-1H-1,2,3-triazol-4-yl)cyclopropyl)-1H-pyrazol-1-yl)phenyl)boronic acid (100 mg, 0.272 mmol) in a mixture of 1,4-dioxane (3 mL) and water (1.00 mL), (R)-1-bromo-3-(1-cyclohexylethoxy)benzene (116 mg, 0.409 mmol), K₂CO₃ (113 mg, 0.817 mmol) and PdCl₂(dppf) (19.93 mg, 0.027 mmol) were added. The reaction was heated in a microwave at 120° C. (high absorption) for 20 mins. The reaction mixture was filtered by StatoSpheres SPEvPL-Thiol MP SPE cartridge and concentrated. The crude product was purified by reverse-phase HPLC under acidic condition to obtain the methyl 1-(3'-((R)-1-cyclohexylethoxy)-[1,1'-biphenyl]-3-yl)-5-((1R,2R)-2-(1-methyl-1H-1,2,3-triazol-4-yl)cyclopropyl)-1H-pyrazole-4-carboxylate (100 mg, 0.19 mmol, 69.9% yield). To it in a mixture of methanol (2.00 mL) and tetrahydrofuran (THF) (2.00 mL), LiOH (65.2 mg, 2.72 mmol) and 0.1 mL of water were added. The reaction mixture was stirred at room temperature for 36 h. The solvent was evaporated and the residue was partitioned between 1 N HCl and ethyl acetate. The organic phase was dried over MgSO₄ and concentrated. The crude product was purified by reverse-phase HPLC under the neutral condition to obtain the title compound (55 mg, 0.108 mmol, 39.5% yield). LC-MS m/z 512.6 (M+H)⁺, 1.25 min (ret. time).

The compounds in Table 8 were prepared by a method similar to the one described for the preparation of 1-(3'-((R)-1-Cyclohexylethoxy)-[1,1'-biphenyl]-3-yl)-5-((1R,2R)-2-(1-methyl-1H-1,2,3-triazol-4-yl)cyclopropyl)-1H-pyrazole-4-carboxylic acid. As is appreciated by those skilled in the art, these analogous examples may involve variations in general reaction conditions.

TABLE 8

| Example | Structure | Name | LCMS [M + H]⁺ | Retention Time (min) |
|---|---|---|---|---|
| 163 | 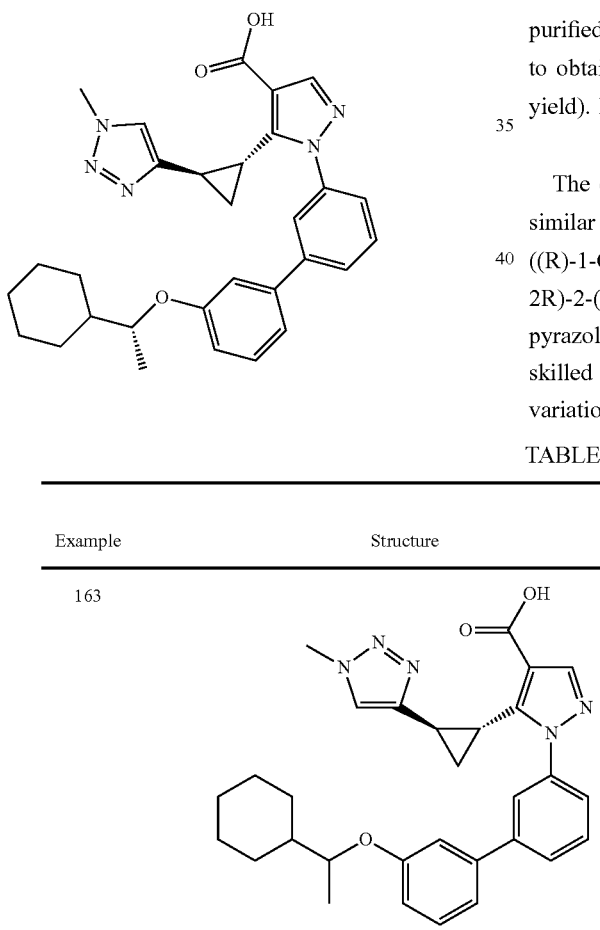 | 1-(3'-(1-Cyclohexylethoxy)-[1,1'-biphenyl]-3-yl)-5-((1R,2R)-2-(1-methyl-1H-1,2,3-triazol-4-yl)cyclopropyl)-1H-pyrazole-4-carboxylic acid | 512.2 | 2.24 |

TABLE 8-continued

| Example | Structure | Name | LCMS [M + H]+ | Retention Time (min) |
|---|---|---|---|---|
| 164 | 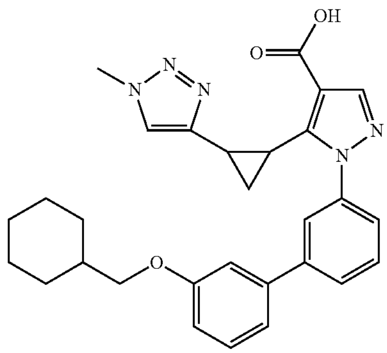 | 1-(3'-(Cyclohexylmethoxy)-[1,1'-biphenyl]-3-yl)-5-(2-(1-methyl-1H-1,2,3-triazol-4-yl)cyclopropyl)-1H-pyrazole-4-carboxylic acid | 498.2 | 2.17 |
| 165 | 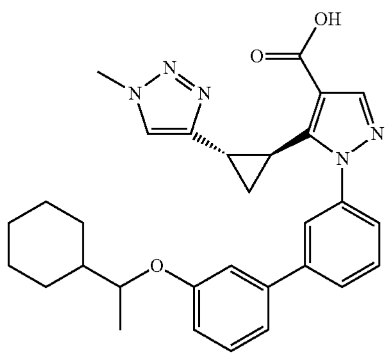 [SMILES: CC(Oc1cccc(-c2cccc(-n3ncc(C(=O)O)c3[C@H]3C[C@@H]3c3cn(C)nn3)c2)c1)C1CCCCC1] | 1-(3'-(1-Cyclohexylethoxy)-[1,1'-biphenyl]-3-yl)-5-((1S,2S)-2-(1-methyl-1H-1,2,3-triazol-4-yl)cyclopropyl)-1H-pyrazole-4-carboxylic acid | 512.2 | 2.24 |
| 166 | 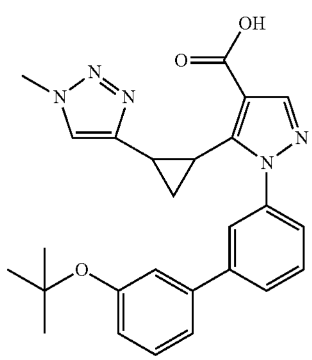 [SMILES: Cn1cc(C2CC2c2c(C(=O)O)cnn2-c2cccc(-c3cccc(OC(C)(C)C)c3)c2)nn1] | 1-(3'-(tert-Butoxy)-[1,1'-biphenyl]-3-yl)-5-(2-(1-methyl-1H-1,2,3-triazol-4-yl)cyclopropyl)-1H-pyrazole-4-carboxylic acid | 498.2 | 2.17 |
| 167 | 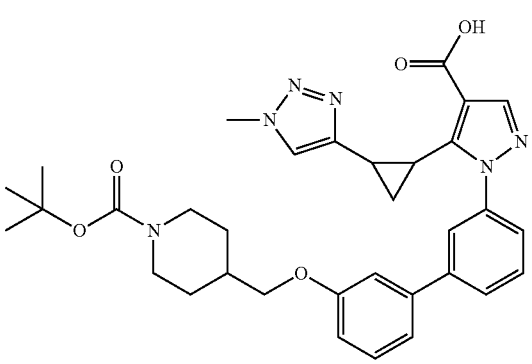 [SMILES: Cn1cc(C2CC2c2c(C(=O)O)cnn2-c2cccc(-c3cccc(OCC4CCN(C(=O)OC(C)(C)C)CC4)c3)c2)nn1] | 1-(3'-((1-(tert-Butoxycarbonyl)piperidin-4-yl)methoxy)-[1,1'-biphenyl]-3-yl)-5-(2-(1-methyl-1H-1,2,3-triazol-4-yl)cyclopropyl)-1H-pyrazole-4-carboxylic acid | 599.2 (H + Na) | 1.99 |

TABLE 8-continued

| Example | Structure | Name | LCMS [M + H]+ | Retention Time (min) |
|---|---|---|---|---|
| 168 | 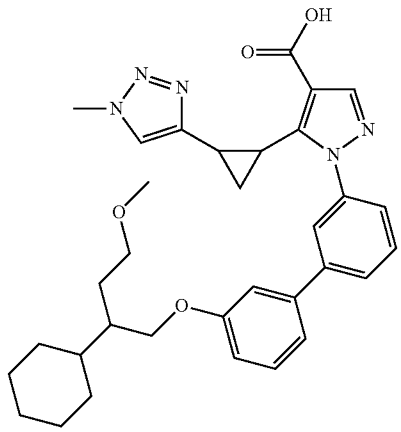 [SMILES: COCCC(COc1cccc(-c2cccc(-n3ncc(C(=O)O)c3C3CC3c3cn(C)nn3)c2)c1)C1CCCCC1] | 1-(3'-(2-Cyclohexyl-4-methoxybutoxy)-[1,1'-biphenyl]-3-yl)-5-(2-(1-methyl-1H-1,2,3-triazol-4-yl)cyclopropyl)-1H-pyrazole-4-carboxylic acid | 570.2 | 2.22 |
| 169 | 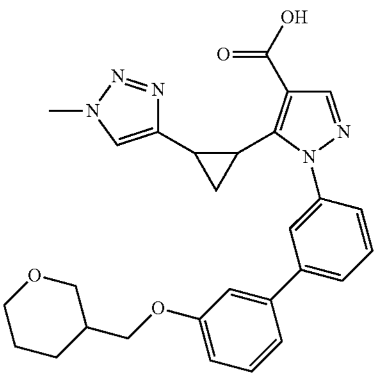 [SMILES: Cn1cc(C2CC2c2c(C(=O)O)cnn2-c2cccc(-c3cccc(OCC4CCCOC4)c3)c2)nn1] | 5-(2-(1-Methyl-1H-1,2,3-triazol-4-yl)cyclopropyl)-1-(3'-((tetrahydro-2H-pyran-3-yl)methoxy)-[1,1'-biphenyl]-3-yl)-1H-pyrazole-4-carboxylic acid | 500.2 | 1.52 |
| 170 | 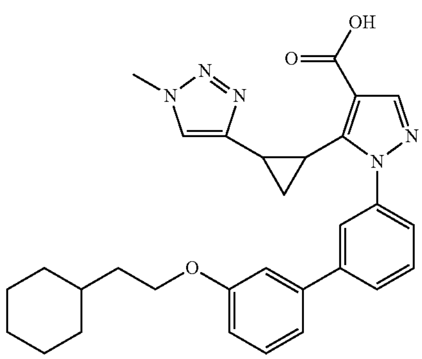 [SMILES: Cn1cc(C2CC2c2c(C(=O)O)cnn2-c2cccc(-c3cccc(OCCC4CCCCC4)c3)c2)nn1] | 1-(3'-(2-Cyclohexylethoxy)-[1,1'-biphenyl]-3-yl)-5-(2-(1-methyl-1H-1,2,3-triazol-4-yl)cyclopropyl)-1H-pyrazole-4-carboxylic acid | 512.2 | 2.27 |
| 171 | 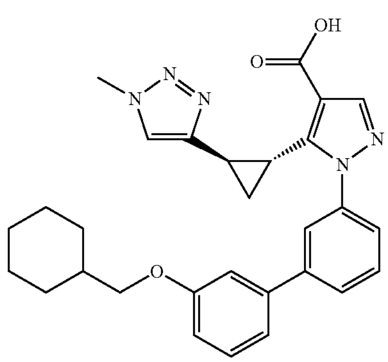 [SMILES: Cn1cc([C@@H]2C[C@H]2c2c(C(=O)O)cnn2-c2cccc(-c3cccc(OCC4CCCCC4)c3)c2)nn1] | 1-(3'-(Cyclohexylmethoxy)-[1,1'-biphenyl]-3-yl)-5-((1R,2R)-2-(1-methyl-1H-1,2,3-triazol-4-yl)cyclopropyl)-1H-pyrazole-4-carboxylic acid | 498.1 | 1.99 |

TABLE 8-continued

| Example | Structure | Name | LCMS [M + H]+ | Retention Time (min) |
|---|---|---|---|---|
| 172 | 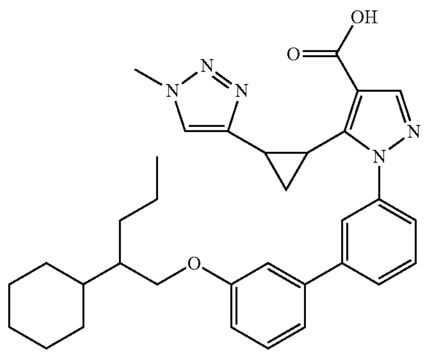 [SMILES: CCCC(COc1cccc(-c2cccc(-n3ncc(C(=O)O)c3C3CC3c3cn(C)nn3)c2)c1)C1CCCCC1] | 1-(3'-((2-Cyclohexylpentyl)oxy)-[1,1'-biphenyl]-3-yl)-5-(2-(1-methyl-1H-1,2,3-triazol-4-yl)cyclopropyl)-1H-pyrazole-4-carboxylic acid | 554.3 | 1.99 |
| 173 | 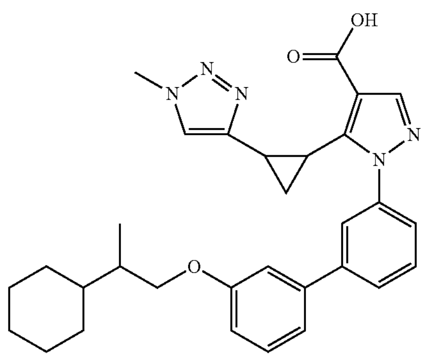 [SMILES: CC(COc1cccc(-c2cccc(-n3ncc(C(=O)O)c3C3CC3c3cn(C)nn3)c2)c1)C1CCCCC1] | 1-(3'-(2-Cyclohexylpropoxy)-[1,1'-biphenyl]-3-yl)-5-(2-(1-methyl-1H-1,2,3-triazol-4-yl)cyclopropyl)-1H-pyrazole-4-carboxylic acid | 526.2 | 1.82 |
| 174 | 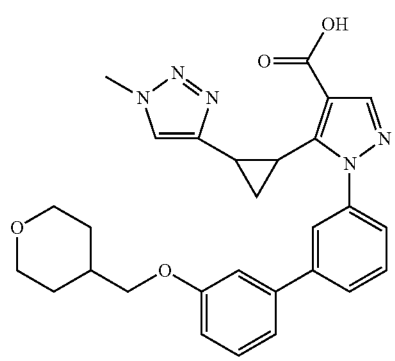 [SMILES: Cn1cc(C2CC2c2c(C(=O)O)cnn2-c2cccc(-c3cccc(OCC4CCOCC4)c3)c2)nn1] | 5-(2-(1-Methyl-1H-1,2,3-triazol-4-yl)cyclopropyl)-1-(3'-((tetrahydro-2H-pyran-4-yl)methoxy)-[1,1'-biphenyl]-3-yl)-1H-pyrazole-4-carboxylic acid | 500.1 | 1.53 |
| 175 | 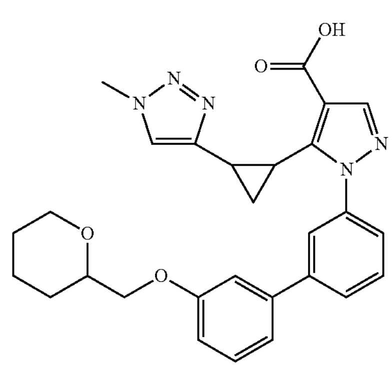 [SMILES: Cn1cc(C2CC2c2c(C(=O)O)cnn2-c2cccc(-c3cccc(OCC4CCCCO4)c3)c2)nn1] | 5-(2-(1-Methyl-1H-1,2,3-triazol-4-yl)cyclopropyl)-1-(3'-((tetrahydro-2H-pyran-2-yl)methoxy)-[1,1'-biphenyl]-3-yl)-1H-pyrazole-4-carboxylic acid | 500.1 | 1.53 |

TABLE 8-continued

| Example | Name | LCMS [M + H]+ | Retention Time (min) |
|---|---|---|---|
| 176 | 1-(3'-(((1R,4S)-4-Methoxycyclohexyl)methoxy)-[1,1'-biphenyl]-3-yl)-5-((1,2-trans)-2-(1-methyl-1H-1,2,3-triazol-4-yl)cyclopropyl)-1H-pyrazole-4-carboxylic acid | 528.2 | 1.91 |
| 177 | 1-(3'-((2-Methoxycyclohexyl)methoxy)-[1,1'-biphenyl]-3-yl)-5-((1,2-trans)-2-(1-methyl-1H-1,2,3-triazol-4-yl)cyclopropyl)-1H-pyrazole-4-carboxylic acid | 528.2 | 1.98 |
| 178 | 1-(3'-((3-Methoxycyclohexyl)methoxy)-[1,1'-biphenyl]-3-yl)-5-((1,2-trans)-2-(1-methyl-1H-1,2,3-triazol-4-yl)cyclopropyl)-1H-pyrazole-4-carboxylic acid | 528.3 | 1.95 |
| 179 | 1-(3'-((Cyclohexylmethyl)thio)-[1,1'-biphenyl]-3-yl)-5-(2-(1-methyl-1H-1,2,3-triazol-4-yl)cyclopropyl)-1H-pyrazole-4-carboxylic acid | 514.2 | 1.84 |

TABLE 8-continued

| Example | Structure | Name | LCMS [M + H]+ | Retention Time (min) |
|---|---|---|---|---|
| 180 | 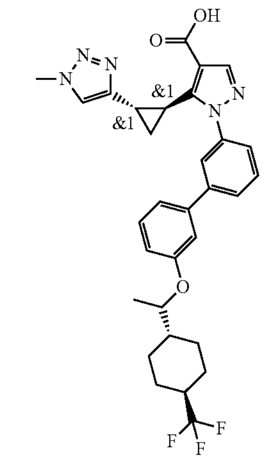 [SMILES: CC(Oc1cccc(-c2cccc(-n3ncc(C(=O)O)c3[C@H]3C[C@@H]3c3cn(C)nn3)c2)c1)[C@H]1CC[C@H](C(F)(F)F)CC1] | 5-((1,2-trans)-2-(1-Methyl-1H-1,2,3-triazol-4-yl)cyclopropyl)-1-(3'-((R)-1-((1R,4R)-4-(trifluoromethyl)cyclohexyl)ethoxy)-[1,1'-biphenyl]-3-yl)-1H-pyrazole-4-carboxylic acid | 580.2 | 1.86 |
| 181 | 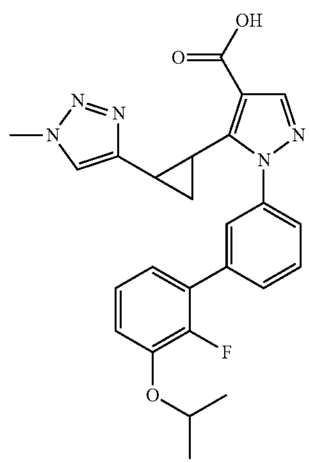 [SMILES: CC(C)Oc1cccc(-c2cccc(-n3ncc(C(=O)O)c3C3CC3c3cn(C)nn3)c2)c1F] | 1-(2'-Fluoro-3'-isopropoxy-[1,1'-biphenyl]-3-yl)-5-(2-(1-methyl-1H-1,2,3-triazol-4-yl)cyclopropyl)-1H-pyrazole-4-carboxylic acid | 462.3 | 1.83 |
| 182 | 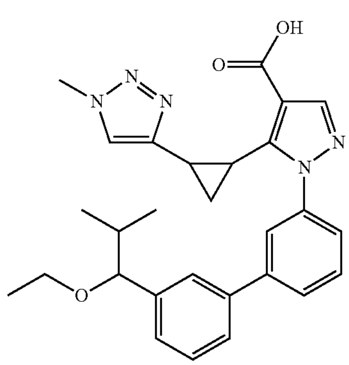 [SMILES: CCOC(c1cccc(-c2cccc(-n3ncc(C(=O)O)c3C3CC3c3cn(C)nn3)c2)c1)C(C)C] | 1-(3'-(1-Ethoxy-2-methylpropyl)-[1,1'-biphenyl]-3-yl)-5-(2-(1-methyl-1H-1,2,3-triazol-4-yl)cyclopropyl)-1H-pyrazole-4-carboxylic acid | 486.1 | 1.99 |

TABLE 8-continued

| Example | Structure | Name | LCMS [M + H]+ | Retention Time (min) |
|---|---|---|---|---|
| 183 | 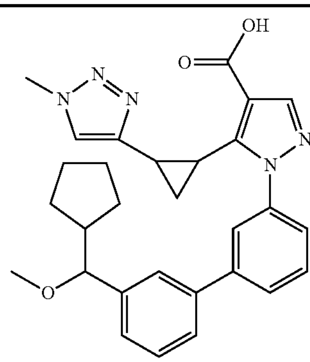 | 1-(3'-(Cyclopentyl(methoxy)methyl)-[1,1'-biphenyl]-3-yl)-5-(2-(1-methyl-1H-1,2,3-triazol-4-yl)cyclopropyl)-1H-pyrazole-4-carboxylic acid | 498.1 | 1.99 |
| 184 | 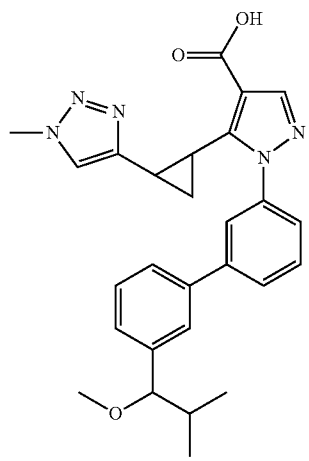 [SMILES: COC(c1cccc(-c2cccc(-n3ncc(C(=O)O)c3C3CC3c3cn(C)nn3)c2)c1)C(C)C] | 1-(3'-(1-Methoxy-2-methylpropyl)-[1,1'-biphenyl]-3-yl)-5-(2-(1-methyl-1H-1,2,3-triazol-4-yl)cyclopropyl)-1H-pyrazole-4-carboxylic acid | 472.1 | 1.93 |

163a) 1-Bromo-3-(1-cyclohexylethoxy)benzene 164a) 1-Bromo-3-(cyclohexylmethoxy)benzene

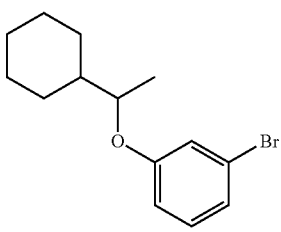 [SMILES: CC(Oc1cccc(Br)c1)C1CCCCC1]

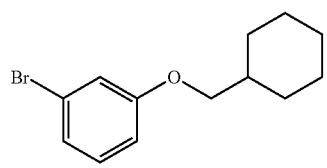

A solution of 3-bromophenol (1.5 g, 8.67 mmol), triphenylphosphine (2.73 g, 10.40 mmol), 1-cyclohexylethanol (1.334 g, 10.40 mmol) in tetrahydrofuran (THF) (10 mL) was added a solution of DIAD (2.023 mL, 10.40 mmol) in tetrahydrofuran (THF) (10 mL) slowly under nitrogen at 25° C. The reaction mixture was stirred at 25° C. for 16 h. 30 mL of water was added and extracted with ethyl acetate (3×). The combined organic phase was washed with brine, dried over $Na_2SO_4$ and concentrated. The residue was purified on silica gel chromatography (hexane:ethyl acetate=10:1) to obtain the title compound 1-bromo-3-(1-cyclohexylethoxy)benzene (1.5 g, 5.30 mmol, 61.1% yield).

A solution of 3-bromophenol (500 mg, 2.89 mmol), (bromomethyl)cyclohexane (1024 mg, 5.78 mmol) in N,N-dimethylformamide (DMF) (5 mL) was added $K_2CO_3$ (799 mg, 5.78 mmol) slowly under nitrogen at room temperature. The mixture reaction was stirred at 150° C. for 4 h. 10 mL of water was added and extracted with ethyl acetate (3×). The combined organic layer was concentrated to obtain the title compound 1-bromo-3-(cyclohexylmethoxy)benzene (780 mg, 2.87 mmol, 99% yield) which was used in next step without further purification. LC-MS m/z 445.25 (M+H)+, 3.26 min (ret. time).

166a) 1-Bromo-3-(tert-butoxy)benzene

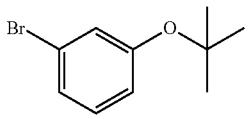

A solution of 3-bromophenol (400 mg, 2.312 mmol) and Boc₂O (1.181 mL, 5.09 mmol) in dichloromethane (DCM) (10 mL) was added Mg(ClO₄)₂ (64.5 mg, 0.231 mmol) slowly under nitrogen at room temperature. The reaction mixture was stirred at 40° C. for 16 h. It was concentrated to obtain the title compound 1-bromo-3-(tert-butoxy)benzene (187 mg, 0.775 mmol, 33.5% yield) which was used in next step without further purification.

166b) tert-Butyl 4-((3-bromophenoxy)methyl)piperidine-1-carboxylate

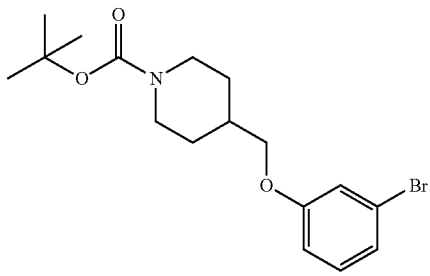 [SMILES: CC(C)(C)OC(=O)N1CCC(COc2cccc(Br)c2)CC1]

A solution of 3-bromophenol (1 g, 5.78 mmol) and triphenylphosphine (1.819 g, 6.94 mmol) in tetrahydrofuran (THF) (30 mL) was added DEAD (121 g, 0.694 mmol) in tetrahydrofuran (THF) (5 mL) slowly under nitrogen at 25° C. The reaction mixture was stirred at 25° C. for 16 h. 50 mL of water was added and extracted with ethyl acetate (3×). The combined organic phase was dried over Na₂SO₄ and concentrated. The crude product was purified by reverse-phase HPLC to obtain the title compound tert-butyl 4-((3-bromophenoxy)methyl)piperidine-1-carboxylate (500 mg, 1.215 mmol, 21.03% yield) which was used for next step without further purification. LC-MS m/z 392.1 (M+H)⁺, 2.32 min (ret. time).

168a) Ethyl 2-cyclohexyl-4-methoxybutanoate

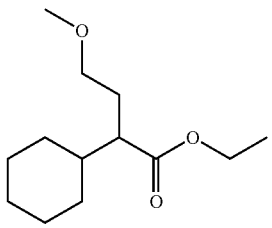 [SMILES: CCOC(=O)C(CCOC)C1CCCCC1]

A solution of ethyl 2-cyclohexylacetate (3 g, 17.62 mmol) in tetrahydrofuran (THF) (30 mL) was added LiHMDS (10.57 mL, 21.15 mmol) slowly under nitrogen at −78° C. The reaction mixture was stirred at −78° C. for 1 h. Then 1-bromo-2-methoxyethane (2.94 g, 21.15 mmol) in 5 mL of THF was added. It was stirred at room temperature for 16 h. 30 mL of water was added and extracted with ethyl acetate (3×). The combined organic phase was concentrated to obtain the title compound ethyl 2-cyclohexyl-4-methoxybutanoate (4 g, 15.77 mmol, 89% yield) which was used in next step without further purification. LC-MS m/z 229.1 (M+H)⁺, 2.13 min (ret. time).

168b) 2-Cyclohexyl-4-methoxybutan-1-ol

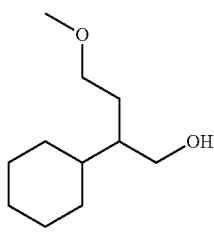

A solution of ethyl 2-cyclohexyl-4-methoxybutanoate (4 g, 17.52 mmol) in tetrahydrofuran (THF) (50 mL) was added LiAlH₄ (1 g, 26.3 mmol) slowly under nitrogen at 0° C. The reaction mixture was stirred at 0° C. for 0.5 h and stirred at room temperature for 2 h. 30 mL of water was added and extracted with ethyl acetate (3×). The combined organic phase was washed with brine, dried over Na₂SO₄ and concentrated. The crude product was purified on silica gel chromatography (hexane:ethyl acetate=4:1) to give the title compound 2-cyclohexyl-4-methoxybutan-1-ol (2 g, 8.59 mmol, 49.0% yield). ¹H NMR (400 MHz, CDCl₃) δ: 3.55-3.50 (m, 2H), 3.42-3.38 (m, 1H), 3.36 (s, 3H), 3.05 (t, J=5.7 Hz, 1H), 1.76-1.68 (m, 4H), 1.44-0.93 (m, 10H).

168c) (1-Iodo-4-methoxybutan-2-yl)cyclohexane

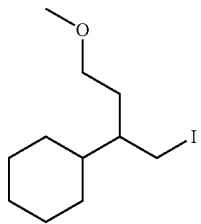

A solution of triphenylphosphine (1690 mg, 6.44 mmol) in tetrahydrofuran (THF) (10 mL) was added imidazole (439 mg, 6.44 mmol) and I₂ (1635 mg, 6.44 mmol) slowly under nitrogen at 25° C. The reaction mixture was stirred at 25° C. for 1 h. Then 2-cyclohexyl-4-methoxybutan-1-ol (1000 mg, 5.37 mmol) in 5 mL of THF was added. The solid was filtered and filtrate was concentrated. The crude product was purified by silica gel chromatography (hexane:ethyl acetate=20:1) to obtain the title compound (1-iodo-4-methoxybutan-2-yl)cyclohexane (1.2 g, 3.65 mmol, 67.9% yield). ¹H NMR (400 MHz, CDCl₃) δ: 3.40 (dd, J=9.9, 3.8 Hz, 3H), 3.33 (s, 3H), 3.31 (d, J=4.6 Hz, 2H), 1.77-1.70 (m, 2H), 1.38-0.81 (m, 12H).

168d) 1-Bromo-3-((1-cyclohexyl-4-methoxybutan-2-yl)oxy)benzene

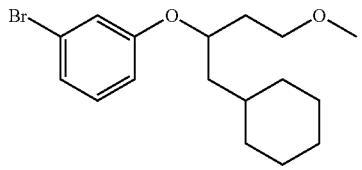 [SMILES: COCCC(CC1CCCCC1)Oc1cccc(Br)c1]

A solution of 3-bromophenol (0.5 g, 2.89 mmol) in N,N-dimethylformamide (DMF) (10 mL) was added (1-iodo-4-methoxybutan-2-yl)cyclohexane hydrochloride (1.154 g, 3.47 mmol) and K₂CO₃ (0.799 g, 5.78 mmol) slowly under nitrogen at room temperature. The reaction mixture was stirred at 150° C. for 16 h. 30 mL of water was added and extracted with ethyl acetate (3×). The combined organic phase was washed with brine, dried over $Na_2SO_4$ and concentrated. The crude product was purified on silica gel chromatography (hexane:ethyl acetate=10:1) to obtain the title compound 1-bromo-3-((1-cyclohexyl-4-methoxybutan-2-yl)oxy)benzene (380 mg, 0.779 mmol, 27.0% yield). ¹H NMR (400 MHz, CDCl₃) δ: 7.12 (t, J=8.2 Hz, 1H), 7.08-7.04 (m, 2H), 6.82 (ddd, J=8.2, 2.3, 1.1 Hz, 1H), 3.48 (t, J=7.2 Hz, 2H), 3.35 (s, 3H), 1.80-1.62 (m, 14H), 1.33-1.18 (m, 4H).

169a) 3-((3-Bromophenoxy)methyl)tetrahydro-2H-pyran

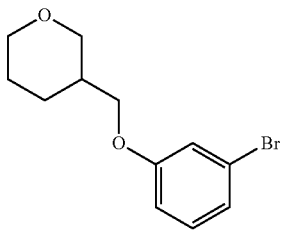 [SMILES: Brc1cccc(OCC2CCCOC2)c1]

A solution of 3-bromophenol (500 mg, 2.89 mmol), triphenylphosphine (758 mg, 2.89 mmol) and (tetrahydro-2H-pyran-3-yl)methanol (420 mg, 3.62 mmol) in tetrahydrofuran (THF) (10 mL) was added DIAD (0.674 mL, 3.47 mmol) in tetrahydrofuran (THF) (10 mL) slowly under nitrogen at 0° C. The reaction mixture was stirred at 25° C. for 16 h. The solvent was evaporated and was purified by reverse-phase HPLC to obtain the title compound 3-((3-bromophenoxy)methyl)tetrahydro-2H-pyran (260 mg, 0.911 mmol, 31.5% yield). LC-MS m/z 271.0 (M+H)⁺, 2.10 min (ret. time).

170a) 1-Bromo-3-(2-cyclohexylethoxy)benzene

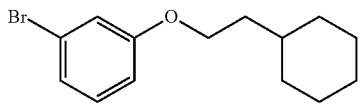 [SMILES: Brc1cccc(OCCC2CCCCC2)c1]

To a solution of 3-bromophenol (500 mg, 2.89 mmol) and (2-bromoethyl)cyclohexane (580 mg, 3.03 mmol) in N,N-dimethylformamide (DMF) (5 mL) was added K₂CO₃ (799 mg, 5.78 mmol) slowly under nitrogen at room temperature. The reaction mixture was stirred at 150° C. for 4 h. 10 mL of water was added and extracted with ethyl acetate (3×). The combined organic phase was concentrated to obtain the title compound 1-bromo-3-(2-cyclohexylethoxy)benzene (700 mg, 1.977 mmol, 68.4% yield) which was used in next step without further purification.

172a) Ethyl 2-cyclohexylpentanoate

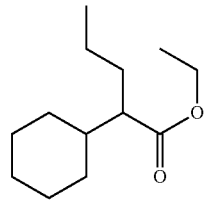

A solution of ethyl 2-cyclohexylacetate (1000 mg, 5.87 mmol) in tetrahydrofuran (THF) (10 mL) was added LDA (6 mL, 6.00 mmol) slowly under nitrogen at −78° C. The reaction mixture was stirred at −78° C. for 1 h. It was added 1-iodopropane (1198 mg, 7.05 mmol) in 5 mL of THF. It was stirred at room temperature for 1 h. 30 mL of water was added and extracted with ethyl acetate (3×). The combined organic phase was washed with brine, dried over $Na_2SO_4$ and concentrated. The crude product purified on silica gel chromatography (hexane:ether=10:1) to obtain the title compound ethyl 2-cyclohexylpentanoate (1.1 g, 5.18 mmol, 88% yield). LC-MS m/z 213.2 (M+H)⁺, 1.98 min (ret. time).

172b) 2-Cyclohexylpentan-1-ol

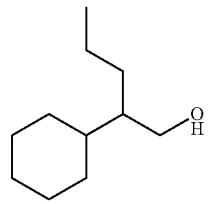

A solution of ethyl 2-cyclohexylpentanoate (1100 mg, 5.18 mmol) in tetrahydrofuran (THF) (30 mL), LiAlH₄ (393 mg, 10.36 mmol) was added slowly under nitrogen at 0° C. The reaction mixture was stirred at 0° C. for 1 h. 10 mL of water was added and extracted with ethyl acetate (3×). The combined organic phase was washed with brine, dried over $Na_2SO_4$ and concentrated to obtain the title compound 2-cyclohexylpentan-1-ol (700 mg, 4.11 mmol, 79% yield) which was used in next step without further purification.

172c) 1-Bromo-3-((2-cyclohexylpentyl)oxy)benzene

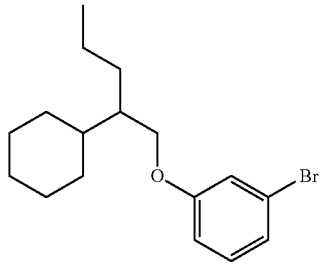 [SMILES: CCCC(COc1cccc(Br)c1)C1CCCCC1]

A solution of 3-bromophenol (400 mg, 2.312 mmol), triphenylphosphine (728 mg, 2.77 mmol) and 2-cyclohexylpentan-1-ol (472 mg, 2.77 mmol) in tetrahydrofuran (THF) (10 mL) was added DIAD (0.539 mL, 2.77 mmol) in tetrahydrofuran (THF) (10 mL) slowly under nitrogen at 25° C. The reaction mixture was stirred at 25° C. for 16 h. 30 mL of water was added and extracted with ethyl acetate (3×). The combined organic phase was washed with brine, dried over $Na_2SO_4$ and concentrated. The crude product was purified on silica gel chromatography (hexane:ethyl acetate=10:1) to obtain the title compound 1-bromo-3-((2-cyclohexylpentyl)oxy)benzene (350 mg, 0.915 mmol, 39.6% yield). $^1$H NMR (400 MHz, $CDCl_3$) δ 7.12 (t, J=8.3 Hz, 1H), 7.08-7.02 (m, 2H), 6.82 (ddd, J=8.3, 2.3, 1.0 Hz, 1H), 3.88 (dd, J=9.2, 5.8 Hz, 1H), 3.81 (dd, J=9.1, 5.5 Hz, 1H), 1.80-1.59 (m, 6H), 1.27 (m, 10H), 0.91 (dd, J=8.6, 4.7 Hz, 3H).

173a) Ethyl 2-cyclohexylpropanoate

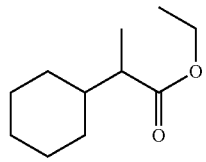

A solution of ethyl 2-cyclohexylacetate (10 g, 58.7 mmol) in tetrahydrofuran (THF) (100 mL) was added LiHMDS (70.5 mL, 70.5 mmol) slowly under nitrogen at −78° C. The reaction mixture was stirred at −78° C. for 1 h. Then iodomethane (10.00 g, 70.5 mmol) in 50 mL of THF was added. The reaction mixture was stirred at room temperature for 1 h. 30 mL of water was added and extracted with ethyl acetate (3×). The combined organic phase was washed with brine, dried over $Na_2SO_4$ and concentrated to obtain the title compound ethyl 2-cyclohexylpropanoate (10 g, 48.8 mmol, 83% yield) which was used in next step without further purification. LC-MS m/z 185.1 (M+H)$^+$, 2.28 min (ret. time).

173b) 2-Cyclohexylpropan-1-ol

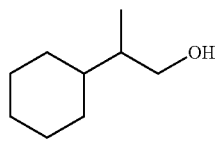

A solution of ethyl 2-cyclohexylpropanoate (10 g, 54.3 mmol) in tetrahydrofuran (THF) (10 mL) was added $LiAlH_4$ (4.12 g, 109 mmol) slowly under nitrogen at 0° C. The reaction mixture was stirred at 0° C. for 0.5 h and stirred at room temperature for 2 h. 30 mL of water was added and extracted with ethyl acetate (3×). The combined organic phase was washed with brine, dried over $Na_2SO_4$ and concentrated. The crude product was purified on silica gel chromatography (hexane:ethyl acetate=10:1) to obtain the title compound 2-cyclohexylpropan-1-ol (7.2 g, 45.6 mmol, 84% yield). $^1$H NMR (400 MHz, $CDCl_3$) δ 3.61 (dd, J=10.2, 5.7 Hz, 1H), 3.50-3.42 (m, 1H), 1.78-1.61 (m, 4H), 1.48 (dd, J=12.7, 6.3 Hz, 1H), 1.37-0.96 (m, 8H), 0.89 (d, J=6.9 Hz, 3H).

173c) 1-Bromo-3-(2-cyclohexylpropoxy)benzene

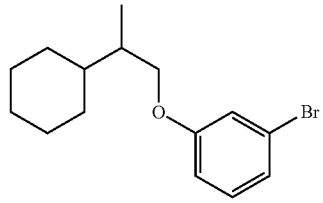 [SMILES: CC(COc1cccc(Br)c1)C1CCCCC1]

A solution of 3-bromophenol (1 g, 5.78 mmol), triphenylphosphine (1.819 g, 6.94 mmol) and 2-cyclohexylpropan-1-ol (0.987 g, 6.94 mmol) in tetrahydrofuran (THF) (10 mL) was added DIAD (1.349 mL, 6.94 mmol) in tetrahydrofuran (THF) (10 mL) slowly under nitrogen at 25° C. The reaction mixture was stirred at 25° C. for 16 h. 30 mL of water was added and extracted with ethyl acetate (3×). The combined organic phase was washed with brine, dried over $Na_2SO_4$ and concentrated. The crude product was purified on silica gel chromatographyl (hexane:ethyl acetate=10:1) to obtain the title compound 1-bromo-3-(2-cyclohexylpropoxy)benzene (1000 mg, 3.03 mmol, 52.4% yield).

174a) (Tetrahydro-2H-pyran-4-yl)methyl Methanesulfonate

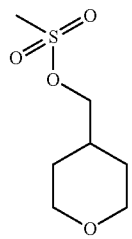

A solution of (tetrahydro-2H-pyran-4-yl)methanol (0.9 g, 7.75 mmol), TEA (2.160 mL, 15.50 mmol) in dichloromethane (DCM) (10 mL) was added methanesulfonyl chloride (0.932 g, 8.14 mmol) in dichloromethane (DCM) (10 mL) slowly under nitrogen at 0° C. The reaction mixture was stirred at room temperature for 12 h. 10 mL of water was added and extracted with ethyl acetate (3×). The combined organic phase was washed with brine, dried over $Na_2SO_4$ and concentrated to obtain the title compound (tetrahydro-2H-pyran-4-yl)methyl methanesulfonate (900 mg, 3.71 mmol, 47.8% yield) which was used in next step without further purification. LC-MS m/z 195.1 (M+H)⁺, 1.29 min (ret. time).

174b) 4-((3-Bromophenoxy)methyl)tetrahydro-2H-pyran

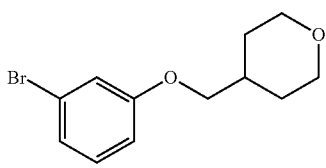 [SMILES: Brc1cccc(OCC2CCOCC2)c1]

A solution of 3-bromophenol (0.5 g, 2.89 mmol) in N,N-dimethylformamide (DMF) (10 mL) was added (tetrahydro-2H-pyran-4-yl)methylmethanesulfonate (0.9 g, 4.63 mmol), $K_2CO_3$ (0.799 g, 5.78 mmol) and KI (0.480 g, 2.89 mmol) slowly under nitrogen at room temperature. The reaction mixture was stirred at 120° C. for 6 h. 10 mL of water was added and extracted with ethyl acetate (3×). The combined organic phase was concentrated. It was purified on silica gel chromatography (petroleum ether:ethyl acetate=5:1) to obtain the title compound 4-((3-bromophenoxy)methyl)tetrahydro-2H-pyran (600 mg, 2.036 mmol, 70.4% yield).

175a) 2-((3-Bromophenoxy)methyl)tetrahydro-2H-pyran

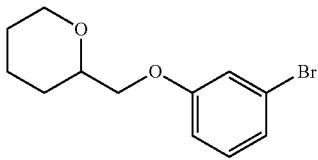 [SMILES: Brc1cccc(OCC2CCCCO2)c1]

A solution of 3-bromophenol (1 g, 5.78 mmol) in DMF (20 mL) was added 2-(bromomethyl)tetrahydro-2H-pyran (1.035 g, 5.78 mmol) and $K_2CO_3$ (2.397 g, 17.34 mmol) slowly under 20° C. The reaction mixture was stirred at 150° C. for 2 h. 10 mL of water was added and extracted with ethyl acetate (3×). The combined organic layer was washed with brine, dried over $Na_2SO_4$ and concentrated. The residue was purified on silica gel chromatography (hexane:ethyl acetate=5:1) to obtain the title compound 2-((3-bromophenoxy)methyl)tetrahydro-2H-pyran (1.53 g, 5.08 mmol, 88% yield). LC-MS m/z 271.0 (M+H)⁺, 2.11 min (ret. time).

176a) (1r,4r)-4-(Hydroxymethyl)cyclohexanol

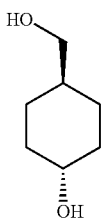

A solution of (1r,4r)-4-hydroxycyclohexanecarboxylic acid (3 g, 20.81 mmol) in tetrahydrofuran (THF) (150 mL) was added $LiAlH_4$ (1.5 g, 39.5 mmol) slowly under nitrogen at room temperature. The reaction mixture was stirred at 60° C. for 16 h. Then it was cooled to 0° C., 1.5 mL of water, 1.5 mL of 10% NaOH, 4.5 mL of water were added. The solid was filtered and the filtrate was concentrated under a stream of nitrogen at 50° C. to obtain the title compound (1r,4r)-4-(hydroxymethyl)cyclohexanol (2000 mg, 14.59 mmol, 70.1% yield) which was used in next step without further purification. ¹H NMR (500 MHz, DMSO-d6) δ: 4.45 (d, J=4.3 Hz, 1H), 4.35 (t, J=5.3 Hz, 1H), 3.31-3.25 (m, 1H), 3.20-3.13 (m, 2H), 1.88-1.76 (m, 2H), 1.73-1.62 (m, 2H), 1.22 (tdd, J=20.9, 9.9, 7.3 Hz, 1H), 1.14-1.01 (m, 2H), 0.86 (qd, J=13.3, 3.2 Hz, 2H).

176b) (1r,4r)-4-((3-Bromophenoxy)methyl)cyclohexanol

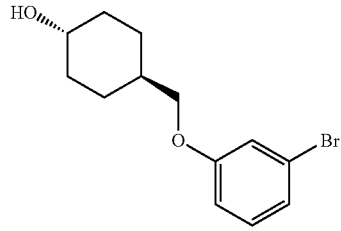 [SMILES: O[C@H]1CC[C@H](COc2cccc(Br)c2)CC1]

A solution of 3-bromophenol (2 g, 11.56 mmol), triphenylphosphine (3.03 g, 11.56 mmol) and (1r,4r)-4-(hydroxymethyl)cyclohexanol (2.5 g, 19.20 mmol) in tetrahydrofuran (THF) (150 mL) was added DIAD (2.70 mL, 13.87 mmol) in tetrahydrofuran (THF) (150 mL) slowly under nitrogen at 25° C. The reaction mixture was stirred at 25° C. for 16 h. The reaction mixture was concentrated. The crude product was purified on silica gel chromatography (hexane:ethyl acetate=4:1) to provide the title compound (1r,4r)-4-((3-bromophenoxy)methyl)cyclohexanol (1.2 g, 2.104 mmol, 18.20% yield) as an oil. 1H NMR (500 MHz, DMSO) δ 7.22 (t, J=8.1 Hz, 1H), 7.14-7.06 (m, 2H), 6.98-6.88 (m, 1H), 4.52 (d, J=4.4 Hz, 1H), 3.90-3.73 (m, 2H), 1.91-1.75 (m, 4H), 1.06 (dd, J=18.7, 8.5 Hz, 2H), 0.84 (ddd, J=13.0, 7.7, 4.6 Hz, 2H).

176c) 1-Bromo-3-(((1r,4r)-4-methoxycyclohexyl)methoxy)benzene

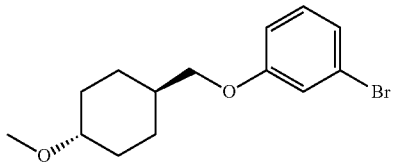 [SMILES: CO[C@H]1CC[C@H](COc2cccc(Br)c2)CC1]

A solution of (1r,4r)-4-((3-bromophenoxy)methyl)cyclohexanol (300 mg, 1.052 mmol) in N,N-dimethylformamide (DMF) (10 mL) was added NaH (168 mg, 4.21 mmol) slowly under nitrogen at 25° C. The reaction mixture was stirred at 25° C. for 1 h. Then iodomethane (597 mg, 4.21 mmol) was added and stirred at 25° C. for 12 h. 30 mL of water was added and extracted with ethyl acetate (3×). The combined organic phase was concentrated under a stream of nitrogen at 50° C. The crude product was purified on silica gel chromatography (petroleum ether:ethyl acetate=5:1) to provide the title compound 1-bromo-3-(((1r,4r)-4-methoxycyclohexyl)methoxy)benzene (250 mg, 0.794 mmol, 75% yield) which was used in next step without further purification. ¹H NMR (500 MHz, CDCl₃) δ 7.12 (t, J=8.0 Hz, 1H), 7.08-7.00 (m, 2H), 6.81 (dd, J=8.2, 1.6 Hz, 1H), 3.74 (d, J=6.3 Hz, 2H), 3.37 (s, 3H), 3.13 (ddd, J=14.8, 9.5, 4.1 Hz, 1H), 2.13 (d, J=9.7 Hz, 2H), 1.99-1.90 (m, 2H), 1.85-1.69 (m, 1H), 1.30-1.19 (m, 3H), 1.16-1.01 (m, 2H).

177a) Ethyl 2-hydroxycyclohexanecarboxylate

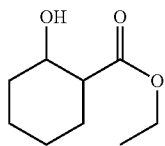

A solution of ethyl 2-oxocyclohexanecarboxylate (10 g, 58.8 mmol) in ethanol (100 mL) was added NaBH₄ (4 g, 106 mmol) slowly under nitrogen at −40° C. The reaction mixture was stirred at −40° C. for 1 h. Then 10 mL of AcOH was added. After the reaction mixture was concentrated, 50 mL of water was added and extracted with ethyl acetate (3×). The combined organic layer was concentrated under a stream of nitrogen at 50° C. The crude product was purified on silica gel chromatography (hexane:ethyl acetate=1:1) to obtain the title compound ethyl 2-hydroxycyclohexanecarboxylate (3 g, 15.68 mmol, 26.7% yield) which was used for next step without further purification. LC-MS m/z 173.1 (M+H)⁺, 1.35 min (ret. time).

177b) 2-(Hydroxymethyl)cyclohexanol

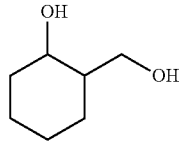

A solution of ethyl 2-hydroxycyclohexanecarboxylate (3 g, 17.42 mmol) in tetrahydrofuran (THF) (50 mL) was added LiAlH₄ (1 g, 26.3 mmol) slowly under nitrogen at 0° C. The reaction mixture was stirred at 25° C. for 2 h. After it was cooled to 0° C., 1 mL of water, 1 mL of 10% NaOH and 3 mL of water were added. The solid was filtered and the filtrate was concentrated under a stream of nitrogen at 50° C. to obtain the title compound 2-(hydroxymethyl)cyclohexanol (2.3 g, 15.90 mmol, 91% yield) which was used in next step without further purification. LC-MS m/z 131.0 (M+H)⁺, 1.34 min (ret. time).

177c) (2-Hydroxycyclohexyl)methyl 4-methylbenzenesulfonate

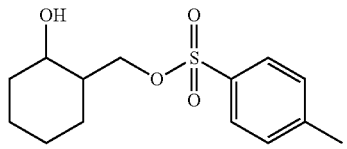 [SMILES: Cc1ccc(S(=O)(=O)OCC2CCCCC2O)cc1]

A solution of 2-(hydroxymethyl)cyclohexanol (2000 mg, 15.36 mmol) in dichloromethane (DCM) (50 mL) was added DMAP (188 mg, 1.536 mmol), TEA (4.28 mL, 30.7 mmol) and 4-methylbenzene-1-sulfonyl chloride (3515 mg, 18.44 mmol) slowly under nitrogen at 0° C. The reaction mixture was stirred at room temperature for 16 h. 30 mL of water was added and extracted with ethyl acetate (3×). The combined organic layer was concentrated under a stream of nitrogen at 50° C. The crude product was purified on silica gel chromatography (hexane:ethyl acetate=4:1) to obtain the title compound (2-hydroxycyclohexyl)methyl 4-methylbenzenesulfonate (1.3 g, 4.11 mmol, 26.8% yield). ¹H NMR (500 MHz, DMSO-d6) δ 7.77 (d, J=8.2 Hz, 2H), 7.48 (d, J=8.0 Hz, 2H), 4.64 (d, J=5.5 Hz, 1H), 4.16 (dd, J=9.3, 3.1 Hz, 1H), 3.94 (dd, J=9.1, 7.5 Hz, 1H), 3.07 (dd, J=9.9, 5.2 Hz, 1H), 2.42 (s, 3H), 1.80 (d, J=9.4 Hz, 1H), 1.70-1.49 (m, 3H), 1.45-1.37 (m, 1H), 1.19-0.89 (m, 4H).

177d) 2-((3-Bromophenoxy)methyl)cyclohexanol

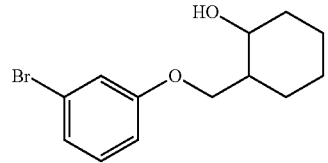 [SMILES: OC1CCCCC1COc1cccc(Br)c1]

A solution of (2-hydroxycyclohexyl)methyl 4-methylbenzenesulfonate (1.3 g, 4.34 mmol) in N,N-dimethylformamide (DMF) (20 mL) was added 3-bromophenol (810 mg, 4.68 mmol), K₂CO₃ (1.200 g, 8.69 mmol) under nitrogen at room temperature. The reaction mixture was stirred at 150° C. for 16 h. 50 mL of water was added and extracted with ethyl acetate (3×). The combined organic layer was concentrated under a stream of nitrogen at 50° C. The crude product was purified by reverse-phase HPLC to provide the title compound 2-((3-bromophenoxy)methyl)cyclohexanol (350 mg, 1.166 mmol, 26.8% yield) which was used for next step without further purification. LC-MS m/z 269.1 (M+H)⁺, 2.15 min (ret. time).

177e) 1-Bromo-3-((2-methoxycyclohexyl)methoxy)benzene

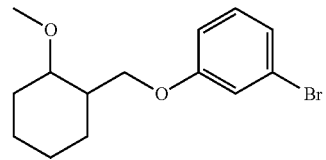 [SMILES: COC1CCCCC1COc1cccc(Br)c1]

A solution of 2-((3-bromophenoxy)methyl)cyclohexanol (100 mg, 0.351 mmol) in N,N-dimethylformamide (DMF) (10 mL) was added NaH (56.1 mg, 1.403 mmol) slowly under nitrogen at 25° C. The reaction mixture was stirred at 25° C. for 1 h. Then iodomethane (199 mg, 1.403 mmol) was added and stirred at 25° C. for 12 h. 30 mL of water was added and extracted with ethyl acetate (3×). The combined organic layer was concentrated under a stream of nitrogen at 50° C. The crude product was purified by reverse-phase HPLC to obtain the title compound 1-bromo-3-((2-methoxycyclohexyl)methoxy)benzene (100 mg, 0.334 mmol, 95% yield) which was used in next step without further purification.

178a) Ethyl 1,4-dioxaspiro[4.5]decane-7-carboxylate

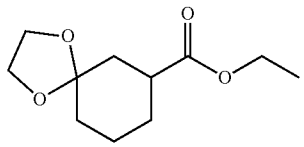

A solution of ethyl 3-oxocyclohexanecarboxylate (4.5 g, 26.4 mmol) in toluene (50 mL) was added ethane-1,2-diol (1.805 g, 29.1 mmol) and TsOH (0.251 g, 1.322 mmol) slowly under nitrogen at room temperature. The reaction mixture was refluxed with Dean-star trap overnight. After the mixture was cooled down, it was diluted with ethyl acetate (60 mL) and washed with saturated $NaHCO_3$ (2×), water and brine. The combined organic layer was dried over $Na_2SO_4$ and concentrated under reduced pressure. The resulting residue was dried under high vacuum to afford the title compound ethyl 1,4-dioxaspiro[4.5]decane-7-carboxylate (5.2 g, 21.84 mmol, 83% yield). LC-MS m/z 215.2 $(M+H)^+$, 1.81 min (ret. time).

178b) 1,4-Dioxaspiro[4.5]decan-7-ylmethanol

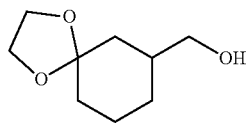 [SMILES: OCC1CCCC2(C1)OCCO2]

A solution of ethyl 1,4-dioxaspiro[4.5]decane-7-carboxylate (5.2 g, 24.27 mmol) in tetrahydrofuran (THF) (200 mL) was added $LiAlH_4$ (1.2 g, 31.6 mmol) slowly under nitrogen at 0° C. The reaction mixture was stirred at 0° C. for 0.5 h and stirred at room temperature for 2 h. It was added 1.2 mL of water, 1.2 mL of 10% NaOH, 3.6 mL of water. The solid was filtered. The filtrate was concentrated to provide the title compound 1,4-dioxaspiro[4.5]decan-7-ylmethanol (4.2 g, 21.95 mmol, 90% yield) which was used in next step without further purification. $^1$H NMR (500 MHz, $CDCl_3$) δ 3.99-3.88 (m, 4H), 3.49 (dd, J=5.7, 3.8 Hz, 2H), 1.87-1.69 (m, 5H), 1.60-1.39 (m, 3H), 1.03-0.89 (m, 1H).

178c) 1,4-Doxaspiro[4.5]decan-7-ylmethyl 4-methylbenzenesulfonate

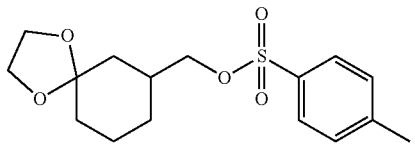 [SMILES: Cc1ccc(S(=O)(=O)OCC2CCCC3(C2)OCCO3)cc1]

A solution of 1,4-dioxaspiro[4.5]decan-7-ylmethanol (3.8 g, 22.06 mmol), DMAP (0.270 g, 2.206 mmol) in dichloromethane (DCM) (100 mL) was added 4-methylbenzene-1-sulfonyl chloride (5.05 g, 26.5 mmol) slowly under nitrogen at 0° C. The reaction mixture was stirred at 25° C. for 16 h. 30 mL of water was added and extracted with ethyl acetate (3×). The combined organic phase was concentrated under a stream of nitrogen at 50° C. The crude product was purified on silica gel chromatography (hexane:ethyl acetate=4:1) to obtain the title compound 1,4-dioxaspiro[4.5]decan-7-ylmethyl 4-methylbenzenesulfonate (6.3 g, 17.76 mmol, 80% yield) which was used for next step without further purification. LC-MS m/z 327.1 $(M+H)^+$, 1.95 min (ret. time).

178d) 7-((3-Bromophenoxy)methyl)-1,4-dioxaspiro[4.5]decane

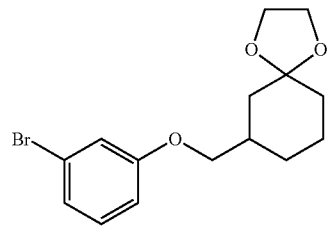 [SMILES: Brc1cccc(OCC2CCCC3(C2)OCCO3)c1]

A solution of 3-bromophenol (3000 mg, 17.34 mmol) in N,N-dimethylformamide (DMF) (100 mL) was added NaH (832 mg, 20.81 mmol) slowly under nitrogen at room temperature. It was stirred at room temperature for 0.5 h. Then 1,4-dioxaspiro[4.5]decan-7-ylmethyl 4-methylbenzenesulfonate (5958 mg, 17.34 mmol) was added. The reaction mixture was stirred at 150° C. for 4 h. 500 mL of water was added and extracted with ethyl acetate (3×). The combined organic layer was washed with brine, dried over $Na_2SO_4$ and concentrated under a stream of nitrogen at 50° C. The crude product was purified on silica gel chromatography (petroleum ether:ethyl acetate=5:1) to provide the title compound 7-((3-bromophenoxy)methyl)-1,4-dioxaspiro[4.5]decane (5.7 g, 16.90 mmol, 97% yield). LC-MS m/z 327.0 $(M+H)^+$, 2.29 min (ret. time).

178e) 3-((3-Bromophenoxy)methyl)cyclohexanone

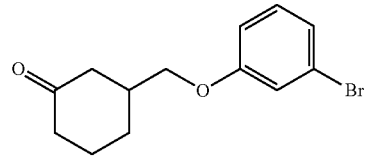 [SMILES: O=C1CCCC(COc2cccc(Br)c2)C1]

A solution of 7-((3-bromophenoxy)methyl)-1,4-dioxaspiro[4.5]decane (5.6 g, 17.11 mmol) in tetrahydrofuran (THF) (100 mL) was added HCl (100 ml, 100 mmol) slowly under nitrogen at 25° C. The reaction mixture was stirred at 25° C. for 12 h. It was extracted with ethyl acetate (3×). The combined organic layer was washed with brine, dried over Na$_2$SO$_4$ and concentrated under a stream of nitrogen at 50° C. to provide the title compound 3-((3-bromophenoxy)methyl)cyclohexanone (3.5 g, 11.12 mmol, 65% yield) which was used for next step without further purification. LC-MS m/z 283.0 (M+H)$^+$, 1.69 min (ret. time).

178f) 3-((3-Bromophenoxy)methyl)cyclohexanol

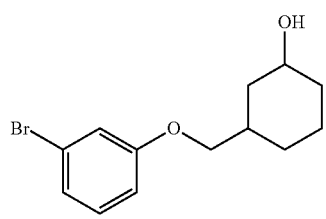 [SMILES: OC1CCCC(COc2cccc(Br)c2)C1]

A solution of 3-((3-bromophenoxy)methyl)cyclohexanone (3500 mg, 12.36 mmol) in methanol (100 mL) was added NaBH$_4$ (468 mg, 12.36 mmol) slowly under nitrogen at 0° C. The reaction mixture was stirred at 0° C. for 0.5 h. 50 mL of water was added and extracted with ethyl acetate (3×). The combined organic layer was concentrated under a stream of nitrogen at 50° C. The crude product was purified on silica gel chromatography (hexane:ethyl acetate=4:1) to obtain the title compound 3-((3-bromophenoxy)methyl)cyclohexanol (1200 mg, 4.21 mmol, 34.0% yield). LC-MS m/z 317.2 (M+Na)$^+$, 1.65 min (ret. time).

178g) 1-Bromo-3-((3-methoxycyclohexyl)methoxy)benzene

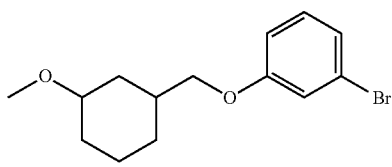 [SMILES: COC1CCCC(COc2cccc(Br)c2)C1]

A solution of 3-((3-bromophenoxy)methyl)cyclohexanol (200 mg, 0.701 mmol) in N,N-dimethylformamide (DMF) (10 mL) was added NaH (112 mg, 2.81 mmol) slowly under nitrogen at 25° C. The reaction mixture was stirred at 25° C. for 1 h. Then iodomethane (398 mg, 2.81 mmol) was added and stirred at 25° C. for 12 h. 30 mL of water was added and extracted with ethyl acetate (3×). The combined organic layer was washed with brine, dried over Na$_2$SO$_4$ and concentrated under a stream of nitrogen at 50° C. The crude product was purified on silica gel chromatography (petroleum ether:ethyl acetate=5:1) to obtain the title compound 1-bromo-3-((3-methoxycyclohexyl)methoxy)benzene (200 mg, 0.668 mmol, 95% yield) which was used for next step without further purification.

179a) (3-Bromophenyl)(cyclohexylmethyl)sulfane

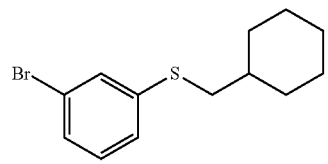

To a solution of 3-bromobenzenethiol (4.158 g, 21.99 mmol) in DMF (30 mL) was added K$_2$CO$_3$ (9.12 g, 66.0 mmol). The reaction mixture was stirred for 30 mins at room temperature. Then (bromomethyl)cyclohexane (4.28 g, 24.19 mmol) was added. The reaction mixture was stirred at 25° C. for 16 h. Then it was poured into water (50 mL) and extracted with ethyl acetate (3×). The combined organic phase was concentrated to obtain the title compound (3-bromophenyl)(cyclohexylmethyl)sulfane (6 g, 18.93 mmol, 86% yield) which was used in the next step without further purification.

180a) (1R,4R)-N-Methoxy-N-methyl-4-(trifluoromethyl)cyclohexanecarboxamide

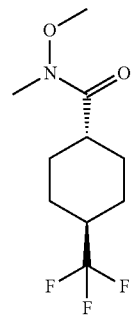 [SMILES: CON(C)C(=O)[C@H]1CC[C@H](C(F)(F)F)CC1]

A solution of (1r,4r)-4-(trifluoromethyl)cyclohexanecarboxylic acid (800 mg, 4.08 mmol) in N,N-dimethylformamide (DMF) (50 mL) was added N,O-dimethylhydroxylamine hydrochloride (477 mg, 4.89 mmol) and TEA (1.421 mL, 10.20 mmol) slowly under nitrogen at 25° C. The reaction mixture was stirred at 25° C. for 16 h. 50 mL of water was added and extracted with ethyl acetate (3×). The combined organic phase was washed with 10% HCl, 10% Na$_2$CO$_3$, brine and concentrated under a stream of nitrogen at 50° C. to obtain the title compound (1r,4r)-N-methoxy-N-methyl-4-(trifluoromethyl)cyclohexanecarboxamide (980 mg, 3.89 mmol, 95% yield) which was used for next step without further purification. LC-MS m/z 240.2 (M+H)$^+$, 1.91 min (ret. time).

180b) 1-((1r,4r)-4-(Trifluoromethyl)cyclohexyl)ethanone

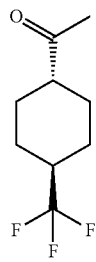

A solution of (1r,4r)-N-methoxy-N-methyl-4-(trifluoromethyl)cyclohexanecarboxamide (980 mg, 4.10 mmol) in tetrahydrofuran (THF) (5 mL) was added methyl magnesium bromide (1.639 mL, 4.92 mmol) slowly under nitrogen at 0° C. The reaction mixture was stirred at 0° C. for 2 h. 5 mL of water was added and extracted with ethyl acetate (3×). The combined organic phase was washed with brine, dried over Na$_2$SO$_4$ and concentrated under a stream of nitrogen at 50° C. to obtain the title compound 1-((1r,4r)-4-(trifluoromethyl)cyclohexyl)ethanone (750 mg, 3.67 mmol, 90% yield) which was used for next step without further purification. GC-MS m/z 194.1 (M+H)$^+$, 7.84 min (ret. time).

180c) (R)-1-((1R,4R)-4-(Trifluoromethyl)cyclohexyl)ethanol

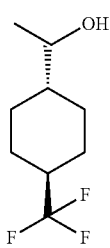

A solution of 1-((1r,4r)-4-(trifluoromethyl)cyclohexyl)ethanone (700 mg, 3.60 mmol) in diethyl ether (20 mL) was added LiAlH$_4$ (164 mg, 4.33 mmol) slowly under nitrogen at 0° C. The reaction mixture was stirred at 0° C. for 2 h. 20 mL of water was added and extracted with ethyl acetate (3×). The combined organic phase was washed with brine, dried over Na$_2$SO$_4$ and concentrated under a stream of nitrogen at 50° C. to obtain the title compound (R)-1-((1r,4R)-4-(trifluoromethyl)cyclohexyl)ethanol (600 mg, 2.75 mmol, 76% yield) which was used for next step without further purification. $^1$H NMR (300 MHz, CDCl$_3$) δ: 4.35 (M, 1H), 3.33 (m, 1H), 1.87 (m, 3H), 1.17 (m, 6H), 1.1 (dd, 3H).

180d) 1-Bromo-3-((R)-1-((1r,4R)-4-(trifluoromethyl)cyclohexyl)ethoxy)benzene

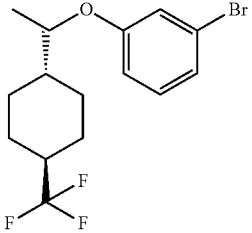

A solution of 3-bromophenol (100 mg, 0.578 mmol), triphenylphosphine (455 mg, 1.734 mmol) and (R)-1-((1r,4R)-4-(trifluoromethyl)cyclohexyl)ethanol (113 mg, 0.578 mmol) in tetrahydrofuran (THF) (5 mL) was added DIAD (0.337 mL, 1.734 mmol) in tetrahydrofuran (THF) (5 mL) slowly under nitrogen at 25° C. The reaction mixture was stirred at 25° C. for 16 h. The reaction mixture was concentrated. it was purified by reverse-phase HPLC (0.05% TFA/H$_2$O:CH$_3$CN=5%~95%) to provide the title compound 1-bromo-3-((R)-1-((1r,4R)-4-(trifluoromethyl)cyclohexyl)ethoxy)benzene (100 mg, 0.270 mmol, 46.8% yield) as an oil. $^1$H NMR (500 MHz, CDCl$_3$) δ 7.12 (t, J=8.1 Hz, 1H), 7.07-7.00 (m, 2H), 6.82-6.77 (m, 1H), 4.17-4.07 (m, 1H), 2.03 (dd, J=29.4, 12.3 Hz, 4H), 1.87 (d, J=12.8 Hz, 1H), 1.61-1.54 (m, 1H), 1.38-1.03 (m, 7H).

181a) 1-Bromo-2-fluoro-3-isopropoxybenzene

A solution of 3-bromo-2-fluorophenol (565 mg, 2.96 mmol) in acetone (20 mL) was added 2-bromopropane (728 mg, 5.92 mmol) and K$_2$CO$_3$ (818 mg, 5.92 mmol) slowly under nitrogen at room temperature. The reaction mixture was stirred at 60° C. for 14 h. 10 mL of water was added and extracted with ethyl acetate (3×). The combined organic phase was concentrated under a stream of nitrogen at 50° C. to obtain the title compound 1-bromo-2-fluoro-3-isopropoxybenzene (700 mg, 2.73 mmol, 92% yield) which was used for next step without further purification.

182a) 1-(3-Bromophenyl)-2-methylpropan-1-ol

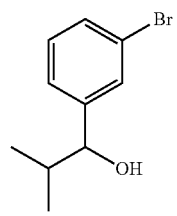

A solution of 3-bromobenzaldehyde (10 g, 54.0 mmol) in tetrahydrofuran (THF) (50 mL) was added isopropyl magnesium chloride (27.0 mL, 54.0 mmol) slowly under nitrogen at 0° C. The reaction mixture was stirred at room temperature for 1 h. 50 mL of aqueous NH$_4$Cl was added and extracted with ethyl acetate (3×). The combined organic phase was washed with brine, dried over Na$_2$SO$_4$ and concentrated under a stream of nitrogen at 50° C. The crude product was purified by reverse-phase HPLC (0.05% TFA/H2O:CH3CN=5%~95%) to obtain the title compound 1-(3-bromophenyl)-2-methylpropan-1-ol (3.2 g, 11.17 mmol, 20.67% yield). LC-MS m/z 213.1 (M+H)$^+$, 1.97 min (ret. time).

182b)
1-Bromo-3-(1-ethoxy-2-methylpropyl)benzene

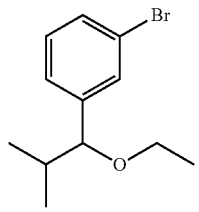

A solution of 1-(3-bromophenyl)-2-methylpropan-1-ol (300 mg, 1.309 mmol) in tetrahydrofuran (THF) (10 mL) was added NaH (300 mg, 7.50 mmol) slowly under nitrogen at room temperature. The reaction mixture was stirred at 60° C. for 0.5 h. It was added iodoethane (1225 mg, 7.86 mmol) slowly and stirred at room temperature for 1 h. 10 mL of water was added and extracted with ethyl acetate (3×). The combined organic phase was concentrated under a stream of nitrogen at 50° C. to obtain the title compound 1-bromo-3-(1-ethoxy-2-methylpropyl)benzene (300 mg, 1.050 mmol, 80% yield) which was used for next step without further purification.

183a) Cyclopentylmagnesium Bromide

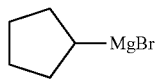

A solution of bromocyclopentane (15 g, 101 mmol) in ether (50 mL) was added to magnesium (2.69 g, 111 mmol) solution in ether (150 mL) slowly under nitrogen at 60° C. The reaction mixture was stirred at 60° C. for 0.5 h. This solution is the title compound 0.5 M of cyclopentylmagnesium bromide (17.69 g, 102 mmol, 101% yield) which was used in next step without further purification.

183b) (3-Bromophenyl)(cyclopentyl)methanol

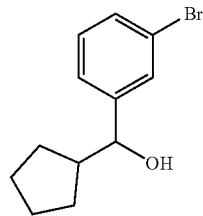 [SMILES: OC(c1cccc(Br)c1)C1CCCC1]

A solution of 3-bromobenzaldehyde (1 g, 5.40 mmol) in tetrahydrofuran (THF) (10 mL) was added cyclopentylmagnesium bromide (10.81 mL, 5.40 mmol) slowly under nitrogen at 25° C. The reaction mixture was stirred at room temperature for 4 h. 50 mL of aqueous NH$_4$Cl was added and extracted with ethyl acetate (3×). The combined organic layer was concentrated under a stream of nitrogen at 50° C. The crude product was purified by reverse-phase HPLC (0.05% TFA/H$_2$O:CH$_3$CN=5%~95%) to obtain the title compound (3-bromophenyl)(cyclopentyl)methanol (200 mg, 0.729 mmol, 13.49% yield) as an oil. LC-MS m/z 239.0 (M+H)$^+$, 2.14 min (ret. time).

183c)
1-Bromo-3-(cyclopentyl(methoxy)methyl)benzene

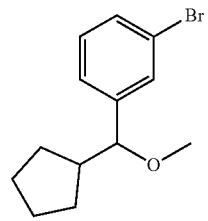

A solution of (3-bromophenyl)(cyclopentyl)methanol (200 mg, 0.784 mmol) in tetrahydrofuran (THF) (10 mL) was added NaH (300 mg, 7.50 mmol) slowly under nitrogen at room temperature. The reaction mixture was stirred at 60° C. for 0.5 h. It was added iodomethane (668 mg, 4.70 mmol) slowly and stirred at room temperature for 1 h. 10 mL of water was added and extracted with ethyl acetate (3×). The combined organic layer was concentrated under a stream of nitrogen at 50° C. to obtain the title compound 1-bromo-3-(cyclopentyl(methoxy)methyl)benzene (200 mg, 0.743 mmol, 95% yield) which was used for next step without further purification.

184a) 1-(3-Bromophenyl)-2-methylpropan-1-ol

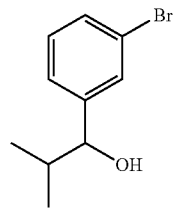

A solution of 3-bromobenzaldehyde (5 g, 27.0 mmol) in tetrahydrofuran (THF) (50 mL) was added isopropylmagnesium chloride (16.21 mL, 32.4 mmol) slowly under nitrogen at 0° C. The reaction mixture was stirred at room temperature for 1 h. 50 mL of aqueous NH$_4$Cl was added and extracted with ethyl acetate (3×). The combined organic layer was concentrated under a stream of nitrogen at 50° C. The crude product was reverse-phase HPLC (0.05% TFA/H$_2$O:CH$_3$CN=5%~95%) to obtain the title compound 1-(3-bromophenyl)-2-methylpropan-1-ol (600 mg, 2.488 mmol, 9.21% yield) as an oil. LC-MS m/z 213.1 (M−18+H)$^+$, 1.97 min (ret. time).

184b)
1-Bromo-3-(1-methoxy-2-methylpropyl)benzene

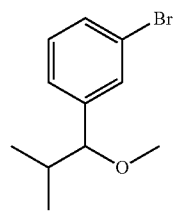

A solution of 1-(3-bromophenyl)-2-methylpropan-1-ol (300 mg, 1.309 mmol) in tetrahydrofuran (THF) (10 mL) was added NaH (300 mg, 7.50 mmol) slowly under nitrogen at room temperature. The reaction mixture was stirred at 60° C. for 0.5 h. Iodomethane (1115 mg, 7.86 mmol) was added at room temperature slowly and stirred for 1 h. 10 mL of water was added and extracted with ethyl acetate (3×). The combined organic layer was washed with brine, dried over Na$_2$SO$_4$ and concentrated under a stream of nitrogen at 50° C. to obtain the title compound 1-bromo-3-(1-methoxy-2-methylpropyl)benzene (350 mg, 1.080 mmol, 82% yield) which was used in next step without further purification.

Example 185. 1-(3'-((4-Chlorocyclohexyl)methoxy)-[1,1'-biphenyl]-3-yl)-5-((1,2-trans)-2-(1-methyl-1H-1,2,3-triazol-4-yl)cyclopropyl)-1H-pyrazole-4-carboxylic Acid

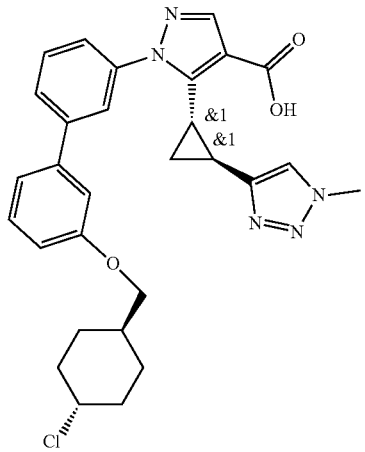 [SMILES: Cn1cc([C@H]2C[C@@H]2c2c(C(=O)O)cnn2-c2cccc(-c3cccc(OC[C@H]4CC[C@H](Cl)CC4)c3)c2)nn1]

185a) Methyl 1-(3'-(((1r,4S)-4-chlorocyclohexyl)methoxy)-[1,1'-biphenyl]-3-yl)-5-((1,2-trans)-2-(1-methyl-1H-1,2,3-triazol-4-yl)cyclopropyl)-1H-pyrazole-4-carboxylate

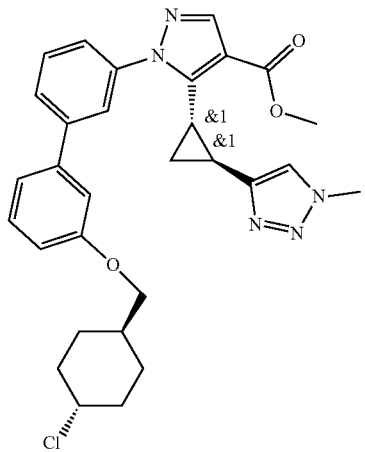 [SMILES: COC(=O)c1cnn(-c2cccc(-c3cccc(OC[C@H]4CC[C@H](Cl)CC4)c3)c2)c1[C@H]1C[C@@H]1c1cn(C)nn1]

A solution of methyl 1-(3'-((2-hydroxycyclohexyl)methoxy)-[1,1'-biphenyl]-3-yl)-5-((1,2-trans)-2-(1-methyl-1H-1,2,3-triazol-4-yl)cyclopropyl)-1H-pyrazole-4-carboxylate (180 mg, 0.341 mmol) in dichloromethane (DCM) (5 mL) was added SOCl$_2$ (0.5 ml, 6.85 mmol) slowly under nitrogen at 20° C. 1 drop of DMF was added. The reaction mixture was stirred at 50° C. for 16 h. The solvent was removed. The residue was purified by reverse-phase HPLC (0.05% TFA/H$_2$O:CH$_3$CN=5%~95%) to obtain the title compound methyl 1-(3'-((2-chlorocyclohexyl)methoxy)-[1,1'-biphenyl]-3-yl)-5-((1,2-trans)-2-(1-methyl-1H-1,2,3-triazol-4-yl)cyclopropyl)-1H-pyrazole-4-carboxylate (90 mg, 0.152 mmol, 44.4% yield). LC-MS m/z 546.2 (M+H)$^+$, 2.28 (ret. time).

185b) 1-(3'-((4-Chlorocyclohexyl)methoxy)-[1,1'-biphenyl]-3-yl)-5-((1,2-trans)-2-(1-methyl-1H-1,2,3-triazol-4-yl)cyclopropyl)-1H-pyrazole-4-carboxylic Acid

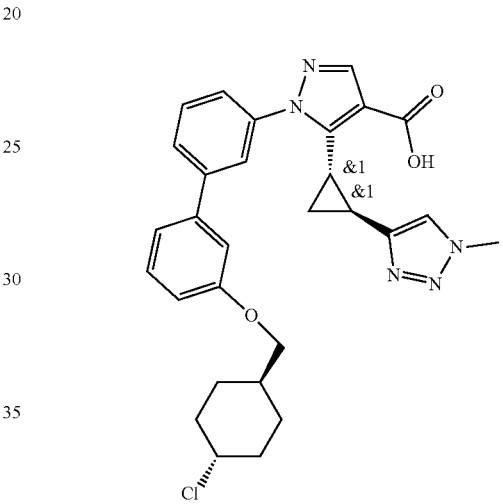

A solution of methyl 1-(3'-((2-chlorocyclohexyl)methoxy)-[1,1'-biphenyl]-3-yl)-5-((1,2-trans)-2-(1-methyl-1H-1,2,3-triazol-4-yl)cyclopropyl)-1H-pyrazole-4-carboxylate (90 mg, 0.165 mmol) in tetrahydrofuran (THF) (5 mL) was added a solution of LiOH (39.5 mg, 1.648 mmol) in water (5 mL) slowly under nitrogen at 25° C. The reaction mixture was stirred at 25° C. for 16 h. After THF was removed, the mixture was added adjusted pHpH=6 with 1N HCl and extracted with ethyl acetate (3×). The combined organic layer was washed with brine, dried over Na$_2$SO$_4$ and concentrated. The residue was purified by reverse-phase HPLC (0.05% TFA/H$_2$O:CH$_3$CN=5%~95%) to obtain the title compound 1-(3'-((2-chlorocyclohexyl)methoxy)-[1,1'-biphenyl]-3-yl)-5-((1,2-trans)-2-(1-methyl-1H-1,2,3-triazol-4-yl)cyclopropyl)-1H-pyrazole-4-carboxylic acid (37 mg, 0.070 mmol, 42.2% yield). LC-MS m/z 531.7 (M+H)$^+$, 1.81 (ret. time).

The compounds in Table 9 were prepared by a method similar to the one described for the preparation of 1-(3'-((2-Chlorocyclohexyl)methoxy)-[1,1'-biphenyl]-3-yl)-5-((1,2-trans)-2-(1-methyl-1H-1,2,3-triazol-4-yl)cyclopropyl)-1H-pyrazole-4-carboxylic acid. As is appreciated by those skilled in the art, these analogous examples may involve variations in general reaction conditions.

TABLE 9

| Example | Structure | Name | LCMS [M + H]⁺ | Retention Time (min) |
|---|---|---|---|---|
| 186 | 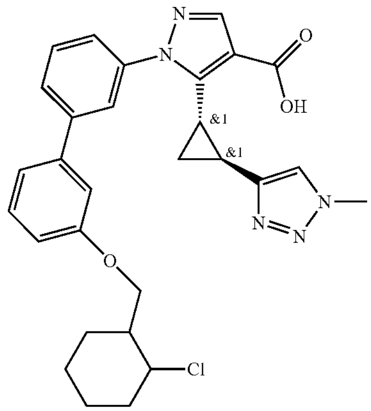 [SMILES: Cn1cc([C@H]2C[C@@H]2c2c(C(=O)O)cnn2-c2cccc(-c3cccc(OCC4CCCCC4Cl)c3)c2)nn1] | 1-(3'-((2-chlorocyclohexyl)methoxy)-[1,1'-biphenyl]-3-yl)-5-((1,2-trans)-2-(1-methyl-1H-1,2,3-triazol-4-yl)cyclopropyl)-1H-pyrazole-4-carboxylic acid | 513.7 | 1.81 |
| 187 | 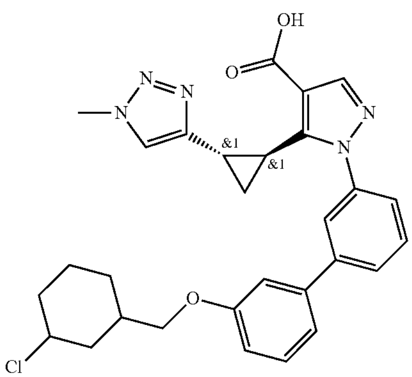 [SMILES: Cn1cc([C@H]2C[C@@H]2c2c(C(=O)O)cnn2-c2cccc(-c3cccc(OCC4CCCC(Cl)C4)c3)c2)nn1] | 1-(3'-((3-chlorocyclohexyl)methoxy)-[1,1'-biphenyl]-3-yl)-5-((1,2-trans)-2-(1-methyl-1H-1,2,3-triazol-4-yl)cyclopropyl)-1H-pyrazole-4-carboxylic acid | 532.2 | 2.06 |

Example 188. 1-(3'-(cyclohexylmethoxy)-[1,1'-biphenyl]-3-yl)-3-methyl-5-((1,2-trans)-(2-(1-methyl-1H-1,2,3-triazol-4-yl)cyclopropyl)-1H-pyrazole-4-carboxylic Acid

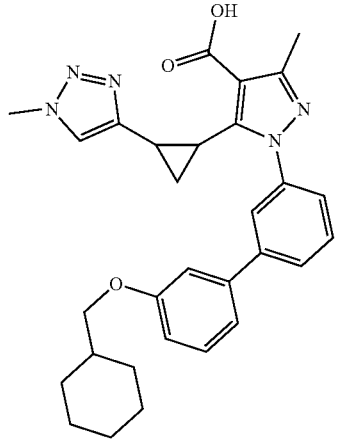 [SMILES: Cc1nn(-c2cccc(-c3cccc(OCC4CCCCC4)c3)c2)c(C2CC2c2cn(C)nn2)c1C(=O)O]

188a) 2-(3-(Cyclohexylmethoxy)phenyl)-4,4,5,5-tetramethyl-1,3,2-dioxaborolane

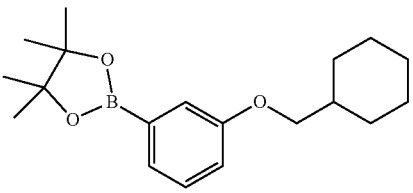 [SMILES: CC1(C)OB(c2cccc(OCC3CCCCC3)c2)OC1(C)C]

A solution of 3-bromophenol (1 g, 5.78 mmol) and (bromomethyl)cyclohexane (1.075 g, 6.07 mmol) in N,N-dimethylformamide (DMF) (5 mL) was added K₂CO₃ (1.598 g, 11.56 mmol) slowly under nitrogen at room temperature. The reaction mixture was stirred at 150° C. for 4 h. 10 mL of water was added and extracted with ethyl acetate (3×). The combined organic phase was washed with brine, dried over Na₂SO₄ and concentrated to obtain 1-bromo-3-(cyclohexylmethoxy)benzene (1.5 g, 5.41 mmol, 94% yield). To a solution of 1-bromo-3-(cyclohexylmethoxy)benzene (1.5 g, 5.57 mmol) in 1,4-dioxane (10 mL) was added potassium acetate (1.094 g, 11.15 mmol), bis(pinacolato)diboron (1.698 g, 6.69 mmol). After the reaction mixture was degassed with argon for 30 mins, (dppf)-$CH_2Cl_2$ adduct (0.455 g, 0.557 mmol) was added. The reaction mixture was stirred at 100° C. for 16 h. After it was cooled to room temperature, it was filtered through celite pad and the filtrate was concentrated. The residue was purified on silica gel chromatography (100% hexane) to obtain the title compound. 2-(3-(cyclohexylmethoxy)phenyl)-4,4,5,5-tetramethyl-1,3,2-dioxaborolane (1.3 g, 4.07 mmol, 73.0% yield) as white solid. The reaction was monitored by TLC.

188b) Methyl 2-(2-(1-methyl-1H-1,2,3-triazol-4-yl)cyclopropanecarbonyl)-3-oxobutanoate

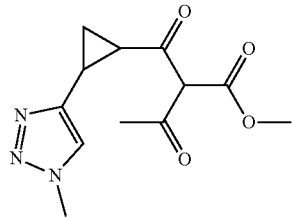 [SMILES: COC(=O)C(C(C)=O)C(=O)C1CC1c1cn(C)nn1]

A solution of methyl 3-(2-(1-methyl-1H-1,2,3-triazol-4-yl)cyclopropyl)-3-oxopropanoate (900 mg, 4.03 mmol) in dichloromethane (DCM) (10 mL) was added pyridine (351 mg, 4.43 mmol) and magnesium chloride (422 mg, 4.43 mmol) slowly under nitrogen at 0° C. The reaction mixture was stirred at 0° C. for 0.5 h. Then acetyl chloride (348 mg, 4.43 mmol) was added slowly. The reaction mixture was stirred at room temperature for 12 h. 30 mL of water was added and extracted with ethyl acetate (3×). The combined organic phase was concentrated to obtain the title compound methyl 2-(2-(1-methyl-1H-1,2,3-triazol-4-yl)cyclopropanecarbonyl)-3-oxobutanoate (820 mg, 2.78 mmol, 69.0% yield) which was used in next step without further purification. LC-MS m/z 266.1 (M+H)$^+$, 1.21 min (ret. time).

188c) Methyl 1-(3-bromophenyl)-3-methyl-5-(2-(1-methyl-1H-1,2,3-triazol-4-yl)cyclopropyl)-1H-pyrazole-4-carboxylate

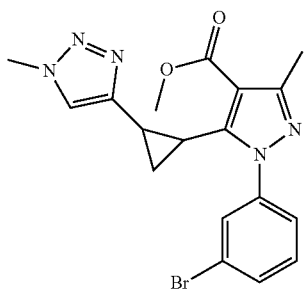

A solution of methyl 2-(2-(1-methyl-1H-1,2,3-triazol-4-yl)cyclopropanecarbonyl)-3-oxobutanoate (0.8 g, 3.02 mmol) in acetic acid (5 mL) was added (3-bromophenyl)hydrazine hydrochloride (0.674 g, 3.02 mmol) in water (5.00 mL) slowly under nitrogen at 20° C. The reaction mixture was stirred at 20° C. for 16 h. Then it was extracted with ethyl acetate (3×). The combined organic phase was concentrated. The crude product was purified on silica gel chromatography (ethyl acetate:hexane=1:1) to obtain the title compound methyl 1-(3-bromophenyl)-3-methyl-5-(2-(1-methyl-1H-1,2,3-triazol-4-yl)cyclopropyl)-1H-pyrazole-4-carboxylate (0.8 g, 1.441 mmol, 47.8% yield). LC-MS m/z 416.1 (M+H)$^+$, 1.86 min (ret. time).

188d) Methyl 1-(3'-(cyclohexylmethoxy)-[1,1'-biphenyl]-3-yl)-3-methyl-5-(2-(1-methyl-1H-1,2,3-triazol-4-yl)cyclopropyl)-1H-pyrazole-4-carboxylate

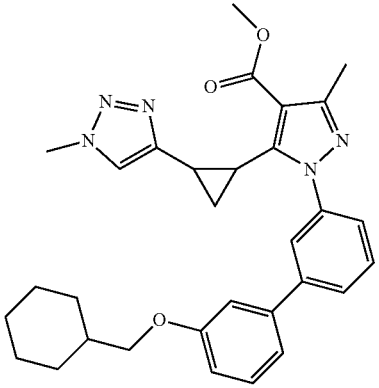 [SMILES: COC(=O)c1c(C)nn(-c2cccc(-c3cccc(OCC4CCCCC4)c3)c2)c1C1CC1c1cn(C)nn1]

A mixture of methyl 1-(3-bromophenyl)-3-methyl-5-(2-(1-methyl-1H-1,2,3-triazol-4-yl)cyclopropyl)-1H-pyrazole-4-carboxylate (200 mg, 0.480 mmol), 2-(3-(cyclohexylmethoxy)phenyl)-4,4,5,5-tetramethyl-1,3,2-dioxaborolane (200 mg, 0.632 mmol), $Na_2CO_3$ (0.480 mL, 1.441 mmol) and $PdCl_2(dppf)$-$CH_2Cl_2$ adduct (39.2 mg, 0.048 mmol) in toluene (5 mL) and methanol (5.00 mL) under nitrogen was stirred at 110° C. for 2 h. After solvent was removed, Then it was adjusted pH=6 with 1N HCl and extracted with ethyl acetate (3×). The combined organic layer was washed with brine, dried over $Na_2SO_4$ and concentrated to obtain the title compound methyl 1-(3'-(cyclohexylmethoxy)-[1,1'-biphenyl]-3-yl)-3-methyl-5-(2-(1-methyl-1H-1,2,3-triazol-4-yl)cyclopropyl)-1H-pyrazole-4-carboxylate (250 mg, 0.333 mmol, 69.3% yield). LC-MS m/z 526.2 (M+H)$^+$, 2.39 min (ret. time).

188e) 1-(3'-(cyclohexylmethoxy)-[1,1'-biphenyl]-3-yl)-3-methyl-5-(2-(1-methyl-1H-1,2,3-triazol-4-yl)cyclopropyl)-1H-pyrazole-4-carboxylic Acid

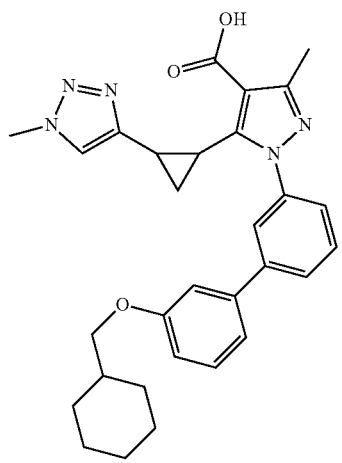 [SMILES: Cc1nn(-c2cccc(-c3cccc(OCC4CCCCC4)c3)c2)c(C2CC2c2cn(C)nn2)c1C(=O)O]

To a solution of methyl 1-(3'-(cyclohexylmethoxy)-[1,1'-biphenyl]-3-yl)-3-methyl-5-(2-(1-methyl-1H-1,2,3-triazol-4-yl)cyclopropyl)-1H-pyrazole-4-carboxylate (250 mg, 0.476 mmol) in tetrahydrofuran (THF) (5.00 mL), a solution of LiOH (114 mg, 4.76 mmol) in water (5 mL) was added under nitrogen. The reaction mixture was stirred at 25° C. for 16 h. After THF was removed, the mixture was adjusted pH=6 with 1 N HCl. The solid was filtered and was washed with ethyl acetate to obtain the title compound 1-(3'-(cyclohexylmethoxy)-[1,1'-biphenyl]-3-yl)-3-methyl-5-(2-(1-methyl-1H-1,2,3-triazol-4-yl)cyclopropyl)-1H-pyrazole-4-carboxylic acid (100 mg, 0.184 mmol, 38.6% yield) as a solid. LC-MS m/z 512.3 (M+H)$^+$, 1.39 min (ret. time).

The compounds in Table 10 were prepared by a method similar to the one described for the preparation of 1-(3'-(cyclohexylmethoxy)-[1,1'-biphenyl]-3-yl)-3-methyl-5-(2-(1-methyl-1H-1,2,3-triazol-4-yl)cyclopropyl)-1H-pyrazole-4-carboxylic acid. As is appreciated by those skilled in the art, these analogous examples may involve variations in general reaction conditions.

TABLE 10

| Example | Structure | Name | LCMS [M + H]$^+$ | Retention Time (min) |
|---|---|---|---|---|
| 189 | 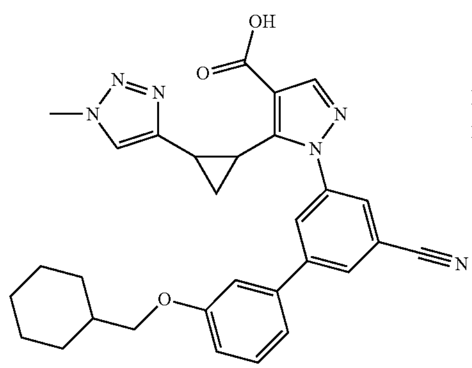 [SMILES: Cn1cc(C2CC2c2c(C(=O)O)cnn2-c2cc(C#N)cc(-c3cccc(OCC4CCCCC4)c3)c2)nn1] | 1-(5-cyano-3'-(cyclohexylmethoxy)-[1,1'-biphenyl]-3-yl)-5-(2-(1-methyl-1H-1,2,3-triazol-4-yl)cyclopropyl)-1H-pyrazole-4-carboxylic acid | 523.3 | 2.14 |
| 190 | 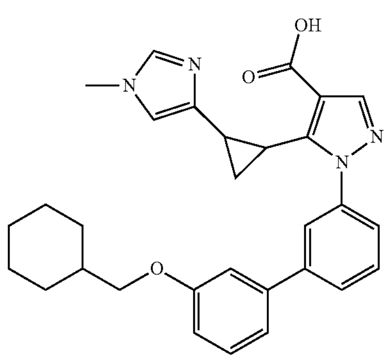 [SMILES: Cn1cnc(C2CC2c2c(C(=O)O)cnn2-c2cccc(-c3cccc(OCC4CCCCC4)c3)c2)c1] | 1-(3'-(cyclohexylmethoxy)-[1,1'-biphenyl]-3-yl)-5-(2-(1-methyl-1H-imidazol-4-yl)cyclopropyl)-1H-pyrazole-4-carboxylic acid | 497.1 | 1.93 |

TABLE 10-continued

| Example | Structure | Name | LCMS [M + H]+ | Retention Time (min) |
| --- | --- | --- | --- | --- |
| 191 | 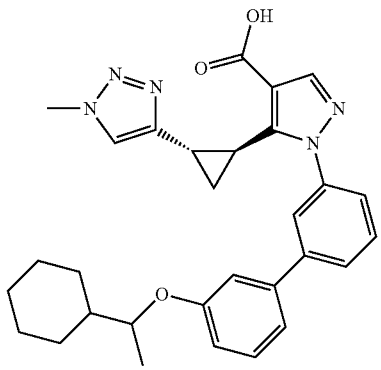 [SMILES: CC(Oc1cccc(-c2cccc(-n3ncc(C(=O)O)c3[C@H]3C[C@@H]3c3cn(C)nn3)c2)c1)C1CCCCC1] | 1-(3'-(1-cyclohexylethoxy)-[1,1'-biphenyl]-3-yl)-5-((1S,2S)-2-(1-methyl-1H-1,2,3-triazol-4-yl)cyclopropyl)-1H-pyrazole-4-carboxylic acid | 526.2 | 2.22 |
| 192 | 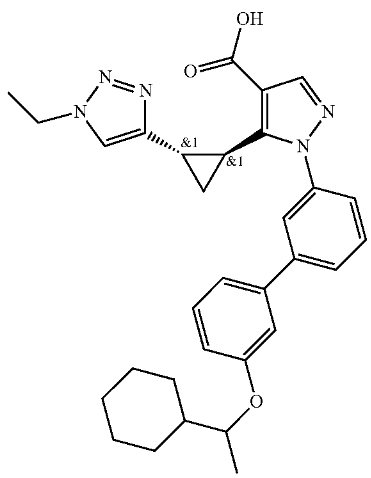 [SMILES: CCn1cc([C@H]2C[C@@H]2c2c(C(=O)O)cnn2-c2cccc(-c3cccc(OC(C)C4CCCCC4)c3)c2)nn1] | 1-(3'-(1-cyclohexylethoxy)-[1,1'-biphenyl]-3-yl)-5-((1,2-trans)-2-(1-ethyl-1H-1,2,3-triazol-4-yl)cyclopropyl)-1H-pyrazole-4-carboxylic acid | 526.2 | 2.25 |
| 193 | 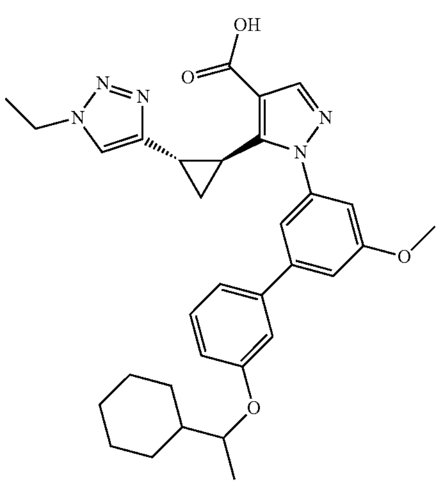 [SMILES: CCn1cc([C@H]2C[C@@H]2c2c(C(=O)O)cnn2-c2cc(OC)cc(-c3cccc(OC(C)C4CCCCC4)c3)c2)nn1] | 1-(3'-(1-cyclohexylethoxy)-5-methoxy-[1,1'-biphenyl]-3-yl)-5-((1S,2S)-2-(1-ethyl-1H-1,2,3-triazol-4-yl)cyclopropyl)-1H-pyrazole-4-carboxylic acid | 542.3 | 2.11 |

TABLE 10-continued

| Example | Structure | Name | LCMS [M + H]+ | Retention Time (min) |
|---|---|---|---|---|
| 194 | 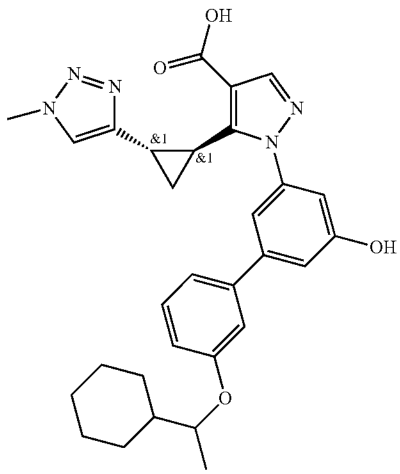 [SMILES: CC(Oc1cccc(-c2cc(O)cc(-n3ncc(C(=O)O)c3[C@H]3C[C@@H]3c3cn(C)nn3)c2)c1)C1CCCCC1] | 1-(3'-(1-cyclohexylethoxy)-5-methoxy-[1,1'-biphenyl]-3-yl)-5-((1,2-trans)-2-(1-ethyl-1H-1,2,3-triazol-4-yl)cyclopropyl)-1H-pyrazole-4-carboxylic acid | 528.2 | 1.70 |
| 195 | 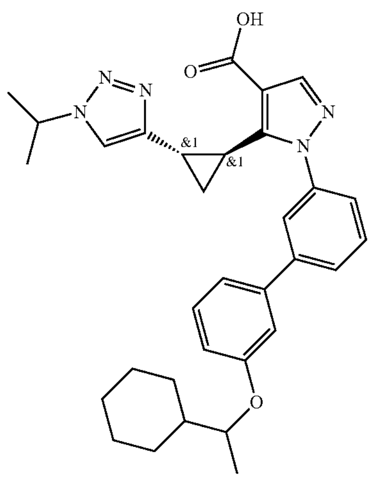 [SMILES: CC(Oc1cccc(-c2cccc(-n3ncc(C(=O)O)c3[C@H]3C[C@@H]3c3cn(C(C)C)nn3)c2)c1)C1CCCCC1] | 1-(3'-(1-cyclohexylethoxy)-[1,1'-biphenyl]-3-yl)-5-((1,2-trans)-2-(1-isopropyl-1H-1,2,3-triazol-4-yl)cyclopropyl)-1H-pyrazole-4-carboxylic acid | 540.2 | 1.93 |

189a) 3-Bromo-5-hydrazinylbenzonitrile

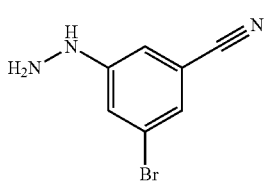 [SMILES: N#Cc1cc(Br)cc(NN)c1]

A solution of 3-amino-5-bromobenzonitrile (0.2 g, 1.015 mmol) in HCl (2 mL, 24.00 mmol) was added sodium nitrite (0.140 g, 2.030 mmol) in water (5 mL) slowly at 0° C. The reaction mixture was stirred at 0° C. for 1 h. Then tin(II) chloride (0.481 g, 2.54 mmol) in HCl (2 mL, 24.00 mmol) was added. The solid was filtered to obtain the title compound 3-bromo-5-hydrazinylbenzonitrile, hydrochloride (200 mg, 0.708 mmol, 69.8% yield). LC-MS m/z 214.0 (M+H)+, 1.25 min (ret. time).

189b) Methyl 1-(3-bromo-5-cyanophenyl)-5-(2-(1-methyl-1H-1,2,3-triazol-4-yl)cyclopropyl)-1H-pyrazole-4-carboxylate

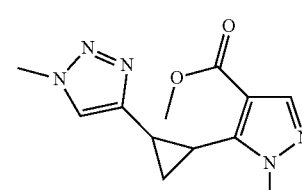

A solution of methyl 3-(dimethylamino)-2-(2-(1-methyl-1H-1,2,3-triazol-4-yl)cyclopropanecarbonyl)acrylate (224 mg, 0.805 mmol) in acetonitrile (5 mL) was added 3-bromo-5-hydrazinylbenzonitrile hydrochloride (200 mg, 0.805 mmol) slowly under nitrogen at 20° C. The reaction mixture was stirred at 20° C. for 16 h. 200 mL of water was added and extracted with ethyl acetate (3×). The combined organic phase was concentrated. The crude product was purified by silica gel chromatography (hexane:ethyl acetate=4:1) to obtain the title compound methyl 1-(3-bromo-5-cyanophenyl)-5-(2-(1-methyl-1H-1,2,3-triazol-4-yl)cyclopropyl)-1H-pyrazole-4-carboxylate (100 mg, 0.225 mmol, 27.9% yield), LC-MS m/z 429.1 (M+H)+, 1.81 min (ret. time).

189c) 1-Bromo-3-(cyclohexylmethoxy)benzene

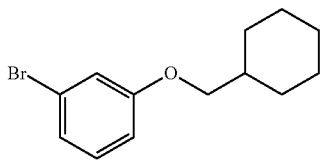 [SMILES: Brc1cccc(OCC2CCCCC2)c1]

A solution of 3-bromophenol (1 g, 5.78 mmol), (bromomethyl)cyclohexane (1.075 g, 6.07 mmol) in N,N-dimethylformamide (DMF) (5 mL) was added K$_2$CO$_3$ (1.598 g, 11.56 mmol) slowly under nitrogen at room temperature. The reaction mixture was stirred at 150° C. for 4 h. 10 mL of water was added and extracted with ethyl acetate (3×). The combined organic phase was concentrated to obtain the title compound 1-bromo-3-(cyclohexylmethoxy)benzene (1.5 g, 5.41 mmol, 94% yield) which was used in next step without further purification.

189d) 2-(3-(Cyclohexylmethoxy)phenyl)-4,4,5,5-tetramethyl-1,3,2-dioxaborolane

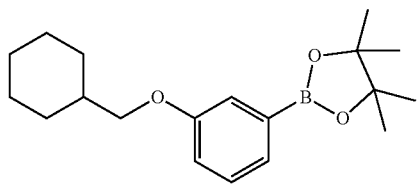 [SMILES: CC1(C)OB(c2cccc(OCC3CCCCC3)c2)OC1(C)C]

To a solution of 1-bromo-3-(cyclohexylmethoxy)benzene (1.5 g, 5.57 mmol) in 1,4-dioxane (10 mL) was added potassium acetate (1.094 g, 11.15 mmol), bis(pinacolato)diboron (1.698 g, 6.69 mmol) and the reaction mixture was degassed with argon for 30 mins and then PdCl$_2$(dppf)-CH$_2$Cl$_2$ adduct (0.455 g, 0.557 mmol) was added. The reaction mixture was stirred at 100° C. for 16 h. After it was cooled to room temperature, it was filtered through celite pad and the filtrate was concentrated. The residue was purified on silica gel chromatography with hexane to obtain the title compound 2-(3-(cyclohexylmethoxy)phenyl)-4,4,5,5-tetramethyl-1,3,2-dioxaborolane (1.3 g, 4.07 mmol, 73.0% yield) as white solid.

190a) (1-Methyl-1H-imidazol-4-yl)methanol

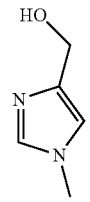

A solution of 1-methyl-1H-imidazole-4-carboxylic acid (25 g, 198 mmol) in tetrahydrofuran (THF) (1000 mL) was added LiAlH$_4$ (15.05 g, 396 mmol) slowly under nitrogen at room temperature. The reaction mixture was stirred at 50° C. for 12 h. It was added 15 mL of water, 15 mL of 10% NaOH, 45 mL of water to the reaction mixture at 0° C. The solid was filtered and the filtrate was concentrated to obtain the title compound (1-methyl-1H-imidazol-4-yl)methanol (13.2 g, 94 mmol, 47.5% yield) which was used for next step without further purification. LC-MS m/z 113.1 (M+H)+, 0.33 min (ret. time).

190b) 1-Methyl-1H-imidazole-4-carbaldehyde

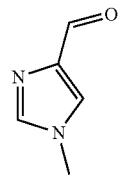

A solution of (1-methyl-1H-imidazol-4-yl)methanol (5 g, 44.6 mmol) in acetone (50 mL) was added manganese(IV) oxide (19.38 g, 223 mmol) slowly under nitrogen at room temperature. The reaction mixture was stirred at 60° C. for 12 h. The solid was filtered and the liquid was concentrated to obtain the title compound 1-methyl-1H-imidazole-4-carbaldehyde (4.12 g, 34.4 mmol, 77% yield) which was used in next step without further purification. LC-MS m/z 111.2 (M+H)+, 0.49 min (ret. time).

190c) (Z)-tert-Butyl 3-(1-methyl-1H-imidazol-4-yl)acrylate

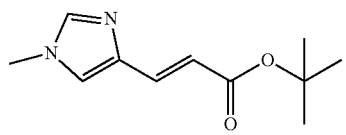

To a solution of tert-butyl 2-(diethoxyphosphoryl)acetate (9.62 g, 38.1 mmol) in tetrahydrofuran (THF) (50 mL), sodium hydride (1.831 g, 45.8 mmol) was added. The reaction mixture was stirred at 0° C. under N$_2$ for 10 mins. Then a solution of 1-methyl-1H-imidazole-4-carbaldehyde (4.2 g, 38.1 mmol) in THF (50 mL) was added and the reaction mixture was stirred at 0° C. for 150 mins. Water (100 mL) was added and extracted with ethyl acetate (3×). The organic layer was washed with water (2×) and brine (2×), dried over Na$_2$SO$_4$ and concentrated. The crude product was purified on silica gel chromatography (hexane:ethyl acetate:TEA=1:1:0.01) to afford the title compound (Z)-tert-butyl 3-(1-methyl-1H-imidazol-4-yl)acrylate (6.1 g, 28.7 mmol, 75% yield) as colorless oil. LC-MS m/z 201.1 (M+H)$^+$, 1.72 min (ret. time).

190d) tert-Butyl 2-(1-methyl-1H-imidazol-4-yl)cyclopropanecarboxylate

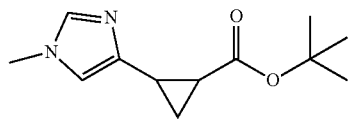 [SMILES: Cn1cnc(C2CC2C(=O)OC(C)(C)C)c1]

To a solution of trimethylsulfoxonium iodide (1.585 g, 7.20 mmol) in dimethyl Sulfoxide (DMSO) (5 mL), sodium hydride (0.288 g, 7.20 mmol) was added. The reaction mixture was stirred at 25° C. under N$_2$ for 1 h. Then a solution of (Z)-tert-butyl 3-(1-methyl-1H-imidazol-4-yl)acrylate (0.5 g, 2.401 mmol) in tetrahydrofuran (THF) (5.00 mL) was added dropwise. The reaction mixture was stirred at 25° C. for 1 h and stirred at 50° C. for another 1 h. 200 mL of ethyl acetate and 50 mL of water were added. The water layer was extracted with ethyl acetate (3×). The combined organic phase was dried over Na$_2$SO$_4$ and concentrated to obtain the title compound tert-butyl 2-(1-methyl-1H-imidazol-4-yl)cyclopropanecarboxylate (520 mg, 2.339 mmol, 97% yield). LC-MS m/z 223.1 (M+H)$^+$, 1.23 min (ret. time).

190e) 2-(1-Methyl-1H-imidazol-4-yl)cyclopropanecarboxylic Acid

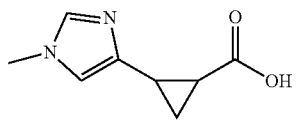

A solution of tert-butyl 2-(1-methyl-1H-imidazol-4-yl)cyclopropanecarboxylate (9.1 g, 40.9 mmol) in hydrogen chloride (4M in 1,4-dioxane, 100 ml, 400 mmol) was stirred slowly at 25° C. under nitrogen for 12 h. The reaction mixture was concentrated to obtain the title compound 2-(1-methyl-1H-imidazol-4-yl)cyclopropanecarboxylic acid, Hydrochloride (5 g, 24.67 mmol, 60.3% yield) which was used in next step without further purification. LC-MS m/z 167.1 (M+H)$^+$, 0.43 min (ret. time).

190f) 2,2-Dimethyl-5-(2-(1-methyl-1H-imidazol-4-yl)cyclopropanecarbonyl)-1,3-dioxane-4,6-dione

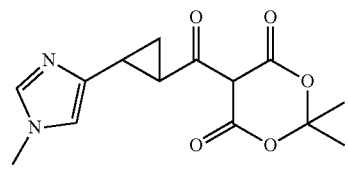

A mixture of 2-(1-methyl-1H-imidazol-4-yl)cyclopropanecarboxylic acid (5.3 g, 31.9 mmol) in dichloromethane (DCM) (100 mL) was added 2,2-dimethyl-1,3-dioxane-4,6-dione (6.90 g, 47.8 mmol), DMAP (5.84 g, 47.8 mmol), EDC (9.17 g, 47.8 mmol) and TEA (4.45 mL, 31.9 mmol). The reaction mixture was stirred at room temperature overnight. The reaction mixture was concentrated. The crude product was purified on silica gel chromatography (DCM: methanol:TEA=50:1:0.01) to obtain the title compound 2,2-dimethyl-5-(2-(1-methyl-1H-imidazol-4-yl)cyclopropanecarbonyl)-1,3-dioxane-4,6-dione (2 g, 4.58 mmol, 14.37% yield) as a oil. LC-MS m/z 293.1 (M+H)$^+$, 1.14 min (ret. time).

190g) Ethyl 3-(2-(1-methyl-1H-imidazol-4-yl)cyclopropyl)-3-oxopropanoate

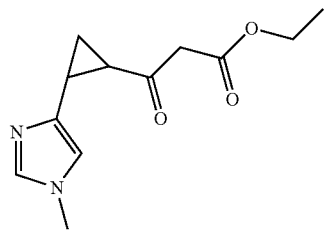 [SMILES: CCOC(=O)CC(=O)C1CC1c1cn(C)cn1]

A solution of 2,2-dimethyl-5-(2-(1-methyl-1H-imidazol-4-yl)cyclopropanecarbonyl)-1,3-dioxane-4,6-dione (2.5 g, 8.55 mmol) in ethanol (100 mL) was stirred at 80° C. for 72 h. The reaction mixture was concentrated to obtain the title compound ethyl 3-(2-(1-methyl-1H-imidazol-4-yl)cyclopropyl)-3-oxopropanoate (2.1 g, 4.09 mmol, 47.8% yield) which was used in next step without further purification. LC-MS m/z 237.1 (M+H)$^+$, 1.57 min (ret. time).

190h) Ethyl 3-(dimethylamino)-2-(2-(1-methyl-1H-imidazol-4-yl)cyclopropanecarbonyl)acrylate

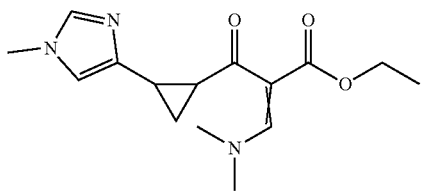 [SMILES: CCOC(=O)C(=CN(C)C)C(=O)C1CC1c1cn(C)cn1]

A solution of ethyl 3-(2-(1-methyl-1H-imidazol-4-yl)cyclopropyl)-3-oxopropanoate (2.1 g, 8.89 mmol) in toluene (50 mL) was added 1,1-dimethoxy-N,N-dimethylmethanamine (1.589 g, 13.33 mmol) slowly under nitrogen at room temperature. The reaction mixture was stirred at 100° C. for 1 h. The reaction mixture was concentrated it. The crude product was purified by reverse-phase HPLC to obtain the title compound ethyl 3-(dimethylamino)-2-(2-(1-methyl-1H-imidazol-4-yl)cyclopropanecarbonyl)acrylate (500 mg, 1.373 mmol, 15.45% yield) as an oil. LC-MS m/z 292.1 (M+H)$^+$, 1.34 min (ret. time).

190i) Ethyl 1-(3-bromophenyl)-5-(2-(1-methyl-1H-imidazol-4-yl)cyclopropyl)-1H-pyrazole-4-carboxylate

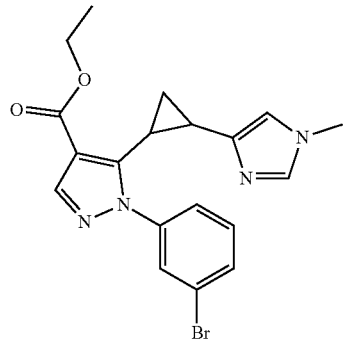 [SMILES: CCOC(=O)c1cnn(-c2cccc(Br)c2)c1C1CC1c1cn(C)cn1]

A solution of ethyl 3-(dimethylamino)-2-(2-(1-methyl-1H-imidazol-4-yl)cyclopropanecarbonyl)acrylate (500 mg, 1.716 mmol) in acetonitrile (5 mL) was added (3-bromophenyl)hydrazine hydrochloride (384 mg, 1.716 mmol) and DIPEA (0.899 mL, 5.15 mmol) slowly under nitrogen at 20° C. Then it was stirred at 20° C. for 16 h. The reaction mixture was concentrated and was purified by reverse-phase HPLC to obtain the title compound ethyl 1-(3-bromophenyl)-5-(2-(1-methyl-1H-imidazol-4-yl)cyclopropyl)-1H-pyrazole-4-carboxylate (500 mg, 1.156 mmol, 67.3% yield) as an oil. LC-MS m/z 417.1 (M+H)$^+$, 1.64 min (ret. time).

191a) 1-Bromo-2-(1-cyclohexylethoxy)benzene

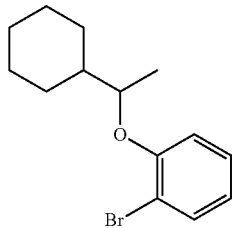 [SMILES: CC(Oc1ccccc1Br)C1CCCCC1]

A solution of 2-bromophenol (400 mg, 2.312 mmol) and triphenylphosphine (728 mg, 2.77 mmol) in tetrahydrofuran (THF) (10 mL) was added DIAD (0.539 mL, 2.77 mmol) in tetrahydrofuran (THF) (10 mL) under nitrogen at 25° C. The reaction mixture was stirred at 25° C. for 16 h. 30 mL of water was added and extracted with ethyl acetate (3×). The combined organic layer was concentrated under a stream of nitrogen at 50° C. It was purified on silica gel chromatography (hexane:ethyl acetate=10:1) to obtain the title compound 1-bromo-2-(1-cyclohexylethoxy)benzene (500 mg, 1.607 mmol, 69.5% yield).

191b) 2-(2-(1-Cyclohexylethoxy)phenyl)-4,4,5,5-tetramethyl-1,3,2-dioxaborolane

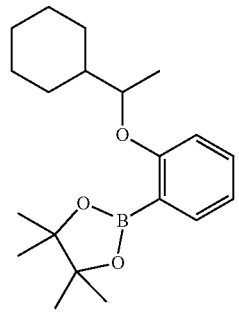 [SMILES: CC(Oc1ccccc1B1OC(C)(C)C(C)(C)O1)C1CCCCC1]

To a solution of 1-bromo-3-(1-cyclohexylethoxy)benzene (3 g, 10.59 mmol) in 1,4-dioxane (50 mL) was added potassium acetate (2.079 g, 21.19 mmol), bis(pinacolato)diboron (3.23 g, 12.71 mmol). The reaction mixture was degassed with argon for 30 mins and then PdCl$_2$(dppf)-CH$_2$Cl$_2$ adduct (0.433 g, 0.530 mmol) was added. The reaction mixture was stirred at 100° C. for 16 h. After it was cooled to room temperature, the reaction mixture was filtered through celite pad and the filtrate was concentrated under vacuum. The residue was purified on silica gel chromatography (hexane) to provide the title compound 2-(3-(1-cyclohexylethoxy)phenyl)-4,4,5,5-tetramethyl-1,3,2-dioxaborolane (3 g, 8.72 mmol, 82% yield) as an oil.

192a) 4-(Diethoxymethyl)-1-ethyl-1H-1,2,3-triazole

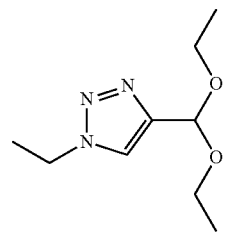

To a solution of iodoethane (36.5 g, 234 mmol) in tetrahydrofuran (THF) (200 mL) and water (200 mL) added NaHCO$_3$ (19.66 g, 234 mmol), CuSO$_4$ (2.491 g, 15.60 mmol), sodium azide (15.22 g, 234 mmol) and sodium (2R)-2-((S)-1,2-dihydroxyethyl)-4-hydroxy-5-oxotetrahydrofuran-3-olate (6.25 g, 31.2 mmol) slowly under nitrogen at room temperature. Then 3,3-diethoxyprop-1-yne (10 g, 78 mmol) was added. The reaction mixture was stirred at 70° C. for 16 h. Then it was extracted with ethyl acetate (3×). The combined organic phase was washed with brine, dried over Na$_2$SO$_4$ and concentrated to obtain the title compound 4-(diethoxymethyl)-1-ethyl-1H-1,2,3-triazole (16 g, 72.3 mmol, 93% yield) which was used in the next step without further purification. LC-MS m/z 200.3 (M+Na)$^+$, 1.78 min (ret. time).

192b) 1-Ethyl-1H-1,2,3-triazole-4-carbaldehyde

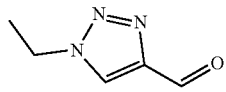

To a solution of 4-(diethoxymethyl)-1-ethyl-1H-1,2,3-triazole (16 g, 80 mmol) in water (20 mL) and DCM (20 mL), 2,2,2-trifluoroacetic acid (15.56 mL, 209 mmol) was added. The reaction mixture was stirred at 25° C. for 1 h. Then it was concentrated to obtain the title compound 1-ethyl-1H-1,2,3-triazole-4-carbaldehyde (10 g, 71.9 mmol, 90% yield) as a yellow solid which was used in the next step without further purification. LC-MS m/z 126.2 (M+Na)$^+$, 0.41 min (ret. time).

192c) (E)-tert-Butyl 3-(1-ethyl-1H-1,2,3-triazol-4-yl)acrylate

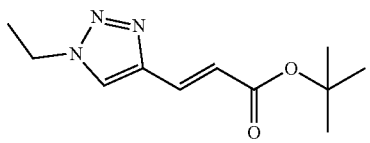 [SMILES: CCn1cc(/C=C/C(=O)OC(C)(C)C)nn1]

To a solution of tert-butyl 2-(diethoxyphosphoryl)acetate (26.6 g, 105 mmol) in tetrahydrofuran (THF) (250 mL), sodium hydride (2.53 g, 105 mmol) was added. The reaction mixture was stirred at 0° C. under N$_2$ for 10 mins. Then a solution of 1-ethyl-1H-1,2,3-triazole-4-carbaldehyde (11 g, 88 mmol) in THF (50 mL) was added dropwise and the reaction mixture was stirred at 0° C. for 15 mins. Water (200 mL) was added and extracted with ethyl acetate (3×). The combined organic layer was washed with water (2×) and brine (2×), dried over Na$_2$SO$_4$ and concentrated. The residue was purified on silica gel chromatography (petroleum ether:ethyl acetate=1:3) to afford the title compound (E)-tert-butyl 3-(1-ethyl-1H-1,2,3-triazol-4-yl)acrylate (18 g, 66.1 mmol, 75% yield) as a colorless oil. LC-MS m/z 224.1 (M+Na)$^+$, 1.77 min (ret. time).

192d) (1,2-trans)-tert-Butyl 2-(1-ethyl-1H-1,2,3-triazol-4-yl)cyclopropanecarboxylate

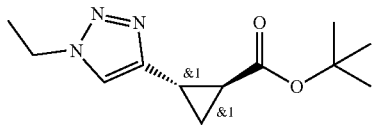 [SMILES: CCn1cc([C@H]2C[C@@H]2C(=O)OC(C)(C)C)nn1]

To a solution of trimethylsulfoxonium iodide (28.1 g, 128 mmol) in dimethyl sulfoxide (DMSO) (300 mL), sodium hydride (5.11 g, 128 mmol) was added. The reaction mixture was stirred at 25° C. under N$_2$ for 1 h. Then a solution of (E)-tert-butyl 3-(1-ethyl-1H-1,2,3-triazol-4-yl)acrylate (19 g, 85 mmol) in tetrahydrofuran (THF) (300 mL) was added dropwise. The reaction mixture was stirred at 25° C. for 1 h and stirred at 50° C. for another 1 h. 200 mL of ethyl acetate and 500 mL of water were added to reaction mixture. The water layer was extracted with ethyl acetate (3×). The combined organic phase was dried with Na$_2$SO$_4$, concentrated to obtain the title compound (1,2-trans)-tert-butyl 2-(1-ethyl-1H-1,2,3-triazol-4-yl)cyclopropanecarboxylate (18 g, 72.1 mmol, 85% yield). LC-MS m/z 238.0 (M+Na)$^+$, 1.57 min (ret. time).

192e) (1,2-trans)-2-(1-Ethyl-1H-1,2,3-triazol-4-yl)cyclopropanecarboxylic Acid

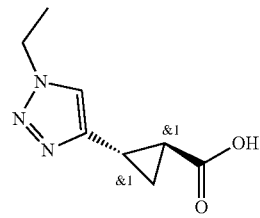

A solution of (1,2-trans)-tert-butyl 2-(1-ethyl-1H-1,2,3-triazol-4-yl)cyclopropanecarboxylate (18 g, 76 mmol) in dichloromethane (DCM) (100 mL) was added TFA (50 ml, 649 mmol) slowly under nitrogen at 40° C. The reaction mixture was stirred at 40° C. for 2 h. The reaction mixture was concentrated and it was washed with ether and ethyl acetate to obtain the title compound (1,2-trans)-2-(1-ethyl-1H-1,2,3-triazol-4-yl)cyclopropanecarboxylic acid (6.5 g, 34.8 mmol, 45.9% yield). LC-MS m/z 182.1 (M+Na)$^+$, 1.13 min (ret. time).

192f) Methyl 3-(dimethylamino)-2-((1,2-trans)-2-(1-ethyl-1H-1,2,3-triazol-4-yl)cyclopropanecarbonyl)acrylate

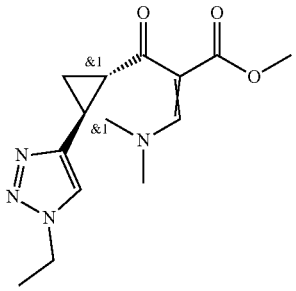 [SMILES: CCn1cc([C@H]2C[C@@H]2C(=O)C(=CN(C)C)C(=O)OC)nn1]

A solution of methyl 3-((1,2-trans)-2-(1-ethyl-1H-1,2,3-triazol-4-yl)cyclopropyl)-3-oxopropanoate (200 mg, 0.843 mmol) in 1,4-dioxane (5 mL) was added DMF-DMA (0.169 mL, 1.259 mmol) slowly under nitrogen at room temperature. The reaction mixture was stirred at 100° C. for 1 h. The reaction mixture was concentrated to obtain the title compound methyl 3-(dimethylamino)-2-((1,2-trans)-2-(1-ethyl-1H-1,2,3-triazol-4-yl)cyclopropanecarbonyl)acrylate (200 mg, 0.445 mmol, 52.8% yield) which was used for next step without further purification. LC-MS m/z 293.1 (M+H)$^+$, 1.34 min (ret. time).

192g) Methyl 1-(3-bromophenyl)-5-((1,2-trans)-2-(1-ethyl-1H-1,2,3-triazol-4-yl)cyclopropyl)-1H-pyrazole-4-carboxylate

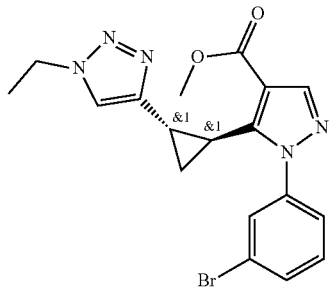 [SMILES: CCn1cc([C@H]2C[C@@H]2c2c(C(=O)OC)cnn2-c2cccc(Br)c2)nn1]

A solution of methyl 3-(dimethylamino)-2-((1,2-trans)-2-(1-ethyl-1H-1,2,3-triazol-4-yl)cyclopropanecarbonyl)acrylate (250 mg, 0.855 mmol) in acetonitrile (10 mL) was added (3-bromophenyl)hydrazine hydrochloride (191 mg, 0.855 mmol) slowly under nitrogen at 20° C. The reaction mixture was stirred at 20° C. for 16 h. After it was concentrated, 200 mL of water was added and extracted with ethyl acetate (3×). The combined organic phase was concentrated under a stream of nitrogen at 50° C. The crude product was purified by silica gel chromatography (hexane:ethyl acetate=1:1) to provide the title compound methyl 1-(3-bromophenyl)-5-((1,2-trans)-2-(1-ethyl-1H-1,2,3-triazol-4-yl)cyclopropyl)-1H-pyrazole-4-carboxylate (100 mg, 0.240 mmol, 28.1% yield). LC-MS m/z 416.2 (M+NH)$^+$, 1.84 min (ret. time).

193a) Methyl 1-(3-bromo-5-methoxyphenyl)-5-((1,2-trans)-2-(1-methyl-1H-1,2,3-triazol-4-yl)cyclopropyl)-1H-pyrazole-4-carboxylate

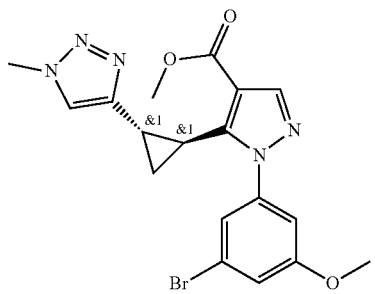

A solution of methyl 3-(dimethylamino)-2-((1,2-trans)-2-(1-methyl-1H-1,2,3-triazol-4-yl)cyclopropanecarbonyl)acrylate (198 mg, 0.710 mmol) in acetonitrile (5 mL) was added (3-bromo-5-methoxyphenyl)hydrazine hydrochloride (200 mg, 0.789 mmol) slowly under nitrogen at 20° C. The reaction mixture was stirred at 20° C. for 16 h. After it was concentrated, 20 mL of water was added and extracted with ethyl acetate (3×). The combined organic phase was concentrated under a stream of nitrogen at 50° C. The crude product was purified by silica gel chromatography (hexane:ethyl acetate=1:1) to provide the title compound methyl 1-(3-bromo-5-methoxyphenyl)-5-((1,2-trans)-2-(1-methyl-1H-1,2,3-triazol-4-yl)cyclopropyl)-1H-pyrazole-4-carboxylate (100 mg, 0.222 mmol, 28.2% yield). LC-MS m/z 432.1 (M+H)$^+$, 1.81 min (ret. time).

194a) Methyl 1-(3-bromo-5-hydroxyphenyl)-5-((1,2-trans)-2-(1-methyl-1H-1,2,3-triazol-4-yl)cyclopropyl)-1H-pyrazole-4-carboxylate

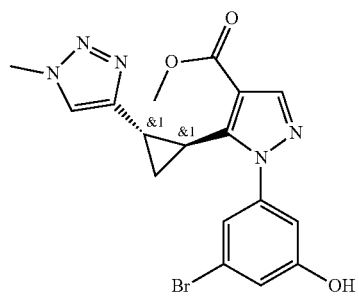 [SMILES: COC(=O)c1cnn(-c2cc(O)cc(Br)c2)c1[C@H]1C[C@@H]1c1cn(C)nn1]

A solution of methyl 3-(dimethylamino)-2-((1,2-trans)-2-(1-methyl-1H-1,2,3-triazol-4-yl)cyclopropanecarbonyl)acrylate (200 mg, 0.719 mmol) in acetonitrile (20 mL) was added 3-bromo-5-hydrazinylphenol hydrochloride (300 mg, 0.939 mmol) slowly under nitrogen at 20° C. The reaction mixture was stirred at 20° C. for 16 h. After it was concentrated, 20 mL of water was added and extracted with ethyl acetate (3×). The combined organic phase was concentrated under a stream of nitrogen at 50° C. The crude product was purified on silica gel chromatography (hexane:ethyl acetate=1:1) to obtain the title compound methyl 1-(3-bromo-5-hydroxyphenyl)-5-((1,2-trans)-2-(1-methyl-1H-1,2,3-triazol-4-yl)cyclopropyl)-1H-pyrazole-4-carboxylate (170 mg, 0.285 mmol, 39.6% yield). LC-MS m/z 418.0 (M+H)$^+$, 1.71 min (ret. time).

195a) 4-(Diethoxymethyl)-1-isopropyl-1H-1,2,3-triazole

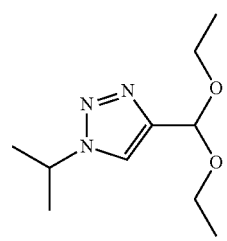

A solution of 2-iodopropane (3.98 g, 23.41 mmol) in tert-butanol (10.00 mL) was added NaHCO$_3$ (1.966 g, 23.41 mmol), copper(II) sulfate (0.249 g, 1.560 mmol), sodium azide (1.522 g, 23.41 mmol), sodium (R)-2-((S)-1,2-dihydroxyethyl)-4-hydroxy-5-oxo-2,5-dihydrofuran-3-olate (0.618 g, 3.12 mmol) and copper(II) sulfate (0.249 g, 1.560 mmol) solution in water (10 mL) slowly under nitrogen at room temperature. Then 3,3-diethoxyprop-1-yne (1 g, 7.80 mmol) was added. The reaction mixture was stirred at 60° C. for 16 h. Then reaction mixture was extracted with ethyl acetate (3×). The combined organic phase was concentrated to obtain the title compound 4-(diethoxymethyl)-1-isopropyl-1H-1,2,3-triazole (1.3 g, 6.10 mmol, 78% yield) which was used in next step without further purification.

195b) 1-Isopropyl-1H-1,2,3-triazole-4-carbaldehyde

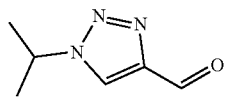

To a solution of 4-(diethoxymethyl)-1-isopropyl-1H-1,2,3-triazole (1.3 g, 6.10 mmol) in water (10 mL) TFA (4.70 mL, 30.5 mmol) was added. The reaction mixture was stirred at 25° C. for 1 h. Then reaction mixture was concentrated to obtain the title compound 1-isopropyl-1H-1,2,3-triazole-4-carbaldehyde (850 mg, 5.62 mmol, 92% yield) which was used in next step without further purification. LC-MS m/z 140.1 (M+H)$^+$, 0.94 min (ret. time).

195c) (E)-tert-Butyl 3-(1-isopropyl-1H-1,2,3-triazol-4-yl)acrylate

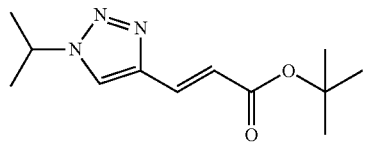 [SMILES: CC(C)n1cc(/C=C/C(=O)OC(C)(C)C)nn1]

To a solution of tert-butyl 2-(diethoxyphosphoryl)acetate (1.695 g, 6.72 mmol) in tetrahydrofuran (THF) (20 mL), sodium hydride (0.293 g, 7.33 mmol) was added. The reaction mixture was stirred at 0° C. under N$_2$ for 10 mins. Then a solution of 1-isopropyl-1H-1,2,3-triazole-4-carbaldehyde (0.85 g, 6.11 mmol) in THF (20 mL) was added dropwise and the reaction was stirred at 0° C. for 15 mins. Water (50 mL) was added and extracted with ethyl acetate (3x). The combined organic layer was washed with water (2x) and brine (2x), dried over Na$_2$SO$_4$ and concentrated. The crude product was purified on silica gel chromatography (hexane:ethyl acetate=1:5) to provide the title compound (E)-tert-butyl 3-(1-isopropyl-1H-1,2,3-triazol-4-yl)acrylate (1000 mg, 4.09 mmol, 66.9% yield) as an oil. LC-MS m/z 238.1 (M+H)$^+$, 1.65 min (ret. time).

195d) (1,2-trans)-tert-Butyl 2-(1-isopropyl-1H-1,2,3-triazol-4-yl)cyclopropanecarboxylate

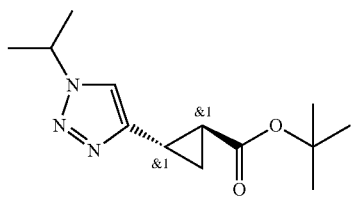 [SMILES: CC(C)n1cc([C@H]2C[C@@H]2C(=O)OC(C)(C)C)nn1]

To a solution of trimethylsulfoxonium iodide (1.855 g, 8.43 mmol) in dimethyl Sulfoxide (DMSO) (30 mL), sodium hydride (0.354 g, 8.85 mmol) was added. The reaction mixture was stirred at 25° C. under N$_2$ for 1 h. Then a solution of (E)-tert-butyl 3-(1-isopropyl-1H-1,2,3-triazol-4-yl)acrylate (1 g, 4.21 mmol) in tetrahydrofuran (THF) (30.0 mL) was added dropwise. The reaction was stirred at 25° C. for 1 h and at 50° C. for another 1 h. 200 mL of ethyl acetate and 50 mL of water were added. The water layer was extracted with ethyl acetate (3x). The combined organic phase was dried with Na$_2$SO$_4$ and concentrated to obtain the title compound (1,2-trans)-tert-butyl 2-(1-isopropyl-1H-1,2,3-triazol-4-yl)cyclopropanecarboxylate (0.8 g, 2.86 mmol, 68.0% yield) which was used in next step without further purification. LC-MS m/z 252.3 (M+H)$^+$, 1.57 min (ret. time).

195e) (1,2-trans)-2-(1-Isopropyl-1H-1,2,3-triazol-4-yl)cyclopropanecarboxylic Acid

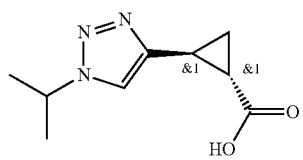

A solution of (1,2-trans)-tert-butyl 2-(1-isopropyl-1H-1,2,3-triazol-4-yl)cyclopropanecarboxylate (0.8 g, 3.18 mmol) in dichloromethane (DCM) (5 mL) was added TFA (2 mL, 26.0 mmol) slowly under nitrogen at 25° C. The reaction mixture was stirred at 25° C. for 4 h. After it was concentrated, 100 mL of ethyl acetate and 100 mL of water were added. Water layer was concentrated to provide the title compound (1,2-trans)-2-(1-isopropyl-1H-1,2,3-triazol-4-yl)cyclopropanecarboxylic acid (0.6 g, 2.77 mmol, 87% yield) as a white solid. LC-MS m/z 196.2 (M+H)$^+$, 1.43 min (ret. time).

195f) Methyl 3-((1,2-trans)-2-(1-isopropyl-1H-1,2,3-triazol-4-yl)cyclopropyl)-3-oxopropanoate

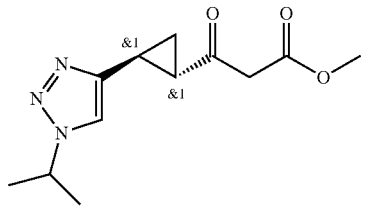 [SMILES: COC(=O)CC(=O)[C@H]1C[C@@H]1c1cn(C(C)C)nn1]

A solution of (1,2-trans)-2-(1-isopropyl-1H-1,2,3-triazol-4-yl)cyclopropanecarboxylic acid (0.4 g, 2.049 mmol) in tetrahydrofuran (THF) (50 mL) was added CDI (0.399 g, 2.459 mmol). The reaction mixture was stirred at 25° C. for 2 h. Then potassium 3-methoxy-3-oxopropanoate (0.480 g, 3.07 mmol) and potassium 3-methoxy-3-oxopropanoate (0.480 g, 3.07 mmol) were added. The reaction mixture was stirred at room temperature overnight. After it was concentrated, ethyl acetate (20 mL) was added. The suspension was washed with 1 M KHSO$_4$, NaHCO$_3$, and brine. The organic layer was dried over Na$_2$SO$_4$ and concentrated to obtain the title compound methyl 3-((1,2-trans)-2-(1-isopropyl-1H-1,2,3-triazol-4-yl)cyclopropyl)-3-oxopropanoate (170 mg, 0.582 mmol, 28.4% yield) as an oil. LC-MS m/z 224.1 (M+H)$^+$, 1.39 min (ret. time).

195g) (Z)-Methyl 3-(dimethylamino)-2-((1,2-trans)-2-(1-isopropyl-1H-1,2,3-triazol-4-yl)cyclopropanecarbonyl)acrylate

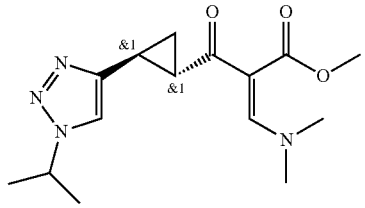 [SMILES: COC(=O)/C(=C\N(C)C)C(=O)[C@H]1C[C@@H]1c1cn(C(C)C)nn1]

A solution of methyl 3-((1,2-trans)-2-(1-isopropyl-1H-1,2,3-triazol-4-yl)cyclopropyl)-3-oxopropanoate (170 mg, 0.677 mmol) in toluene (10 mL) was added DMF-DMA (0.272 mL, 2.030 mmol) and TsOH (1.287 mg, 6.77 μmol) slowly under nitrogen at room temperature. The reaction mixture was stirred at 100° C. for 1 h. The solvent was concentrated. The crude product was purified on silica gel chromatography (DCM:methanol=20:1) to obtain the title compound methyl 3-(dimethylamino)-2-((1,2-trans)-2-(1-isopropyl-1H-1,2,3-triazol-4-yl)cyclopropanecarbonyl)acrylate (200 mg, 0.516 mmol, 76% yield) as an oil. LC-MS m/z 307.1 (M+H)$^+$, 1.24 min (ret. time).

195h) Methyl 1-(3-bromophenyl)-5-((1,2-trans)-2-(1-isopropyl-1H-1,2,3-triazol-4-yl)cyclopropyl)-1H-pyrazole-4-carboxylate

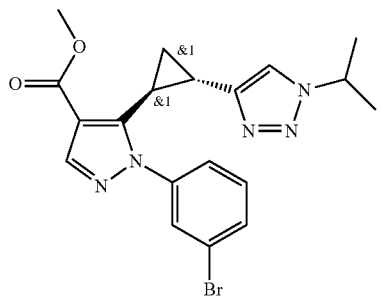 [SMILES: COC(=O)c1cnn(-c2cccc(Br)c2)c1[C@H]1C[C@@H]1c1cn(C(C)C)nn1]

A solution of methyl 3-(dimethylamino)-2-((1,2-trans)-2-(1-isopropyl-1H-1,2,3-triazol-4-yl)cyclopropanecarbonyl)acrylate (200 mg, 0.653 mmol) in acetonitrile (100 mL) was added (3-bromophenyl)hydrazine hydrochloride (200 mg, 0.850 mmol) and DIPEA (0.296 mL, 1.697 mmol) slowly under nitrogen at 20° C. The reaction mixture was stirred at 20° C. for 16 h. 500 mL of water was added. The solid was filtered and washed with hexane (3×), dried with high vacuum to obtain the title compound methyl 1-(3-bromophenyl)-5-((1,2-trans)-2-(1-isopropyl-1H-1,2,3-triazol-4-yl)cyclopropyl)-1H-pyrazole-4-carboxylate (130 mg, 0.287 mmol, 44.0% yield) as a solid. LC-MS m/z 430.1 (M+H)$^+$, 1.93 min (ret. time).

Example 196. 5-(2-(1-Methyl-1H-1,2,3-triazol-4-yl)cyclopropyl)-1-(6-(3-((R)-2-propylpiperidine-1-carbonyl)phenyl)pyridin-2-yl)-1H-pyrazole-4-carboxylic Acid

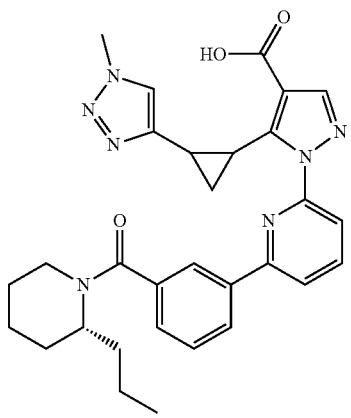 [SMILES: CCC[C@@H]1CCCCN1C(=O)c1cccc(-c2cccc(-n3ncc(C(=O)O)c3C3CC3c3cn(C)nn3)n2)c1]

196a) Methyl 1-(6-bromopyridin-2-yl)-5-(2-(1-methyl-1H-1,2,3-triazol-4-yl)cyclopropyl)-1H-pyrazole-4-carboxylate

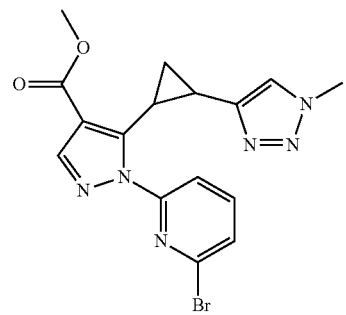 [SMILES: COC(=O)c1cnn(-c2cccc(Br)n2)c1C1CC1c1cn(C)nn1]

A solution of methyl 3-(dimethylamino)-2-(2-(1-methyl-1H-1,2,3-triazol-4-yl)cyclopropanecarbonyl)acrylate (300 mg, 1.078 mmol) in acetonitrile (5 mL) was added 2-bromo-6-hydrazinylpyridine (213 mg, 1.078 mmol) slowly under nitrogen at 20° C. The reaction mixture was stirred at 20° C. for 16 h. The solid was filtered and washed with ether (5 mL), dried with high vacuum to obtain the title compound methyl 1-(6-bromopyridin-2-yl)-5-(2-(1-methyl-1H-1,2,3-triazol-4-yl)cyclopropyl)-1H-pyrazole-4-carboxylate (200 mg, 0.496 mmol, 46.0% yield) which was used in next step without further purification. LC-MS m/z 405.1 (M+H)$^+$, 1.64 min (ret. time).

196b) Methyl 1-(6-(3-(tert-butoxycarbonyl)phenyl)pyridin-2-yl)-5-(2-(1-methyl-1H-1,2,3-triazol-4-yl)cyclopropyl)-1H-pyrazole-4-carboxylate

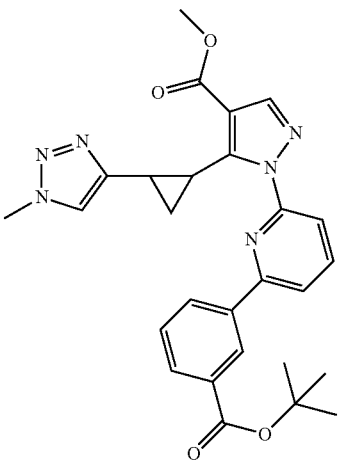 [SMILES: COC(=O)c1cnn(-c2cccc(-c3cccc(C(=O)OC(C)(C)C)c3)n2)c1C1CC1c1cn(C)nn1]

A mixture of methyl 1-(6-bromopyridin-2-yl)-5-(2-(1-methyl-1H-1,2,3-triazol-4-yl)cyclopropyl)-1H-pyrazole-4-carboxylate (250 mg, 0.620 mmol), (3-(tert-butoxycarbonyl)phenyl)boronic acid (145 mg, 0.651 mmol) and Na$_2$CO$_3$ (0.620 mL, 1.860 mmol) in toluene (5 mL) and methanol (3 mL) under nitrogen was stirred at 110° C. for 2 h. 10 mL of water was added and extracted with ethyl acetate (3×). The combined organic phase was washed with brine, dried over Na$_2$SO$_4$ and concentrated under a stream of nitrogen at 50° C. The crude product was purified on silica gel chromatography (petroleum ether:ethyl acetate=1:1) to provide the title compound methyl 1-(6-(3-(tert-butoxycarbonyl)phenyl)pyridin-2-yl)-5-(2-(1-methyl-1H-1,2,3-triazol-4-yl)cyclopropyl)-1H-pyrazole-4-carboxylate (250 mg, 0.455 mmol, 73.3% yield). LC-MS m/z 501.4 (M+H)$^+$, 2.01 min (ret. time).

196c) 3-(6-(4-(Methoxycarbonyl)-5-(2-(1-methyl-1H-1,2,3-triazol-4-yl)cyclopropyl)-1H-pyrazol-1-yl)pyridin-2-yl)benzoic Acid

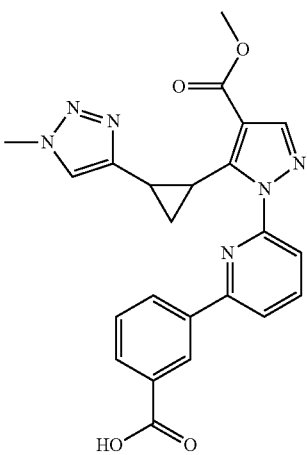 [SMILES: COC(=O)c1cnn(-c2cccc(-c3cccc(C(=O)O)c3)n2)c1C1CC1c1cn(C)nn1]

A solution of methyl 1-(6-(3-(tert-butoxycarbonyl)phenyl)pyridin-2-yl)-5-(2-(1-methyl-1H-1,2,3-triazol-4-yl)cyclopropyl)-1H-pyrazole-4-carboxylate (250 mg, 0.499 mmol) in dichloromethane (DCM) (3 mL) was added TFA (0.5 ml, 6.49 mmol) slowly under nitrogen at 25° C. The reaction mixture was stirred at 25° C. for 2 h. The reaction mixture was concentrated to obtain the title compound 3-(6-(4-(methoxycarbonyl)-5-(2-(1-methyl-1H-1,2,3-triazol-4-yl)cyclopropyl)-1H-pyrazol-1-yl)pyridin-2-yl)benzoic acid (200 mg, 0.405 mmol, 81% yield) which was used in next step without further purification. LC-MS m/z 445.1 (M+H)$^+$, 1.66 min (ret. time).

196d) Methyl 5-(2-(1-methyl-1H-1,2,3-triazol-4-yl)cyclopropyl)-1-(6-(3-((R)-2-propylpiperidine-1-carbonyl)phenyl)pyridin-2-yl)-1H-pyrazole-4-carboxylate

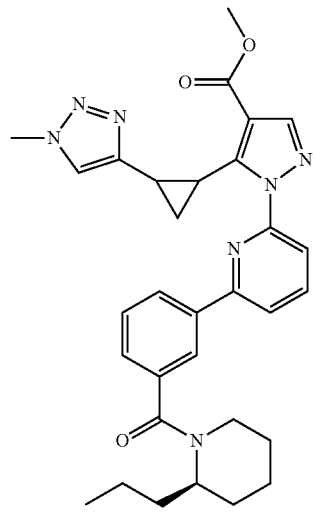 [SMILES: CCC[C@@H]1CCCCN1C(=O)c1cccc(-c2cccc(-n3ncc(C(=O)OC)c3C3CC3c3cn(C)nn3)n2)c1]

To a solution of 3-(6-(4-(methoxycarbonyl)-5-(2-(1-methyl-1H-1,2,3-triazol-4-yl)cyclopropyl)-1H-pyrazol-1-yl)pyridin-2-yl)benzoic acid, trifluoroacetic acid salt (219 mg, 0.393 mmol), (R)-2-propylpiperidine (50 mg, 0.393 mmol), HATU (179 mg, 0.472 mmol) in dichloromethane (DCM) (3 mL) and N,N-Dimethylformamide (DMF) (2 mL) was added DIPEA (0.343 mL, 1.965 mmol) slowly under nitrogen at 25° C. The reaction mixture was stirred at 25° C. for 16 h. 20 mL of water was added and extracted with ethyl acetate (3×). The combined organic layer was concentrated under a stream of nitrogen at 50° C. The crude product was purified on silica gel chromatography (ethyl acetate:methanol=50:1) to obtain the title compound methyl 5-(2-(1-methyl-1H-1,2,3-triazol-4-yl)cyclopropyl)-1-(6-(3-((R)-2-propylpiperidine-1-carbonyl)phenyl)pyridin-2-yl)-1H-pyrazole-4-carboxylate (200 mg, 0.318 mmol, 81% yield). LC-MS m/z 554.3 (M+H)$^+$, 2.02 min (ret. time).

196e) 5-(2-(1-Methyl-1H-1,2,3-triazol-4-yl)cyclopropyl)-1-(6-(3-((R)-2-propylpiperidine-1-carbonyl)phenyl)pyridin-2-yl)-1H-pyrazole-4-carboxylic Acid

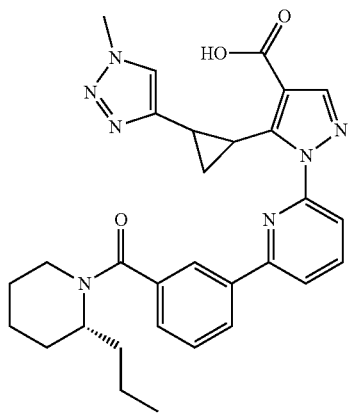 [SMILES: CCC[C@@H]1CCCCN1C(=O)c1cccc(-c2cccc(-n3ncc(C(=O)O)c3C3CC3c3cn(C)nn3)n2)c1]

A solution of methyl 5-(2-(1-methyl-1H-1,2,3-triazol-4-yl)cyclopropyl)-1-(6-(3-((R)-2-propylpiperidine-1-carbonyl)phenyl)pyridin-2-yl)-1H-pyrazole-4-carboxylate (200 mg, 0.361 mmol) in tetrahydrofuran (THF) (3 mL) and methanol (3.00 mL) was added a solution of LiOH (200 mg, 8.35 mmol) in water (5 mL) under nitrogen at 25° C. The reaction mixture was stirred at 25° C. for 16 h. It was adjusted pH=3 with 1 N HCl and extracted with ethyl acetate (3×). The combined organic layer was washed with brine, dried over $Na_2SO_4$ and concentrated. The residue was purified by reverse-phase HPLC (0.05% TFA/$H_2O$: $CH_3CN$=5%~95%) to obtain the title compound 5-(2-(1-methyl-1H-1,2,3-triazol-4-yl)cyclopropyl)-1-(6-(3-((R)-2-propylpiperidine-1-carbonyl)phenyl)pyridin-2-yl)-1H-pyrazole-4-carboxylic acid (60 mg, 0.109 mmol, 30.2% yield) as a white solid. LC-MS m/z 540.2 (M+H)$^+$, 1.82 min (ret. time).

The compounds in Table 11 were prepared by a method similar to the one described for the preparation of 5-(2-(1-Methyl-1H-1,2,3-triazol-4-yl)cyclopropyl)-1-(6-(3-((R)-2-propylpiperidine-1-carbonyl)phenyl)pyridin-2-yl)-1H-pyrazole-4-carboxylic acid. As is appreciated by those skilled in the art, these analogous examples may involve variations in general reaction conditions.

TABLE 11

| Example | Structure | Name | LCMS [M + H]$^+$ | Retention Time (min) |
|---|---|---|---|---|
| 197 | 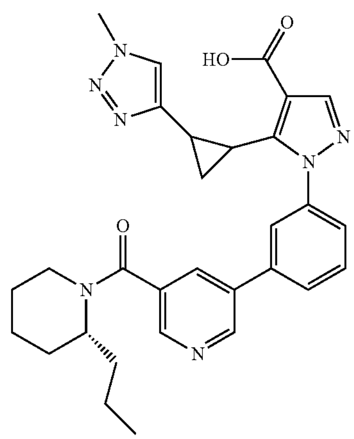 [SMILES: CCC[C@@H]1CCCCN1C(=O)c1cncc(-c2cccc(-n3ncc(C(=O)O)c3C3CC3c3cn(C)nn3)c2)c1] | 5-(2-(1-Methyl-1H-1,2,3-triazol-4-yl)cyclopropyl)-1-(3-(5-((R)-2-propylpiperidine-1-carbonyl)pyridin-3-yl)phenyl)-1H-pyrazole-4-carboxylic acid | 540.2 | 1.68 |
| 198 | 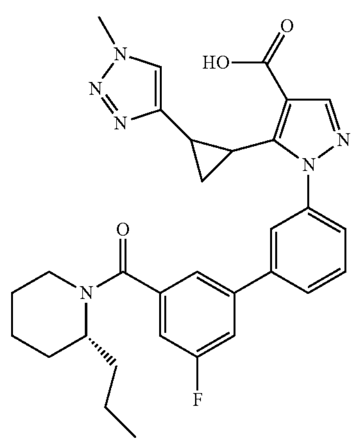 [SMILES: CCC[C@@H]1CCCCN1C(=O)c1cc(F)cc(-c2cccc(-n3ncc(C(=O)O)c3C3CC3c3cn(C)nn3)c2)c1] | 1-(3'-Fluoro-5'-((R)-2-propylpiperidine-1-carbonyl)-[1,1'-biphenyl]-3-yl)-5-(2-(1-methyl-1H-1,2,3-triazol-4-yl)cyclopropyl)-1H-pyrazole-4-carboxylic acid | 557.1 | 1.91 |

TABLE 11-continued

| Example | Structure | Name | LCMS [M + H]+ | Retention Time (min) |
|---------|-----------|------|---------------|----------------------|
| 199 | 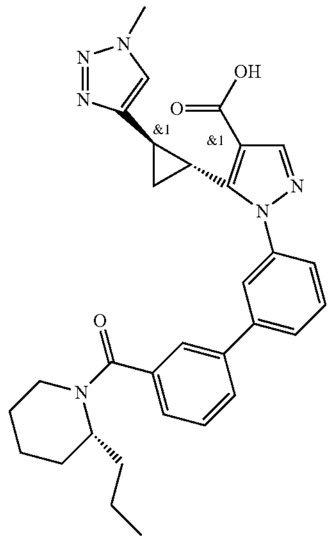 [SMILES: CCC[C@@H]1CCCCN1C(=O)c1cccc(-c2cccc(-n3ncc(C(=O)O)c3[C@@H]3C[C@H]3c3cn(C)nn3)c2)c1] | 5-((1,2-trans)-2-(1-methyl-1H-1,2,3-triazol-4-yl)cyclopropyl)-1-(3'-((R)-2-propylpiperidine-1-carbonyl)-[1,1'-biphenyl]-3-yl)-1H-pyrazole-4-carboxylic acid | 539.2 | 1.01 |
| 200 | 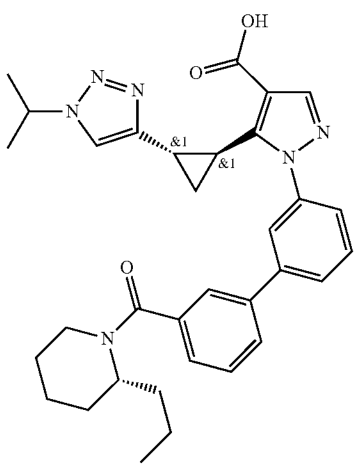 [SMILES: CCC[C@@H]1CCCCN1C(=O)c1cccc(-c2cccc(-n3ncc(C(=O)O)c3[C@H]3C[C@@H]3c3cn(C(C)C)nn3)c2)c1] | 5-((1,2-trans)-2-(1-Isopropyl-1H-1,2,3-triazol-4-yl)cyclopropyl)-1-3'-(R)-2-propylpiperidine-1-carbonyl)-[1,1'-biphenyl]-3-yl)-1H-pyrazole-4-carboxylic acid | 567.2 | 1.68 |
| 201 | 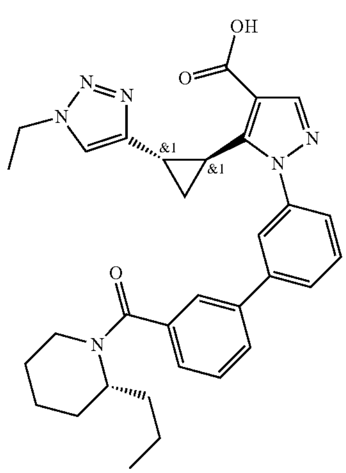 [SMILES: CCC[C@@H]1CCCCN1C(=O)c1cccc(-c2cccc(-n3ncc(C(=O)O)c3[C@H]3C[C@@H]3c3cn(CC)nn3)c2)c1] | 5-((1,2-trans)-2-(1-Ethyl-1H-1,2,3-triazol-4-yl)cyclopropyl)-1-(3'-((R)-2-propylpiperidine-1-carbonyl)-[1,1'-biphenyl]-3-yl)-1H-pyrazole-4-carboxylic acid | 553.3 | 1.74 |

TABLE 11-continued

| Example | Structure | Name | LCMS [M + H]+ | Retention Time (min) |
|---|---|---|---|---|
| 202 | 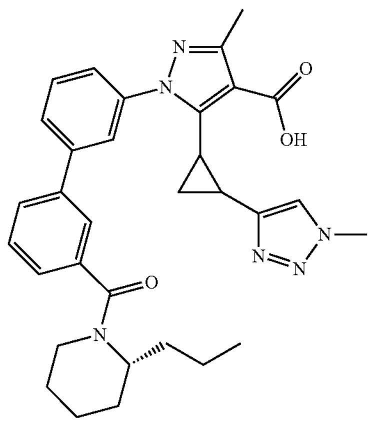 [SMILES: CCC[C@@H]1CCCCN1C(=O)c1cccc(-c2cccc(-n3nc(C)c(C(=O)O)c3C3CC3c3cn(C)nn3)c2)c1] | 3-Methyl-5-(2-(1-methyl-1H-1,2,3-triazol-4-yl)cyclopropyl)-1-(3'-((R)-2-propylpiperidine-1-carbonyl)-[1,1'-biphenyl]-3-yl)-1H-pyrazole-4-carboxylic acid | 553.3 | 1.93 |
| 203 | 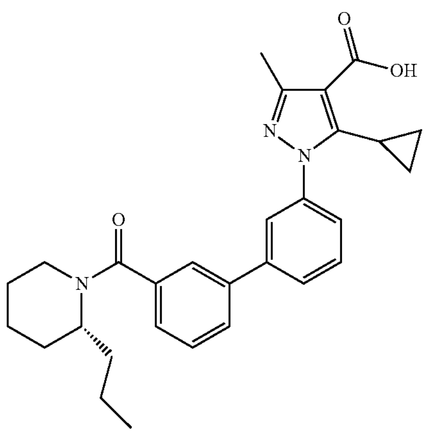 [SMILES: CCC[C@@H]1CCCCN1C(=O)c1cccc(-c2cccc(-n3nc(C)c(C(=O)O)c3C3CC3)c2)c1] | (R)-5-Cyclopropyl-3-methyl-1-(3'-(2-propylpiperidine-1-carbonyl)-[1,1'-biphenyl]-3-yl)-1H-pyrazole-4-carboxylic acid | 472.3 | 2.07 |

197a) (R)-(5-Bromopyridin-3-yl)(2-propylpiperidin-1-yl)methanone

A solution of 5-bromonicotinic acid (79 mg, 0.393 mmol) in dichloromethane (DCM) (5 mL) was added oxalyl chloride (0.138 mL, 1.572 mmol) slowly under nitrogen at 25° C. The reaction mixture was stirred at 25° C. for 2 h. After the reaction mixture was concentrated, it was dissolved in 5 mL of DCM, (R)-2-propylpiperidine (50 mg, 0.393 mmol) and DIPEA (0.275 mL, 1.572 mmol) were added under $N_2$. The reaction mixture was stirred at room temperature for another 2 h. 10 mL of water was added and extracted with ethyl acetate (3×). The combined organic layer was concentrated under a stream of nitrogen at 50° C. to obtain the title compound (R)-(5-bromopyridin-3-yl)(2-propylpiperidin-1-yl)methanone (100 mg, 0.292 mmol, 74.4% yield) which was used in next step without further purification. LC-MS m/z 313.0 (M+H)+, 1.94 min (ret. time).

197b) Methyl 5-(2-(1-methyl-1H-1,2,3-triazol-4-yl)cyclopropyl)-1-(3-(5-((R)-2-propylpiperidine-1-carbonyl)pyridin-3-yl)phenyl)-1H-pyrazole-4-carboxylate A mixture of methyl 5-(2-(1-methyl-1H-1,2,3-triazol-4-yl)cyclopropyl)-1-(3-(4,4,5,5-tetramethyl-1,3,2-dioxaborolan-2-yl)phenyl)-1H-pyrazole-4-carboxylate (144 mg, 0.321 mmol), (R)-(5-bromopyridin-3-yl)(2-propylpiperidin-1-yl) methanone (100 mg, 0.321 mmol) and Na$_2$CO$_3$ (0.321 mL, 0.964 mmol) in toluene (5 mL) and methanol (3 ml) under nitrogen was stirred at 110° C. for 2 h. 10 mL of water was added and extracted with ethyl acetate (3×). The combined organic layer was concentrated under a stream of nitrogen at 50° C. It was purified on silica gel chromatography (petroleum ether:ethyl acetate=1:1) to obtain the title compound methyl 5-(2-(1-methyl-1H-1,2,3-triazol-4-yl)cyclopropyl)-1-(3-(5-((R)-2-propylpiperidine-1-carbonyl)pyridin-3-yl)phenyl)-1H-pyrazole-4-carboxylate (100 mg, 0.146 mmol, 45.5% yield). LC-MS m/z 554.2 (M+H)$^+$, 1.86 min (ret. time).

198a) (R)-(3-Bromo-5-fluorophenyl)(2-propylpiperidin-1-yl)methanone

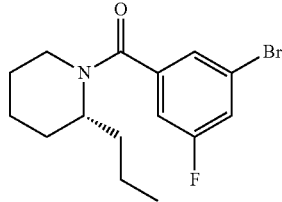 [SMILES: CCC[C@@H]1CCCCN1C(=O)c1cc(F)cc(Br)c1]

A solution of 3-bromo-5-fluorobenzoic acid (86 mg, 0.393 mmol) in dichloromethane (DCM) (5 mL) was added oxalyl chloride (0.138 mL, 1.572 mmol) slowly under nitrogen at 25° C. The reaction mixture was stirred at 25° C. for 2 h. After it was concentrated, it was re-dissolved in 5 mL of DCM, (R)-2-propylpiperidine (50 mg, 0.393 mmol) and DIPEA (0.275 mL, 1.572 mmol) were added. The reaction mixture was stirred at room temperature for 2 h. 10 mL of water was added and extracted with ethyl acetate (3×). The combined organic layer was concentrated under a stream of nitrogen at 50° C. to obtain the title compound (R)-(3-bromo-5-fluorophenyl)(2-propylpiperidin-1-yl)methanone (110 mg, 0.315 mmol, 80% yield) which was used in next step without further purification. LC-MS m/z 330.1 (M+H)$^+$, 2.13 min (ret. time).

198b) Methyl 1-(3'-fluoro-5'-((R)-2-propylpiperidine-1-carbonyl)-[1,1'-biphenyl]-3-yl)-5-(2-(1-methyl-1H-1,2,3-triazol-4-yl)cyclopropyl)-1H-pyrazole-4-carboxylate

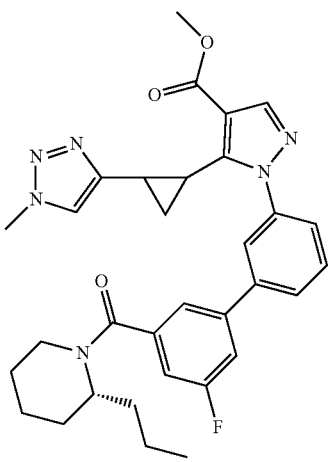 [SMILES: CCC[C@@H]1CCCCN1C(=O)c1cc(F)cc(-c2cccc(-n3ncc(C(=O)OC)c3C3CC3c3cn(C)nn3)c2)c1]

A mixture of methyl 5-(2-(1-methyl-1H-1,2,3-triazol-4-yl)cyclopropyl)-1-(3-(4,4,5,5-tetramethyl-1,3,2-dioxaborolan-2-yl)phenyl)-1H-pyrazole-4-carboxylate (137 mg, 0.305 mmol), (R)-(3-bromo-5-fluorophenyl)(2-propylpiperidin-1-yl)methanone (100 mg, 0.305 mmol) and Na$_2$CO$_3$ (0.305 mL, 0.914 mmol) in toluene (5 mL) and methanol (3 ml) under nitrogen was stirred at 110° C. for 2 h. 10 mL of water was added and extracted with ethyl acetate (3×). The combined organic layer was concentrated under a stream of nitrogen at 50° C. It was purified on silica gel chromatography (hexane:ethyl acetate=1:1) to obtain the title compound methyl 1-(3'-fluoro-5'-((R)-2-propylpiperidine-1-carbonyl)-[1,1'-biphenyl]-3-yl)-5-(2-(1-methyl-1H-1,2,3-triazol-4-yl)cyclopropyl)-1H-pyrazole-4-carboxylate (100 mg, 0.089 mmol, 29.3% yield) which was used in next step without further purification. LC-MS m/z 571.3 (M+H)$^+$, 2.08 min (ret. time).

199a) (R)-(3-Bromophenyl)(2-propylpiperidin-1-yl)methanone

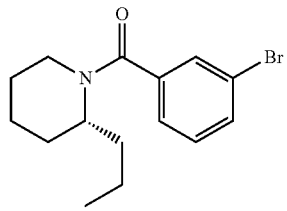 [SMILES: CCC[C@@H]1CCCCN1C(=O)c1cccc(Br)c1]

To a solution of 3-bromobenzoic acid (348 mg, 1.729 mmol) in dichloromethane (DCM) (10 mL), HATU (657 mg, 1.729 mmol) was added. After 10 mins, (R)-2-propylpiperidine (200 mg, 1.572 mmol) and DIEA (0.686 mL, 3.93 mmol) were added. The reaction mixture was stirred at room temperature for 4 h. Then it was partitioned between CH$_2$Cl$_2$ and saturated NaHCO$_3$ solution. The water layer was extracted with CH$_2$Cl$_2$ (2×). The combined organic phase was dried over MgSO$_4$ and concentrated. The crude product was then purified on a silica cartridge (24 g) with a Combiflash Companion, eluting at 30 mL/min with a gradient running from 100% hexanes to 100% EtOAc/hexanes over 35 min) to obtain the title compound (440 mg, 1.418 mmol, 90% yield). LC-MS m/z 310.0/312.0 (M+H)$^+$, 1.17 min (ret. time).

199b) Ethyl 5-((1,2-trans)-2-(1-methyl-1H-1,2,3-triazol-4-yl)cyclopropyl)-1-(3'-((R)-2-propylpiperidine-1-carbonyl)-[1,1'-biphenyl]-3-yl)-1H-pyrazole-4-carboxylate

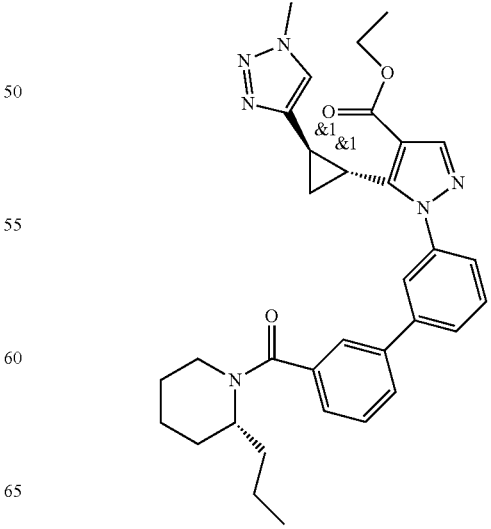

To a solution of rac-(3-(4-(ethoxycarbonyl)-5-(2-(1-methyl-1H-1,2,3-triazol-4-yl)cyclopropyl)-1H-pyrazol-1-yl)phenyl)boronic acid (246 mg, 0.645 mmol) in 1,4-dioxane (6 mL) and water (2.00 mL), (R)-(3-bromophenyl)(2-propylpiperidin-1-yl)methanone (100 mg, 0.322 mmol), Na$_2$CO$_3$ (102 mg, 0.967 mmol) and PdCl$_2$(dppf) (23.59 mg, 0.032 mmol) were added. The reaction mixture was stirred at 100° C. for 50 mins. The solvent was evaporated. The crude product was purified on silica gel chromatography (hexane/ethyl Acetate) to obtain the title compound (87 mg, 0.154 mmol, 47.6% yield). LC-MS m/z 567.2 (M+H)$^+$, 1.16 min (ret. time).

200a) (R)-(2-Propylpiperidin-1-yl)(3-(4,4,5,5-tetramethyl-1,3,2-dioxaborolan-2-yl)phenyl)methanone

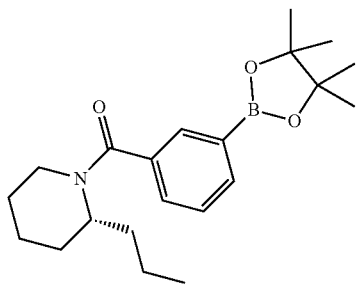 [SMILES: CCC[C@@H]1CCCCN1C(=O)c1cccc(B2OC(C)(C)C(C)(C)O2)c1]

To a solution of (R)-(3-bromophenyl)(2-propylpiperidin-1-yl)methanone (612 mg, 1.973 mmol) in 1,4-dioxane (50 mL) was added potassium acetate (387 mg, 3.95 mmol), bis(pinacolato)diboron (601 mg, 2.367 mmol) and the reaction mixture was degassed with argon for 30 min. Then PdCl$_2$(dppf)-CH$_2$Cl$_2$ adduct (81 mg, 0.099 mmol) was added. The reaction mixture was stirred at 100° C. for 16 h. After the reaction mixture was cooled and filtered through celite pad. The filtrate was concentrated under vacuum. The residue was purified on silica gel chromatography (hexane:ethyl acetate=3:1) to obtain the title compound (R)-(2-propylpiperidin-1-yl)(3-(4,4,5,5-tetramethyl-1,3,2-dioxaborolan-2-yl)phenyl)methanone (586 mg, 1.312 mmol, 66.5% yield) as white solid. LC-MS m/z 358.3 (M+H)$^+$, 2.27 min (ret. time).

200b) Methyl 5-((1,2-trans)-2-(1-isopropyl-1H-1,2,3-triazol-4-yl)cyclopropyl)-1-(3'-((R)-2-propylpiperidine-1-carbonyl)-[1,1'-biphenyl]-3-yl)-1H-pyrazole-4-carboxylate

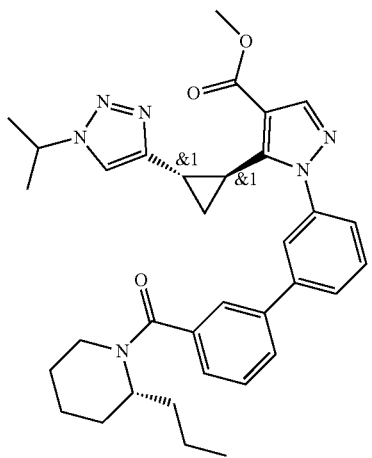 [SMILES: CCC[C@@H]1CCCCN1C(=O)c1cccc(-c2cccc(-n3ncc(C(=O)OC)c3[C@H]3C[C@@H]3c3cn(C(C)C)nn3)c2)c1]

A mixture of methyl 1-(3-bromophenyl)-5-((1,2-trans)-2-(1-isopropyl-1H-1,2,3-triazol-4-yl)cyclopropyl)-1H-pyrazole-4-carboxylate (75 mg, 0.174 mmol), (R)-(2-propylpiperidin-1-yl)(3-(4,4,5,5-tetramethyl-1,3,2-dioxaborolan-2-yl)phenyl)methanone (74.7 mg, 0.209 mmol), Na$_2$CO$_3$ (0.174 mL, 0.523 mmol) and PdCl$_2$(dppf)-CH$_2$Cl$_2$ adduct (14.23 mg, 0.017 mmol) in toluene (5 mL) and methanol (5.00 mL) under nitrogen was stirred at 110° C. for 2 h. 10 mL of water was added and extracted with ethyl acetate (3×). The combined organic layer was washed with brine, dried over Na$_2$SO$_4$ and concentrated under a stream of nitrogen at 50° C. It was purified on silica gel chromatography (hexane:ethyl acetate=1:1) to obtain the title compound methyl 5-((1,2-trans)-2-(1-isopropyl-1H-1,2,3-triazol-4-yl)cyclopropyl)-1-(3'-((R)-2-propylpiperidine-1-carbonyl)-[1,1'-biphenyl]-3-yl)-1H-pyrazole-4-carboxylate (80 mg, 0.129 mmol, 74.3% yield). LC-MS m/z 567.2 (M+H)$^+$, 1.97 min (ret. time).

201a) Methyl 5-((1,2-trans)-2-(1-ethyl-1H-1,2,3-triazol-4-yl)cyclopropyl)-1-(3'-((R)-2-propylpiperidine-1-carbonyl)-[1,1'-biphenyl]-3-yl)-1H-pyrazole-4-carboxylate

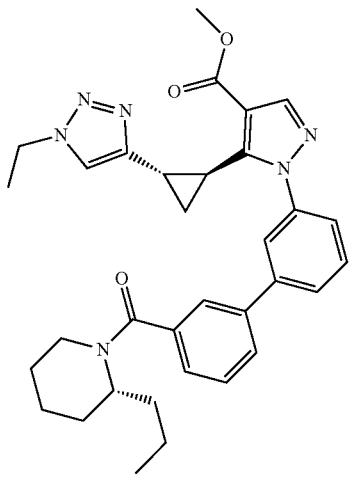 [SMILES: CCC[C@@H]1CCCCN1C(=O)c1cccc(-c2cccc(-n3ncc(C(=O)OC)c3[C@H]3C[C@@H]3c3cn(CC)nn3)c2)c1]

A mixture of methyl 1-(3-bromophenyl)-5-((1,2-trans)-2-(1-ethyl-1H-1,2,3-triazol-4-yl)cyclopropyl)-1H-pyrazole-4-carboxylate (100 mg, 0.240 mmol), (R)-(2-propylpiperidin-1-yl)(3-(4,4,5,5-tetramethyl-1,3,2-dioxaborolan-2-yl)phenyl)methanone (86 mg, 0.240 mmol), Na$_2$CO$_3$ (0.240 mL, 0.721 mmol) and PdCl$_2$(dppf)-CH$_2$Cl$_2$ adduct (19.62 mg, 0.024 mmol) in toluene (5 mL) and methanol (5.00 mL) under nitrogen was stirred at 110° C. for 2 h. 10 mL of water was added and extracted with ethyl acetate (3×). The combined organic layer was concentrated under a stream of nitrogen at 50° C. The crude product was purified on silica gel chromatography (hexane:ethyl acetate=1:1) to obtain the title compound methyl 5-((1,2-trans)-2-(1-ethyl-1H-1,2,3-triazol-4-yl)cyclopropyl)-1-(3'-((R)-2-propylpiperidine-1-carbonyl)-[1,1'-biphenyl]-3-yl)-1H-pyrazole-4-carboxylate (80 mg, 0.137 mmol, 57.0% yield). LC-MS m/z 567.2 (M+H)$^+$, 1.97 min (ret. time).

202a) Methyl 1-(3'-(tert-butoxycarbonyl)-[1,1'-biphenyl]-3-yl)-3-methyl-5-(2-(1-methyl-1H-1,2,3-triazol-4-yl)cyclopropyl)-1H-pyrazole-4-carboxylate

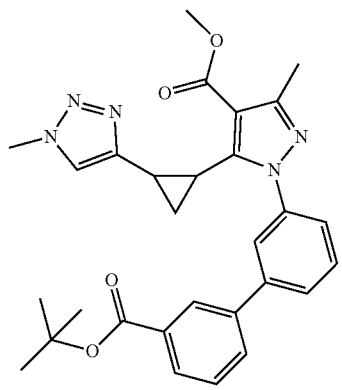 [SMILES: COC(=O)c1c(C)nn(-c2cccc(-c3cccc(C(=O)OC(C)(C)C)c3)c2)c1C1CC1c1cn(C)nn1]

A mixture of methyl 1-(3-bromophenyl)-3-methyl-5-(2-(1-methyl-1H-1,2,3-triazol-4-yl)cyclopropyl)-1H-pyrazole-4-carboxylate (500 mg, 1.201 mmol), (3-(tert-butoxycarbonyl)phenyl)boronic acid (320 mg, 1.441 mmol), $Na_2CO_3$ (1.201 mL, 3.60 mmol) and $PdCl_2$(dppf)-$CH_2Cl_2$ adduct (98 mg, 0.120 mmol) in toluene (5 mL) and methanol (5.00 mL) under nitrogen was stirred at 110° C. for 2 h. 10 mL of water was added and extracted with ethyl acetate (3×). The combined organic layer was concentrated under a stream of nitrogen at 50° C. The crude product was purified on silica gel chromatography (hexane:ethyl acetate=1:1) to obtain the title compound methyl 1-(3'-(tert-butoxycarbonyl)-[1,1'-biphenyl]-3-yl)-3-methyl-5-(2-(1-methyl-1H-1,2,3-triazol-4-yl)cyclopropyl)-1H-pyrazole-4-carboxylate (600 mg, 0.748 mmol, 62.2% yield). LC-MS m/z 514.2 (M+H)$^+$, 2.17 min (ret. time).

202b) 3'-(4-(Methoxycarbonyl)-3-methyl-5-(2-(1-methyl-1H-1,2,3-triazol-4-yl)cyclopropyl)-1H-pyrazol-1-yl)-[1,1'-biphenyl]-3-carboxylic Acid

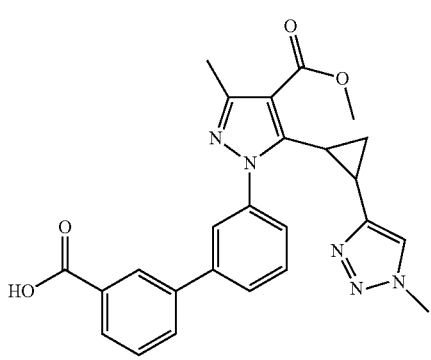 [SMILES: COC(=O)c1c(C)nn(-c2cccc(-c3cccc(C(=O)O)c3)c2)c1C1CC1c1cn(C)nn1]

A solution of methyl 1-(3'-(tert-butoxycarbonyl)-[1,1'-biphenyl]-3-yl)-3-methyl-5-(2-(1-methyl-1H-1,2,3-triazol-4-yl)cyclopropyl)-1H-pyrazole-4-carboxylate (600 mg, 1.168 mmol) in dichloromethane (DCM) (5 mL) was added TFA (2 mL, 26.0 mmol) under nitrogen at 25° C. The reaction mixture was stirred at 25° C. for 12 h. Then it was concentrated and washed with hexane to obtain the title compound 3'-(4-(methoxycarbonyl)-3-methyl-5-(2-(1-methyl-1H-1,2,3-triazol-4-yl)cyclopropyl)-1H-pyrazol-1-yl)-[1,1'-biphenyl]-3-carboxylic acid (350 mg, 0.612 mmol, 52.4% yield) which was used in next step without further purification. LC-MS m/z 457.8 (M+H)$^+$, 1.51 min (ret. time).

202c) Methyl 3-methyl-5-(2-(1-methyl-1H-1,2,3-triazol-4-yl)cyclopropyl)-1-(3'-((R)-2-propylpiperidine-1-carbonyl)-[1,1'-biphenyl]-3-yl)-1H-pyrazole-4-carboxylate

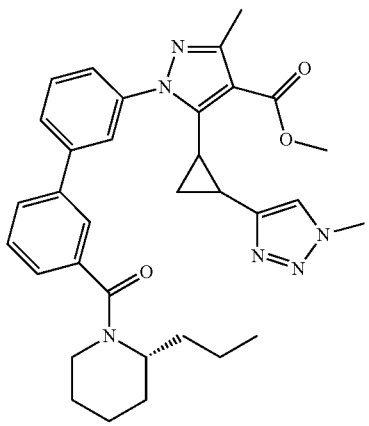 [SMILES: CCC[C@@H]1CCCCN1C(=O)c1cccc(-c2cccc(-n3nc(C)c(C(=O)OC)c3C3CC3c3cn(C)nn3)c2)c1]

A solution of 3'-(4-(methoxycarbonyl)-3-methyl-5-(2-(1-methyl-1H-1,2,3-triazol-4-yl)cyclopropyl)-1H-pyrazol-1-yl)-[1,1'-biphenyl]-3-carboxylic acid (350 mg, 0.765 mmol) in dichloromethane (DCM) (5 mL) was added (R)-2-propylpiperidine (97 mg, 0.765 mmol), HOBT (176 mg, 1.148 mmol), EDC (220 mg, 1.148 mmol) and DIPEA (0.267 mL, 1.530 mmol) slowly under nitrogen at 25° C. The reaction mixture was stirred at 25° C. for 16 h. 30 mL of water was added and extracted with ethyl acetate (3×). The combined organic layer was concentrated under a stream of nitrogen at 50° C. The crude product was purified on silica gel chromatography (hexane:ethyl acetate) to obtain the title compound methyl 3-methyl-5-(2-(1-methyl-1H-1,2,3-triazol-4-yl)cyclopropyl)-1-(3'-((R)-2-propylpiperidine-1-carbonyl)-[1,1'-biphenyl]-3-yl)-1H-pyrazole-4-carboxylate (250 mg, 0.410 mmol, 53.6% yield). LC-MS m/z 567.3 (M+H)$^+$, 2.18 min (ret. time).

203a) Methyl 2-(cyclopropanecarbonyl)-3-oxobutanoate

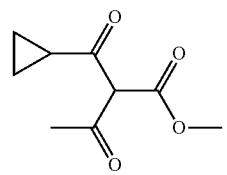

A solution of methyl 3-cyclopropyl-3-oxopropanoate (10 g, 70.3 mmol) in dichloromethane (DCM) (200 mL) was added pyridine (6.12 g, 77 mmol), magnesium chloride (7.03 g, 73.9 mmol) slowly under nitrogen at 0° C. The reaction mixture was stirred at 0° C. for 0.5 h. Acetyl chloride (6.07 g, 77 mmol) was added slowly. The reaction mixture was stirred at room temperature for 12 h. 30 mL of water was added and extracted with ethyl acetate (3×). The combined organic layer was concentrated under a stream of nitrogen at 50° C. to obtain the title compound methyl 2-(cyclopropanecarbonyl)-3-oxobutanoate (10 g, 48.9 mmol, 69.5% yield) which was used in next step without further purification. LC-MS m/z 185.1 (M+H)+, 1.86 min (ret. time).

203b) Methyl 1-(3-bromophenyl)-5-cyclopropyl-3-methyl-1H-pyrazole-4-carboxylate

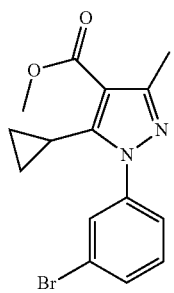 [SMILES: COC(=O)c1c(C)nn(-c2cccc(Br)c2)c1C1CC1]

A solution of methyl 2-(cyclopropanecarbonyl)-3-oxobutanoate (5 g, 27.1 mmol) in acetic acid (50 mL) was added (3-bromophenyl)hydrazine hydrochloride (6.07 g, 27.1 mmol) in water (50.0 mL) slowly under nitrogen at 20° C. The reaction mixture was stirred at 20° C. for 16 h. 20 mL of water was added and extracted with ethyl acetate (3×). The combined organic layer was concentrated under a stream of nitrogen at 50° C. The crude product was purified on silica gel chromatography (hexane:ethyl acetate=1:1) to obtain the title compound methyl 1-(3-bromophenyl)-5-cyclopropyl-3-methyl-1H-pyrazole-4-carboxylate (3 g, 8.95 mmol, 33.0% yield). LC-MS m/z 337.0 (M+H)+, 2.09 min (ret. time).

203c) Methyl 1-(3'-(tert-butoxycarbonyl)-[1,1'-biphenyl]-3-yl)-5-cyclopropyl-3-methyl-1H-pyrazole-4-carboxylate

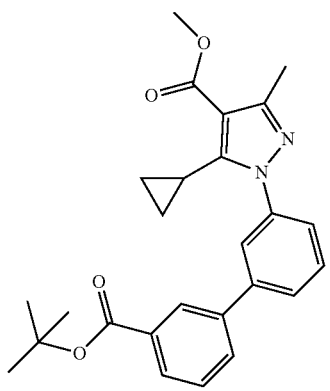 [SMILES: COC(=O)c1c(C)nn(-c2cccc(-c3cccc(C(=O)OC(C)(C)C)c3)c2)c1C1CC1]

A mixture of methyl 1-(3-bromophenyl)-5-cyclopropyl-3-methyl-1H-pyrazole-4-carboxylate (300 mg, 0.895 mmol), (3-(tert-butoxycarbonyl)phenyl)boronic acid (219 mg, 0.984 mmol), Na₂CO₃ (0.895 mL, 2.68 mmol) and PdCl₂(dppf)-CH₂Cl₂ adduct (73.1 mg, 0.089 mmol) in tolu-ene (5 mL) and ethanol (5 mL) under nitrogen was stirred at 110° C. for 2 h. 10 mL of water was added and extracted with ethyl acetate (3×). The combined organic layer was concentrated under a stream of nitrogen at 50° C. The crude product was purified on silica gel chromatography (hexane:ethyl acetate=10:1) to obtain the title compound methyl 1-(3'-(tert-butoxycarbonyl)-[1,1'-biphenyl]-3-yl)-5-cyclopropyl-3-methyl-1H-pyrazole-4-carboxylate (260 mg, 0.589 mmol, 65.8% yield). LC-MS m/z 433.2 (M+H)+, 1.99 min (ret. time).

203d) 3'-(5-Cyclopropyl-4-(methoxycarbonyl)-3-methyl-1H-pyrazol-1-yl)-[1,1'-biphenyl]-3-carboxylic Acid

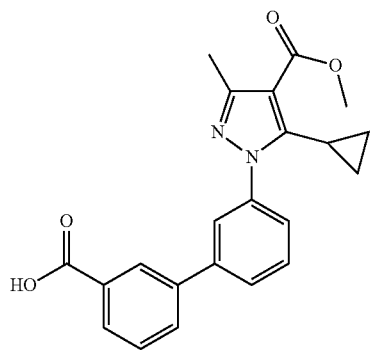 [SMILES: COC(=O)c1c(C)nn(-c2cccc(-c3cccc(C(=O)O)c3)c2)c1C1CC1]

A solution of methyl 1-(3'-(tert-butoxycarbonyl)-[1,1'-biphenyl]-3-yl)-5-cyclopropyl-3-methyl-1H-pyrazole-4-carboxylate (260 mg, 0.601 mmol) in dichloromethane (DCM) (5 mL) was added TFA (2 ml, 26.0 mmol) under nitrogen at 25° C. The reaction mixture was stirred at 25° C. for 12 h. The reaction mixture was concentrated to obtain the title compound 3'-(5-cyclopropyl-4-(methoxycarbonyl)-3-methyl-1H-pyrazol-1-yl)-[1,1'-biphenyl]-3-carboxylic acid (220 mg, 0.538 mmol, 89% yield) which was used in next step without further purification. LC-MS m/z 377.1 (M+H)+, 1.64 min (ret. time).

203f) (R)-Methyl 5-cyclopropyl-3-methyl-1-(3'-(2-propylpiperidine-1-carbonyl)-[1,1'-biphenyl]-3-yl)-1H-pyrazole-4-carboxylate

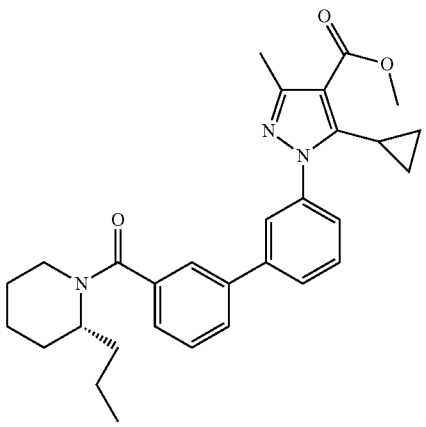 [SMILES: CCC[C@@H]1CCCCN1C(=O)c1cccc(-c2cccc(-n3nc(C)c(C(=O)OC)c3C3CC3)c2)c1]

A solution of 3'-(5-cyclopropyl-4-(methoxycarbonyl)-3-methyl-1H-pyrazol-1-yl)-[1,1'-biphenyl]-3-carboxylic acid (220 mg, 0.584 mmol) in dichloromethane (DCM) (5 mL) was added (R)-2-propylpiperidine (74.4 mg, 0.584 mmol), HOBt (134 mg, 0.877 mmol), EDC (168 mg, 0.877 mmol) and DIPEA (0.204 mL, 1.169 mmol) slowly under nitrogen at 25° C. The reaction mixture was stirred at 25° C. for 1 h. 30 mL of water was added and extracted with ethyl acetate (3×). The combined organic layer was concentrated under a stream of nitrogen at 50° C. to obtain the title compound (R)-methyl 5-cyclopropyl-3-methyl-1-(3'-(2-propylpiperidine-1-carbonyl)-[1,1'-biphenyl]-3-yl)-1H-pyrazole-4-carboxylate (200 mg, 0.375 mmol, 64.1% yield) which was used in next step without further purification. LC-MS m/z 486.1 (M+H)$^+$, 2.35 min (ret. time).

Example 204. 1-(6-(3-(6,6-Dimethyl-5,6-dihydrocyclopenta[c]pyrazol-1(4H)-yl)phenyl)pyridin-2-yl)-5-(trifluoromethyl)-1H-pyrazole-4-carboxylic Acid

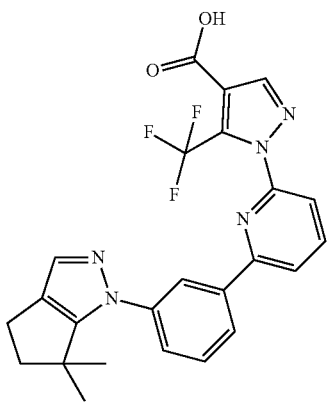 [SMILES: CC1(C)CCc2cnn(-c3cccc(-c4cccc(-n5ncc(C(=O)O)c5C(F)(F)F)n4)c3)c21]

204a) 5-((Dimethylamino)methylene)-2,2-dimethyl-cyclopentanone

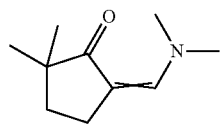

A mixture of 2,2-dimethylcyclopentanone (1 g, 8.92 mmol) and 1-tert-butoxy-N,N,N',N'-tetramethylmethanediamine (1.554 g, 8.92 mmol) was stirred under nitrogen at room temperature. The reaction mixture was stirred at 110° C. for 1 h. The reaction mixture was concentrated to obtain the title compound 5-((dimethylamino)methylene)-2,2-dimethylcyclopentanone (1.4 g, 8.37 mmol, 94% yield) as an oil which was used in next step without further purification. LC-MS m/z 168.1 (M+H)$^+$, 1.55 min (ret. time).

204b) 1-(3-Bromophenyl)-6,6-dimethyl-1,4,5,6-tetrahydrocyclopenta[c]pyrazole

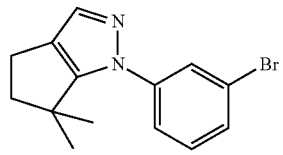 [SMILES: CC1(C)CCc2cnn(-c3cccc(Br)c3)c21]

A solution of 5-((dimethylamino)methylene)-2,2-dimethylcyclopentanone (1000 mg, 5.98 mmol) in acetic Acid (20 mL) was added (3-bromophenyl)hydrazine hydrochloride (1336 mg, 5.98 mmol) slowly under nitrogen at room temperature. The reaction mixture was stirred at 120° C. for 3 h. After the reaction mixture was concentrated, 50 mL of aqueous Na$_2$CO$_3$ was added and extracted with ethyl acetate (3×). The combined organic layer was concentrated under a stream of nitrogen at 50° C. The crude product was purified on silica gel chromatography (hexane:ethyl acetate=20:1) to obtain the title compound 1-(3-bromophenyl)-6,6-dimethyl-1,4,5,6-tetrahydrocyclopenta[c]pyrazole (880 mg, 2.66 mmol, 44.5% yield) which was used in next step without further purification. LC-MS m/z 293.1 (M+H)$^+$, 2.25 min (ret. time).

204c) 6,6-dimethyl-1-(3-(4,4,5,5-tetramethyl-1,3,2-dioxaborolan-2-yl)phenyl)-1,4,5,6-tetrahydrocyclopenta[c]pyrazole

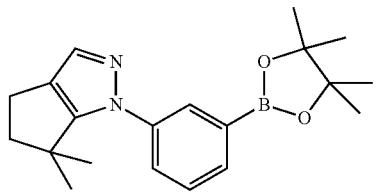 [SMILES: CC1(C)CCc2cnn(-c3cccc(B4OC(C)(C)C(C)(C)O4)c3)c21]

To a solution of 1-(3-bromophenyl)-6,6-dimethyl-1,4,5,6-tetrahydrocyclopenta[c]pyrazole (500 mg, 1.717 mmol) in 1,4-dioxane (50 mL) was added potassium acetate (337 mg, 3.43 mmol), bis(pinacolato)diboron (523 mg, 2.061 mmol). After the reaction mixture was degassed with argon for 30 mins, PdCl$_2$(dppf)-CH$_2$Cl$_2$ adduct (70.1 mg, 0.086 mmol) was added. The reaction mixture was stirred at 100° C. for 16 h. The mixture was filtered through celite pad and the filtrate was concentrated under vacuum. The crude residue was purified on silica gel chromatography (hexane:ethyl acetate=10:1) to obtain the title compound 6,6-dimethyl-1-(3-(4,4,5,5-tetramethyl-1,3,2-dioxaborolan-2-yl)phenyl)-1,4,5,6-tetrahydrocyclopenta[c]pyrazole (500 mg, 1.064 mmol, 62.0% yield) as a white solid. LC-MS m/z 339.2 (M+H)$^+$, 2.35 min (ret. time).

204d) Ethyl 1-(6-bromopyridin-2-yl)-5-(trifluoromethyl)-1H-pyrazole-4-carboxylate

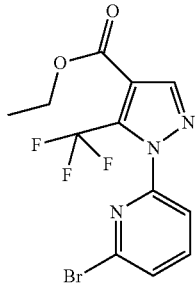 [SMILES: CCOC(=O)c1cnn(-c2cccc(Br)n2)c1C(F)(F)F]

To a solution of ethyl 2-(ethoxymethylene)-4,4,4-trifluoro-3-oxobutanoate (3.51 g, 14.63 mmol) in ethanol (50 mL) was added 2-bromo-6-hydrazinylpyridine (2.5 g, 13.30 mmol) slowly under nitrogen at −20° C. The reaction mixture was stirred at 20° C. for 16 h. The solvent was removed. The residue was purified on silica gel chromatography (hexane:ethyl acetate=20:1) to obtain the title compound ethyl 1-(6-bromopyridin-2-yl)-5-(trifluoromethyl)-1H-pyrazole-4-carboxylate (2.5 g, 6.66 mmol, 50.1% yield) as a solid. LC-MS m/z 366.0 (M+H)$^+$, 2.20 min (ret. time).

204e) Ethyl 1-(6-(3-(6,6-dimethyl-5,6-dihydrocyclopenta[c]pyrazol-1(4H)-yl)phenyl)pyridin-2-yl)-5-(trifluoromethyl)-1H-pyrazole-4-carboxylate

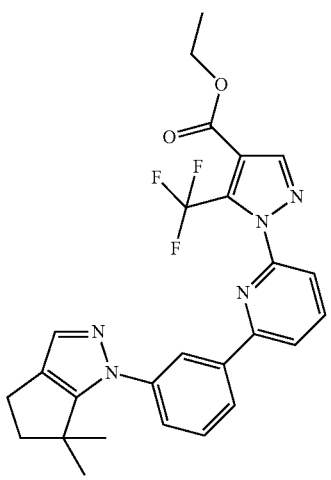 [SMILES: CCOC(=O)c1cnn(-c2cccc(-c3cccc(-n4ncc5c4C(C)(C)CC5)c3)n2)c1C(F)(F)F]

A mixture of ethyl 1-(6-bromopyridin-2-yl)-5-(trifluoromethyl)-1H-pyrazole-4-carboxylate (100 mg, 0.275 mmol), 6,6-dimethyl-1-(3-(4,4,5,5-tetramethyl-1,3,2-dioxaborolan-2-yl)phenyl)-1,4,5,6-tetrahydrocyclopenta[c]pyrazole (139 mg, 0.412 mmol), Na$_2$CO$_3$ (0.275 mL, 0.824 mmol) and PdCl$_2$(dppf)-CH$_2$Cl$_2$ adduct (22.43 mg, 0.027 mmol) in 1,4-dioxane (6 mL) and water (2 mL) under nitrogen was stirred at 110° C. for 2 h. After the solvent was removed, 10 mL of water was added and extracted with ethyl acetate (3×). The combined organic layer was washed with brine, dried over Na$_2$SO$_4$ and concentrated. The residue was purified on silica gel chromatography (hexane:ethyl acetate=1:2) to obtain the title compound ethyl 1-(6-(3-(6,6-dimethyl-5,6-dihydrocyclopenta[c]pyrazol-1(4H)-yl)phenyl)pyridin-2-yl)-5-(trifluoromethyl)-1H-pyrazole-4-carboxylate (100 mg, 0.151 mmol, 55.1% yield). LC-MS m/z 496.1 (M+H)$^+$, 2.32 min (ret. time).

204f) 1-(6-(3-(6,6-Dimethyl-5,6-dihydrocyclopenta[c]pyrazol-1(4H)-yl)phenyl)pyridin-2-yl)-5-(trifluoromethyl)-1H-pyrazole-4-carboxylic Acid

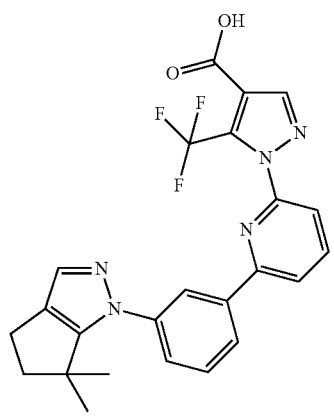 [SMILES: CC1(C)CCc2cnn(-c3cccc(-c4cccc(-n5ncc(C(=O)O)c5C(F)(F)F)n4)c3)c21]

To a solution of ethyl 1-(6-(3-(6,6-dimethyl-5,6-dihydrocyclopenta[c]pyrazol-1(4H)-yl)phenyl)pyridin-2-yl)-5-(trifluoromethyl)-1H-pyrazole-4-carboxylate (100 mg, 0.202 mmol) in tetrahydrofuran (THF) (2.000 mL), LiOH (48.3 mg, 2.018 mmol) in water (2 mL) was added. The reaction mixture was stirred at 25° C. for 16 h. After THF was removed, it was adjusted pH=6 with 1 N HCl. The solid was filtered and was purified by reverse-phase HPLC (0.05% TFA/H$_2$O:CH$_3$CN=5%~95%) to obtain the title compound 1-(6-(3-(6,6-dimethyl-5,6-dihydrocyclopenta[c]pyrazol-1(4H)-yl)phenyl)pyridin-2-yl)-5-(trifluoromethyl)-1H-pyrazole-4-carboxylic acid (56 mg, 0.120 mmol, 59.4% yield) as a solid. LC-MS m/z 468.1 (M+H)$^+$, 1.69 min (ret. time).

Example 205. 5-Cyclopropyl-1-(3'-(6-methyl-6-propyl-5,6-dihydrocyclopenta[c]pyrazol-1(4H)-yl)-[1,1'-biphenyl]-3-yl)-1H-pyrazole-4-carboxylic Acid

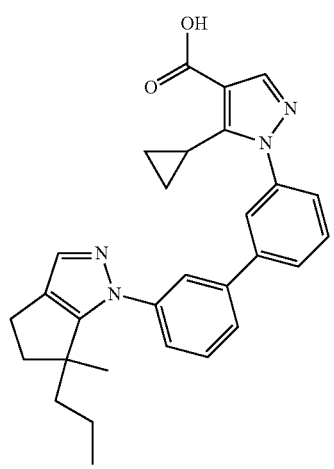 [SMILES: CCCC1(C)CCc2cnn(-c3cccc(-c4cccc(-n5ncc(C(=O)O)c5C5CC5)c4)c3)c21]

205a) (1-Chloropropyl)(phenyl)sulfane

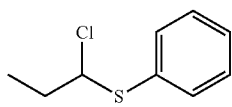

To a solution of phenyl(propyl)sulfane (1500 mg, 9.85 mmol) in CCl$_4$ (20 mL, 207 mmol) at room temperature, NCS (1579 mg, 11.82 mmol) was added. The reaction mixture was stirred at room temperature for 4 h. The solid was filtered and filtrate was evaporated to obtain the title compound (1809 mg, 9.69 mmol, 98% yield) which was used in next step without further purification. $^1$H NMR (400 MHz, chloroform-d) ppm: 1.10-1.25 (m, 3H) 2.02-2.31 (m, 2H) 5.14-5.38 (m, 1H) 7.39-7.68 (m, 5H).

205b) 2-Methyl-2-(1-(phenylthio)propyl)cyclopentanone

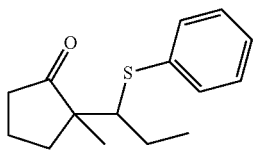 [SMILES: CCC(Sc1ccccc1)C1(C)CCCC1=O]

To a solution of trimethyl((2-methylcyclopent-1-en-1-yl)oxy)silane (1500 mg, 8.81 mmol) in dichloromethane (DCM) (20 mL) at room temperature, (1-chloropropyl)(phenyl)sulfane (1809 mg, 9.69 mmol) and zinc(II) bromide (198 mg, 0.881 mmol) were added. The reaction mixture was stirred at room temperature for 16 h. Then it was filtered with celite and evaporated. The crude product was purified on silica gel chromatography to obtain the title compound (1.109 g, 4.46 mmol, 50.7% yield). LC-MS m/z 249.2 (M+H)$^+$, 1.17 min (ret. time).

205c) 2-Methyl-2-propylcyclopentanone

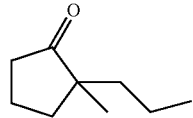

To a solution of 2-methyl-2-(1-(phenylthio)propyl)cyclopentanone (500 mg, 2.013 mmol) in acetone (20 mL), W-2 Rancy nickel (591 mg, 10.07 mmol) was added. The reaction mixture was stirred at room temperature for 2 h. Then it was filtered with celite and concentrated to obtain the title compound (450 mg, 3.21 159% yield) which was carried over to next step without further purification. LC-MS m/z 140.1 (M+H)$^+$, 0.75 min (ret. time).

205d) (E)-5-((Dimethylamino)methylene)-2-methyl-2-propylcyclopentanone

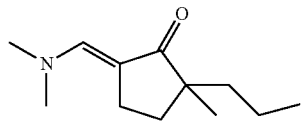

To 2-methyl-2-propylcyclopentanone (500 mg, 3.57 mmol) in flask, 1-tert-butoxy-N,N,N',N'-tetramethylmethanediamine (736 µl, 3.57 mmol) was added. The reaction mixture was stirred at 120° C. for 1 h. This reaction mixture was carried over to next step without further purification. LC-MS m/z 195.9 (M+H)$^+$, 0.93 min (ret. time).

205e) Ethyl 5-cyclopropyl-1-(3'-(6-methyl-6-propyl-5,6-dihydrocyclopenta[c]pyrazol-1(4H)-yl)-[1,1'-biphenyl]-3-yl)-1H-pyrazole-4-carboxylate

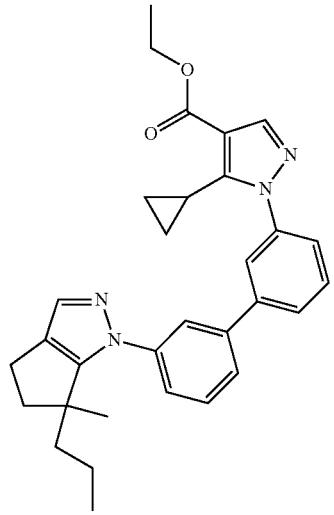 [SMILES: CCCC1(C)CCc2cnn(-c3cccc(-c4cccc(-n5ncc(C(=O)OCC)c5C5CC5)c4)c3)c21]

To a solution of ethyl 5-cyclopropyl-1-(3'-hydrazinyl-[1,1'-biphenyl]-3-yl)-1H-pyrazole-4-carboxylate (900 mg, 2.483 mmol) in acetic acid (5 mL), (E)-5-((dimethylamino)methylene)-2-methyl-2-propylcyclopentanone (485 mg, 2.483 mmol) was added at room temperature. Then the reaction mixture was stirred at 100° C. for 90 mins. 1N NaOH was added to pH=7 and extracted with ethyl acetate (3×). The combined organic phase was dried over MgSO$_4$ and concentrated. The crude product was purified by reverse-phase HPLC to obtain the title compound (23 mg, 0.046 mmol, 1.873% yield). $^1$H NMR (400 MHz, DMSO-d$_6$) ppm 0.43-1.61 (m, 15H) 2.01-2.42 (m, 2H) 2.55 (br. s., 4H) 4.27 (d, J=7.03 Hz, 3H) 7.22-8.20 (m, 10H).

205f) 5-Cyclopropyl-1-(3'-(6-methyl-6-propyl-5,6-dihydrocyclopenta[c]pyrazol-1(4H)-yl)-[1,1'-biphenyl]-3-yl)-1H-pyrazole-4-carboxylic Acid

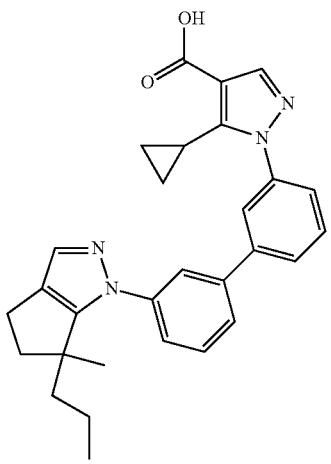 [SMILES: CCCC1(C)CCc2cnn(-c3cccc(-c4cccc(-n5ncc(C(=O)O)c5C5CC5)c4)c3)c21]

To a solution of ethyl 5-cyclopropyl-1-(3'-(6-methyl-6-propyl-5,6-dihydrocyclopenta[c]pyrazol-1(4H)-yl)-[1,1'-biphenyl]-3-yl)-1H-pyrazole-4-carboxylate (23 mg, 0.046 mmol) in methanol (1 mL), LiOH (11.14 mg, 0.465 mmol) and 0.1 mL of water were added. The reaction mixture was stirred at room temperature for 16 h. 1N HCl was added to pH=1. The solvent was evaporated. The crude product was purified by reverse-phase HPLC to obtain the title compound (3.2 mg, 0.00686 mmol, 14.75% yield). LC-MS m/z 467.4 (M+H)$^+$, 1.24 min (ret. time).

Example 206. 1-(3'-(6-Butyl-5,6-dihydrocyclopenta[c]pyrazol-1(4H)-yl)-[1,1'-biphenyl]-3-yl)-5-cyclopropyl-1H-pyrazole-4-carboxylic Acid

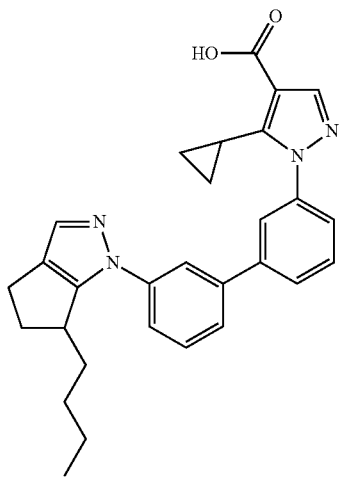 [SMILES: CCCCC1CCc2cnn(-c3cccc(-c4cccc(-n5ncc(C(=O)O)c5C5CC5)c4)c3)c21]

206a) 2-Butyl-5-(((dimethylamino)methylene)cyclopentanone

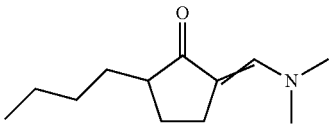

1-tert-butoxy-N,N,N',N'-tetramethylmethanediamine (186 mg, 1.070 mmol) was added dropwise to 2-butylcyclopentanone (150 mg, 1.070 mmol) under nitrogen atmosphere at ambient temperature. The reaction mixture was stirred at ambient temperature under nitrogen for 1 h, then at 110° C. for 2.5 h. The reaction mixture was stored in the refrigerator overnight. The crude product was carried forward. LC-MS m/z 196.1 (M+H)$^+$, 0.91 min (ret. time)

206b) tert-Butyl 2-(3-bromophenyl)hydrazinecarboxylate

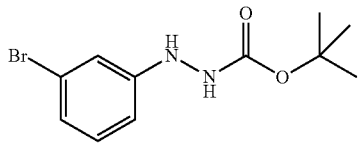 [SMILES: CC(C)(C)OC(=O)NNc1cccc(Br)c1]

To a solution of (3-bromophenyl)hydrazine hydrochloride (3.28 g, 14.66 mmol) and triethylamine (6.13 mL, 44.0 mmol) in dichloromethane (DCM) (20 mL) was added di-tert-butyl dicarbonate (3.40 mL, 14.66 mmol). The reaction mixture was stirred at ambient temperature for 93 h. The reaction mixture was quenched with water and extracted with DCM twice. The combined organic layer was dried over sodium sulfate, filtered and concentrated to afford the title compound (4.1815 g, 14.56 mmol, 99% yield). LC-MS m/z 287.0 (M+H)$^+$, 0.96 min (ret. time).

206c) Ethyl 5-cyclopropyl-1-(3'-hydrazinyl-[1,1'-biphenyl]-3-yl)-1H-pyrazole-4-carboxylate

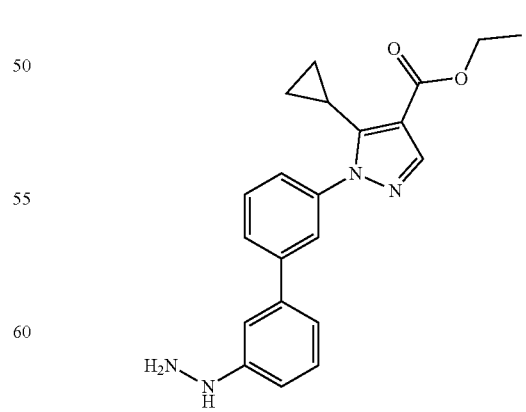

To a solution of ethyl 1-(3'-(2-(tert-butoxycarbonyl)hydrazinyl)-[1,1'-biphenyl]-3-yl)-5-cyclopropyl-1H-pyrazole-4-carboxylate (650 mg, 1.405 mmol) in dichloromethane (DCM) (6 mL) was added 4N HCl in dioxane (1.405 mL, 5.62 mmol). The reaction mixture was stirred at ambient temperature for 17 h. The solvent was evaporated to afford the crude product. Soluble impurities were removed from the crude product via trituration with ether to afford the title compound (260.2 mg, 0.718 mmol, 51.1% yield) as an HCl salt. LC-MS m/z 363.1 (M+H)$^+$, 0.84 min (ret. time).

206d) 1-(3'-(6-Butyl-5,6-dihydrocyclopenta[c]pyrazol-1(4H)-yl)-[1,1'-biphenyl]-3-yl)-5-cyclopropyl-1H-pyrazole-4-carboxylic Acid

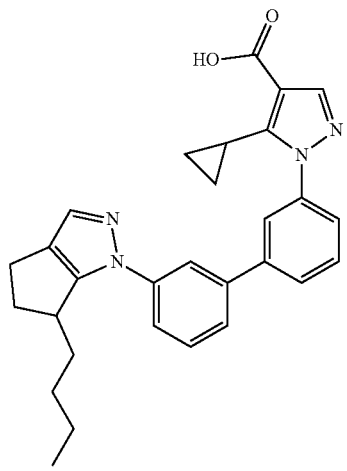 [SMILES: CCCCC1CCc2cnn(-c3cccc(-c4cccc(-n5ncc(C(=O)O)c5C5CC5)c4)c3)c21]

To a solution of ethyl 5-cyclopropyl-1-(3'-hydrazinyl-[1,1'-biphenyl]-3-yl)-1H-pyrazole-4-carboxylate hydrochloride (70 mg, 0.175 mmol) in acetic acid (1.5 mL) was added 2-butyl-5-((dimethylamino)methylene)cyclopentanone (34.3 mg, 0.175 mmol). The reaction mixture was stirred at reflux for 3 h. The reaction mixture was neutralized with 2.5 M NaOH and concentrated. To the crude product was added methanol (1.500 mL), tetrahydrofuran (THF) (1 mL) and LiOH (0.877 mL, 1.755 mmol). The reaction mixture was stirred at ambient temperature for 20 h. To the reaction mixture was added 2 M LiOH (0.5 mL). The reaction mixture was stirred at ambient temperature for 69 h. To the reaction mixture was added 2 M LiOH (1 mL). The reaction mixture was stirred at ambient temperature for 22 h. To the reaction mixture was added 2 M LiOH (1 mL). The reaction mixture was stirred at ambient temperature for 24 h. The reaction mixture was transferred to a microwave vessel and concentrated. The reaction was stirred at ambient temperature over night. The reaction vessel was heated at high absorption in a Biotage microwave for 30 min at 80° C. LCMS showed similar conversion. The reaction vessel was heated in a Biotage microwave at high absorption for 45 min at 100° C. LCMS showed no further conversion. To the reaction vessel was added DMSO (0.5 mL). The reaction vessel was heated in a Biotage microwave at high absorption for 1 hr at 85° C. LCMS showed no further conversion. The reaction mixture was concentrated. The mixture was washed with DCM and filtered. LCMS of the filtrate showed ester product. The filtrate was concentrated and diluted with H$_2$O and extracted with EtOAc (3×). The combined organic fractions were concentrated to afford the crude product. To the reaction mixture was added MeOH (1 mL, THF (0.5 mL), and 2 M LiOH (0.8 mL). The reaction vessel was heated in a Biotage microwave at high absorption for 45 min at 100° C. The reaction mixture was neutralized with 1 N HCl and concentrated. The crude product was dissolved in DMSO (2 mL) and purified on a Gilson HPLC, eluting at 20 mL/min with a linear gradient running from 40% CH$_3$CN/H$_2$O (0.1% TFA) to 90% CH$_3$CN/H$_2$O (0.1% TFA) over 15 min. The desired fractions were concentrated to afford the title compound (12.41 mg, 0.027 mmol, 15.16% yield). LC-MS m/z 467.3 (M+H)$^+$, 1.28 min (ret. time); $^1$H NMR (400 MHz, methanol-d4) δ ppm: 0.67 (d, J=5.52 Hz, 2H) 0.73 (t, J=6.53 Hz, 3H) 0.95 (d, J=8.28 Hz, 2H) 1.18 (m, J=14.20, 7.00, 7.00 Hz, 4H) 1.29-1.41 (m, 2H) 1.53-1.63 (m, 1H) 2.09-2.18 (m, 1H) 2.34 (m, J=8.60, 4.10, 4.10 Hz, 1H) 2.61-2.78 (m, 2H) 2.87 (m, J=13.40, 6.10 Hz, 1H) 3.57 (d, J=4.02 Hz, 1H) 7.41 (s, 1H) 7.63 (m, J=4.30 Hz, 3H) 7.66-7.74 (m, 2H) 7.83-7.92 (m, 3H) 8.04 (s, 1H).

Example 207. 5-Cyclopropyl-1-(3'-(6-cyclopropyl-5,6-dihydrocyclopenta[c]pyrazol-1(4H)-yl)-[1,1'-biphenyl]-3-yl)-1H-pyrazole-4-carboxylic Acid

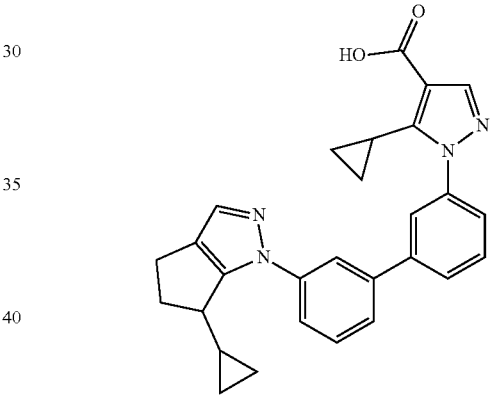

207a) 2-Cyclopropyl-5-((dimethylamino)methylene)cyclopentanone

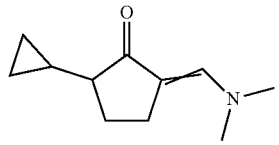

1-tert-Butoxy-N,N,N',N'-tetramethylmethanediamine (166 μL, 0.805 mmol) was added dropwise to a vial containing 2-cyclopropylcyclopentanone (100 mg, 0.805 mmol) under nitrogen atmosphere at ambient temperature. The reaction mixture was stirred at ambient temperature under nitrogen atmosphere for 1 h, then at 110° C. for 2 h. The reaction mixture was concentrated to afford the title compound (156.3 mg, 0.872 mmol, 108% yield). It was carried forward to subsequent reactions. LC-MS m/z 180.0 (M+H)$^+$, 0.70 min (ret. time).

207b) 5-Cyclopropyl-1-(3'-(6-cyclopropyl-5,6-dihydrocyclopenta[c]pyrazol-1(4H)-yl)-[1,1'-biphenyl]-3-yl)-1H-pyrazole-4-carboxylic Acid

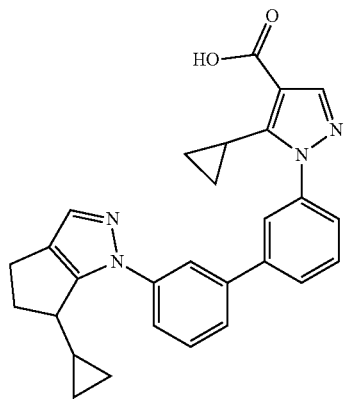 [SMILES: O=C(O)c1cnn(-c2cccc(-c3cccc(-n4ncc5c4C(C4CC4)CC5)c3)c2)c1C1CC1]

To a solution of ethyl 5-cyclopropyl-1-(3'-(6-cyclopropyl-5,6-dihydrocyclopenta[c]pyrazol-1(4H)-yl)-[1,1'-biphenyl]-3-yl)-1H-pyrazole-4-carboxylate (43.7 mg, 0.091 mmol) in methanol (0.5 mL) was added 2M LiOH (0.274 mL, 0.548 mmol). The reaction vessel was stirred at ambient temperature for 17 h. To the reaction mixture was added 2M LiOH (0.137 mL, 0.274 mmol). The reaction mixture was stirred at ambient temperature for 3 h. The reaction mixture was stirred at ambient temperature for 4 h. The reaction mixture was neutralized with 1 N HCl and concentrated. The crude product was dissolved in MeOH (1 mL) and purified on a Gilson HPLC eluting at 20 mL/min with a linear gradient running from 40% $CH_3CN/H_2O$ (0.1% TFA) to 90% $CH_3CN/H_2O$ (0.1% TFA) over 15 min. The desired fraction was concentrated to afford the title compound (6.2 mg, 0.014 mmol, 15.07% yield). LC-MS m/z $(M+H)^+$, 1.22 min (ret. time) $^1$H NMR (400 MHz, methanol-d4) δ ppm: 0.03 (d, J=4.52 Hz, 1H) 0.03-0.14 (m, 1H) 0.14-0.25 (m, 1H) 0.35 (dd, J=8.53, 4.02 Hz, 1H) 0.67 (d, J=4.27 Hz, 1H) 0.78-0.90 (m, 1H) 0.91-1.03 (m, 2H) 2.08-2.20 (m, 1H) 2.45 (dd, J=8.03, 4.27 Hz, 1H) 2.59-2.70 (m, 1H) 2.73-2.94 (m, 3H) 3.03-3.11 (m, 1H) 7.45 (s, 1H) 7.63 (d, J=4.77 Hz, 6H) 7.83-7.88 (m, 1H) 7.89-7.97 (m, 2H) 8.02-8.06 (m, 1H).

Example 208. 1-(3'-(6,6-Dimethyl-5,6-dihydrocyclopenta[c]pyrazol-1(4H)-yl)-[1,1'-biphenyl]-3-yl)-5-((1S,2S)-2-(1-methyl-1H-1,2,3-triazol-4-yl)cyclopropyl)-1H-pyrazole-4-carboxylic Acid

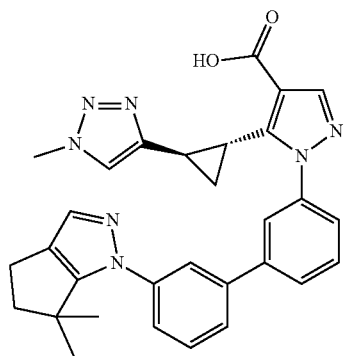 [SMILES: Cn1cc([C@@H]2C[C@H]2c2c(C(=O)O)cnn2-c2cccc(-c3cccc(-n4ncc5c4C(C)(C)CC5)c3)c2)nn1]

208a) 5-((Dimethylamino)methylene)-2,2-dimethylcyclopentanone

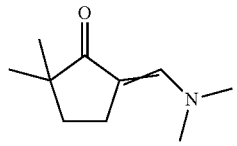

1-tert-Butoxy-N,N,N',N'-tetramethylmethanediamine (184 μL, 0.892 mmol) was added dropwise to a vial containing 2,2-dimethylcyclopentanone (100 mg, 0.892 mmol) under nitrogen atmosphere at ambient temperature. The reaction mixture was stirred at ambient temperature under nitrogen atmosphere for 45 min, then at 110° C. for 2 h. The reaction mixture was concentrated to give the title compound (168.9 mg, 1.010 mmol, 113% yield), which was carried forward to subsequent reactions. LC-MS m/z 167.9 $(M+H)^+$, 0.69 min (ret. time).

208b) Ethyl 1-(3'-(2-(tert-butoxycarbonyl)hydrazinyl)-[1,1'-biphenyl]-3-yl)-5-((1S,2S)-2-(1-methyl-1H-1,2,3-triazol-4-yl)cyclopropyl)-1H-pyrazole-4-carboxylate

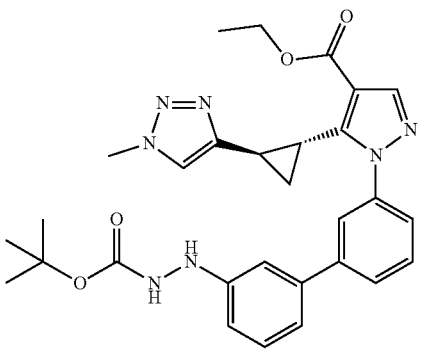 [SMILES: CCOC(=O)c1cnn(-c2cccc(-c3cccc(NNC(=O)OC(C)(C)C)c3)c2)c1[C@@H]1C[C@H]1c1cn(C)nn1]

To a solution of (3-(4-(ethoxycarbonyl)-5-((1S,2S)-2-(1-methyl-1H-1,2,3-triazol-4-yl)cyclopropyl)-1H-pyrazol-1-yl)phenyl)boronic acid (100 mg, 0.262 mmol) in 1,4-dioxane (1 mL) and water (0.333 mL) was added tert-butyl 2-(3-bromophenyl)hydrazinecarboxylate (113 mg, 0.394 mmol), $PdCl_2(dppf)$ (19.20 mg, 0.026 mmol) and potassium carbonate (51.5 mg, 0.525 mmol). The reaction vessel was heated in a Biotage microwave at high absorption for 15 min at 100° C. After cooling the reaction, the reaction was filtered, extracted with EtOAc (3×5 mL) and concentrated. The crude product was purified on a silica cartridge (12 g) with a Combiflash Companion, eluting at 35 mL/min with a gradient running from 0% EtOAc/hexanes to 60% EtOAc/hexanes. The desired fractions were concentrated to afford the title compound (50.6 mg, 0.093 mmol, 35.5% yield). LC-MS m/z 544.3 $(M+H)^+$, 1.06 min (ret. time).

208c) Ethyl 1-(3'-hydrazinyl-[1,1'-biphenyl]-3-yl)-5-((1S,2S)-2-(1-methyl-1H-1,2,3-triazol-4-yl)cyclopropyl)-1H-pyrazole-4-carboxylate Hydrochloride

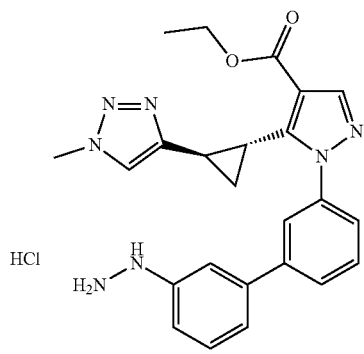 [SMILES: Cl ; CCOC(=O)c1cnn(-c2cccc(-c3cccc(NN)c3)c2)c1[C@@H]1C[C@H]1c1cn(C)nn1]

To a solution of ethyl 1-(3'-(2-(tert-butoxycarbonyl)hydrazinyl)-[1,1'-biphenyl]-3-yl)-5-((1S,2S)-2-(1-methyl-1H-1,2,3-triazol-4-yl)cyclopropyl)-1H-pyrazole-4-carboxylate (50.6 mg, 0.093 mmol) in dichloromethane (DCM) (0.5 mL) was added HCl in dioxane (0.140 mL, 0.558 mmol). The reaction mixture was stirred at ambient temperature for 24 h. The reaction mixture was concentrated to afford the title compound (49.5 mg, 0.103 mmol, 111% yield) as HCl salt. LC-MS m/z 444.2 (M+H)$^+$, 0.73 min (ret. time).

208d) Ethyl 1-(3'-(6,6-dimethyl-5,6-dihydrocyclopenta[c]pyrazol-1(4H)-yl)-[1,1'-biphenyl]-3-yl)-5-((1S,2S)-2-(1-methyl-1H-1,2,3-triazol-4-yl)cyclopropyl)-1H-pyrazole-4-carboxylate

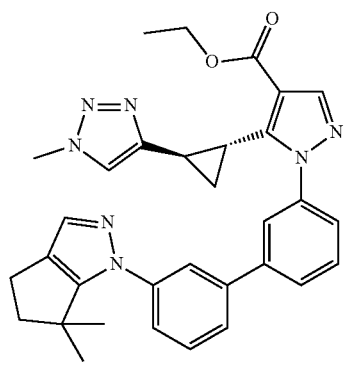 [SMILES: CCOC(=O)c1cnn(-c2cccc(-c3cccc(-n4ncc5c4C(C)(C)CC5)c3)c2)c1[C@@H]1C[C@H]1c1cn(C)nn1]

To a solution of ethyl 1-(3'-hydrazinyl-[1,1'-biphenyl]-3-yl)-5-((1S,2S)-2-(1-methyl-1H-1,2,3-triazol-4-yl)cyclopropyl)-1H-pyrazole-4-carboxylate hydrochloride (49.5 mg, 0.103 mmol) in acetic acid (1 mL) was added 5-((dimethylamino)methylene)-2,2-dimethylcyclopentanone (17.25 mg, 0.103 mmol). The reaction mixture was stirred at reflux for 2 h. The reaction mixture was stirred at reflux for an additional 2 h. The reaction mixture was neutralized with NaOH and concentrated. The remaining solid residue was diluted with water and extracted with EtOAc (3×). The combined organic layers were concentrated. The crude product was dissolved in DMSO (2 mL) and purified on a Gilson HPLC, eluting at 20 mL/min with a linear gradient running from 40% CH$_3$CN/H$_2$O to 90% CH$_3$CN/H$_2$O over 15 min. The desired fractions were concentrated to afford the title compound (15.4 mg, 0.028 mmol, 27.3% yield). LC-MS m/z 548.3 (M+H)$^+$, 1.21 min (ret. time).

208e) 1-(3'-(6,6-Dimethyl-5,6-dihydrocyclopenta[c]pyrazol-1(4H)-yl)-[1,1'-biphenyl]-3-yl)-5-((1S,2S)-2-(1-methyl-1H-1,2,3-triazol-4-yl)cyclopropyl)-1H-pyrazole-4-carboxylic Acid

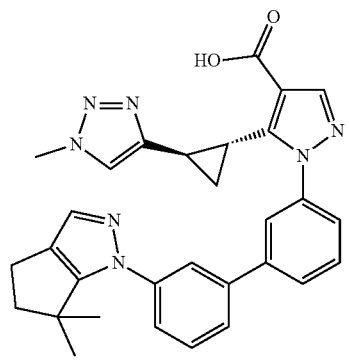 [SMILES: Cn1cc([C@@H]2C[C@H]2c2c(C(=O)O)cnn2-c2cccc(-c3cccc(-n4ncc5c4C(C)(C)CC5)c3)c2)nn1]

To a solution of ethyl 1-(3'-(6,6-dimethyl-5,6-dihydrocyclopenta[c]pyrazol-1(4H)-yl)-[1,1'-biphenyl]-3-yl)-5-((1S,2S)-2-(1-methyl-1H-1,2,3-triazol-4-yl)cyclopropyl)-1H-pyrazole-4-carboxylate (15.4 mg, 0.028 mmol) in methanol (0.25 mL) was added 2M LiOH (0.084 mL, 0.169 mmol). The reaction vessel was stirred at ambient temperature for 72 h. LCMS showed evidence of desired product and methyl ester. To the reaction mixture was added 2M LiOH (0.084 mL, 0.169 mmol). The reaction mixture was stirred at ambient temperature for 27 h. LCMS showed minor evidence of methyl ester. To the reaction mixture was added 2M LiOH (0.084 mL, 0.169 mmol). The reaction mixture was stirred at 30° C. for 7 h. LCMS showed evidence of methyl ester. The reaction mixture was stirred at 50° C. for 18 h. LCMS showed reaction complete. The reaction mixture was neutralized with 1 N HCl and concentrated. The crude product was dissolved in DMSO (1 mL) and purified on a Gilson HPLC, eluting at 20 mL/min with a linear gradient running from 40% CH$_3$CN/H$_2$O (0.1% TFA) to 80% CH$_3$CN/H$_2$O (0.1% TFA) over 15 min. The desired fractions were concentrated to afford the title compound (12.83 mg, 0.025 mmol, 88% yield). LC-MS m/z 520.4 (M+H)$^+$, 0.98 min (ret. time)$^1$H NMR (400 MHz, methanol-d4) δ ppm: 1.28 (s, 6H) 1.32-1.40 (m, 1H) 1.51-1.59 (m, 1H) 2.15-2.23 (m, 1H) 2.39-2.46 (m, 2H) 2.53-2.61 (m, 1H) 2.65-2.73 (m, 3H) 3.88 (s, 3H) 7.39 (s, 1H) 7.45 (s, 1H) 7.48-7.54 (m, 1H) 7.57-7.72 (m, 5H) 7.78-7.85 (m, 2H) 8.08 (s, 1H).

Example 209. 5-Cyclopropyl-1-(3'-(5-ethyl-1,2,4-oxadiazol-3-yl)-[1,1'-biphenyl]-3-yl)-1H-pyrazole-4-carboxylic Acid

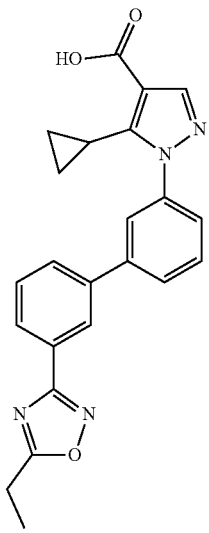 [SMILES: CCc1nc(-c2cccc(-c3cccc(-n4ncc(C(=O)O)c4C4CC4)c3)c2)no1]

209a) 3-Bromo-N'-hydroxybenzimidamide

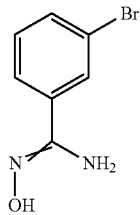

To a solution of 3-bromobenzonitrile in methanol was added hydroxylamine hydrochloride and sodium bicarbonate. The reaction mixture was heated to 65° C. for 3 h in a sealed microwave vessel. The reaction mixture was concentrated. The reaction mixture was diluted with H$_2$O (5 mL) and extracted with EtOAc (3×5 mL). The combined organic layer was dried over MgSO$_4$, filtered and concentrated to afford the title compound (292.6 mg, 1.361 mmol, 124% yield). LC-MS m/z 214.9 (M+H)$^+$, 0.16 min (ret. time).

209b) 3-(3-Bromophenyl)-5-ethyl-1,2,4-oxadiazole

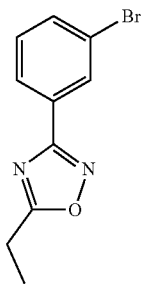

To a solution of propionic acid (0.143 mL, 1.905 mmol) in N,N-dimethylformamide (DMF) (6 mL) was added CDI (309 mg, 1.905 mmol). The reaction mixture was stirred at ambient temperature for 30 min. Then to the reaction mixture was added 3-bromo-N'-hydroxybenzimidamide (292.6 mg, 1.361 mmol). The reaction mixture was stirred at 120° C. for 4 h. The reaction mixture was diluted with H$_2$O (10 mL) and extracted with EtOAc (3×10 mL). The combined organic layer was dried over MgSO$_4$, filtered and concentrated to afford the title compound (316.3 mg, 1.250 mmol, 92% yield). LC-MS m/z 252.9 (M+H)$^+$, 1.09 min (ret. time).

209c) Ethyl 5-cyclopropyl-1-(3'-(5-ethyl-1,2,4-oxadiazol-3-yl)-[1,1'-biphenyl]-3-yl)-1H-pyrazole-4-carboxylate

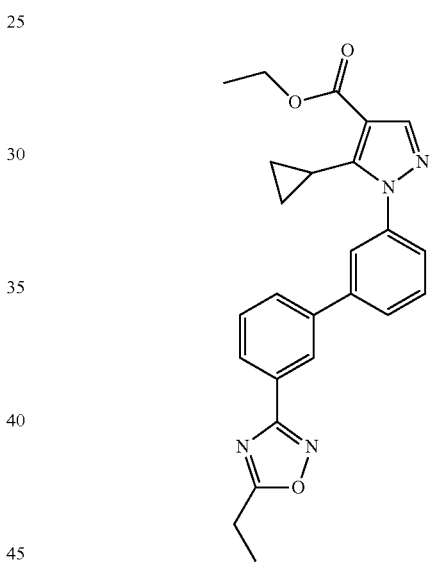

To a solution of ethyl 5-cyclopropyl-1-(3-(4,4,5,5-tetramethyl-1,3,2-dioxaborolan-2-yl)phenyl)-1H-pyrazole-4-carboxylate (80 mg, 0.209 mmol), 3-(3-bromophenyl)-5-ethyl-1,2,4-oxadiazole (53.0 mg, 0.209 mmol) and potassium carbonate (57.8 mg, 0.419 mmol) in 1,4-dioxane (1.2 mL) and water (0.400 mL) was added PdCl$_2$(dppf) (15.31 mg, 0.021 mmol). The reaction vessel was heated in a Biotage microwave at high absorption for 15 min at 100° C. LCMS showed evidence of desired product and boronic ester starting material. To the reaction mixture was added 3-(3-bromophenyl)-5-ethyl-1,2,4-oxadiazole (1 eq). The reaction vessel was heated in a Biotage microwave at high absorption for 15 min at 100° C. The reaction mixture was stirred at ambient temperature 17 h. The reaction mixture was filtered, diluted with H$_2$O (5 mL), and extracted with EtOAC (3×5 mL twice). The combined organic phase was back extracted with brine, dried over MgSO₄, filtered and concentrated to afford the crude product. The crude product was dissolved in DMSO (2 mL) and purified on a Gilson HPLC eluting at 20 mL/min with a linear gradient running from 50% CH₃CN/H₂O to 90% CH₃CN/H₂O over 15 min. The desired fractions were concentrated to afford the title compound (31.1 mg, 0.073 mmol, 34.7% yield). LC-MS m/z 429.1 (M+H)⁺, 1.30 min (ret. time).

209d) 5-Cyclopropyl-1-(3'-(5-ethyl-1,2,4-oxadiazol-3-yl)-[1,1'-biphenyl]-3-yl)-1H-pyrazole-4-carboxylic Acid

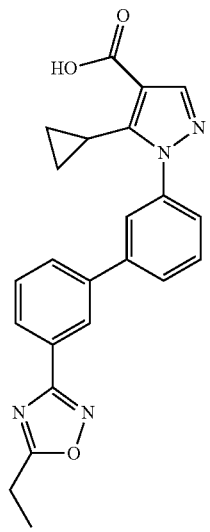 [SMILES: CCc1nc(-c2cccc(-c3cccc(-n4ncc(C(=O)O)c4C4CC4)c3)c2)no1]

To a solution of ethyl 5-cyclopropyl-1-(3'-(5-ethyl-1,2,4-oxadiazol-3-yl)-[1,1'-biphenyl]-3-yl)-1H-pyrazole-4-carboxylate (31.1 mg, 0.073 mmol) in methanol (0.5 mL) was added 2M LiOH (0.218 mL, 0.435 mmol). The reaction mixture was stirred at ambient temperature for 17 h. LCMS showed evidence of starting material, methyl ester and desired product. To the reaction mixture was added 2M LiOH (0.109 mL, 0.2175 mmol). The reaction mixture was stirred at ambient temperature for 89 h. To the reaction mixture was added DMSO (2 mL) and concentrated. The crude product was purified on a Gilson HPLC eluting at 20 mL/min with a linear gradient running from 40% CH₃CN/H₂O (0.1% TFA) to 90% CH₃CN/H₂O (0.1% TFA) over 15 min. The desired fractions were concentrated to afford the title compound (7.11 mg, 0.018 mmol, 24.46% yield). LC-MS m/z 401.1 (M+H)⁺, 1.06 min (ret. time) ¹H NMR (400 MHz, methanol-d₄) δ ppm: 0.69 (d, J=5.02 Hz, 2H) 0.93-1.02 (m, 2H) 1.47 (t, J=7.53 Hz, 3H) 2.09-2.19 (m, 1H) 2.68 (s, 1H) 2.99-3.10 (m, 2H) 7.66 (dd, J=17.07, 8.53 Hz, 3H) 7.85 (d, J=7.78 Hz, 1H) 7.89 (br. s., 2H) 8.04 (s, 1H) 8.09 (d, J=7.78 Hz, 1H) 8.38 (s, 1H).

The compounds in Table 12 were prepared by a method similar to the one described for the preparation of 5-cyclopropyl-1-(3'-(5-ethyl-1,2,4-oxadiazol-3-yl)-[1,1'-biphenyl]-3-yl)-1H-pyrazole-4-carboxylic acid. As is appreciated by those skilled in the art, these analogous examples may involve variations in general reaction conditions.

TABLE 12

| Example | Structure | Name | LCMS [M + H]⁺ | Retention time (min) |
|---|---|---|---|---|
| 210 | 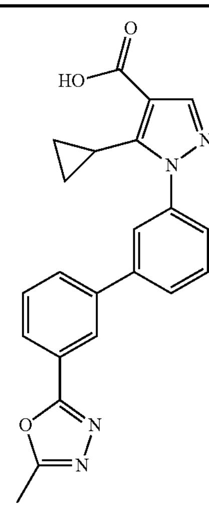 | 5S-Cyclopropyl-1-(3'-(5-methyl-1,3,4-oxadiazol-2-yl)-[1,1'-biphenyl]-3-yl)-1H-pyrazole-4-carboxylic acid | 387.1 | 0.86 |

TABLE 12-continued

| Example | Structure | Name | LCMS [M + H]+ | Retention time (min) |
|---|---|---|---|---|
| 211 | 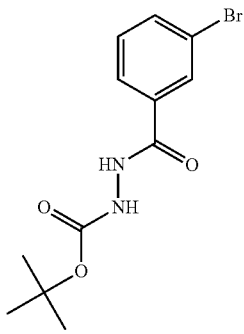 [SMILES: CC(C)(C)OC(=O)NNC(=O)c1cccc(Br)c1] | 5-Cyclopropyl-1-(3'-(5-methyl-1,2,4-oxadiazol-3-yl)-[1,1'-biphenyl]-3-yl)-1H-pyrazole-4-carboxylic acid | 387.4 | 0.95 |

210a) tert-Butyl 2-(3-bromobenzoyl)hydrazinecarboxylate

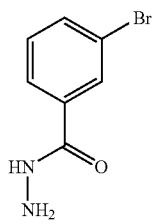

CDI (202 mg, 1.244 mmol) was added to a solution of 3-bromobenzoic acid (250 mg, 1.244 mmol) in tetrahydrofuran (THF) (6 mL). The reaction mixture was stirred at reflux for about 15 min (corresponding to the end of $CO_2$ evolution) and tert-butyl hydrazinecarboxylate (82 mg, 0.622 mmol) was added. The reaction mixture was stirred at reflux for 5.5 h. The reaction mixture was stirred at ambient temperature overnight. The reaction mixture was concentrated and then diluted with $H_2O$ (5 mL) and extracted with EtOAc (3×5 mL). The combined organic layer was dried over $MgSO_4$, filtered and concentrated to afford the crude product. The crude product was dissolved in DCM and purified on a silica cartridge (24 g) with a Combiflash Companion, eluting at 35 mL/min with a gradient running from 0% EtOAc/hexane to 40% EtOAc/hexane over 30 min. The desired fractions were concentrated to afford the title compound (121.0 mg, 0.384 mmol, 30.9% yield). LC-MS m/z 314.7 (M+H)+, 0.81 min (ret. time).

210b) 3-Bromobenzohydrazide

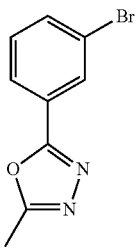

To a solution of tert-butyl 2-(3-bromobenzoyl)hydrazinecarboxylate (121.0 mg, 0.384 mmol) in dichloromethane (DCM) (2 mL) was added 4 M HCl in dioxane (0.576 mL, 2.304 mmol). The reaction mixture was stirred at ambient temperature for 16.5 h. The reaction mixture was concentrated to afford the title compound (55.0 mg, 0.256 mmol, 66.6% yield). LC-MS m/z 215.0 (M+H)+, 0.49 min (ret. time).

210c) 2-(3-Bromophenyl)-5-methyl-1,3,4-oxadiazole

A solution of 3-bromobenzohydrazide (55.0 mg, 0.256 mmol) and triethyl orthoacetate (1132 μL, 6.14 mmol) was stirred at 110° C. for 3.5 h. LCMS showed good conversion.

The reaction mixture was concentrated. The crude product was taken up in DCM (~1 mL) and purified on a silica cartridge (12 g) with a Combiflash Companion, eluting at 20 mL/min with a gradient running from 0% EtOAc/hexanes to 40% EtOAc/hexanes over 25 min. The desired fractions were concentrated on the rotary evaporator to afford the title compound (51.1 mg, 0.214 mmol, 84% yield). LC-MS m/z 240.9 (M+H)+, 0.81 min (ret. time).

211a) 3-Bromo-N'-hydroxybenzimidamide

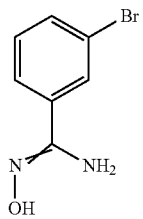

To a solution of 3-bromobenzonitrile (200 mg, 1.099 mmol) in methanol (5 mL) was added hydroxylamine hydrochloride (84 mg, 1.209 mmol) and sodium bicarbonate (138 mg, 1.648 mmol). The reaction mixture was heated to 65° C. for 3 h in a sealed microwave vessel. The reaction mixture was concentrated. The reaction mixture was diluted with H$_2$O (5 mL) and extracted with EtOAc (3×5 mL). The combined organic layer was dried over MgSO$_4$, filtered and concentrated to afford the title compound (218.2 mg, 1.015 mmol, 92% yield). LC-MS m/z 214.9 (M+H)+, 0.41 min (ret. time).

211b)
3-(3-Bromophenyl)-5-methyl-1,2,4-oxadiazole

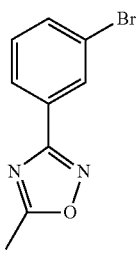

To a solution of acetic acid (0.081 mL, 1.421 mmol) in N,N-dimethylformamide (DMF) (6 mL) was added CDI (230 mg, 1.421 mmol). The reaction mixture was stirred at ambient temperature for 30 min. Then to the reaction mixture was added 3-bromo-N'-hydroxybenzimidamide (218.2 mg, 1.015 mmol). The reaction mixture was stirred at 120° C. for 4 h. The reaction mixture was diluted with H$_2$O (10 mL) and extracted with EtOAc (3×10 mL). The combined organic layer was dried over MgSO$_4$, filtered and concentrated to afford the title compound (201.9 mg, 0.845 mmol, 83% yield). LC-MS m/z 238.8 (M+H)+, 0.96 min (ret. time).

Example 212. 1-(3'-(6,6-Dimethyl-5,6-dihydrocyclopenta[c]pyrazol-1(4H)-yl)-[1,1'-biphenyl]-3-yl)-5-(2-(1-methyl-1H-1,2,3-triazol-4-yl)cyclopropyl)-1H-pyrazole-4-carboxylic Acid

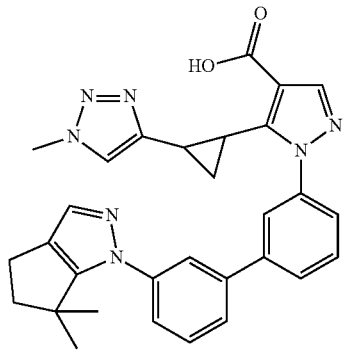 [SMILES: Cn1cc(C2CC2c2c(C(=O)O)cnn2-c2cccc(-c3cccc(-n4ncc5c4C(C)(C)CC5)c3)c2)nn1]

To a solution of ethyl 1-(3'-hydrazinyl-[1,1'-biphenyl]-3-yl)-5-(2-(1-methyl-1H-1,2,3-triazol-4-yl)cyclopropyl)-1H-pyrazole-4-carboxylate hydrochloride (80.6 mg, 0.168 mmol) in acetic acid (1.5 mL) was added 5-((dimethylamino)methylene)-2,2-dimethylcyclopentanone (28.1 mg, 0.168 mmol). The reaction mixture was stirred at reflux for 3.5 h. The reaction mixture was neutralized with 1 M NaOH and concentrated. The crude product was dissolved in MeOH (1 mL) and to the reaction mixture was added LiOH (0.504 mL, 1.008 mmol). The reaction vessel was heated in a Biotage microwave at high absorption for 30 min at 80° C. The reaction mixture was filtered to remove the solid impurities and concentrated. To the reaction mixture was added MeOH (1.5 mL), THF (1 mL) and LiOH (0.504 mL, 1.008 mmol). The reaction mixture was stirred at ambient temperature for 80 h. It was acidified with 6 N HCl, 1 mL DMSO was added. The reaction mixture was concentrated and filtered. It was purified with preparative HPLC under acidic conditions to give the title compound (40.9 mg, 0.079 mmol, 46.9% yield) as solid. LC-MS m/z 520.2 (M+H)+, 0.98 min (ret. time); $^1$H NMR (400 MHz, DMSO-d$_6$) δ ppm: 1.25 (s, 6H) 1.41 (br. s., 1H) 2.14 (d, J=8.78 Hz, 1H) 2.35 (t, J=6.40 Hz, 2H) 2.57-2.64 (m, 4H) 3.81 (s, 3H) 7.38 (s, 1H) 7.50 (s, 2H) 7.57-7.68 (m, 4H) 7.72 (s, 1H) 7.81 (d, J=6.78 Hz, 1H) 7.86 (s, 1H) 8.02 (s, 1H).

Example 213. 5-(2-(1-Methyl-1H-pyrazol-4-yl)cyclopropyl)-1-(3'-((R)-2-propylpiperidine-1-carbonyl)-[1,1'-biphenyl]-3-yl)-1H-pyrazole-4-carboxylic Acid

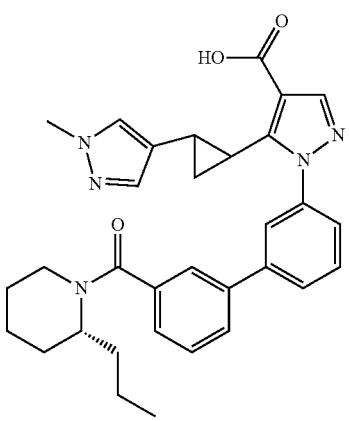 [SMILES: CCC[C@@H]1CCCCN1C(=O)c1cccc(-c2cccc(-n3ncc(C(=O)O)c3C3CC3c3cnn(C)c3)c2)c1]

213a) Methyl 5-(2-(1-methyl-1H-pyrazol-4-yl)cyclopropyl)-1-(3'-((R)-2-propylpiperidine-1-carbonyl)-[1,1'-biphenyl]-3-yl)-1H-pyrazole-4-carboxylate

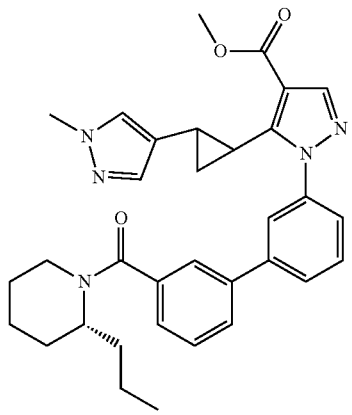 [SMILES: CCC[C@@H]1CCCCN1C(=O)c1cccc(-c2cccc(-n3ncc(C(=O)OC)c3C3CC3c3cnn(C)c3)c2)c1]

A mixture of (R)-(2-propylpiperidin-1-yl)(3-(4,4,5,5-tetramethyl-1,3,2-dioxaborolan-2-yl)phenyl)methanone (78 mg, 0.219 mmol), (R)-(3-(2-propylpiperidine-1-carbonyl)phenyl)boronic acid (60.3 mg, 0.219 mmol) methyl 1-(3-bromophenyl)-5-(2-(1-methyl-1H-pyrazol-4-yl)cyclopropyl)-1H-pyrazole-4-carboxylate (0.075 mL, 0.199 mmol), $Na_2CO_3$ (63.4 mg, 0.598 mmol) and $PdCl_2$(dppf) (14.59 mg, 0.020 mmol) in 1,4-dioxane (3 mL) and water (1 mL) was degassed for 5 min and then heated under microwave for 15 min at 100° C. It was passed through celite and washed with ethyl acetate. It was extracted with ethyl acetate twice. The organic layer was washed with brine and then concentrated to give crude product. The reaction mixture was purified by silica gel chromatography (Combiflash) (product came out at 100% ethyl acetate in hexane). Desired fractions were concentrated to give the title compound (65 mg, 0.118 mmol, 59.1% yield). LC-MS m/z 552.3 (M+H)$^+$, 1.20 min (ret. time).

213b) 5-(2-(1-Methyl-1H-pyrazol-4-yl)cyclopropyl)-1-(3'-((R)-2-propylpiperidine-1-carbonyl)-[1,1'-biphenyl]-3-yl)-1H-pyrazole-4-carboxylic Acid

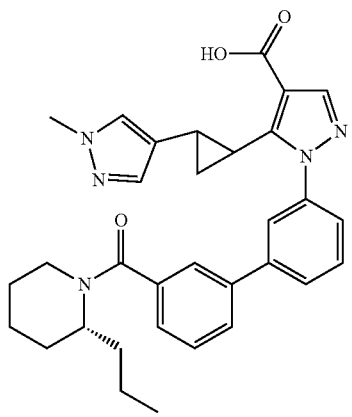 [SMILES: CCC[C@@H]1CCCCN1C(=O)c1cccc(-c2cccc(-n3ncc(C(=O)O)c3C3CC3c3cnn(C)c3)c2)c1]

To a solution of methyl 5-(2-(1-methyl-1H-pyrazol-4-yl)cyclopropyl)-1-(3'-((R)-2-propylpiperidine-1-carbonyl)-[1,1'-biphenyl]-3-yl)-1H-pyrazole-4-carboxylate (65 mg, 0.118 mmol) in MeOH (2 mL) was added 2M LiOH (0.353 mL, 0.707 mmol). The reaction mixture was heated with μwave at 80° C. for 30 min. It was acidified with 6N HCl, 0.5 mL DMSO was added. It was concentrated to give the crude material. It was filtered and purified with preparative HPLC under acidic conditions. The title compound (55.2 mg, 0.103 mmol, 87% yield) was obtained as solid. LC-MS m/z 538.3 (M+H)$^+$, 1.07 min (ret. time).

Example 214. 1-(2'-Fluoro-3'-((R)-2-propylpiperidine-1-carbonyl)-[1,1'-biphenyl]-3-yl)-5-(2-(1-methyl-1H-pyrazol-4-yl)cyclopropyl)-1H-pyrazole-4-carboxylic Acid

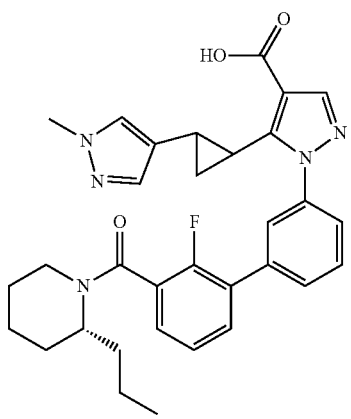 [SMILES: CCC[C@@H]1CCCCN1C(=O)c1cccc(-c2cccc(-n3ncc(C(=O)O)c3C3CC3c3cnn(C)c3)c2)c1F]

214a) Methyl 1-(2'-fluoro-3'-((R)-2-propylpiperidine-1-carbonyl)-[1,1'-biphenyl]-3-yl)-5-(2-(1-methyl-1H-pyrazol-4-yl)cyclopropyl)-1H-pyrazole-4-carboxylate

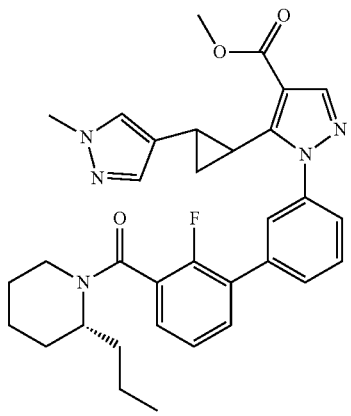 [SMILES: CCC[C@@H]1CCCCN1C(=O)c1cccc(-c2cccc(-n3ncc(C(=O)OC)c3C3CC3c3cnn(C)c3)c2)c1F]

A mixture of (R)-(2-fluoro-3-(4,4,5,5-tetramethyl-1,3,2-dioxaborolan-2-yl)phenyl)(2-propylpiperidin-1-yl)methanone (82 mg, 0.219 mmol), (R)-(2-fluoro-3-(2-propylpiperidine-1-carbonyl)phenyl)boronic acid (64.3 mg, 0.219 mmol) methyl 1-(3-bromophenyl)-5-(2-(1-methyl-1H-pyrazol-4-yl)cyclopropyl)-1H-pyrazole-4-carboxylate (0.075 mL, 0.199 mmol), $Na_2CO_3$ (63.4 mg, 0.598 mmol) and $PdCl_2$(dppf) (14.59 mg, 0.020 mmol) in 1,4-dioxane (3 mL)

and water (1 mL) was degassed for 5 min and then heated under microwave for 15 min at 100° C. It was passed through celite and washed with ethyl acetate. It was extracted with ethyl acetate twice. The organic layer was washed with brine and then concentrated to give crude product. The reaction mixture was purified by silica gel chromatography (Combiflash) (product came out at 100% ethyl acetate in hexane). Desired fractions were concentrated to give the title compound (73 mg, 0.128 mmol, 64.3% yield). LC-MS m/z 570.3 (M+H)+, 1.20 min (ret. time).

214b) 1-(2'-Fluoro-3'-((R)-2-propylpiperidine-1-carbonyl)-[1,1'-biphenyl]-3-yl)-5-(2-(1-methyl-1H-pyrazol-4-yl)cyclopropyl)-1H-pyrazole-4-carboxylic Acid

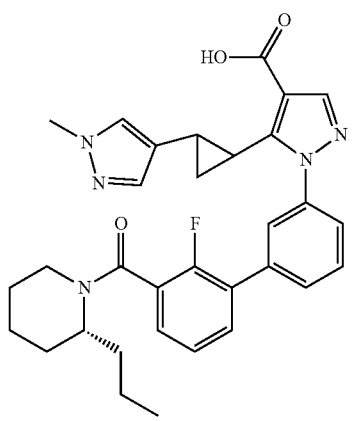 [SMILES: CCC[C@@H]1CCCCN1C(=O)c1cccc(-c2cccc(-n3ncc(C(=O)O)c3C3CC3c3cnn(C)c3)c2)c1F]

To a solution of methyl 1-(2'-fluoro-3'-((R)-2-propylpiperidine-1-carbonyl)-[1,1'-biphenyl]-3-yl)-5-(2-(1-methyl-1H-pyrazol-4-yl)cyclopropyl)-1H-pyrazole-4-carboxylate (74 mg, 0.130 mmol) in MeOH (2 mL) was added 2M LiOH (0.390 mL, 0.779 mmol). The reaction mixture was heated with μwave at 80° C. for 30 min. It was acidified with 6N HCl, 0.5 mL DMSO was added. It was concentrated with V10 to give the crude material. It was filtered and purified with preparative HPLC under acidic conditions. The title compound (72.7 mg, 0.131 mmol, 101% yield) was obtained as solid. LC-MS m/z 556.3 (M+H)+, 1.07 min (ret. time).

Example 215. 1-(3'-(2-Cyclohexylacetyl)-[1,1'-biphenyl]-3-yl)-5-(2-(1-methyl-1H-1,2,3-triazol-4-yl)cyclopropyl)-1H-pyrazole-4-carboxylic Acid

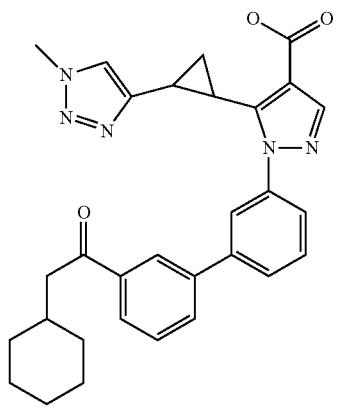 [SMILES: Cn1cc(C2CC2c2c(C(=O)O)cnn2-c2cccc(-c3cccc(C(=O)CC4CCCCC4)c3)c2)nn1]

215a) 1-(3-Bromophenyl)-2-cyclohexylethanol

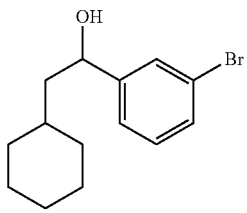 [SMILES: OC(CC1CCCCC1)c1cccc(Br)c1]

(Bromomethyl)cyclohexane (5 g, 28.2 mmol) was added under argon to magnesium (0.686 g, 28.2 mmol) turnings in anhydrous tetrahydrofuran (THF) (50 mL) containing catalytic amount of iodine (0.717 g, 2.82 mmol). It was refluxed for 3 h. The reaction mixture was cool to ambient temperature and added to a solution of 3-bromobenzaldehyde (5.22 g, 28.2 mmol) in tetrahydrofuran (THF) (50 mL) at 0° C. The reaction mixture was stirred at ambient temperature for 18 h. The reaction mixture was quenched with cold water, extracted with EtOAc twice. The combined organic layer was washed with brine solution, dried over anhydrous Na2SO4. It was filtrated and the filtrate was concentrated. The crude residue was purified on flash column chromatography eluting with EtOAC:hexane (4:96) to give the title compound (2 g, 7.06 mmol, 25.01% yield). $^1$H NMR (400 MHz, DMSO-d6) δ: 0.75-1.00 (m, 2H), 1.01-1.28 (m, 3H), 1.27-1.42 (m, 2H), 1.44-1.54 (m, 1H), 1.55-1.70 (m, 4H), 1.78 (br d, J=12.72 Hz, 1H), 4.53-4.67 (m, 1H), 5.17 (d, J=4.82 Hz, 1H), 7.23-7.32 (m, 2H), 7.36-7.43 (m, 1H), 7.45-7.54 (m, 1H).

215b) 1-(3-Bromophenyl)-2-cyclohexylethanone

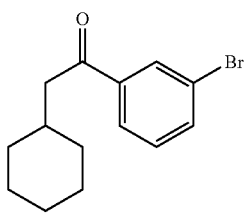 [SMILES: O=C(CC1CCCCC1)c1cccc(Br)c1]

To a solution of 1-(3-bromophenyl)-2-cyclohexylethanol (100 mg, 0.353 mmol) in dichloromethane (DCM) (10 mL) at 0° C. was added Dess-Martin periodinane (225 mg, 0.530 mmol). It was stir for 2 h at RT. The reaction mixture was passed through celite. The filtrate was concentrated. The crude compound was purified through column chromatography eluting with ethyl acetate:hexane (5:95). The desired fractions were concentrated to give the title compound (30 mg, 0.050 mmol, 14.13% yield) as liquid. LC-MS m/z 281.16 (M+H)+, 3.16 min (ret. time).

215c) Ethyl 1-(3'-(2-cyclohexylacetyl)-[1,1'-biphenyl]-3-yl)-5-(2-(1-methyl-1H-1,2,3-triazol-4-yl)cyclopropyl)-1H-pyrazole-4-carboxylate

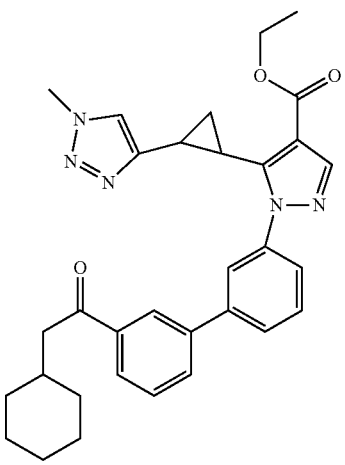 [SMILES: CCOC(=O)c1cnn(-c2cccc(-c3cccc(C(=O)CC4CCCCC4)c3)c2)c1C1CC1c1cn(C)nn1]

To a solution of 1-(3-bromophenyl)-2-cyclohexylethanone (100 mg, 0.356 mmol) in 1,4-dioxane (3 mL) and water (3.00 mL) was added ethyl 5-(2-(1-methyl-1H-1,2,3-triazol-4-yl)cyclopropyl)-1-(3-(4,4,5,5-tetramethyl-1,3,2-dioxaborolan-2-yl)phenyl)-1H-pyrazole-4-carboxylate (181 mg, 0.391 mmol). It was degassed with argon for 10 min. Then $K_2CO_3$ (98 mg, 0.711 mmol) and tetrakis(triphenylphosphine)palladium(0) (41.1 mg, 0.036 mmol) were added and degassed for 20 min. The reaction mixture was stirred at 95° C. for 16 h. The reaction mixture was diluted with water and extracted with EtOAc. The organic layer was washed with brine, dried over $Na_2SO_4$, filtered and concentrated. The crude compound was purified through column chromatography eluting with EtOAc:hexane (2:8). Desired fractions were concentrated to give the title compound (130 mg). LC-MS m/z 538.2 (M+H)$^+$, 4.12 min (ret. time).

215d) 1-(3'-(2-Cyclohexylacetyl)-[1,1'-biphenyl]-3-yl)-5-(2-(1-methyl-1H-1,2,3-triazol-4-yl)cyclopropyl)-1H-pyrazole-4-carboxylic Acid

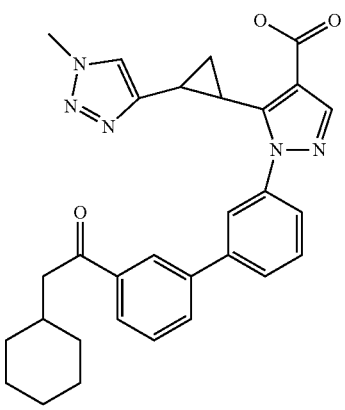 [SMILES: Cn1cc(C2CC2c2c(C(=O)O)cnn2-c2cccc(-c3cccc(C(=O)CC4CCCCC4)c3)c2)nn1]

To a solution of ethyl 1-(3'-(2-cyclohexylacetyl)-[1,1'-biphenyl]-3-yl)-5-(2-(1-methyl-1H-1,2,3-triazol-4-yl)cyclopropyl)-1H-pyrazole-4-carboxylate (210 mg, 0.391 mmol) in ethanol (20 mL) at 0° C. was added 1N sodium hydroxide (5 mL, 0.391 mmol). The reaction mixture was stir for 4 h at RT. The reaction mixture was concentrated, neutralized with 1N HCl and extracted with (1:9) MeOH & DCM twice. The combined organic layer was dried over anhydrous $Na_2SO_4$, filtered and concentrated. The crude residue was purified with preparative HPLC (with 0.1% formic acid as modifier) to give the title compound (70 mg, 0.137 mmol, 31.8% yield) as white solid. LC-MS m/z 510.30 (M+H)$^+$, 2.60 min (ret. time).

Example 216. 1-(3'-(2-Cyclohexyl-1-methoxyethyl)-[1,1'-biphenyl]-3-yl)-5-(2-(1-methyl-1H-1,2,3-triazol-4-yl)cyclopropyl)-1H-pyrazole-4-carboxylic Acid

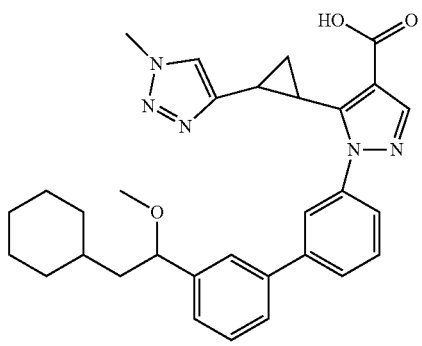 [SMILES: COC(CC1CCCCC1)c1cccc(-c2cccc(-n3ncc(C(=O)O)c3C3CC3c3cn(C)nn3)c2)c1]

216a) 1-Bromo-3-(2-cyclohexyl-1-methoxyethyl)benzene

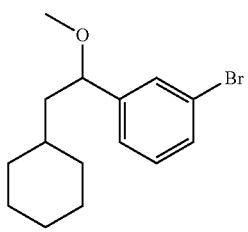 [SMILES: COC(CC1CCCCC1)c1cccc(Br)c1]

To a solution of 1-(3-bromophenyl)-2-cyclohexylethanol (500 mg, 1.766 mmol) in DMF (10 mL) at 0° C. was added NaH (63.6 mg, 2.65 mmol). It was stirred for 1 h, and then MeI (0.110 mL, 1.766 mmol) was added at 0° C. The reaction mixture was stirred for 2 h at ambient temperature. The reaction mixture was quenched with cold water and extracted with EtOAc. The organic layer was washed with cold water twice and brine solution. It was dried over $Na_2SO_4$, filtered and concentrated. The crude residue was purified through column chromatography eluting with EtOAc & hexane (2:98). The desired fractions were concentrated to give the title compound (250 mg, 0.841 mmol, 47.6% yield) as light yellow liquid. $^1$H NMR (CDCl$_3$) δ: 0.83-1.00 (m, 2H), 1.10-1.29 (m, 3H), 1.30-1.45 (m, 2H), 1.54-1.79 (m, 6H), 3.19 (s, 3H), 4.14 (br dd, J=8.77, 4.38 Hz, 1H), 7.13-7.23 (m, 2H), 7.32-7.52 (m, 2H).

216b) Ethyl 1-(3'-(2-cyclohexyl-1-methoxyethyl)-[1,1'-biphenyl]-3-yl)-5-(2-(1-methyl-1H-1,2,3-triazol-4-yl)cyclopropyl)-1H-pyrazole-4-carboxylate

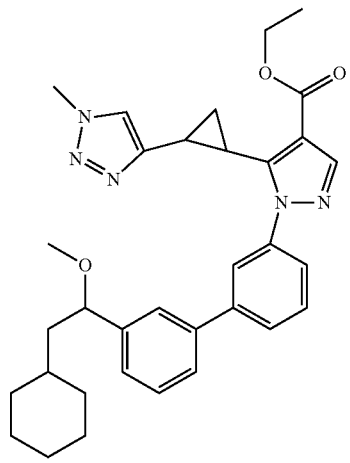 [SMILES: CCOC(=O)c1cnn(-c2cccc(-c3cccc(C(CC4CCCCC4)OC)c3)c2)c1C1CC1c1cn(C)nn1]

To a solution of 1-bromo-3-(2-cyclohexyl-1-methoxyethyl)benzene (50 mg, 0.168 mmol) in 1,4-dioxane (5 mL) and water (5.00 mL) was added ethyl 5-(2-(1-methyl-1H-1,2,3-triazol-4-yl)cyclopropyl)-1-(3-(4,4,5,5-tetramethyl-1,3,2-dioxaborolan-2-yl)phenyl)-1H-pyrazole-4-carboxylate (78 mg, 0.168 mmol). It was degassed with argon for 10 min. K₂CO₃ (46.5 mg, 0.336 mmol) and Pd(Ph₃P)₄ (9.72 mg, 8.41 μmol) were added and degassed for 20 min. The reaction mixture was stirred at 95° C. for 16 h. The reaction mixture was diluted with water and extracted with EtOAc. The organic layer was washed with brine, dried over Na₂SO₄, filtered and concentrated. The crude compound was purified through column chromatography eluting with EtOAc & hexane (2:8). The desired fractions were concentrated to give the title compound (70 mg, 0.087 mmol, 52.0% yield). LC-MS m/z 554.42 (M+H)⁺, 3.19 min (ret. time).

216c) 1-(3'-(2-Cyclohexyl-1-methoxyethyl)-[1,1'-biphenyl]-3-yl)-5-(2-(1-methyl-1H-1,2,3-triazol-4-yl)cyclopropyl)-1H-pyrazole-4-carboxylic Acid To a solution of ethyl 1-(3'-(2-cyclohexyl-1-methoxyethyl)-[1,1'-biphenyl]-3-yl)-5-(2-(1-methyl-1H-1,2,3-triazol-4-yl)cyclopropyl)-1H-pyrazole-4-carboxylate (70 mg, 0.126 mmol) in ethanol (3 mL) at 0° C. was added 1N NaOH (3 mL, 0.126 mmol). The reaction mixture was stir for 4 h at ambient temperature. The reaction mixture was concentrated and neutralized with 1 N HCl and extracted with (1:9) MeOH & DCM twice. The combined organic layer was dried over anhydrous Na₂SO₄, filtered and concentrated. The crude residue was purified with preparative HPLC (with 0.1% formic acid as modifier) to give the title compound (30 mg, 0.057 mmol, 37.3% yield) as white solid. LC-MS m/z 526.29 (M+H)⁺, 2.80 min (ret. time).

The compounds in Table 13 were prepared by a method similar to the one described for the preparation of 1-(3'-(2-cyclohexyl-1-methoxyethyl)-[1,1'-biphenyl]-3-yl)-5-(2-(1-methyl-1H-1,2,3-triazol-4-yl)cyclopropyl)-1H-pyrazole-4-carboxylic acid. As is appreciated by those skilled in the art, these analogous examples may involve variations in general reaction conditions.

TABLE 13

| Example | Structure | Name | LCMS [M + H]⁺ | Retention time (min) |
|---|---|---|---|---|
| 217 | 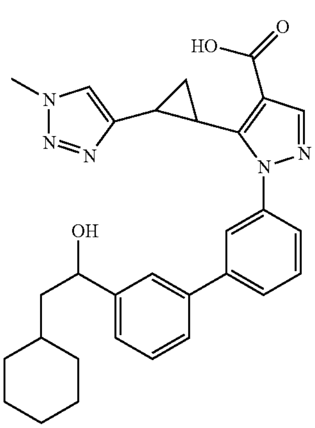 [SMILES: Cn1cc(C2CC2c2c(C(=O)O)cnn2-c2cccc(-c3cccc(C(O)CC4CCCCC4)c3)c2)nn1] | 1-(3'-(2-Cyclohexyl-1-hydroxyethyl)-[1,1'-biphenyl]-3-yl)-5-(2-(1-methyl-1H-1,2,3-triazol-4-yl)cyclopropyl)-1H-pyrazole-4-carboxylic acid | 512.36 | 2.45 |

Example 218. 1-(3'-((1-Cyclohexylpropan-2-yl)oxy)-[1,1'-biphenyl]-3-yl)-5-(2-(1-methyl-1H-1,2,3-triazol-4-yl)cyclopropyl)-1H-pyrazole-4-carboxylic Acid

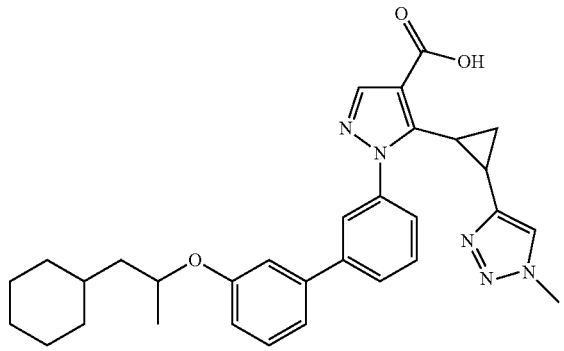 [SMILES: CC(CC1CCCCC1)Oc1cccc(-c2cccc(-n3ncc(C(=O)O)c3C3CC3c3cn(C)nn3)c2)c1]

218a) 1-Cyclohexylpropan-2-ol

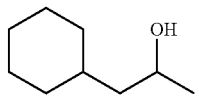

To a solution of 1-cyclohexylpropan-2-one (1 g, 7.13 mmol) in methanol (10 mL) at 0° C. was added NaBH$_4$ (0.540 g, 14.26 mmol) and stirred for 15 min. Then the reaction mixture was allowed to warm to ambient temperature and stirred for 2 h. The reaction mixture was quenched with ice water solution and extracted with DCM (3×30 mL). The combined organic layer was washed with water (50 mL) and brine solution (50 mL), dried over anhydrous Na$_2$SO$_4$ and concentrated to give the title compound (800 mg, 5.62 mmol, 79% yield). $^1$H NMR (CDCl$_3$) δ: 3.91 (br d, J=5.5 Hz, 1H), 1.69 (br s, 1H), 1.62-1.70 (m, 2H), 1.30-1.44 (m, 2H), 0.90-1.29 (m, 8H).

218b) (2-Chloropropyl)cyclohexane

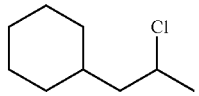

To a solution of 1-cyclohexylpropan-2-ol (800 mg, 5.62 mmol) in dichloromethane (DCM) (15 mL) at 0° C. was added thionyl chloride (0.821 mL, 11.25 mmol) and stirred for 15 min. Then reaction mixture was allowed to warm to ambient temperature and stirred for 2 h. The reaction mixture was quenched with saturated bicarbonate solution and extracted with DCM (3×30 mL). The combined organic layer was washed with water (50 mL) and brine solution (50 mL), dried over anhydrous Na$_2$SO$_4$ and concentrated under reduced pressure to afford the title compound (500 mg, 3.11 mmol, 55.3% yield). $^1$H NMR (CDCl$_3$) δ: 4.54-4.83 (m, 1H), 1.78 (br d, J=12.1 Hz, 1H), 1.52-1.72 (m, 5H), 1.09-1.50 (m, 8H), 0.82-0.99 (m, 2H).

218c) Ethyl 1-(3'-hydroxy-[1,1'-biphenyl]-3-yl)-5-(2-(1-methyl-1H-1,2,3-triazol-4-yl)cyclopropyl)-1H-pyrazole-4-carboxylate

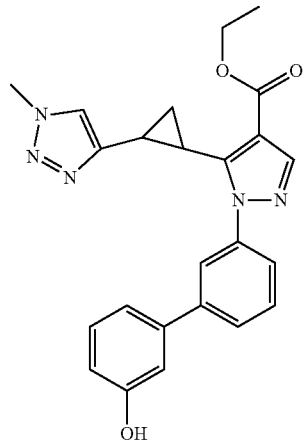 [SMILES: CCOC(=O)c1cnn(-c2cccc(-c3cccc(O)c3)c2)c1C1CC1c1cn(C)nn1]

To a solution of ethyl 1-(3-bromophenyl)-5-(2-(1-methyl-1H-1,2,3-triazol-4-yl)cyclopropyl)-1H-pyrazole-4-carboxylate (2 g, 4.80 mmol) in tetrahydrofuran (THF) (15 mL) and water (3 mL) was added sodium carbonate (1.018 g, 9.61 mmol), (3-hydroxyphenyl)boronic acid (0.795 g, 5.77 mmol). It was degassed for 10 min. Pd(Ph$_3$P)$_4$ (0.555 g, 0.480 mmol) was added and purged with nitrogen and heated at 70° C. for 5 h. The crude residue was diluted with water (200 mL) and extracted with ethyl acetate (2×200 mL). The combined organic layer was washed with brine solution (100 mL) and dried over anhydrous Na$_2$SO$_4$, filtered and concentrated. The crude residue was purified on flash column chromatography eluting with 15% ethyl acetate in hexane. The desired fractions were concentrated to give the title compound (1.5 g, 3.21 mmol, 66.9% yield) as brown solid. LC-MS m/z 430.24 (M+H)$^+$, 2.064 min (ret. time).

218d) Ethyl 1-(3'-((1-cyclohexylpropan-2-yl)oxy)-[1,1'-biphenyl]-3-yl)-5-(2-(1-methyl-1H-1,2,3-triazol-4-yl)cyclopropyl)-1H-pyrazole-4-carboxylate

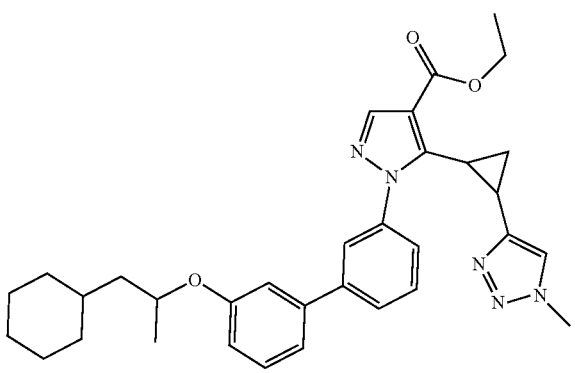 [SMILES: CCOC(=O)c1cnn(-c2cccc(-c3cccc(OC(C)CC4CCCCC4)c3)c2)c1C1CC1c1cn(C)nn1]

To a solution of ethyl 1-(3'-hydroxy-[1,1'-biphenyl]-3-yl)-5-(2-(1-methyl-1H-1,2,3-triazol-4-yl)cyclopropyl)-1H-pyrazole-4-carboxylate (300 mg, 0.699 mmol) in N,N-dimethylformamide (DMF) (10 mL) at ambient temperature was added Cs$_2$CO$_3$ (455 mg, 1.397 mmol). The reaction mixture was stirred at 120° C. for 4 h. The reaction mixture was diluted with water and extracted with EtOAc (2×30 mL). The combined organic layer was washed with brine (10 mL) solution, dried over anhydrous Na$_2$SO$_4$, filtered and concentrated. The crude residue was purified on flash column chromatography eluting with 2.5% MeOH in DCM. The desired fractions were concentrated to give the title compound (200 mg, 0.241 mmol, 34.4% yield) as a brown solid. LC-MS m/z 540.45 (M+H)$^+$, 3.25 min (ret. time).

218e) 1-(3'-((1-Cyclohexylpropan-2-yl)oxy)-[1,1'-biphenyl]-3-yl)-5-(2-(1-methyl-1H-1,2,3-triazol-4-yl)cyclopropyl)-1H-pyrazole-4-carboxylic Acid

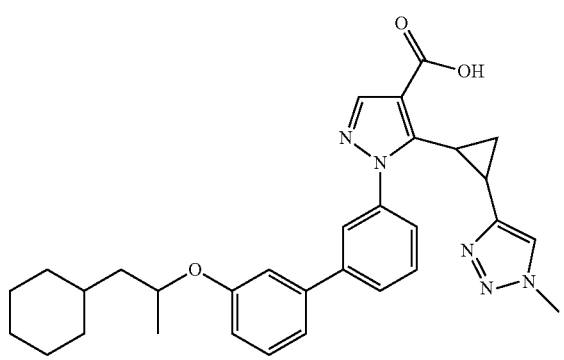 [SMILES: CC(CC1CCCCC1)Oc1cccc(-c2cccc(-n3ncc(C(=O)O)c3C3CC3c3cn(C)nn3)c2)c1]

To a solution of ethyl 1-(3'-((1-cyclohexylpropan-2-yl)oxy)-[1,1'-biphenyl]-3-yl)-5-(2-(1-methyl-1H-1,2,3-triazol-4-yl)cyclopropyl)-1H-pyrazole-4-carboxylate (200 mg, 0.361 mmol) in ethanol (5 mL) at 25° C. was added 1N NaOH in water (0.361 mL, 0.361 mmol). It was stirred for 5 h. The reaction mixture was concentrated. The residue was acidified with 1N HCl solution to pH 4. Solid was precipitated. It was filtered, washed with water and dried to afford the crude residue. It was purified with Prep HPLC (with 10 mM ammonium bicarbonate as modifier) to give the title compound (37 mg, 0.069 mmol, 19.20% yield) as white solid. LC-MS m/z 526.43 (M+H)$^+$, 2.96 min (ret. time).

The compounds in Table 14 were prepared by a method similar to the one described for the preparation of 1-(3'-((1-cyclohexylpropan-2-yl)oxy)-[1,1'-biphenyl]-3-yl)-5-(2-(1-methyl-1H-1,2,3-triazol-4-yl)cyclopropyl)-1H-pyrazole-4-carboxylic acid. As is appreciated by those skilled in the art, these analogous examples may involve variations in general reaction conditions.

TABLE 14

| Example | Structure | Name | LCMS [M + H]$^+$ | Retention time (min) |
|---|---|---|---|---|
| 219 | 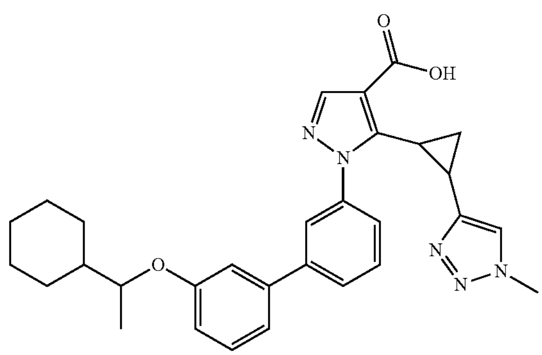 [SMILES: CC(Oc1cccc(-c2cccc(-n3ncc(C(=O)O)c3C3CC3c3cn(C)nn3)c2)c1)C1CCCCC1] | 1-(3'-(1-Cyclohexylethoxy)-[1,1'-biphenyl]-3-yl)-5-(2-(1-methyl-1H-1,2,3-triazol-4-yl)cyclopropyl)-1H-pyrazole-4-carboxylic acid | 512.36 | 2.84 |
| 220 | 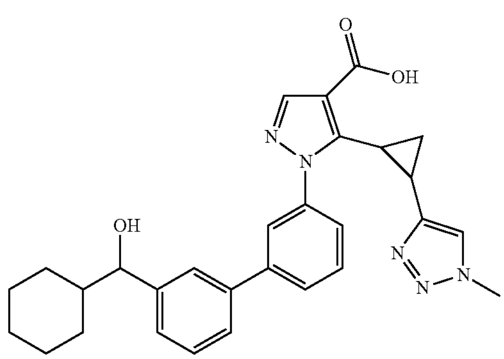 [SMILES: Cn1cc(C2CC2c2c(C(=O)O)cnn2-c2cccc(-c3cccc(C(O)C4CCCCC4)c3)c2)nn1] | 1-(3'-(Cyclohexyl(hydroxy)methyl)-[1,1'-biphenyl]-3-yl)-5-(2-(1-methyl-1H-1,2,3-triazol-4-yl)cyclopropyl)-1H-pyrazole-4-carboxylic acid | 498.28 | 2.32 |

TABLE 14-continued

| Example | Structure | Name | LCMS [M + H]+ | Retention time (min) |
|---|---|---|---|---|
| 221 | 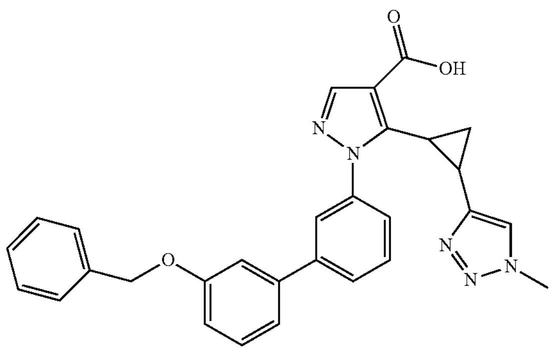 [SMILES: Cn1cc(C2CC2c2c(C(=O)O)cnn2-c2cccc(-c3cccc(OCc4ccccc4)c3)c2)nn1] | 1-(3'-Benzyloxy)-[1,1'-biphenyl]-3-yl)-5-(2-(1-methyl-1H-1,2,3-triazol-4-yl)cyclopropyl)-1H-pyrazole-4-carboxylic acid | 492.2 | 2.653 |
| 222 | 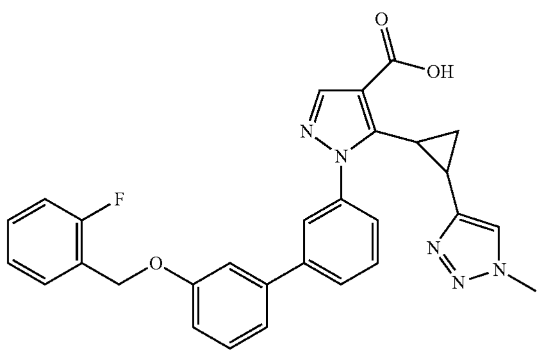 [SMILES: Cn1cc(C2CC2c2c(C(=O)O)cnn2-c2cccc(-c3cccc(OCc4ccccc4F)c3)c2)nn1] | 1-(3'-((2-Fluorobenzyl)oxy)-[1,1'-biphenyl]-3-yl)-5-(2-(1-methyl-1H-1,2,3-triazol-4-yl)cyclopropyl)-1H-pyrazole-4-carboxylic acid | 510.25 | 2.429 |
| 223 | 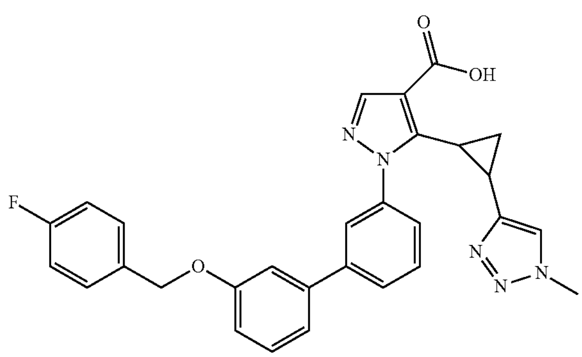 [SMILES: Cn1cc(C2CC2c2c(C(=O)O)cnn2-c2cccc(-c3cccc(OCc4ccc(F)cc4)c3)c2)nn1] | 1-(3'-((4-Fluorobenzyl)oxy)-[1,1'-biphenyl]-3-yl)-5-(2-(1-methyl-1H-1,2,3-triazol-4-yl)cyclopropyl)-1H-pyrazole-4-carboxylic acid | 510.25 | 2.429 |
| 224 | 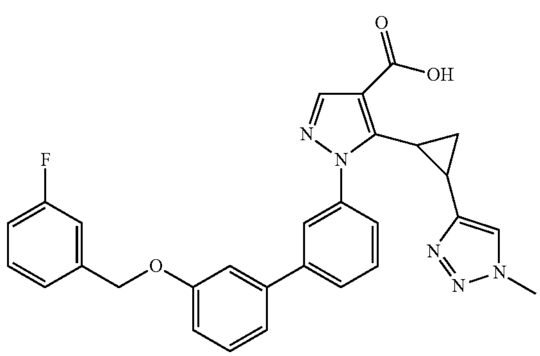 [SMILES: Cn1cc(C2CC2c2c(C(=O)O)cnn2-c2cccc(-c3cccc(OCc4cccc(F)c4)c3)c2)nn1] | 1-(3'-((3-Fluorobenzyl)oxy)-[1,1'-biphenyl]-3-yl)-5-(2-(1-methyl-1H-1,2,3-triazol-4-yl)cyclopropyl)-1H-pyrazole-4-carboxylic acid | 510.28 | 2.429 |

TABLE 14-continued

| Example | Structure | Name | LCMS [M + H]⁺ | Retention time (min) |
|---|---|---|---|---|
| 225 | 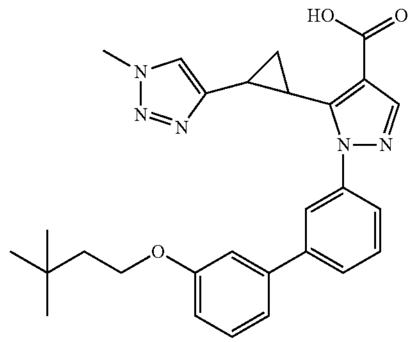 [SMILES: Cn1cc(C2CC2c2c(C(=O)O)cnn2-c2cccc(-c3cccc(OCCC(C)(C)C)c3)c2)nn1] | 1-(3'-(3,3-Dimethylbutoxy)-[1,1'-biphenyl]-3-yl)-5-(2-(1-methyl-1H-1,2,3-triazol-4-yl)cyclopropyl)-1H-pyrazole-4-carboxylic acid | 486.34 | 2.693 |
| 226 | 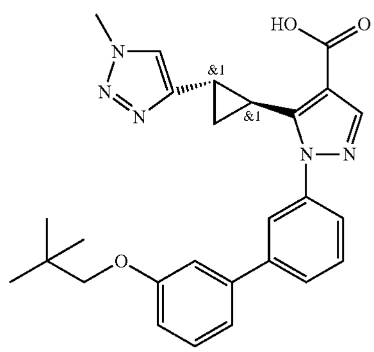 [SMILES: Cn1cc([C@H]2C[C@@H]2c2c(C(=O)O)cnn2-c2cccc(-c3cccc(OCC(C)(C)C)c3)c2)nn1] | 5-((1,2-trans)-2-(1-Methyl-1H-1,2,3-triazol-4-yl)cyclopropyl)-1-(3'-(neopentyloxy)-[1,1'-biphenyl]-3-yl)-1H-pyrazole-4-carboxylic acid | 472.34 | 2.58 |

219a) (1-Chloroethyl)cyclohexane

To a solution of 1-cyclohexylethanol (500 mg, 3.90 mmol) in dichloromethane (DCM) (15 mL) at 0° C. was added thionyl chloride (0.569 mL, 7.80 mmol) and stirred for 15 min. The reaction mixture was allowed to warm to ambient temperature and stirred for 2 h. The reaction mixture was quenched with saturated bicarbonate solution and extracted with DCM (3×30 mL). The combined organic layer was washed with water (50 mL) and brine solution (50 mL), dried over anhydrous $Na_2SO_4$ and concentrated under reduced pressure to afford the title compound (350 mg, 2.387 mmol, 61.2% yield). ¹H NMR (CDCl₃) δ: 4.23-4.57 (m, 1H), 1.57-1.91 (m, 5H), 1.41-1.56 (m, 1H), 1.16-1.37 (m, 5H), 0.90-1.15 (m, 3H).

220a) (3-Bromophenyl)(cyclohexyl)methanol

To a solution of magnesium (0.149 g, 6.13 mmol) in dry tetrahydrofuran (THF) (10 mL) was added catalytic amount of iodine. A solution of bromocyclohexane (1 g, 6.13 mmol) in tetrahydrofuran (THF) (10 mL) was added and reflux for 3 h. The reaction mixture was added to 3-bromobenzaldehyde (1.135 g, 6.13 mmol) in tetrahydrofuran (THF) (10 mL). It was stirred at ambient temperature for 16 h. The reaction mixture was quenched with ammonium chloride solution (50 mL), extracted with ethyl acetate (2×100 mL). The combined organic layer was washed with water (50 mL), brine (50 mL) and concentrated. The crude residue was purified on flash column chromatography eluting with 1.5% ethyl acetate in hexane. The desired fractions were concentrated to give the title compound (200 mg, 0.543 mmol, 17.72% yield) as colorless oil. ¹H NMR (DMSO-d₆) δ: 7.44 (s, 1H), 7.36-7.42 (m, 1H), 7.19-7.31 (m, 2H), 5.17 (d, J=4.6 Hz, 1H), 4.19-4.30 (m, 1H), 1.75 (br d, J=12.7 Hz, 1H), 1.53-1.70 (m, 3H), 1.38-1.50 (m, 1H), 1.34 (br d, J=12.7 Hz, 1H), 1.03-1.22 (m, 3H), 0.88-1.02 (m, 2H).

Example 227. 5-(2-(1-Methyl-1H-1,2,3-triazol-4-yl)cyclopropyl)-1-(3'-(1-(tetrahydro-2H-pyran-4-yl)ethoxy)-[1,1'-biphenyl]-3-yl)-1H-pyrazole-4-carboxylic Acid

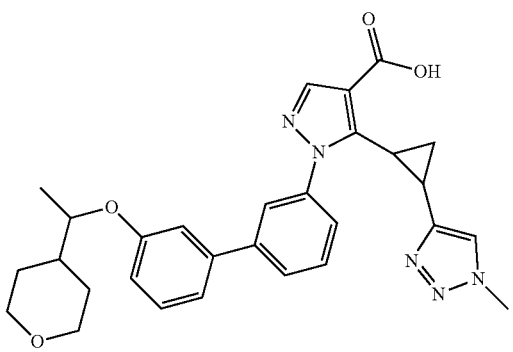 [SMILES: CC(Oc1cccc(-c2cccc(-n3ncc(C(=O)O)c3C3CC3c3cn(C)nn3)c2)c1)C1CCOCC1]

227a) Ethyl 5-(2-(1-methyl-1H-1,2,3-triazol-4-yl)cyclopropyl)-1-(3'-(1-(tetrahydro-2H-pyran-4-yl)ethoxy)-[1,1'-biphenyl]-3-yl)-1H-pyrazole-4-carboxylate

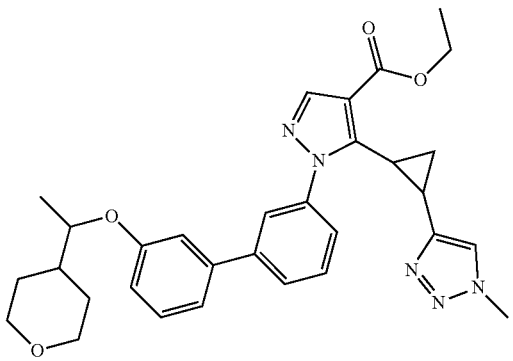 [SMILES: CCOC(=O)c1cnn(-c2cccc(-c3cccc(OC(C)C4CCOCC4)c3)c2)c1C1CC1c1cn(C)nn1]

To a solution of ethyl 1-(3'-hydroxy-[1,1'-biphenyl]-3-yl)-5-(2-(1-methyl-1H-1,2,3-triazol-4-yl)cyclopropyl)-1H-pyrazole-4-carboxylate (500 mg, 1.164 mmol) in dichloromethane (DCM) (50 mL) was added triphenylphosphine (611 mg, 2.328 mmol), (Z)-diazene-1,2-diylbis(piperidin-1-ylmethanone) (587 mg, 2.328 mmol), and 1-(tetrahydro-2H-pyran-4-yl)ethanol (167 mg, 1.281 mmol). It was stirred at ambient temperature for 16 h. The reaction mixture quenched with ice cold water (30 mL) and extracted with EtOAc (2×30 mL). The combined organic layer was washed with cold water (20 mL), brine (20 mL) solution and then concentrated to give the title compound (500 mg, 0.382 mmol, 32.9% yield) as a white solid. LC-MS m/z 542.36 (M+H)$^+$, 3.73 min (ret. time).

227b) 5-(2-(1-Methyl-1H-1,2,3-triazol-4-yl)cyclopropyl)-1-(3'-(1-(tetrahydro-2H-pyran-4-yl)ethoxy)-[1,1'-biphenyl]-3-yl)-1H-pyrazole-4-carboxylic Acid

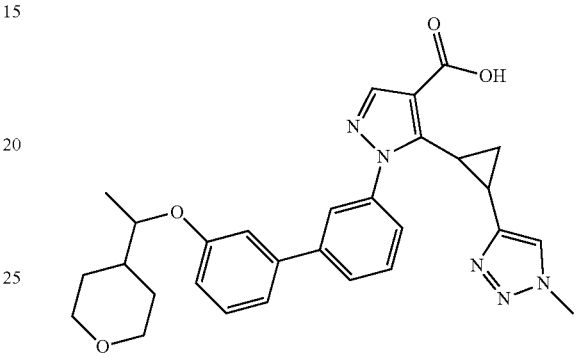

To a solution of ethyl 5-(2-(1-methyl-1H-1,2,3-triazol-4-yl)cyclopropyl)-1-(3'-(1-(tetrahydro-2H-pyran-4-yl)ethoxy)-[1,1'-biphenyl]-3-yl)-1H-pyrazole-4-carboxylate (200 mg, 0.369 mmol) in ethanol (5 mL) was added 1N NaOH (5 mL, 5.00 mmol). It was stirred for 5 h. The reaction mixture was concentrated. The residue was acidified with 1N HCl solution to pH 4. Solid was precipitated. It was filtered and the solid was washed with water and dried. It was purified with prep HPLC (0.1% formic acid as modifier) to give the title compound (47 mg, 0.091 mmol, 38.8% yield) as an off-white solid. LC-MS m/z 514.38 (M+H)$^+$, 2.19 min (ret. time).

The compounds in Table 15 were prepared by a method similar to the one described for the preparation of 5-(2-(1-methyl-1H-1,2,3-triazol-4-yl)cyclopropyl)-1-(3'-(1-(tetrahydro-2H-pyran-4-yl)ethoxy)-[1,1'-biphenyl]-3-yl)-1H-pyrazole-4-carboxylic acid. As is appreciated by those skilled in the art, these analogous examples may involve variations in general reaction conditions.

TABLE 15

| Example | Structure | Name | LCMS [M + H]$^+$ | Retention time (min) |
|---|---|---|---|---|
| 228 | 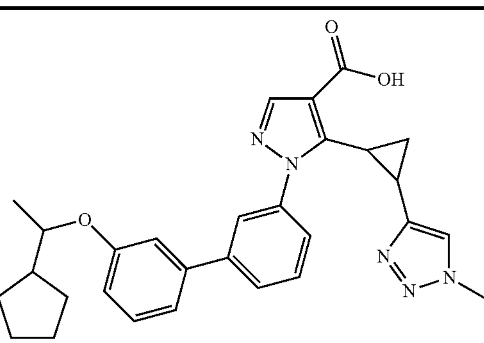 | 1-(3'-(1-Cyclopentylethoxy)-[1,1'-biphenyl]-3-yl)-5-(2-(1-methyl-1H-1,2,3-triazol-4-yl)cyclopropyl)-1H-pyrazole-4-carboxylic acid | 498.39 | 2.71 |

TABLE 15-continued

| Example | Name | LCMS [M + H]+ | Retention time (min) |
|---|---|---|---|
| 229 | 1-(3'-Cyclohexyloxy)-[1,1'-biphenyl]-3-yl)-5-(2-(1-methyl-1H-1,2,3-triazol-4-yl)cyclopropyl)-1H-pyrazole-4-carboxylic acid | 484.33 | 2.587 |
| 230 | 1-(3'-(1-Cycloheptylethoxy)-[1,1'-biphenyl]-3-yl)-5-((1,2-trans)-2-(1-methyl-1H-1,2,3-triazol-4-yl)cyclopropyl)-1H-pyrazole-4-carboxylic acid | 526.41 | 2.953 |
| 231 | 1-(3'-(1-Cyclopropylethoxy)-[1,1'-biphenyl]-3-yl)-5-(2-(1-methyl-1H-1,2,3-triazol-4-yl)cyclopropyl)-1H-pyrazole-4-carboxylic acid | 470.30 | 2.33 |
| 232 | 1-(3'-((1-(tert-Butoxycarbonyl)piperidin-3-yl)oxy)-[1,1'-biphenyl]-3-yl)-5-(2-(1-methyl-1H-1,2,3-triazol-4-yl)cyclopropyl)-1H-pyrazole-4-carboxylic acid | 585.37 | 2.44 |

230a) Cycloheptylmethanol

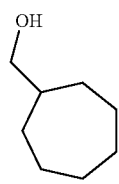

To a solution of cycloheptanecarboxylic acid (2 g, 14.07 mmol) in tetrahydrofuran (THF) (25 mL) at 0° C. was added aluminum (111) lithium hydride (14.07 mL, 14.07 mmol) slowly and stirred for 4 h. The reaction was quenched with saturated $Na_2SO_4$ solution (5 mL) and extracted with EtOAc (2×50 mL). The combined organic layer was washed with brine solution (50 mL) and dried over anhydrous $Na_2SO_4$, filtered and concentrated to give the title compound (1.3 g, 10.14 mmol, 72.1% yield) as liquid. $^1$H NMR (400 MHz, DMSO-d6) δ: 4.36 (t, J=5.3 Hz, 1H), 3.15 (dd, J=5.5, 6.6 Hz, 2H), 1.74-1.56 (m, 4H), 1.56-1.30 (m, 7H), 1.14-1.02 (m, 2H).

230b) Cycloheptanecarbaldehyde

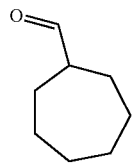

To a solution of cycloheptylmethanol (1.3 g, 10.14 mmol) in dichloromethane (DCM) (30 mL) at 10° C. was added Dess-Martin periodinane (6.88 g, 16.22 mmol). It was stirred for 3 h. The reaction mixture was filtered through celite pad and the filtrate was concentrated. The crude residue was purified on flash column chromatography eluting with 5% EtOAc in hexane. The desired fractions were concentrated to give the title compound (800 mg, 6.34 mmol, 62.5% yield) as color less liquid. $^1$H NMR (400 MHz, CDCl$_3$) δ: 9.64 (d, J=1.1 Hz, 1H), 2.44-2.34 (m, 1H), 2.02-1.89 (m, 2H), 1.75-1.63 (m, 3H), 1.63-1.47 (m, 10H).

230c) 1-Cycloheptylethanol

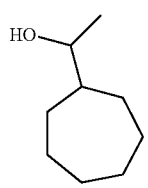

To a solution of cycloheptanecarbaldehyde (800 mg, 6.34 mmol) in tetrahydrofuran (THF) (20 mL) at −40° C. was added methylmagnesium bromide (6.34 mL, 9.51 mmol) slowly for 1 h. The reaction mixture was quenched with ammonium chloride solution (20 mL) and extracted with EtOAc (2×10 mL). The combined organic layer was washed with brine solution (20 mL), dried over anhydrous $Na_2SO_4$, filtered and concentrated to give the title compound (500 mg, 3.52 mmol, 55.5% yield) as color less liquid. $^1$H NMR (400 MHz, CDCl$_3$) δ: 3.73-3.60 (m, 1H), 1.76-1.65 (m, 4H), 1.61-1.40 (m, 10H), 1.31-1.21 (m, 2H), 1.13 (d, J=6.1 Hz, 3H).

Example 233. 1-(3'-(2-Cyclohexylethyl)-[1,1'-biphenyl]-3-yl)-5-(2-(1-methyl-1H-1,2,3-triazol-4-yl)cyclopropyl)-1H-pyrazole-4-carboxylic Acid

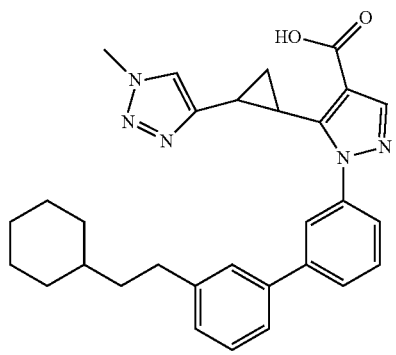 [SMILES: Cn1cc(C2CC2c2c(C(=O)O)cnn2-c2cccc(-c3cccc(CCC4CCCCC4)c3)c2)nn1]

233a) 4,4,5,5-Tetramethyl-2-(3-vinylphenyl)-1,3,2-dioxaborolane

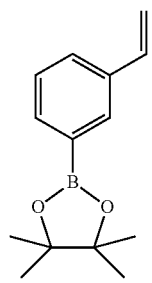 [SMILES: C=Cc1cccc(B2OC(C)(C)C(C)(C)O2)c1]

To a solution of 1-bromo-3-vinylbenzene (500 mg, 2.73 mmol) in 1,4-dioxane (10 mL) was added bis(pinacolato)diboron (832 mg, 3.28 mmol) and potassium acetate (536 mg, 5.46 mmol). The reaction mixture was degassed with argon for 10 min then PdCl$_2$(dppf)-CH$_2$Cl$_2$ adduct (112 mg, 0.137 mmol) was added. The reaction mixture was heated to 90° C. for 3 h. The reaction mixture was cool to 0° C., quenched with cold water, extracted with EtOAc twice. The combined organic layer was washed with brine solution, dried over anhydrous Na$_2$SO$_4$, filtered and concentrated. The crude residue was purified on flash column chromatography eluting with EtOAC:Hexane (4:96). Desired fractions were concentrated to give the title compound (300 mg, 1.304 mmol, 47.7% yield) as liquid. $^1$H NMR (400 MHz, chloroform-d) δ ppm: 1.35 (s, 12H) 5.24 (d, J=10.96 Hz, 1H) 5.78 (d, J=17.54 Hz, 1H) 7.30-7.36 (m, 1H) 7.48-7.54 (m, 1H) 7.70 (d, J=7.23 Hz, 1H) 7.84 (s, 1H).

233b) (E)-2-(3-(2-Cyclohexylvinyl)phenyl)-4,4,5,5-tetramethyl-1,3,2-dioxaborolane

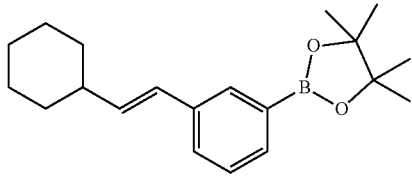 [SMILES: CC1(C)OB(c2cccc(/C=C/C3CCCCC3)c2)OC1(C)C]

To a solution of 4,4,5,5-tetramethyl-2-(3-vinylphenyl)-1,3,2-dioxaborolane (500 mg, 2.173 mmol) in dichloromethane (DCM) (10 mL) at ambient temperature was added vinylcyclohexane (1197 mg, 10.86 mmol) and Grubbs II (55.3 mg, 0.065 mmol). The reaction was stirred at 45° C. for 8 h. The reaction mixture was cool to 0° C., quenched with cold water, extracted with DCM twice. The combined organic layer was washed with brine solution, dried over anhydrous $Na_2SO_4$, filtered and concentrated. The crude residue was purified on flash column chromatography eluting with EtOAC:Hexane (2:98). Desired fractions were concentrated to give the title compound (250 mg, 0.801 mmol, 36.8% yield). $^1H$ NMR (400 MHz, chloroform-d) δ ppm: 1.28-1.36 (m, 17H) 1.67 (br d, J=12.50 Hz, 1H) 1.69-1.85 (m, 5H) 6.18-6.25 (m, 1H) 6.32-6.38 (m, 1H) 7.30 (d, J=7.45 Hz, 1H) 7.42 (br d, J=7.67 Hz, 1H) 7.62 (d, J=7.23 Hz, 1H) 7.77-7.81 (m, 1H).

233c) 2-(3-(2-Cyclohexylethyl)phenyl)-4,4,5,5-tetramethyl-1,3,2-dioxaborolane

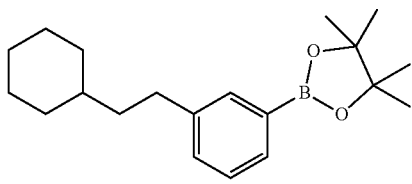 [SMILES: CC1(C)OB(c2cccc(CCC3CCCCC3)c2)OC1(C)C]

To a solution of (E)-2-(3-(2-cyclohexylvinyl)phenyl)-4,4,5,5-tetramethyl-1,3,2-dioxaborolane (250 mg, 0.801 mmol) in ethanol (10 mL) was added 10% Pd—C (85 mg, 0.801 mmol). The reaction mixture was stirred at ambient temperature for 6 h under hydrogen atmosphere. The reaction mixture was filtrated through celite. The filtrate was concentrated to give the title compound (200 mg, 0.636 mmol, 79% yield). $^1H$ NMR (400 MHz, chloroform-d) δ ppm: 1.17-1.30 (m, 5H) 1.35 (s, 12H) 1.50 (br d, J=3.51 Hz, 1H) 1.64-1.81 (m, 5H) 2.57-2.64 (m, 2H) 3.70 (s, 2H) 7.28 (br s, 2H) 7.62 (s, 2H).

233d) Ethyl 1-(3'-(2-cyclohexylethyl)-[1,1'-biphenyl]-3-yl)-5-(2-(1-methyl-1H-1,2,3-triazol-4-yl)cyclopropyl)-1H-pyrazole-4-carboxylate

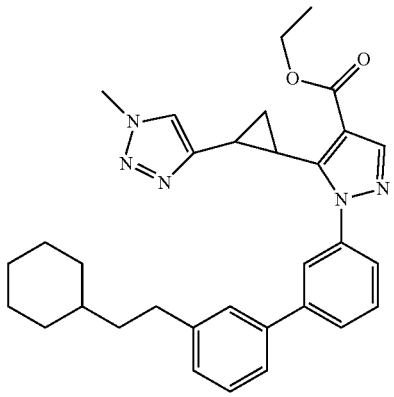 [SMILES: CCOC(=O)c1cnn(-c2cccc(-c3cccc(CCC4CCCCC4)c3)c2)c1C1CC1c1cn(C)nn1]

To a solution of ethyl 1-(3-bromophenyl)-5-(2-(1-methyl-1H-1,2,3-triazol-4-yl)cyclopropyl)-1H-pyrazole-4-carboxylate (80 mg, 0.192 mmol), 2-(3-(2-cyclohexylethyl)phenyl)-4,4,5,5-tetramethyl-1,3,2-dioxaborolane (60.4 mg, 0.192 mmol) in 1,4-dioxane (5 mL) and water (5 mL) was added $K_2CO_3$ (66.4 mg, 0.480 mmol), degassed with nitrogen for 20 min, followed by the addition of Tetrakis (22.21 mg, 0.019 mmol). The reaction mixture was stirred at 90° C. for 6 h. The reaction mixture was cool to 0° C., quenched with cold water, extracted with twice EtOAc, brine solution. The organic layer was dried under anhydrous $Na_2SO_4$, filtered and the filtrate was concentrated to give the title compound (90 mg, 0.091 mmol, 47.1% yield) as liquid. The product was carried to next step without any further purification. LC-MS m/z 524.3 $(M+H)^+$, 3.54 min (ret. time).

233e) 1-(3'-(2-Cyclohexylethyl)-[1,1'-biphenyl]-3-yl)-5-(2-(1-methyl-1H-1,2,3-triazol-4-yl)cyclopropyl)-1H-pyrazole-4-carboxylic Acid

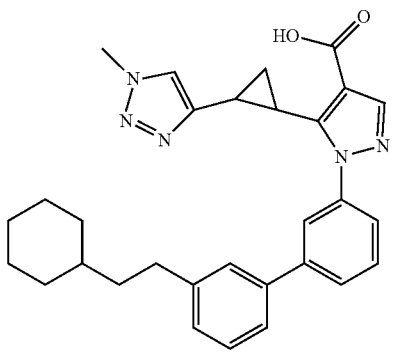 [SMILES: Cn1cc(C2CC2c2c(C(=O)O)cnn2-c2cccc(-c3cccc(CCC4CCCCC4)c3)c2)nn1]

To a solution of ethyl 1-(3'-(2-cyclohexylethyl)-[1,1'-biphenyl]-3-yl)-5-(2-(1-methyl-1H-1,2,3-triazol-4-yl)cyclopropyl)-1H-pyrazole-4-carboxylate (280 mg, 0.535 mmol) in ethanol (10 mL) at 0° C. was added 10% NaOH (20 mL, 0.535 mmol). The reaction was stirred at ambient temperature for 16 h. The reaction mixture was concentrated, neutralized with 2N HCl, extracted with DCM twice. The combined organic layer was washed with brine solution, dried over anhydrous Na$_2$SO$_4$, filtered. The filtrate was concentrated. The crude residue was purified with Prep HPLC (10 mm ammonium bicarbonate as modifier) to give the title compound (80 mg, 0.160 mmol, 29.8% yield) as white solid. LC-MS m/z 496.35 (M+H)$^+$, 3.01 min (ret. time).

Example 234. 1-(2'-Fluoro-3'-((tetrahydro-2H-pyran-4-yl)oxy)-[1,1'-biphenyl]-3-yl)-5-(2-(1-methyl-1H-1,2,3-triazol-4-yl)cyclopropyl)-1H-pyrazole-4-carboxylic Acid

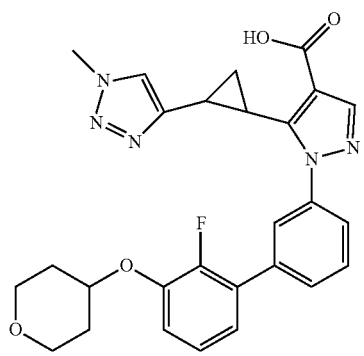 [SMILES: Cn1cc(C2CC2c2c(C(=O)O)cnn2-c2cccc(-c3cccc(OC4CCOCC4)c3F)c2)nn1]

234a) Ethyl 1-(2'-fluoro-3'-hydroxy-[1,1'-biphenyl]-3-yl)-5-(2-(1-methyl-1H-1,2,3-triazol-4-yl)cyclopropyl)-1H-pyrazole-4-carboxylate

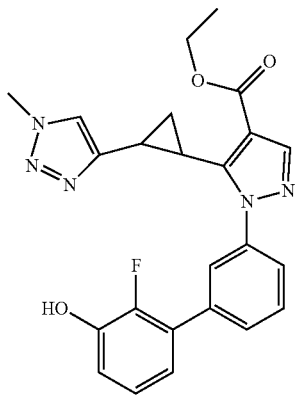 [SMILES: CCOC(=O)c1cnn(-c2cccc(-c3cccc(O)c3F)c2)c1C1CC1c1cn(C)nn1]

To a solution of ethyl 1-(3-bromophenyl)-5-(2-(1-methyl-1H-1,2,3-triazol-4-yl)cyclopropyl)-1H-pyrazole-4-carboxylate (400 mg, 0.961 mmol) in tetrahydrofuran (THF) (2 mL) was added (2-fluoro-3-hydroxyphenyl)boronic acid (180 mg, 1.153 mmol), sodium carbonate (204 mg, 1.922 mmol) and water (0.5 mL). The reaction mixture was degassed with argon for 15 min, then tetrakis(triphenylphosphine)palladium(0) (111 mg, 0.096 mmol) was added under nitrogen atmosphere. It was heated at 75° C. for 16 h. The reaction mixture was diluted with water and extracted with ethyl acetate (2×30 mL). The combined organic layer was washed with brine solution (20 mL), dried over anhydrous Na$_2$SO$_4$ and concentrated. The crude residue was purified by column chromatography eluting with 60% ethyl acetate in n-hexane. Desired fractions were concentrated to give the title compound (450 mg, 0.961 mmol, 100% yield). LC-MS m/z 448.35 (M+H)$^+$, 3.26 min (ret. time).

234b) Ethyl 1-(2'-fluoro-3'-((tetrahydro-2H-pyran-4-yl)oxy)-[1,1'-biphenyl]-3-yl)-5-(2-(1-methyl-1H-1,2,3-triazol-4-yl)cyclopropyl)-1H-pyrazole-4-carboxylate

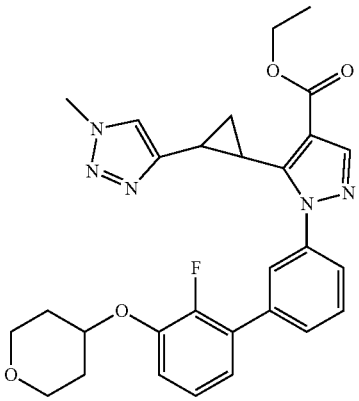 [SMILES: CCOC(=O)c1cnn(-c2cccc(-c3cccc(OC4CCOCC4)c3F)c2)c1C1CC1c1cn(C)nn1]

To a solution of ethyl 1-(2'-fluoro-3'-hydroxy-[1,1'-biphenyl]-3-yl)-5-(2-(1-methyl-1H-1,2,3-triazol-4-yl)cyclopropyl)-1H-pyrazole-4-carboxylate (450 mg, 1.006 mmol) in N,N-dimethylformamide (DMF) (5 mL) was added Cs$_2$CO$_3$ (655 mg, 2.011 mmol) and 4-bromotetrahydro-2H-pyran (232 mg, 1.408 mmol). It was heated in Microwave at 120° C. for 2 h. The reaction mixture was diluted with water and extracted with ethyl acetate (2×30 mL). The combined organic layer was washed with chilled water (3×30 mL) and then brine solution (30 mL), dried over anhydrous Na$_2$SO$_4$ and concentrated. The crude residue was purified by column chromatography eluting with 1% methanol in DCM. Desired fractions were concentrated to give the title compound (200 mg, 0.217 mmol, 21.58% yield). LC-MS m/z 532.23 (M+H)$^+$, 2.36 min (ret. time).

234c) 1-(2'-Fluoro-3'-((tetrahydro-2H-pyran-4-yl)oxy)-[1,1'-biphenyl]-3-yl)-5-(2-(1-methyl-1H-1,2,3-triazol-4-yl)cyclopropyl)-1H-pyrazole-4-carboxylic Acid

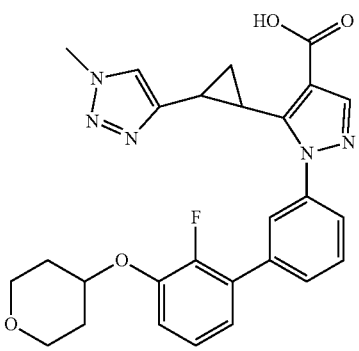 [SMILES: Cn1cc(C2CC2c2c(C(=O)O)cnn2-c2cccc(-c3cccc(OC4CCOCC4)c3F)c2)nn1]

To a solution of ethyl 1-(2'-fluoro-3'-((tetrahydro-2H-pyran-4-yl)oxy)-[1,1'-biphenyl]-3-yl)-5-(2-(1-methyl-1H-1,2,3-triazol-4-yl)cyclopropyl)-1H-pyrazole-4-carboxylate (200 mg, 0.376 mmol) in ethanol (5 mL) was added NaOH (2 mL, 4.00 mmol) and stirred for 2 h. The reaction mixture was concentrated and the residue was diluted with ice and acidified with 1 N HCl solution to pH 4. Solid was precipitated. It was stirred for 20 min and then filtered. Solid was dried and then purified by column chromatography eluting with 4% methanol in DCM. Desired fractions were concentrated to give the title compound (90 mg, 0.170 mmol, 45.3% yield) as white solid. LC-MS m/z 504.2 (M+H)$^+$, 2.00 min (ret. time).

Example 235. 5-(2-(1-Methyl-1H-1,2,3-triazol-4-yl)cyclopropyl)-1-(3'-(1-phenylethoxy)-[1,1'-biphenyl]-3-yl)-1H-pyrazole-4-carboxylic Acid

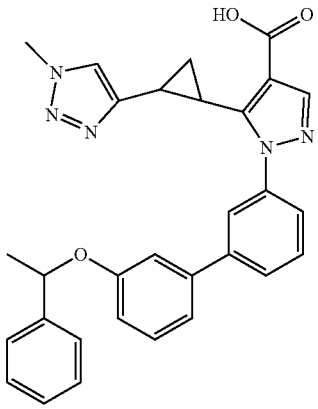 [SMILES: CC(Oc1cccc(-c2cccc(-n3ncc(C(=O)O)c3C3CC3c3cn(C)nn3)c2)c1)c1ccccc1]

235a) Ethyl 5-(2-(1-methyl-1H-1,2,3-triazol-4-yl)cyclopropyl)-1-(3'-(1-phenylethoxy)-[1,1'-biphenyl]-3-yl)-1H-pyrazole-4-carboxylate N33934-50-A1

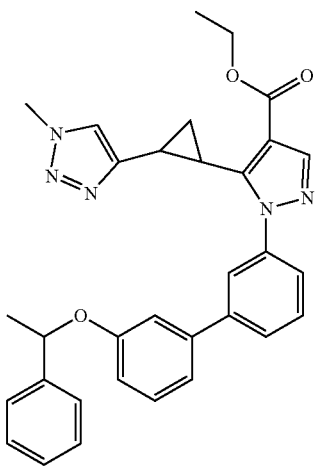 [SMILES: CCOC(=O)c1cnn(-c2cccc(-c3cccc(OC(C)c4ccccc4)c3)c2)c1C1CC1c1cn(C)nn1]

To a solution of ethyl 1-(3'-hydroxy-[1,1'-biphenyl]-3-yl)-5-(2-(1-methyl-1H-1,2,3-triazol-4-yl)cyclopropyl)-1H-pyrazole-4-carboxylate (200 mg, 0.466 mmol) and potassium carbonate (129 mg, 0.931 mmol) in N,N-dimethylformamide (DMF) (10 mL) was added (1-bromoethyl)benzene (129 mg, 0.699 mmol) at RT and stirred at 100° C. for 10 h. The reaction was cooled to RT and diluted with Ice water (20 mL) and extracted with EtOAc (2×20 mL). The combined organic layer was washed with brine solution (20 mL) and dried over anhydrous Na$_2$SO$_4$, filtered and concentrated to give the title compound (200 mg, 0.375 mmol, 80% yield). LCMS m/z 534.37 (M+H)$^+$, 2.787 min (ret. time).

235b) 5-(2-(1-Methyl-1H-1,2,3-triazol-4-yl)cyclopropyl)-1-(3'-(1-phenylethoxy)-[1,1'-biphenyl]-3-yl)-1H-pyrazole-4-carboxylic Acid

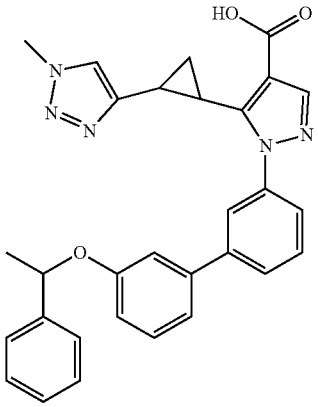 [SMILES: CC(Oc1cccc(-c2cccc(-n3ncc(C(=O)O)c3C3CC3c3cn(C)nn3)c2)c1)c1ccccc1]

To a solution of ethyl 5-(2-(1-methyl-1H-1,2,3-triazol-4-yl)cyclopropyl)-1-(3'-(1-phenylethoxy)-[1,1'-biphenyl]-3-yl)-1H-pyrazole-4-carboxylate (120 mg, 0.225 mmol) in ethanol (5 mL) at RT was added NaOH (0.112 mL, 0.225 mmol) and stirred for 4 h. The reaction mixture was concentrated. It was acidified with 2 N HCl solution to pH 2 and the aqueous layer was extracted with EtOAc (2×20 mL). The combined organic layer was washed with brine solution (20 mL), dried over anhydrous Na$_2$SO$_4$, filtered and concentrated. It was purified through Prep HPLC (0.1% formic acid as modifier) to give the title compound (28 mg, 0.055 mmol, 24.40% yield) as an off-white solid. LCMS m/z 506.41 (M+H)$^+$, 2.38 min (ret. time).

The compounds in Table 16 were prepared by a method similar to the one described for the preparation of 5-(2-(1-methyl-1H-1,2,3-triazol-4-yl)cyclopropyl)-1-(3'-(1-phenylethoxy)-[1,1'-biphenyl]-3-yl)-1H-pyrazole-4-carboxylic acid. As is appreciated by those skilled in the art, these analogous examples may involve variations in general reaction conditions.

TABLE 16

| Example | Structure | Name | LCMS [M + H]+ | Retention time (min) |
|---|---|---|---|---|
| 236 | 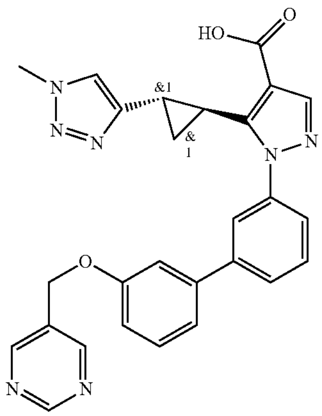 [SMILES: Cn1cc([C@H]2C[C@@H]2c2c(C(=O)O)cnn2-c2cccc(-c3cccc(OCc4cncnc4)c3)c2)nn1] | 5-((1,2-trans)-2-(1-Methyl-1H-1,2,3-triazol-4-yl)cyclopropyl)-1-(3'-(pyrimidin-5-ylmethoxy)-[1,1'-biphenyl]-3-yl)-1H-pyrazole-4-carboxylic acid | 494.30 | 1.826 |

236a) 5-(Bromomethyl)pyrimidine

To a solution of pyrimidin-5-ylmethanol (300 mg, 2.72 mmol) in dichloromethane (DCM) (15 mL) at 0° C. was added tribromophosphine (0.257 mL, 2.72 mmol) and stirred for 2 h. The reaction mixture was quenched with ice water (20 mL) and extracted with DCM (2×20 mL). The combined organic layer was washed with brine solution (20 mL), dried over anhydrous Na$_2$SO$_4$, filtered and concentrated to give the title compound (200 mg, 1.156 mmol, 42.4% yield). $^1$H NMR (400 MHz, CDCl$_3$) δ: 9.16 (s, 1H), 8.78 (s, 2H), 4.44 (s, 2H).

Example 237. 1-(3'-([1,1'-Biphenyl]-4-ylmethoxy)-[1,1'-biphenyl]-3-yl)-5-((1,2-trans)-2-(1-methyl-1H-1,2,3-triazol-4-yl)cyclopropyl)-1H-pyrazole-4-carboxylic Acid

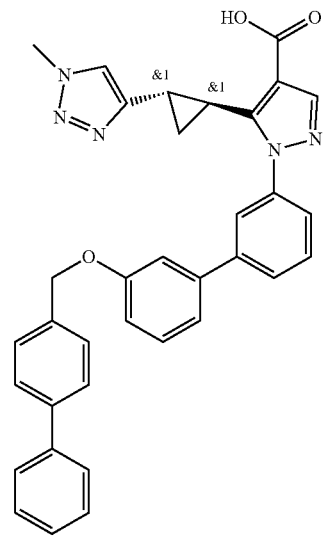 [SMILES: Cn1cc([C@H]2C[C@@H]2c2c(C(=O)O)cnn2-c2cccc(-c3cccc(OCc4ccc(-c5ccccc5)cc4)c3)c2)nn1]

237a) Ethyl 1-(3'-([1,1'-biphenyl]-4-ylmethoxy)-[1,1'-biphenyl]-3-yl)-5-((1,2-trans)-2-(1-methyl-1H-1,2,3-triazol-4-yl)cyclopropyl)-1H-pyrazole-4-carboxylate

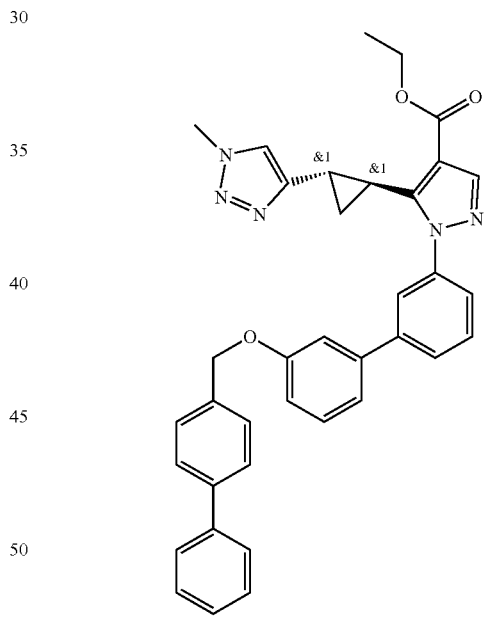

To a solution of ethyl 1-(3'-hydroxy-[1,1'-biphenyl]-3-yl)-5-((1,2-trans)-2-(1-methyl-1H-1,2,3-triazol-4-yl)cyclopropyl)-1H-pyrazole-4-carboxylate (100 mg, 0.233 mmol) in N,N-dimethylformamide (DMF) (2 mL) at 10° C. was added NaH (18.63 mg, 0.466 mmol). 4-(Bromomethyl)-1,1'-biphenyl (86 mg, 0.349 mmol) was added after 10 min and stirred for 10 h. The reaction diluted with ice water (10 mL) and extracted with EtOAc (2×20 mL). The combined organic layer was washed with brine solution (20 mL), dried over anhydrous Na$_2$SO$_4$, filtered and concentrated. The crude residue was purified on flash column chromatography eluting with EtOAc:hexane (5:5). Desired fractions were concentrated to give the title compound (120 mg, 0.181 mmol, 78% yield) as a white solid. LCMS m/z 596.17 (M+H)$^+$, 3.025 min (ret. time).

237b) 1-(3'-([1,1'-Biphenyl]-4-ylmethoxy)-[1,1'-biphenyl]-3-yl)-5-((1,2-trans)-2-(1-methyl-1H-1,2,3-triazol-4-yl)cyclopropyl)-1H-pyrazole-4-carboxylic Acid

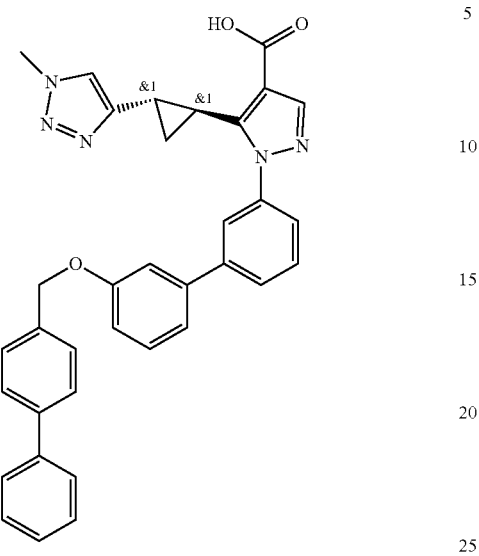

To a solution of ethyl 1-(3'-([1,1'-biphenyl]-4-ylmethoxy)-[1,1'-biphenyl]-3-yl)-5-((1,2-trans)-2-(1-methyl-1H-1,2,3-triazol-4-yl)cyclopropyl)-1H-pyrazole-4-carboxylate (120 mg, 0.201 mmol) in ethanol (5 mL) at RT was added NaOH (0.201 mL, 0.403 mmol). It was stirred for 6 h. The reaction concentrated and diluted with ice water (10 mL), acidified with 1N HCl to pH 2. The obtained white precipitate was filtered and washed with hexane and dried to give the title compound (90 mg, 0.157 mmol, 78% yield) as an off-white solid. LCMS m/z 568.20 (M+H)$^+$, 2.717 min (ret. time).

The compounds in Table 17 were prepared by a method similar to the one described for the preparation of 1-(3'-([1,1'-biphenyl]-4-ylmethoxy)-[1,1'-biphenyl]-3-yl)-5-((1,2-trans)-2-(1-methyl-1H-1,2,3-triazol-4-yl)cyclopropyl)-1H-pyrazole-4-carboxylic acid. As is appreciated by those skilled in the art, these analogous examples may involve variations in general reaction conditions.

TABLE 17

| Example | Structure | Name | LCMS [M + H]$^+$ | Retention time (min) |
|---|---|---|---|---|
| 238 | 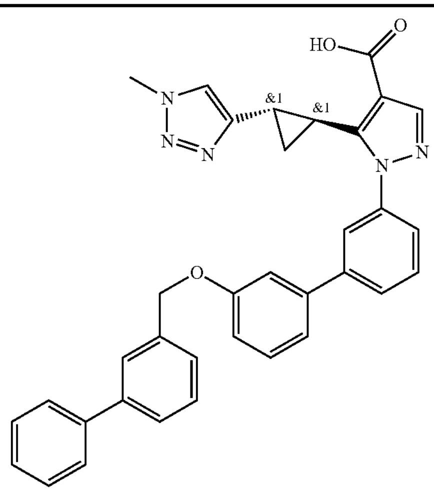 | 1-(3'-([1,1'-Biphenyl]-3-ylmethoxy)-[1,1'-biphenyl]-3-yl)-5-((1,2-trans)-2-(1-methyl-1H-1,2,3-triazol-4-yl)cyclopropyl)-1H-pyrazole-4-carboxylic acid | 567.9 | 3.363 |

Example 239. 1-(3'-(1-([1,1'-Biphenyl]-3-yl)ethoxy)-[1,1'-biphenyl]-3-yl)-5-((1,2-trans)-2-(1-methyl-1H-1,2,3-triazol-4-yl)cyclopropyl)-1H-pyrazole-4-carboxylic Acid

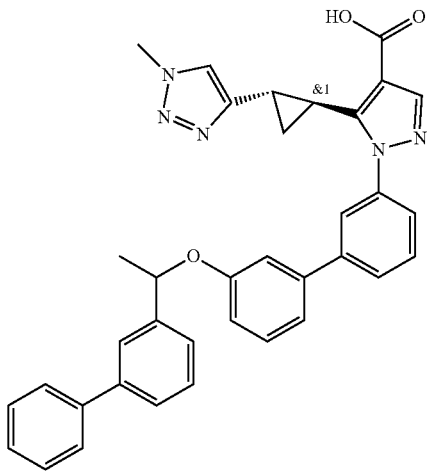 [SMILES: CC(Oc1cccc(-c2cccc(-n3ncc(C(=O)O)c3[C@H]3C[C@@H]3c3cn(C)nn3)c2)c1)c1cccc(-c2ccccc2)c1]

239a) 1-([1,1'-Biphenyl]-3-yl)ethanol

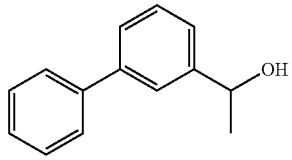

To a solution of 1-([1,1'-biphenyl]-3-yl)ethanone (200 mg, 1.019 mmol) in methanol (10 mL) at ambient temperature was added $NaBH_4$ (38.6 mg, 1.019 mmol) slowly. It was stirred at RT for 5 h. Solvent was evaporated under vacuum. The residue was diluted with water (20 mL) and extracted with DCM (2×20 mL). The combined organic layer was washed with brine solution (20 mL) and dried over anhydrous $Na_2SO_4$, filtered and concentrated to give the title compound (150 mg, 0.741 mmol, 72.7% yield). LCMS m/z 181.06 (M−OH)$^+$, 2.245 min (ret. time).

239b) Ethyl 1-(3'-(1-([1,1'-biphenyl]-3-yl)ethoxy)-[1,1'-biphenyl]-3-yl)-5-((1,2-trans)-2-(1-methyl-1H-1,2,3-triazol-4-yl)cyclopropyl)-1H-pyrazole-4-carboxylate

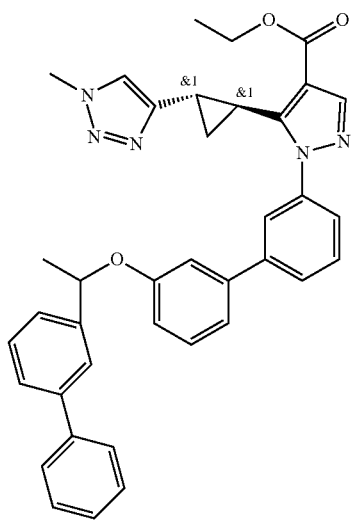 [SMILES: CCOC(=O)c1cnn(-c2cccc(-c3cccc(OC(C)c4cccc(-c5ccccc5)c4)c3)c2)c1[C@H]1C[C@@H]1c1cn(C)nn1]

To a solution of 1-([1,1'-biphenyl]-3-yl)ethanol (55.4 mg, 0.279 mmol), 1-([1,1'-biphenyl]-3-yl)ethanol (55.4 mg, 0.279 mmol) and tributylphosphine (70.7 mg, 0.349 mmol) in tetrahydrofuran (THF) (5 mL) at 10° C. was added (E)-diazene-1,2-diylbis(piperidin-1-ylmethanone) (88 mg, 0.349 mmol) slowly and allowed to stir at ambient temperature for 16 h. The reaction mixture was diluted with water (20 mL) and extracted with DCM (2×20 mL). The combined organic layer was washed with brine solution (20 mL), dried over anhydrous $Na_2SO_4$, filtered and concentrated. The crude residue was purified on flash column chromatography eluting with EtOAc:hexane (5:5). Desired fractions were concentrated to give the title compound (110 mg, 0.137 mmol, 58.8% yield) as an off-white solid. LCMS m/z 610.26 (M+H)$^+$, 7.190 min (ret. time).

239c) 1-(3'-(1-([1,1'-Biphenyl]-3-yl)ethoxy)-[1,1'-biphenyl]-3-yl)-5-((1,2-trans)-2-(1-methyl-1H-1,2,3-triazol-4-yl)cyclopropyl)-1H-pyrazole-4-carboxylic Acid

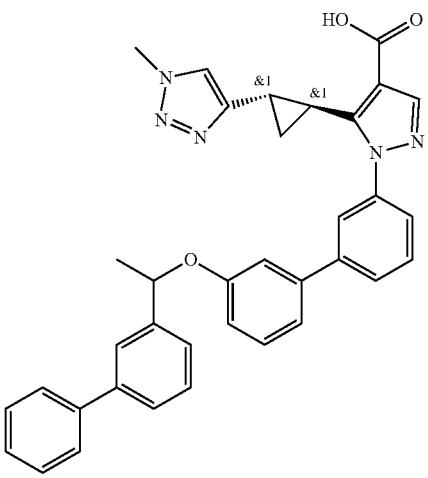 [SMILES: CC(Oc1cccc(-c2cccc(-n3ncc(C(=O)O)c3[C@H]3C[C@@H]3c3cn(C)nn3)c2)c1)c1cccc(-c2ccccc2)c1]

To a solution of ethyl 1-(3'-(1-([1,1'-biphenyl]-3-yl)ethoxy)-[1,1'-biphenyl]-3-yl)-5-((1,2-trans)-2-(1-methyl-1H-1,2,3-triazol-4-yl)cyclopropyl)-1H-pyrazole-4-carboxylate (110 mg, 0.180 mmol) in ethanol (5 mL) at RT was added NaOH (0.180 mL, 0.361 mmol). It was stirred for 6 h. Solvent was concentrated and the residue was diluted with ice water (10 mL), acidified with 1N HCl to pH 2. The obtained white precipitate was filtered, washed with hexane and dried It was purified with Prep HPLC (using 0.1% formic acid as modifier) to give the title compound (41 mg, 0.070 mmol, 57.8% yield) as a white solid. LCMS m/z 582.13 (M+H)$^+$, 2.743 min (ret. time).

The compound in Table 18 were prepared by a method similar to the one described for the preparation of 1-(3'-(1-([1,1'-biphenyl]-3-yl)ethoxy)-[1,1'-biphenyl]-3-yl)-5-((1,2-trans)-2-(1-methyl-1H-1,2,3-triazol-4-yl)cyclopropyl)-1H-pyrazole-4-carboxylic acid. As is appreciated by those skilled in the art, these analogous examples may involve variations in general reaction conditions.

TABLE 7

| Example | Structure | Name | LCMS [M + H]+ | Retention time (min) |
|---|---|---|---|---|
| 240 | 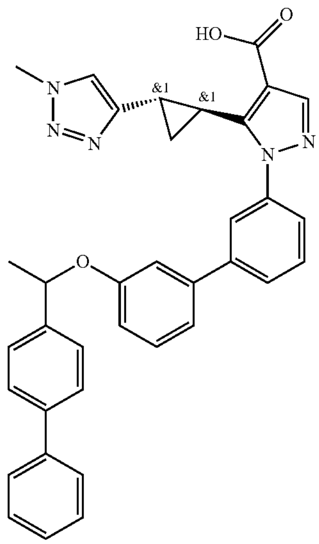 [SMILES: CC(Oc1cccc(-c2cccc(-n3ncc(C(=O)O)c3[C@H]3C[C@@H]3c3cn(C)nn3)c2)c1)c1ccc(-c2ccccc2)cc1] | 1-(3'-(1-([1,1'-Biphenyl]-4-yl)ethoxy)-[1,1'-biphenyl]-3-yl)-5-((1,2-trans)-2-(1-methyl-1H-1,2,3-triazol-4-yl)cyclopropyl)-1H-pyrazole-4-carboxylic acid | 582.30 | 2.775 |

Example 241. 1-(4'-(1-Cyclohexylethoxy)-[1,1'-biphenyl]-3-yl)-5-((1,2-trans)-2-(1-methyl-1H-1,2,3-triazol-4-yl)cyclopropyl)-1H-pyrazole-4-carboxylic Acid

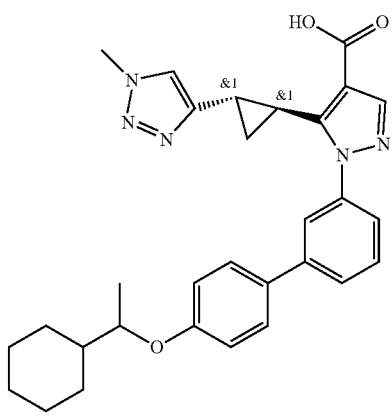 [SMILES: CC(Oc1ccc(-c2cccc(-n3ncc(C(=O)O)c3[C@H]3C[C@@H]3c3cn(C)nn3)c2)cc1)C1CCCCC1]

241a) 1-Cyclohexylethyl methanesulfonate

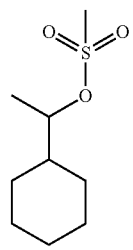

To a solution of 1-cyclohexylethanol (200 mg, 1.560 mmol) and TEA (0.435 mL, 3.12 mmol) in dichloromethane (DCM) (10 mL) at 0° C. was added methanesulfonyl chloride (0.182 mL, 2.340 mmol) and stirred for 2 h. The reaction mixture was diluted with saturated NaHCO$_3$ solution (20 mL) and extracted with DCM (2×20 mL). The combined organic layer was washed with brine solution (10 mL) and dried over anhydrous Na$_2$SO$_4$, filtered and concentrated to give the title compound (200 mg, 0.969 mmol, 62.1% yield). $^1$H NMR (400 MHz, chloroform-d) δ ppm: 1.00-1.30 (m, 5H), 1.39 (d, J=6.36 Hz, 3H) 1.52-1.56 (m, 1H) 1.64-1.87 (m, 5H) 2.99 (s, 3H) 4.60 (quin, J=6.25 Hz, 1H).

241b) Ethyl 1-(4'-(1-cyclohexylethoxy)-[1,1'-biphenyl]-3-yl)-5-((1,2-trans)-2-(1-methyl-1H-1,2,3-triazol-4-yl)cyclopropyl)-1H-pyrazole-4-carboxylate

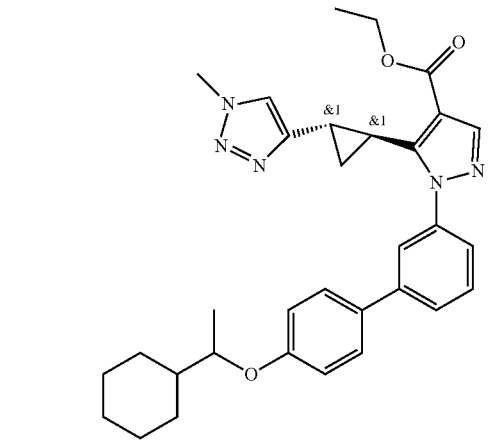 [SMILES: CCOC(=O)c1cnn(-c2cccc(-c3ccc(OC(C)C4CCCCC4)cc3)c2)c1[C@H]1C[C@@H]1c1cn(C)nn1]

To a solution of ethyl 1-(4'-hydroxy-[1,1'-biphenyl]-3-yl)-5-((1,2-trans)-2-(1-methyl-1H-1,2,3-triazol-4-yl)cyclopropyl)-1H-pyrazole-4-carboxylate (200 mg, 0.466 mmol), 1-cyclohexylethyl methanesulfonate (144 mg, 0.699 mmol) in N,N-dimethylformamide (DMF) (2 mL) at RT was added K$_2$CO$_3$ (129 mg, 0.931 mmol). It was stirred at 100° C. for 12 h. The reaction mixture was cooled to RT and diluted with water (20 mL) and extracted with EtOAc (2×20 mL). The combined organic layer was washed with brine solution (20 mL) and dried over anhydrous Na$_2$SO$_4$, filtered and concentrated. The crude residue was purified on flash column chromatography eluting with EtOAc:Hexane (5:5). Desired fractions were concentrated to give the title compound (130 mg, 0.216 mmol, 46.5% yield) as white solid. LCMS m/z 540.26 (M+H)$^+$, 4.187 min (ret. time).

241c) 1-(4'-(1-Cyclohexylethoxy)-[1,1'-biphenyl]-3-yl)-5-((1,2-trans)-2-(1-methyl-1H-1,2,3-triazol-4-yl)cyclopropyl)-1H-pyrazole-4-carboxylic Acid

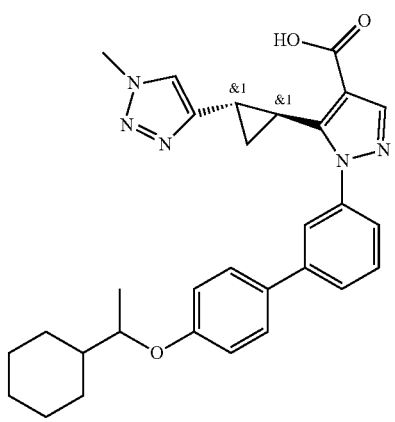 [SMILES: CC(Oc1ccc(-c2cccc(-n3ncc(C(=O)O)c3[C@H]3C[C@@H]3c3cn(C)nn3)c2)cc1)C1CCCCC1]

To a solution of ethyl 1-(4'-(1-cyclohexylethoxy)-[1,1'-biphenyl]-3-yl)-5-((1,2-trans)-2-(1-methyl-1H-1,2,3-triazol-4-yl)cyclopropyl)-1H-pyrazole-4-carboxylate (130 mg, 0.241 mmol) in ethanol (1 mL) at RT was added NaOH (0.602 mL, 1.204 mmol). It was stirred for 10 h. The reaction mixture was diluted with ice water (10 mL) and acidified with 2 N HCl solution to pH 3. Solid was filtered and washed with diethyl ether and hexane to give the title compound (53 mg, 0.099 mmol, 41.1% yield) as a white solid. LCMS m/z 512.18 (M+H)$^+$, 2.847 min (ret. time)

The compound in Table 19 were prepared by a method similar to the one described for the preparation of 1-(4'-(1-Cyclohexylethoxy)-[1,1'-biphenyl]-3-yl)-5-((1,2-trans)-2-(1-methyl-1H-1,2,3-triazol-4-yl)cyclopropyl)-1H-pyrazole-4-carboxylic. As is appreciated by those skilled in the art, these analogous examples may involve variations in general reaction conditions.

TABLE 19

| Example | Structure | Name | LCMS [M + H]$^+$ | Retention time (min) |
|---|---|---|---|---|
| 242 | 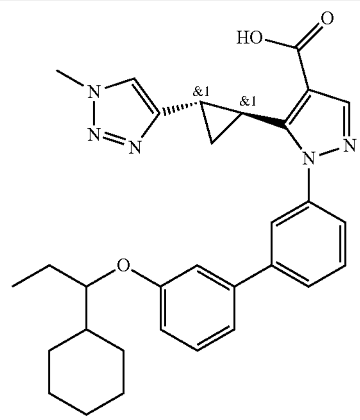 [SMILES: CCC(Oc1cccc(-c2cccc(-n3ncc(C(=O)O)c3[C@H]3C[C@@H]3c3cn(C)nn3)c2)c1)C1CCCCC1] | 1-(3'-(1-Cyclohexylpropoxy)-[1,1'-biphenyl]-3-yl)-5-((1,2-trans)-2-(1-methyl-1H-1,2,3-triazol-4-yl)cyclopropyl)-1H-pyrazole-4-carboxylic acid | 526.26 | 2.952 |

242a) 1-Cyclohexylpropan-1-ol

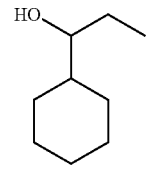

To a solution of cyclohexanecarbaldehyde (500 mg, 4.46 mmol) in tetrahydrofuran (THF) (20 mL) at −40° C. was added ethylmagnesium bromide (4.46 mL, 6.69 mmol) slowly for 1 h. The reaction mixture was quenched with ammonium chloride solution (20 mL) and extracted with EtOAc (2×10 mL). The combined organic layer was washed with brine solution (20 mL) and dried over anhydrous Na$_2$SO$_4$, filtered and concentrated to give the title compound (300 mg, 2.109 mmol, 47.3% yield) as color less liquid. $^1$H NMR (400 MHz, chloroform-d) δ ppm: 0.85 (t, J=7.56 Hz, 3H) 1.01-1.31 (m, 5H) 1.31-1.60 (m, 2H) 1.60-1.85 (m, 6H) 3.28 (br s, 1H) 3.44 (br d, J=6.36 Hz, 1H).

242b) 1-Cyclohexylpropyl methanesulfonate

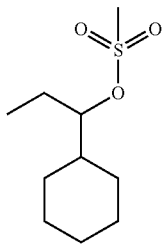

To a solution of 1-cyclohexylpropan-1-ol (200 mg, 1.406 mmol) and TEA (0.392 mL, 2.81 mmol) in dichloromethane (DCM) (10 mL) at 0° C. was added methanesulfonyl chloride (0.164 mL, 2.109 mmol). It was stirred for 2 h. The reaction mixture was diluted with saturated NaHCO$_3$ (20 mL) and extracted with DCM (2×20 mL). The combined organic layer was washed with brine solution (10 mL) and dried over anhydrous Na$_2$SO$_4$, filtered and concentrated to give the title compound (200 mg, 0.908 mmol, 64.6% yield). $^1$H NMR (400 MHz, chloroform-d) δ ppm: 0.97 (t, J=7.45 Hz, 3H) 1.04 (br d, J=10.74 Hz, 2H) 1.07-1.07 (m, 1H) 1.07-1.28 (m, 2H) 1.37-1.59 (m, 2H) 1.64-1.81 (m, 6H) 2.98 (s, 3H) 4.43-4.52 (m, 1H).

Example 243. 1-(3'-(Cyclohexanecarbonyl)-[1,1'-biphenyl]-3-yl)-5-(2-(1-methyl-1H-1,2,3-triazol-4-yl)cyclopropyl)-1H-pyrazole-4-carboxylic Acid

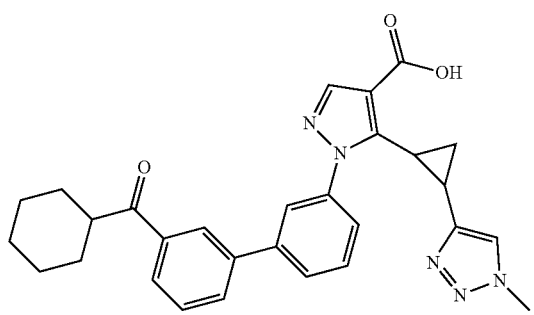 [SMILES: Cn1cc(C2CC2c2c(C(=O)O)cnn2-c2cccc(-c3cccc(C(=O)C4CCCCC4)c3)c2)nn1]

243a) (3-Bromophenyl)(cyclohexyl)methanol

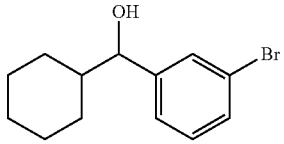 [SMILES: OC(c1cccc(Br)c1)C1CCCCC1]

To a solution of magnesium (0.298 g, 12.27 mmol) in dry tetrahydrofuran (THF) (20 mL), was added iodine (0.156 g, 0.613 mmol), and bromocyclohexane (2 g, 12.27 mmol) in tetrahydrofuran (THF) (20 mL). It was reflux for 3 h. The reaction mixture was added to a solution of 3-bromobenzaldehyde (2.269 g, 12.27 mmol) in tetrahydrofuran (THF) (20 mL) and stirred at RT for 16 h. The reaction mixture was quenched with ammonium chloride solution (100 mL), and extracted with ethyl acetate (2×200 mL). The combined organic layer was washed with water (100 mL), brine (50 mL) and concentrated. The crude residue was purified on flash column chromatography eluting with 1.5% ethyl acetate in hexane. Desired fractions were concentrated to give the title compound (1.2 g, 2.93 mmol, 23.90% yield) as colorless oil. $^1$H NMR (DMSO-d6, 400 MHz): δ 7.41 (s, 1H), 7.36 (br dd, J=5.6, 2.1 Hz, 1H), 7.12-7.25 (m, 2H), 5.13 (d, J=4.4 Hz, 1H), 4.17-4.26 (m, 1H), 1.72 (br d, J=12.7 Hz, 1H), 1.44-1.64 (m, 3H), 1.17-1.42 (m, 2H), 0.98-1.14 (m, 3H), 0.85-0.96 ppm (m, 2H).

243b) (3-Bromophenyl)(cyclohexyl)methanone

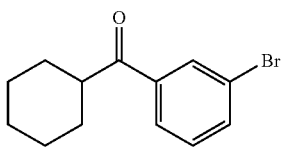 [SMILES: O=C(c1cccc(Br)c1)C1CCCCC1]

To a solution of (3-bromophenyl)(cyclohexyl)methanol (100 mg, 0.372 mmol) in dichloromethane (DCM) (20 mL) at 20° C. was added Dess-Martin periodinane (158 mg, 0.372 mmol). It was stirred for 5 h. The reaction mixture was filtered through celite pad and the filtrate was concentrated. The crude product was purified on flash column chromatography eluting with EtOAC:hexane (0.5:9.5). Desired fractions were concentrated to give the title compound (50 mg, 0.187 mmol, 50.4% yield). $^1$H NMR (CDCl$_3$, 400 MHz): δ 8.05 (t, J=1.6 Hz, 1H), 7.85 (d, J=7.9 Hz, 1H), 7.67 (dd, J=7.9, 0.9 Hz, 1H), 7.34 (t, J=7.8 Hz, 1H), 3.19 (tt, J=11.1, 3.2 Hz, 1H), 1.80-1.94 (m, 4H), 1.64-1.78 (m, 1H), 1.21-1.57 ppm (m, 5H).

243c) Ethyl 1-(3'-(cyclohexanecarbonyl)-[1,1'-biphenyl]-3-yl)-5-(2-(1-methyl-1H-1,2,3-triazol-4-yl)cyclopropyl)-1H-pyrazole-4-carboxylate

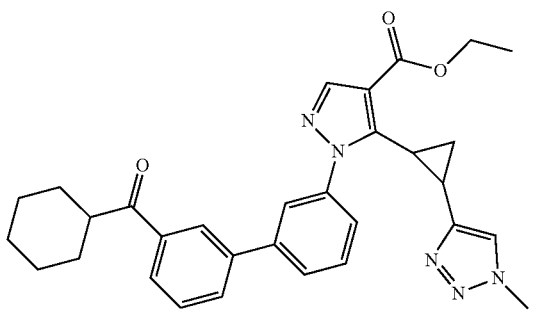 [SMILES: CCOC(=O)c1cnn(-c2cccc(-c3cccc(C(=O)C4CCCCC4)c3)c2)c1C1CC1c1cn(C)nn1]

To a solution of ethyl 5-(2-(1-methyl-1H-1,2,3-triazol-4-yl)cyclopropyl)-1-(3-(4,4,5,5-tetramethyl-1,3,2-dioxaborolan-2-yl)phenyl)-1H-pyrazole-4-carboxylate (113 mg, 0.243 mmol) in tetrahydrofuran (THF) (10 mL) and water (2 mL) was added sodium carbonate (19.84 mg, 0.187 mmol), (3-bromophenyl)(cyclohexyl)methanone (50 mg, 0.187 mmol) and purged with nitrogen for 10 min. Pd(Ph$_3$P)$_4$ (21.63 mg, 0.019 mmol) was added and purged with nitrogen. It was heated at 70° C. for 5 h. The reaction mixture was diluted with ice water and extracted with EtOAc. The combined organic layer was washed with brine solution and dried over anhydrous Na₂SO₄, filtered and concentrated. The crude residue was purified on flash column chromatography eluting with EtOAc:Hexane (5:5). Desired fractions were concentrated to give the title compound (50 mg, 0.055 mmol, 29.2% yield). LC-MS m/z 524.1.9 (M+H)$^+$, 4.090 min (ret. time).

243d) 1-(3'-(Cyclohexanecarbonyl)-[1,1'-biphenyl]-3-yl)-5-(2-(1-methyl-1H-1,2,3-triazol-4-yl)cyclopropyl)-1H-pyrazole-4-carboxylic Acid

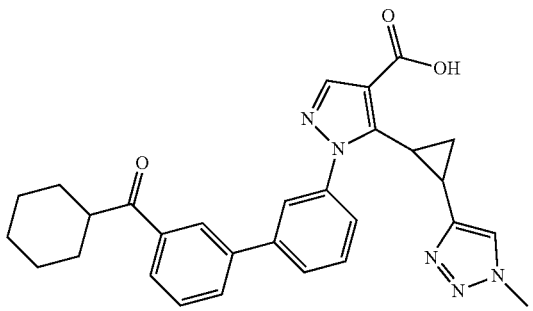 [SMILES: Cn1cc(C2CC2c2c(C(=O)O)cnn2-c2cccc(-c3cccc(C(=O)C4CCCCC4)c3)c2)nn1]

To a solution of ethyl 1-(3'-(cyclohexanecarbonyl)-[1,1'-biphenyl]-3-yl)-5-(2-(1-methyl-1H-1,2,3-triazol-4-yl)cyclopropyl)-1H-pyrazole-4-carboxylate (50 mg, 0.095 mmol) in ethanol (5 mL) was added NaOH (0.048 mL, 0.095 mmol) and the reaction mixture was stirred at 25° C. for 3 h. It was concentrated and the residue was diluted with ice water, acidified with 1 N HCl solution to pH 3. The obtained solid was filtered and washed with water and dried. It was purified with Prep HPLC (0.1% formic acid as modifier) to give the title compound (51 mg, 0.102 mmol, 45.8% yield) as a white solid. LC-MS m/z 496.26 (M+H)$^+$, 2.46 min (ret. time).

The compounds in Table 20 were prepared by a method similar to the one described for the preparation of 1-(3'-(cyclohexanecarbonyl)-[1,1'-biphenyl]-3-yl)-5-(2-(1-methyl-1H-1,2,3-triazol-4-yl)cyclopropyl)-1H-pyrazole-4-carboxylic acid. As is appreciated by those skilled in the art, these analogous examples may involve variations in general reaction conditions.

244a)
1-Bromo-3-(cyclohexyl(methoxy)methyl)benzene

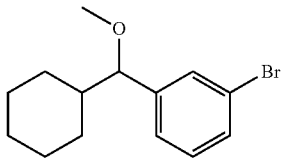 [SMILES: COC(c1cccc(Br)c1)C1CCCCC1]

To a solution of (3-bromophenyl)(cyclohexyl)methanol (100 mg, 0.372 mmol) in N,N-dimethylformamide (DMF) (2 mL) at 0° C. was added NaH (8.92 mg, 0.372 mmol). The reaction was stirred at same temperature for 1 h. At the same temperature was added MeI (0.023 mL, 0.372 mmol) dropwise and the reaction mixture was allowed to stir at ambient temperature for 1 h. The reaction mixture was diluted with ice water and extracted with EtOAc. The organic layer was washed with brine solution and dried over anhydrous Na₂SO₄, filtered and concentrated to give the title compound (80 mg, 0.282 mmol, 76% yield). $^1$H NMR (CDCl₃, 400 MHz) δ: 7.33-7.44 (m, 2H), 7.18 (dt, J=14.0, 7.7 Hz, 2H), 3.75 (d, J=7.2 Hz, 1H), 3.19 (S, 3H), 1.97 (br d, J=12.9 Hz, 1H), 1.63-1.78 (m, 1H), 1.03-1.36 (m, 5H), 0.80-1.02 ppm (m, 4H).

Example 245. 1-(3'-(2-cyclohexylethoxy)-[1,1'-biphenyl]-3-yl)-5-(trans-2-(1-methyl-1H-1,2,3-triazol-4-yl)cyclopropyl)-1H-pyrazole-4-carboxylic Acid

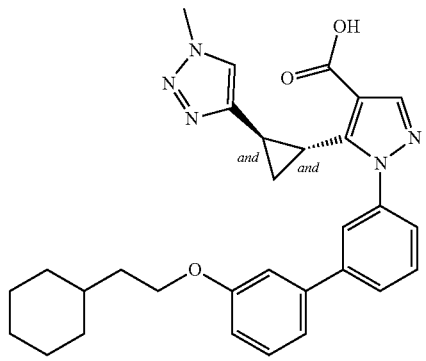 [SMILES: Cn1cc([C@@H]2C[C@H]2c2c(C(=O)O)cnn2-c2cccc(-c3cccc(OCCC4CCCCC4)c3)c2)nn1]

TABLE 20

| Example | Structure | Name | LCMS [M + H]$^+$ | Retention time (min) |
|---|---|---|---|---|
| 244 | 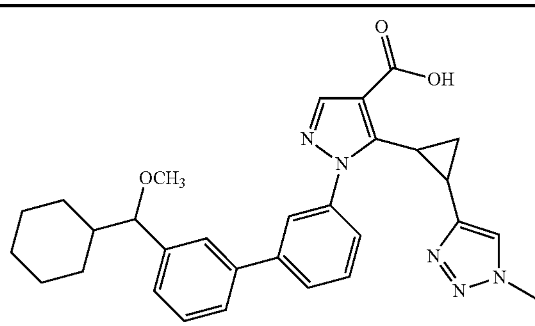 | 1-(3'-(Cyclohexyl(methoxy)methyl)-[1,1'-biphenyl]-3-yl)-5-(2-(1-methyl-1H-1,2,3-triazol-4-yl)cyclopropyl)-1H-pyrazole-4-carboxylic acid | 512.32 | 2.73 |

245a) Methyl 1-(3'-(2-cyclohexylethoxy)-[1,1'-biphenyl]-3-yl)-5-(trans-2-(1-methyl-1H-1,2,3-triazol-4-yl)cyclopropyl)-1H-pyrazole-4-carboxylate

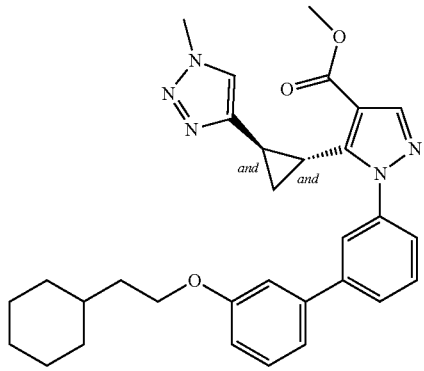 [SMILES: COC(=O)c1cnn(-c2cccc(-c3cccc(OCCC4CCCCC4)c3)c2)c1[C@@H]1C[C@H]1c1cn(C)nn1]

To a solution of methyl 1-(3'-hydroxy-[1,1'-biphenyl]-3-yl)-5-(trans-2-(1-methyl-1H-1,2,3-triazol-4-yl)cyclopropyl)-1H-pyrazole-4-carboxylate (108 mg, 0.260 mmol) in tetrahydrofuran (THF) (10 mL), 2-cyclohexylethanol (0.073 mL, 0.520 mmol), DIAD (0.101 mL, 0.520 mmol) and triphenylphosphine (136 mg, 0.520 mmol) were added at room temperature under nitrogen. The reaction was stirred for 18 h at room temperature. The solvent was evaporated and the crude residue was purified by silica gel chromatography to afford the title compound (130 mg, 0.247 mmol, 95% yield). LC-MS m/z 526.5 (M+H)+, 1.39 min (ret. time).

245b) 1-(3'-(2-Cyclohexylethoxy)-[1,1'-biphenyl]-3-yl)-5-(trans-2-(1-methyl-1H-1,2,3-triazol-4-yl)cyclopropyl)-1H-pyrazole-4-carboxylic Acid

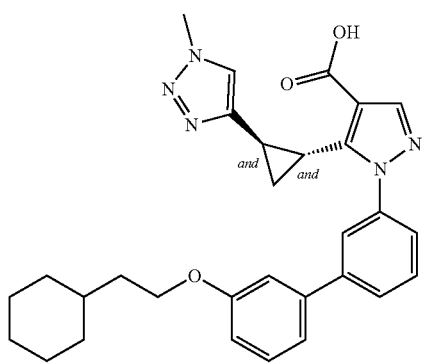 [SMILES: Cn1cc([C@@H]2C[C@H]2c2c(C(=O)O)cnn2-c2cccc(-c3cccc(OCCC4CCCCC4)c3)c2)nn1]

To a solution of methyl 1-(3'-(2-cyclohexylethoxy)-[1,1'-biphenyl]-3-yl)-5-(trans-2-(1-methyl-1H-1,2,3-triazol-4-yl)cyclopropyl)-1H-pyrazole-4-carboxylate (130 mg, 0.247 mmol) in methanol (3.0 mL) and water (0.3 mL) was added LiOH (130 mg, 5.43 mmol). The reaction was stirred for 80 h at room temperature. The reaction mixture was acidified with 1N aqueous HCl to pH=2. The solvent was removed in vacuo. The crude residue was purified by using Gilson HPLC under neutral condition to the title compound (71 mg, 0.139 mmol, 56.1% yield). LC-MS m/z 512.1 (M+H)+, 1.36 min (ret. time).

Example 246. 1-(3-(5-(Cyclohexylmethoxy)pyridin-3-yl)phenyl)-5-(trans-2-(1-methyl-1H-1,2,3-triazol-4-yl)cyclopropyl)-1H-pyrazole-4-carboxylic Acid

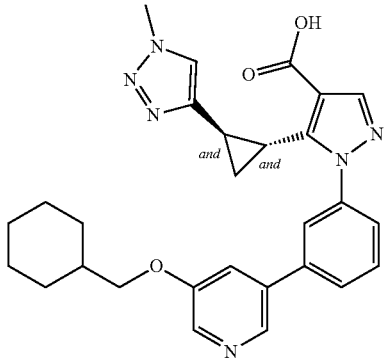 [SMILES: Cn1cc([C@@H]2C[C@H]2c2c(C(=O)O)cnn2-c2cccc(-c3cncc(OCC4CCCCC4)c3)c2)nn1]

246a) 3-Bromo-5-(cyclohexylmethoxy)pyridine

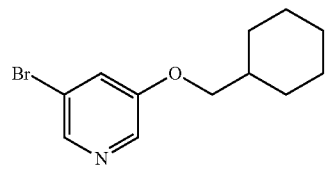 [SMILES: Brc1cncc(OCC2CCCCC2)c1]

To a solution of 5-bromopyridin-3-ol (400 mg, 2.299 mmol) in tetrahydrofuran (THF) (10 mL), cyclohexylmethanol (0.57 mL, 4.60 mmol), DIAD (0.89 mL, 4.60 mmol) and triphenylphosphine (120.6 mg, 4.60 mmol) were added at 25° C. under nitrogen. The reaction was stirred for 20 h at room temperature. The solvent was evaporated and the crude residue was purified by silica gel chromatography (hexanes/EtOAc) to afford 3-bromo-5-(cyclohexylmethoxy)pyridine (0.3692 g, 1.367 mmol, 59.4% yield). LC-MS m/z 269.8/271.8 (M+H)+, 1.27 min (ret. time).

246b) 1-(3-(5-(Cyclohexylmethoxy)pyridin-3-yl)phenyl)-5-(trans-2-(1-methyl-1H-1,2,3-triazol-4-yl)cyclopropyl)-1H-pyrazole-4-carboxylic Acid

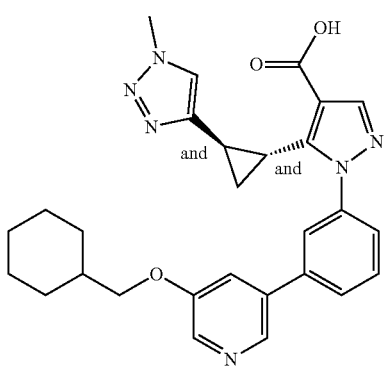 [SMILES: Cn1cc([C@@H]2C[C@H]2c2c(C(=O)O)cnn2-c2cccc(-c3cncc(OCC4CCCCC4)c3)c2)nn1]

To a solution of ethyl 5-(trans-2-(1-methyl-1H-1,2,3-triazol-4-yl)cyclopropyl)-1-(3-(4,4,5,5-tetramethyl-1,3,2-dioxaborolan-2-yl)phenyl)-1H-pyrazole-4-carboxylate (150 mg, 0.324 mmol) in a mixture of 1,4-dioxane (3.0 mL) and water (1.0 mL), 3-bromo-5-(cyclohexylmethoxy)pyridine (96 mg, 0.356 mmol), K₂CO₃ (134 mg, 0.971 mmol) were added. PdCl₂(dppf) (23.7 mg, 0.032 mmol) was then added. The reaction mixture was heated to 120° C. for 20 mins under microwave irradiation. The reaction mixture was extracted with EtOAc, dried with magnesium sulfate, filtered, and the solvent was evaporated by rotary evaporator. The crude residue was diluted with methanol (2.0 mL). LiOH (78 mg, 3.24 mmol) was added along with 10 drops of water to this solution. The reaction mixture was stirred for 16 h at room temperature. The reaction mixture was acidified with 1.0 N aqueous HCl to pH=2. The solvent was evaporated and the crude residue was purified using Gilson HPLC under neutral condition to afford the title compound (16 mg, 0.032 mmol, 9.91% yield). LC-MS m/z 499.5 (M+H)⁺, 0.89 min (ret. time).

Example 247. 5-(trans-2-(1-Methyl-1H-1,2,3-triazol-4-yl)cyclopropyl)-1-(3'-(piperidin-1-ylmethyl)-[1,1'-biphenyl]-3-yl)-1H-pyrazole-4-carboxylic Acid

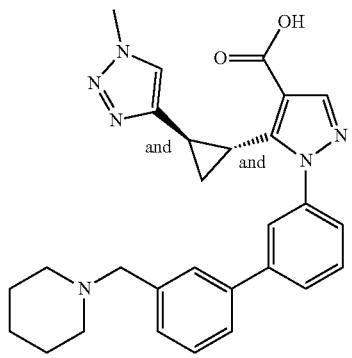 [SMILES: Cn1cc([C@@H]2C[C@H]2c2c(C(=O)O)cnn2-c2cccc(-c3cccc(CN4CCCCC4)c3)c2)nn1]

247a) Methyl 5-(trans-2-(1-methyl-1H-1,2,3-triazol-4-yl)cyclopropyl)-1-(3-(4,4,5,5-tetramethyl-1,3,2-dioxaborolan-2-yl)phenyl)-1H-pyrazole-4-carboxylate and ethyl 5-(trans-2-(1-methyl-1H-1,2,3-triazol-4-yl)cyclopropyl)-1-(3-(4,4,5,5-tetramethyl-1,3,2-dioxaborolan-2-yl)phenyl)-1H-pyrazole-4-carboxylate

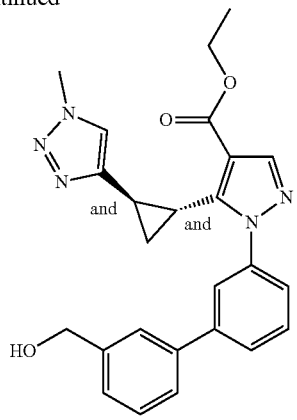

To a solution of methyl 5-(trans-2-(1-methyl-1H-1,2,3-triazol-4-yl)cyclopropyl)-1-(3-(4,4,5,5-tetramethyl-1,3,2-dioxaborolan-2-yl)phenyl)-1H-pyrazole-4-carboxylate (820 mg, 1.825 mmol) and ethyl 5-(2-(1-methyl-1H-1,2,3-triazol-4-yl)cyclopropyl)-1-(3-(4,4,5,5-tetramethyl-1,3,2-dioxaborolan-2-yl)phenyl)-1H-pyrazole-4-carboxylate (180 mg, 0.390 mmol) in 1,4-dioxane (9.0 mL) and water (3.0 mL), (3-bromophenyl)methanol (0.534 mL, 4.45 mmol) and potassium acetate (874 mg, 8.90 mmol) was added. The reaction mixture was degassed for 2 mins. PdCl₂(dppf) (163 mg, 0.223 mmol) was added. The reaction mixture was heated to 120° C. for 20 mins under microwave irradiation. The reaction mixture was cooled to room temperature and extracted with EtOAc. The organic layers were dried with magnesium sulfate, filtered, and the solvent was removed in vacuo. The crude residue was purified by silica gel chromatography (gradient EtOAc/hexanes, product eluted with 100% EtOAc) to afford the products as a mixture of methyl and ethyl esters that were carried to the next step without separation (704 mg). LC-MS m/z 430.1 (M+H)⁺, 0.84 min (ret. time) and LC-MS m/z 444.1 (M+H)⁺, 0.89 min (ret. time).

247b) Methyl 1-(3'-(chloromethyl)-[1,1'-biphenyl]-3-yl)-5-(trans-2-(1-methyl-1H-1,2,3-triazol-4-yl)cyclopropyl)-1H-pyrazole-4-carboxylate and ethyl 1-(3'-(chloromethyl)-[1,1'-biphenyl]-3-yl)-5-(trans-2-(1-methyl-1H-1,2,3-triazol-4-yl)cyclopropyl)-1H-pyrazole-4-carboxylate

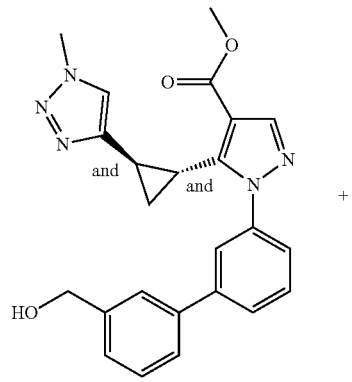 +

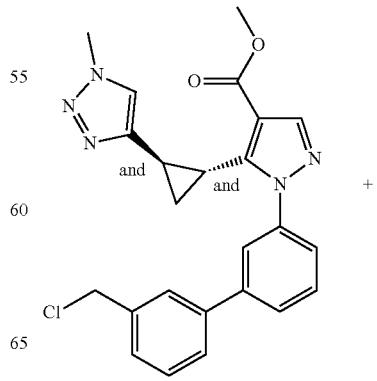 +

-continued

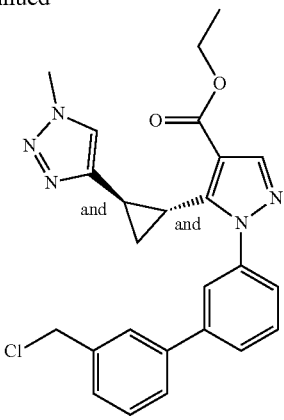

To a solution of a mixture of methyl 1-(3'-(hydroxymethyl)-[1,1'-biphenyl]-3-yl)-5-(trans-2-(1-methyl-1H-1,2,3-triazol-4-yl)cyclopropyl)-1H-pyrazole-4-carboxylate and methyl 1-(3'-(hydroxymethyl)-[1,1'-biphenyl]-3-yl)-5-(trans-2-(1-methyl-1H-1,2,3-triazol-4-yl)cyclopropyl)-1H-pyrazole-4-carboxylate from Example 247a (704 mg, about a 2:1 mixture by UV detection) in dichloromethane (20 mL), thionyl chloride (0.24 mL, 3.28 mmol) was added. The reaction mixture was stirred at room temperature for 1.5 h. The solvent was evaporated and the crude material (100 mg) was carried to next step without further purification. LC-MS m/z 448.1 (M+H)$^+$, 1.09 min (ret. time) and LC-MS m/z 462.1 (M+H)$^+$, 1.14 min (ret. time).

247c) Methyl 5-(trans-2-(1-methyl-1H-1,2,3-triazol-4-yl)cyclopropyl)-1-(3'-(piperidin-1-ylmethyl)-[1,1'-biphenyl]-3-yl)-1H-pyrazole-4-carboxylate and ethyl 5-(trans-2-(1-methyl-1H-1,2,3-triazol-4-yl)cyclopropyl)-1-(3'-(piperidin-1-ylmethyl)-[1,1'-biphenyl]-3-yl)-1H-pyrazole-4-carboxylate

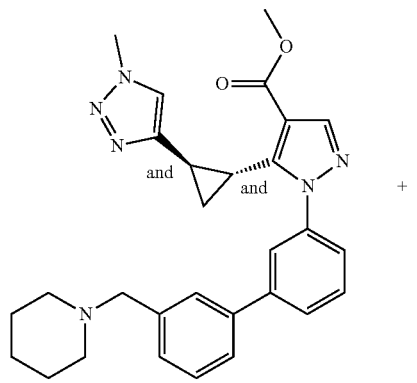

+

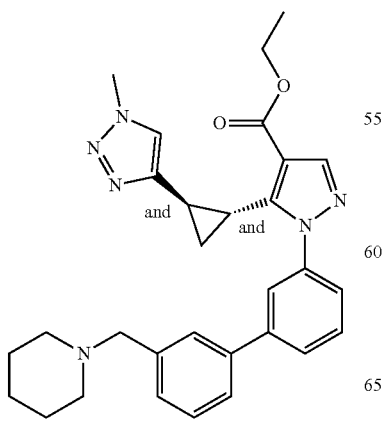

To a solution of a mixture of methyl- and ethyl 1-(3'-(chloromethyl)-[1,1'-biphenyl]-3-yl)-5-(trans-2-(1-methyl-1H-1,2,3-triazol-4-yl)cyclopropyl)-1H-pyrazole-4-carboxylate from Example 165b (100 mg, about a 2:1 mixture by UV detection) in N,N-dimethylformamide (DMF) (2 mL), piperidine (0.033 mL, 0.335 mmol) and potassium carbonate (93 mg, 0.670 mmol) were added. The reaction mixture was heated to 80° C. for 2 h. The reaction mixture was cooled room temperature and extracted with EtOAc, dried with magnesium sulfate, filtered, and the solvent was evaporated by rotary evaporator. The crude material (100 mg) was carried to the next step without any further purification. LC-MS m/z 497.1 (M+H)$^+$, 0.80 min (ret. time) and LC-MS m/z 511.2 (M+H)$^+$, 0.88 min (ret. time).

247d) 5-(trans-2-(1-Methyl-1H-1,2,3-triazol-4-yl)cyclopropyl)-1-(3'-(piperidin-1-ylmethyl)-[1,1'-biphenyl]-3-yl)-1H-pyrazole-4-carboxylic Acid

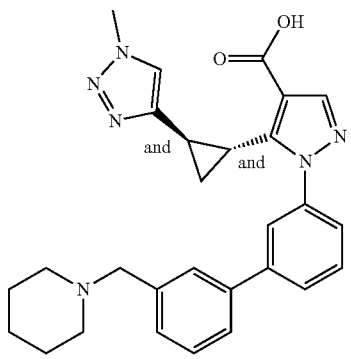 [SMILES: Cn1cc([C@@H]2C[C@H]2c2c(C(=O)O)cnn2-c2cccc(-c3cccc(CN4CCCCC4)c3)c2)nn1]

To a solution of a mixture of ethyl- and methyl 5-(trans-2-(1-methyl-1H-1,2,3-triazol-4-yl)cyclopropyl)-1-(3'-(piperidin-1-ylmethyl)-[1,1'-biphenyl]-3-yl)-1H-pyrazole-4-carboxylate from Example 247c (100 mg) in methanol (2.0 mL) and water (0.2 mL), LiOH (120 mg, 5.01 mmol) was added at room temperature. The reaction was stirred for 18 h at room temperature. The reaction mixture was acidified with 1.0 N aqueous HCl to pH=2. The solvent was evaporated using a Biotage V-10 evaporator. The concentrated crude residue was purified by using Gilson HPLC under neutral condition to afford the title compound (12 mg, 0.025 mmol, 12.35% yield). LC-MS m/z 483.1 (M+H)$^+$, 0.68 min (ret. time).

Example 248. 5-(trans-2-(1-Methyl-1H-1,2,3-triazol-4-yl)cyclopropyl)-1-(3'-(morpholinomethyl)-[1,1'-biphenyl]-3-yl)-1H-pyrazole-4-carboxylic Acid

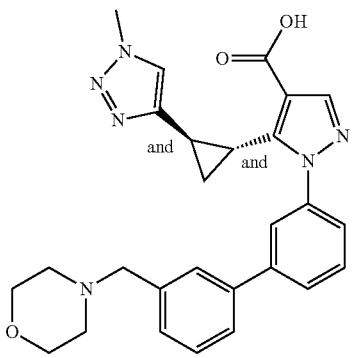 [SMILES: Cn1cc([C@@H]2C[C@H]2c2c(C(=O)O)cnn2-c2cccc(-c3cccc(CN4CCOCC4)c3)c2)nn1]

248a) Methyl 5-(trans-2-(1-methyl-1H-1,2,3-triazol-4-yl)cyclopropyl)-1-(3'-(morpholinomethyl)-[1,1'-biphenyl]-3-yl)-1H-pyrazole-4-carboxylate and ethyl 5-(trans-2-(1-methyl-1H-1,2,3-triazol-4-yl)cyclopropyl)-1-(3'-(morpholinomethyl)-[1,1'-biphenyl]-3-yl)-1H-pyrazole-4-carboxylate 248b) 5-(trans-2-(1-Methyl-1H-1,2,3-triazol-4-yl)cyclopropyl)-1-(3'-(morpholinomethyl)-[1,1'-biphenyl]-3-yl)-1H-pyrazole-4-carboxylic Acid

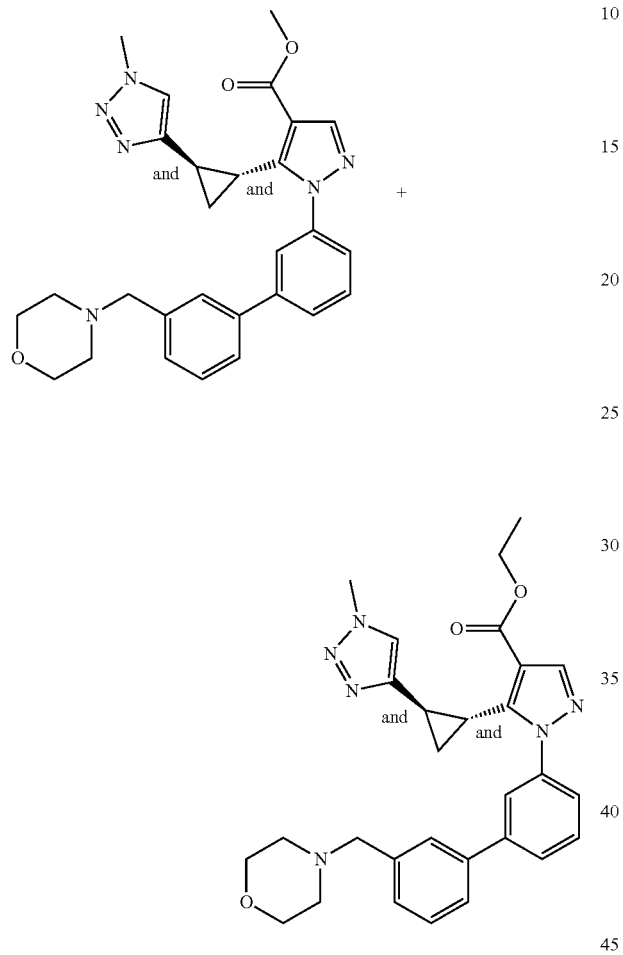

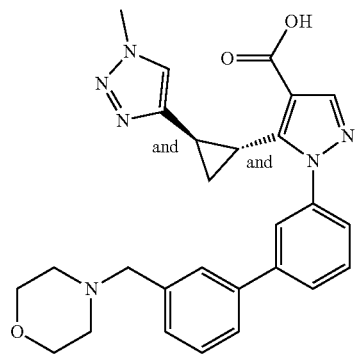 [SMILES: Cn1cc([C@@H]2C[C@H]2c2c(C(=O)O)cnn2-c2cccc(-c3cccc(CN4CCOCC4)c3)c2)nn1]

To a solution of a mixture of ethyl- and methyl 5-(trans-2-(1-methyl-1H-1,2,3-triazol-4-yl)cyclopropyl)-1-(3'-(piperidin-1-ylmethyl)-[1,1'-biphenyl]-3-yl)-1H-pyrazole-4-carboxylate from Example 166a (100 mg) in methanol (2 mL) and water (0.2 mL), LiOH (96 mg, 4.01 mmol) was added at room temperature. The reaction was stirred for 18 h at room temperature. Excess LiOH was added and the reaction was stirred at room temperature for 80 h. The reaction mixture was acidified with 1.0 N aqueous HCl to pH=2. The solvent was evaporated using a Biotage V-10 evaporator. The concentrated crude residue was purified by using Gilson HPLC under neutral condition to afford the title compound (14.3 mg, 0.030 mmol, 14.71% yield). LC-MS m/z 485.1 (M+H)⁺, 0.64 min (ret. time).

Example 249. 1-(6-(3-(1-Cyclohexylethoxy)phenyl)pyridin-2-yl)-5-(trans-2-(1-methyl-1H-1,2,3-triazol-4-yl)cyclopropyl)-1H-pyrazole-4-carboxylic Acid
249a) rac-Methyl 1-(6-(3-hydroxyphenyl)pyridin-2-yl)-5-((1R,2R)-2-(1-methyl-1H-1,2,3-triazol-4-yl)cyclopropyl)-1H-pyrazole-4-carboxylate

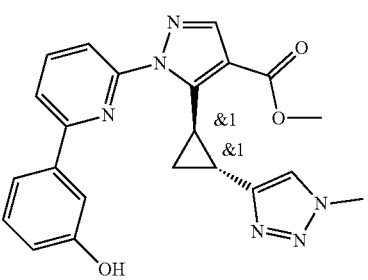 [SMILES: COC(=O)c1cnn(-c2cccc(-c3cccc(O)c3)n2)c1[C@@H]1C[C@H]1c1cn(C)nn1]

To a solution of a mixture of methyl- and ethyl 1-(3'-(chloromethyl)-[1,1'-biphenyl]-3-yl)-5-(trans-2-(1-methyl-1H-1,2,3-triazol-4-yl)cyclopropyl)-1H-pyrazole-4-carboxylate from Example 165b (97 mg, about a 2:1 mixture by UV detection) in N,N-dimethylformamide (DMF) (2 mL), morpholine (0.028 mL, 0.325 mmol) and potassium carbonate (90 mg, 0.650 mmol) were added. The reaction mixture was heated to 70° C. for 2 h. The reaction mixture was cooled room temperature and extracted with EtOAc. The combined organic layers were dried with magnesium sulfate, filtered, and the solvent was evaporated by rotary evaporator. The crude material (100 mg) and was carried to the next step without any further purification. LC-MS m/z 499.1 (M+H)⁺, 0.70 min (ret. time) and LC-MS m/z 513.2 (M+H)⁺, 0.78 min (ret. time).

To a solution of rac-methyl 1-(6-bromopyridin-2-yl)-5-((1R,2R)-2-(1-methyl-1H-1,2,3-triazol-4-yl)cyclopropyl)-1H-pyrazole-4-carboxylate (190 mg, 0.471 mmol) in 1,4-dioxane (3 mL) and water (1.000 mL), (3-hydroxyphenyl)boronic acid (130 mg, 0.942 mmol) and PdCl₂(dppf) (34.5 mg, 0.047 mmol) was added. Then the reaction mixture was degassed for 2 mins. Then potassium carbonate (260 mg, 1.885 mmol) was added. The reaction was heated in a microwave at 120° C. (high absorption) for 20 mins. The reaction mixture was extracted with ethyl acetate, dried with magnesium sulfate and the solvent was evaporated by rotary evaporator. The crude product was purified by silica gel chromatography (hexanes:ethyl acetate followed by (hexanes:ethyl Acetate/EtOH (3:1)) to obtain the title compound rac-methyl 1-(6-(3-hydroxyphenyl)pyridin-2-yl)-5-((1R,2R)-2-(1-methyl-1H-1,2,3-triazol-4-yl)cyclopropyl)-1H-pyrazole-4-carboxylate (100 mg, 0.240 mmol, 51.0% yield). LC-MS m/z 417.4 (M+H)+, 0.74 min (ret. time).

249b) Methyl 1-(6-(3-(1-cyclohexylethoxy)phenyl)pyridin-2-yl)-5-(trans-2-(1-methyl-1H-1,2,3-triazol-4-yl)cyclopropyl)-1H-pyrazole-4-carboxylate

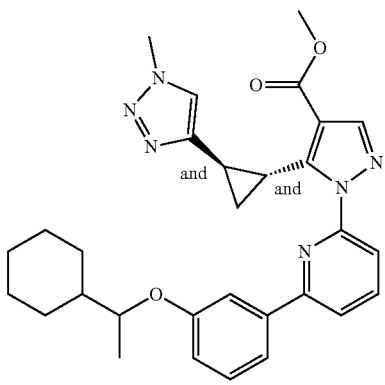 [SMILES: COC(=O)c1cnn(-c2cccc(-c3cccc(OC(C)C4CCCCC4)c3)n2)c1[C@@H]1C[C@H]1c1cn(C)nn1]

To a solution of methyl 1-(6-(3-hydroxyphenyl)pyridin-2-yl)-5-(trans-2-(1-methyl-1H-1,2,3-triazol-4-yl)cyclopropyl)-1H-pyrazole-4-carboxylate (100 mg, 0.240 mmol) in tetrahydrofuran (THF) (10 mL), 1-cyclohexylethanol (0.40 mL, 2.88 mmol), DIAD (0.56 mL, 2.88 mmol) and triphenylphosphine (756 mg, 2.88 mmol) were added at room temperature under nitrogen. The reaction was stirred for 16 h at room temperature. The reaction was recharged with 1-cyclohexylethanol (0.40 mL, 2.88 mmol), DIAD (0.56 mL, 2.88 mmol) and triphenylphosphine (756 mg, 2.88 mmol) and the reaction mixture was stirred for 5 additional h at room temperature. The solvent was evaporated and the crude residue was purified by silica gel chromatography (hexanes/EtOAc eluent). Triphenylphosphine oxide eluted along with the target compound. The combined fractions were collected, concentrated in vacuo, and purified by Gilson HPLC to provide the title compound (83 mg, 0.158 mmol, 65.6% yield). LC-MS m/z 527.3 (M+H)+, 1.30 min (ret. time).

249c) 5-(trans-2-(1-Methyl-1H-1,2,3-triazol-4-yl)cyclopropyl)-1-(3'-(morpholinomethyl)-[1,1'-biphenyl]-3-yl)-1H-pyrazole-4-carboxylic Acid

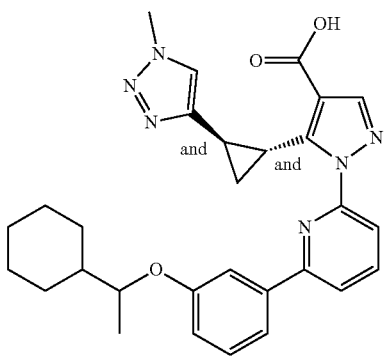 [SMILES: CC(Oc1cccc(-c2cccc(-n3ncc(C(=O)O)c3[C@@H]3C[C@H]3c3cn(C)nn3)n2)c1)C1CCCCC1]

To a solution of methyl 1-(6-(3-(1-cyclohexylethoxy)phenyl)pyridin-2-yl)-5-(trans-2-(1-methyl-1H-1,2,3-triazol-4-yl)cyclopropyl)-1H-pyrazole-4-carboxylate (83 mg, 0.158 mmol) in methanol (4.0 mL) and water (2.0 mL), LiOH (72 mg, 2.36 mmol) was added at room temperature. The reaction was stirred for 16 h at room temperature. Additional LiOH (72 mg, 2.36 mmol) was added to the reaction mixture and was it stirred for 4 additional h at 40° C. The reaction mixture was acidified with 1.0 N aqueous HCl to pH=3. The reaction mixture was extracted with EtOAc. The combined organic layers were concentrated in vacuo. The crude residue was purified by Gilson HPLC under neutral condition to afford the title compound (51.5 mg, 0.100 mmol, 63.7% yield). LC-MS m/z 513.5 (M+H)+, 1.16 min (ret. time).

Example 250. 1-(3'-(6,6-Dimethyl-5,6-dihydrocyclopenta[c]pyrazol-1(4H)-yl)-[1,1'-biphenyl]-3-yl)-5-(trifluoromethyl)-1H-pyrazole-4-carboxylic Acid

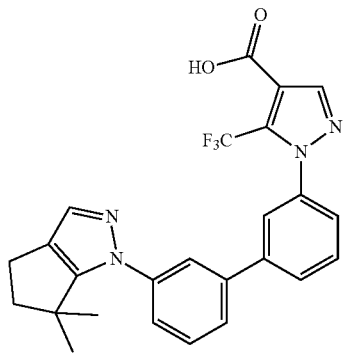 [SMILES: CC1(C)CCc2cnn(-c3cccc(-c4cccc(-n5ncc(C(=O)O)c5C(F)(F)F)c4)c3)c21]

250a) Ethyl 1-(3'-(2-(tert-butoxycarbonyl)hydrazinyl)-[1,1'-biphenyl]-3-yl)-5-(trifluoromethyl)-1H-pyrazole-4-carboxylate

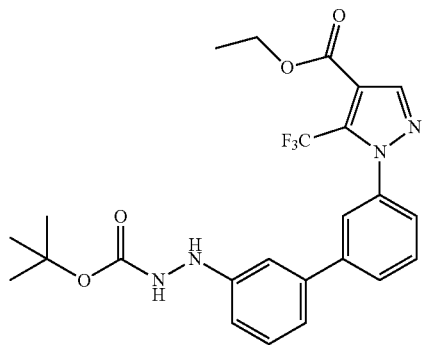 [SMILES: CCOC(=O)c1cnn(-c2cccc(-c3cccc(NNC(=O)OC(C)(C)C)c3)c2)c1C(F)(F)F]

To a solution of ethyl 1-(3-(4,4,5,5-tetramethyl-1,3,2-dioxaborolan-2-yl)phenyl)-5-(trifluoromethyl)-1H-pyrazole-4-carboxylate (300 mg, 0.731 mmol) in 1,4-dioxane (5.0 mL) and water (1.7 mL), tert-butyl 2-(3-bromophenyl)hydrazinecarboxylate (420 mg, 1.463 mmol) and $K_2CO_3$ (404 mg, 2.93 mmol) were added. Then the reaction mixture was degassed for 2 mins. $PdCl_2(dppf)$ (53.5 mg, 0.073 mmol) was added. The reaction heated to 120° C. for 20 min under microwave irradiation. The reaction mixture was extracted with EtOAc, dried with magnesium sulfate, filtered and the solvent was evaporated. The crude residue was purified by silica gel chromatography (hexanes/EtOAc eluent) to obtain the title compound (183 mg, 0.373 mmol, 51.0% yield). LC-MS m/z 425.2 (M–tBu)⁺, 1.22 min (ret. time).

250b) Ethyl 1-(3'-hydrazinyl-[1,1'-biphenyl]-3-yl)-5-(trifluoromethyl)-1H-pyrazole-4-carboxylate

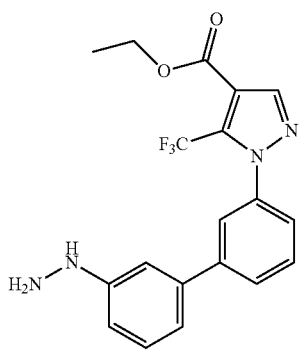 [SMILES: CCOC(=O)c1cnn(-c2cccc(-c3cccc(NN)c3)c2)c1C(F)(F)F]

To a solution of ethyl 1-(3'-(2-(tert-butoxycarbonyl)hydrazinyl)-[1,1'-biphenyl]-3-yl)-5-(trifluoromethyl)-1H-pyrazole-4-carboxylate (183 mg, 0.373 mmol) in dichloromethane (3 mL), HCl in dioxane (0.56 mL, 2.239 mmol) was added. The reaction mixture was stirred for 2 h 30 min at room temperature. An additional amount of 4N HCl in 1,4-dioxane (0.56 mL, 2.239 mmol) was added to reaction mixture and was stirred for another addition 1 hour 30 min at room temperature. An additional amount 4N HCl in 1,4-dioxane (1.12 mL, 4.45 mmol) was added to the reaction mixture and was stirred for 4 h at room temperature. The solvent removed in vacuo to provide the title compound to afford the title compound as the di-HCl salt (140 mg, 0.359 mmol, 96% yield). LC-MS m/z 391.3 (M+H)⁺, 0.82 min (ret. time).

250c) Ethyl 1-(3'-(6,6-dimethyl-5,6-dihydrocyclopenta[c]pyrazol-1(4H)-yl)-[1,1'-biphenyl]-3-yl)-5-(trifluoromethyl)-1H-pyrazole-4-carboxylate

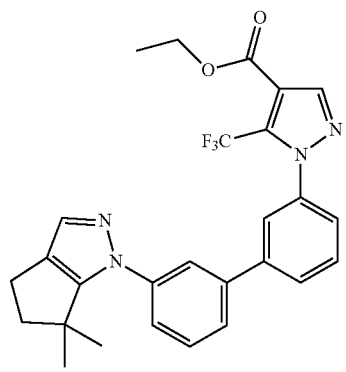 [SMILES: CCOC(=O)c1cnn(-c2cccc(-c3cccc(-n4ncc5c4C(C)(C)CC5)c3)c2)c1C(F)(F)F]

To a solution of the di-HCl salt of ethyl 1-(3'-hydrazinyl-[1,1'-biphenyl]-3-yl)-5-(trifluoromethyl)-1H-pyrazole-4-carboxylate (150 mg, 0.384 mmol) in acetic acid (2.0 mL) and methanol (1.5 mL), 5-((dimethylamino)methylene)-2,2-dimethylcyclopentanone (64.3 mg, 0.384 mmol) was added. Then the reaction mixture was stirred for 3 h at 100° C. The solvent was removed in vacuo. The crude residue was purified by Gilson HPLC to afford the title compound (130 mg, 0.263 mmol, 68.4% yield). LC-MS m/z 495.4 (M+H)⁺, 1.39 min (ret. time).

250d) 1-(3'-(6,6-Dimethyl-5,6-dihydrocyclopenta[c]pyrazol-1(4H)-yl)-[1,1'-biphenyl]-3-yl)-5-(trifluoromethyl)-1H-pyrazole-4-carboxylic Acid

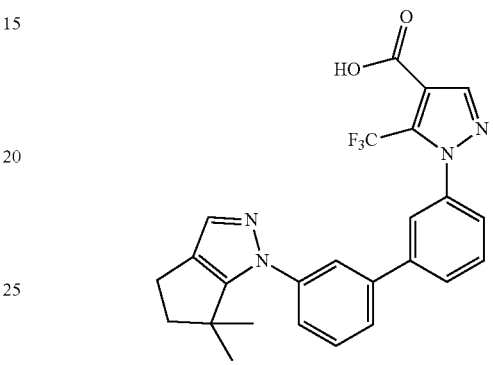

To a solution of ethyl 1-(3'-(6,6-dimethyl-5,6-dihydrocyclopenta[c]pyrazol-1(4H)-yl)-[1,1'-biphenyl]-3-yl)-5-(trifluoromethyl)-1H-pyrazole-4-carboxylate (130 mg, 0.263 mmol) in and methanol (3.0 mL) and water (1.5 mL), LiOH (94 mg, 3.94 mmol) was added at room temperature. The reaction was stirred for 16 h at room temperature. The reaction mixture was acidified with 1.0 N aqueous HCl to pH=3. The reaction mixture was extracted with EtOAc. The combined organic layers were concentrated in vacuo. The crude residue was purified by Gilson HPLC under neutral condition to afford the title compound (30 mg, 0.064 mmol, 24.46% yield). LC-MS m/z 467.2 (M+H)⁺, 1.26 min (ret. time).

Example 251. 1-(6-(3-(6,6-Dimethyl-5,6-dihydrocyclopenta[c]pyrazol-1(4H)-yl)phenyl)pyridin-2-yl)-5-(trans-2-(1-methyl-1H-1,2,3-triazol-4-yl)cyclopropyl)-1H-pyrazole-4-carboxylic Acid

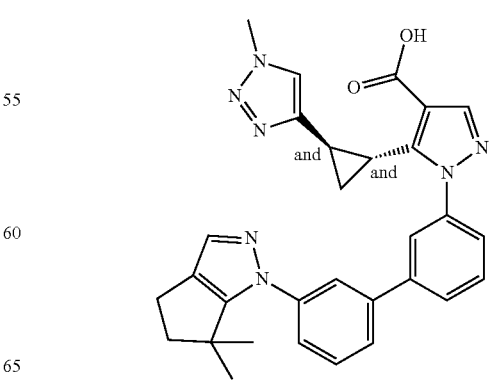

251a) Methyl 1-(6-(3-(6,6-dimethyl-5,6-dihydrocyclopenta[c]pyrazol-1(4H)-yl)phenyl)pyridin-2-yl)-5-(trans-2-(1-methyl-1H-1,2,3-triazol-4-yl)cyclopropyl)-1H-pyrazole-4-carboxylate

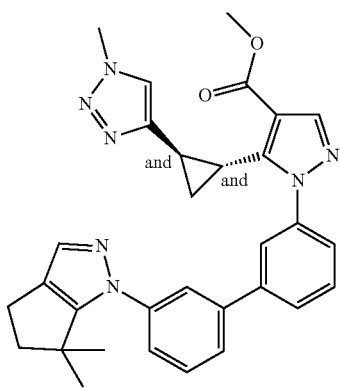 [SMILES: COC(=O)c1cnn(-c2cccc(-c3cccc(-n4ncc5c4C(C)(C)CC5)c3)c2)c1[C@@H]1C[C@H]1c1cn(C)nn1]

A solution of methyl 1-(6-bromopyridin-2-yl)-5-(trans-2-(1-methyl-1H-1,2,3-triazol-4-yl)cyclopropyl)-1H-pyrazole-4-carboxylate (100 mg, 0.248 mmol) and 6,6-dimethyl-1-(3-(4,4,5,5-tetramethyl-1,3,2-dioxaborolan-2-yl)phenyl)-1,4,5,6-tetrahydrocyclopenta[c]pyrazole (151 mg, 0.446 mmol) in 1,4-dioxane (4.0 mL) was degassed for 2 mins. PdCl$_2$(dppf) (18.1 mg, 0.025 mmol) was added. The reaction mixture was heated to 120° C. for 20 min under microwave irradiation. The reaction was cooled to room temperature and then extracted with EtOAc, dried with magnesium sulfate, filtered and the solvent was concentrated in vacuo. The crude residue was purified by silica gel chromatography (hexanes/EtOAc followed by hexanes/(3:1 EtOAc/EtOH) to afford the title compound. LC-MS m/z 535.2 (M+H)$^+$, 1.05 min (ret. time).

251b) 1-(6-(3-(6,6-Dimethyl-5,6-dihydrocyclopenta[c]pyrazol-1(4H)-yl)phenyl)pyridin-2-yl)-5-(trans-2-(1-methyl-1H-1,2,3-triazol-4-yl)cyclopropyl)-1H-pyrazole-4-carboxylic Acid

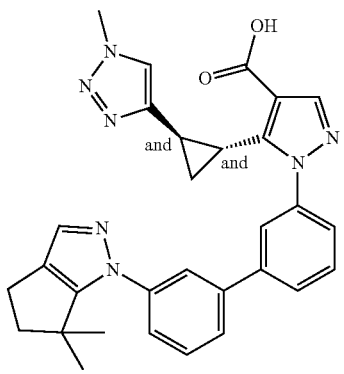 [SMILES: Cn1cc([C@@H]2C[C@H]2c2c(C(=O)O)cnn2-c2cccc(-c3cccc(-n4ncc5c4C(C)(C)CC5)c3)c2)nn1]

To a solution of methyl 1-(6-(3-(6,6-dimethyl-5,6-dihydrocyclopenta[c]pyrazol-1(4H)-yl)phenyl)pyridin-2-yl)-5-(trans-2-(1-methyl-1H-1,2,3-triazol-4-yl)cyclopropyl)-1H-pyrazole-4-carboxylate (100 mg, 0.187 mmol) in methanol (2.0 mL) and water (1.0 mL) was added LiOH (67.2 mg, 2.81 mmol). The reaction mixture was stirred for 1 hour 30 min at 56° C. The reaction mixture was acidified with 1.0 N aqueous HCl to pH=3. The methanol was evaporated by Biotage V-10 and the resulting mixture was extracted with EtOAc. The combined organic solvent was concentrated in vacuo. The crude residue was purified by Gilson HPLC under neutral condition to afford the title compound (24 mg, 0.046 mmol, 24.65% yield). LC-MS m/z 521.4 (M+H)$^+$, 0.91 min (ret. time).

Example 252. 1-(3'-((4-Ethyl-4,5-dihydro-1H-benzo[c]azepin-2(3H)-yl)methyl)-[1,1'-biphenyl]-3-yl)-5-(trans-2-(1-methyl-1H-1,2,3-triazol-4-yl)cyclopropyl)-1H-pyrazole-4-carboxylic Acid

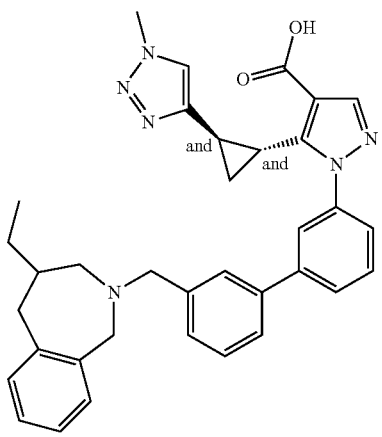 [SMILES: CCC1Cc2ccccc2CN(Cc2cccc(-c3cccc(-n4ncc(C(=O)O)c4[C@@H]4C[C@H]4c4cn(C)nn4)c3)c2)C1]

252a) Ethyl 1-(3'-((4-ethyl-4,5-dihydro-1H-benzo[c]azepin-2(3H)-yl)methyl)-[1,1'-biphenyl]-3-yl)-5-(trans-2-(1-methyl-1H-1,2,3-triazol-4-yl)cyclopropyl)-1H-pyrazole-4-carboxylate

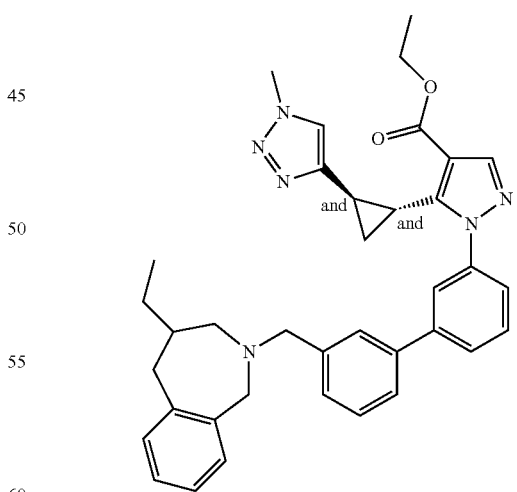

To a solution of ethyl 1-(3'-(chloromethyl)-[1,1'-biphenyl]-3-yl)-5-(trans-2-(1-methyl-1H-1,2,3-triazol-4-yl)cyclopropyl)-1H-pyrazole-4-carboxylate (70 mg, 0.152 mmol) in N,N-dimethylformamide (DMF) (2.0 mL), 4-ethyl-2,3,4,5-tetrahydro-1H-benzo[c]azepine hydrochloride (48.1 mg, 0.227 mmol) and K$_2$CO$_3$ (84 mg, 0.606 mmol) were added.

The reaction mixture was heated to 80° C. and stirred for 1.5 h. The reaction was cooled to room temperature and the solvent was evaporated using Biotage V-10 to afford the title compound (91 mg, 0.152 mmol, 100% yield) which was carried to the next step without any purification. LC-MS m/z 604.6 (M+H)+, 0.94 min (ret. time).

252b) 1-(3'-((4-Ethyl-4,5-dihydro-1H-benzo[c]azepin-2(3H)-yl)methyl)-[1,1'-biphenyl]-3-yl)-5-(trans-2-(1-methyl-1H-1,2,3-triazol-4-yl)cyclopropyl)-1H-pyrazole-4-carboxylic Acid

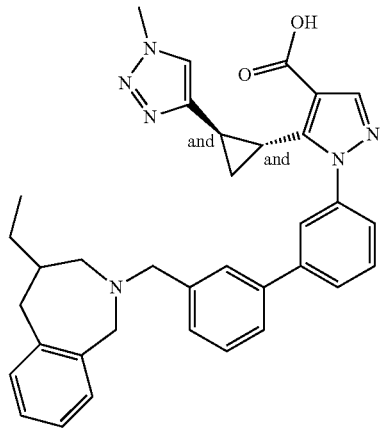 [SMILES: CCC1Cc2ccccc2CN(Cc2cccc(-c3cccc(-n4ncc(C(=O)O)c4[C@@H]4C[C@H]4c4cn(C)nn4)c3)c2)C1]

To a solution ethyl 1-(3'-((4-ethyl-4,5-dihydro-1H-benzo[c]azepin-2(3H)-yl)methyl)-[1,1'-biphenyl]-3-yl)-5-(trans-2-(1-methyl-1H-1,2,3-triazol-4-yl)cyclopropyl)-1H-pyrazole-4-carboxylate (65 mg, 0.108 mmol) in methanol (2.0 mL) and water (1.0 mL), LiOH (25.8 mg, 1.077 mmol) was added. The reaction mixture was heated to 60° C. for 40 min. The reaction mixture was acidified with 1.0 N aqueous HCl to pH=3. The methanol was evaporated by Biotage V-10 and the resulting aqueous layer was extracted with EtOAc. The organic solvent was concentrated in vacuo. The crude residue was purified by Gilson HPLC under neutral conditions afford the title compound (56 mg, 0.098 mmol, 91% yield). LC-MS m/z 573.2 (M+H)+, 0.82 min (ret. time).

Example 253. 1-(3'-(((R)-2-Ethyl-2,3-dihydrobenzo[f][1,4]oxazepin-4(5H)-yl)methyl)-[1,1'-biphenyl]-3-yl)-5-(trans-2-(1-methyl-1H-1,2,3-triazol-4-yl)cyclopropyl)-1H-pyrazole-4-carboxylic Acid

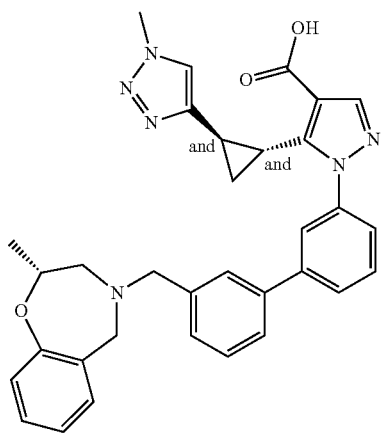 [SMILES: C[C@@H]1CN(Cc2cccc(-c3cccc(-n4ncc(C(=O)O)c4[C@@H]4C[C@H]4c4cn(C)nn4)c3)c2)Cc2ccccc2O1]

253a) Ethyl 1-(3'-(chloromethyl)-[1,1'-biphenyl]-3-yl)-5-((trans)-2-(1-methyl-1H-1,2,3-triazol-4-yl)cyclopropyl)-1H-pyrazole-4-carboxylate

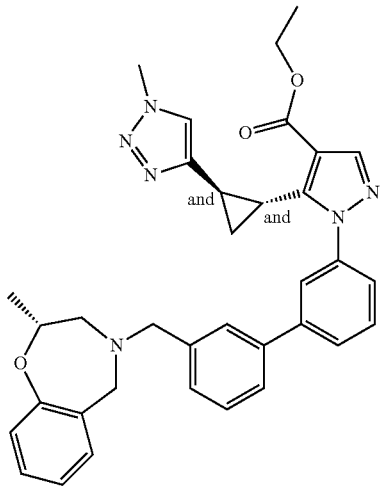 [SMILES: CCOC(=O)c1cnn(-c2cccc(-c3cccc(CN4Cc5ccccc5O[C@H](C)C4)c3)c2)c1[C@@H]1C[C@H]1c1cn(C)nn1]

To a solution of ethyl 1-(3'-(chloromethyl)-[1,1'-biphenyl]-3-yl)-5-(trans-2-(1-methyl-1H-1,2,3-triazol-4-yl)cyclopropyl)-1H-pyrazole-4-carboxylate (70 mg, 0.152 mmol) in N,N-dimethylformamide (DMF) (2.0 mL), (R)-2-methyl-2,3,4,5-tetrahydrobenzo[f][1,4]oxazepine hydrochloride (45.4 mg, 0.227 mmol), $K_2CO_3$ (84 mg, 0.606 mmol) and sodium iodide (45.4 mg, 0.303 mmol) were added. The reaction mixture was heated to 80° C. and stirred for 2 h. The reaction was cooled the room temperature and the solvent was removed using a Biotage V-10 evaporator to provide the title compound (89 mg, 0.152 mmol, 100% yield), which was carried to the next step without further purification. LC-MS m/z 589.2 (M+H)+, 0.88 min (ret. time).

253b) 1-(3'-(((R)-2-Ethyl-2,3-dihydrobenzo[f][1,4]oxazepin-4(5H)-yl)methyl)-[1,1'-biphenyl]-3-yl)-5-(trans-2-(1-methyl-1H-1,2,3-triazol-4-yl)cyclopropyl)-1H-pyrazole-4-carboxylic Acid

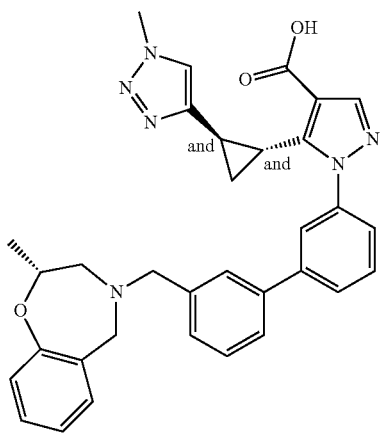 [SMILES: C[C@@H]1CN(Cc2cccc(-c3cccc(-n4ncc(C(=O)O)c4[C@@H]4C[C@H]4c4cn(C)nn4)c3)c2)Cc2ccccc2O1]

To a solution provide ethyl 5-(trans-2-(1-methyl-1H-1,2,3-triazol-4-yl)cyclopropyl)-1-(3'-(((R)-2-methyl-2,3-dihydrobenzo[f][1,4]oxazepin-4(5H)-yl)methyl)-[1,1'-biphenyl]-3-yl)-1H-pyrazole-4-carboxylate (63.4 mg, 0.108 mmol) in methanol (2.0 mL) and water (1.0 mL), LiOH (25.8 mg, 1.077 mmol) was added. The reaction mixture was heated to 60° C. for 40 min. The reaction mixture was acidified with 1.0 N aqueous HCl to pH=3. The methanol was removed with a Biotage V-10 evaporator and the resulting aqueous layer was extracted with EtOAc. The organic solvent was concentrated in vacuo. The crude residue was purified by Gilson HPLC under neutral conditions afford the title compound (19 mg, 0.034 mmol, 31.5% yield). LC-MS m/z 561.1 (M+H)+, 0.77 min (ret. time).

Example 254. 1-(3'-((2,2-Dimethyl-2,3-dihydrobenzo[f][1,4]oxazepin-4(5H)-yl)methyl)-[1,1'-biphenyl]-3-yl)-5-(trans-2-(1-methyl-1H-1,2,3-triazol-4-yl)cyclopropyl)-1H-pyrazole-4-carboxylic Acid

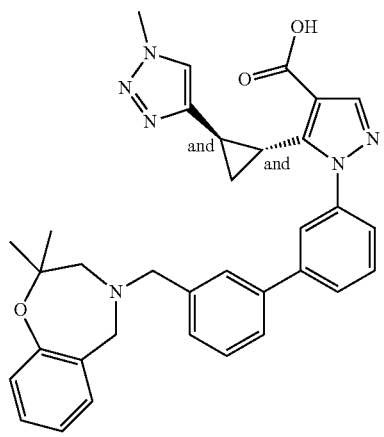 [SMILES: Cn1cc([C@@H]2C[C@H]2c2c(C(=O)O)cnn2-c2cccc(-c3cccc(CN4Cc5ccccc5OC(C)(C)C4)c3)c2)nn1]

254a) Ethyl 1-(3'-(chloromethyl)-[1,1'-biphenyl]-3-yl)-5-(trans-2-(1-methyl-1H-1,2,3-triazol-4-yl)cyclopropyl)-1H-pyrazole-4-carboxylate

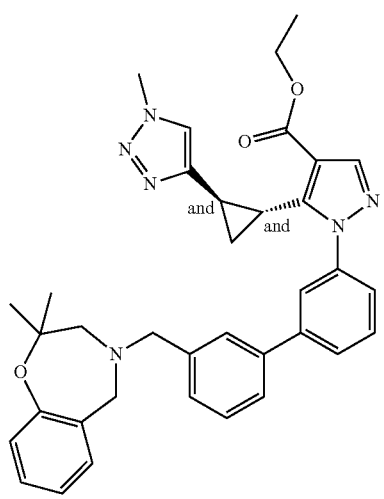 [SMILES: CCOC(=O)c1cnn(-c2cccc(-c3cccc(CN4Cc5ccccc5OC(C)(C)C4)c3)c2)c1[C@@H]1C[C@H]1c1cn(C)nn1]

To a solution of ethyl 1-(3'-(chloromethyl)-[1,1'-biphenyl]-3-yl)-5-(trans-2-(1-methyl-1H-1,2,3-triazol-4-yl)cyclopropyl)-1H-pyrazole-4-carboxylate (70 mg, 0.152 mmol) in N,N-dimethylformamide (DMF) (2 mL), 2,2-dimethyl-2,3,4,5-tetrahydrobenzo[f][1,4]oxazepine hydrochloride (48.6 mg, 0.227 mmol), K$_2$CO$_3$ (84 mg, 0.606 mmol) and sodium iodide (45.4 mg, 0.303 mmol) were added. The reaction mixture was heated to 80° C. and stirred for 2 h. The reaction was cooled the room temperature and the solvent was removed using a Biotage V-10 evaporator to provide the title compound (91 mg, 0.152 mmol, 100% yield), which was carried to the next step without further purification. LC-MS m/z 603.5 (M+H)+, 0.90 min (ret. time).

254b) 1-(3'-((2,2-Dimethyl-2,3-dihydrobenzo[f][1,4]oxazepin-4(5H)-yl)methyl)-[1,1'-biphenyl]-3-yl)-5-(trans-2-(1-methyl-1H-1,2,3-triazol-4-yl)cyclopropyl)-1H-pyrazole-4-carboxylic Acid

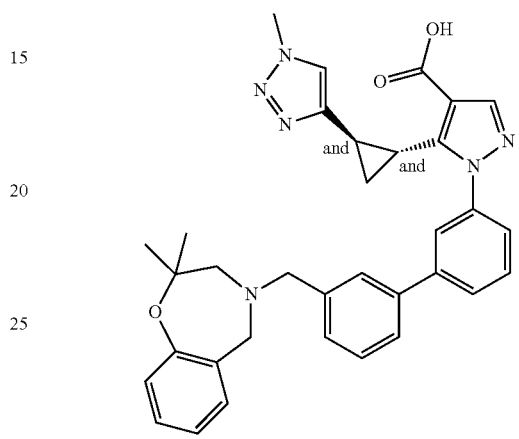

To a solution provide ethyl 1-(3'-((2,2-dimethyl-2,3-dihydrobenzo[f][1,4]oxazepin-4(5H)-yl)methyl)-[1,1'-biphenyl]-3-yl)-5-(trans-2-(1-methyl-1H-1,2,3-triazol-4-yl)cyclopropyl)-1H-pyrazole-4-carboxylate (64.9 mg, 0.108 mmol) in methanol (2.0 mL) and water (1.0 mL), LiOH (25.8 mg, 1.077 mmol) was added. The reaction mixture was heated to 60° C. for 40 min. The reaction mixture was acidified with 1.0 N aqueous HCl to pH=3. The methanol was removed with a Biotage V-10 evaporator and the resulting aqueous layer was extracted with EtOAc. The organic solvent was concentrated in vacuo. The crude residue was purified by Gilson HPLC under neutral conditions afford the title compound (14 mg, 0.024 mmol, 22.6% yield). LC-MS m/z 575.4 (M+H)+, 0.75 min (ret. time).

Example 255. 1-(3'-(((R)-4-Ethyl-1,1-dioxido-3,4-dihydro-2H-benzo[b][1,4,5]oxathiazepin-2-yl)methyl)-[1,1'-biphenyl]-3-yl)-5-(trans-2-(1-methyl-1H-1,2,3-triazol-4-yl)cyclopropyl)-1H-pyrazole-4-carboxylic Acid

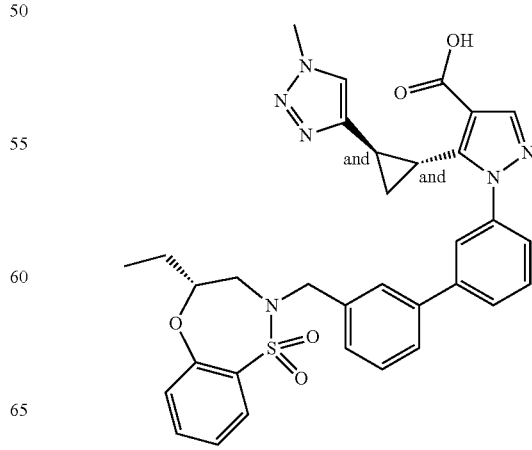

255a) Methyl 1-(3'-(hydroxymethyl)-[1,1'-biphenyl]-3-yl)-5-(trans-2-(1-methyl-1H-1,2,3-triazol-4-yl)cyclopropyl)-1H-pyrazole-4-carboxylate To a solution of rac-methyl 1-(3-bromophenyl)-5-((1R,2R)-2-(1-methyl-1H-1,2,3-triazol-4-yl)cyclopropyl)-1H-pyrazole-4-carboxylate (330 mg, 0.820 mmol) in 1,4-dioxane (9 mL), (3-(hydroxymethyl)phenyl)boronic acid (249 mg, 1.641 mmol) and potassium acetate (322 mg, 3.28 mmol) were added. Then the reaction mixture was degassed for 2 mins. Then PdCl$_2$(dppf) (60.0 mg, 0.082 mmol) was added. The reaction was heated in a microwave at 120° C. (high absorption) for 25 mins. The reaction mixture was extracted with ethyl acetate, dried with magnesium sulfate and the solvent was evaporated by rotary evaporator. The crude product was purified with silica gel chromatography (hexanes:ethyl acetate and then hexanes:(ethyl acetate:EtOH, 3:1)) to obtain the title compound rac-methyl 1-(3'-(hydroxymethyl)-[1,1'-biphenyl]-3-yl)-5-((1R,2R)-2-(1-methyl-1H-1,2,3-triazol-4-yl)cyclopropyl)-1H-pyrazole-4-carboxylate (209 mg, 0.487 mmol, 59.3% yield). LC-MS m/z 430.2 (M+H)$^+$, 0.77 min (ret. time).

255b) Methyl 1-(3'-(((R)-4-ethyl-1,1-dioxido-3,4-dihydro-2H-benzo[b][1,4,5]oxathiazepin-2-yl)methyl)-[1,1'-biphenyl]-3-yl)-5-(trans-2-(1-methyl-1H-1,2,3-triazol-4-yl)cyclopropyl)-1H-pyrazole-4-carboxylate

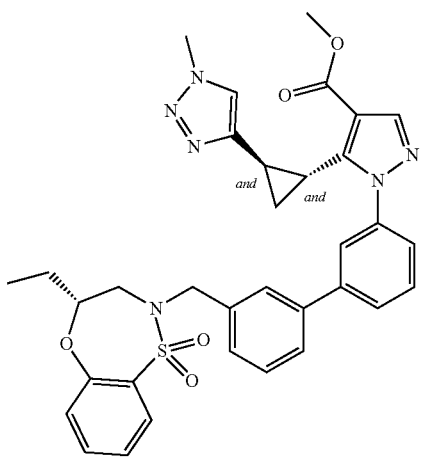 [SMILES: CC[C@@H]1CN(Cc2cccc(-c3cccc(-n4ncc(C(=O)OC)c4[C@@H]4C[C@H]4c4cn(C)nn4)c3)c2)S(=O)(=O)c2ccccc2O1]

To a solution of methyl 1-(3'-(hydroxymethyl)-[1,1'-biphenyl]-3-yl)-5-(trans-2-(1-methyl-1H-1,2,3-triazol-4-yl)cyclopropyl)-1H-pyrazole-4-carboxylate (85 mg, 0.198 mmol) in tetrahydrofuran (THF) (6.0 mL), (R)-4-ethyl-3,4-dihydro-2H-benzo[b][1,4,5]oxathiazepine 1,1-dioxide (90 mg, 0.396 mmol), DIAD (0.231 mL, 1.188 mmol) and triphenylphosphine (311 mg, 1.188 mmol) were added at room temperature under nitrogen. The reaction was stirred for 18 h at room temperature. Then The solvent was evaporated and the crude residue was purified by silica gel chromatography to afford the title compound (120 mg, 0.188 mmol, 95% yield). LC-MS m/z 639.3 (M+H)$^+$, 1.14 min (ret. time).

255c) 1-(3'-(((R)-4-Ethyl-1,1-dioxido-3,4-dihydro-2H-benzo[b][1,4,5]oxathiazepin-2-yl)methyl)-[1,1'-biphenyl]-3-yl)-5-(trans-2-(1-methyl-1H-1,2,3-triazol-4-yl)cyclopropyl)-1H-pyrazole-4-carboxylic Acid

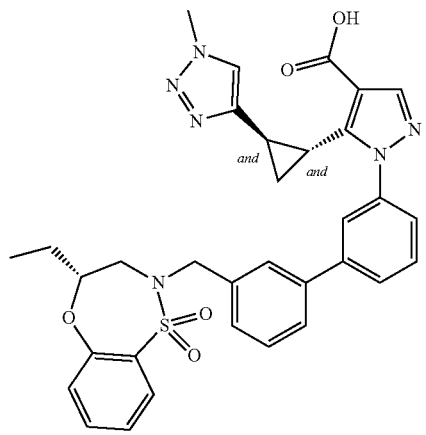 [SMILES: CC[C@@H]1CN(Cc2cccc(-c3cccc(-n4ncc(C(=O)O)c4[C@@H]4C[C@H]4c4cn(C)nn4)c3)c2)S(=O)(=O)c2ccccc2O1]

To a solution of methyl 1-(3'-(((R)-4-ethyl-1,1-dioxido-3,4-dihydro-2H-benzo[b][1,4,5]oxathiazepin-2-yl)methyl)-[1,1'-biphenyl]-3-yl)-5-(trans-2-(1-methyl-1H-1,2,3-triazol-4-yl)cyclopropyl)-1H-pyrazole-4-carboxylate (120 mg, 0.188 mmol) in methanol (2.0 mL) and water (1.0 mL), LiOH (45.0 mg, 1.879 mmol) was added at room temperature. The reaction mixture was stirred for 1 hour 30 min at 60° C. The reaction mixture was acidified with 1.0 N aqueous HCl to pH=3. The methanol was removed with a Biotage V-10 evaporator and the resulting aqueous mixture was extracted with EtOAc. The organic solvent was separated and concentrated in vacuo. The crude residue was purified using Gilson HPLC under neutral condition to afford the title compound (18 mg, 0.029 mmol, 15.34% yield). LC-MS m/z 625.2 (M+H)$^+$, 1.02 min (ret. time).

Example 256. 1-(3'-((2,3-Dihydrobenzo[f][1,4]oxazepin-4(5H)-yl)methyl)-[1,1'-biphenyl]-3-yl)-5-(trans-2-(1-methyl-1H-1,2,3-triazol-4-yl)cyclopropyl)-1H-pyrazole-4-carboxylic Acid

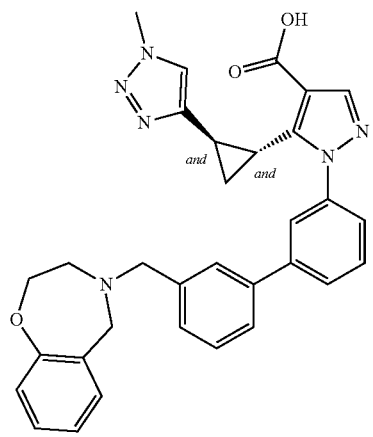 [SMILES: Cn1cc([C@@H]2C[C@H]2c2c(C(=O)O)cnn2-c2cccc(-c3cccc(CN4CCOc5ccccc5C4)c3)c2)nn1]

585

256a) Ethyl 1-(3'-((2,3-dihydrobenzo[f][1,4]oxaze-pin-4(5H)-yl)methyl)-[1,1'-biphenyl]-3-yl)-5-(trans-2-(1-methyl-1H-1,2,3-triazol-4-yl)cyclopropyl)-1H-pyrazole-4-carboxylate

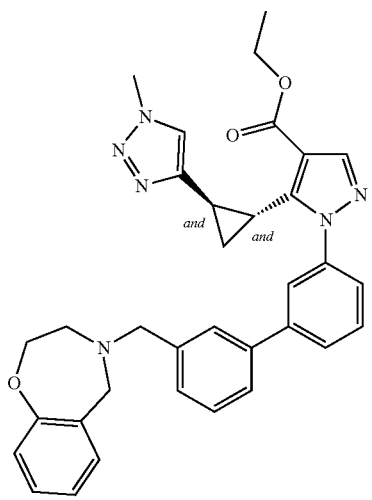 [SMILES: CCOC(=O)c1cnn(-c2cccc(-c3cccc(CN4CCOc5ccccc5C4)c3)c2)c1[C@@H]1C[C@H]1c1cn(C)nn1]

To a solution of ethyl 1-(3'-(chloromethyl)-[1,1'-biphenyl]-3-yl)-5-(trans-2-(1-methyl-1H-1,2,3-triazol-4-yl)cyclopropyl)-1H-pyrazole-4-carboxylate (60 mg, 0.130 mmol) in N,N-dimethylformamide (DMF) (2 mL), 2,3,4,5-tetrahydrobenzo[f][1,4]oxazepine (0.020 mL, 0.143 mmol), K$_2$CO$_3$ (71.8 mg, 0.520 mmol) and sodium iodide (38.9 mg, 0.260 mmol) were added. The reaction mixture was heated to 80° C. for 1 hour. The solvent DMF was removed using a Biotage V-10 evaporator. The resulting crude residue was taken up in EtOAc, dried with magnesium sulfate, filtered and the solvent was concentrated in vacuo the provide the title compound (70 mg, 0.122 mmol, 94% yield) that was used in the next step without further purification LC-MS m/z 575.3 (M+H)$^+$, 0.86 min (ret. time).

256b) 1-(3'-((2,3-Dihydrobenzo[f][1,4]oxazepin-4(5H)-yl)methyl)-[1,1'-biphenyl]-3-yl)-5-(trans-2-(1-methyl-1H-1,2,3-triazol-4-yl)cyclopropyl)-1H-pyrazole-4-carboxylic Acid

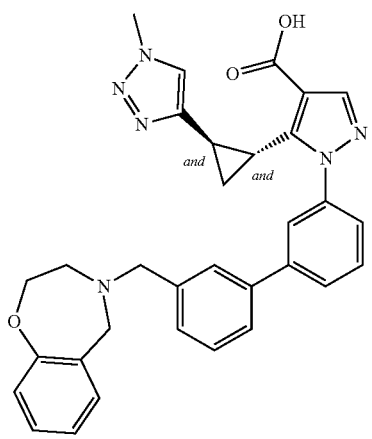 [SMILES: Cn1cc([C@@H]2C[C@H]2c2c(C(=O)O)cnn2-c2cccc(-c3cccc(CN4CCOc5ccccc5C4)c3)c2)nn1]

586

To a solution of ethyl 1-(3'-((2,3-dihydrobenzo[f][1,4]oxazepin-4(5H)-yl)methyl)-[1,1'-biphenyl]-3-yl)-5-(trans-2-(1-methyl-1H-1,2,3-triazol-4-yl)cyclopropyl)-1H-pyrazole-4-carboxylate (70 mg, 0.122 mmol, 94% yield) in methanol (2.0 mL) and water (1.0 mL), LiOH (40.4 mg, 1.689 mmol) was added at room temperature. The reaction mixture was stirred for 1 hour at 60° C. The reaction mixture was acidified with 1.0 N aqueous HCl to pH=3. The methanol was removed using a Biotage V-10 evaporator and the resulting aqueous reaction mixture was extracted with EtOAc. The organic layer was separated and concentrated in vacuo. The crude residue was purified by Gilson HPLC under neutral condition to afford the title compound (30 mg, 0.055 mmol, 42.3% yield). LC-MS m/z 547.3 (M+H)$^+$, 0.75 min (ret. time).

Example 257. 1-(3'-((R)-2-Ethyl-2,3,4,5-tetrahydrobenzo[f][1,4]oxazepine-4-carbonyl)-[1,1'-biphenyl]-3-yl)-5-(trans-(2-(1-methyl-1H-1,2,3-triazol-4-yl)cyclopropyl)-1H-pyrazole-4-carboxylic Acid

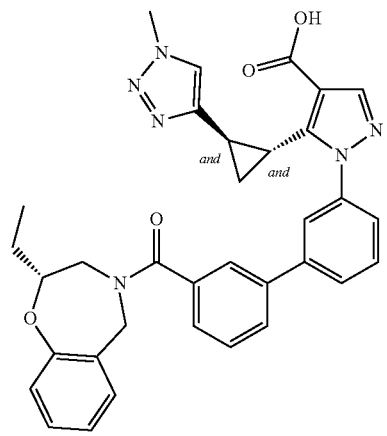 [SMILES: CC[C@@H]1CN(C(=O)c2cccc(-c3cccc(-n4ncc(C(=O)O)c4[C@@H]4C[C@H]4c4cn(C)nn4)c3)c2)Cc2ccccc2O1]

257a) (R)-(3-bromophenyl)(2-ethyl-2,3-dihydrobenzo[f][1,4]oxazepin-4(5H)-yl)methanone

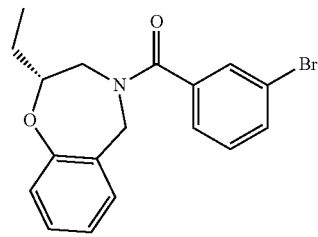 [SMILES: CC[C@@H]1CN(C(=O)c2cccc(Br)c2)Cc2ccccc2O1]

To a solution of (R)-2-ethyl-2,3,4,5-tetrahydrobenzo[f][1,4]oxazepine (90 mg, 0.508 mmol) in dichloromethane (DCM) (4 mL), HATU (212 mg, 0.559 mmol) was added at room temperature. After 10 min, 3-bromobenzoic acid (122 mg, 0.609 mmol) and DIEA (0.266 mL, 1.523 mmol) were added. The reaction was stirred for 16 h at room temperature The reaction mixture was partitioned between EtOAc and water. The organic layer was dried with magnesium sulfate, filtered and the solvent was concentrated in vacuo. The crude residue was purified by silica gel chromatography (hexanes/EtOAc eluent) to afford (R)-(3-bromophenyl)(2-ethyl-2,3-dihydrobenzo[f][1,4]oxazepin-4(5H)-yl)methanone (68 mg, 0.189 mmol, 37.2% yield). LC-MS m/z 360.1/362.1 (M+H)$^+$, 1.12 min (ret. time).

257b) Ethyl 1-(3'-((R)-2-ethyl-2,3,4,5-tetrahydrobenzo[f][1,4]oxazepine-4-carbonyl)-[1,1'-biphenyl]-3-yl)-5-(trans-2-(1-methyl-1H-1,2,3-triazol-4-yl)cyclopropyl)-1H-pyrazole-4-carboxylate

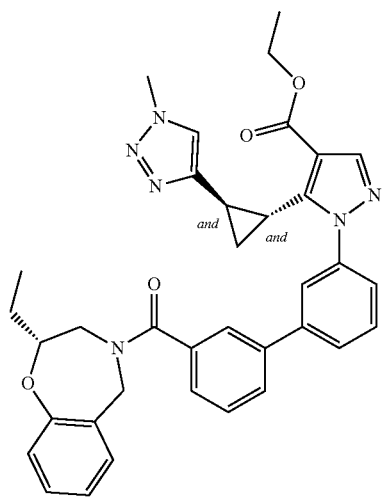 [SMILES: CCOC(=O)c1cnn(-c2cccc(-c3cccc(C(=O)N4Cc5ccccc5O[C@H](CC)C4)c3)c2)c1[C@@H]1C[C@H]1c1cn(C)nn1]

To a solution of ethyl 5-(trans-2-(1-methyl-1H-1,2,3-triazol-4-yl)cyclopropyl)-1-(3-(4,4,5,5-tetramethyl-1,3,2-dioxaborolan-2-yl)phenyl)-1H-pyrazole-4-carboxylate (96 mg, 0.208 mmol) in 1,4-dioxane (3.0 mL) and water (1.0 mL), (R)-(3-bromophenyl)(2-ethyl-2,3-dihydrobenzo[f][1,4]oxazepin-4(5H)-yl)methanone (68 mg, 0.189 mmol) and potassium acetate (55.6 mg, 0.566 mmol) were added. The reaction mixture was degassed for 2 min. PdCl$_2$(dppf) (13.81 mg, 0.019 mmol) was added and the reaction heated for 20 min at 120° C. under microwave irradiation. The reaction mixture was extracted with EtOAc. The organic layers were dried with magnesium sulfate, filtered and the solvent was removed in vacuo. The crude residue was purified by Gilson HPLC under acidic conditions to afford the title compound (80 mg, 0.130 mmol, 68.7% yield). LC-MS m/z 617.5 (M+H)$^+$, 1.13 min (ret. time).

257c) 1-(3'-((R)-2-Ethyl-2,3,4,5-tetrahydrobenzo[f][1,4]oxazepine-4-carbonyl)-[1,1'-biphenyl]-3-yl)-5-(trans-2-(1-methyl-1H-1,2,3-triazol-4-yl)cyclopropyl)-1H-pyrazole-4-carboxylic Acid

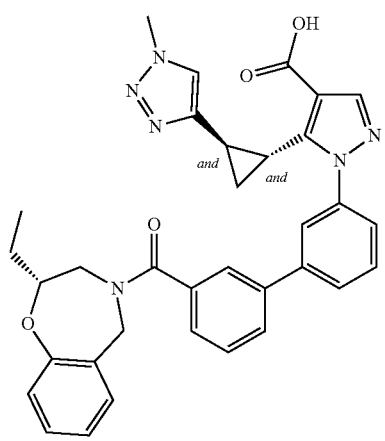 [SMILES: CC[C@@H]1CN(C(=O)c2cccc(-c3cccc(-n4ncc(C(=O)O)c4[C@@H]4C[C@H]4c4cn(C)nn4)c3)c2)Cc2ccccc2O1]

Ethyl 1-(3'-((R)-2-ethyl-2,3,4,5-tetrahydrobenzo[f][1,4]oxazepine-4-carbonyl)-[1,1'-biphenyl]-3-yl)-5-(trans-2-(1-methyl-1H-1,2,3-triazol-4-yl)cyclopropyl)-1H-pyrazole-4-carboxylate (80 mg, 0.130 mmol) was dissolved in methanol (1.0 mL) and water (1.0 mL). To this solution, LiOH (45.2 mg, 1.888 mmol) was added at room temperature. The reaction mixture was stirred for 40 min at 60° C. The reaction mixture was acidified with 1.0 N aqueous HCl to pH=3. The methanol was removed using a Biotage V-10 evaporator and the resulting reaction mixture was purified with Gilson HPLC under neutral condition to afford the title compound (60 mg, 0.102 mmol, 54.0% yield). LC-MS m/z 589.1 (M+H)$^+$, 0.98 min (ret. time).

Example 258. 1-(2'-Fluoro-3'-(piperidine-1-carbonyl)-[1,1'-biphenyl]-3-yl)-5-(trans-2-(1-methyl-1H-1,2,3-triazol-4-yl)cyclopropyl)-1H-pyrazole-4-carboxylic Acid

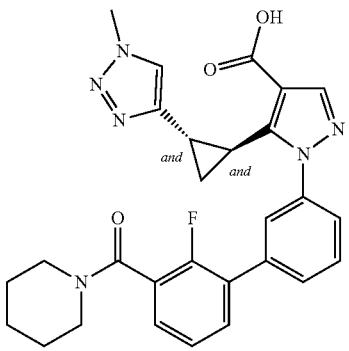 [SMILES: Cn1cc([C@H]2C[C@@H]2c2c(C(=O)O)cnn2-c2cccc(-c3cccc(C(=O)N4CCCCC4)c3F)c2)nn1]

258a) (2-Fluoro-3-(4,4,5,5-tetramethyl-1,3,2-dioxaborolan-2-yl)phenyl)(piperidin-1-yl)methanone

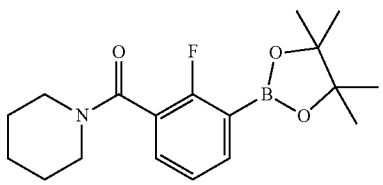 [SMILES: CC1(C)OB(c2cccc(C(=O)N3CCCCC3)c2F)OC1(C)C]

To a solution of 2-fluoro-3-(4,4,5,5-tetramethyl-1,3,2-dioxaborolan-2-yl)benzoic acid (250 mg, 0.940 mmol) in dichloromethane (DCM) (5.0 mL), piperidine (0.093 mL, 0.940 mmol), HATU (357 mg, 0.940 mmol) and DIPEA (0.41 mL, 2.349 mmol) were added. The reaction mixture was stirred at room temperature for 2 h. The reaction mixture was quenched with saturated aqueous NaHCO$_3$. The organic layer was separated and then washed with water and brine. The aqueous phase was backextracted with DCM. The organic layers were combined, dried over magnesium sulfate, filtered and concentrated under reduced pressure. The crude material was purified by silica gel chromatography (0-100% EtOAc/hexanes gradient) to afford 242 mg of the title compound. LC-MS m/z 334.3 (M+H)$^+$, 1.04 min (ret. time).

258b) Ethyl 1-(2'-fluoro-3'-(piperidine-1-carbonyl)-[1,1'-biphenyl]-3-yl)-5-(trans-2-(1-methyl-1H-1,2,3-triazol-4-yl)cyclopropyl)-1H-pyrazole-4-carboxylate

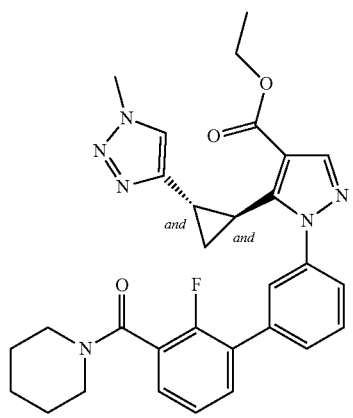 [SMILES: CCOC(=O)c1cnn(-c2cccc(-c3cccc(C(=O)N4CCCCC4)c3F)c2)c1[C@H]1C[C@@H]1c1cn(C)nn1]

To a solution of (2-fluoro-3-(4,4,5,5-tetramethyl-1,3,2-dioxaborolan-2-yl)phenyl)(piperidin-1-yl)methanone (100 mg, 0.300 mmol) in ethanol (1.0 mL) and toluene (3.0 mL) was added ethyl 1-(3-bromophenyl)-5-(trans-2-(1-methyl-1H-1,2,3-triazol-4-yl)cyclopropyl)-1H-pyrazole-4-carboxylate (80 mg, 0.192 mmol) and sodium carbonate (61.1 mg, 0.577 mmol). PdCl$_2$(dppf) (14.1 mg, 0.019 mmol) was then added. The reaction mixture was stirred at 95° C. for 17 h. The reaction mixture was cooled to room temperature and partitioned between water and EtOAc. The organic phase was washed with water and then brine. The aqueous phase was extracted with EtOAc. The organic phases were combined, dried over magnesium sulfate, filtered and concentrated under reduced pressure. The crude material was purified by Gilson HPLC (solubilisation solvent: DMSO; acidic condition; eluent graduation: 30-90% ACN) to get 88.2 mg of the title compound (85% yield). LC-MS m/z 543.4 (M+H)$^+$, 0.98 min (ret. time).

258c) 1-(2'-Fluoro-3'-(piperidine-1-carbonyl)-[1,1'-biphenyl]-3-yl)-5-(trans-2-(1-methyl-1H-1,2,3-triazol-4-yl)cyclopropyl)-1H-pyrazole-4-carboxylic Acid

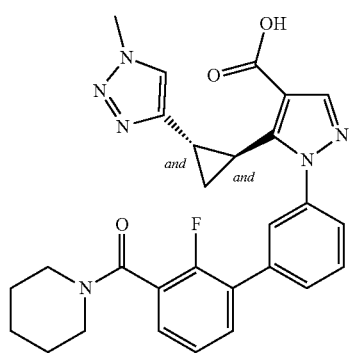 [SMILES: Cn1cc([C@H]2C[C@@H]2c2c(C(=O)O)cnn2-c2cccc(-c3cccc(C(=O)N4CCCCC4)c3F)c2)nn1]

To a solution of ethyl 1-(2'-fluoro-3'-(piperidine-1-carbonyl)-[1,1'-biphenyl]-3-yl)-5-(trans-2-(1-methyl-1H-1,2,3-triazol-4-yl)cyclopropyl)-1H-pyrazole-4-carboxylate (90 mg, 0.166 mmol) in ethanol (3.0 mL) and a few drops of water, LiOH (199 mg, 8.29 mmol) was added. The reaction mixture was stirred at 25° C. for 16 h. The reaction mixture was quenched with 1N aqueous HCl to pH=1. It was then partitioned between DCM and water. The organic phase was dried over magnesium sulfate, filtered and concentrated under reduced pressure. The crude material was then purified by Gilson HPLC (neutral condition; graduation: 20-80% ACN) to get 49.5 mg of desired product (58% yield). LC-MS m/z 515.3 (M+H)$^+$, 0.84 min (ret. time)

Example 259. 1-(2'-Fluoro-3'-(3,3-dimethylpiperidine-1-carbonyl)-[1,1'-biphenyl]-3-yl)-5-(trans-2-(1-methyl-1H-1,2,3-triazol-4-yl)cyclopropyl)-1H-pyrazole-4-carboxylic Acid

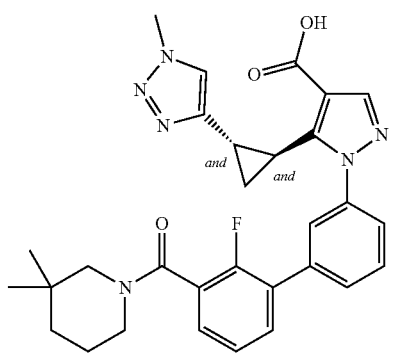 [SMILES: Cn1cc([C@H]2C[C@@H]2c2c(C(=O)O)cnn2-c2cccc(-c3cccc(C(=O)N4CCCC(C)(C)C4)c3F)c2)nn1]

259a) (3,3-Dimethylpiperidin-1-yl)(2-fluoro-3-(4,4,5,5-tetramethyl-1,3,2-dioxaborolan-2-yl)phenyl)methanone and (3-(3,3-dimethylpiperidine-1-carbonyl)-2-fluorophenyl)boronic Acid

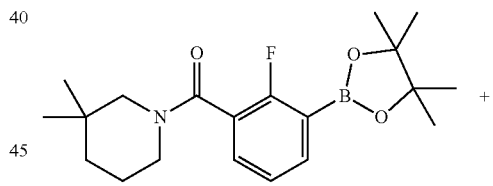

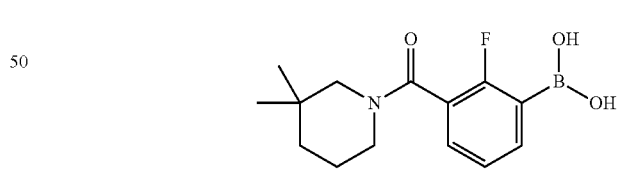

To a solution of 2-fluoro-3-(4,4,5,5-tetramethyl-1,3,2-dioxaborolan-2-yl)benzoic acid (250 mg, 0.940 mmol) in dichloromethane (DCM) (5.0 mL), 3,3-dimethylpiperidine (0.12 mL, 0.940 mmol), HATU (357 mg, 0.940 mmol) and DIPEA (0.41 mL, 2.349 mmol) were added. The reaction mixture was stirred at room temperature for 2 h. The reaction mixture was quenched with saturated aqueous NaHCO$_3$. The organic layer was separated and then washed with water and brine. The aqueous phase was backextracted with DCM. The organic layers were combined, dried over magnesium sulfate, filtered and concentrated under reduced pressure. The crude material was purified by silica gel chromatography (0-100% EtOAc/hexanes gradient) to afford 242 mg of a 3:2 mixture of (3,3-dimethylpiperidin-1-yl)(2-fluoro-3-(4,4,5,5-tetramethyl-1,3,2-dioxaborolan-2-yl)phenyl)methanone and (3-(3,3-dimethylpiperidine-1-carbonyl)-2-fluorophenyl)boronic acid. LC-MS m/z 362.3 (M+H)$^+$, 1.15 min (ret. time) and m/z 280.2 (M+H)$^+$, 0.74 min (ret. time), respectively.

259b) Ethyl 1-(3'-(3,3-dimethylpiperidine-1-carbonyl)-2'-fluoro-[1,1'-biphenyl]-3-yl)-5-(trans-2-(1-methyl-1H-1,2,3-triazol-4-yl)cyclopropyl)-1H-pyrazole-4-carboxylate

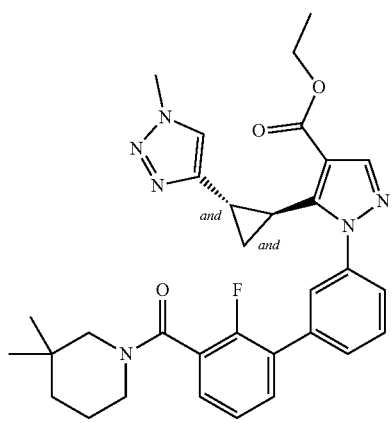 [SMILES: CCOC(=O)c1cnn(-c2cccc(-c3cccc(C(=O)N4CCCC(C)(C)C4)c3F)c2)c1[C@H]1C[C@@H]1c1cn(C)nn1]

To a solution a 3:2 mixture of (3,3-dimethylpiperidin-1-yl)(2-fluoro-3-(4,4,5,5-tetramethyl-1,3,2-dioxaborolan-2-yl)phenyl)methanone and (3-(3,3-dimethylpiperidine-1-carbonyl)-2-fluorophenyl)boronic acid (Example 93a, 90 mg) in ethanol (1.0 mL) and toluene (3.0 mL), ethyl 1-(3-bromophenyl)-5-(trans-2-(1-methyl-1H-1,2,3-triazol-4-yl)cyclopropyl)-1H-pyrazole-4-carboxylate (80 mg, 0.192 mmol) and sodium carbonate (61.1 mg, 0.577 mmol) were added. PdCl$_2$(dppf) (141 mg, 0.192 mmol) was added. The reaction mixture was stirred at 95° C. for 3.5 h. The reaction was recharged with the boronic ester (50 mg) and the reaction mixture was stirred at 95° C. for 2 h. The reaction was still incomplete. The reaction was once more recharged with boronic ester (60 mg), sodium carbonate (80 mg) and PdCl$_2$(dppf) (15 mg). The reaction mixture was stirred at 95° C. for 16 h. EtOAc (15 mL) was added to the reaction mixture. This organic layer was then washed with water (1×15 mL) and then brine (2×10 mL). The aqueous phase was backextracted with EtOAc (2×20 mL). The combined organic layers were dried over magnesium sulfate, filtered and concentrated under reduced pressure. The crude material was purified by Gilson HPLC (acidic condition; graduation: 30-90% of ACN for 10 min) to afford 118 mg of the title compound (94% yield). LC-MS m/z 571.6 (M+H)$^+$, 1.07 min (ret. time).

259c) 1-(2'-Fluoro-3'-(3,3-dimethylpiperidine-1-carbonyl)-[1,1'-biphenyl]-3-yl)-5-(trans-2-(1-methyl-1H-1,2,3-triazol-4-yl)cyclopropyl)-1H-pyrazole-4-carboxylic Acid

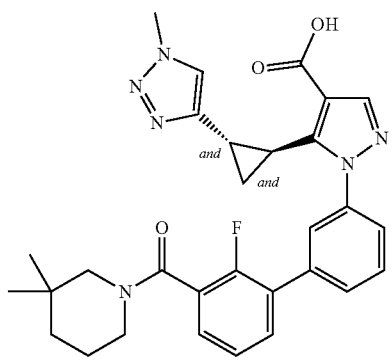 [SMILES: Cn1cc([C@H]2C[C@@H]2c2c(C(=O)O)cnn2-c2cccc(-c3cccc(C(=O)N4CCCC(C)(C)C4)c3F)c2)nn1]

To a solution of ethyl 1-(3'-(3,3-dimethylpiperidine-1-carbonyl)-2'-fluoro-[1,1'-biphenyl]-3-yl)-5-(trans-2-(1-methyl-1H-1,2,3-triazol-4-yl)cyclopropyl)-1H-pyrazole-4-carboxylate (115 mg, 0.202 mmol) in ethanol (3.0 mL) and a few drops of water, LiOH (241 mg, 10.08 mmol) was added. The reaction mixture was stirred at 25° C. for 72 h. The reaction mixture was quenched with 1N aqueous HCl to pH=1. It was then partitioned between DCM and water. The organic phase was separated and dried over magnesium sulfate, filtered and concentrated under reduced pressure. The crude material was purified by Gilson HPLC (neutral condition; graduation: 20-80% of ACN for 10 min) to afford the title compound (34.3 mg, 31.4% yield). LC-MS m/z 543.5 (M+H)$^+$, 0.92 min (ret. time).

Example 260. 1-(2'-Fluoro-3'-(azepane-1-carbonyl)-[1,1'-biphenyl]-3-yl)-5-(trans-2-(1-methyl-1H-1,2,3-triazol-4-yl)cyclopropyl)-1H-pyrazole-4-carboxylic Acid

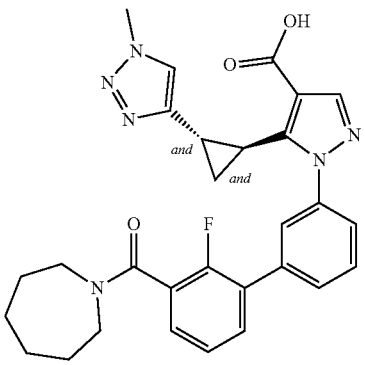 [SMILES: Cn1cc([C@H]2C[C@@H]2c2c(C(=O)O)cnn2-c2cccc(-c3cccc(C(=O)N4CCCCCC4)c3F)c2)nn1]

260a) Azepan-1-yl(2-fluoro-3-(4,4,5,5-tetramethyl-1,3,2-dioxaborolan-2-yl)phenyl)methanone

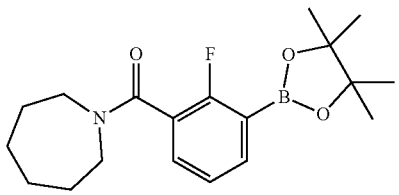 [SMILES: CC1(C)OB(c2cccc(C(=O)N3CCCCCC3)c2F)OC1(C)C]

To a solution of 2-fluoro-3-(4,4,5,5-tetramethyl-1,3,2-dioxaborolan-2-yl)benzoic acid (250 mg, 0.940 mmol) in dichloromethane (DCM) (5.0 mL), azepane (0.13 mL, 1.128 mmol), HATU (357 mg, 0.940 mmol) and DIPEA (0.41 mL, 2.349 mmol) were added. The reaction mixture was stirred at room temperature for 19.5 h. The reaction mixture was quenched with saturated aqueous NaHCO$_3$ and diluted with DCM (5 mL). The organic layer was separated and then washed with water (2×15 mL) and brine (1×15 mL). The aqueous phase was backextracted with DCM (1×20 mL). The organic layers were combined, dried over magnesium sulfate, filtered and concentrated under reduced pressure. The crude material was purified by silica gel chromatography (0-80% EtOAc/hexanes gradient) to afford 200 mg of the title compound (61.2% yield). LC-MS m/z 362.3 (M+H)$^+$, 1.15 min (ret. time)

260b) Ethyl 1-(3'-(azepane-1-carbonyl)-2'-fluoro-[1,1'-biphenyl]-3-yl)-5-(trans-2-(1-methyl-1H-1,2,3-triazol-4-yl)cyclopropyl)-1H-pyrazole-4-carboxylate

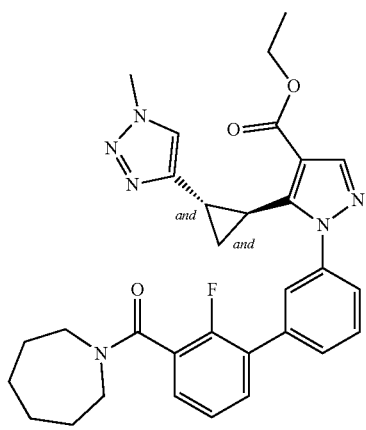 [SMILES: CCOC(=O)c1cnn(-c2cccc(-c3cccc(C(=O)N4CCCCCC4)c3F)c2)c1[C@H]1C[C@@H]1c1cn(C)nn1]

To a solution of azepan-1-yl(2-fluoro-3-(4,4,5,5-tetramethyl-1,3,2-dioxaborolan-2-yl)phenyl)methanone (110 mg, 0.317 mmol) in ethanol (1.0 mL) and toluene (3.0 mL), ethyl 1-(3-bromophenyl)-5-(trans-2-(1-methyl-1H-1,2,3-triazol-4-yl)cyclopropyl)-1H-pyrazole-4-carboxylate (80 mg, 0.192 mmol) and sodium carbonate (61.1 mg, 0.577 mmol) were added. PdCl$_2$(dppf) (141 mg, 0.192 mmol) was then added. The reaction mixture was stirred at 95° C. for 18 h. The reaction was cooled to room temperature and the mixture was partitioned between water and EtOAc. The organic layer was separated and with water and brine. The aqueous phase was backextracted with EtOAc. The combined organic layers were combined, dried over magnesium sulfate, filtered and concentrated under reduced pressure. The crude material was purified by Gilson HPLC (solubilisation solvent: DMSO; acidic condition; graduation: 30-90% of ACN for 10 min) to get 105.6 mg title compound (60.0% yield). LC-MS m/z 571.6 (M+H)$^+$, 1.07 min (ret. time).

260c) 1-(2'-Fluoro-3'-(azepane-1-carbonyl)-[1,1'-biphenyl]-3-yl)-5-(trans-2-(1-methyl-1H-1,2,3-triazol-4-yl)cyclopropyl)-1H-pyrazole-4-carboxylic Acid

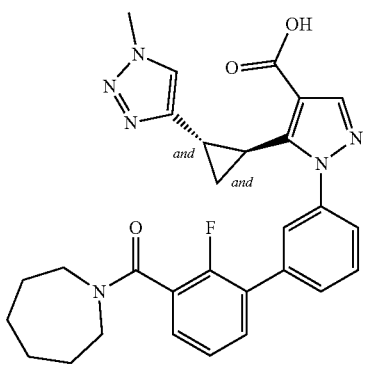 [SMILES: Cn1cc([C@H]2C[C@@H]2c2c(C(=O)O)cnn2-c2cccc(-c3cccc(C(=O)N4CCCCCC4)c3F)c2)nn1]

To a solution of ethyl 1-(3'-(azepane-1-carbonyl)-2'-fluoro-[1,1'-biphenyl]-3-yl)-5-(2-(1-methyl-1H-1,2,3-triazol-4-yl)cyclopropyl)-1H-pyrazole-4-carboxylate (105 mg, 0.189 mmol) in ethanol (3.0 mL) and a few drops of water, LiOH (226 mg, 9.43 mmol) was added. The reaction mixture was stirred at 25° C. for 72 h. The reaction mixture was quenched with 1N aqueous HCl to pH=1. It was then partitioned between DCM and water. The organic phase was separated and dried over magnesium sulfate, filtered and concentrated under reduced pressure. The crude material was purified by Gilson HPLC (neutral condition; graduation: 20-80% of ACN for 10 min) to afford the title compound (34.6 mg, 33.0% yield). LC-MS m/z 557.0 (M+H)$^+$, 1.00 min (ret. time).

Example 261. 1-(3'-((2R,6S)-2,6-Dimethylpiperidine-1-carbonyl)-2'-fluoro-[1,1'-biphenyl]-3-yl)-5-(trans-2-(1-methyl-1H-1,2,3-triazol-4-yl)cyclopropyl)-1H-pyrazole-4-carboxylic Acid

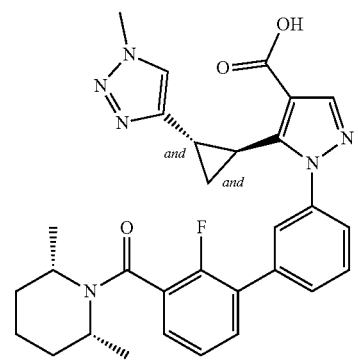 [SMILES: C[C@@H]1CCC[C@H](C)N1C(=O)c1cccc(-c2cccc(-n3ncc(C(=O)O)c3[C@H]3C[C@@H]3c3cn(C)nn3)c2)c1F]

261a) ((2R,6S)-2,6-Dimethylpiperidin-1-yl)(2-fluoro-3-(4,4,5,5-tetramethyl-1,3,2-dioxaborolan-2-yl)2-fluorophenyl)methanone

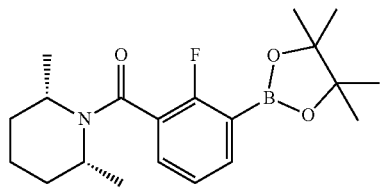 [SMILES: C[C@@H]1CCC[C@H](C)N1C(=O)c1cccc(B2OC(C)(C)C(C)(C)O2)c1F]

To a solution of 2-fluoro-3-(4,4,5,5-tetramethyl-1,3,2-dioxaborolan-2-yl)benzoic acid (250 mg, 0.940 mmol) in dichloromethane (DCM) (5.0 mL), (2R,6S)-2,6-dimethylpiperidine (106 mg, 0.940 mmol), HATU (357 mg, 0.940 mmol) and DIPEA (0.41 mL, 2.349 mmol) were added. The reaction mixture was stirred at room temperature for 19 h. The reaction mixture was partitioned between water and DCM. The organic phase was separated and dried over magnesium sulfate, filtered and concentrate under reduced pressure. The title compound was isolated (155 mg, 45.7% yield) was used in the next step without further purification. LC-MS m/z 362.4 (M+H)$^+$, 1.15 min (ret. time).

261b) Ethyl 1-(3'-((2R,6S)-2,6-dimethylpiperidine-1-carbonyl)-2'-fluoro-[1,1'-biphenyl]-3-yl)-5-(trans-2-(1-methyl-1H-1,2,3-triazol-4-yl)cyclopropyl)-1H-pyrazole-4-carboxylate

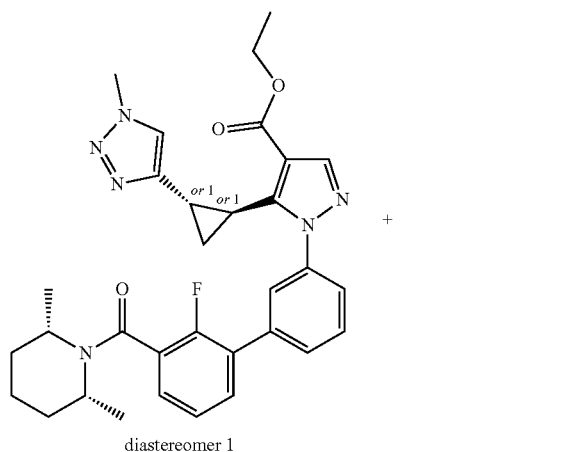

To a solution of ((2R,6S)-2,6-dimethylpiperidin-1-yl)(2-fluoro-3-(4,4,5,5-tetramethyl-1,3,2-dioxaborolan-2-yl)2-fluorophenyl)methanone (107.7 mg, 0.298 mmol) in ethanol (1.0 mL) and toluene (3.0 mL), ethyl 1-(3-bromophenyl)-5-(trans-2-(1-methyl-1H-1,2,3-triazol-4-yl)cyclopropyl)-1H-pyrazole-4-carboxylate (80 mg, 0.192 mmol) and sodium carbonate (61.1 mg, 0.577 mmol) were added. Tetrakis(triphenylphosphine)palladium(0) (22.2 mg, 0.019 mmol) was added. The reaction mixture was stirred at 95° C. for 16 h. Addition boronic acid (53.2 mg. 0.193 mmol), sodium carbonate (60 mg, 0.577 mmol) and tetrakis(triphenylphosphine)palladium(0) (20 mg, 0.018 mmol) were added. The reaction mixture was stirred at 95° C. for 4 h. The reaction mixture was partitioned between water and EtOAc. The organic phase was separated and washed with water and brine. The aqueous phase was backextracted with EtOAc. The combined organic layers were dried over magnesium sulfate, filtered and concentrated under reduced pressure. The crude material was then purified by Gilson HPLC (acidic condition; graduation: 40-90% of ACN for 10 min) to afford the title compound as separated diastereomers of trans cyclopropyl groups of unconfirmed diastereomeric relation: 47.8 mg of diastereomer 1 (42.3% yield) and 18.9 mg of diastereomer 2 (13.8% yield). LC-MS m/z 571.5 (M+H)$^+$, 1.09 min (ret. time) and LC-MS m/z 571.5 (M+H)$^+$, 1.08 min (ret. time), respectively.

261c) 1-(3'-((2R,6S)-2,6-Dimethylpiperidine-1-carbonyl)-2'-fluoro-[1,1'-biphenyl]-3-yl)-5-(trans-2-(1-methyl-1H-1,2,3-triazol-4-yl)cyclopropyl)-1H-pyrazole-4-carboxylic Acid

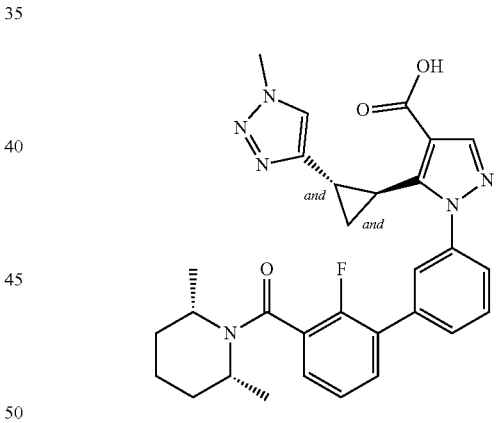

To a solution of ethyl 1-(3'-((2R,6S)-2,6-dimethylpiperidine-1-carbonyl)-2'-fluoro-[1,1'-biphenyl]-3-yl)-5-(trans-2-(1-methyl-1H-1,2,3-triazol-4-yl)cyclopropyl)-1H-pyrazole-4-carboxylate from Example 261b (40 mg, 0.070 mmol, diastereomer 1) in ethanol (3.0 mL) and water (0.2 mL), LiOH (84 mg, 3.50 mmol) was added. The reaction mixture was stirred at 25° C. for 16 h. The reaction mixture was quenched with 1N aqueous HCl to pH=1. It was then partitioned between DCM and water. The organic phase separated and dried over magnesium sulfate, filtered and concentrated under reduced pressure. The crude material was then purified by Gilson HPLC (neutral condition) to get 3.5 mg of desired product. (9.2% yield). LC-MS m/z 543.5 (M+H)$^+$, 0.92 min (ret. time).

Example 262. 1-(3'-((2R,6S)-2,6-dimethylpiperi-dine-1-carbonyl)-2'-fluoro-[1,1'-biphenyl]-3-yl)-5-(trans-2-(1-methyl-1H-1,2,3-triazol-4-yl)cyclopropyl)-1H-pyrazole-4-carboxylic Acid

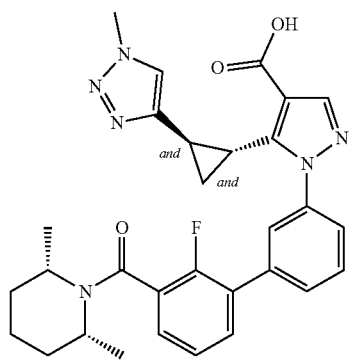 [SMILES: C[C@@H]1CCC[C@H](C)N1C(=O)c1cccc(-c2cccc(-n3ncc(C(=O)O)c3[C@@H]3C[C@H]3c3cn(C)nn3)c2)c1F]

262a) 1-(3'-((2R,6S)-2,6-dimethylpiperidine-1-carbonyl)-2'-fluoro-[1,1'-biphenyl]-3-yl)-5-(trans-2-(1-methyl-1H-1,2,3-triazol-4-yl)cyclopropyl)-1H-pyrazole-4-carboxylic Acid To a solution of ethyl 1-(3'-((2R,6S)-2,6-dimethylpiperidine-1-carbonyl)-2'-fluoro-[1,1'-biphenyl]-3-yl)-5-(trans-2-(1-methyl-1H-1,2,3-triazol-4-yl)cyclopropyl)-1H-pyrazole-4-carboxylate from Example 261 b (18 mg, 0.032 mmol, diastereomer 2) in ethanol (3.0 mL) and water (0.2 mL), LiOH (38 mg, 1.58 mmol) was added. The reaction mixture was stirred at 25° C. for 16 h. The reaction mixture was quenched with 1N aqueous HCl to pH=1. It was then partitioned between DCM and water. The organic phase separated and dried over magnesium sulfate, filtered and concentrated under reduced pressure. The crude material was then purified by Gilson HPLC (neutral condition) to get 3.5 mg of desired product. (9.2% yield). LC-MS m/z 543.5 (M+H)+, 0.93 min (ret. time).

Example 263. 1-(3'-(3,5-Dimethylpiperidine-1-carbonyl)-2'-fluoro-[1,1'-biphenyl]-3-yl)-5-(2-(1-methyl-1H-1,2,3-triazol-4-yl)cyclopropyl)-1H-pyrazole-4-carboxylic Acid

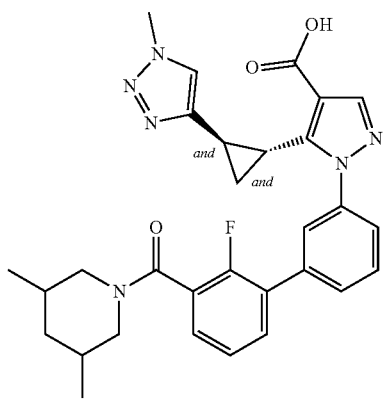 [SMILES: CC1CC(C)CN(C(=O)c2cccc(-c3cccc(-n4ncc(C(=O)O)c4[C@@H]4C[C@H]4c4cn(C)nn4)c3)c2F)C1]

263a) (3,5-Dimethylpiperidin-1-yl)(2-fluoro-3-(4,4,5,5-tetramethyl-1,3,2-dioxaborolan-2-yl)phenyl)methanone

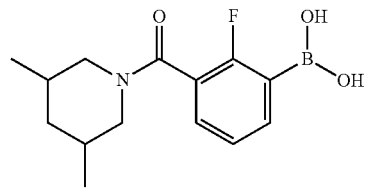 [SMILES: CC1CC(C)CN(C(=O)c2cccc(B(O)O)c2F)C1]

To a solution of 2-fluoro-3-(4,4,5,5-tetramethyl-1,3,2-dioxaborolan-2-yl)benzoic acid (250 mg, 0.940 mmol) in dichloromethane (DCM) (5.0 mL), 3,5-dimethylpiperidine (106 mg, 0.940 mmol), HATU (357 mg, 0.940 mmol) and DIPEA (0.41 mL, 2.349 mmol) were added. The reaction mixture was stirred at room temperature. After 18 h, more 3,5-dimethylpiperidine (50 mg, 0.442 mmol)), HATU (180 mg, 0.473 mmol) and DIPEA (0.2 mL, 1.169 mmol)) were added. The reaction mixture was stirred at room temperature for 30 h. The reaction mixture was quenched with saturated aqueous NaHCO3 and then washed with water and brine. The aqueous phase was backextracted with DCM. The combined organic layers were combined, dried over magnesium sulfate, filtered and concentrated under reduced pressure. The crude material was purified by silica gel chromatography (0-100% EtOAc/hexanes gradient) to afford 213 mg of the title compound (64.1% yield). LC-MS m/z 362.3 (M+H)+, 1.18 min (ret. time).

263b) Ethyl 1-(3'-(3,5-dimethylpiperidine-1-carbonyl)-2'-fluoro-[1,1'-biphenyl]-3-yl)-5-(trans-2-(1-methyl-1H-1,2,3-triazol-4-yl)cyclopropyl)-1H-pyrazole-4-carboxylate

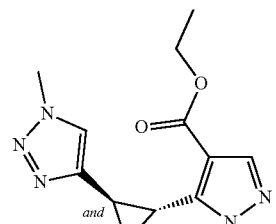
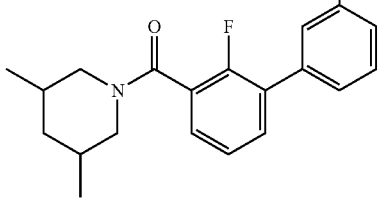

To a solution of (3,5-dimethylpiperidin-1-yl)(2-fluoro-3-(4,4,5,5-tetramethyl-1,3,2-dioxaborolan-2-yl)phenyl)methanone (110 mg, 0.304 mmol) in ethanol (1.33 mL) and toluene (4.0 mL), ethyl 1-(3-bromophenyl)-5-(trans-2-(1-methyl-1H-1,2,3-triazol-4-yl)cyclopropyl)-1H-pyrazole-4-carboxylate (80 mg, 0.192 mmol) and sodium carbonate (100 mg, 0.943 mmol) were added. PdCl2(dppf) (20 mg, 0.027 mmol) was added. The reaction mixture was stirred at 95° C. for 20 h. The reaction was cooled to room temperature and EtOAc (15 mL) was added to the reaction mixture. The organic layer was then washed with water (1×15 mL)

and brine (2×10 mL). The aqueous laphase was backextracted with EtOAc (2×20 mL). The combined organic layers were combined, dried over magnesium sulfate, filtered and concentrated under reduced pressure. The crude material was then purified by Gilson HPLC (acidic condition; graduation: 40-90% of ACN for 10 min) to afford the title compound (93.4 mg, 81.0% yield) in about a 7:1 ratio of unconfirmed diastereomers on the piperidine ring. LC-MS m/z 571.3 (M+H)$^+$, 1.14 min (ret. time, minor) and 1.17 min (ret. time, major).

263c) 1-(3'-(3,5-Dimethylpiperidine-1-carbonyl)-2'-fluoro-[1,1'-biphenyl]-3-yl)-5-(2-(1-methyl-1H-1,2,3-triazol-4-yl)cyclopropyl)-1H-pyrazole-4-carboxylic Acid

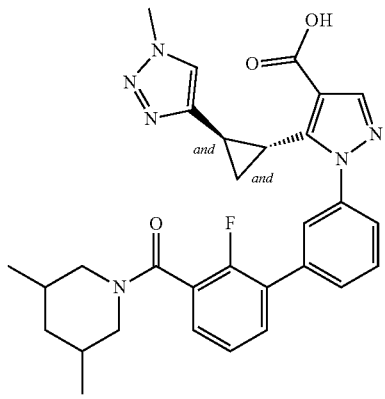 [SMILES: CC1CC(C)CN(C(=O)c2cccc(-c3cccc(-n4ncc(C(=O)O)c4[C@@H]4C[C@H]4c4cn(C)nn4)c3)c2F)C1]

To a solution of ethyl 1-(3'-(3,5-dimethylpiperidine-1-carbonyl)-2'-fluoro-[1,1'-biphenyl]-3-yl)-5-(trans-2-(1-methyl-1H-1,2,3-triazol-4-yl)cyclopropyl)-1H-pyrazole-4-carboxylate (87 mg, 0.152 mmol) in ethanol (3.0 mL) and in a few drops of water, LiOH (183 mg, 7.62 mmol) was added. The reaction mixture was stirred at 25° C. for 46 h. The reaction mixture was quenched with 1N aqueous HCl to pH=1. It was then partitioned between DCM and water. The organic phase was separated and dried over magnesium sulfate, filtered and concentrated under reduced pressure. The crude material was then purified by Gilson HPLC (neutral condition; graduation: 30-90% of ACN for 10 min) to get 44.2 mg of the title product (51.8% yield). LC-MS m/z 543.1 (M+H)$^+$, 0.96 min (ret. time).

Example 264. 1-(3'-(2-(Methoxymethyl)piperidine-1-carbonyl)-2'-fluoro-[1,1'-biphenyl]-3-yl)-5-(trans-2-(1-methyl-1H-1,2,3-triazol-4-yl)cyclopropyl)-1H-pyrazole-4-carboxylic Acid

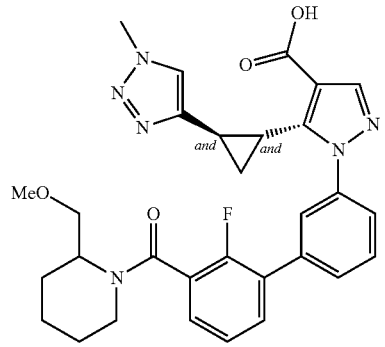

264a) (2-Fluoro-3-(4,4,5,5-tetramethyl-1,3,2-dioxaborolan-2-yl)phenyl)(2-(methoxymethyl)piperidin-1-yl)methanone and (2-fluoro-3-(2-(methoxymethyl)piperidine-1-carbonyl)phenyl)boronic Acid

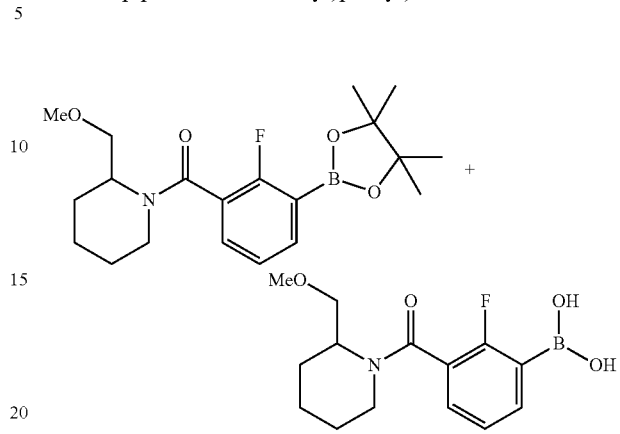

To a solution of 2-fluoro-3-(4,4,5,5-tetramethyl-1,3,2-dioxaborolan-2-yl)benzoic acid (250 mg, 0.940 mmol) in dichloromethane (DCM) (5 mL), 2-(methoxymethyl)piperidine (158 mg, 1.221 mmol), HATU (357 mg, 0.940 mmol) and DIPEA (0.410 mL, 2.349 mmol) were added. The reaction mixture was stirred at room temperature for 25 h. The reaction mixture was quenched with saturated aqueous NaHCO$_3$ and then washed with water and brine. The aqueous phase was backextracted with DCM. The combined organic layers were combined, dried over magnesium sulfate, filtered and concentrated under reduced pressure. The crude material was purified by silica gel chromatography (0-100% EtOAc/hexanes gradient) to afford 236.3 mg of a mixture of pinacol ester and boronic acid. LC-MS m/z 378.4 (M+H)$^+$, 1.06 min (ret. time) and m/z 296.3 (M+H)$^+$, 0.64 min (ret. time), respectively.

264b) Ethyl 1-(2'-fluoro-3'-(2-(methoxymethyl)piperidine-1-carbonyl)-[1,1'-biphenyl]-3-yl)-5-(trans-2-(1-methyl-1H-1,2,3-triazol-4-yl)cyclopropyl)-1H-pyrazole-4-carboxylate

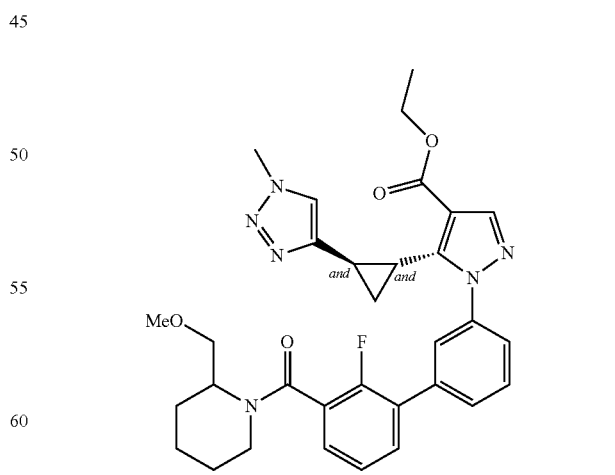

To a solution of the mixture of (2-fluoro-3-(4,4,5,5-tetramethyl-1,3,2-dioxaborolan-2-yl)phenyl)(2-(methoxymethyl)piperidin-1-yl)methanone and (2-fluoro-3-(2-(methoxymethyl)piperidine-1-carbonyl)phenyl)boronic acid (113 mg) in ethanol (1.0 mL) and toluene (3.0 mL), ethyl 1-(3-bromophenyl)-5-(trans-2-(1-methyl-1H-1,2,3-triazol-4-yl)cyclopropyl)-1H-pyrazole-4-carboxylate (80 mg, 0.192 mmol) and sodium carbonate (61.1 mg, 0.577 mmol) were added. PdCl$_2$(dppf) (141 mg, 0.192 mmol) was added. The reaction mixture was heated to 95° C. for 16.5 h, at which point additional boron reagent (66 mg) was added and the reaction heated to 95° C. for 2.5 h. The reaction was still incomplete so additional sodium carbonate (65 mg, 0.602 mmol) and PdCl$_2$(dppf) (15 mg, 0.020 mmol) was added. The reaction was heated to 95° C. for 1.5 h to push the reaction to completion. The reaction was cooled to room temperature and EtOAc (10 mL) was added to the reaction mixture. The organic layer was then washed with water (2×10 mL) and brine (1×10 mL). The aqueous laphase was backextracted with EtOAc (2×15 mL). The combined organic layers were combined, dried over magnesium sulfate, filtered and concentrated under reduced pressure. The crude material was then purified by Gilson HPLC (acidic condition; graduation: 40-90% of ACN for 10 min) to afford the title compound (133 mg, quantatative yield). LC-MS m/z 587.2 (M+H)$^+$, 1.00 min (ret. time, minor) and 1.17 min (ret. time, major).

264c) 1-(3'-(2-(Methoxymethyl)piperidine-1-carbonyl)-2'-fluoro-[1,1'-biphenyl]-3-yl)-5-(trans-2-(1-methyl-1H-1,2,3-triazol-4-yl)cyclopropyl)-1H-pyrazole-4-carboxylic Acid

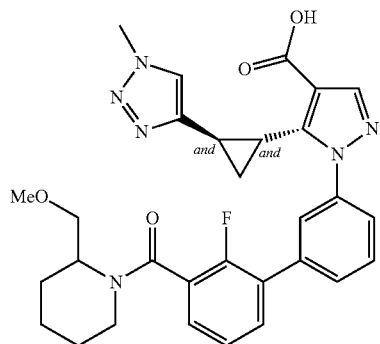

To a solution of ethyl 1-(2'-fluoro-3'-(2-(methoxymethyl)piperidine-1-carbonyl)-[1,1'-biphenyl]-3-yl)-5-(trans-2-(1-methyl-1H-1,2,3-triazol-4-yl)cyclopropyl)-1H-pyrazole-4-carboxylate (130 mg, 0.222 mmol) in ethanol (3.0 mL) and in a few drops of water, LiOH (265 mg, 11.08 mmol) was added. The reaction mixture was heated at 80° C. for 9.5 h and 100° C. for 3 h under microwave irradiation. The reaction mixture was cooled to room temperature and quenched with 1N aqueous HCl to pH=1. It was then partitioned between DCM and water. The organic phase was separated and dried over magnesium sulfate, filtered and concentrated under reduced pressure. The crude material was then purified by Gilson HPLC (neutral condition; graduation: 30-80% of ACN for 10 min) to get 43.1 mg of the title product (51.8% yield). LC-MS m/z 559.2 (M+H)$^+$, 0.87 min (ret. time).

Example 265. 1-(3'-((Cyclopropylmethyl)carbamoyl)-2'-fluoro-[1,1'-biphenyl]-3-yl)-5-(trans-2-(1-methyl-1H-1,2,3-triazol-4-yl)cyclopropyl)-1H-pyrazole-4-carboxylic Acid

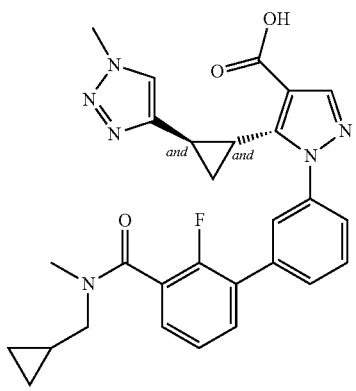

265a) (3-((Cyclopropylmethyl)carbamoyl)-2-fluorophenyl)boronic Acid

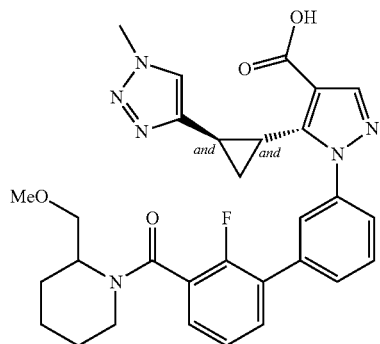

To a solution of 2-fluoro-3-(4,4,5,5-tetramethyl-1,3,2-dioxaborolan-2-yl)benzoic acid (500 mg, 1.879 mmol) in dichloromethane (DCM) (10 mL), cyclopropylmethanamine (0.19 mL, 2.255 mmol), HATU (715 mg, 1.879 mmol) and DIPEA (0.82 mL, 4.70 mmol) were added.

The reaction mixture was stirred at room temperature for 22 h. The reaction mixture was quenched with saturated aqueous NaHCO$_3$. The organic layer was separated and then washed with water and brine. The aqueous layer was backextracted with DCM. The combined organic layers were combined, dried over magnesium sulfate, filtered and concentrated under reduced pressure. The crude material was purified by silica gel chromatography (0-60% EtOAc/hexanes: eluent) to afford 440.3 mg of the title compound (73% yield). LC-MS m/z 319.9 (M+H)$^+$, 1.02 min (ret. time).

265b) (3-(((Cyclopropylmethyl)(methyl)carbamoyl)-2-fluorophenyl)boronic Acid and N-(cyclopropylmethyl)-2-fluoro-N-methyl-3-(4,4,5,5-tetramethyl-1,3,2-dioxaborolan-2-yl)benzamide

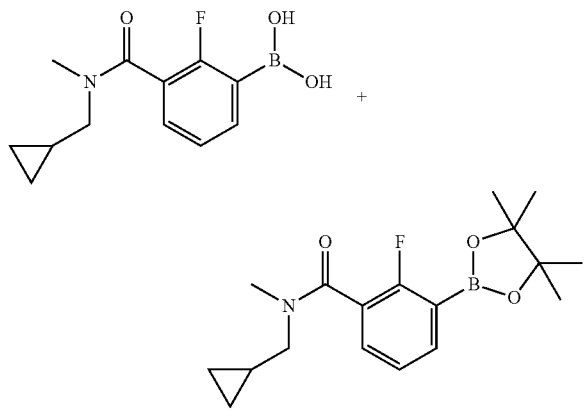

To a solution of N-(cyclopropylmethyl)-2-fluoro-N-methyl-3-(4,4,5,5-tetramethyl-1,3,2-dioxaborolan-2-yl)benzamide (210 mg, 0.658 mmol) in DMF (5 mL), iodomethane (0.091 mL. 1.455 mmol) and sodium hydride (68 mg, 1.766 mmol, 60% dispersion) The reaction mixture was stirred at 80° C. for 5 h. The reaction mixture was cooled to room temperature and carefully quenched with water. This mixture was diluted with DCM and then the organic layer was washed with water and brine. The aqueous phase was backextracted with DCM. The combined organic layers were combined, dried over magnesium sulfate, filtered and concentrated under reduced pressure. The crude material was purified by silica gel chromatography (0-60% EtOAc/hexanes gradient) to afford 64 mg of a 1:1 mixture of the boronic acid and pinacolatoboronate ester. LC-MS m/z 252.2 (M+H)$^+$, 0.62 min (ret. time) and m/z 334.1 (M+H)$^+$, 1.10 min (ret. time), respectively.

265c) Ethyl 1-(3'-((cyclopropylmethyl)(methyl)carbamoyl)-2'-fluoro-[1,1'-biphenyl]-3-yl)-5-(trans-2-(1-methyl-1H-1,2,3-triazol-4-yl)cyclopropyl)-1H-pyrazole-4-carboxylate

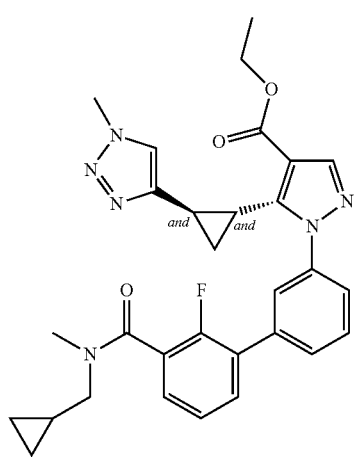

To a solution of (3-((cyclopropylmethyl)(methyl)carbamoyl)-2-fluorophenyl)boronic acid and ester from Example 265b (62.7 mg) in ethanol (1.0 mL) and toluene (3.0 mL), ethyl 1-(3-bromophenyl)-5-(trans-2-(1-methyl-1H-1,2,3-triazol-4-yl)cyclopropyl)-1H-pyrazole-4-carboxylate (80 mg, 0.192 mmol) and sodium carbonate (61.1 mg, 0.577 mmol) were added. PdCl$_2$(dppf) (14.1 mg, 0.019 mmol) was added. The reaction mixture was heated to 95° C. for 21 h, at which point additional sodium carbonate (70 mg, 0.679 mmol) and PdCl$_2$(dppf) (20 mg, 0.027 mmol) was added and further heated to 100° C. for 2 h to push the reaction to completion. The reaction was cooled to room temperature and DCM (10 mL) was added to the reaction mixture. The organic layer was then washed with water (2×10 mL) and brine (1×10 mL). The aqueous layer was backextracted with DCM (2×15 mL). The combined organic layers were combined, dried over magnesium sulfate, filtered and concentrated under reduced pressure. The crude material was then purified by Gilson HPLC (acidic condition; graduation: 35-70% of ACN for 10 min) to afford the title compound (39 mg, 25.4% yield). LC-MS m/z 543.2 (M+H)$^+$, 1.04 min (ret. time).

265d) 1-(3'-((Cyclopropylmethyl)carbamoyl)-2'-fluoro-[1,1'-biphenyl]-3-yl)-5-(trans-2-(1-methyl-1H-1,2,3-triazol-4-yl)cyclopropyl)-1H-pyrazole-4-carboxylic Acid To a solution of ethyl 1-(3'-((cyclopropylmethyl)(methyl)carbamoyl)-2'-fluoro-[1,1'-biphenyl]-3-yl)-5-(trans-2-(1-methyl-1H-1,2,3-triazol-4-yl)cyclopropyl)-1H-pyrazole-4-carboxylate (39 mg, 0.072 mmol) in ethanol (2.0 mL) and water (0.1 mL), LiOH (51.6 mg, 2.16 mmol) was added. The reaction mixture was heated at 80° C. for 9.5 h and 100° C. for 3 h under microwave irradiation. The reaction mixture was cooled to room temperature and quenched with 1N aqueous HCl to pH=1. It was then partitioned between DCM and water. The organic phase was separated and dried over magnesium sulfate, filtered and concentrated under reduced pressure. The crude material was then purified by Gilson HPLC (neutral condition) to get 4 mg of the title product (10.8% yield). LC-MS m/z 515.2 (M+H)$^+$, 0.89 min (ret. time)

Example 266. 1-(2'-Fluoro-3'(isobutyl(methyl)carbamoyl)-[1,1'-biphenyl]-3-yl)-5-(trans-2-(1-methyl-1H-1,2,3-triazol-4-yl)cyclopropyl)-1H-pyrazole-4-carboxylic Acid

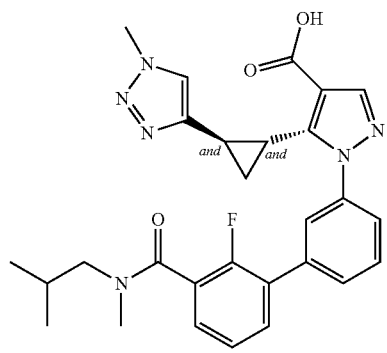

266a) 2-Fluoro-N-isobutyl-N-methyl-3-(4,4,5,5-tetramethyl-1,3,2-dioxaborolan-2yl)benzamide and (2-fluoro-3-(isobutyl(methyl)carbamoyl)phenyl) boronic Acid

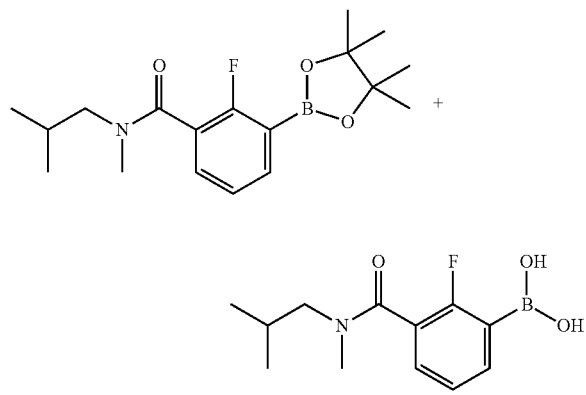

To a solution of (2-fluoro-3-(isobutyl(methyl)carbamoyl)phenyl)boronic acid (100 mg, 0.395 mmol) in dichloromethane (DCM) (5.0 mL), N,2-dimethylpropan-1-amine (0.133 mL, 1.315 mmol), HATU (357 mg, 0.940 mmol) and DIPEA (0.41 mL, 2.349 mmol) were added. The reaction mixture was stirred at room temperature for 3 h. The reaction mixture was quenched with saturated aqueous NaHCO₃ and then washed with water and brine. The aqueous phase was backextracted with DCM. The combined organic layers were combined, dried over magnesium sulfate, filtered and concentrated under reduced pressure. The crude material was purified by silica gel chromatography (0-60% EtOAc/hexanes gradient) to afford 271.5 mg of a 2:1 mixture of the pinacolboron ester to the boronic acid. LC-MS m/z 336.1 (M+H)⁺, 1.13 min (ret. time) and m/z 254.0 (M+H)⁺, 0.67 min (ret. time).

266b) Ethyl 1-(2'-fluoro-3'-(isobutyl(methyl)carbamoyl)-[1,1'-biphenyl]-3-yl)-5-(trans-2-(1-methyl-1H-1,2,3-triazol-4-yl)cyclopropyl)-1H-pyrazole-4-carboxylate

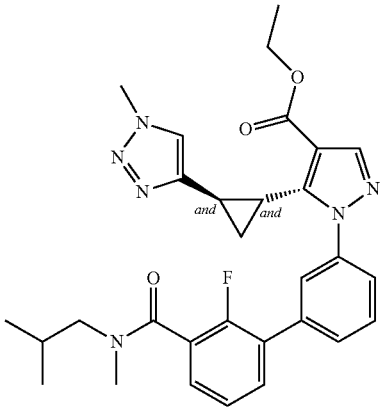

To a solution of a mixture of (2-fluoro-3-(isobutyl(methyl)carbamoyl)phenyl)boronic acid and 2-fluoro-N-isobutyl-N-methyl-3-(4,4,5,5-tetramethyl-1,3,2-dioxaborolan-2yl)benzamide (Example 100a, 100 mg) in ethanol (1.0 mL) and toluene (3.0 mL), ethyl 1-(3-bromophenyl)-5-(trans-2-(1-methyl-1H-1,2,3-triazol-4-yl)cyclopropyl)-1H-pyrazole-4-carboxylate (80 mg, 0.192 mmol) and sodium carbonate (61.1 mg, 0.577 mmol) were added. PdCl₂(dppf) (14.1 mg, 0.019 mmol) was added. The reaction mixture was heated to 95° C. for 23.5 h and further heated to 95° C. under microwave irradiation for 2 h. In order to push the reaction to completion, additional boronic acid (90 mg, 0.305 mmol), sodium carbonate (70 mg, 0.660 mmol), and PdCl₂(dppf) (17.6 mg, 0.024 mmol) was added. The reaction was cooled to room temperature and the mixture was partitioned between EtOAc and water. The organic layer was separated and washed with water (2×10 mL) and brine (1×10 mL). The aqueous phase was backextracted with EtOAc (2×15 mL). The combined organic layers were combined, dried over magnesium sulfate, filtered and concentrated under reduced pressure. The crude material was then purified by Gilson HPLC (acidic condition; graduation: 35-85%) to afford the title compound (54.1 mg, 46.0% yield). LC-MS m/z 545.2 (M+H)⁺, 1.08 min (ret. time).

266c) 1-(2'-Fluoro-3'(isobutyl(methyl)carbamoyl)-[1,1'-biphenyl]-3-yl)-5-(trans-2-(1-methyl-1H-1,2,3-triazol-4-yl)cyclopropyl)-1H-pyrazole-4-carboxylic Acid

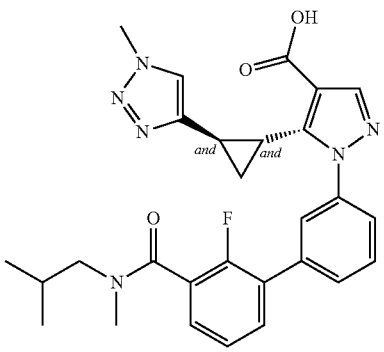

To a solution of ethyl 1-(2'-fluoro-3'-(isobutyl(methyl)carbamoyl)-[1,1'-biphenyl]-3-yl)-5-(trans-2-(1-methyl-1H-1,2,3-triazol-4-yl)cyclopropyl)-1H-pyrazole-4-carboxylate (39 mg, 0.072 mmol) in ethanol (2.0 mL) and water (0.1 mL), LiOH (51.4 mg, 2.15 mmol) was added. The reaction mixture was heated at 80° C. for 1.5 h under microwave irradiation. It was further heated under microwave irradiation to 90° C. for 1 h. The reaction mixture was cooled to room temperature and quenched with 1N aqueous HCl to pH=1. It was then partitioned between DCM and water. The organic phase was separated and dried over magnesium sulfate, filtered and concentrated under reduced pressure. The crude material was then purified by Gilson HPLC (neutral condition; graduation: 30-80% of ACN for 10 min) to afford 24.3 mg of the title product (65.7% yield). LC-MS m/z 517.1 (M+H)$^+$, 0.89 min (ret. time).

Example 267. 1-(3'-((S)-2-(Ethoxymethyl)pyrrolidine-1-carbonyl)-[1,1'-biphenyl]-3-yl)-5-(trans-2-(1-methyl-1H-1,2,3-triazol-4-yl)cyclopropyl)-1H-pyrazole-4-carboxylic Acid

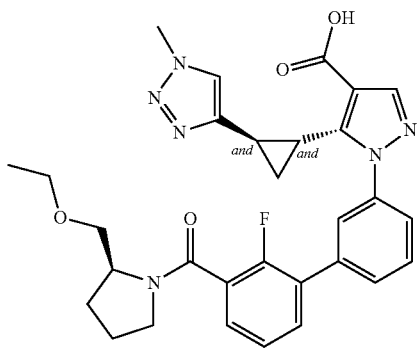

267a) (S)-(2-(ethoxymethyl)pyrrolidin-1-yl)(2-fluoro-3-(4,4,5,5-tetramethyl-1,3,2-dioxaborolan-2-yl)phenyl)methanone

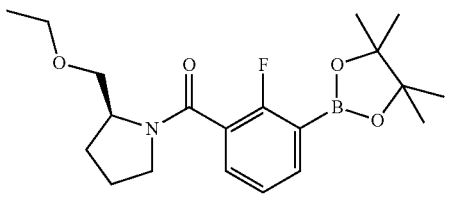 [SMILES: CCOC[C@@H]1CCCN1C(=O)c1cccc(B2OC(C)(C)C(C)(C)O2)c1F]

To a solution of 2-fluoro-3-(4,4,5,5-tetramethyl-1,3,2-dioxaborolan-2-yl)benzoic acid (250 mg, 0.940 mmol) in dichloromethane (DCM) (5.0 mL), N,2-dimethylpropan-1-amine (0.13 mL, 1.315 mmol), HATU (357 mg, 0.940 mmol) and DIPEA (0.41 mL, 2.349 mmol) were added. The reaction mixture was stirred at room temperature for 3 h. The reaction mixture was quenched with saturated aqueous NaHCO$_3$ and then washed with water and brine. The aqueous phase was backextracted with DCM. The combined organic layers were combined, dried over magnesium sulfate, filtered and concentrated under reduced pressure. The crude material was purified by silica gel chromatography (0-60% EtOAc/hexanes gradient) to afford 271.5 mg of the title compound (86% yield). LC-MS m/z 336.1 (M+H)$^+$, 1.13 min (ret. time).

267b) Ethyl 1-(3'-((S)-2-(ethoxymethyl)pyrrolidine-1-carbonyl)-2'-fluoro-[1,1'-biphenyl]-3-yl)-5-(trans-2-(1-methyl-1H-1,2,3-triazol-4-yl)cyclopropyl)-1H-pyrazole-4-carboxylate

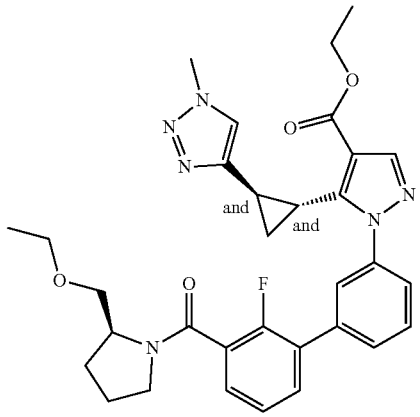 [SMILES: CCOC[C@@H]1CCCN1C(=O)c1cccc(-c2cccc(-n3ncc(C(=O)OCC)c3[C@@H]3C[C@H]3c3cn(C)nn3)c2)c1F]

To a solution of (S)-(3-(2-(ethoxymethyl)pyrrolidine-1-carbonyl)-2-fluorophenyl)boronic acid (100 mg, 0.339 mmol) in ethanol (1.0 mL) and toluene (3.0 mL), ethyl 1-(3-bromophenyl)-5-(trans-2-(1-methyl-1H-1,2,3-triazol-4-yl)cyclopropyl)-1H-pyrazole-4-carboxylate (100 mg, 0.240 mmol) and sodium carbonate (76 mg, 0.721 mmol) were added. PdCl$_2$(dppf) (17.6 mg, 0.024 mmol) was added. The reaction mixture was heated to 95° C. for 2 h. An additional amount of boronic acid (36 mg, 0.112 mmol) was added and further heated to 95° C. under microwave irradiation for 30 min. In order to push the reaction to completion, additional boronic acid (90 mg, 0.305 mmol), sodium carbonate (70 mg, 0.660 mmol), and PdCl$_2$(dppf) (17.6 mg, 0.024 mmol) was added and it was heated to 95° C. under microwave irradiation for 1 h. The reaction was cooled to room temperature and the mixture was partitioned between EtOAc and water. The organic layer was separated and washed with water (2×10 mL) and brine (1×10 mL). The aqueous phase was backextracted with EtOAc (2×15 mL). The combined organic layers were combined, dried over magnesium sulfate, filtered and concentrated under reduced pressure. The crude material was then purified by Gilson HPLC (acidic condition; graduation: 30-90%) to afford the title compound (104.3 mg, 98% yield). LC-MS m/z 587.1 (M+H)$^+$, 1.02 min (ret. time).

267c) 1-(3'-((S)-2-(Ethoxymethyl)pyrrolidine-1-carbonyl)-[1,1'-biphenyl]-3-yl)-5-(trans-2-(1-methyl-1H-1,2,3-triazol-4-yl)cyclopropyl)-1H-pyrazole-4-carboxylic Acid

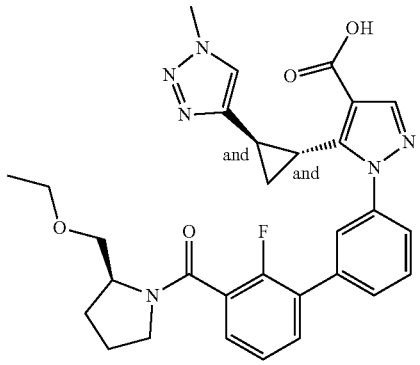 [SMILES: CCOC[C@@H]1CCCN1C(=O)c1cccc(-c2cccc(-n3ncc(C(=O)O)c3[C@@H]3C[C@H]3c3cn(C)nn3)c2)c1F]

To a solution of ethyl 1-(3'-((S)-2-(ethoxymethyl)pyrrolidine-1-carbonyl)-2'-fluoro-[1,1'-biphenyl]-3-yl)-5-(trans-2-(1-methyl-1H-1,2,3-triazol-4-yl)cyclopropyl)-1H-pyrazole-4-carboxylate (140 mg, 0.239 mmol) in ethanol (2.0 mL) and water (0.1 mL), LiOH (171 mg, 7.16 mmol) was added. The reaction mixture was heated at 80° C. for 1.5 h under microwave irradiation. It was further heated under microwave irradiation to 90° C. for 1 h and 100° C. for 6.25 h. The reaction proceeded to about 85% consumption of starting material. The reaction mixture was cooled to room temperature and quenched with 1N aqueous HCl to pH=1. It was then partitioned between DCM and water. The organic phase was separated and dried over magnesium sulfate, filtered and concentrated under reduced pressure. The crude material was then purified by Gilson HPLC (neutral condition; graduation: 35-85% of ACN for 10 min) to afford 61 mg of the title product (43.5% yield). LC-MS m/z 559.2 (M+H)$^+$, 0.91 min (ret. time).

Example 268. 1-(3'-((R)-2-(Ethoxymethyl)pyrrolidine-1-carbonyl)-[1,1'-biphenyl]-3-yl)-5-(trans-2-(1-methyl-1H-1,2,3-triazol-4-yl)cyclopropyl)-1H-pyrazole-4-carboxylic Acid

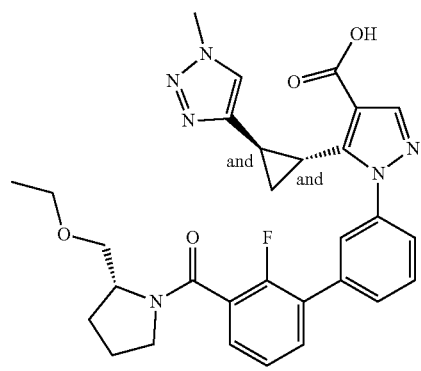 [SMILES: CCOC[C@H]1CCCN1C(=O)c1cccc(-c2cccc(-n3ncc(C(=O)O)c3[C@@H]3C[C@H]3c3cn(C)nn3)c2)c1F]

268a) (R)-(3-(2-(ethoxymethyl)pyrrolidine-1-carbonyl)-2-fluorophenyl)boronic acid and (R)-(2-(ethoxymethyl)pyrrolidin-1-yl)(2-fluoro-3-(4,4,5,5-tetramethyl-1,3,2-dioxaborolan-2-yl)phenyl)methanone

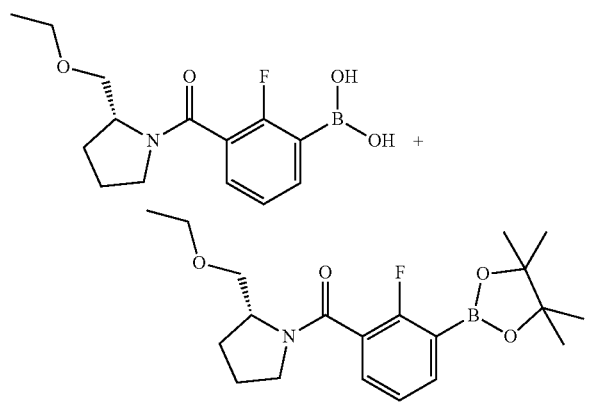

To a solution of 2-fluoro-3-(4,4,5,5-tetramethyl-1,3,2-dioxaborolan-2-yl)benzoic acid (297 mg, 1.12 mmol) in dichloromethane (DCM) (5 mL), (R)-2-(ethoxymethyl)pyrrolidine hydrochloride (222 mg, 1.315 mmol), HATU (424 mg, 1.12 mmol) and DIPEA (0.487 mL, 2.79 mmol) were added. The reaction mixture was stirred at room temperature for 18 h. The reaction mixture was quenched with saturated aqueous NaHCO$_3$ and then washed with water and brine. The aqueous phase was backextracted with DCM. The combined organic layers were combined, dried over magnesium sulfate, filtered and concentrated under reduced pressure. The crude material was purified by silica gel chromatography (0-60% EtOAc/hexanes gradient) to afford 169 mg of the title compound in a 3:1 ratio of the boronic acid to the ester (39% yield). LC-MS m/z 296.0 (M+H)$^+$, 0.64 min (ret. time) and m/z 378.1 (M+H)$^+$, 1.08 min (ret. time), respectively.

268b) Ethyl 1-(3'-((R)-2-(ethoxymethyl)pyrrolidine-1-carbonyl)-2'-fluoro-[1,1'-biphenyl]-3-yl)-5-(trans-2-(1-methyl-1H-1,2,3-triazol-4-yl)cyclopropyl)-1H-pyrazole-4-carboxylate

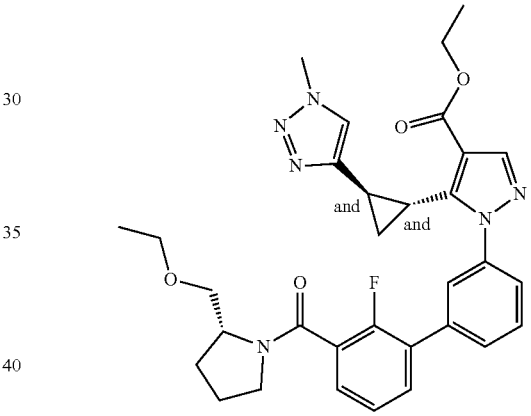

To a solution of a mixture of (R)-(3-(2-(ethoxymethyl)pyrrolidine-1-carbonyl)-2-fluorophenyl)boronic acid and (R)-(2-(ethoxymethyl)pyrrolidin-1-yl)(2-fluoro-3-(4,4,5,5-tetramethyl-1,3,2-dioxaborolan-2-yl)phenyl)methanone (Example 267a, 100 mg) in ethanol (1.0 mL) and toluene (3.0 mL), ethyl 1-(3-bromophenyl)-5-(trans-2-(1-methyl-1H-1,2,3-triazol-4-yl)cyclopropyl)-1H-pyrazole-4-carboxylate (100 mg, 0.240 mmol) and sodium carbonate (76 mg, 0.721 mmol) were added. PdCl$_2$(dppf) (17.6 mg, 0.024 mmol) was added. The reaction mixture was heated to 95° C. for 6.5 h. An additional amount of the mixture of boronic acid/ester (Example 268a, 70 mg) was added and the reaction was heated to 90° C. 23.5 h. The reaction was cooled to room temperature and the mixture was partitioned between EtOAc and water. The organic layer was separated and washed with water (2×10 mL) and brine (1×10 mL). The aqueous phase was backextracted with EtOAc (2×15 mL). The combined organic layers were combined, dried over magnesium sulfate, filtered and concentrated under reduced pressure. The crude material was then purified by Gilson HPLC (acidic condition; graduation: 30-90%) to afford the title compound (132.7 mg, 75% yield). LC-MS m/z 587.3 (M+H)$^+$, 1.07 min (ret. time).

268c) 1-(3'-((R)-2-(Ethoxymethyl)pyrrolidine-1-carbonyl)-[1,1'-biphenyl]-3-yl)-5-(trans-2-(1-methyl-1H-1,2,3-triazol-4-yl)cyclopropyl)-1H-pyrazole-4-carboxylic Acid

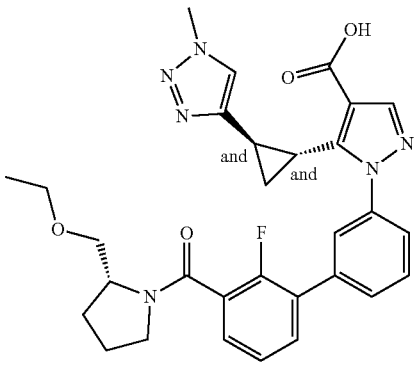 [SMILES: CCOC[C@H]1CCCN1C(=O)c1cccc(-c2cccc(-n3ncc(C(=O)O)c3[C@@H]3C[C@H]3c3cn(C)nn3)c2)c1F]

To a solution of ethyl 1-(3'-((R)-2-(ethoxymethyl)pyrrolidine-1-carbonyl)-2'-fluoro-[1,1'-biphenyl]-3-yl)-5-(trans-2-(1-methyl-1H-1,2,3-triazol-4-yl)cyclopropyl)-1H-pyrazole-4-carboxylate (130 mg, 0.222 mmol) in ethanol (2.0 mL) and water (0.1 mL), LiOH (159 mg, 6.65 mmol) was added. The reaction mixture was heated at 100° C. for 3.5 h under microwave irradiation. It was further heated under microwave irradiation to 90° C. for 1 h and 100° C. for 6.25 h. The reaction mixture was cooled to room temperature and quenched with 1N aqueous HCl to pH=1. It was then partitioned between DCM and water. The organic phase was separated and dried over magnesium sulfate, filtered and concentrated under reduced pressure. The crude material was then purified by Gilson HPLC (neutral condition; graduation: 30-90% of ACN for 10 min) to afford 57.3 mg of the title product (44.9% yield). LC-MS m/z 559.4 (M+H)$^+$, 0.89 min (ret. time)

Example 269. 1-(3'-((R)-2-(Ethoxymethyl)pyrrolidine-1-carbonyl)-[1,1'-biphenyl]-3-yl)-5-(trans-2-(1-methyl-1H-1,2,3-triazol-4-yl)cyclopropyl)-1H-pyrazole-4-carboxylic Acid

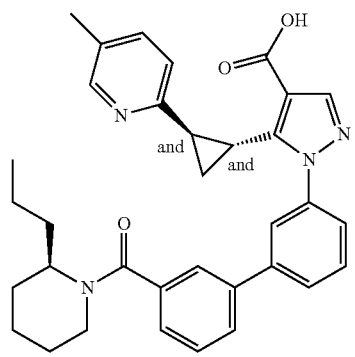 [SMILES: CCC[C@@H]1CCCCN1C(=O)c1cccc(-c2cccc(-n3ncc(C(=O)O)c3[C@@H]3C[C@H]3c3ccc(C)cn3)c2)c1]

269a) (E)-tert-Butyl 3-(5-methylpyridin-2-yl)acrylate N31061-83-A1

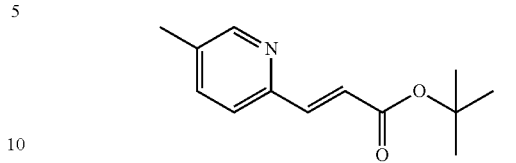

To a solution of 5-methylpicolinaldehyde (2000 mg, 16.51 mmol) in tetrahydrofuran (THF) (5 mL) at 0° C. was added tert-butyl 2-(triphenylphosphoranylidene)acetate (9322 mg, 24.77 mmol). The reaction mixture was stirred at 0° C. for 10 min, then it was warmed to room temperature and stirred for more 24 h. Ethyl acetate (10 mL) was added to the reaction mixture. It was then washed with water (2×) and brine. Aqueous phase was extracted with ethyl acetate (2×). Organic layers were combined, dried over magnesium sulfate, filtered and concentrated under reduced pressure. The crude material was purified by reverse-phase HPLC (acidic condition; graduation: 30-55% of ACN (0.1% TFA) over 10 min) to obtain the title compound (2.3472 g, 9.63 mmol, 58.3% yield). LC-MS m/z 220.1 (M+H)$^+$, 0.76 min (ret. time)

269b) 2-(5-Methylpyridin-2-yl)cyclopropanecarboxylic Acid

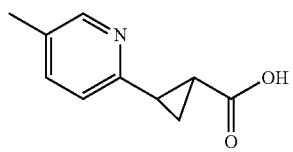

To a solution of trimethylsulfoxonium iodide (1393 mg, 6.33 mmol) in dimethyl sulfoxide (DMSO) (50 mL), sodium hydride (253 mg, 6.33 mmol) was added. The reaction mixture was stirred at room temperature under N$_2$ for 1 h. Then a solution of (E)-tert-butyl 3-(5-methylpyridin-2-yl)acrylate (925 mg, 4.22 mmol) in tetrahydrofuran (THF) (50 mL) was added by dropwise. The reaction mixture was stirred at room temperature for 1 h and at 50° C. for 16 h. It was added 200 mL of ethyl acetate and 50 mL of water. The water layer was extracted with ethyl acetate (3×). The combined organic phase was dried with MgSO4 and concentrated. To crude product in dichloromethane (DCM) (10.0 mL), TFA (3.25 mL, 42.2 mmol) was added at room temperature. Then the reaction mixture was stirred at room temperature for 16 h. Then the solvent was evaporated to obtain the title compound (560 mg, 3.16 mmol, 74.9% yield) which was carried over to next step without further purification. LC-MS m/z 177.9 (M+H)$^+$, 0.4 min (ret. time)

269c) Methyl 3-(2-(5-methylpyridin-2-yl)cyclopropyl)-3-oxopropanoate

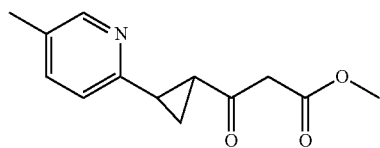

To a solution of 2-(5-methylpyridin-2-yl)cyclopropanecarboxylic acid (560 mg, 3.16 mmol) in tetrahydrofuran (THF) (10 mL) at room temperature, CDI (564 mg, 3.48 mmol) was added slowly. After it was stirred for 30 min, a mixture of magnesium chloride (602 mg, 6.32 mmol) and potassium 3-methoxy-3-oxopropanoate (1481 mg, 9.48 mmol) were added. The reaction mixture was stirred at room temperature for 16 h. It was quenched with water and then extracted with ethyl acetate (2×). The combined organic phase was washed with brine, dried over MgSO$_4$, filtered and concentrated to obtain the title compound (530 mg, 2.272 mmol, 71.9% yield) which was carried over to next step without further purification. LC-MS m/z 234.0 (M+H)$^+$, 0.44 min (ret. time)

269d) Methyl 3-(dimethylamino)-2-(2-(5-methylpyridin-2-yl)cyclopropanecarbonyl)acrylate

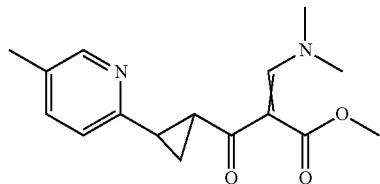

To a solution of methyl 3-(2-(5-methylpyridin-2-yl)cyclopropyl)-3-oxopropanoate (500 mg, 2.144 mmol) in 1,4-dioxane (10 mL), 1,1-dimethoxy-N,N-dimethylmethanamine (383 mg, 3.22 mmol) was added. The reaction mixture was stirred at 25° C. for 4 h. The solvent was evaporated. The crude product was purified by silica gel chromatography [hexane/ethyl acetate:EtOH(3:1)] to obtain the title compound (319 mg, 1.106 mmol., 51.6% yield). LC-MS m/z 289.2 (M+H)$^+$, 0.51 min (ret. time)

269e) rac-Methyl 1-(6-bromopyridin-2-yl)-5-((1,2-trans)-2-(1-methyl-1H-1,2,3-triazol-4-yl)cyclopropyl)-1H-pyrazole-4-carboxylate To a solution of methyl 3-(dimethylamino)-2-(2-(5-methylpyridin-2-yl)cyclopropanecarbonyl)acrylate (319 mg, 1.106 mmol) in ethanol (5 mL), (3-bromophenyl)hydrazine hydrochloride (272 mg, 1.217 mmol) and Et$_3$N (0.463 mL, 3.32 mmol) were added. The reaction mixture was stirred at room temperature for 4 h. The solvent was evaporated under Biotage V-10 and purified by silica gel chromatography (ethyl acetate/hexane) to obtain the title compound (343 mg, 0.832 mmol, 75% yield). LC-MS m/z 412.1/414.1 (M+H)$^+$, 0.75 min (ret. time)

269f) (R)-(2-propylpiperidine-1-carbonyl)phenyl)boronic acid and (R)-(2-propylpiperidin-1-yl)(3-(4,4,5,5-tetramethyl-1,3,2-dioxaborolan-2-yl)phenyl)methanone

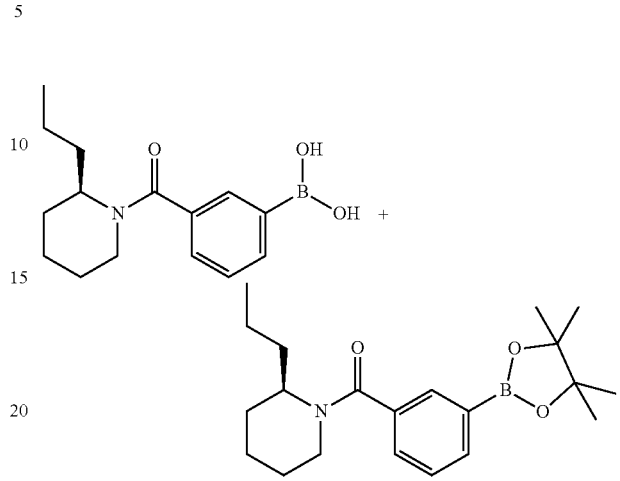

To a solution of 3-(4,4,5,5-tetramethyl-1,3,2-dioxaborolan-2-yl)benzoic acid (250 mg, 1.008 mmol) in dichloromethane (DCM) (5.0 mL), (R)-2-propylpiperidine (128 mg, 1.008 mmol), HATU (383 mg, 1.01 mmol) and DIPEA (0.44 mL, 2.52 mmol) were added. The reaction mixture was stirred at room temperature for 22 h. The reaction was recharged with an additional amount of 4,4,5,5-tetramethyl-1,3,2-dioxaborolan-2-yl)benzoic acid (50 mg, 0.202 mmol), HATU (77 mg, 0.202 mmol) and DIPEA (0.09 mL, 0.503 mmol) and stirred for 72 h. The reaction mixture was quenched with saturated aqueous NaHCO$_3$ and then washed with water and brine. The aqueous phase was backextracted with DCM. The combined organic layers were combined, dried over magnesium sulfate, filtered and concentrated under reduced pressure. A 1:1 ratio of the boronic acid to the ester was isolated and carried to the next step without further purification (391 mg, approximately an 80% yield). LC-MS m/z 276.1 (M+H)$^+$, 0.81 min (ret. time) and m/z 358.2 (M+H)$^+$, 1.25 min (ret. time), respectively.

269g) Methyl 5-(trans-2-(5-methylpyridin-2-yl)cyclopropyl)-1-(3'-((R)-2-propylpiperidine-1-carbonyl)-[1,1'-biphenyl]-3-yl)-1H-pyrazole-4-carboxylate

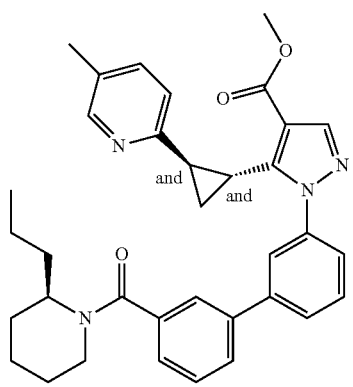 [SMILES: CCC[C@@H]1CCCCN1C(=O)c1cccc(-c2cccc(-n3ncc(C(=O)OC)c3[C@@H]3C[C@H]3c3ccc(C)cn3)c2)c1]

To a solution of a mixture of ((R)-(2-propylpiperidine-1-carbonyl)phenyl)boronic acid and (R)-(2-propylpiperidin-1- yl)(3-(4,4,5,5-tetramethyl-1,3,2-dioxaborolan-2-yl)phenyl)methanone (Example 268a, 137 mg) in ethanol (1.0 mL) and toluene (3.0 mL), methyl 1-(3-bromophenyl)-5-(trans-2-(5-methylpyridin-2-yl)cyclopropyl)-1H-pyrazole-4-carboxylate (72 mg, 0.175 mmol) and sodium carbonate (61 mg, 0.576 mmol) were added. PdCl$_2$(dppf) (15 mg, 0.021 mmol) was added. The reaction mixture was heated to 95° C. for 3 h. The reaction was cooled to room temperature and the mixture was partitioned between EtOAc and water. The organic layer was separated and washed with water (2×10 mL) and brine (1×10 mL). The aqueous phase was backextracted with EtOAc (2×10 mL). The combined organic layers were combined, dried over magnesium sulfate, filtered and concentrated under reduced pressure. The crude material was then purified by Gilson HPLC (acidic condition; graduation: 20-90%) to afford the title compound (32 mg, 75% yield). LC-MS m/z 563.4 (M+H)$^+$, 1.00 min (ret. time).

269h) 1-(3'-((R)-2-(Ethoxymethyl)pyrrolidine-1-carbonyl)-[1,1'-biphenyl]-3-yl)-5-(trans-2-(1-methyl-1H-1,2,3-triazol-4-yl)cyclopropyl)-1H-pyrazole-4-carboxylic Acid

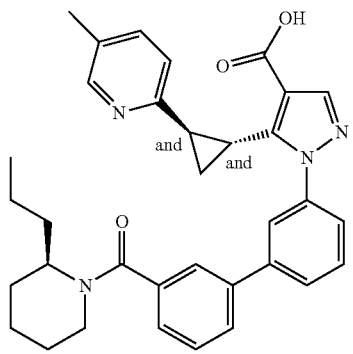 [SMILES: CCC[C@@H]1CCCCN1C(=O)c1cccc(-c2cccc(-n3ncc(C(=O)O)c3[C@@H]3C[C@H]3c3ccc(C)cn3)c2)c1]

To a solution of methyl 5-(trans-2-(5-methylpyridin-2-yl)cyclopropyl)-1-(3'-((R)-2-propylpiperidine-1-carbonyl)-[1,1'-biphenyl]-3-yl)-1H-pyrazole-4-carboxylate (32 mg, 0.057 mmol) in ethanol (3.0 mL) and water (0.1 mL), LiOH (66.4 mg, 2.27 mmol) was added. The reaction mixture was stirred at room temperature for 45 h. It was further heated under microwave irradiation to 90° C. for 1 h and 100° C. for 6.25 h. The reaction mixture was quenched with 1N aqueous HCl to pH=1. This mixture was extracted with EtOAc (5 mL). The organic phase was separated and washed with water (1×10 mL) and brine (1×10 mL). The aqueous phase was backextracted with EtOAc (1×10 mL). The combined organic layers were dried over magnesium sulfate, filtered and concentrated under reduced pressure. The crude material was then purified by Gilson HPLC (neutral condition) to afford 8.8 mg of the title product (28.9% yield). LC-MS m/z 549.6 (M+H)$^+$, 0.94 min (ret. time).

What is claimed is:
1. A compound of Formula (I):

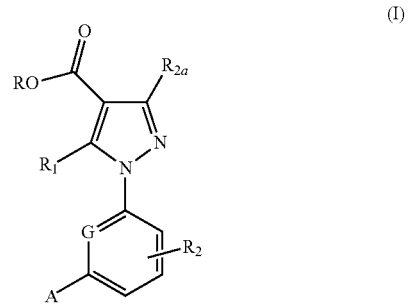

wherein:
R is hydrogen or —C$_{1-5}$alkyl, wherein —C$_{1-5}$alkyl is unsubstituted or substituted by one or two substituents independently selected from —OH, —OC(O)—C$_{1-5}$alkyl, —OC(O)-phenyl, —OC(O)—O—C$_{1-5}$alkyl,

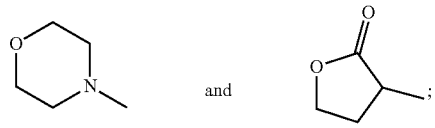

R$_1$ is —CF$_3$, —C$_{3-7}$cycloalkyl, or —C$_{4-7}$heterocycloalkyl, wherein the —C$_{3-7}$cycloalkyl, or —C$_{4-7}$heterocycloalkyl is unsubstituted or substituted by one or two substituents independently selected from —C$_{1-3}$alkyl, phenyl, triazolyl, pyridyl, pyridazinyl, imidazolyl, pyrazolyl, isoxazolyl, halo, —NR$_9$—C(O)—R$_{10}$ and —C(O)R$_{10}$, and wherein each of the phenyl, triazolyl, pyridyl, pyridazinyl, imidazolyl, pyrazolyl and isoxazolyl is unsubstituted or substituted by one or two substituents independently selected from halo, phenyl, and —C$_{1-7}$alkyl optionally substituted with phenyl, —N(CH$_3$)$_2$, —CF$_3$, —OH, —C$_{3-7}$cycloalkyl optionally substituted with C$_{1-3}$alkyl, and —C$_{3-7}$heterocylcoalkyl optionally substituted with —C$_{1-3}$ alkyl or —C(O)—C$_{1-4}$alkyl;
or R$_1$ is —C$_{2-3}$alkyl-R$_{11}$;
R$_{2a}$ is hydrogen, halo, or —C$_{1-3}$alkyl;
R$_2$ is hydrogen, halo, —CN, —O—C$_{1-3}$alkyl, —OH, or —C$_{1-3}$alkyl;
G is CH or N;
A is

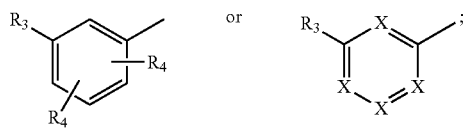

R$_3$ is —(CH$_2$)$_n$—C(O)NR$_5$R$_6$, —(CH$_2$)$_n$—C(R$_{14}$)(R$_{15}$)—NR$_5$R$_6$, —(CH$_2$)$_n$—S(O)NR$_5$R$_6$

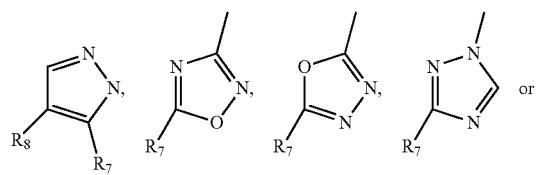

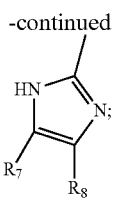

or R₃ is —O—C₁₋₆alkyl, —C₁₋₆ alkyl, —C₄₋₇heterocycloalkyl, —O—C₄₋₇ heterocycloalkyl, —N—R₁₂R₁₃, —C₃₋₇ cycloalkyl, —O—C₃₋₇ cycloalkyl, —S—C₁₋₃ alkyl, —S—C₄₋₇heterocycloalkyl, S—C₃₋₇ cycloalkyl, —S(O)—C₁₋₃alkyl, —S(O)—C₄₋₇ heterocycloalkyl, —S(O)—C₃₋₇ cycloalkyl, —S(O)₂—C₁₋₃alkyl, —S(O)₂ —C₄₋₇ heterocycloalkyl, or —S(O)₂—C₃₋₇ cycloalkyl, wherein each of —O—C₁₋₆alkyl, —C₁₋₆ alkyl, —C₄₋₇heterocycloalkyl, —O—C₄₋₇ heterocycloalkyl, —C₃₋₇ cycloalkyl, —O—C₃₋₇ cycloalkyl, —S—C₁₋₃alkyl, —S—C₄₋₇heterocycloalkyl, S—C₃₋₇ cycloalkyl, —S(O)—C₁₋₃alkyl, —S(O)—C₄₋₇ heterocycloalkyl, —S(O)—C₃₋₇ cycloalkyl, —S(O)₂—C₁₋₃ alkyl, —S(O)₂—C₄₋₇ heterocycloalkyl, or —S(O)₂—C₃₋₇ cycloalkyl, is unsubstituted or substituted by one or two substituents independently selected from —C₁₋₇ alkyl, —C₃₋₇ cycloalkyl, —OH, =O, —O—C₁₋₅ alkyl, CF₃, —C₄₋₇heterocycloalkyl, phenyl, pyridyl, pyrazolyl, pyridazinyl, pyrimidinyl, pyrazinyl, and triazolyl, and wherein each of —C₁₋₇ alkyl, —C₃₋₇ cycloalkyl, —O—C₁₋₃ alkyl, —C₄₋₇ heterocycloalkyl, phenyl, pyridyl, pyrazolyl, pyridazinyl, pyrimidinyl, pyrazinyl, or triazolyl is unsubstituted or further substituted by one or more substituents independently selected from —C₁₋₅ alkyl, —CF₃, —OC₁₋₃alkyl, phenyl, —C(O)—O—C₁₋₅alkyl and halo;

Each R₄ is independently hydrogen, halo or —C₁₋₃alkyl,

R₅ and R₆ are independently H, —C₁₋₆ alkyl, —C₃₋₇ cycloalkyl or —C₄₋₇ heterocycloalkyl, wherein each of —C₁₋₆ alkyl, —C₃₋₇ cycloalkyl or —C₄₋₇ heterocycloalkyl is unsubstituted or substituted by one or more substituents selected from F, —CH—F₂, —CF₃, —(CH₂)ₙ—O—(CH₂)ₘ—CH₃, and —C₃₋₇cycloalkyl;

or R₅ and R₆ together with the nitrogen atom to which they are attached form a 5-8-membered ring, an 8-11-membered bicyclic ring or a 9-10-membered bridged bicyclic ring, wherein each 5-8-membered ring, 8-11-membered bicyclic ring, or 9-10-membered bridged bicyclic ring optionally includes one —S(O)₂, one or more oxygen ring atoms or one or more nitrogen ring atoms, and wherein each 5-8-membered ring, 8-11-membered bicyclic ring, or 9-10-membered bridged bicyclic ring is unsubstituted or substituted by one, two or three substituents independently selected from —C₁₋₅ alkyl, —C₃₋₇cycloalkyl, —C₄₋₇heterocycloalkyl, halogen, —CHF₂, —CF₃, and —(CH₂)ₙ—O—(CH₂)ₘ—CH₃;

or R₅ and R₆ together with the nitrogen atom to which they are attached form 4-azaspiro[2.5]octane, 7-azaspiro[4.5]decane, 2-oxa-8-azaspiro[5.5]undecane, 6-oxa-9-azaspiro[4.5]decane, 2-oxa-8-azaspiro[5.5]undecane, 1-azaspiro[4.5]decane, 2,3,4,5-tetrahydrobenzo[f][1,4]oxazepine or 2,3,4,5-tetrahydro-1H-benzo[c]azepine;

R₇ and R₈ are independently H, —C₁₋₆ alkyl, —C₃₋₇ cycloalkyl or —C₄₋₇ heterocycloalkyl, wherein each of —C₁₋₆ alkyl, —C₃₋₇ cycloalkyl or —C₄₋₇ heterocycloalkyl is unsubstituted or substituted by one or two substituents independently selected from F, —CHF₂, —CF₃, and —(CH₂)ₙ—O—(CH₂)ₘ—CH₃;

or R₇ and R₈ together with the carbon atoms to which they are attached form a 5-8-membered ring, which optionally includes one or more oxygen or nitrogen atoms as ring atoms, and wherein the 5-8-membered ring is unsubstituted or substituted by one or two substituents independently selected from —C₁₋₅ alkyl, —C₃₋₇ cycloalkyl, —C₄₋₇ heterocycloalkyl, F, —CHF₂, —CF₃, =O, and —(CH₂)ₙ—O—(CH₂)ₘ—CH₃;

R₉ is H or —C₁₋₃alkyl;

R₁₀ is —C₁₋₃alkyl;

R₁₁ is aryl, triazolyl, pyridyl, pyridazinyl, imidazolyl, or pyrazolyl, wherein each of aryl, triazolyl, pyridyl, pyridazinyl, imidazolyl, or pyrazolyl is unsubstituted or substituted by one or two substituents independently selected from —C₁₋₃alkyl and halo;

R₁₂ and R₁₃ are independently C₄₋₇ heterocycloalkyl, —C₁₋₃ alkyl or —C₃₋₇ cycloalkyl, wherein each of the —C₄₋₇ heterocycloalkyl, —C₁₋₃ alkyl or —C₃₋₇ cycloalkyl is unsubstituted or substituted by one or two substituents independently selected from —C₁₋₇alkyl, —C₃₋₇cycloalkyl, —OH, =O, —O—C₁₋₅alkyl, —C₄₋₇ heterocycloalkyl, phenyl, pyridyl, pyrazolyl, pyridazinyl, pyrimidinyl, pyrazinyl, and triazolyl, and wherein each of the —C₁₋₇alkyl, —C₃₋₇cycloalkyl, —O—C₁₋₅ alkyl, —C₄₋₇heterocycloalkyl, phenyl, pyridyl, pyrazolyl, pyridazinyl, pyrimidinyl, pyrazinyl, or triazolyl is further optionally substituted by one or more substituents independently selected from —C₁₋₅alkyl and halo;

R₁₄ is hydrogen or —C₁₋₃alkyl;

R₁₅ is hydrogen or —C₁₋₃alkyl;

Each X is CR₄ or N provided only one X is N;

Each n is independently 0 or 1;

Each m is independently 0 or 1;

or a pharmaceutically acceptable salt thereof.

2. The compound of Formula (I) according to claim 1, wherein:

R is hydrogen;

R₁ is —C₃₋₇cycloalkyl, wherein the C₃₋₇cycloalkyl is unsubstituted or substituted by one substituent independently selected from triazolyl, pyridyl and pyridazinyl, and wherein the triazolyl, pyridyl, or pyridazinyl is unsubstituted or substituted by —C₁₋₃alkyl;

R₂ is hydrogen, or F;

R₂ₐ is hydrogen;

G is CH or N;

A is

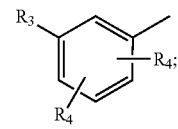

R₃ is —(CH₂)ₙ—C(O)N(R₅)(R₆); —(CH₂)ₙ—C(R₁₄)(R₁₅)—N(R₅)(R₆), —(CH₂)ₙ—S(O)NR₅R₆ or

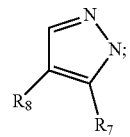

or R₃ is —O—$C_{1-3}$alkyl, —$C_{1-6}$alkyl, —$C_{4-7}$heterocycloalkyl, —O—$C_{4-7}$heterocycloalkyl, or, —O—$C_{3-7}$cycloalkyl, wherein each of —O—$C_{1-3}$alkyl, —$C_{1-6}$alkyl, —$C_{4-7}$heterocycloalkyl, —O—$C_{4-7}$heterocycloalkyl, or, —O—$C_{3-7}$cycloalkyl is unsubstituted or substituted by one or two substituents independently selected from —$C_{1-7}$alkyl, —$C_{3-7}$ cycloalkyl, =O, —O—$C_{1-5}$alkyl, and —$C_{4-7}$heterocycloalkyl, and wherein each of the —$C_{1-7}$alkyl, —$C_{3-7}$cycloalkyl, —O—$C_{1-3}$alkyl, or —$C_{4-7}$heterocycloalkyl is unsubstituted or further substituted by one or two substituents independently substituted by —$C_{1-5}$alkyl, —$CF_3$, —O—$C_{1-3}$alkyl, phenyl or halo;

Each $R_4$ is independently hydrogen or F;

$R_5$ and $R_6$ together with the nitrogen atom to which they are attached form a 5-8-membered ring, an 8-11-membered bicyclic ring or a 9-10-membered bridged bicyclic ring, wherein each 5-8-membered ring, 8-11-membered bicyclic ring, or 9-10-membered bridged bicyclic ring optionally includes one —$S(O)_2$, one or more oxygen ring atoms or one or more nitrogen ring atoms, and wherein each 5-8-membered ring, 8-11-membered bicyclic ring, or 9-10-membered bridged bicyclic ring is unsubstituted or substituted by one, two or three substituents independently selected from —$C_{1-5}$alkyl, —$C_{3-7}$cycloalkyl, —$C_{4-7}$heterocycloalkyl, halogen, —$CHF_2$, —$CF_3$, and —$(CH_2)_n$—O—$(CH_2)_n$—$CH_3$;

or $R_5$ and $R_6$ together with the nitrogen atom to which they are attached form 4-azaspiro[2.5]octane, 7-azaspiro[4.5]decane, 2-oxa-8-azaspiro[5.5]undecane, 6-oxa-9-azaspiro[4.5]decane, 2-oxa-8-azaspiro[5.5]undecane, 1-azaspiro[4.5]decane, 2,3,4,5-tetrahydrobenzo[f][1,4]oxazepine or 2,3,4,5-tetrahydro-1H-benzo[c]azepine;

$R_7$ and $R_8$ are independently H, —$C_{1-6}$ alkyl or —$C_{3-7}$ cycloalkyl wherein each of —$C_{1-6}$ alkyl or —$C_{3-7}$ cycloalkyl is unsubstituted or substituted by one or two substituents independently selected from F, —$CHF_2$, —$CF_3$ and —$(CH_2)_n$—O—$(CH_2)_m$—$CH_3$;

or $R_7$ and $R_8$ together with the carbon atoms to which they are attached form a 5-8 membered ring, which optionally includes one or more oxygen atoms or one or more nitrogen atoms as ring atoms, and wherein the 5-8-membered ring is unsubstituted or substituted by one or two substituents independently selected from —$C_{1-5}$ alkyl, F, —$CHF_2$ and —$CF_3$;

$R_{14}$ is hydrogen;
$R_{15}$ is hydrogen;
Each X is CH;
Each n is independently 0 or 1;
Each m is independently 0 or 1;
or a pharmaceutically acceptable salt thereof.

3. The compound of Formula (I) according to claim 1, wherein:
R is hydrogen or —$C_{1-5}$alkyl, wherein —$C_{1-5}$alkyl is unsubstituted or substituted by one or two substituents independently selected from —OH, —OC(O)—$C_{1-5}$ alkyl, —OC(O)-phenyl, —OC(O)—O—$C_{1-5}$ alkyl,

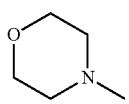 and 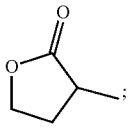;

$R_1$ is $C_3$cycloalkyl, wherein the $C_3$cycloalkyl is substituted or unsubstituted by one substituent independently selected from triazolyl, pyridyl, and pyridazinyl, and the triazolyl, pyridyl, and pyridazinyl is unsubstituted or substituted by $C_{1-3}$alkyl;

$R_2$ is hydrogen;
$R_{2a}$ is hydrogen;
G is CH;
A is

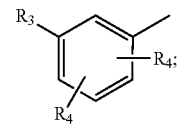

$R_3$ is $(CH_2)_n$—C(O)N($R_5$)($R_6$); $(CH_2)_n$, —C($R_{14}$)($R_{15}$)—N($R_5$)($R_6$), or

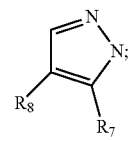

or $R_3$ is O—$C_{1-3}$alkyl, $C_{1-6}$alkyl, $C_{4-7}$heterocycloalkyl, O—$C_{4-7}$heterocycloalkyl, or —O—$C_{3-7}$cycloalkyl; wherein each of the moieties $R_3$ is unsubstituted or substituted by one or two substituents independently selected from $C_{1-7}$alkyl, $C_{3-7}$cycloalkyl, =O, —O—$C_{1-5}$ alkyl, and $C_{4-7}$ heterocycloalkyl, and wherein the $C_{1-7}$ alkyl, $C_{3-7}$ cycloalkyl, —O—$C_{1-3}$ alkyl, and $C_{4-7}$ heterocycloalkyl, is further unsubstituted or substituted by one or two substituents independently selected from $C_{1-5}$ alkyl, $CF_3$, O—$C_{1-3}$alkyl, phenyl and halo;

Each $R_4$ is independently hydrogen or F;

$R_5$ and $R_6$ together with the nitrogen atom to which they are attached form a 5-8 member ring or a 8-11 member bicyclic ring or a 9 or 10-membered bridged bicyclic ring, each of which optionally includes oxygen or another nitrogen as ring atoms, and each of which is unsubstituted or substituted by one or two substituents independently selected from $C_{1-5}$ alkyl, F, $CHF_2$, $CF_3$, and $(CH_2)_n$—O—$(CH_2)_m$—$CH_3$; or $R_5$ and $R_6$ together with the nitrogen atom to which they are attached form 4-azaspiro[2.5]octane, 7-azaspiro[4.5]decane, 2-oxa-8-azaspiro[5.5]undecane, 6-oxa-9-azaspiro[4.5]decane, 2-oxa-8-azaspiro[5.5]undecane, 1-azaspiro[4.5]decane, or 2,3,4,5-tetrahydrobenzo[f][1,4]oxazepine; 2,3,4,5-tetrahydro-1H-benzo[c]azepine;

$R_7$ and $R_8$ are independently H, $C_{1-6}$ alkyl, or $C_{3-7}$ cycloalkyl, each of which is unsubstituted or substituted by one or two substituents selected from F, $CHF_2$, $CF_3$, and $(CH_2)_n$—O—$(CH_2)_m$—$CH_3$; or $R_7$ and $R_8$ together with the carbon atoms to which they are attached form a 5-8-member ring, which optionally includes oxygen or another nitrogen as ring atoms, which is unsubstituted or substituted by one or two substituents independently selected from $C_{1-5}$ alkyl, F, $CHF_2$, and $CF_3$;

$R_{14}$ is hydrogen;
$R_{15}$ is hydrogen;

Each X is CH;
Each n is independently 0;
Each m is independently 0 or 1;
or a pharmaceutically acceptable salt thereof.

4. The compound of Formula (I) according to claim 1, wherein:
R is hydrogen or $C_{1-5}$alkyl wherein $C_{1-5}$alkyl is unsubstituted or substituted by one or more substituents independently selected from —OH, —OC(O)—$C_{1-5}$alkyl, —OC(O)-phenyl and —OC(O)—O—$C_{1-5}$alkyl;
$R_1$ is —$CF_3$, —$C_{3-7}$cycloalkyl, wherein the —$C_{3-7}$cycloalkyl is unsubstituted or substituted by one or two substituents independently selected from triazolyl, pyridyl and halo, and wherein each of the triazolyl and pyridyl is unsubstituted or substituted by one or two substituents independently selected from phenyl, halo, —$C_{1-7}$alkyl optionally substituted with phenyl, —$N(CH_3)_2$, —$CF_3$, —OH, and —$C_{3-7}$cycloalkyl optionally substituted with one or two of —$C_{1-3}$alkyl or —$C_{3-7}$heterocylcoalkyl optionally substituted with one or two of —$C_{1-3}$alkyl or —C(O)—$C_{1-4}$alkyl;
or $R_1$ is —$C_{2-3}$alkyl-$R_{11}$;
$R_{2a}$ is hydrogen or —$C_{1-3}$alkyl;
$R_2$ is hydrogen, halo or —$C_{1-3}$alkyl;
G is CH or N;
A is

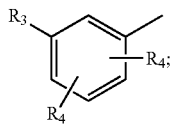

$R_3$ is —$(CH_2)_n$—C(O)$NR_5R_6$, —$(CH_2)_n$—C($R_{14}$)($R_{15}$)—N($R_5$)($R_6$), or

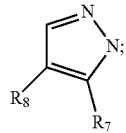

or $R_3$ is —O—$C_{1-6}$alkyl, —$C_{1-6}$alkyl, —$C_{4-7}$heterocycloalkyl, —O—$C_{4-7}$heterocycloalkyl, or —O—$C_{3-7}$cycloalkyl, wherein each of —O—$C_{1-6}$alkyl, —$C_{1-6}$alkyl, —$C_{4-7}$heterocycloalkyl, —O—$C_{4-7}$heterocycloalkyl, and —O—$C_{3-7}$cycloalkyl is unsubstituted or substituted by one or two substituents independently selected from —$C_{1-7}$alkyl, —$C_{3-7}$cycloalkyl, =O, —O—$C_{1-5}$alkyl, and —$C_{4-7}$heterocycloalkyl, and wherein each of the —$C_{1-7}$alkyl, —$C_{3-7}$cycloalkyl, —O—$C_{1-5}$alkyl, and $C_{4-7}$ heterocycloalkyl, is further substituted by one or two substituents independently selected from —$C_{1-5}$alkyl, $CF_3$, O—$C_{1-3}$alkyl, phenyl and halo;
Each $R_4$ is independently hydrogen, halo or —$C_{1-3}$ alkyl;
$R_5$ and $R_6$ are independently H, —$C_{1-6}$ alkyl, —$C_{3-7}$ cycloalkyl or —$C_{4-7}$ heterocycloalkyl, wherein each of —$C_{1-6}$ alkyl, —$C_{3-7}$ cycloalkyl or —$C_{4-7}$ heterocycloalkyl is unsubstituted or substituted by one or two substituents independently selected from F, —CH—$F_2$, —$CF_3$, —$(CH_2)_n$—O—$(CH_2)_m$—$CH_3$, and —$C_{3-7}$cycloalkyl;

$R_5$ and $R_6$ together with the nitrogen atom to which they are attached form a 5-8-membered ring, an 8-11-membered bicyclic ring or a 9-10-membered bridged bicyclic ring, wherein each 5-8-membered ring, 8-11-membered bicyclic ring, or 9-10-membered bridged bicyclic ring optionally includes one —$S(O)_2$, one or more oxygen ring atoms or one or more nitrogen ring atoms, and wherein each 5-8-membered ring, 8-11-membered bicyclic ring, or 9-10-membered bridged bicyclic ring is unsubstituted or substituted by one, two or three substituents independently selected from —$C_{1-5}$alkyl, —$C_{3-7}$cycloalkyl, —$C_{4-7}$heterocycloalkyl, halogen, —$CHF_2$, —$CF_3$, and —$(CH_2)_n$—O—$(CH_2)_m$—$CH_3$;
or $R_5$ and $R_6$ together with the nitrogen atom to which they are attached form 4-azaspiro[2.5]octane, 7-azaspiro[4.5]decane, 2-oxa-8-azaspiro[5.5]undecane, 6-oxa-9-azaspiro[4.5]decane, 2-oxa-8-azaspiro[5.5]undecane, 1-azaspiro[4.5]decane, 2,3,4,5-tetrahydrobenzo[f][1,4]oxazepane, or 2,3,4,5-tetrahydro-1H-benzo[c]azepine;
$R_7$ and $R_8$ are independently H, —$C_{1-6}$alkyl, —$C_{3-7}$cycloalkyl or —$C_{4-7}$ heterocycloalkyl, wherein each of —$C_{1-6}$ alkyl, —$C_{3-7}$ cycloalkyl or —$C_{4-7}$ heterocycloalkyl is unsubstituted or substituted by one or two substituents independently selected from F, —$CHF_2$, —$CF_3$, and —$(CH_2)_n$—O—$(CH_2)_m$—$CH_3$;
or $R_7$ and $R_8$ together with the carbon atoms to which they are attached form a 5-8-membered ring, which optionally includes one or more oxygen or one or more nitrogen atoms as ring atoms, and wherein the 5-8-membered ring is unsubstituted or substituted by one or two substituents independently selected from —$C_{1-5}$ alkyl, —$C_{3-7}$ cycloalkyl, —$C_{4-7}$ heterocycloalkyl, F, —$CHF_2$, —$CF_3$, =O, and —$(CH_2)_n$—O—$(CH_2)_m$—$CH_3$;
$R_9$ is H or —$C_{1-3}$alkyl;
$R_{10}$ is —$C_{1-3}$alkyl;
$R_{11}$ is aryl or triazolyl;
$R_{12}$ and $R_{13}$ are independently $C_{4-7}$ heterocycloalkyl, —$C_{1-3}$ alkyl or —$C_{3-7}$ cycloalkyl, wherein each of —$C_{4-7}$ heterocycloalkyl, —$C_{1-3}$ alkyl or —$C_{3-7}$ cycloalkyl is unsubstituted or substituted by one or two substituents independently selected from —$C_{1-7}$alkyl, —$C_{3-7}$cycloalkyl, —OH, =O, —O—$C_{1-5}$alkyl, —$C_{4-7}$ heterocycloalkyl, phenyl, pyridyl, pyrazolyl, pyridazinyl, pyrimidinyl, pyrazinyl, and triazolyl, and wherein —$C_{1-7}$alkyl, —$C_{3-7}$cycloalkyl, —O—$C_{1-3}$alkyl, —$C_{4-7}$ heterocycloalkyl, phenyl, pyridyl, pyrazolyl, pyridazinyl, pyrimidinyl, pyrazinyl, or triazolyl is further optionally substituted by one or more substituents independently selected from —$C_{1-5}$alkyl and halo;
$R_{14}$ is hydrogen or —$C_{1-3}$alkyl;
$R_{15}$ is hydrogen or —$C_{1-3}$alkyl;
Each X is $CR_4$ or N provided only one X is N;
Each n is independently 0 or 1;
Each m is independently 0 or 1;
or a pharmaceutically acceptable salt thereof.

5. The compound of Formula (I) according to claim 1, wherein,
R is hydrogen;
$R_1$ is —$C_{3-7}$cycloalkyl, wherein the —$C_{3-7}$cycloalkyl is unsubstituted or substituted by one substituent selected from triazolyl, pyridyl and pyridazinyl, and wherein the, triazolyl, pyridyl, and pyridazinyl is optionally substituted by —$C_{1-3}$alkyl;
$R_{2a}$ is hydrogen or methyl;
$R_2$ is hydrogen or F;
G is CH or N;

A is

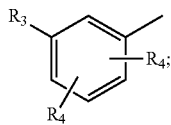

$R_3$ is —$(CH_2)_n$—C(O)N($R_5$)($R_6$), —$(CH_2)_n$—C($R_{14}$)($R_{15}$)—N($R_5$)($R_6$), or

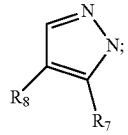

or $R_3$ is —O—$C_{1-6}$alkyl, —$C_{1-6}$ alkyl, —$C_{4-7}$heterocycloalkyl, —O—$C_{4-7}$heterocycloalkyl, or —O—$C_{3-7}$cycloalkyl, wherein each of —O—$C_{1-6}$alkyl, —$C_{1-6}$ alkyl, —$C_{4-7}$heterocycloalkyl, —O—$C_{4-7}$ heterocycloalkyl, and —O—$C_{3-7}$cycloalkyl is unsubstituted or substituted by one or two substituents independently selected from —$C_{1-7}$alkyl, —$C_{3-7}$cycloalkyl, =O, —O—$C_{1-5}$alkyl, and —$C_{4-7}$heterocycloalkyl, and wherein each of the —$C_{1-7}$alkyl, —$C_{3-7}$cycloalkyl, —O—$C_{1-5}$alkyl, and $C_{4-7}$ heterocycloalkyl, is further substituted by one or two substituents independently selected from —$C_{1-5}$alkyl, $CF_3$, O—$C_{1-3}$alkyl, phenyl and halo;

$R_4$ is independently hydrogen or F;

$R_5$ and $R_6$ together with the nitrogen atom to which they are attached form a 5-8-membered ring, an 8-11-membered bicyclic ring or a 9-10-membered bridged bicyclic ring, wherein each 5-8-membered ring, 8-11-membered bicyclic ring, or 9-10-membered bridged bicyclic ring optionally includes one —S(O)$_2$ one or more oxygen ring atoms or one or more nitrogen ring atoms, and wherein each 5-8-membered ring, 8-11-membered bicyclic ring, or 9-10-membered bridged bicyclic ring is unsubstituted or substituted by one, two or three substituents independently selected from —$C_{1-5}$alkyl, —$C_{3-7}$cycloalkyl, —$C_{4-7}$heterocycloalkyl, halogen, —$CHF_2$, —$CF_3$, and —$(CH_2)_n$—O—$(CH_2)_m$—$CH_3$;

or $R_5$ and $R_6$ together with the nitrogen atom to which they are attached form 4-azaspiro[2.5]octane, 7-azaspiro[4.5]decane, 2-oxa-8-azaspiro[5.5]undecane, 6-oxa-9-azaspiro[4.5]decane, 2-oxa-8-azaspiro[5.5]undecane, 1-azaspiro[4.5]decane, 2,3,4,5-tetrahydrobenzo[f][1,4]oxazepane, or 2,3,4,5-tetrahydro-1H-benzo[c]azepine;

$R_7$ and $R_8$ are independently H, —$C_{1-6}$ alkyl or —$C_{3-7}$ cycloalkyl, wherein each of —$C_{1-6}$ alkyl, or —$C_{3-7}$ cycloalkyl is unsubstituted or substituted by one or two substituents independently selected from F, —$CHF_2$, —$CF_3$, and —$(CH_2)_n$—O—$(CH_2)_m$—$CH_3$;

or $R_7$ and $R_8$ together with the carbon atoms to which they are attached form a 5-8-membered ring, which optionally includes one or more oxygen or one or more nitrogen atoms as ring atoms, and wherein the 5-8-membered ring is unsubstituted or substituted by one or two substituents independently selected from —$C_{1-5}$ alkyl, F, —$CHF_2$, and —$CF_3$;

$R_{14}$ is hydrogen;
$R_{15}$ is hydrogen;
X is CH;
n is independently 0 or 1;
m is independently 0 or 1;
or a pharmaceutically acceptable salt thereof.

6. The compound of Formula (I) according to claim 1, wherein,

R is hydrogen;
$R_1$ is cyclopropyl, wherein the cyclopropyl ring is unsubstituted or substituted by one substituent selected from triazolyl, pyridyl, and pyridazinyl, and wherein the triazolyl, pyridyl, and pyridazinyl is unsubstituted or substituted by $C_{1-3}$alkyl;
$R_{2a}$ is hydrogen;
$R_2$ is hydrogen;
G is CH;
A is

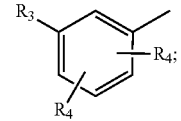

$R_3$ is —$(CH_2)_n$—C(O)N($R_5$)($R_6$), —$(CH_2)_n$—C($R_{14}$)($R_{15}$)—N($R_5$)($R_6$);

or $R_3$ is —O—$C_{1-6}$alkyl, —$C_{1-6}$ alkyl, —$C_{4-7}$heterocycloalkyl, —O—$C_{4-7}$heterocycloalkyl, or —O—$C_{3-7}$ cycloalkyl wherein each of —O—$C_{1-6}$alkyl, —$C_{1-6}$ alkyl, —$C_{4-7}$heterocycloalkyl, —O—$C_{4-7}$ heterocycloalkyl, and —O—$C_{3-7}$cycloalkyl is unsubstituted or substituted by one or two substituents independently selected from —$C_{1-7}$alkyl, —$C_{3-7}$cycloalkyl, =O, —O—$C_{1-5}$alkyl, and —$C_{4-7}$heterocycloalkyl, and wherein each of the —$C_{1-7}$alkyl, —$C_{3-7}$cycloalkyl, —O—$C_{1-5}$alkyl, and $C_{4-7}$ heterocycloalkyl, is further substituted by one or two substituents independently selected from —$C_{1-5}$alkyl, $CF_3$, O—$C_{1-3}$alkyl, phenyl and halo;

$R_4$ is independently hydrogen or F;

$R_5$ and $R_6$ together with the nitrogen atom to which they are attached form a 5-8-membered ring, an 8-11-membered bicyclic ring or a 9-10-membered bridged bicyclic ring, wherein each 5-8-membered ring, 8-11-membered bicyclic ring, or 9-10-membered bridged bicyclic ring optionally includes one —S(O)$_2$, one or more oxygen ring atoms or one or more nitrogen ring atoms, and wherein each 5-8-membered ring, 8-11-membered bicyclic ring, or 9-10-membered bridged bicyclic ring is unsubstituted or substituted by one, two or three substituents independently selected from —$C_{1-5}$alkyl, —$C_{3-7}$cycloalkyl, —$C_{4-7}$heterocycloalkyl, halogen, —$CHF_2$, —$CF_3$, and —$(CH_2)_n$—O—$(CH_2)_m$—$CH_3$;

or $R_5$ and $R_6$ together with the nitrogen atom to which they are attached form 4-azaspiro[2.5]octane, 7-azaspiro[4.5]decane, 2-oxa-8-azaspiro[5.5]undecane, 6-oxa-9-azaspiro[4.5]decane, 2-oxa-8-azaspiro[5.5]undecane, 1-azaspiro[4.5]decane, 2,3,4,5-tetrahydrobenzo[f][1,4]oxazepane, or 2,3,4,5-tetrahydro-1H-benzo[c]azepine;

$R_7$ and $R_8$ are independently H, —$C_{1-6}$ alkyl or —$C_{3-7}$ cycloalkyl wherein each of —$C_{1-6}$ alkyl, or —$C_{3-7}$ cycloalkyl is unsubstituted or substituted by one or two substituents independently selected from F, —$CHF_2$, —$CF_3$, and —$(CH_2)_n$—O—$(CH_2)_m$—$CH_3$;

or $R_7$ and $R_8$ together with the carbon atoms to which they are attached form a 5-8-membered ring, which optionally includes one or more oxygen or one or more nitrogen atoms as ring atoms, and wherein the 5-8-membered ring is unsubstituted or substituted by one or two substituents independently selected from —$C_{1-5}$alkyl, F, —$CHF_2$, and —$CF_3$;

$R_{14}$ is hydrogen;
$R_{15}$ is hydrogen;
X is CH;
n is 0;
m is independently 0 or 1;
or a pharmaceutically acceptable salt thereof.

7. The compound of Formula (I) according to claim 1, wherein

R is hydrogen;
$R_1$ is —$CF_3$, —$C_{3-7}$cycloalkyl, wherein —$C_{3-7}$cycloalkyl is substituted by one or two substituents independently selected from triazolyl, pyridyl and halo, and wherein each of triazolyl or pyridyl is unsubstituted or substituted by one or two substituents independently selected from halo, phenyl, —$C_{1-7}$alkyl optionally substituted with phenyl, —$N(CH_3)_2$, —$CF_3$, —OH, and —$C_{3-7}$cycloalkyl optionally substituted with —$C_{1-3}$alkyl, —$C_{3-7}$heterocylcoalkyl optionally substituted with —$C_{1-3}$alkyl or —C(O)—$C_{1-4}$alkyl;
$R_{2a}$ is hydrogen or methyl;
$R_2$ is hydrogen, halo or —$C_{1-3}$alkyl;
G is CH;
A is $R_3$ is —$(CH_2)_n$—$C(O)NR_5R_6$ or Each $R_4$ is independently hydrogen, halo or —$C_{1-3}$alkyl,
$R_5$ and $R_6$ are independently —$C_{1-6}$alkyl or —$C_{3-7}$cycloalkyl, wherein each of —$C_{1-6}$alkyl, —$C_{3-7}$cycloalkyl is unsubstituted or substituted by one or more substituents selected from F, —CH—$F_2$, —$CF_3$, —$(CH_2)_n$—O—$(CH_2)_m$—$CH_3$, and —$C_{3-7}$cycloalkyl;
or $R_5$ and $R_6$ together with the nitrogen atom to which they are attached form a 5-8-membered ring, wherein said 5-8-membered ring optionally includes one or more oxygen ring atoms or another nitrogen ring atom, and wherein said 5-8-membered ring is unsubstituted or substituted by one or two substituents independently selected from —$C_{1-5}$alkyl;
$R_7$ and $R_8$ are independently H, —$C_{1-6}$alkyl, —$C_{3-7}$cycloalkyl or —$C_{4-7}$heterocycloalkyl, wherein each of —$C_{1-6}$alkyl, —$C_{3-7}$cycloalkyl or —$C_{4-7}$heterocycloalkyl is unsubstituted or substituted by one or more substituents selected from F, —$CHF_2$, —$CF_3$, and —$(CH_2)_n$—O—$(CH_2)_m$—$CH_3$;
or $R_7$ and $R_8$ together with the carbon atoms to which they are attached form a 5-8-membered ring, which optionally includes one or more oxygen atoms or one or more nitrogen atoms as ring atoms, and wherein the 5-8-membered ring is unsubstituted or substituted by one or two substituents independently selected from —$C_{1-5}$alkyl, —$C_{3-7}$cycloalkyl, —$C_{4-7}$heterocycloalkyl, F, —$CHF_2$, —$CF_3$, =O, and —$(CH_2)_n$—O—$(CH_2)_m$—$CH_3$;
X is CH;
n is 0;
m is independently 0 or 1;
or a pharmaceutically acceptable salt thereof.

8. A compound of claim 1 selected from:
5-Cyclopentyl-1-{3-[3-(dimethylcarbamoyl)-2-fluorophenyl]phenyl}-1H-pyrazole-4-carboxylic acid,
1-{3-[3-(Dimethylcarbamoyl)-2-fluorophenyl]phenyl}-5-(trifluoromethyl)-1H-pyrazole-4-carboxylic acid,
1-(3-{3-[Cyclopentyl(methyl)carbamoyl]-2-fluorophenyl}phenyl)-5-cyclopropyl-1H-pyrazole-4-carboxylic acid,
5-Cyclopropyl-1-(3-{2-fluoro-3-[methyl(2-methylpropyl)carbamoyl]phenyl}phenyl)-1H-pyrazole-4-carboxylic acid,
1-(3-{3-[Cyclohexyl(methyl)carbamoyl]-2-fluorophenyl}phenyl)-5-cyclopropyl-1H-pyrazole-4-carboxylic acid,
5-Cyclopropyl-1-{3-[3-(3,3-dimethylpiperidine-1-carbonyl)-2-fluorophenyl]phenyl}-1H-pyrazole-4-carboxylic acid,
1-{3-[3-(azepane-1-carbonyl)-2-fluorophenyl]phenyl}-5-cyclopropyl-1H-pyrazole-4-carboxylic acid,
1-(3-{3-[Bis(cyclopropylmethyl)carbamoyl]-2-fluorophenyl}phenyl)-5-cyclopropyl-1H-pyrazole-4-carboxylic acid,
5-Cyclopropyl-1-(3-{3-[(cyclopropylmethyl)(propyl)carbamoyl]-2-fluorophenyl}phenyl)-1H-pyrazole-4-carboxylic acid,
1-{3-[3-(Azepane-1-carbonyl)phenyl]phenyl}-5-cyclopropyl-1H-pyrazole-4-carboxylic acid,
1-{3-[3-(propan-2-yloxy)phenyl]phenyl}-5-(trifluoromethyl)-1H-pyrazole-4-carboxylic acid,
1-(3-{3-[(Cyclopentylmethyl)(methyl)carbamoyl]-2-fluorophenyl}phenyl)-5-cyclopropyl-1H-pyrazole-4-carboxylic acid,
5-[(cis)-3-Acetamidocyclopentyl]-1-{3-[2-fluoro-3-(propan-2-yloxy)phenyl]phenyl}-1H-pyrazole-4-carboxylic acid (cis racemate),
1-(3-{3-[(Cyclopentylmethyl)(cyclopropylmethyl)carbamoyl]-2-fluorophenyl}phenyl)-5-cyclopropyl-1H-pyrazole-4-carboxylic acid,
1-(3-{2-Chloro-3-[(cyclopropylmethyl)(propyl)carbamoyl]phenyl}phenyl)-5-cyclopropyl-1H-pyrazole-4-carboxylic acid,
5-Cyclopropyl-1-(3-{3-[(cyclopropylmethyl)(propyl)carbamoyl]-2-methylphenyl}phenyl)-1H-pyrazole-4-carboxylic acid,
5-Cyclopropyl-1-{3-[2-fluoro-3-(2-propylpiperidine-1-carbonyl)phenyl]phenyl}-1H-pyrazole-4-carboxylic acid,
5-Cyclopropyl-1-(3-{2-fluoro-3-[3-(trifluoromethyl)piperidine-1-carbonyl]phenyl}phenyl)-1H-pyrazole-4-carboxylic acid,
1-[3-(3-{4-Azaspiro[2.5]octane-4-carbonyl}-2-fluorophenyl)phenyl]-5-cyclopropyl-1H-pyrazole-4-carboxylic acid, 5-Cyclopropyl-1-{3-[2-fluoro-3-(piperidine-1-carbonyl)phenyl]phenyl}-1H-pyrazole-4-carboxylic acid, 5-Cyclopropyl-1-(3-{3-[(2R,6S)-2,6-dimethylpiperidine-1-carbonyl]-2-fluorophenyl}phenyl)-1H-pyrazole-4-carboxylic acid, 5-Cyclopropyl-1-(3-{2-fluoro-3-[2-(methoxymethyl)piperidine-1-carbonyl]phenyl}phenyl)-1H-pyrazole-4-carboxylic acid, 5-Cyclopropyl-1-(3-{3-[(cyclopropylmethyl)(3,3,3-trifluoropropyl)carbamoyl]-2-fluorophenyl}phenyl)-1H-pyrazole-4-carboxylic acid, 5-Cyclopropyl-1-{3-[3-(2,5-dimethylpyrrolidine-1-carbonyl)-2-fluorophenyl]phenyl}-1H-pyrazole-4-carboxylic acid, 1-{3-[3-(2-Propylpiperidine-1-carbonyl)phenyl]phenyl}-5-(trifluoromethyl)-1H-pyrazole-4-carboxylic acid, 5-Cyclopropyl-1-{3-[2-fluoro-3-(2-propylpyrrolidine-1-carbonyl)phenyl]phenyl}-1H-pyrazole-4-carboxylic acid, 5-Cyclopropyl-1-{3-[2-fluoro-3-(3-propylmorpholine-4-carbonyl)phenyl]phenyl}-1H-pyrazole-4-carboxylic acid, 5-Cyclopropyl-1-(3-{2-fluoro-3-[2-(2-methylpropyl)piperidine-1-carbonyl]phenyl}phenyl)-1H-pyrazole-4-carboxylic acid, 5-Cyclopropyl-1-{3-[2-fluoro-3-(4-methylazepane-1-carbonyl)phenyl]phenyl}-1H-pyrazole-4-carboxylic acid, 5-Cyclopropyl-1-{3-[3-(2,5-dimethylpiperidine-1-carbonyl)-2-fluorophenyl]phenyl}-1H-pyrazole-4-carboxylic acid, 5-Cyclopropyl-1-{3-[3-(decahydroquinoline-1-carbonyl)-2-fluorophenyl]phenyl}-1H-pyrazole-4-carboxylic acid, 5-cyclopropyl-1-[3-(2-fluoro-3-{3-oxa-8-azabicyclo[3.2.1]octane-8-carbonyl}phenyl)phenyl]-1H-pyrazole-4-carboxylic acid, 1-{3-[3-(2-Cyclopentylpiperidine-1-carbonyl)-2-fluorophenyl]phenyl}-5-cyclopropyl-1H-pyrazole-4-carboxylic acid, 1-[3-(3-{9-azabicyclo[3.3.1]nonane-9-carbonyl}-2-fluorophenyl)phenyl]-5-cyclopropyl-1H-pyrazole-4-carboxylic acid, 1-[3-(3-{7-Azaspiro[4.5]decane-7-carbonyl}-2-fluorophenyl)phenyl]-5-cyclopropyl-1H-pyrazole-4-carboxylic acid, 5-Cyclopropyl-1-{3-[3-(5-methyl-1H-pyrazol-1-yl)phenyl]phenyl}-1H-pyrazole-4-carboxylic acid, 5-Cyclopropyl-1-(3-{2-fluoro-3-[(2R)-2-propylpiperidine-1-carbonyl]phenyl}phenyl)-1H-pyrazole-4-carboxylic acid, 5-Cyclopropyl-1-(3-{2-fluoro-3-[2-(3,3,3-trifluoropropyl)piperidine-1-carbonyl]phenyl}phenyl)-1H-pyrazole-4-carboxylic acid, 5-cyclopropyl-1-{3-[2-fluoro-3-(5-methyl-1H-pyrazol-1-yl)phenyl]phenyl}-1H-pyrazole-4-carboxylic acid, 1-{3-[3-(2-propylpiperidine-1-carbonyl)phenyl]phenyl}-5-[2-(pyridin-3-yl)cyclopropyl]-1H-pyrazole-4-carboxylic acid, 1-[3'-(2-Propyl-piperidine-1-carbonyl)-biphenyl-3-yl]-5-(2-pyridazin-3-yl-cyclopropyl)-1H-pyrazole-4-carboxylic acid, 5-[2-(1-methyl-1H-1,2,3-triazol-4-yl)cyclopropyl]-1-{3-[3-(2-propylpiperidine-1-carbonyl)phenyl]phenyl}-1H-pyrazole-4-carboxylic acid, 5-Cyclopropyl-1-[3-(2-fluoro-3-{2-oxa-8-azaspiro[5.5]undecane-8-carbonyl}phenyl)phenyl]-1H-pyrazole-4-carboxylic acid, 5-cyclopropyl-1-[3-(2-fluoro-3-{6-oxa-9-azaspiro[4.5]decane-9-carbonyl}phenyl)phenyl]-1H-pyrazole-4-carboxylic acid, 5-cyclopropyl-1-(3-{2-fluoro-3-[(2S,5R)-2-methyl-5-propylmorpholine-4-carbonyl]phenyl}phenyl)-1H-pyrazole-4-carboxylic acid, 5-(1-Acetylpiperidin-4-yl)-1-{3-[3-dimethylcarbamoyl)phenyl]phenyl}-1H-pyrazole-4-carboxylic acid, 1-(3-{3-[(cyclopropylmethyl)(methyl)carbamoyl]-2-fluorophenyl}phenyl)-5-(trifluoromethyl)-1H-pyrazole-4-carboxylic acid, 5-cyclopropyl-1-(3-{3-[(cyclopropylmethyl)(methyl)carbamoyl]-2-fluorophenyl}phenyl)-1H-pyrazole-4-carboxylic acid, 1-{3-[3-(dimethylcarbamoyl)phenyl]phenyl}-5-(3-phenylcyclobutyl)-1H-pyrazole-4-carboxylic acid, 5-Cyclopropyl-1-[3'-(tetrahydro-furan-2-yl)-biphenyl-3-yl]-1H-pyrazole-4-carboxylic acid, 5-[(1S,2S)-2-(1-methyl-1H-1,2,3-triazol-4-yl)(cyclopropyl]-1-(3-{3-[(2R)-2-propylpiperidine-1-carbonyl]phenyl}phenyl)-1H-pyrazole-4-carboxylic acid, 5-[(1R,2R)-2-(1-methyl-1H-1,2,3-triazol-4-yl)cyclopropyl]-1-(3-{3-[(2R)-2-propylpiperidine-1-carbonyl]phenyl}phenyl)-1H-pyrazole-4-carboxylic acid, 1-{3-[3-(2-propylpiperidine-1-carbonyl)phenyl]phenyl}-5-[2-(pyridin-3-yl)cyclopropyl]-1H-pyrazole-4-carboxylic acid, 5-Cyclopropyl-1-[3'-(3,5-dimethyl-piperidine-1-carbonyl)-2'-fluoro-biphenyl-3-yl]-1H-pyrazole-4-carboxylic acid, 5-Cyclopropyl-1-{3-[2-fluoro-3-((2-S)-2-propylpiperidine-1-carbonyl)phenyl]phenyl}-1H-pyrazole-4-carboxylic acid, (R)-1-(2'-Fluoro-3'-(2-propylpiperidine-1-carbonyl)-[1,1'-biphenyl]-3-yl)-5-(2-(1-methyl-1H-1,2,3-triazol-4-yl)ethyl)-1H-pyrazole-4-carboxylic acid, 1-(2'-Fluoro-3'-(2-propylpiperidine-1-carbonyl)-[1,1'-biphenyl]-3-yl)-5-(2-(1-methyl-1H-1,2,3-triazol-4-yl)ethyl)-1H-pyrazole-4-carboxylic acid, 1-(2'-Fluoro-3'-((R)-2-propylpiperidine-1-carbonyl)-[1,1'-biphenyl]-3-yl)-5-(2-(1-methyl-1H-1,2,3-triazol-4-yl)cyclopropyl)-1H-pyrazole-4-carboxylic acid, (R)-5-(2-(1-Methyl-1H-1,2,3-triazol-4-yl)ethyl)-1-(3'-(2-propylpiperidine-1-carbonyl)-[1,1'-biphenyl]-3-yl)-1H-pyrazole-4-carboxylic acid, 1-(3'-Isopropoxy-[1,1'-biphenyl]-3-yl)-5-(2-(1-methyl-1H-1,2,3-triazol-4-yl)cyclopropyl)-1H-pyrazole-4-carboxylic acid, 1-(3'-(1-Cyclohexylethoxy)-[1,1'-biphenyl]-3-yl)-5-cyclopropyl-1H-pyrazole-4-carboxylic acid, 5-Cyclopropyl-1-(3'-(5,6-dihydrocyclopenta[c]pyrazol-1(4H)-yl)-[1,1'-biphenyl]-3-yl)-1H-pyrazole-4-carboxylic acid, 5-cyclopropyl-1-(3'-(4,5,6,7-tetrahydro-1H-indazol-1-yl)-[1,1'-biphenyl]-3-yl)-1H-pyrazole-4-carboxylic acid, 5-Cyclopropyl-1-(3'-(6,6-dimethyl-5,6-dihydrocyclopenta[c]pyrazol-1(4H)-yl)-[1,1'-biphenyl]-3-yl)-1H-pyrazole-4-carboxylic acid, 1-(3'-((S)-1-Cyclohexylethoxy)-[1,1'-biphenyl]-3-yl)-5-((1R,2R)-2-(1-methyl-1H-1,2,3-triazol-4-yl)cyclopropyl)-1H-pyrazole-4-carboxylic acid, 1-(3'-(((R)-2-Ethyl-2,3-dihydrobenzo[f][1,4]oxazepin-4(5H)-yl)methyl)-[1,1'-biphenyl]-3-yl)-5-((1R,2R)-2-(1-methyl-1H-1,2,3-triazol-4-yl)cyclopropyl)-1H-pyrazole-4-carboxylic acid, 1-(6-(3-Isopropoxyphenyl)pyridin-2-yl)-5-(trifluoromethyl)-1H-pyrazole-4-carboxylic acid,
5-(2,2-Difluorocyclopropyl)-1-(3'-((R)-2-propylpiperidine-1-carbonyl)-[1,1'-biphenyl]-3-yl)-1H-pyrazole-4-carboxylic acid,
1-(3'-((S)-1-Cyclohexylethoxy)-[1,1'-biphenyl]-3-yl)-5-((1R,2R)-2-(1-methyl-1H-1,2,3-triazol-4-yl)cyclopropyl)-1H-pyrazole-4-carboxylate, Sodium salt,
Barium 1-(3'-((S)-1-Cyclohexylethoxy)-[1,1'-biphenyl]-3-yl)-5-((1R,2R)-2-(1-methyl-1H-1,2,3-triazol-4-yl)cyclopropyl)-1H-pyrazole-4-carboxylate hydroxide,
Calcium 1-(3'-((S)-1-Cyclohexylethoxy)-[1,1'-biphenyl]-3-yl)-5-((1R,2R)-2-(1-methyl-1H-1,2,3-triazol-4-yl)cyclopropyl)-1H-pyrazole-4-carboxylate hydroxide,
1-(3'-((S)-1-Cyclohexylethoxy)-2'-methyl-[1,1'-biphenyl]-3-yl)-5-(trans-2-(1-methyl-1H-1,2,3-triazol-4-yl)cyclopropyl)-1H-pyrazole-4-carboxylic acid,
1-(3'-(Cyclohexylmethoxy)-2'-methyl-[1,1'-biphenyl]-3-yl)-5-(trans-2-(1-methyl-1H-1,2,3-triazol-4-yl)cyclopropyl)-1H-pyrazole-4-carboxylic acid,
1-(3'-((S)-1-Cycloheptylethoxy)-[1,1'-biphenyl]-3-yl)-5-((1R,2R)-2-(1-methyl-1H-1,2,3-triazol-4-yl)cyclopropyl)-1H-pyrazole-4-carboxylic acid,
1-(3'-((R)-1-Cycloheptylethoxy)-[1,1'-biphenyl]-3-yl)-5-((1R,2R)-2-(1-methyl-1H-1,2,3-triazol-4-yl)cyclopropyl)-1H-pyrazole-4-carboxylic acid,
1-(3'-((S)-1-Cyclohexylethoxy)-[1,1'-biphenyl]-3-yl)-5-(trans-2-(1-methyl-1H-1,2,3-triazol-4-yl)cyclopropyl)-1H-pyrazole-4-carboxylic acid,
1-(3'-((S)-1-Cyclohexylethoxy)-[1,1'-biphenyl]-3-yl)-5-(trans-2-(1-ethyl-1H-1,2,3-triazol-4-yl)cyclopropyl)-1H-pyrazole-4-carboxylic acid,
1-(3'-((S)-1-Cyclohexylethoxy)-[1,1'-biphenyl]-3-yl)-5-(trans-2-(1-(oxetan-3-yl)-1H-1,2,3-triazol-4-yl)cyclopropyl)-1H-pyrazole-4-carboxylic acid,
5-(trans-2-(1-Cyclobutyl-1H-1,2,3-triazol-4-yl)cyclopropyl)-1-(3'-((S)-1-cyclohexylethoxy)-[1,1'-biphenyl]-3-yl)-1H-pyrazole-4-carboxylic acid,
1-(3'-((S)-1-Cyclohexylethoxy)-[1,1'-biphenyl]-3-yl)-5-(trans-2-(1-cyclopropyl-1H-1,2,3-triazol-4-yl)cyclopropyl)-1H-pyrazole-4-carboxylic acid,
5-(trans-2-(1-(1-(tert-Butoxycarbonyl)azetidin-3-yl)-1H-1,2,3-triazol-4-yl)cyclopropyl)-1-(3'-((S)-1-cyclohexylethoxy)-[1,1'-biphenyl]-3-yl)-1H-pyrazole-4-carboxylic acid,
5-(trans-2-(1-(1-(tert-Butoxycarbonyl)piperidin-4-yl)-1H-1,2,3-triazol-4-yl)cyclopropyl)-1-(3'-((S)-1-cyclohexylethoxy)-[1,1'-biphenyl]-3-yl)-1H-pyrazole-4-carboxylic acid,
1-(3'-((S)-1-Cyclohexylethoxy)-[1,1'-biphenyl]-3-yl)-5-(trans-2-(1-(1-methylpiperidin-4-yl)-1H-1,2,3-triazol-4-yl)cyclopropyl)-1H-pyrazole-4-carboxylic acid,
1-(3'-((S)-1-Cyclohexylethoxy)-[1,1'-biphenyl]-3-yl)-5-(trans-2-(1-(tetrahydro-2H-pyran-4-yl)-1H-1,2,3-triazol-4-yl)cyclopropyl)-1H-pyrazole-4-carboxylic acid,
5-(trans-2-(1-Cyclohexyl-1H-1,2,3-triazol-4-yl)cyclopropyl)-1-(3'-((S)-1-cyclohexylethoxy)-[1,1'-biphenyl]-3-yl)-1H-pyrazole-4-carboxylic acid,
5-(trans-2-(1-(Azetidin-3-yl)-1H-1,2,3-triazol-4-)cyclopropyl)-1-(3'-((S)-1-cyclohexylethoxy)-[1,1'-biphenyl]-3-yl)-1H-pyrazole-4-carboxylic acid,
1-(3'-((S)-1-cyclohexylethoxy)-[1,1'-biphenyl]-3-yl)-5-(trans-2-(1-(piperidin-4-yl)-1H-1,2,3-triazol-4-yl)cyclopropyl)-1H-pyrazole-4-carboxylic acid,
5-(trans-2-(1-Benzyl-1H-1,2,3-triazol-4-yl)cyclopropyl)-1-(3'-((S)-1-cyclohexylethoxy)-[1,1'-biphenyl]-3-yl)-1H-pyrazole-4-carboxylic acid,
1-(3'-((S)-1-Cyclohexylethoxy)-[1,1'-biphenyl]-3-yl)-5-(trans-2-(1-(2-(dimethylamino)ethyl)-1H-1,2,3-triazol-4-yl)cyclopropyl)-1H-pyrazole-4-carboxylic acid,
1-(3'-((S)-1-Cyclohexylethoxy)-[1,1'-biphenyl]-3-yl)-5-(trans-2-(1-(2,2,2-trifluoroethyl)-1H-1,2,3-triazol-4-yl)cyclopropyl)-1H-pyrazole-4-carboxylic acid,
1-(3'-((S)-1-Cyclohexylethoxy)-[1,1'-biphenyl]-3-yl)-5-(trans-2-(1-(2-hydroxyethyl)-1H-1,2,3-triazol-4-yl)cyclopropyl)-1H-pyrazole-4-carboxylic acid,
1-(3'-((S)-1-Cyclohexylethoxy)-[1,1'-biphenyl]-3-yl)-5-(trans-2-(1-isopropyl-1H-1,2,3-triazol-4-yl)cyclopropyl)-1H-pyrazole-4-carboxylic acid,
1-(3'-((S)-1-Cyclohexylethoxy)-[1,1'-biphenyl]-3-yl)-5-((1,2-trans)-2-(1-phenyl-1H-1,2,3-triazol-4-yl)cyclopropyl)-1H-pyrazole-4-carboxylic acid,
5-(trans-2-(1H-1,2,3-Triazol-4-yl)cyclopropyl)-1-(3'-((S)-1-cyclohexylethoxy)-[1,1'-biphenyl]-3-yl)-1H-pyrazole-4-carboxylic acid,
1-(3'-((S)-1-Cyclohexylethoxy)-[1,1'-biphenyl]-3-yl)-5-(trans-2-(1-(1-methylazetidin-3-yl)-1H-1,2,3-triazol-4-yl)cyclopropyl)-1H-pyrazole-4-carboxylic acid,
1-(3'-((S)-1-Cyclohexylethoxy)-[1,1'-biphenyl]-3-yl)-5-((1R,2R)-2-(1-(tetrahydro-2H-pyran-4-yl)-1H-1,2,3-triazol-4-yl)cyclopropyl)-1H-pyrazole-4-carboxylic acid,
1-(3'-((S)-1-Cyclohexylethoxy)-[1,1'-biphenyl]-3-yl)-5-((1S,2S)-2-(1-(tetrahydro-2H-pyran-4-yl)-1H-1,2,3-triazol-4-yl)cyclopropyl)-1H-pyrazole-4-carboxylic acid,
1-(3'-((S)-1-Cyclohexylethoxy)-[1,1'-biphenyl]-3-yl)-5-((1R,2R)-2-(1-(2,2,2-trifluoroethyl)-1H-1,2,3-triazol-4-yl)cyclopropyl)-1H-pyrazole-4-carboxylic acid,
1-(3'-((S)-1-Cyclohexylethoxy)-[1,1'-biphenyl]-3-yl)-5-((1R,2R)-2-(1-cyclopropyl-1H-1,2,3-triazol-4-yl)cyclopropyl)-1H-pyrazole-4-carboxylic acid,
5-((1R,2R)-2-(1H-1,2,3-Triazol-4-yl)cyclopropyl)-1-(3'-((S)-1-cyclohexylethoxy)-[1,1'-biphenyl]-3-yl)-1H-pyrazole-4-carboxylic acid,
5-((1S,2S)-2-(1H-1,2,3-Triazol-4-yl)cyclopropyl)-1-(3'-((S)-1-cyclohexylethoxy)-[1,1'-biphenyl]-3-yl)-1H-pyrazole-4-carboxylic acid,
1-(3'-((S)-1-cyclohexylethoxy)-[1,1'-biphenyl]-3-yl)-5-(cis-2-(1-methyl-1H-1,2,3-triazol-4-yl)cyclopropyl)-1H-pyrazole-4-carboxylic acid,
1-(3'-((S)-1-Cyclohexylethoxy)-[1,1'-biphenyl]-3-yl)-5-(trans-2-(3-hydroxypropyl)cyclopropyl)-1H-pyrazole-4-carboxylic acid,
1-(3'-((S)-1-cyclohexylethoxy)-[1,1'-biphenyl]-3-yl)-5-(trans-2-(1-methyl-1H-pyrazol-4-yl)cyclopropyl)-1H-pyrazole-4-carboxylic acid,
1-(3'-((S)-1-cyclohexylethoxy)-2'-fluoro-[1,1'-biphenyl]-3-yl)-5-((1R,2R)-2-(1-methyl-1H-1,2,3-triazol-4-yl)cyclopropyl)-1H-pyrazole-4-carboxylic acid,
Ethyl 1-(3'-((S)-1-cyclohexylethoxy)-[1,1'-biphenyl]-3-yl)-5-((1R,2R)-2-(1-methyl-1H-1,2,3-triazol-4-yl)cyclopropyl)-1H-pyrazole-4-carboxylate,
2-Oxotetrahydrofuran-3-yl 1-(3'-((S)-1-cyclohexylethoxy)-[1,1'-biphenyl]-3-yl)-5-((1R,2R)-2-(1-methyl-1H-1,2,3-triazol-4-yl)cyclopropyl)-1H-pyrazole-4-carboxylate,
2-Hydroxyethyl 1-(3'-((S)-1-cyclohexylethoxy)-[1,1'-biphenyl]-3-yl)-5-((1R,2R)-2-(1-methyl-1H-1,2,3-triazol-4-yl)cyclopropyl)-1H-pyrazole-4-carboxylate,
2-Morpholinoethyl 1-(3'-((S)-1-cyclohexylethoxy)-[1,1'-biphenyl]-3-yl)-5-((1R,2R)-2-(1-methyl-1H-1,2,3-triazol-4-yl)cyclopropyl)-1H-pyrazole-4-carboxylate, (Pivaloyloxy)methyl 1-(3'-((S)-1-cyclohexylethoxy)-[1,1'-biphenyl]-3-yl)-5-((1R,2R)-2-(1-methyl-1H-1,2,3-triazol-4-yl)cyclopropyl)-1H-pyrazole-4-carboxylate,
Acetoxymethyl 1-(3'-((S)-1-cyclohexylethoxy)-[1,1'-biphenyl]-3-yl)-5-((1R,2R)-2-(1-methyl-1H-1,2,3-triazol-4-yl)cyclopropyl)-1H-pyrazole-4-carboxylate,
(Benzoyloxy)methyl 1-(3'-((S)-1-cyclohexylethoxy)-[1,1'-biphenyl]-3-yl)-5-((1R,2R)-2-(1-methyl-1H-1,2,3-triazol-4-yl)cyclopropyl)-1H-pyrazole-4-carboxylate,
((tert-Butoxycarbonyl)oxy)methyl 1-(3'-((S)-1-cyclohexylethoxy)-[1,1'-biphenyl]-3-yl)-5-((1R,2R)-2-(1-methyl-1H-1,2,3-triazol-4-yl)cyclopropyl)-1H-pyrazole-4-carboxylate,
rac-1-(3'-((E)-2-Cyclohexylvinyl)-[1,1'-biphenyl]-3-yl)-5-(trans-2-(1-methyl-1H-1,2,3-triazol-4-yl)cyclopropyl)-1H-pyrazole-4-carboxylic acid,
rac-1-(3'-(2-Cyclohexylethyl)-[1,1'-biphenyl]-3-yl)-5-(-2-(1-methyl-1H-1,2,3-triazol-4-yl)cyclopropyl)-1H-pyrazole-4-carboxylic acid,
1-(3'-((S)-1-cyclohexylethoxy)-[1,1'-biphenyl]-3-yl)-5-((1R,2R)-2-(3-methylisoxazol-5-yl)cyclopropyl)-1H-pyrazole-4-carboxylic acid,
1-(3'-((R) or (S)-2-Cyclohexylpropyl)-[1,1'-biphenyl]-3-yl)-5-((1R,2R)-2-(1-methyl-1H-1,2,3-triazol-4-yl)cyclopropyl)-1H-pyrazole-4-carboxylic acid,
1-(3'-((R) or (S)-2-Cyclohexylpropyl)-[1,1'-biphenyl]-3-yl)-5-((1R,2R)-2-(1-methyl-1H-1,2,3-triazol-4-yl)cyclopropyl)-1H-pyrazole-4-carboxylic acid,
1-(2'-fluoro-3'-((R)-2-propylpiperidine-1-carbonyl)-[1,1'-biphenyl]-3-yl)-5-(trans-2-(3-methylisoxazol-5-yl)cyclopropyl)-1H-pyrazole-4-carboxylic acid,
Methyl 1-(3'-((3-ethyl-2,3-dihydrobenzo[f][1,4]oxazepin-4(5H)-yl)methyl)-[1,1'-biphenyl]-3-yl)-5-((1,2-trans)-2-(1-methyl-1H-1,2,3-triazol-4-yl)cyclopropyl)-1H-pyrazole-4-carboxylate,
1-(3'-(((S)-3-Ethyl-2,3-dihydrobenzo[f][1,4]oxazepin-4(5H)-yl)methyl)-[1,1'-biphenyl]-3-yl)-5-((1R,2R)-2-(1-methyl-1H-1,2,3-triazol-4-yl)cyclopropyl)-1H-pyrazole-4-carboxylic acid,
1-(3'-(((R)-3-Ethyl-2,3-dihydrobenzo[f][1,4]oxazepin-4(5H)-yl)methyl)-[1,1'-biphenyl]-3-yl)-5-((1R,2R)-2-(1-methyl-1H-1,2,3-triazol-4-yl)cyclopropyl)-1H-pyrazole-4-carboxylic acid,
1-(3'-(((S)-5-Ethyl-2,3-dihydrobenzo[f][1,4]oxazepin-4(5H)-yl)methyl)-[1,1'-biphenyl]-3-yl)-5-((1R,2R)-2-(1-methyl-1H-1,2,3-triazol-4-yl)cyclopropyl)-1H-pyrazole-4-carboxylic acid (isomer 2),
1-(3'-(((S)-5-Ethyl-2,3-dihydrobenzo[f][1,4]oxazepin-4(5H)-yl)methyl)-[1,1'-biphenyl]-3-yl)-5-((1R,2R)-2-(1-methyl-1H-1,2,3-triazol-4-yl)cyclopropyl)-1H-pyrazole-4-carboxylic acid (isomer 1),
1-(3'-((5-Ethyl-2,3-dihydrobenzo[f][1,4]oxazepin-4(5H)-yl)methyl)-[1,1'-biphenyl]-3-yl)-5-((1,2-trans)-2-(1-methyl-1H-1,2,3-triazol-4-yl)cyclopropyl)-1H-pyrazole-4-carboxylic acid,
1-(3'-(((S)-5-Ethyl-2,2-dimethyl-2,3-dihydrobenzo[f][1,4]oxazepin-4(5H)-yl)methyl)-[1,1'-biphenyl]-3-yl)-5-((1R,2R)-2-(1-methyl-1H-1,2,3-triazol-4-yl)cyclopropyl)-1H-pyrazole-4-carboxylic acid (isomer 1),
1-(3'-(((R)-5-Ethyl-2,2-dimethyl-2,3-dihydrobenzo[f][1,4]oxazepin-4(5H)-yl)methyl)-[1,1'-biphenyl]-3-yl)-5-((1R,2R)-2-(1-methyl-1H-1,2,3-triazol-4-yl)cyclopropyl)-1H-pyrazole-4-carboxylic acid (isomer 2),
1-(3'-((4,4-dimethyl-4,5-dihydro-1H-benzo[c]azepin-2(3H)-yl)methyl)-[1,1'-biphenyl]-3-yl)-5-((1,2-trans)-2-(1-methyl-1H-1,2,3-triazol-4-yl)cyclopropyl)-1H-pyrazole-4-carboxylic acid,
1-(3'-((1-Ethyl-2,3-dihydro-1H-benzo[e][1,4]diazepin-4(5H)-yl)methyl)-[1,1'-biphenyl]-3-yl)-5-((1,2-trans)-2-(1-methyl-1H-1,2,3-triazol-4-yl)cyclopropyl)-1H-pyrazole-4-carboxylic acid,
1-(3'-(((R)-2-ethyl-2,3-dihydrobenzo[f][1,4]oxazepin-4(5H)-yl)methyl)-[1,1'-biphenyl]-3-yl)-5-((1,2-trans)-2-(1-isopropyl-1H-1,2,3-triazol-4-yl)cyclopropyl)-1H-pyrazole-4-carboxylic acid,
1-(3'-(((R)-2-ethyl-2,3-dihydrobenzo[f][1,4]oxazepin-4(5H)-yl)methyl)-[1,1'-biphenyl]-3-yl)-5-(2-(1-methyl-1H-1,2,3-triazol-4-yl)cyclopropyl)-1H-pyrazole-4-carboxylic acid,
1-(3'-(((R)-4-Methyl-1,1-dioxido-4,5-dihydrobenzo[1,2]thiazepin-2(3H)-yl)methyl)-[1,1'-biphenyl]-3-yl)-5-((1R,2R)-2-(1-methyl-1H-1,2,3-triazol-4-yl)cyclopropyl)-1H-pyrazole-4-carboxylic acid,
1-(3'-(((S)-8-Bromo-4-methyl-1,1-dioxido-4,5-dihydrobenzo[f][1,2]thiazepin-2(3H)-yl)methyl)-2'-fluoro-[1,1'-biphenyl]-3-yl)-5-((1R,2R)-2-(1-methyl-1H-1,2,3-triazol-4-yl)cyclopropyl)-1H-pyrazole-4-carboxylic acid,
1-(3'-(((S)-4-methyl-1,1-dioxido-4,5-dihydrobenzo[1,2]thiazepin-2(3H)-yl)methyl)-[1,1'-biphenyl]-3-yl)-5-((1R,2R)-2-(1-methyl-1H-1,2,3-triazol-4-yl)cyclopropyl)-1H-pyrazole-4-carboxylic acid,
1-(3'-(((S)-4-methyl-1,1-dioxido-4,5-dihydrobenzo[1,2]thiazepin-2(3H)-yl)methyl)-[1,1'-biphenyl]-3-yl)-5-((1S,2S)-2-(1-methyl-1H-1,2,3-triazol-4-yl)cyclopropyl)-1H-pyrazole-4-carboxylic acid,
1-(3'-(((S)-8-bromo-4-methyl-1,1-dioxido-4,5-dihydrobenzo[f][1,2]thiazepin-2(3H)-yl)methyl)-[1,1'-biphenyl]-3-yl)-5-((1R,2R)-2-(1-methyl-1H-1,2,3-triazol-4-yl)cyclopropyl)-1H-pyrazole-4-carboxylic acid (isomer 1),
1-(3'-(((R)-8-bromo-4-methyl-1,1-dioxido-4,5-dihydrobenzo[f][1,2]thiazepin-2(3H)-yl)methyl)-[1,1'-biphenyl]-3-yl)-5-((1R,2R)-2-(1-methyl-1H-1,2,3-triazol-4-yl)cyclopropyl)-1H-pyrazole-4-carboxylic acid (isomer 2),
1-(3'-(((S)-4-methyl-1,1-dioxido-4,5-dihydrobenzo[f][1,2]thiazepin-2(3H)-yl)methyl)-[1,1'-biphenyl]-3-yl)-5-((1,2-trans)-2-(1-methyl-1H-1,2,3-triazol-4-yl)cyclopropyl)-1H-pyrazole-4-carboxylic acid,
1-(3'-(((R)-4-methyl-1,1-dioxido-4,5-dihydrobenzo[f][1,2]thiazepin-2(3H)-yl)methyl)-[1,1'-biphenyl]-3-yl)-5-((1,2-trans)-2-(1-methyl-1H-1,2,3-triazol-4-yl)cyclopropyl)-1H-pyrazole-4-carboxylic acid,
1-(3'-(((R)-4-ethyl-1,1-dioxido-3,4-dihydro-2H-pyrido[2,3-b][1,4,5]oxathiazepin-2-yl)methyl)-[1,1'-biphenyl]-3-yl)-5-((1,2-trans)-2-(1-methyl-1H-1,2,3-triazol-4-yl)cyclopropyl)-1H-pyrazole-4-carboxylic acid,
1-(3'-((5-Ethyl-1,1-dioxido-4,5-dihydrobenzo[f][1,2,5]thiadiazepin-2(3H)-yl)methyl)-[1,1'-biphenyl]-3-yl)-5-((1R,2R)-2-(1-methyl-1H-1,2,3-triazol-4-yl)cyclopropyl)-1H-pyrazole-4-carboxylic acid,
1-(3'-((5-methyl-1,1-dioxido-4,5-dihydrobenzo[f][1,2,5]thiadiazepin-2(3H)-yl)methyl)-[1,1'-biphenyl]-3-yl)-5-((1,2-trans)-2-(1-methyl-1H-1,2,3-triazol-4-yl)cyclopropyl)-1H-pyrazole-4-carboxylic acid,
1-(3'-((2,2-Dimethyl-2,3-dihydrobenzo[f][1,4]oxazepin-4(5H)-yl)sulfonyl)-[1,1'-biphenyl]-3-yl)-5-((1,2-trans)-2-(1-methyl-1H-1,2,3-triazol-4-yl)cyclopropyl)-1H-pyrazole-4-carboxylic acid,
5-((1,2-trans)-2-(1-Methyl-1H-1,2,3-triazol-4-yl)cyclopropyl)-1-(3'-((2-propylpiperidin-1-yl)sulfonyl)-[1,1'-biphenyl]-3-yl)-1H-pyrazole-4-carboxylic acid, 5-((1,2-trans)-2-(1-Methyl-1H-1,2,3-triazol-4-yl)cyclopropyl)-1-(3'-(piperidin-1-ylsulfonyl)-[1,1'-biphenyl]-3-yl)-1H-pyrazole-4-carboxylic acid, 5-((1,2-trans)-2-(1-Methyl-1H-1,2,3-triazol-4-yl)cyclopropyl)-1-(3'-((tetrahydro-2H-thiopyran-3-yl)methoxy)-[1,1'-biphenyl]-3-yl)-1H-pyrazole-4-carboxylic acid, 1-(3'-((4,4-Difluorocyclohexyl)methoxy)-[1,1'-biphenyl]-3-yl)-5-((1,2-trans)-2-(1-methyl-1H-1,2,3-triazol-4-yl)cyclopropyl)-1H-pyrazole-4-carboxylic acid, 5-((1,2-trans)-2-(1-Methyl-1H-1,2,3-triazol-4-yl)cyclopropyl)-1-(3'-(((1r,4R)-4-(trifluoromethyl)cyclohexyl)methoxy)-[1,1'-biphenyl]-3-yl)-1H-pyrazole-4-carboxylic acid, 5-((1,2-trans)-2-(1-Methyl-1H-1,2,3-triazol-4-yl)cyclopropyl)-1-(3'-((3-(trifluoromethyl)cyclohexyl)methoxy)-[1,1'-biphenyl]-3-yl)-1H-pyrazole-4-carboxylic acid, 5-((1,2-trans)-2-(1-Methyl-1H-1,2,3-triazol-4-yl)cyclopropyl)-1-(3'-((2-(trifluoromethyl)cyclohexyl)methoxy)-[1,1'-biphenyl]-3-yl)-1H-pyrazole-4-carboxylic acid, 5-((1,2-trans)-2-(1-Methyl-1H-1,2,3-triazol-4-yl)cyclopropyl)-1-(3'-((tetrahydro-2H-thiopyran-4-yl)methoxy)-[1,1'-biphenyl]-3-yl)-1H-pyrazole-4-carboxylic acid, 1-(3'-((4-Ethylcyclohexyl)methoxy)-[1,1'-biphenyl]-3-yl)-5-((1,2-trans)-2-(1-methyl-1H-1,2,3-triazol-4-yl)cyclopropyl)-1H-pyrazole-4-carboxylic acid, 1-(3'-(Cyclohexylmethoxy)-[1,1'-biphenyl]-3-yl)-5-(2-(1-methyl-1H-1,2,3-triazol-4-yl)ethyl)-1H-pyrazole-4-carboxylic acid, 1-(3'-(Cyclohexylmethoxy)-2'-fluoro-[1,1'-biphenyl]-3-yl)-5-((1,2-trans)-2-(1-methyl-1H-1,2,3-triazol-4-yl)cyclopropyl)-1H-pyrazole-4-carboxylic acid, 5-Cyclopropyl-1-(3'-(4-(1-methyl-1H-1,2,3-triazol-4-yl)butoxy)-[1,1'-biphenyl]-3-yl)-1H-pyrazole-4-carboxylic acid, 5-(2-(1-Methyl-1H-1,2,3-triazol-4-yl)cyclopropyl)-1-(5-methyl-3'-((R)-2-propylpiperidine-1-carbonyl)-[1,1'-biphenyl]-3-yl)-1H-pyrazole-4-carboxylic acid, 5-((1R,2R)-2-(1-Methyl-1H-1,2,3-triazol-4-yl)cyclopropyl)-1-(5-methyl-3'-((R)-2-propylpiperidine-1-carbonyl)-[1,1'-biphenyl]-3-yl)-1H-pyrazole-4-carboxylic acid (isomer 1), 5-((1S,2S)-2-(1-methyl-1H-1,2,3-triazol-4-yl)cyclopropyl)-1-(5-methyl-3'-((R)-2-propylpiperidine-1-carbonyl)-[1,1'-biphenyl]-3-yl)-1H-pyrazole-4-carboxylic acid (isomer 2), 1-(3'-(1-Cyclohexyl-2,2,2-trifluoroethoxy)-[1,1'-biphenyl]-3-yl)-5-((1,2-trans)-2-(1-methyl-1H-1,2,3-triazol-4-yl)cyclopropyl)-1H-pyrazole-4-carboxylic acid, 1-(3'-(dimethylcarbamoyl)-[1,1'-biphenyl]-3-yl)-5-(2-(1-ethyl-1H-1,2,3-triazol-4-yl)cyclopropyl)-1H-pyrazole-4-carboxylic acid, 5-(2-(5-Methylisoxazol-4-yl)cyclopropyl)-1-(3'-((R)-2-propylpiperidine-1-carbonyl)-[1,1'-biphenyl]-3-yl)-1H-pyrazole-4-carboxylic acid, 1-(5-Chloro-3'-((R)-2-propylpiperidine-1-carbonyl)-[1,1'-biphenyl]-3-yl)-5-(2-(1-methyl-1H-1,2,3-triazol-4-yl)cyclopropyl)-1H-pyrazole-4-carboxylic acid compound with 2,2,2-trifluoroacetic acid (1:1), 1-(3'-((1-Cyclohexylpropan-2-yl)oxy)-[1,1'-biphenyl]-3-yl)-5-cyclopropyl-1H-pyrazole-4-carboxylic acid, 1-(3'-((R)-1-Cyclohexylethoxy)-[1,1'-biphenyl]-3-yl)-5-((1R,2R)-2-(1-methyl-1H-1,2,3-triazol-4-yl)cyclopropyl)-1H-pyrazole-4-carboxylic acid, 1-(3'-(1-Cyclohexylethoxy)-[1,1'-biphenyl]-3-yl)-5-((1R,2R)-2-(1-methyl-1H-1,2,3-triazol-4-yl)cyclopropyl)-1H-pyrazole-4-carboxylic acid, 1-(3'-(Cyclohexylmethoxy)-[1,1'-biphenyl]-3-yl)-5-(2-(1-methyl-1H-1,2,3-triazol-4-yl)cyclopropyl)-1H-pyrazole-4-carboxylic acid, 1-(3'-(1-Cyclohexylethoxy)-[1,1'-biphenyl]-3-yl)-5-((1S,2S)-2-(1-methyl-1H-1,2,3-triazol-4-yl)cyclopropyl)-1H-pyrazole-4-carboxylic acid, 1-(3'-(tert-Butoxy)-[1,1'-biphenyl]-3-yl)-5-(2-(1-methyl-1H-1,2,3-triazol-4-yl)cyclopropyl)-1H-pyrazole-4-carboxylic acid, 1-(3'-((1-(tert-Butoxycarbonyl)piperidin-4-yl)methoxy)-[1,1'-biphenyl]-3-yl)-5-(2-(1-methyl-1H-1,2,3-triazol-4-yl)cyclopropyl)-1H-pyrazole-4-carboxylic acid, 1-(3'-(2-Cyclohexyl-4-methoxybutoxy)-[1,1'-biphenyl]-3-yl)-5-(2-(1-methyl-1H-1,2,3-triazol-4-yl)cyclopropyl)-1H-pyrazole-4-carboxylic acid, 5-(2-(1-Methyl-1H-1,2,3-triazol-4-yl)cyclopropyl)-1-(3'-((tetrahydro-2H-pyran-3-yl)methoxy)-[1,1'-biphenyl]-3-yl)-1H-pyrazole-4-carboxylic acid, 1-(3'-(2-Cyclohexylethoxy)-[1,1'-biphenyl]-3-yl)-5-(2-(1-methyl-1H-1,2,3-triazol-4-yl)cyclopropyl)-1H-pyrazole-4-carboxylic acid, 1-(3'-(Cyclohexylmethoxy)-[1,1'-biphenyl]-3-yl)-5-((1R,2R)-2-(1-methyl-1H-1,2,3-triazol-4-yl)cyclopropyl)-1H-pyrazole-4-carboxylic acid, 1-(3'-((2-Cyclohexylpentyl)oxy)-[1,1'-biphenyl]-3-yl)-5-(2-(1-methyl-1H-1,2,3-triazol-4-yl)cyclopropyl)-1H-pyrazole-4-carboxylic acid, 1-(3'-(2-Cyclohexylpropoxy)-[1,1'-biphenyl]-3-yl)-5-(2-(1-methyl-1H-1,2,3-triazol-4-yl)cyclopropyl)-1H-pyrazole-4-carboxylic acid, 5-(2-(1-Methyl-1H-1,2,3-triazol-4-yl)cyclopropyl)-1-(3'-((tetrahydro-2H-pyran-4-yl)methoxy)-[1,1'-biphenyl]-3-yl)-1H-pyrazole-4-carboxylic acid, 5-(2-(1-Methyl-1H-1,2,3-triazol-4-yl)cycclopropyl)-1-(3'-((tetrahydro-2H-pyran-2-yl)methoxy)-[1,1'-biphenyl]-3-yl)-1H-pyrazole-4-carboxylic acid, 1-(3'-(((1R,4S)-4-Methoxycyclohexyl)methoxy)-[1,1'-biphenyl]-3-yl)-5-((1,2-trans)-2-(1-methyl-1H-1,2,3-triazol-4-yl)cyclopropyl)-1H-pyrazole-4-carboxylic acid, 1-(3'-((2-Methoxycyclohexyl)methoxy)-[1,1'-biphenyl]-3-yl)-5-((1,2-trans)-2-(1-methyl-1H-1,2,3-triazol-4-yl)cyclopropyl)-1H-pyrazole-4-carboxylic acid, 1-(3'-((3-Methoxycyclohexyl)methoxy)-[1,1'-biphenyl]-3-yl)-5-((1,2-trans)-2-(1-methyl-1H-1,2,3-triazol-4-yl)cyclopropyl)-1H-pyrazole-4-carboxylic acid, 1-(3'-((Cyclohexylmethyl)thio)-[1,1'-biphenyl]-3-yl)-5-(2-(1-methyl-1H-1,2,3-triazol-4-yl)cyclopropyl)-1H-pyrazole-4-carboxylic acid, 5-((1,2-trans)-2-(1-Methyl-1H-1,2,3-triazol-4-yl)cyclopropyl)-1-(3'-((R)-1-((1R,4R)-4-(trifluoromethyl)cyclohexyl)ethoxy)-[1,1'-biphenyl]-3-yl)-1H-pyrazole-4-carboxylic acid, 1-(2'-Fluoro-3'-isopropoxy-[1,1'-biphenyl]-3-yl)-5-(2-(1-methyl-1H-1,2,3-triazol-4-yl)cyclopropyl)-1H-pyrazole-4-carboxylic acid, 1-(3'-(1-Ethoxy-2-methylpropyl)-[1,1'-biphenyl]-3-yl)-5-(2-(1-methyl-1H-1,2,3-triazol-4-yl)cyclopropyl)-1H-pyrazole-4-carboxylic acid, 1-(3'-(Cyclopentyl(methoxy)methyl)-[1,1'-biphenyl]-3-yl)-5-(2-(1-methyl-1H-1,2,3-triazol-4-yl)cyclopropyl)-1H-pyrazole-4-carboxylic acid, 1-(3'-(1-Methoxy-2-methylpropyl)-[1,1'-biphenyl]-3-yl)-5-(2-(1-methyl-1H-1,2,3-triazol-4-yl)cyclopropyl)-1H-pyrazole-4-carboxylic acid, 1-(3'-((4-Chlorocyclohexyl)methoxy)-[1,1'-biphenyl]-3-yl)-5-((1,2-trans)-2-(1-methyl-1H-1,2,3-triazol-4-yl)cyclopropyl)-1H-pyrazole-4-carboxylic acid, 1-(3'-((2-chlorocyclohexyl)methoxy)-[1,1'-biphenyl]-3-yl)-5-((1,2-trans)-2-(1-methyl-1H-1,2,3-triazol-4-yl)cyclopropyl)-1H-pyrazole-4-carboxylic acid, 1-(3'-((3-chlorocyclohexyl)methoxy)-[1,1'-biphenyl]-3-yl)-5-((1,2-trans)-2-(1-methyl-1H-1,2,3-triazol-4-yl)cyclopropyl)-1H-pyrazole-4-carboxylic acid, 1-(3'-(cyclohexylmethoxy)-[1,1'-biphenyl]-3-yl)-3-methyl-5-((1,2-trans)-(2-(1-methyl-1H-1,2,3-triazol-4-yl)cyclopropyl)-1H-pyrazole-4-carboxylic acid, 1-(5-cyano-3'-(cyclohexylmethoxy)-[1,1'-biphenyl]-3-yl)-5-(2-(1-methyl-1H-1,2,3-triazol-4-yl)cyclopropyl)-1H-pyrazole-4-carboxylic acid, 1-(3'-(cyclohexylmethoxy)-[1,1'-biphenyl]-3-yl)-5-(2-(1-methyl-1H-imidazol-4-yl)cyclopropyl)-1H-pyrazole-4-carboxylic acid, 1-(3'-(1-cyclohexylethoxy)-[1,1'-biphenyl]-3-yl)-5-((1S,2S)-2-(1-methyl-1H-1,2,3-triazol-4-yl)cyclopropyl)-1H-pyrazole-4-carboxylic acid, 1-(3'-(1-cyclohexylethoxy)-[1,1'-biphenyl]-3-yl)-5-((1,2-trans)-2-(1-ethyl-1H-1,2,3-triazol-4-yl)cyclopropyl)-1H-pyrazole-4-carboxylic acid, 1-(3'-(1-cyclohexylethoxy)-5-methoxy-[1,1'-biphenyl]-3-yl)-5-((1S,2S)-2-(1-ethyl-1H-1,2,3-triazol-4-yl)cyclopropyl)-1H-pyrazole-4-carboxylic acid, 1-(3'-(1-cyclohexylethoxy)-5-methoxy-[1,1'-biphenyl]-3-yl)-5-((1,2-trans)-2-(1-ethyl-1H-1,2,3-triazol-4-yl)cyclopropyl)-1H-pyrazole-4-carboxylic acid, 1-(3'-(1-cyclohexylethoxy)-[1,1'-biphenyl]-3-yl)-5-((1,2-trans)-2-(1-isopropyl-1H-1,2,3-triazol-4-yl)cyclopropyl)-1H-pyrazole-4-carboxylic acid, 5-(2-(1-Methyl-1H-1,2,3-triazol-4-yl)cyclopropyl)-1-(6-(3-((R)-2-propylpiperidine-1-carbonyl)phenyl)pyridin-2-yl)-1H-pyrazole-4-carboxylic acid, 5-(2-(1-Methyl-1H-1,2,3-triazol-4-yl)cyclopropyl)-1-(3-(5-((R)-2-propylpiperidine-1-carbonyl)pyridin-3-yl)phenyl)-1H-pyrazole-4-carboxylic acid, 1-(3'-Fluoro-5'-((R)-2-propylpiperidine-1-carbonyl)-[1,1'-biphenyl]-3-yl)-5-(2-(1-methyl-1H-1,2,3-triazol-4-yl)cyclopropyl)-1H-pyrazole-4-carboxylic acid, 5-((1,2-trans)-2-(1-methyl-1H-1,2,3-triazol-4-yl)cyclopropyl)-1-(3'-((R)-2-propylpiperidine-1-carbonyl)-[1,1'-biphenyl]-3-yl)-1H-pyrazole-4-carboxylic acid, 5-((1,2-trans)-2-(1-Isopropyl-1H-1,2,3-triazol-4-yl)cyclopropyl)-1-(3'-((R)-2-propylpiperidine-1-carbonyl)-[1,1'-biphenyl]-3-yl)-1H-pyrazole-4-carboxylic acid, 5-((1,2-trans)-2-(1-Ethyl-1H-1,2,3-triazol-4-yl)cyclopropyl)-1-(3'-((R)-2-propylpiperidine-1-carbonyl)-[1,1'-biphenyl]-3-yl)-1H-pyrazole-4-carboxylic acid, 3-Methyl-5-(2-(1-methyl-1H-1,2,3-triazol-4-yl)cyclopropyl)-1-(3'-((R)-2-propylpiperidine-1-carbonyl)-[1,1'-biphenyl]-3-yl)-1H-pyrazole-4-carboxylic acid, (R)-5-Cyclopropyl-3-methyl-1-(3'-(2-propylpiperidine-1-carbonyl)-[1,1'-biphenyl]-3-yl)-1H-pyrazole-4-carboxylic acid, 1-(6-(3-(6,6-Dimethyl-5,6-dihydrocyclopenta[c]pyrazol-1(4H)-yl)phenyl)pyridin-2-yl)-5-(trifluoromethyl)-1H-pyrazole-4-carboxylic acid, 5-Cyclopropyl-1-(3'-(6-methyl-6-propyl-5,6-dihydrocyclopenta[c]pyrazol-1(4H)-yl)-[1,1'-biphenyl]-3-yl)-1H-pyrazole-4-carboxylic acid, 1-(3'-(6-Butyl-5,6-dihydrocyclopenta[c]pyrazol-1(4H)-yl)-[1,1'-biphenyl]-3-yl)-5-cyclopropyl-1H-pyrazole-4-carboxylic acid, 5-Cyclopropyl-1-(3'-(6-cyclopropyl-5,6-dihydrocyclopenta[c]pyrazol-1(4H)-yl)-[1,1-'-biphenyl]-3-yl)-1H-pyrazole-4-carboxylic acid, 1-(3'-(6,6-Dimethyl-5,6-dihydrocyclopenta[c]pyrazol-1(4H)-yl)-[1,1'-biphenyl]-3-yl)-5-((1S,2S)-2-(1-methyl-1H-1,2,3-triazol-4-yl)cyclopropyl)-1H-pyrazole-4-carboxylic acid, 5-Cyclopropyl-1-(3'-(5-ethyl-1,2,4-oxadiazol-3-yl)-[1,1'-biphenyl]-3-yl)-1H-pyrazole-4-carboxylic acid, 5-Cyclopropyl-1-(3'-(5-methyl-1,3,4-oxadiazol-2-yl)-[1,1'-biphenyl]-3-yl)-1H-pyrazole-4-carboxylic acid, 5-Cyclopropyl-1-(3'-(5-methyl-1,2,4-oxadiazol-3-yl)-[1,1'-biphenyl]-3-yl)-1H-pyrazole-4-carboxylic acid, 1-(3'-(6,6-Dimethyl-5,6-dihydrocyclopenta[c]pyrazol-1(4H)-yl)-[1,1'-biphenyl]-3-yl)-5-(2-(1-methyl-1H-1,2,3-triazol-4-yl)cyclopropyl)-1H-pyrazole-4-carboxylic acid, 5-(2-(1-Methyl-1H-pyrazol-4-yl)cyclopropyl)-1-(3'-((R)-2-propylpiperidine-1-carbonyl)-[1,1'-biphenyl]-3-yl)-1H-pyrazole-4-carboxylic acid, 1-(2'-Fluoro-3'-((R)-2-propylpiperidine-1-carbonyl)-[1,1'-biphenyl]-3-yl)-5-(2-(1-methyl-1H-pyrazol-4-yl)cyclopropyl)-1H-pyrazole-4-carboxylic acid, 1-(3'-(2-Cyclohexylacetyl)-[1,1'-biphenyl]-3-yl)-5-(2-(1-methyl-1H-1,2,3-triazol-4-yl)cyclopropyl)-1H-pyrazole-4-carboxylic acid, 1-(3'-(2-Cyclohexyl-1-methoxyethyl)-[1,1'-biphenyl]-3-yl)-5-(2-(1-methyl-1H-1,2,3-triazol-4-yl)cyclopropyl)-1H-pyrazole-4-carboxylic acid, 1-(3'-(2-Cyclohexyl-1-hydroxyethyl)-[1,1'-biphenyl]-3-yl)-5-(2-(1-methyl-1H-1,2,3-triazol-4-yl)cyclopropyl)-1H-pyrazole-4-carboxylic acid, 1-(3'-((1-Cyclohexylpropan-2-yl)oxy)-[1,1'-biphenyl]-3-yl)-5-(2-(1-methyl-1H-1,2,3-triazol-4-yl)cyclopropyl)-1H-pyrazole-4-carboxylic acid, 1-(3'-(1-Cyclohexylethoxy)-[1,1'-biphenyl]-3-yl)-5-(2-(1-methyl-1H-1,2,3-triazol-4-yl)cyclopropyl)-1H-pyrazole-4-carboxylic acid, 1-(3'-(Cyclohexyl(hydroxy)methyl)-[1,1'-biphenyl]-3-yl)-5-(2-(1-methyl-1H-1,2,3-triazol-4-yl)cyclopropyl)-1H-pyrazole-4-carboxylic acid, 1-(3'-(Benzyloxy)-[1,1'-biphenyl]-3-yl)-5-(2-(1-methyl-1H-1,2,3-triazol-4-yl)cyclopropyl)-1H-pyrazole-4-carboxylic acid, 1-(3'-((2-Fluorobenzyl)oxy)-[1,1'-biphenyl]-3-yl)-5-(2-(1-methyl-1H-1,2,3-triazol-4-yl)cyclopropyl)-1H-pyrazole-4-carboxylic acid, 1-(3'-((4-Fluorobenzyl)oxy)-[1,1'-biphenyl]-3-yl)-5-(2-(1-methyl-1H-1,2,3-triazol-4-yl)cyclopropyl)-1H-pyrazole-4-carboxylic acid, 1-(3'-((3-Fluorobenzyl)oxy)-[1,1'-biphenyl]-3-yl)-5-(2-(1-methyl-1H-1,2,3-triazol-4-yl)cyclopropyl)-1H-pyrazole-4-carboxylic acid, 1-(3'-(3,3-Dimethylbutoxy)-[1,1'-biphenyl]-3-yl)-5-(2-(1-methyl-1H-1,2,3-triazol-4-yl)cyclopropyl)-1H-pyrazole-4-carboxylic acid, 5-((1,2-trans)-2-(1-Methyl-1H-1,2,3-triazol-4-yl)cyclopropyl)-1-(3'-(neopentyloxy)-[1,1'-biphenyl]-3-yl)-1H-pyrazole-4-carboxylic acid, 5-(2-(1-Methyl-1H-1,2,3-triazol-4-yl)cyclopropyl)-1-(3'-(1-(tetrahydro-2H-pyran-4-yl)ethoxy)-[1,1'-biphenyl]-3-yl)-1H-pyrazole-4-carboxylic acid, 1-(3'-(1-Cyclopentylethoxy)-[1,1'-biphenyl]-3-yl)-5-(2-(1-methyl-1H-1,2,3-triazol-4-yl)cyclopropyl)-1H-pyrazole-4-carboxylic acid, 1-(3'-(Cyclohexyloxy)-[1,1'-biphenyl]-3-yl)-5-(2-(1-methyl-1H-1,2,3-triazol-4-yl)cyclopropyl)-1H-pyrazole-4-carboxylic acid, 1-(3'-(1-Cycloheptylethoxy)-[1,1'-biphenyl]-3-yl)-5-((1,2-trans)-2-(1-methyl-1H-1,2,3-triazol-4-yl)cyclopropyl)-1H-pyrazole-4-carboxylic acid, 1-(3'-(1-Cyclopropylethoxy)-[1,1'-biphenyl]-3-yl)-5-(2-(1-methyl-1H-1,2,3-triazol-4-yl)cyclopropyl)-1H-pyrazole-4-carboxylic acid, 1-(3'-((1-(tert-Butoxycarbonyl)piperidin-3-yl)oxy)-[1,1'-biphenyl]-3-yl)-5-(2-(1-methyl-1H-1,2,3-triazol-4-yl)cyclopropyl)-1H-pyrazole-4-carboxylic acid, 1-(3'-(2-Cyclohexylethyl)-[1,1'-biphenyl]-3-yl)-5-(2-(1-methyl-1H-1,2,3-triazol-4-yl)cyclopropyl)-1H-pyrazole-4-carboxylic acid, 1-(2'-Fluoro-3'-((tetrahydro-2H-pyran-4-yl)oxy)-[1,1'-biphenyl]-3-yl)-5-(2-(1-methyl-1H-1,2,3-triazol-4-yl)cyclopropyl)-1H-pyrazole-4-carboxylic acid, 5-(2-(1-Methyl-1H-1,2,3-triazol-4-yl)cyclopropyl)-1-(3'-(1-phenylethoxy)-[1,1'-biphenyl]-3-yl)-1H-pyrazole-4-carboxylic acid, 5-((1,2-trans)-2-(1-Methyl-1H-1,2,3-triazol-4-yl)cyclopropyl)-1-(3'-(pyrimidin-5-ylmethoxy)-[1,1'-biphenyl]-3-yl)-1H-pyrazole-4-carboxylic acid, 1-(3'-([1,1'-Biphenyl]-4-ylmethoxy)-[1,1'-biphenyl]-3-yl)-5-((1,2-trans)-2-(1-methyl-1H-1,2,3-triazol-4-yl)cyclopropyl)-1H-pyrazole-4-carboxylic acid, 1-(3'-([1,1'-Biphenyl]-3-ylmethoxy)-[1,1'-biphenyl]-3-yl)-5-((1,2-trans)-2-(1-methyl-1H-1,2,3-triazol-4-yl)cyclopropyl)-1H-pyrazole-4-carboxylic acid, 1-(3'-(1-([1,1'-Biphenyl]-3-yl)ethoxy)-[1,1'-biphenyl]-3-yl)-5-((1,2-trans)-2-(1-methyl-1H-1,2,3-triazol-4-yl)cyclopropyl)-1H-pyrazole-4-carboxylic acid, 1-(3'-(1-([1,1'-Biphenyl]-4-yl)ethoxy)-[1,1'-biphenyl]-3-yl)-5-((1,2-trans)-2-(1-methyl-1H-1,2,3-triazol-4-yl)cyclopropyl)-1H-pyrazole-4-carboxylic acid, 1-(4'-(1-Cyclohexylethoxy)-[1,1'-biphenyl]-3-yl)-5-((1,2-trans)-2-(1-methyl-1H-1,2,3-triazol-4-yl)cyclopropyl)-1H-pyrazole-4-carboxylic acid, 1-(3'-(1-Cyclohexylpropoxy)-[1,1'-biphenyl]-3-yl)-5-((1,2-trans)-2-(1-methyl-1H-1,2,3-triazol-4-yl)cyclopropyl)-1H-pyrazole-4-carboxylic acid, 1-(3'-(Cyclohexanecarbonyl)-[1,1'-biphenyl]-3-yl)-5-(2-(1-methyl-1H-1,2,3-triazol-4-yl)cyclopropyl)-1H-pyrazole-4-carboxylic acid, 1-(3'-(Cyclohexyl(methoxy)methyl)-[1,1'-biphenyl]-3-yl)-5-(2-(1-methyl-1H-1,2,3-triazol-4-yl)cyclopropyl)-1H-pyrazole-4-carboxylic acid, 1-(3'-(2-cyclohexylethoxy)-[1,1'-biphenyl]-3-yl)-5-(trans-2-(1-methyl-1H-1,2,3-triazol-4-yl)cyclopropyl)-1H-pyrazole-4-carboxylic acid, 1-(3-(5-(Cyclohexylmethoxy)pyridin-3-yl)phenyl)-5-(trans-2-(1-methyl-1H-1,2,3-triazol-4-yl)cyclopropyl)-1H-pyrazole-4-carboxylic acid, 5-(trans-2-(1-methyl-1H-1,2,3-triazol-4-yl)cyclopropyl)-1-(3'-(piperidin-1-ylmethyl)-[1,1'-biphenyl]-3-yl)-1H-pyrazole-4-carboxylic acid, 5-(trans-2-(1-Methyl-1H-1,2,3-triazol-4-yl)cyclopropyl)-1-(3'-(morpholinomethyl)-[1,1'-biphenyl]-3-yl)-1H-pyrazole-4-carboxylic acid, 1-(6-(3-(1-Cyclohexylethoxy)phenyl)pyridin-2-yl)-5-(trans-2-(1-methyl-1H-1,2,3-triazol-4-yl)cyclopropyl)-1H-pyrazole-4-carboxylic acid, 1-(3'-(6,6-Dimethyl-5,6-dihydrocyclopenta[c]pyrazol-1(4H)-yl)-[1,1'-biphenyl]-3-yl)-5-(trifluoromethyl)-1H-pyrazole-4-carboxylic acid, 1-(6-(3-(6,6-Dimethyl-5,6-dihydrocyclopenta[c]pyrazol-1(4H)-yl)phenyl)pyridin-2-yl)-5-(trans-2-(1-methyl-1H-1,2,3-triazol-4-yl)cyclopropyl)-1H-pyrazole-4-carboxylic acid, 1-(3'-((4-Ethyl-4,5-dihydro-1H-benzo[c]azepin-2(3H)-yl)methyl)-[1,1'-biphenyl]-3-yl)-5-(trans-2-(1-methyl-1H-1,2,3-triazol-4-yl)cyclopropyl)-1H-pyrazole-4-carboxylic acid, 1-(3'-(((R)-2-Ethyl-2,3-dihydrobenzo[f][1,4]oxazepin-4(5H)-yl)methyl)-[1,1'-biphenyl]-3-yl)-5-(trans-2-(1-methyl-1H-1,2,3-triazol-4-yl)cyclopropyl)-1H-pyrazole-4-carboxylic acid, 1-(3'-((2,2-Dimethyl-2,3-dihydrobenzo[f][1,4]oxazepin-4(5H)-yl)methyl)-[1,1'-biphenyl]-3-yl)-5-(trans-2-(1-methyl-1H-1,2,3-triazol-4-yl)cyclopropyl)-1H-pyrazole-4-carboxylic acid, 1-(3'-(((R)-4-Ethyl-1,1-dioxido-3,4-dihydro-2H-benzo[b][1,4,5]oxathiazepin-2-yl)methyl)-[1,1'-biphenyl]-3-yl)-5-(trans-2-(1-methyl-1H-1,2,3-triazol-4-yl)cyclopropyl)-1H-pyrazole-4-carboxylic acid, 1-(3'-((2,3-Dihydrobenzo[f][1,4]oxazepin-4(5H)-yl)methyl)-[1,1'-biphenyl]-3-yl)-5-(trans-2-(1-methyl-1H-1,2,3-triazol-4-yl)cyclopropyl)-1H-pyrazole-4-carboxylic acid, 1-(3'-((R)-2-Ethyl-2,3,4,5-tetrahydrobenzo[f][1,4]oxazepine-4-carbonyl)-[1,1'-biphenyl]-3-yl)-5-(trans-(2-(1-methyl-1H-1,2,3-triazol-4-yl)cyclopropyl)-1H-pyrazole-4-carboxylic acid, 1-(2'-Fluoro-3'-(piperidine-1-carbonyl)-[1,1'-biphenyl]-3-yl)-5-(trans-2-(1-methyl-1H-1,2,3-triazol-4-yl)cyclopropyl)-1H-pyrazole-4-carboxylic acid, 1-(2'-Fluoro-3'-(3,3-dimethylpiperidine-1-carbonyl)-[1,1'-biphenyl]-3-yl)-5-(trans-2-(1-methyl-1H-1,2,3-triazol-4-yl)cyclopropyl)-1H-pyrazole-4-carboxylic acid, 1-(2'-Fluoro-3'-(azepane-1-carbonyl)-[1,1'-biphenyl]-3-yl)-5-(trans-2-(1-methyl-1H-1,2,3-triazol-4-yl)cyclopropyl)-1H-pyrazole-4-carboxylic acid, 1-(3'-((2R,6S)-2,6-Dimethylpiperidine-1-carbonyl)-2'-fluoro-[1,1'-biphenyl]-3-yl)-5-(trans-2-(1-methyl-1H-1,2,3-triazol-4-yl)cyclopropyl)-1H-pyrazole-4-carboxylic acid, 1-(3'-((2R,6S)-2,6-dimethylpiperidine-1-carbonyl)-2'-fluoro-[1,1'-biphenyl]-3-yl)-5-(trans-2-(1-methyl-1H-1,2,3-triazol-4-yl)cyclopropyl)-1H-pyrazole-4-carboxylic acid, 1-(3'-(3,5-Dimethylpiperidine-1-carbonyl)-2'-fluoro-[1,1'-biphenyl]-3-yl)-5-(2-(1-methyl-1H-1,2,3-triazol-4-yl)cyclopropyl)-1H-pyrazole-4-carboxylic acid, 1-(3'-(2-(Methoxymethyl)piperidine-1-carbonyl)-2'-fluoro-[1,1'-biphenyl]-3-yl)-5-(trans-2-(1-methyl-1H-1,2,3-triazol-4-yl)cyclopropyl)-1H-pyrazole-4-carboxylic acid, 1-(3'-((Cyclopropylmethyl)carbamoyl)-2'-fluoro-[1,1'-biphenyl]-3-yl)-5-(trans-2-(1-methyl-1H-1,2,3-triazol-4-yl)cyclopropyl)-1H-pyrazole-4-carboxylic acid, 1-(2'-Fluoro-3'(isobutyl(methyl)carbamoyl)-[1,1'-biphenyl]-3-yl)-5-(trans-2-(1-methyl-1H-1,2,3-triazol-4-yl)cyclopropyl)-1H-pyrazole-4-carboxylic acid, 1-(3'-((S)-2-(Ethoxymethyl)pyrrolidine-1-carbonyl)-[1,1'-biphenyl]-3-yl)-5-(trans-2-(1-methyl-1H-1,2,3-triazol-4-yl)cyclopropyl)-1H-pyrazole-4-carboxylic acid, 1-(3'-((R)-2-(Ethoxymethyl)pyrrolidine-1-carbonyl)-[1,1'-biphenyl]-3-yl)-5-(trans-2-(1-methyl-1H-1,2,3-triazol-4-yl)cyclopropyl)-1H-pyrazole-4-carboxylic acid, and 1-(3'-((R)-2-(Ethoxymethyl)pyrrolidine-1-carbonyl)-[1,1'-biphenyl]-3-yl)-5-(trans-2-(1-methyl-1H-1,2,3-triazol-4-yl)cyclopropyl)-1H-pyrazole-4-carboxylic acid.

9. A pharmaceutical composition comprising a compound of claim 1 and a pharmaceutically acceptable carrier or excipient.

10. A method of treating respiratory and non-respiratory disorders, selected from the group consisting of COPD, asthma, fibrosis, chronic asthma and acute asthma, lung disease secondary to environmental exposures, acute lung infection, chronic lung infection, al antitrypsin disease, cystic fibrosis, autoimmune diseases, diabetic nephropathy, chronic kidney disease, sepsis-induced acute kidney injury, acute kidney injury (AKI), kidney disease or malfunction seen during kidney transplantation, Pulmonary Arterial Hypertension, atherosclerosis, hypertension, heart failure, acute coronary syndrome, myocardial infarction, myocardial repair, cardiac remodeling, cardiac arrhythmias, Parkinson's disease (PD), Alzheimer's disease (AD), Friedreich's Ataxia (FA), amyotrophic lateral sclerosis (ALS), multiple sclerosis (MS), inflammatory bowel disease, colon cancer, neovascular (dry) AMD and neovascular (wet) AMD, eye injury, Fuchs Endothelial Corneal Dystrophy (FECD), uveitis or other inflammatory eye conditions, Non-alcoholic Steatohepatitis (NASH), toxin-induced liver disease, acetaminophen-induced hepatic disease, viral hepatitis, cirrhosis, psoriasis, dermatitis/topical effects of radiation, immunosuppression due to radiation exposure, Preeclampsia, and high altitude sickness, which comprises administering to a human having said disorder, a compound of claim 1.

11. The method according to claim 10 wherein the compound is administered orally.

12. The method according to claim 10 wherein the compound is administered intravenously.

13. The method according to claim 10 wherein the compound is administered by inhalation.

14. The method according to claim 10 wherein the disease is COPD.

15. The method according to claim 14 wherein the compound is administered by inhalation.

* * * * *